United States Patent
Miller et al.

(10) Patent No.: US 9,308,236 B2
(45) Date of Patent: Apr. 12, 2016

(54) MACROCYCLIC INHIBITORS OF THE PD-1/PD-L1 AND CD80(B7-1)/PD-L1 PROTEIN/PROTEIN INTERACTIONS

(71) Applicant: Bristol-Myers Squibb Company, Princeton, NJ (US)

(72) Inventors: Michael Matthew Miller, Pennington, NJ (US); Claudio Mapelli, Langhorne, PA (US); Martin Patrick Allen, Flemington, NJ (US); Michael S. Bowsher, Prospect, CT (US); Kenneth M. Boy, Durham, CT (US); Eric P. Gillis, Cheshire, CT (US); David R. Langley, Meriden, CT (US); Eric Mull, Guilford, CT (US); Maude A. Poirier, Pennington, NJ (US); Nishith Sanghvi, Franklin Park, NJ (US); Li-Qiang Sun, Glastonbury, CT (US); Daniel J. Tenney, Madison, CT (US); Kap-Sun Yeung, Madison, CT (US); Juliang Zhu, North Haven, CT (US); Patrick C. Reid, Tokyo (JP); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/201,977

(22) Filed: Mar. 10, 2014

(65) Prior Publication Data

US 2014/0294898 A1    Oct. 2, 2014

Related U.S. Application Data

(60) Provisional application No. 61/918,184, filed on Dec. 19, 2013, provisional application No. 61/794,589, filed on Mar. 15, 2013.

(51) Int. Cl.
| | | |
|---|---|---|
| *C07K 7/56* | (2006.01) |
| *A61K 38/12* | (2006.01) |
| *C07K 7/08* | (2006.01) |
| *G01N 33/68* | (2006.01) |
| *A61K 38/10* | (2006.01) |
| *A61K 39/39* | (2006.01) |
| *A61K 45/06* | (2006.01) |
| *G01N 33/574* | (2006.01) |
| *A61K 38/00* | (2006.01) |

(52) U.S. Cl.
CPC ............... *A61K 38/10* (2013.01); *A61K 39/39* (2013.01); *A61K 45/06* (2013.01); *C07K 7/08* (2013.01); *C07K 7/56* (2013.01); *G01N 33/574* (2013.01); *A61K 38/00* (2013.01); *G01N 2333/70532* (2013.01); *G01N 2500/02* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,869,451 | A | 2/1999 | Dower et al. |
| 2010/0168380 | A1 | 7/2010 | Suga et al. |
| 2013/0178394 | A1 | 7/2013 | Suga et al. |
| 2014/0018257 | A1 | 1/2014 | Suga et al. |

FOREIGN PATENT DOCUMENTS

| | | |
|---|---|---|
| WO | WO 00/26353 | 5/2000 |
| WO | WO 2010/027828 | 3/2010 |
| WO | WO 2011/161699 | 12/2011 |
| WO | WO 2012/168944 | 12/2012 |
| WO | WO 2013/144704 | 10/2013 |
| WO | WO 2013/182240 | 12/2013 |
| WO | WO 2013/183707 | 12/2013 |
| WO | WO 2014/151006 | 9/2014 |
| WO | WO 2015/033303 | 3/2015 |
| WO | WO 2015/044900 | 4/2015 |

OTHER PUBLICATIONS

Hayashi, Y. et al., "In Vitro Selection of Anti-Akt2 Thioether-Macrocyclic Peptides Leading to Isoform-Selective Inhibitors", ACS Chemical Biology, vol. 7, pp. 607-613 (2012).

Morimoto, J. et al., "Discovery of Macrocyclic Peptides Armed with a Mechanism-Based Warhead: Isoform-Selective Inhibition of Human Deacetylase SIRT2", Angewandte Chemie, International Edition, vol. 51, pp. 3423-3427 (2012).

Yamagishi, Y. et al., "Natural Product-Like Macrocyclic N-Methyl-Peptide Inhibitors against a Ubiquitin Ligase Uncovered from a Ribosome-Expressed De Novo Library", Chemistry & Biology, vol. 18, pp. 1562-1570 (2011).

Bristol-Myers Squibb Company, International Patent Application No. PCT/US14/55093, filed Sep. 11, 2014.

*Primary Examiner* — Julie Ha
*Assistant Examiner* — Kristina M Hellman
(74) *Attorney, Agent, or Firm* — Pamela A. Mingo; Stephen C. D'Amico

(57) ABSTRACT

The present disclosure provides novel macrocyclic peptides which inhibit the PD-1/PD-L1 and PD-L1/CD80 protein/protein interaction, and thus are useful for the amelioration of various diseases, including cancer and infectious diseases.

5 Claims, 13 Drawing Sheets

FIG. 4

| Inhibitor | PD-1/PD-L1 HTRF Binding Assay (IC$_{50}$, nM) Binding Pairs | | | |
|---|---|---|---|---|
| | PD-1/PD-L1 | PD-1/PD-L2 | CD80/PD-L1 | CD80/CTLA4 |
| αPD-1 | 0.60 | 3.33 | >100 | >100 |
| αPD-L1 | 6.09 | >100 | 1.02 | >100 |
| Compound No. 99 | 90.9 | >10,000 | 78.2 | >10,000 |
| Compound No. 2 | 14.4 | >10,000 | 15.2 | >10,000 |
| Compound No. 1 | 5.60 | >10,000 | 7.04 | >10,000 |
| Compound No. 71 | 1.03 | >10,000 | 3.57 | >10,000 |

FIG. 5

| Cell Line: | Jurkat PD-1 | LK35.2-hPD-L1 | L2987 |
|---|---|---|---|
| Ligand: | sPD-L1-Ig | sPD-1-Ig | sPD-1-Ig |
| *Antibodies* | | | |
| αPD-1 (MDX-1106) | 0.18 | 0.91 | 4.12 |
| αPD-L1 | 1.67 | 0.08 | 0.03 |
| *PD-L1 Macrocyclic Peptides* | | | |
| Compound No. 99 | 120 | 207 | 150 |
| Compound No. 2 | 79 | 11 | 73 |
| Compound No. 1 | 26 | 6 | 12 |
| Compound No. 71 | 5 | 1 | 1 |

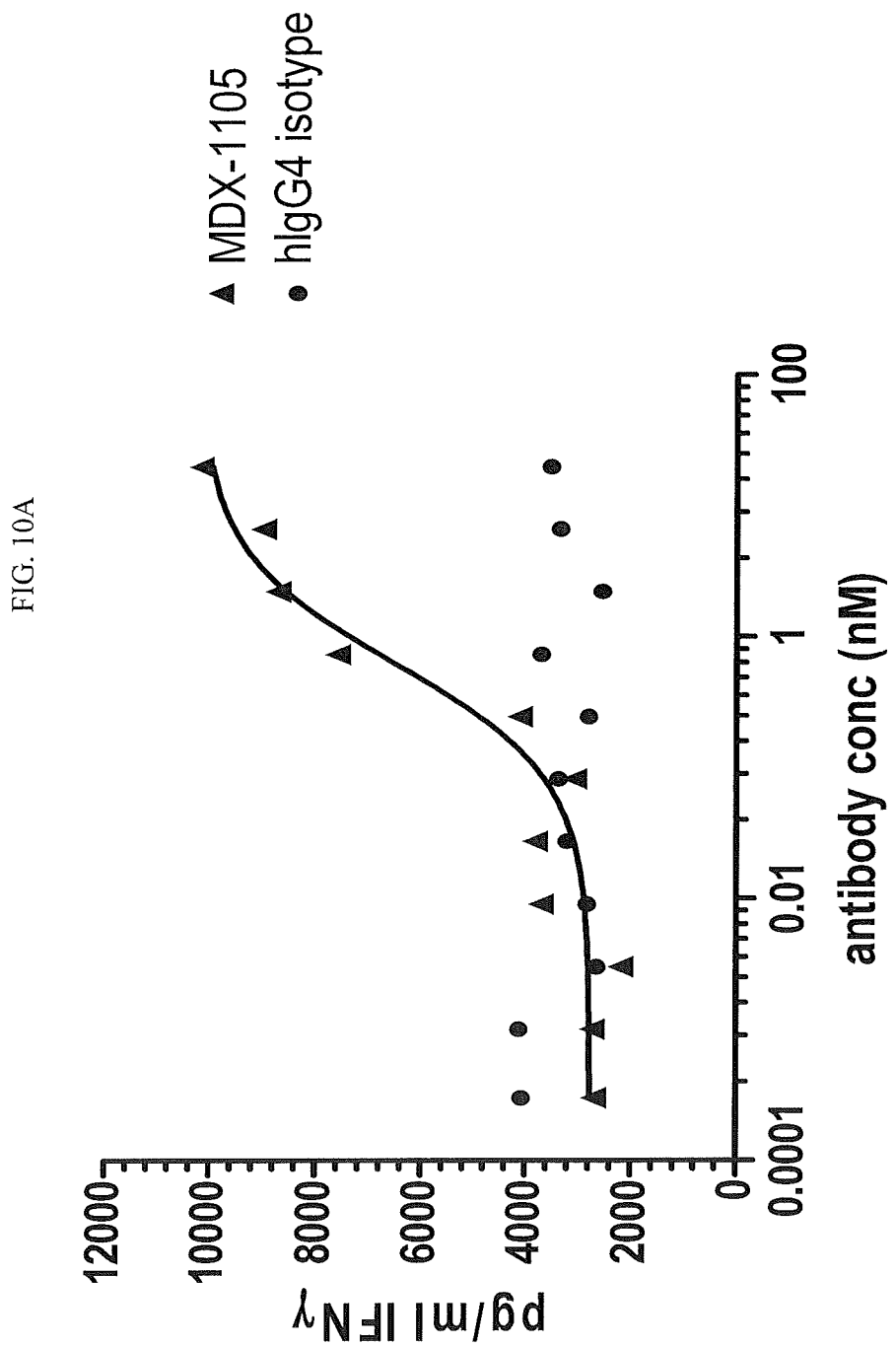

| Inhibitor | αPD-L1 (MDX-1105) | Compound No. 71 | Compound No. 1 | Compound No. 2 | Compound No. 99 |
|---|---|---|---|---|---|
| $EC_{50}$, nM | 0.600 | 300 | 400 | 400 | >10,000 |

FIG. 11

| Inhibitor: | αPD-L1 | | Compound No. 71 | | DMSO control |
|---|---|---|---|---|---|
| Antigen: | Mean | Fold | Mean | Fold | Mean |
| HIV-GAG Pool 1 | 258.0 | 1.0 | 291.0 | 1.1 | 271.0 |
| HIV-GAG Pool 2 | 105.0 | 21.0 | 56.5 | 11.3 | 5.0 |
| HIV-GAG Pool 3 | 38.0 | 0.6 | 55.0 | 0.9 | 64.5 |
| HIV-GAG Pool 4 | 216.0 | 1.6 | 157.0 | 1.2 | 132.5 |
| HIV-GAG Pool 5 | 32.5 | 0.5 | 94.5 | 1.4 | 65.5 |
| HIV-GAG Pool 6 | 448.0 | 0.9 | 470.5 | 0.9 | 506.5 |

MACROCYCLIC INHIBITORS OF THE PD-1/PD-L1 AND CD80(B7-1)/PD-L1 PROTEIN/PROTEIN INTERACTIONS

This application claims priority to U.S. Provisional Patent Application 61/918,184, filed Dec. 19, 2013 and U.S. Provisional Patent Application 61/794,589, filed Mar. 15, 2013, hereby incorporated by reference in their entireties.

The present disclosure provides novel macrocyclic peptides which inhibit the PD-1/PD-L1 and CD80/PD-L1 protein/protein interaction, and are thus useful for the amelioration of various diseases, including cancer and infectious diseases.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al., *Curr. Opin. Immunol.*, 14:779-782 (2002); Bennett et al., *J. Immunol.*, 170:711-718 (2003)).

The PD-1 protein is a 55 kDa type I transmembrane protein that is part of the Ig gene superfamily (Agata et al., *Int. Immunol.*, 8:765-772 (1996)). PD-1 contains a membrane proximal immunoreceptor tyrosine inhibitory motif (ITIM) and a membrane distal tyrosine-based switch motif (ITSM) (Thomas, M. L., *J. Exp. Med.*, 181:1953-1956 (1995); Vivier, E. et al., *Immunol. Today*, 18:286-291 (1997)). Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be down-regulated upon interaction with cells expressing PD-L1 or PD-L2 (Freeman et al., *J. Exp. Med.*, 192:1027-1034 (2000); Latchman et al., *Nat. Immunol.*, 2:261-268 (2001); Carter et al., *Eur. J. Immunol.*, 32:634-643 (2002)). Both PD-L1 and PD-L2 are B7 protein family members that bind to PD-1, but do not bind to other CD28 family members. The PD-L1 ligand is abundant in a variety of human cancers (Dong et al., *Nat. Med.*, 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med.*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 with PD-L1, and the effect is additive when the interaction of PD-1 with PD-L2 is blocked as well (Iwai et al., *Proc. Natl. Acad. Sci. USA*, 99:12293-12297 (2002); Brown et al., *J. Immunol.*, 170:1257-1266 (2003)).

PD-L1 has also been shown to interact with CD80 (Butte M J et al, *Immunity;* 27:111-122 (2007)). The interaction PD-L1/CD80 on expressing immune cells has been shown to be an inhibitory one. Blockade of this interaction has been shown to abrogate this inhibitory interaction (Paterson A M, et al., *J. Immunol.*, 187:1097-1105 (2011); Yang J, et al. *J Immunol.* August 1; 187(3):1113-9 (2011)).

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self tolerance (Keir, M. E. et al., *Annu. Rev. Immunol.*, 26:Epub (2008)). Chronic antigen stimulation, such as that which occurs during tumor disease or chronic infections, results in T cells that express elevated levels of PD-1 and are dysfunctional with respect to activity towards the chronic antigen (reviewed in Kim et al., *Curr. Opin.* 1 mm. (2010)). This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1 (Brahmer et al., *New Engl. J. Med.* (2012)). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong, H. et al., "B7-H1 pathway and its role in the evasion of tumor immunity", *J. Mol. Med.*, 81(5):281-287 (2003); Dong, H. et al., "Tumor-associated B7-H1 promotes T-cell apoptosis: a potential mechanism of immune evasion", *Nat. Med.*, 8(8): 793-800 (2002)).

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection (Barber, D. L. et al., "Restoring function in exhausted CD8 T cells during chronic viral infection", *Nature,* 439(7077):682-687 (2006)). Humanized mice infected with HIV-1 show enhanced protection against viremia and viral depletion of CD4+ T cells (Palmer et al., *J. Immunol.* (2013)). Blockade of PD-1/PD-L1 through monoclonal antibodies to PD-L1 can restore in vitro antigen-specific functionality to T cells from HIV patients (Day, *Nature* (2006); Petrovas, *J. Exp. Med.* (2006); Trautman, *Nature Med.* (2006); D'Souza, *J. Immunol.* (2007); Zhang, *Blood* (2007); Kaufmann, *Nature Imm.* (2007); Kasu, *J. Immunol.* (2010); Porichis, *Blood* (2011)), HCV patients (Golden-Mason, *J. Virol.* (2007); Jeung, *J. Leuk. Biol.* (2007); Urbani, *J. Hepatol.* (2008); Nakamoto, *PLoS Path.* (2009); Nakamoto, *Gastroenterology* (2008)) and HBV patients (Boni, *J. Virol.* (2007); Fisicaro, *Gastro.* (2010); Fisicaro et al., *Gastroenterology* (2012); Boni et al., *Gastro.* (2012); Penna et al., *J. Hep.* (2012); Raziorrough, *Hepatology* (2009); Liang, *World J. Gastro.* (2010); Zhang, *Gastro.* (2008)).

Blockade of the PD-L1/CD80 interaction has also been shown to stimulate immunity (Yang J., et al., *J Immunol.* August 1; 187(3):1113-9 (2011)). Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., *Nat Rev Immunol* (2013)). These include increased levels of PD-1 and PD-L1 (Guignant, et al, *Crit. Care* (2011)), Cells from septic shock patients with increased levels of PD-1 and PD-L1 exhibit an increased level of T cell apoptosis. Antibodies directed to PD-L1, can reduce the level of Immune cell apoptosis (Zhang et al, *Crit. Care* (2011)). Furthermore, mice lacking PD-1 expression are more resistant to septic shock symptoms than wildtype mice. Yang J., et al. *J Immunol.* August 1; 187(3):1113-9 (2011)). Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection (Ha, S. J. et al., "Enhancing therapeutic vaccination by blocking PD-1-mediated inhibitory signals during chronic infection", *J. Exp. Med.*, 205(3):543-555 (2008); Finnefrock, A. C. et al., "PD-1 blockade in rhesus macaques: impact on chronic infection and prophylactic vaccination", *J. Immunol.*, 182(2): 980-987 (2009); Song, M.-Y. et al., "Enhancement of vaccine-induced primary and memory CD8+ t-cell responses by soluble PD-1", *J. Immunother.*, 34(3):297-306 (2011)).

The molecules described herein demonstrate the ability to block the interaction of PD-L1 with PD-1, in both biochemical and cell-based experimental systems. These results are consistent with a potential for therapeutic administration to enhance immunity in cancer or chronic infection, including therapeutic vaccine.

The macrocyclic peptides described herein are capable of inhibiting the interaction of PD-L1 with PD-1 and with CD80. These compounds have demonstrated highly efficacious binding to PD-L1, blockade of the interaction of PD-L1 with either PD-1 or CD80, and are capable of promoting enhanced T cell functional activity, thus making them candidates for parenteral, oral, pulmonary, nasal, buccal and sustained release formulations.

In one embodiment the present disclosure provides a compound of formula (I)

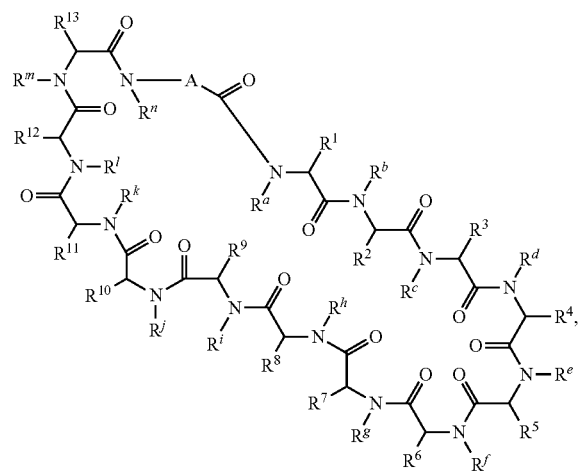

(I)

or a pharmaceutically acceptable salt thereof, wherein:
A is selected from a bond,

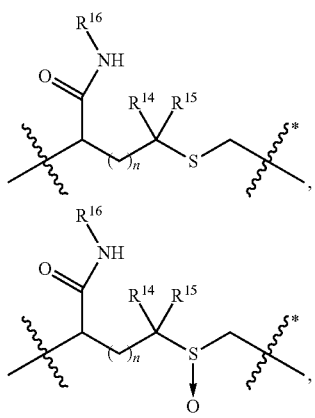

-continued

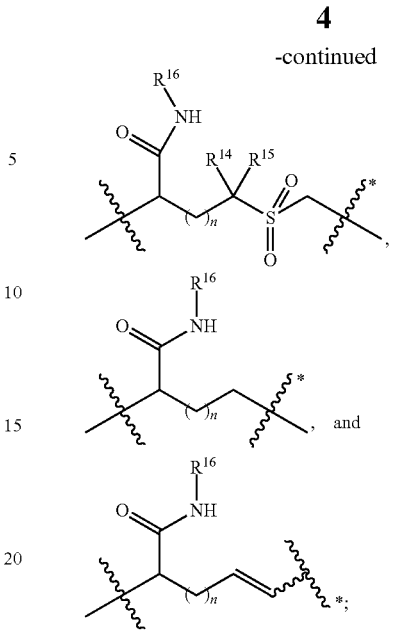

wherein:
⁎ denotes the point of attachment to the carbonyl group and ⁎ denotes the point of attachment to the nitrogen atom;
n is 0 or 1;
$R^{14}$ and $R^{15}$ are independently selected from hydrogen and methyl; and
$R^{16}$ is selected from hydrogen, —$CHR^{17}C(O)NH_2$, —$CHR^{17}C(O)NHCHR^{18}C(O)NH_2$, and —$CHR^{17}C(O)NHCHR^{18}C(O)NHCH_2C(O)NH_2$;
wherein $R^{17}$ is selected from hydrogen and —$CH_2OH$ and wherein $R^{18}$ is selected from hydrogen and methyl;
$R^c$, $R^f$, $R^h$, $R^i$, $R^m$, and $R^n$ are hydrogen;
$R^a$, $R^e$, $R^j$, and $R^k$, are each independently selected from hydrogen and methyl;
$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;
$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;
$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^1$ is methyl or, $R^1$ and $R^{12}$, together with the atoms to which they are attached, form a ring selected from azetidine and pyrollidine, wherein each ring is optionally substituted with one to four independently selected from amino, cyano, methyl, halo, and hydroxy.

In another embodiment the present disclosure provides a compound of formula (I), or a pharmaceutically acceptable salt thereof, wherein A is

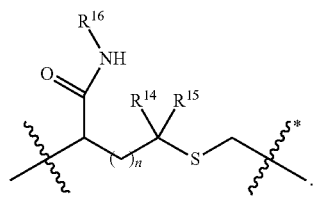

In another embodiment the present disclosure provides a compound of formula (I),
or a pharmaceutically acceptable salt thereof, wherein A is

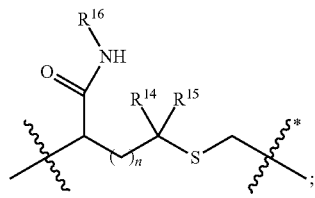

$R^d$ is methyl or, $R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, hydroxy, and phenyl;

$R^g$ is methyl or, $R^g$ and $R^7$, together with the atoms to which they are attached, form a ring selected from azetidine, pyrollidine, morpholine, piperidine, piperazine, and tetrahydrothiazole; wherein each ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^k$ is methyl or, $R^k$ and $R^{11}$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy.

In another embodiment the present disclosure provides a compound of formula (I), or a pharmaceutically acceptable salt thereof, wherein A is

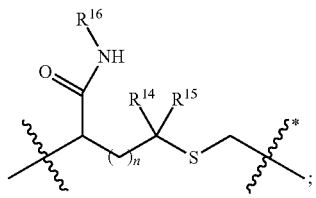

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^k$ is methyl.

In another embodiment the present disclosure provides a compound of formula (I), or a pharmaceutically acceptable salt thereof, wherein A is

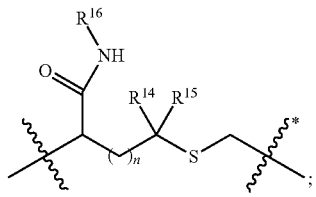

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group;

$R^k$ is methyl; and $R^8$ is selected from:

azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl; and indolyl$C_1$-$C_3$alkyl, wherein the indolyl part is optionally substituted with one group selected from $C_1$-$C_3$alkyl, cyano, halo, and hydroxy.

In another embodiment the present disclosure provides a compound of formula (I),
or a pharmaceutically acceptable salt thereof, wherein A is

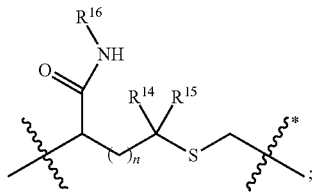

$R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group;

$R^k$ is methyl; and $R^8$ is 3-indolyl$C_1$-$C_3$alkyl optionally substituted with one group selected from $C_1$-$C_3$alkyl, halo, hydroxy, or cyano.

In another embodiment the present disclosure provides a compound of formula (II)

(II)

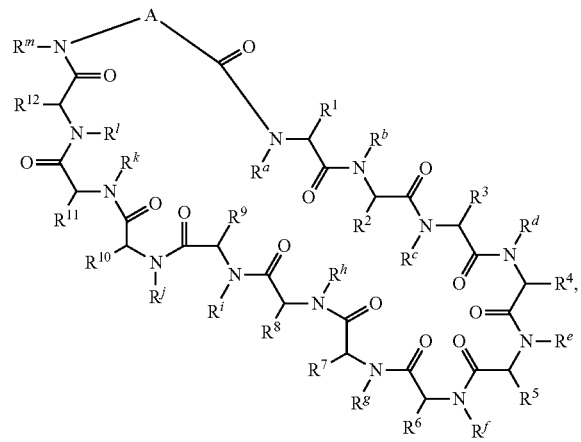

or a pharmaceutically acceptable salt thereof, wherein:
A is selected from a bond,

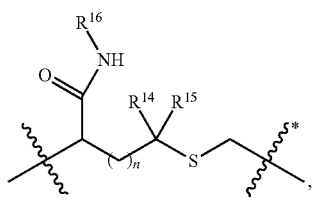

-continued

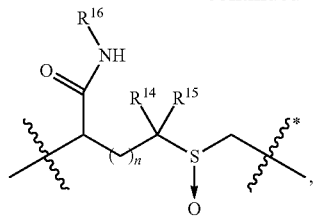

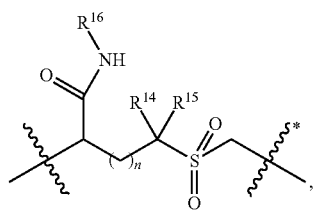

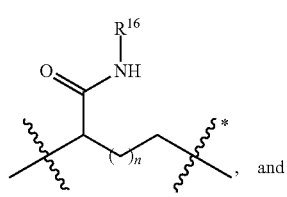

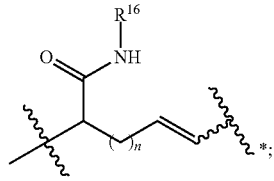

wherein:
⁎ denotes the point of attachment to the carbonyl group and ⁎ denotes the point of attachment to the nitrogen atom;

n is 0 or 1;

$R^{14}$ and $R^{15}$ are independently selected from hydrogen and methyl; and $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$;

wherein $R^{17}$ is selected from hydrogen and —CH$_2$OH and wherein $R^{18}$ is selected from hydrogen and methyl;

$R^a$, $R^f$, $R^j$, $R^k$, $R^l$, and $R^m$ are hydrogen;

$R^b$ and $R^c$ are methyl;

$R^g$ is selected from hydrogen and methyl;

$R^1$, $R^2$, $R^3$, $R^4$, $R^5$, $R^6$, $R^7$, $R^8$, $R^9$, $R^{10}$, $R^{11}$, and $R^{12}$ are independently selected from a natural amino acid side chain and an unnatural amino acid side chain or form a ring with the corresponding vicinal R group as described below;

$R^d$ is selected from hydrogen and methyl, or, $R^d$ and $R^4$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;

$R^e$ is selected from hydrogen and methyl, or, $R^e$ and $R^5$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy;

$R^h$ is selected from hydrogen and methyl, or, $R^h$ and $R^8$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy; and $R^i$ is selected from hydrogen and methyl, or, $R^i$ and $R^9$, together with the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, halomethyl, and hydroxy.

In another embodiment the present disclosure provides a compound of formula (II), or a pharmaceutically acceptable salt thereof, wherein A is

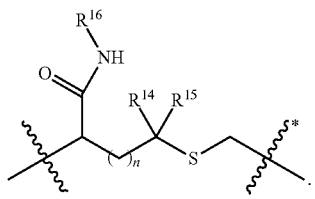

In another embodiment the present disclosure provides a compound of formula (II), or a pharmaceutically acceptable salt thereof, wherein A is

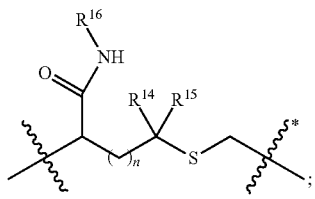

$R^d$ is methyl, or, $R^d$ and $R^4$, together with the atoms to which they are attached selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy;

$R^g$ is methyl; and $R^i$ is methyl, or, $R^i$ and $R^9$, together with the atoms to which they are attached selected from selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy.

In another embodiment the present disclosure provides a compound of formula (II), or a pharmaceutically acceptable salt thereof, wherein A is

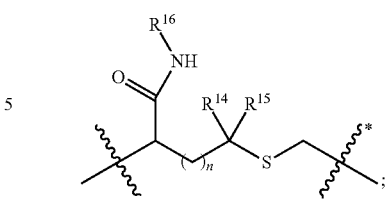

$R^d$ is methyl, or, $R^d$ and $R^4$, together with the atoms to which they are attached selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy;

$R^g$ is methyl;

$R^i$ is methyl, or, $R^i$ and $R^9$, together with the atoms to which they are attached selected from selected from azetidine, pyrollidine, morpholine, piperidine, piperazine, and tetrahydrothiazole; wherein each ring is optionally substituted with one or two groups independently selected from amino, cyano, methyl, halo, halomethyl, and hydroxy; and $R^7$ is phenyl$C_1$-$C_3$alkyl optionally substituted with a fluoro group.

In another embodiment the present disclosure provides a method of enhancing, stimulating, and/or increasing the immune response in a subject in need thereof, said method comprising administering to the subject a therapeutically effective amount of at least one macrocyclic peptide described herein. In another embodiment the method further comprises administering an additional agent prior to, after, or simultaneously with the macrocyclic peptide or peptides described herein. In another embodiment the additional agent is an antimicrobial agent, an antiviral agent, a cytotoxic agent, and/or an immune response modifier.

In another embodiment the present disclosure provides a method of inhibiting growth, proliferation, or metastasis of cancer cells in a subject in need thereof, said method comprising administering to the subject a therapeutically effective amount of one or more macrocyclic peptides described herein. In another embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In another embodiment the present disclosure provides a method of treating an infectious disease in a subject in need thereof, the method comprising administering to the subject a therapeutically effective amount of at least one macrocyclic peptide described herein. In another embodiment the infectious disease is caused by a virus. In another embodiment the virus is selected from HIV, Hepatitis A, Hepatitis B, Hepatitis C, herpes virus, and influenza.

In another embodiment the present disclosure provides a method of treating septic shock in a subject in need thereof, the method comprising administering to the subject a therapeutically effective amount of one or more macrocyclic peptides described herein.

In another embodiment the present disclosure provides a method blocking the interaction of PD-L1 with PD-1 and/or CD80 in a subject, said method comprising administering to the subject a therapeutically effective amount of at least one macrocyclic peptide described herein.

In compounds of formula (I) and (II) where the R side chains are part of a ring that is substituted with methyl, it is understood that the methyl group may be on any substitutable carbon atom in the ring, including the carbon that is part of the macrocyclic parent structure.

In compounds of formula (I), preferred $R^1$ side chains are: phenylalanine, tyrosine, 3-thien-2-yl, 4-methylphenylalanine, 4-chlorophenylalanine, 3-methoxyphenylalananie, isotryptophan, 3-methylphenylalanine, 1-naphthylalanine, 3,4-difluorophenylalanine, 4-fluorophenylalanine, 3,4-dimethoxyphenylalanine, 3,4-dichlorophenylalanine, 4-difluoromethylphenylalanine, 2-methylphenylalanine, 2-naphthylalanine, tryptophan, 4-pyridinyl, 4-bromophenylalanine, 3-pyridinyl, 4-trifluoromethylphenylalanine, 4-carboxyphenylalanine, 4-methoxyphenylalanine, biphenylalanine, and 3-chlorophenylalanine; and 2,4-diaminobutane.

In compounds of formula (I) where $R^2$ is not part of a ring, preferred $R^2$ side chains are: alanine, serine, and glycine.

In compounds of formula (I), preferred $R^3$ side chains are: asparagine, aspartic acid, glutamic acid, glutamine, serine, ornithine, lysine, histidine, threonine, leucine, alanine, 2,3-diaminopropane, and 2,4-diaminobutane.

In compounds of formula (I) where $R^4$ is not part of a ring, preferred $R^4$ side chains are: valine, alanine, isoleucine, and glycine.

In compounds of formula (I), preferred $R^5$ side chains are: histidine, asparagine, 2,3-diaminopropane, serine, glycine, 2,4-diaminobutane, threonine, alanine, lysine, aspartic acid, alanine, and 3-thiazolylalanine In compounds of formula (I), preferred $R^6$ side chains are: leucine, aspartic acid, asparagine, glutamic acid, glutamine, serine, lysine, 3-cyclohexane, threonine, ornithine, 2,4-diaminobutane, alanine, arginine, and ornithine ($COCH_3$).

In compounds of formula (I) where $R^7$ is not part of a ring, preferred $R^7$ side chains are: glycine, 2,4-diaminobutane, serine, lysine, arginine, ornithine, histidine, asparagine, glutamine, alanine, and 2,4-diaminobutane (C(O)cyclobutane).

In compounds of formula (I) preferred $R^8$ side chains are tryptophan and 1,2-benzisothiazolinylalanine In compounds of formula (I) preferred $R^9$ side chains are: serine, histidine, lysine, ornithine, 2,4-dibutylamine, threonine, lysine, glycine, glutamic acid, valine, 2,3-diaminopropane, arginine, aspartic acid, and tyrosine.

In compounds of formula (I) preferred $R^{10}$ side chains are: tryptophan, benzisothiazolylalanine, 1-napthylalanine, 5-fluorotryptophan, methionine, 7-methyltryptophan, 5-chlorotryptophan, and -methyltryptophan.

In compounds of formula (I) preferred $R^{11}$ side chains are: norleucine, leucine, asparagine, phenylalanine, methionine, ethoxymethane, alanine, tryptophan, isoleucine, phenylpropane, glutamic acid, hexane, and heptane.

In compounds of formula (I) where $R^{12}$ is not part of a ring, preferred $R^{12}$ side chains are: norleucine, alanine, ethoxymethane, methionine, serine, phenylalanine, methoxyethane, leucine, tryptophan, isoleucine, glutamic acid, hexane, heptane, and glycine.

In compounds of formula (I) preferred $R^{13}$ side chains: arginine, ornithine, alanine, 2,4-diaminobutane, 2,3-diaminopropane, leucine, aspartic acid, glutamic acid, serine, lysine, threonine, cyclopropylmethane, glycine, valine, isoleucine, histidine, and 2-aminobutane.

In compounds of formula (II) preferred $R^1$ side chains are: phenylalanine, 3-methoxyphenylalanine, 2-fluorophenylalanine, 3-fluorophenylalanine, 4-fluorophenylalanine, 3,4-difluorophenylalanine, 3,5-difluorophenylalanine, 3,4,5-trifluorophenylalanine, 3-fluoro, 4-chlorophenylalanine, 3-chloro, 4-fluorophenylalanine, 3-chlorophenylalanine, 4-chlorophenylalanine, 3,4-dichlorophenylalanine, 3,5-dichlorophenylalanine, 3,5-dichloro, 4-fluorophenylalanine, 3-chloro, 4,5-difluorophenylalanine, 4-bromophenylalanine, 4-nitrophenylalanine, 3-trifluoromethylphenylalanine, 4-trifluoromethylphenylalanine, and 3-pyridylalanine.

In compounds of formula (II), preferred $R^2$ side chains are: phenylalanine, alanine, histidine, tyrosine, tryptophan, glutamic acid, 1-naphthylalanine, 2-naphthylalanine, 2-benzothiazolylalanine, 3-pyridinylalanine, and 4-pyridinylalanine In compounds of formula (II), preferred $R^3$ side chains are: norleucine, alanine, tyrosine, glutamic acid, leucine, and isoleucine.

In compounds of formula (II) where $R^4$ is not part of a ring, preferred $R^4$ side chains are: glycine, and alanine In compounds of formula (II) where $R^5$ is not part of a ring, preferred $R^5$ side chains are: aspartic acid, glutamic acid, arginine, lysine, asparagine, serine, 2,4-diaminobutane, 2,3-diaminopropane, and 2-aminobutane.

In compounds of formula (II) preferred $R^6$ side chains are: valine, leucine, isoleucine, N-methylthreonine, and cyclohexylmethane.

In compounds of formula (II) preferred $R^7$ side chains are: phenylalanine and 3-fluorophenylalanine.

In compounds of formula (II) where $R^8$ is not part of a ring, preferred $R^8$ side chains are: tyrosine, 3-iodotyrosine, leucine, arginine, glutamic acid, glutamine, pentafluorophenylalanine, 4-aminophenylalanine, 4-aminomethylphenylalanine, 3,4-dimethoxyphenylalanine, tryptophan, 5-chlorotryptophan, 5-hydroxytryptophan, isotryptophan, lysine, ornithine, and 2,3-diaminopropane.

In compounds of formula (II) preferred $R^{10}$ side chains are: tryptophan, 5-chlorotryptophan, 7-azatryptophan, isotryptophan, 3-benzothiazolylalanine, and 1-napththylalanine In compounds of formula (II) preferred $R^{11}$ side chains are tyrosine, 4-fluorophenylalanine, 4-aminomethylphenylalanine, 4-aminophenylalanine, and 3,4-dihydroxyphenylalanine In compounds of formula (II) preferred $R^{12}$ side chains are: leucine, tyrosine, arginine, lysine, ornithine, glutamic acid, phenylalanine, 4-methylphenylalanine, 4-chlorophenylalanine, 4-aminomethylphenyalanine, norleucine, cyclohexylalanine, 2,4-diaminobutane, and 2,3-diaminopropane.

In compounds of formula (II), when $R^4$ and $R^9$ are part of a ring the preferred stereochemistry is that of the D-isomer and when $R^5$ and $R^8$ are part of a ring the preferred stereochemistry is that of the L isomer.

One embodiment of the subject matter described herein is directed to a polypeptide comprising a sequence of Formula I(a):

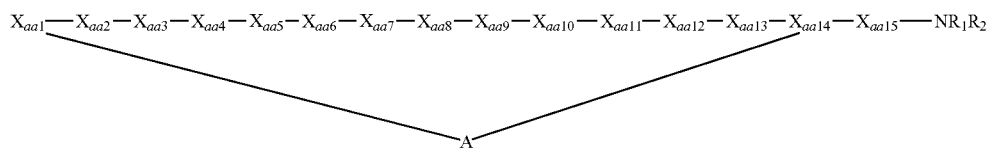

wherein,

A is an organic or peptidic linker between $X_{aa1}$ and $X_{aa14}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or N-methylated alkyl amino acid;

$X_{aa3}$ is a naturally or nonnaturally occurring hydrophilic or alkyl or polar amino acid;

$X_{aa4}$ is a naturally or nonnaturally occurring amino acid, an alkyl amino acid or a N-methylated alkyl amino acid;

$X_{aa5}$ is a naturally or nonnaturally occurring heteroaromatic amino acid or a positively charged amino acid or an alkyl amino acid;

$X_{aa6}$ is a naturally or nonnaturally occurring hydrophilic or hydrophobic or positively or negatively charged amino acid;

$X_{aa7}$ is a naturally or nonnaturally occurring N-methylated or non-N-methylated hydrophilic or hydrophobic or positively or negatively charged amino acid;

$X_{aa8}$ is a naturally or nonnaturally occurring aromatic or heteroaromatic or arylalkyl or heteroarylalkyl amino acid;

$X_{aa9}$ is a naturally or nonnaturally occurring hydrophilic or hydrophobic or positively or negatively charged amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally N-methylated or non-N-methylated alkyl or heteroalkyl or aromatic or heteroaromatic occurring amino acid;

$X_{aa12}$ is a naturally or nonnaturally N-methylated or non-N-methylated alkyl or heteroalkyl or aromatic or heteroaromatic occurring amino acid;

$X_{aa13}$ is a naturally or nonnaturally occurring hydrophilic or hydrophobic or positively or negatively charged amino acid;

$X_{aa14}$ is a naturally or nonnaturally occurring amino acid possessing a functional group that can be appropriately activated to react with one end of linker A to yield a cyclic peptide;

$X_{aa15}$ is a naturally or nonnaturally occurring amino acid or a spacer followed by a tag or a spacer followed by a solubilizing or a PK-enhancing element.

In another embodiment, the subject matter described herein is directed to a polypeptide comprising a sequence of Formula I(b):

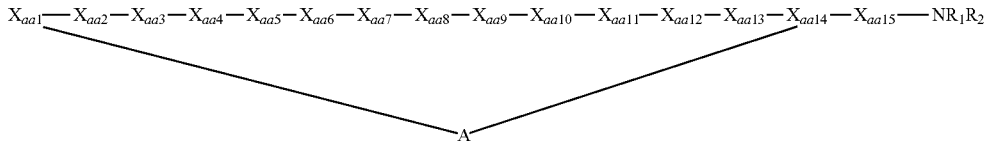

wherein,

A is an electrophilic moiety such as a Michael acceptor or a chloro- or bromoacetyl group which is capable of reacting with a sulfhydryl group present on residue $X_{aa14}$ to form a covalent thioether bond, thereby yielding a macrocyclic peptide; wherein such thioether bond may or may not be oxidized to the corresponding diastereomeric sulfoxides;

and wherein A can be optionally present; and wherein, if A is present, it can be a Gly or other spacer with a free amine, which can be used to cyclize the peptide via amide bond formation with a carboxyl group on the side chain of $X_{aa14}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa14}$, thereby providing an N-terminus to side chain lactam cyclic peptide;

and wherein, if A is present, it can be a Gly or other spacer with a free amine, which can be used to cyclize the peptide via amide bond formation with the C-terminal α-carboxyl group of $X_{aa15}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa15}$, thereby providing a head-to-tail cyclic peptide;

$X_{aa1}$ is a naturally or nonnaturally occurring amino acid comprising L-Phe, L-Ala, L-Trp, L-Tyr, L-Phe(4-OMe), L-Phe(4-F), L-Phe(4-Cl), L-Phe(4-Br), L-Phe(4-Me), L-Phe(4-CF$_3$), L-Phe(4-t-Bu), L-Phe(penta-F), L-1-Nal, L-2-Nal, L-Bip, L-$^m$Phe, L-Tic, L-3-Pya, L-4-Pya, L-Tza, L-3-Tha;

$X_{aa2}$ is a naturally or nonnaturally occurring amino acid selected from the group consisting of L-Ala, L-$^m$Ala, $^m$Gly, L-$^m$Val;

$X_{aa3}$ is selected from the group consisting of Gly, L-Asn and L-Ala;

$X_{aa4}$ is a naturally or nonnaturally occurring amino acid comprising L-Pro, L-Ala, L-α-Me-Pro, L-Pro(4R—OH), L-Pro(4R-OBzl), L-Pro(4R—NH$_2$), L-Pro(3R-Ph), L-Pro(4S-Ph), L-Pro(5R-Ph), L-Azt, L-Pip, L-Oic, L-2,3-Methano-Pro, L-3,4-Methano-Pro, L-Val, L-Leu, L-Ile, L-$^m$Ala, L-$^m$Val, L-$^m$Leu, L-Tza;

$X_{aa5}$ is a naturally or nonnaturally occurring amino acid selected from the group consisting of L-His, L-Ala, L-Tza, L-Arg, L-Lys, L-Orn, L-Dab and L-Dap;

$X_{aa6}$ is a naturally or nonnaturally occurring amino acid comprising L-Leu, L-Ala, L-Arg, L-His, L-Glu and L-Asp;

$X_{aa7}$ is a naturally or nonnaturally occurring amino acid comprising $^m$Gly, Gly, L-$^m$Ala, D-$^m$Ala, L-Pro, L-Ser, L-$^m$Ser L-Dab, L-Arg and L-His;

$X_{aa8}$ is L-Trp, L-Phe, L-Tyr, L-His, L-Phe(penta-F), L-Tza, L-Bzt, L-1-Nal, L-2-Nal, L-2-Pya, L-3-Pya, L-4-Pya;

$X_{aa9}$ is a naturally or nonnaturally occurring amino acid comprising L-Ser, L-Ala, L-Arg and D-Asn;

$X_{aa10}$ is a naturally or nonnaturally occurring amino acid selected from the group consisting of L-Trp, L-Ala, L-Met, L-Nle, L-Leu and L-Ile, L-Phe, L-Tyr, L-His, L-Phe(penta-F), L-Tza, L-Bzt, L-1-Nal, L-2-Nal, L-2-Pya, L-3-Pya, L-4-Pya;

$X_{aa11}$ is a naturally or nonnaturally occurring amino acid comprising L-$^m$Nle, L-Nle, L-$^m$Ala, L-Ala, L-Phe, L-$^m$Phe and L-$^m$Leu, L-Ser, D-Nle and L-Pro;

$X_{aa12}$ is a naturally or nonnaturally occurring amino acid comprising L-$^m$Nle, L-Nle, L-$^m$Ala, L-Ala, L-Phe, L-$^m$Phe, L-$^m$Leu and L-Pro;

$X_{aa13}$ is a naturally or nonnaturally occurring amino acid comprising L-Arg, L-Ala, L-Leu, L-Lys, L-Asp, L-Glu, L-His;

$X_{aa14}$ is selected from the group consisting of L-Cys, D-Cys, Asp, Glu, Gly, L-homo-Cys, D-homo-Cys, L-Pen, D-Pen, L-$^m$Cys and D-$^m$Cys;

$X_{aa15}$ is Gly or Gly followed by a PEG spacer comprised of at least two ethylene glycol units, or Gly followed by a PEG spacer comprised of at least two ethylene glycol units followed by a tag such as biotin, or Gly followed by a spacer followed by a PK-enhancing element;

wherein $X_{aa15}$ is optionally present and wherein the C-terminal carbonyl carbon of said amino acid is attached to a hydroxyl group to form a carboxylic acid or to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa15}$ is not present, the C-terminal carbonyl carbon of $X_{aa14}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula I(c):

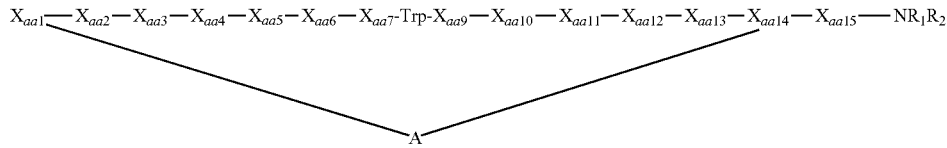

wherein,

A is an electrophilic moiety such as a Michael acceptor or a chloro- or bromoacetyl group which is capable of reacting with a sulfhydryl group present on residue $X_{aa14}$ to form a covalent thioether bond, thereby yielding a macrocyclic peptide; wherein such thioether bond may or may not be oxidized to the corresponding diastereomeric sulfoxides;

and wherein A can be optionally present; and wherein, if A is present, it can be a Gly or other spacer with a free amine, which can be used to cyclize the peptide via amide bond formation with a carboxyl group on the side chain of $X_{aa14}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa14}$, thereby providing an N-terminus to side chain lactam cyclic peptide;

and wherein, if A is present, it can by a Gly or other spacer with a free amine, which can be used to cyclize the peptide via amide bond formation with the C-terminal α-carboxyl group of $X_{aa15}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa15}$, thereby providing a head-to-tail cyclic peptide;

$X_{aa1}$ is a naturally or nonnaturally occurring amino acid comprising L-Phe, L-Ala, L-Trp, L-Tyr, L-Phe(4-OMe), L-Phe(4-F), L-Phe(4-Cl), L-Phe(4-Br), L-Phe(4-Me), L-Phe(4-CF$_3$), L-Phe(4-t-Bu), L-Phe(penta-F), L-1-Nal, L-2-Nal, L-Bip, L-$^m$Phe, L-Tic, L-3-Pya, L-4-Pya, L-Tza, L-3-Tha;

$X_{aa2}$ is a naturally or nonnaturally occurring amino acid selected from the group consisting of L-Ala, L-$^m$Ala, $^m$Gly, L-$^m$Val;

$X_{aa3}$ is selected from the group consisting of Gly, L-Asn and L-Ala;

$X_{aa4}$ is a naturally or nonnaturally occurring amino acid comprising L-Pro, L-Ala, L-α-Me-Pro, L-Pro(4R—OH), L-Pro(4R—NH$_2$), L-Pro(4S-Ph), L-Azt, L-Pip and L-Oic;

$X_{aa5}$ is a naturally or nonnaturally occurring amino acid selected from the group consisting of L-His and L-Ala;

$X_{aa6}$ is a naturally or nonnaturally occurring amino acid comprising L-Leu, L-Ala, L-Arg and L-Asp;

$X_{aa7}$ is a naturally or nonnaturally occurring amino acid comprising $^m$Gly, Gly, L-$^m$Ala, D-$^m$Ala, L-Pro, L-Ser, L-$^m$Ser L-Dab, L-Arg and L-His;

$X_{aa9}$ is a naturally or nonnaturally occurring amino acid comprising L-Ser, L-Ala, L-Arg and D-Asn;

$X_{aa10}$ is a naturally or nonnaturally occurring amino acid selected from the group consisting of L-Trp, L-Ala, L-Met, L-Leu and L-Ile;

$X_{aa11}$ is a naturally or nonnaturally occurring amino acid comprising L-$^m$Nle, L-Nle, L-$^m$Ala, L-Ala, L-Phe, L-$^m$Phe and L-$^m$Leu, L-Ser and D-Nle;

$X_{aa12}$ is a naturally or nonnaturally occurring amino acid comprising L-$^m$Nle, L-Nle, L-$^m$Ala and L-Ala;

$X_{aa13}$ is a naturally or nonnaturally occurring amino acid comprising L-Arg, L-Ala and L-Leu;

$X_{aa14}$ is selected from the group consisting of L-Cys, D-Cys, Asp, Glu and Gly;

$X_{aa15}$ is Gly or Gly followed by a PEG spacer comprised of at least two ethylene glycol units, or Gly followed by a PEG spacer comprised of at least two ethylene glycol units followed by a tag such as biotin;

wherein $X_{aa15}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa15}$ is not present, the C-terminal carbonyl carbon of $X_{aa14}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula II(a):

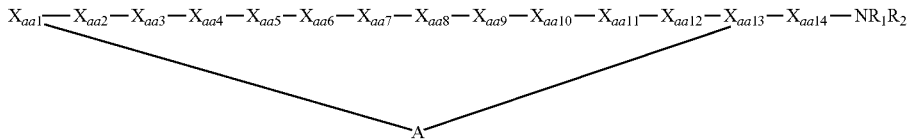

wherein,

A is an organic or peptidic linker between $X_{aa1}$ and $X_{aa13}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or aromatic N-methylated amino acid;

$X_{aa3}$ is a naturally or nonnaturally occurring hydrophobic N-methylated amino acid;

$X_{aa4}$ is a naturally or nonnaturally occurring hydrophobic N-methylated amino acid;

$X_{aa5}$ is a naturally or nonnaturally occurring alkyl amino acid or a positively or negatively charged amino acid;

$X_{aa6}$ is a naturally or nonnaturally occurring hydrophobic amino acid;

$X_{aa7}$ is a naturally or nonnaturally occurring N-methylated or non-N-methylated aromatic or heteroaromatic or alkyl or heteroarylalkyl amino acid;

$X_{aa8}$ is a naturally or nonnaturally occurring aromatic or heteroaromatic or arylalkyl or heteroarylalkyl amino acid or an alkyl amino acid;

$X_{aa9}$ is a naturally or nonnaturally occurring N-methylated or non-N-methylated aromatic or heteroaromatic or alkyl or heteroarylalkyl amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally occurring aromatic or heteroaromatic or arylalkyl or heteroarylalkyl or alkyl or heteroalkyl amino acid;

$X_{aa12}$ is a naturally or nonnaturally occurring aromatic or heteroaromatic or arylalkyl or heteroarylalkyl or alkyl or heteroalkyl amino acid;

$X_{aa13}$ is a naturally or nonnaturally occurring amino acid possessing a functional group that can be appropriately activated to react with one end of linker A to yield a cyclic peptide;

$X_{aa14}$ is a naturally or nonnaturally occurring amino acid or a spacer or a spacer followed by a tag or a spacer followed by a solubilizing or a PK-enhancing element.

In another embodiment, the subject matter described herein is directed to a polypeptide comprising a sequence of Formula II(b):

and wherein A can be optionally present; and wherein, if A is present, it can be a Gly or other spacer with a free amino terminus, which can be used to cyclize the peptide via amide bond formation with a carboxyl group on the side chain of $X_{aa13}$, thereby providing an N-terminus to side chain lactam cyclic peptide; and wherein, if A is not present, the N-terminal amino group of the $X_{aa1}$ residue can be used to cyclize the peptide via amide bond formation with a carboxyl group on the side chain of $X_{aa13}$, thereby providing an N-terminus to side chain lactam cyclic peptide;

and wherein, if A is present, it can be a Gly or other spacer with a free amino terminus, which can be used to cyclize the peptide via amide bond formation with the C-terminal α-carboxyl group of $X_{aa14}$, thereby providing a head-to-tail cyclic peptide; and wherein, if A is not present, the N-terminal amino group of the $X_{aa1}$ amino acid can be used to cyclize the peptide via amide bond formation with the C-terminal α-carboxyl group of $X_{aa14}$, thereby providing a head-to-tail cyclic peptide;

$X_{aa1}$ is a naturally or nonnaturally occurring amino acid comprising Phe and Ala;

$X_{aa2}$ is a naturally or nonnaturally occurring amino acid comprising $^m$Phe and $^m$Ala;

$X_{aa3}$ is a naturally or nonnaturally occurring amino acid comprising $^m$Nle and $^m$Ala;

$X_{aa4}$ is a naturally or nonnaturally occurring amino acid comprising $^m$Gly, Gly and $^m$Ala;

$X_{aa5}$ is a naturally or nonnaturally occurring amino acid comprising Asp and Ala;

$X_{aa6}$ is a naturally or nonnaturally occurring amino acid comprising Val (preferred) and Ala;

$X_{aa7}$ is a naturally or nonnaturally occurring amino acid comprising $^m$Phe and Phe;

$X_{aa8}$ is a naturally or nonnaturally occurring amino acid selected from the group consisting of Tyr and Ala;

$X_{aa9}$ is a naturally or nonnaturally occurring amino acid comprising $^m$Gly $^m$Ala and Gly;

$X_{aa11}$ is a naturally or nonnaturally occurring amino acid comprising Tyr and Ala;

$X_{aa12}$ is a naturally or nonnaturally occurring amino acid comprising Leu and Ala;

$X_{aa13}$ is a naturally or nonnaturally occurring amino acid comprising L-Cys, D-Cys, Asp, Glu and Gly;

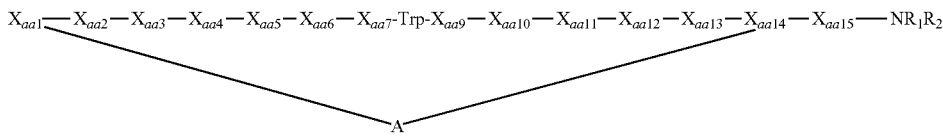

wherein,

A is an electrophilic moiety such as a Michael acceptor or a chloro- or bromoacetyl group which is capable of reacting with a sulfhydryl group present on residue $X_{aa13}$ to form a covalent thioether bond, thereby yielding a macrocyclic peptide; wherein such thioether bond may or may not be oxidized to the corresponding diastereomeric sulfoxides;

$X_{aa14}$ is Gly or Gly followed by a PEG spacer comprised of at least two ethylene glycol units, or Gly followed by a PEG spacer comprised of at least two ethylene glycol units followed by a tag such as biotin, wherein $X_{aa14}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa14}$ is not present, the C-terminal carbonyl carbon of $X_{aa13}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula III(a):

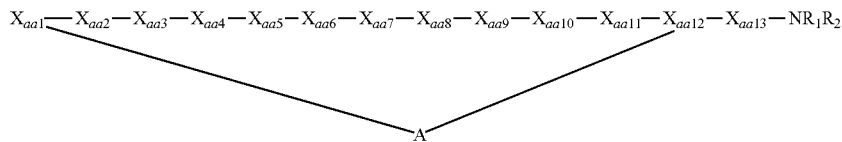

wherein,

A is an organic or peptidic linker between $X_{aa1}$ and $X_{aa12}$, thereby providing a macrocyclic peptide;

$X_{aa1}$ is a naturally or nonnaturally occurring aromatic or heteroaromatic or alkyl or heteroaryl alkyl amino acid;

$X_{aa2}$ is a naturally or nonnaturally occurring alkyl or aromatic or charged amino acid;

$X_{aa3}$ is a naturally or nonnaturally occurring aromatic or heteroaromatic or alkyl or heteroaryl alkyl amino acid;

$X_{aa4}$ is a naturally or nonnaturally occurring aromatic or heteroaromatic or alkyl or heteroarylalkyl amino acid;

$X_{aa5}$ is a naturally or nonnaturally occurring alkyl or heteroalkyl or aromatic or heteroaromatic or heteroarylalkyl amino acid;

$X_{aa6}$ is a naturally or nonnaturally occurring heteroaromatic or positively charged amino acid;

$X_{aa7}$ is a naturally or nonnaturally occurring polar or charged amino acid;

$X_{aa8}$ is a naturally or nonnaturally occurring positively charged amino acid;

$X_{aa9}$ is a naturally or nonnaturally occurring alkyl or heteroalkyl or aromatic or heteroaromatic or heteroarylalkyl amino acid;

$X_{aa10}$ is a naturally or nonnaturally occurring aromatic or heteroaromatic or arylalkyl or heteroarylalkyl or alkyl or heteroalkyl amino acid;

$X_{aa11}$ is a naturally or nonnaturally occurring aromatic or heteroaromatic or arylalkyl or heteroarylalkyl or heteroalkyl or a positively charged amino acid;

$X_{aa12}$ is a naturally or nonnaturally occurring amino acid possessing a functional group that can be appropriately activated to react with one end of linker A to yield a cyclic peptide;

$X_{aa13}$ is a naturally or nonnaturally occurring amino acid or a spacer or a spacer followed by a tag or a spacer followed by a solubilizing or a PK-enhancing element.

In another embodiment, the subject matter described herein is directed to a polypeptide comprising a sequence of Formula III(b):

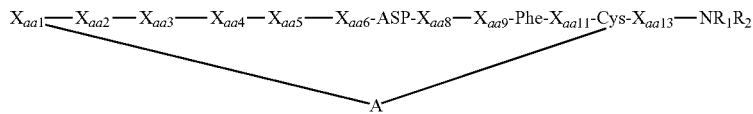

wherein,

A is an electrophilic moiety such as a Michael acceptor or a chloro- or bromoacetyl group which is capable of reacting with the sulfhydryl group of $Cys^{12}$ to form a covalent thioether bond, thereby yielding a macrocyclic peptide; wherein such thioether bond may or may not be oxidized to the corresponding diastereomeric sulfoxides;

$X_{aa1}$ is selected from Phe and D-Phe;

$X_{aa2}$ is selected from Leu, Arg and Phe;

$X_{aa3}$ is selected from Ile, Leu and Phe;

$X_{aa4}$ is selected from Val, Tyr and Phe;

$X_{aa5}$ is selected from Ile and Val;

$X_{aa6}$ is selected from Arg and His;

$X_{aa8}$ is selected from Arg;

$X_{aa9}$ is selected from Val, Leu, Tyr and Phe;

$X_{aa11}$ is selected from Arg and Tyr;

$X_{aa13}$ is Gly or Gly followed by a PEG spacer comprised of at least two ethylene glycol units, wherein $X_{aa13}$ is optionally present and wherein the C-terminal carbonyl carbon of said amino acid is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group;

wherein, if $X_{aa13}$ is not present, the C-terminal carbonyl carbon of $Cys^{12}$ is attached to a nitrogen to form a carboxamide ($NH_2$), an alkyl carboxamide ($NHR_1$), or a dialkylcarboxamide ($NR_1R_2$);

wherein each of $R_1$ and $R_2$ is an alkyl or arylalkyl group.

In another embodiment, the subject matter described herein is directed to a polypeptide comprising a sequence of Formula I(d):

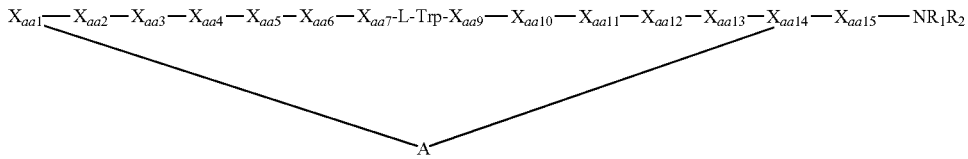

wherein,

A is a chloroacetyl group attached to the α-amine of the N-terminal $X_{aa1}$ residue which is capable of reacting with a sulfhydryl group present on residue $X_{aa14}$ to form a covalent thioether bond, thereby providing a macrocyclic peptide; wherein such thioether bond may or may not be oxidized to the corresponding diastereomeric sulfoxides;

and wherein, $X_{aa1}$ is selected from the group consisting of L-Phe, L-Trp, L-Tyr, L-Phe(4-OMe), L-Phe(4-F), L-Phe(4-Cl), L-Phe(4-Br), L-Phe(4-Me), L-Phe(4-CF$_3$), L-1-Nal, L-2-Nal, L-Bip, L-3-Pya, L-4-Pya, L-3-Tha;

$X_{aa2}$ is selected from the group consisting of L-Ala, L-$^m$Ala, $^m$Gly;

$X_{aa3}$ is selected from the group consisting of L-Ala and L-Asn;

$X_{aa4}$ is selected from the group consisting of L-Pro, L-Ala, L-α-Me-Pro, L-Pro(4-OH), L-Pro(4-NH$_2$), L-Pro(4S-Ph), L-Azt, L-Pip and L-Oic;

$X_{aa5}$ is selected from the group consisting of L-Ala, L-His and L-Leu;

$X_{aa6}$ is selected from the group consisting of L-Ala, L-Arg, L-Asp, L-His and L-Leu;

$X_{aa7}$ is selected from the group consisting of $^m$Gly, Gly, L-$^m$Ala, D-$^m$Ala, L-Pro, L-Ser, L-$^m$Ser, L-Dab, L-Arg and L-His;

$X_{aa9}$ is selected from the group consisting of L-Ala, L-Arg and L-Ser;

$X_{aa10}$ selected from the group consisting of L-Trp, L-Met and L-Bzt;

$X_{aa11}$ is selected from the group consisting of L-Nle, L-$^m$Nle, L-$^m$Ala, L-Phe, L-$^m$Phe and L-$^m$Leu and L-$^m$Ser;

$X_{aa12}$ is selected from the group consisting of L-$^m$Nle and L-$^m$Ala;

$X_{aa13}$ is selected from the group consisting of L-Ala, L-Arg and L-Leu;

$X_{aa14}$ is selected from the group consisting of L-Cys and D-Cys;

$X_{aa15}$ is Gly or Gly followed by a PEG spacer comprised of twelve ethylene glycol units;

wherein $X_{aa15}$ is optionally present and wherein the C-terminal carbonyl carbon of said amino acid is attached to a nitrogen to form a carboxamide (CONH$_2$);

wherein, if $X_{aa15}$ is not present, the C-terminal carbonyl carbon of $X_{aa14}$ is attached to a nitrogen to form a carboxamide (CONH$_2$).

In another embodiment, the subject matter described herein is directed to a polypeptide comprising a sequence of Formula II(c):

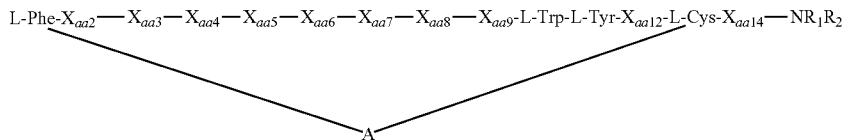

wherein,

A is a chloroacetyl group attached to the α-amine of the N-terminal $X_{aa1}$ residue which is capable of reacting with a sulfhydryl group present on the Cys$^{13}$ residue to form a covalent thioether bond, thereby yielding a macrocyclic peptide; wherein such thioether bond may or may not be oxidized to the corresponding diastereomeric sulfoxides;

and wherein $X_{aa2}$ is selected from the group consisting of L-$^m$Ala and L-$^m$Phe;

$X_{aa3}$ is selected from the group consisting of L-$^m$Ala and L-$^m$Nle;

$X_{aa4}$ is selected from the group consisting of Gly, $^m$Gly and L-$^m$Ala;

$X_{aa5}$ is selected from the group consisting of L-Ala and L-Asp;

$X_{aa6}$ is selected from the group consisting of L-Ala and L-Val;

$X_{aa7}$ is selected from the group consisting of L-Phe and L-$^m$Phe;

$X_{aa8}$ is selected from the group consisting of L-Ala and L-Tyr;

$X_{aa9}$ is selected from the group consisting of Gly, $^m$Gly and L-$^m$Ala;

$X_{aa12}$ is selected from the group consisting of L-Leu and L-Ala;

$X_{aa14}$ is Gly or Gly followed by a PEG spacer comprised of twelve ethylene glycol units, wherein the C-terminal carbonyl carbon of $X_{aa14}$ or of $X_{aa14}$ followed by a PEG spacer is attached to a nitrogen to form a carboxamide (CONH$_2$).

In another embodiment, the subject matter described herein is directed to a polypeptide comprising a sequence of Formula III(c):

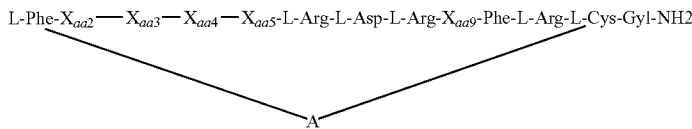

wherein,

A is a chloroacetyl group attached to the α-amine of the N-terminal L-Phe residue which is capable of reacting with a sulfhydryl group present on the L-Cys$^{12}$ residue to form a covalent thioether bond, thereby yielding a macrocyclic peptide;

and wherein, $X_{aa2}$ is selected from L-Leu, L-Arg and L-Phe;
$X_{aa3}$ is selected from L-Ile and L-Phe;
$X_{aa4}$ is selected from L-Phe, L-Tyr and L-Val;
$X_{aa5}$ is selected from L-Ile and L-Val;
$X_{aa9}$ is selected from L-Leu, L-Phe, L-Tyr and L-Val;

wherein the C-terminal carbonyl carbon of Gly$^{13}$ is attached to a nitrogen to form a carboxamide ($CONH_2$).

The present disclosure is also directed to a macrocyclic peptides comprising a sequence provided in Formula I.

The present disclosure is also directed to macrocyclic peptides comprising a sequence provided in Formula I(a).

The present disclosure is also directed to macrocyclic peptides comprising a sequence provided in Formula I(b).

The present disclosure is also directed to macrocyclic peptides comprising a sequence provided in Formula I(c).

The present disclosure is also directed to macrocyclic peptides comprising a sequence provided in Formula I(d).

The present disclosure is also directed to macrocyclic peptides comprising a sequence provided in Formula II.

The present disclosure is also directed to macrocyclic peptides comprising a sequence provided in Formula II(a).

The present disclosure is also directed to macrocyclic peptides comprising a sequence provided in Formula II(b).

The present disclosure is also directed to macrocyclic peptides comprising a sequence provided in Formula II(c).

The present disclosure is also directed to macrocyclic peptides comprising a sequence provided in Formula III.

The present disclosure is also directed to macrocyclic peptides comprising a sequence provided in Formula III(a).

The present disclosure is also directed to macrocyclic peptides comprising a sequence provided in Formula III(b).

The present disclosure is also directed to macrocyclic peptides comprising a sequence provided in Formula III(c).

The present disclosure is also directed to macrocyclic peptides comprising a sequence provided in Formula IV.

The present disclosure is also directed to macrocyclic peptides comprising a sequence provided in Formula V.

The present disclosure is also directed to macrocyclic peptides comprising a sequence provided in Formula VI.

The present disclosure is also directed to macrocyclic peptides comprising a sequence provided in Formula VII.

The present disclosure is also directed to macrocyclic peptides comprising a sequence selected from the group consisting of: Compound Nos. 1, 2, 3, 4, 71, and 99.

The present disclosure is also directed to macrocyclic peptides comprising a sequence selected from those described herein.

The present disclosure is also directed to methods of using the macrocyclic peptides of the present disclosure to ameliorate and/or treat hyperproliferative disorders and/or viral disorders.

The present disclosure is also directed to a method of modulating an immune response in a subject comprising administering to the subject one or more macrocyclic peptides comprising the sequence selected from the peptides described herein.

The present disclosure is also directed to a method of enhancing, stimulating or increasing the immune response in the subject comprising administering to the subject one or more macrocyclic peptides comprising the sequence selected from those described herein.

The present disclosure is also directed to a method of promoting immune system inhibition of the growth of tumor cells in a subject, comprising administering to a subject a therapeutically effective amount of one or more macrocyclic peptides comprising the sequence selected from those peptides described herein.

The present disclosure is also directed to a method of treating an infectious disease in a subject, comprising administering to a subject a therapeutically effective amount of one or more macrocyclic peptides comprising the sequence selected from those peptides described herein The present disclosure is also directed to combinations comprising a sequence selected from the macrocyclic peptides described herein, with another agent, such an antimicrobial therapy, antiviral therapy, an additional immunomodulatory therapy, a vaccine, or a cancer chemotherapeutic agent.

BRIEF DESCRIPTION OF THE FIGURES

FIG. 4—HTRF selectivity panel. As shown, the data demonstrate the macrocyclic peptides are binding to PD-L1 because they interfere with PD-L1 binding to PD-1 and CD80, but their binding is selective because the peptides do not block PD-1/PD-L2 or CD80/CTLA4 interactions.

FIG. 5—Cell binding assay of select macrocyclic peptides of the present disclosure. As shown, the macrocyclic peptides of the present disclosure block binding of recombinant PD-L1-Ig to Jurkat-PD-1 cells, and also block binding of recombinant PD-1-Ig to either L2987 (adenocarcinoma cell line with endogenous PD-L1 expression) or LK35.2-hPD-L1 (mouse B cell line over-expressing hPD-L1. The anti-PD-L1 antibody is an internal antibody developed by Bristol-Myers Squibb Company).

FIGS. 10A-C—Anti-PD-L1 antibody and peptides both promote IFNγ secretion by CMV-specific T cells in a dose-dependent manner. The most robust response was generated by the antibody directed to PD-L1 (MDX-1105) (Anti-PD-1 Ab#1, $EC_{50}$ 0.6 nM; FIG. 10A) followed by Compound No. 71 ($EC_{50}$ 300 nM; FIG. 10B), Compound No. 1 ($EC_{50}$ 400 nM), Compound No. 2 ($EC_{50}$ 400 nM), and Compound No. 99 ($EC_{50}$>10,000 nM). Numerical $EC_{50}$ results for MDX-1105 and Compound No. 71, Compound No. 1, Compound No. 2, and Compound No. 99 are provided in FIG. 10C. These results suggest that PD-L1 binding of the macrocyclic peptide inhibitors of the present disclosure can enhance IFNγ release in a memory T cell population generated from previous exposure to a persistent antigen.

FIG. 11—Anti-PD-L1 antibody macrocyclic peptides both promote IFNγ secretion by HIV-specific T cells in a dose-dependent manner. The mean IFNγ spot forming cells (SFC) per well was calculated from duplicate wells and any background present in the unstimulated wells (<25 SFC) has been subtracted. Data are also presented as the fold increase over the DMSO control treatment. The anti-PD-L1 antibody and peptide both enhance IFNγ secretion by HIV-specific T cells responding to at least 1 of the 6 HIV-Gag antigen pools. These results show that PD-L1 binding with a peptide inhibitor can enhance IFNγ release from the T cell population responding to an ongoing chronic viral infection, similar to the anti-PD-L1 antibody.

Figure 1:
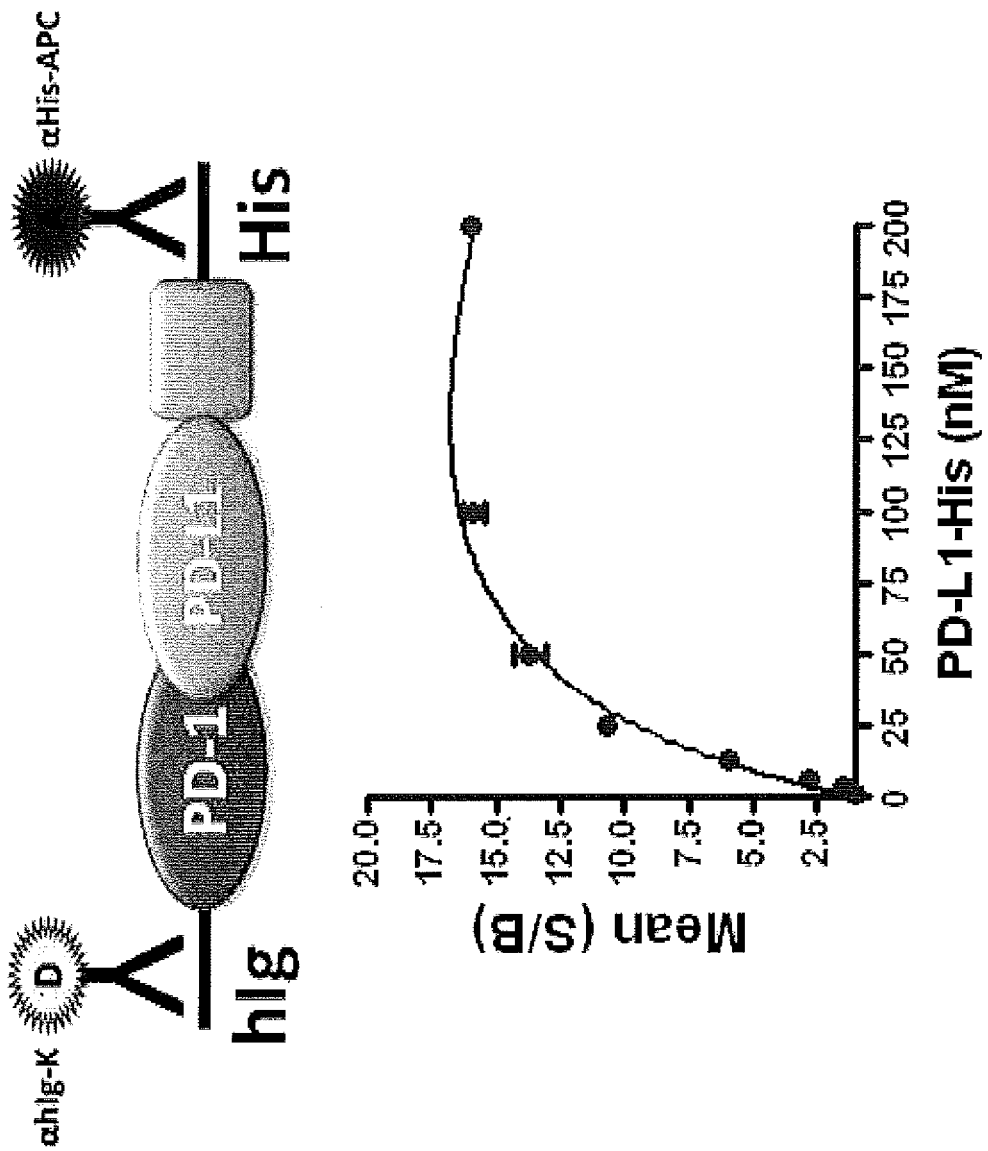
FIG. 1—Provides a schematic representation of the PD-1/PD-L1 biochemical binding assay formatted as a homogeneous time-resolved fluorescence format (HTRF) assay utilized for measuring the ability of the macrocyclic peptides to bind with PD-L1.

In accordance with the present disclosure, we have discovered peptides that specifically bind to PD-L1 and are capable of inhibiting the interaction of PD-L1 with PD-1 and CD80. These macrocyclic peptides exhibit in vitro immunomodulatory efficacy thus making them therapeutic candidates for the treatment of various diseases including cancer and infectious diseases.

The terms "specific binding" or "specifically bind" refer to the interaction between a protein and a binding molecule, such as a compound or ligand. The interaction is dependent upon the presence of a particular structure (i.e., an enzyme binding site, an antigenic determinant or epitope) of the protein that is recognized by the binding molecule. For example, if a compound has specific binding for protein binding site "A", the presence of the compound in a reaction containing a protein including binding site A, and a labeled peptide that specifically binds to protein binding site A will reduce the amount of labeled peptide bound to the protein. In contrast, nonspecific binding of a compound to the protein does not result in a concentration-dependent displacement of the labeled peptide from the protein.

Other embodiments include polypeptides comprising the following structures:

Formula IV

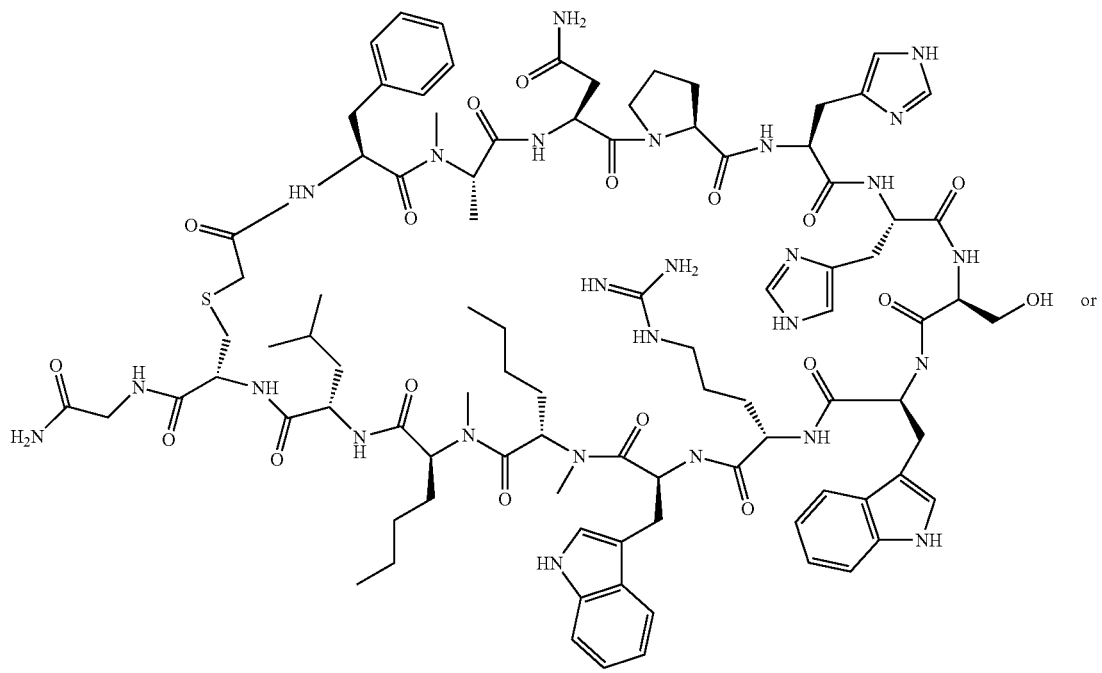

or

-continued
Formula V
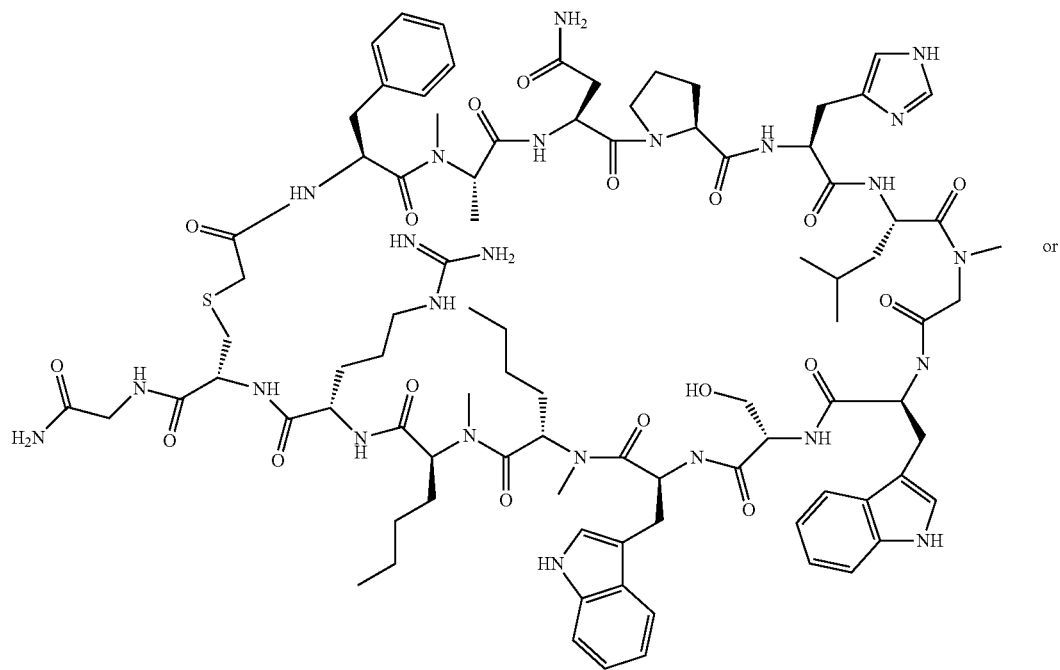
Formula VI
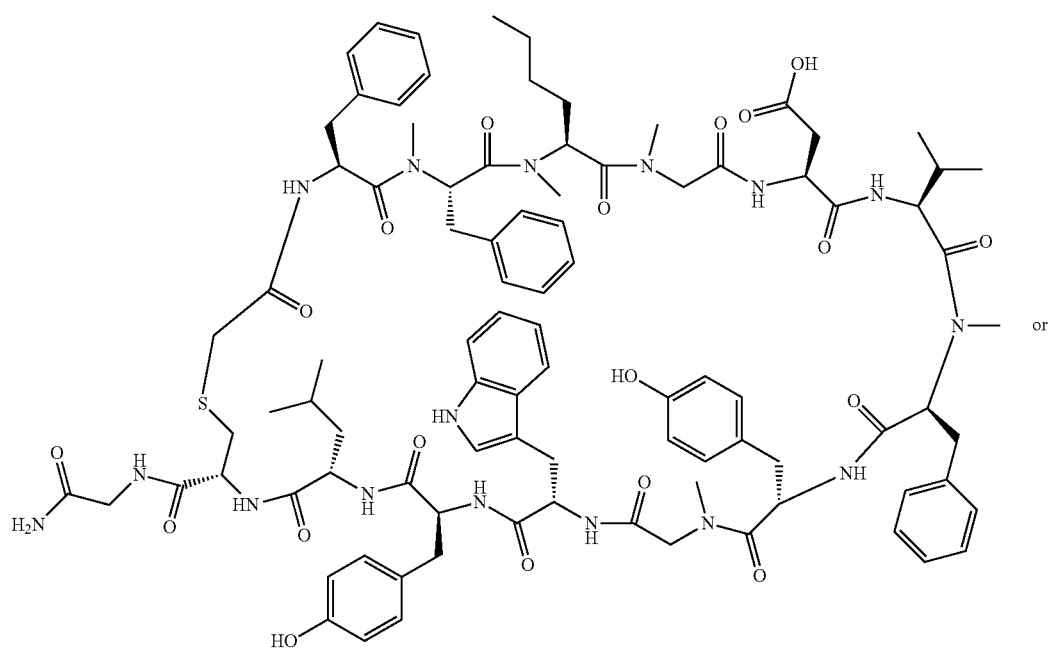
or

Formula VII

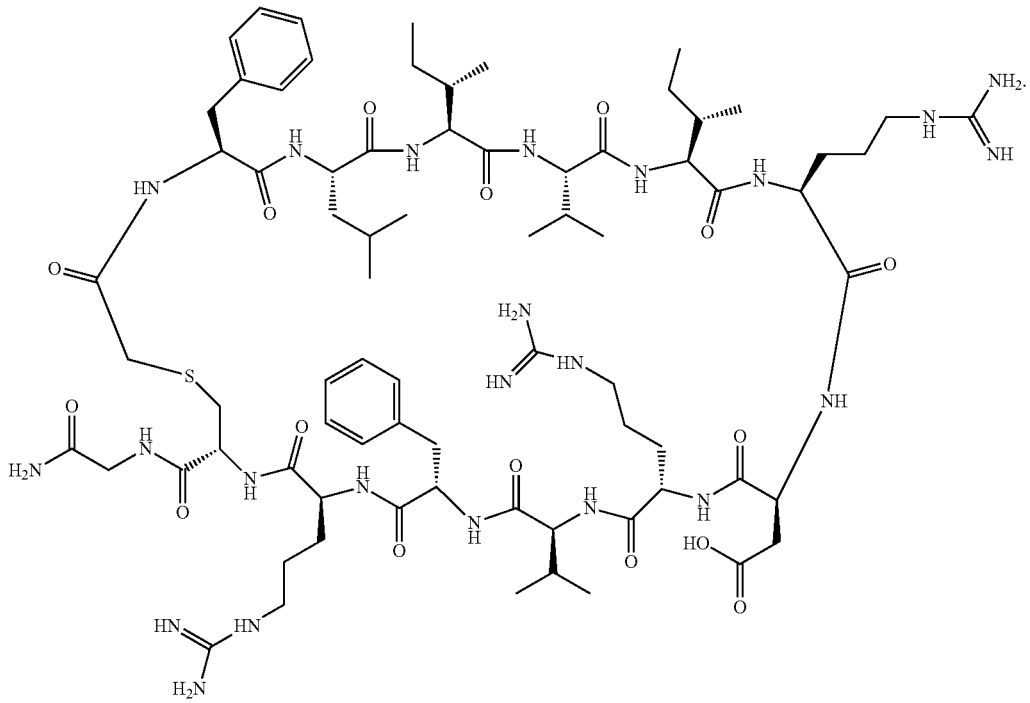

Another embodiment is a pharmaceutical composition comprising a polypeptide of Formula I(a), I(b), I(c), II(a), II(b), III(a), III(b), IV, V, VI, or VII, or a peptide comprising at least one of the macrocyclic peptides described herein.

Another embodiment is directed to a pharmaceutical combination comprising a polypeptide of Formula I(a), I(b), I(c), II(a), II(b), III(a), III(b), IV, V, VI, or VII or a macrocyclic peptide described herein, and at least one therapeutic agent selected from the group consisting of an antimicrobial, an antiviral, anti-cancer, anti-diabetic agent, an anti-obesity agent, an anti-hypertensive agent, an anti-atherosclerotic agent and a lipid-lowering agent.

Another embodiment is directed to a pharmaceutical combination of a polypeptide of Formula I(a), I(b), I(c), II(a), II(b), III(a), III(b), IV, V, VI, or VII, or a macrocyclic peptide described herein, with another agent disclosed herein.

Another embodiment is directed to a method for treating or delaying the progression or onset of cancer and/or virology disorder, which comprises administering to a mammalian species in need of treatment a therapeutically effective amount of a polypeptide of Formula I(a), I(b), I(c), II(a), II(b), III(a), III(b), IV, V, VI, or VII, or a macrocyclic peptide described herein.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

An additional aspect of the subject matter described herein is the use of the disclosed peptides as radiolabeled ligands for development of ligand binding assays or for monitoring of in vivo adsorption, metabolism, distribution, receptor binding or occupancy, or compound disposition. For example, a macrocyclic peptide described herein may be prepared using the radioactive isotope $^{125}I$ and the resulting radiolabeled peptide may be used to develop a binding assay or for metabolism studies. Alternatively, and for the same purpose, a macrocyclic peptide described herein may be converted to a radiolabeled form by catalytic tritiation using methods known to those skilled in the art.

The macrocyclic peptides of the present disclosure can also be used as PET imaging agents by adding a radioactive tracer using methods known to those skilled in the art.

Preferred peptides include at least one of the macrocyclic peptides provided herein and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

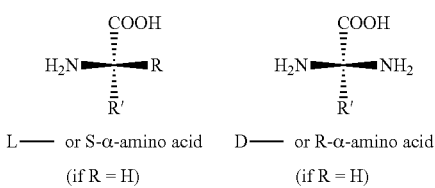

L —— or S-α-amino acid (if R = H)    D —— or R-α-amino acid (if R = H)

where R and R' are as discussed herein.

Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'" (prime) substituents equal hydrogen, the amino acid is glycine and is not chiral.

The term "naturally occurring amino acid side chain," as used herein, refers to side chain of any of the naturally occurring amino acids (i.e., alanine, arginine, asparagine, aspartic acid, cysteine, glutamine, glutamic acid, glycine, -histidine, isoleucine, leucine, lysine, methionine, phenylalanine, proline, serine, threonine, tryptophan, tyrosine, and valine) usually in the S-configuration (i.e., the L-amino acid).

The term "non-naturally occurring amino acid side chain," as used herein, refers to a side chain of any naturally occurring amino acid usually in the R-configuration (i.e., the D-amino acid) or to a group other than a naturally occurring amino acid side chain in R- or S-configuration (i.e., the D- or L-amino acid, respectively) selected from:

$C_2$-$C_7$alkenyl, $C_1$-$C_3$alkoxy$C_1$-$C_3$alkyl, $C_1$-$C_6$alkoxycarbonyl$C_1$-$C_3$alkyl, $C_1$-$C_7$alkyl, $C_1$-$C_3$alkylsulfanyl$C_1$-$C_3$alkyl, amido$C_1$-$C_3$alkyl, amino$C_1$-$C_3$alkyl, azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, carboxy$C_1$-$C_3$alkyl, $C_3$-$C_6$cycloalkyl$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl;

biphenyl$C_1$-$C_3$alkyl wherein the biphenyl is optionally substituted with a methyl group;

indolyl$C_1$-$C_3$alkyl, wherein the indolyl part is optionally substituted with one group selected from $C_1$-$C_3$alkyl, carboxy$C_1$-$C_3$alkyl, halo, hydroxy, and phenyl, wherein the phenyl is further optionally substituted by one, two, or three groups independently selected from $C_1$-$C_3$alkoxy, $C_1$-$C_3$alkyl, and halo;

$NR^aR^b(C_1$-$C_7$alkyl), wherein $R^a$ and $R^b$ are independently selected from hydrogen, $C_2$-$C_4$alkenyloxycarbonyl, $C_1$-$C_3$alkyl, $C_1$-$C_3$alkylcarbonyl, $C_3$-$C_6$cycloalkylcarbonyl, furanylcarbonyl, and phenylcarbonyl. When the alkyl linker contains more than one carbon an additional $NR^aR^b$ group can be on the chain.

$NR^cR^d$carbonyl$C_1$-$C_3$alkyl, wherein $R^c$ and $R^d$ are independently selected from hydrogen, $C_1$-$C_3$alkyl, and triphenylmethyl;

phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —NC(NH$_2$)$_2$, nitro, and —OP(O)(OH)$_2$; and phenoxy$C_1$-$C_3$alkyl wherein the phenyl is optionally substituted with a $C_1$-$C_3$alkyl group.

The term "$C_2$-$C_4$alkenyl," as used herein, refers to a straight or branched chain group of two to four carbon atoms containing at least one carbon-carbon double bond.

The term "$C_2$-$C_7$alkenyl," as used herein, refers to a straight or branched chain group of two to seven carbon atoms containing at least one carbon-carbon double bond.

The term "$C_2$-$C_4$alkenyloxy," as used herein, refers to a $C_2$-$C_4$alkenyl group attached to the parent molecular moiety through an oxygen atom.

The term "$C_1$-$C_3$alkoxy," as used herein, refers to a $C_1$-$C_3$alkyl group attached to the parent molecular moiety through an oxygen atom.

The term "$C_1$-$C_4$alkoxy," as used herein, refers to a $C_1$-$C_4$alkyl group attached to the parent molecular moiety through an oxygen atom.

The term "$C_1$-$C_6$alkoxy," as used herein, refers to a $C_1$-$C_6$alkyl group attached to the parent molecular moiety through an oxygen atom.

The term "$C_1$-$C_3$alkoxy$C_1$-$C_3$alkyl," as used herein, refers to a $C_1$-$C_3$alkoxy group attached to the parent molecular moiety through a $C_1$-$C_3$alkyl group.

The term "$C_1$-$C_6$alkoxycarbonyl," as used herein, refers to a $C_1$-$C_6$alkoxy group attached to the parent molecular moiety through a carbonyl group.

The term "$C_1$-$C_6$alkoxycarbonyl$C_1$-$C_3$alkyl," as used herein, refers to a $C_1$-$C_6$alkoxycarbonyl group attached to the parent molecular moiety through a $C_1$-$C_3$alkyl group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_3$alkylcarbonyl," as used herein, refers to a C1-C3alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl group attached to the parent molecular moiety through a $C_1$-$C_3$alkyl group.

The term "$C_1$-$C_3$alkylsulfonyl," as used herein, refers to a $C_1$-$C_3$alkyl group attached to the parent molecular moiety through a sulfonyl group.

The term "$C_1$-$C_3$alkylsulfonylamino," as used herein, refers to a $C_1$-$C_3$alkylsulfonyl group attached to the parent molecular moiety through an amino group.

The term "amido," as used herein, refers to —C(O)NH$_2$.

The term "amido$C_1$-$C_3$alkyl," as used herein, refers to an amido group attached to the parent molecular moiety through a $C_1$-$C_3$alkyl group.

The term "amino," as used herein, refers to —NH$_2$.

The term "amino$C_1$-$C_3$alkyl," as used herein, refers to an amino group attached to the parent molecular moiety through a $C_1$-$C_3$alkyl group.

The term "aminosulfonyl," as used herein, refers to an amino group attached to the parent molecular moiety through a sulfonyl group.

The term "azaindolyl$C_1$-$C_3$alkyl," as used herein, refers to an azaindolyl group attached to the parent molecular through a $C_1$-$C_3$alkyl group. The azaindolyl group can be attached to the alkyl moiety through any substitutable atom in the group.

The term "benzothiazolyl$C_1$-$C_3$alkyl," as used herein, refers to an benzothiazolyl group attached to the parent molecular through a $C_1$-$C_3$alkyl group. The benzothiazolyl group can be attached to the alkyl moiety through any substitutable atom in the group.

The term "benzothienyl$C_1$-$C_3$alkyl," as used herein, refers to a benzothienyl group attached to the parent molecular through a $C_1$-$C_3$alkyl group. The benzothienyl group can be attached to the alkyl moiety through any substitutable atom in the group.

The term "benzyloxy," as used herein, refers to a benzyl group attached to the parent molecular moiety through an oxygen atom.

The term "benzyloxy$C_1$-$C_3$alkyl," as used herein, refers to a benzyloxy group attached to the parent molecular moiety through a $C_1$-$C_3$alkyl group.

The term "biphenyl$C_1$-$C_3$alkyl," as used herein, refers to a biphenyl group attached to the parent molecular moiety through a $C_1$-$C_3$alkyl group. The biphenyl group can be attached to the alkyl moiety through any substitutable atom in the group.

The term "carbonyl," as used herein, refers to —C(O)—.

The term "carboxy," as used herein, refers to —$CO_2H$.

The term "carboxy$C_1$-$C_3$alkyl," as used herein, refers to a carboxy group attached to the parent molecular moiety through a $C_1$-$C_3$alkyl group.

The term "cyano," as used herein, refers to —CN.

The term "$C_3$-$C_6$cycloalkyl," as used herein, refers to a saturated monocyclic, hydrocarbon ring system having three to six carbon atoms and zero heteroatoms.

The term "$C_3$-$C_6$cycloalkyl$C_1$-$C_3$alkyl," as used herein, refers to a $C_3$-$C_6$cycloalkyl group attached to the parent molecular moiety through a $C_1$-$C_3$alkyl group.

The term "$C_3$-$C_6$cycloalkylcarbonyl," as used herein, refers to a $C_3$-$C_6$ cycloalkyl group attached to the parent molecular moiety through a carbonyl group.

The term "furanyl$C_1$-$C_3$alkyl," as used herein, refers to a furanyl group attached to the parent molecular moiety through a $C_1$-$C_3$alkyl group. The furanyl group can be attached to the alkyl moiety through any substitutable atom in the group.

The term "furanylcarbonyl," as used herein, refers to a furanyl group attached to the parent molecular moiety through a carbonyl group.

The terms "halo" and "halogen," as used herein, refer to F, Cl, Br, or I.

The term "halo$C_1$-$C_3$alkyl," as used herein, refers to a $C_1$-$C_3$alkyl group substituted with one, two, or three halogen atoms.

The term "halomethyl," as used herein, refers to a methyl group substituted with one, two, or three halogen atoms.

The term "hydroxy," as used herein, refers to —OH.

The term "imidazolyl$C_1$-$C_3$alkyl," as used herein, refers to an imidazolyl group attached to the parent molecular moiety through a $C_1$-$C_3$alkyl group. The imidazolyl group can be attached to the alkyl moiety through any substitutable atom in the group.

The term "indolyl$C_1$-$C_3$alkyl," as used herein, refers to an indolyl group attached to the parent molecular moiety through a $C_1$-$C_3$alkyl group. The indolyl group can be attached to the alkyl moiety through any substitutable atom in the group.

The term "naphthyl$C_1$-$C_3$alkyl," as used herein, refers to a naphthyl group attached to the parent molecular moiety through a $C_1$-$C_3$alkyl group. The naphthyl group can be attached to the alkyl moiety through any substitutable atom in the group.

The term "nitro," as used herein, refers to —$NO_2$.

The term "$NR^aR^b$," as used herein, refers to two groups, $R^a$ and $R^b$, which are attached to the parent molecular moiety through a nitrogen atom. $R^a$ and $R^b$ are independently selected from hydrogen, $C_2$-$C_4$alkenyloxycarbonyl, $C_1$-$C_3$alkylcarbonyl, $C_3$-$C_6$cycloalkylcarbonyl, furanylcarbonyl, and phenylcarbonyl.

The term "$NR^aR^b(C_1$-$C_3)$alkyl," as used herein, refers to an $NR^aR^b$ group attached to the parent molecular moiety through a $C_1$-$C_3$alkyl group.

The term "$NR^cR^d$," as used herein, refers to two groups, $R^c$ and $R^d$, which are attached to the parent molecular moiety through a nitrogen atom. $R^c$ and $R^d$ are independently selected from hydrogen, $C_1$-$C_3$alkyl, and triphenylmethyl.

The term "$NR^cR^d$carbonyl," as used herein, refers to an $NR^cR^d$ group attached to the parent molecular moiety through a carbonyl group.

The term "$NR^cR^d$carbonyl$C_1$-$C_3$alkyl," as used herein, refers to an $NR^cR^d$carbonyl group attached to the parent molecular moiety through a $C_1$-$C_3$alkyl group.

The term "phenoxy," as used herein, refers to a phenyl group attached to the parent molecular moiety through an oxygen atom.

The term "phenoxy$C_1$-$C_3$alkyl," as used herein, refers to a phenoxy group attached to the parent molecular moiety through a $C_1$-$C_3$alkyl group.

The term "phenyl$C_1$-$C_3$alkyl," as used herein, refers to a phenyl group attached to the parent molecular moiety through a $C_1$-$C_3$alkyl group.

The term "phenylcarbonyl," as used herein, refers to a phenyl group attached to the parent molecular moiety through a carbonyl group.

The term "pyridinyl$C_1$-$C_3$alkyl," as used herein, refers to a pyridinyl group attached to the parent molecular moiety through a $C_1$-$C_3$alkyl group. The pyridinyl group can be attached to the alkyl moiety through any substitutable atom in the group.

The term "sulfanyl," as used herein, refers to —S—.

The term "sulfonyl," as used herein, refers to —$SO_2$—.

The term "thiazolyl$C_1$-$C_3$alkyl," as used herein, refers to a thiazolyl group attached to the parent molecular moiety through a $C_1$-$C_3$alkyl group. The thiazolyl group can be attached to the alkyl moiety through any substitutable atom in the group.

The term "thienyl$C_1$-$C_3$alkyl," as used herein, refers to a thienyl group attached to the parent molecular moiety through a $C_1$-$C_3$alkyl group. The thienyl group can be attached to the alkyl moiety through any substitutable atom in the group.

The term "treating" refers to: (i) preventing a disease, disorder, or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

Unless otherwise indicated, the term "alkyl" as employed herein alone or as part of another group includes, without limitation, both straight and branched chain hydrocarbons, containing 1 to 40 carbons, preferably 1 to 20 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, alkynyl, hydroxy, arylalkyl, cycloalkyl, cycloalkylalkyl, alkoxy, arylalkyloxy, heteroaryloxy, heteroarylalkyloxy, alkanoyl, halo, hydroxyl, thio, nitro, cyano, carboxyl, carbonyl

carboxamido, amino, alkylamino, dialkylamino, amido, alkylamino, arylamido, heteroarylamido, azido, guanidino, amidino, phosphonic, phosphinic, sulfonic, sulfonamido, haloaryl, $CF_3$, $OCF_2$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes, without limitation, saturated or partially unsaturated (containing 1 or 2 double bonds) cyclic hydrocarbon groups containing 1 to 3 rings, appended or fused, including monocyclic alkyl, bicyclic alkyl and tricyclic alkyl, containing a total of 3 to 20 carbons forming the rings, preferably 4 to 7 carbons, forming each ring; which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

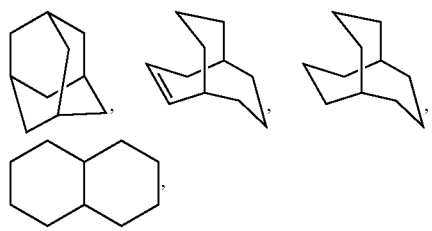

any of which groups may be optionally substituted through any available carbon atoms with 1 or more groups selected from hydrogen, halo, haloalkyl, alkyl, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, carboxyl, carbonyl

carboxamido, amino, substituted amino wherein the amino includes 1 or 2 substituents (which are alkyl, aryl or any of the other aryl compounds mentioned in the definitions), amido, azido, guanidino, amidino, phosphonic, phosphinic, sulfonic, sulfonamido, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "aryl" as employed herein alone or as part of another group refers, without limitation, to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or heterocycloalkyl rings) and may be optionally substituted through any available carbon atoms with 1 or more groups selected from hydrogen, alkyl, halo, haloalkyl, alkoxy, haloalkoxy, alkenyl, trifluoromethyl, trifluoromethoxy, alkynyl, cycloalkylalkyl, fluorenyl, heterocycloalkyl, heterocycloalkylalkyl, aryl, heteroaryl, arylalkyl, aryloxy, aryloxyalkyl, arylalkoxy, arylthio, arylazo, heteroarylalkyl, heteroarylalkenyl, heteroaryloxy, heteroarylalkyloxy, heteroarylalkyloxyalkyl, hydroxy, nitro, oxo, cyano, amino, substituted amino wherein the amino includes 1 or 2 substituents (which are alkyl, cycloalkyl, heterocycloalkyl, heteroaryl, or aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, cycloalkylaminocarbonyl, arylaminocarbonyl, heteroarylaminocarbonyl, heteroarylalkylaminocarbonyl alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of alkyl substituents as set out above.

The term "arylalkyl" as used herein alone or as part of another group refers, without limitation, to alkyl groups as defined above having an aryl substituent, such as benzyl, phenethyl or naphthylpropyl, wherein said aryl and/or alkyl groups may optionally be substituted as defined above.

The term "alkoxy", "aryloxy", "heteroaryloxy", "arylalkyloxy", or "heteroarylalkyloxy" as employed herein alone or as part of another group includes, without limitation, an alkyl or aryl group as defined above linked through an oxygen atom.

The term "heterocyclo", "heterocycle", "heterocyclyl" or "heterocyclic", as used herein, represents, without limitation, an unsubstituted or substituted stable 4-, 5-, 6-, or 7-membered monocyclic ring system which may be saturated or unsaturated, and which consists of carbon atoms and from one to four heteroatoms selected from nitrogen, sulfur, oxygen and/or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, tetrahydrofuranyl, tetrahydrothiophenyl pyrrolidinyl, piperidinyl, piperazinyl, oxopyrrolidinyl, oxopiperazinyl, oxopiperidinyl and oxadiazolyl. Optionally a heterocyclo group may be substituted with one or more functional groups, such as those described for "alkyl" or "aryl".

The term "heterocycloalkyl" as used herein alone or as part of another group refers, without limitation, to alkyl groups as defined above having a heterocycloalkyl substituent, wherein said "heterocyclo" and/or alkyl groups may optionally be substituted as defined above.

The term "heteroaryl" as used herein refers, without limitation, to a 5-, 6- or 7-membered aromatic heterocyclic ring which contains one or more heteroatoms selected from nitrogen, sulfur, oxygen and/or a SO or $SO_2$ group. Such rings may be fused to another aryl or heteroaryl ring and include possible N-oxides; examples of such heteroaryl groups include, but are not limited to, furan, pyrrole, thiophene, pyridine, pyrimidine, pyrazine, pyridazine, isoxazole, oxazole, imidazole and the like. Optionally a heteroaryl group may be substituted with one or more functional groups commonly attached to such chains, such as those described for "alkyl" or "aryl".

The term "heteroarylalkyl" as used herein alone or as part of another group refers, without limitation, to alkyl groups as defined above having a heteroaryl substituent, wherein said heteroaryl and/or alkyl groups may optionally be substituted as defined above.

The "inhibitory concentration" of PD-1/PD-L1 inhibitor is intended to mean the concentration at which a compound screened in an assay of the disclosure inhibits a measurable percentage of the interaction of PD-1 with PD-L1. Examples of "inhibitory concentration" values range from $IC_{50}$ to $IC_{90}$, and are preferably, $IC_{50}$, $IC_{60}$, $IC_{70}$, $IC_{80}$, or $IC_{90}$, which represent 50%, 60%, 70%, 80% or 90% reduction in PD-1/PD-L1 binding activity, respectively. More preferably, the "inhibitory concentration" is measured as the $IC_{50}$ value. It is understood that another designation for $IC_{50}$ is the half-maximal inhibitory concentration.

Binding of the macrocyclic peptides to PD-L1 can be measured, for example, by methods such as homogeneous time-resolved fluorescence (HTRF), Surface Plasmon Resonance (SPR), isothermal titration calorimetry (ITC), nuclear magnetic resonance spectroscopy (NMR), and the like. Further, binding of the macrocyclic peptides to PD-L1 expressed on the surface of cells can be measured as described herein in cellular binding assays.

Administration of a therapeutic agent described herein includes, without limitation, administration of a therapeutically effective amount of therapeutic agent. The term "therapeutically effective amount" as used herein refers, without limitation, to an amount of a therapeutic agent to treat or prevent a condition treatable by administration of a composition of the PD-1/PD-L1 binding inhibitors described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

The macrocyclic peptides of the present disclosure show potent binding activity to PD-L1, both in HTRF assays, as well as cellular binding assays. In addition, the macrocyclic peptides also demonstrate biological activity in CMV recall and HIV Elispot assays demonstrating their utility in ameliorating and/or treating hyperproliferative disorders, such as cancer, and virology indications, including HIV.

In another aspect, the disclosure pertains to methods of inhibiting growth of tumor cells in a subject using the macrocyclic peptides of the present disclosure. As demonstrated herein, the macrocyclic peptides of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancement of HIV-specific T cell IFNg secretion. As a result, the macrocyclic peptides of the present disclosure are useful for modifying an immune response, treating diseases such as cancer or infectious disease, stimulating a protective autoimmune response or to stimulate antigen-specific immune responses (e.g., by coadministration of PD-L1 blocking peptides with an antigen of interest).

In order that the present disclosure may be more readily understood, certain terms are first defined. Additional definitions are set forth throughout the detailed description.

The terms "Programmed Death Ligand 1", "Programmed Cell Death Ligand 1", "Protein PD-L1", "PD-L1", "PDL1", "PDCDL1", "hPD-L1", "hPD-L1", "CD274" and "B7-H1" are used interchangeably, and include variants, isoforms, species homologs of human PD-L1, and analogs having at least one common epitope with PD-L1. The complete PD-L1 sequence can be found under GENBANK® Accession No. NP_054862.

The terms "Programmed Death 1", "Programmed Cell Death 1", "Protein PD-1", "PD-1", "PD1", "PDCD1", "hPD-1" and "hPD-I" are used interchangeably, and include variants, isoforms, species homologs of human PD-1, and analogs having at least one common epitope with PD-1. The complete PD-1 sequence can be found under GENBANK® Accession No. U64863.

The terms "cytotoxic T lymphocyte-associated antigen-4", "CTLA-4", "CTLA4", "CTLA-4 antigen" and "CD152" (see, e.g., Murata, *Am. J. Pathol.*, 155:453-460 (1999)) are used interchangeably, and include variants, isoforms, species homologs of human CTLA-4, and analogs having at least one common epitope with CTLA-4 (see, e.g., Balzano, *Int. J. Cancer Suppl.*, 7:28-32 (1992)). The complete CTLA-4 nucleic acid sequence can be found under GENBANK® Accession No. L15006.

The term "immune response" refers to the action of, for example, lymphocytes, antigen presenting cells, phagocytic cells, granulocytes, and soluble macromolecules produced by the above cells or the liver (including macrocyclic peptides, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the PD-1 receptor.

The term "macrocyclic peptide derivatives" refers to any modified form of the macrocyclic peptides disclosed herein, e.g., mutations, isoforms, peptides with altered linker backbones, conjugates with an antibody and/or another agent, etc.

As used herein, a macrocyclic peptide of the present disclosure that "specifically binds to human PD-L1" is intended to refer to a macrocyclic peptide that binds to human PD-L1 with an $IC_{50}$ of less than about 200 nM, less than about 150 nM, less than about 100 nM, less than about 80 nM, less than about 60 nM, less than about 40 nM, less than about 20 nM, less than about 15 nM, less than about 10 nM, less than about 5 nM, less than about 1 nM, or less. In this context, the term "about" shall be construed to mean anywhere between ±1, 2, 3, 4, 5, 6, 7, 8, 9, 10, 11, 12, 13, 14, 15, 16, 17, 18, 19, or 20 nM more or less than the cited amount.

The term "treatment" or "therapy" refers to administering an active agent with the purpose to cure, heal, alleviate, relieve, alter, remedy, ameliorate, improve, or affect a condition (e.g., a disease), the symptoms of the condition, or to prevent or delay the onset of the symptoms, complications, biochemical indicia of a disease, or otherwise arrest or inhibit further development of the disease, condition, or disorder in a statistically significant manner.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within one or more than one standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

Competition Assays

Figure 9:
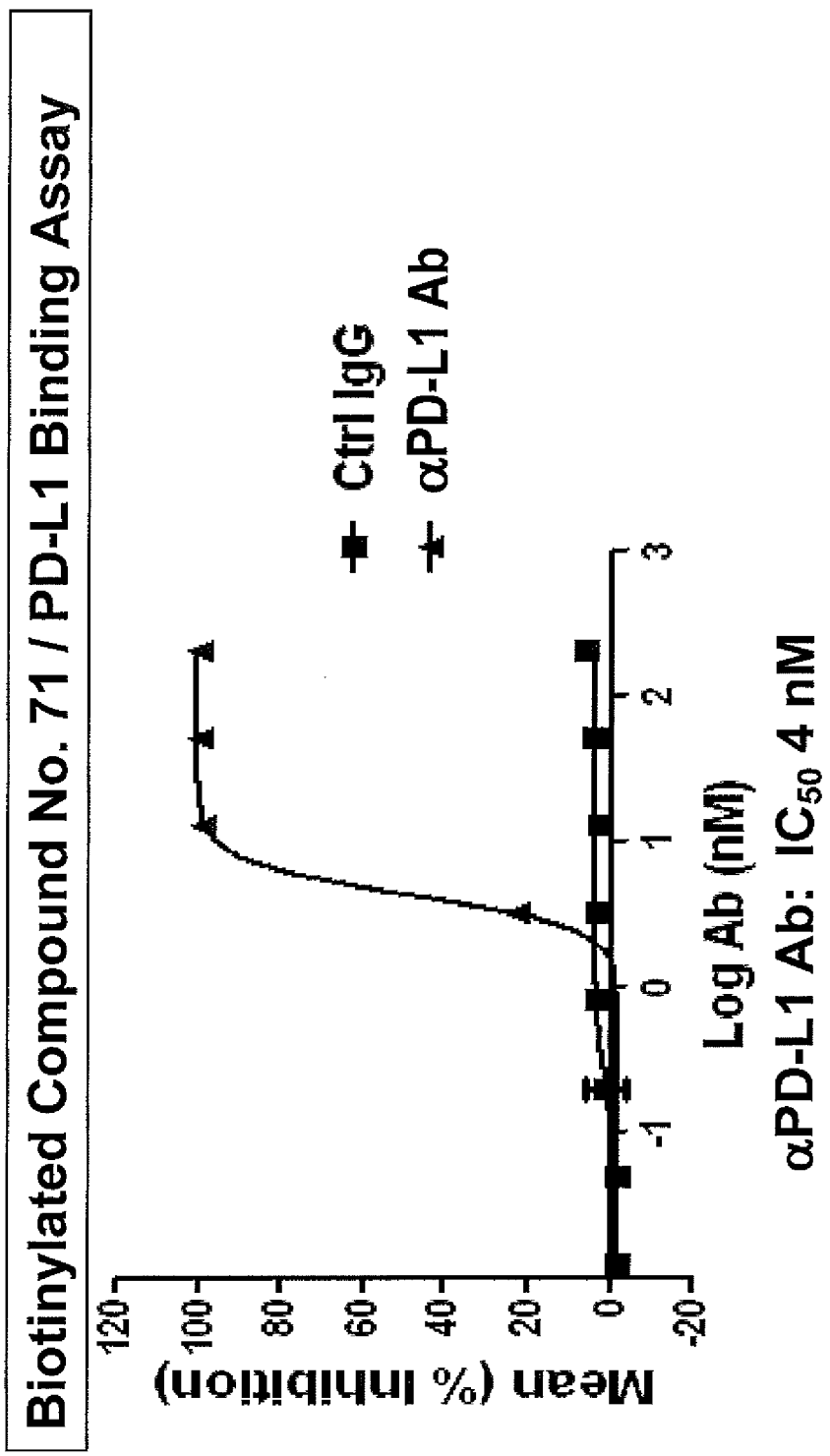
FIG. 9—Biotinylated Compound No. 71/PD-L1 Binding Assay—Anti-PD-L1 Antibody. As shown, the anti-PD-L1 monoclonal antibody is capable of blocking biotinylated Compound No. 71 to PD-L1 using the HTRF assay. These results suggest these peptides bind to the same binding site as the anti-PD-L1 monoclonal antibody.

The present disclosure is also directed to macrocyclic peptides that are capable of competing with the binding of a reference anti-PD-L1 antibody (MDX-1105) by at least about 20%, at least about 30%, at least about 40%, at least about 50%, at least about 60%, at least about 70%, at least about 80%, at least about 90%, and at least about 100%. Such macrocyclic peptides may share structural homology with one or more macrocyclic peptides disclosed herein, including mutant, conservative substitution, functional substitution, and deletion forms, provided they specific bind to PD-L1. For example, if a macrocyclic peptide binds substantially to the same region of PD-L1 as a reference anti-PD-L1 antibody, the macrocyclic peptide should bind to an epitope of PD-L1 that at least overlaps with the PD-L1 epitope that the anti-PD-L1 monoclonal antibody binds to. The overlapping region can range from one amino acid residue to several hundred amino acid residues. The macrocyclic peptide should then compete with and/or block the binding of the anti-PD-L1 monoclonal antibody to PD-L1 and thereby decrease the binding of the anti-PD-L1 monoclonal antibody to PD-L1, preferably by at least about 50% in a competition assay. (See FIG. 9).

Anti-PD-L1 antibodies that may be used as reference antibodies for competition assay purposes are known in the art. For example, the following representative anti-PD-L1 antibodies may be used: MDX-1105 (BMS); L01X-C (Serono), L1X3 (Serono), MSB-0010718C (Serono), and PD-L1 Probody (CytomX), and the PD-L1 antibodies disclosed in co-owned WO 2007/005874.

Anti-PD-1 antibodies that may be used as reference antibodies for competition assay purposes are known in the art. For example, the following representative anti-PD-1 antibodies may be used: nivolumab (BMS); 17D8, 2D3, 4H1, 4A11, 7D3 and 5F4 each disclosed in co-owned U.S. Pat. No. 8,008,449 (BMS), MK-3475 (Merck, disclosed in U.S. Pat. No. 8,168,757), and the antibodies disclosed in U.S. Pat. No. 7,488,802.

Variant Macrocyclic Peptides

In yet another embodiment, a macrocyclic peptide of the disclosure comprises amino acid sequences that are homologous to the amino acid sequences of the macrocyclic peptides described herein, and wherein the macrocyclic peptides retain the desired functional and/or biological properties of the macrocyclic peptide of the disclosure.

For example, the disclosure provides a macrocyclic peptide, or antigen-binding portion thereof, comprising: an amino acid sequence that is at least 80% homologous to an amino acid sequence selected from the compounds described herein; and the macrocyclic peptide exhibits one or more of the following properties:

(a) the macrocyclic peptide binds to human PD-L1 with an $IC_{50}$ of 200 nM or less;

(b) the macrocyclic peptide does not substantially bind to human CD28, CTLA-4 or ICOS;

(c) the macrocyclic peptide increases CMV-specific T cell IFNγ secretion;

(d) the macrocyclic peptide increases HIV-specific T cell IFNγ secretion;

(e) the macrocyclic peptide binds to human PD-1 and one or more of the following: cynomolgus monkey PD-1; woodchuck PD-1, and/or mouse PD-1;

(f) the macrocyclic peptide inhibits the binding of PD-L1 and/or PD-L2 to PD-1;

(g) the macrocyclic peptide is capable of competing with binding of anti-PD-1 monoclonal antibodies, including nivolumab (BMS-936558, MDX-1106);

(h) the macrocyclic peptide inhibits tumor cell growth in a cellular assay and/or in vivo assay; and/or (i) the macrocyclic peptide inhibits HIV in a cellular assay and/or in vivo assay.

In other embodiments, the macrocyclic peptide amino acid sequences may be about 80%, about 85%, about 86%, about 87%, about 88%, about 89%, about 90%, about 91%, about 92%, about 93%, about 94%, about 95%, about 96%, about 97%, about 98% or about 99% homologous to the sequences set forth above. In this context, the term "about" shall be construed to mean anywhere between 1, 2, 3, 4, or 5 percent more or less than the cited amount. A macrocyclic peptide of the present disclosure having sequences with high identity (i.e., 80% or greater) to the sequences set forth above, can be obtained by mutating the sequences during chemical synthesis, for example, followed by testing of the altered macrocyclic peptide for retained function (i.e., the functions set forth in (a) through (i) above) using the functional assays described herein. The biological and/or functional activity of the variant macrocyclic peptide amino acid sequences may be at least about 1×, 2×, 3×, 4×, 5×, 6×, 7×, 8×, 9×, or 10× more than the reference macrocyclic peptide on which the variant is based. In this context, the term "about" shall be construed to mean anywhere between 0.1×, 0.2×, 0.3×, 0.4×, 0.5×, 0.6×, 0.7×, 0.8×, or 0.9× more or less than the cited amount.

As used herein, the percent homology between two amino acid sequences is equivalent to the percent identity between the two sequences. The percent identity between the two sequences is a function of the number of identical positions shared by the sequences (i.e., % homology=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of Meyers E. et al., (Comput. Appi. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman et al. (J. Mol. Biol., 48:444-453 (1970)) algorithm which has been incorporated into the GAP program in the GCG® software package using either a Blossum 62 matrix or a PAM250 matrix, and a gap weight of 16, 14, 12, 10, 8, 6, or 4 and a length weight of 1, 2, 3, 4, 5, or 6.

Macrocyclic Peptides with Conservative Modifications

In yet another embodiment, a macrocyclic peptide of the disclosure comprises amino acid sequences that are homologous to the amino acid sequences of the macrocyclic peptides described herein, and wherein the macrocyclic peptides retain the desired functional and/or biological properties of the macrocyclic peptide of the disclosure.

For example, the disclosure provides a macrocyclic peptide, or antigen-binding portion thereof, comprising: an amino acid sequence that is at least 80% homologous to an amino acid sequence selected from the macrocyclic peptides described herein, wherein one or more amino acids have been substituted with a conservative amino acid; and the macrocyclic peptide exhibits one or more of the following properties:

(a) the macrocyclic peptide binds to human PD-L1 with an $IC_{50}$ of 200 nM or less (b) the macrocyclic peptide does not substantially bind to human CD28, CTLA-4 or ICOS;

(c) the macrocyclic peptide increases CMV-specific T cell IFNγ secretion;

(d) the macrocyclic peptide increases HIV-specific T cell IFNγ secretion;

(e) the macrocyclic peptide binds to human PD-L1 and one or more of the following: cynomolgus monkey PD-L1; woodchuck PD-L1, and/or mouse PD-L1;

(f) the macrocyclic peptide inhibits the binding of PD-L1 and/or PD-L2 to PD-1;

(g) the macrocyclic peptide is capable of competing with binding of anti-PD-1 monoclonal antibodies, including nivolumab (BMS-936558, MDX-1106);

(h) the macrocyclic peptide inhibits tumor cell growth in a cellular assay and/or in vivo assay; and/or (i) the macrocyclic peptide inhibits HIV in a cellular assay and/or in vivo assay.

As used herein, the term "conservative sequence modifications" is intended to refer to amino acid modifications that do not significantly affect or alter the binding characteristics of the macrocyclic peptide containing the amino acid sequence. Such conservative modifications include amino acid substitutions, additions and deletions. Modifications can be introduced into an antibody of the disclosure by standard techniques known in the art, such as substitution of peptide amidites during chemical synthesis, site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the antigen binding regions of macrocyclic peptides of the disclosure can be replaced with other amino acid residues from the same side chain family and the altered antibody can be tested for retained function (i.e., the functions set forth in (a) thru (i) above) using the functional assays described herein. Conservative amino acid substitutions may also be selected from one or more non-naturally occurring amino acids disclosed herein.

Pharmaceutical Compositions

The disclosure further relates to the polypeptides described herein wherein the sequence comprises one or more amino acid deletions from either the C-terminus and/or the N-terminus.

In preferred embodiments, the following N-terminal Compound No. 99 deletion polypeptides are encompassed by the present disclosure: X1-X13, X2-X13, X3-X13, X4-X13, X5-X13, X6-X13, X7-X13, X8-X13, X9-X13, X10-X13, X11-X13, and/or X12-X13 of Compound No. 99, wherein each X is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 99 deletion polypeptides are encompassed by the present disclosure: X1-X13, X1-X12, X1-X11, X1-X10, X1-X9, X1-X8, X1-X7, X1-X6, X1-X5, X1-X4 and/or X1-X3 of Compound No. 99, wherein each X is representative of an amino acid at the indicated position for each peptide as outlined herein. The present disclosure also encompasses cyclic forms of these deletion mutants using the linking chemistries described elsewhere herein.

In preferred embodiments, the following N-terminal Compound No. 1 deletion polypeptides are encompassed by the present disclosure: X1-X15, X2-X15, X3-X15, X4-X15, X5-X15, X6-X15, X7-X15, X8-X15, X9-X15, X10-X15, X11-X15, and/or X12-X15 of Compound No. 1, wherein each 1 is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 1 deletion polypeptides are encompassed by the present disclosure: X1-X15, X1-X14, X1-X13, X1-X12, X1-X11, X1-X10, X1-X9, X1-X8, X1-X7, X1-X6, X1-X5, X1-X4 and/or X1-X3 of Compound No. 1, wherein each X is representative of an amino acid at the indicated position for each peptide as outlined herein. The present disclosure also encompasses cyclic forms of these deletion mutants using the linking chemistries described elsewhere herein.

In preferred embodiments, the following N-terminal Compound No. 71 deletion polypeptides are encompassed by the present disclosure: X1-X14, X2-X14, X3-X14, X4-X14, X5-X14, X6-X14, X7-X14, X8-X14, X9-X14, X10-X14, X11-X14, and/or X12-X14 of Compound No. 71, wherein each X is representative of an amino acid at the indicated position for each peptide as outlined herein. The present disclosure also encompasses cyclic forms of these deletion mutants using the linking chemistries described elsewhere herein.

In preferred embodiments, the following C-terminal Compound No. 71 deletion polypeptides are encompassed by the present disclosure: X1-X14, X1-X13, X1-X12, X1-X11, X1-X10, X1-X9, X1-X8, X1-X7, X1-X6, X1-X5, X1-X4 and/or X1-X3 of Compound No. 71, wherein each X is representative of an amino acid at the indicated position for each peptide as outlined herein. The present disclosure also encompasses cyclic forms of these deletion mutants using the linking chemistries described elsewhere herein.

In another aspect, the present disclosure provides a composition, e.g., a pharmaceutical composition, containing one or a combination of macrocyclic peptides, or antigen-binding portion(s) thereof, of the present disclosure, formulated together with a pharmaceutically acceptable carrier. Such compositions may include one or a combination of (e.g., two or more different) macrocyclic peptides, or immunoconjugates or bispecific molecules of the disclosure. For example, a pharmaceutical composition of the disclosure can comprise a combination of macrocyclic peptides (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a macrocyclic peptide combined with at least one other anti-inflammatory or immunosuppressant agent. Examples of therapeutic agents that can be used in combination therapy are described in greater detail below in the section on uses of the macrocyclic peptides of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a macrocyclic peptide, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" refers to a salt that retains the desired biological activity of the parent compound and does not impart any undesired toxicological effects (see e.g., Berge, S. M. et al., *J. Pharm. Sci.*, 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the macrocyclic peptide, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, bi-weekly, tri-weekly, weekly, once every two weeks, once every three weeks, once every four weeks, once a month, once every 3 months or once every three to 6 months. Preferred dosage regimens for a macrocyclic peptide of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more macrocyclic peptides with different binding specificities are administered simultaneously, in which case the dosage of each compound administered falls within the ranges indicated. The compounds are usually administered on multiple occasions. Intervals between single dosages can be, for example, weekly, monthly, every three months or yearly. Intervals can also be irregular as indicated by measuring blood levels of macrocyclic peptide to the target antigen in the patient. In some methods, dosage is adjusted to achieve a plasma antibody concentration of about 1-1000 .mu.g/ml and in some methods about 25-300 .mu.g/ml.

Alternatively, the macrocyclic peptide can be administered as a sustained release formulation, in which case less frequent administration is required. Dosage and frequency vary depending on the half-life of the macrocyclic peptide in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a macrocyclic peptide of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth and/or HIV can be evaluated in an animal model system predictive of efficacy in human tumors or viral efficacy. Alternatively, this property of a composition can be evaluated by examining the ability of the compound to inhibit, such inhibition in vitro by assays known to the skilled practitioner. A therapeutically effective amount of a therapeutic compound can decrease tumor size, decrease viral load, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising a macrocyclic peptide and an anti-CTLA-4 antibody, as described herein. The kit may also further comprise instructions for use in the treatment of a hyperproliferative disease (such as cancer as described herein) and/or anti-viral disease.

A composition of the present disclosure can be administered via one or more routes of administration using one or more of a variety of methods known in the art. As will be appreciated by the skilled artisan, the route and/or mode of administration will vary depending upon the desired results. Preferred routes of administration for macrocyclic peptides of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a macrocyclic peptide of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., Sustained and Controlled Release Drug Delivery Systems, Marcel Dekker, Inc., New York (1978).

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the macrocyclic peptides of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522,811, 5,374,548, and 5,399,331. The liposomes may comprise one or more moieties which are selectively transported into specific cells or organs, thus enhance targeted drug delivery (see, e.g., Ranade, V. V., J. Clin. Pharmacol., 29:685 (1989)). Exemplary targeting moieties include folate or biotin (see, e.g., U.S. Pat. No. 5,416,016 to Low et al.); mannosides (Umezawa et al., Biochem. Biophys. Res. Commun., 153:1038 (1988)); macrocyclic peptides (Bloeman, P. G. et al., FEBS Lett., 357:140 (1995); Owais, M. et al., Antimicrob. Agents Chemother., 39:180 (1995)); surfactant protein A receptor (Briscoe et al., Am. J. Physiol., 1233:134 (1995)); p 120 (Schreier et al., J. Biol. Chem., 269:9090 (1994)); see also Keinanen, K. et al., FEBS Lett., 346:123 (1994); Killion, J. J. et al., Immunomethods 4:273 (1994).

Uses and Methods of the Disclosure

The macrocyclic peptides, compositions and methods of the present disclosure have numerous in vitro and in vivo utilities involving, for example, detection of PD-L1 or enhancement of immune response by blockade of PD-L1. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the antibody, or antigen-binding portion thereof, of the disclosure such that the immune response in the subject is modified. Preferably, the response is enhanced, stimulated or up-regulated. In other respects, the macrocyclic peptide may have anti-cyno, anti-mouse, and/or anti-woodchuck binding and therapeutic activity.

As used herein, the term "subject" is intended to include human and non-human animals. Non-human animals includes all vertebrates, e.g., mammals and non-mammals, such as non-human primates, sheep, dogs, cats, cows, horses, chickens, woodchuck, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the macrocyclic peptides can be administered together with an antigen of interest. When macrocyclic peptides to PD-L1 are administered together with another agent, the two can be administered in either order or simultaneously.

The disclosure further provides methods for detecting the presence of human, woodchuck, cyno, and/or mouse PD-L1 antigen in a sample, or measuring the amount of human, woodchuck, cyno, and/or mouse PD-L1 antigen, comprising contacting the sample, and a control sample, with a reference monoclonal antibody, or an antigen-binding portion thereof, which specifically binds to human, woodchuck, cyno, and/or mouse PD-L1, under conditions that allow for formation of a complex between the antibody or portion thereof and human, woodchuck, cyno, and/or mouse PD-L1. The formation of a complex is then detected, wherein a difference complex formation between the sample compared to the control sample is indicative the presence of human, woodchuck, cyno, and/or mouse PD-L1 antigen in the sample.

Given the specific binding of the macrocyclic peptides of the disclosure for PD-L1, compared to CD28, ICOS and CTLA-4, the macrocyclic peptides of the disclosure can be used to specifically detect PD-L1 expression on the surface of cells and, moreover, can be used to purify PD-L1 via immunoaffinity purification.

Cancer

Blockade of PD-1 by macrocyclic peptides can enhance the immune response to cancerous cells in the patient. The ligand for PD-1, PD-L1, is not expressed in normal human cells, but is abundant in a variety of human cancers (Dong et al., Nat. Med., 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med.*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 to PD-L1 and the effect is additive when the interaction of PD-1 to PD-L2 is blocked as well (Iwai et al., *Proc. Natl. Acad. Sci.*, 99:12293-12297 (2002); Brown et al., *J. Immunol.*, 170:1257-1266 (2003)). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present disclosure relates to treatment of a subject in vivo using a macrocyclic peptide such that growth of cancerous tumors is inhibited. A macrocyclic peptide may be used alone to inhibit the growth of cancerous tumors. Alternatively, a macrocyclic peptide may be used in conjunction with other immunogenic agents, standard cancer treatments, or other macrocyclic peptides, as described below.

Accordingly, in one embodiment, the disclosure provides a method of inhibiting growth of tumor cells in a subject, comprising administering to the subject a therapeutically effective amount of a macrocyclic peptide, or antigen-binding portion thereof.

Preferred cancers whose growth may be inhibited using the macrocyclic peptides of the disclosure include cancers typically responsive to immunotherapy. Non-limiting examples of preferred cancers for treatment include melanoma (e.g., metastatic malignant melanoma), renal cell carcinoma (e.g., clear cell carcinoma), prostate cancer (e.g., hormone refractory prostate adenocarcinoma and castration-resistant prostate cancer), breast cancer, colorectal cancer and lung cancer (e.g., squamous and non-squamous non-small cell lung cancer). Additionally, the disclosure includes refractory or recurrent malignancies whose growth may be inhibited using the macrocyclic peptides of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, colon cancer, rectal cancer, cancer of the anal region, stomach/gastric cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al., *Int. Immunol.*, 17:133-144 (2005)).

Optionally, macrocyclic peptides to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo, N. et al., Cancer Vaccines, Chapter 61, pp. 3023-3043, in DeVita, V. et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90: 3539-3543 (1993)).

The study of gene expression and large scale gene expression patterns in various tumors has led to the definition of so called tumor specific antigens (Rosenberg, S. A., *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R. et al., *Science*, 269:1585-1588 (1995); Tamura, Y. et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al., *Nat. Med.*, 4:328-332 (1998)). DCs may also be transduced by genetic means to express these tumor antigens as well. DCs have also been fused directly to tumor cells for the purposes of immunization (Kugler, A. et al., *Nat. Med.*, 6:332-336 (2000)). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al., *Cancer Res.*, 58:5301-5304 (1998)). An example of such a combination is a macrocyclic peptide in combination with decarbazine for the treatment of melanoma. Another example of such a combination is a macrocyclic peptide in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade Inhibition of angiogenesis leads to tumor cell death which may feed tumor antigen into host antigen presentation pathways.

PD-L1 blocking macrocyclic peptides can also be used in combination with bispecific macrocyclic peptides that target Fc alpha or Fc gamma receptor-expressing effectors cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al., *J. Exp. Med.*, 163: 1037-1050 (1986)), IL-10 (Howard, M. et al., *Immunology Today*, 13:198-200 (1992)), and Fas ligand (Hahne, M. et al., *Science*, 274:1363-1365 (1996)). Macrocyclic peptides to each of these entities may be used in combination with anti-PD-L1 to counteract the effects of the immunosuppressive agent and favor tumor immune responses by the host.

Other macrocyclic peptides which may be used to activate host immune responsiveness can be used in combination with anti-PD-L1. These include molecules on the surface of dendritic cells which activate DC function and antigen presentation. Anti-CD40 macrocyclic peptides are able to substitute effectively for T cell helper activity (Ridge, J. et al., *Nature*, 393:474-478 (1998)) and can be used in conjunction with PD-1 antibodies (Ito, N. et al., *Immunobiology*, 201(5):527-540 (2000)). Activating macrocyclic peptides to T cell costimulatory molecules such as CTLA-4 (e.g., U.S. Pat. No. 5,811,097), OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence of macrocyclic peptides may be expected to increase the frequency and activity of the adoptively transferred T cells.

Infectious Diseases

Other methods of the disclosure are used to treat patients that have been exposed to particular toxins or pathogens. Accordingly, another aspect of the disclosure provides a method of treating an infectious disease in a subject comprising administering to the subject a macrocyclic peptide of the present disclosure, or antigen-binding portion thereof, such that the subject is treated for the infectious disease. Preferably, the antibody is a human anti-human PD-L1 macrocyclic peptide (such as any of the macrocyclic peptides described herein). Additionally or alternatively, the antibody can be a chimeric or humanized antibody.

Similar to its application to tumors as discussed above, antibody mediated PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, and C), Influenza, Herpes, Giardia, Malaria (Butler, N. S. et al., *Nature Immunology* 13, 188-195 (2012); Hafalla, J. C. R., et al. *PLOS Pathogens*; Feb. 2, 2012)), Leishmania, Staphylococcus aureus, Pseudomonas Aeruginosa. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, *klebsiella, proteus, serratia,* pseudomonas, *legionella,* diphtheria, *salmonella,* bacilli, cholera, tetanus, botulism, anthrax, plague, leptospirosis, and Lyme disease bacteria.

Some examples of pathogenic fungi causing infections treatable by methods of the disclosure include *Candida* (albicans, krusei, glabrata, tropicalis, etc.), *Cryptococcus neoformans, Aspergillus* (fumigatus, niger, etc.), Genus *Mucorales* (mucor, *absidia,* rhizophus), *Sporothrix schenkii, Blastomyces dermatitidis, Paracoccidioides brasiliensis, Coccidioides immitis* and *Histoplasma capsulatum.*

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis.*

In all of the above methods, PD-L1 blockade can be combined with other forms of immunotherapy such as cytokine treatment (e.g., interferons, agents targeting VEGF activity or VEGF-receptors, GM-CSF, G-CSF, IL-2), or bispecific antibody therapy, which provides for enhanced presentation of tumor antigens (see, e.g., Holliger, *Proc. Natl. Acad. Sci. USA,* 90:6444-6448 (1993); Poljak, *Structure,* 2:1121-1123 (1994)).

Autoimmune Reactions

The macrocyclic peptides may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al., *Proc. Natl. Acad. Sci. USA,* 96:2982-2987 (1999)); autoimmune prostatitis evoked by TRAMP tumor cell vaccines (Hurwitz, A., supra (2000)), melanoma peptide antigen vaccination and vitiligo observed in human clinical trials (Rosenberg, S. A. et al., *J. Immunother. Emphasis Tumor Immunol.,* 19(1):81-84 (1996)).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., *Nature,* 400:173-177 (1999)).

Other self proteins may also be used as targets such as IgE for the treatment of allergy and asthma, and TNF.alpha for rheumatoid arthritis. Finally, antibody responses to various hormones may be induced by the use of the macrocycles disclosed herein. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 macrocycles can be used for induction of therapeutic autoimmune responses to treat patients having an inappropriate accumulation of other self-antigens, such as amyloid deposits, including A.beta. in Alzheimer's disease, cytokines such as TNF.alpha., and IgE.

Vaccines

The macrocyclic peptides may be used to stimulate antigen-specific immune responses by coadministration of an anti-PD-1 macrocycle with an antigen of interest (e.g., a vaccine). Accordingly, in another aspect the disclosure provides a method of enhancing an immune response to an antigen in a subject, comprising administering to the subject: (i) the antigen; and (ii) an anti-PD-1 macrocycle, or antigen-binding portion thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the compositions (e.g., macrocyclic peptides, multispecific and bispecific molecules and immunoconjugates) of the disclosure in vivo and in vitro are well known in the art and can be selected by those of ordinary skill. For example, the compositions can be administered by injection (e.g., intravenous or subcutaneous). Suitable dosages of the molecules used will depend on the age and weight of the subject and the concentration and/or formulation of the composition.

As previously described the macrocyclic peptides of the disclosure can be co-administered with one or other more therapeutic agents, e.g., a cytotoxic agent, a radiotoxic agent or an immunosuppressive agent. The peptide can be linked to the agent (as an immunocomplex) or can be administered separate from the agent. In the latter case (separate administration), the peptide can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the macrocyclic peptides, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the peptides.

Also within the scope of the present disclosure are kits comprising the compositions of the disclosure (e.g., macrocyclic peptides, bispecific or multispecific molecules, or immunoconjugates) and instructions for use. The kit can further contain at least one additional reagent, or one or more additional macrocyclic peptides of the disclosure (e.g., a human antibody having a complementary activity which binds to an epitope in PD-L1 antigen distinct from the macrocycle). Kits typically include a label indicating the intended use of the contents of the kit. The term label includes any writing, or recorded material supplied on or with the kit, or which otherwise accompanies the kit.

Combination Therapy

The combination of the macrocyclic peptides of the present disclosure with another PD-L1 antagonist and/or CTLA-4 antagonist is useful for enhancement of an immune response against a hyperproliferative disease by blockade of PD-L1 and CTLA-4. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject an antibody combination, or a combination of antigen-binding portions thereof, of the disclosure such that the immune response in the subject is modified. Preferably, the response is enhanced, stimulated or up-regulated. In another embodiment, the instant disclosure provides a method of altering adverse events associated with treatment of a hyperproliferative disease with an immunostimulatory therapeutic agent, comprising administering a macrocyclic peptide of the present disclosure and a subtherapeutic dose of anti-CTLA-4 antibody to a subject.

Blockade of PD-L1 and CTLA-4 by macrocyclic peptides can enhance the immune response to cancerous cells in the patient. Cancers whose growth may be inhibited using the macrocyclic peptides of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

In certain embodiments, the combination of therapeutic agents containing at least one macrocyclic peptide discussed herein may be administered concurrently as a single composition in a pharmaceutically acceptable carrier, or concurrently as separate compositions wherein each agent can be administered sequentially. For example, an anti-CTLA-4 antibody and a macrocyclic peptide of the present disclosure can be administered sequentially, such as anti-CTLA-4 being administered first and the macrocyclic peptide second, or the macrocyclic peptide being administered first and anti-CTLA-4 second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a combination anti-CTLA-4 antibody and the macrocyclic peptide may be concurrent, the second administration may be sequential with anti-CTLA-4 first and the macrocyclic peptide second, and the third administration may be sequential with the macrocyclic peptide first and anti-CTLA-4 second, etc. Another representative dosing scheme may involve a first administration that is sequential with the macrocyclic peptide first and anti-CTLA-4 second, and subsequent administrations may be concurrent.

Optionally, the combination of the macrocyclic peptide and anti-CTLA-4 agent can be further combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

A combined PD-L1 macrocyclic peptide and CTLA-4 blockade can be further combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo et al., Cancer Vaccines, Chapter 61, pp. 3023-3043 in DeVita et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90:3539-3543 (1993)).

The study of gene expression and large scale gene expression patterns in various tumors has led to the definition of so called tumor specific antigens (Rosenberg, *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-L1 macrocyclic peptide and CTLA-4 blockade using the antibody compositions described herein may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al., *Science,* 266: 2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 macrocyclic peptide blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269:1585-1588 (1995); Tamura et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle et al., *Nat. Med.*, 4:328-332 (1998)). DCs may also be transduced by genetic means to express these tumor antigens as well. DCs have also been fused directly to tumor cells for the purposes of immunization (Kugler et al., *Nat. Med.*, 6:332-336 (2000)). As a method of vaccination, DC immunization may be effectively further combined with a combined anti-PD-L1 macrocyclic peptide and CTLA-4 blockade to activate more potent anti-tumor responses.

A combined anti-PD-L1 macrocyclic peptide and CTLA-4 blockade may also be further combined with standard cancer treatments. For example, a combined macrocyclic peptide and CTLA-4 blockade may be effectively combined with chemotherapeutic regimes. In these instances, as is observed with the combination of a macrocyclic peptide and anti-CTLA-4 agent, it may be possible to reduce the dose of other chemotherapeutic reagent administered with the combination of the instant disclosure (Mokyr et al., *Cancer Res.*, 58:5301-5304 (1998)). An example of such a combination is a combination of a macrocyclic peptide and anti-CTLA-4 agent further in combination with decarbazine for the treatment of melanoma. Another example is a combination of a macrocyclic peptide and anti-CTLA-4 agent further in combination with interleukin-2 (IL-2) for the treatment of melanoma. The scientific rationale behind the combined use of PD-L1 macrocyclic peptide and CTLA-4 blockade with chemotherapy is that cell death, which is a consequence of the cytotoxic action of most chemotherapeutic compounds, should result in increased levels of tumor antigen in the antigen presentation pathway. Other combination therapies that may result in synergy with a combined anti-PD-L1 macrocyclic peptide and CTLA-4 blockade through cell death include radiation, surgery, or hormone deprivation. Each of these protocols creates a source of tumor antigen in the host. Angiogenesis inhibitors may also be combined with a combined PD-L1 and CTLA-4 blockade. Inhibition of angiogenesis leads to tumor cell death, which may also be a source of tumor antigen to be fed into host antigen presentation pathways.

A combination of PD-L1 and CTLA-4 blocking agents can also be used in combination with bispecific macrocyclic peptides that target Fc.alpha. or Fc.gamma. receptor-expressing effector cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of a combined PD-1 and CTLA-4 blockade. Alternatively, antigen may be delivered directly to DCs by the use of bispecific macrocyclic peptides which bind to tumor antigen and a dendritic cell specific cell surface marker.

In another example, a combination of a macrocyclic peptide and anti-CTLA-4 agent can be used in conjunction with anti-neoplastic macrocyclic agents, such as RITUXAN® (rituximab), HERCEPTIN® (trastuzumab), BEXXAR® (tositumomab), ZEVALIN® (ibritumomab), CAMPATH® (alemtuzumab), Lymphocide (eprtuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4 or PD-L1. In an exemplary embodiment, a treatment of a hyperproliferative disease (e.g., a cancer tumor) may include an anti-cancer antibody in combination with a macrocyclic peptide and anti-CTLA-4 agents, concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-.beta. (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). In another example, antibodies to each of these entities may be further combined with a macrocyclic peptide and anti-CTLA-4 combination to counteract the effects of immunosuppressive agents and favor anti-tumor immune responses by the host.

Other agents that may be used to activate host immune responsiveness can be further used in combination with a macrocyclic peptide of the present disclosure. These include molecules on the surface of dendritic cells that activate DC function and antigen presentation. Anti-CD40 macrocyclic peptides are able to substitute effectively for T cell helper activity (Ridge, J. et al., *Nature*, 393:474-478 (1998)) and can be used in conjunction with the macrocyclic peptides of the present disclosure, either alone or in combination with an anti-CTLA-4 combination (Ito, N. et al., *Immunobiology*, 201(5):527-540 (2000)). Activating macrocyclic peptides to T cell costimulatory molecules, such as OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A macrocyclic peptide of the present disclosure, either alone or in combination with CTLA-4 blockade, can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence a macrocyclic peptide of the present disclosure, either alone or in combination with an anti-CTLA-4 antagonist, may be expected to increase the frequency and activity of the adoptively transferred T cells.

In certain embodiments, the present disclosure provides a method for altering an adverse event associated with treatment of a hyperproliferative disease with an immunostimulatory agent, comprising administering a macrocyclic peptide of the present disclosure in combination with a subtherapeutic dose of anti-CTLA-4 antibody to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such treatment, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a macrocyclic peptide of the present disclosure, either alone or in combination with CTLA-4 blockade, can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid is budesonide. Budesonide is a locally-acting glucocorticosteroid, which is extensively metabolized, primarily by the liver, following oral administration. ENTOCORT® EC (Astra-Zeneca) is a pH- and time-dependent oral formulation of budesonide developed to optimize drug delivery to the ileum and throughout the colon. ENTOCORT® EC is approved in the U.S. for the treatment of mild to moderate Crohn's disease involving the ileum and/or ascending colon. The usual oral dosage of ENTOCORT® EC for the treatment of Crohn's disease is 6 to 9 mg/day. ENTOCORT® EC is released in the intestines before being absorbed and retained in the gut mucosa. Once it passes through the gut mucosa target tissue, ENTOCORT® EC is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT® EC can result in systemic glucocorticoid effects such as hypercorticism and adrenal suppression. See *Physicians' Desk Reference Supplement*, 58th Edition, 608-610 (2004).

In still further embodiments, a combination PD-L1 and CTLA-4 blockade (i.e., immunostimulatory therapeutic macrocyclic peptides anti-PD-L1 and anti-CTLA-4) in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

Dosage and Formulation

A suitable peptide of Formula I, or more specifically a macrocyclic peptide described herein, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in *The Pharmacological Basis of Therapeutics*, Chapter 1, p. 1 (1975); *Remington's Pharmaceutical Sciences*, 18th Edition, Mack Publishing Co., Easton, Pa. (1990)).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company (1995), a standard reference text in this field.

Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Peptide Synthesis

The macrocyclic peptides of the present disclosure can be produced by methods known in the art, such as they can be synthesized chemically, recombinantly in a cell free system, recombinantly within a cell or can be isolated from a biological source. Chemical synthesis of a macrocyclic peptide of the present disclosure can be carried out using a variety of art recognized methods, including stepwise solid phase synthesis, semi-synthesis through the conformationally-assisted religation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., *Fmoc Solid Phase Synthesis*, Oxford University Press, Oxford (2000); Barany, G. et al., *The Peptides: Analysis, Synthesis, Biology*, Vol. 2: "Special Methods in Peptide Synthesis, Part A", pp. 3-284, Gross, E. et al., eds., Academic Press, New York (1980); and in Stewart, J. M. et al., *Solid-Phase Peptide Synthesis*, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

Useful Fmoc amino acids derivatives are shown below.

Examples of Orthogonally Protected Amino Acids used in Solid Phase Synthesis

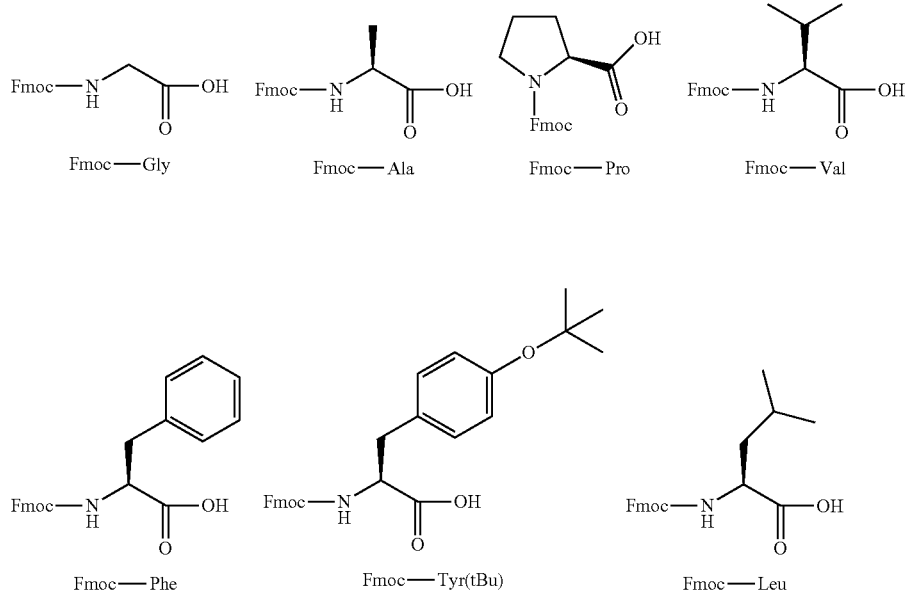

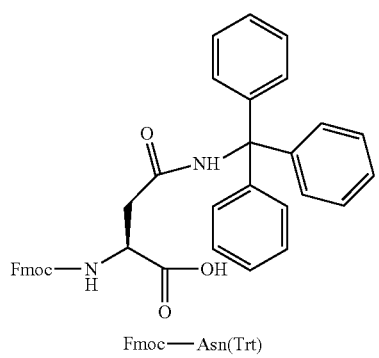
Fmoc—Asn(Trt)
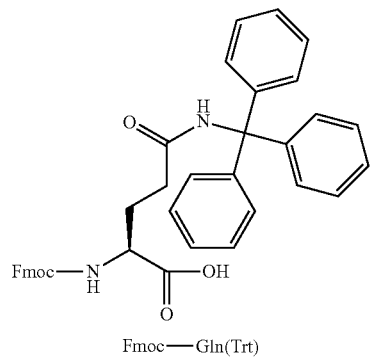
Fmoc—Gln(Trt)
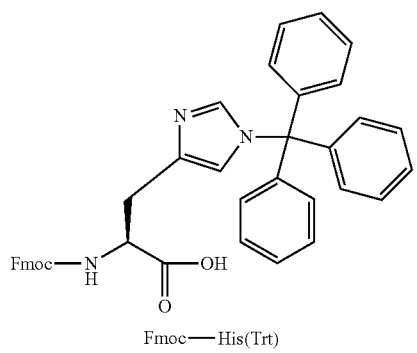
Fmoc—His(Trt)
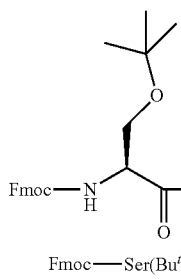
Fmoc—Ser(Bu$^t$)
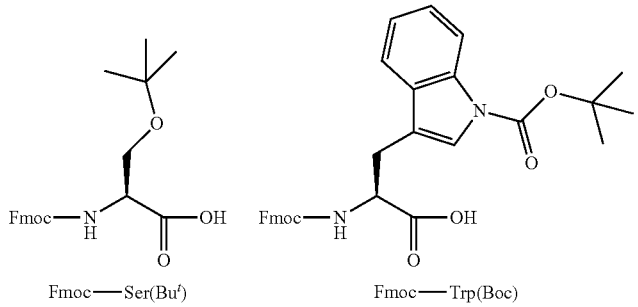
Fmoc—Trp(Boc)
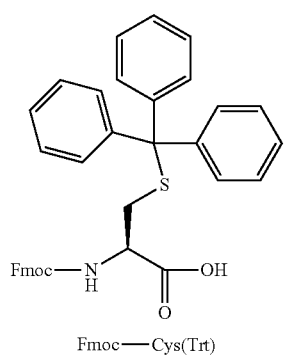
Fmoc—Cys(Trt)
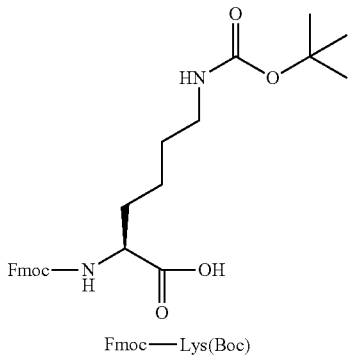
Fmoc—Lys(Boc)
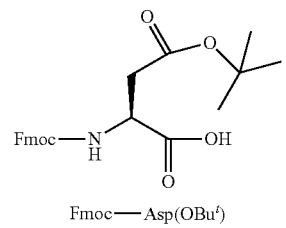
Fmoc—Asp(OBu$^t$)
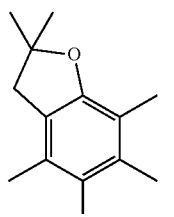
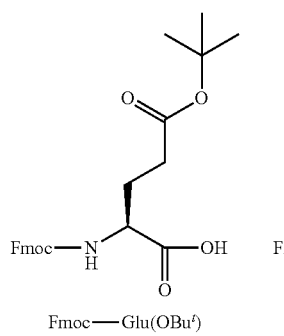
Fmoc—Glu(OBu$^t$)
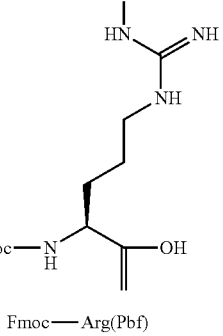
Fmoc—Arg(Pbf)

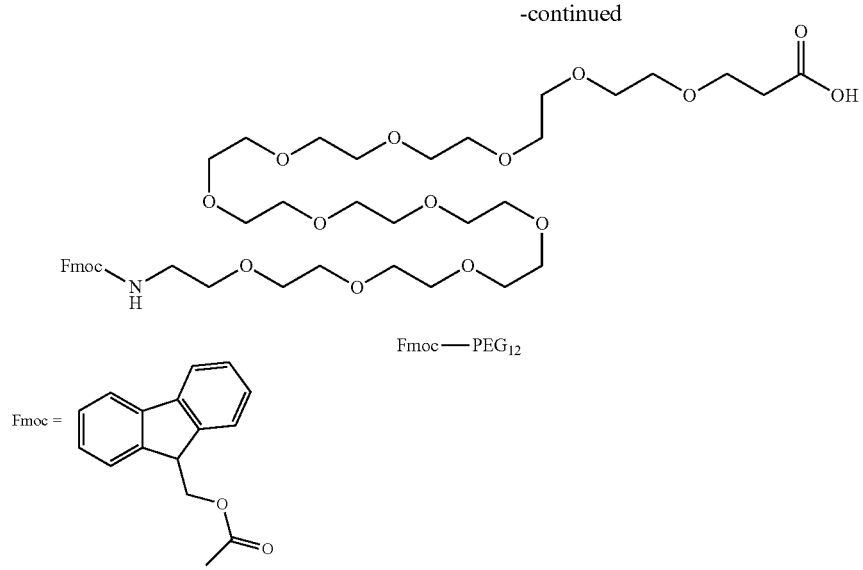

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

List of non-naturally occurring amino acids referred to herein is provided below.

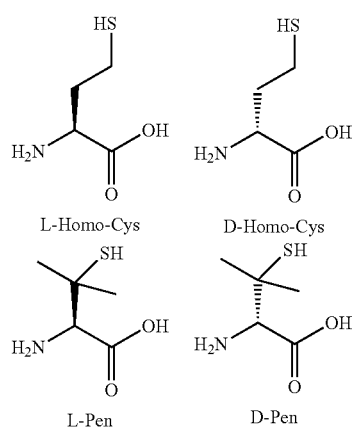

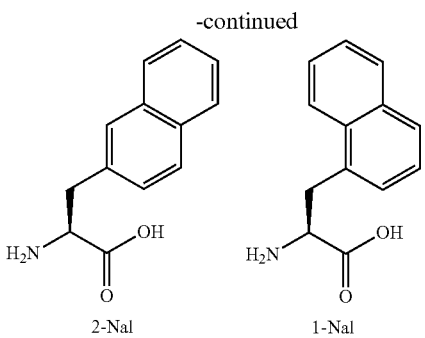

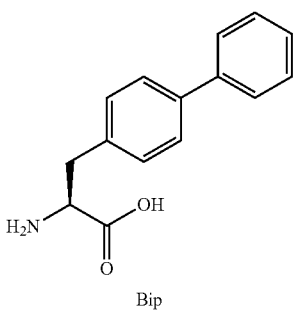

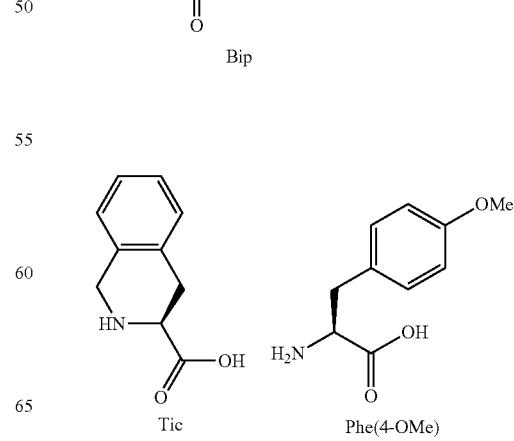

-continued
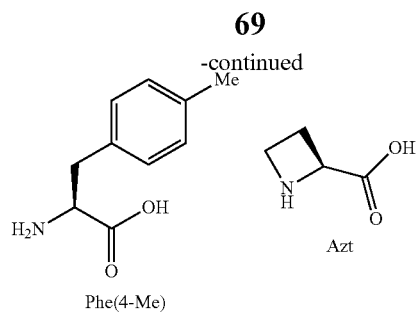
Phe(4-Me)  Azt
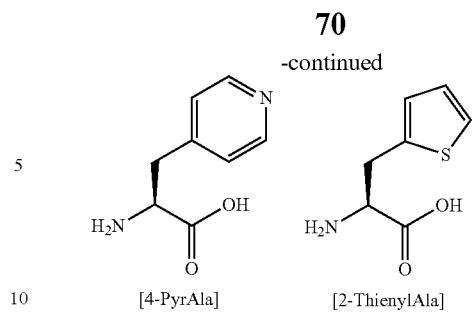
[4-PyrAla]  [2-ThienylAla]
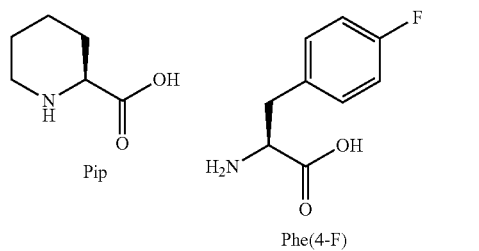
Pip  Phe(4-F)
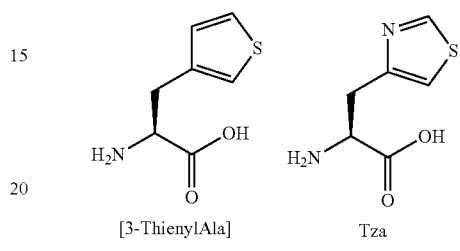
[3-ThienylAla]  Tza
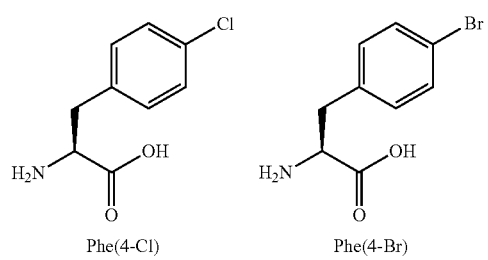
Phe(4-Cl)  Phe(4-Br)
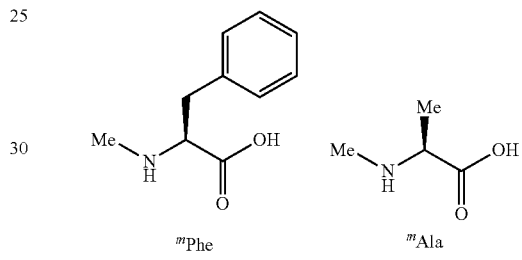
$^m$Phe  $^m$Ala
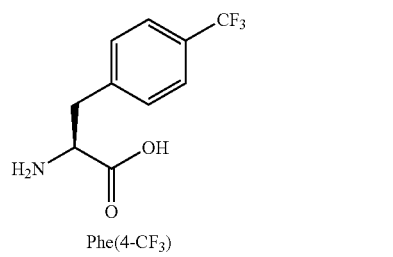
Phe(4-CF$_3$)
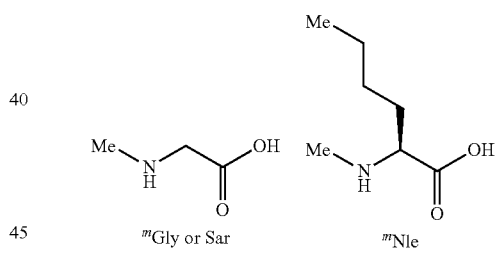
$^m$Gly or Sar  $^m$Nle
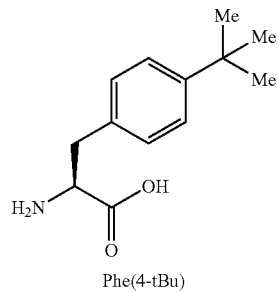
Phe(4-tBu)
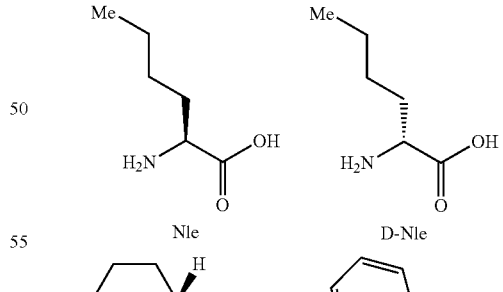
Nle  D-Nle
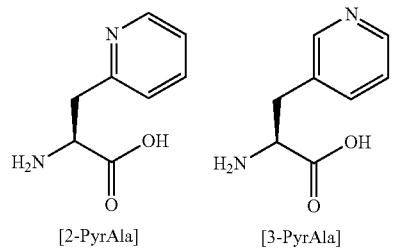
[2-PyrAla]  [3-PyrAla]
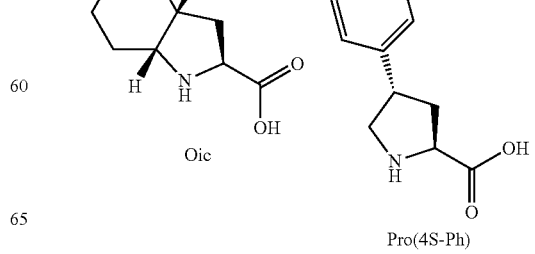
Oic  Pro(4S-Ph)

-continued

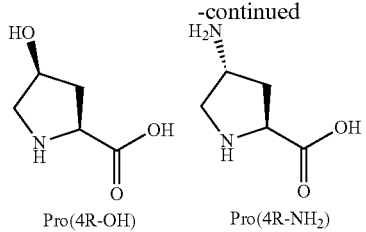

Pro(4R-OH)  Pro(4R-NH₂)

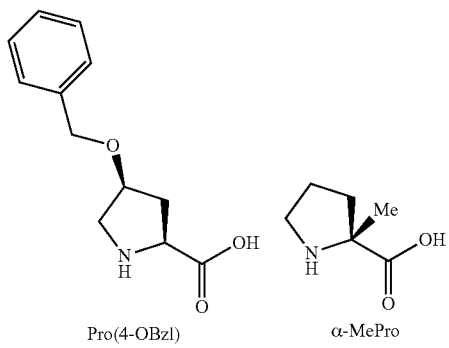

Pro(4-OBzl)  α-MePro

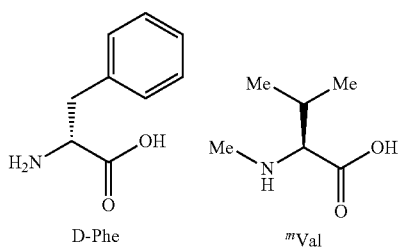

D-Phe  ᵐVal

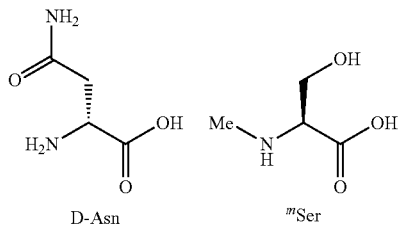

D-Asn  ᵐSer

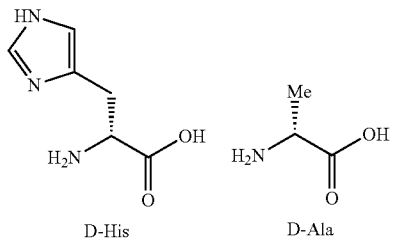

D-His  D-Ala

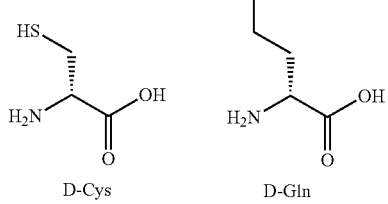

D-Cys  D-Gln

-continued

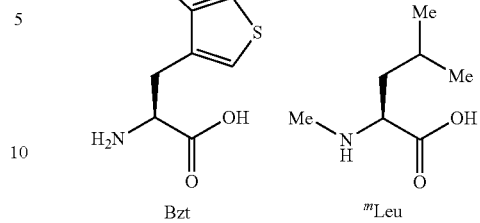

Bzt  ᵐLeu

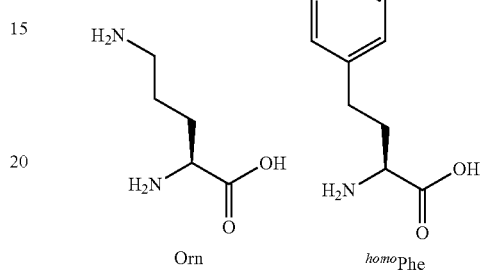

Orn  ʰᵒᵐᵒPhe

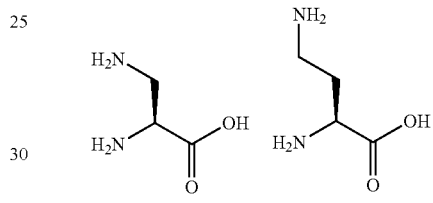

Dap  Dab

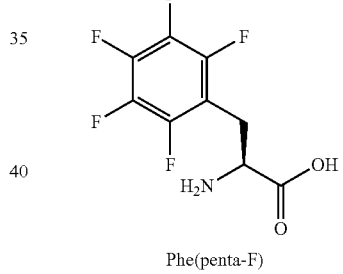

Phe(penta-F)

The following abbreviations are employed in the Examples and elsewhere herein:
Ph=phenyl
Bn=benzyl
i-Bu=iso-butyl
i-Pr=iso-propyl
Me=methyl
Et=ethyl
Pr=n-propyl
Bu=n-butyl
t-Bu=tert-butyl
Trt=trityl
TMS=trimethylsilyl
TIS=triisopropylsilane
Et₂O=diethyl ether
HOAc or AcOH=acetic acid
MeCN or AcCN=acetonitrile
DMF=N,N-dimethylformamide
EtOAc=ethyl acetate
THF=tetrahydrofuran
TFA=trifluoroacetic acid
TFE=α,α,α-trifluoroethanol Et₂NH=diethylamine
NMM=N-methylmorpholine
NMP=N-methylpyrrolidone
DCM=dichloromethane
TEA=triethylamine
min.=minute(s)
h or hr=hour(s)
L=liter
mL or ml=milliliter
µL=microliter
g=gram(s)
mg=milligram(s)
mol=mole(s)
mmol=millimole(s)
meq=milliequivalent
rt or RT=room temperature
sat or sat'd=saturated
aq.=aqueous
mp=melting point
BOP reagent=benzotriazol-1-yloxy-tris-dimethylaminophosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyluronium hexafluorophosphate
HATU=O-(7-Azabenzotriazol-1-yl)-1,1,3,3-tetramethyluronim hexafluorophosphate
HCTU=2-(6-Chloro-1-H-benzotriazol-1-yl)-1,1,3,3-tetramethyluronium hexafluorophosphate
T3P=2,4,6-tripropyl-1,3,5,2,4,6-trioxatriphosphorinane-2,4,6-trioxide
DMAP=4-(dimethylamino)pyridine
DIEA=diisopropylethylamine
Fmoc or FMOC=fluorenylmethyloxycarbonyl
Boc or BOC=tert-butyloxycarbonyl
HOBT or HOBT.H₂O=1-hydroxybenzotriazole hydrate
Cl-HOBt=6-Chloro-benzotriazole
HOAT=1-hydroxy-7-azabenzotriazole
HPLC=high performance liquid chromatography
LC/MS=high performance liquid chromatography/mass spectrometry
MS or Mass Spec=mass spectrometry
NMR=nuclear magnetic resonance
Sc or SC=sub-cutaneous
IP or ip=intra-peritoneal

EXAMPLES

Example 1

Solid Phase Peptide Synthesis and Cyclization of Peptides

The procedures described in this Example, either in whole or in part where noted, were used to synthesize the macrocyclic peptides shown in Tables 1, 2, 3, 4 and 5.

TABLE 1

FORMULA I PEPTIDE SERIES±

| Compound No. | A | 1 | 2 | 3 | 4 | 5 | 6 | 7 | 8 | 9 |
|---|---|---|---|---|---|---|---|---|---|---|
| 1 | ClAc | F | ᵐAla | N | P | H | L | Sar | W | S |
| 2 | ClAc | F | ᵐAla | N | P | H | H | S | W | R |
| 3 | ClAc | F | ᵐAla | N | P | H | R | S | W | R |
| 4 | ClAc | F | ᵐAla | N | P | L | R | S | W | R |
| 5 | ClAc | A | ᵐAla | N | P | H | L | Sar | W | S |
| 6 | ClAc | F | A | N | P | H | L | Sar | W | S |
| 7 | ClAc | F | Sar | N | P | H | L | Sar | W | S |
| 8 | ClAc | F | ᵐAla | A | P | H | L | Sar | W | S |
| 9 | ClAc | F | ᵐAla | N | A | H | L | Sar | W | S |
| 10 | ClAc | F | ᵐAla | N | P | A | L | Sar | W | S |
| 11 | ClAc | F | ᵐAla | N | P | H | A | Sar | W | S |
| 12 | ClAc | F | ᵐAla | N | P | H | L | G | W | S |
| 13 | ClAc | F | ᵐAla | N | P | H | L | ᵐAla | W | S |
| 14 | ClAc | F | ᵐAla | N | P | H | L | D-ᵐAla | W | S |
| 15 | ClAc | F | ᵐAla | N | P | H | L | Sar | A | S |
| 16 | ClAc | F | ᵐAla | N | P | H | L | Sar | W | A |
| 17 | ClAc | F | ᵐAla | N | P | H | L | Sar | W | S |
| 18 | ClAc | F | ᵐAla | N | P | H | L | Sar | W | S |
| 19 | ClAc | F | ᵐAla | N | P | H | L | Sar | W | S |
| 20 | ClAc | F | ᵐAla | N | P | H | L | Sar | W | S |
| 21 | ClAc | F | ᵐAla | N | P | H | L | Sar | W | S |
| 22 | ClAc | F | ᵐAla | N | P | H | L | Sar | W | S |
| 23 | ClAc | F | ᵐAla | N | P | H | L | Sar | W | S |
| 24 | ClAc | F | ᵐAla | N | P | H | L | Sar | W | S |
| 25 | ClAc | Trp | ᵐAla | N | P | H | L | Sar | W | S |
| 26 | ClAc | 2-Nal | ᵐAla | N | P | H | L | Sar | W | S |
| 27 | ClAc | 1-Nal | ᵐAla | N | P | H | L | Sar | W | S |
| 28 | ClAc | Bip | ᵐAla | N | P | H | L | Sar | W | S |
| 29 | ClAc | Tic | ᵐAla | N | P | H | L | Sar | W | S |
| 30 | ClAc | Tyr | ᵐAla | N | P | H | L | Sar | W | S |
| 31 | ClAc | Phe(4-OMe) | ᵐAla | N | P | H | L | Sar | W | S |
| 32 | ClAc | Phe(4-F) | ᵐAla | N | P | H | L | Sar | W | S |
| 33 | ClAc | Phe(4-Cl) | ᵐAla | N | P | H | L | Sar | W | S |
| 34 | ClAc | Phe(4-Br) | ᵐAla | N | P | H | L | Sar | W | S |
| 35 | ClAc | Phe(4-CF₃) | ᵐAla | N | P | H | L | Sar | W | S |
| 36 | ClAc | Phe(4-Me) | ᵐAla | N | P | H | L | Sar | W | S |
| 37 | ClAc | Phe(4-tBu) | ᵐAla | N | P | H | L | Sar | W | S |
| 38 | ClAc | 3-PyrAla | ᵐAla | N | P | H | L | Sar | W | S |

TABLE 1-continued

FORMULA I PEPTIDE SERIES±

| | | | | | | | | | | |
|---|---|---|---|---|---|---|---|---|---|---|
| 39 | ClAc | 4-PyrAla | ᵐAla | N | P | H | L | Sar | W | S |
| 40 | ClAc | 3-ThienylAla | ᵐAla | N | P | H | L | Sar | W | S |
| 41 | ClAc | F | ᵐVal | N | P | H | L | Sar | W | S |
| 42 | ClAc | F | ᵐAla | D-Asn | P | H | L | Sar | W | S |
| 43 | ClAc | F | ᵐAla | Gly | P | H | L | Sar | W | S |
| 44 | ClAc | F | ᵐAla | N | Pip | H | L | Sar | W | S |
| 45 | ClAc | F | ᵐAla | N | Oic | H | L | Sar | W | S |
| 46 | ClAc | F | ᵐAla | N | Pro(4-Ph) | H | L | Sar | W | S |
| 47 | ClAc | F | ᵐAla | N | Pro(4-OH) | H | L | Sar | W | S |
| 48 | ClAc | F | ᵐAla | N | Pro(4-NH$_2$) | H | L | Sar | W | S |
| 49 | ClAc | F | ᵐAla | N | α-Me-Pro | H | L | Sar | W | S |
| 50 | ClAc | F | ᵐAla | N | Azt | H | L | Sar | W | S |
| 51 | ClAc | F | ᵐAla | N | P | H | Asp | Sar | W | S |
| 52 | ClAc | F | ᵐAla | N | P | H | L | Dab | W | S |
| 53 | ClAc | F | ᵐAla | N | P | H | L | His | W | S |
| 54 | ClAc | F | ᵐAla | N | P | H | L | Arg | W | S |
| 55 | ClAc | F | ᵐAla | N | P | H | L | Pro | W | S |
| 56 | ClAc | F | ᵐAla | N | P | H | L | ᵐSer | W | S |
| 57 | ClAc | F | ᵐAla | N | P | H | L | Ser | W | S |
| 58 | ClAc | F | ᵐAla | N | P | H | L | Sar | W | ᴰAsn |
| 59 | ClAc | F | ᵐAla | N | P | H | L | Sar | W | ᴰGln |
| 60 | ClAc | F | ᵐAla | N | P | H | L | Sar | W | Ala |
| 61 | ClAc | F | ᵐAla | N | P | H | L | Sar | W | S |
| 62 | ClAc | F | ᵐAla | N | P | H | L | Sar | W | S |
| 63 | ClAc | F | ᵐAla | N | P | H | L | Sar | W | S |
| 64 | ClAc | F | ᵐAla | N | P | H | L | Sar | W | S |
| 65 | ClAc | F | ᵐAla | N | P | H | L | Sar | W | S |
| 66 | ClAc | F | ᵐAla | N | P | H | L | Sar | W | S |
| 67 | ClAc | F | ᵐAla | N | P | H | L | Sar | W | S |
| 68 | ClAc | F | ᵐAla | N | P | H | L | Sar | W | S |
| 69 | ClAc | F | ᵐAla | N | P | H | L | Sar | W | S |
| 70 | ClAc | F | ᵐAla | N | P | H | L | Sar | W | S |

| Compound | | | Peptide Sequence | | | | | | MS | |
|---|---|---|---|---|---|---|---|---|---|---|
| No. | A | 10 | 11 | 12 | 13 | 14 | 15 | | Predicted | Observed |
| 1 | ClAc | W | ᵐNle | ᵐNle | R | C | G | NH$_2$ | 1852.19 | 926.7 (M + 2) |
| 2 | ClAc | W | ᵐNle | ᵐNle | L | C | G | NH$_2$ | 1918.25 | 959.9 (M + 2) |
| 3 | ClAc | W | ᵐNle | ᵐNle | L | C | G | NH$_2$ | 1937.3 | 970.0 (M + 2) |
| 4 | ClAc | W | ᵐNle | ᵐNle | L | C | G | NH$_2$ | 1894.27 | 948.3 (M + 2) |
| 5 | ClAc | W | ᵐNle | ᵐNle | R | C | G | NH$_2$ | 1776.09 | 888.7 (M + 2) |
| 6 | ClAc | W | ᵐNle | ᵐNle | R | C | G | NH$_2$ | 1838.16 | 920.3 (M + 2) |
| 7 | ClAc | W | ᵐNle | ᵐNle | R | C | G | NH$_2$ | 1838.16 | 920.2 (M + 2) |
| 8 | ClAc | W | ᵐNle | ᵐNle | R | C | G | NH$_2$ | 1809.17 | 906.5 (M + 2) |
| 9 | ClAc | W | ᵐNle | ᵐNle | R | C | G | NH$_2$ | 1826.15 | 914.3 (M + 2) |
| 10 | ClAc | W | ᵐNle | ᵐNle | R | C | G | NH$_2$ | 1786.13 | 894.4 (M + 2) |
| 11 | ClAc | W | ᵐNle | ᵐNle | R | C | G | NH$_2$ | 1810.11 | 905.8 (M + 2) |
| 12 | ClAc | W | ᵐNle | ᵐNle | R | C | G | NH$_2$ | 1838.16 | 919.8 (M + 2) |
| 13 | ClAc | W | ᵐNle | ᵐNle | R | C | G | NH$_2$ | 1866.22 | 1866.9 |
| 14 | ClAc | W | ᵐNle | ᵐNle | R | C | G | NH$_2$ | 1866.22 | 933.9 (M + 2) |
| 15 | ClAc | W | ᵐNle | ᵐNle | R | C | G | NH$_2$ | 1737.06 | 869.6 (M + 2) |
| 16 | ClAc | W | ᵐNle | ᵐNle | R | C | G | NH$_2$ | 1836.19 | 918.8 (M + 2) |
| 17 | ClAc | A | ᵐNle | ᵐNle | R | C | G | NH$_2$ | 1737.06 | 869.3 (M + 2) |
| 18 | ClAc | W | Nle | ᵐNle | R | C | G | NH$_2$ | 1838.16 | 919.8 (M + 2) |
| 19 | ClAc | W | ᵐAla | ᵐNle | R | C | G | NH$_2$ | 1810.11 | 906.3 (M + 2) |
| 20 | ClAc | W | ᵐNle | Nle | R | C | G | NH$_2$ | 1838.16 | 919.8 (M + 2) |
| 21 | ClAc | W | ᵐNle | ᵐAla | R | C | G | NH$_2$ | 1810.11 | 905.8 (M + 2) |
| 22 | ClAc | W | ᵐNle | ᵐNle | A | C | G | NH$_2$ | 1767.08 | 884.5 (M + 2) |
| 23 | ClAc | W | ᵐNle | ᵐNle | R | ᴰCys | G | NH$_2$ | 1852.19 | 926.8 (M + 2) |
| 24 | ClAc | W | ᵐNle | ᵐNle | R | C | NH$_2$ | | 1795.14 | 898.2 (M + 2) |
| 25 | ClAc | W | ᵐNle | ᵐNle | R | C | G | NH$_2$ | 1891.23 | 946.4 (M + 2) |
| 26 | ClAc | W | ᵐNle | ᵐNle | R | C | G | NH$_2$ | 1902.25 | 951.7 (M + 2) |
| 27 | ClAc | W | ᵐNle | ᵐNle | R | C | G | NH$_2$ | 1902.25 | 1903.7 |
| 28 | ClAc | W | ᵐNle | ᵐNle | R | C | G | NH$_2$ | 1928.29 | 964.9 (M + 2) |
| 29 | ClAc | W | ᵐNle | ᵐNle | R | C | G | NH$_2$ | 1864.20 | 933.2 (M + 2) |
| 30 | ClAc | W | ᵐNle | ᵐNle | R | C | G | NH$_2$ | 1868.19 | 934.8 (M + 2) |
| 31 | ClAc | W | ᵐNle | ᵐNle | R | C | G | NH$_2$ | 1882.22 | 942.0 (M + 2) |
| 32 | ClAc | W | ᵐNle | ᵐNle | R | C | G | NH$_2$ | 1870.18 | 936.6 (M + 2) |
| 33 | ClAc | W | ᵐNle | ᵐNle | R | C | G | NH$_2$ | 1886.64 | 943.6 (M + 2) |
| 34 | ClAc | W | ᵐNle | ᵐNle | R | C | G | NH$_2$ | 1931.09 | 966.3 (M + 2) |
| 35 | ClAc | W | ᵐNle | ᵐNle | R | C | G | NH$_2$ | 1920.19 | 960.9 (M + 2) |
| 36 | ClAc | W | ᵐNle | ᵐNle | R | C | G | NH$_2$ | 1866.22 | 933.9 (M + 2) |
| 37 | ClAc | W | ᵐNle | ᵐNle | R | C | G | NH$_2$ | 1908.30 | 954.6 (M + 2) |
| 38 | ClAc | W | ᵐNle | ᵐNle | R | C | G | NH$_2$ | 1853.18 | 928.0 (M + 2) |
| 39 | ClAc | W | ᵐNle | ᵐNle | R | C | G | NH$_2$ | 1853.18 | 927.6 (M + 2) |
| 40 | ClAc | W | ᵐNle | ᵐNle | R | C | G | NH$_2$ | 1858.22 | 929.9 (M + 2) |
| 41 | ClAc | W | ᵐNle | ᵐNle | R | C | G | NH$_2$ | 1880.2 | 941.2 (M + 2) |

TABLE 1-continued

FORMULA I PEPTIDE SERIES[±]

| | | | | | | | | | | |
|---|---|---|---|---|---|---|---|---|---|---|
| 42 | ClAc | W | mNle | mNle | R | C | G | NH$_2$ | 1852.16 | 926.9 (M + 2) |
| 43 | ClAc | W | mNle | mNle | R | C | G | NH$_2$ | 1795.1 | 898.6 (M + 2) |
| 44 | ClAc | W | mNle | mNle | R | C | G | NH$_2$ | 1866.22 | 934.7 (M + 2) |
| 45 | ClAc | W | mNle | mNle | R | C | G | NH$_2$ | 1906.28 | 953.6 (M + 2) |
| 46 | ClAc | W | mNle | mNle | R | C | G | NH$_2$ | 1928.29 | 965.0 (M + 2) |
| 47 | ClAc | W | mNle | mNle | R | C | G | NH$_2$ | 1868.19 | 935.0 (M + 2) |
| 48 | ClAc | W | mNle | mNle | R | C | G | NH$_2$ | 1867.21 | 934.4 (M + 2) |
| 49 | ClAc | W | mNle | mNle | R | C | G | NH$_2$ | 1866.22 | 934.0 (M + 2) |
| 50 | ClAc | W | mNle | mNle | R | C | G | NH$_2$ | 1838.16 | 919.9 (M + 2) |
| 51 | ClAc | W | mNle | mNle | R | C | G | NH$_2$ | 1854.1 | 928.0 (M + 2) |
| 52 | ClAc | W | mNle | mNle | R | C | G | NH$_2$ | 1881.23 | 941.5 (M + 2) |
| 53 | ClAc | W | mNle | mNle | R | C | G | NH$_2$ | 1918.25 | 959.8 (M + 2) |
| 54 | ClAc | W | mNle | mNle | R | C | G | NH$_2$ | 1937.30 | 969.7 (M + 2) |
| 55 | ClAc | W | mNle | mNle | R | C | G | NH$_2$ | 1878.23 | 940.2 (M + 2) |
| 56 | ClAc | W | mNle | mNle | R | C | G | NH$_2$ | 1882.19 | 941.9 (M + 2) |
| 57 | ClAc | W | mNle | mNle | R | C | G | NH$_2$ | 1868.17 | 934.8 (M + 2) |
| 58 | ClAc | W | mNle | mNle | R | C | G | NH$_2$ | 1879.22 | 940.5 (M + 2) |
| 59 | ClAc | W | mNle | mNle | R | C | G | NH$_2$ | 1894.2 | 947.6 (M + 2) |
| 60 | ClAc | W | mNle | mNle | Ala | C | G | NH$_2$ | 1751.08 | 876.3 (M + 2) |
| 61 | ClAc | Met | mNle | mNle | R | C | G | NH$_2$ | 1797.18 | 899.6 (M + 2) |
| 62 | ClAc | Ile | mNle | mNle | R | C | G | NH$_2$ | 1779.11 | 890.3 (M + 2) |
| 63 | ClAc | Leu | mNle | mNle | R | C | G | NH$_2$ | 1779.14 | 890.7 (M + 2) |
| 64 | ClAc | Bzt | mNle | mNle | R | C | G | NH$_2$ | 1869.21 | 935.7 (M + 2) |
| 65 | ClAc | W | mLeu | mNle | R | C | G | NH$_2$ | 1852.19 | 926.9 (M + 2) |
| 66 | ClAc | W | mSer | mNle | R | C | G | NH$_2$ | 1826.11 | 914.3 (M + 2) |
| 67 | ClAc | W | mPhe | mNle | R | C | G | NH$_2$ | 1886.21 | 943.9 (M + 2) |
| 68 | ClAc | W | Ser | mNle | R | C | G | NH$_2$ | 1812.08 | 906.8 (M + 2) |
| 69 | ClAc | W | Phe | mNle | R | C | G | NH$_2$ | 1872.18 | 936.6 (M + 2) |
| 70 | ClAc | W | DNle | mNle | R | C | G | NH$_2$ | 1838.1 | 920.1 (M + 2) |

[±]Compound Nos. 1 to 70 are macrocyclic peptides cyclized via the moiety listed at the A position with a downstream cysteine.

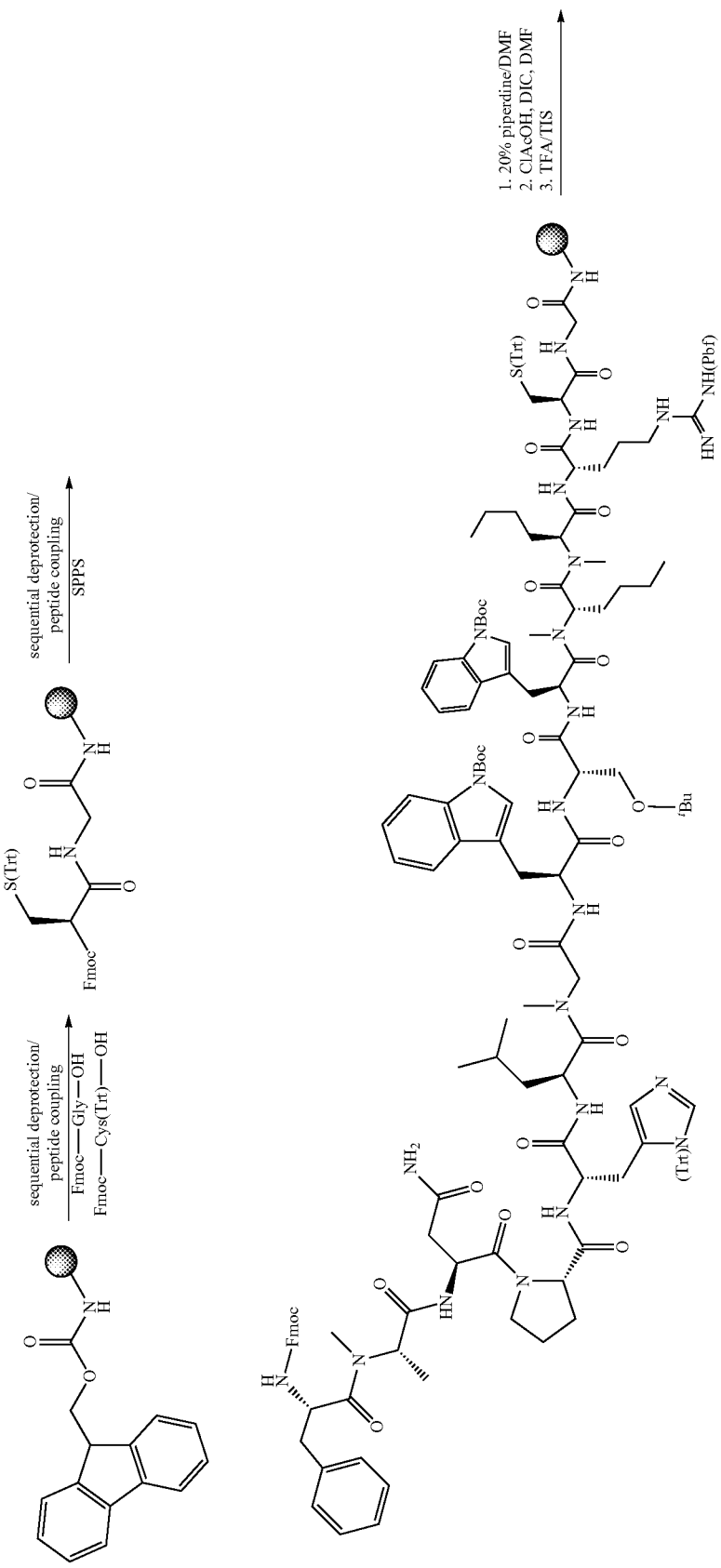
SCHEME 1-COMMON SYNTHETIC METHOD USED FOR THIOETHER-CYCLIZED PEPTIDES (EXAMPLES 2 THRU 88)

-continued
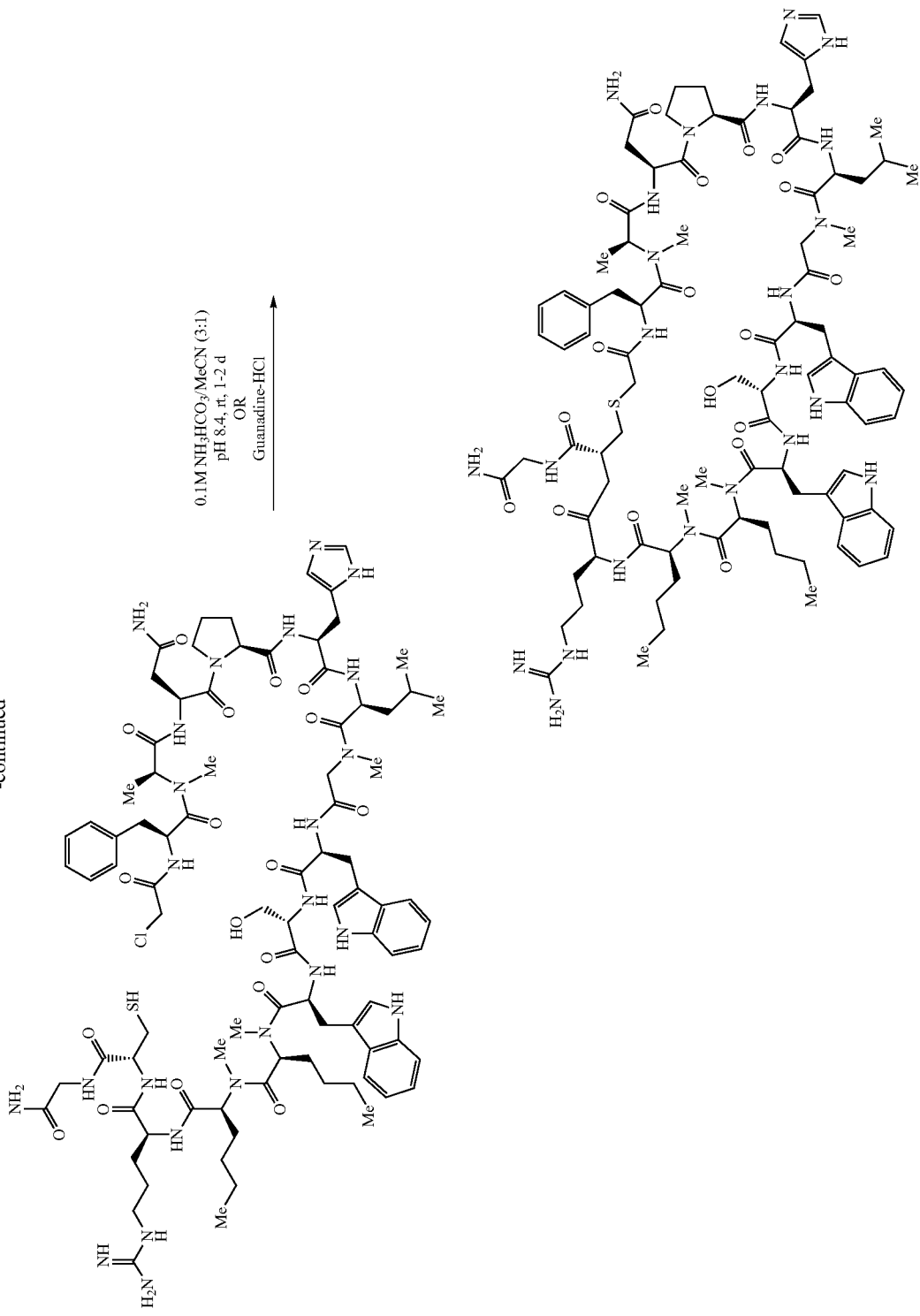

General protocol for solid-phase peptide synthesis and macrocyclization. On a Symphony Peptide Synthesizer (Protein Technology Inc. Tucson, Ariz.), Prelude Peptide Synthesizer (Protein Technology Inc. Tucson, Ariz.), or Liberty (CEM Matthews, N.C.), Sieber Amide resin (0.71 mmol/g, 0.100 mmol, 141 mg) was swelled with DMF (7 mL×4 min) and mixed with a gentle stream of $N_2$ every 30 seconds. The solvent was drained and the following method was used to couple the first amino acid: the Fmoc group was removed from the resin-supported building block by washing the resin twice with a solution of 20% piperidine in DMF (5 mL and 2.5 minutes per wash) and mixing with a gentle stream of $N_2$ every 30 seconds. The resin was washed three times with DMF (5-8 mL and 1.5 min per wash). 2-((((9H-Fluoren-9-yl)methoxy)carbonyl)amino)acetic acid (0.2 M solution in DMF, 0.5 mmol) was then added, followed by coupling activator (i.e., HATU (Chem-Impex Int'l, 0.4M solution in DMF, 1.25 mL, 0.5 mmol)) and base (i.e., N-methyl morpholine (Aldrich, 0.8 M in DMF, 1.25 mL, 1 mmol)). The reaction mixture was agitated by a gentle stream of nitrogen for 1 h. The reagents were drained from the reaction vessel, and the resin was washed three times with DMF (5 mL×1.5 min). It should be noted that the typical reagents for the Liberty CEM were the following: HCTU (0.45 M in DMF) as the coupling activator, DIEA (2 M in NMP) as the base, and 5% piperazine in DMF with 0.1 M HOBt as the deprotect solution.

The resulting resin-supported Fmoc-protected dipeptide was then sequentially deprotected and coupled with third amino acid and so forth in an iterative fashion to give the desired resin-supported product.

LCMS analysis was performed on a peptide aliquot, which was cleaved from the resin (analytical amount was treated with a TFA/TIS (96:4) solution (0.2 mL) at room temperature. Following confirmation of the desired linear sequence, the Fmoc group was removed from the N-terminus upon washing the resin twice with a solution of 20% piperidine in DMF (5 mL and 2.5 minutes per wash) and vortexing the slurry. The resin was washed with DMF (2×5 mL). To the peptide-resin was added in succession 2-chloroacetic acid (0.6 mmol, 57 mg), DMF (5.26 mL), and DIC (0.6 mmol, 93 µL). The new slurry was vortexed for 1-2 days as which point the peptide-resin was washed with DMF (1×5 mL×1 min) and DCM (3×DCM×1 min).

The peptide was deprotected and cleaved from the resin upon treatment with a TFA/TIS (96:4) solution (10 mL) for 1 h. The resin was removed by filtration, washed with cleavage cocktail (2×1 mL), the combined filtrates were added to $Et_2O$ (10-15 mL) and the solution was chilled at 0° C. in order to effect the peptide to precipitate out of solution. The slurry is centrifuged to pellet the solids and the supernatant was decanted. Fresh $Et_2O$ (25 mL) was added and the process was repeated three times to wash the solids. To the wet solids was added a solution of 0.1 M $NH_4HCO_3$/Acetonitrile (from 1/1 to 3/1 (v/v), pH=8.6) or 6 M guanidine HCl in 100 mM $NaH_2PO_4$ (pH=8.4). The solution was stirred for 1-2 days and monitored by LCMS. The reaction solution was purified by preparative HPLC to obtain the desired product.

GENERAL ANALYTICAL PROTOCOLS AND SYNTHESIS METHODS[±]

[±]The following analysis protocols and synthetic methods were used in Examples 1 through 4000.
Analytical Data:
Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.
Analysis LCMS Condition A:
Column: BEH C18, 2.1×50 mm, 1.7-µm particles; Mobile Phase A: water with 0.05% TFA; Mobile Phase B:Acetonitrile with 0.05% TFA; Temperature: 50° C.; Gradient: 2% B to 98% B over 2 minutes, then a 0.5 minutes hold at 98% B; Flow: 0.8 mL/min;
Detection: UV at 220 nm.
Analysis LCMS Condition B:
Column: BEH C18, 2.1×50 mm, 1.7-µm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.
Analysis LCMS Condition C:
Column: BEH C18, 2.1×50 mm, 1.7-µm particles; Mobile Phase A: water with 0.2% Formic Acid and 0.01% TFA; Mobile Phase B: Acetonitrile with 0.2% Formic acid an 0.01% TFA; Temperature: 50° C.; Gradient: 2% B to 80% B over 2 minutes, 80% B to 98% B over 0.1 minute then a 0.5 minutes hold at 98% B; Flow: 0.8 mL/min; Detection: UV at 220 nm.
Analysis LCMS Condition D:
Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.
Analysis LCMS Condition E:
Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; temperature: 50° C.; Gradient: 0-100% B over 3 minutes, then a 0.75-minute hold at 100% B; Flow: 1.11 mL/min; Detection: UV at 220 nm.
Analysis LCMS Condition F:
Column: Waters Xbridge C18, 2.1×50 mm; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 minutes, then a 1-minute hold at 100% B; Flow: 4 mL/min; Detection: UV at 220 nm.
Analysis LCMS Condition G:
Finnigan LTQ Mass Spectrometer; column: PHENOMENEX® Jupiter C4, 1×50 mm; Mobile Phase A: 1% formic acid in water; Mobile Phase B: 0.1% formic acid in acetonitrile; Temperature: 30° C.; Gradient: 1% B, 1 min. hold; 1-95% B over 3 min., then a 3-min. hold at 95% B; Flow: 0.15 mL/min.
Analysis HPLC Condition A:
Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 35% B to 80% B over 25 min.; Flow: 1 mL/min; Detection: UV at 217 nm.

Analysis HPLC Condition B:
  Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 75% B over 25 min.; Flow: 1 mL/min; Detection: UV at 217 nm.
Analysis HPLC Condition C:
  Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 20% B to 70% B over 25 min.; Flow: 1 mL/min; Detection: UV at 217 nm.
Analysis HPLC Condition D:
  Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 15% B to 65% B over 25 min.; Flow: 1 mL/min; Detection: UV at 217 nm.
Analysis HPLC Condition E:
  Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 60% B over 20 min.; Flow: 1.25 mL/min; Detection: UV at 217 nm.
Analysis HPLC Condition F:
  Column: YMC Pack ODS-AQ 3 um 150×4.6 mm Mobile Phase A: water with 0.1% TFA; Mobile Phase B: Acetonitrile with 0.1% TFA; Temperature: 60° C.; Gradient: from 25% B to 65% B over 20 min.; Flow: 1.25 mL/min; Detection: UV at 217 nm.
Analysis HPLC Condition G:
  Column: Sunfire C18 3.5 um, 3.0×150 mm; Mobile Phase A: 5:95 acetonitrile:water with 0.05% trifluoroacetic acid; Mobile Phase B: 95:5 acetonitrile:water with 0.05% trifluoroacetic acid; temperature: 50° C.; Gradient: 10-100% B over 12 minutes, then a 3-minute hold at 100% B; Flow: 1 mL/min; Detection: UV at 220 nm.
Analysis HPLC Condition H:
  Column: Xbridge Phenyl 3.5×150 um, Mobile Phase A: 5:95 acetonitrile:water with 0.05% trifluoroacetic acid; Mobile Phase B: 95:5 acetonitrile:water with 0.05% trifluoroacetic acid; temperature: 50° C.; Gradient: 10-100% B over 12 minutes, then a 3-minute hold at 100% B; Flow: 1 mL/min; Detection: UV at 220 nm.
Analysis HPLC Condition I:
  Column: PHENOMENEX® Luna 5 u C18(2) 150×4.6 mm; mobile Phase A: water with 0.1% trifluoroacetic acid, mobile Phase B: acetonitrile with 0.1% trifluoroacetic acid, Gradient 5-100% B over 20 min, then a 5 minute hold at 100% B; Flow 1 mL/min, Detection: UV at 220
Analysis HPLC Condition J:
  Column: PHENOMENEX® Luna 5 u C18(2) 150×4.6 mm; mobile Phase A: water with 0.1% trifluoroacetic acid, mobile Phase B: acetonitrile with 0.1% trifluoroacetic acid, Gradient 10-100% B over 20 min, then a 5 minute hold at 100% B; Flow 1 mL/min, Detection: UV at 220
General Procedures:
Prelude Method A:
  All manipulations were performed under automation on a Prelude peptide synthesizer (Protein Technologies). All procedures unless noted were performed in a 10 or 45 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. DMF=dimethylformamide; DIC=N,N'-diisopropylcarbodiimide; HOAt=1-hydroxy 7-azabenzotriazole; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.
  Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH
  The procedures of "Prelude Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of Fmoc-N-methyl amino acids and coupling to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.
Resin-Swelling Procedure:
  To a 40 mL polypropylene solid-phase reaction vessel was added Merrifield:Sieber resin (140 mg, 0.100 mmol). The resin was washed three times as follows: to the reaction vessel was added DMF (5.0 mL) and DCM (5.0 mL), upon which the mixture was periodically agitated with N2 bubbling from the bottom of the reaction vessel for 10 minutes before the solvent was drained.
Single-Coupling Procedure:
  To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added a solution of the amino acid and HOAt (0.2M in DMF, 5.0 mL, 10 eq), then DIC (0.2M in DMF, 5.0 mL, 10 eq). The mixture was periodically agitated for 60 min, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride: DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added a solution of the amino acid and HOAt (0.2M in DMF, 5.0 mL, 5 eq), then DIC (0.2M in DMF, 5.0 mL, 5 eq). The mixture was periodically agitated for 300 min, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA: DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained. The resin was washed successively three times as follows: for each wash, DMF (4.0 mL) was added to top of the vessel and the resulting mixture was periodically agitated for 90 seconds before the solution was drained. The resin was washed successively four times as follows: for each wash, DCM (4.0 mL) was added to top of the vessel and the resulting mixture was periodically agitated for 90 seconds before the solution was drained.

Prelude Method B:

All manipulations were performed under automation on a Prelude peptide synthesizer (Protein Technologies). All procedures were performed in a 10 or 45 mL polypropylene tube fitted with a bottom frit. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. DMF=dimethylformamide; HCTU=2-(6-Chloro-1-H-benzotriazol-1-yl)-1,1,3,3-tetramethyluronium; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method B" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 30 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 15 minutes, then the reaction solution was drained through the frit. The resin was washed successively 3 times with DMF (4.0 mL) through the top of the vessel and the resulting mixture was periodically agitated for 60 seconds before the solution was drained through the frit. To the reaction vessel was added the amino acid (0.2M in DMF, 5.0 mL, 10 eq), then HCTU (0.2M in DMF, 5.0 mL, 10 eq), and finally DIPEA (0.8M in DMF, 2.5 mL, 20 eq). The mixture was periodically agitated for 15 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 10 eq), then HCTU (0.2M in DMF, 2.5 mL, 10 eq), and finally NMM (0.8M in DMF, 1.5 mL, 12 eq). The mixture was periodically agitated for 12 hrs, then the reaction solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure A:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Chloroacetic Acid Coupling Procedure B:

To the reaction vessel containing the resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Prelude Method C:

All manipulations were performed under automation on a Prelude peptide synthesizer (Protein Technologies). All procedures unless noted were performed in a 10 or 45 mL polypropylene tube fitted with a bottom frit. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method C" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. The Final wash of the Resin used the "Final Wash procedure" described below Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with $N_2$ bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU (0.2M in DMF, 5.0 mL, 10 eq), and finally DIPEA (0.8M in DMF, 2.5 mL, 20 eq). The mixture was periodically agitated for 60 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally DIPEA (0.8M in DMF, 1.5 mL, 12 eq). The mixture was periodically agitated for 300 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, 5 eq), then HATU (0.2M in DMF, 2.5 mL, 5 eq), and finally DIPEA (0.8M in DMF, 1.5 mL, 12 eq). The mixture was periodically agitated for 300 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Custom Amino Acids-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 0.5 to 2.5 mL, 1 to 5 eq), then HATU (0.2M in DMF, 0.5 to 2.5 mL, 1 to 5 eq), and finally DIPEA (0.8M in DMF, 0.5 to 1.5 mL, 4 to 12 eq). The mixture was periodically agitated for 60 minutes to 600 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Final Wash Procedure:

The resin was washed successively two times as follows: for each wash, DMF (4.0 mL) was added through the top of the vessel and the resulting mixture was periodically agitated for 90 seconds before the solution was drained through the frit. The resin was washed successively four times as follows: for each wash, DCM (4.0 mL) was added through the top of the vessel and the resulting mixture was periodically agitated for 90 seconds before the solution was drained through the frit. The resulting resin was used directly in the next step.

Chloroacetic Acid Coupling Procedure:

Note Manuel step. To the reaction vessel containing the resin from the previous step was added piperidine:DMF (20:80 v/v, 5.0 mL). The mixture was shaken at Room temperature for 5 minutes and then the solution was drained through the frit. The resin was washed successively five times as follows: for each wash, DMF (4.0 mL) was added through the top of the vessel and the resulting mixture was agitated before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was shaken at room temperature for 12 to 18 hours, then the solution was drained through the frit. The resin was washed successively three times as follows: for each wash, DMF (4.0 mL) was added to top of the vessel and the resulting mixture was agitated for 90 seconds before the solution was drained through the frit. The resin was washed successively four times as follows: for each wash, $CH_2Cl_2$ (4.0 mL) was added to top of the vessel and the resulting mixture was periodically agitated for 90 seconds before the solution was drained through the frit.

Prelude Method D:

All manipulations were performed under automation on a Prelude peptide synthesizer (Protein Technologies). All procedures unless noted were performed in a 10 or 45 mL polypropylene tube fitted with a bottom frit. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method D" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. The Final wash of the Resin used the "Final Wash procedure" described below Resin-Swelling Procedure:

To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 minutes before the solvent was drained through the frit.

Single-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 15 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:

To the reaction vessel containing resin from the previous step was added piperidine:DMF (20:80 v/v, 5.0 mL). The mixture was periodically agitated for 3 minutes and then the solution was drained through the frit. To the reaction vessel was added piperidine:DMF (20:80 v/v, 5.0 mL). The mixture was periodically agitated for 3 minutes and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added the amino (0.2M in DMF, 1.25 mL, 2.5 eq), then HATU (0.2M in DMF, 1.25 mL, 2.5 eq), and finally DIPEA (0.8M in DMF, 0.75 mL, 5 eq). The mixture was periodically agitated for 30 minutes, then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1: 89 v/v/v, 5.0 mL). The mixture was periodically agitated for 15 minutes, then the solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1: 89 v/v/v, 5.0 mL). The mixture was periodically agitated for 15 minutes, then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Final Wash Procedure:

The resin was washed successively two times as follows: for each wash, DMF (4.0 mL) was added through the top of the vessel and the resulting mixture was periodically agitated for 90 seconds before the solution was drained through the frit. The resin was washed successively four times as follows: for each wash, DCM (4.0 mL) was added through the top of the vessel and the resulting mixture was periodically agitated for 90 seconds before the solution was drained through the frit. The resulting resin was used directly in the next step.

Chloroacetic Acid Coupling Procedure:

Note Manuel step. To the reaction vessel containing the resin from the previous step was added piperidine:DMF (20:80 v/v, 5.0 mL). The mixture was shaken at Room temperature for 5 minutes and then the solution was drained through the frit. The resin was washed successively five times as follows: for each wash, DMF (4.0 mL) was added through the top of the vessel and the resulting mixture was agitated before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was shaken at room temperature for 12 to 18 hours, then the solution was drained through the frit. The resin was washed successively three times as follows: for each wash, DMF (4.0 mL) was added to top of the vessel and the resulting mixture was agitated for 90 seconds before the solution was drained through the frit. The resin was washed successively four times as follows: for each wash, $CH_2Cl_2$ (4.0 mL) was added to top of the vessel and the resulting mixture was periodically agitated for 90 seconds before the solution was drained through the frit.

CEM Method A:

All manipulations were performed under automation on a CEM Liberty microwave peptide synthesizer (CEM Corporation). All procedures unless noted were performed in a 30 or 125 mL polypropylene tube fitted with a bottom frit to a CEM Discovery microwave unit. The tube connects to a the CEM Liberty synthesizer through both the bottom and the top of the tube. DMF and DCM can be added through the top and bottom of the tube, which washes down the sides of the tube equally. All solutions are removed through the bottom of the tube except while transferring resin from the top. "Periodic bubbling" describes a brief bubbling of $N_2$ gas through the bottom frit. Amino acid solutions were generally not used beyond three weeks from preparation. HATU solution were used within 5 days of preparation. DMF=dimeth- ylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other Common resins Such as Rink, ChloroTrityl, or other acid sensitive linkers can be employed in the synthesis, Seiber amide resin is used unless otherwise noted in specific examples. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc[N-Me]Nle-OH; Fmoc-Orn(Boc)-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "CEM Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed above.

Resin-Swelling Procedure:

To 50 mL polypropylene conical tube was added Merrifield:Sieber resin (140 mg, 0.100 mmol). Then DMF (7 mL) was added to the tube followed by DCM (7 mL). The resin was then transferred to the reaction vessel from top of the vessel. The procedure is repeated additionally two times. DMF (7 mL) was added followed by DCM (7 mL). The resin was allowed to swell with N2 bubbling from the bottom of the reaction vessel for 15 minutes before the solvent was drained through the frit.

Standard Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Double-Couple Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 minutes at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Secondary Amine Coupling Procedure:

To the reaction vessel containing resin from the previous step was added a solution of 5% piperazine and 0.1 M HOBt in DMF (7 mL). The mixture was periodically agitated for 3 minutes at 75° C. and then the solution was drained. This procedure was repeated one more time. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HCTU (0.5M in DMF, 1.0 mL, 5 eq), and DIPEA (2M in NMP, 0.5 mL, 10 eq). The mixture was mixed by $N_2$ bubbling for 5 minutes at 75° C. for all amino acids (50° C. for Fmoc-Cys(Trt)-OH and Fmoc-His(Trt)-OH), followed by 6 hrs with no heating. After draining, the resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained. The resin was washed successively three times as follows: DMF (7 mL) wash from top, followed by DMF (7 mL) wash from bottom and finally with DMF (7 mL) wash from top. The resulting resin was used directly in the next step.

Custom Amino Acids-Coupling Procedure:

To the reaction vessel containing resin from the previous step was added a solution of piperidine:DMF (20:80 v/v, 5.0 mL). The mixture was periodically agitated for 3 minutes and then the solution was drained through the frit. To the reaction vessel was added a solution of piperidine:DMF (20:80 v/v, 5.0 mL). The mixture was periodically agitated for 3 minutes and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid solution (1.25 mL to 5 mL, 2.5 eq to 10 eq) containing HATU (2.5 eq to 10 eq), and finally DIPEA (2M in NMP, 0.5 mL to 1 mL, 20 eq). The mixture was mixed by N2 bubbling for 5 minutes to 2 hours at 25° C. to 75° C., then the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 minutes at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Symphony Method A:

All manipulations were performed under automation on a Symphony peptide synthesizer (Protein Technologies). All procedures unless noted were performed in a Symphony polypropylene tube fitted with a bottom frit. The tube connects to a the Symphony peptide synthesizer through both the bottom and the top of the tube. All Solvents, DMF, DCM, amino acids and reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 15 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; NMM=n-Methyl morpholine; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1%

DVB, 0.71 mmol/g loading. Other common Acid sensitive resins can also be used in the synthesis such as Rink or functionalized Chloro trityl Resin. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Symphony Method A" describes an experiment performed on a 0.050 mmol scale, where the scale is determined by the amount of Sieber linker bound to the resin. This scale corresponds to approximately 70 mg of the Sieber-Merrifield resin described above. All procedures can be scaled beyond 0.050 mmol scale by adjusting the described volumes by the multiple of the scale. Prior to amino acid coupling, all peptide synthesis sequences began with a resin-swelling procedure, described below as "Swelling procedure". Coupling of amino acids to a primary amine N-terminus used the "Standard-coupling procedure" described below. Coupling of amino acids to a secondary amine N-terminus used the "Double-coupling", custom amino acids are coupled via a manual Blank addition of the amino acid "Blank coupling" described below.

Swelling Procedure:

To a Symphony polypropylene solid-phase reaction vessel was added Merrifield:Sieber resin (70 mg, 0.050 mmol). The resin was washed (swelled) three times as follows: to the reaction vessel was added DMF (2.5 mL) upon which the mixture was periodically agitated with N2 bubbling from the bottom of the reaction vessel for 10 minutes before the solvent was drained through the frit. To the reaction vessel was added piperidine:DMF (20:80 v/v, 2.5 mL). The mixture was periodically agitated for 2.5 minutes and then the solution was drained through the frit. The resin was washed successively six times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed three times as follows: to the reaction vessel was added DMF (2.5 mL) upon which the mixture was periodically agitated with N2 bubbling from the bottom of the reaction vessel for 30 seconds before the solvent was drained through the frit. The resulting resin was used directly in the next step.

Standard-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Secondary Amine-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. The resulting resin was used directly in the next step.

Custom Amino Acids-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. The synthesis was paused by the Symphony software to add to the reaction vessel manually the custom amino acid (0.2M in DMF, 1.25 mL, 5 eq), then restart automation: to add HATU (0.2M in DMF, 1.25 mL, 5 eq), and finally NMM (0.8M in DMF, 1.25 mL, 10 eq). The mixture was periodically agitated for 300 minutes, then the reaction solution was drained through the frit. The resin was washed six times as follows with DMF (2.5 mL) was added through the bottom of the vessel and the resulting mixture was periodically agitated for 30 seconds before the solution was drained through the frit. To the reaction vessel was added the Ac$_2$O/DIPEA/DMF (v/v/v 1:1:3 2.5 mL) the mixture was periodically agitated for 10 minutes, then the reaction solution was drained through the frit. The resin was washed successively three times as follows: for each wash, DMF (2.5 mL) was added through the bottom of the vessel and the resulting mixture was periodically agitated for 90 seconds before the solution was drained through the frit. The resulting resin was used directly in the next step.

Symphony Method B:

All manipulations were performed under automation on a Symphony peptide synthesizer (Protein Technologies). All procedures unless noted were performed in a Symphony polypropylene tube fitted with a bottom frit. The tube connects to a the Symphony peptide synthesizer through both the bottom and the top of the tube. All Solvents, DMF, DCM, amino acids and reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 15 seconds. Amino acid solutions were generally not used beyond three weeks from preparation. HATU solution were used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; NMM=n-Methyl morpholine; DIEA or DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Other common Acid sensitive resins can also be used in the synthesis such as Rink or functionalized Chloro trityl Resin. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Symphony Method B" describes an experiment performed on a 0.050 mmol scale, where the scale is determined by the amount of Sieber linker bound to the resin. This scale corresponds to approximately 70 mg of the Sieber-Merrifield resin described above. All procedures can be scaled beyond 0.050 mmol scale by adjusting the described volumes by the multiple of the scale. Prior to amino acid coupling, all peptide synthesis sequences began with a resin-swelling procedure, described below as "Swelling procedure". Coupling of amino acids to a primary amine N-terminus used the "Standard-coupling procedure" described below. Coupling of amino acids to a secondary amine N-terminus used the "Secondary amine-coupling procedure B", Custom amino acids are coupled via a manual Blank addition of the amino acid "Custom amino acids-coupling procedure" described below, and ChloroAcetyl Anhydride is added to the final position of the sequence using the "final capping procedure" described below.

Swelling Procedure:

To a Symphony polypropylene solid-phase reaction vessel was added Merrifield:Sieber resin (70 mg, 0.050 mmol). The resin was washed (swelled) three times as follows: to the reaction vessel was added DMF (2.5 mL) upon which the mixture was periodically agitated with N$_2$ bubbling from the bottom of the reaction vessel for 10 minutes before the solvent was drained through the frit. To the reaction vessel was added piperidine:DMF (20:80 v/v, 2.5 mL). The mixture was periodically agitated for 2.5 minutes and then the solution was drained through the frit. The resin was washed successively six times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed with DMF (6.25 mL) added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 10 minutes, then the reaction solution was drained through the frit. The resin was washed three times as follows: to the reaction vessel was added DMF (2.5 mL) upon which the mixture was periodically agitated with N2 bubbling from the bottom of the reaction vessel for 30 seconds before the solvent was drained through the frit. The resulting resin was used directly in the next step.

Standard-Coupling Procedure:

The resin was washed three times as follows: to the reaction vessel was added DMF (2.5 mL) upon which the mixture was periodically agitated with N$_2$ bubbling from the bottom of the reaction vessel for 30 seconds before the solvent was drained through the frit. To the reaction vessel was added piperidine:DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added Ac$_2$O/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Secondary Amine-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added the amino acid (0.2M in DMF, 1.25 mL, 5 eq), then HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed successively three times as follows: for each wash, DMF (2.5 mL) was added through the bottom of the vessel and the resulting mixture was periodically agitated for 30 seconds before the solution was drained through the frit. To the reaction vessel was added Ac2O/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Custom Amino Acids-Coupling Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. The System was paused by the system for the manual addition of the custom amino acid to the reaction vessel (0.2M in DMF, 1.25 mL, 5 eq), then the automation was restarted to add to the reaction vesicle HATU (0.2M in DMF, 1.25 mL, 5 eq), and finally NMM (0.8M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added Ac2O/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 90 seconds before the solution was drained through the frit. The resulting resin was used directly in the next step.

Final Capping Procedure:

The resin was washed three times as follows: to the reaction vessel was added DMF (2.5 mL) upon which the mixture was periodically agitated with $N_2$ bubbling from the bottom of the reaction vessel for 30 seconds before the solvent was drained through the frit. To the reaction vessel was added piperidine: DMF (20:80 v/v, 2.5 mL). The mixture was periodically agitated for 2.5 minutes and then the solution was drained through the frit. The resin was washed 6 times as follows: for each wash, DMF (2.5 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed with DMF (6.25 mL) was added through the bottom of the vessel and the resulting mixture was periodically agitated for 30 seconds before the solution was drained through the frit. To the reaction vessel was added NMM (0.8M in DMF, 1.25 mL, 10 eq) followed by the addition of the Chloroacetic anhydride (0.4M in DMF, 1.25 mL, 10 eq). The mixture was periodically agitated for 15 minutes, then the reaction solution was drained through the frit. The resin was washed 6 times as follows: DMF (2.5 mL) was added through the bottom of the vessel and the resulting mixture was periodically agitated for 30 seconds before the solution was drained through the frit. To the reaction vessel was added $Ac_2O$/DIPEA/DMF (v/v/v 1:1:3 2.5 mL) the mixture was periodically agitated for 10 minutes, then the reaction solution was drained through the frit. The resin was washed successively six times as follows: for each wash, DMF (2.5 mL) was added through the bottom of the vessel and the resulting mixture was periodically agitated for 30 seconds before the solution was drained through the frit. The resin was washed successively four times as follows: for each wash, DCM (2.5 mL) was added through the bottom of the vessel and the resulting mixture was periodically agitated for 30 seconds before the solution was drained through the frit. The resulting resin was then dried with a stream of Nitrogen for 10 mins.

Global Deprotection Method A:

All manipulations were performed manually unless noted otherwise. The procedure of "Global Deprotection Method A" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:water:triisopropylsilane:dithiothreitol (92.5:2.5:2.5:2.5 v:v:v:w). The resin was removed from the reaction vessel and transferred to a 25 mL syringe equipped with a frit. To the syringe was added the "deprotection solution" (5.0 mL). The mixture was mixed in a shaker for 85 min. The solution was filtered through, concentrated and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method B:

All manipulations were performed manually unless noted otherwise. The procedure of "Global Deprotection Method B" describes an experiment performed on a 0.04 mmol scale, where the scale is determined by the amount of Sieber linker bound to the resin. The procedure can be scaled beyond 0.04 mmol scale by adjusting the described volumes by the multiple of the scale. A "deprotection solution" was prepared using trifluoroacetic acid:triisopropylsilane (96:4; v:v). The resin was removed from the reaction vessel and transferred to a 10 mL syringe equipped with a frit. To the syringe was added the "deprotection solution" (2.0-3.0 mL). The mixture was mixed in a shaker for 1 h or 1.5 h. The solution was filtered through, washed with deprotection solution (0.5 mL), concentrated and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method C:

All manipulations were performed manually unless noted. The procedure of "Global Deprotection Method C" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a Bio-Rad tube. To the Bio-Rad tube was added the "deprotection solution" (4.0 mL). The mixture was mixed in a shaker for 60 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method D:

All manipulations were performed manually unless noted otherwise. The procedure of "Global Deprotection Method B" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (94:3:3 v:v:w). The resin was removed from the reaction vessel and transferred to a 25 mL syringe equipped with a frit. To the syringe was added the "deprotection solution" (5.0 mL). The mixture was mixed in a shaker for 5 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method E:

All manipulations were performed manually unless noted. The procedure of "Global Deprotection Method E" describes an experiment performed on a 0.100 mmol scale, where the scale is determined by the amount of Fmoc Gly-ClTrt linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a Bio-Rad tube. To the Bio-Rad tube was added the "deprotection solution" (2.0 mL). The mixture was mixed in a shaker for 3 minutes. The solution was filtered, and collected in a Centrifuge tube. To the Bio-Rad tube was added the "deprotection solution" (2.0 mL). The mixture was mixed in a shaker for 3 minutes. The solution was filtered, and collected in a Centrifuge tube. To the Bio-Rad tube was added the "deprotection solution" (2.0 mL). The mixture was mixed in a shaker for 3 minutes. The solution was filtered, and collected in a Centrifuge tube. The solution in the Centrifuge tube was allowed to stand for 60 minutes. The collected solution was then diluted with diethyl ether (30 mL), and precipitate formed. The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Global Deprotection Method F:

All manipulations were performed manually unless noted. The procedure of "Global Deprotection Method F" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (95:2.5:2.5 v:v:w). The resin was removed from the reaction vessel and transferred to a 6 mls Bio-Rad tube. To the Bio-Rad was added the "deprotection solution" (4.0 mL). The mixture was mixed in a shaker for 90 minutes. The solution was filtered through and diluted in diethyl ether (30 mL). The precipitated solid was centrifuged for 3 minutes. The supernatant solution was decanted and the solid was resuspended diethyl ether (25 mL). The suspension was centrifuged for 3 minutes. The supernatant was decanted and the remaining solid was suspended diethyl ether (25 mL). The suspension was centrifuged for 3 minutes. The supernatant was decanted and the remaining solid was dried under high vacuum. The crude peptide was obtained as a white to off-white solid.

Cyclization Method A

All manipulations were performed manually unless noted otherwise. The procedure of "Cyclization Method A" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 8M Guanidine/

50 mM TRIS (1:3) (pH 8.6) (7 mL:18 mL or similar ratio), and the solution was then adjusted to pH=8.5-9.0 using aq NaOH (1.0M), if necessary. The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Cyclization Method C:

All manipulations were performed manually unless noted. The procedure of "Cyclization Method C" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL:24 mL or similar ratio), and the solution was then carefully adjusted to pH=8.5-9.0 using aq NaOH (1.0M). The solution was then mixed using a shaker for 12 to 18 hours. The reaction solution was concentrated and the residue was then dissolved in acetonitrile:water. This solution was subjected to reverse-phase HPLC purification to afford the desired cyclic peptide.

Cyclization Method D:

All manipulations were performed manually unless noted. The procedure of "Cyclization Method D" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL:24 mL), and the solution was then carefully adjusted to pH=8.5-9.0 using aq NaOH (1.0M). The solution was then mixed with stirring for 12 to 18 hours. The reaction solution was concentrated and the residue was then dissolved in acetonitrile:water. This solution was subjected to reverse-phase HPLC purification to afford the desired cyclic peptide.

Cyclization Method E:

All manipulations were performed manually unless noted. The procedure of "Cyclization Method E" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of aqueous 6M guanidine HCl buffer (15 mL), the solution was then mixed with stirring for 12 to 18 hours. The reaction solution was concentrated and 15 mL of DMSO was added to the residue affording a slurry which was filtered. This filtered solution was subjected to reverse-phase HPLC purification to afford the desired cyclic peptide.

Manual Coupling Procedure A:

To Bio-Rad reaction vessel containing resin from the previous step was added piperidine:DMF (20:80 v/v, 5.0 mL). The mixture was periodically shaken for 5 minutes and then the solution was drained through the frit. The resin was washed successively five times as follows: for each wash, DMF (4.0 mL) was added through the top of the vessel and the resulting mixture was shaken for 60 seconds before the solution was drained through the frit. To the reaction vessel was added the amino acid (1.2-10 equivalents) typical (0.2M in DMF, 2.5 mL, 5 eq), then HATU (1.210 equivalents) typical (0.2M in DMF, 2.5 mL, 5 eq), and finally DIPEA (2.4-20 equivalents) typical (0.8M in DMF, 1.25 mL, 10 eq). The mixture was shaken for 60 minutes to 18 hours, then the reaction solution was drained through the frit. The resin was washed successively four times as follows: for each wash, DMF (4.0 mL) was added through the top of the vessel and the resulting mixture was shaken for 60 seconds before the solution was drained through the frit.

N-methylation on-resin Method A. (Turner, R. A.; Hauksson, N. E.; Gipe, J. H.; Lokey, R. S. *Org. Lett.* 2013, 15(19), 5012-5015):

All manipulations were performed manually unless noted. The procedure of "N-methylation on-resin Method A" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale.

The resin was transferred into a 25 mL fritted syringe. To the resin was added piperidine:DMF (20:80 v/v, 5.0 mL). The mixture was shaken for 3 min. and then the solution was drained through the frit. The resin was washed 3 times with DMF (4.0 mL). To the reaction vessel was added piperidine:DMF (20:80 v/v, 4.0 mL). The mixture was shaken for 3 min. and then the solution was drained through the frit. The resin was washed successively three times with DMF (4.0 mL) and three times with DCM (4.0 mL). The resin was suspended in DMF (2.0 mL) and ETHYL TRIFLUOROACETATE (0.119 ml, 1.00 mmol), 1,8-DIAZABICYCLO[5.4.0]UNDEC-7-ENE (0.181 ml, 1.20 mmol). The mixture was placed on a shaker for 60 min. The solution was drained through the frit. The resin was washed successively three times with DMF (4.0 mL) and three times with DCM (4.0 mL).

The resin was washed three times with dry THF (2.0 mL) to remove any residual water. In an oven dried 4.0 mL vial was added THF (1.0 mL) and TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit and the resin was washed with three times with dry THF (2.0 mL) to remove any residual water. In an oven dried 4.0 mL vial was added THF (1.0 mL), TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit. The resin was washed successively three times with DMF (4.0 mL) and three times with DCM (4.0 mL). The resin was suspended in Ethanol (1.0 mL) and THF (1.0 mL), and SODIUM BOROHYDRIDE (37.8 mg, 1.000 mmol) was added. The mixture was stirred for 30 min. and drained. The resin was washed successively three times with DMF (4.0 mL) and three times with DCM (4.0 mL).

Microcleavage A:

To a small <10 mg sample of resin is added 2 drops of TIS and 1 mL of Trifluoroacetic acid, shake at rt. After 1 h, remove a small aliquot and dilute with 0.5 mL Acetonitrile, filter, and obtain analysis by LC-MS.

Synthesis protocols for specific peptides disclosed herein are provided in the following Examples.

Examples 2 thru 71 provide synthesis schemes for the Formula I(a) to I(d) macrocyclic peptides.

Examples 72 thru 88 provide synthesis schemes for the Formula II(a) to II(c) macrocyclic peptides.

Examples 100 thru 116 provide synthesis schemes for the Formula III(a) to III(c) macrocyclic peptides.

Examples 116 thru 119 provide synthesis schemes for the C-terminally PEGylated macrocyclic peptides of Formulas I and II.

Example 2

Synthesis of Compound No. 1

Molecular Weight: 1852.17

To a 40 mL polypropylene solid-phase reaction vessel was added Sieber resin (140 mg, 0.100 mmol), and the reaction vessel was placed on the Prelude peptide synthesizer. The following procedures were then performed sequentially:

"CEM Method A: Resin-swelling procedure" was followed;
"CEM Method A: Single-coupling procedure" was followed with Fmoc-Gly-OH;
"CEM Method A: Single-coupling procedure" was followed with Fmoc-Cys(Trt)-OH;
"CEM Method A: Double-coupling procedure" was followed with Fmoc-Arg(Pbf)-OH;
"CEM Method A: Single-coupling procedure" was followed with Fmoc-[N-Me]Nle-OH;
"CEM Method A: Single-coupling procedure" was followed with Fmoc-[N-Me]Nle-OH;
"CEM Method A: Single-coupling procedure" was followed with Fmoc-Trp(Boc)-OH;
"CEM Method A: Single-coupling procedure" was followed with Fmoc-Ser(tBu)-OH;
"CEM Method A: Single-coupling procedure" was followed with Fmoc-Trp(Boc)-OH;
"CEM Method A: Single-coupling procedure" was followed with Fmoc-[N-Me]Gly-OH;
"CEM Method A: Single-coupling procedure" was followed with Fmoc-Leu-OH;
"CEM Method A: Single-coupling procedure" was followed with Fmoc-His(Trt)-OH;
"CEM Method A: Single-coupling procedure" was followed with Fmoc-Pro-OH;
"CEM Method A: Single-coupling procedure" was followed with Fmoc-Asn(Trt)-OH;
"CEM Method A: Single-coupling procedure" was followed with Fmoc-[N-Me]Ala-OH;
"CEM Method A: Single-coupling procedure" was followed with Fmoc-Phe-OH;
"Chloroacetyl chloride coupling procedure A" was followed;
"Global Deprotection Method A" was followed;
"Cyclization Method A" was followed.

The crude material was purified via preparative HPLC using the following conditions: Column: PHENOMENEX® C18 Luna, 20×250 mm, 5-µm particles; Mobile Phase A: 0.1% TFA in water; Mobile Phase B: 0.1% TFA in AcCN; gradient: 20-70% B over 50 min.; Flow: 15 mL/min. Fractions containing the desired product were combined and dried by lyophilization. The yield of product was 16 mg, and its estimated purity by HPLC analysis was 97%.

Analysis LCMS Condition A: retention time=1.30 min.; ESI-MS(+) m/z 926.7 (M+2H).

Analysis HPLC Condition A: retention time=11.16 min.

Example 3

Synthesis of Compound No. 2

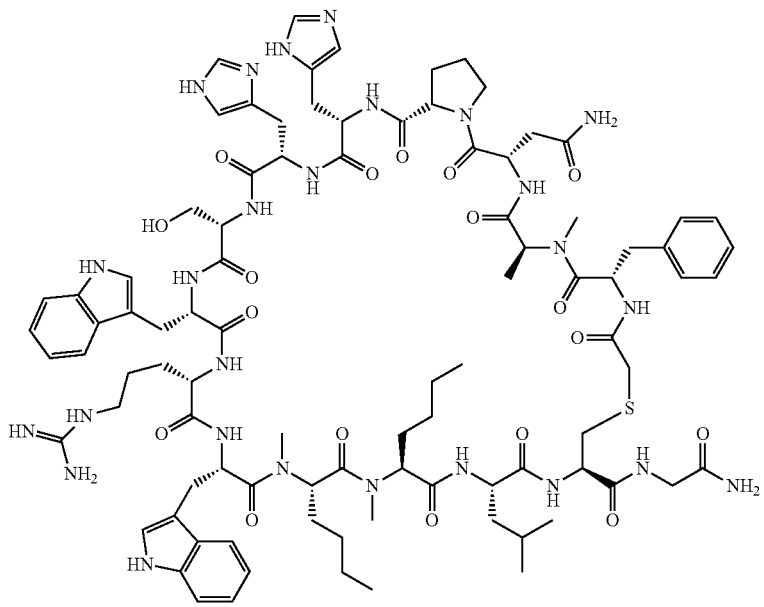

Molecular Weight: 1918.23

Example 0003 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method A", and "Cyclization Method A".

The crude material was purified via preparative HPLC using the following conditions: Column: PHENOMENEX® C18 Luna, 20×250 mm, 5-μm particles; Mobile Phase A: 0.1% TFA in water; Mobile Phase B: 0.1% TFA in AcCN; gradient: 20-75% B over 55 min.; Flow: 15 mL/min. Fractions containing the desired product were combined and dried by lyophilization. The yield of product was 18 mg, and its estimated purity by HPLC analysis was 93

Analysis LCMS Condition A: retention time=1.19 min.; ESI-MS(+) m/z 959.8 (M+2H).

Analysis HPLC Condition B: retention time=14.49 min.

Example 4

Synthesis of Compound No. 3

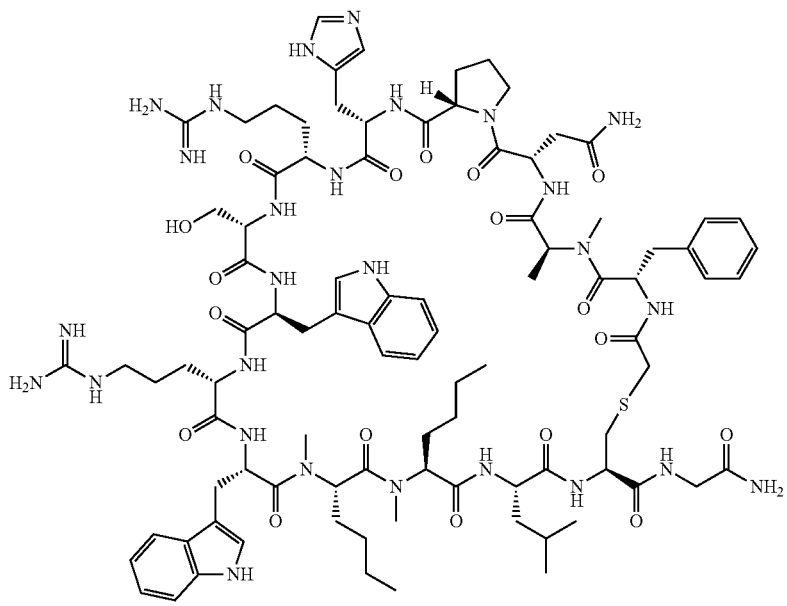

Molecular Weight: 1937.28

Example 0004 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-μm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 8.1 mg, and its estimated purity by HPLC analysis was 98%.

Analysis LCMS Condition A: retention time=1.21 min.; ESI-MS(+) m/z 970.0 (M+2H).

Analysis HPLC Condition B: retention time=19.91 min.

Example 5

Synthesis of Compound No. 4

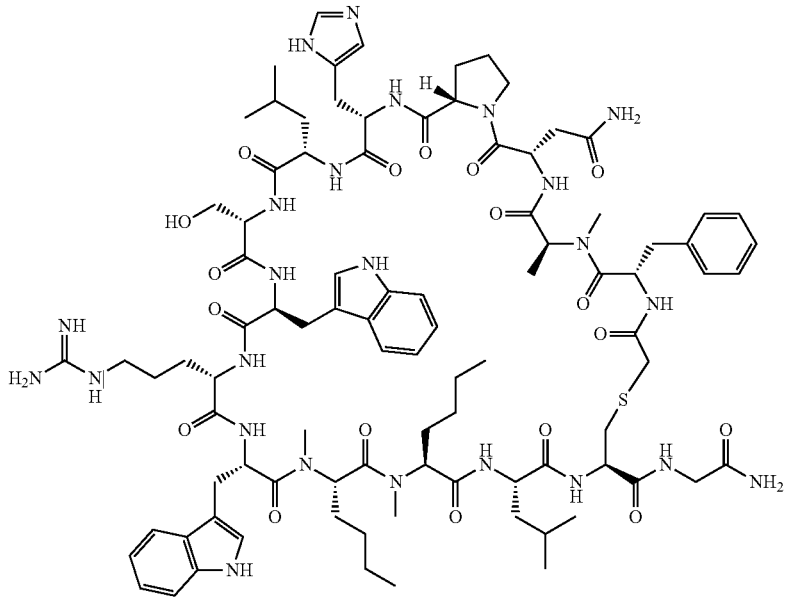

Example 5

Example 0005 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-μm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 2.1 mg, and its estimated. purity by HPLC analysis was 99%.

Analysis LCMS Condition A: retention time=1.28 min.; ESI-MS(+) m/z 948.3 (M+2H).

Analysis HPLC Condition C: retention time=19.03 min.

Example 6

Synthesis of Compound No. 5

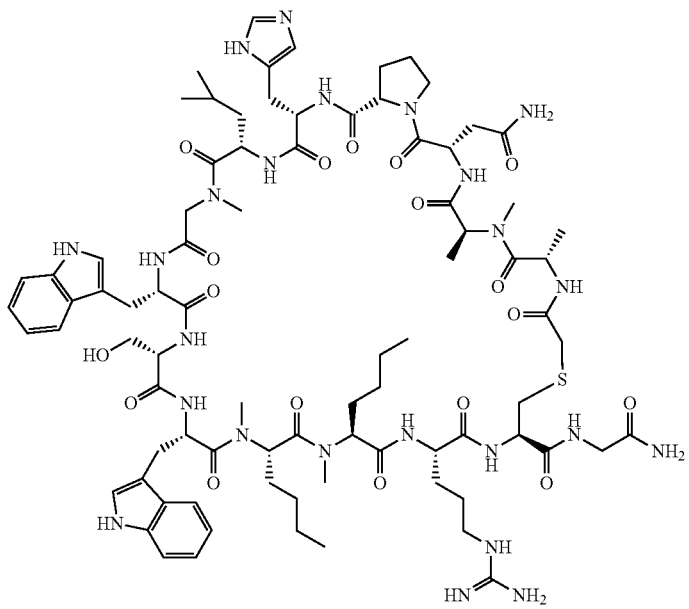

Molecular Weight: 1776.07

To a 40 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method A: Resin-swelling procedure" was followed;

"Prelude Method A: Single-coupling procedure" was followed;

"Prelude Method A: Secondary amine coupling procedure" was followed for couplings of the Fmoc-N-Methyl amino acids and for couplings to a secondary amine N-terminus;

"Prelude Method A: Chloroacetyl chloride coupling procedure A" was followed;

"Global Deprotection Method C" was followed;

"Cyclization Method C" was followed.

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 20-65% B over 25 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 98% by "Analysis LCMS conditions B and D".

Analysis LCMS condition B: Retention time=1.412 min; ESI-MS(+) m/z 888.75 (M+2H).

Analysis LCMS condition D: Retention time=1.539 min; ESI-MS(+) m/z 888.50 (M+2H).

Example 7

Synthesis of Compound No. 6

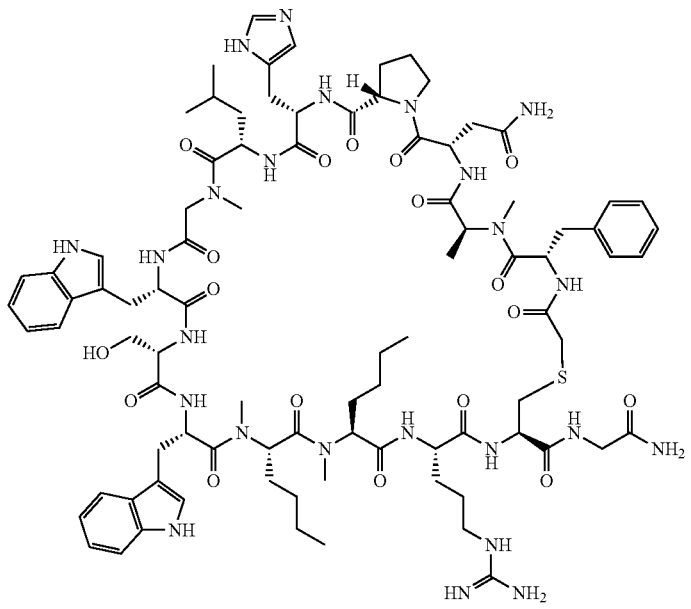

Molecular Weight: 1838.14

Example 0007 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-µm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 24 mg, and its estimated purity by HPLC analysis was 99%.

Analysis LCMS Condition A: retention time=1.20 min.; ESI-MS(+) m/z 920.3 (M+2H).

Analysis HPLC Condition C: retention time=15.66 min.

Example 8

Synthesis of Compound No. 7

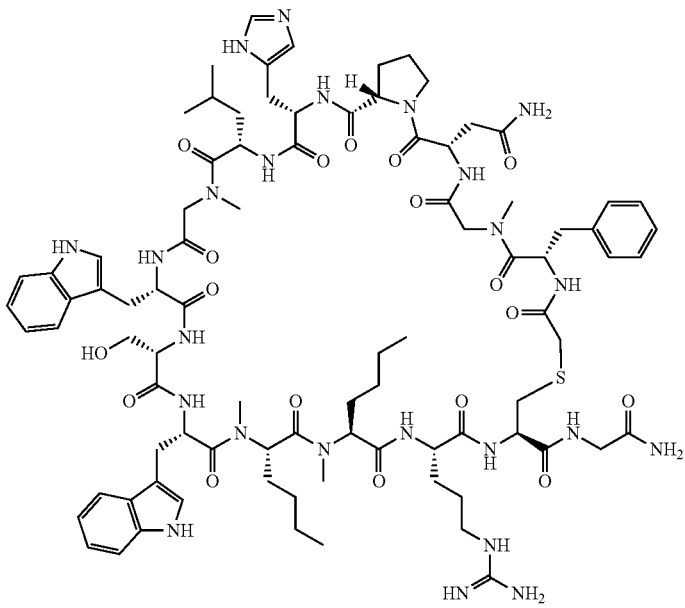

Molecular Weight: 1838.14

Example 0008 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-μm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 11.5 mg, and its estimated purity by HPLC analysis was 97%.

Analysis LCMS Condition A: retention time=1.24 min.; ESI-MS(+) m/z 920.2 (M+2H).

Analysis HPLC Condition C: retention time=16.39 min.

Example 9

Synthesis of Compound No. 8

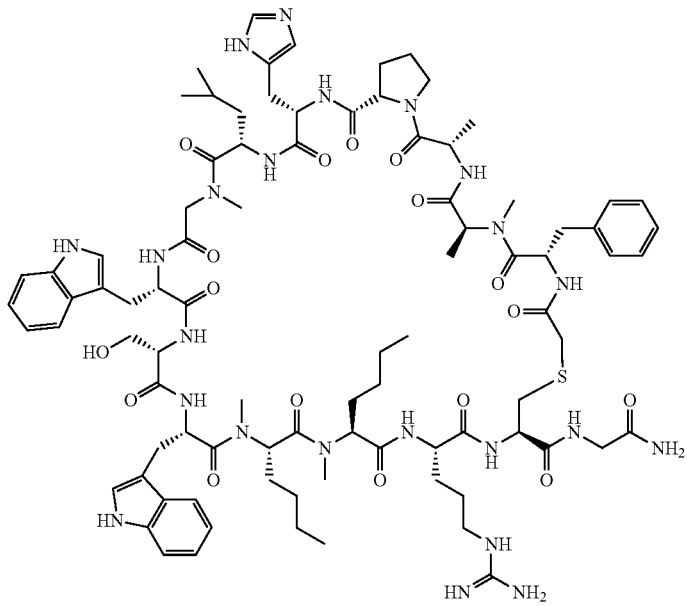

Molecular Weight: 1809.14

Example 0009 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-μm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 12 mg, and its estimated purity by HPLC analysis was 92%.

Analysis LCMS Condition A: retention time=1.27 min.; ESI-MS(+) m/z 905.8 (M+2H).

Analysis HPLC Condition C: retention time=17.18 min.

Example 10

Synthesis of Compound No. 9

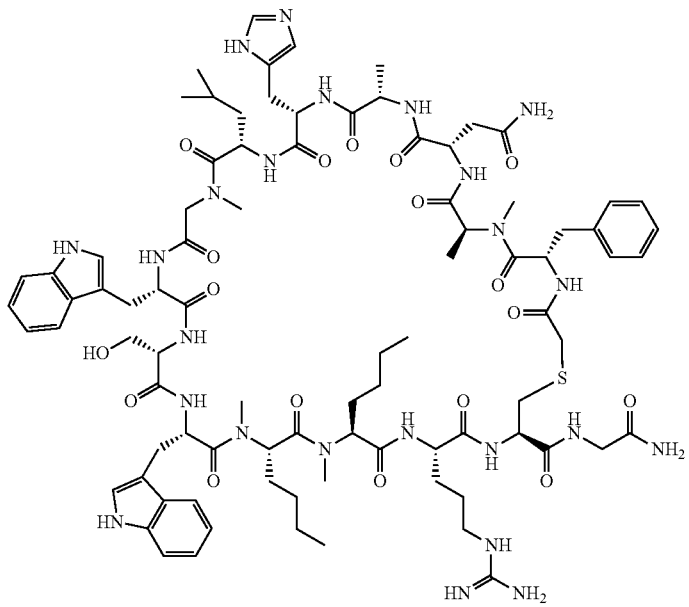

Molecular Weight: 1826.13

Example 0010 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-μm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 16 mg, and its estimated purity by HPLC analysis was 93%.

Analysis LCMS Condition A: retention time=1.26 min.; ESI-MS(+) m/z 914.3 (M+2H).

Analysis HPLC Condition C: retention time=16.98 min.

Example 11

Synthesis of Compound No. 10

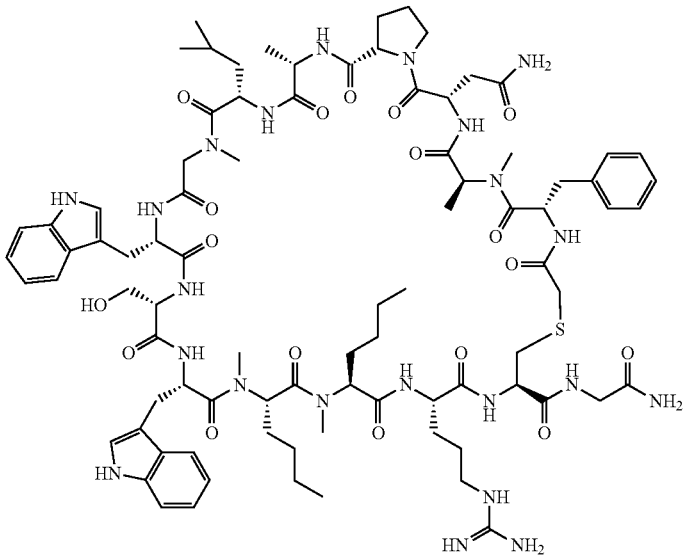

Molecular Weight: 1786.11

Example 0011 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC AQ-ODS, 20×250 mm, 5-µm particles, heated to 60° C.; Mobile Phase A: 0.1% TFA in water; Mobile Phase B: 0.1% TFA in AcCN; gradient: 10-70% B over 60 min.; Flow: 15 mL/min. Fractions containing the desired product were combined and dried by lyophilization. The yield of product was 3.9 mg, and its estimated purity by HPLC analysis was 99%.

Analysis LCMS Condition A: retention time=1.45 min.; ESI-MS(+) m/z 894.2 (M+2H).

Analysis HPLC Condition D: retention time=23.00 min.

Example 12

Synthesis of Compound No. 11

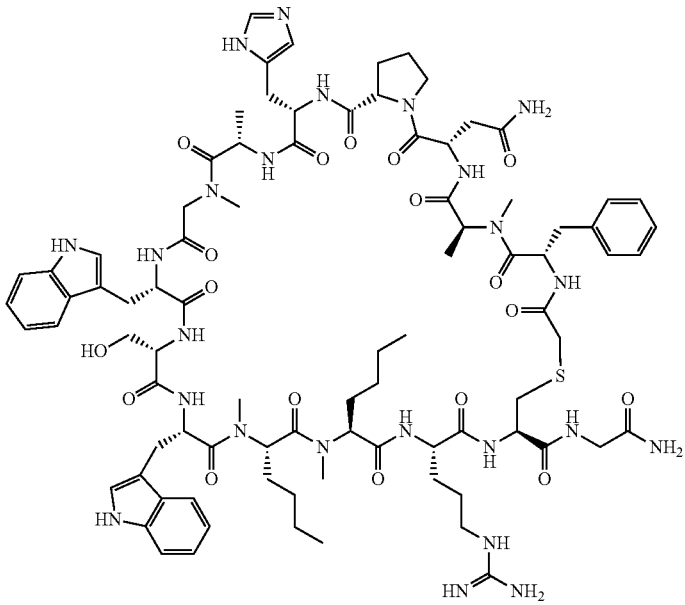

Molecular Weight: 1810.09

Example 0012 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: PHENOMENEX® C18 Luna, 20×250 mm, 5-µm particles, heated to 60° C.; Mobile Phase A: 0.1% TFA in water; Mobile Phase B: 0.1% TFA in AcCN; gradient: 25-75% B over 45 min.; Flow: 15 mL/min. Fractions containing the desired product were combined and dried by lyophilization. The yield of product was 3.6 mg, and its estimated purity by HPLC analysis was 99%.

Analysis LCMS Condition G: ESI-MS(+) m/z 905.8 (M+2H).

Analysis HPLC Condition E: retention time=14.68 min.

Example 13

Synthesis of Compound No. 12

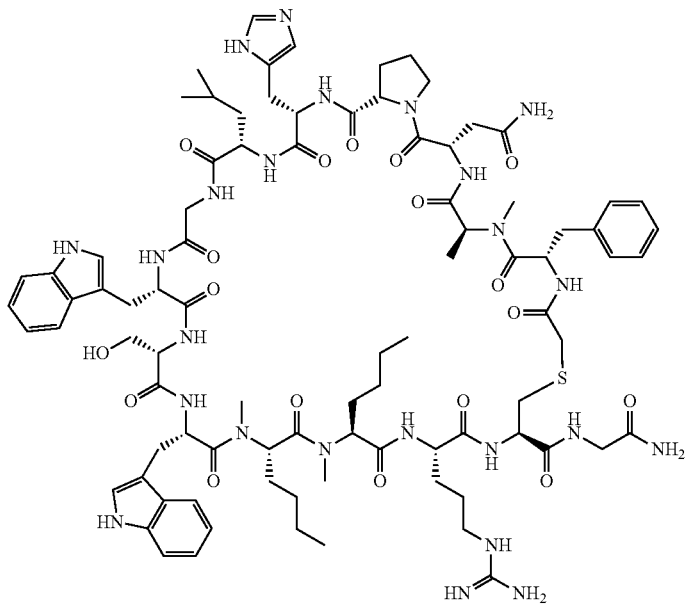

Molecular Weight: 1838.14

Example 0013 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method B", and "Cyclization Method C".

The crude material was purified via preparative HPLC using the following conditions: Column: YMC ODS-AQ, 20×250 mm, 5-µm particles, heated to 60° C.; Mobile Phase A: 0.1% TFA in water; Mobile Phase B: 0.1% TFA in AcCN; gradient: 25-70% B over 60 min.; Flow: 15 mL/min. Fractions containing the desired product were combined and dried by lyophilization. The yield of product was 3.0 mg, and its estimated purity by HPLC analysis was 92%.

Analysis LCMS Condition G: retention time=4.06 min.; ESI-MS(+) m/z 919.8 (M+2H).

Analysis HPLC Condition E: retention time=13.71 min.

Example 14

Synthesis of Compound No. 13

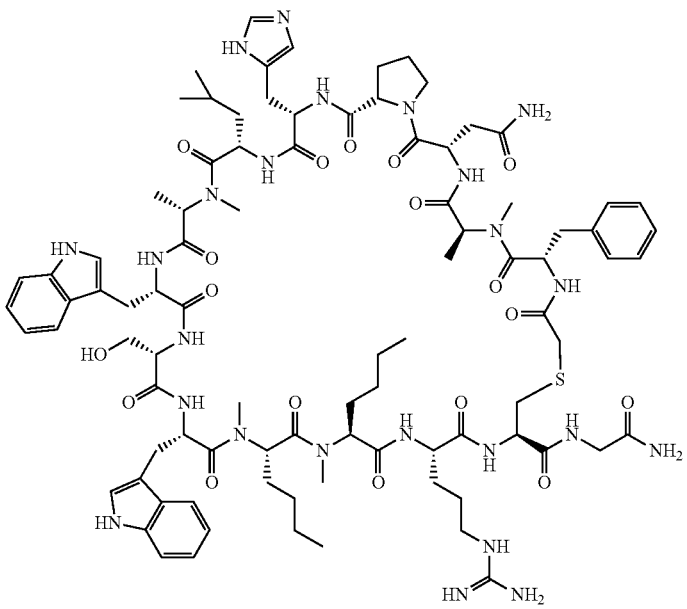

Molecular Weight: 1866.19

Example 0014 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 25-65% B over 25 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 95% by "Analysis LCMS conditions B and D".

Analysis LCMS condition B: Retention time=1.683 min; ESI-MS(+) m/z 933.70 (M+2H).

Analysis LCMS condition D: Retention time=1.750 min; ESI-MS(+) m/z 933.95 (M+2H).

Example 15

Synthesis of Compound No. 14

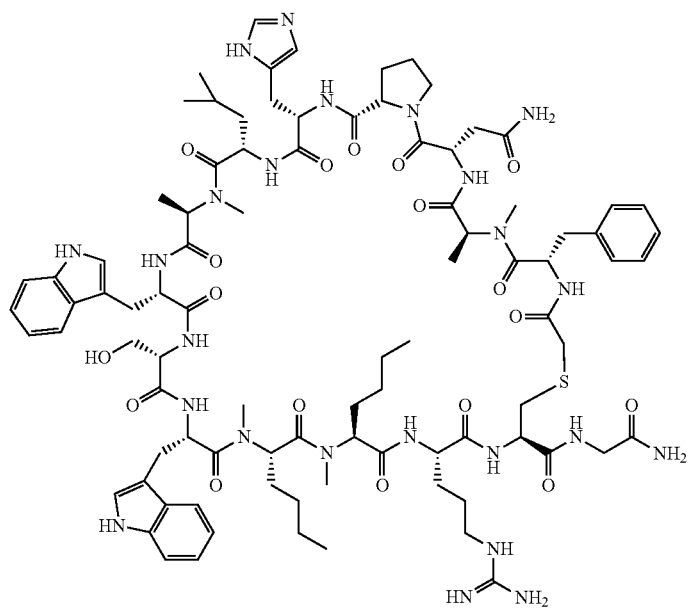

Molecular Weight: 1866.19

Example 0015 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 20-60% B over 25 minutes, then a 5-minute hold at 100% B; Flow: 20 mL/min. Fractions containing the desired product were combined and dried via centrifugal evaporation. The yield of the product was 13.3 mg, and its estimated purity by LCMS analysis was 98% by "Analysis LCMS conditions B and D".

Analysis LCMS condition B: Retention time=1.566 min; ESI-MS(+) m/z 933.95 (M+2H).

Analysis LCMS condition D: Retention time=1.630 min; ESI-MS(+) m/z 934.00 (M+2H).

Example 16

Synthesis of Compound No. 15

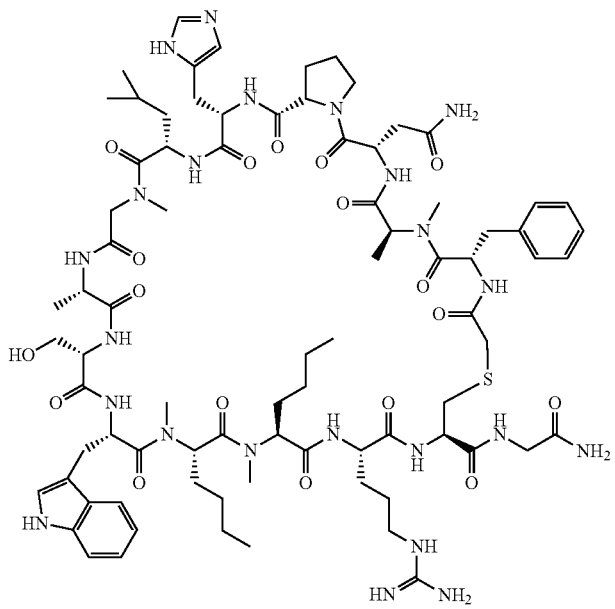

Molecular Weight: 1737.04

Example 0016 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "CEM Method A: Coupling to N-Methyl Amino Acid procedure", "Chloroacetyl chloride coupling procedure A", "Global Deprotection Method B", and "Cyclization Method C".

The crude material was purified via preparative HPLC using the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-60% B over 60 min.; Flow: 15 mL/min. Fractions containing the desired product were combined and dried by lyophilization. The yield of product was 7.0 mg, and its estimated purity by HPLC analysis was 93%.

Analysis LCMS Condition A: retention time=1.15 min.; ESI-MS(+) m/z 869.6 (M+2H).

Analysis HPLC Condition E: retention time=10.49 min.

Example 17

Synthesis of Compound No. 16

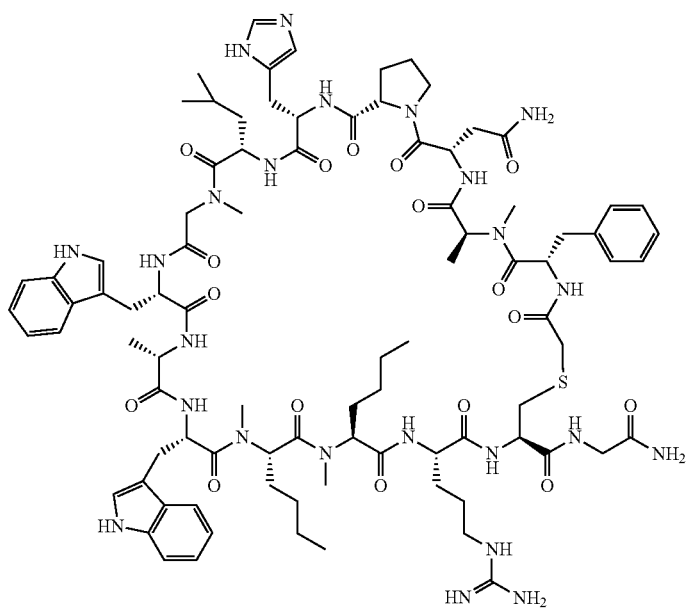

Molecular Weight: 1836.17

Example 0017 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "CEM Method A: Coupling to N-Methyl Amino Acid procedure", "Chloroacetyl chloride coupling procedure A", "Global Deprotection Method B", and "Cyclization Method C".

The crude material was purified via preparative HPLC using the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-60% B over 60 min.; Flow: 15 mL/min. Fractions containing the desired product were combined and dried by lyophilization. The yield of product was 8.4 mg, and its estimated purity by HPLC analysis was 99%.

Analysis LCMS Condition G: retention time=3.76 min.; ESI-MS(+) m/z 919.8 (M+2H).

Analysis HPLC Condition E: retention time=14.69 min.

Example 18

Synthesis of Compound No. 17

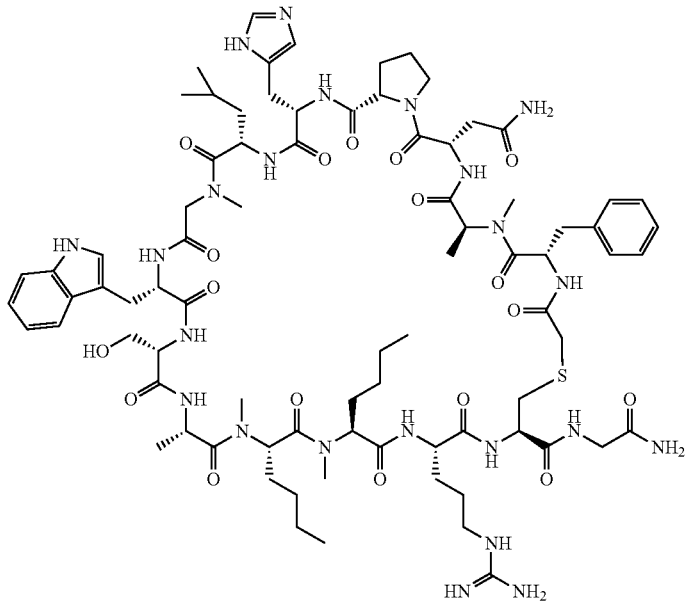

Molecular Weight: 1737.04

Example 0018 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "CEM Method A: Coupling to N-Methyl Amino Acid procedure", "Chloroacetyl chloride coupling procedure A", "Global Deprotection Method B", and "Cyclization Method C".

The crude material was purified via preparative HPLC using the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-65% B over 60 min.; Flow: 15 mL/min. Fractions containing the desired product were combined and dried by lyophilization. The yield of product was 10.5 mg, and its estimated purity by HPLC analysis was 93%.

Analysis LCMS Condition G: retention time=3.60 min.; ESI-MS(+) m/z 869.3 (M+2H).

Analysis HPLC Condition F: retention time=11.75 min.

Example 19

Synthesis of Compound No. 18

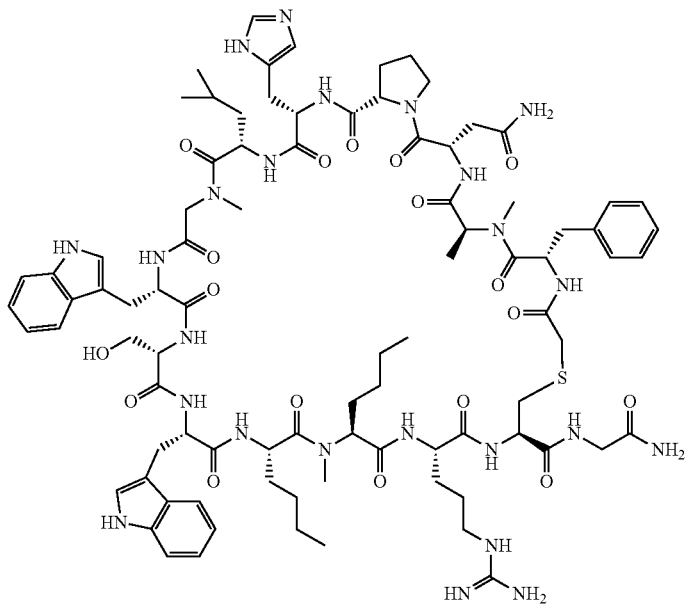

Molecular Weight: 1838.14

To a 40 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method B: Resin-swelling procedure" was followed;

"Prelude Method B: Double-coupling procedure" was followed for couplings to primary amine N-terminus;

"Prelude Method B: Secondary amine coupling procedure" was followed for couplings to secondary amine N-terminus;

"Prelude Method A: Chloroacetyl chloride coupling procedure A" was followed;

"Global Deprotection Method B" was followed;

"Cyclization Method C" was followed.

The crude material was purified via preparative HPLC with the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-75% B over 45 min.; Flow: 15 mL/min. Fractions containing the desired product were combined and dried by lyophilization. The yield of the product was 15 mg, and its estimated purity by HPLC analysis was 95%.

Analysis LCMS Condition G: retention time=3.53 min.; ESI-MS(+) m/z 919.8 (M+2H).

Analysis HPLC Condition F: retention time=15.29 min.

Example 20

Synthesis of Compound No. 19

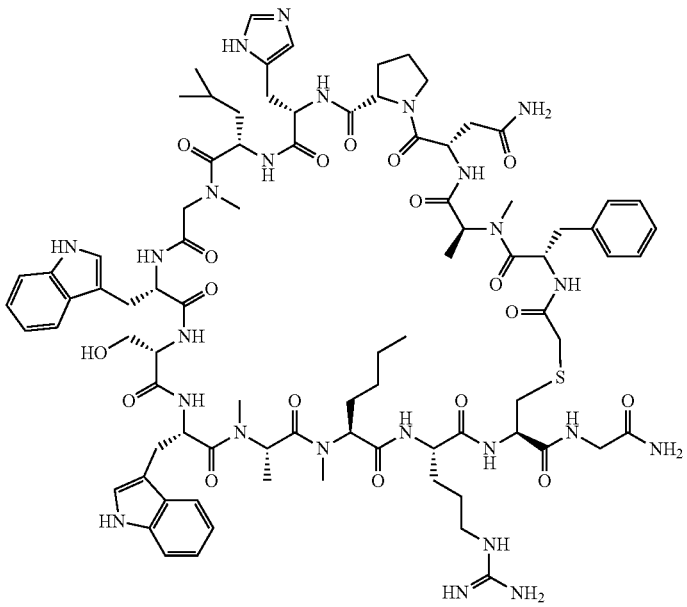

Molecular Weight: 1810.09

Example 0020 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 15-55% B over 25 minutes, then a 5-minute hold at 55% B; Flow: 20 mL/min. Fractions containing the desired product were combined and dried via centrifugal evaporation. The yield of the product was 23.6 mg, and its estimated purity by LCMS analysis was 97% by "Analysis LCMS conditions B and D".

Analysis LCMS condition B: Retention time=1.434 min; ESI-MS(+) m/z 906.30 (M+2H).

Analysis LCMS condition D: Retention time=1.483 min; ESI-MS(+) m/z 905.70 (M+2H).

Example 21

Synthesis of Compound No. 20

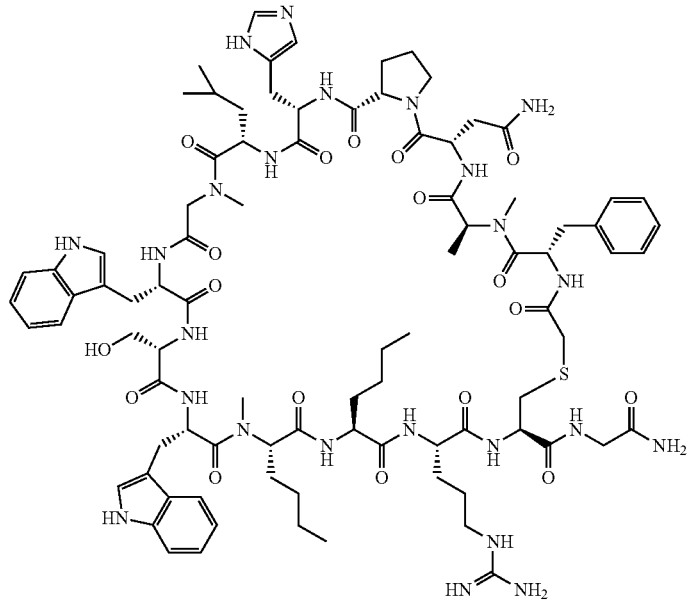

Molecular Weight: 1838.14

Example 0021 was prepared following the general synthetic sequence described for the preparation of Example 0019, composed of the following general procedures: "Prelude Method B: Resin-swelling procedure", "Prelude Method B: Double-coupling procedure" for couplings to primary amine N-terminus; "Prelude Method B: Secondary amine coupling procedure" for couplings to secondary amine N-terminus; "Prelude Method A: Chloroacetyl chloride coupling procedure A", "Global Deprotection Method B" and "Cyclization Method C".

The crude material was purified via preparative HPLC with the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-65% B over 45 min.; Flow: 15 mL/min. Fractions containing the desired product were combined and dried by lyophilization. The yield of the product was 21.3 mg, and its estimated purity by HPLC analysis was 91%.

Analysis LCMS Condition G: retention time=3.84 min.; ESI-MS(+) m/z 919.8 (M+2H).

Analysis HPLC Condition E: retention time=16.82 min.

Example 22

Synthesis of Compound No. 21

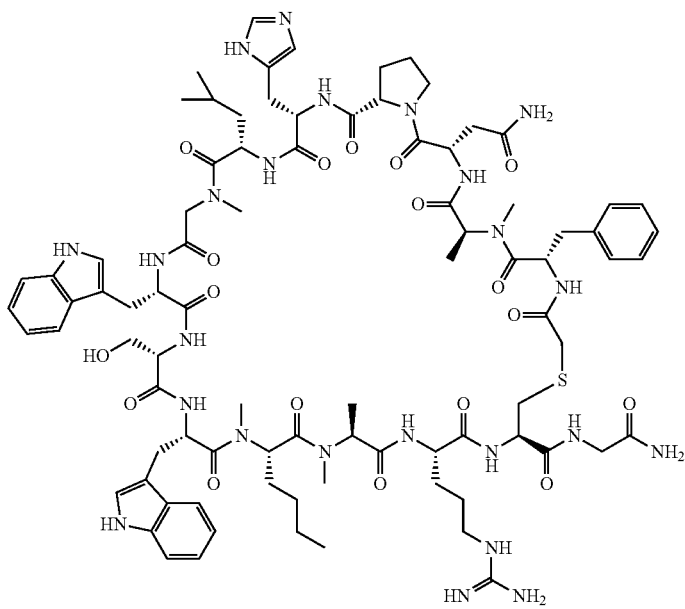

Molecular Weight: 1810.09

Example 0022 was prepared following the general synthetic sequence described for the preparation of Example 0019, composed of the following general procedures: "Prelude Method B: Resin-swelling procedure", "Prelude Method B: Double-coupling procedure" for couplings to primary amine N-terminus; "Prelude Method B: Secondary amine coupling procedure" for couplings to secondary amine N-terminus; "Prelude Method A: Chloroacetyl chloride coupling procedure A", "Global Deprotection Method B" and "Cyclization Method C".

The crude material was purified via preparative HPLC with the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-50% B over 45 min.; Flow: 15 mL/min. Fractions containing the desired product were combined and dried by lyophilization. The yield of the product was 7.5 mg, and its estimated purity by HPLC analysis was 99%.

Analysis LCMS Condition G: retention time=3.89 min.; ESI-MS(+) m/z 905.8 (M+2H).

Analysis HPLC Condition E: retention time=13.23 min.

Example 23

Synthesis of Compound No. 22

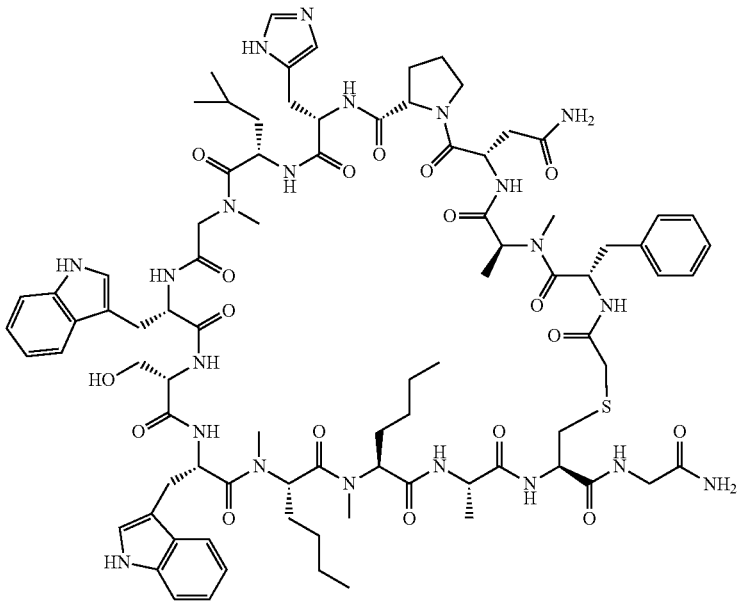

Molecular Weight: 1767.06

Example 0023 was prepared following the general synthetic sequence described for the preparation of Example 0019, composed of the following general procedures: "Prelude Method B: Resin-swelling procedure", "Prelude Method B: Double-coupling procedure" for couplings to primary amine N-terminus; "Prelude Method B: Secondary amine coupling procedure" for couplings to secondary amine N-terminus; "Prelude Method A: Chloroacetyl chloride coupling procedure A", "Global Deprotection Method B" and "Cyclization Method C".

The crude material was purified via preparative HPLC with the following conditions: Column: YMC ODS-AQ, 20×250 mm, 5-μm particles, heated to 60° C.; Mobile Phase A: 0.1% TFA in water; Mobile Phase B: 0.1% TFA in AcCN; gradient: 25-70% B over 45 min.; Flow: 15 mL/min. Fractions containing the desired product were combined and dried by lyophilization. The yield of the product was 25 mg, and its estimated purity by HPLC analysis was 99%.

Analysis LCMS Condition G: retention time=3.91 min.; ESI-MS(+) m/z 884.5 (M+2H).

Analysis HPLC Condition E: retention time=13.23 min.

Example 24

Synthesis of Compound No. 23

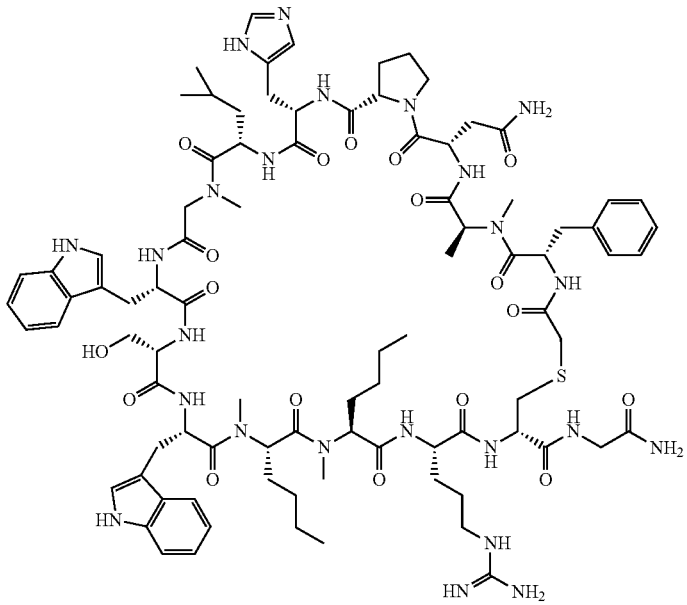

Molecular Weight: 1852.17

Example 0024 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 15-55% B over 25 minutes, then a 5-minute hold at 55% B; Flow: 20 mL/min. Fractions containing the desired product were combined and dried via centrifugal evaporation. The yield of the product was 10.8 mg, and its estimated purity by LCMS analysis was 98% by "Analysis LCMS conditions B and D".

Analysis LCMS condition B: Retention time=1.505 min; ESI-MS(+) m/z 926.70 (M+2H).

Analysis LCMS condition D: Retention time=1.537 min; ESI-MS(+) m/z 926.80 (M+2H).

Example 25

Synthesis of Compound No. 24

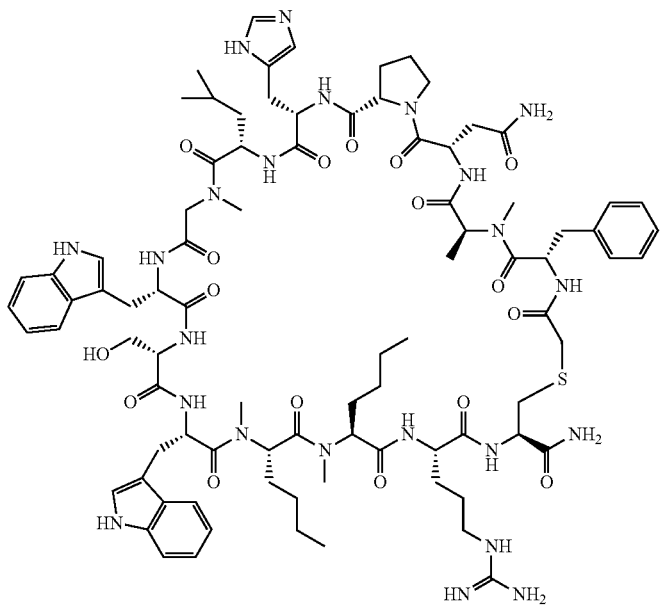

Molecular Weight: 1795.12

Example 0025 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 20-60% B over 25 minutes, then a 5-minute hold at 60% B; Flow: 20 mL/min. Fractions containing the desired product were combined and dried via centrifugal evaporation. The yield of the product was 9.9 mg, and its estimated purity by LCMS analysis was 100% by "Analysis LCMS conditions B and D".

Analysis LCMS condition B: Retention time=1.676 min; ESI-MS(+) m/z 898.20 (M+2H).

Analysis LCMS condition D: Retention time=1.749 min; ESI-MS(+) m/z 898.45 (M+2H).

Example 26

Synthesis of Compound No. 25

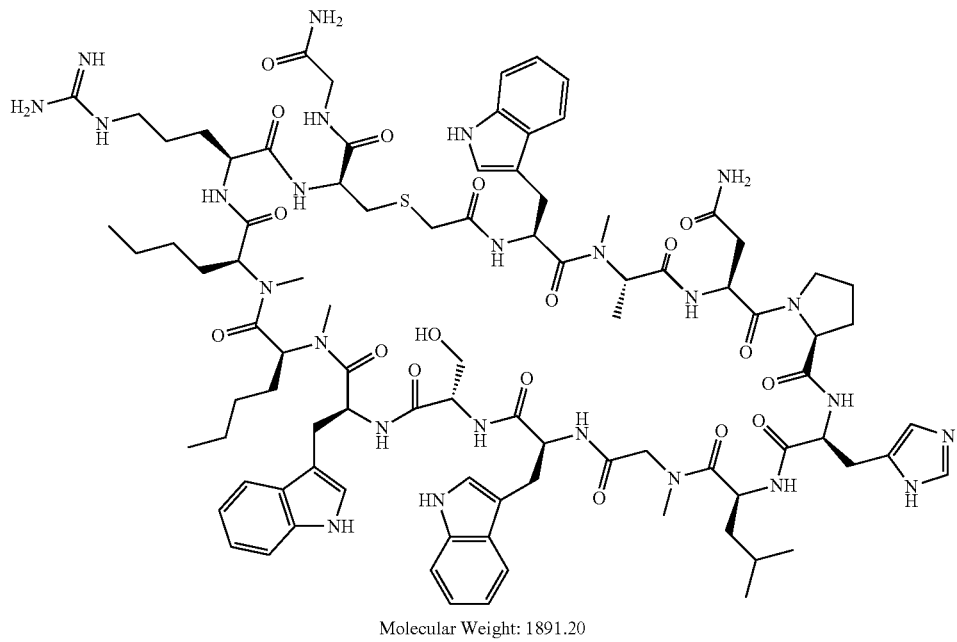 [SMILES: CCCC[C@H]1C(=O)N(C)[C@@H](CCCC)C(=O)N[C@@H](CCCNC(=N)N)C(=O)N[C@@H](C(=O)NCC(N)=O)CSCC(=O)N[C@@H](Cc2c[nH]c3ccccc23)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N(C)CC(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1891.20

Example 0026 was prepared starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-Trp(Boc)-OH was used in the first amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 1.7 mg, and its estimated purity by LCMS analysis was 100%.

Analysis LCMS Condition D: Retention time=1.65 min; ESI-MS(+) m/z 946.4 (M+2H).

Analysis LCMS Condition E: Retention time=1.58 min; ESI-MS(+) m/z 946.4 (M+2H).

Example 27

Synthesis of Compound No. 26

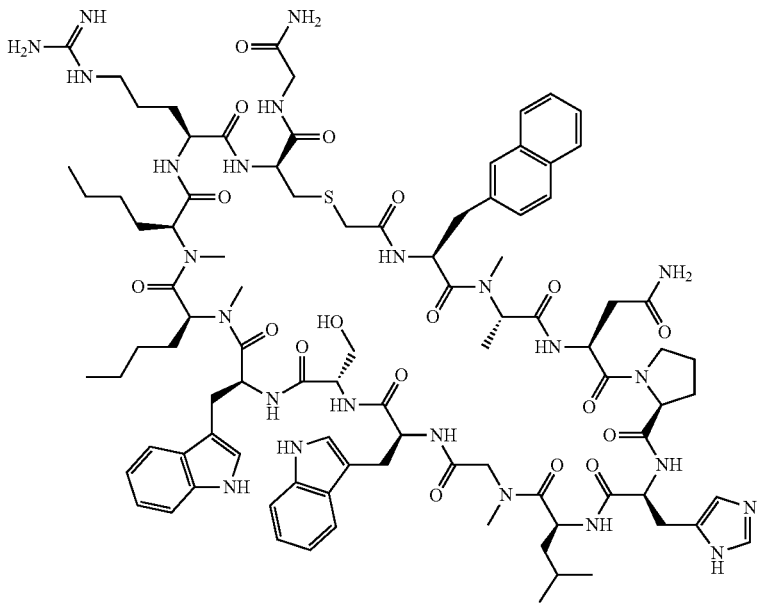

Molecular Weight: 1902.23

Example 0027 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-2-Nal-OH was used in the first amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 4.4 mg, and its estimated purity by LCMS analysis was 100%.

Analysis LCMS Condition D: Retention time=1.84 min; ESI-MS(+) m/z 951.9 (M+2H).

Analysis LCMS Condition E: Retention time=1.77 min; ESI-MS(+) m/z 951.7 (M+2H).

Example 28

Synthesis of Compound No. 27

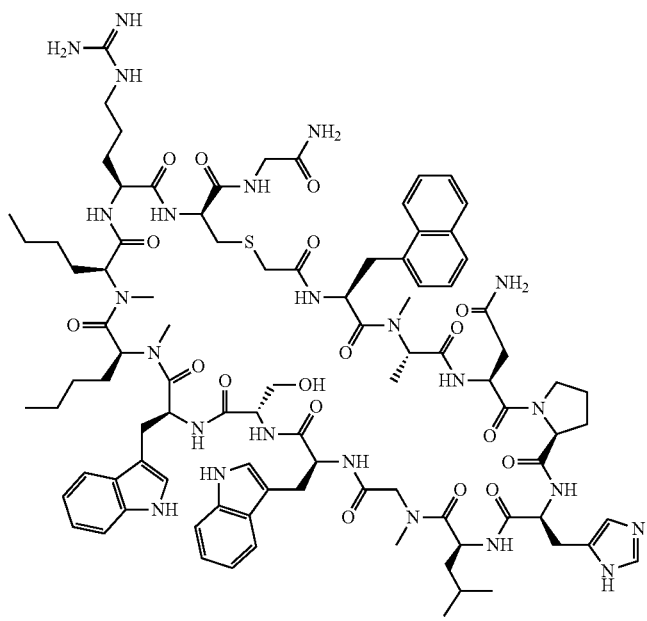

Molecular Weight: 1902.23

Example 0028 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-1-Nal-OH was used in the first amino acid coupling step.

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 3.2 mg, and its estimated purity by LCMS analysis was 99.8%.

Analysis LCMS Condition A: Retention time=0.83 min; ESI-MS(+) m/z 1903.7 (M+H), 952.3 (M+2H).

Analysis HPLC Condition J: Retention time=13.9 min

Example 29

Synthesis of Compound No. 28

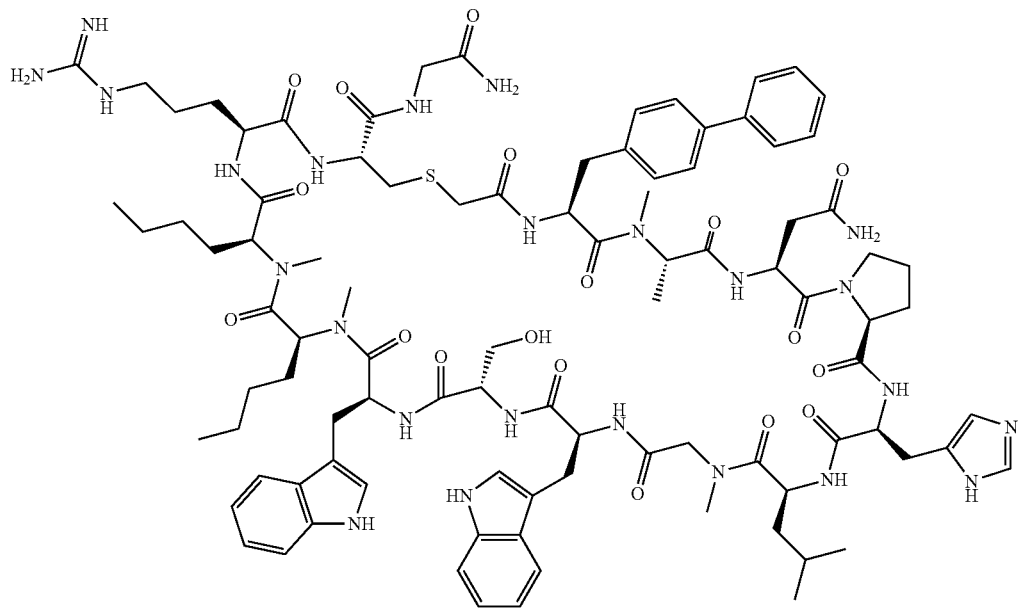

Molecular Weight: 1928.26

Example 0029 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-Bip-OH was used in the first amino acid coupling step.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 100%.

Analysis LCMS Condition D: Retention time=1.91 min; ESI-MS(+) m/z 964.9 (M+2H).

Analysis LCMS Condition E: Retention time=1.84 min; ESI-MS(+) m/z 964.9 (M+2H).

Example 30

Synthesis of Compound No. 29

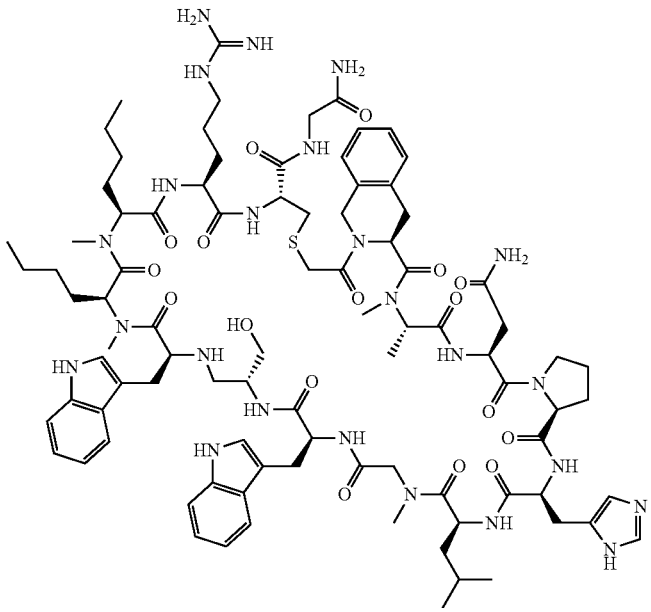

Molecular Weight: 1864.18

Example 0030 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-1-Tiq-OH was used in the first amino acid coupling step.

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 2.2 mg, and its estimated purity by LCMS analysis was 100%.

Analysis LCMS Condition A: Retention time=0.81 min; ESI-MS(+) m/z 933.2 (M+2H)

Analysis HPLC Condition J: Retention time=13.85 min

Example 31

Synthesis of Compound No. 30

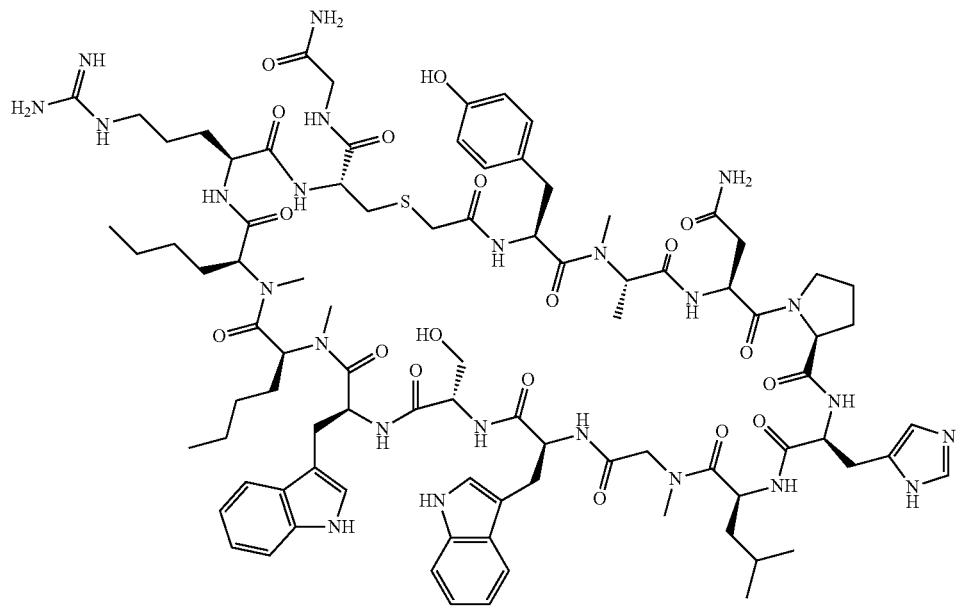

Molecular Weight: 1868.17

Example 0031 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-Tyr(tBu)-OH was used in the first amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 60% B; Flow: 20 mL/min. Fractions containing the desired product were combined and dried via centrifugal evaporation. The yield of the product was 1.8 mg, and its estimated purity by LCMS analysis was 100%.

Analysis LCMS Condition D: Retention time=1.48 min; ESI-MS(+) m/z 934.8 (M+2H).

Analysis LCMS Condition E: Retention time=1.45 min; ESI-MS(+) m/z 934.8 (M+2H).

Example 32

Synthesis of Compound No. 31

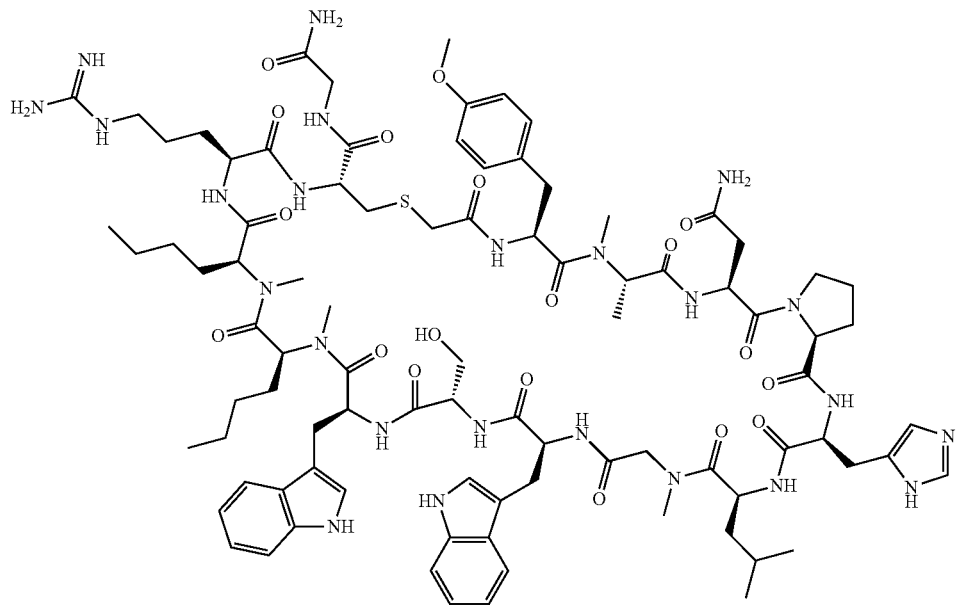

Molecular Weight: 1882.19

Example 0032 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-methoxy-Phe-OH was used in the first amino acid coupling step.

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 1.1 mg, and its estimated purity by LCMS analysis was 99.6%.

Analysis LCMS Condition A: Retention time=0.78 min; ESI-MS(+) m/z 942.0 (M+2H)

Analysis HPLC Condition J: Retention time=13.27 min

Example 33

Synthesis of Compound No. 32

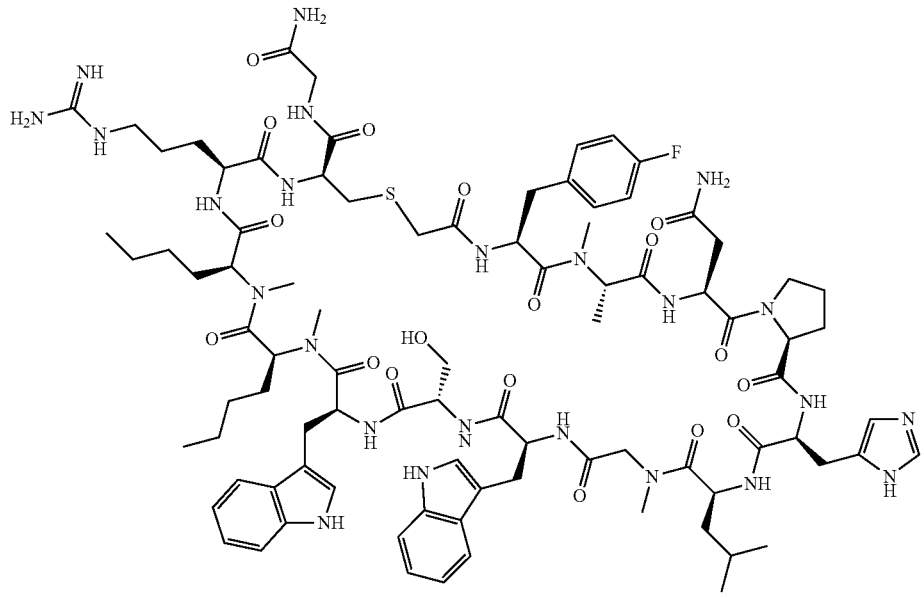

Molecular Weight: 1870.16

Example 0033 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-Fluoro-Phe-OH was used in the First amino acid coupling step.

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 0.85 mg, and its estimated purity by LCMS analysis was 99.8%.

Analysis LCMS Condition A: Retention time=0.78 min; ESI-MS(+) m/z 936.6 (M+2H)

Analysis HPLC Condition J: Retention time=13.58 min

Example 34

Synthesis of Compound No. 33

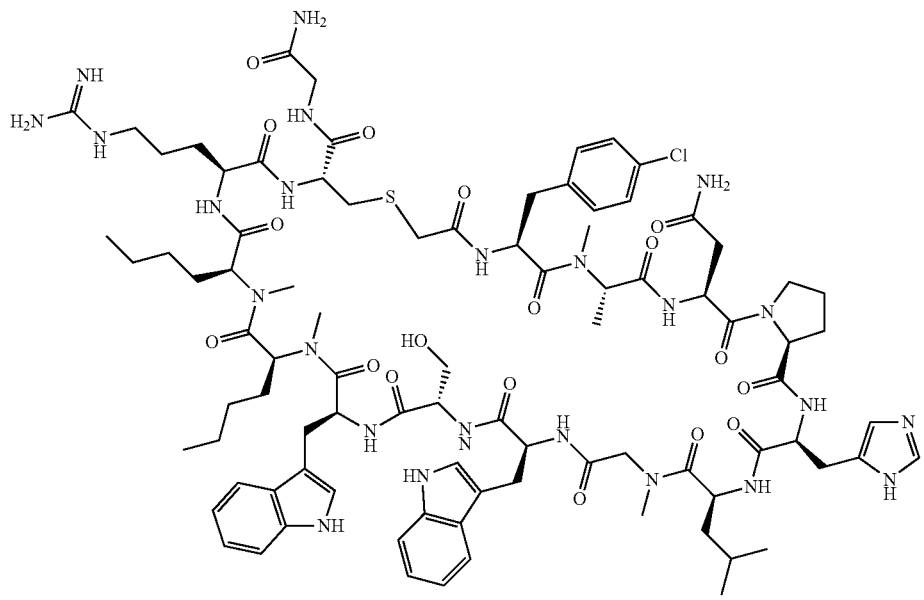

Molecular Weight: 1886.61

Example 0034 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-Chloro-Phe-OH was used in the first amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 0-minute hold at 100% B; Flow: 20 mL/min. Fractions containing the desired product were combined and dried via centrifugal evaporation. The yield of the product was 2.7 mg, and its estimated purity by LCMS analysis was 100%.

Analysis LCMS Condition D: Retention time=1.80 min; ESI-MS(+) m/z 944.1 (M+2H).

Analysis LCMS Condition E: Retention time=1.73 min; ESI-MS(+) m/z 943.6 (M+2H).

Example 35

Synthesis of Compound No. 34

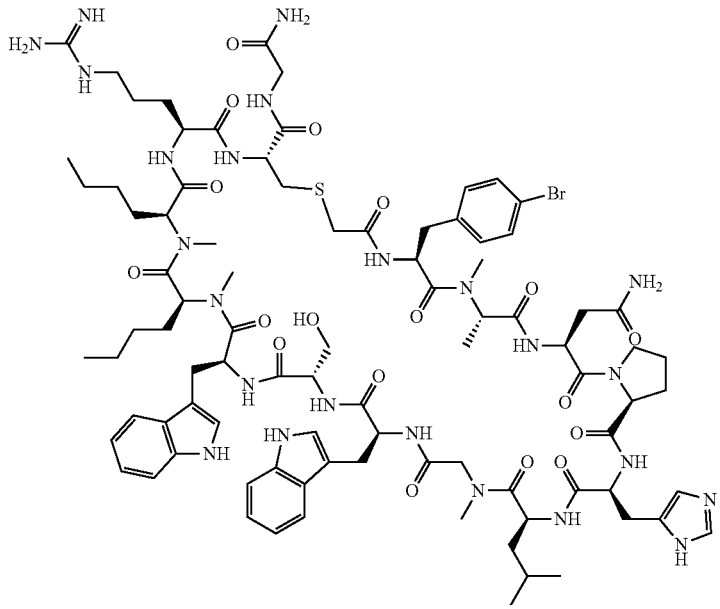

Molecular Weight: 1931.06

Example 0035 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-Bromo-Phe-OH was used in the first amino acid coupling step.

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 0.8 mg, and its estimated purity by LCMS analysis was 99.7%.

Analysis LCMS Condition A: Retention time=0.83 min; ESI-MS(+) m/z 966.3 (M+2H)

Analysis HPLC Condition J: Retention time=13.99 min

Example 36

Synthesis of Compound No. 35

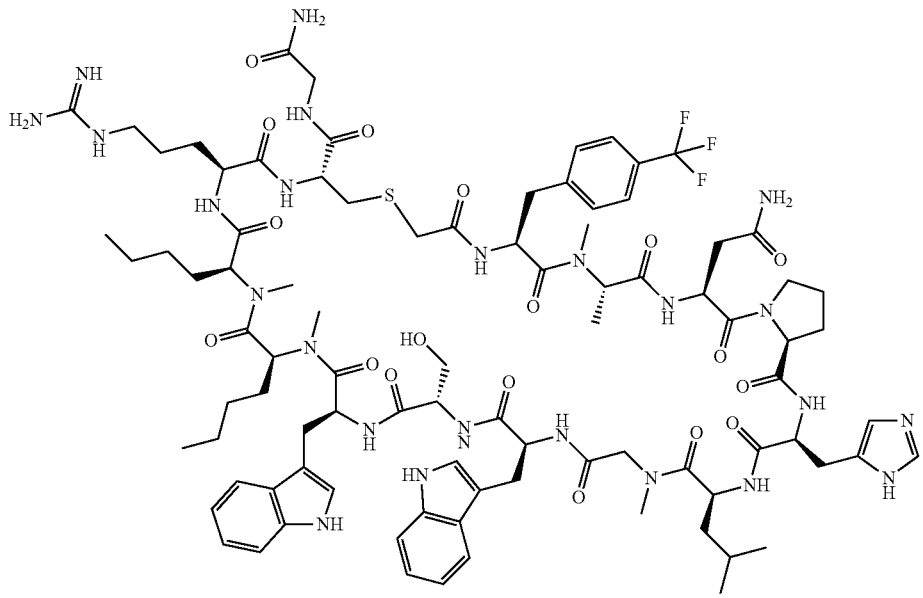

Molecular Weight: 1920.17

Example 0036 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-trifluoromethyl-Phe-OH was used in the first amino acid coupling step.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 minutes, then a 5-minute hold at 100% B; Flow: 20 mL/min. Fractions containing the Desired product were combined and dried via centrifugal evaporation. The yield of the product was 1.5 mg, and its estimated purity by LCMS analysis was 91%.

Analysis LCMS Condition D: Retention time=1.824 min; ESI-MS(+) m/z 960.90 (M+2H)

Analysis LCMS Condition E: Retention time=1.59 min; ESI-MS(+) m/z 960.4 (M+2H)

Example 37

Synthesis of Compound No. 36

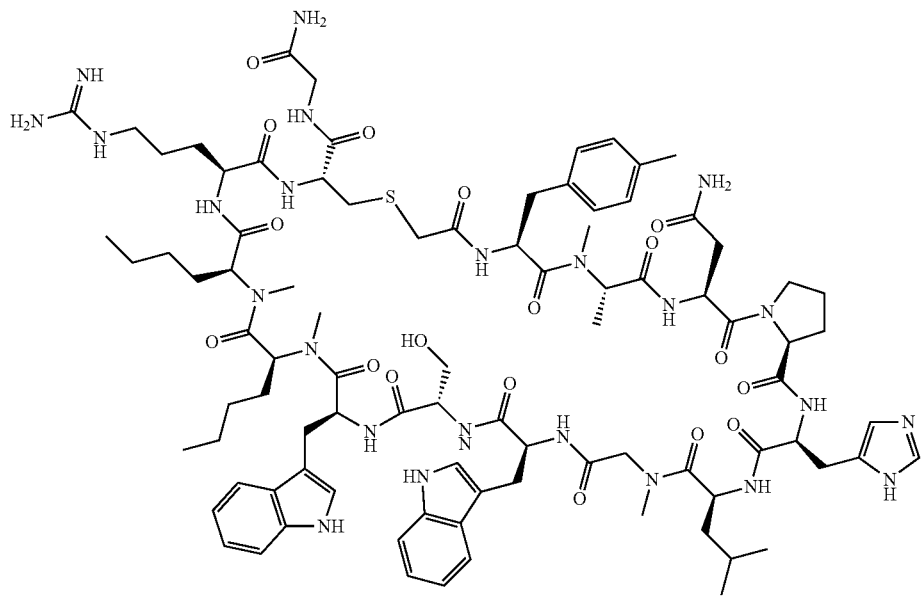

Molecular Weight: 1866.19

Example 0037 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-methyl-Phe-OH was used in the first amino acid coupling step.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 100%.

Analysis LCMS Condition D: Retention time=1.847 min; ESI-MS(+) m/z 933.9 (M+2H).

Analysis LCMS Condition E: Retention time=1.742 min; ESI-MS(+) m/z 933.9 (M+2H).

Example 38

Synthesis of Compound No. 37

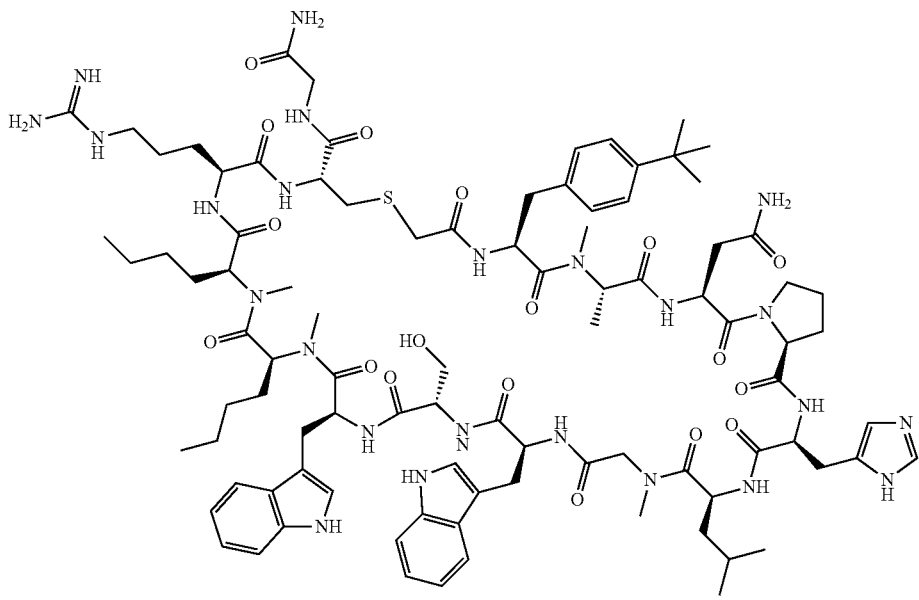

Molecular Weight: 1908.27

Example 0038 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-t-Butyl-Phe-OH was used in the first amino acid coupling step.

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 25 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 95%.

Analysis LCMS Condition D: Retention time=2.003 min; ESI-MS(+) m/z 954.6 (M+2H).

Analysis LCMS Condition E: Retention time=1.786 min; ESI-MS(+) m/z 954.6 (M+2H).

Example 39

Synthesis of Compound No. 38

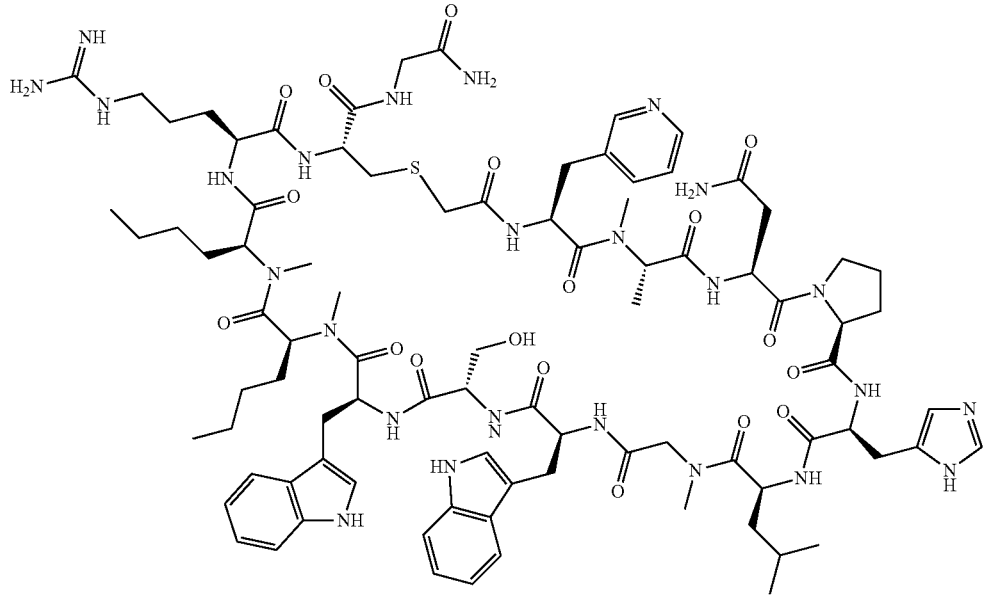

Molecular Weight: 1853.16

Example 0039 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-3-Pyr-OH was used in the first amino acid coupling step.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-55% B over 25 minutes, then a 5-minute hold at 100% B; Flow: 20 mL/min. Fractions containing the desired product were combined and dried via centrifugal evaporation. The yield of the product was 1.2 mg, and its estimated purity by LCMS analysis was 96%.

Analysis LCMS Condition D: Retention time=1.47 min; ESI-MS(+) m/z 927.4 (M+2H).

Analysis LCMS Condition E: Retention time=1.13 min; ESI-MS(+) m/z 927.4 (M+2H).

Example 40

Synthesis of Compound No. 39

Example 0040 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-4-Pyr-OH was used in the first amino acid coupling step.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-55% B over 25 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 94%.

Analysis LCMS Condition D: Retention time=1.448 min; ESI-MS(+) m/z 927.55 (M+2H).

Analysis LCMS Condition E: Retention time=1.121 min; ESI-MS(+) m/z 927.65 (M+2H).

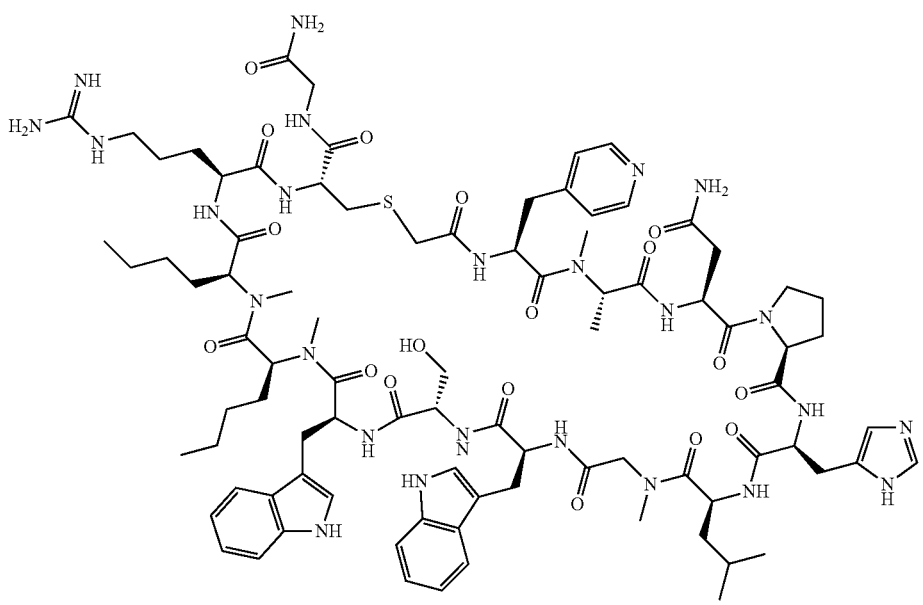

Molecular Weight: 1853.16

Example 41

Synthesis of Compound No. 40

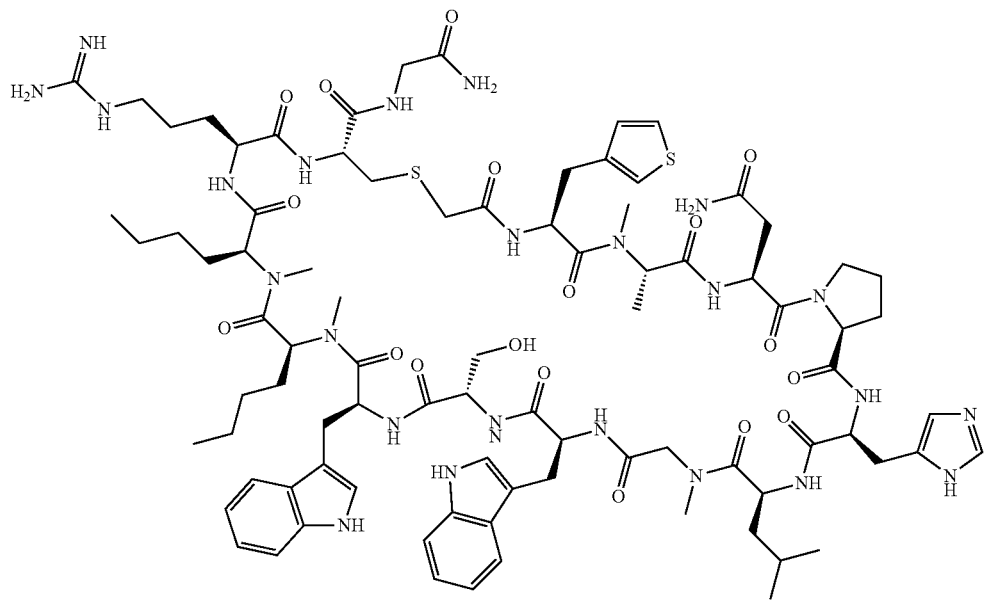

Molecular Weight: 1858.20

Example 0041 was prepared, starting with Intermediate Resin I, following the general synthetic sequence described for the preparation of Example 0001, composed of the following general procedures: "Manual Coupling procedure A", "Chloroacetic acid coupling procedure B", "Global Deprotection Method C", and "Cyclization Method D". Fmoc-3-thienyl Alanine-OH was used in the first amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.6 mg, and its estimated purity by LCMS analysis was 100%.

Analysis LCMS Condition D: Retention time=1.649 min; ESI-MS(+) m/z 1858.8 (M+1), 929.9 (M+2H).

Analysis LCMS Condition E: Retention time=1.589 min; ESI-MS(+) m/z 929.9 (M+2H).

Example 42

Synthesis of Compound No. 41

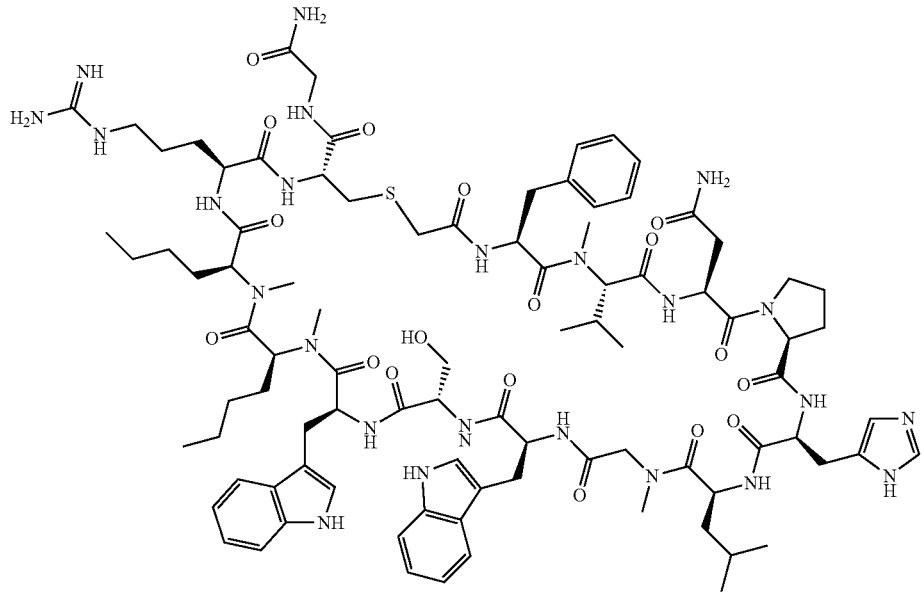

Molecular Weight: 1880.22

Example 0042 was prepared, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final wash procedure", Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 1.5 mg, and its estimated purity by LCMS analysis was 100%.

Analysis LCMS Condition A: Retention time=0.79 min; ESI-MS(+) m/z 941.2 (M+2H)

Analysis HPLC Condition J: Retention time=13.45 min

Example 43

Synthesis of Compound No. 42

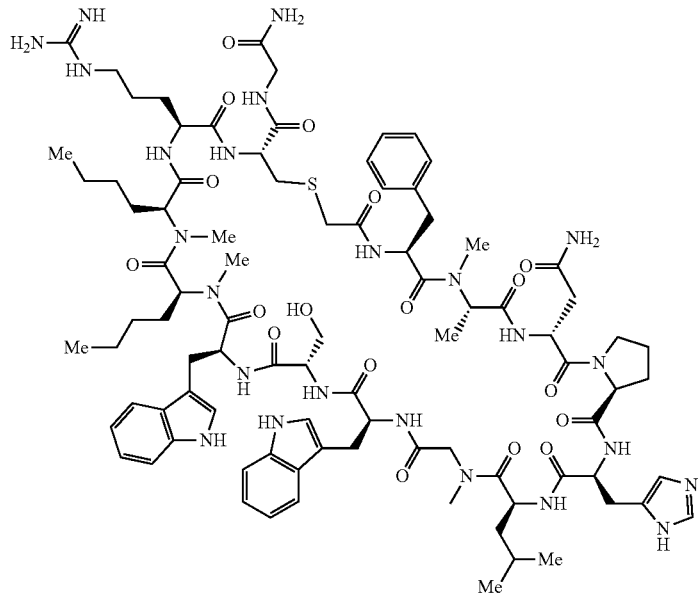

Molecular Weight: 1852.17

Example 0043 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 minutes, then a 0-minute hold at 100% B; Flow: 20 mL/min. Fractions containing the desired product were combined and dried via centrifugal evaporation. The yield of the product was 4.8 mg, and its estimated purity by LCMS analysis was 90%.

Analysis LCMS Condition D: Retention time=1.553 min; ESI-MS(+) m/z 926.9 (M+2H).

Analysis LCMS Condition E: Retention time=1.356 min; ESI-MS(+) m/z 926.7 (M+2H).

Example 44

Synthesis of Compound No. 43

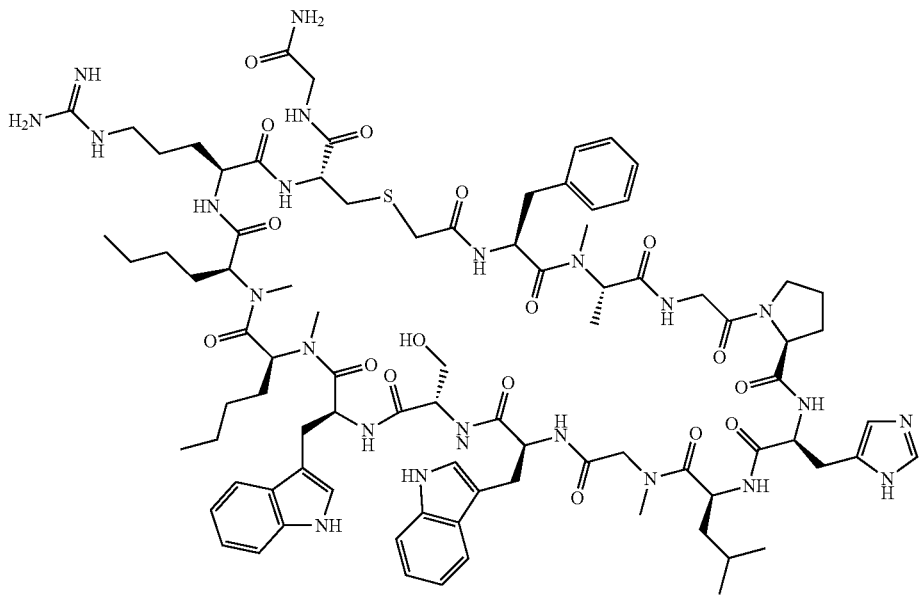

Molecular Weight: 1795.12

Example 0044 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final wash procedure", "Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 2.8 mg, and its estimated purity by LCMS analysis was 99.2%.

Analysis LCMS Condition A: Retention time=0.76 min; ESI-MS(+) m/z 898.6 (M+2H).

Analysis HPLC Condition J: Retention time=12.91 min.

Example 45

Synthesis of Compound No. 44

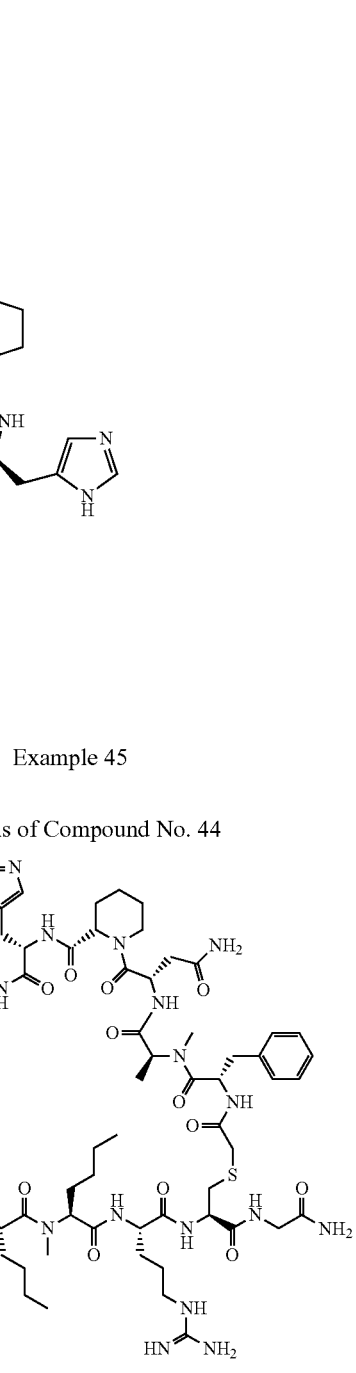

Molecular Weight: 1866.19

Example 0045 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 20-60% B over 25 minutes; Flow: 20 mL/min. Fractions containing the desired product were combined and dried via centrifugal evaporation. The yield of the product was 5.9 mg, and its estimated purity by LCMS analysis was 98% by "Analysis LCMS conditions B and D".

Analysis LCMS condition B: Retention time=1.547 min; ESI-MS(+) m/z 934.65 (M+2H).

Analysis LCMS condition D: Retention time=1.732 min; ESI-MS(+) m/z 933.95 (M+2H).

Example 46

Synthesis of Compound No. 45

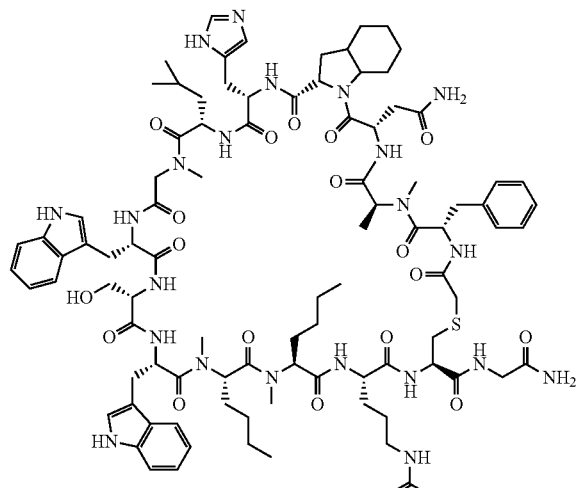

Molecular Weight: 1906.26

Example 0046 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 30-70% B over 25 minutes; Flow: 20 mL/min. Fractions containing the desired product were combined and dried via centrifugal evaporation. The yield of the product was 2.5 mg, and its estimated purity by LCMS analysis was 95% by "Analysis LCMS conditions B and D".

Analysis LCMS condition B: Retention time=1.710 min; ESI-MS(+) m/z 954.20 (M+2H).

Analysis LCMS condition D: Retention time=1.966 min; ESI-MS(+) m/z 954.20 (M+2H).

Example 47

Synthesis of Compound No. 46

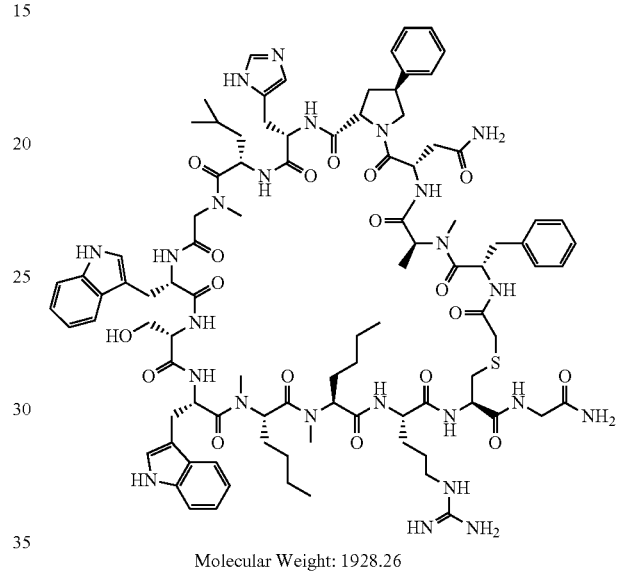

Molecular Weight: 1928.26

Example 0047 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 25-70% B over 25 minutes; Flow: 20 mL/min. Fractions containing the desired product were combined and dried via centrifugal evaporation. The yield of the product was 2.4 mg, and its estimated purity by LCMS analysis was 96% by "Analysis LCMS conditions B and D".

Analysis LCMS condition B: Retention time=1.851 min; ESI-MS(+) m/z 964.95 (M+2H).

Analysis LCMS condition D: Retention time=1.957 min; ESI-MS(+) m/z 964.75 (M+2H).

Example 48

Synthesis of Compound No. 47

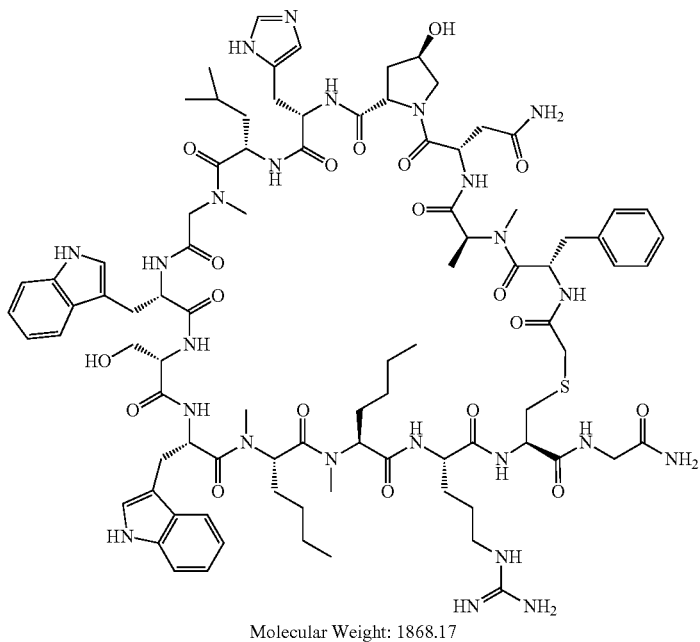

Molecular Weight: 1868.17

Example 48 was prepared following the general synthetic sequence described for the preparation of Example 6, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% TFA; Mobile Phase B: 95:5 acetonitrile:water with 0.1% TFA; Gradient: 15-60% B over 25 minutes; Flow: 20 mL/min. Fractions containing the desired product were combined and dried via centrifugal evaporation. The yield of the product was 4.5 mg, and its estimated purity by LCMS analysis was 98% by "Analysis LCMS conditions B and D".

Analysis LCMS condition B: Retention time=1.486 min; ESI-MS(+) m/z 934.95 (M+2H).

Analysis LCMS condition D: Retention time=1.636 min; ESI-MS(+) m/z 935.00 (M+2H).

Example 49

Synthesis of Compound No. 48

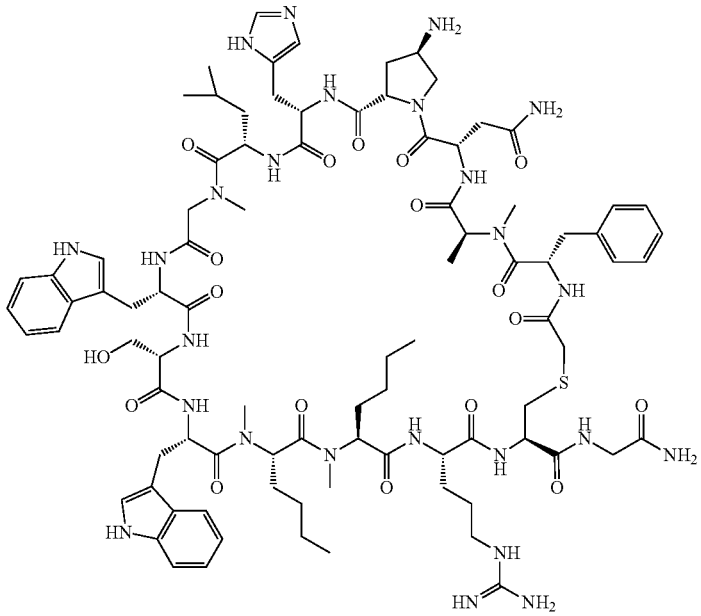

Molecular Weight: 1867.18

Example 0049 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 20-65% B over 25 minutes, then a 5-minute hold at 65% B; Flow: 20 mL/min. Fractions containing the desired product were combined and dried via centrifugal evaporation. The yield of the product was 8.7 mg, and its estimated purity by LCMS analysis was 99% by "Analysis LCMS conditions B and D".

Analysis LCMS condition B: Retention time=1.290 min; ESI-MS(+) m/z 934.45 (M+2H).

Analysis LCMS condition D: Retention time=1.567 min; ESI-MS(+) m/z 934.55 (M+2H).

Example 50

Synthesis of Compound No. 49

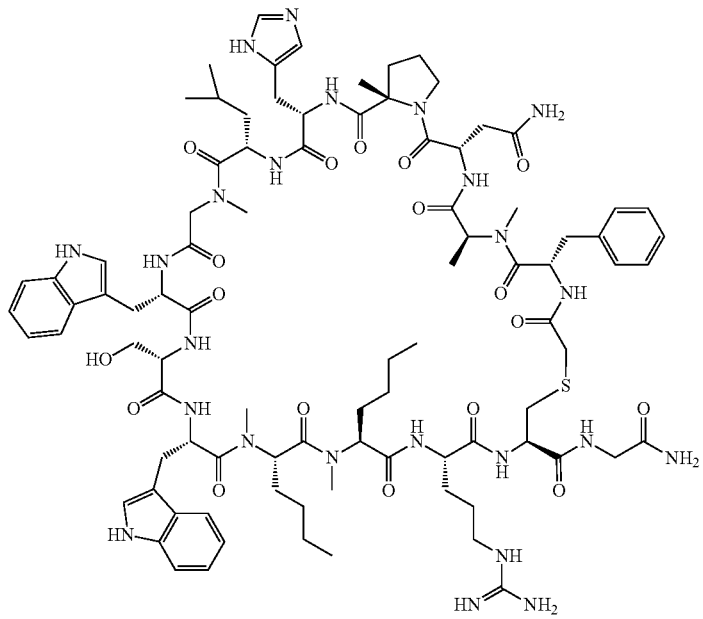

Molecular Weight: 1866.19

Example 0050 was prepared following the general synthetic sequence described for the preparation of Example 006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 15-60% B over 25 minutes, then a 5-minute hold at 60% B; Flow: 20 mL/min. Fractions containing the desired product were combined and dried via centrifugal evaporation. The yield of the product was 6.7 mg, and its estimated purity by LCMS analysis was 99% by "Analysis LCMS conditions B and D".

Analysis LCMS condition B: Retention time=1.623 min; ESI-MS(+) m/z 933.95 (M+2H).

Analysis LCMS condition D: Retention time=1.841 min; ESI-MS(+) m/z 933.95 (M+2H).

Example 51

Synthesis of Compound No. 50

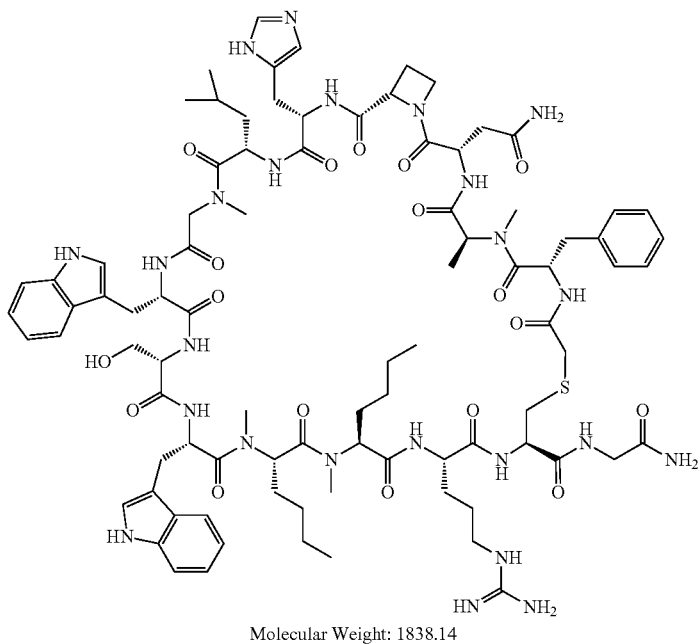

Molecular Weight: 1838.14

Example 0051 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure"; "Prelude Method A: Chloroacetyl chloride coupling procedure A", "Global Deprotection Method C" and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% TFA; Mobile Phase B: 95:5 acetonitrile:water with 0.1% TFA; Gradient: 15-60% B over 25 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 97% by "Analysis LCMS conditions B and D".

Analysis LCMS condition B: Retention time=1.476 min; ESI-MS(+) m/z 920.00 (M+2H).

Analysis LCMS condition D: Retention time=1.670 min; ESI-MS(+) m/z 919.95 (M+2H).

Example 52

Synthesis of Compound No. 51

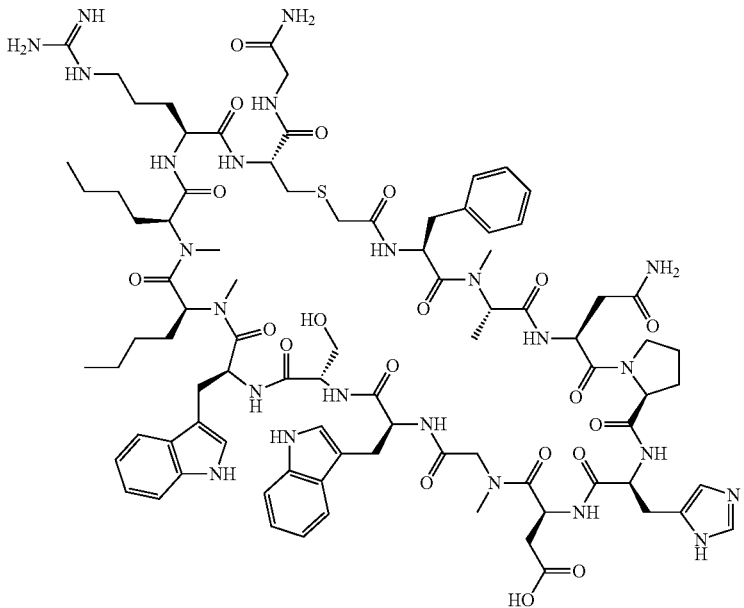

Molecular Weight: 1854.10

Example 0052 was prepared, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final wash procedure", Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 3.3 mg, and its estimated purity by LCMS analysis was 97.5%.

Analysis LCMS Condition A: Retention time=0.80 min; ESI-MS(+) m/z 928.0 (M+2H).

Analysis HPLC Condition J: Retention time=13.38 min.

Example 53

Synthesis of Compound No. 52

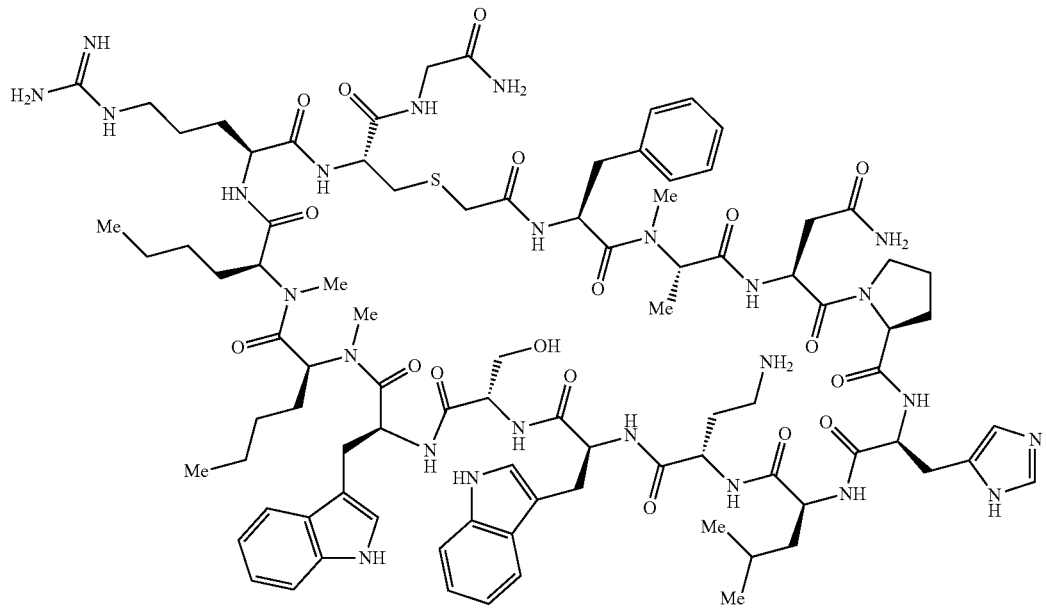

Molecular Weight: 1881.21

Example 0053 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 0.6 mg, and its estimated purity by LCMS analysis was 100%.

Analysis LCMS Condition D: Retention time=1.390 min; ESI-MS(+) m/z 941.35 (M+2H), 1881.85 (M+H).

Analysis LCMS Condition E: Retention time=1.355 min; ESI-MS(+) m/z 941.50 (M+2H).

Example 54

Synthesis of Compound No. 53

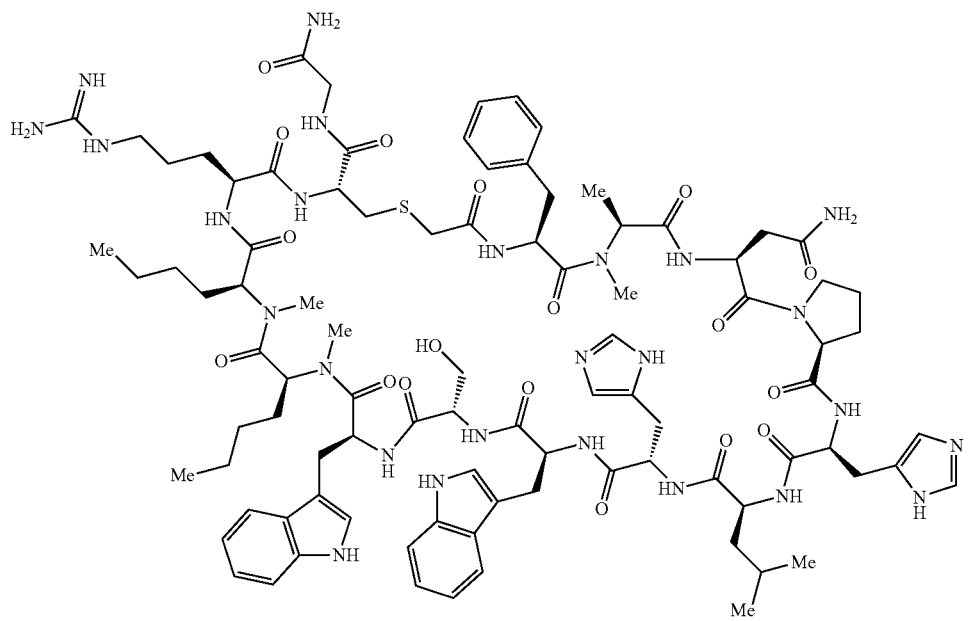

Molecular Weight: 1918.23

Example 0054 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 100%.

Analysis LCMS Condition D: Retention time=1.682 min; ESI-MS(+) m/z 959.85 (M+2H).

Analysis LCMS Condition E: Retention time=1.607 min; ESI-MS(+) m/z 959.85 (M+2H).

Example 55

Synthesis of Compound No. 54

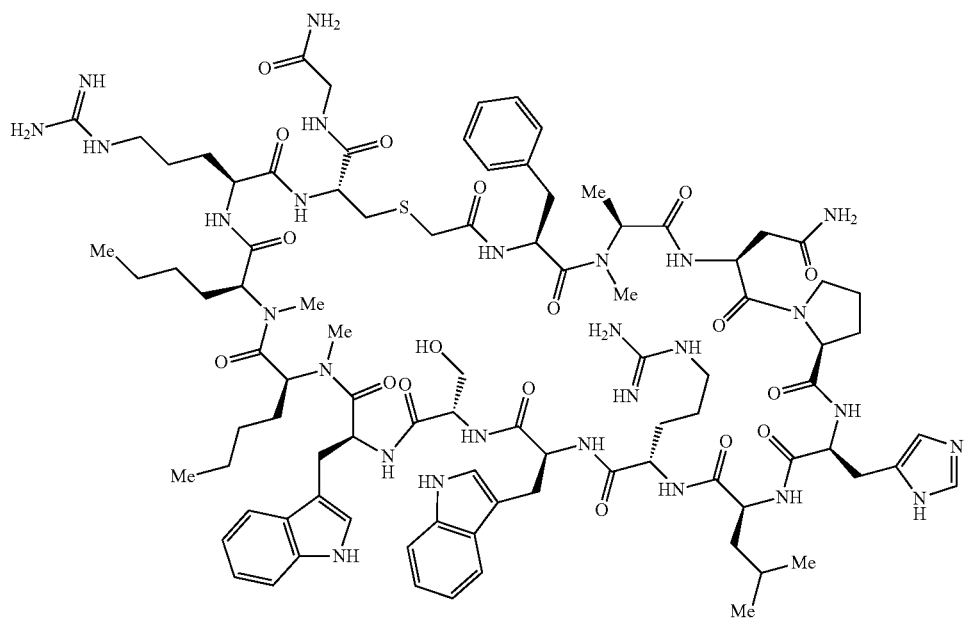

Molecular Weight: 1937.28

Example 0055 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 0-minute hold at 55% B; Flow: 20 mL/min. Fractions containing the desired product were combined and dried via centrifugal evaporation. The yield of the product was 1.5 mg, and its estimated purity by LCMS analysis was 100%.

Analysis LCMS Condition D: Retention time=1.398 min; ESI-MS(+) m/z 969.45 (M+2H).

Analysis LCMS Condition E: Retention time=1.360 min; ESI-MS(+) m/z 969.75 (M+2H).

Example 56

Synthesis of Compound No. 55

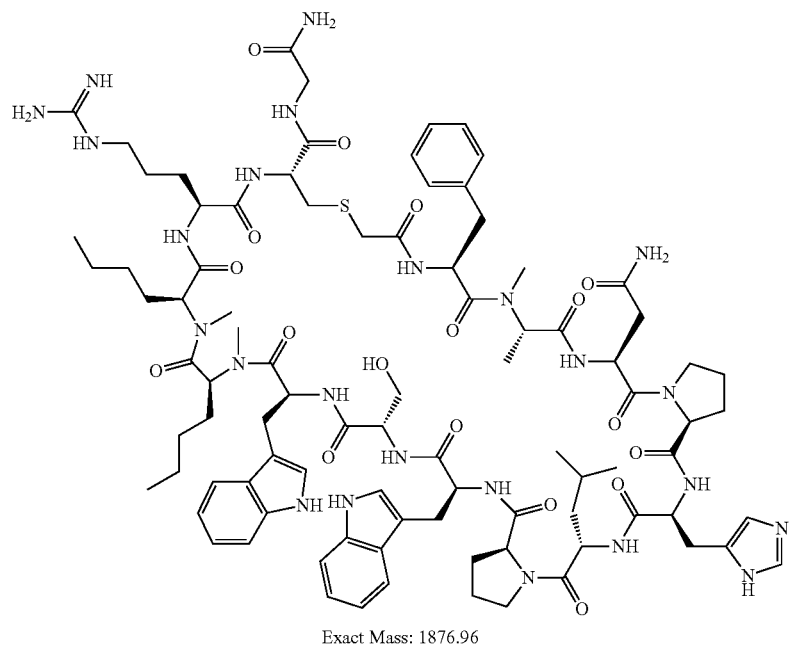 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccccc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Exact Mass: 1876.96

Example 0056 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 5.0 mg, and its estimated purity by LCMS analysis was 100%.

Analysis LCMS Condition D: Retention time=1.67 min; ESI-MS(+) m/z 940.2 (M+2H).

Analysis LCMS Condition E: Retention time=1.73 min; ESI-MS(+) m/z 940.2 (M+2H).

Example 57
Synthesis of Compound No. 56

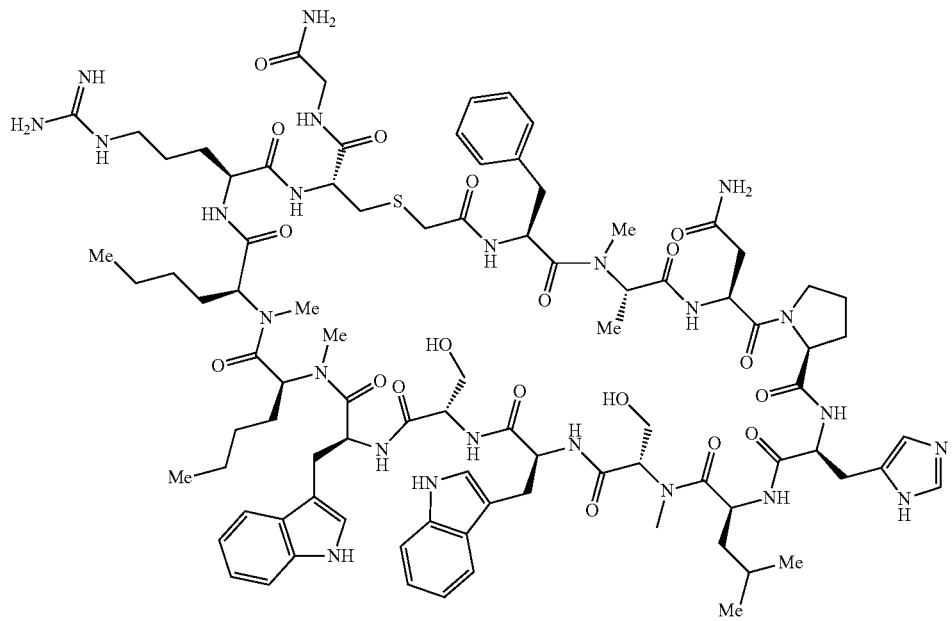

Molecular Weight: 1882.19

Example 0057 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 minutes, then a 0-minute hold at 100% B; Flow: 20 mL/min. Fractions containing the desired product were combined and dried via centrifugal evaporation. The yield of the product was 4.0 mg, and its estimated purity by LCMS analysis was 98%.

Analysis LCMS Condition D: Retention time=1.714 min; ESI-MS(+) m/z 1882.85 (M+1), 941.90 (M+2)

Analysis LCMS Condition E: Retention time=1.532 min; ESI-MS(+) m/z 941.90 (M+2)

Example 58
Synthesis of Compound No. 57

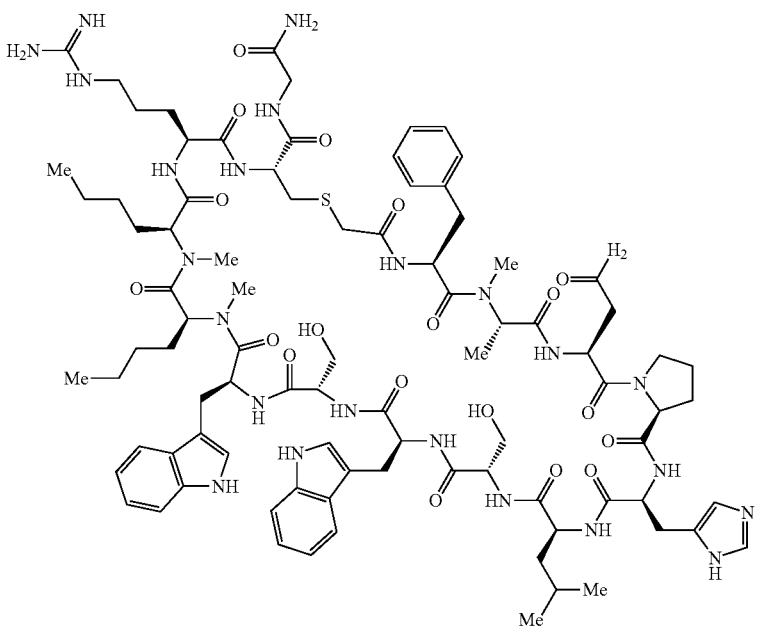

Molecular Weight: 1868.17

Example 0058 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 3.68 mg, and its estimated purity by LCMS analysis was 97.4%.

Analysis LCMS Condition D: Retention time=1.714 min; ESI-MS(+) m/z 1868.85 (M+1), 934.85 (M+2)

Analysis LCMS Condition E: Retention time=1.526 min; ESI-MS(+) m/z 934.65 (M+2)

Example 59

Synthesis of Compound No. 58

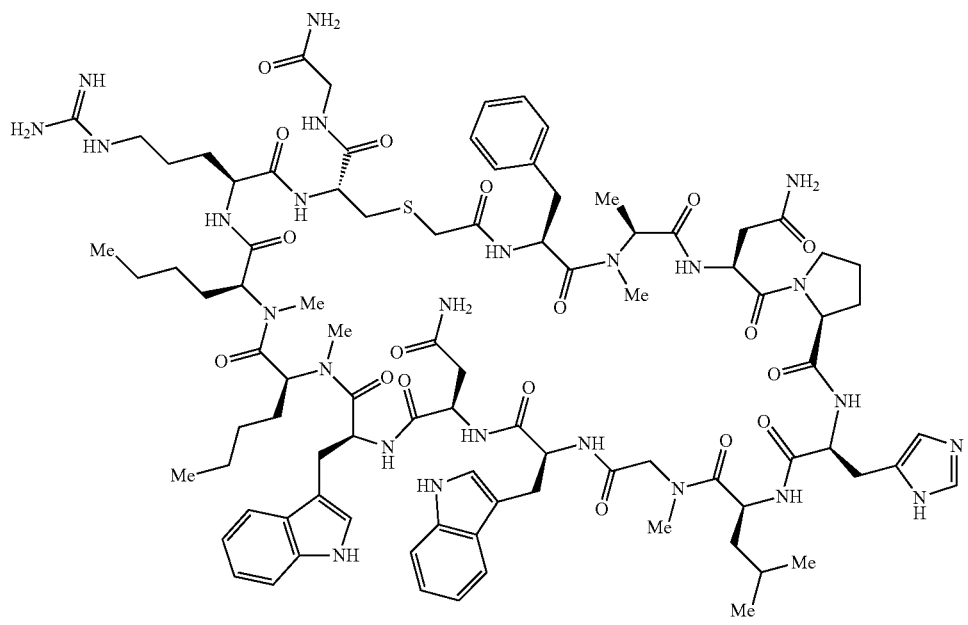

Molecular Weight: 1879.19

Example 0059 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.45 mg, and its estimated purity by LCMS analysis was 99%.

Analysis LCMS Condition D: Retention time=1.454 min; ESI-MS(+) m/z 1879.90 (M+1), 940.55 (M+2)

Example 60

Synthesis of Compound No. 59

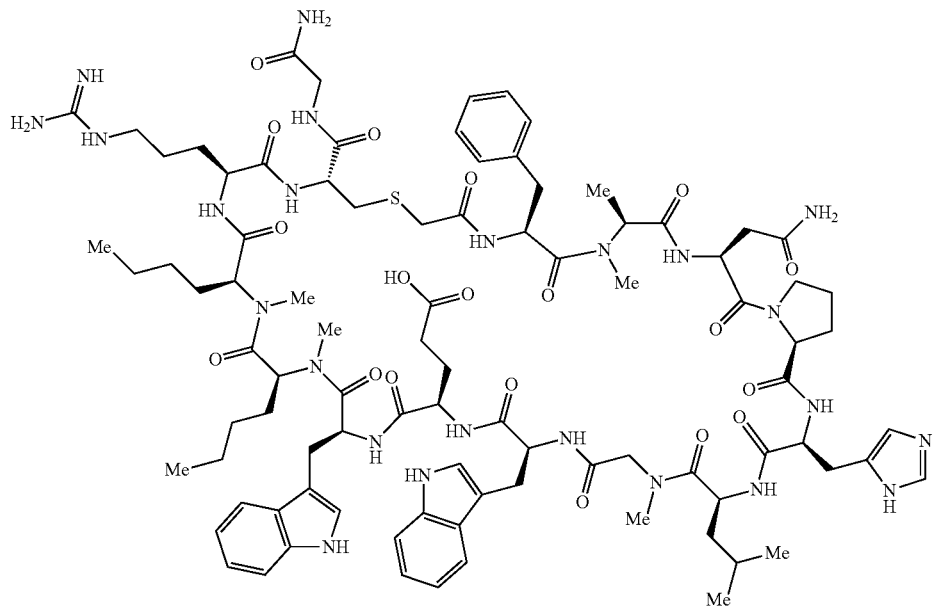

Molecular Weight: 1894.20

Example 0060 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 3.7 mg, and its estimated purity by LCMS analysis was 94.4%.

Analysis LCMS Condition D: Retention time=1.452 min; ESI-MS(+) m/z 947.60 (M+2)

Analysis LCMS Condition E: Retention time=1.257 min; ESI-MS(+) m/z 947.65 (M+2)

Example 61

Synthesis of Compound No. 60

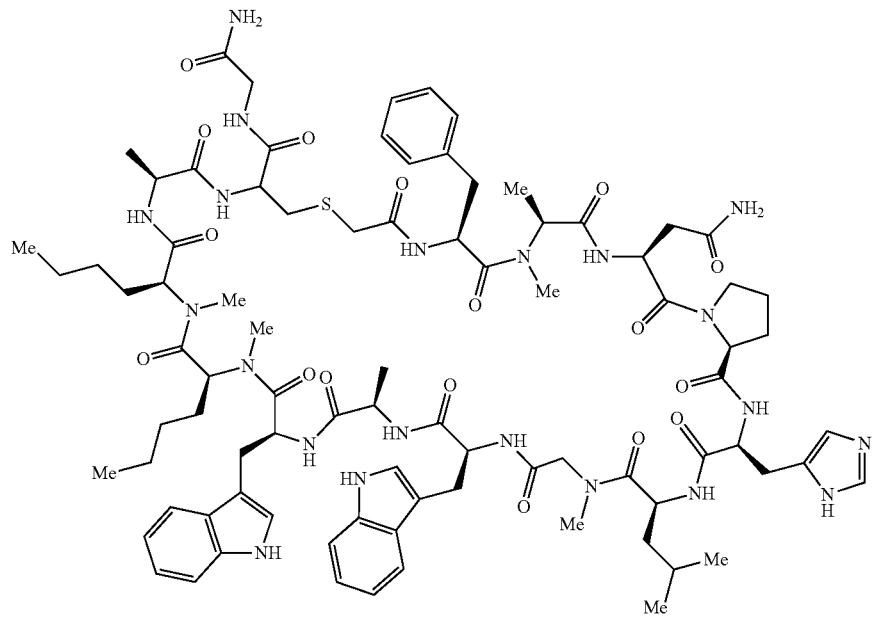

Molecular Weight: 1751.06

Example 0061 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 2.1 mg, and its estimated purity by LCMS analysis was 92.5%.

Analysis LCMS Condition D: Retention time=1.800 min; ESI-MS(+) m/z 1751.85 (M+1), 876.35 (M+2)

Analysis LCMS Condition E: Retention time=1.620 min; ESI-MS(+) m/z 876.35 (M+2)

Example 62

Synthesis of Compound No. 61

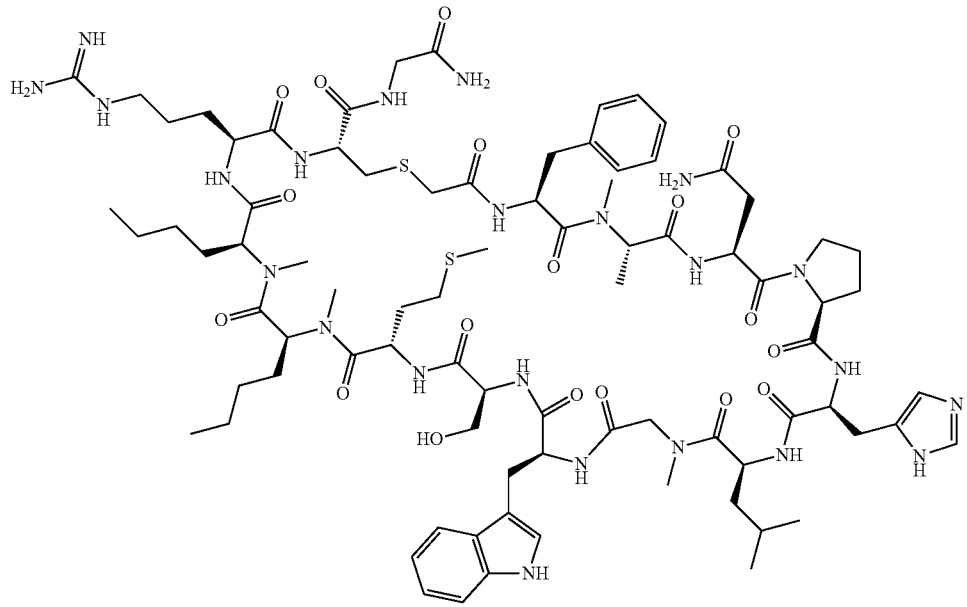

Molecular Weight: 1797.15

Example 0062 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 0-minute hold at 100% B; Flow: 20 mL/min. Fractions containing the desired product were combined and dried via centrifugal evaporation. The yield of the product was 3.1 mg, and its estimated purity by LCMS analysis was 100%.

Analysis LCMS Condition D: Retention time=1.616 min; ESI-MS(+) m/z 899.40 (M+2H).

Analysis LCMS Condition E: Retention time=1.558 min; ESI-MS(+) m/z 899.35 (M+2H).

Example 63

Synthesis of Compound No. 62

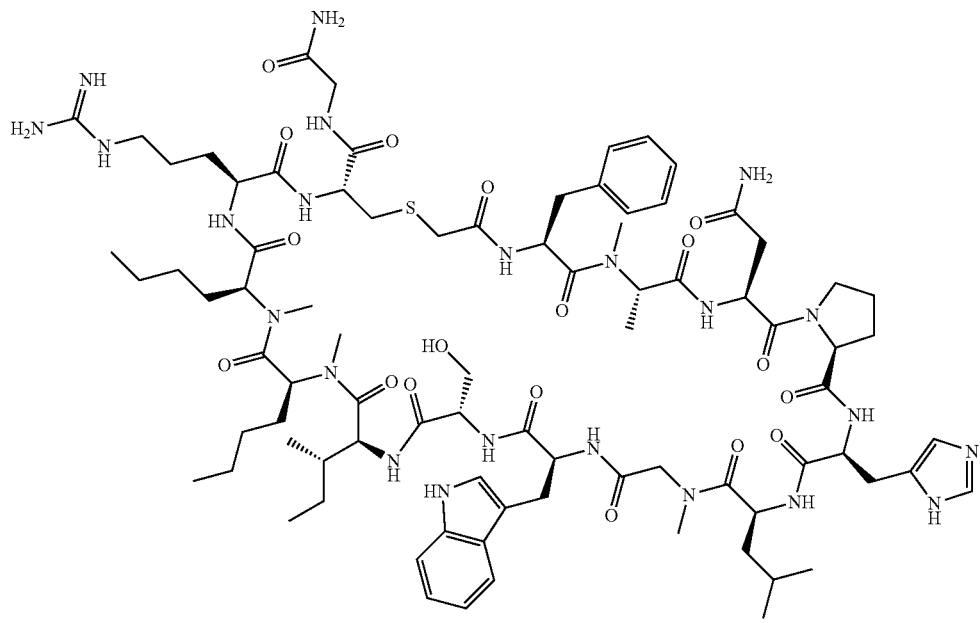

Molecular Weight: 1779.12

Example 0063 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 99%.

Analysis LCMS Condition D: Retention time=1.575 min; ESI-MS(+) m/z 1779.90 (M+1), 890.30 (M+2)

Analysis LCMS Condition E: Retention time=1.37 min; ESI-MS(+) m/z 889.9 (M+2H).

Example 64

Synthesis of Compound No. 63

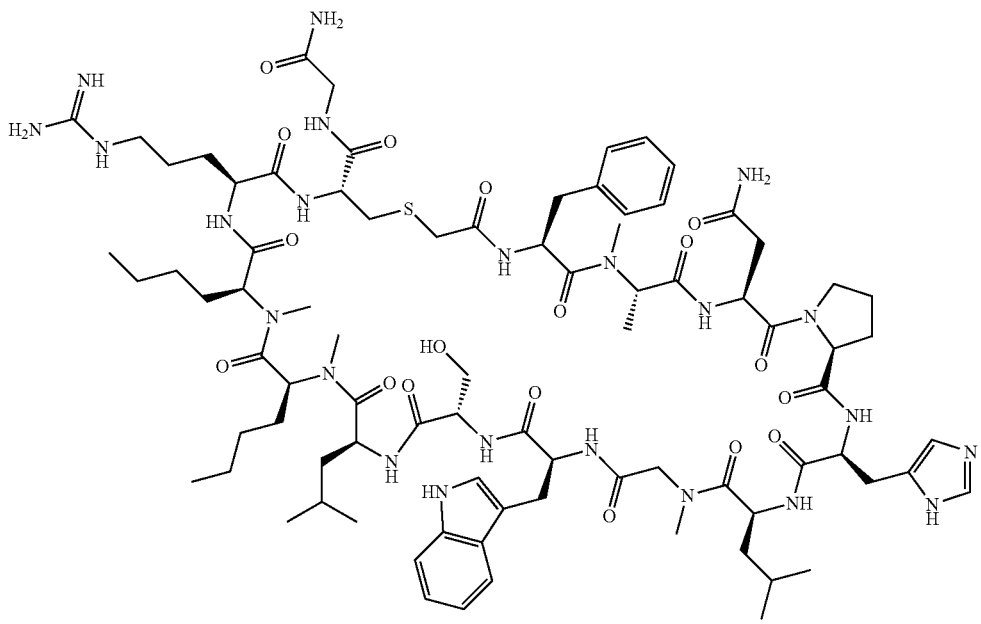

Molecular Weight: 1779.12

Example 0064 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 3.5 mg, and its estimated purity by LCMS analysis was 100%.

Analysis LCMS Condition D: Retention time=1.65 min; ESI-MS(+) m/z 890.4 (M+2H).

Analysis LCMS Condition E: Retention time=1.54 min; ESI-MS(+) m/z 890.3 (M+2H).

Example 65

Synthesis of Compound No. 64

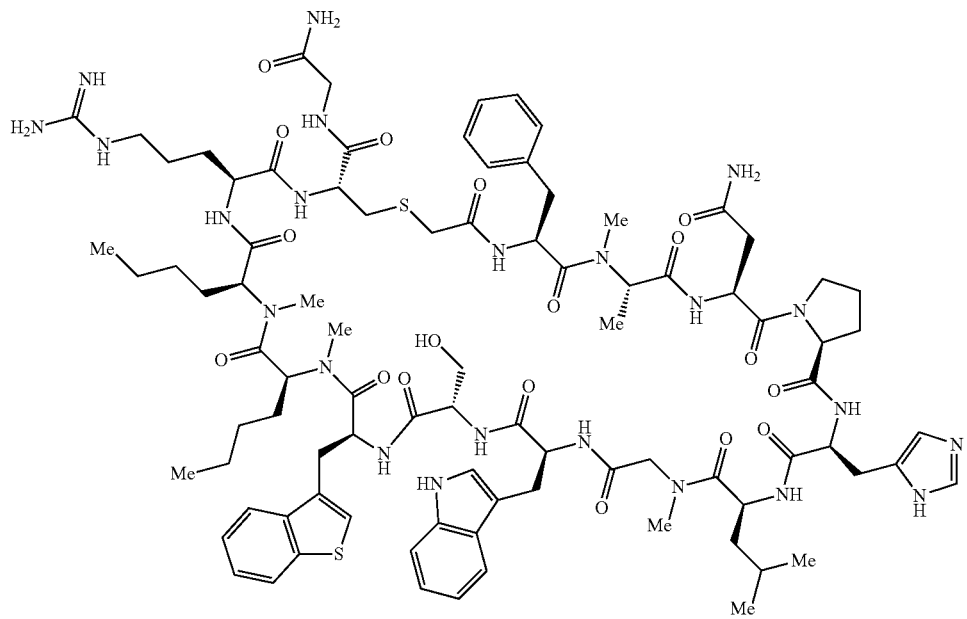

Molecular Weight: 1869.22

Example 0065 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 2.1 mg, and its estimated purity by LCMS analysis was 96.4%.

Analysis LCMS Condition D: Retention time=1.847 min; ESI-MS(+) m/z 935.70 (M+2)

Analysis LCMS Condition E: Retention time=1.658 min; ESI-MS(+) m/z 935.60 (M+2)

Example 66

Synthesis of Compound No. 65

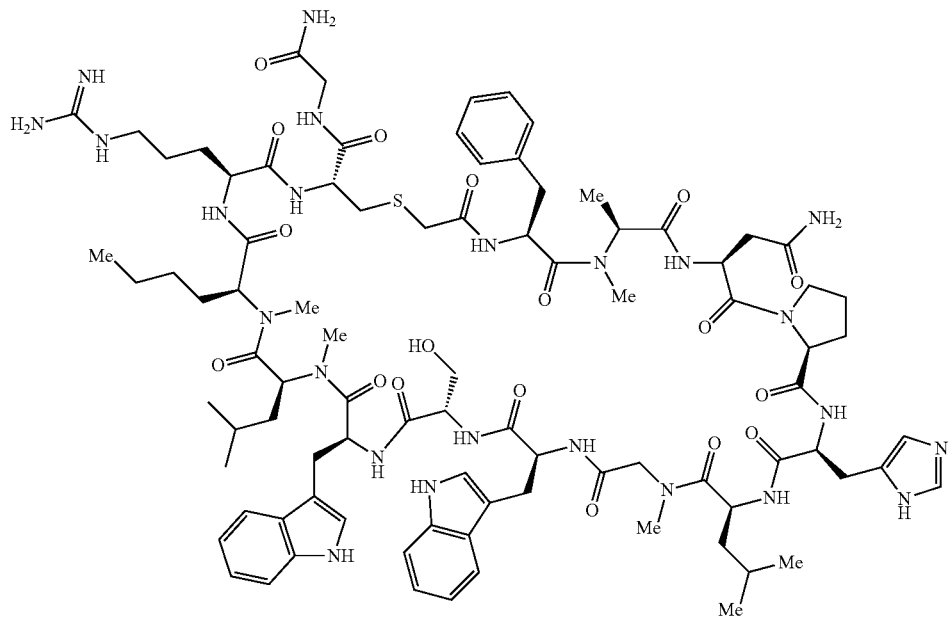

Molecular Weight: 1852.17

Example 0066 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.44 mg, and its estimated purity by LCMS analysis was 100%.

Analysis LCMS Condition D: Retention time=1.605 min; ESI-MS(+) m/z 926.95 (M+2)

Example 67

Synthesis of Compound No. 66

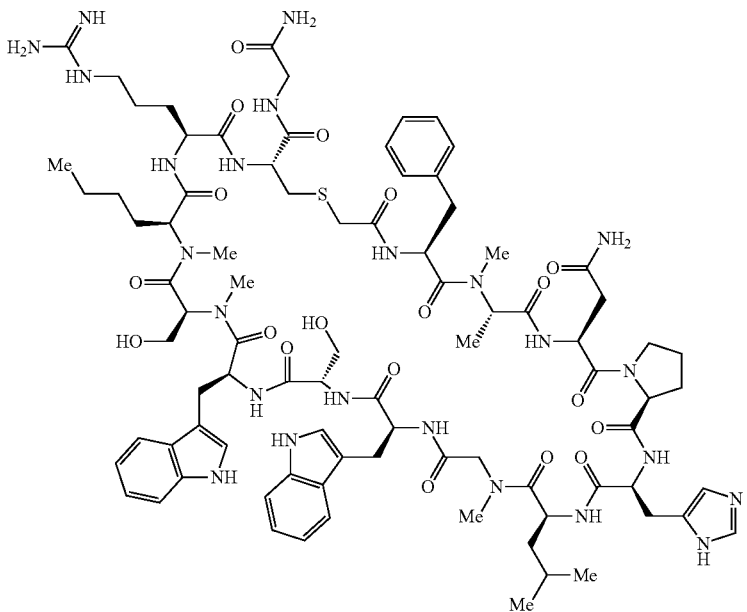

Molecular Weight: 1826.09

Example 0067 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.41 mg, and its estimated purity by LCMS analysis was 97.3%.

Analysis LCMS Condition D: Retention time=1.388 min; ESI-MS(+) m/z 914.35 (M+2)

Analysis LCMS Condition E: Retention time=1.228 min; ESI-MS(+) m/z 914.30 (M+2)

Example 68

Synthesis of Compound No. 67

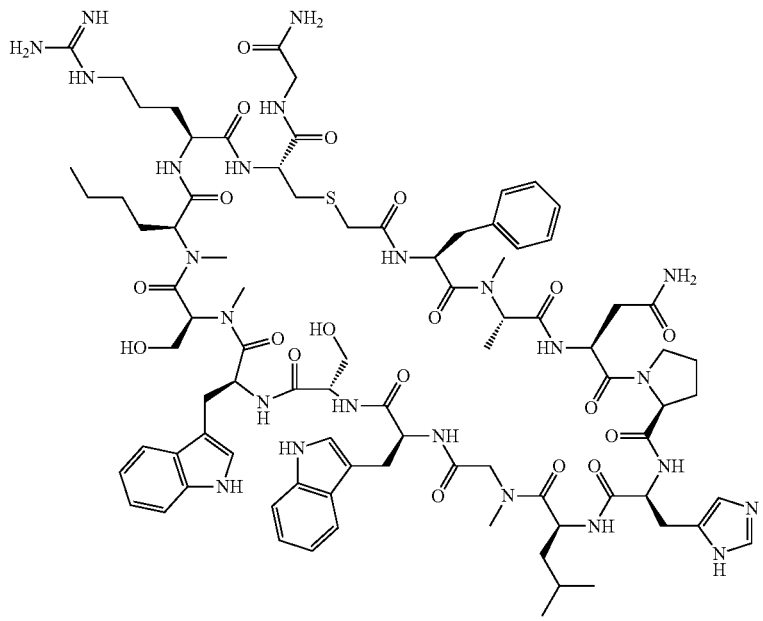

Molecular Weight: 1886.18

Example 0068 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 minutes, then a 5-minute hold at 100% B; Flow: 20 mL/min. Fractions containing the desired product were combined and dried via centrifugal evaporation. The yield of the product was 12.9 mg, and its estimated purity by LCMS analysis was 98%.

Analysis LCMS Condition D: Retention time=1.659 min; ESI-MS(+) m/z 1886.80 (M+1), 943.90 (M+2)

Analysis LCMS Condition E: Retention time=1.449 min; ESI-MS(+) m/z 943.90 (M+2)

Example 69

Synthesis of Compound No. 68

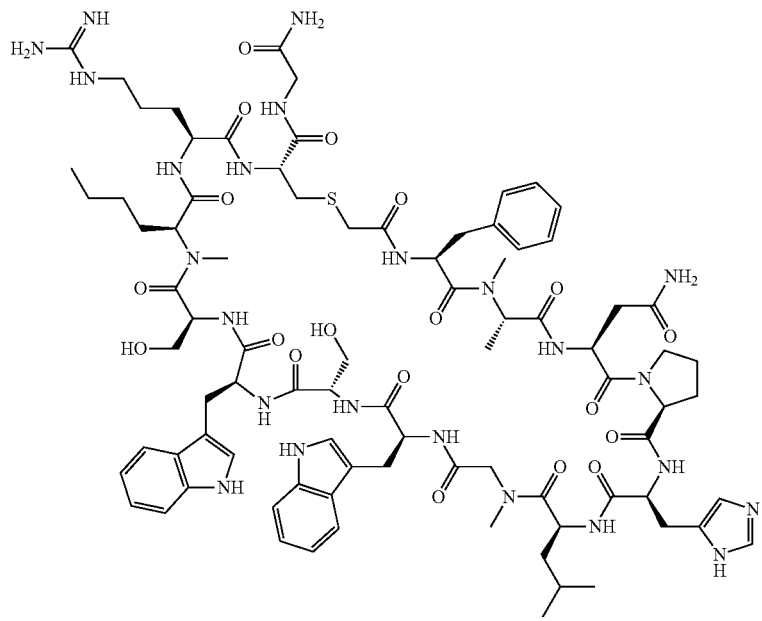

Molecular Weight: 1812.06

Example 0069 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 25 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 95%.

Analysis LCMS Condition D: Retention time=1.402 min; ESI-MS(+) m/z 1812.80 (M+1), 906.80 (M+2)

Analysis LCMS Condition E: Retention time=1.216 min; ESI-MS(+) m/z 906.80 (M+2)

Example 70

Synthesis of Compound No. 69

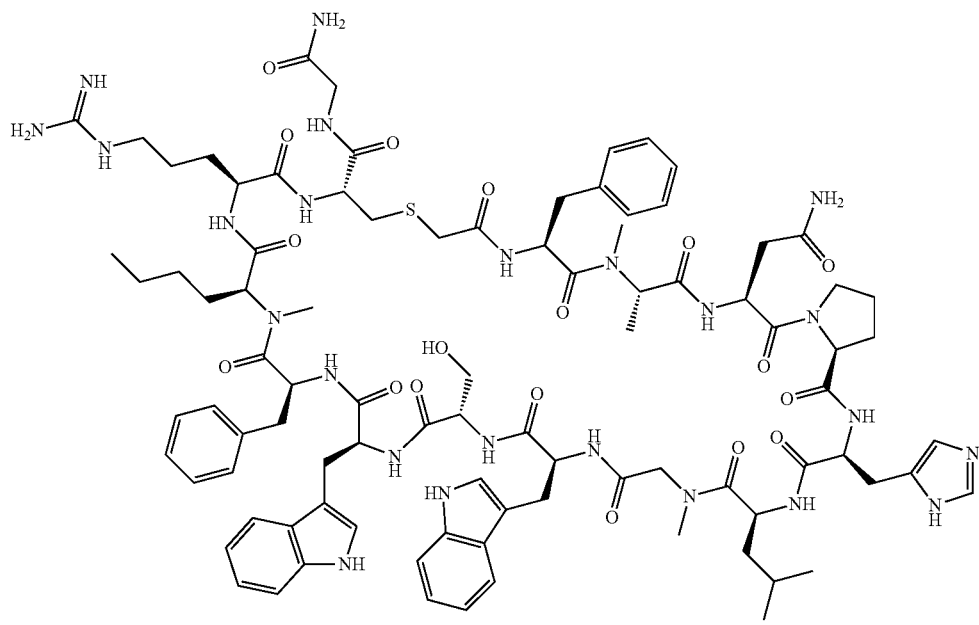

Molecular Weight: 1872.16

Example 0070 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 98%.

Analysis LCMS Condition D: Retention time=1.590 min; ESI-MS(+) m/z 1872.85 (M+1), 936.90 (M+2)

Analysis LCMS Condition E: Retention time=1.377 min; ESI-MS(+) m/z 936.65 (M+2)

Example 71

Synthesis of Compound No. 70

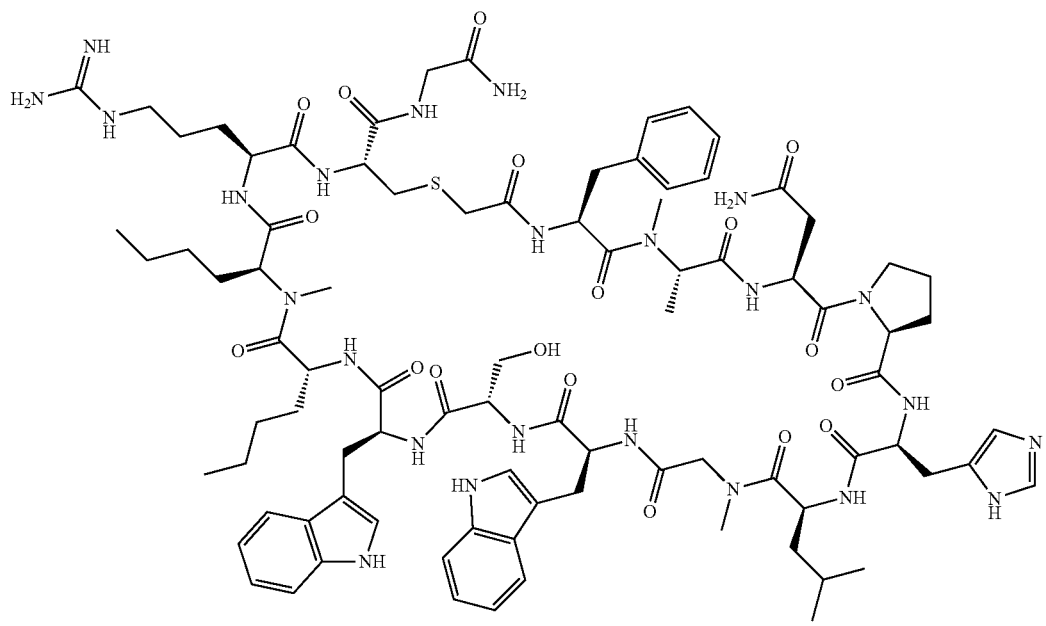

Molecular Weight: 1838.14

Example 0071 was prepared, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final wash procedure", Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 3-minute hold at 100% B; Flow: 20 mL/min. Fractions containing the desired product were combined and dried via centrifugal evaporation. The yield of the product was 1.1 mg, and its estimated purity by LCMS analysis was 97.9%.

Analysis LCMS Condition A: Retention time=0.80 min; ESI-MS(+) m/z 920.1 (M+2H)

Analysis HPLC Condition J: Retention time=13.01 min

TABLE 2

FORMULA II PEPTIDE SERIES⁺

| Compound No. | A | 1 | 2 | 3 | 4 | 5 | 6 | 7 | 8 | 9 | 10 | 11 | 12 | 13 | 14 | MS Predicted | Observed |
|---|---|---|---|---|---|---|---|---|---|---|---|---|---|---|---|---|---|
| 71 | ClAc | F | ᵐPhe | ᵐNle | Sar | D | V | ᵐPhe | Y | Sar | W | Y | L | C | G NH₂ | 1796.11 | 898.8 (M + 2) |
| 72 | ClAc | A | ᵐPhe | ᵐNle | Sar | D | V | ᵐPhe | Y | Sar | W | Y | L | C | G NH₂ | 1720.02 | 1720.4 |
| 73 | ClAc | F | ᵐAla | ᵐNle | Sar | D | V | ᵐPhe | Y | Sar | W | Y | L | C | G NH₂ | 1720.02 | 1721.1 |
| 74 | ClAc | F | Phe | ᵐNle | Sar | D | V | ᵐPhe | Y | Sar | W | Y | L | C | G NH₂ | 1782.09 | 1782.8 |
| 75 | ClAc | F | ᵐPhe | ᵐAla | Sar | D | V | ᵐPhe | Y | Sar | W | Y | L | C | G NH₂ | 1754.03 | 1754.7 |
| 76 | ClAc | F | ᵐPhe | Nle | Sar | D | V | ᵐPhe | Y | Sar | W | Y | L | C | G NH₂ | 1782.09 | 892.1 (M + 2) |
| 77 | ClAc | F | ᵐPhe | ᵐNle | ᵐAla | D | V | ᵐPhe | Y | Sar | W | Y | L | C | G NH₂ | 1810.14 | 1811.1 |
| 78 | ClAc | F | ᵐPhe | ᵐNle | Gly | D | V | ᵐPhe | Y | Sar | W | Y | L | C | G NH₂ | 1782.09 | 1782.8 |
| 79 | ClAc | F | ᵐPhe | ᵐNle | Sar | A | V | ᵐPhe | Y | Sar | W | Y | L | C | G NH₂ | 1752.11 | 1753.8 |
| 80 | ClAc | F | ᵐPhe | ᵐNle | Sar | D | A | ᵐPhe | Y | Sar | W | Y | L | C | G NH₂ | 1768.06 | 1769.0 |
| 81 | ClAc | F | ᵐPhe | ᵐNle | Sar | D | V | ᵐAla | Y | Sar | W | Y | L | C | G NH₂ | 1720.02 | 861.0 (M + 2) |
| 82 | ClAc | F | ᵐPhe | ᵐNle | Sar | D | V | Phe | Y | Sar | W | Y | L | C | G NH₂ | 1782.09 | 891.7 (M + 2) |
| 83 | ClAc | F | ᵐPhe | ᵐNle | Sar | D | V | ᵐPhe | A | Sar | W | Y | L | C | G NH₂ | 1704.02 | 852.8 (M + 2) |
| 84 | ClAc | F | ᵐPhe | ᵐNle | Sar | D | V | ᵐPhe | Y | ᵐAla | W | Y | L | C | G NH₂ | 1810.14 | 960.3 (M + 2) |
| 85 | ClAc | F | ᵐPhe | ᵐNle | Sar | D | V | ᵐPhe | Y | Gly | W | Y | L | C | G NH₂ | 1782.09 | 891.9 (M + 2) |
| 86 | ClAc | F | ᵐPhe | ᵐNle | Sar | D | V | ᵐPhe | Y | Sar | W | A | L | C | G NH₂ | 1704.02 | 852.3 (M + 2) |
| 87 | ClAc | F | ᵐPhe | ᵐNle | Sar | D | V | ᵐPhe | Y | Sar | W | Y | A | C | G NH₂ | 1754.03 | 877.1 (M + 2) |

⁺Compound Nos. 71 to 87 are macrocyclic peptides cyclized via the moiety listed at the A position with a downstream cysteine.

Example 72

Synthesis of Compound No. 71

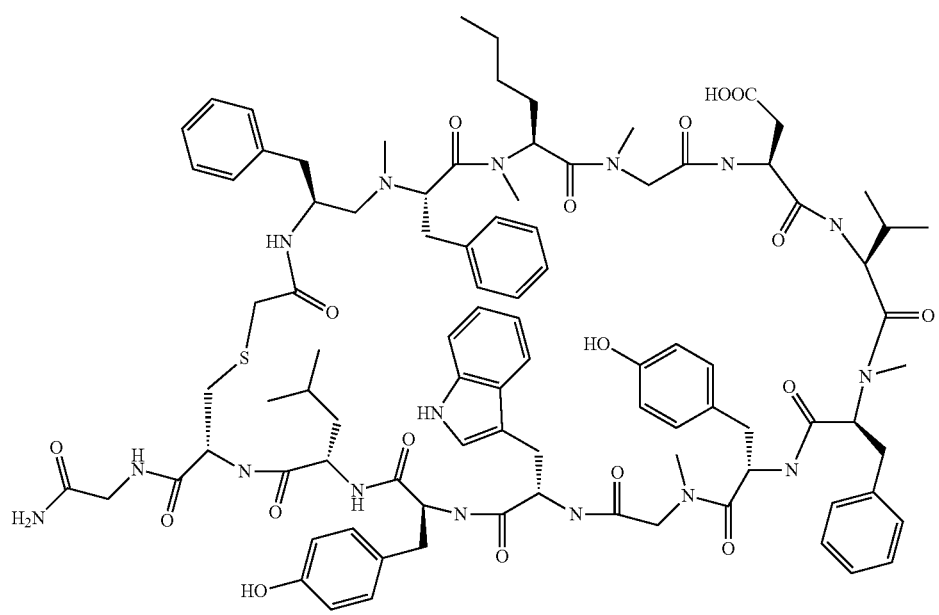

Molecular Weight: 1796.09

To a 40 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method A: Resin-swelling procedure" was followed;

"Prelude Method A: Single-coupling procedure" was followed with Fmoc-Gly-OH;

"Prelude Method A: Single-coupling procedure" was followed with Fmoc-Cys(Trt)-OH;

"Prelude Method A: Single-coupling procedure" was followed with Fmoc-Leu-OH;

"Prelude Method A: Single-coupling procedure" was followed with Fmoc-Tyr(tBu)-OH;

"Prelude Method A: Single-coupling procedure" was followed with Fmoc-Trp(Boc)-OH;

"Prelude Method A: Single-coupling procedure" was followed with Fmoc-Sar-OH;

"Prelude Method A: Custom amino acids-coupling procedure" was followed with Fmoc-Tyr(tBu)-OH using 10 eq for 10 h;

"Prelude Method A: Single-coupling procedure" was followed with Fmoc-[N-Me]Phe-OH;

"Prelude Method A: Secondary amine-coupling procedure" was followed with Fmoc-Val-OH;

"Prelude Method A: Single-coupling procedure" was followed with Fmoc-Asp(OtBu)-OH;

"Prelude Method A: Secondary amine-coupling procedure" was followed with Fmoc-Sar-OH;

"Prelude Method A: Secondary amine-coupling procedure" was followed with Fmoc-[N-Me]Nle-OH;

"Prelude Method A: Secondary amine-coupling procedure" was followed with Fmoc-[N-Me]Phe-OH;

"Prelude Method A: Secondary amine-coupling procedure" was followed with Fmoc-Phe-OH;

"Prelude Method A: Chloroacetyl chloride coupling procedure A" was followed;

"Global Deprotection Method B" was followed;

"Cyclization Method C" was followed.

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 25-95% B in A over 50 min., then a 5-minute hold at 95% B; Flow: 15 mL/min. Fractions containing the desired product were combined and dried. The yield of product was 28.6 mg, and its estimated purity was 98% by HPLC "Analysis Condition B" using a gradient of 35% to 95% B in A over 30 min.

Analysis condition A: Retention time=1.451 min; ESI-MS (+) m/z 899.3 (M+2H).

ESI-HRMS(+) m/z: Calculated: 898.4313 (M+2H). Found: 898.4294.

Example 73

Synthesis of Compound No. 72

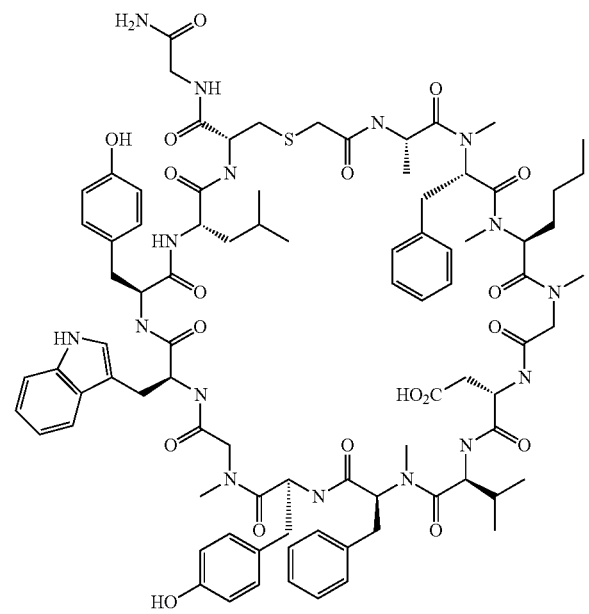

Molecular Weight: 1720.00

Example 0073 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E".

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 100.0%.

Analysis LCMS Condition A: Retention time=0.85 min; ESI-MS(+) m/z 860.96 (M+2H)

Analysis HPLC Condition J: Retention time=14.696 min

Example 74
Synthesis of Compound No. 73

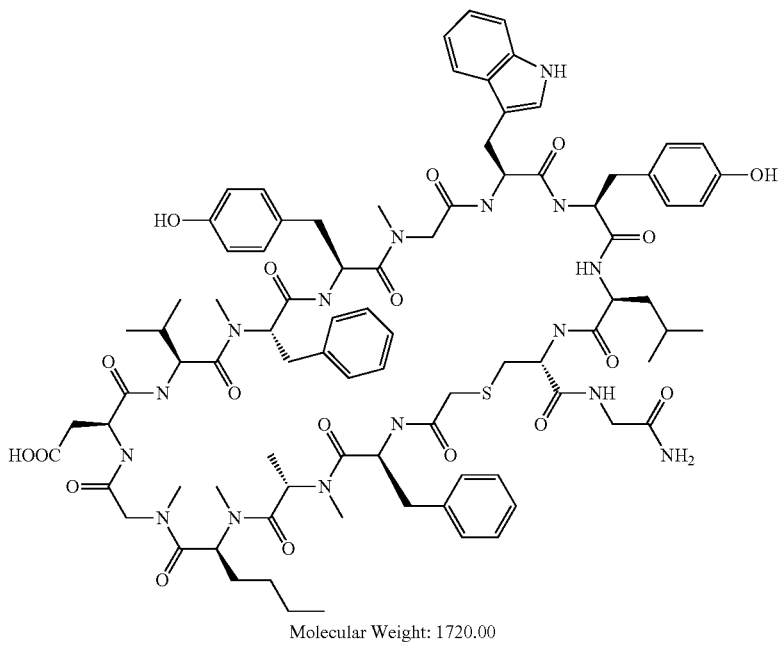 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](C)C(=O)N1C]

Molecular Weight: 1720.00

Example 0074 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E".

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 99%.

Analysis LCMS Condition A: Retention time=0.87 min; ESI-MS(+) m/z 861.1 (M+2)

Analysis HPLC Condition J: Retention time=14.82 min

Example 75
Synthesis of Compound No. 74

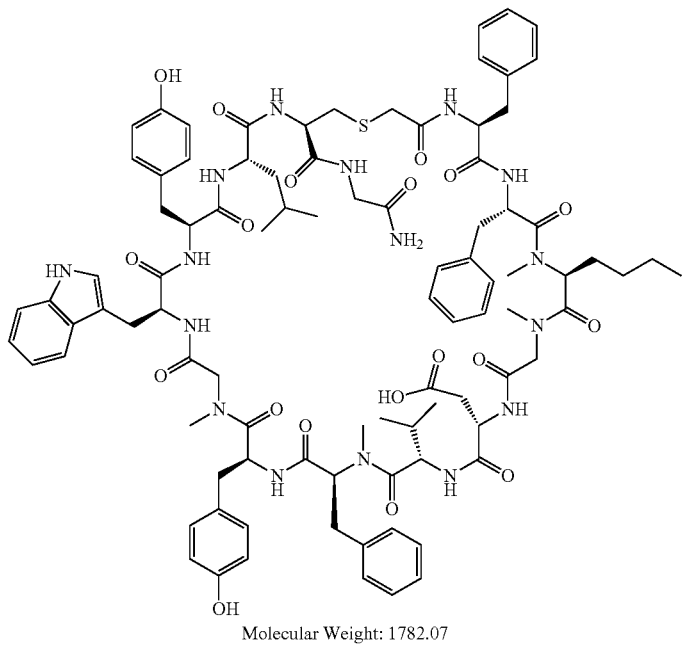 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N[C@@H](Cc2ccccc2)C(=O)N1C]

Molecular Weight: 1782.07

Example 0075 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.7 mg, and its estimated purity by LCMS analysis was 95%.

Analysis LCMS Condition E: Retention time=1.98 min; ESI-MS(+) m/z 1783.2 (M+1)

Example 76

Synthesis of Compound No. 7

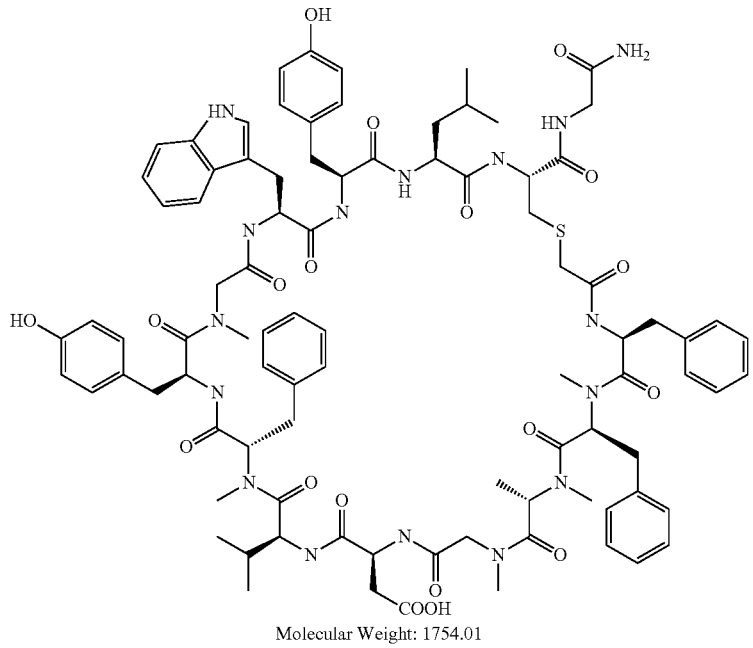 [SMILES: CC(C)C[C@@H]1NC(=O)[C@H](Cc2ccc(O)cc2)NC(=O)[C@H](Cc2c[nH]c3ccccc23)NC(=O)CN(C)C(=O)[C@H](Cc2ccc(O)cc2)NC(=O)[C@H](Cc2ccccc2)N(C)C(=O)[C@H](C(C)C)NC(=O)[C@H](CC(=O)O)NC(=O)CN(C)C(=O)[C@H](C)N(C)C(=O)[C@H](Cc2ccccc2)N(C)C(=O)[C@H](Cc2ccccc2)NC(=O)CSC[C@@H](C(=O)NCC(N)=O)NC1=O]

Molecular Weight: 1754.01

Example 0076 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E".

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 99.6%.

Analysis LCMS Condition A: Retention time=0.83 min; ESI-MS(+) m/z 1754.7 (M+H), 878.0 (M+2H)

Analysis HPLC Condition J: Retention time=14.44 min

Example 77

Synthesis of Compound No. 76

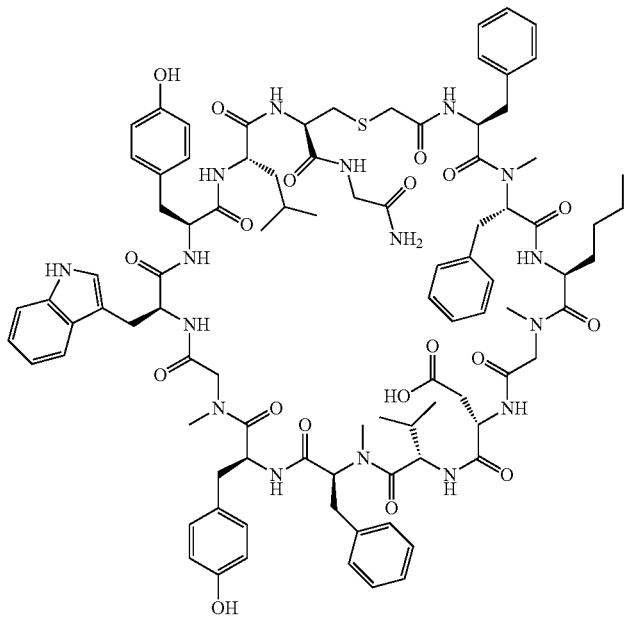

Molecular Weight: 1782.07

Example 0077 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 1.3 mg, and its estimated purity by LCMS analysis was 100%.

Analysis LCMS Condition D: Retention time=1.610 min; ESI-MS(+) m/z 1782.75 (M+1), 891.60 (M+2)

Analysis LCMS Condition E: Retention time=1.775 min; ESI-MS(+) m/z 892.10 (M+2)

Example 78

Synthesis of Compound No. 77

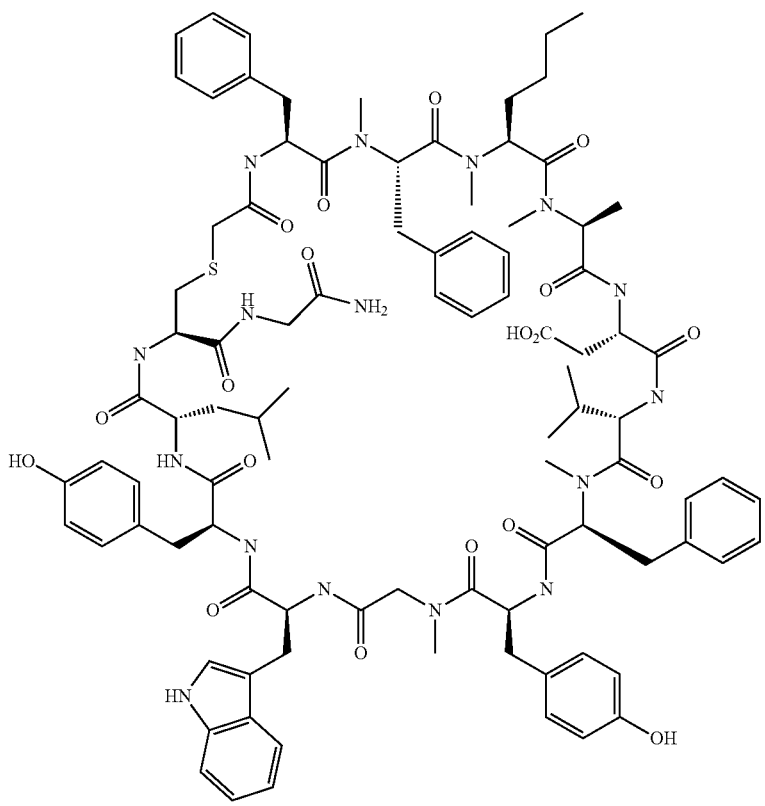

Molecular Weight: 1810.12

Example 0078 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E". Fmoc-N-Me-Ala-OH was used in the eleventh amino acid coupling step.

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 97.7%.

Analysis LCMS Condition A: Retention time=0.94 min; ESI-MS(+) m/z 1811.1 (M+H), 906.0 (M+2H).

Analysis HPLC Condition J: Retention time=16.38 min

Example 79

Synthesis of Compound No. 78

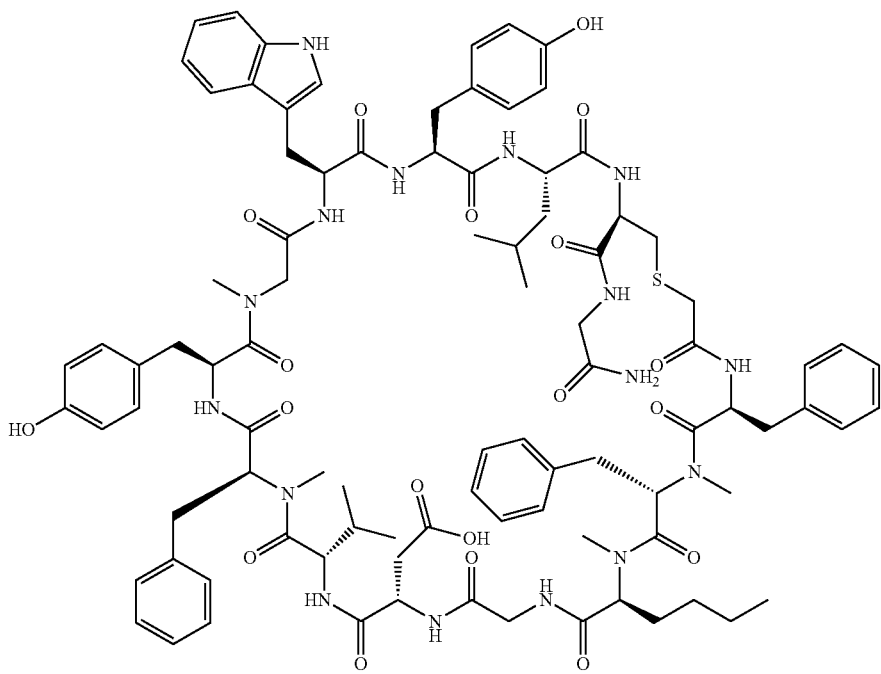

Molecular Weight: 1782.07

Example 0079 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 0-minute hold at 100% B; Flow: 20 mL/min. Fractions containing the desired product were combined and dried via centrifugal evaporation. The yield of the product was 2.0 mg, and its estimated purity by LCMS analysis was 97%.

Analysis LCMS Condition D: Retention time=1.591 min; ESI-MS(+) m/z 1782.80 (M+1), 891.85 (M+2)

Analysis LCMS Condition E: Retention time=1.634 min; ESI-MS(+) m/z 891.60 (M+2)

Example 80

Synthesis of Compound No. 79

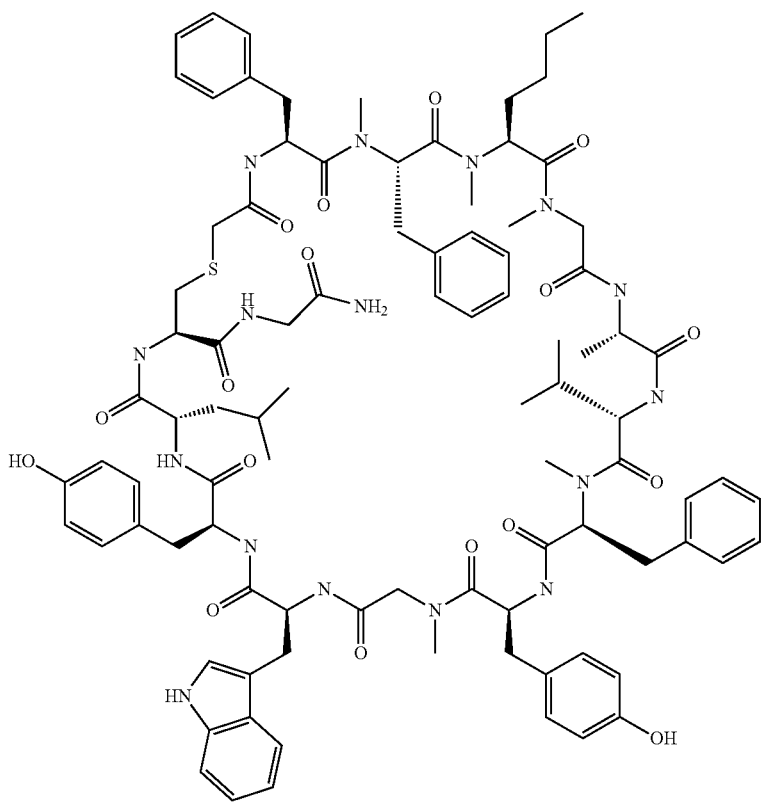

Molecular Weight: 1752.08

Example 0080 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E".

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10 1000% B over 20 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 95.7%.

Analysis LCMS Condition A: Retention time=0.94 min; ESI-MS(+) m/z 1753.8 (M+H), 877.0 (M+2H)

Analysis HPLC Condition J: Retention time=16.19 min

Example 81

Synthesis of Compound No. 80

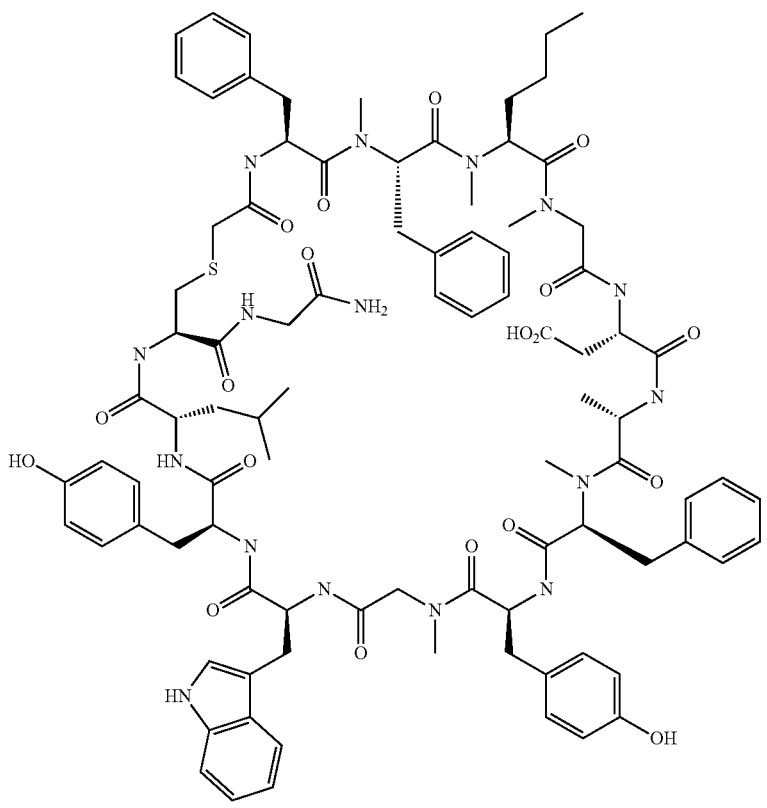

Molecular Weight: 1768.04

Example 0081 was prepared following the general synthetic sequence described for the preparation of Example 0001, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method E".

The crude material was purified via preparative LC with the following conditions: Column: PHENOMENEX® Luna C18, 30×100 mm; Mobile Phase A: 5:95 acetonitrile:water with 0.1% trifluoroacetic acid; Mobile Phase B: 95:5 acetonitrile:water with 0.1% trifluoroacetic acid; Gradient: 10-1000% B over 20 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 100%.

Analysis LCMS Condition A: Retention time=0.86 min; ESI-MS(+) m/z 1769.0 (M+H), 884.8 (M+2H)

Analysis HPLC Condition J: Retention time=14.89 min

Example 82

Synthesis of Compound No. 81

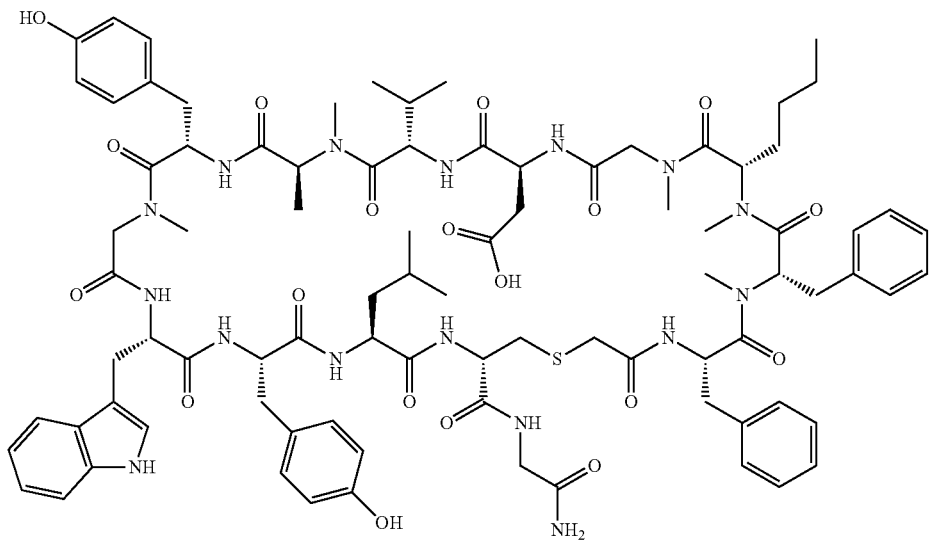

Molecular Weight: 1720.00

Example 0082 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method E".

The crude material was purified via preparative HPLC with the following conditions: 4×2 mL injections on a 30×100 C18 column with a gradient of 10 to 100% Acetonitrile in Water, 0.1% TFA as modifier over 20 mins. The yield of the product was 4.0 mg, and its estimated purity by HPLC analysis was 90%.

Analysis LCMS Condition A: Retention time=0.85 min; ESI-MS(+) m/z 861.0 (M+2)

Analysis HPLC Condition J: Retention time=14.249 min

Example 83

Synthesis of Compound No. 82

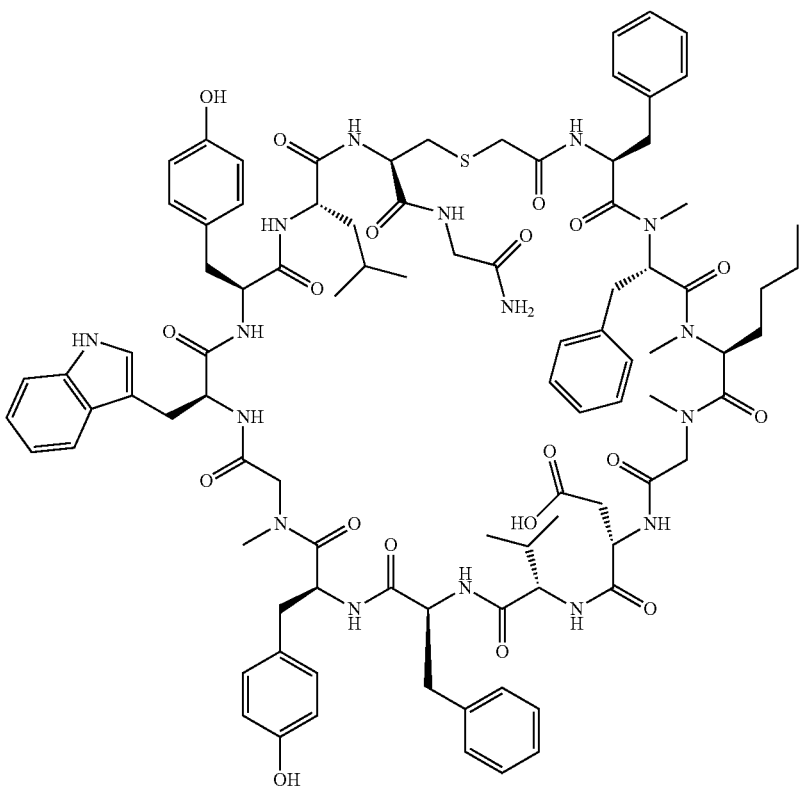

Molecular Weight: 1782.07

Example 0083 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 1.1 mg, and its estimated purity by LCMS analysis was 100%.

Analysis LCMS Condition D: Retention time=1.587 min; ESI-MS(+) m/z 1782.75 (M+1), 891.65 (M+2)

Analysis LCMS Condition E: Retention time=1.750 min; ESI-MS(+) m/z 891.70 (M+2)

Example 84

Synthesis of Compound No. 83

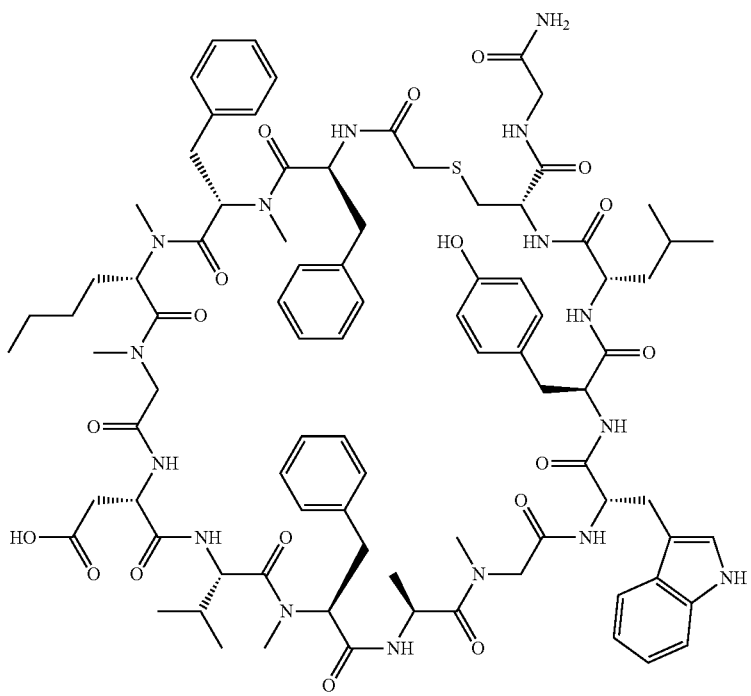

Molecular Weight: 1704.00

Example 0084 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method E".

The crude material was purified via preparative HPLC with the following conditions: 4×2 ml, injections on a 30×100 C18 column with a gradient of 10 to 100% Acetonitrile in Water, 0.1% TFA as modifier over 20 mins. The yield of the product was 1.04 mg, and its estimated purity by HPLC analysis was 91%.

Analysis LCMS Condition A: Retention time=0.91 min; ESI-MS(+) m/z 852.8 (M+2H) Analysis HPLC Condition J: Retention time=16.012 min Example 85

Synthesis of Compound No. 84

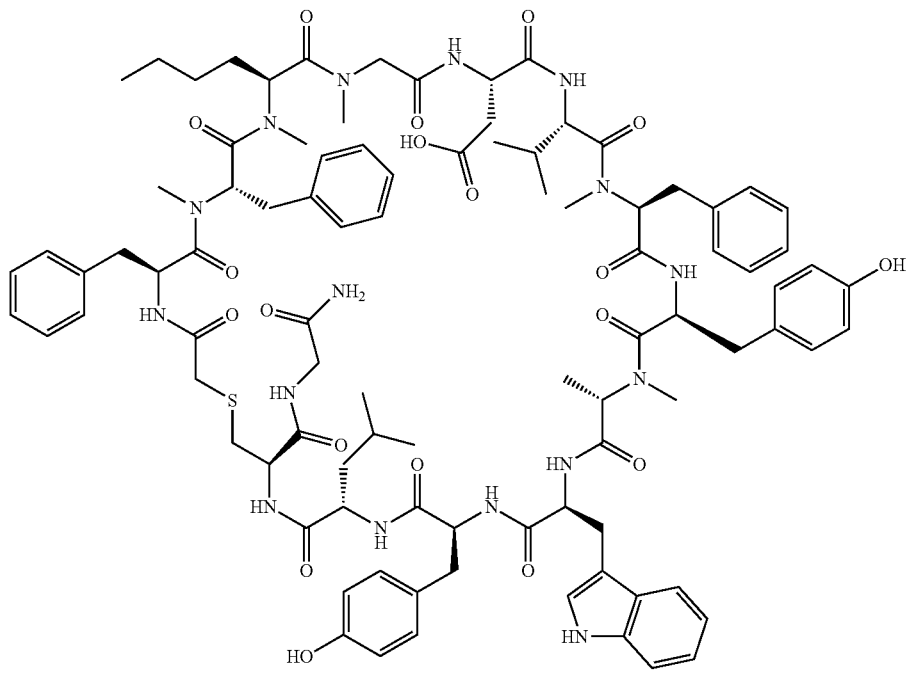

Molecular Weight: 1810.12

Example 0085 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method E".

The crude material was purified via preparative HPLC with the following conditions: 4×2 mL injections on a 30×100 C18 column with a gradient of 10 to 100% Acetonitrile in Water, 0.1% TFA as modifier over 20 mins. The yield of the product was 1.01 mg, and its estimated purity by HPLC analysis was 98%.

Analysis LCMS Condition A: Retention time=0.93 min; ESI-MS(+) m/z 906.3 (M+2H)

Analysis HPLC Condition J. Retention time=16.484 min

Example 86

Synthesis of Compound No. 85

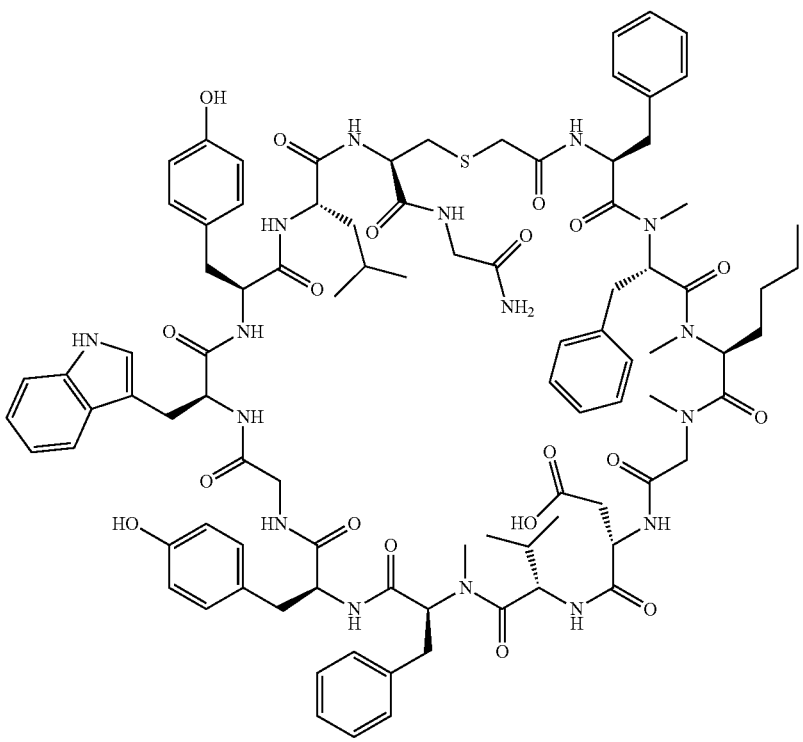

Molecular Weight: 1782.07

Example 0086 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 0.5 mg, and its estimated purity by LCMS analysis was 96%.

Analysis LCMS Condition D: Retention time=1.611 min; ESI-MS(+) m/z 1782.70 (M+1), 891.80 (M+2)

Analysis LCMS Condition E: Retention time=1.783 min; ESI-MS(+) m/z 891.95 (M+2)

Example 87

Synthesis of Compound No. 86

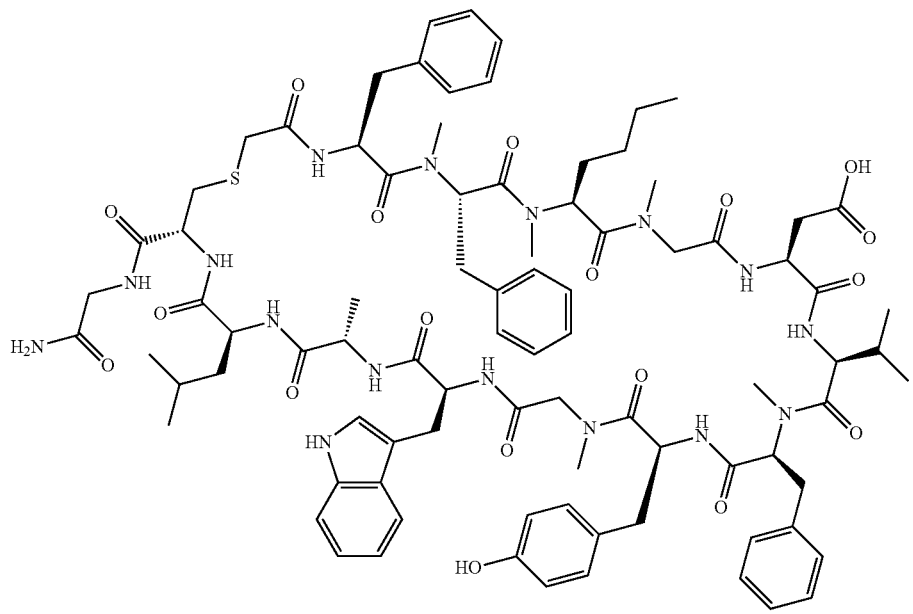

Molecular Weight: 1704.00

Example 0087 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method E".

The crude material was purified via preparative HPLC with the following conditions: 4×2 mL injections on a 30×100 C18 column with a gradient of 10 to 100% Acetonitrile in Water, 0.1% TFA as modifier over 20 mins. The yield of the product was 1.53 mg, and its estimated purity by HPLC analysis was 97%.

Analysis LCMS Condition A: Retention time=0.92 min; ESI-MS(+) m/z 852.3 (M+2)

Analysis HPLC Condition J. Retention time=16.044 min

Example 88

Synthesis of Compound No. 87

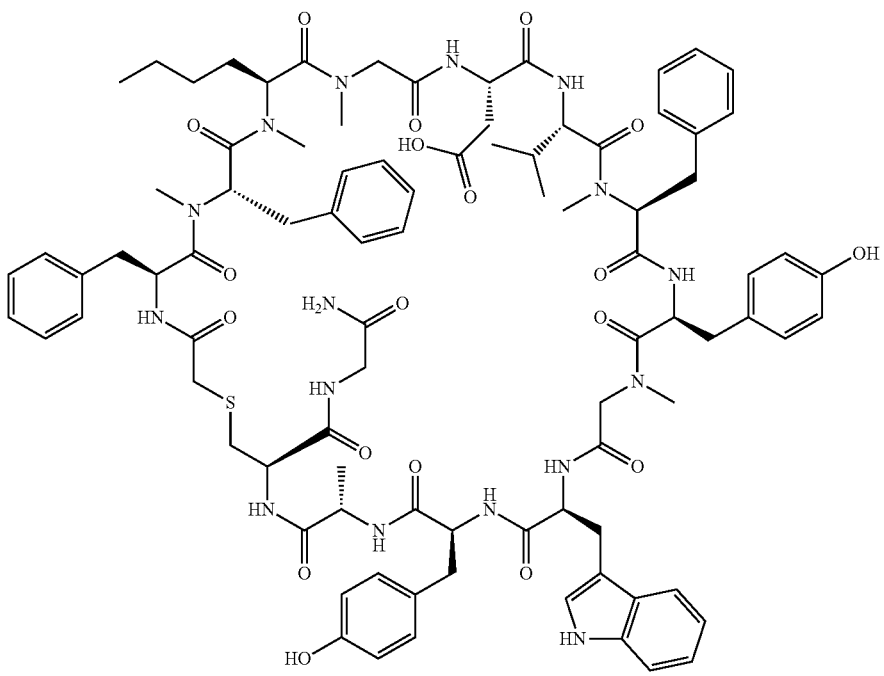

Molecular Weight: 1754.01

Example 0088 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method E".

The crude material was purified via preparative HPLC with the following conditions: 4×2 mL injections on a 30×100 C18 column with a gradient of 10 to 100% Acetonitrile in Water, 0.1% TFA as modifier over 20 mins. The yield of the product was 1 mg, and its estimated purity by HPLC analysis was 92%.

Analysis LCMS Condition A: Retention time=0.88 min; ESI-MS(+) m/z 877.1 (M+2H)

Analysis HPLC Condition J: Retention time=15.511 min

TABLE 3

SULFOXIDE AND LACTAM LINKERS FOR COMPOUND NOS. 1 AND 71 PEPTIDES[+][*]

| Compound No. | A | 1 | 2 | 3 | 4 | 5 | 6 | 7 | 8 | 9 | 10 | 11 | 12 | 13 |
|---|---|---|---|---|---|---|---|---|---|---|---|---|---|---|
| 88 | ClAc | F | $^m$Ala | N | P | H | L | $^m$Gly | W | S | W | $^m$Nle | $^m$Nle | R |
| 89 | ClAc | F | $^m$Phe | $^m$Nle | $^m$Gly | D | V | $^m$Phe | Y | $^m$Gly | W | Y | L | C(SO) |
| 90 | ClAc | F | $^m$Phe | $^m$Nle | $^m$Gly | D | V | $^m$Phe | Y | $^m$Gly | W | Y | L | C(SO) |

Lactams (between residues indicated)

| Compound No. | A | 1 | 2 | 3 | 4 | 5 | 6 | 7 | 8 | 9 | 10 | 11 | 12 | 13 |
|---|---|---|---|---|---|---|---|---|---|---|---|---|---|---|
| 91 |   | F | $^m$Ala | N | P | H | L | $^m$Gly | W | S | W | $^m$Nle | $^m$Nle | R |
| 92 |   | F | $^m$Ala | N | P | H | L | $^m$Gly | W | S | W | $^m$Nle | $^m$Nle | R |
| 93 | G | F | $^m$Ala | N | P | H | L | $^m$Gly | W | S | W | $^m$Nle | $^m$Nle | R |
| 94 | G | F | $^m$Ala | N | P | H | L | $^m$Gly | W | S | W | $^m$Nle | $^m$Nle | R |
| 95 | G | F | $^m$Phe | $^m$Nle | $^m$Gly | D | V | $^m$Phe | Y | $^m$Gly | W | Y | L | D |
| 96 | G | F | $^m$Phe | $^m$Nle | $^m$Gly | D | V | $^m$Phe | Y | $^m$Gly | W | Y | L | E |
| 97 |   | F | $^m$Phe | $^m$Nle | $^m$Gly | D | V | $^m$Phe | Y | $^m$Gly | W | Y | L | D |
| 98 |   | F | $^m$Phe | $^m$Nle | $^m$Gly | D | V | $^m$Phe | Y | $^m$Gly | W | Y | L | G |

| Compound No. | A | 14 | 15 |   | MS Predicted | MS Observed | Comments |
|---|---|---|---|---|---|---|---|
| 88 | ClAc | C(SO) | G | NH$_2$ | 1868.19 | 935.4 (M + 2) | Sulfoxides of Compound No. 1 (diast. mixt.) |
| 89 | ClAc |   | G | NH$_2$ | 1812.11 | 907.4 (M + 2) | Sulfoxide of Compound No. 71 (Isomer A) |
| 90 | ClAc |   | G | NH$_2$ | 1812.11 | 907.4 (M + 2) | Sulfoxide of Compound No. 71 (Isomer B) |

Lactams (between residues indicated)

| Compound No. | A | 14 | 15 |   | MS Predicted | MS Observed | Comments |
|---|---|---|---|---|---|---|---|
| 91 |   | D | G | NH$_2$ | 1806.08 | 904.3 (M + 2) | Phe$^1$-Asp$^{14}$ Lactam |
| 92 |   | E | G | NH$_2$ | 1820.12 | 911.1 (M + 2) | Phe$^1$-Glu$^{14}$ Lactam |
| 93 | G | D | G | NH$_2$ | 1863.13 | 932.8 (M + 2) | Gly$^0$-Asp$^{14}$ Lactam |
| 94 | G | E | G | NH$_2$ | 1877.15 | 939.5 (M + 2) | Gly$^0$-Glu$^{14}$ Lactam |
| 95 |   |   | G | NH$_2$ | 1807.05 | 904.7 (M + 2) | Gly$^0$-Asp$^{13}$ Lactam |
| 96 |   |   | G | NH$_2$ | 1821.08 | 911.6 (M + 2) | Gly$^0$-Glu$^{13}$ Lactam |
| 97 |   |   | G | NH$_2$ | 1750.00 | 876.2 (M + 2) | Phe$^1$-Asp$^{13}$ Lactam |
| 98 |   |   |   | NH$_2$ | 1635.90 | 819.0 (M + 2) | Phe$^1$-Gly$^{13}$ Lactam (head-to-tail) |

[+]Compound Nos. 88 to 90 are macrocyclic peptides cyclized via the moiety listed at the A position with a downstream cysteine.

[*]Compound Nos. 91 thru 98 are macrocyclic lactam peptides cyclized via the amino acids noted under the comment section.

Example 89

Synthesis of Compound No. 88 Sulfoxide Diastereomeric Mixture of Compound No. 1

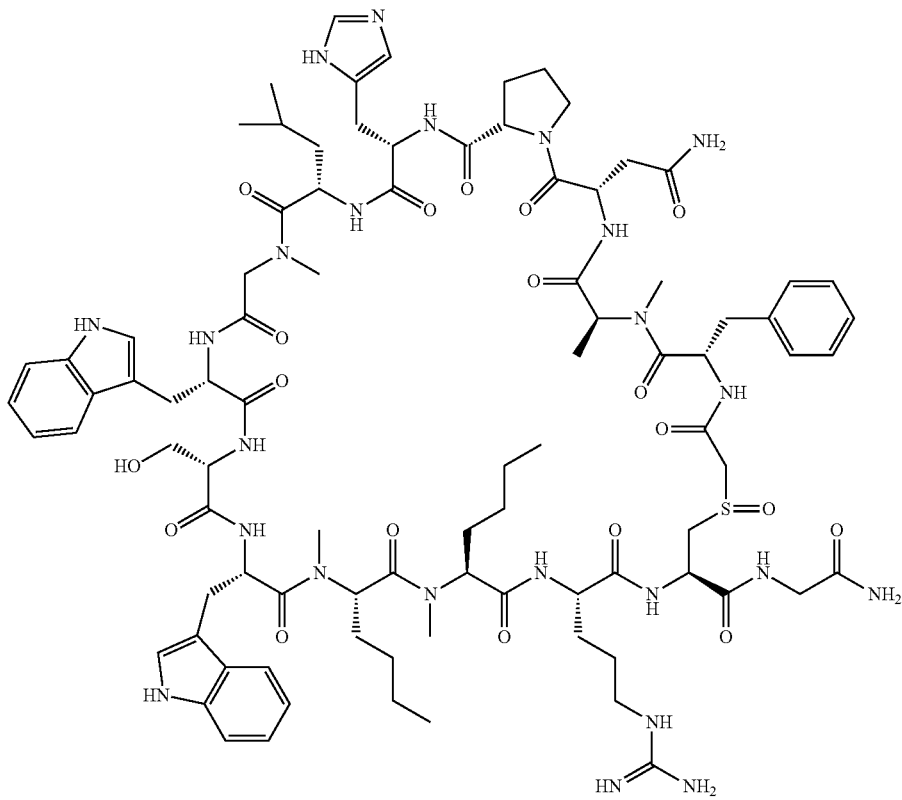

Molecular Weight: 1868.17

Example 89 [Compound No. 88] was prepared by oxidation of the macrocyclic peptide of Example 2 using the following procedure: to a solution of the macrocyclic peptide of Example 2 (1.6 mg) in 1 mL of 50 mM $NH_4HCO_4$/Acetonitrile (1:1) was added a 1 mg/mL solution of m-chloroperbenzoic acid (0.9 eq) in Acetonitrile. The reaction mixture was stirred at room temperature for 18 h.

The crude product was purified via preparative HPLC using the following conditions: Column: PHENOMENEX® C18 Luna, 20×250 mm, 5-μm particles; Mobile Phase A: 0.1% TFA in water; Mobile Phase B: 0.1% TFA in AcCN; gradient: 20-75% B in A over 55 min.; Flow: 15 mL/min. Fractions containing the desired product were combined and dried by lyophilization. The yield of the product was 0.91 mg, and its estimated purity by HPLC analysis was 98%.

Analysis LCMS Condition C: Retention time=1.16 min; ESI-MS(+) m/z 935.4 (M+2H).

Analysis HPLC Condition A: Retention times=9.19 min and 9.41 min for the partially resolved diastereomers.

Example 90

Synthesis of Compound Nos. 89 and 90 [Sulfoxides of Compound No. 71]

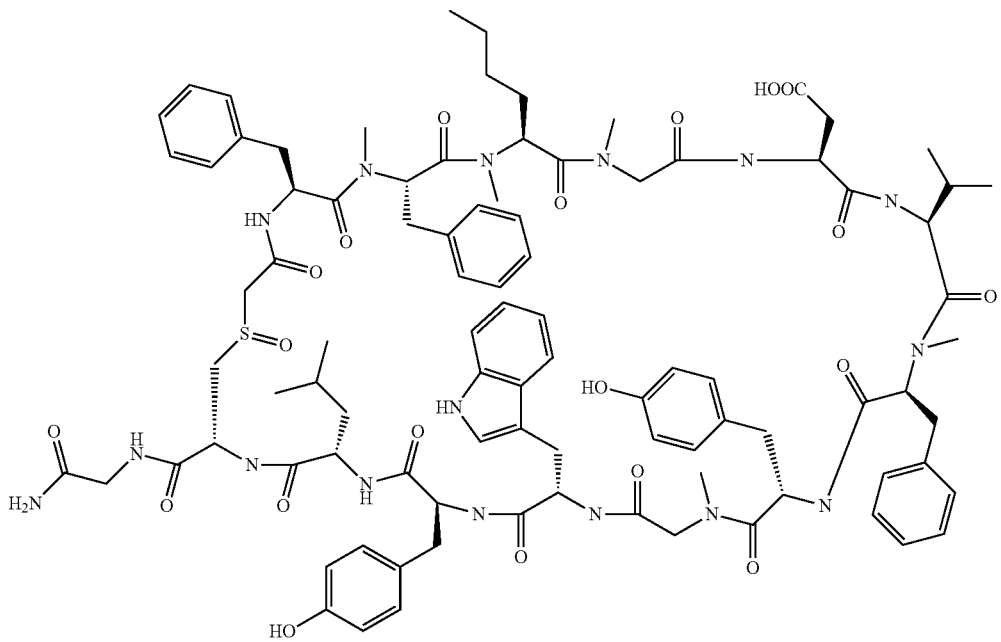

Molecular Weight: 1812.09

The synthesis of the compounds of Example 90 (Compound Nos. 89 and 90) was performed by oxidation of the macrocyclic peptide of Example 71 using the following procedure: to a solution of the peptide of Example 71 (1.4 mg) in 1 mL of 50 mM $NH_4HCO_4$/Acetonitrile (1:1) was added a 1 mg/mL solution in Acetonitrile of m-chloroperbenzoic acid (m-CPBA) (0.9 eq). The reaction mixture was stirred at room temperature for 18 h.

The crude product was purified via preparative HPLC using the following conditions: Column: PHENOMENEX® C18 Luna, 20×250 mm, 5-μm particles; Mobile Phase A: 0.1% TFA in water; Mobile Phase B: 0.1% TFA in AcCN; gradient: 20-75% B over 55 min.; Flow: 15 mL/min. Two isomeric products were separated, Isomer A (Compound No. 89) and Isomer B (Compound No. 90). The fractions containing them were combined and dried by lyophilization. The yield of the faster eluting Isomer A (Compound No. 89) was 0.49 mg, and its estimated purity by HPLC analysis was 98%.

Analysis LCMS Condition C: Retention time=1.62 min; ESI-MS(+) m/z 907.4 (M+2H).

Analysis HPLC Condition G: Retention time=12.72 min.

The yield of the slower eluting Isomer B (Compound No. 90) was 0.49 mg, and its estimated purity by HPLC analysis was 99%.

Analysis LCMS Condition C: Retention time=1.65 min; ESI-MS(+) m/z 907.4 (M+2H).

Analysis HPLC Condition G: Retention time=13.61 min.

Example 92

Synthesis of Compound No. 91

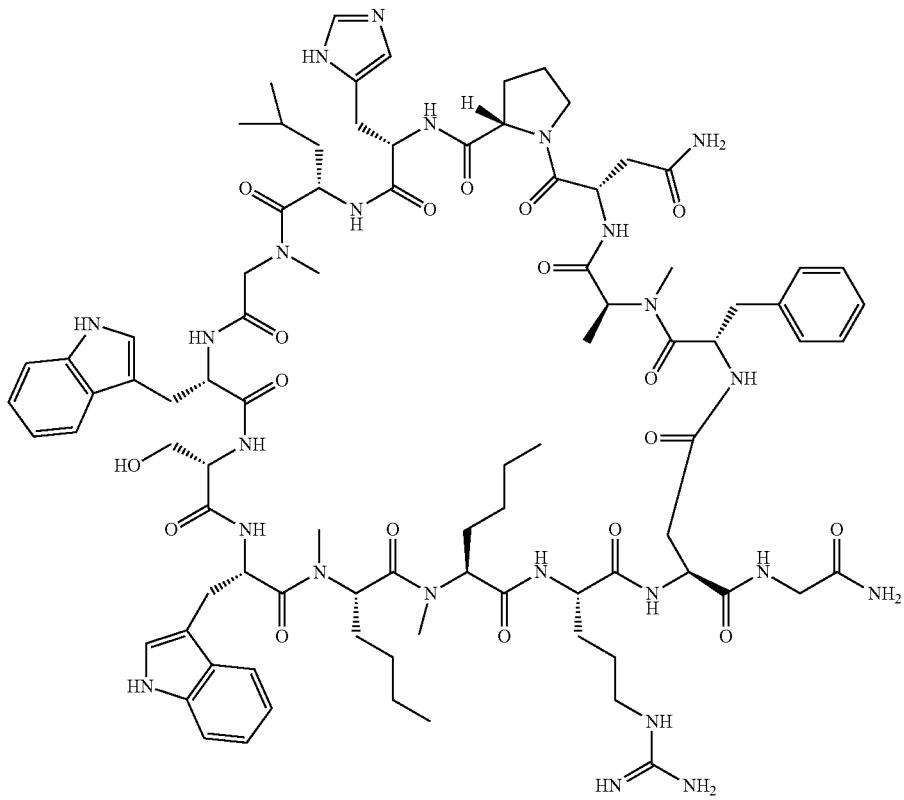

Molecular Weight: 1806.08

Example 92 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure". Fmoc-Asp(O-2-PhiPr)-OH was used as the orthogonal protection of the Asp$^{14}$ residue. After the last Fmoc removal, the peptidyl-resin was cleaved from the solid support by treating it four times with DCM/TIS/TFA (96:3:1; v:v:v) (4 mL) for 5 min. This step also removed the 2-phenylisopropyl ester from the Asp$^{14}$ residue. The protected peptide (70.4 mg) was cyclized using 1 eq. of T3P (50% EtOAc) and 2 eq. of DIEA in (1:1) Acetonitrile/DCM (20 mL). The reaction was allowed to proceed for 18 h. The solvents were removed under reduced pressure and the resulting solid was treated with (50:46:4) TFA/DCM/TIS (4 mL) for 1.5 h at rt. The reaction mixture was concentrated in vacuo. Addition of ether (20 mL) and cooling to 0° C. for 15 min, produced a solid, which was washed with ether and dried, to yield 27 mg of crude product. The crude material was purified via preparative LC/MS using the following conditions: Column: YMC ODS-AQ, 20×250 mm, 5-μm particles, heated to 60° C.; Mobile Phase A: 0.1% TFA in water; Mobile Phase B: 0.1% TFA in Acetonitrile; Gradient: 20-60% B over 60 minutes; Flow: 15 mL/min. Fractions containing the desired product were combined and dried via lyophilization. The yield of product was 1.7 mg, and its estimated purity by HPLC analysis was 93%.

Analysis LCMS Condition A: retention time=0.97 min.; ESI-MS(+) m/z 904.3 (M+2H).

Analysis HPLC Condition E: retention time=10.11 min.

Example 93

Synthesis of Compound No. 92

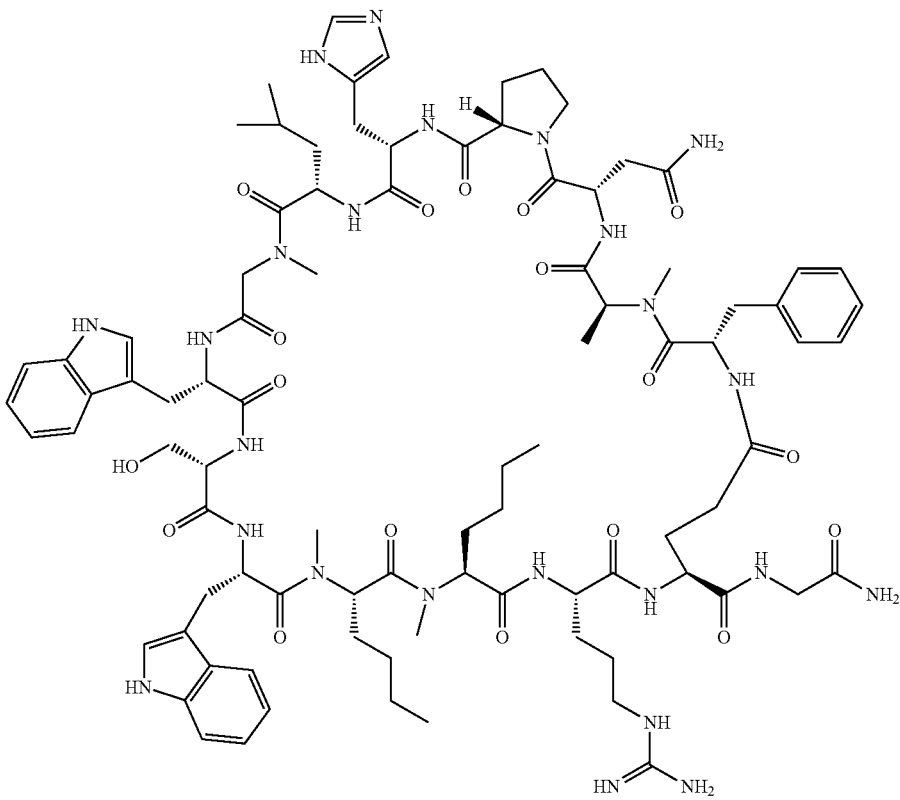

Molecular Weight: 1820.10

Example 93 was prepared following the general synthetic sequence described for the preparation of Example 92, except that Fmoc-Glu(O-2-PhiPr)-OH was used at position 14. After release of the protected peptide from the solid support, T3P-mediated cyclization of the resulting protected peptide and TFA-mediated side chain deprotection yielded the crude product (28 mg), which was purified via preparative LC/MS using the following conditions: Column: YMC ODS-AQ, 20×250 mm, 5-μm particles, heated to 60° C.; Mobile Phase A: 0.1% TFA in water; Mobile Phase B: 0.1% TFA in Acetonitrile; Gradient: 25-75% B over 75 minutes; Flow: 15 mL/min. Fractions containing the desired product were combined and dried via lyophilization. The yield of product was 6.3 mg, and its estimated purity by HPLC analysis was 97.5%.

Analysis LCMS Condition G: retention time=3.88 min.; ESI-MS(+) m/z 911.08 (M+2H).

Analysis HPLC Condition H: retention time=12.04 min.

Example 94

Synthesis of Compound No. 93

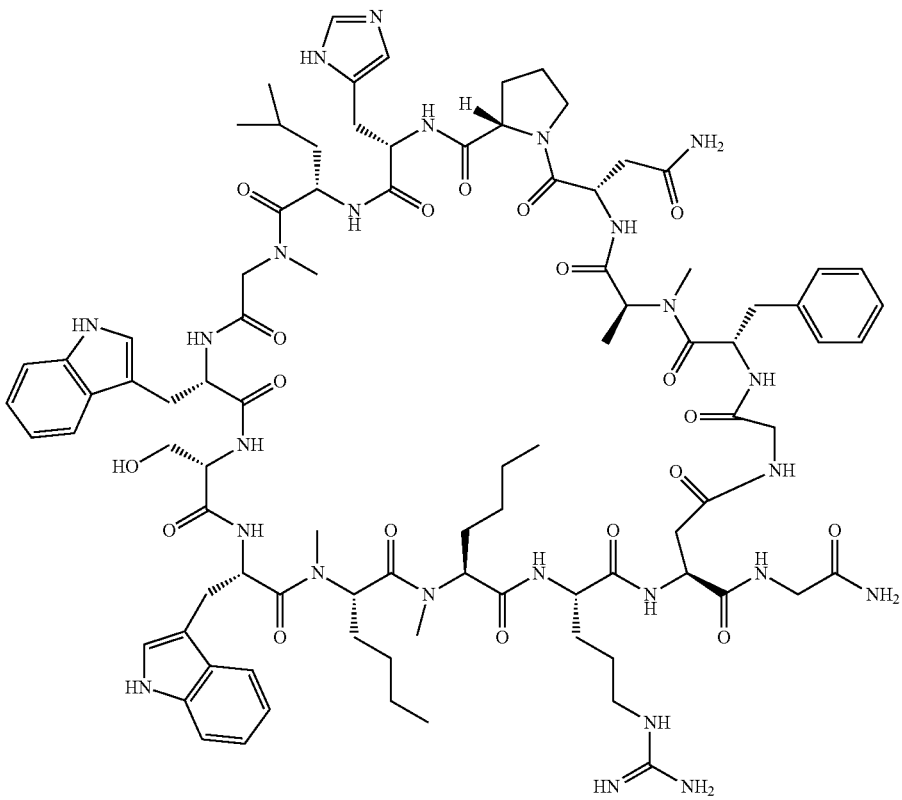

Molecular Weight: 1863.13

Example 94 was prepared following the general synthetic sequence described for the preparation of Example 92, except that an additional Fmoc-Gly-OH was coupled at the N-terminus. After release from the solid support, T3P-mediated cyclization of the resulting protected peptide and TFA-mediated side chain deprotection, the crude product (25 mg) was purified via preparative LC/MS using the following conditions: Column: YMC ODS-AQ, 20×250 mm, 5-μm particles, heated to 60° C.; Mobile Phase A: 0.1% TFA in water; Mobile Phase B: 0.1% TFA in Acetonitrile; Gradient: 20-60% B over 60 minutes; Flow: 15 mL/min. Fractions containing the desired product were combined and dried via lyophilization. The yield of the product was 1.0 mg, and its estimated purity by HPLC analysis was 95%.

Analysis LCMS Condition A: retention time=1.00 min.; ESI-MS(+) m/z 932.8 (M+2H).

Analysis HPLC Condition E: retention time=11.07 min.

Example 95

Synthesis of Compound No. 94

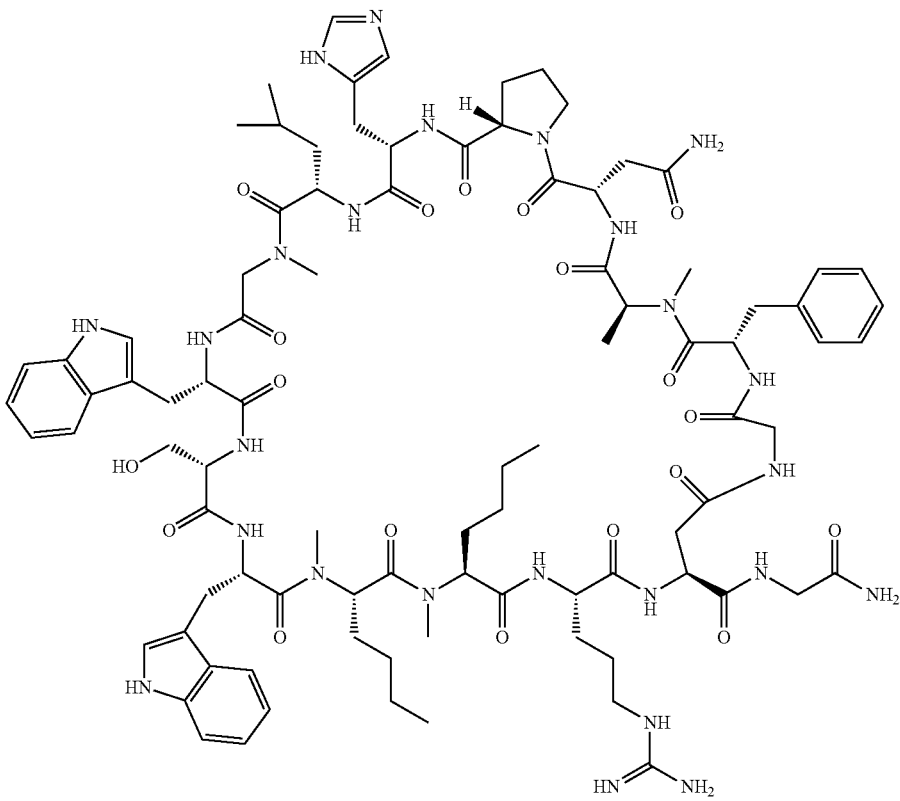

Molecular Weight: 1877.15

Example 95 was prepared following the general synthetic sequence described for the preparation of Example 93, except that an additional Fmoc-Gly-OH was coupled at the N-terminus. After release from the solid support, T3P-mediated cyclization of the resulting protected peptide and TFA-mediated side chain deprotection, the crude product (25 mg) was purified via preparative LC/MS using the following conditions: Column: YMC ODS-AQ, 20×250 mm, 5-μm particles, heated to 60° C.; Mobile Phase A: 0.1% TFA in water; Mobile Phase B: 0.1% TFA in Acetonitrile; Gradient: 20-60% B over 60 minutes; Flow: 15 mL/min. Fractions containing the desired product were combined and dried via lyophilization. The yield of the product was 3.8 mg, and its estimated purity by HPLC analysis was 98%.

Analysis LCMS Condition G: retention time=4.27 min.; ESI-MS(+) m/z 939.5 (M+2H).

Analysis HPLC Condition E: retention time=13.76 min.

Example 96

Synthesis of Compound No. 95

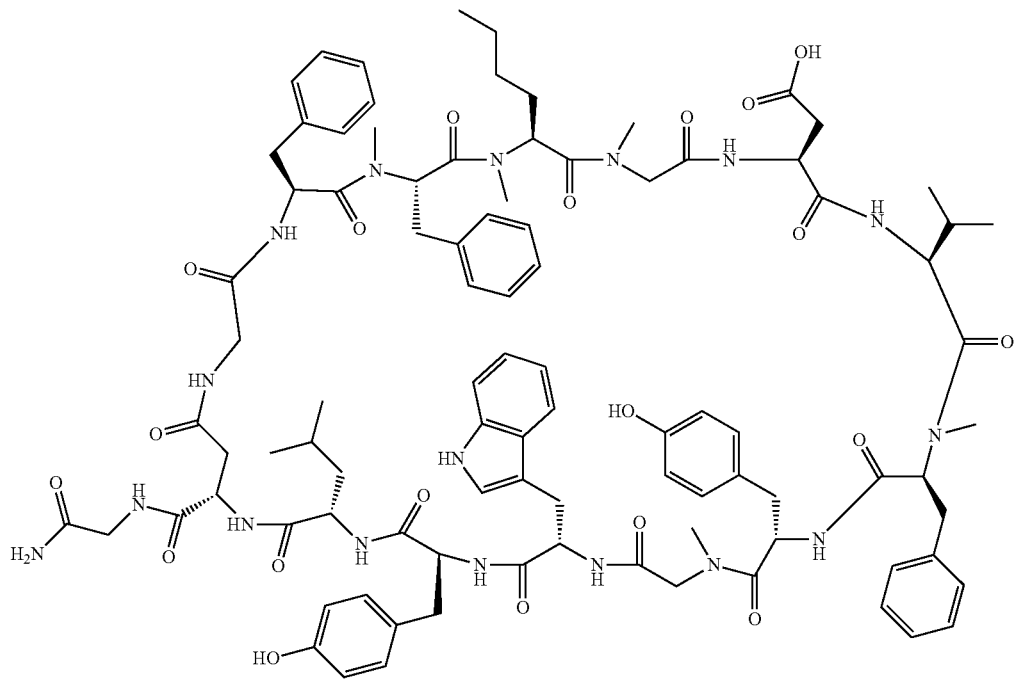

Molecular Weight: 1807.05

Example 96 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure". Fmoc-Asp(O-2-PhiPr)-OH was used as the orthogonal protection of the Asp$^{13}$ residue. After the last Fmoc removal, the peptidyl-resin was cleaved from the solid support by treating it five times with DCM/TIS/TFA (96:3:1; v:v:v) (5 mL) for 1 min. This step also removed the 2-phenylisopropyl ester from the Asp$^{13}$ residue. The filtrates were collected in a flask containing 1.5 mL pyridine. The filtrates were then extracted with water (3×5 mL). The organic phase was dried to yield an oil, which was then lyophilized from MeCN/water (1:2) to yield a solid product (100 mg). A portion of the product (34 mg, 0.017 mmol) was cyclized using 1 eq. of HATU and 2 eq. of DIEA in (1:9) DMF/DCM (17 mL). The reaction was allowed to proceed for 18 h. The solvents were removed under reduced pressure and the resulting solid was treated with (95:5) TFA/TIS (6 mL) for 5 min. at rt. Addition of ether (20 mL) produced a solid, which was washed with ether and dried. The crude product was purified via preparative LC/MS using the following conditions: Column: PHENOMENEX® C18 Luna, 20×250 mm, 5-μm particles; Mobile Phase A: 0.1% TFA in water; Mobile Phase B: 0.1% TFA in Acetonitrile; Gradient: 30-95% B over 50 minutes; Flow: 15 mL/min. Fractions containing the desired product were combined and dried via lyophilization. The yield of the product was 1.9 mg, and its estimated purity by HPLC analysis was 95%.

Analysis LCMS Condition A: retention time=1.40 min.; ESI-MS(+) m/z 904.7 (M+2H).

Analysis HPLC Condition G: retention time=13.54 min.

Example 97
Synthesis of Compound No. 96

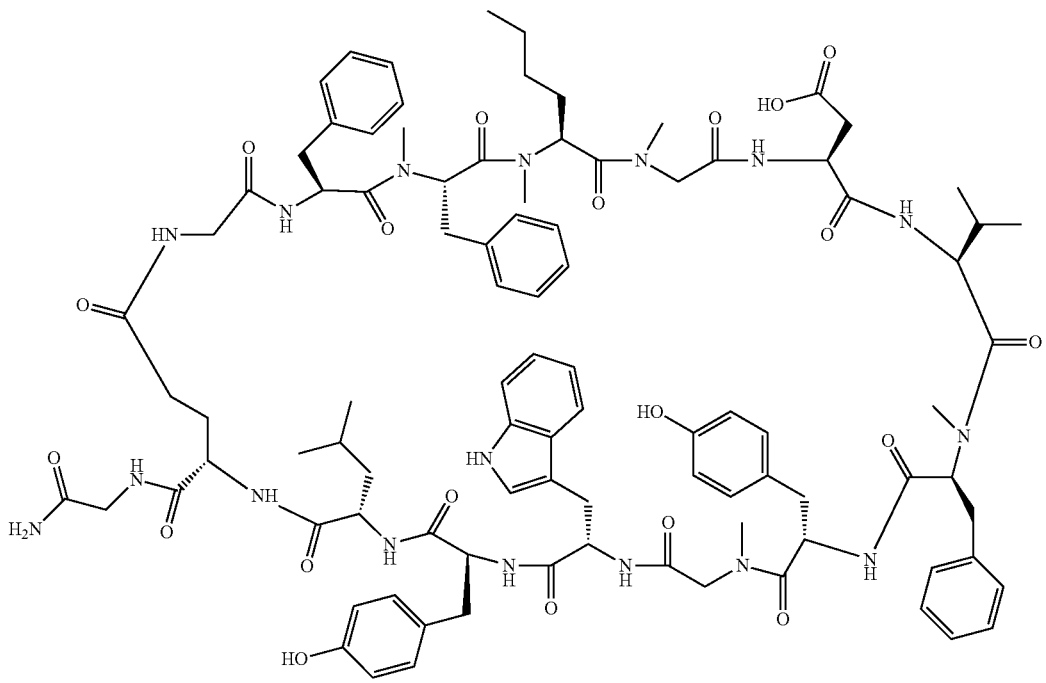

Molecular Weight: 1821.08

Example 97 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure". Fmoc-Glu(O-2-PhiPr)-OH was used as the orthogonal protection of the $Glu^{13}$ residue. After the last Fmoc removal, the peptidyl-resin was cleaved from the solid support by treating it five times with DCM/TIS/TFA (96:3:1; v:v:v) (5 mL) for 1 min. This step also removed the 2-phenylisopropyl ester from the $Glu^{13}$ residue. The filtrates were collected in a flask containing 1.5 mL pyridine and were then extracted with water (3×5 mL). The organic phase was evaporated to yield an oil, which was then lyophilized from MeCN/water (1:2) to yield a solid product (36 mg). The peptide was deprotected using TFA/TIS/water (96:2:2:) for 5 mins and was then precipitated in ether, washed with ether and dried. The protected peptide (32 mg, 0.015 mmol) mg) was cyclized using 1 eq. of HATU and 2 eq. of DIEA in DMF (30 mL). The reaction was allowed to proceed for 18 h. The solvent was removed under reduced pressure and the residue was precipitated with water, washed and dried. The resulting solid was treated with (48:48:4) TFA/DCM/TIS (3 mL) for 5 min. at room temperature. Addition of ether (20 mL) produced a solid, which was washed with ether and dried, to yield a solid product. The crude product was purified via preparative LC/MS using the following conditions: Column: YMC ODS-AQ, 20×250 mm, 5-μm particles, heated to 60° C.; Mobile Phase A: 0.1% TFA in water; Mobile Phase B: 0.1% TFA in Acetonitrile; Gradient: 20-60% B over 60 minutes; Flow: 15 mL/min. Fractions containing the desired product were combined and dried via lyophilization. The yield of the product was 0.4 mg, and its estimated purity by HPLC analysis was 99%.

Analysis LCMS Condition C: retention time=1.63 min.; ESI-MS(+) m/z 911.9 (M+2H).

Analysis HPLC Condition I: retention time=12.50 min.

Example 98
Synthesis of Compound No. 97

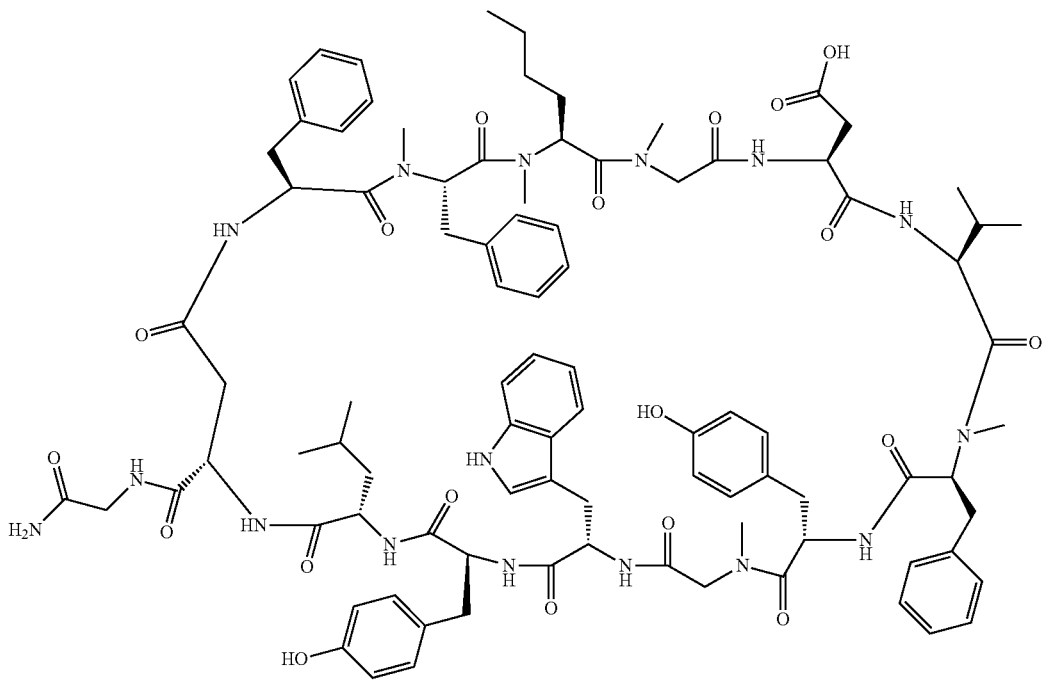

Molecular Weight: 1750.00

Example 98 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure". Fmoc-Asp(O-2-PhiPr)-OH was used as the orthogonal protection of the Asp$^{13}$ residue. After the last Fmoc removal, the peptidyl-resin was cleaved from the solid support by treating it five times with DCM/TIS/TFA (96:3:1; v:v:v) (5 mL) for 1 min. This step also removed the 2-phenylisopropyl ester from the Asp$^{13}$ residue. The filtrates were collected in a flask containing 1.5 mL pyridine. The filtrates were then extracted with water (3×5 mL). The organic phase was dried to yield an oil, which was then lyophilized from MeN/water (1:2) to yield a solid product (97 mg). A portion of the product (35 mg, 0.017 mmol) was cyclized using 1 eq. of HATU and 2 eq. of DIEA in (1:9) DMF/Acetonitrile (17 mL). The reaction was allowed to proceed for 18 hrs. The solvents were removed under reduced pressure and the residue was redissolved in Acetonitrile (1 mL) and then precipitated with water (2 mL). The collected peptide was redissolved in DCM and extracted with water (2×5 mL). The organic layer was then dried over sodium sulfate, filtered and dried to afford 97 mg of protected peptide. This was treated with (95:5) TFA/TIS (6 mL) for 5 min at rt. Addition of ether (20 mL) produced a solid, which was washed with ether and dried. The crude product was purified via preparative LC/MS using the following conditions: Column: PHENOMENEX® C18 Luna, 20×250 mm, 5-μm particles; Mobile Phase A: 0.1% TFA in water; Mobile Phase B: 0.1% TFA in Acetonitrile; Gradient: 30-95% B over 50 minutes; Flow: 15 mL/min. Fractions containing the desired product were combined and dried via lyophilization. The yield of the product was 1.0 mg, and its estimated purity by HPLC analysis was 82%.

Analysis LCMS Condition A: retention time=1.42 min.; ESI-MS(+) m/z 876.2 (M+2H).

Analysis HPLC Condition G: retention time=14.01 min.

Example 99

Synthesis of Compound No. 98

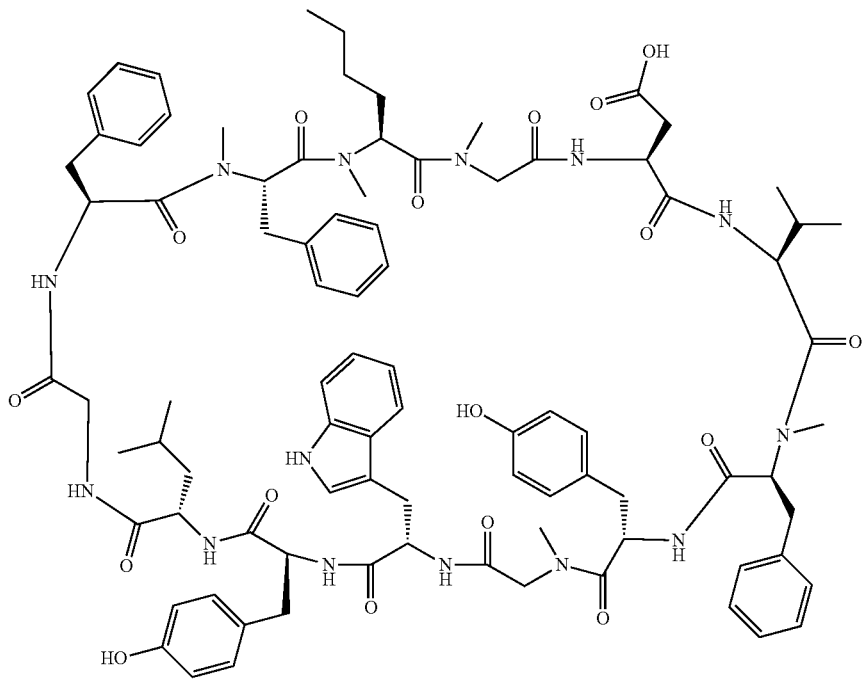

Molecular Weight: 1635.90

Example 99 was prepared following the general synthetic sequence described for the preparation of Example 0006, composed of the following general procedures: "Prelude Method A: Resin-swelling procedure", "Prelude Method A: Single-coupling procedure", "Prelude Method A: Secondary amine coupling procedure". The synthesis was started from H-Gly-2-Cl-trityl resin (Novabiochem, 0.6 mmole/g). After the last Fmoc removal, the peptidyl-resin was cleaved from the solid support by treating it five times with DCM/TIS/TFA (96:3:1; v:v:v) (5 mL) for 1 min. The filtrates were collected in a flask containing 1.5 mL pyridine. The filtrates were then extracted with water (3×5 mL). The organic phase was evaporated to yield an oil, which was then lyophilized from MeCN/water (1:2) to yield a solid product (221 mg). A portion of the product (10 mg, 0.005 mmol) was cyclized using 1 eq. of HATU and 2 eq. of DIEA in (1:9) DMF/DCM (17 mL). The reaction was allowed to proceed for 18 hrs. The solvents were removed under reduced pressure and the residue was redissolved in Acetonitrile (1 mL) and then precipitated with water (2 mL). The collected peptide was redissolved in DCM and extracted with water (2×5 mL). The organic layer was then dried over sodium sulfate, filtered and dried to afford 17 mg of protected peptide. This was treated with (95:5) TFA/TIS (6 mL) for 5 min. at room temperature. Addition of ether (20 mL), and cooling to 0° C. for 10 min. produced a solid, which was washed with ether and dried. The crude product was purified via preparative LC/MS using the following conditions: Column: PHENOMENEX® C18 Luna, 20×250 mm, 5-μm particles; Mobile Phase A: 0.1% TFA in water; Mobile Phase B: 0.1% TFA in Acetonitrile; Gradient: 30-95% B over 50 minutes; Flow: 15 mL/min. Fractions containing the desired product were combined and dried via lyophilization. The yield of product was 0.81 mg, and its estimated purity by HPLC analysis was 99%.

Analysis LCMS Condition A: retention time=1.55 min.; ESI-MS(+) m/z 819.0 (M+2H).

Analysis HPLC Condition G: retention time=16.15 min.

TABLE 4

| FORMULA III PEPTIDE SERIES± | | | | | | | | | | | | | | | | | |
|---|---|---|---|---|---|---|---|---|---|---|---|---|---|---|---|---|---|
| Compound | | | | | Peptide Sequence | | | | | | | | | | | MS | |
| No. | A | 1 | 2 | 3 | 4 | 5 | 6 | 7 | 8 | 9 | 10 | 11 | 12 | 13 | 14 | Predicted | Observed |
| 99 | ClAc | F | L | I | V | I | R | D | R | V | F | R | C | G | NH$_2$ | 1632.99 | 817.6 (M + 2) |
| 100 | ClAc | F | R | I | V | I | R | D | R | V | F | R | C | G | NH$_2$ | 1676.02 | 839.1 (M + 2) |

TABLE 4-continued

FORMULA III PEPTIDE SERIES[+]

| Compound No. | A | 1 | 2 | 3 | 4 | 5 | 6 | 7 | 8 | 9 | 10 | 11 | 12 | 13 | 14 | MS Predicted | MS Observed |
|---|---|---|---|---|---|---|---|---|---|---|---|---|---|---|---|---|---|
| 101 | ClAc | F | F | I | V | I | R | D | R | V | F | R | C | G | $NH_2$ | 1667.01 | 834.8 (M + 2) |
| 102 | ClAc | F | D-Phe | I | V | I | R | D | R | V | F | R | C | G | $NH_2$ | 1667.01 | 834.7 (M + 2) |
| 103 | ClAc | F | L | L | V | I | R | D | R | V | F | R | C | G | $NH_2$ | 1632.99 | 817.7 (M + 2) |
| 104 | ClAc | F | L | F | V | I | R | D | R | V | F | R | C | G | $NH_2$ | 1667.01 | 834.6 (M + 2) |
| 105 | ClAc | F | L | I | Y | I | R | D | R | V | F | R | C | G | $NH_2$ | 1697.03 | 849.6 (M + 2) |
| 106 | ClAc | F | L | I | F | I | R | D | R | V | F | R | C | G | $NH_2$ | 1681.04 | 841.7 (M + 2) |
| 107 | ClAc | F | L | I | V | V | R | D | R | V | F | R | C | G | $NH_2$ | 1618.97 | 810.6 (M + 2) |
| 108 | ClAc | F | L | I | V | I | H | D | R | V | F | R | C | G | $NH_2$ | 1613.95 | 808.1 (M + 2) |
| 109 | ClAc | F | L | I | V | I | L | D | R | V | F | R | C | G | $NH_2$ | 1589.96 | 796.3 (M + 2) |
| 110 | ClAc | F | L | I | V | I | R | D | R | L | F | R | C | G | $NH_2$ | 1647.02 | 824.7 (M + 2) |
| 111 | ClAc | F | L | I | V | I | R | D | R | F | F | R | C | G | $NH_2$ | 1681.04 | 841.5 (M + 2) |
| 112 | ClAc | F | L | I | V | I | R | D | R | Y | F | R | C | G | $NH_2$ | 1697.03 | 849.7 (M + 2) |
| 113 | ClAc | F | L | I | V | I | R | D | R | V | F | Y | C | G | $NH_2$ | 1639.98 | 821.1 (M + 2) |
| 114 | ClAc | F | L | I | V | I | R | D | R | V | F | P | C | G | $NH_2$ | 1573.92 | 788.0 (M + 2) |
| 115 | ClAc | F | F | L | V | I | R | D | R | V | F | R | C | G | $NH_2$ | 1667.01 | 834.5 (M + 2) |

[+]Compound Nos. 99 to 115 are macrocyclic peptides cyclized via the moiety listed at the A position with a downstream cysteine.

Example 100

Synthesis of Compound No. 99

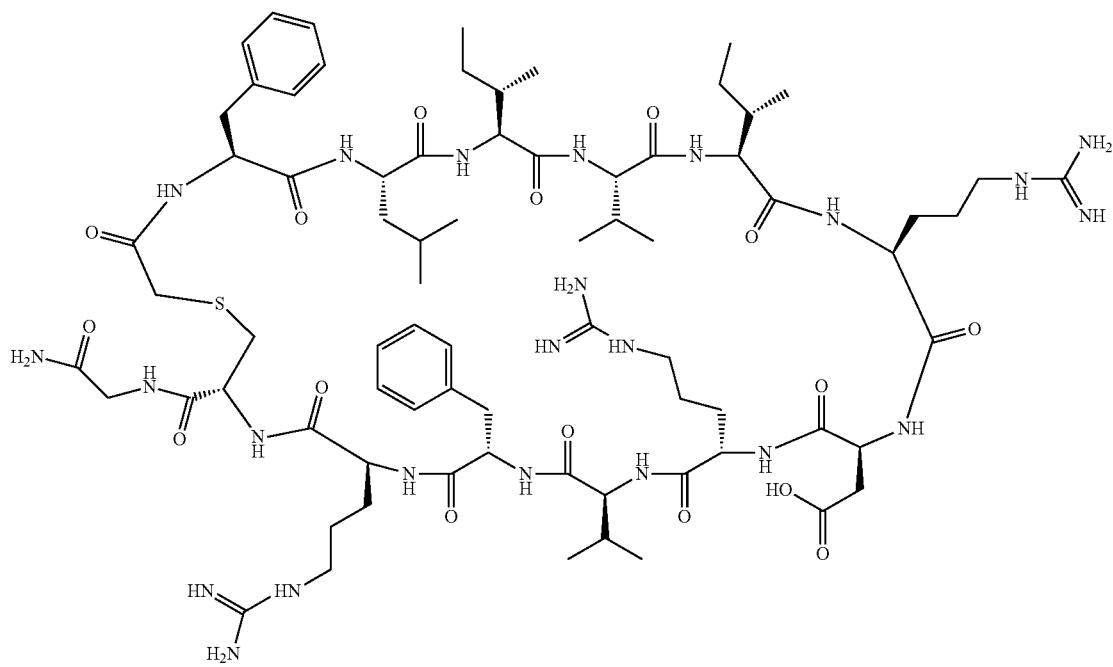

Molecular Weight: 1632.97

Example 100 was prepared following the general synthetic sequence described for the preparation of Example 0019, composed of the following general procedures: "Prelude Method B: Resin-swelling procedure", "Prelude Method B: Double-coupling procedure" for couplings to primary amine N-terminus; "Prelude Method B: Secondary amine coupling procedure" for couplings to secondary amine N-terminus; "Prelude Method A: Chloroacetic acid coupling procedure A", "Global Deprotection Method A" and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 6.4 mg, and its estimated purity by HPLC analysis was 99%.

Analysis LCMS Condition A: retention time=0.90 min.; ESI-MS(+) m/z 817.6 (M+2H).

Analysis HPLC Condition F: retention time=9.21 min.

Example 101

Synthesis of Compound No. 100

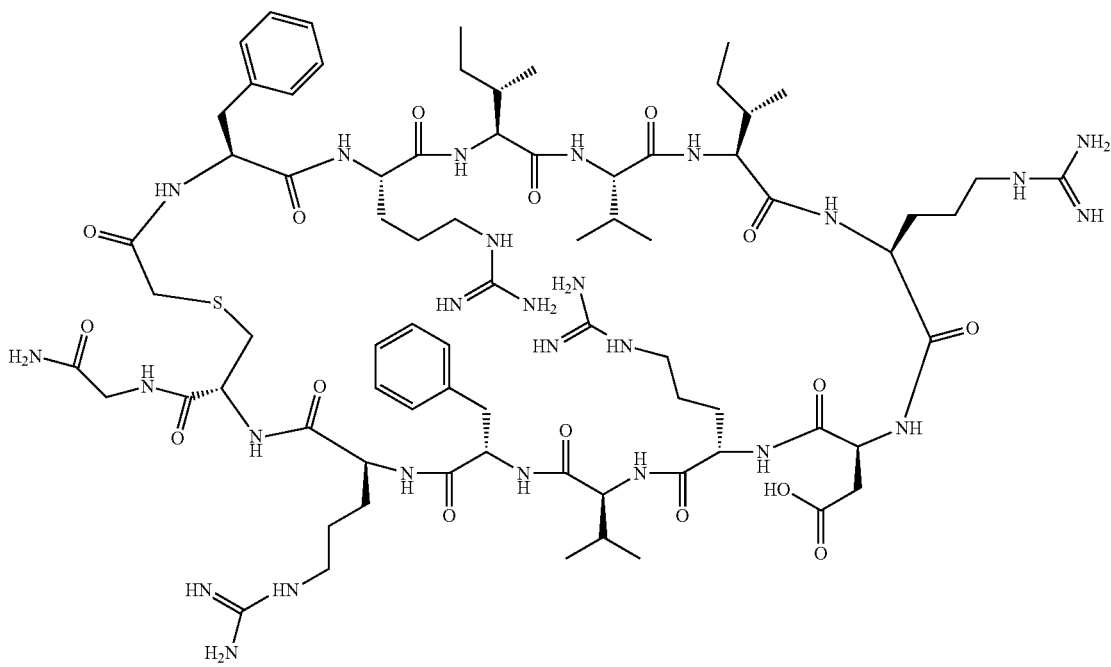

Molecular Weight: 1676.00

Example 101 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure A", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 15-55% B over 40 min.; Flow: 15 mL/min. Fractions containing the desired product were combined and dried by lyophilization. The yield of product was 6.0 mg, and its estimated purity by HPLC analysis was 95%.

Analysis LCMS Condition A: retention time=0.82 min.; ESI-MS(+) m/z 839.1 (M+2H).

Analysis HPLC Condition E: retention time=10.22 min.

Example 102

Synthesis of Compound No. 101

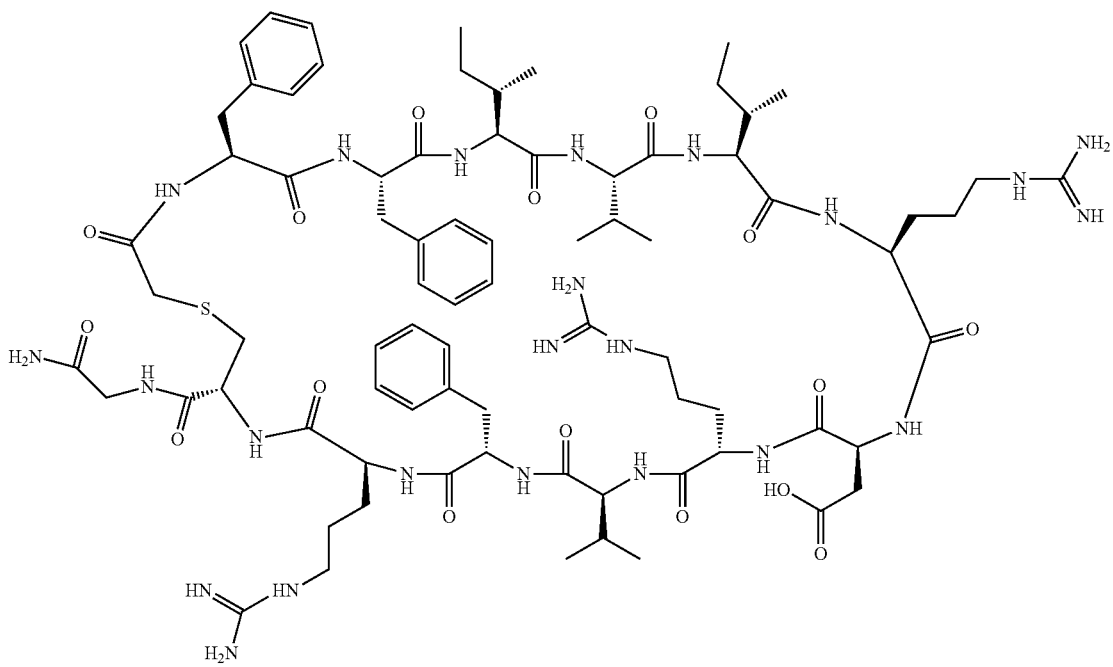

Molecular Weight: 1666.99

Example 102 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 6.0 mg, and its estimated purity by HPLC analysis was 98%.

Analysis LCMS Condition A: retention time=0.93 min.; ESI-MS(+) m/z 834.8 (M+2H).

Analysis HPLC Condition F: retention time=9.57 min.

Example 103

Synthesis of Compound No. 102

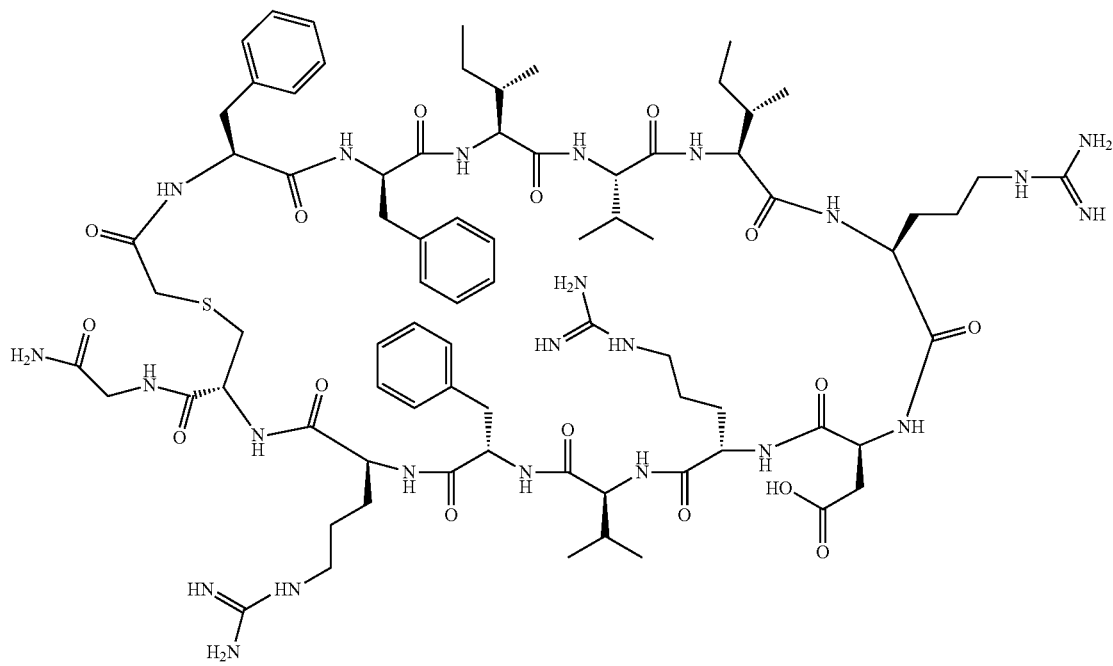

Molecular Weight: 1666.99

Example 103 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 4.7 mg, and its estimated purity by HPLC analysis was 99%.

Analysis LCMS Condition A: retention time=1.05 min.; ESI-MS(+) m/z 834.7 (M+2H).
Analysis HPLC Condition F: retention time=12.03 min.

Example 104

Synthesis of Compound No. 103

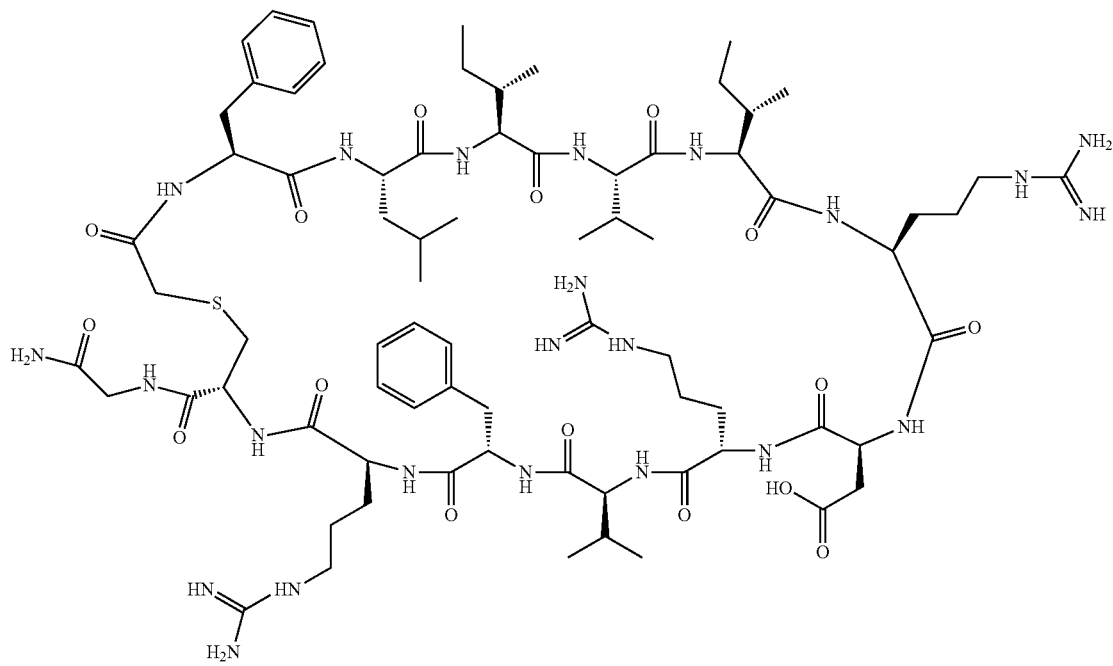

Molecular Weight: 1632.97

Example 104 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 4.9 mg, and its estimated purity by HPLC analysis was 96%.

Analysis LCMS Condition A: retention time=0.94 min.; ESI-MS(+) m/z 817.7 (M+2H).

Analysis HPLC Condition F: retention time=9.61 min.

Example 105

Synthesis of Compound No. 104

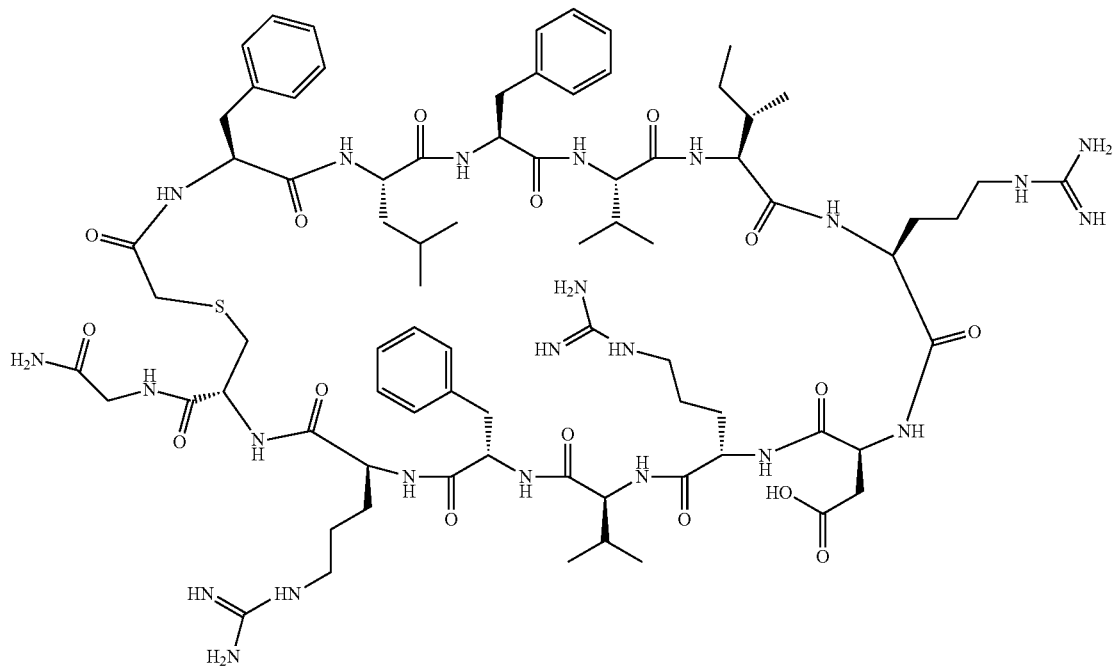

Molecular Weight: 1666.99

Example 105 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-µm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 8.4 mg, and its estimated purity by HPLC analysis was 91%.

Analysis LCMS Condition A: retention time=0.96 min.; ESI-MS(+) m/z 834.6 (M+2H).
Analysis HPLC Condition F: retention time=10.20 min.

Example 106

Synthesis of Compound No. 105

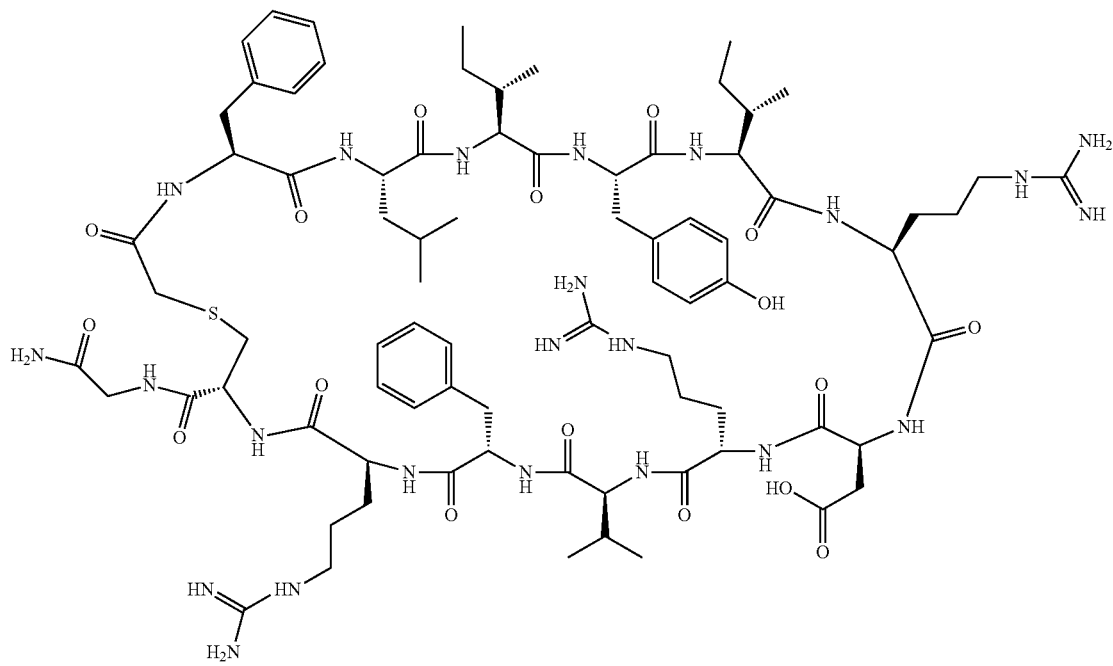

Molecular Weight: 1697.01

Example 106 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 7.5 mg, and its estimated purity by HPLC analysis was 95%.

Analysis LCMS Condition A: retention time=0.93 min.; ESI-MS(+) m/z 849.6 (M+2H).

Analysis HPLC Condition F: retention time=9.43 min.

Example 107

Synthesis of Compound No. 106

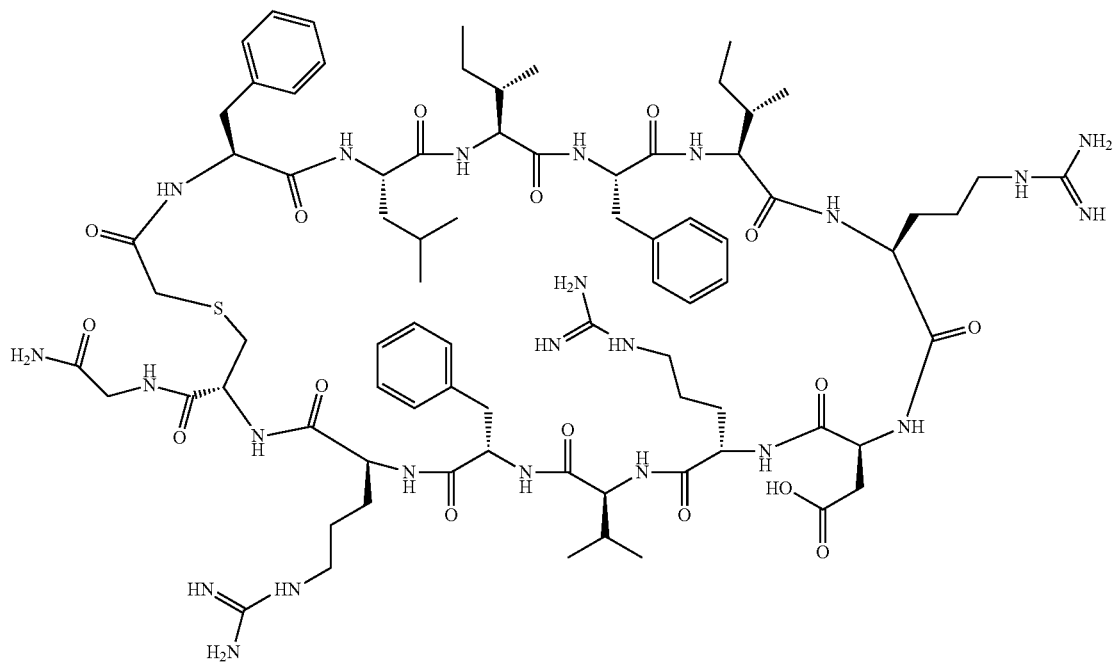

Molecular Weight: 1681.02

Example 107 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-µm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 6.8 mg, and its estimated purity by HPLC analysis was 96%.

Analysis LCMS Condition A: retention time=1.00 min.; ESI-MS(+) m/z 841.7 (M+2H).

Analysis HPLC Condition F: retention time=10.80 min.

Example 108

Synthesis of Compound No. 107

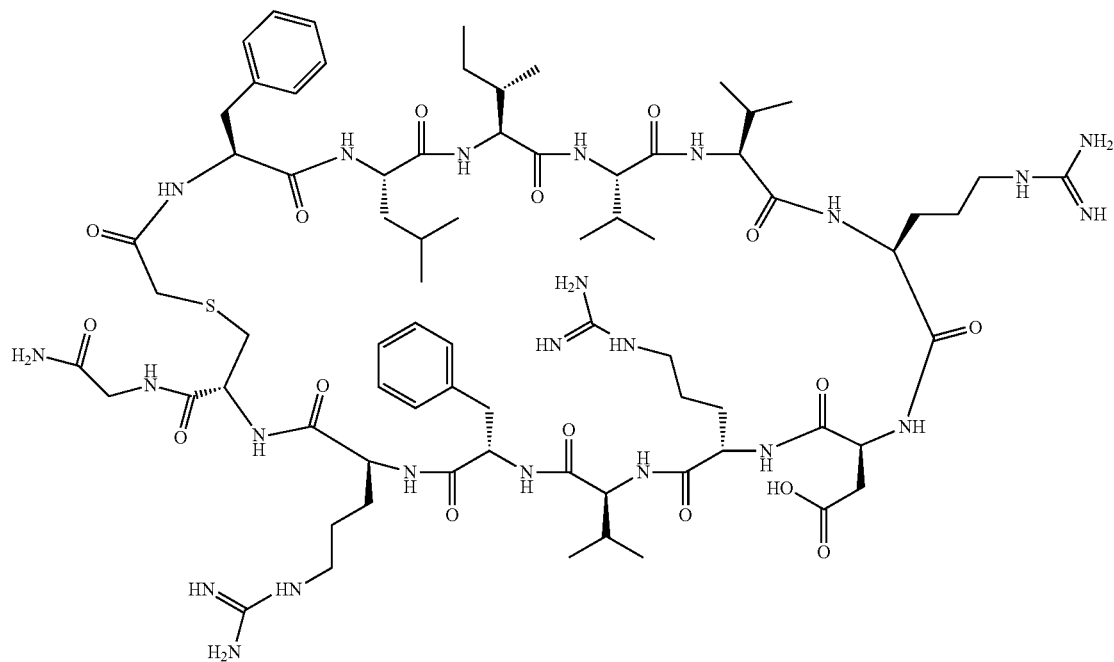

Molecular Weight: 1618.95

Example 108 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 8.8 mg, and its estimated purity by HPLC analysis was 98%.

Analysis LCMS Condition A: retention time=0.90 min.; ESI-MS(+) m/z 810.6 (M+2H).

Analysis HPLC Condition F: retention time=8.70 min.

Example 109

Synthesis of Compound No. 108

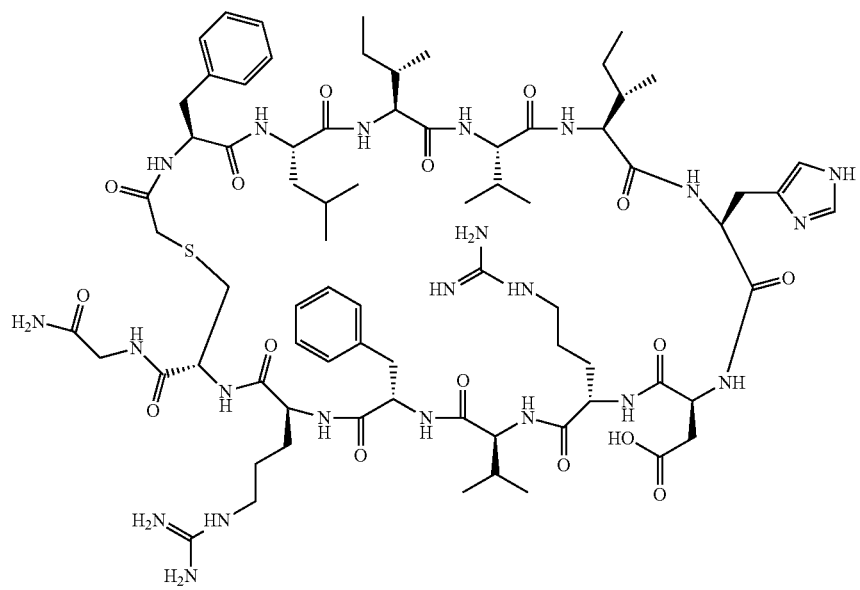

Molecular Weight: 1613.93

Example 109 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 6.3 mg, and its estimated purity by HPLC analysis was 98%.

Analysis LCMS Condition A: retention time=0.89 min.; ESI-MS(+) m/z 808.1 (M+2H).

Analysis HPLC Condition F: retention time=8.65 min.

Example 110

Synthesis of Compound No. 109

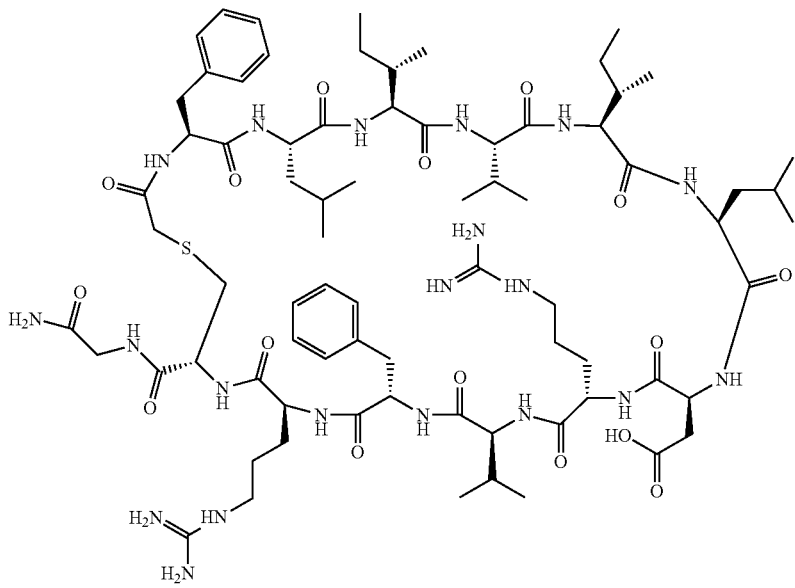

Molecular Weight: 1589.94

Example 110 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 30-80% B over 40 min.; Flow: 15 mL/min. Fractions containing the desired product were combined and dried by lyophilization. The yield of product was 6.3 mg, and its estimated purity by HPLC analysis was 98%.

Analysis LCMS Condition A: retention time=1.18 min.; ESI-MS(+) m/z 796.3 (M+2H).

Analysis HPLC Condition J: retention time=9.00 min.

Example 111

Synthesis of Compound No. 110

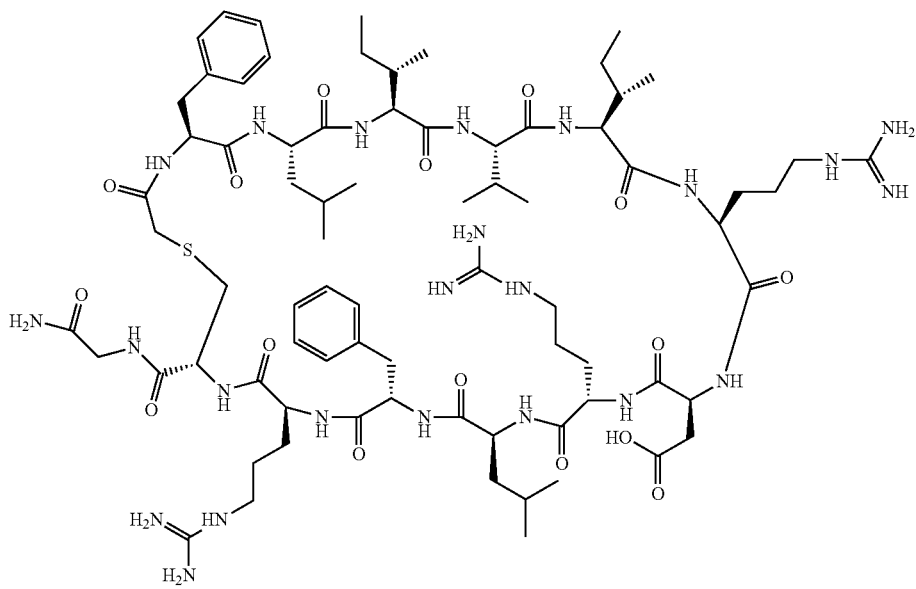

Molecular Weight: 1647.00

Example 111 was prepared following the general synthetic sequence described for the preparation of Example 0002, composed of the following general procedures: "CEM Method A: Resin-swelling procedure", "CEM Method A:

Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 3.4 mg, and its estimated purity by HPLC analysis was 95%.

Analysis LCMS Condition A: retention time=0.96 min.; ESI-MS(+) m/z 824.7 (M+2H).

Analysis HPLC Condition F: retention time=9.98 min.

Example 112

Synthesis of Compound No. 111

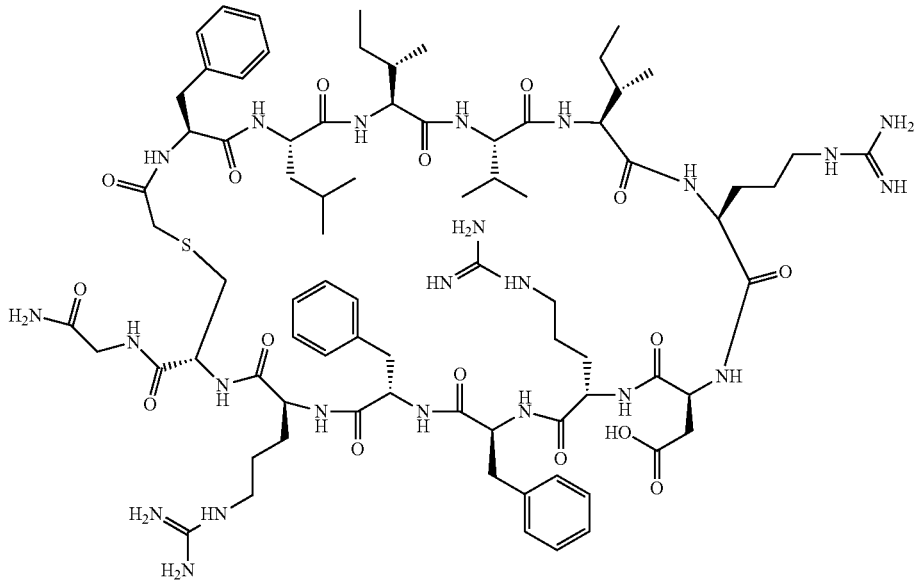

Molecular Weight: 1681.02

Example 112 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure A", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 13 mg, and its estimated purity by HPLC analysis was 95%.

Analysis LCMS Condition A: retention time=0.98 min.; ESI-MS(+) m/z 841.5 (M+2H).

Analysis HPLC Condition F: retention time=10.49 min.

Example 113

Synthesis of Compound No. 112

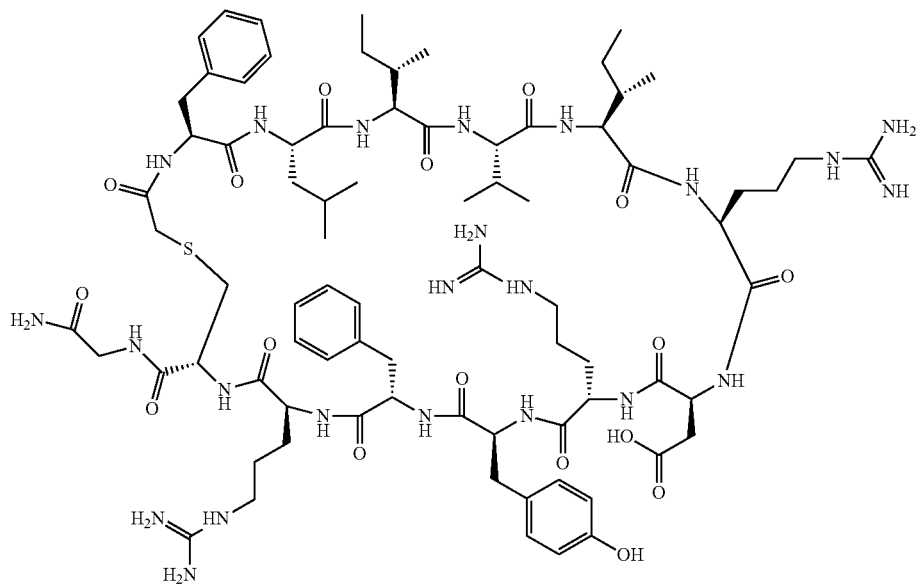

Molecular Weight: 1697.01

Example 113 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 5.4 mg, and its estimated purity by HPLC analysis was 98%.

Analysis LCMS Condition A: retention time=0.95 min.; ESI-MS(+) m/z 849.7 (M+2H).

Analysis HPLC Condition F: retention time=9.72 min.

Example 114

Synthesis of Compound No. 113

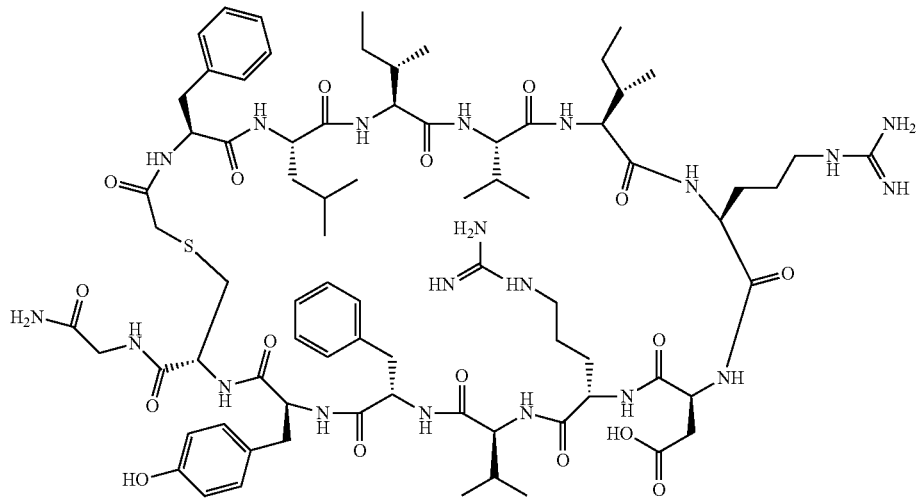

Molecular Weight: 1639.96

Example 114 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure B", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 2.2 mg, and its estimated purity by HPLC analysis was 94%.

Analysis LCMS Condition A: retention time=1.02 min.; ESI-MS(+) m/z 821.1 (M+2H).

Analysis HPLC Condition F: retention time=11.30 min.

Example 115

Synthesis of Compound No. 114

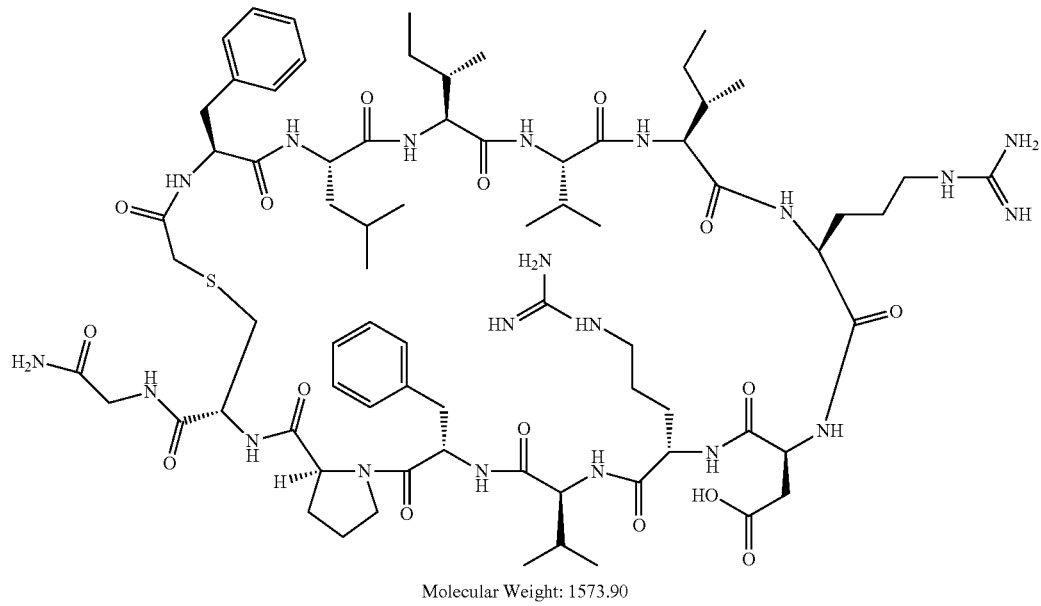 [SMILES: CC[C@H](C)[C@@H]1NC(=O)[C@H](CC(C)C)NC(=O)[C@H](Cc2ccccc2)NC(=O)CSC[C@@H](C(=O)NCC(N)=O)NC(=O)[C@@H]2CCCN2C(=O)[C@H](Cc2ccccc2)NC(=O)[C@H](C(C)C)NC(=O)[C@H](CCCNC(=N)N)NC(=O)[C@H](CC(=O)O)NC(=O)[C@H](CCCNC(=N)N)NC(=O)[C@H]([C@@H](C)CC)NC(=O)[C@H](C(C)C)NC1=O]

Molecular Weight: 1573.90

Example 115 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure A", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 12.5 mg, and its estimated purity by HPLC analysis was 99%.

Analysis LCMS Condition A: Retention time=1.06 min; ESI-MS(+) m/z 788.0 (M+2H)

Analysis HPLC Condition F: Retention time=11.88 min

Example 116

Synthesis of Compound No. 115

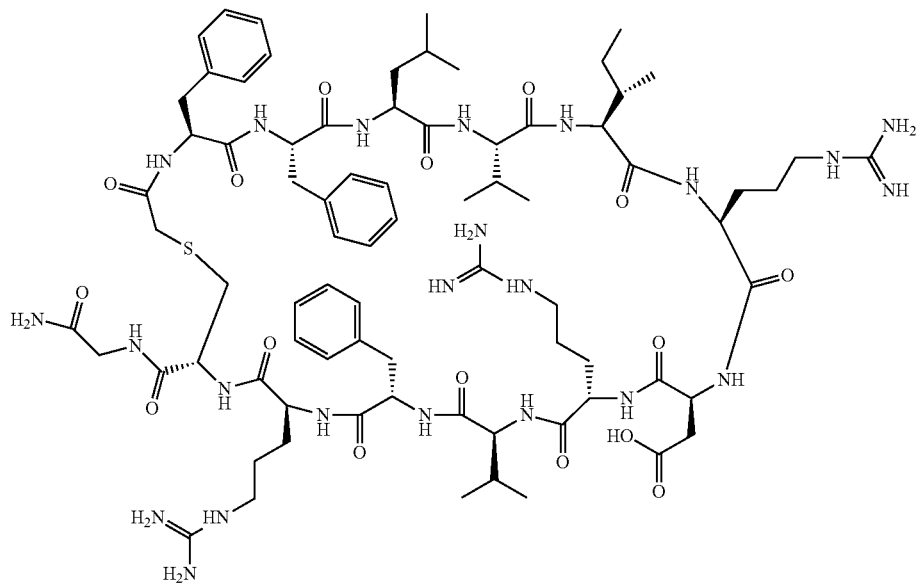

Molecular Weight: 1666.99

Example 116 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetic acid coupling procedure A", "Global Deprotection Method A", and "Cyclization Method A".

The crude material was purified via preparative HPLC using the following conditions: Column: YMC ODS-AQ, 20×250 mm, 5-μm particles; Mobile Phase A: 0.1% TFA in water; Mobile Phase B: 0.1% TFA in MeCN; gradient: 20-60% B over 40 min.; Flow: 15 mL/min. Fractions containing the desired product were combined and dried by lyophilization. The yield of product was 8.4 mg, and its estimated purity by HPLC analysis was 96%.

Analysis LCMS Condition A: Retention time=0.95 min; ESI-MS(+) m/z 834.5 (M+2H)

Analysis HPLC Condition F: Retention time=10.01 min

TABLE 5

C-TERMINALLY PEGYLATED PEPTIDES OF FORMULAS I AND II[±]

| Compound No. | Peptide Sequence | | | | | | | | | | | | | | | | MS | |
|---|---|---|---|---|---|---|---|---|---|---|---|---|---|---|---|---|---|---|
| | A | 1 | 2 | 3 | 4 | 5 | 6 | 7 | 8 | 9 | 10 | 11 | 12 | 13 | 14 | 15 | Predicted | Observed |
| 116 | ClAc | F | $^m$Ala | N | P | H | L | Sar | W | S | W | $^m$Nle | $^m$Nle | R | C | G | PEG$_{12}$-NH$_2$ | 2451.90 | 1226.6 (M + 2) |
| 117 | ClAc | F | $^m$Ala | N | P | H | H | S | W | R | W | $^m$Nle | $^m$Nle | L | C | G | PEG$_{12}$-NH$_2$ | 2517.96 | 1260.1 (M + 2) |
| 118 | ClAc | F | $^m$Phe | $^m$Nle | Sar | D | V | $^m$Phe | Y | Sar | W | Y | L | C | G | PEG$_{12}$-NH$_2$ | 2395.82 | 1198.7 (M + 2) |

[±]Compound Nos. 116 to 118 are macrocyclic peptides cyclized via the moiety listed at the A position with a downstream cysteine.

Example 117

Synthesis of Compound No. 116

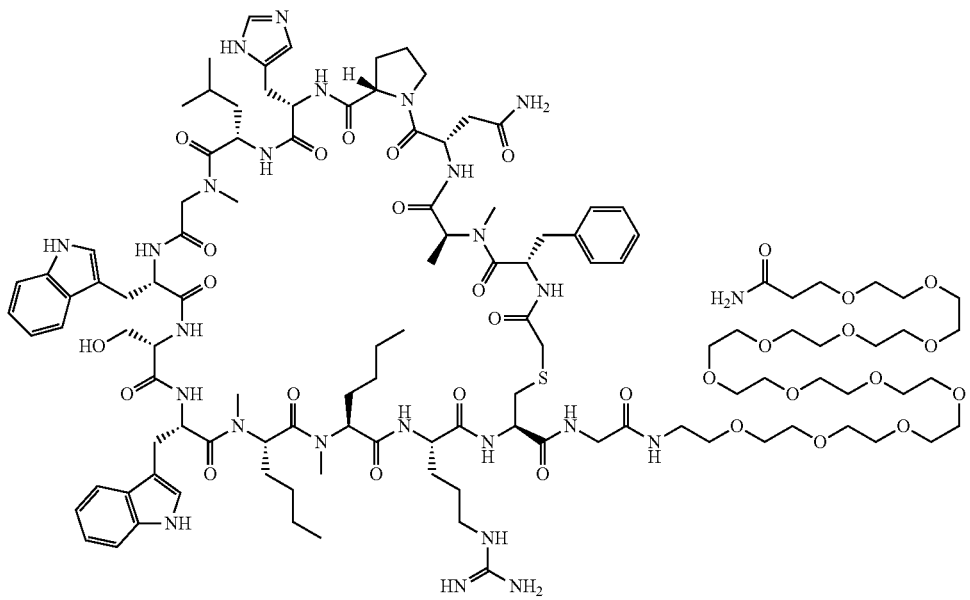

Molecular Weight: 2451.88

Example 117 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method E", and "Cyclization Method C". The starting resin was Fmoc-PEG$_{12}$-Sieber amide resin (0.05 mmol), which was prepared manually by coupling of O—(N-FMOC-2-AMINOETHYL)-O'-(2-CARBOXYETHYL)-UNDECAETHYLENEGLYCOL to Sieber Amide resin according to the following procedure: Seiber Amide Resin (0.60 mmol, 0.846 g, 0.71 mmole/g) was washed with DCM (8 mL) for 5 min. and DMF (8 mL) for 5 min. The resin was treated twice with 5% piperazine in DMF (8 mL) for 5 min and then washed once with methanol (8 mL) and six times with DMF (8 mL). To a solution of O—(N-FMOC-2-AMINOETHYL)-O'-(2-CARBOXYETHYL)-UNDECAETHYLENEGLYCOL (0.715 g, 0.851 mmol) in DMF (4 mL) was added 0.45 M HCTU in DMF (1.8 ml, 0.810 mmol) and 2 M DIEA in NMP (0.85 ml, 1.70 mmol). The resulting solution was stirred and added to the resin. The reaction was allowed to proceed for 18 hrs. The resin was washed three times with DMF (8 mL) and three times with DCM washes (8 mL). An Fmoc determination on an aliquot of dry resin provided a substitution of 0.26 mmol/g. This was used to determine the amount of starting resin equivalent to 0.05 or 0.1 mmol, depending on the scale required.

The crude material was purified via preparative HPLC using the following conditions: Column: YMC ODS-AQ, 20×250 mm, 5-µm particles; Mobile Phase A: 0.1% TFA in water; Mobile Phase B: 0.1% TFA in MeCN; gradient: 20-80% B over 60 min.; Flow: 15 mL/min. Fractions containing the desired product were combined and dried by lyophilization. The yield of product was 6.2 mg, and its estimated purity by HPLC analysis was 98%.

Analysis LCMS Condition A: Retention time=1.31 min.; ESI-MS(+) m/z 1226.6 (M+2H)

Analysis HPLC Condition B: Retention time=16.08 min

Example 118

Synthesis of Compound No. 117

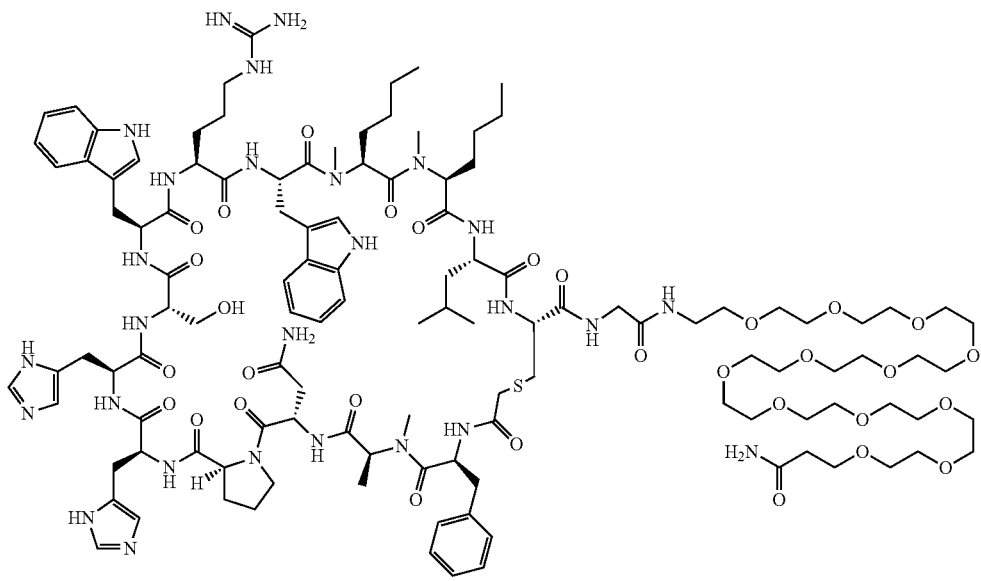

Molecular Weight: 2517.94

Example 118 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method E", and "Cyclization Method C". The starting resin was Fmoc-$PEG_{12}$-Sieber amide resin (0.05 mmol), prepared as described in Example 117

The crude material was purified via preparative HPLC using the following conditions: Column: YMC ODS-AQ, 20×250 mm, 5-µm particles; Mobile Phase A: 0.1% TFA in water; Mobile Phase B: 0.1% TFA in MeCN; gradient: 25-50% B over 50 min.; Flow: 15 mL/min. Fractions containing the desired product were combined and dried by lyophilization. The yield of product was 3.2 mg, and its estimated purity by HPLC analysis was 91.4%.

Analysis LCMS Condition A: Retention time=1.22 min; ESI-MS(+) m/z 1260.1 (M+2H)

Analysis HPLC Condition B: Retention time=14.75 min

Example 119

Synthesis of Compound No. 118

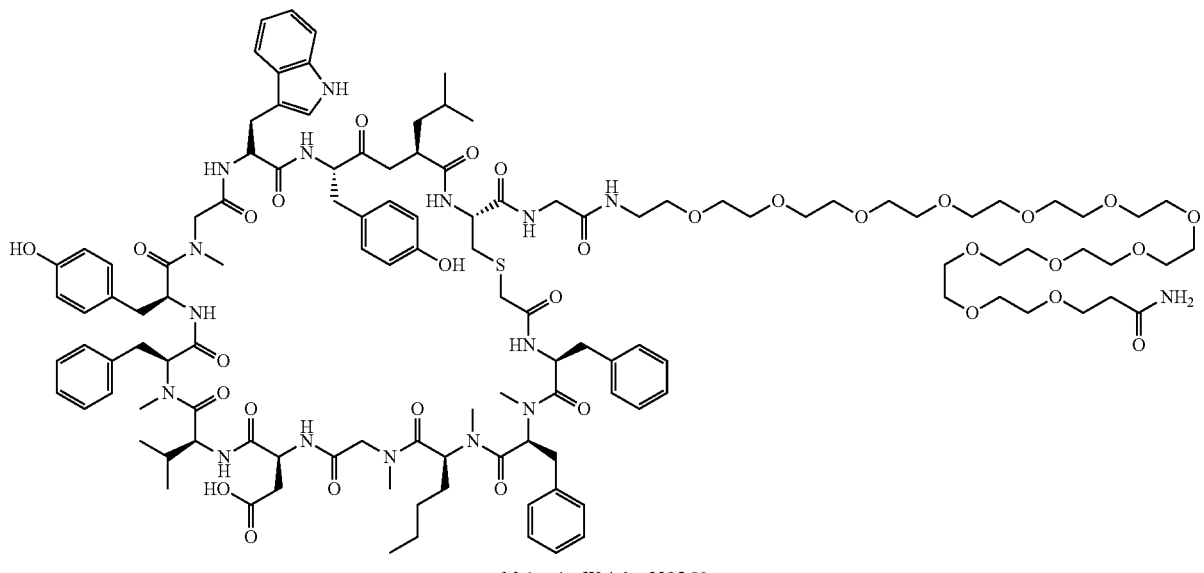

Molecular Weight: 2395.80

Example 119 was prepared following the general synthetic sequence described for the preparation of Example 0002, composed of the following general procedures: "CEM Method A: Resin-swelling procedure", "CEM Method A: Single-coupling procedure", "CEM Method A: Double-coupling procedure", "Chloroacetyl chloride coupling procedure A", "Global Deprotection Method F", and "Cyclization Method C". The starting resin was Fmoc-PEG$_{12}$-Sieber amide resin (0.05 mmol), prepared as described in Example 117

The crude material was purified via preparative HPLC using the following conditions: Column: YMC ODS-AQ, 20×250 mm, 5-µm particles; Mobile Phase A: 0.1% TFA in water; Mobile Phase B: 0.1% TFA in MeCN; gradient: 20-90% B over 60 min.; Flow: 15 mL/min. Fractions containing the desired product were combined and dried by lyophilization. The yield of product was 5.3 mg, and its estimated purity by HPLC analysis was 96%.

Analysis LCMS Condition A: Retention time=1.44 min; ESI-MS(+) m/z 1198.7 (M+2H).

Analysis HPLC Condition K: Retention time=14.22 min

Custom Amino Acids (S)-2-((((9H-fluoren-9-yl)methoxy)carbonyl)amino)-3-(cyclobutanecarboxamido)propanoic acid Cyclobutanecarbonyl chloride (72.7 mg, 0.613 mmol) and NaOH (0.735 mL, 0.735 mmol) were dropped at the same time to a stirred solution of (S)-2-((((9H-fluoren-9-yl)methoxy)carbonyl)amino)-3-aminopropanoic acid (200 mg, 0.613 mmol) in THF (1.5 mL) and NaOH (1N, 0.8 mL) at 0° C. The reaction mixture was allowed to stir at rt for 1 h at which time LC-MS showed the desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (156 mg, 61%).

Analysis LCMS Condition A: Retention time=0.94 min; ESI-MS(+) m/z 409.1 (M+H)

$^1$H NMR (400 MHz, methanol-d$_4$) δ 7.80 (d, J=7.5 Hz, 2H), 7.67 (br s, 2H), 7.44-7.35 (m, 2H), 7.35-7.27 (m, 2H), 4.37-4.31 (m, 2H), 4.23 (s, 1H), 3.55-3.48 (m, 1H), 3.14 (s, 2H), 2.31-2.08 (m, 7H)

(S)-2-((((9H-fluoren-9-yl)methoxy)carbonyl)amino)-3-(cyclopentanecarboxamido)propanoic acid

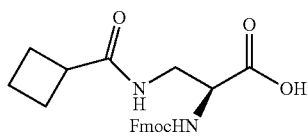

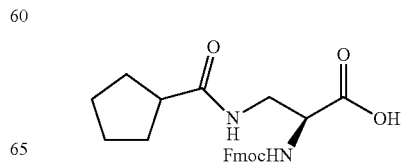

Cyclopentanecarbonyl chloride (81 mg, 0.613 mmol) and NaOH (0.735 mL, 0.735 mmol) were dropped at the same time to a stirred solution of (S)-2-((((9H-fluoren-9-yl)methoxy)carbonyl)amino)-3-aminopropanoic acid (200 mg, 0.613 mmol) in THF (1.5 mL) and NaOH (1N, 0.8 mL) at 0° C. The reaction mixture was allowed to stir at rt for 1 h at which time LC-MS showed the desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (142 mg, 54%).

Analysis LCMS Condition A: Retention time=0.99 min; ESI-MS(+) m/z 423.1 (M+H)

$^1$H NMR (400 MHz, methanol-$d_4$) δ 7.80 (d, J=7.5 Hz, 2H), 7.67 (t, J=6.4 Hz, 2H), 7.44-7.37 (m, 2H), 7.35-7.27 (m, 2H), 4.38-4.31 (m, 2H), 4.27-4.19 (m, 1H), 3.69-3.47 (m, 2H), 2.61 (s, 1H), 1.88-1.53 (m, 9H)

(S)-2-((((9H-fluoren-9-yl)methoxy)carbonyl)amino)-3-benzamidopropanoic acid

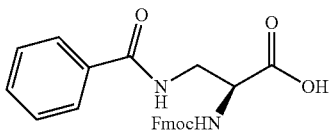

Benzoyl chloride (86 mg, 0.613 mmol) and NaOH (0.735 mL, 0.735 mmol) were dropped at the same time to a stirred solution of (S)-2-((((9H-fluoren-9-yl)methoxy)carbonyl)amino)-3-aminopropanoic acid (200 mg, 0.613 mmol) in THF (1.5 mL) and NaOH (1N, 0.8 mL) at 0° C. The reaction mixture was allowed to stir at rt for 1 h at which time LC-MS showed desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (149 mg, 52%).

Analysis LCMS Condition A: Retention time=0.96 min; ESI-MS(+) m/z 431.0 (M+H)

$^1$H NMR (400 MHz, methanol-$d_4$) δ 7.84-7.75 (m, 4H), 7.64 (d, J=7.5 Hz, 2H), 7.52 (d, J=7.3 Hz, 1H), 7.48-7.41 (m, 2H), 7.37 (t, J=7.5 Hz, 2H), 7.31-7.22 (m, 2H), 4.54-4.47 (m, 1H), 4.33 (dd, J=7.0, 3.3 Hz, 2H), 4.24-4.17 (m, 1H), 3.89-3.73 (m, 2H)

(S)-2-((((9H-fluoren-9-yl)methoxy)carbonyl)amino)-4-(cyclobutanecarboxamido)butanoic acid

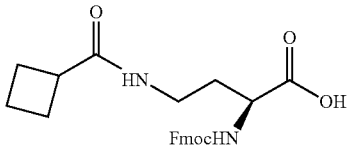

Cyclobutanecarbonyl chloride (69.7 mg, 0.588 mmol) and NaOH (0.705 mL, 0.705 mmol) were dropped at the same time to a stirred solution of (S)-2-((((9H-fluoren-9-yl)methoxy)carbonyl)amino)-4-aminobutanoic acid (200 mg, 0.588 mmol) in THF (1.5 mL) and of NaOH (1N, 0.7 mL) at 0° C. The reaction mixture was allowed to stir at rt for 1 h at which time LC-MS showed desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (92.6 mg, 37%).

Analysis LCMS Condition A: Retention time=0.94 min; ESI-MS(+) m/z 423.1 (M+H)

$^1$H NMR (400 MHz, methanol-$d_4$) δ 7.80 (d, J=7.5 Hz, 2H), 7.72-7.65 (m, 2H), 7.43-7.36 (m, 2H), 7.35-7.28 (m, 2H), 4.41-4.32 (m, 2H), 4.28-4.15 (m, 2H), 3.20 (d, J=7.0 Hz, 1H), 3.08 (s, 1H), 2.31-2.04 (m, 6H), 1.97 (d, J=9.9 Hz, 1H), 1.84 (d, J=7.3 Hz, 2H)

(S)-2-((((9H-fluoren-9-yl)methoxy)carbonyl)amino)-4-(cyclopentanecarboxamido)butanoic acid

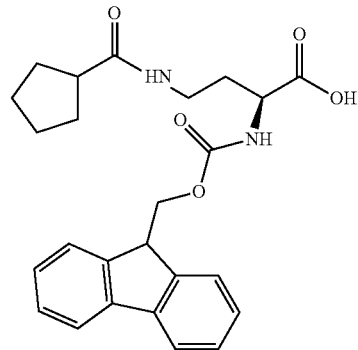 [SMILES: O=C(N[C@@H](CCNC(=O)C1CCCC1)C(=O)O)OCC1c2ccccc2-c2ccccc21]

Cyclopentanecarbonyl chloride (78 mg, 0.588 mmol) and NaOH (0.705 mL, 0.705 mmol) were dropped at the same time to a stirred solution of (S)-2-((((9H-fluoren-9-yl)methoxy)carbonyl)amino)-4-aminobutanoic acid (200 mg, 0.588 mmol) in THF (1.5 mL) and of NaOH (1N, 0.7 mL) at 0° C. The reaction mixture was allowed to stir at rt for 1 h at which time LC-MS showed desired product peak. The reaction solution was acidified with 1N HCl and extracted with EtOAc (60 mL×1). The crude materials were purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (84.1 mg, 33%).

Analysis LCMS Condition A: Retention time=0.98 min; ESI-MS(+) m/z 437.1 (M+H)

$^1$H NMR (400 MHz, methanol-$d_4$) δ 7.79 (d, J=7.5 Hz, 2H), 7.72-7.64 (m, 2H), 7.42-7.35 (m, 2H), 7.34-7.26 (m, 2H), 4.41-4.30 (m, 2H), 4.26-4.14 (m, 2H), 3.24-3.13 (m, 1H), 2.59 (t, J=7.8 Hz, 1H), 2.05 (s, 1H), 1.91-1.62 (m, 8H), 1.64-1.50 (m, 2H)

(S)-2-((((9H-fluoren-9-yl)methoxy)carbonyl)amino)-4-(cyclohexanecarboxamido)butanoic acid

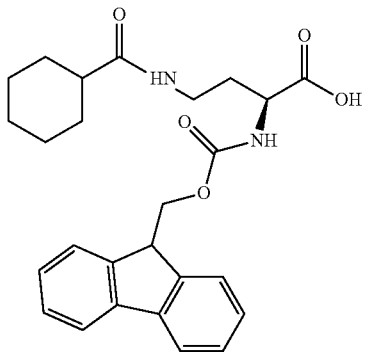 [SMILES: O=C(N[C@@H](CCNC(=O)C1CCCCC1)C(=O)O)OCC1c2ccccc2-c2ccccc21]

Cyclohexanecarbonyl chloride (86 mg, 0.588 mmol) and NaOH (0.705 mL, 0.705 mmol) were dropped at the same time to a stirred solution of (S)-2-((((9H-fluoren-9-yl)methoxy)carbonyl)amino)-4-aminobutanoic acid (200 mg, 0.588 mmol) in THF (1.5 mL) and of NaOH (1N, 0.7 mL) at 0° C. The reaction mixture was allowed to stir at rt for 1 h at which time LC-MS showed desired product peak. The reaction solution was acidified with 1N HCl and extracted with EtOAc (60 mL×1). The crude materials were purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (201 mg, 70%).

Analysis LCMS Condition A: Retention time=1.01 min; ESI-MS(+) m/z 451.2 (M+H)

$^1$H NMR (400 MHz, methanol-$d_4$): δ 7.79 (d, J=7.5 Hz, 2H), 7.73-7.65 (m, 2H), 7.43-7.35 (m, 2H), 7.34-7.26 (m, 2H), 4.42-4.30 (m, 2H), 4.27-4.15 (m, 2H), 3.18 (d, J=7.3 Hz, 1H), 2.15 (s, 1H), 2.10-2.01 (m, 1H), 1.89-1.72 (m, 5H), 1.68 (d, J=10.3 Hz, 1H), 1.49-1.17 (m, 6H)

(S)-2-((((9H-fluoren-9-yl)methoxy)carbonyl)amino)-4-benzamidobutanoic acid

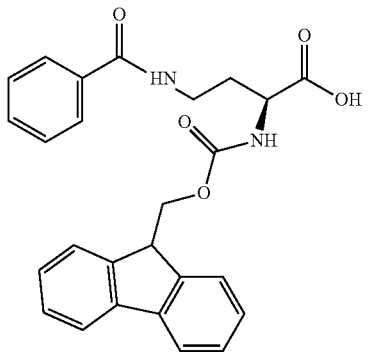 [SMILES: O=C(N[C@@H](CCNC(=O)c1ccccc1)C(=O)O)OCC1c2ccccc2-c2ccccc21]

Benzoyl chloride (83 mg, 0.588 mmol) and NaOH (0.705 mL, 0.705 mmol) were dropped at the same time to a stirred solution of (S)-2-((((9H-fluoren-9-yl)methoxy)carbonyl)amino)-4-aminobutanoic acid (200 mg, 0.588 mmol) in THF (1.5 mL) and of NaOH (1N, 0.7 mL) at 0° C. The reaction mixture was allowed to stir at rt for 1 h at which time LC-MS showed desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (160 mg, 57%).

Analysis LCMS Condition A: Retention time=0.97 min; ESI-MS(+) m/z 445.1 (M+H)

$^1$H NMR (400 MHz, methanol-$d_4$) δ 7.82 (t, J=8.6 Hz, 4H), 7.74-7.67 (m, 2H), 7.56-7.50 (m, 1H), 7.49-7.42 (m, 2H), 7.42-7.36 (m, 2H), 7.35-7.26 (m, 2H), 4.39 (dd, J=7.0, 2.0 Hz, 2H), 4.32-4.21 (m, 2H), 3.62-3.52 (m, 1H), 3.45-3.35 (m, 1H), 2.20 (d, J=5.1 Hz, 1H), 1.99 (d, J=8.1 Hz, 1H)

(S)-2-((((9H-fluoren-9-yl)methoxy)carbonyl)amino)-4-(furan-2-carboxamido)butanoic acid

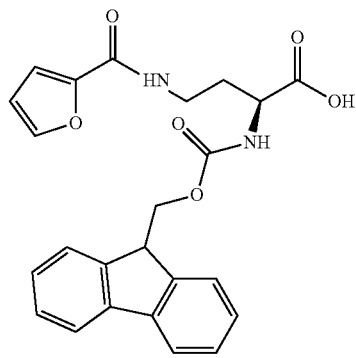 [SMILES: O=C(N[C@@H](CCNC(=O)c1ccco1)C(=O)O)OCC1c2ccccc2-c2ccccc21]

Furan-2-carbonyl chloride (77 mg, 0.588 mmol) and NaOH (0.705 mL, 0.705 mmol) were dropped at the same time to a stirred solution of (S)-2-((((9H-fluoren-9-yl)methoxy)carbonyl)amino)-4-aminobutanoic acid (200 mg, 0.588 mmol) in THF (1.5 mL) and of NaOH (1N, 0.7 mL) at 0° C. The reaction mixture was allowed to stir at rt for 1 h at which time LC-MS showed desired product peak. The reaction solution was acidified with 1N HCl and extracted with EtOAc (60 mL×1). The crude was purified via flash chromatography (ISCO, silica gel, 12 g column; flow rate 30 mL/min, 100% DCM to 20% MeOH/DCM). Fractions containing the desired product were combined and dried via centrifugal evaporation to provide the title compound (107 mg, 41%).

Analysis LCMS Condition A: Retention time=0.92 min; ESI-MS(+) m/z 435.0 (M+H)

$^1$H NMR (400 MHz, methanol-$d_4$) δ 7.80 (d, J=7.7 Hz, 2H), 7.73-7.66 (m, 2H), 7.63 (s, 1H), 7.44-7.35 (m, 2H), 7.34-7.26 (m, 2H), 7.09 (d, J=3.3 Hz, 1H), 6.56 (dd, J=3.4, 1.7 Hz, 1H), 4.41-4.35 (m, 2H), 4.28-4.19 (m, 2H), 3.51 (dd, J=13.8, 7.4 Hz, 1H), 3.43-3.34 (m, 1H), 2.24-2.12 (m, 1H), 1.94 (d, J=7.3 Hz, 1H)

Intermediate Resins for Examples 1001-3000

Preparation of Intermediate Resin A

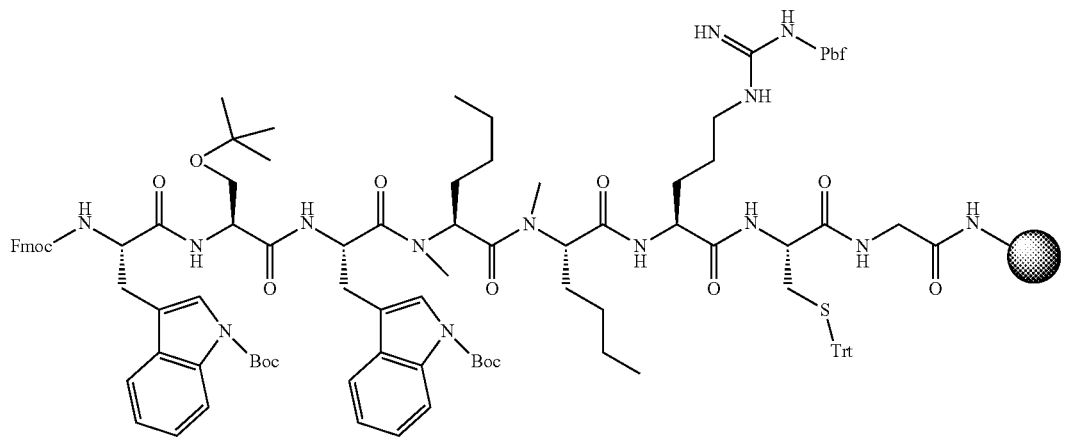

To a 125 mL reactor was added Sieber resin (1410 mg, 1 mmol) and the vessel was placed on the CEM Liberty microwave peptide synthesizer. The following procedures were then performed sequentially:

"CEM Method A: Resin-swelling procedure" was followed;

"CEM Method A: Standard coupling procedure" was followed with Fmoc-Gly-OH;

"CEM Method A: Standard coupling procedure" was followed with Fmoc-Cys(Trt)-OH;

"CEM Method A: Standard coupling procedure" was followed with Fmoc-Arg(PBF)-OH;

"CEM Method A: Double-couple Coupling procedure" was followed with Fmoc-[N-Me]Nle-OH;

"CEM Method A: Double-couple Coupling procedure" was followed with Fmoc-[N-Me]Nle-OH "CEM Method A: Double-couple Coupling procedure" was followed with Fmoc-Trp-OH using 2.5 eq for 30 mins;

"CEM Method A: Standard coupling procedure" was followed with Fmoc-Ser(tBu)-OH;

"CEM Method A: Standard coupling procedure" was followed with Fmoc-Trp-OH;

The resulting resin was transferred to a 100 mL polypropylene tube and washed DCM (40 mL×3). Finally, the resin was dried under vacuum and used as a intermediate for synthesis.

Microcleavage A was followed.

Analysis LCMS Condition A: Retention time=0.89 min, ESI-MS(+) m/z 1271.2 (M+H).

Preparation of Intermediate Resin B

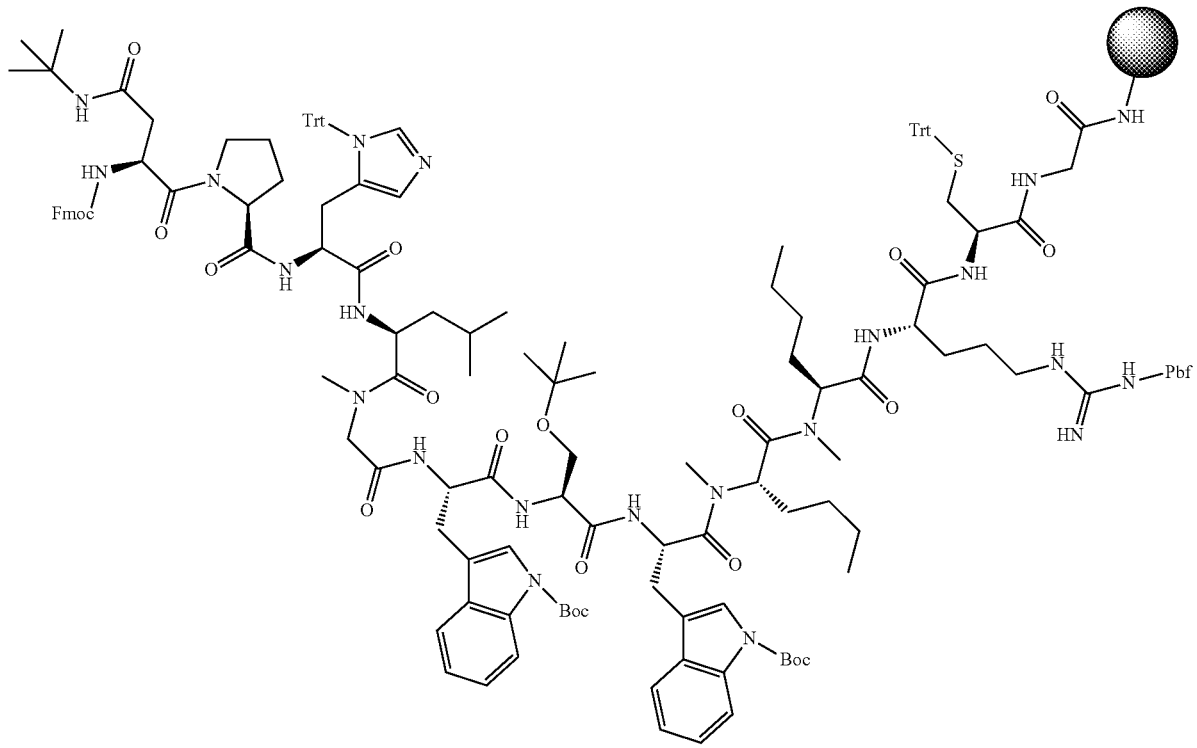

To a 125 mL reactor was added Sieber resin (1410 mg, 1 mmol), and the vessel was placed on the CEM Liberty microwave peptide synthesizer. The following procedures were then performed sequentially:

"CEM Method A: Resin-swelling procedure" was followed;

"CEM Method A: Standard coupling procedure" was followed with Fmoc-Gly-OH;

"CEM Method A: Standard coupling procedure" was followed with Fmoc-Cys(Trt)-OH;

"CEM Method A: Standard coupling procedure" was followed with Fmoc-Arg(PBF)—OH;

"CEM Method A: Double-couple Coupling procedure" was followed with Fmoc-[N-Me]Nle-OH;

"CEM Method A: Double-couple Coupling procedure" was followed with Fmoc-[N-Me]Nle-OH;

"CEM Method A: Double-couple Coupling procedure" was followed with Fmoc-Trp(Boc)-OH;

"CEM Method A: Standard coupling procedure" was followed with Fmoc-Ser(tBu)-OH;

"CEM Method A: Standard coupling procedure" was followed with Fmoc-Trp-OH;

"CEM Method A: Standard coupling procedure" was followed with Fmoc-Sar-OH;

"CEM Method A: Double-couple Coupling procedure" was followed with Fmoc-Leu-OH;

"CEM Method A: Standard coupling procedure" was followed with Fmoc-His(Trt)-OH;

"CEM Method A: Standard coupling procedure" was followed with Fmoc-Pro-OH;

"CEM Method A: Double-couple Coupling procedure" was followed with Fmoc-Asn(tBu)-OH;

The resulting resin was transferred to a 100 mL polypropylene tube equipped with a frit and washed with DCM (40 mL×3). Finally, the resin was dried under vacuum and used as a intermediate for synthesis.

Microcleavage A was followed.
Analysis LCMS Condition A: Retention time=1.0 min, ESI-MS(+) m/z 966.6 (M+2H+1CO$_2$).

Preparation of Intermediate Resin C

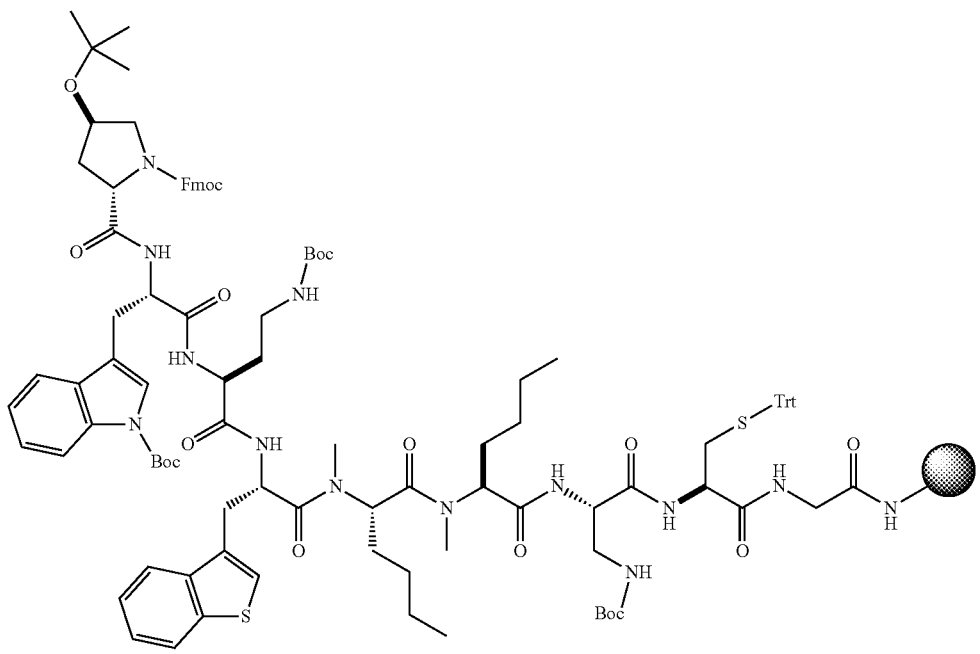

To a 125 mL reactor was added Rink Amide resin (1640 mg, 1 mmol), and the vessel was placed on the CEM Liberty microwave peptide synthesizer. The following procedures were then performed sequentially:

"CEM Method A: Resin-swelling procedure" was followed;

"CEM Method A: Standard coupling procedure" was followed with Fmoc-Gly-OH;

"CEM Method A: Standard coupling procedure" was followed with Fmoc-Cys(Trt)-OH;

"CEM Method A: Standard coupling procedure" was followed with Fmoc-Dap(Boc)-OH;

"CEM Method A: Double-couple Coupling procedure" was followed with Fmoc-Bzt-OH;

"CEM Method A: Double-couple Coupling procedure" was followed with Fmoc-[N-Me]Nle-OH;

"CEM Method A: Double-couple Coupling procedure" was followed with Fmoc-Trp-OH;

"CEM Method A: Standard coupling procedure" was followed with Fmoc-Dab(Boc)-OH;

"CEM Method A: Standard coupling procedure" was followed with Fmoc-Trp-OH;

"CEM Method A: Standard coupling procedure" was followed with Fmoc-Hyp(tBu)-OH;

The resulting resin was transferred to a 100 mL polypropylene tube equipped with a frit and washed with DCM (40 mL×3). Finally, the resin was dried under vacuum and used as a intermediate for synthesis.

Microcleavage A was followed.

Analysis LCMS Condition A: Retention time=0.81 min, ESI-MS(+) m/z 672.2 (M+2H).

Preparation of Intermediate Resin D

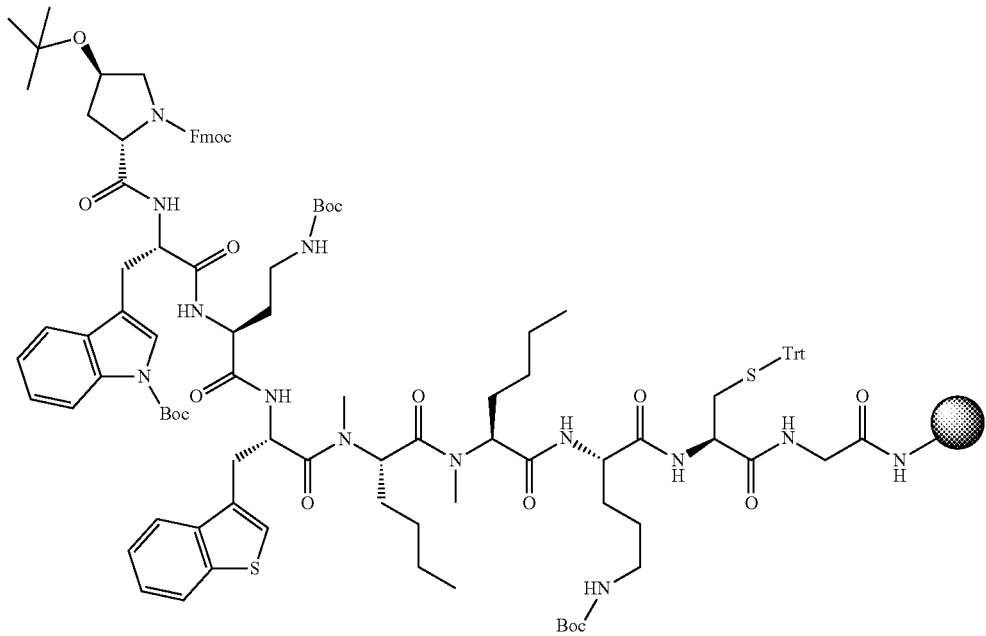

To a 125 mL reactor was added Rink resin (1640 mg, 1 mmol), and the vessel was placed on the CEM Liberty microwave peptide synthesizer. The following procedures were then performed sequentially:

"CEM Method A: Resin-swelling procedure" was followed;

"CEM Method A: Standard coupling procedure" was followed with Fmoc-Gly-OH;

"CEM Method A: Standard coupling procedure" was followed with Fmoc-Cys(Trt)-OH;

"CEM Method A: Standard coupling procedure" was followed with Fmoc-Orn(Boc)-OH;

"CEM Method A: Double-couple Coupling procedure" was followed with Fmoc-[N-Me]Nle-OH;

"CEM Method A: Double-couple Coupling procedure" was followed with Fmoc-[N-Me]Nle-OH;

"CEM Method A: Double-couple Coupling procedure" was followed with Fmoc-Bzt-OH;

"CEM Method A: Standard coupling procedure" was followed with Fmoc-Dab(Boc)-OH;

"CEM Method A: Standard coupling procedure" was followed with Fmoc-Trp-OH;

"CEM Method A: Standard coupling procedure" was followed with Fmoc-Hyp(tBu)-OH;

The resulting resin was transferred to a 100 mL polypropylene tube equipped with a frit and washed with DCM (40 mL×3). Finally, the resin was dried under vacuum and used as a intermediate for synthesis.

Microcleavage A was followed.

Analysis LCMS Condition A: Retention time=0.77 min, ESI-MS(+) m/z 708.2 (M+2H+1CO2).

Preparation of Intermediate Resin E

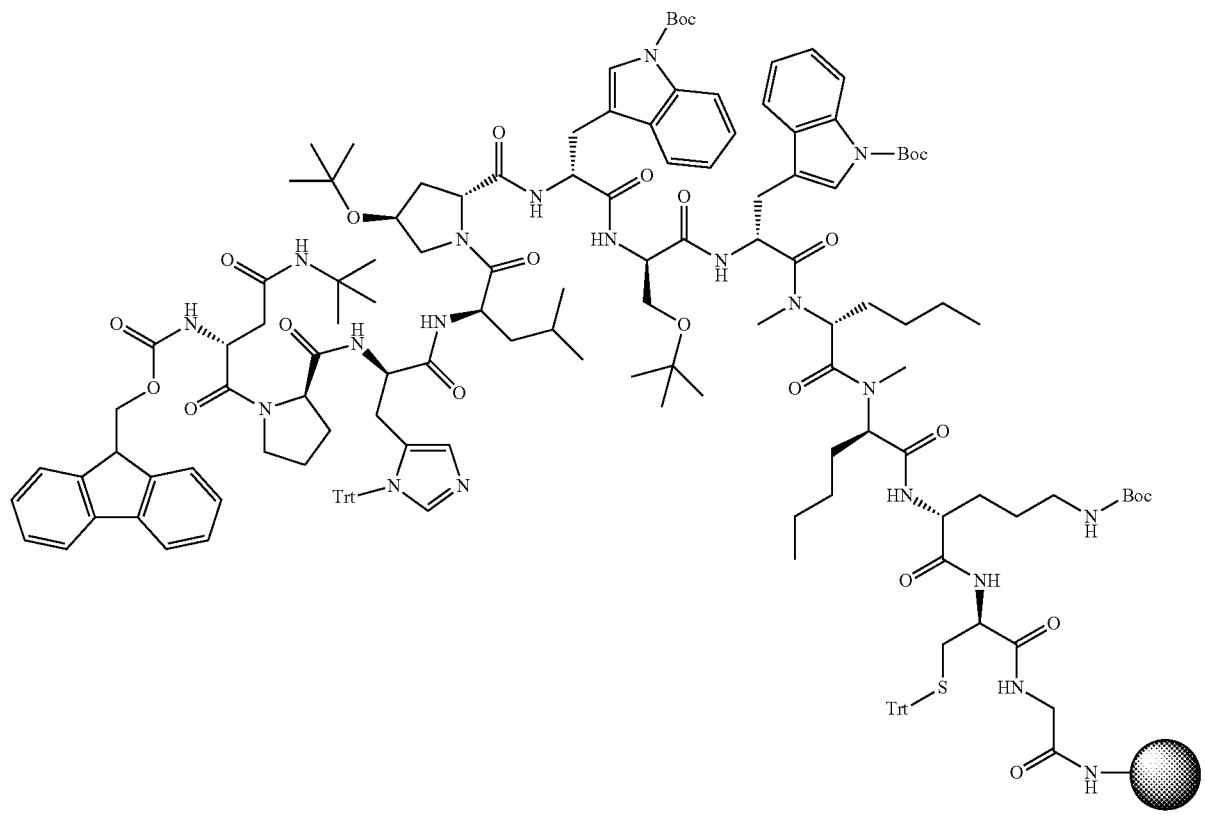

To a 45 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method C: Resin-swelling procedure" was followed;

"Prelude Method C: Single-coupling procedure" was followed with Fmoc-Gly-OH;

"Prelude Method C: Single-coupling procedure" was followed with Fmoc-Cys(Trt)-OH;

"Prelude Method C: Single-coupling procedure" was followed with Fmoc-Orn(Boc)-OH;

"Prelude Method C: Single-coupling procedure" was followed with Fmoc-NMeNle-OH;

"Prelude Method C: Secondary amine-coupling procedure" was followed with Fmoc-MeNleOH;

"Prelude Method C: Secondary amine-coupling procedure" was followed with Fmoc-Trp(Boc)-OH;

"Prelude Method C: Single-coupling procedure" was followed with Fmoc-Ser(tBu)-OH;

"Prelude Method C: Single-coupling procedure" was followed with Fmoc-Trp(Boc)-OH;

"Prelude Method C: Single-coupling procedure" was followed with Fmoc-Hyp(tBu)-OH;

"Prelude Method C: Secondary amine-coupling procedure" was followed with Fmoc-Leu-OH;

"Prelude Method C: Single-coupling procedure" was followed with Fmoc-His(Boc)-OH;

"Prelude Method C: Single-coupling procedure" was followed with Fmoc-Pro-OH;

"Prelude Method C: Secondary amine-coupling procedure" was followed with Fmoc-Asn(tBu)-OH;

"Prelude Method C: Final Wash procedure" was followed

The resulting resin was transferred to a 6 mL Bio-Rad tube equipped with a frit and washed with DCM (4 mL×3). Finally, the resin was dried under vacuum and used as a intermediate for synthesis. The crude material was used as an intermediate for synthesis without analysis.

Preparation of Intermediate Resin F

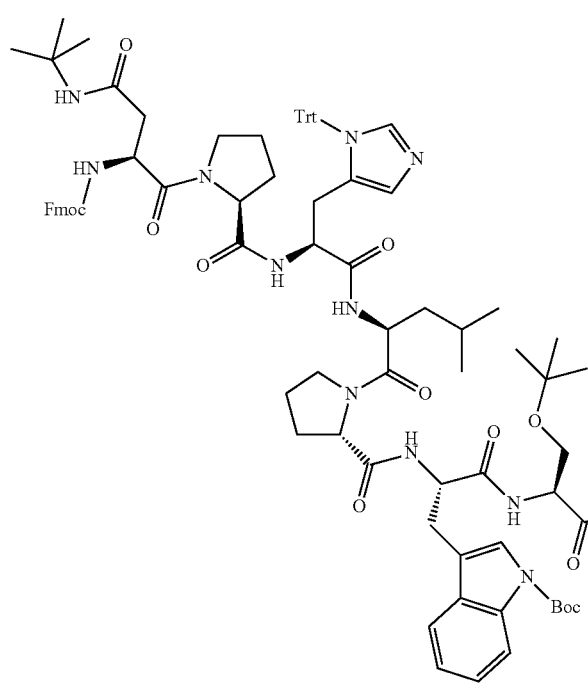

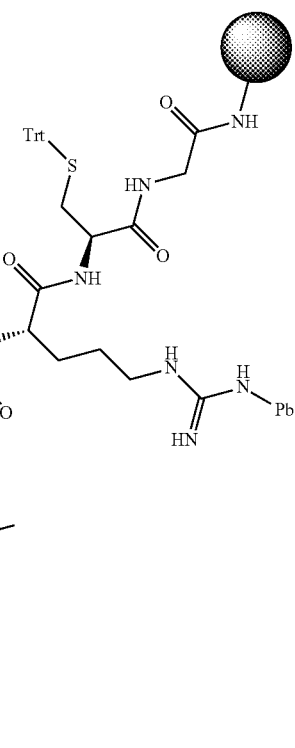

To a 125 mL reactor was added Rink resin (1640 mg, 1 mmol), and the vessel was placed on the CEM Liberty microwave peptide synthesizer. The following procedures were then performed sequentially:

"CEM Method A: Resin-swelling procedure" was followed;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Arg(PBF)-OH;
"CEM Method A: Double-couple Coupling procedure" was followed with Fmoc-[N-Me]Nle-OH;
"CEM Method A: Double-couple Coupling procedure" was followed with Fmoc-[N-Me]Nle-OH;
"CEM Method A: Double-couple Coupling procedure" was followed with Fmoc-Bzt-OH;
"CEM Method A: Standard coupling procedure" was followed with Fmoc-Ser(tBu)-OH;
"CEM Method A: Standard coupling procedure" was followed with Fmoc-Trp-OH;
"CEM Method A: Standard coupling procedure" was followed with Fmoc-Pro-OH;
"CEM Method A: Double-couple Coupling procedure" was followed with Fmoc-Leu-OH;
"CEM Method A: Standard coupling procedure" was followed with Fmoc-His(Trt)-OH;
"CEM Method A: Standard coupling procedure" was followed with Fmoc-Pro-OH;
"CEM Method A: Double-couple Coupling procedure" was followed with Fmoc-Asn(tBu)-OH;

The resulting resin was transferred to a 100 mL polypropylene tube equipped with a frit and washed with DCM (40 mL×3). Finally, the resin was dried under vacuum and used as a intermediate for synthesis.

Microcleavage A was followed.

Analysis LCMS Condition A: Retention time=0.83 min, ESI-MS(+) m/z 945.7 (M+2H).

Preparation of Intermediate Resin G

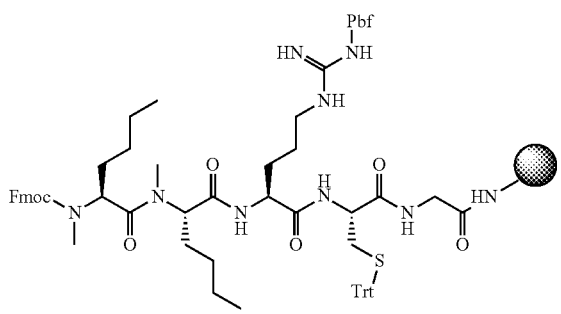

To a 45 mL polypropylene solid-phase reaction vessel was added Sieber resin (140 mg, 0.100 mmol), and the reaction vessel was placed on the Prelude peptide synthesizer. The following procedures were then performed sequentially:

"Prelude Method C: Resin-swelling procedure" was followed;
"Prelude Method C: Single-coupling procedure" was followed with Fmoc-Gly-OH;
"Prelude Method C: Single-coupling procedure" was followed with Fmoc-Cys(Trt)-OH;

"Prelude Method C: Single-coupling procedure" was followed with Fmoc-Orn(Boc)-OH;
"Prelude Method C: Single-coupling procedure" was followed with Fmoc-NMeNle-OH;
"Prelude Method C: Secondary amine-coupling procedure" was followed with Fmoc-MeNle-OH;
"Prelude Method C: Final Wash procedure" was followed.

The resulting resin was transferred to a Bio-Rad tube equipped with a frit and washed DCM (4 mL×3).

Microcleavage A was performed.

Analysis LCMS Condition A: Retention time=0.91 min, ESI-MS(+) m/z 810.5 (M+H).

Preparation of Intermediate Resin H

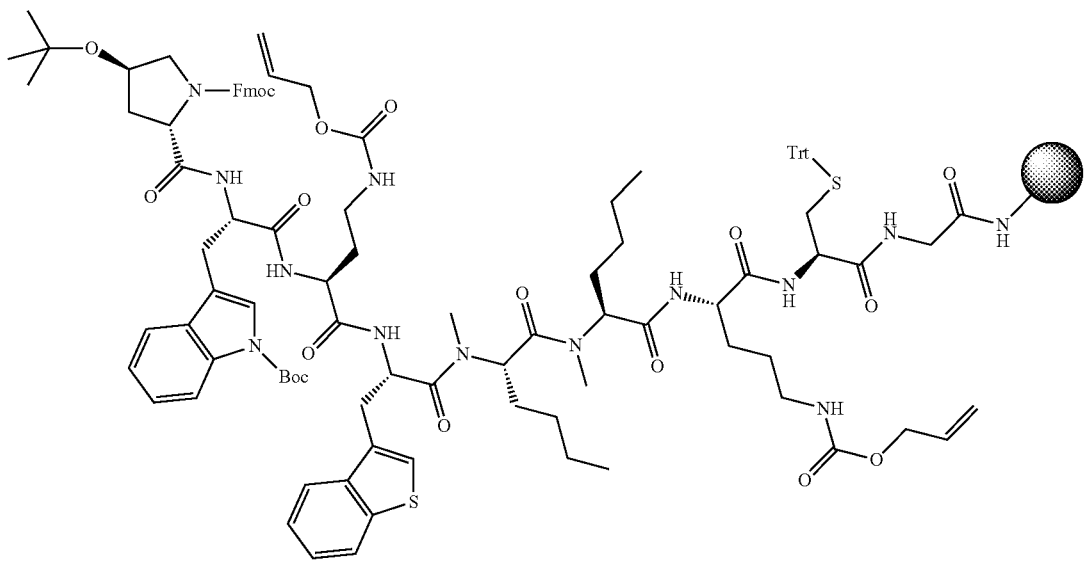

To a 125 mL reactor was added Rink resin (1640 mg, 1 mmol), and the vessel was placed on the CEM Liberty microwave peptide synthesizer. The following procedures were then performed sequentially:
"CEM Method A: Resin-swelling procedure" was followed;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Orn(Alloc)-OH;
"CEM Method A: Double-couple Coupling procedure" was followed with Fmoc-[N-Me]Nle-OH;
"CEM Method A: Double-couple Coupling procedure" was followed with Fmoc-[N-Me]Nle-OH;
"CEM Method A: Double-couple Coupling procedure" was followed with Fmoc-Bzt-OH;
"CEM Method A: Standard coupling procedure" was followed with Fmoc-Dab(Alloc)-OH;
"CEM Method A: Standard coupling procedure" was followed with Fmoc-Trp(Boc)-OH;
"CEM Method A: Standard coupling procedure" was followed with Fmoc-Hyp(tBu)-OH;

The resulting resin was transferred to a 100 mL polypropylene tube equipped with a frit and washed with DCM (40 mL×3). Finally, the resin was dried under vacuum and used as a intermediate for synthesis.

Preparation of Example 1001

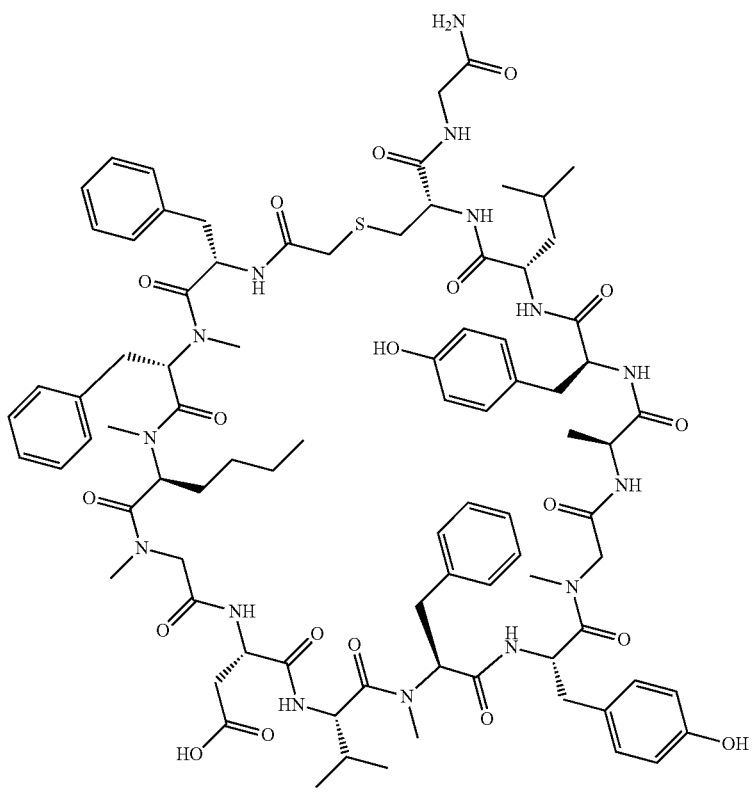

Molecular Weight: 1680.96

Example 1001 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 minutes, then a 5-minute hold at 100% B; Flow: 20 mL/min. Fractions containing the desired product were combined and dried via centrifugal evaporation. The yield of the product was 0.8 mg, and its estimated purity by LCMS analysis was 100%.

Analysis LCMS Condition D: Retention time=1.49 min; ESI-MS(+) m/z 841.20 (M+2H)

Analysis LCMS Condition E: Retention time=1.60 min; ESI-MS(+) m/z 841.20 (M+2H)

Preparation of Example 1002

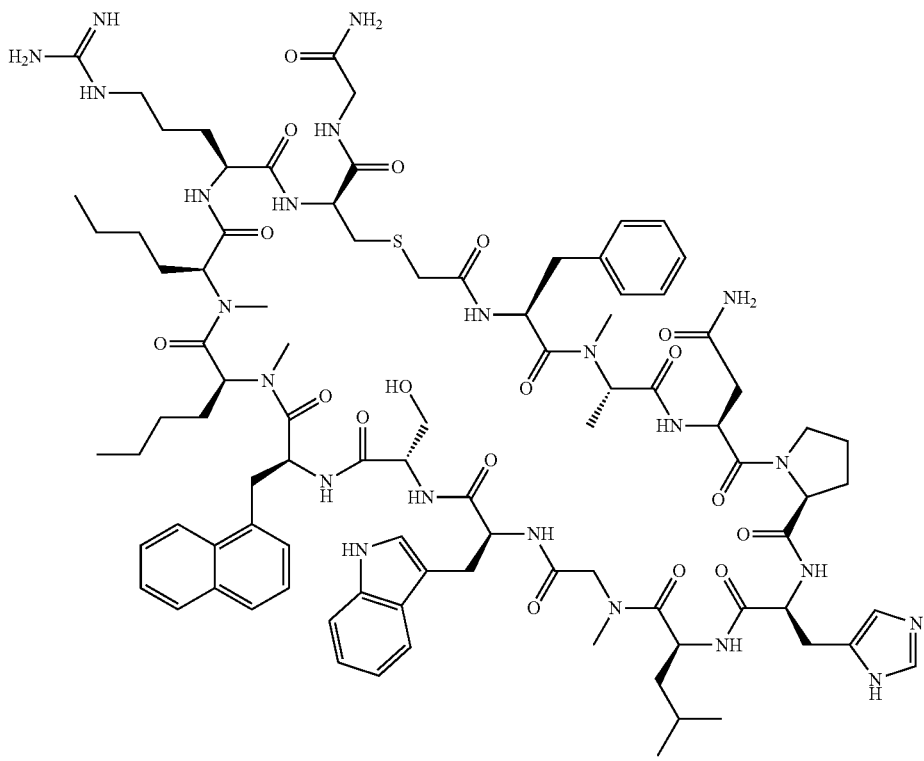

Molecular Weight: 1863.19

Example 1002 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 89%.

Analysis LCMS Condition D: Retention time=1.94 min; ESI-MS(+) m/z 932.50 (M+2H)

Analysis LCMS Condition E: Retention time=1.77 min; ESI-MS(+) m/z 932.60 (M+2H)

Preparation of Example 1003

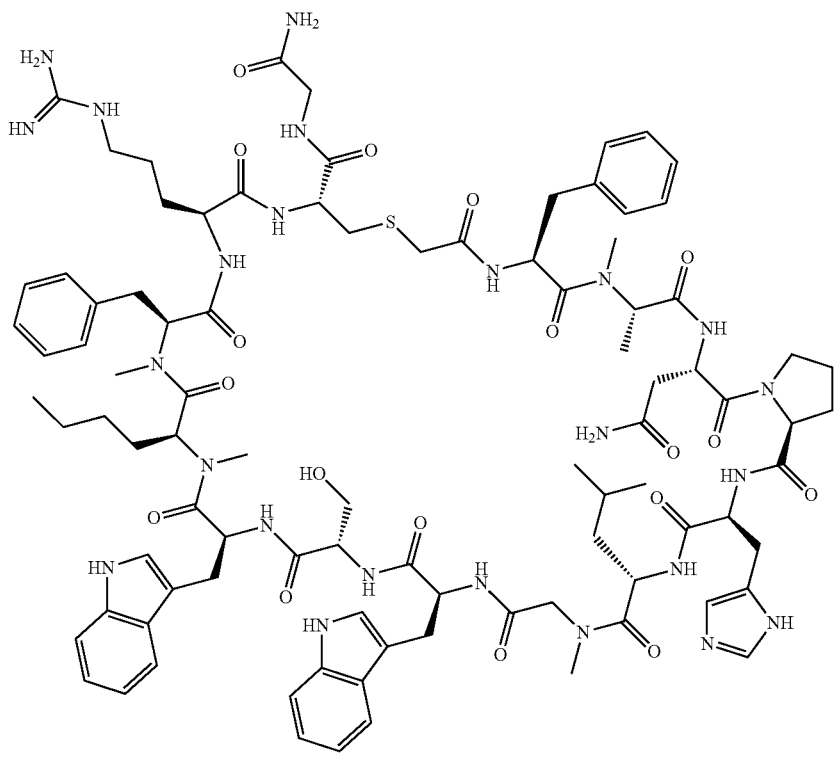

Molecular Weight: 1886.18

Example 1003 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 6.1 mg, and its estimated purity by LCMS analysis was 100%.

Analysis LCMS Condition D: Retention time=1.59 min; ESI-MS(+) m/z 943.7 (M+2H)

Analysis LCMS Condition E: Retention time=1.54 min; ESI-MS(+) m/z 944.0 (M+2H)

Preparation of Example 1004

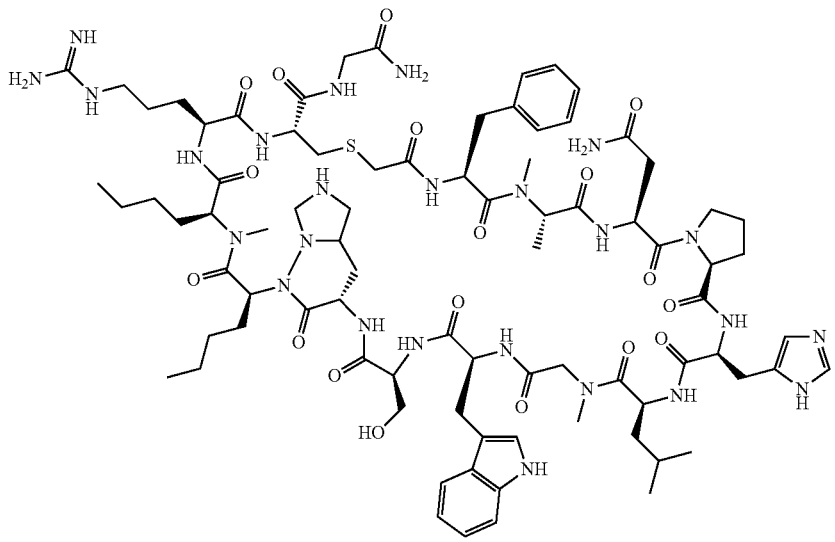

Molecular Weight: 1803.10

Example 1004 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 6.2 mg, and its estimated purity by LCMS analysis was 100%.

Analysis LCMS Condition D: Retention time=1.33 min; ESI-MS(+) m/z 902.1 (M+2H)

Analysis LCMS Condition E: Retention time=1.20 min; ESI-MS(+) m/z 902.0 (M+2H)

Preparation of Example 1005

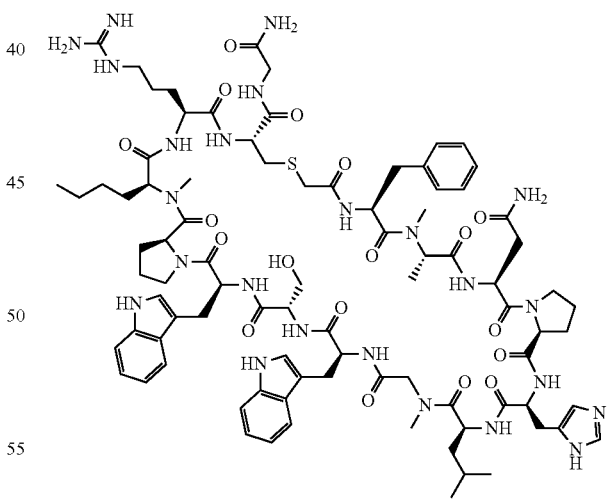

Molecular Weight: 1822.10

Example 1005 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 0-minute hold at 100% B; Flow: 20 mL/min. Fractions containing the desired product were combined and dried via centrifugal evaporation. The yield of the product was 9.0 mg, and its estimated purity by LCMS analysis was 91%.

Analysis LCMS Condition D: Retention time=1.49 min; ESI-MS(+) m/z 911.85 (M+2H)

Analysis LCMS Condition E: Retention time=1.40 min; ESI-MS(+) m/z 911.6 (M+2H)

Preparation of Example 1006

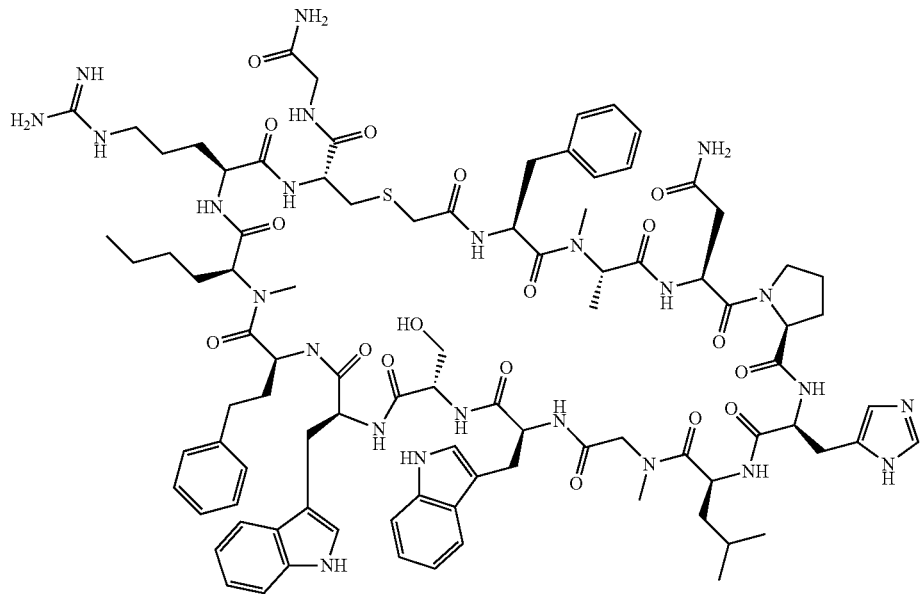

Molecular Weight: 1886.18

Example 1006 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 95%.

Analysis LCMS Condition D: Retention time=1.64 min; ESI-MS(+) m/z 943.90 (M+2H)

Analysis LCMS Condition E: Retention time=1.54 min; ESI-MS(+) m/z 944.25 (M+2H)

Preparation of Example 1007

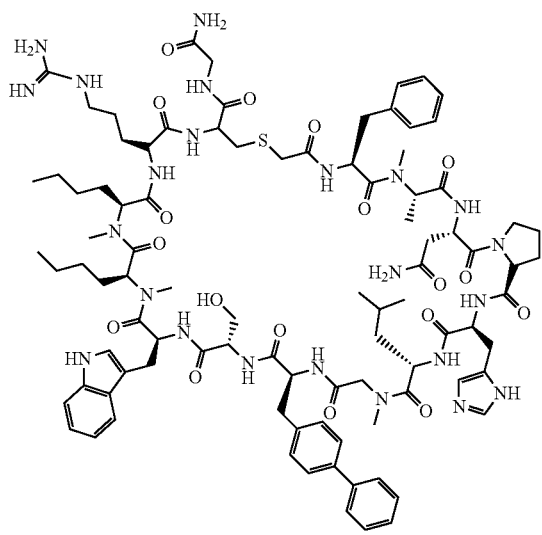

Molecular Weight: 1889.23

Example 1007 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 19.2 mg, and its estimated purity by LCMS analysis was 90%.

Analysis LCMS Condition D: Retention time=1.83 min; ESI-MS(+) m/z 946.10 (M+2H)

Analysis LCMS Condition E: Retention time=1.74 min; ESI-MS(+) m/z 945.15 (M+2H)

Preparation of Example 1009

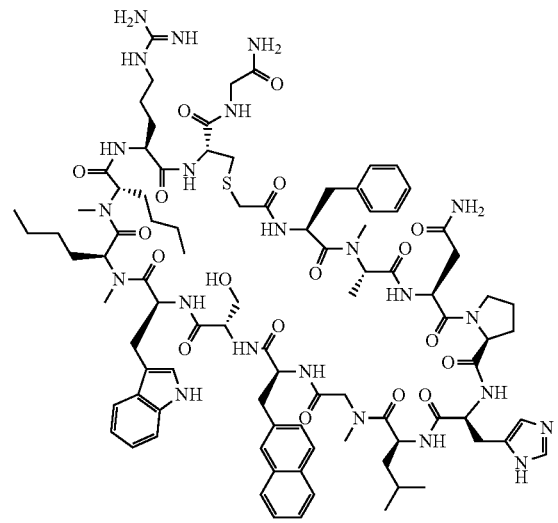

Molecular Weight: 1863.19

Example 1009 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 0-minute hold at 100% B; Flow: 20 mL/min. Fractions containing the desired product were combined and dried via centrifugal evaporation. The yield of the product was 9.0 mg, and its estimated purity by LCMS analysis was 95%.

Analysis LCMS Condition D: Retention time=1.77 min; ESI-MS(+) m/z 932.40 (M+2H)

Analysis LCMS Condition E: Retention time=1.68 min; ESI-MS(+) m/z 932.20 (M+2H)

Preparation of Example 1010

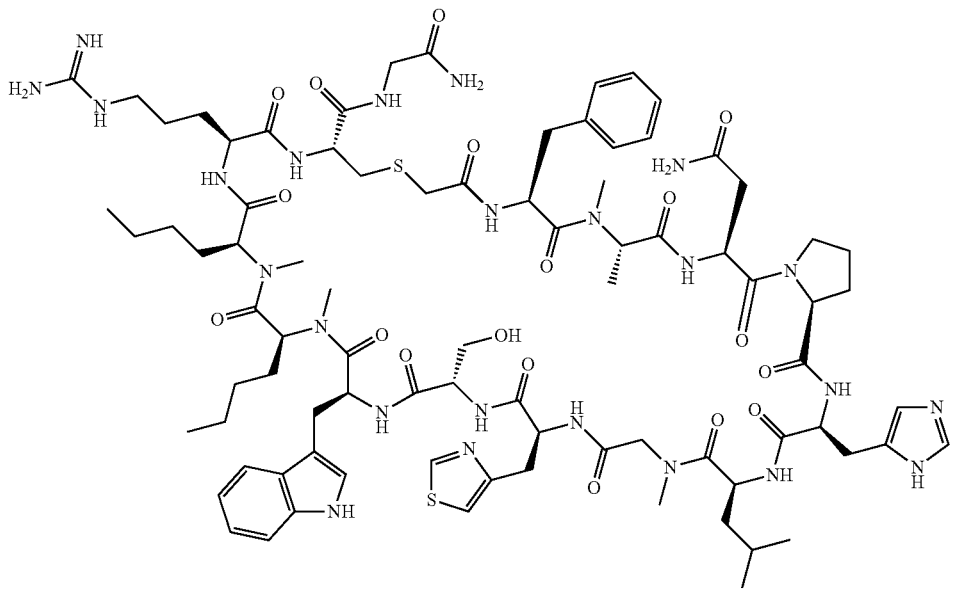

Molecular Weight: 1820.15

Example 1010 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 0-minute hold at 100% B; Flow: 20 mL/min. Fractions containing the desired product were combined and dried via centrifugal evaporation. The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 1 mg, and its estimated purity by LCMS analysis was 100%.

Analysis LCMS Condition D: Retention time=1.47 min; ESI-MS(+) m/z 911.25 (M+2H)

Analysis LCMS Condition E: Retention time=1.40 min; ESI-MS(+) m/z 910.60 (M+2H)

Preparation of Example 1011

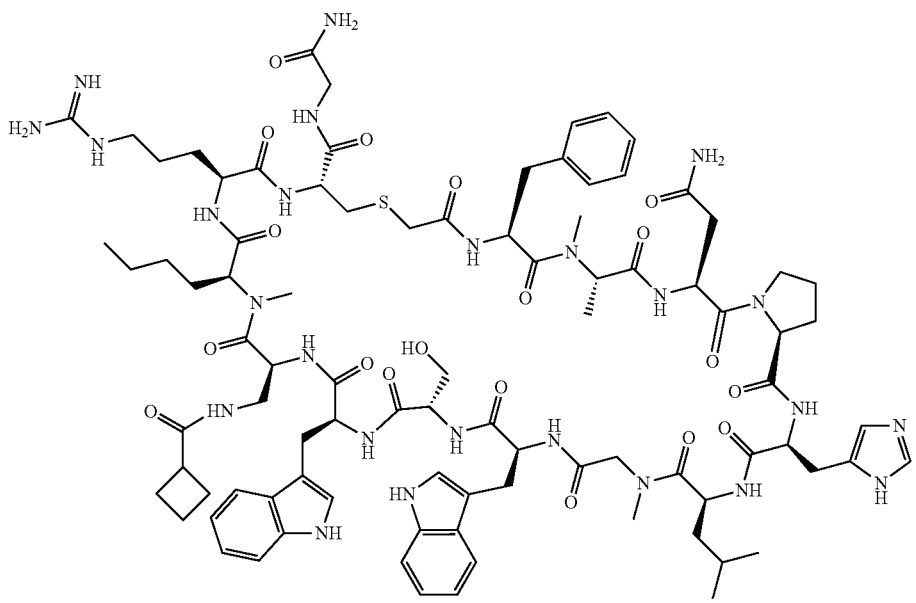

Molecular Weight: 1893.18

Example 1011 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3-(cyclobutanecarboxamido)propanoic acid was used in the "Custom amino acids-coupling procedure".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 65% B; Flow: 20 mL/min. Fractions containing the desired product were combined and dried via centrifugal evaporation. The yield of the product was 2.9 mg, and its estimated purity by LCMS analysis was 98%.

Analysis LCMS Condition D: Retention time=1.45 min; ESI-MS(+) m/z 947.65 (M+2H)

Analysis LCMS Condition E: Retention time=1.39 min; ESI-MS(+) m/z 947.35 (M+2H)

Preparation of Example 1012

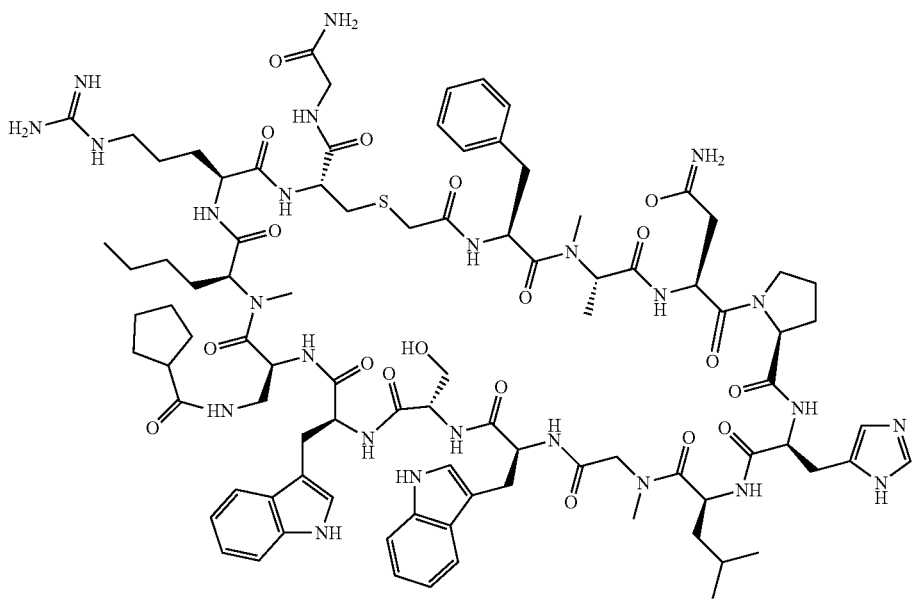

Molecular Weight: 1907.20

Example 1012 was prepared following the general synthetic sequence described for the preparation of Example 00011, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3-(cyclopentanecarboxamido)propanoic acid was used in the "Custom amino acids-coupling procedure".

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 94%.

Analysis LCMS Condition D: Retention time=1.50 min; ESI-MS(+) m/z 954.30 (M+2H)

Analysis LCMS Condition E: Retention time=1.43 min; ESI-MS(+) m/z 954.20 (M+2H)

Preparation of Example 1013

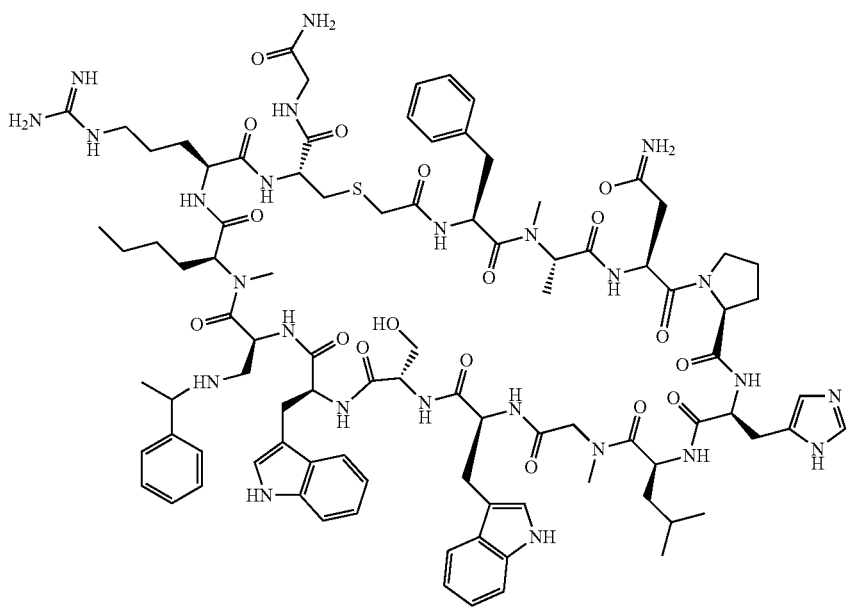

Molecular Weight: 1915.18

Example 1013 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3-benzamidopropanoic acid was used in the "Custom amino acids-coupling procedure".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-80% B over 25 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 90%.

Analysis LCMS Condition D: Retention time=1.48 min; ESI-MS(+) m/z 958.75 (M+2H)

Analysis LCMS Condition E: Retention time=1.41 min; ESI-MS(+) m/z 958.35 (M+2H)

Preparation of Example 1014

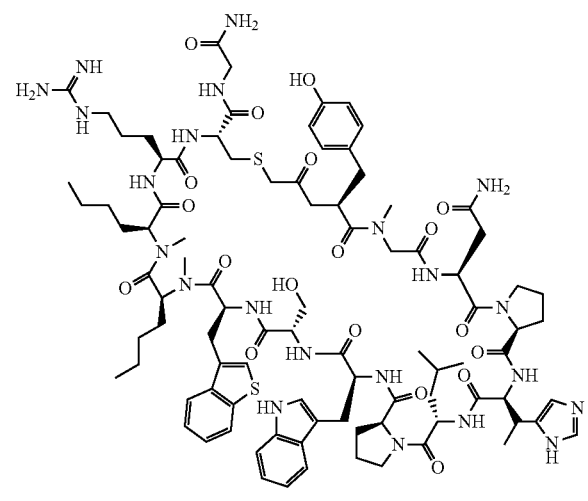

Molecular Weight: 1911.25

Example 1014 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-50% B over 25 minutes, then a 5-minute hold at 100% B; Flow: 20 mL/min. Fractions containing the desired product were combined and dried via centrifugal evaporation. The yield of the product was 6 mg, and its estimated purity by LCMS analysis was 92%.

Analysis LCMS Condition D: Retention time=1.65 min; ESI-MS(+) m/z 956.30 (M+2H)

Analysis LCMS Condition E: Retention time=1.57 min; ESI-MS(+) m/z 956.30 (M+2H)

Preparation of Example 1015

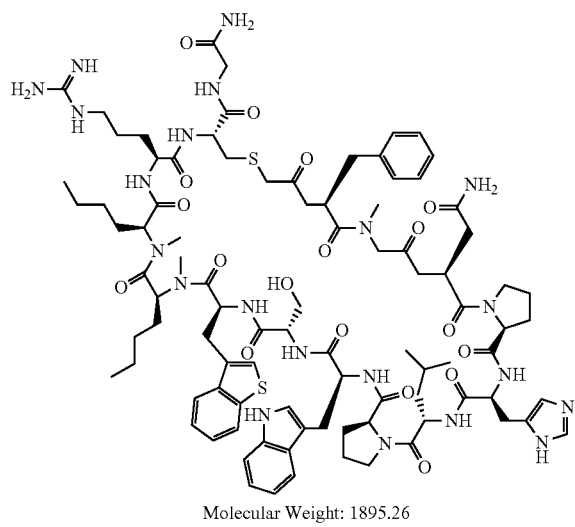 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)C[C@@H](Cc2ccccc2)C(=O)N(C)CC(=O)C[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1895.26

Example 1015 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-70% B over 25 minutes, then a 5-minute hold at 70% B; Flow: 20 mL/min. Fractions containing the desired product were combined and dried via centrifugal evaporation. The yield of the product was 13.7 mg, and its estimated purity by LCMS analysis was 92%.

Analysis LCMS Condition D: Retention time=1.83 min; ESI-MS(+) m/z 948.45 (M+2H)

Analysis LCMS Condition E: Retention time=1.73 min; ESI-MS(+) m/z 948.40 (M+2H)

Preparation of Example 1016

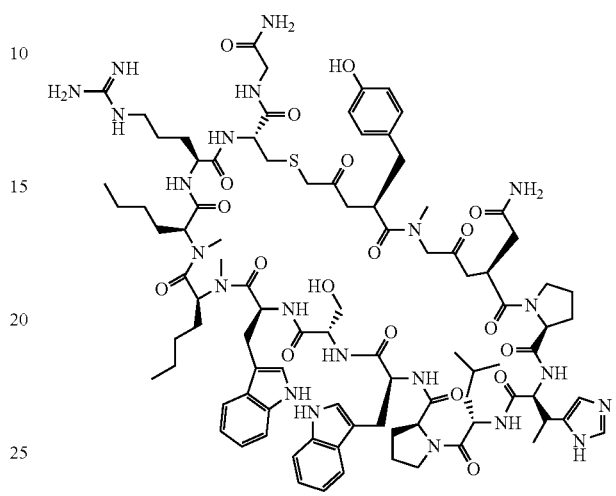

Molecular Weight: 1894.20

Example 1016 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 1.6 mg, and its estimated purity by LCMS analysis was 97%.

Analysis LCMS Condition D: Retention time=1.50 min; ESI-MS(+) m/z 948.20 (M+2H)

Analysis LCMS Condition E: Retention time=1.43 min; ESI-MS(+) m/z 948.15 (M+2H)

Preparation of Example 1017

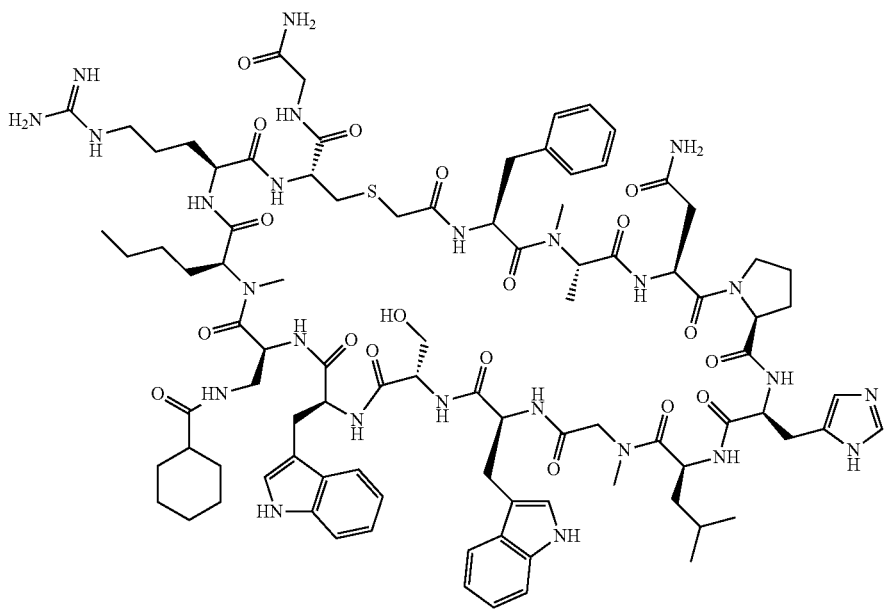

Molecular Weight: 1921.23

Example 1017 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3-(cyclohexanecarboxamido)propanoic acid was used in the "Custom amino acids-coupling procedure".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 95%.

Analysis LCMS Condition D: Retention time=1.45 min; ESI-MS(+) m/z 961.3 (M+2H)

Analysis LCMS Condition E: Retention time=1.42 min; ESI-MS(+) m/z 961.6 (M+2H)

Preparation of Example 1018

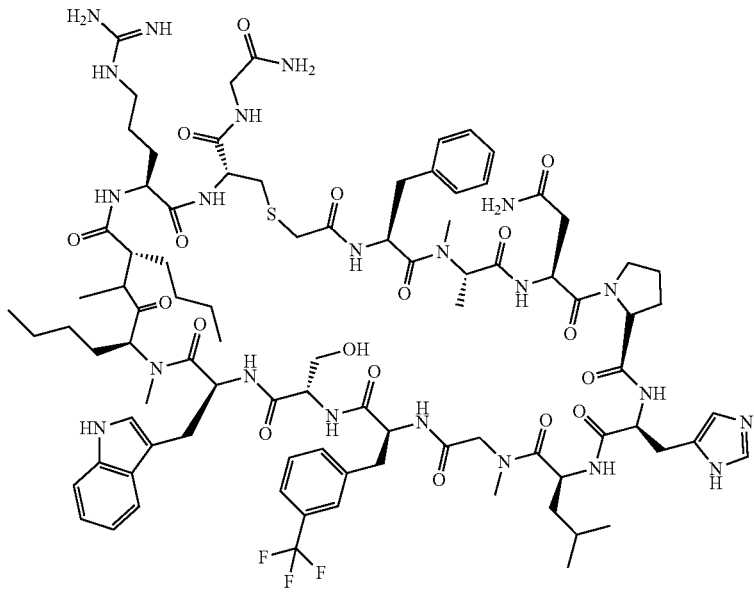

Molecular Weight: 1881.13

Example 1018 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 6.2 mg, and its estimated purity by LCMS analysis was 99%.

Analysis LCMS Condition D: Retention time=1.63 min; ESI-MS(+) m/z 941.3 (M+2H)

Analysis LCMS Condition E: Retention time=1.61 min; ESI-MS(+) m/z 942.0 (M+2H)

Preparation of Example 1019

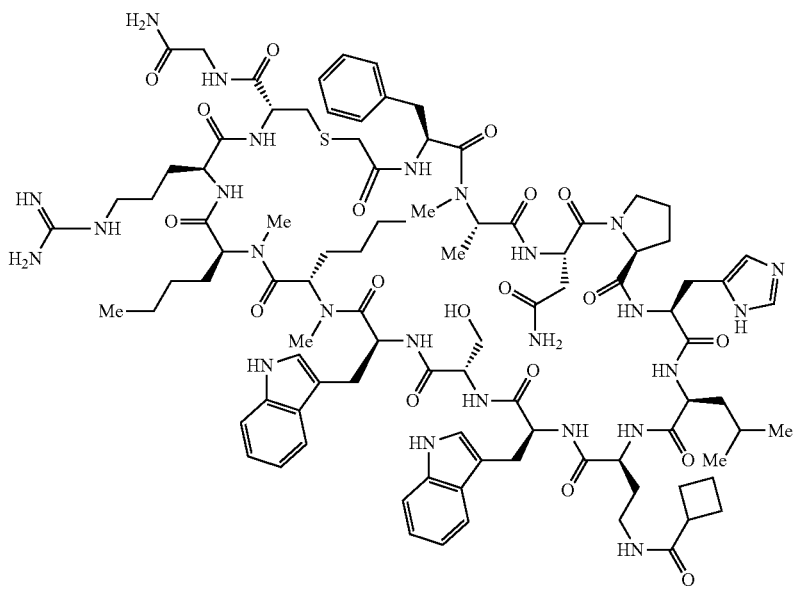

Molecular Weight: 1963.31

Example 1019 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-4-(cyclobutanecarboxamido)butanoic acid was used in the "Custom amino acids-coupling procedure".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 97%.

Analysis LCMS Condition D: Retention time=1.80 min; ESI-MS(+) m/z 982.50 (M+2H)

Analysis LCMS Condition E: Retention time=1.69 min; ESI-MS(+) m/z 982.25 (M+2H)

Preparation of Example 1020

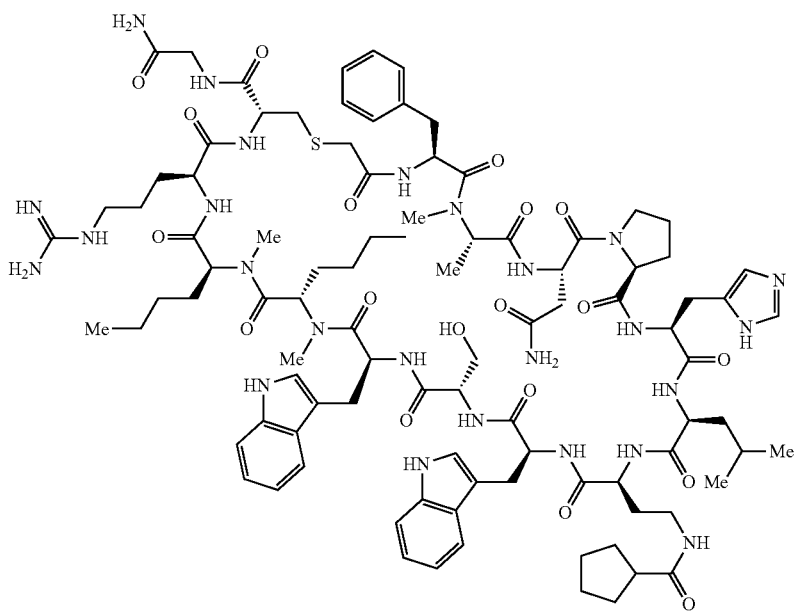

Molecular Weight: 1977.34

Example 1020 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-4-(cyclopentanecarboxamido)butanoic acid was used in the "Custom amino acids-coupling procedure".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation. The yield of the product was 3 mg, and its estimated purity by LCMS analysis was 89%.

Analysis LCMS Condition D: Retention time=1.84 min; ESI-MS(+) m/z 989.30 (M+2H)

Analysis LCMS Condition E: Retention time=1.74 min; ESI-MS(+) m/z 989.45 (M+2H)

Preparation of Example 1021

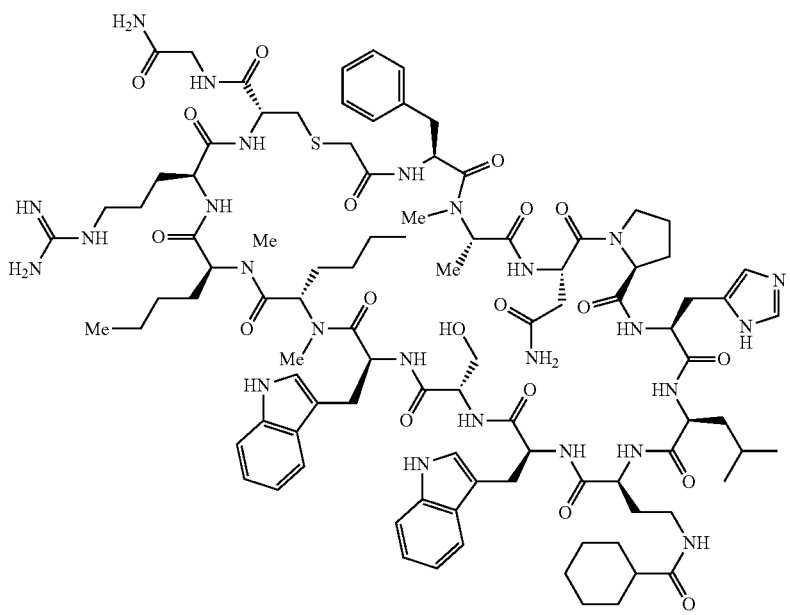

Molecular Weight: 1991.36

Example 1021 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-(((((9H-fluoren-9-yl)methoxy)carbonyl)amino)-4-(cyclohexanecarboxamido)butanoic acid was used in the "Custom amino acids-coupling procedure".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 97%.

Analysis LCMS Condition D: Retention time=1.87 min; ESI-MS(+) m/z 996.75 (M+2H)

Analysis LCMS Condition E: Retention time=1.77 min; ESI-MS(+) m/z 996.75 (M+2H)

Preparation of Example 1022

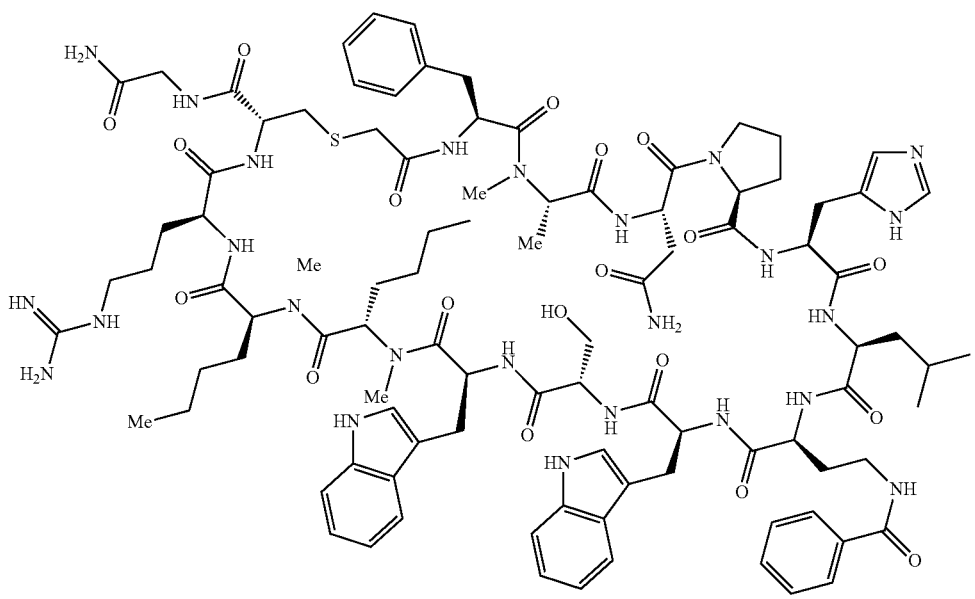

Molecular Weight: 1985.32

Example 1022 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-4-benzamidobutanoic acid was used in the "Custom amino acids-coupling procedure".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 96%.

Analysis LCMS Condition D: Retention time=1.82 min; ESI-MS(+) m/z 993.35 (M+2H)

Analysis LCMS Condition E: Retention time=1.71 min; ESI-MS(+) m/z 993.45 (M+2H)

Preparation of Example 1023

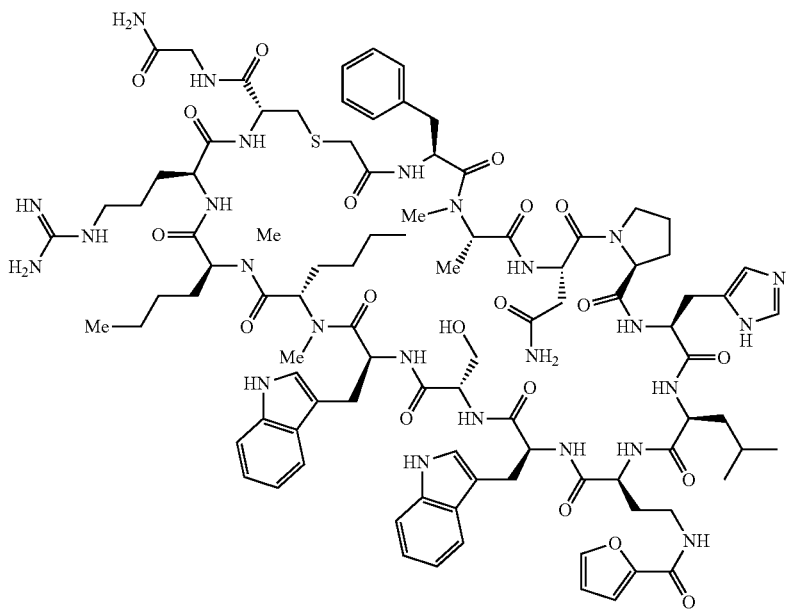

Molecular Weight: 1975.28

Example 1023 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-4-(furan-2-carboxamido)butanoic acid was used in the "Custom amino acids-coupling procedure".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 95%.

Analysis LCMS Condition D: Retention time=1.76 min; ESI-MS(+) m/z 988.75 (M+2H)

Analysis LCMS Condition E: Retention time=1.68 min; ESI-MS(+) m/z 988.75 (M+2H)

Preparation of Example 1024

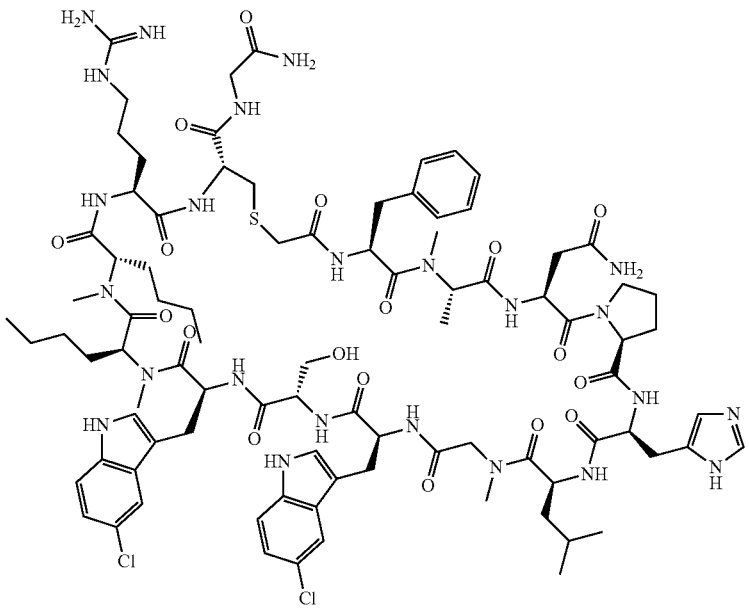

Molecular Weight: 1921.06

Example 1024 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 6.6 mg, and its estimated purity by LCMS analysis was 99%.

Analysis LCMS Condition D: Retention time=1.87 min; ESI-MS(+) m/z 961.2 (M+2H)

Analysis LCMS Condition E: Retention time=1.78 min; ESI-MS(+) m/z 961.3 (M+2H)

Preparation of Example 1025

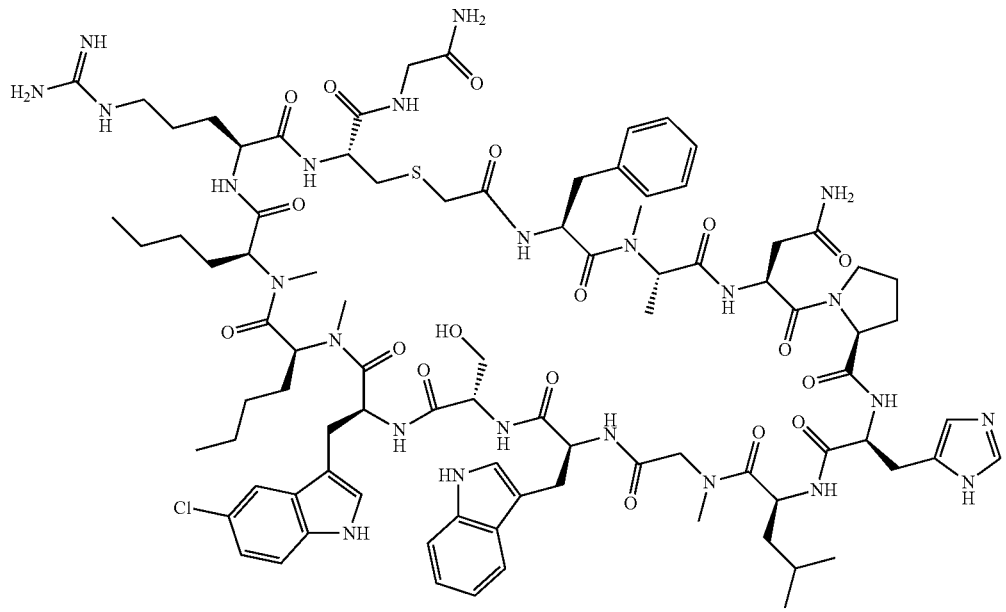

Molecular Weight: 1886.61

Example 1025 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 10.1 mg, and its estimated purity by LCMS analysis was 96%.

Analysis LCMS Condition D: Retention time=1.79 min; ESI-MS(+) m/z 944.1 (M+2H)

Analysis LCMS Condition E: Retention time=1.71 min; ESI-MS(+) m/z 944.1 (M+2H)

Preparation of Example 1026

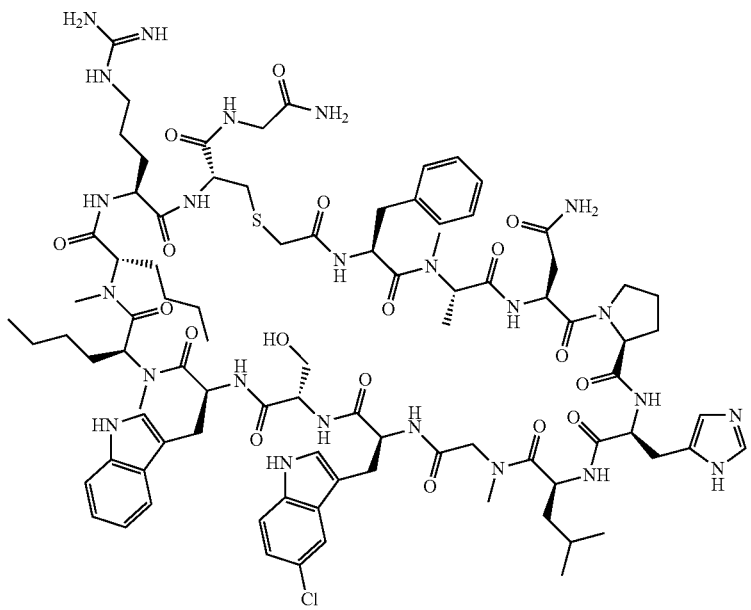

Molecular Weight: 1886.61

Example 1026 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 minutes, then a 5-minute hold at 100% B; Flow: 20 mL/min. Fractions containing the desired product were combined and dried via centrifugal evaporation. The yield of the product was 6.0 mg, and its estimated purity by LCMS analysis was 97%.

Analysis LCMS Condition D: Retention time=1.83 min; ESI-MS(+) m/z 944.8 (M+2H)

Analysis LCMS Condition E: Retention time=1.74 min; ESI-MS(+) m/z 944.6 (M+2H)

Preparation of Example 1028

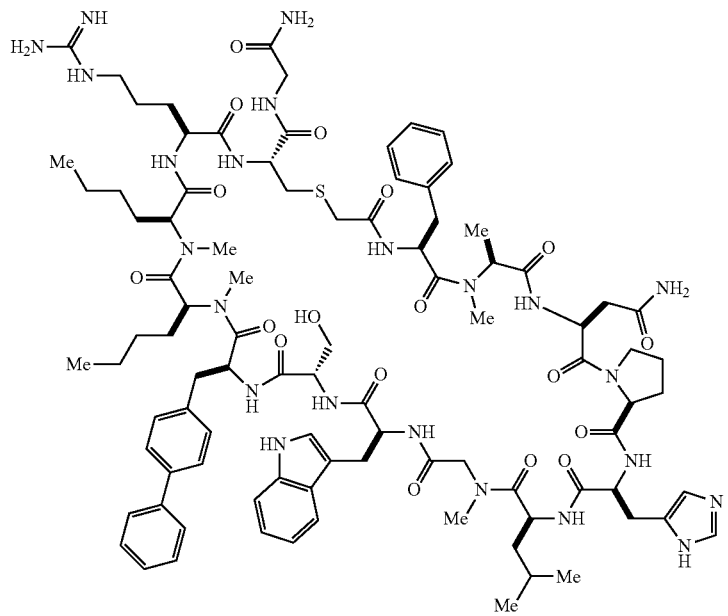

Molecular Weight: 1889.23

Example 1028 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 minutes, then a 5-minute hold at 100% B; Flow: 20 mL/min. Fractions containing the desired product were combined and dried via centrifugal evaporation. The yield of the product was 8.1 mg, and its estimated purity by LCMS analysis was 92%.

Analysis LCMS Condition D: Retention time=1.91 min; ESI-MS(+) m/z 945.7 (M+2H)

Analysis LCMS Condition E: Retention time=1.84 min; ESI-MS(+) m/z 945.6 (M+2H)

Preparation of Example 1029

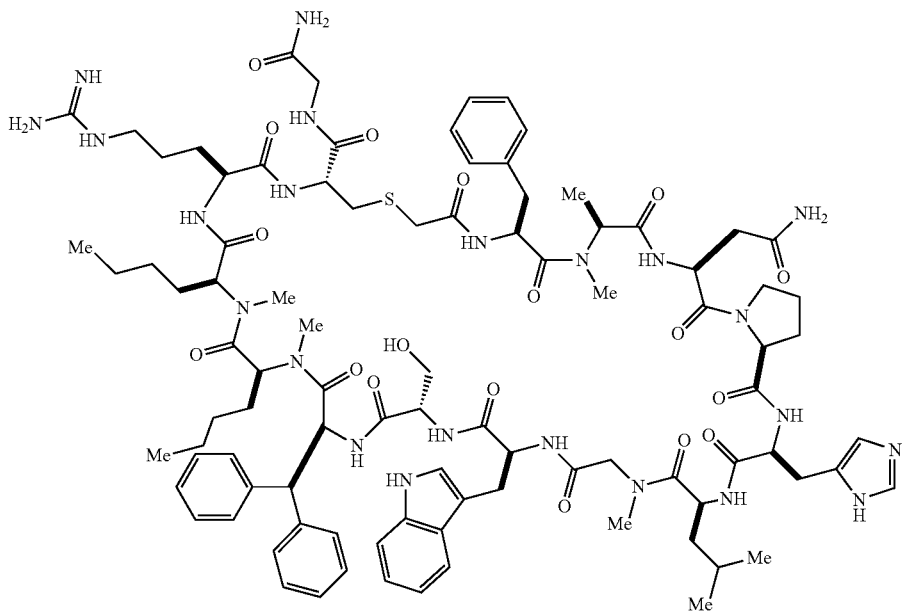

Molecular Weight: 1889.23

Example 1029 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 97%.

Analysis LCMS Condition D: Retention time=1.80 min; ESI-MS(+) m/z 946.5 (M+2H)

Analysis LCMS Condition E: Retention time=1.70 min; ESI-MS(+) m/z 946.5 (M+2H)

Preparation of Example 1030

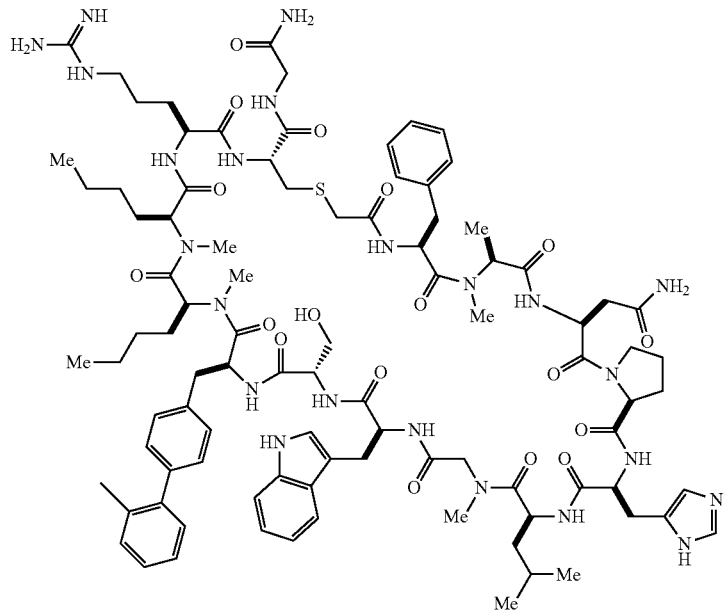

Molecular Weight: 1903.25

Example 1030 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 97%.

Analysis LCMS Condition D: Retention time=1.95 min; ESI-MS(+) m/z 953.7 (M+2H)

Analysis LCMS Condition E: Retention time=1.91 min; ESI-MS(+) m/z 952.9 (M+2H)

Preparation of Example 1031

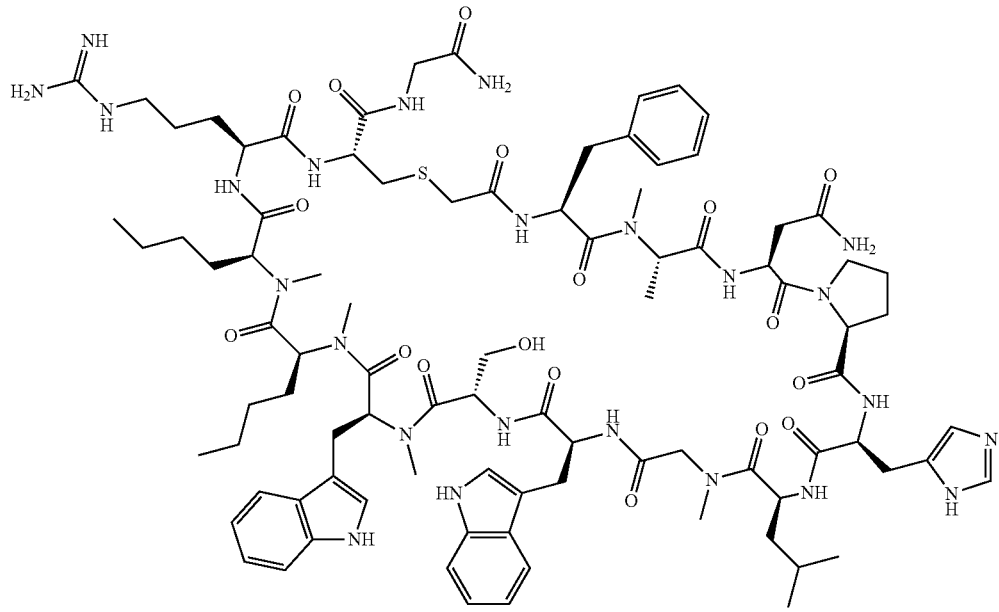

Molecular Weight: 1866.19

Example 1031 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 25 minutes, then a 5-minute hold at 100% B; Flow: 20 mL/min. Fractions containing the desired product were combined and dried via centrifugal evaporation. The yield of the product was 7.1 mg, and its estimated purity by LCMS analysis was 100%.

Analysis LCMS Condition D: Retention time=1.62 min; ESI-MS(+) m/z 934.0 (M+2H)

Analysis LCMS Condition E: Retention time=1.57 min; ESI-MS(+) m/z 934.2 (M+2H)

Preparation of Example 1032

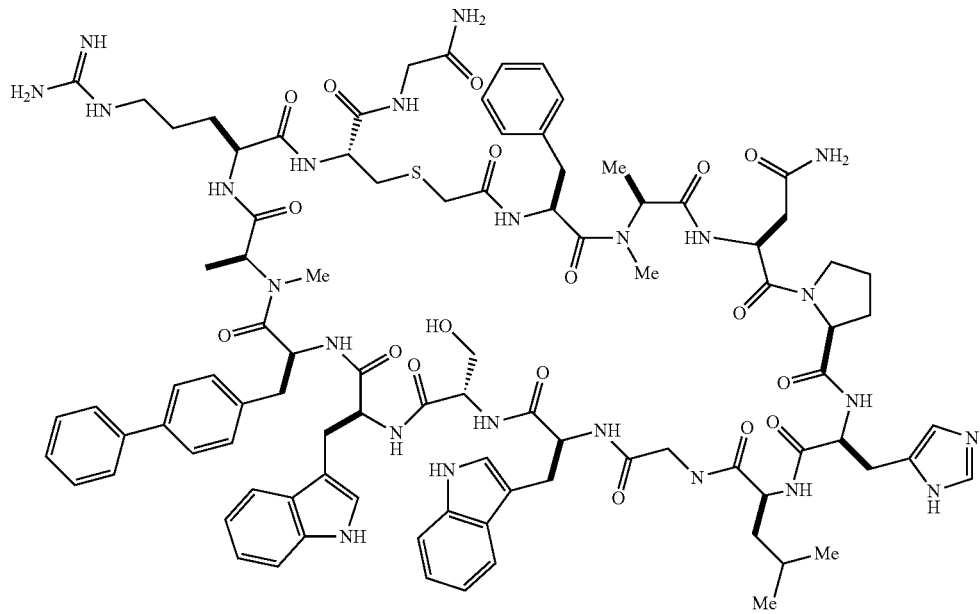

Molecular Weight: 1906.17

Example 1032 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 10-minute hold at 55% B; Flow: 20 mL/min. Fractions containing the desired product were combined and dried via centrifugal evaporation. The yield of the product was 10.3 mg, and its estimated purity by LCMS analysis was 99%.

Analysis LCMS Condition D: Retention time=1.62 min; ESI-MS(+) m/z 953.9 (M+2H)

Analysis LCMS Condition E: Retention time=1.58 min; ESI-MS(+) m/z 954.5 (M+2H)

Preparation of Example 1033

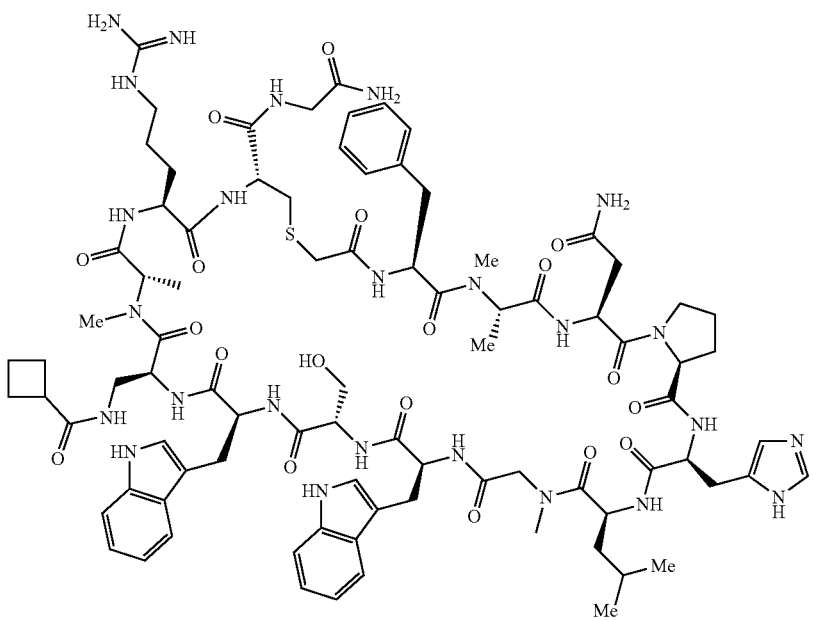

Molecular Weight: 1851.10

Example 1033 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-3-(cyclobutanecarboxamido)propanoic acid was used in the "Custom amino acids-coupling procedure".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 25 minutes, then a 10-minute hold at 50% B; Flow: 20 mL/min. Fractions containing the desired product were combined and dried via centrifugal evaporation. The yield of the product was 8.8 mg, and its estimated purity by LCMS analysis was 97%.

Analysis LCMS Condition D: Retention time=1.31 min; ESI-MS(+) m/z 926.1 (M+2H)

Analysis LCMS Condition E: Retention time=1.29 min; ESI-MS(+) m/z 926.2 (M+2H)

Preparation of Example 1034

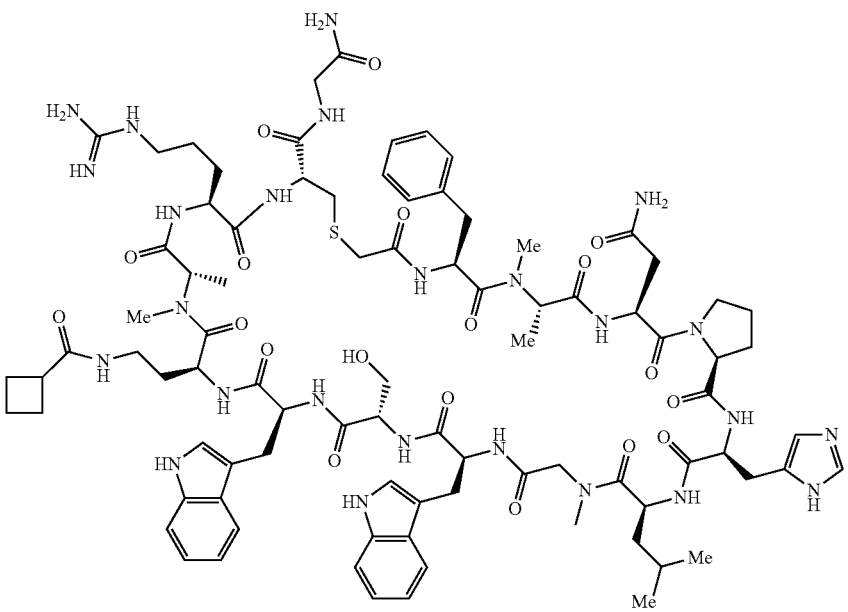

Molecular Weight: 1865.12

Example 1034 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D". (S)-2-((((9H-fluoren-9-yl)methoxy)carbonyl)amino)-4-(cyclobutanecarboxamido)butanoic acid was used in the "Custom amino acids-coupling procedure".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 98%.

Analysis LCMS Condition D: Retention time=1.31 min; ESI-MS(+) m/z 933.3 (M+2H)

Analysis LCMS Condition E: Retention time=1.30 min; ESI-MS(+) m/z 933.3 (M+2H)

Preparation of Example 1035

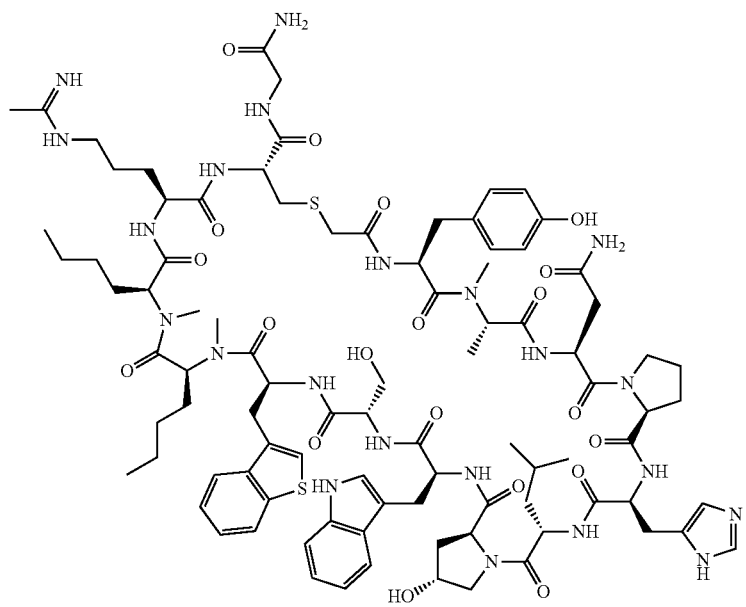

Molecular Weight: 1927.25

Example 1035 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 95%.

Analysis LCMS Condition D: Retention time=1.69 min; ESI-MS(+) m/z 965.1 (M+2H)

Analysis LCMS Condition E: Retention time=1.62 min; ESI-MS(+) m/z 964.6 (M+2H)

Preparation of Example 1036

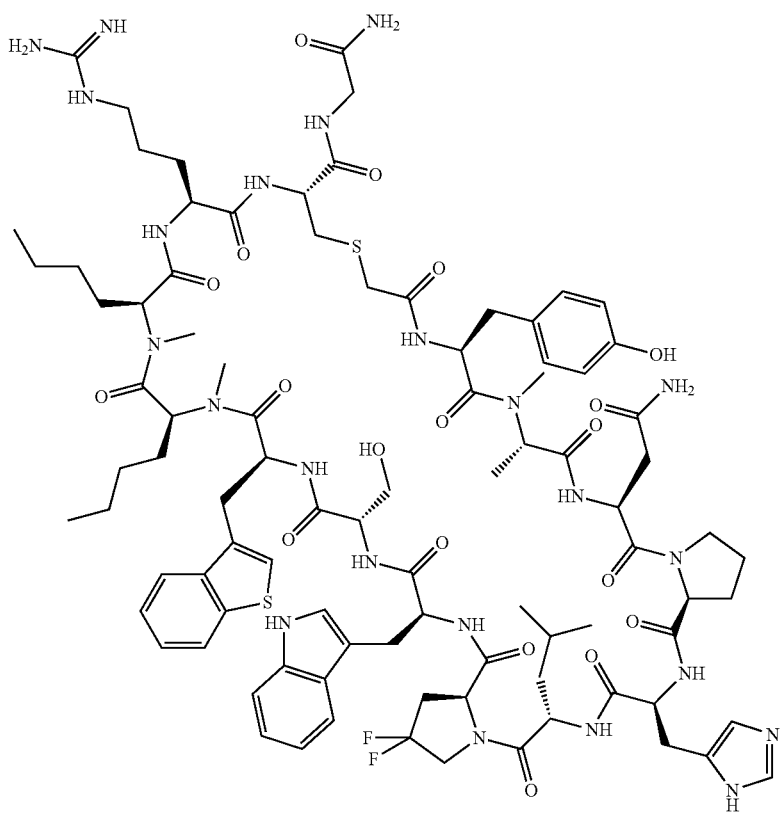

Molecular Weight: 1947.24

Example 1036 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 5.7 mg, and its estimated purity by LCMS analysis was 95%.

Analysis LCMS Condition D: Retention time=1.74 min; ESI-MS(+) m/z 974.9 (M+2H)

Analysis LCMS Condition E: Retention time=1.67 min; ESI-MS(+) m/z 974.8 (M+2H)

Preparation of Example 1037

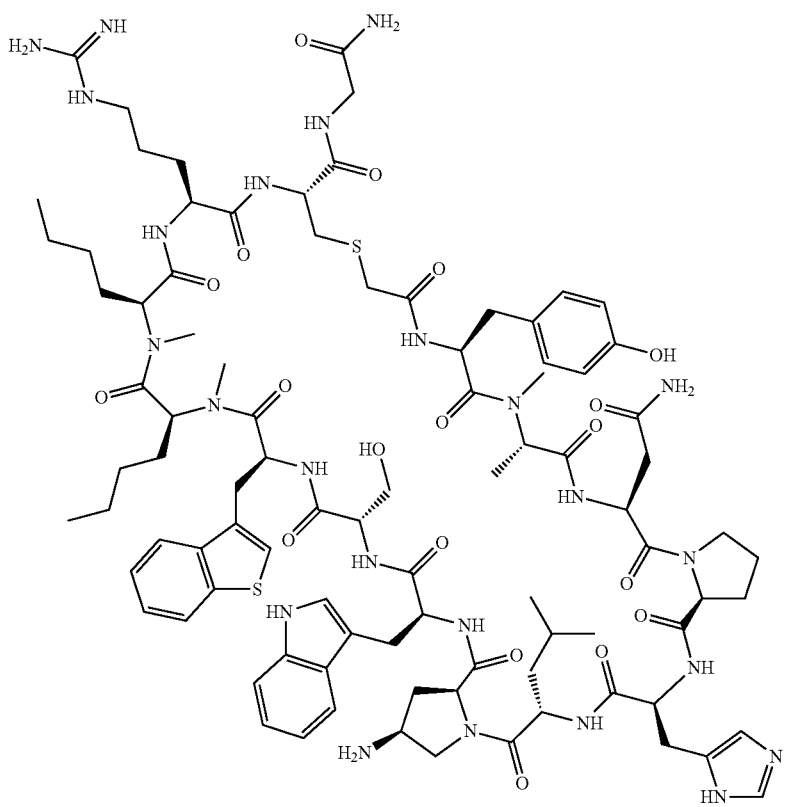

Molecular Weight: 1926.27

Example 1037 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 98%.

Analysis LCMS Condition D: Retention time=1.70 min; ESI-MS(+) m/z 964.3 (M+2H)

Analysis LCMS Condition E: Retention time=1.60 min; ESI-MS(+) m/z 964.0 (M+2H)

Preparation of Example 1038

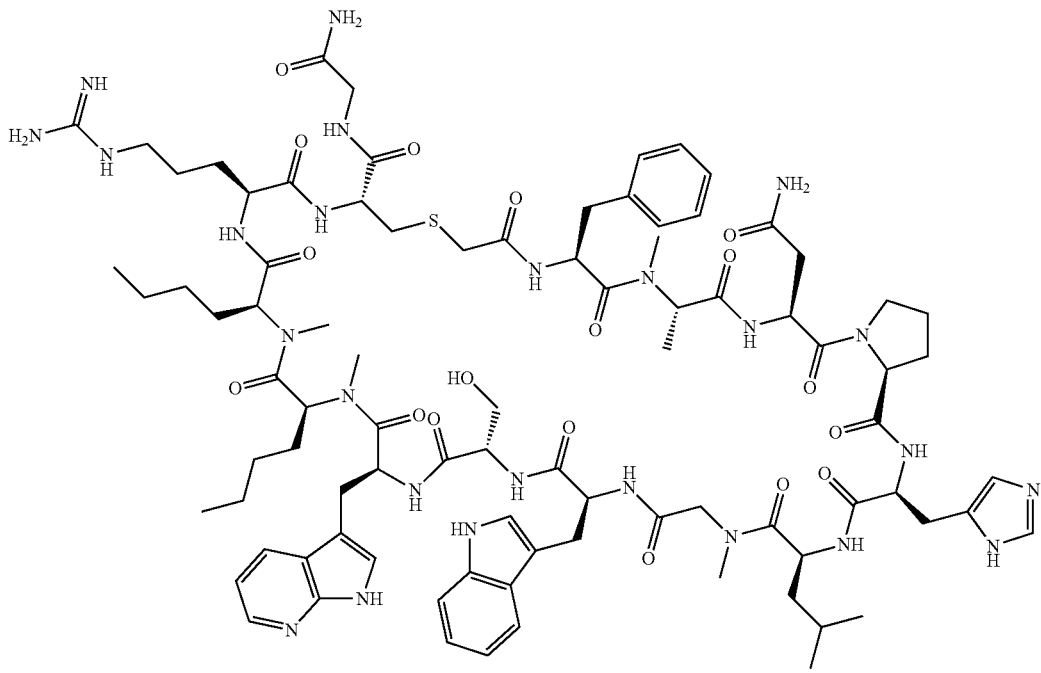

Molecular Weight: 1853.16

Example 1038 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 93%.

Analysis LCMS Condition D: Retention time=1.47 min; ESI-MS(+) m/z 927.5 (M+2H)

Analysis LCMS Condition E: Retention time=1.32 min; ESI-MS(+) m/z 927.3 (M+2H)

Preparation of Example 1039

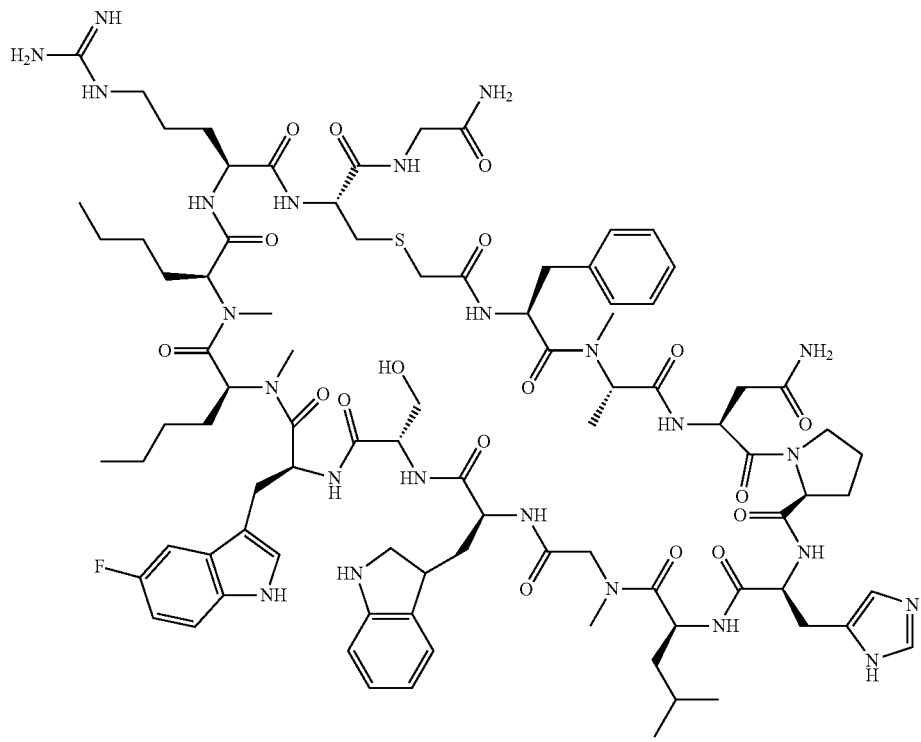

Molecular Weight: 1870.16

Example 1039 was following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 99%.

Analysis LCMS Condition D: Retention time=1.69 min; ESI-MS(+) m/z 936.0 (M+2H)

Analysis LCMS Condition E: Retention time=1.65 min; ESI-MS(+) m/z 935.8 (M+2H)

Preparation of Example 1040

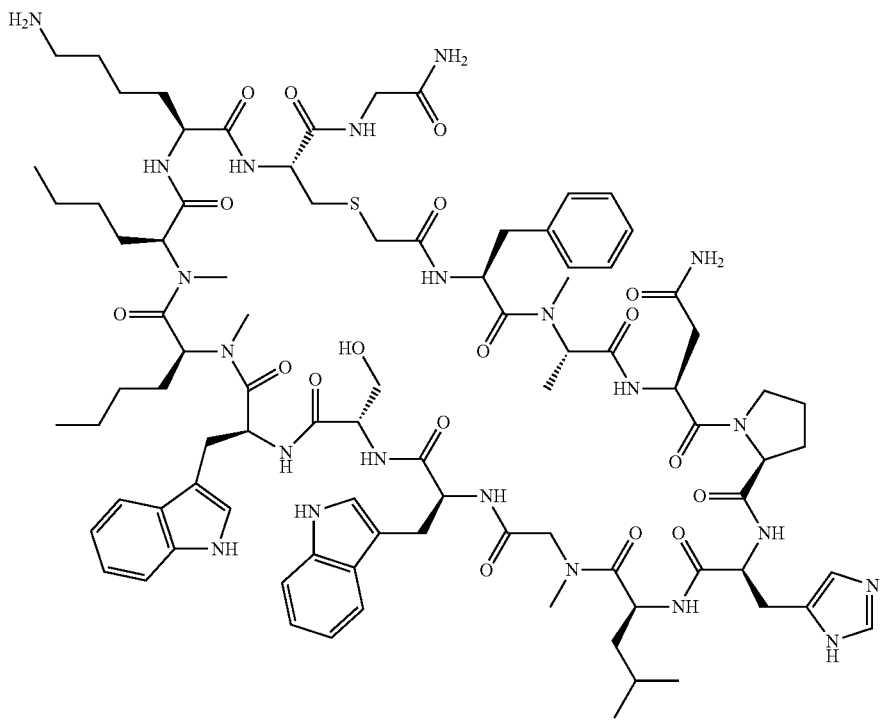

Molecular Weight: 1824.15

Example 1040 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 99%.

Analysis LCMS Condition D: Retention time=1.69 min; ESI-MS(+) m/z 913.7 (M+2H)

Analysis LCMS Condition E: Retention time=1.65 min; ESI-MS(+) m/z 912.9 (M+2H)

Preparation of Example 1041

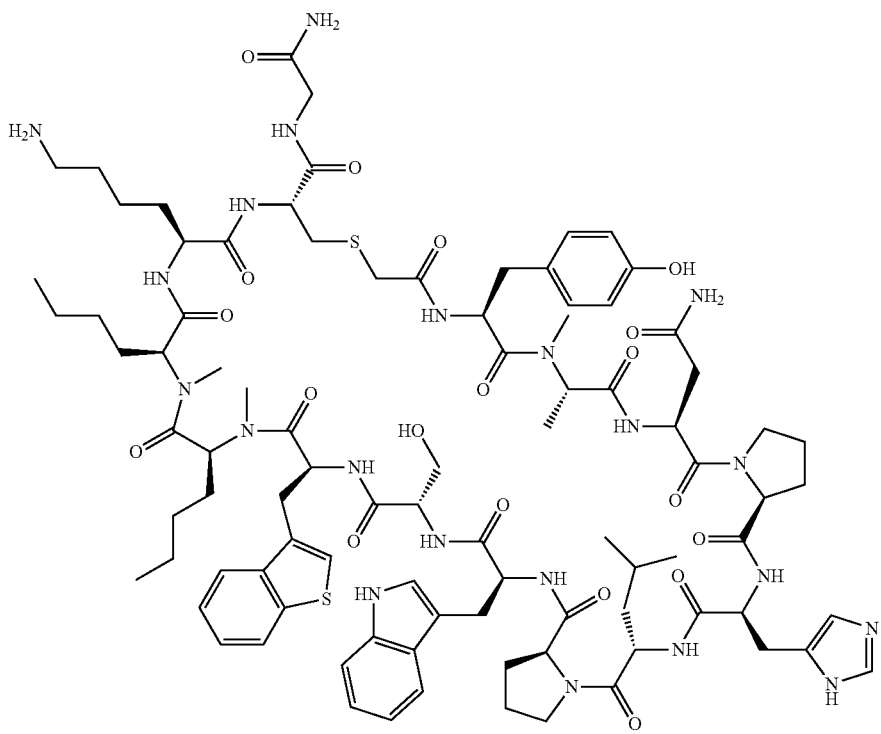

Molecular Weight: 1883.24

Example 1041 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions:

Column: Waters XBridge C18, 19×250 mm, 5-µm particles; Mobile Phase A: 5:95 acetonitrile:water with 10-mM ammonium acetate;

Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 92%.

Analysis LCMS Condition D: Retention time=1.56 min; ESI-MS(+) m/z 942.6 (M+2H)

Analysis LCMS Condition E: Retention time=1.55 min; ESI-MS(+) m/z 942.7 (M+2H)

Preparation of Example 1042

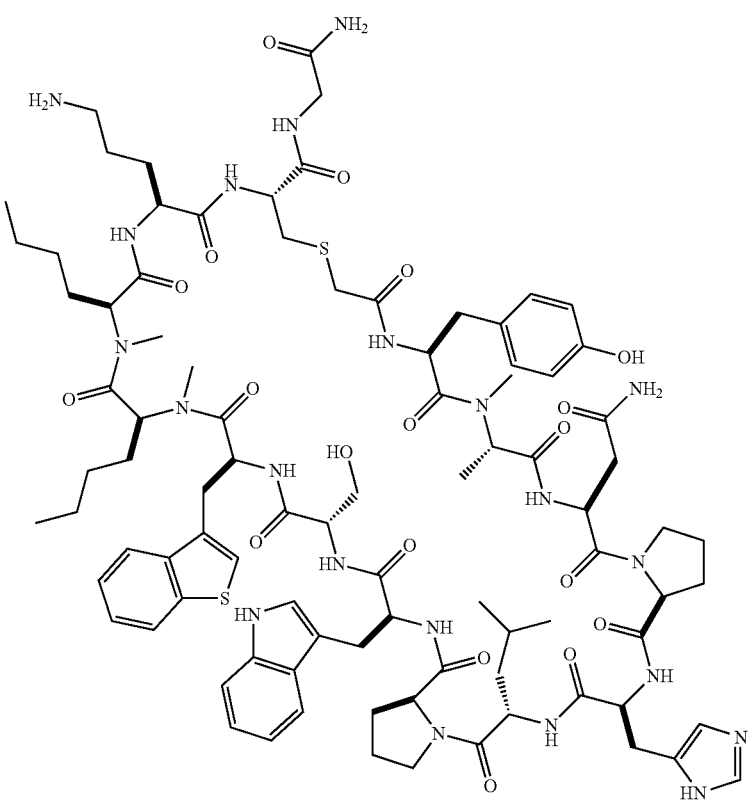

Molecular Weight: 1869.21

Example 1042 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 99%.

Analysis LCMS Condition D: Retention time=1.57 min; ESI-MS(+) m/z 935.7 (M+2H)

Analysis LCMS Condition E: Retention time=1.57 min; ESI-MS(+) m/z 935.3 (M+2H)

Preparation of Example 1043

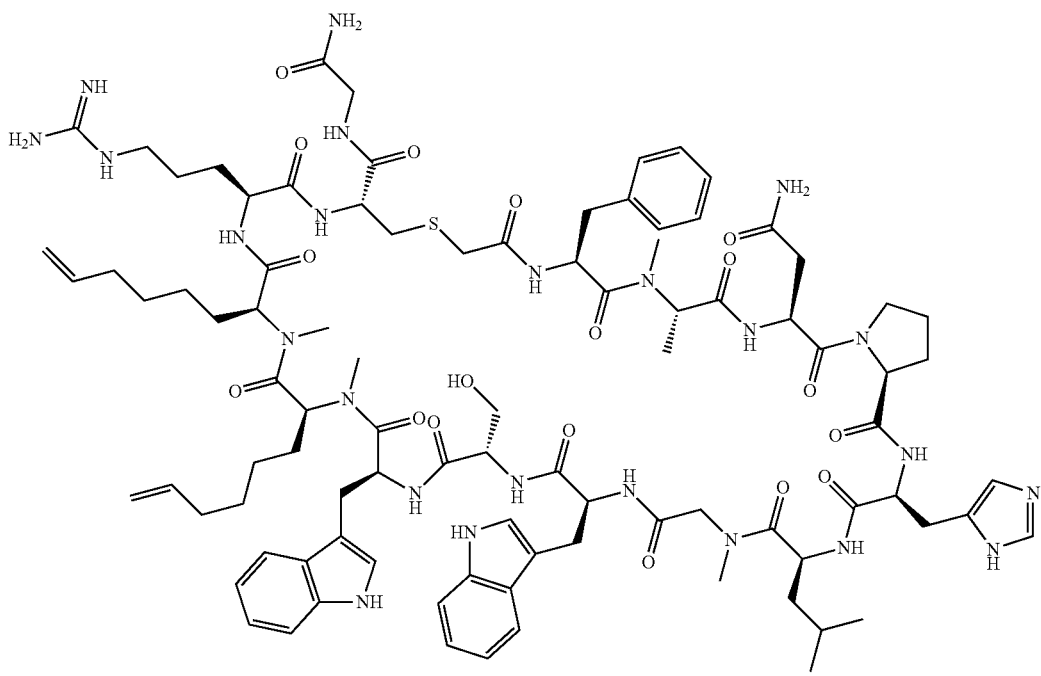

Molecular Weight: 1904.24

Example 1043 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative HPLC with the following conditions: Column: PHENOMENEX® Luna Axia C18, 30×250; Mobile Phase A: 5:95 acetonitrile:water with 0.1% TFA; Mobile Phase B: 95:5 acetonitrile:water with 0.1% TFA; Gradient: 10-100% B over 30 minutes, then a 5-minute hold at 100% B; Flow: 20 mL/min. Fractions containing the desired product were combined and dried via centrifugal evaporation. The yield of the product was 15 mg, and its estimated purity by HPLC analysis was 99%.

Analysis LCMS Condition A: Retention time=0.9 min; ESI-MS(+) m/z 953.1 (M+2H)

Analysis HPLC Condition I: Retention Time=14.98 min

Preparation of Example 1044

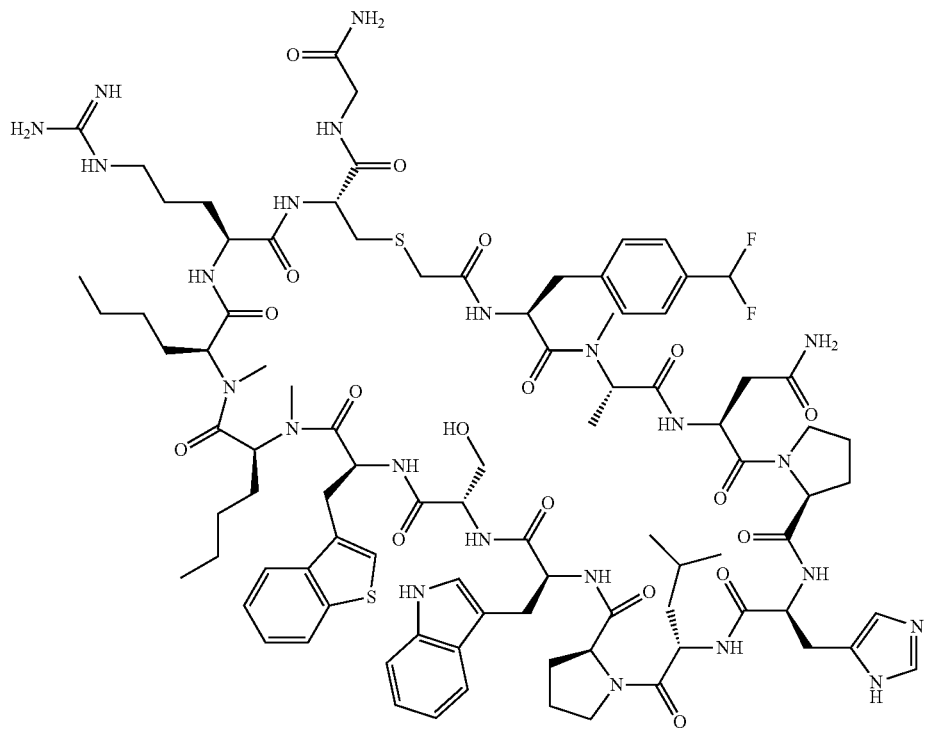

Molecular Weight: 1945.26

Example 1044 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 minutes, then a 10-minute hold at 65% B; Flow: 20 mL/min. Fractions containing the desired product were combined and dried via centrifugal evaporation. The yield of the product was 8.6 mg, and its estimated purity by LCMS analysis was 100%.

Analysis LCMS Condition D: Retention time=1.85 min; ESI-MS(+) m/z 973.6 (M+2H)

Analysis LCMS Condition E: Retention time=1.78 min; ESI-MS(+) m/z 973.3 (M+2H)

Preparation of Example 1045

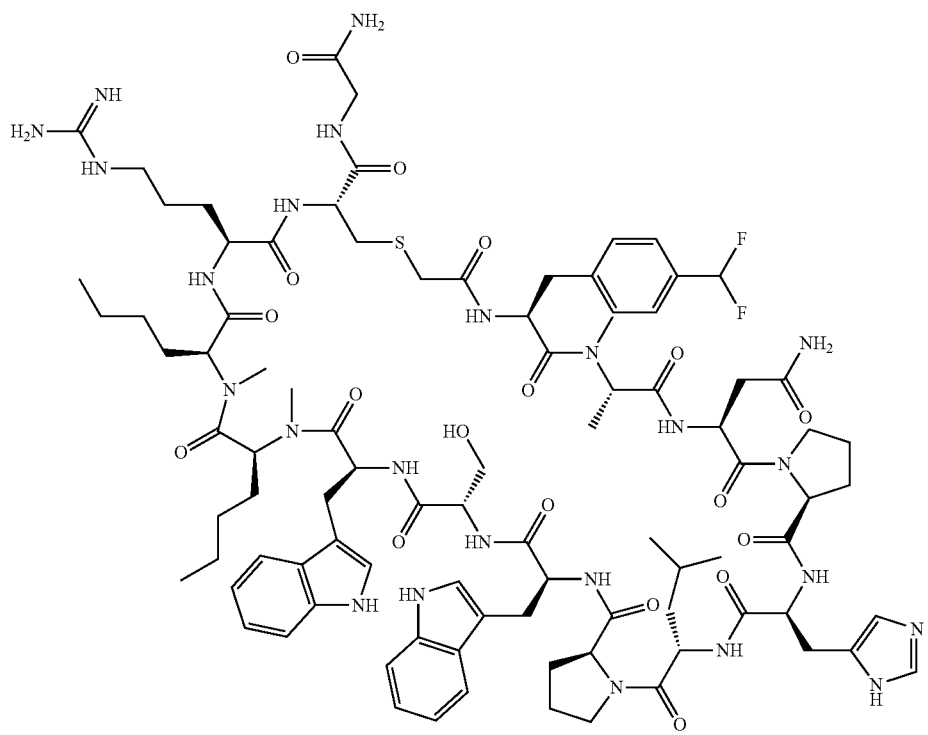

Molecular Weight: 1928.21

Example 1045 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 10-minute hold at 60% B; Flow: 20 mL/min. Fractions containing the desired product were combined and dried via centrifugal evaporation. The yield of the product was 9.0 mg, and its estimated purity by LCMS analysis was 94%.

Analysis LCMS Condition D: Retention time=1.70 min; ESI-MS(+) m/z 964.9 (M+2H)

Analysis LCMS Condition E: Retention time=1.65 min; ESI-MS(+) m/z 964.8 (M+2H)

Preparation of Example 1046

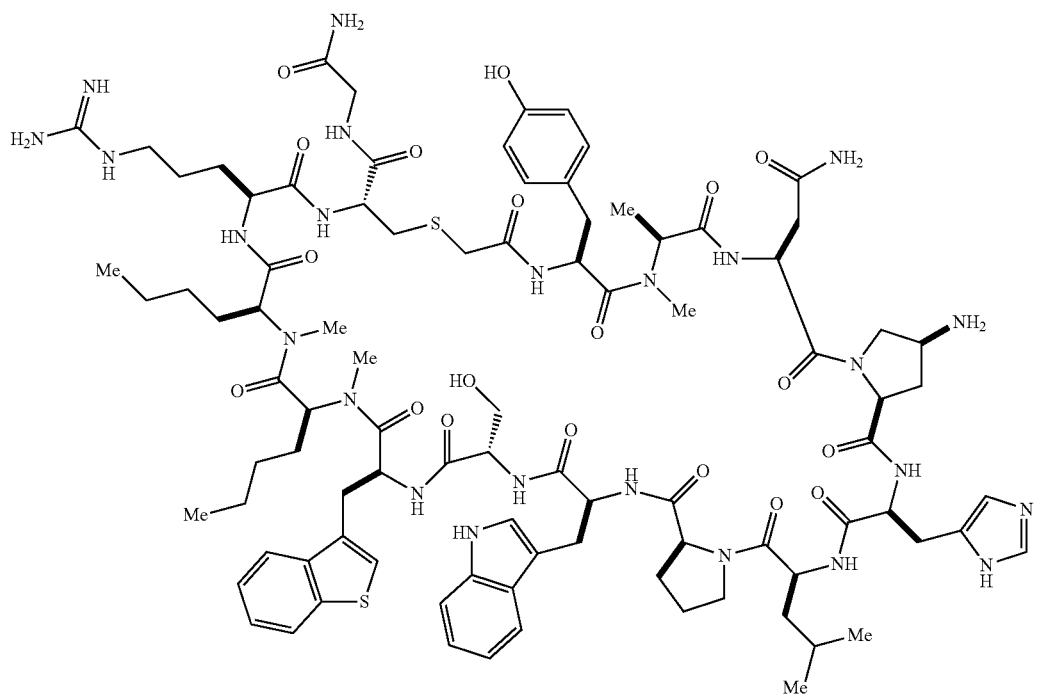

Molecular Weight: 1926.27

Example 1046 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 100%.

Analysis LCMS Condition D: Retention time=1.51 min; ESI-MS(+) m/z 964.5 (M+2H)

Analysis LCMS Condition E: Retention time=1.38 min; ESI-MS(+) m/z 963.8 (M+2H)

Preparation of Example 1047

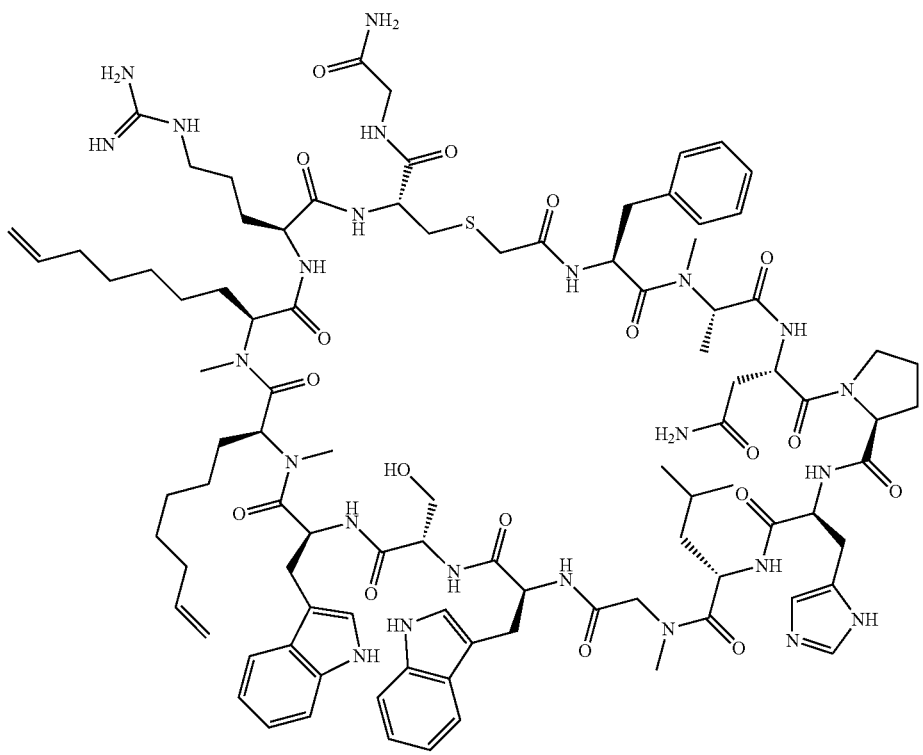

Molecular Weight: 1932.30

Example 1047 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative HPLC with the following conditions: Column: PHENOMENEX® Luna Axia C18, 30×250; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 30 minutes, then a 5-minute hold at 100% B; Flow: 20 mL/min. Fractions containing the desired product were combined and dried via centrifugal evaporation. The yield of the product was 26 mg, and its estimated purity by HPLC analysis was 100%.

Analysis LCMS Condition A: Retention time=0.94 min; ESI-MS(+) m/z 967.0 (M+2H)

Analysis HPLC Condition I: Retention Time=15.58 min

Preparation of Example 1048

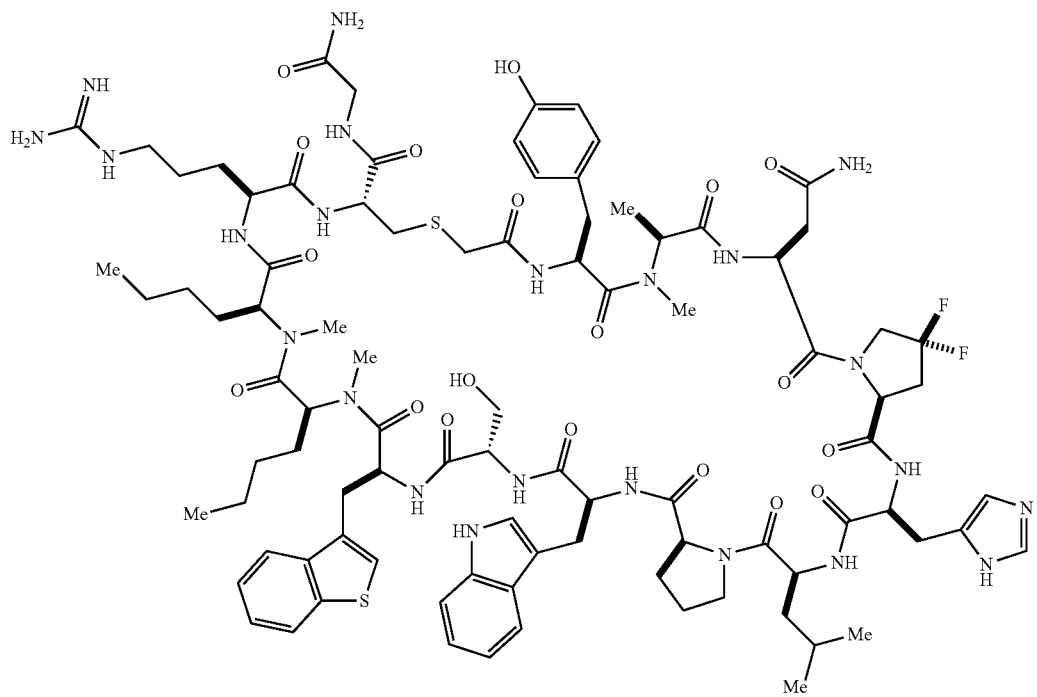

Molecular Weight: 1947.24

Example 1048 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 97%.

Analysis LCMS Condition D: Retention time=1.65 min; ESI-MS(+) m/z 974.6 (M+2H)

Analysis LCMS Condition E: Retention time=1.62 min; ESI-MS(+) m/z 974.8 (M+2H)

Preparation of Example 1049

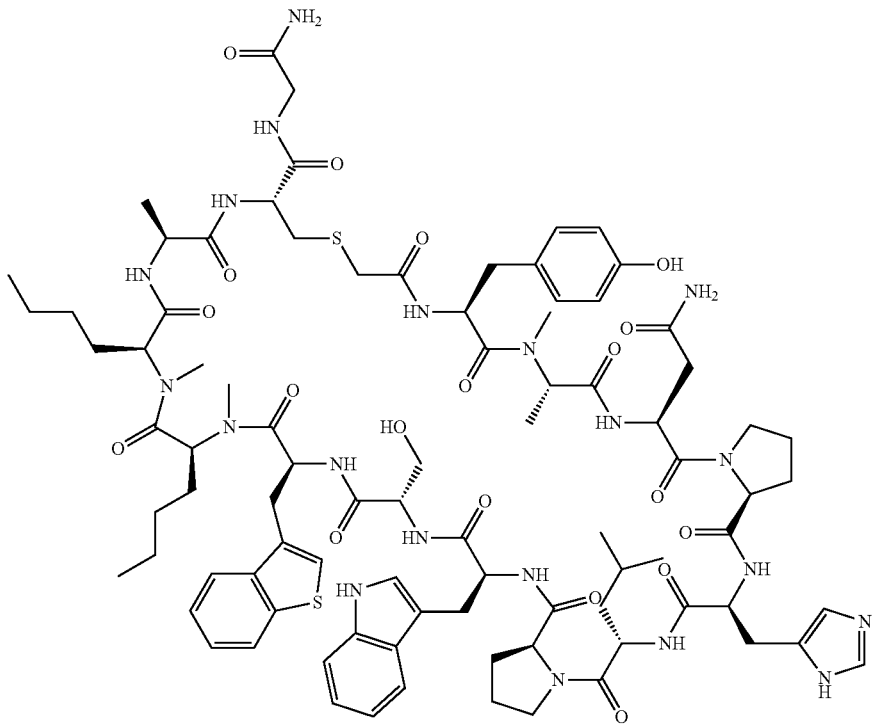

Molecular Weight: 1826.15

Example 1049 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 10-minute hold at 60% B; Flow: 20 mL/min. Fractions containing the desired product were combined and dried via centrifugal evaporation. The yield of the product was 6.5 mg, and its estimated purity by LCMS analysis was 93%.

Analysis LCMS Condition D: Retention time=1.67 min; ESI-MS(+) m/z 914.1 (M+2H)

Analysis LCMS Condition E: Retention time=1.67 min; ESI-MS(+) m/z 913.8 (M+2H)

Preparation of Example 1050

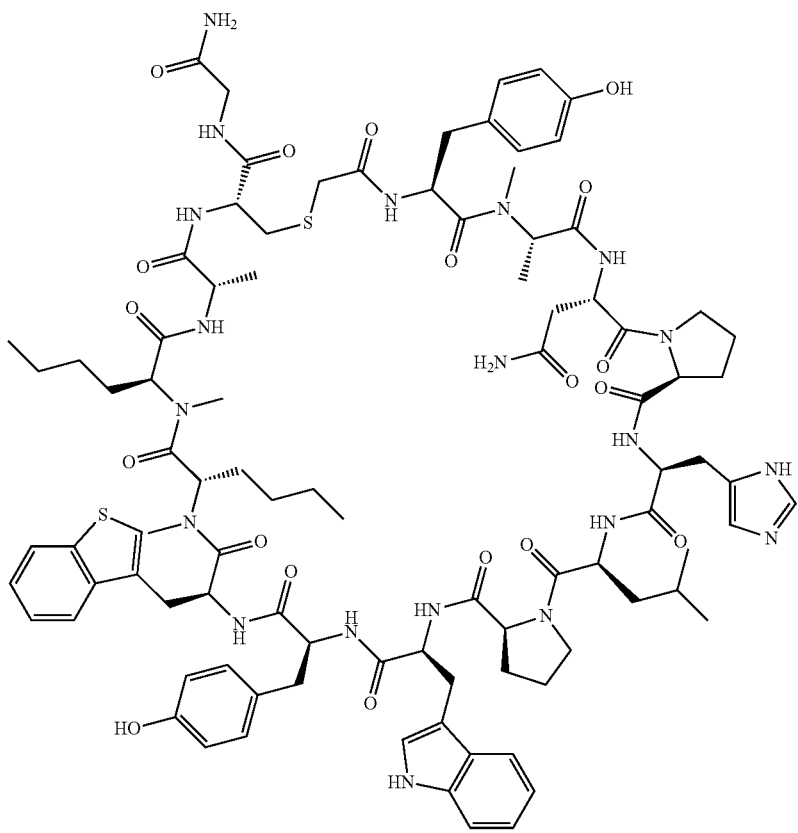

Molecular Weight: 1902.24

Example 1050 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 10-minute hold at 60% B; Flow: 20 mL/min. Fractions containing the desired product were combined and dried via centrifugal evaporation. The yield of the product was 7.1 mg, and its estimated purity by LCMS analysis was 92%.

Analysis LCMS Condition D: Retention time=1.73 min; ESI-MS(+) m/z 952.0 (M+2H)

Analysis LCMS Condition E: Retention time=1.72 min; ESI-MS(+) m/z 951.7 (M+2H)

Preparation of Example 1051

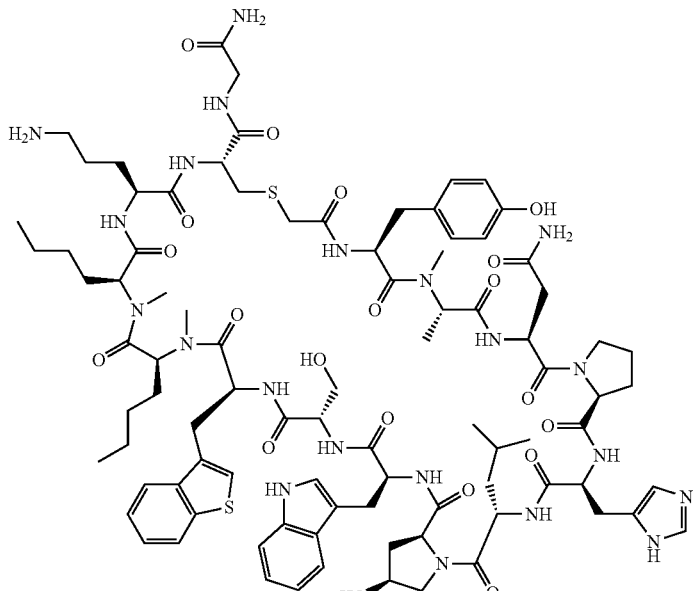

Molecular Weight: 1885.21

Example 1051 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 9.5 mg and its estimated purity by LCMS analysis was 99%.

Analysis LCMS Condition D: Retention time=1.54 min; ESI-MS(+) m/z 943.3 (M+2H)

Analysis LCMS Condition E: Retention time=1.51 min; ESI-MS(+) m/z 943.5 (M+2H)

Preparation of Example 1052

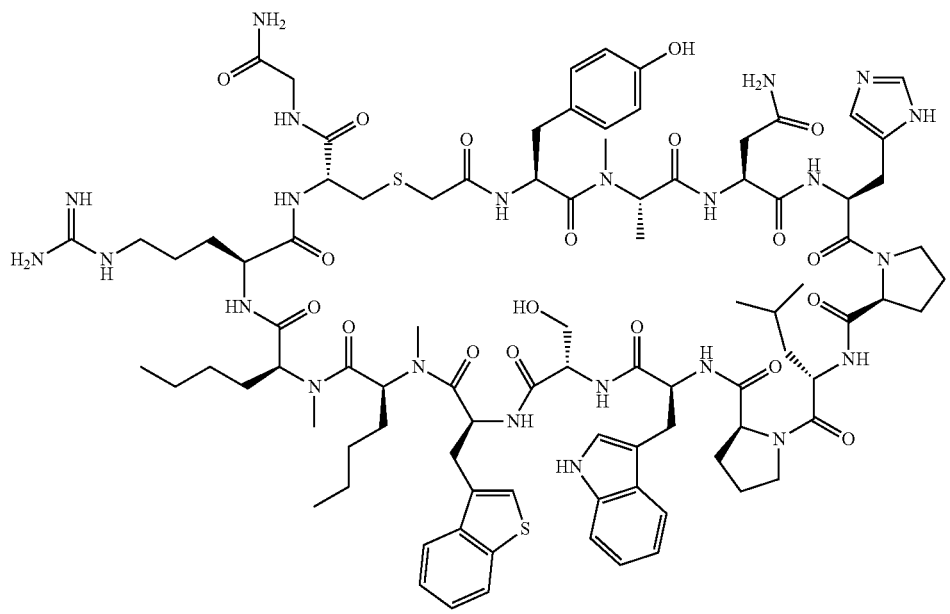

Molecular Weight: 1911.25

Example 1052 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum of acetonitrile and water, frozen and lyophilized to give a white amorphous solid. The yield of the product was 1.1 mg, and its estimated purity by HPLC analysis was 95%.

Analysis LCMS Condition A Retention time=0.8 min, ESI-MS(+) m/z 956.9 (M+H)

Analysis HPLC Condition G: Retention time=7.8 min

Analysis HPLC Condition H: Retention time=9.35 min

Preparation of Example 1053

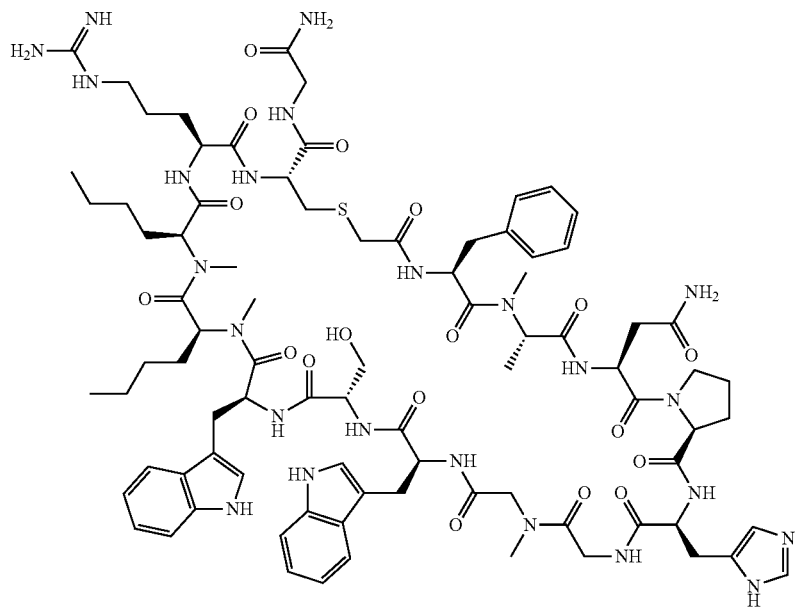

Molecular Weight: 1796.06

Example 1053 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 0.5 mg, and its estimated purity by HPLC analysis was 95%.

Analysis LCMS Condition A: Retention time=0.78 min; ESI-MS(+) m/z 899.0 (M+2H).

Analysis HPLC Condition J: Retention time=12.74 min

Preparation of Example 1054

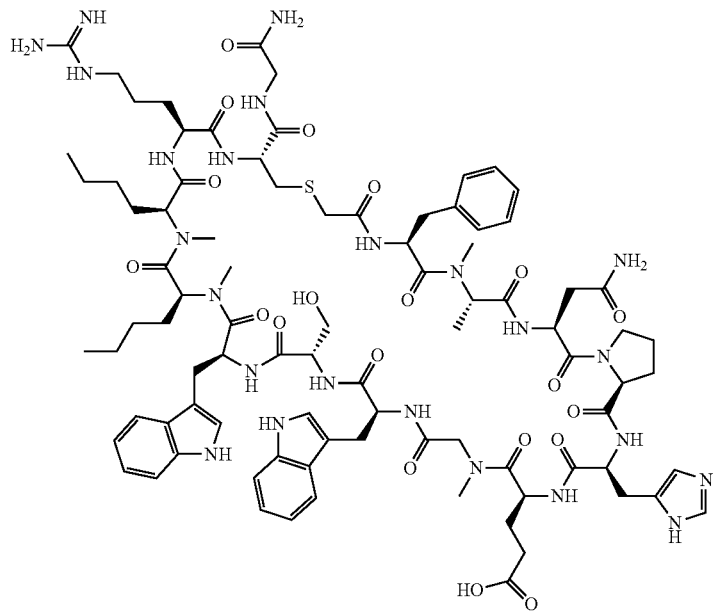

Molecular Weight: 1868.12

Example 1054 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 4.7 mg, and its estimated purity by HPLC analysis was 100%.

Analysis LCMS Condition A: Retention time=0.81 min; ESI-MS(+) m/z 935.4 (M+2H).

Analysis HPLC Condition J: Retention time=13.48 min.

Preparation of Example 1055

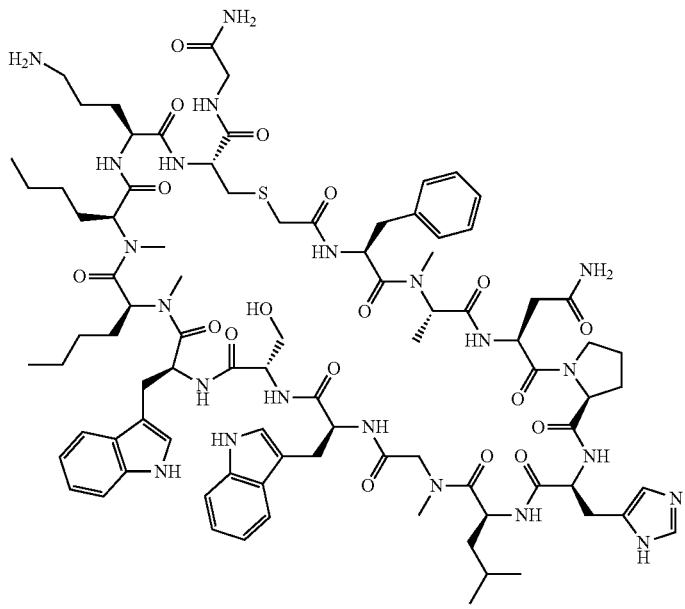

Molecular Weight: 1810.13

Example 1055 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D"

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 1.6 mg, and its estimated purity by HPLC analysis was 100%.

Analysis LCMS Condition A: Retention time=0.81 min; ESI-MS(+) m/z 906.2 (M+2H)

Analysis HPLC Condition J: Retention time=13.54 min

Preparation of Example 1056

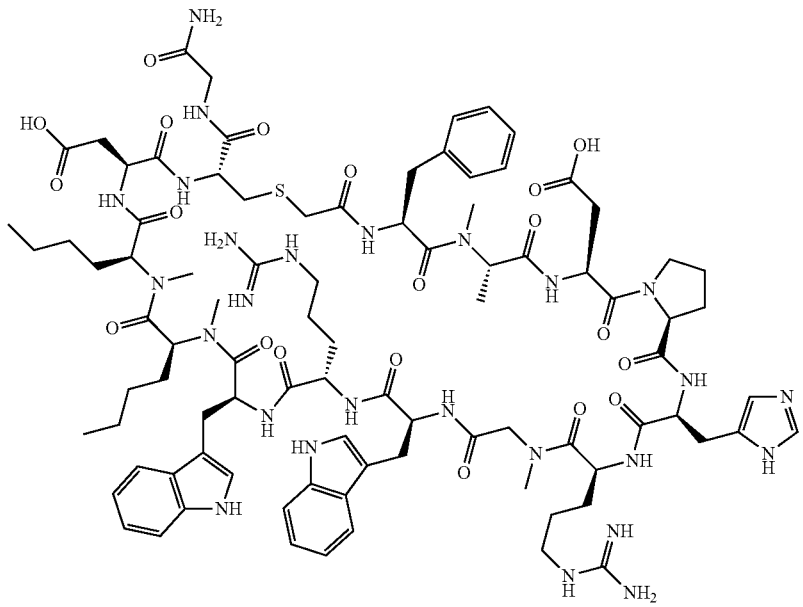

Molecular Weight: 1924.19

Example 1056 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 3.6 mg, and its estimated purity by HPLC analysis was 99.2%.

Analysis LCMS Condition A: Retention time=0.78 min; ESI-MS(+) m/z 963.1 (M+2H)

Analysis HPLC Condition J: Retention time=12.33 min

Preparation of Example 1057

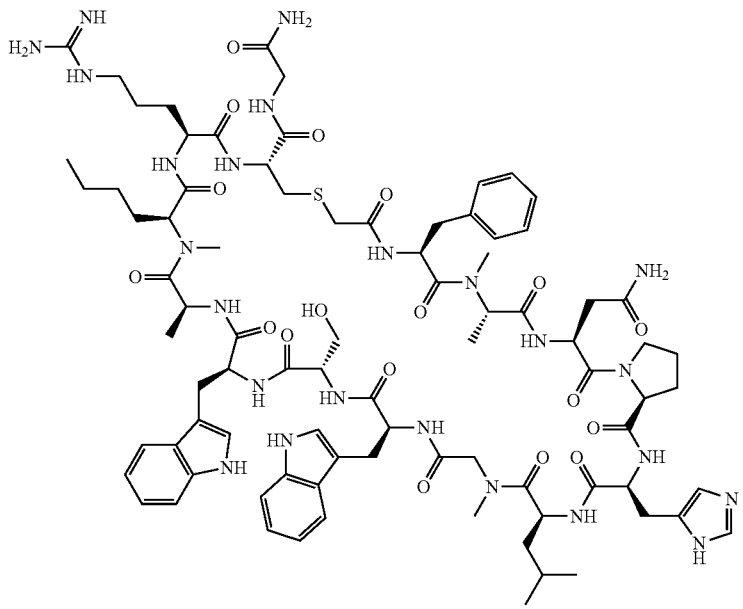

Molecular Weight: 1796.06

Example 1057 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via 2 preparative HPLC injections with the following conditions: Column: PHENOMENEX® Luna 5 u C18(2) 30×100; Mobile Phase A: 0.1% TFA in water; Mobile Phase B: 0.1% TFA in acetonitrile; Gradient: 0-100% B over 20 minutes, then a 5-minute Hold at 100% B; Flow: 15 mL/min. Fractions containing the desired product were combined and dried via centrifugal evaporation. The product was dissolved in a minimum if acetonitrile and water, frozen and lyophilized to give a white amorphous solid. The yield of the product was 8.7 mg, and its estimated purity by HPLC analysis was 99.5%.

Analysis LCMS Condition A: Retention time=0.71 min; ESI-MS(+) m/z 899.1 (M+2H)

Analysis HPLC Condition J. Retention time=11.76 min

Preparation of Example 1058

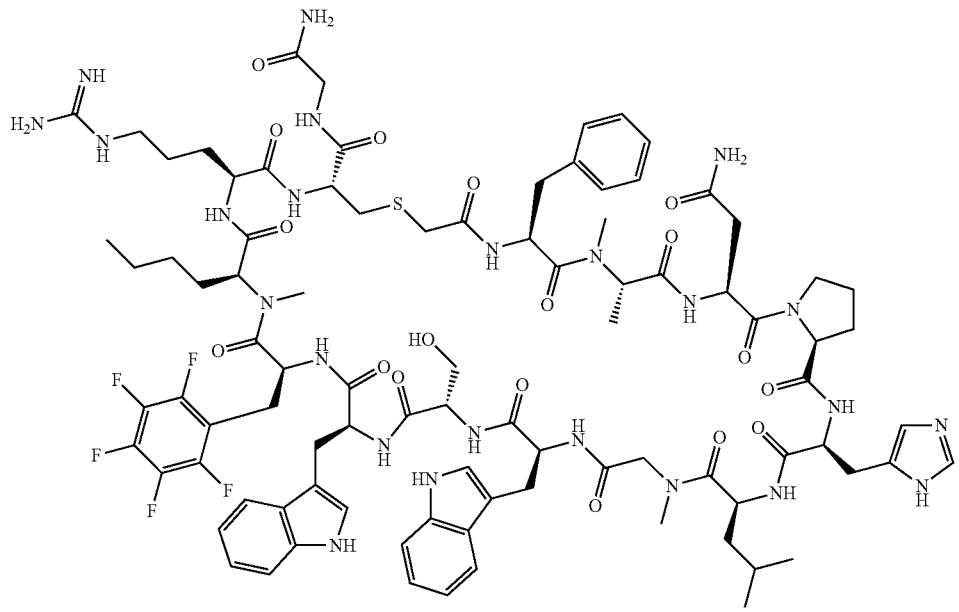

Molecular Weight: 1962.11

Example 1058 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 minutes, then a 0-minute hold at 100% B; Flow: 20 mL/min. Fractions containing the desired product were combined and dried via centrifugal evaporation. The yield of the product was 6.7 mg, and its estimated purity by LCMS analysis was 96%.

Analysis LCMS Condition D: Retention time=1.59 min; ESI-MS(+) m/z 981.6 (M+2H).

Analysis LCMS Condition E: Retention time=1.51 min; ESI-MS(+) m/z 981.7 (M+2H).

Preparation of Example 1059

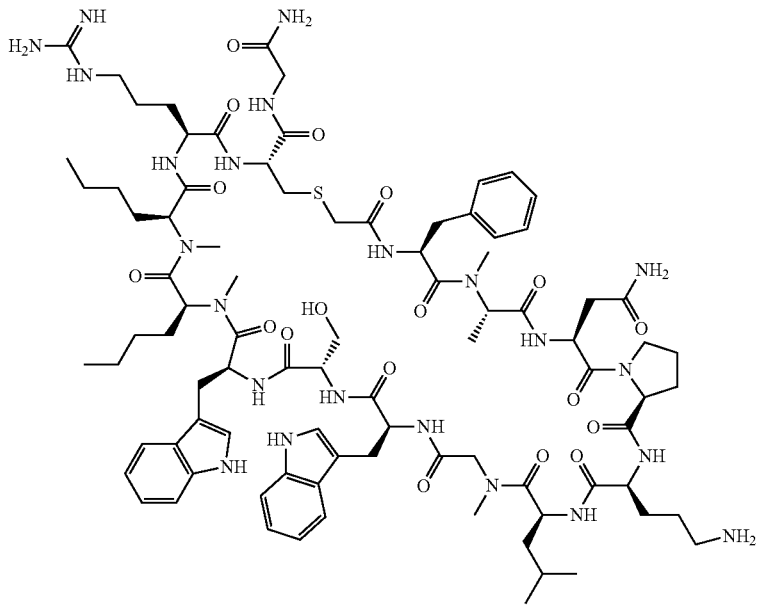

Molecular Weight: 1829.17

Example 1059 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 11.9 mg, and its estimated purity by LCMS analysis was 98%.

Analysis LCMS Condition D: Retention time=1.66 min; ESI-MS(+) m/z 915.4 (M+2H).

Analysis LCMS Condition E: Retention time=1.64 min; ESI-MS(+) m/z 915.4 (M+2H).

Preparation of Example 1060

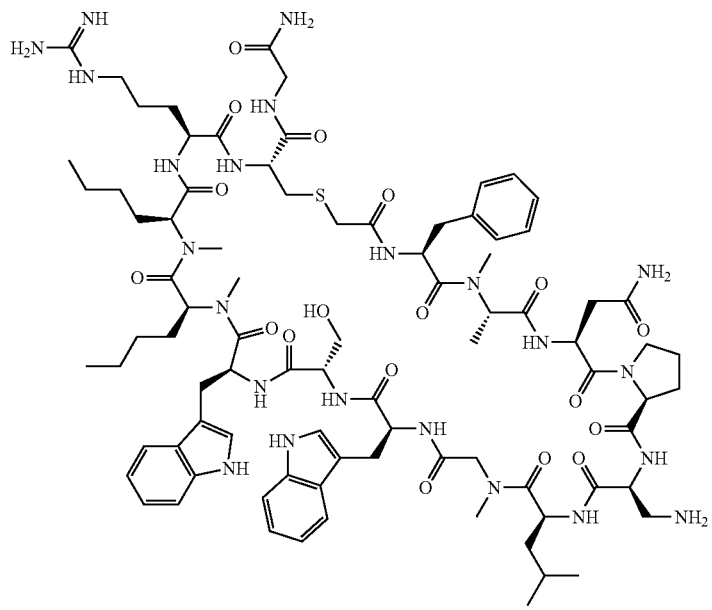

Molecular Weight: 1801.12

Example 1060 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 98%.

Analysis LCMS Condition D: Retention time=1.71 min; ESI-MS(+) m/z 901.6 (M+2H).

Analysis LCMS Condition E: Retention time=1.68 min; ESI-MS(+) m/z 901.3 (M+2H).

Preparation of Example 1061

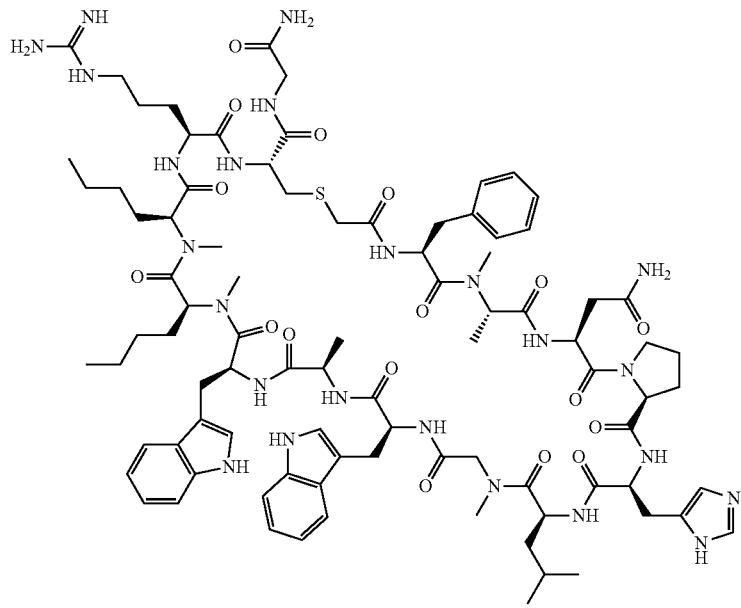

Molecular Weight: 1836.17

Example 1061 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 4.6 mg, and its estimated purity by LCMS analysis was 93%.

Analysis LCMS Condition D: Retention time=1.56 min; ESI-MS(+) m/z 919.0 (M+2H).

Analysis LCMS Condition E: Retention time=1.64 min; ESI-MS(+) m/z 919.0 (M+2H).

Preparation of Example 1062

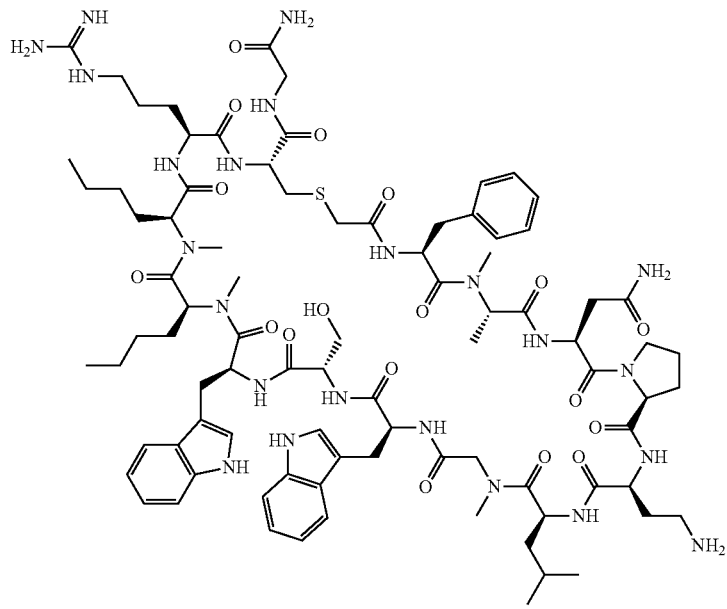

Molecular Weight: 1815.15

Example 1062 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 96%.

Analysis LCMS Condition D: Retention time=1.68 min; ESI-MS(+) m/z 908.8 (M+2H).

Analysis LCMS Condition E: Retention time=1.67 min; ESI-MS(+) m/z 908.8 (M+2H).

Preparation of Example 1063

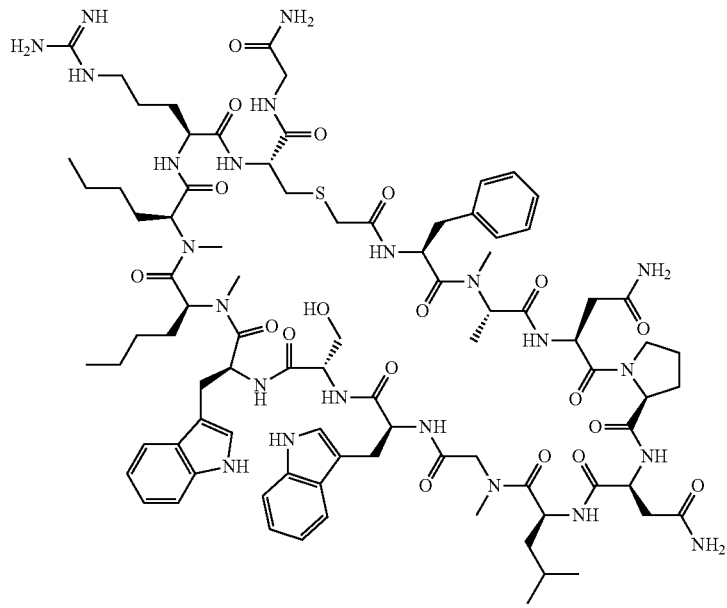

Molecular Weight: 1829.13

Example 1063 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 98%.

Analysis LCMS Condition D: Retention time=1.74 min; ESI-MS(+) m/z 915.8 (M+2H).

Analysis LCMS Condition E: Retention time=1.74 min; ESI-MS(+) m/z 915.8 (M+2H).

Preparation of Example 1064

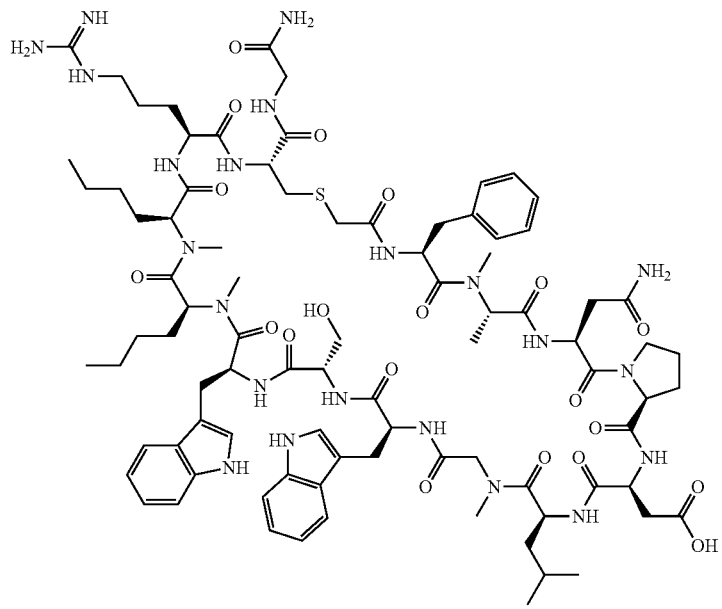

Molecular Weight: 1830.12

Example 1064 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 97%.

Analysis LCMS Condition D: Retention time=1.61 min; ESI-MS(+) m/z 916.3 (M+2H).

Analysis LCMS Condition E: Retention time=1.76 min; ESI-MS(+) m/z 916.2 (M+2H).

Preparation of Example 1065

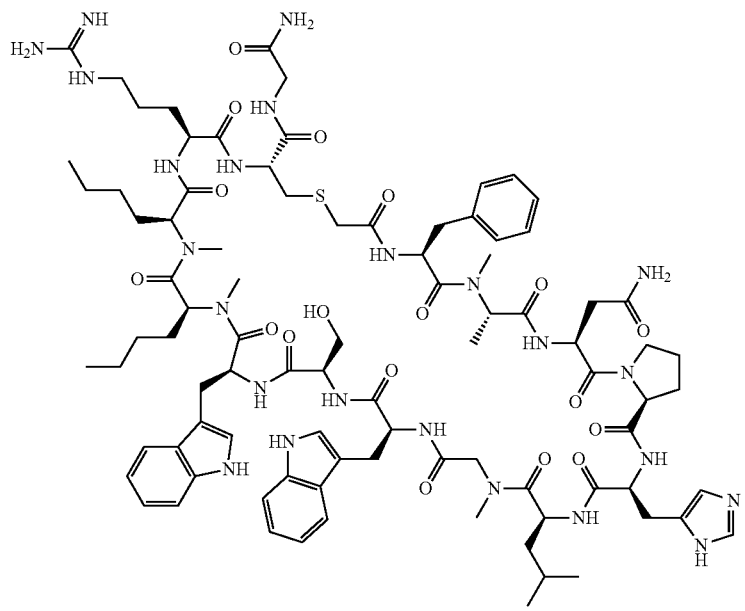

Molecular Weight: 1852.17

Example 1065 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 7 mg, and its estimated purity by LCMS analysis was 93%.

Analysis LCMS Condition D: Retention time=1.50 min; ESI-MS(+) m/z 927.2 (M+2H).

Analysis LCMS Condition E: Retention time=1.74 min; ESI-MS(+) m/z 927.2 (M+2H).

Preparation of Example 1066

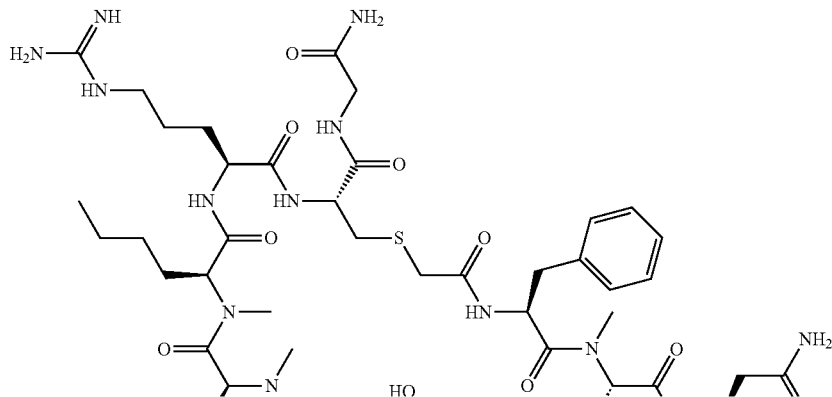

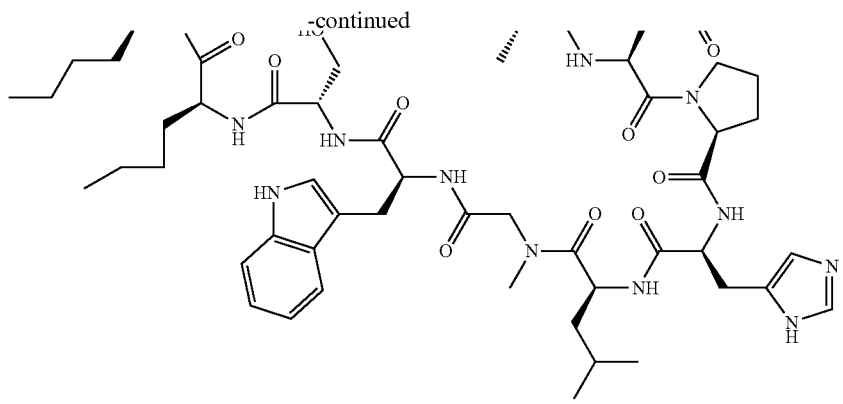

molecular weight: 1779.12

Example 1066 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 30 minutes, Flow: 20 mL/min. Fractions containing the desired product were combined and dried via centrifugal evaporation. The yield of the product was 4.9 mg, and its estimated purity by LC analysis was 100%.

Analysis LCMS Condition A: Retention time=0.78 min; ESI-MS(+) m/z 890.5 (M+2H).

Analysis HPLC Condition J: Retention time=13.4 min.

Preparation of Example 1067

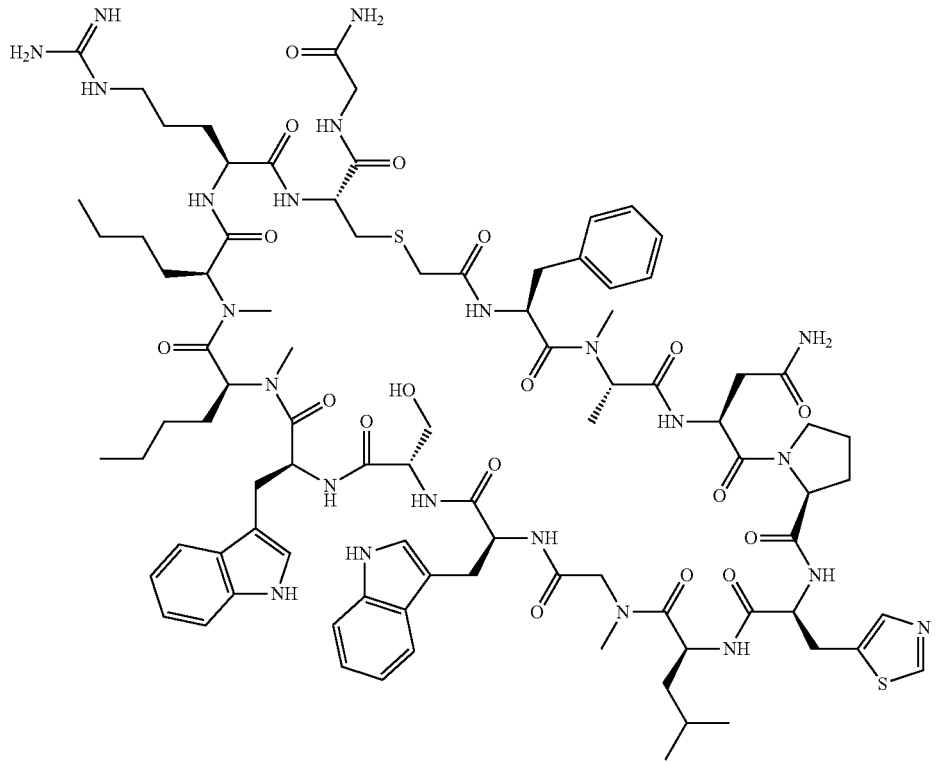

molecular weight: 1869.22

Example 1067 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: PHENOMENEX® Luna C18, 30×1000 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 30 minutes, Flow: 20 mL/min. Fractions containing the desired product were combined and dried via centrifugal evaporation. The yield of the product was 1.6 mg, and its estimated purity by LC analysis was 95%.

Analysis LCMS Condition A: Retention time=0.93 min; ESI-MS(+) m/z 935.7 (M+2H)

Analysis HPLC Condition J: Retention time=14.92 min

Preparation of Example 1068

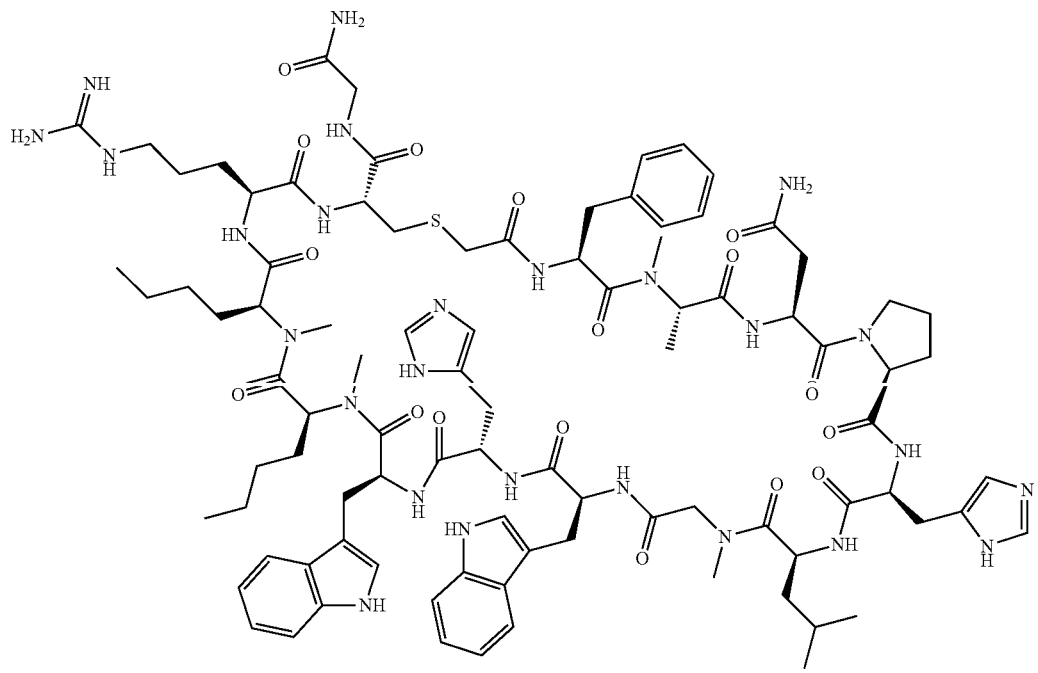

Molecular Weight: 1902.23

Example 1068 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column; PHENOMENEX® Luna C18, 30×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-1000% B over 30 minutes, then a 5-minute hold at 100% B; Flow: 20 mL/min, 2 2 ml injections. Fractions containing the desired product were combined and dried via centrifugal evaporation. The yield of the product was 3.3 mg, and its estimated purity by LC 100% using analysis Condition J.

Analysis LCMS Condition A: Retention time=0.79 min; ESI-MS(+) m/z 952.4 (M+2H).

Analysis HPLC Condition J: Retention time=12.99 min.

Preparation of Example 1069

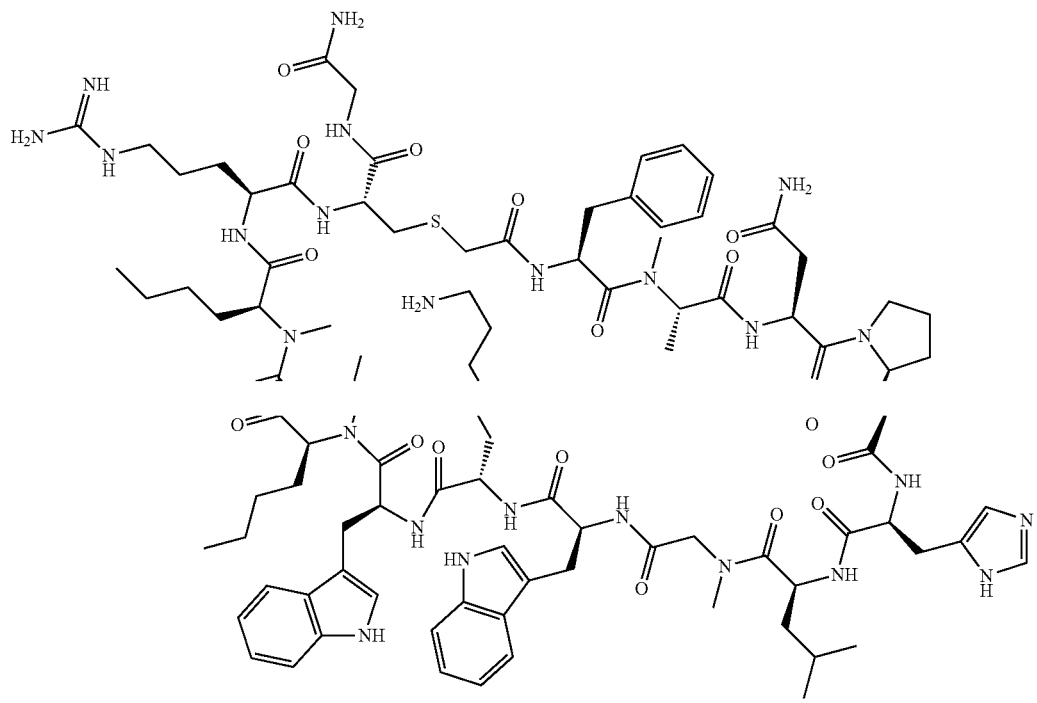

Molecular Weight: 1893.26

Example 1069 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column; PHENOMENEX® Luna C18, 30×1000 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 30 minutes, then a 5-minute hold at 100% B; Flow: 20 mL/min, 2 2 ml injections. Fractions containing the desired product were combined and dried via centrifugal evaporation. The yield of the product was 4.7 mg, and its estimated purity by LC 95.5% using 3 LC analysis methods.

Analysis LCMS Condition A: Retention time=0.81 min; ESI-MS(+) m/z 947.5 (M+2H).

Analysis HPLC Condition J: Retention time=13.13 min.

Analysis HPLC Condition G: Retention time=9.14 min.

Analysis HPLC Condition H: Retention time=10.76 min.

Preparation of Example 1070

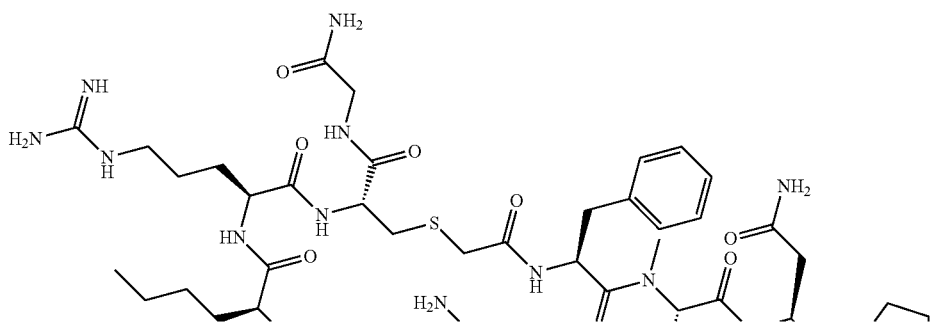

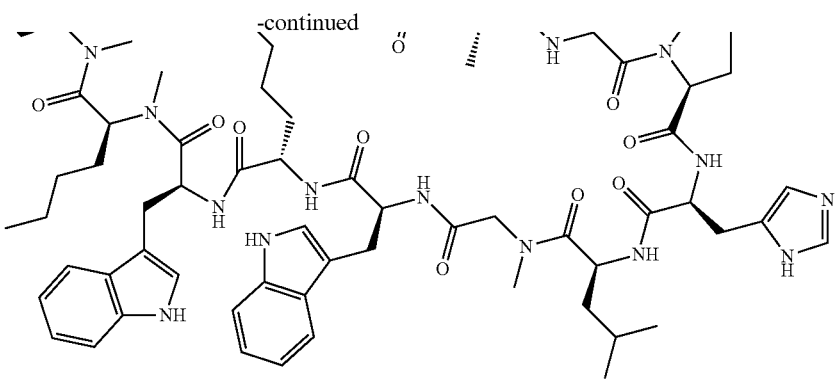

Molecular Weight: 1879.24

Example 1070 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column; PHENOMENEX® Luna C18, 30×100 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-100% B over 30 minutes, then a 5-minute hold at 100% B; Flow: 20 mL/min, 2 2 ml injections. Fractions containing the desired product were combined and dried via centrifugal evaporation. The yield of the product was 6 mg, and its estimated purity by LC 100%.

Analysis LCMS Condition A: Retention time=0.82 min; ESI-MS(+) m/z 940.7 (M+2H).

Analysis HPLC Condition J: Retention time=13.0 min.

Preparation of Example 1071

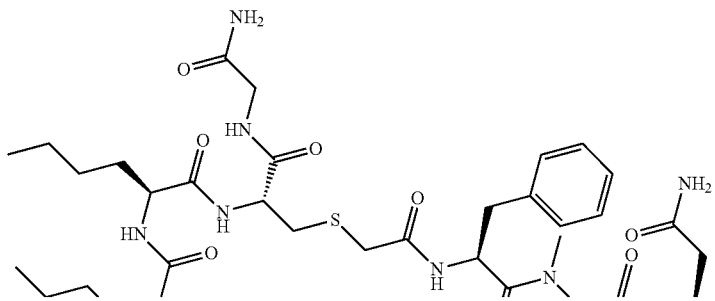

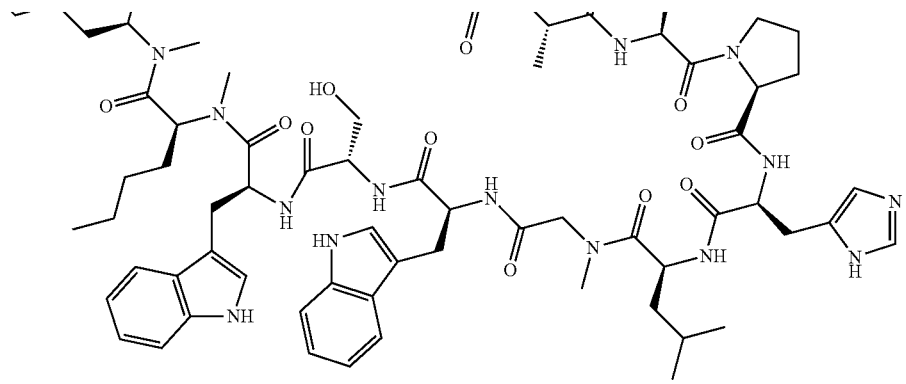

Molecular Weight: 1809.14

Example 1071 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column PHENOMENEX® Luna C18, 30×100 mm, 5-μm particles; 0 to 100% acetonitrile in water with 0.1% TFA as modifier, over 30 mins. Fractions containing the desired product were combined and dried via centrifugal evaporation. The yield of the product was 5.5 mg, and its estimated purity by LC 100%.

Analysis LCMS Condition A: Retention time=0.88 min; ESI-MS(+) m/z 905.7 (M+2H).
Analysis HPLC Condition J: Retention time=14.83 min.

Example 1072 was prepared starting with Intermediate Resin B, using Manual Coupling procedure A, "Chloroacetic acid coupling procedure B", "Global Deprotection Method C", and "Cyclization Method D".

The crude material was purified via preparative LC with the following conditions: Column PHENOMENEX® Luna C18, 30×100 mm, 5-μm particles; 0 to 100% acetonitrile in water with 0.1% TFA as modifier, over 30 mins. Fractions containing the desired product were combined and dried via centrifugal evaporation. The yield of the product was 13.3 mg, and its estimated purity by LC 100%.

Analysis LCMS Condition A: Retention time=0.7 min; ESI-MS(+) m/z 922.9 (M+2H).

Analysis HPLC Condition J: Retention time=11.36 min.

Preparation of Example 1072

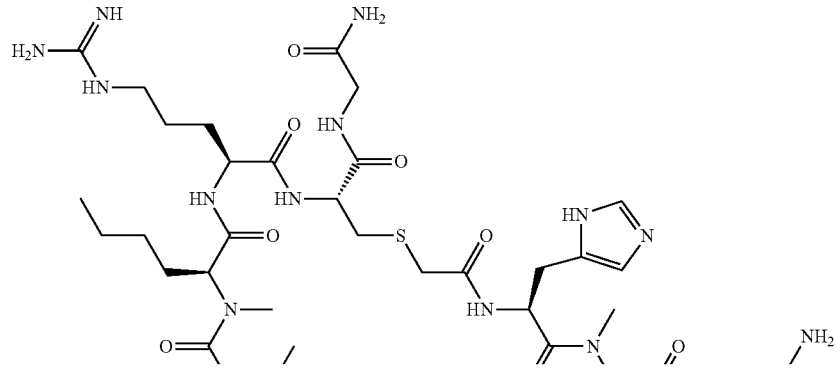

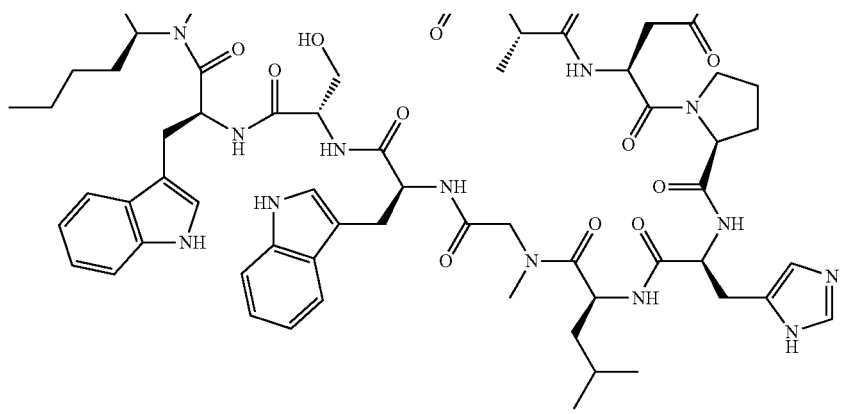

Molecular Weight: 1842.13

Preparation of Example 1073

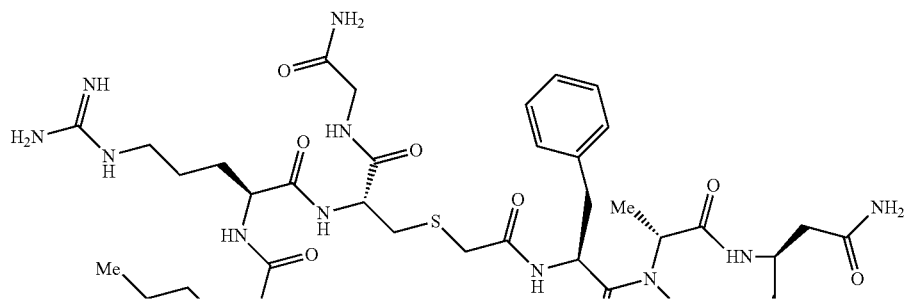

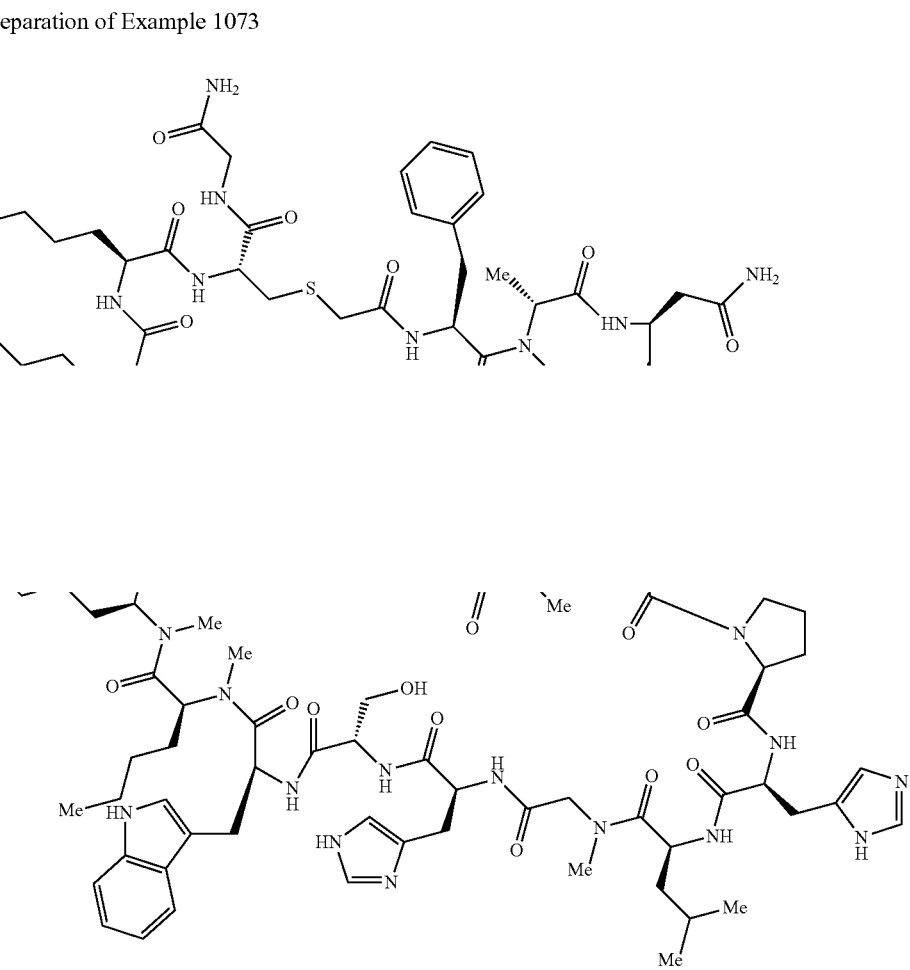

Molecular Weight: 1803.10

Example 1073 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column PHENOMENEX® Luna C18, 30×100 mm, 5-μm particles; 0 to 100% acetonitrile in water with 0.1% TFA as modifier, over 30 mins. Fractions containing the desired product were combined and dried via centrifugal evaporation. The yield of the product was 3 mg, and its estimated purity by LC 100%.

Analysis LCMS Condition A: Retention time=0.71 min; ESI-MS(+) m/z 902.7 (M+2H).

Analysis HPLC Condition J: Retention time=11.15 min.

Preparation of Example 1074

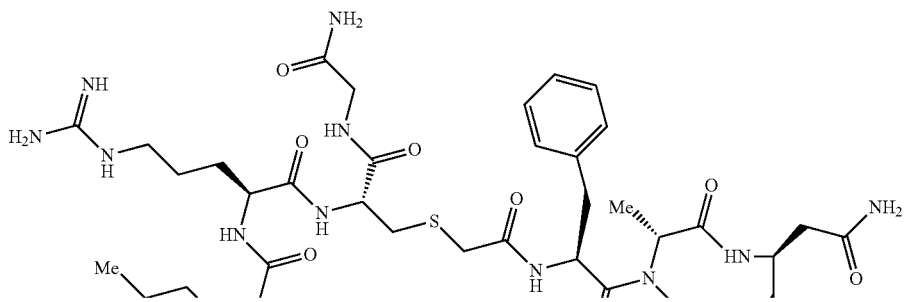

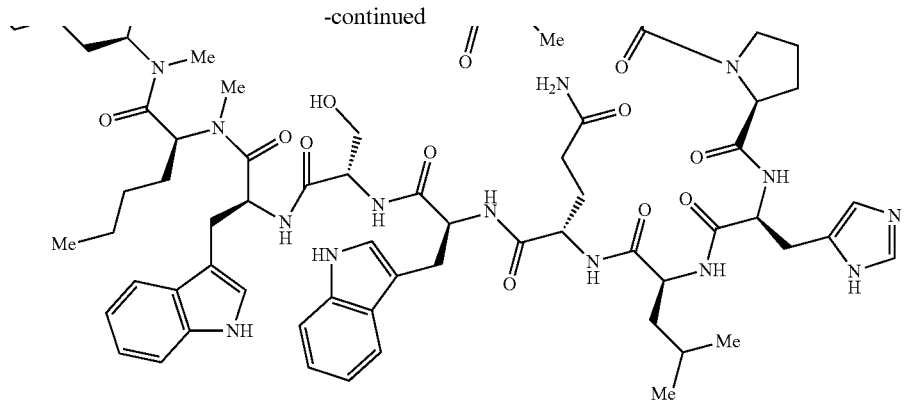

Molecular Weight: 1909.22

Example 1074 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC with the following conditions: Column PHENOMENEX® Luna C18, 30×100 mm, 5-μm particles; 0 to 100% acetonitrile in water with 0.1% TFA as modifier, over 30 mins. Fractions containing the desired product were combined and dried via centrifugal evaporation. The yield of the product was 3.8 mg, and its estimated purity by LC 100%.

Analysis LCMS Condition A: Retention time=0.84 min; ESI-MS(+) m/z 955.8 (M+2H).

Analysis HPLC Condition J. Retention time=13.34 min.

Preparation of Example 1075

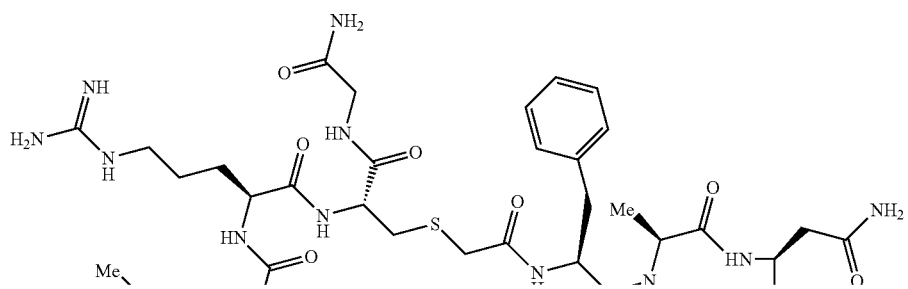

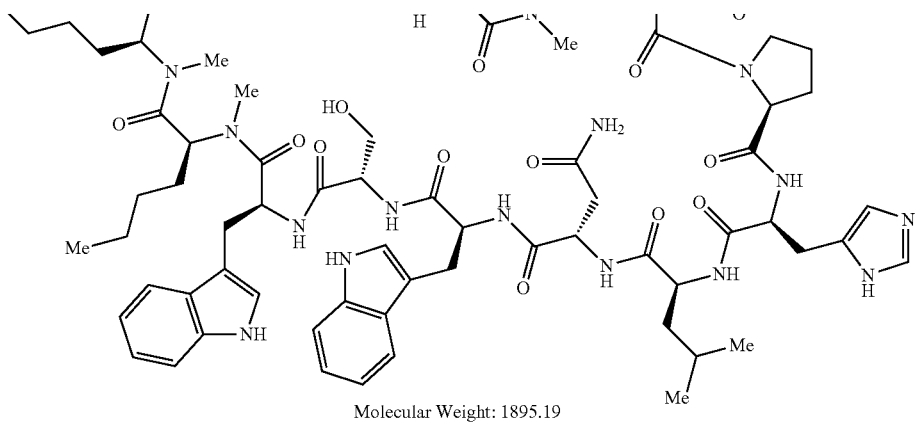

Molecular Weight: 1895.19

Example 1075 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC with the following conditions: Column PHENOMENEX® Luna C18, 30×100 mm, 5-μm particles; 0 to 100% acetonitrile in water with 0.1% TFA as modifier, over 30 mins. Fractions containing the desired product were combined and dried via centrifugal evaporation. The yield of the product was 3.8 mg, and its estimated purity by LC 100%.

Analysis LCMS Condition A: Retention time=0.8 min; ESI-MS(+) m/z 948.9 (M+2H).

Analysis HPLC Condition J: Retention time=13.34 min.

Example 1076 was prepared on Fmoc-Gly-O-cltrityl resin, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 93%.

Analysis LCMS Condition D: Retention time=1.74 min; ESI-MS(+) m/z 927.7 (M+2H).

Analysis LCMS Condition E: Retention time=1.66 min; ESI-MS(+) m/z 927.4 (M+2H).

Preparation of Example 1076

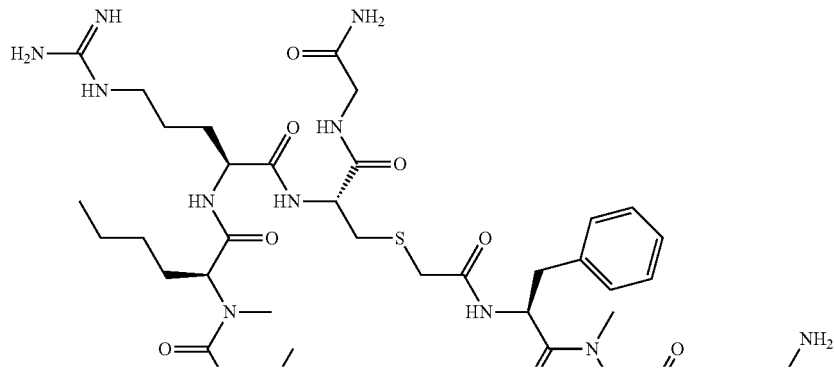

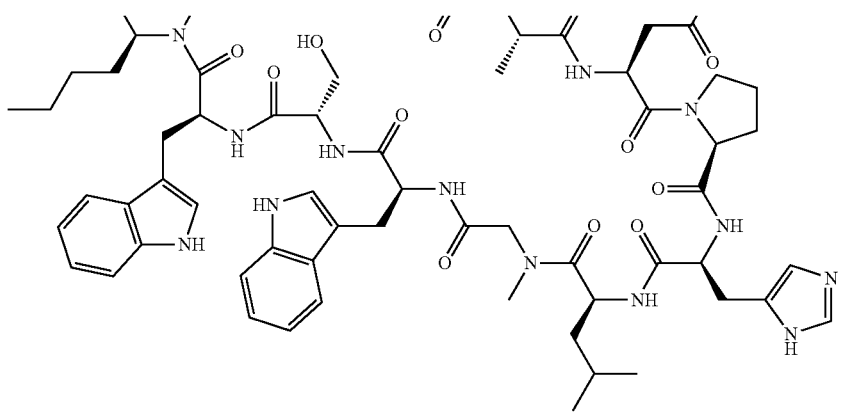

Molecular Weight: 1853.15

Preparation of Example 1077

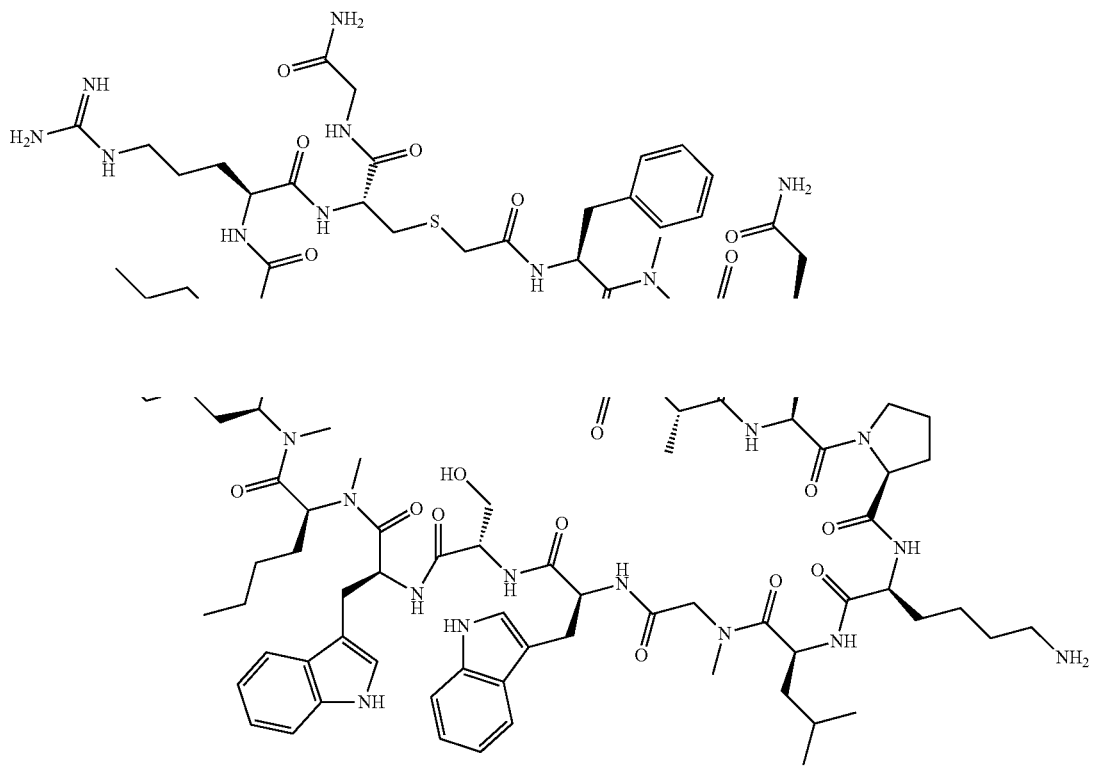

Molecular Weight: 1843.20

Example 1077 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 1.8 mg, and its estimated purity by LCMS analysis was 94%.

Analysis LCMS Condition D: Retention time=1.65 min; ESI-MS(+) m/z 922.4 (M+2H).

Analysis LCMS Condition E: Retention time=1.66 min; ESI-MS(+) m/z 922.3 (M+2H).

Preparation of Example 1078

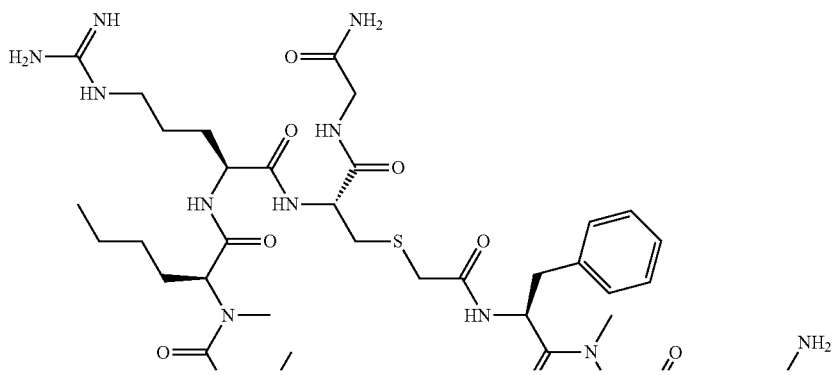

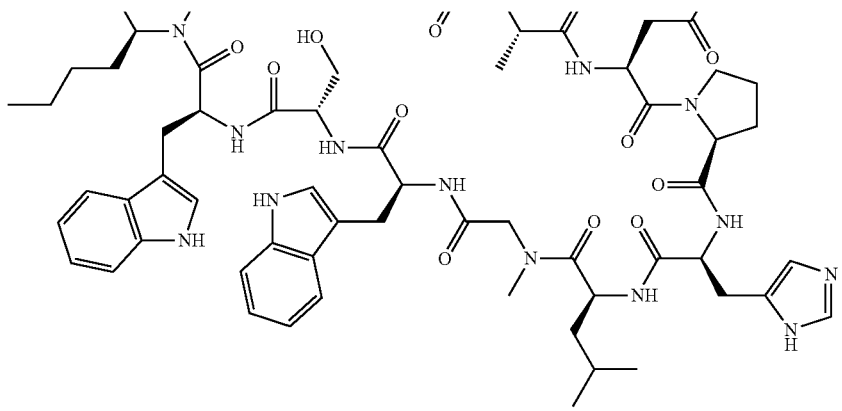

Molecular Weight: 1866.19

Example 1078 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 1 mg, and its estimated purity by LCMS analysis was 89%.

Analysis LCMS Condition D: Retention time=1.54 min; ESI-MS(+) m/z 933.7 (M+2H).

Analysis LCMS Condition E: Retention time=1.47 min; ESI-MS(+) m/z 933.7 (M+2H).

Preparation of Example 1080

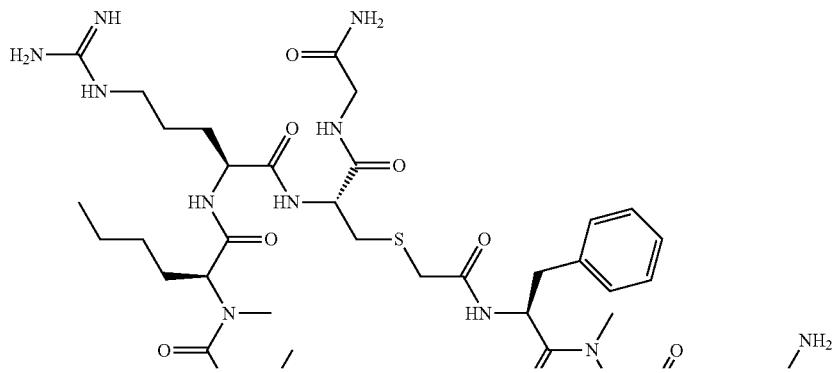

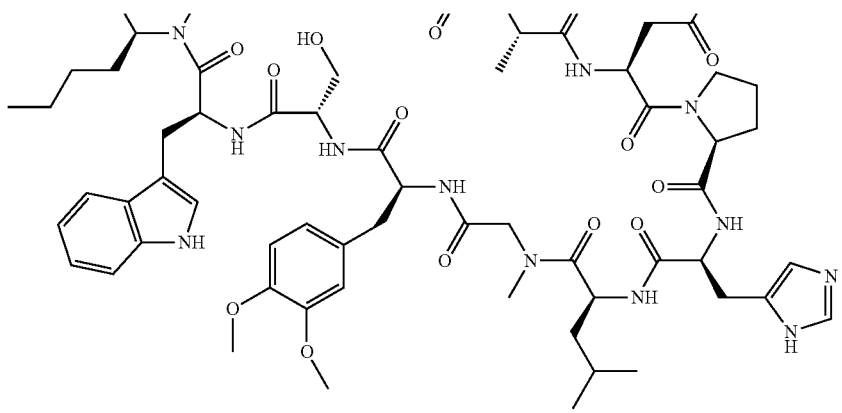

Molecular Weight: 1873.18

Example 1080 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". (S)-2-((((9H-fluoren-9-yl)methoxy)carbonyl)amino)-3-(3,4-dimethoxyphenyl)propanoic acid was used the eighth amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 92%.

Analysis LCMS Condition D: Retention time=1.55 min; ESI-MS(+) m/z 937.5 (M+2H).

Analysis LCMS Condition E: Retention time=1.48 min; ESI-MS(+) m/z 937.5 (M+2H).

Preparation of Example 1081

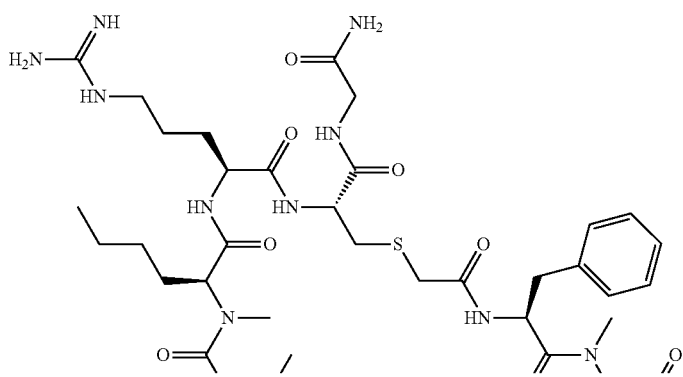

-continued

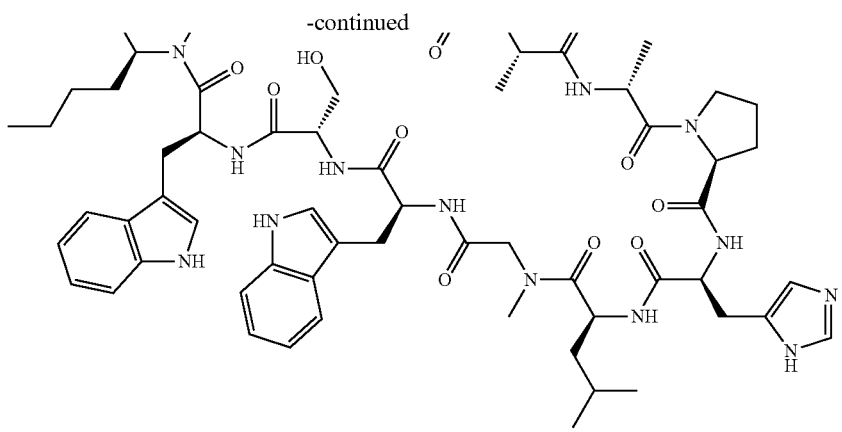

MolecularWeight: 1809.14

Example 1081 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 5-minute hold at 100% B; Flow: 20 mL/min. Fractions containing the desired product were combined and dried via centrifugal evaporation. The yield of the product was 0.6 mg, and its estimated purity by LCMS analysis was 94%.

Analysis LCMS Condition D: Retention time=1.62 min; ESI-MS(+) m/z 905.5 (M+2H).

Analysis LCMS Condition E: Retention time=1.54 min; ESI-MS(+) m/z 905.5 (M+2H).

Preparation of Example 1082

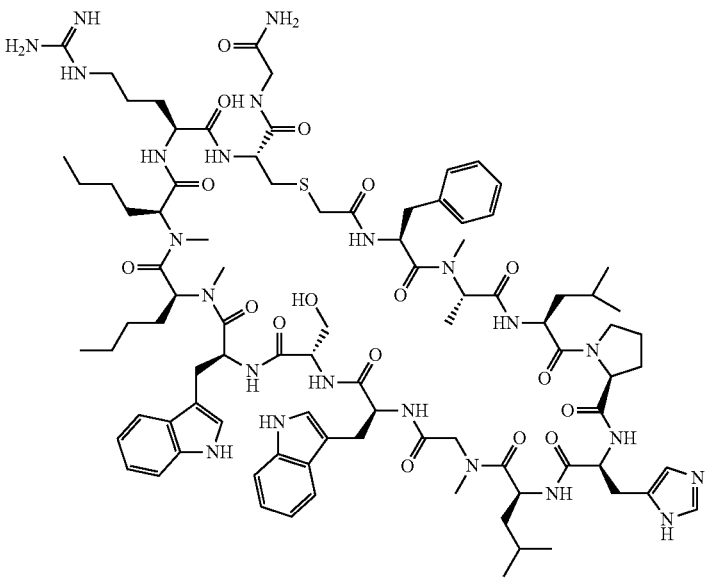

Molecular Weight: 1851.22

Example 1082 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 99%.

Analysis LCMS Condition D: Retention time=1.75 min; ESI-MS(+) m/z 926.3 (M+2H).

Analysis LCMS Condition E: Retention time=1.58 min; ESI-MS(+) m/z 926.3 (M+2H).

Preparation of Example 1083

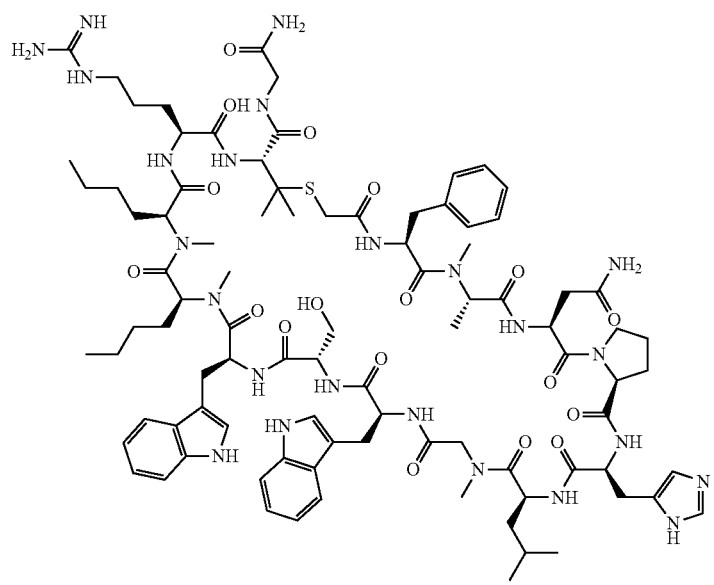

Molecular Weight: 1880.22

Example 1083 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". (R)-2-((((9H-fluoren-9-yl)methoxy)carbonyl)amino)-3-methyl-3-(tritylthio)butanoic acid was used the second amino acid coupling step.

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 20-70% B over 25 minutes, then a 5-minute hold at 100% B; Flow: 20 mL/min. Fractions containing the desired product were combined and dried via centrifugal evaporation. The yield of the product was 10.91 mg and its estimated purity by LCMS analysis was 98%.

Analysis LCMS Condition D: Retention time=1.73 min; ESI-MS(+) m/z 941.2 (M+2H).

Analysis LCMS Condition E: Retention time=1.65 min; ESI-MS(+) m/z 940.9 (M+2H).

Preparation of Example 1084

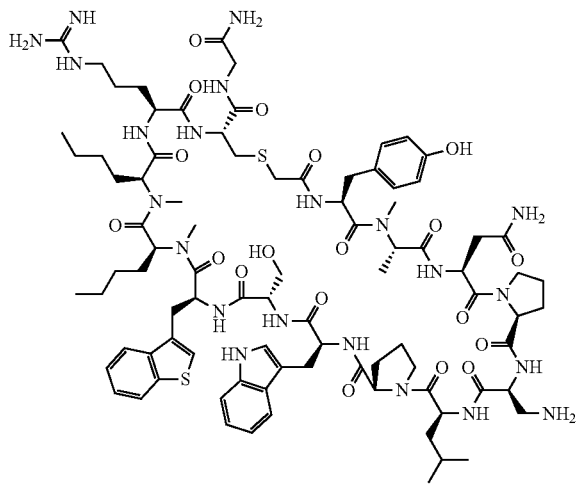

Molecular Weight: 1860.21

Example 1084 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 minutes, then a 5-minute hold at 100% B; Flow: 20 mL/min. Fractions containing the desired product were combined and dried via centrifugal evaporation. The yield of the product was 5 mg, and its estimated purity by LCMS analysis was 95%.

Analysis LCMS Condition D: Retention time=1.51 min; ESI-MS(+) m/z 930.8 (M+2H).

Analysis LCMS Condition E: Retention time=1.51 min; ESI-MS(+) m/z 930.8 (M+2H).

Preparation of Example 1085

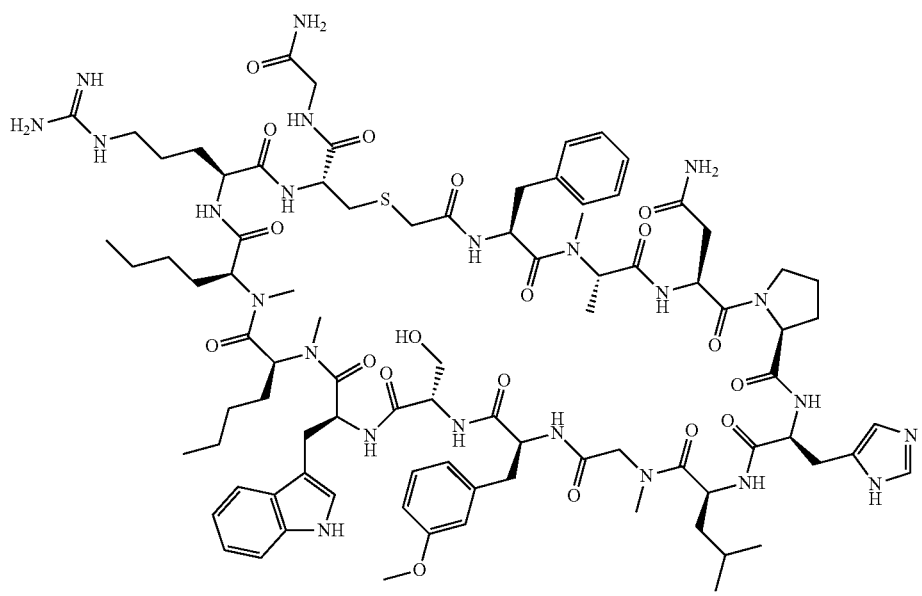

Molecular Weight: 1843.16

Example 1085 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". (S)-2-((((9H-fluoren-9-yl)methoxy)carbonyl)amino)-3-(3-methoxyphenyl)propanoic acid is used in the eighth amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 13 mg and its estimated purity by LCMS analysis was 99%.

Analysis LCMS Condition D: Retention time=1.51 min; ESI-MS(+) m/z 922.6 (M+2H).

Analysis LCMS Condition E: Retention time=1.51 min; ESI-MS(+) m/z 922.5 (M+2H).

Preparation of Example 1086

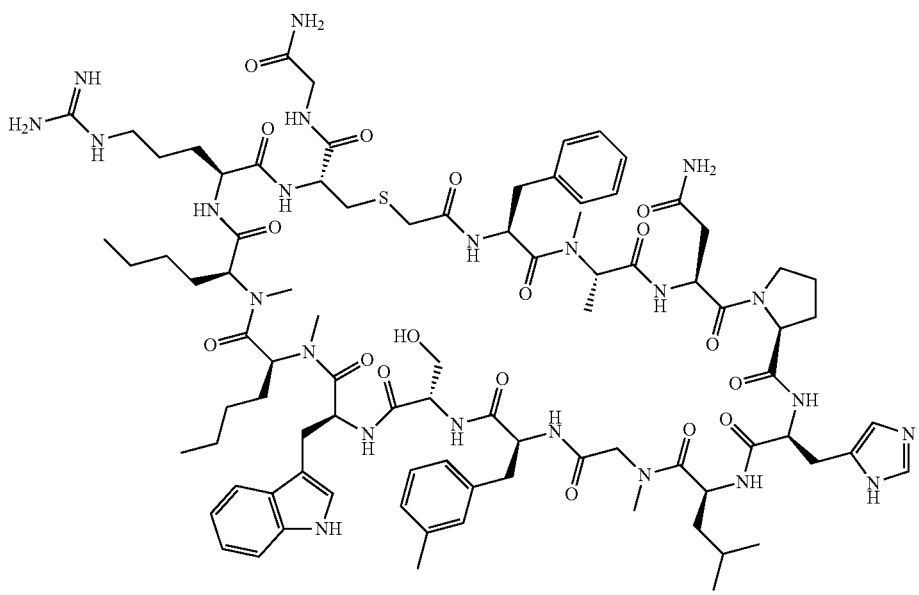

Molecular Weight: 1827.16

Example 1086 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". (S)-2-((((9H-fluoren-9-yl)methoxy)carbonyl)amino)-3-(3-methylphenyl)propanoic acid is used in the eighth amino acid coupling step.

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 0-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis LCMS Condition D: Retention time=1.55 min; ESI-MS(+) m/z 914.2 (M+2H).

Analysis LCMS Condition E: Retention time=1.52 min; ESI-MS(+) m/z 914.5 (M+2H).

Preparation of Example 1087

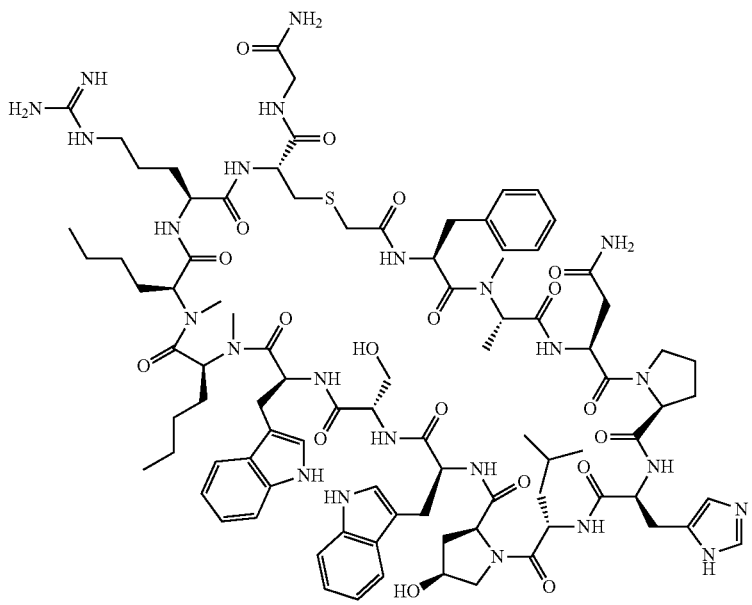

Molecular Weight: 1894.20

Example 1087 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 99%.

Analysis LCMS Condition D: Retention time=1.79 min; ESI-MS(+) m/z 948.3 (M+2H).

Analysis LCMS Condition E: Retention time=1.73 min; ESI-MS(+) m/z 947.9 (M+2H).

Preparation of Example 1088

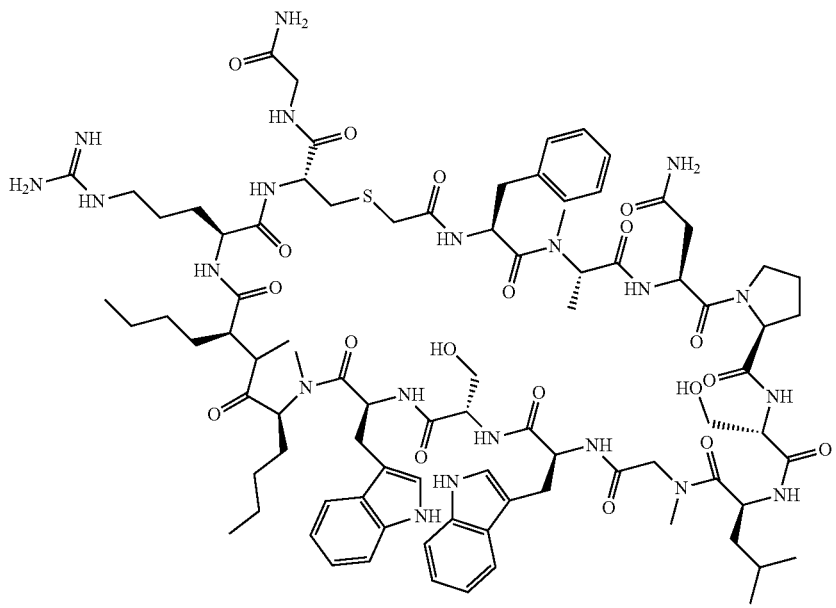

Molecular Weight: 1802.11

Example 1088 was prepared form Intermediate Resin A, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 4.6 mg, and its estimated purity by LCMS analysis was 98%.

Analysis LCMS Condition D: Retention time=1.81 min; ESI-MS(+) m/z 902.0 (M+2H).

Analysis LCMS Condition E: Retention time=1.83 min; ESI-MS(+) m/z 902.0 (M+2H).

Preparation of Example 1089

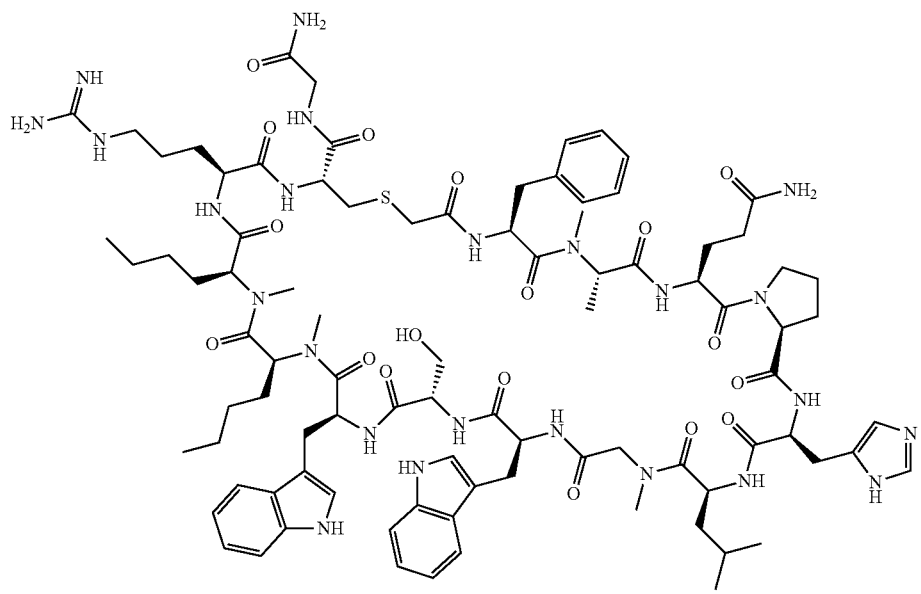

Molecular Weight: 1866.19

Example 1089 was prepared form Intermediate Resin A, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 98%.

Analysis LCMS Condition D: Retention time=1.68 min; ESI-MS(+) m/z 934.0 (M+2H).

Analysis LCMS Condition E: Retention time=1.59 min; ESI-MS(+) m/z 934.3 (M+2H).

Preparation of Example 1090

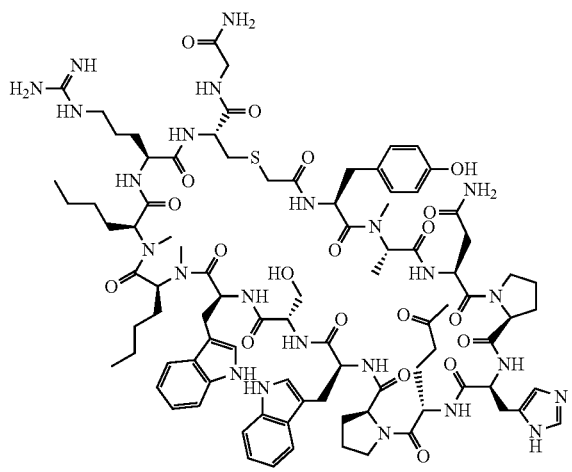

Molecular Weight: 1910.16

Preparation of Example 1091

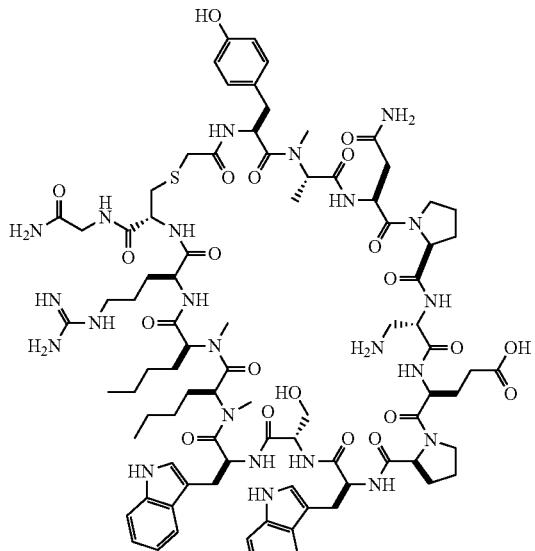

Molecular Weight: 1859.11

Example 1090 was prepared form Intermediate Resin A, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 0-minute hold at 100% B; Flow: 20 mL/min. Fractions containing the desired product were combined and dried via centrifugal evaporation. The yield of the product was 12.1 mg, and its estimated purity by LCMS analysis was 93%.

Analysis LCMS Condition D: Retention time=1.46 min; ESI-MS(+) m/z 956.0 (M+2H).

Analysis LCMS Condition E: Retention time=1.46 min; ESI-MS(+) m/z 955.9 (M+2H).

Example 1091 was prepared form Intermediate Resin A, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 10-minute hold at 60% B; Flow: 20 mL/min. Fractions containing the desired product were combined and dried via centrifugal evaporation. The yield of the product was 9.1 mg, and its estimated purity by LCMS analysis was 99%.

Analysis LCMS Condition D: Retention time=1.46 min; ESI-MS(+) m/z 930.9 (M+2H).

Analysis LCMS Condition E: Retention time=1.47 min; ESI-MS(+) m/z 930.7 (M+2H).

Preparation of Example 1092

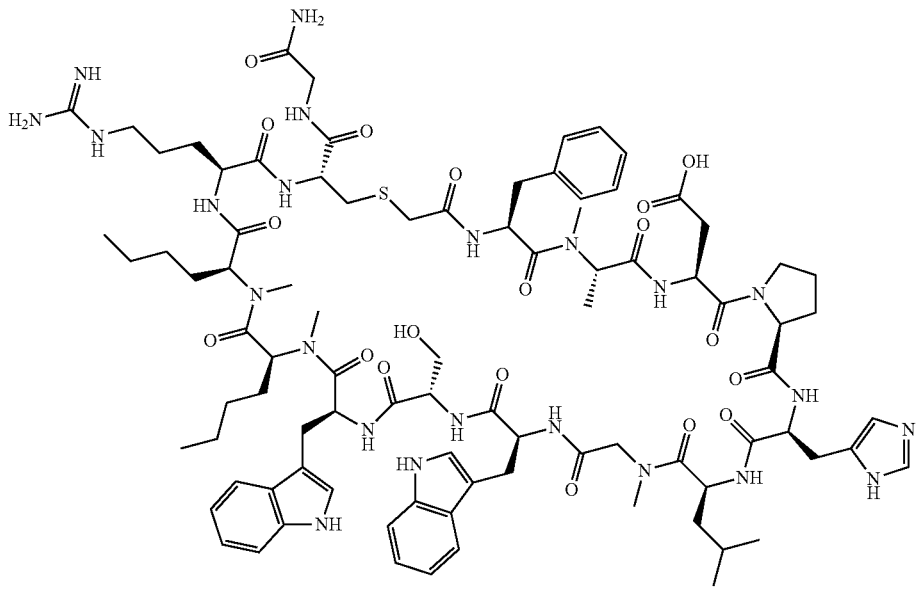

Molecular Weight: 1853.15

Example 1092 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 1.4 mg, and its estimated purity by LCMS analysis was 100%.

Analysis LCMS Condition D: Retention time=1.70 min; ESI-MS(+) m/z 927.3 (M+2H).

Analysis LCMS Condition E: Retention time=1.71 min; ESI-MS(+) m/z 927.3 (M+2H).

Preparation of Example 1093

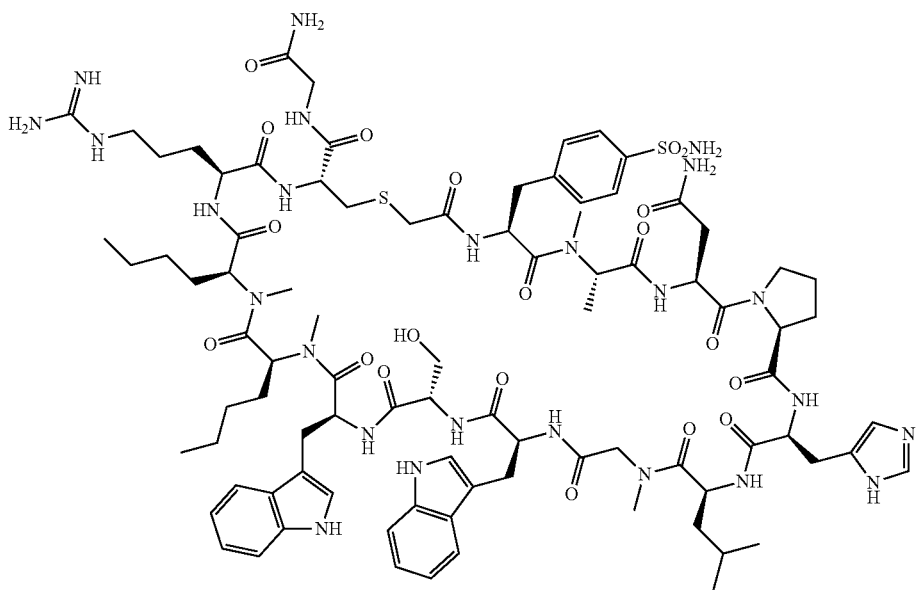

Molecular Weight: 1931.25

Example 1093 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(4-sulfamoylphenyl)propanoic acid, was used in the amino acid coupling step.

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 99%.

Analysis LCMS Condition D: Retention time=1.48 min; ESI-MS(+) m/z 966.7 (M+2H).

Analysis LCMS Condition E: Retention time=1.45 min; ESI-MS(+) m/z 966.2 (M+2H).

Preparation of Example 1094

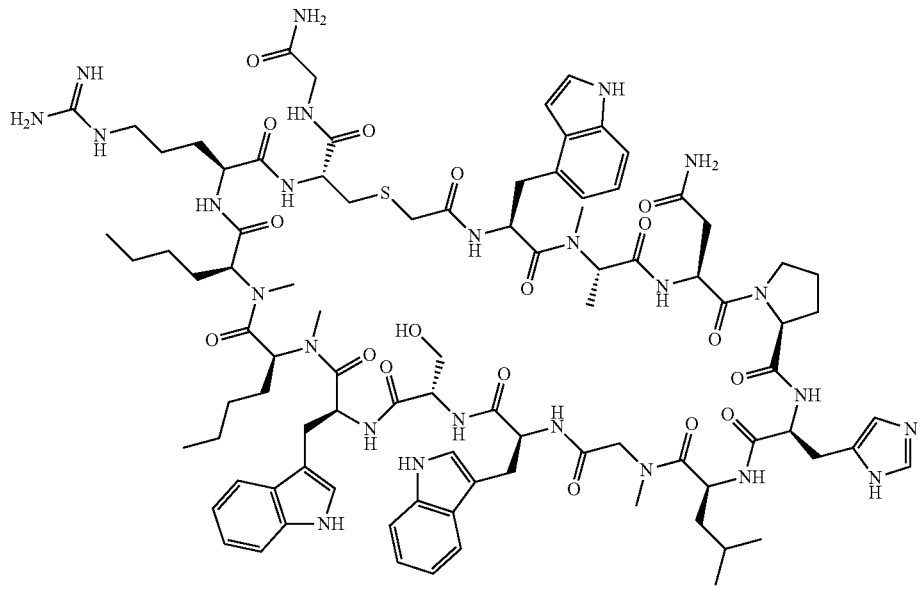

Molecular Weight: 1891.20

Example 1094 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(1-(tert-butoxycarbonyl)-1H-indol-4-yl)propanoic acid was used in the amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 100%.

Analysis LCMS Condition D: Retention time=1.66 min; ESI-MS(+) m/z 946.6 (M+2H).

Analysis LCMS Condition E: Retention time=1.62 min; ESI-MS(+) m/z 946.6 (M+2H).

Preparation of Example 1095

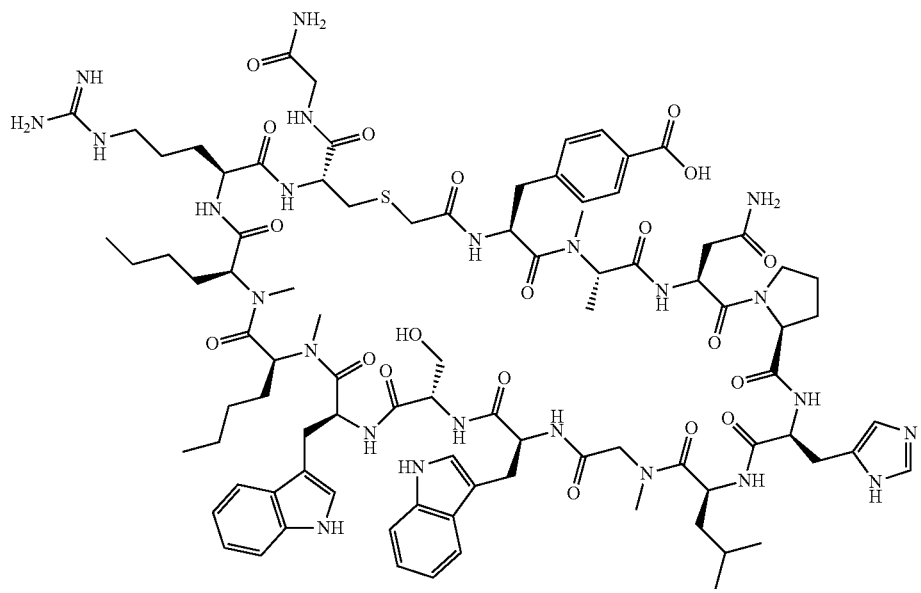

Molecular Weight: 1896.18

Example 1095 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(4-(tert-butoxycarbonyl)phenyl)propanoic acid was used in the amino acid coupling step.

The crude material was purified via preparative LC/MS with the following conditions: Column: XBridge C18 300, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 100%.

Analysis LCMS Condition D: Retention time=1.38 min; ESI-MS(+) m/z 949.3 (M+2H).

Analysis LCMS Condition E: Retention time=1.44 min; ESI-MS(+) m/z 949.2 (M+2H).

Preparation of Example 1096

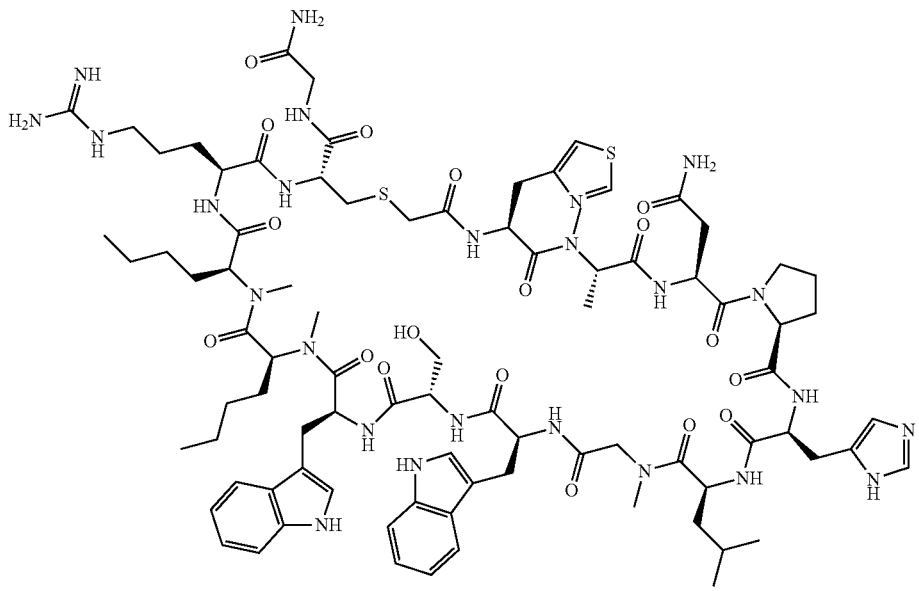

Molecular Weight: 1859.18

Example 1096 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(thiazol-4-yl)propanoic acid was used in the amino acid coupling step.

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 100%.

Analysis LCMS Condition D: Retention time=1.49 min; ESI-MS(+) m/z 930.6 (M+2H).

Analysis LCMS Condition E: Retention time=1.45 min; ESI-MS(+) m/z 930.7 (M+2H).

Preparation of Example 1097

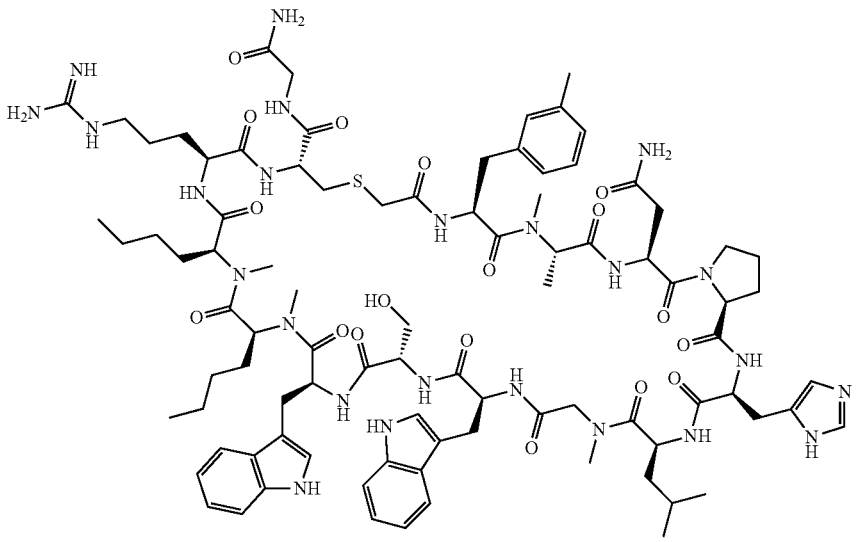

Molecular Weight: 1866.19

Example 1097 was prepared starting with Intermediate Resin B, using Manuel Coupling procedure A, Chloroacetic acid coupling procedure B "Global Deprotection Method C", and "Cyclization Method D". (S)-2-((((9H-fluoren-9-yl)methoxy)carbonyl)amino)-3-(m-tolyl)propanoic acid was used in the amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 98%.

Analysis LCMS Condition D: Retention time=1.87 min; ESI-MS(+) m/z 934.1 (M+2H).

Analysis LCMS Condition E: Retention time=1.79 min; ESI-MS(+) m/z 934.1 (M+2H)

Preparation of Example 1098

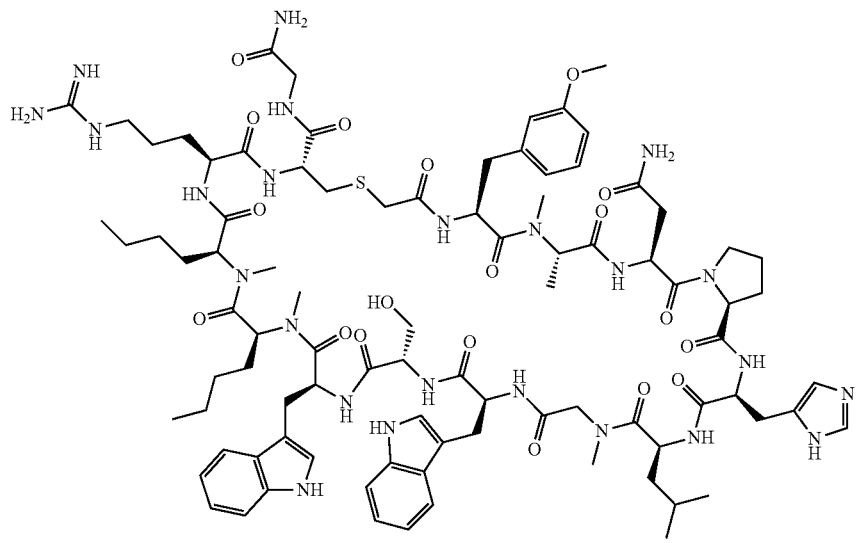

Molecular Weight: 1882.19

Example 1098 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(3-methoxyphenyl)propanoic acid was used in the amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 5.1 mg, and its estimated purity by LCMS analysis was 100%.

Analysis LCMS Condition D: Retention time=1.78 min; ESI-MS(+) m/z 942.2 (M+2H).

Analysis LCMS Condition E: Retention time=1.71 min; ESI-MS(+) m/z 942.1 (M+2H).

Preparation of Example 1099

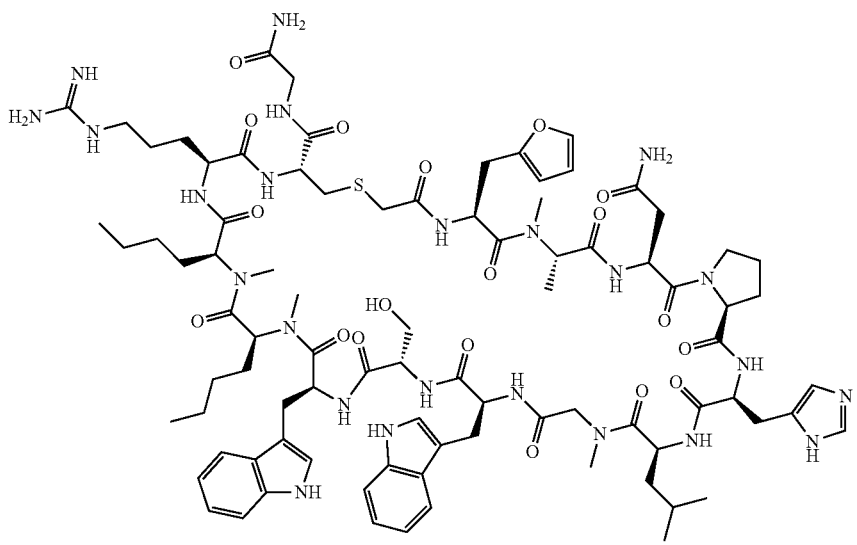

Molecular Weight: 1842.13

Example 1099 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(furan-2-yl)propanoic acid was used in the amino acid coupling step.

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 100%.

Analysis LCMS Condition D: Retention time=1.65 min; ESI-MS(+) m/z 922.1 (M+2H).

Analysis LCMS Condition E: Retention time=1.56 min; ESI-MS(+) m/z 922.2 (M+2H).

Preparation of Example 1100

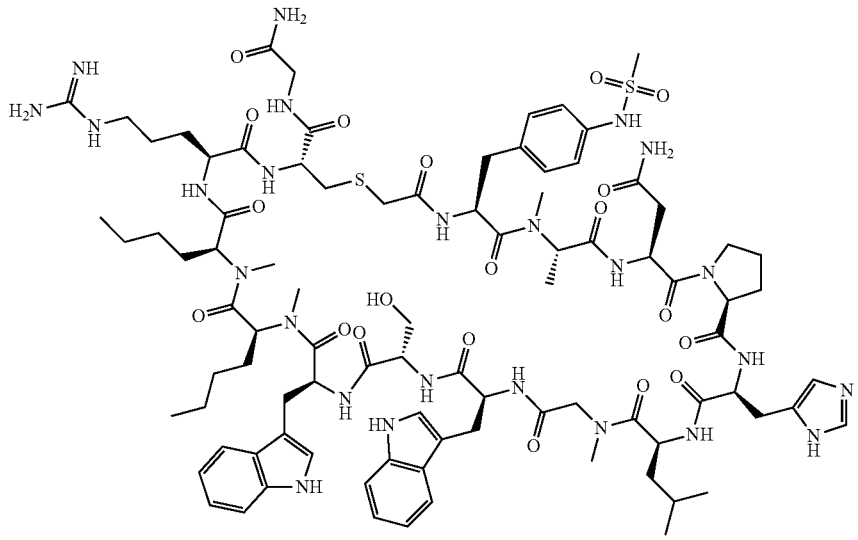

Molecular Weight: 1945.27

Example 1100 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(4-(methylsulfonamido)phenyl)propanoic acid was used in the amino acid coupling step.

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 100%.

Analysis LCMS Condition D: Retention time=1.47 min; ESI-MS(+) m/z 973.9 (M+2H).

Analysis LCMS Condition E: Retention time=1.56 min; ESI-MS(+) m/z 973.5 (M+2H).

Preparation of Example 1101

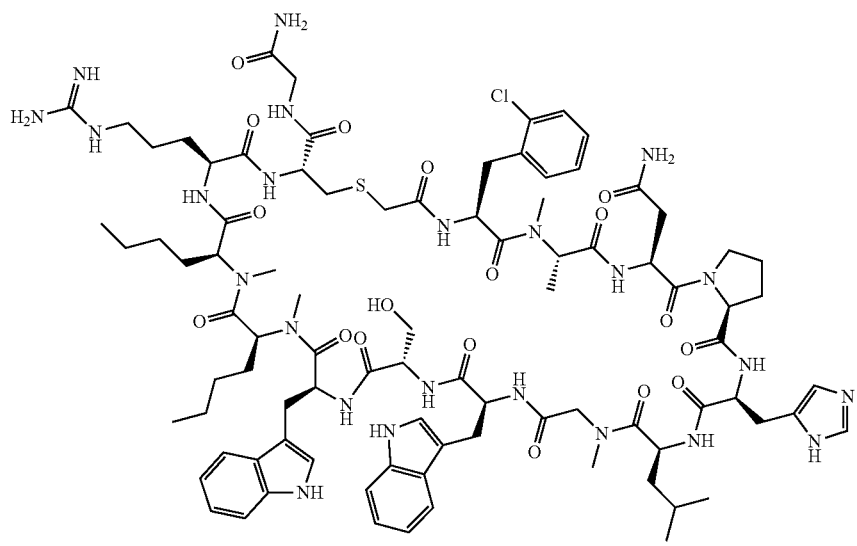

Molecular Weight: 1886.61

Example 1101 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(2-chlorophenyl)propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 5.3 mg, and its estimated purity by LCMS analysis was 99%.

Analysis LCMS Condition D: Retention time=1.73 min; ESI-MS(+) m/z 945.0 (M+2H).

Analysis LCMS Condition E: Retention time=1.64 min; ESI-MS(+) m/z 944.2 (M+2H).

Preparation of Example 1102

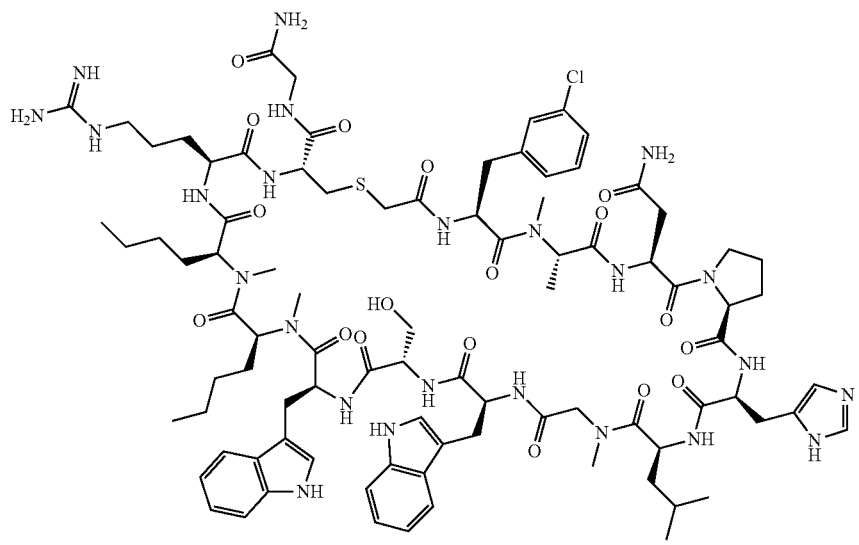

Molecular Weight: 1886.61

Example 1102 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(3-chlorophenyl)propanoic acid was used in the amino acid coupling step.

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 4.6 mg, and its estimated purity by LCMS analysis was 98%.

Analysis LCMS Condition D: Retention time=1.77 min; ESI-MS(+) m/z 944.7 (M+2H).

Analysis LCMS Condition E: Retention time=1.71 min; ESI-MS(+) m/z 944.4 (M+2H).

Preparation of Example 1103

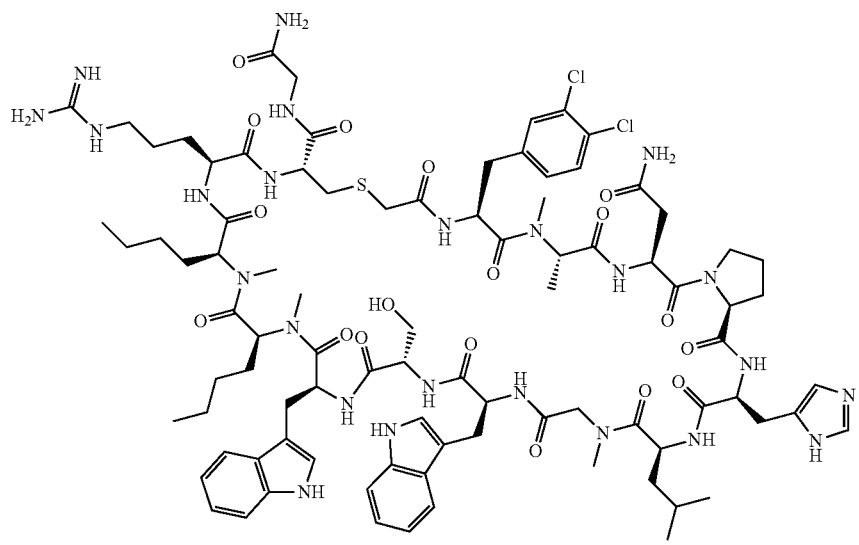

Molecular Weight: 1921.06

Example 1103 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(3,4-dichlorophenyl)propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 2.5 mg, and its estimated purity by LCMS analysis was 98%.

Analysis LCMS Condition D: Retention time=1.85 min; ESI-MS(+) m/z 961.9 (M+2H).

Analysis LCMS Condition E: Retention time=1.75 min; ESI-MS(+) m/z 961.3 (M+2H).

Preparation of Example 1104

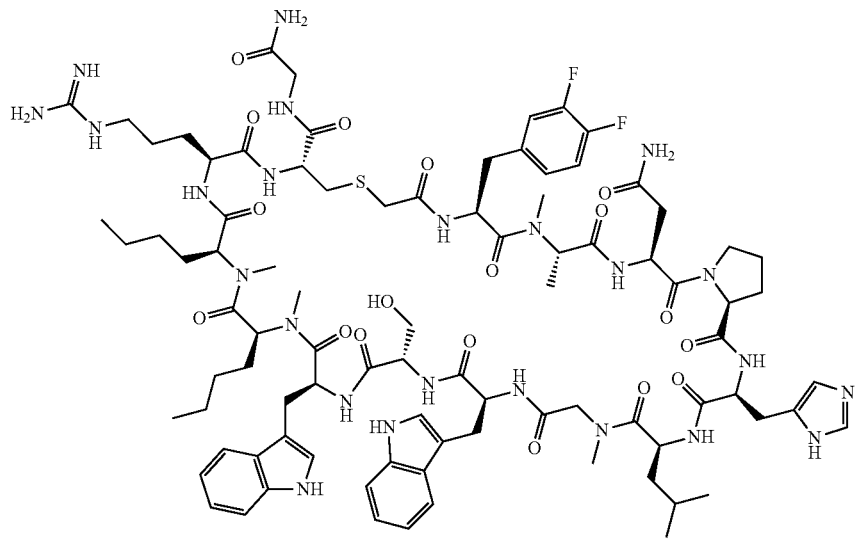

Molecular Weight: 1888.15

Example 1104 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(3,4-difluorophenyl)propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 4.9 mg, and its estimated purity by LCMS analysis was 98%.

Analysis LCMS Condition D: Retention time=1.75 min; ESI-MS(+) m/z 945.2 (M+2H).

Analysis LCMS Condition E: Retention time=1.66 min; ESI-MS(+) m/z 945.2 (M+2H).

Preparation of Example 1105

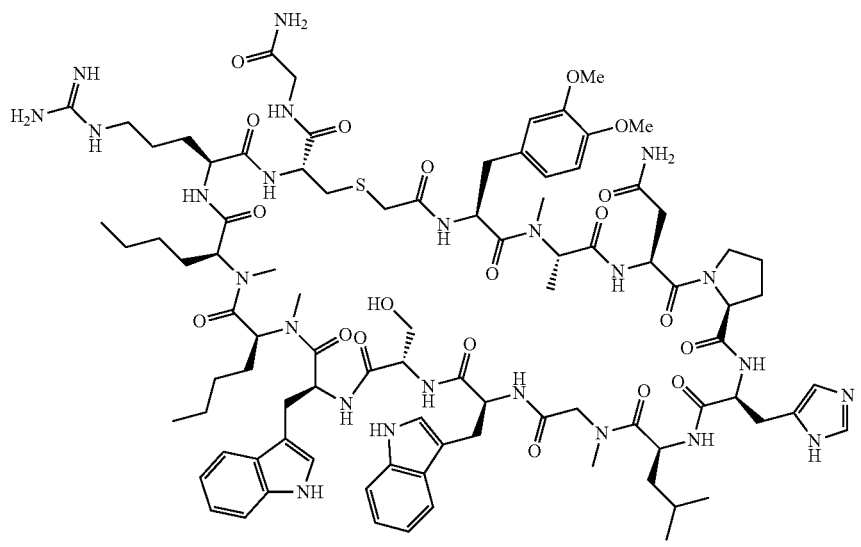

Molecular Weight: 1912.22

Example 1105 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl)methoxy)carbonyl)amino)-3-(3,4-dimethoxyphenyl)propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 10-minute hold at 55% B; Flow: 20 mL/min. Fractions containing the desired product were combined and dried via centrifugal evaporation. The yield of the product was 5.9 mg, and its estimated purity by LCMS analysis was 100%.

Analysis LCMS Condition D: Retention time=1.62 min; ESI-MS(+) m/z 956.9 (M+2H).

Analysis LCMS Condition E: Retention time=1.56 min; ESI-MS(+) m/z 956.9 (M+2H).

Preparation of Example 1106

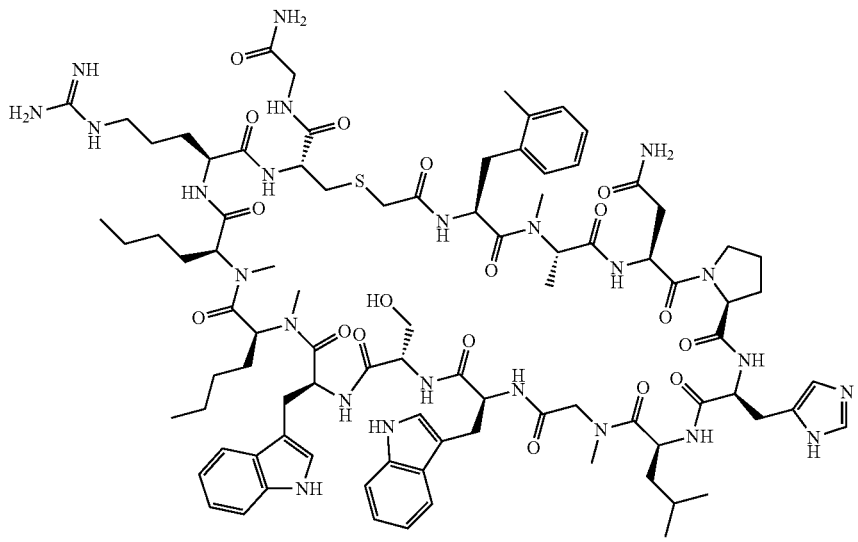

Molecular Weight: 1866.19

Example 1106 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl) methoxy)carbonyl)amino)-3-(o-tolyl)propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 6.0 mg, and its estimated purity by LCMS analysis was 99%.

Analysis LCMS Condition D: Retention time=1.79 min; ESI-MS(+) m/z 934.2 (M+2H).

Analysis LCMS Condition E: Retention time=1.72 min; ESI-MS(+) m/z 934.0 (M+2H).

Preparation of Example 1107

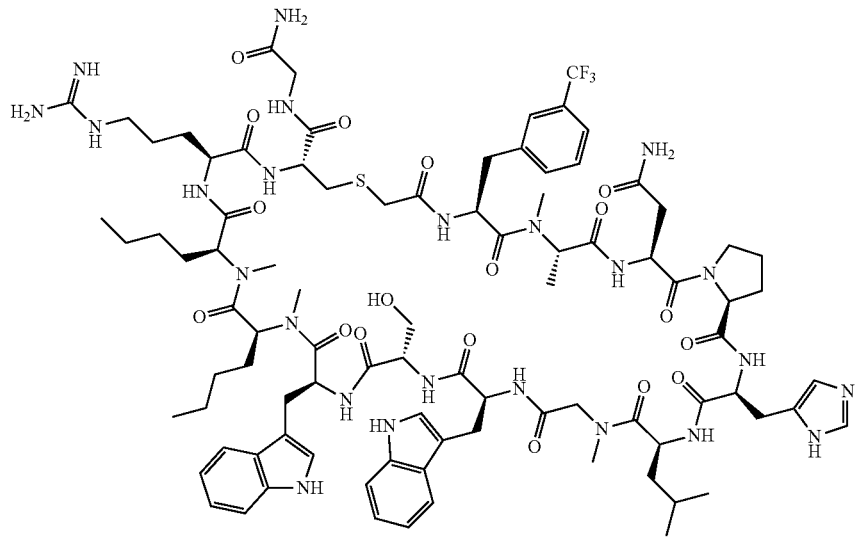

Molecular Weight: 1920.17

Example 1107 was prepared starting with Intermediate Resin B, using Manual Coupling procedure A, "Chloroacetic acid coupling procedure B", "Global Deprotection Method C", and "Cyclization Method D". (S)-2-((((9H-fluoren-9-yl) methoxy)carbonyl)amino)-3-(3-(trifluoromethyl)phenyl) propanoic acid was used in the amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 6.7 mg, and its estimated purity by LCMS analysis was 95%.

Analysis LCMS Condition D: Retention time=1.78 min; ESI-MS(+) m/z 961.2 (M+2H).

Analysis LCMS Condition E: Retention time=1.75 min; ESI-MS(+) m/z 961.0 (M+2H).

Preparation of Example 1108

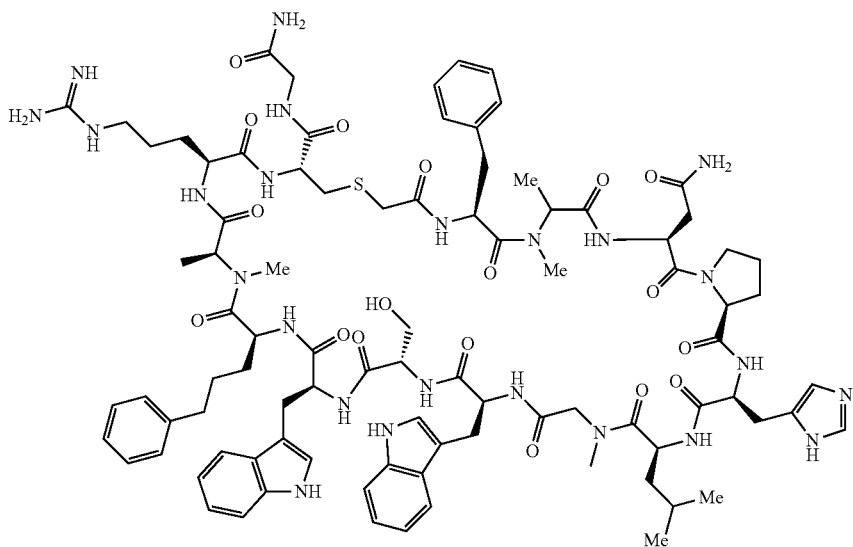

Molecular Weight: 1858.13

Example 1108 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". Fmoc-N-Me-Ala-OH is used in the fourth amino acid coupling step, and (S)-2-((((9H-fluoren-9-yl)methoxy)carbonyl)amino)-5-phenyl-pentanoic acid was used in the fifth amino acid coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mm ammonium acetate; Gradient: 15-55% B over 25 minutes, then a 10-minute hold at 55% B; Flow: 20 mL/min. Fractions containing the desired product were combined and dried via centrifugal evaporation. The yield of the product was 2 mg, and its estimated purity by LCMS analysis was 91%.

Analysis LCMS Condition D: Retention time=1.52 min; ESI-MS(+) m/z 930.1 (M+2H).

Analysis LCMS Condition E: Retention time=1.48 min; ESI-MS(+) m/z 930.0 (M+2H).

Preparation of Example 1110

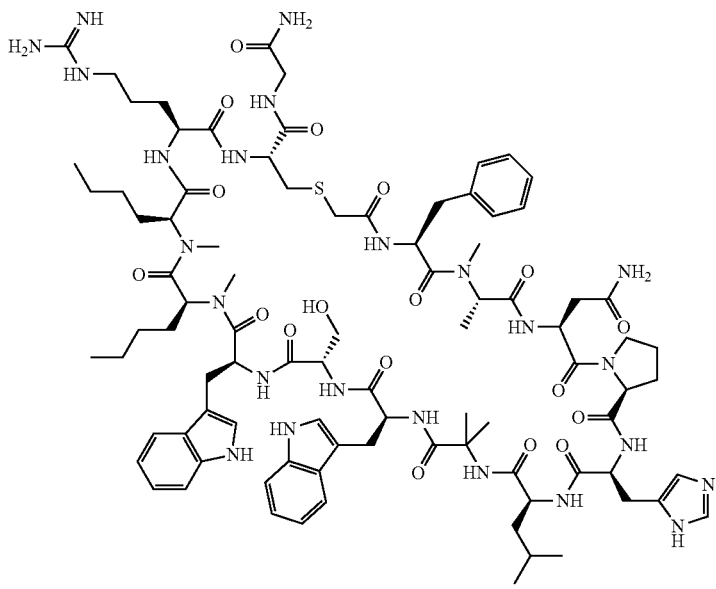

Molecular Weight: 1866.19

Example 1110 was prepared starting with Intermediate Resin A, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D". 2-((((9H-fluoren-9-yl)methoxy)carbonyl) amino)-2-methylpropanoic acid was used in the first coupling step to Intermediate Resin A.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 6.0 mg, and its estimated purity by LCMS analysis was 100%.

Analysis LCMS Condition D: Retention time=1.60 min; ESI-MS(+) m/z 934.0 (M+2H).

Analysis LCMS Condition E: Retention time=1.52 min; ESI-MS(+) m/z 933.9 (M+2H).

Preparation of Example 1112

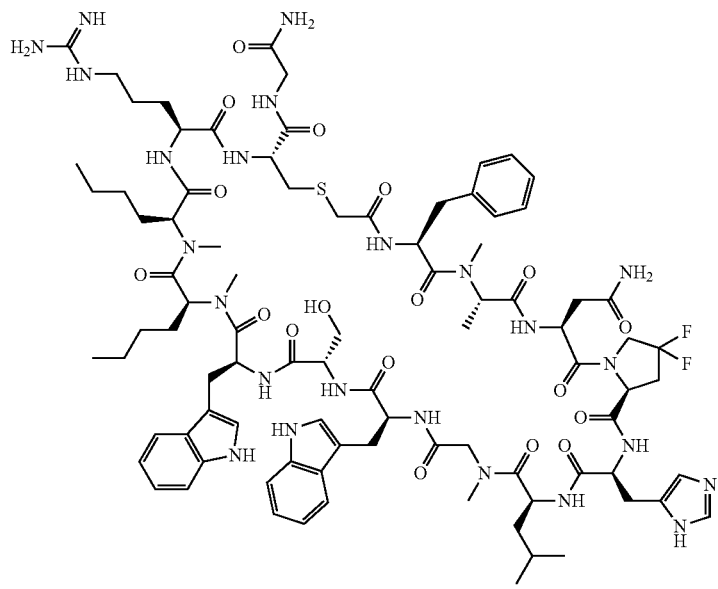

Molecular Weight: 1888.15

Example 1112 was prepared starting with Intermediate Resin A, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D". (S)-1-(((9H-fluoren-9-yl)methoxy)carbonyl)-4,4-difluoropyrrolidine-2-carboxylic acid was used in the fourth coupling step.

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation. The yield of the product was 4.9 mg, and its estimated purity by LCMS analysis was 100%.

Analysis LCMS Condition D: Retention time=1.74 min; ESI-MS(+) m/z 944.9 (M+2H).

Analysis LCMS Condition E: Retention time=1.70 min; ESI-MS(+) m/z 944.9 (M+2H).

Preparation of Example 1113

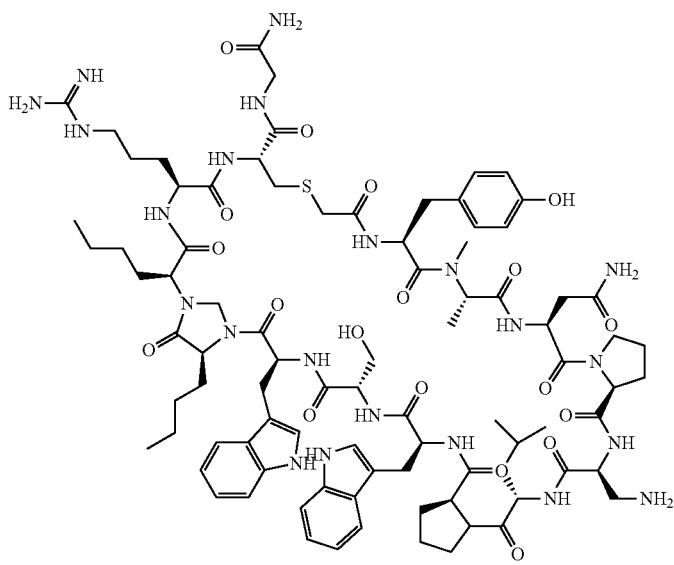

Molecular Weight: 1843.16

Example 1113 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 10.5 mg, and its estimated purity by LCMS analysis was 100%.

Analysis LCMS Condition D: Retention time=1.45 min; ESI-MS(+) m/z 922.7 (M+2H).

Analysis LCMS Condition E: Retention time=1.43 min; ESI-MS(+) m/z 922.4 (M+2H).

Preparation of Example 1114

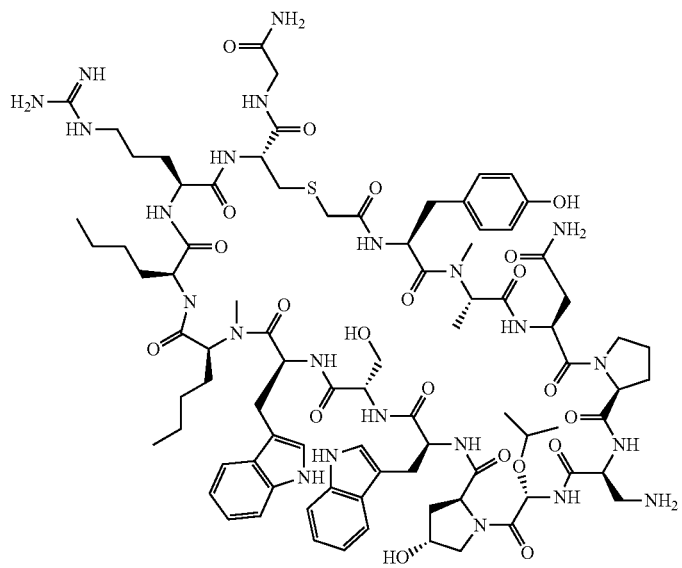

Molecular Weight: 1859.16

Example 1114 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 100%.

Analysis LCMS Condition D: Retention time=1.43 min; ESI-MS(+) m/z 930.6 (M+2H).

Analysis LCMS Condition E: Retention time=1.40 min; ESI-MS(+) m/z 930.2 (M+2H).

Preparation of Example 1115

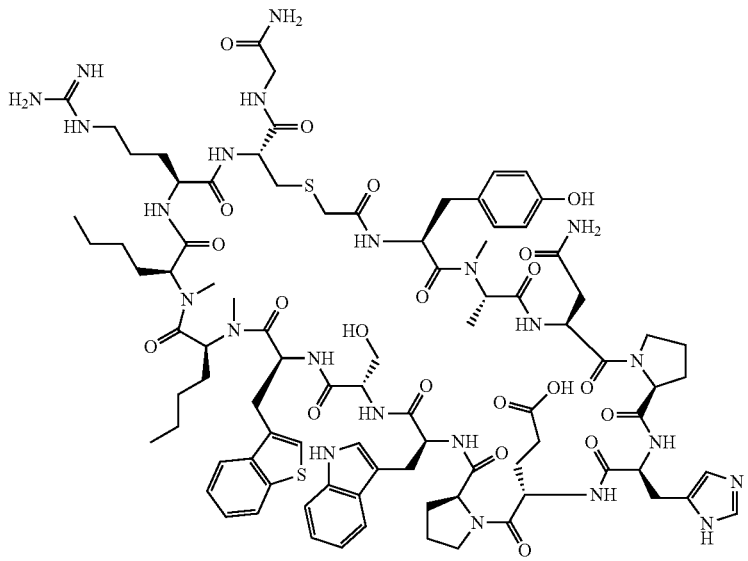

Molecular Weight: 1927.21

Example 1115 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 100%.

Analysis LCMS Condition D: Retention time=1.57 min; ESI-MS(+) m/z 964.8 (M+2H).

Analysis LCMS Condition E: Retention time=1.40 min; ESI-MS(+) m/z 964.4 (M+2H).

Preparation of Example 1116

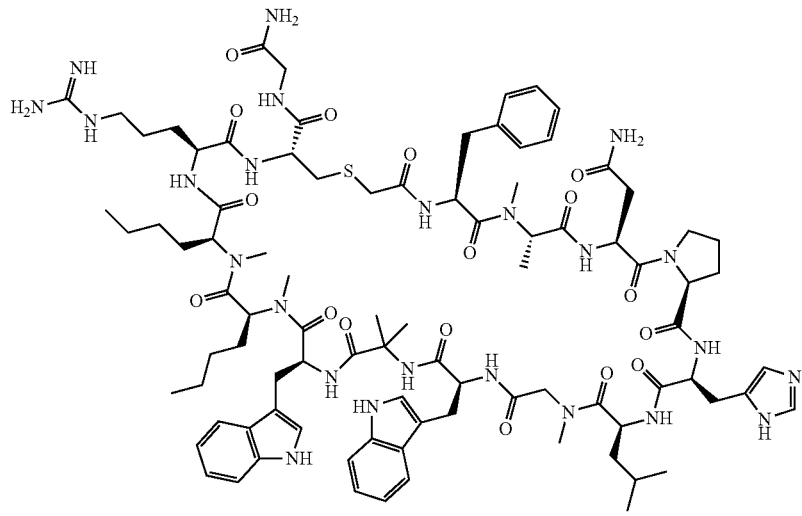

Molecular Weight: 1850.19

Example 1116 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 100%.

Analysis LCMS Condition D: Retention time=1.58 min; ESI-MS(+) m/z 926.7 (M+2H).

Analysis LCMS Condition E: Retention time=1.51 min; ESI-MS(+) m/z 926.2 (M+2H).

Preparation of Example 1117

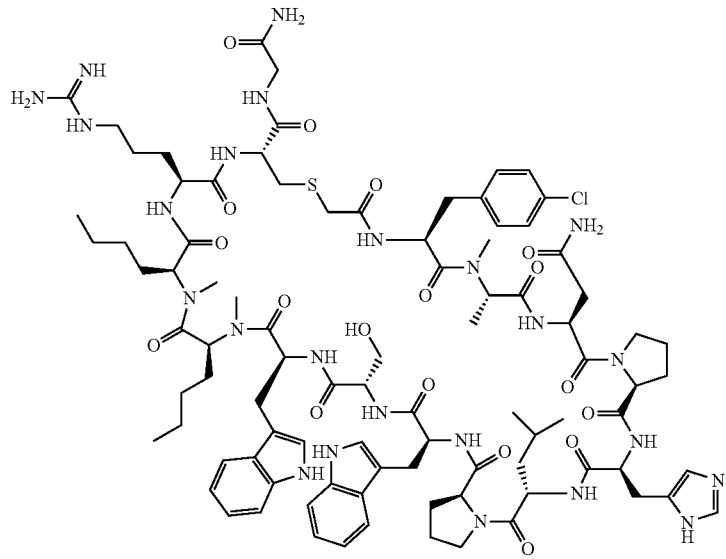

Molecular Weight: 1912.65

Example 1117 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 25 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 100%.

Analysis LCMS Condition D: Retention time=1.86 min; ESI-MS(+) m/z 957.0 (M+2H).

Analysis LCMS Condition E: Retention time=1.79 min; ESI-MS(+) m/z 956.8 (M+2H).

Preparation of Example 1118

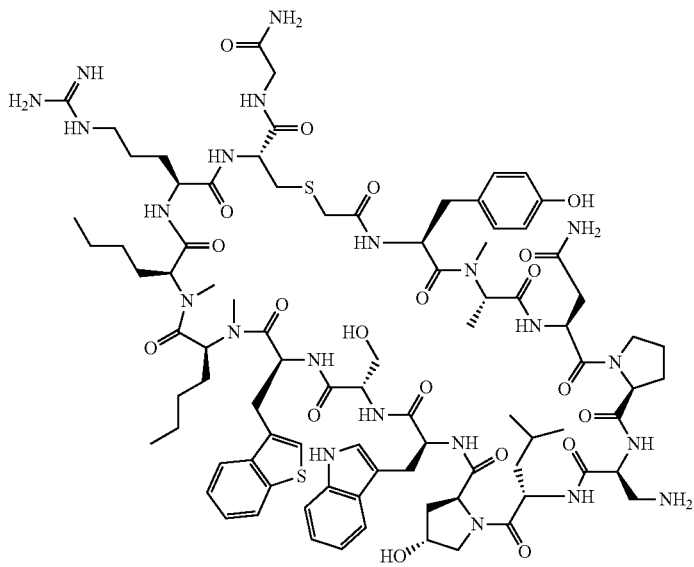

Molecular Weight: 1876.21

Example 1118 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 10.2 mg, and its estimated purity by LCMS analysis was 100%.

Analysis LCMS Condition D: Retention time=1.56 min; ESI-MS(+) m/z 939.0 (M+2H).

Analysis LCMS Condition E: Retention time=1.56 min; ESI-MS(+) m/z 938.7 (M+2H).

ESI-HRMS(+) m/z:
Calculated: 938.4553 (M+2H).
Found: 938.4529 (M+2H).

Preparation of Example 1119

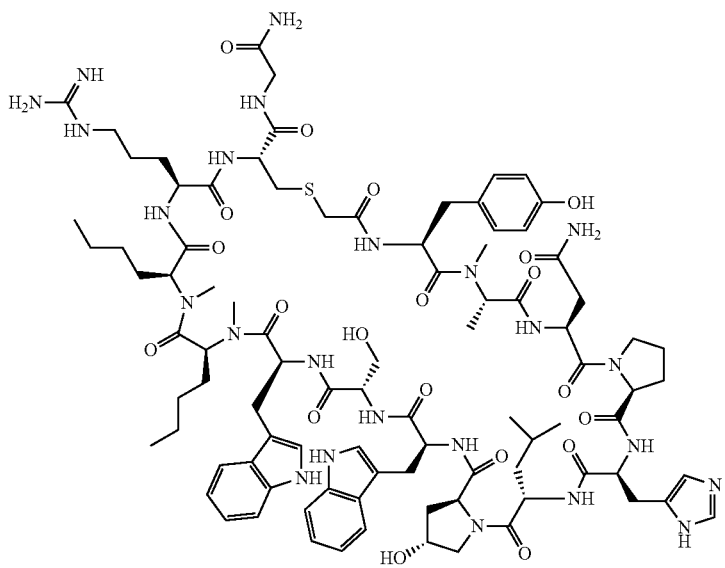

Molecular Weight: 1910.20

Example 1119 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 97%.

Analysis LCMS Condition D: Retention time=1.43 min; ESI-MS(+) m/z 955.7 (M+2H).

Analysis LCMS Condition E: Retention time=1.41 min; ESI-MS(+) m/z 955.6 (M+2H).

Preparation of Example 1120

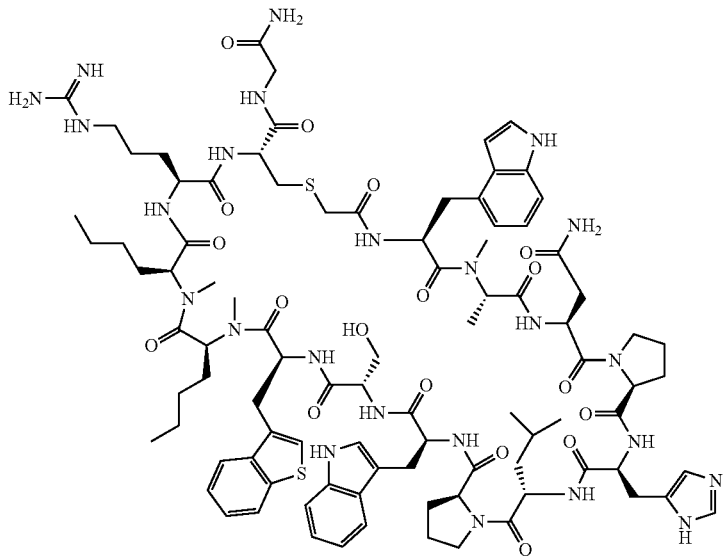

Molecular Weight: 1934.29

Example 1120 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 99%.

Analysis LCMS Condition D: Retention time=1.71 min; ESI-MS(+) m/z 967.8 (M+2H).

Analysis LCMS Condition E: Retention time=1.67 min; ESI-MS(+) m/z 968.2 (M+2H).

Preparation of Example 1121

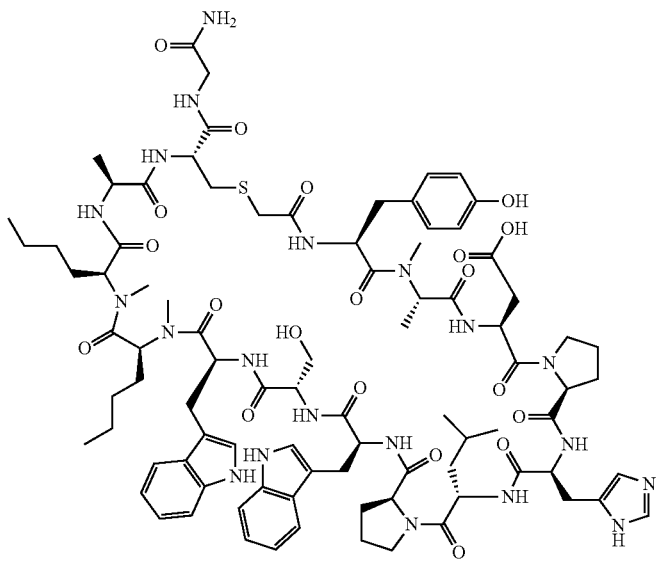

Molecular Weight: 1810.08

Example 1121 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 96%.

Analysis LCMS Condition D: Retention time=1.56 min; ESI-MS(+) m/z 906.2 (M+2H).

Analysis LCMS Condition E: Retention time=1.59 min; ESI-MS(+) m/z 906.2 (M+2H).

Preparation of Example 1122

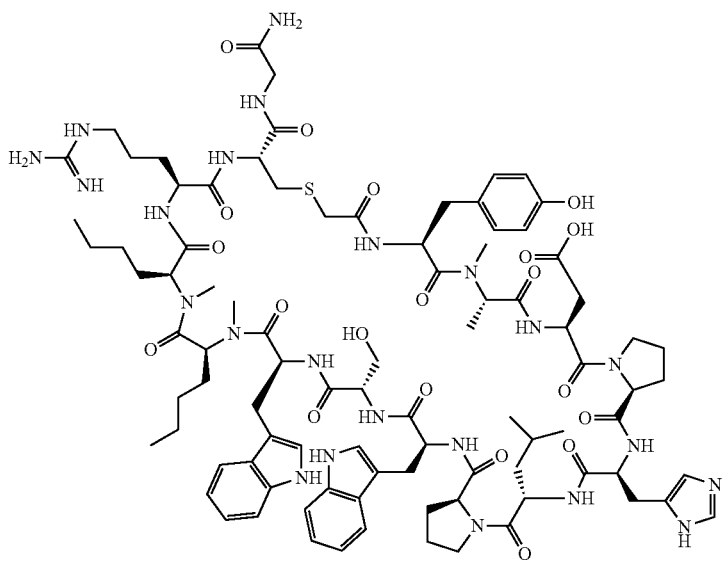

Molecular Weight: 1895.19

Example 1122 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 99%.

Analysis LCMS Condition D: Retention time=1.49 min; ESI-MS(+) m/z 948.8 (M+2H).

Analysis LCMS Condition E: Retention time=1.49 min; ESI-MS(+) m/z 948.8 (M+2H).

Preparation of Example 1123

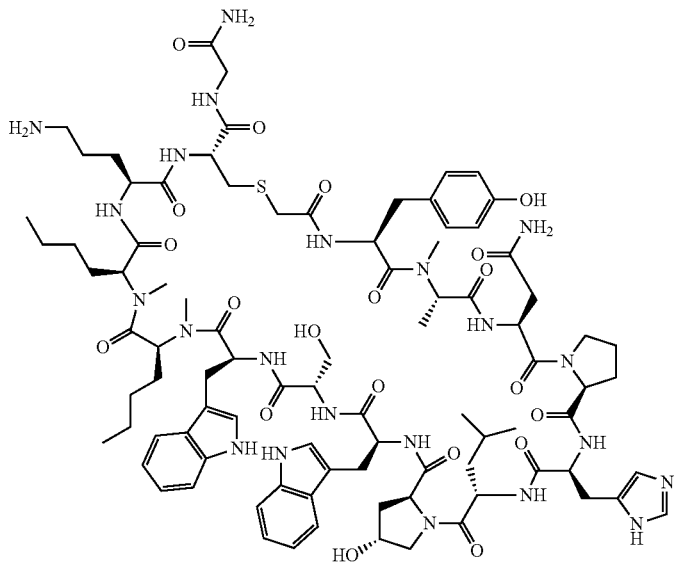

Molecular Weight: 1868.16

Example 1123 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 21.0 mg, and its estimated purity by LCMS analysis was 100%.

Analysis LCMS Condition D: Retention time=1.47 min; ESI-MS(+) m/z 935.3 (M+2H).

Analysis LCMS Condition E: Retention time=1.44 min; ESI-MS(+) m/z 935.3 (M+2H).

Preparation of Example 1124

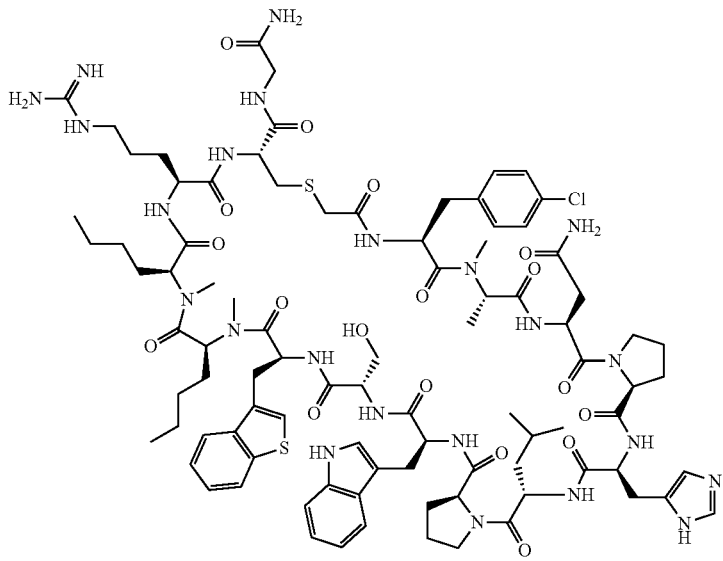

Molecular Weight: 1929.70

Example 1124 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 95%.

Analysis LCMS Condition D: Retention time=2.03 min; ESI-MS(+) m/z 966.0 (M+2H).

Analysis LCMS Condition E: Retention time=1.99 min; ESI-MS(+) m/z 965.9 (M+2H).

Preparation of Example 1125

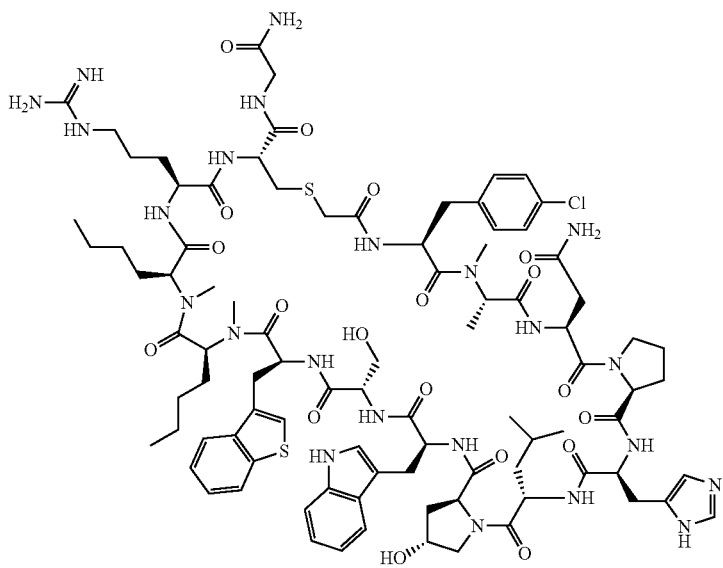

Molecular Weight: 1945.70

Example 1125 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 100%.

Analysis LCMS Condition D: Retention time=1.97 min; ESI-MS(+) m/z 974.5 (M+2H).

Analysis LCMS Condition E: Retention time=1.90 min; ESI-MS(+) m/z 973.4 (M+2H).

Preparation of Example 1126

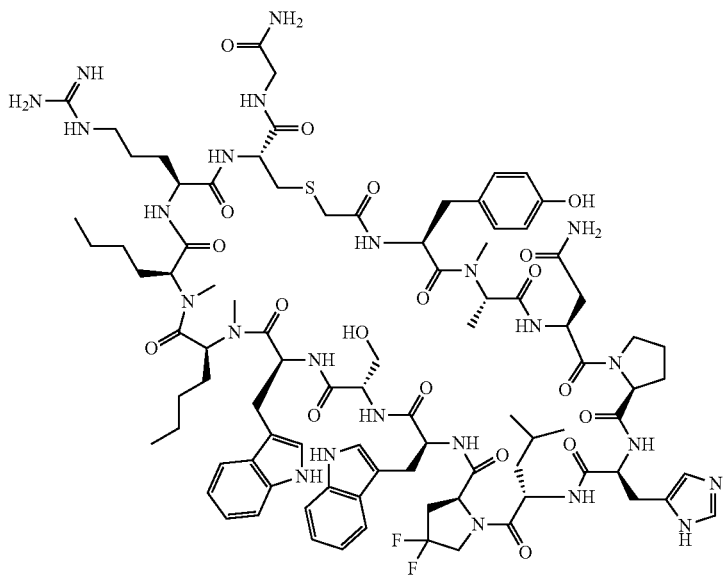

Molecular Weight: 1930.19

Example 1126 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation.

The yield of the product was 2.7 mg, and its estimated purity by LCMS analysis was 98%.

Analysis LCMS Condition D: Retention time=1.49 min; ESI-MS(+) m/z 965.8 (M+2H).

Analysis LCMS Condition E: Retention time=1.59 min; ESI-MS(+) m/z 966.3 (M+2H).

Preparation of Example 1127

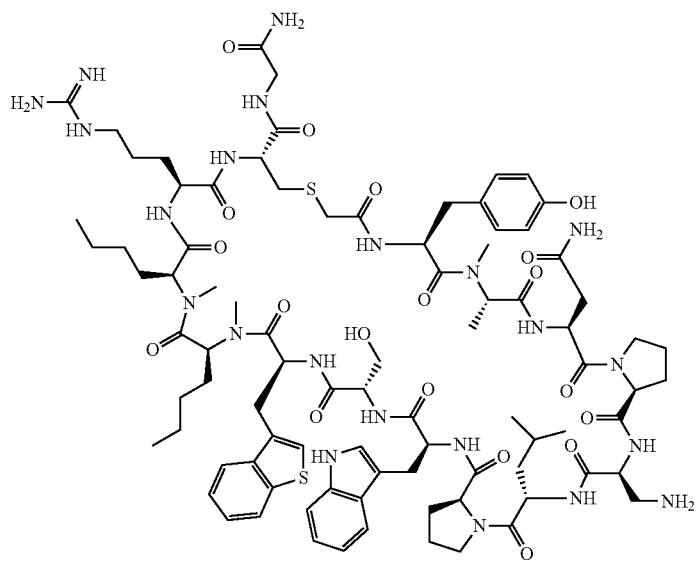

Molecular Weight: 1876.16

Example 1127 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 95%.

Analysis LCMS Condition D: Retention time=1.57 min; ESI-MS(+) m/z 939.4 (M+2H).

Analysis LCMS Condition E: Retention time=1.6 min; ESI-MS(+) m/z 938.9 (M+2H).

Preparation of Example 1128

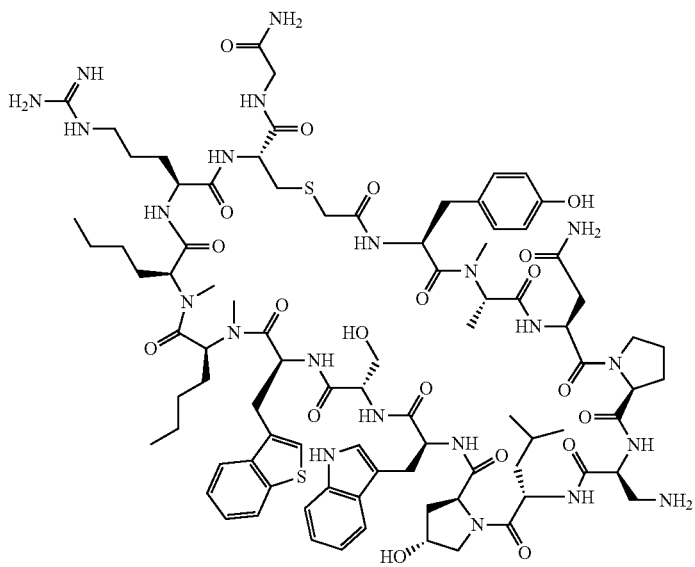

Molecular Weight: 1892.16

Example 1128 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 0.8 mg, and its estimated purity by LCMS analysis was 95%.

Analysis LCMS Condition D: Retention time=1.59 min; ESI-MS(+) m/z 947.3 (M+2H).

Analysis LCMS Condition E: Retention time=1.60 min; ESI-MS(+) m/z 947.1 (M+2H).

Preparation of Example 1129

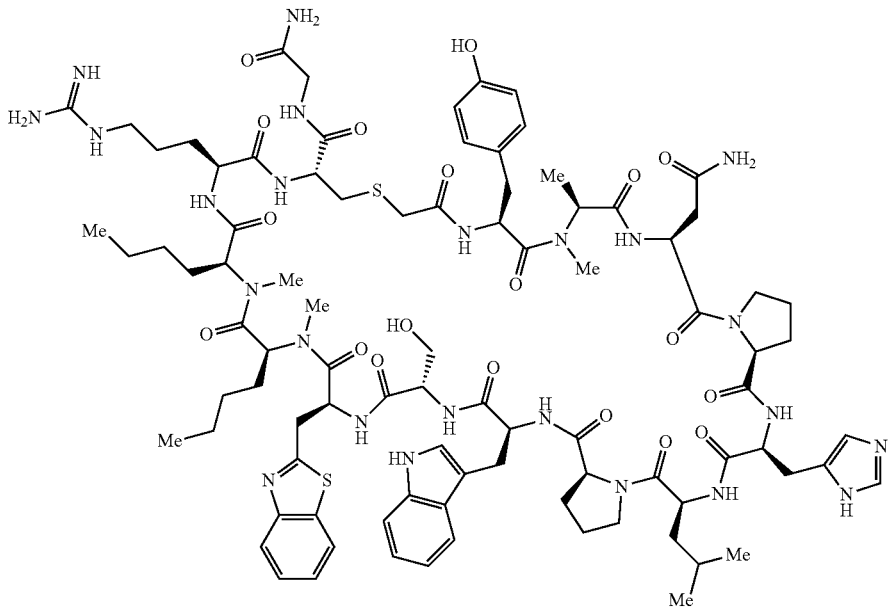

Molecular Weight: 1912.24

Example 1129 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 0.8 mg, and its estimated purity by LCMS analysis was 90%.

Analysis LCMS Condition D: Retention time=1.55 min; ESI-MS(+) m/z 957.3 (M+2H).

Analysis LCMS Condition E: Retention time=1.51 min; ESI-MS(+) m/z 956.7 (M+2H).

Preparation of Example 1130

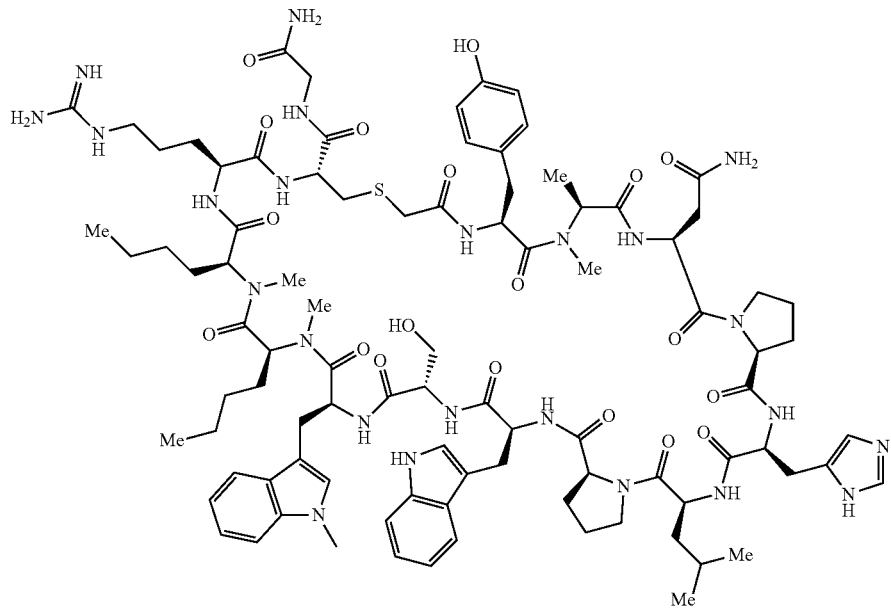

Molecular Weight: 1908.23

Example 1130 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D". Fmoc-(D/L)-Trp(Me)-OH was used in the sixth amino acid coupling step.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 97%.

Analysis LCMS Condition D: Retention time=1.64 min; ESI-MS(+) m/z 955.5 (M+2H).

Analysis LCMS Condition E: Retention time=1.61 min; ESI-MS(+) m/z 955.4 (M+2H).

Preparation of Example 1131

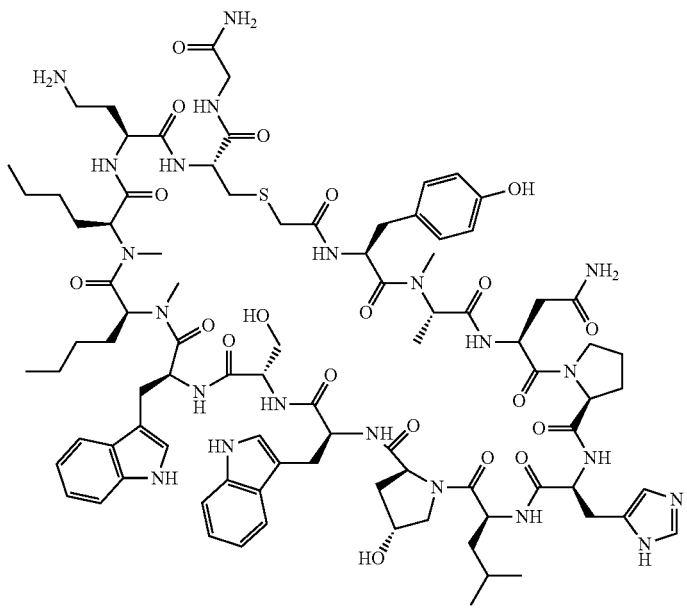

Molecular Weight: 1854.14

Example 1131 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 99%.

Analysis LCMS Condition D: Retention time=1.46 min; ESI-MS(+) m/z 928.2 (M+2H).

Analysis LCMS Condition E: Retention time=1.44 min; ESI-MS(+) m/z 928.1 (M+2H).

Preparation of Example 1132

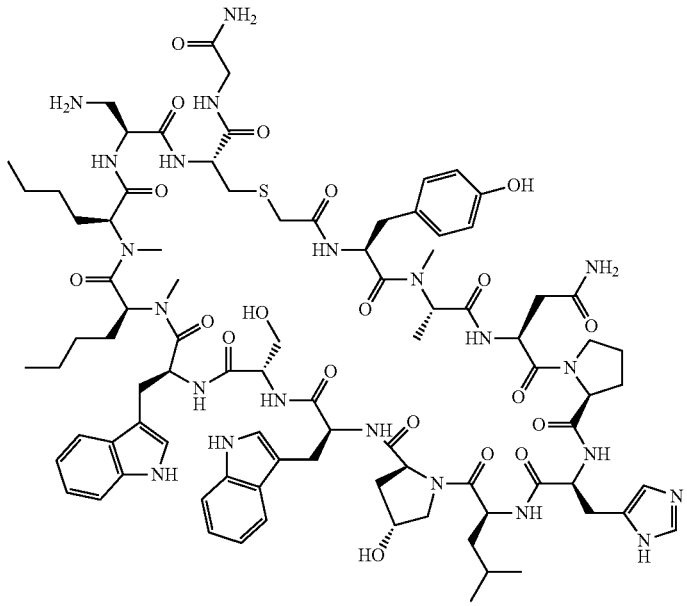

Molecular Weight: 1840.11

Example 1132 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis LCMS Condition D: Retention time=1.52 min; ESI-MS(+) m/z 921.2 (M+2H).

Analysis LCMS Condition E: Retention time=1.46 min; ESI-MS(+) m/z 921.2 (M+2H).

Preparation of Example 1133

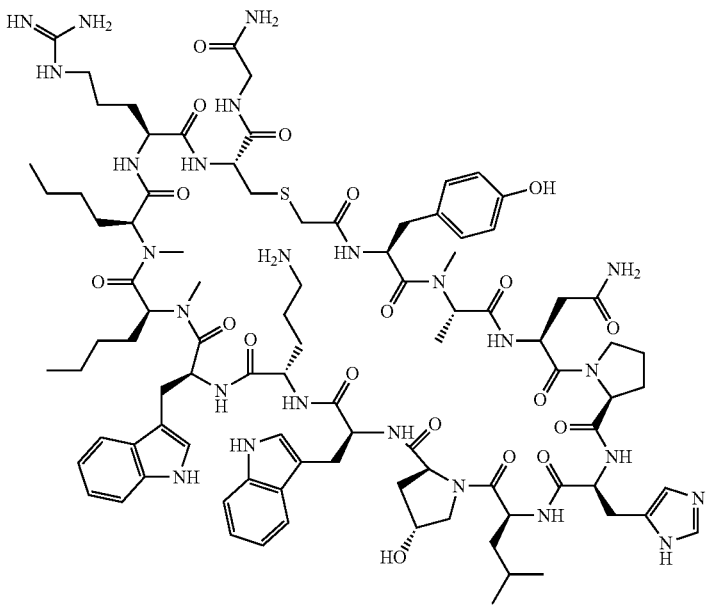

Molecular Weight: 1937.27

Example 1133 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 0.8 mg, and its estimated purity by LCMS analysis was 92%.

Analysis LCMS Condition D: Retention time=1.41 min; ESI-MS(+) m/z 969.9 (M+2H).

Analysis LCMS Condition E: Retention time=1.35 min; ESI-MS(+) m/z 969.8 (M+2H).

Preparation of Example 1134

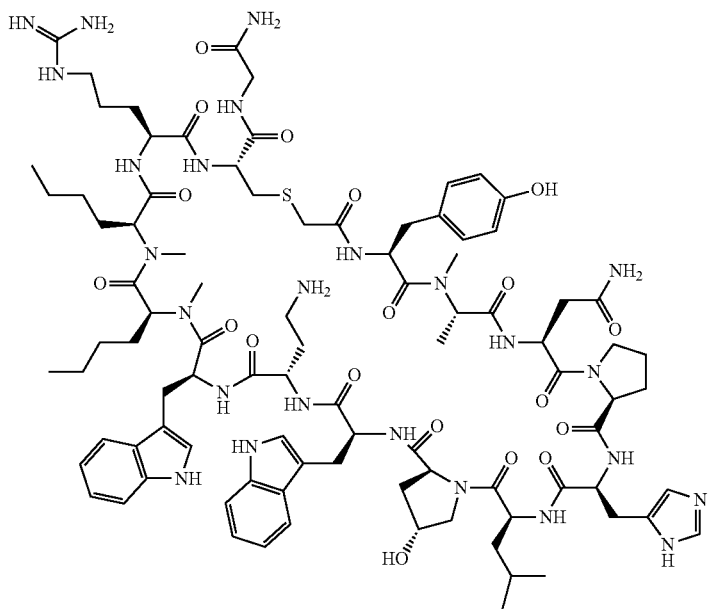

Molecular Weight: 1923.25

Example 1134 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 25 minutes, then a 5-minute hold at 100% B; Flow: 20 mL/min. Fractions containing the desired product were combined and dried via centrifugal evaporation. The yield of the product was 1.9 mg, and its estimated purity by LCMS analysis was 100%.

Analysis LCMS Condition D: Retention time=1.41 min; ESI-MS(+) m/z 962.8 (M+2H).

Analysis LCMS Condition E: Retention time=1.35 min; ESI-MS(+) m/z 962.4 (M+2H).

Preparation of Example 1135

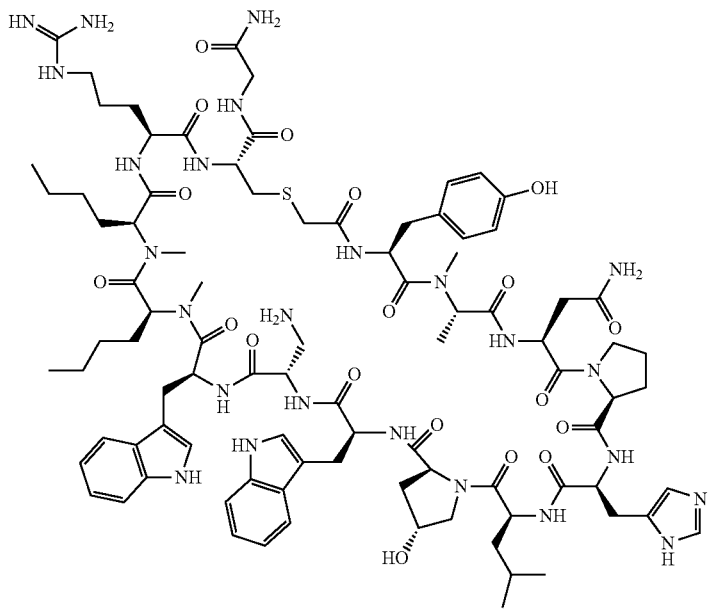

Molecular Weight: 1909.22

Example 1135 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 8.2 mg, and its estimated purity by LCMS analysis was 98%.

Analysis LCMS Condition D: Retention time=1.43 min; ESI-MS(+) m/z 955.8 (M+2H).

Analysis LCMS Condition E: Retention time=1.31 min; ESI-MS(+) m/z 955.5 (M+2H).

Preparation of Example 1136

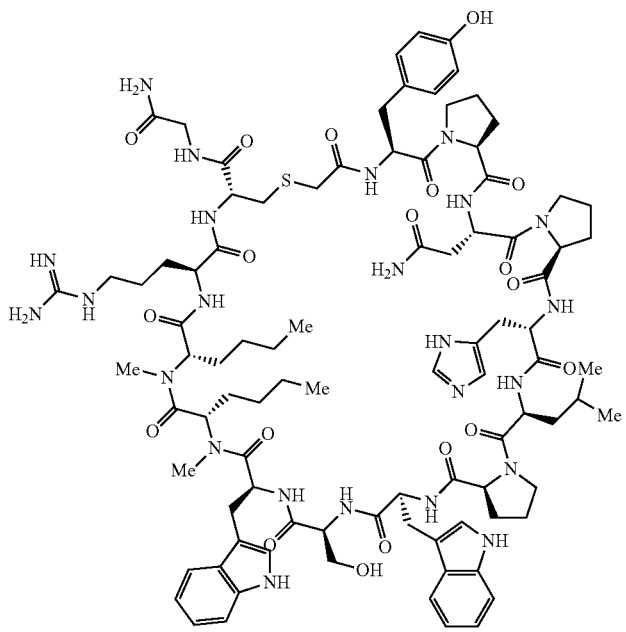

Molecular Weight: 1906.22

Example 1136 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 6.2 mg, and its estimated purity by LCMS analysis was 94%.

Analysis LCMS Condition D: Retention time=1.44 min; ESI-MS(+) m/z 954.1 (M+2H).

Analysis LCMS Condition E: Retention time=1.40 min; ESI-MS(+) m/z 953.8 (M+2H).

Preparation of Example 1137

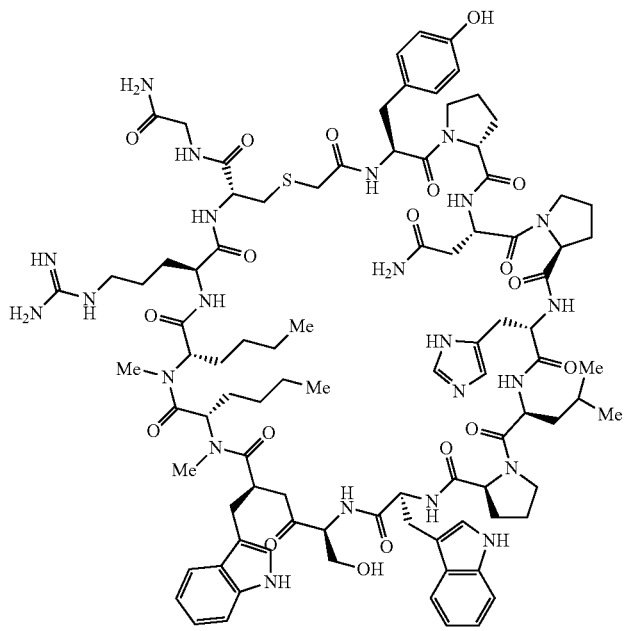

Molecular Weight: 1906.22

Example 1137 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 100%.

Analysis LCMS Condition D: Retention time=1.46 min; ESI-MS(+) m/z 954.3 (M+2H).

Analysis LCMS Condition E: Retention time=1.43 min; ESI-MS(+) m/z 953.8 (M+2H).

Preparation of Example 1138

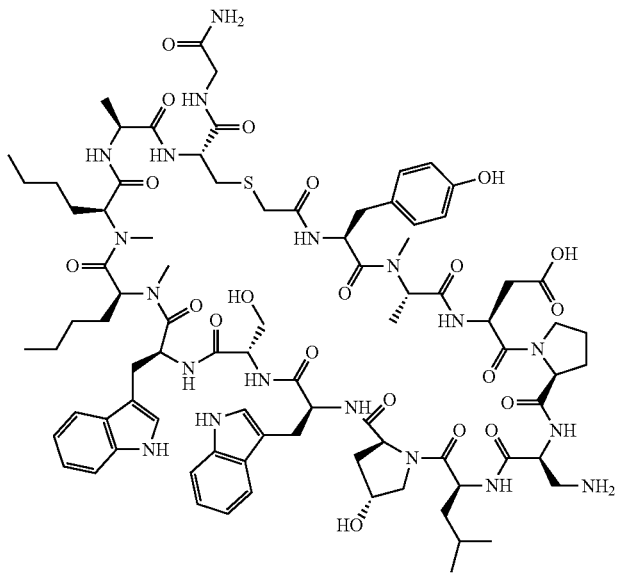

Molecular Weight: 1775.03

Example 1138 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 23.0 mg, and its estimated purity by LCMS analysis was 98%.

Analysis LCMS Condition D: Retention time=1.46 min; ESI-MS(+) m/z 888.1 (M+2H).

Analysis LCMS Condition E: Retention time=1.46 min; ESI-MS(+) m/z 888.2 (M+2H).

Preparation of Example 1139

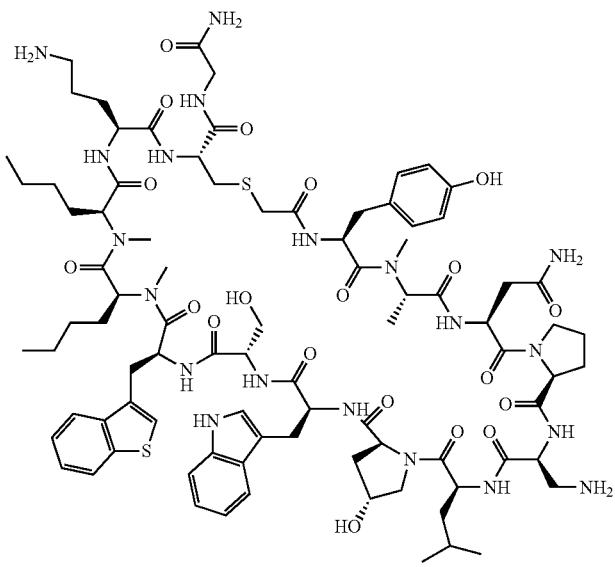

Molecular Weight: 1834.17

Example 1139 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 14.2 mg, and its estimated purity by LCMS analysis was 97%.

Analysis LCMS Condition D: Retention time=1.46 min; ESI-MS(+) m/z 917.8 (M+2H).

Analysis LCMS Condition E: Retention time=1.52 min; ESI-MS(+) m/z 917.8 (M+2H).

Preparation of Example 1140

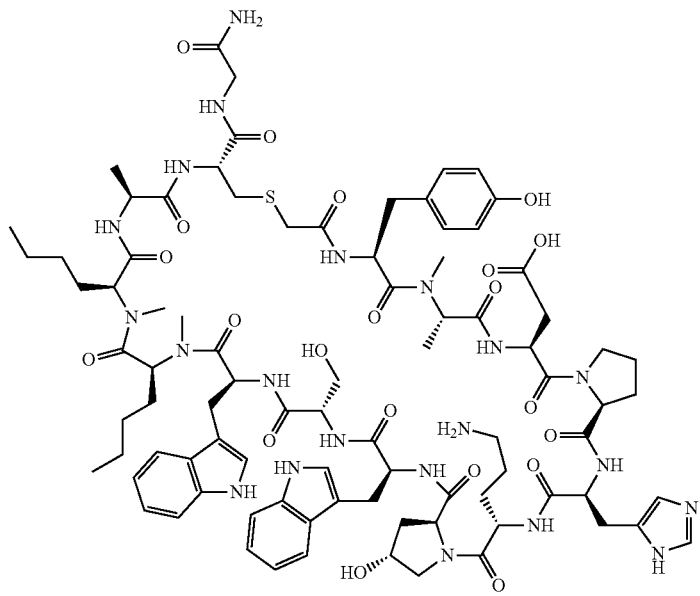

Molecular Weight: 1827.07

Example 1140 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 91%.

Analysis LCMS Condition D: Retention time=1.42 min; ESI-MS(+) m/z 914.2 (M+2H).

Analysis LCMS Condition E: Retention time=1.36 min; ESI-MS(+) m/z 914.6 (M+2H).

Preparation of Example 1141

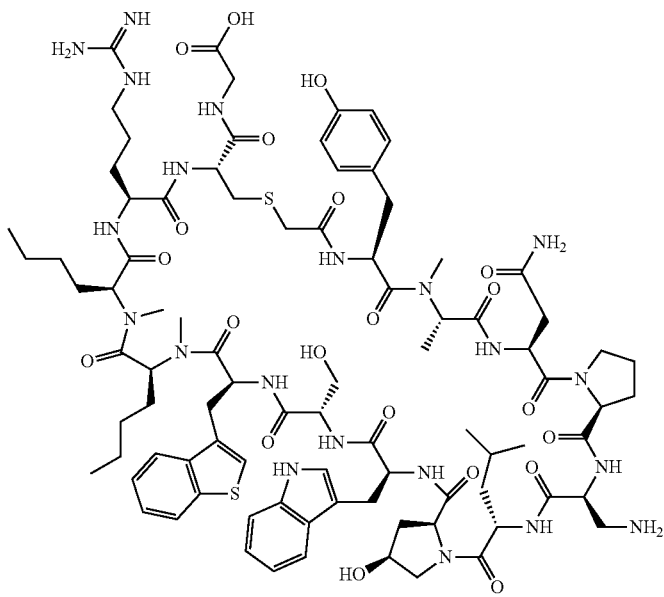

Molecular Weight: 1877.19

Example 1141 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 12.5 mg, and its estimated purity by LCMS analysis was 93%.

Analysis LCMS Condition D: Retention time=1.59 min; ESI-MS(+) m/z 939.3 (M+2H).

Analysis LCMS Condition E: Retention time=1.57 min; ESI-MS(+) m/z 940.4 (M+2H).

Preparation of Example 1142

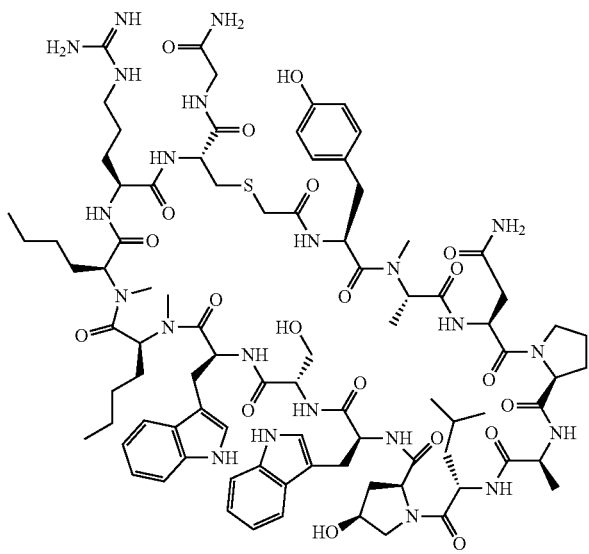

Molecular Weight: 1844.14

Example 1142 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 7-minute hold at 100% B; Flow: 20 mL/min. Fractions containing the desired product were combined and dried via centrifugal evaporation. The yield of the product was 21.3 mg, and its estimated purity by LCMS analysis was 99%.

Analysis LCMS Condition D: Retention time=1.49 min; ESI-MS(+) m/z 923.3 (M+2H).

Analysis LCMS Condition E: Retention time=1.49 min; ESI-MS(+) m/z 923.3 (M+2H).

Preparation of Example 1143

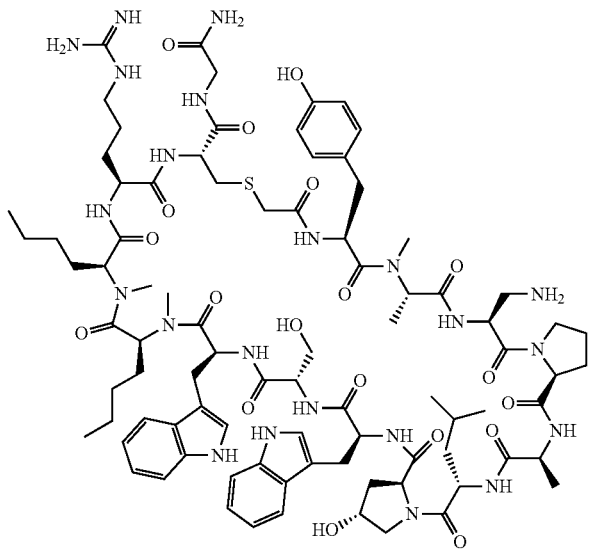

Molecular Weight: 1816.13

Example 1143 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 10-minute hold at 100% B; Flow: 20 mL/min. Fractions containing the desired product were combined and dried via centrifugal evaporation. The yield of the product was 16.4 mg, and its estimated purity by LCMS analysis was 92%.

Analysis LCMS Condition D: Retention time=1.43 min; ESI-MS(+) m/z 908.9 (M+2H).

Analysis LCMS Condition E: Retention time=1.38 min; ESI-MS(+) m/z 909.3 (M+2H).

Preparation of Example 1144

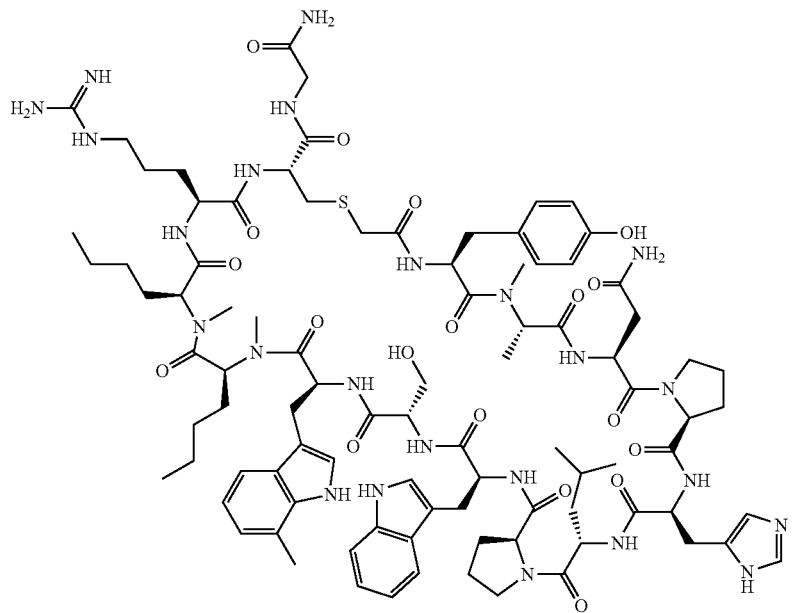

Molecular Weight: 1908.23

Example 1144 was prepared starting from Intermediate Resin G following the general synthetic sequence described for the preparation of Example 0001, Starting from composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D". (S)-2-((((9H-fluoren-9-yl)methoxy)carbonyl)amino)-3-(7-methyl-1H-indol-3-yl)propanoic acid was used in the first coupling to the Intermediate Resin G.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 1.0 mg, and its estimated purity by LCMS analysis was 96%.

Analysis LCMS Condition D: Retention time=1.54 min; ESI-MS(+) m/z 955.1 (M+2H).

Analysis LCMS Condition E: Retention time=1.49 min; ESI-MS(+) m/z 955.0 (M+2H).

Preparation of Example 1145

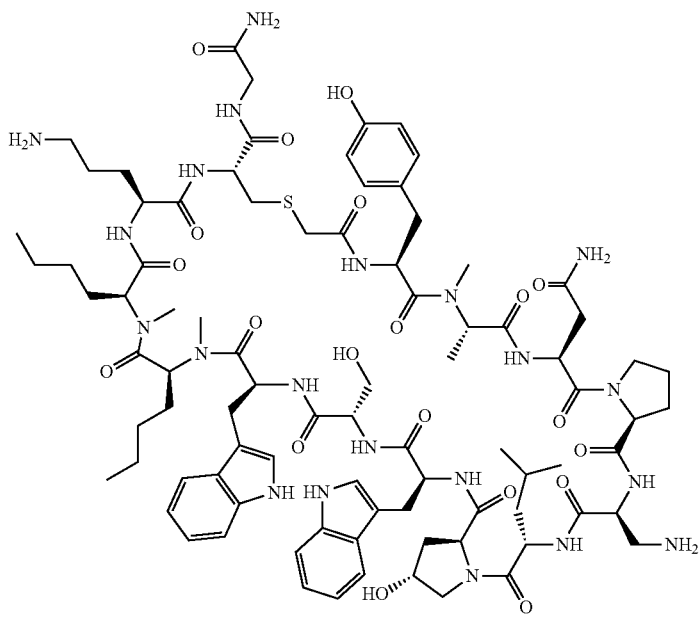

Molecular Weight: 1817.12

Example 1145 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 92%.

Analysis LCMS Condition D: Retention time=1.39 min; ESI-MS(+) m/z 909.3 (M+2H).

Analysis LCMS Condition E: Retention time=1.4 min; ESI-MS(+) m/z 909.5 (M+2H).

Preparation of Example 1146

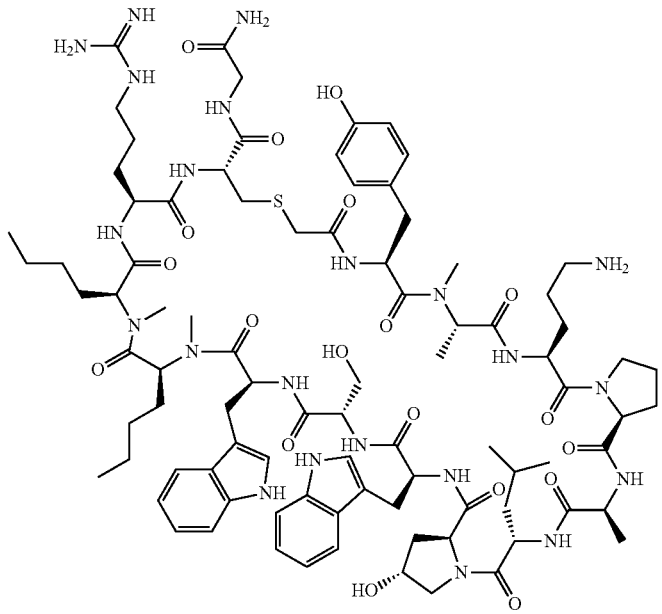

Molecular Weight: 1844.19

Example 1146 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge shield rp18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-55% B over 25 minutes, then a 5-minute hold at 55% B; Flow: 20 mL/min. Fractions containing the desired product were combined and dried via centrifugal evaporation. The yield of the product was 22.4 mg, and its estimated purity by LCMS analysis was 98%.

Analysis LCMS Condition D: Retention time=1.31 min; ESI-MS(+) m/z 922.8 (M+2H).

Analysis LCMS Condition E: Retention time=1.38 min; ESI-MS(+) m/z 922.8 (M+2H).

Preparation of Example 1147

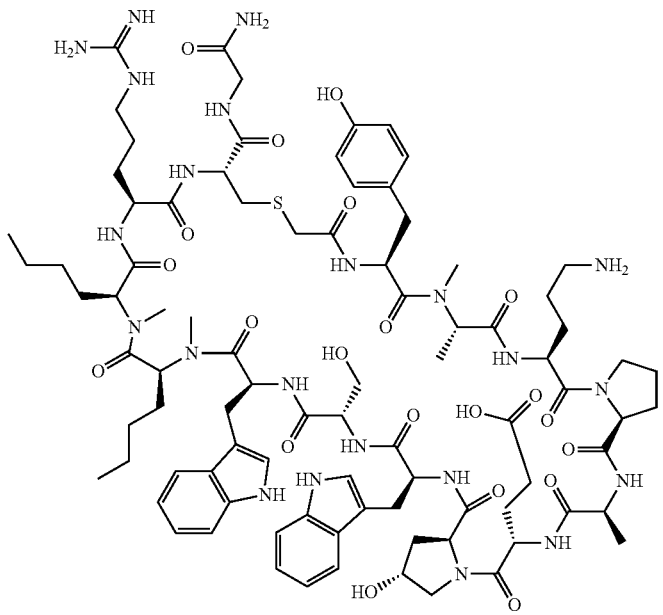

Molecular Weight: 1860.14

Example 1147 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 99%.

Analysis LCMS Condition D: Retention time=1.38 min; ESI-MS(+) m/z 931.3 (M+2H).

Analysis LCMS Condition E: Retention time=1.38 min; ESI-MS(+) m/z 931.1 (M+2H).

Preparation of Example 1148

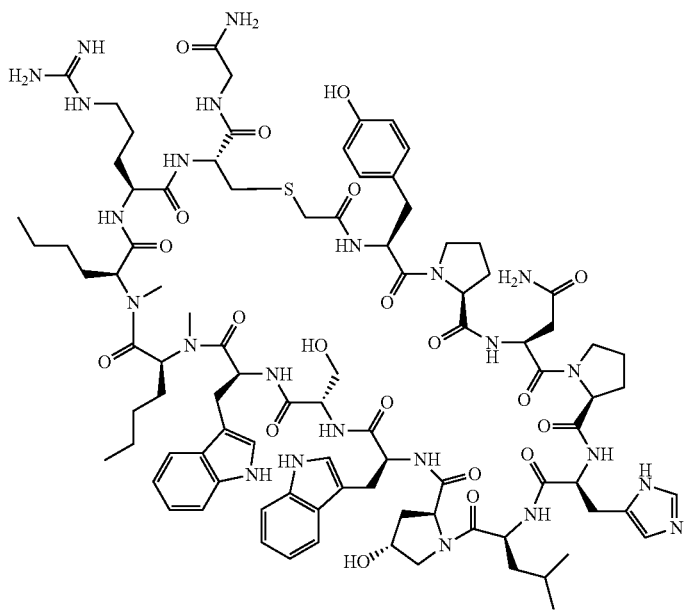

Molecular Weight: 1922.21

Example 1148 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-70% B over 25 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 93%.

Analysis LCMS Condition D: Retention time=1.37 min; ESI-MS(+) m/z 962.2 (M+2H).

Analysis LCMS Condition E: Retention time=1.35 min; ESI-MS(+) m/z 961.8 (M+2H).

Preparation of Example 1149

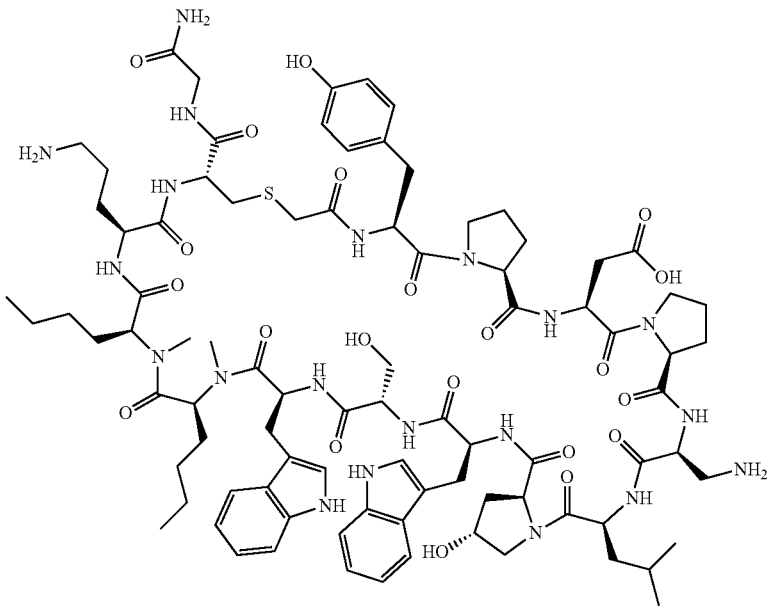

Molecular Weight: 1830.11

Example 1149 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 55.2 mg, and its estimated purity by LCMS analysis was 96%.

Analysis LCMS Condition D: Retention time=1.32 min; ESI-MS(+) m/z 915.8 (M+2H).

Analysis LCMS Condition E: Retention time=1.31 min; ESI-MS(+) m/z 916.0 (M+2H).

Preparation of Example 1150

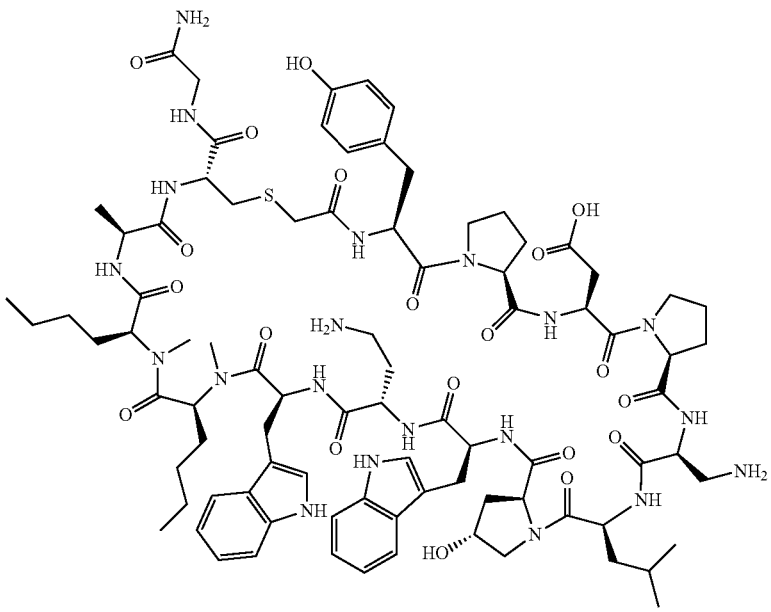

Molecular Weight: 1800.09

Example 1150 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 47.7 mg, and its estimated purity by LCMS analysis was 98%.

Analysis LCMS Condition D: Retention time=1.33 min; ESI-MS(+) m/z 901.0 (M+2H).

Analysis LCMS Condition E: Retention time=1.34 min; ESI-MS(+) m/z 900.7 (M+2H).

Preparation of Example 1151

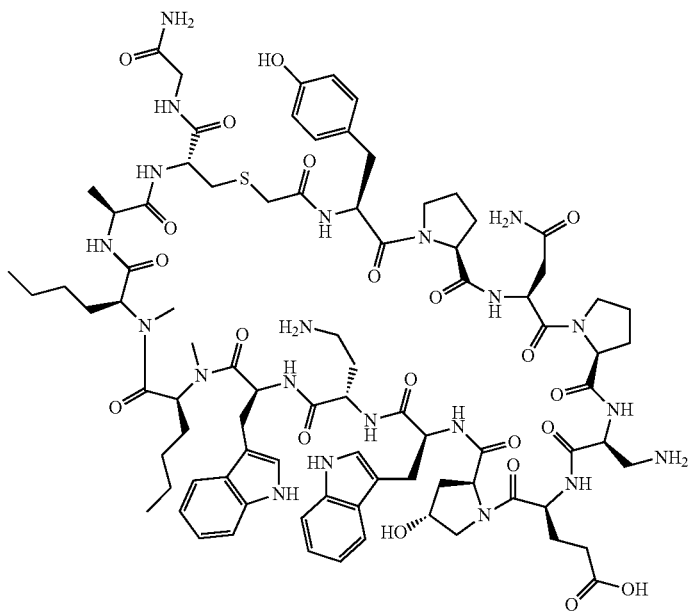

Molecular Weight: 1815.06

Example 1151 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 53.0 mg, and its estimated purity by LCMS analysis was 100%.

Analysis LCMS Condition D: Retention time=1.31 min; ESI-MS(+) m/z 908.2 (M+2H).

Analysis LCMS Condition E: Retention time=1.30 min; ESI-MS(+) m/z 908.4 (M+2H).

Preparation of Example 1152

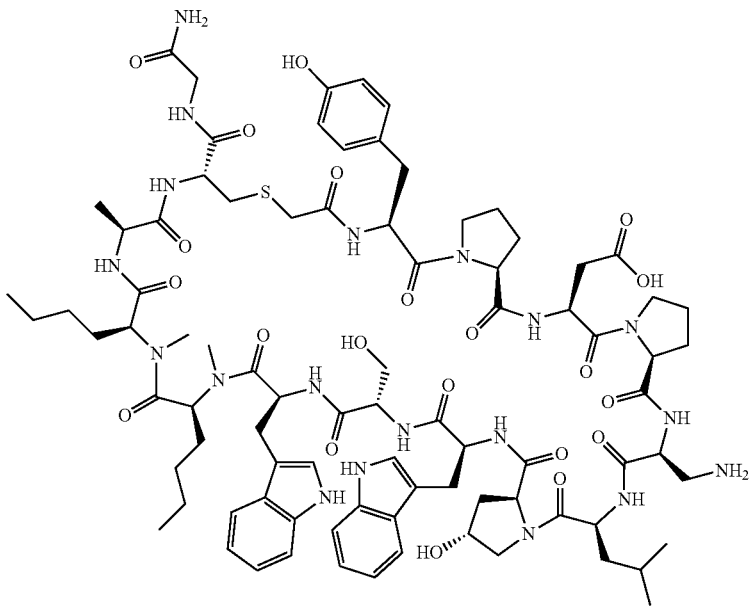

Molecular Weight: 1787.04

Example 1152 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 28.0 mg, and its estimated purity by LCMS analysis was 94%.

Analysis LCMS Condition D: Retention time=1.41 min; ESI-MS(+) m/z 894.1 (M+2H).

Analysis LCMS Condition E: Retention time=1.40 min; ESI-MS(+) m/z 894.1 (M+2H).

Preparation of Example 1153

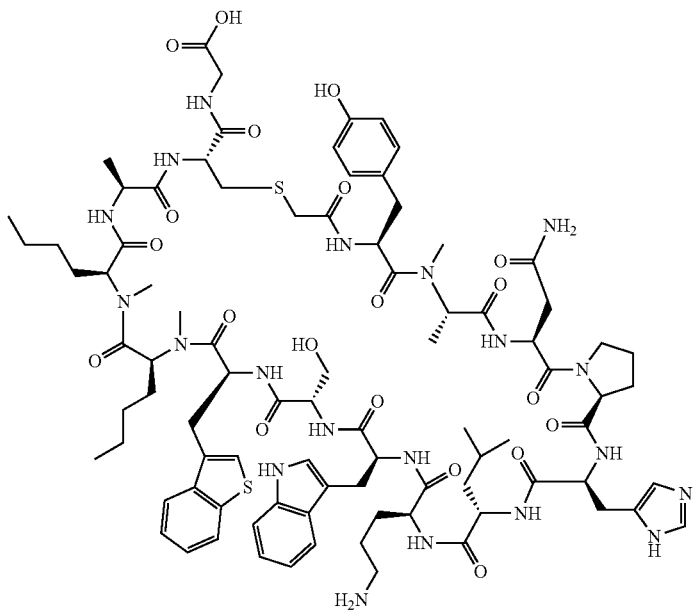

Molecular Weight: 1844.16

Example 1153 was prepared following the general synthetic sequence described for the preparation of Example 0001, starting with Fmoc-Gly-O-chlorotrityl Resin, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method E", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 0.9 mg and its estimated purity by LCMS analysis was 92%.

Analysis LCMS Condition D: Retention time=1.67 min; ESI-MS(+) m/z 922.7 (M+2H).

Analysis LCMS Condition E: Retention time=1.60 min; ESI-MS(+) m/z 923.3 (M+2H).

Preparation of Example 1154

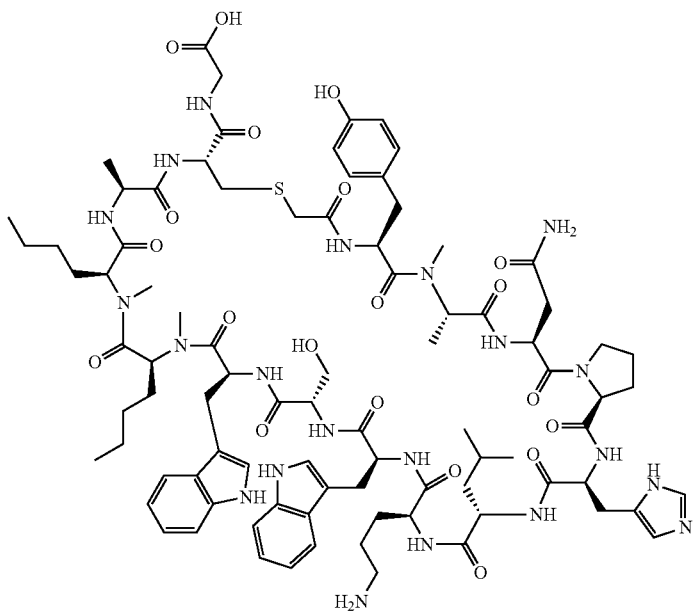

Molecular Weight: 1827.11

Example 1154 was prepared following the general synthetic sequence described for the preparation of Example 0001, starting with Fmoc-Gly-O-chlorotrityl Resin, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method E", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 100%.

Analysis LCMS Condition D: Retention time=1.51 min; ESI-MS(+) m/z 914.2 (M+2H).

Analysis LCMS Condition E: Retention time=1.44 min; ESI-MS(+) m/z 914.2 (M+2H).

ESI-HRMS(+) m/z:

Calculated: 913.9560 (M+2H).

Found: 913.9529 (M+2H).

Preparation of Example 1155

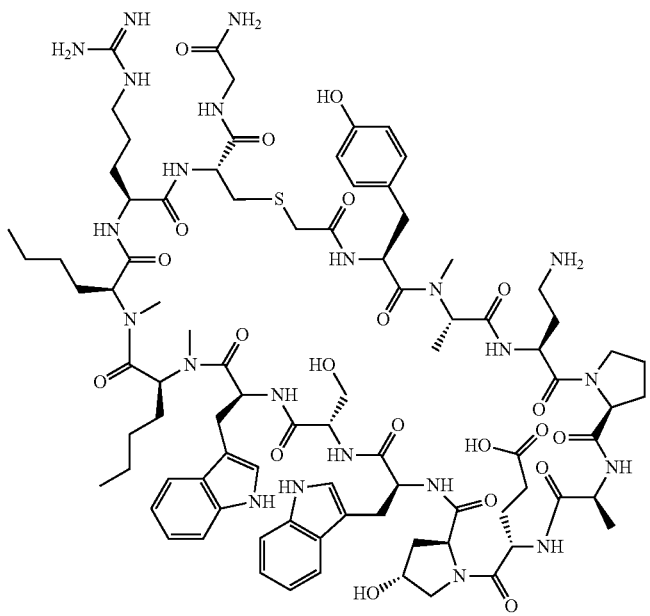

Molecular Weight: 1846.12

Example 1155 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 96%.

Analysis LCMS Condition D: Retention time=1.4 min; ESI-MS(+) m/z 923.8 (M+2H).

Analysis LCMS Condition E: Retention time=1.35 min; ESI-MS(+) m/z 923.9 (M+2H).

Preparation of Example 1156

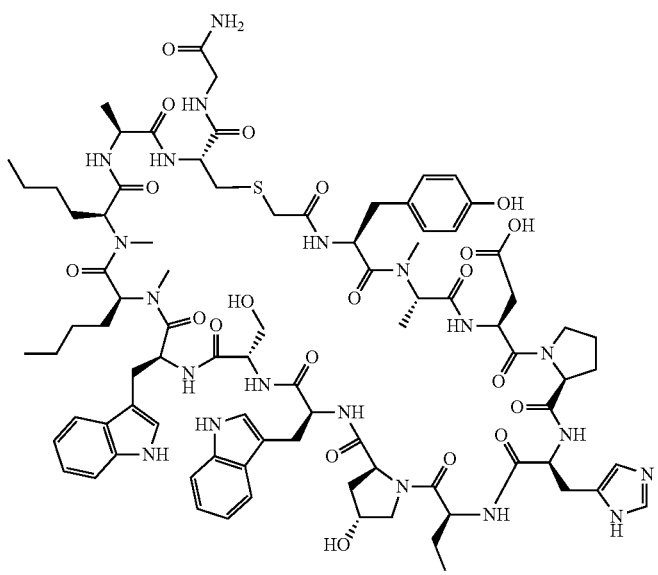

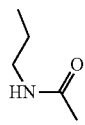

Molecular Weight: 1869.11

Example 1156 was prepared by treating Example 1140 (29 mg, 0.016 mmol) with a premade solution of HATU (7.24 mg, 0.019 mmol) in DMF (2 mL), and DIEA (6.93 µA, 0.040 mmol). Stir at RT overnight.

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 7.9 mg, and its estimated purity by LCMS analysis was 97%.

Analysis LCMS Condition D: Retention time=1.42 min; ESI-MS(+) m/z 935.2 (M+2H).

Analysis LCMS Condition E: Retention time=1.40 min; ESI-MS(+) m/z 935.2 (M+2H).

Preparation of Example 1157

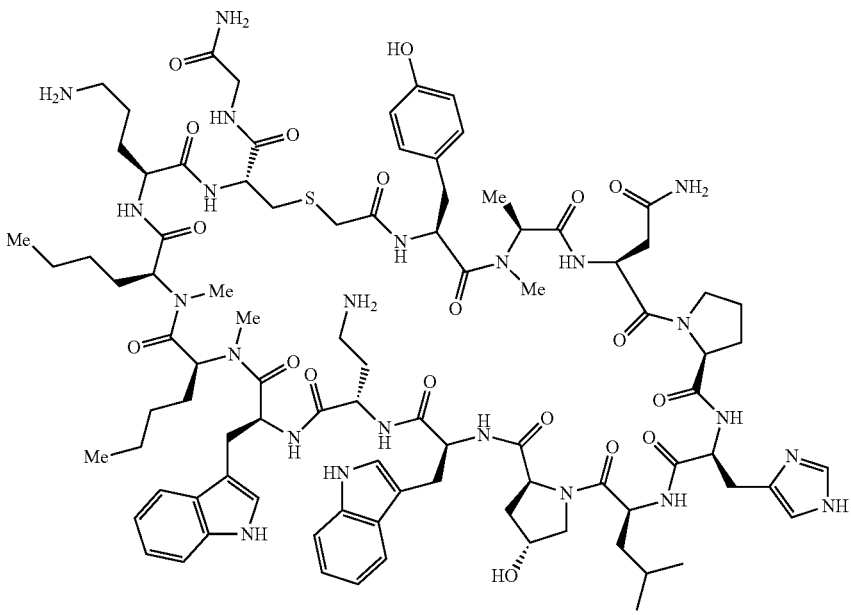

Molecular Weight: 1881.21

Example 1157 was prepared, following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 98%.

Analysis LCMS Condition D: Retention time=1.35 min; ESI-MS(+) m/z 941.6 (M+2H).

Analysis LCMS Condition E: Retention time=1.38 min; ESI-MS(+) m/z 941.4 (M+2H).

Preparation of Example 1158

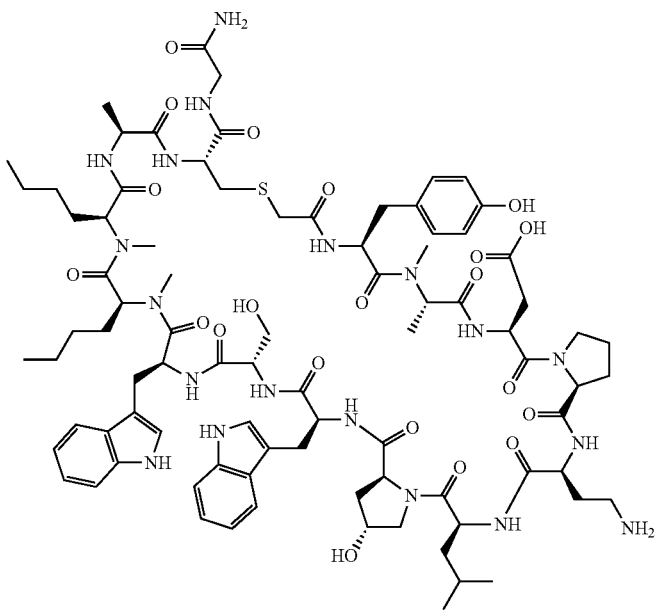

Molecular Weight: 1789.06

Example 1158 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 19.5 mg, and its estimated purity by LCMS analysis was 92%.

Analysis LCMS Condition D: Retention time=1.47 min; ESI-MS(+) m/z 895.2 (M+2H).

Analysis LCMS Condition E: Retention time=1.48 min; ESI-MS(+) m/z 895.8 (M+2H).

Preparation of Example 1159

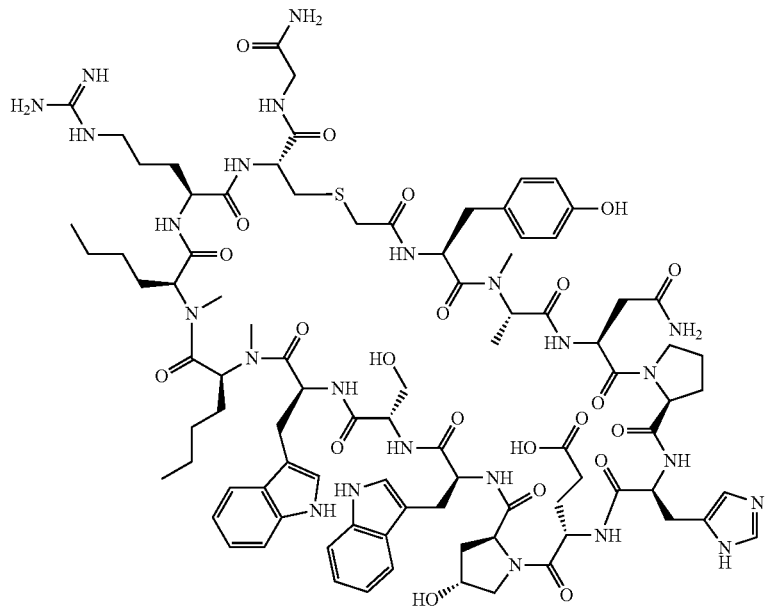

Molecular Weight: 1926.16

Example 1159 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 25 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 100%.

Analysis LCMS Condition D: Retention time=1.42 min; ESI-MS(+) m/z 964.2 (M+2H).

Analysis LCMS Condition E: Retention time=1.39 min; ESI-MS(+) m/z 964.0 (M+2H).

Preparation of Example 1160

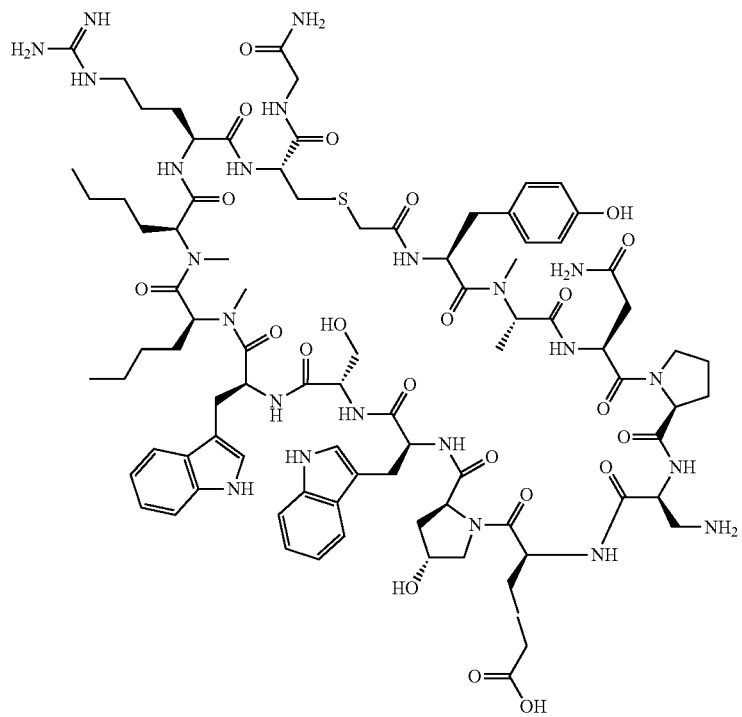

Molecular Weight: 1875.11

Example 1160 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 99%.

Analysis LCMS Condition D: Retention time=1.41 min; ESI-MS(+) m/z 938.4 (M+2H).

Analysis LCMS Condition E: Retention time=1.40 min; ESI-MS(+) m/z 938.5 (M+2H).

Preparation of Example 1161

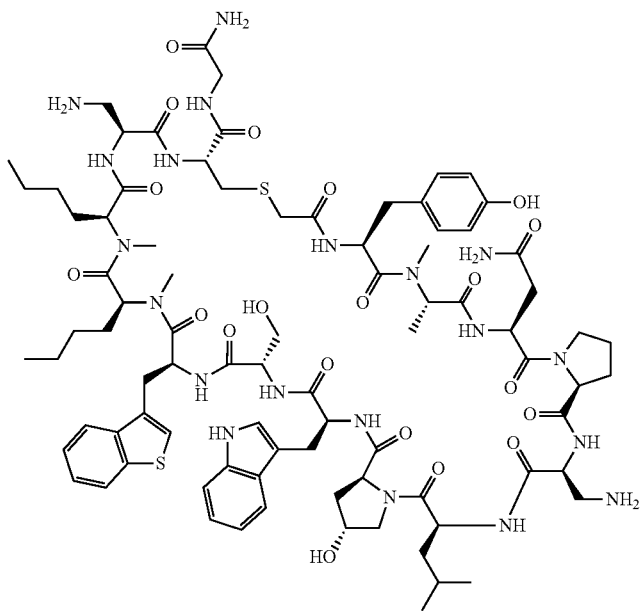

Molecular Weight: 1806.11

Example 1161 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 100%.

Analysis LCMS Condition D: Retention time=1.64 min; ESI-MS(+) m/z 903.8 (M+2H).

Analysis LCMS Condition E: Retention time=1.58 min; ESI-MS(+) m/z 904.0 (M+2H).

Preparation of Example 1162

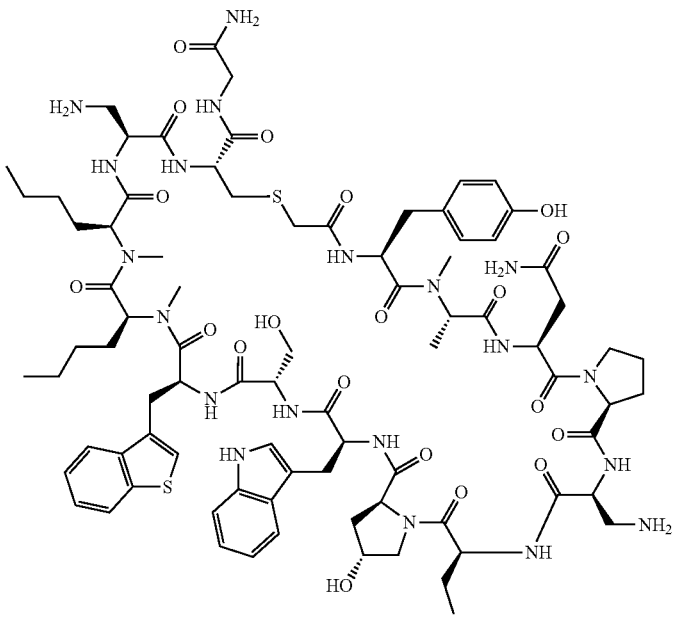

Molecular Weight: 1822.07

Example 1162 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 11.3 mg, and its estimated purity by LCMS analysis was 100%.

Analysis LCMS Condition D: Retention time=1.61 min; ESI-MS(+) m/z 912.3 (M+2H).

Analysis LCMS Condition E: Retention time=1.57 min; ESI-MS(+) m/z 911.7 (M+2H).

Preparation of Example 1163

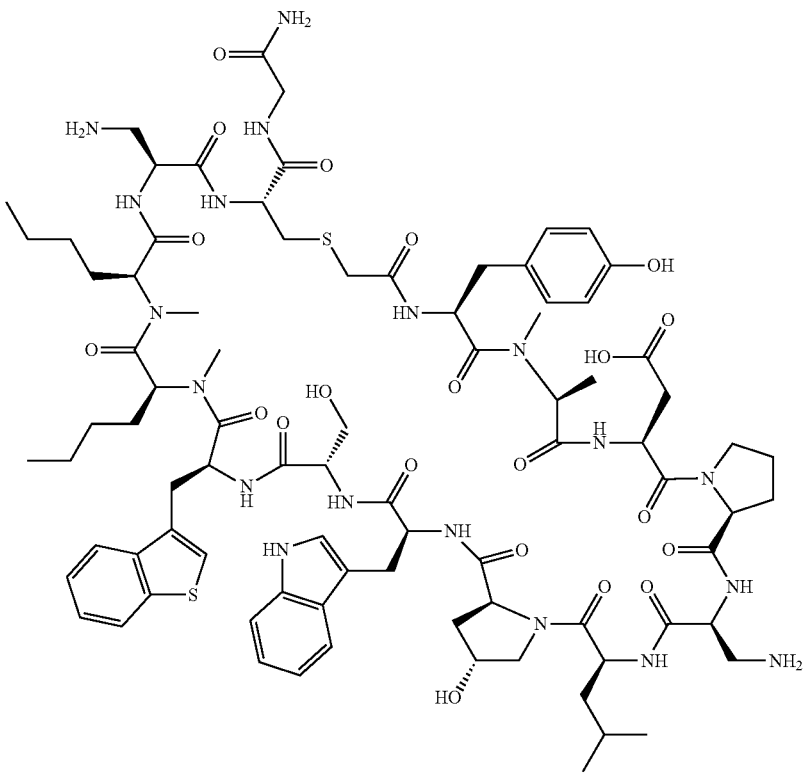

Molecular Weight: 1807.10

Example 1163 was prepared, using Rink Resin, following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 16.8 mg, and its estimated purity by LCMS analysis was 100%.

Analysis LCMS Condition D: Retention time=1.61 min; ESI-MS(+) m/z 904.4 (M+2H).

Analysis LCMS Condition E: Retention time=1.58 min; ESI-MS(+) m/z 904.3 (M+2H).

Preparation of Example 1164

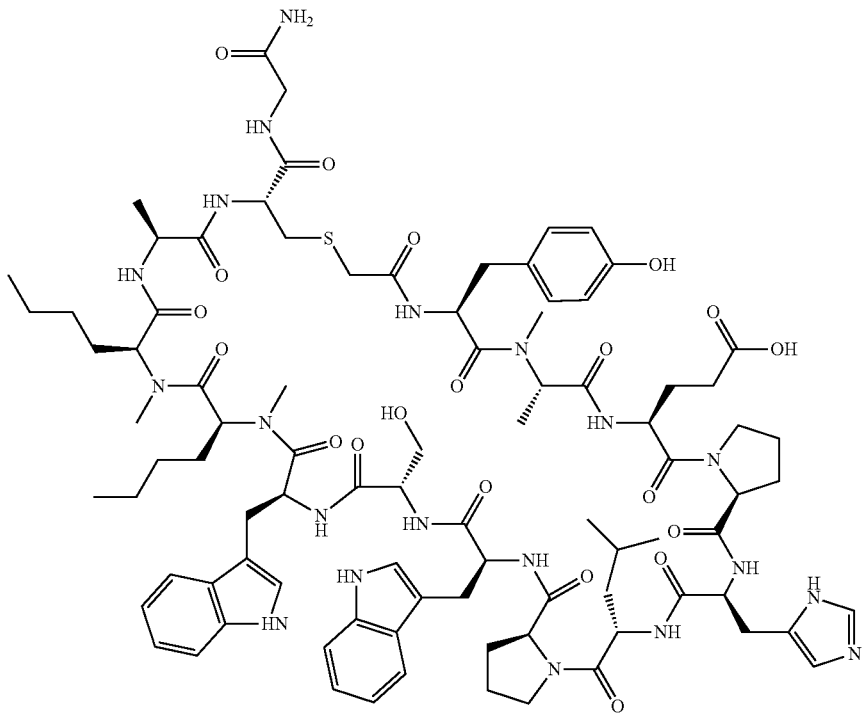

Molecular Weight: 1824.11

Example 1164 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 7.1 mg, and its estimated purity by LCMS analysis was 92%.

Analysis LCMS Condition D: Retention time=1.45 min; ESI-MS(+) m/z 912.8 (M+2H).

Analysis LCMS Condition E: Retention time=1.50 min; ESI-MS(+) m/z 912.5 (M+2H).

Preparation of Example 1165

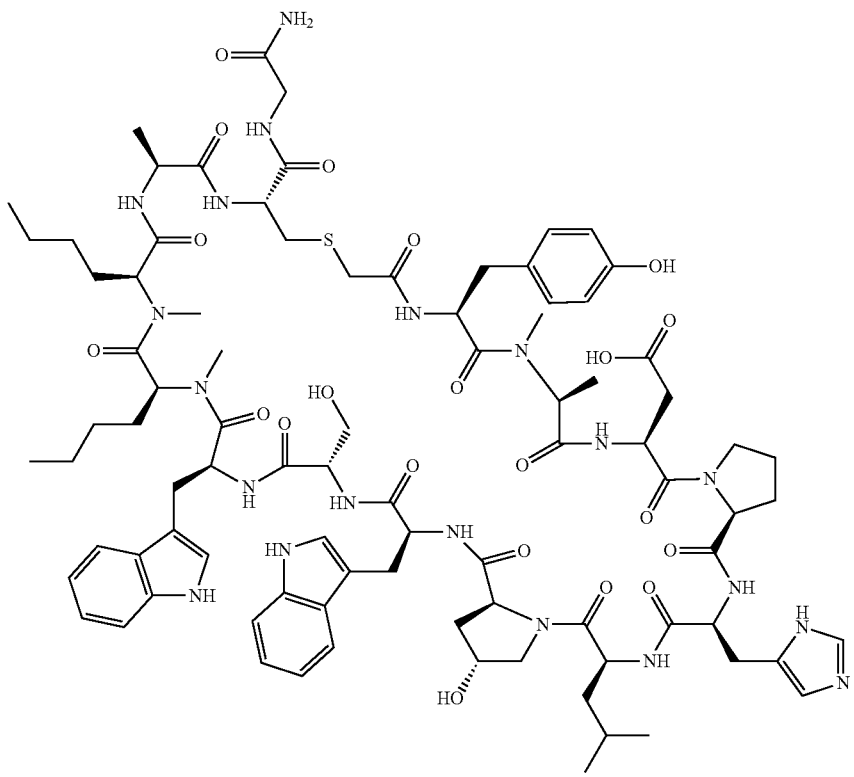

Molecular Weight: 1826.08

Example 1165 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge Shield RP18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5 minute hold at 100% B; Flow: 20 mL/min. Fractions containing the desired product were combined and dried via centrifugal evaporation. The yield of the product was 11.4 mg, and its estimated purity by LCMS analysis was 100%.

Analysis LCMS Condition D: Retention time=1.45 min; ESI-MS(+) m/z 913.8 (M+2H).

Analysis LCMS Condition E: Retention time=1.46 min; ESI-MS(+) m/z 913.7 (M+2H).

Preparation of Example 1166

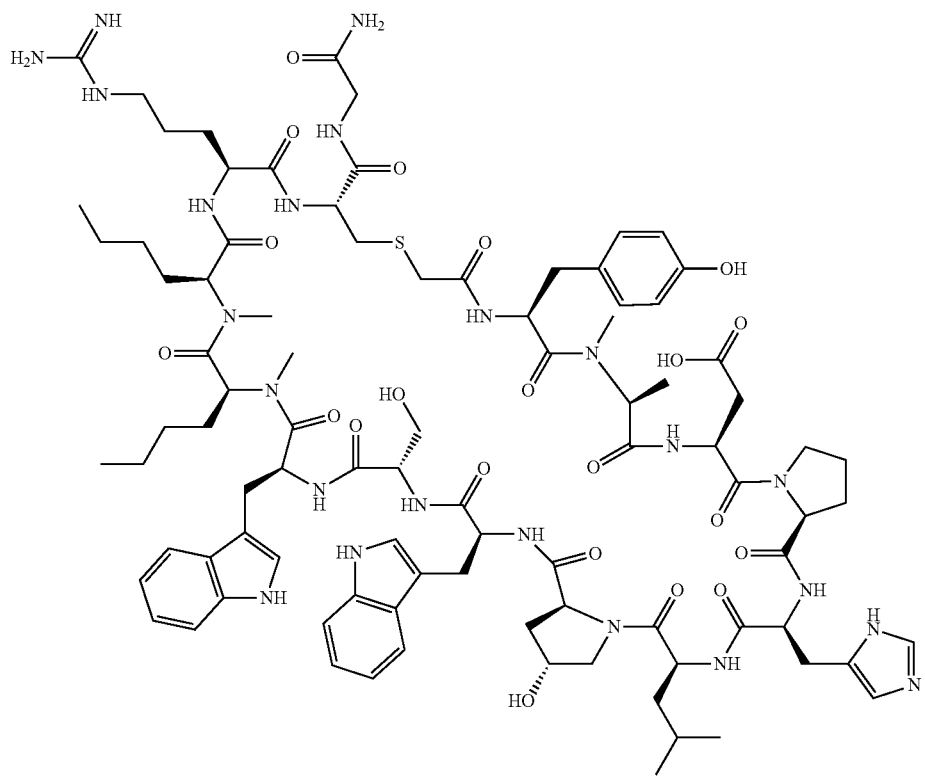

Molecular Weight: 1911.19

Example 1166 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge Shield RP18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5 minute hold at 100% B; Flow: 20 mL/min. Fractions containing the desired product were combined and dried via centrifugal evaporation. The yield of the product was 8.6 mg, and its estimated purity by LCMS analysis was 100%.

Analysis LCMS Condition D: Retention time=1.38 min; ESI-MS(+) m/z 956.2 (M+2H).

Analysis LCMS Condition E: Retention time=1.38 min; ESI-MS(+) m/z 956.4 (M+2H).

Preparation of Example 1167

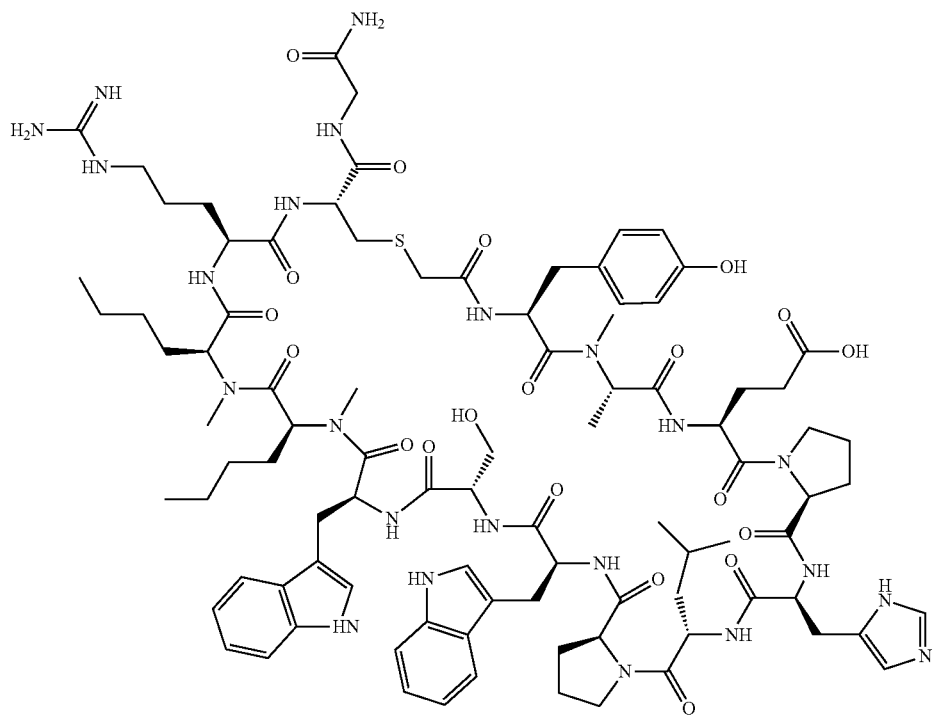

Molecular Weight: 1909.22

Example 1167 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 9.2 mg, and its estimated purity by LCMS analysis was 99%.

Analysis LCMS Condition D: Retention time=1.4 min; ESI-MS(+) m/z 955.3 (M+2H).

Analysis LCMS Condition E: Retention time=1.38 min; ESI-MS(+) m/z 955.3 (M+2H).

Preparation of Example 1168

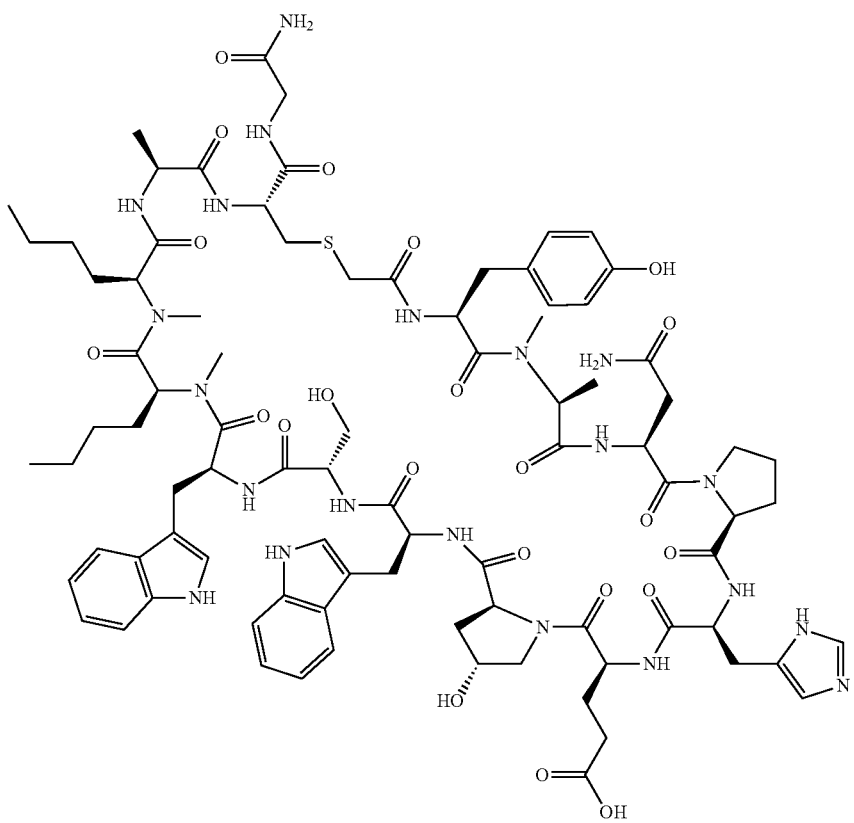

Molecular Weight: 1841.05

Example 1168 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 21.6 mg, and its estimated purity by LCMS analysis was 93%.

Analysis LCMS Condition D: Retention time=1.41 min; ESI-MS(+) m/z 921.7 (M+2H).

Analysis LCMS Condition E: Retention time=1.42 min; ESI-MS(+) m/z 921.2 (M+2H).

Preparation of Example 1169

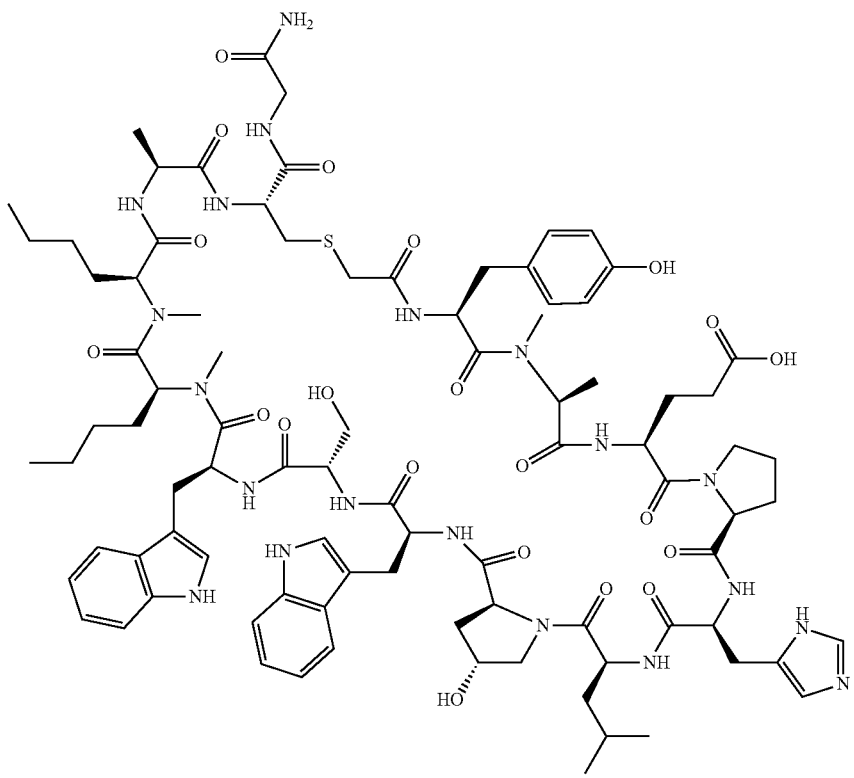

Molecular Weight: 1840.11

Example 1169 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge Shield RP18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5 minute hold at 100% B; Flow: 20 mL/min. Fractions containing the desired product were combined and dried via centrifugal evaporation. The yield of the product was 7.6 mg, and its estimated purity by LCMS analysis was 90%.

Analysis LCMS Condition D: Retention time=1.41 min; ESI-MS(+) m/z 921.1 (M+2H).

Analysis LCMS Condition E: Retention time=1.42 min; ESI-MS(+) m/z 921.5 (M+2H).

Preparation of Example 1170

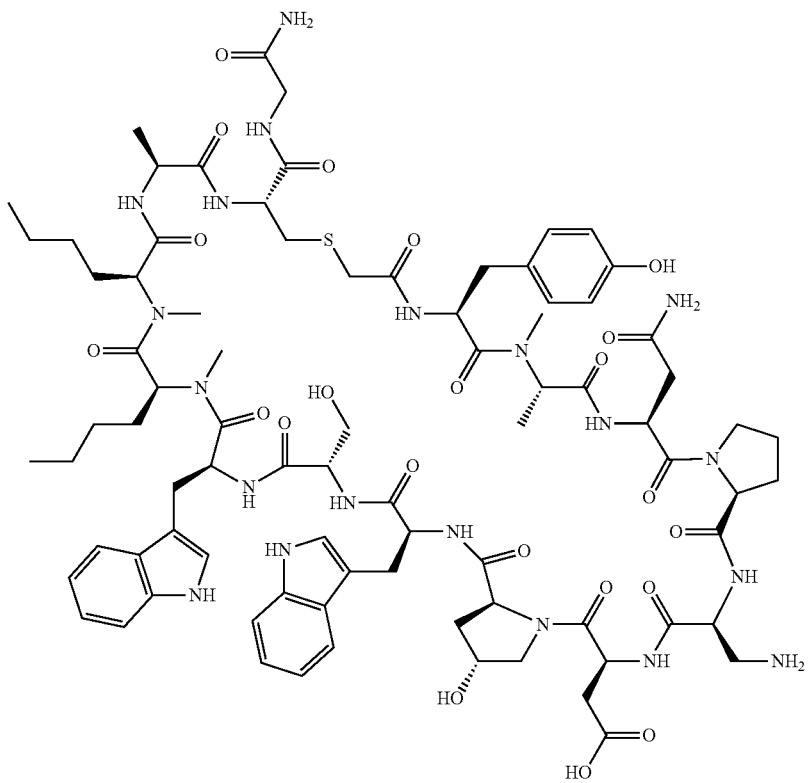

Molecular Weight: 1775.98

Example 1170 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 95%.

Analysis LCMS Condition D: Retention time=1.44 min; ESI-MS(+) m/z 889.3 (M+2H).

Analysis LCMS Condition E: Retention time=1.51 min; ESI-MS(+) m/z 888.7 (M+2H).

Preparation of Example 1171

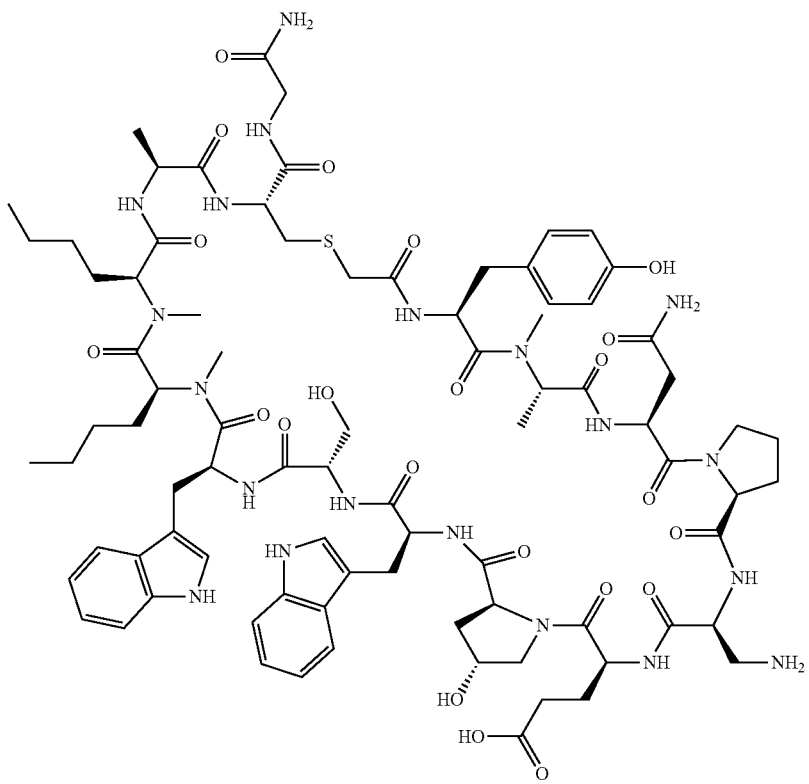

Molecular Weight: 1788.83

Example 1171 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 19.6 mg, and its estimated purity by LCMS analysis was 98%.

Analysis LCMS Condition D: Retention time=1.43 min; ESI-MS(+) m/z 895.7 (M+2H).

Analysis LCMS Condition E: Retention time=1.43 min; ESI-MS(+) m/z 895.7 (M+2H).

Preparation of Example 1172

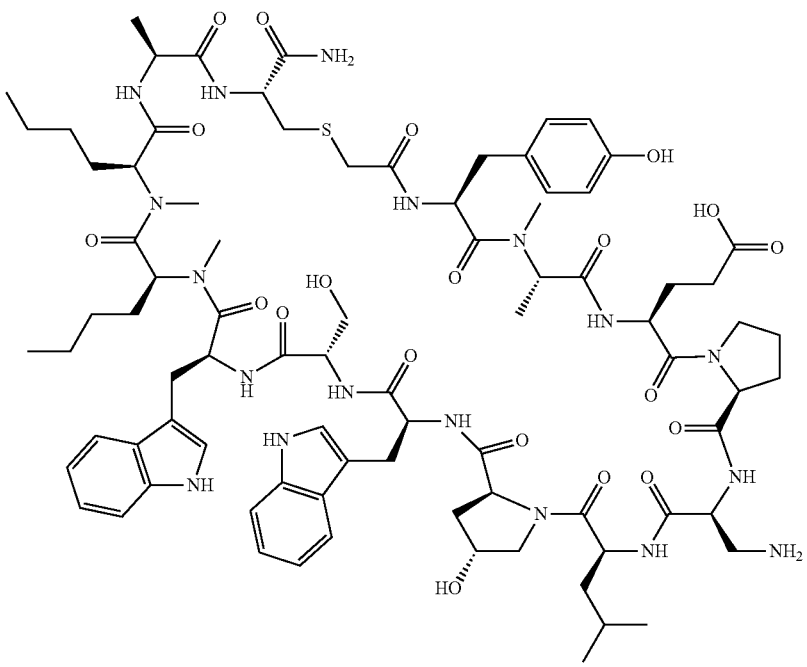

Molecular Weight: 1732.01

Example 1172 was prepared following the general synthetic sequence described for the preparation of Example 0001, composed of the following general procedures: "CEM Method A: Resin-swelling procedure", "CEM Method A: Standard coupling procedure", "CEM Method A: Double-couple Coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 6.9 mg, and its estimated purity by LCMS analysis was 100%.

Analysis LCMS Condition D: Retention time=1.53 min; ESI-MS(+) m/z 867.0 (M+2H).

Analysis LCMS Condition E: Retention time=1.56 min; ESI-MS(+) m/z 867.0 (M+2H).

Preparation of Example 1173

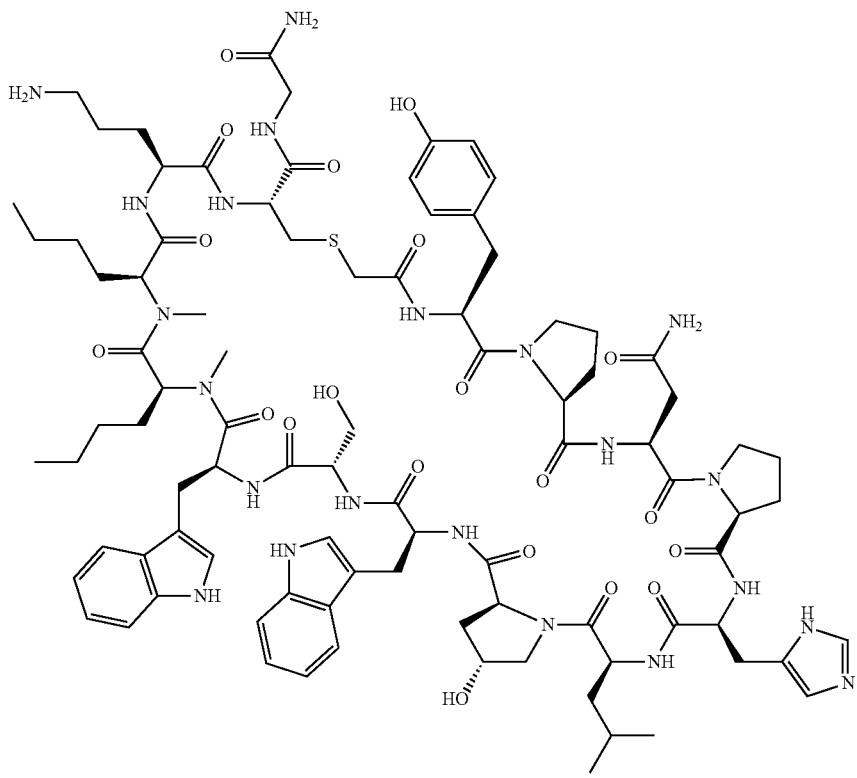

Molecular Weight: 1880.17

Example 1173 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 40.2 mg, and its estimated purity by LCMS analysis was 99%.

Analysis LCMS Condition D: Retention time=1.37 min; ESI-MS(+) m/z 940.9 (M+2H).
Analysis LCMS Condition E: Retention time=1.32 min; ESI-MS(+) m/z 941.0 (M+2H).

Preparation of Example 1174

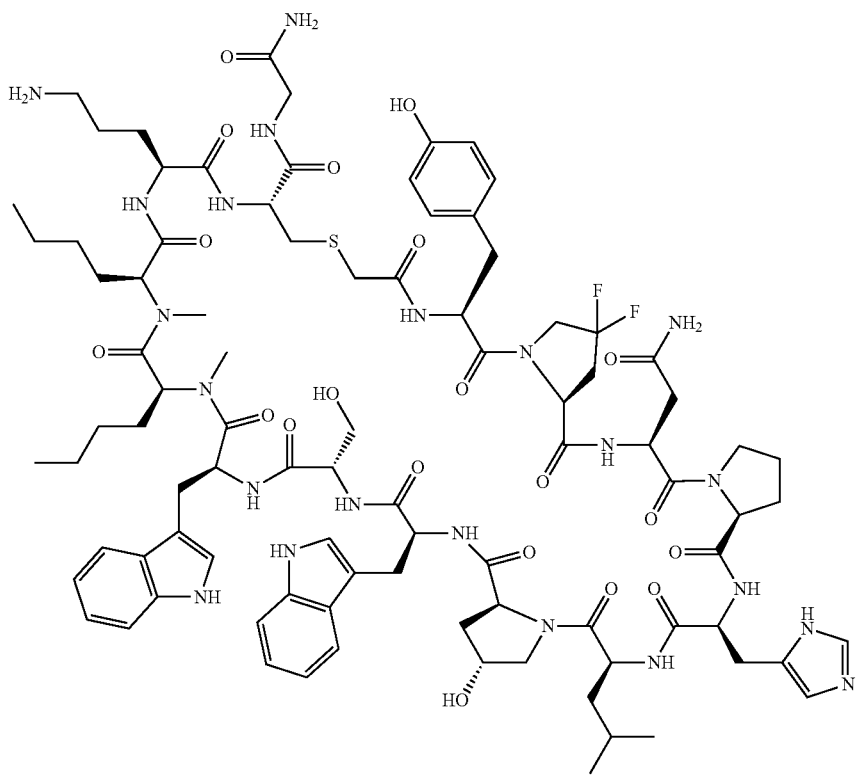

Molecular Weight: 1916.16

Example 1174 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 37.3 mg, and its estimated purity by LCMS analysis was 91%.

Analysis LCMS Condition D: Retention time=1.44 min; ESI-MS(+) m/z 958.7 (M+2H).
Analysis LCMS Condition E: Retention time=1.39 min; ESI-MS(+) m/z 959.2 (M+2H).

Preparation of Example 1175

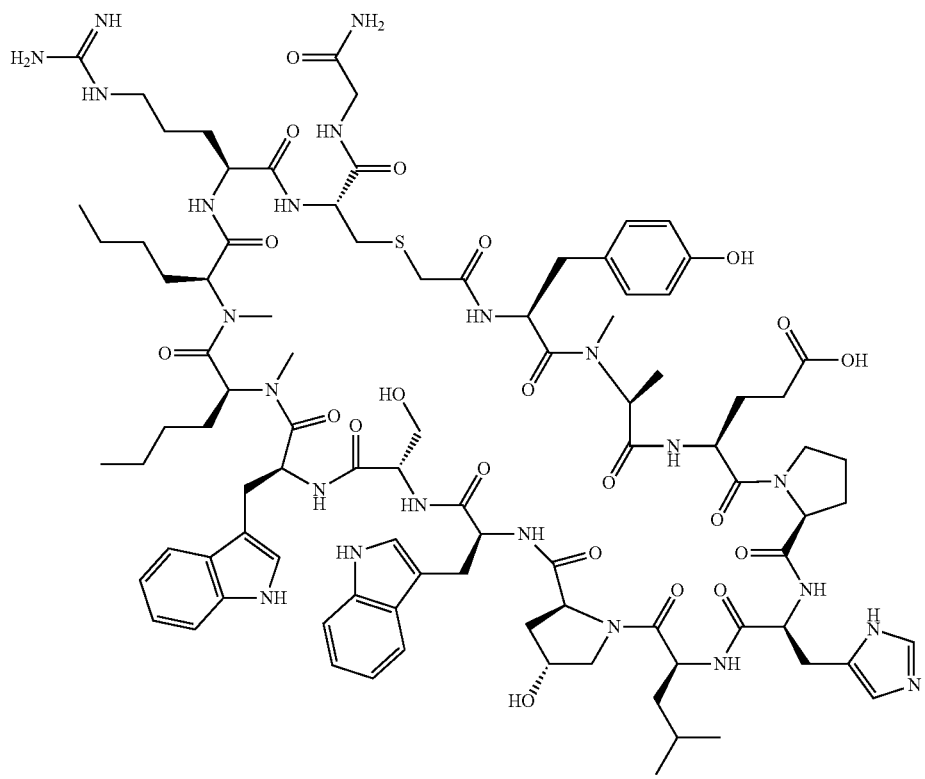

Molecular Weight: 1925.22

Example 1175 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 26.2 mg, and its estimated purity by LCMS analysis was 100%.

Analysis LCMS Condition D: Retention time=1.44 min; ESI-MS(+) m/z 963.7 (M+2H).
Analysis LCMS Condition E: Retention time=1.41 min; ESI-MS(+) m/z 963.6 (M+2H).

Preparation of Example 1176

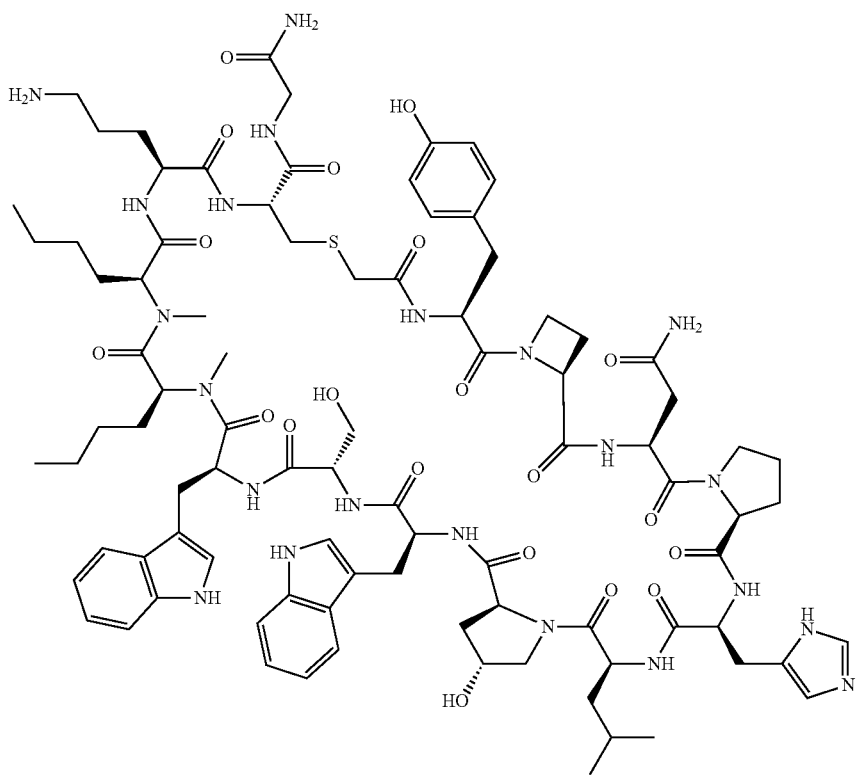

Molecular Weight: 1866.15

Example 1176 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 35.8 mg, and its estimated purity by LCMS analysis was 98%.

Analysis LCMS Condition D: Retention time=1.37 min; ESI-MS(+) m/z 934.1 (M+2H).

Analysis LCMS Condition E: Retention time=1.32 min; ESI-MS(+) m/z 933.9 (M+2H).

ESI-HRMS(+) m/z:

Calculated: 933.4614 (M+2H).

Found: 933.4596 (M+2H).

Preparation of Example 1177

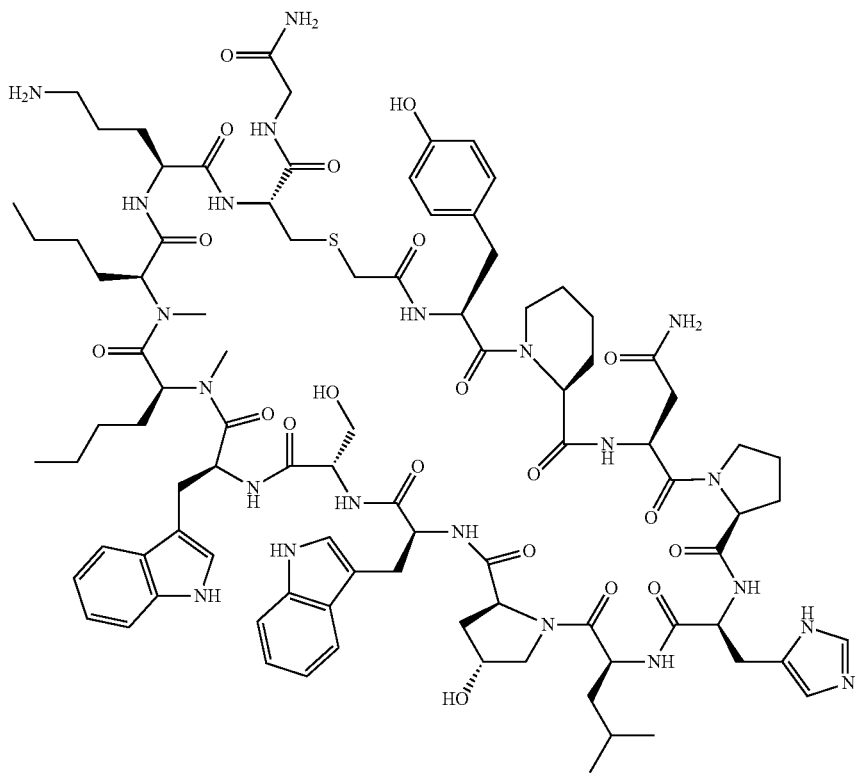

Molecular Weight: 1894.20

Example 1177 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 99%.

Analysis LCMS Condition D: Retention time=1.45 min; ESI-MS(+) m/z 948.0 (M+2H).

Analysis LCMS Condition E: Retention time=1.39 min; ESI-MS(+) m/z 947.7 (M+2H).

Preparation of Example 1178

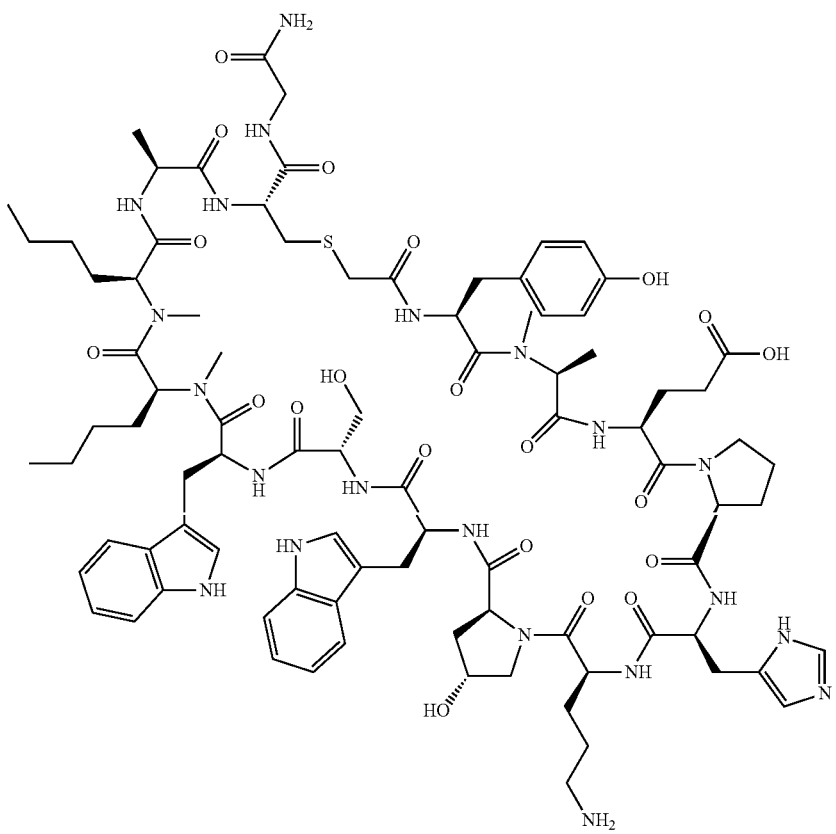

Molecular Weight: 1841.10

Example 1178 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 100%.

Analysis LCMS Condition D: Retention time=1.39 min; ESI-MS(+) m/z 921.1 (M+2H).

Analysis LCMS Condition E: Retention time=1.32 min; ESI-MS(+) m/z 921.0 (M+2H).

Preparation of Example 1179

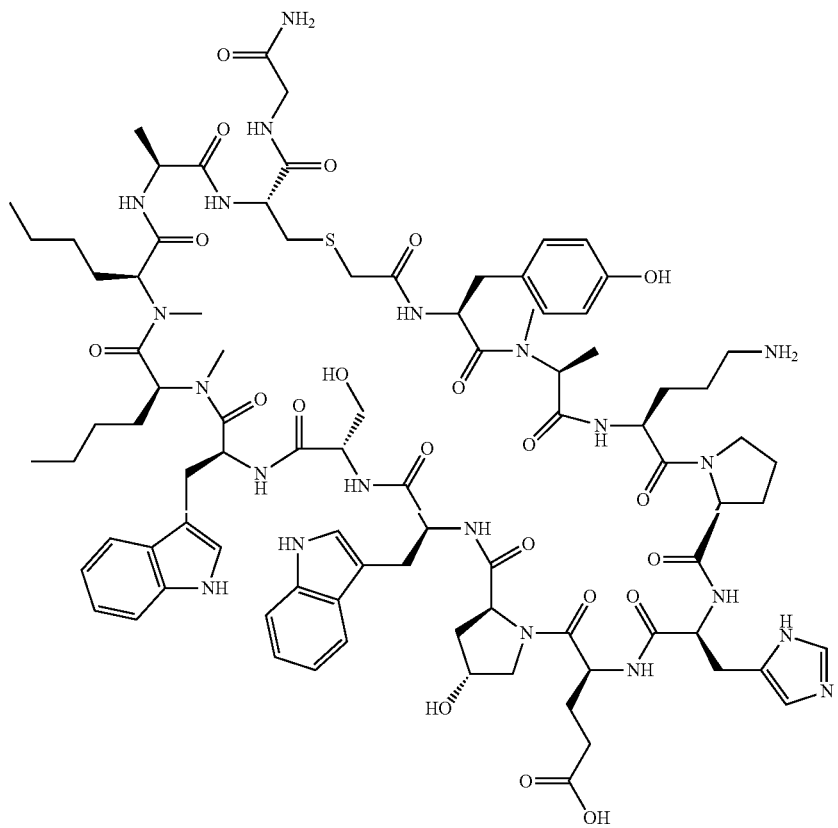

Molecular Weight: 1841.10

Example 1179 was prepared, using Rink Resin, following the general synthetic sequence described for the preparation of Example 0001, composed of the following general procedures: "Prelude Method D: Resin-swelling procedure", "Prelude Method D: Single-coupling procedure", "Prelude Method D: Secondary amine-coupling procedure", "Prelude Method D: Final Wash procedure", "Chloroacetic acid coupling procedure B", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-61% B over 25 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 92%.

Analysis LCMS Condition D: Retention time=1.49 min; ESI-MS(+) m/z 921.6 (M+2H).

Analysis LCMS Condition E: Retention time=1.41 min; ESI-MS(+) m/z 921.6 (M+2H).

Preparation of Example 1180

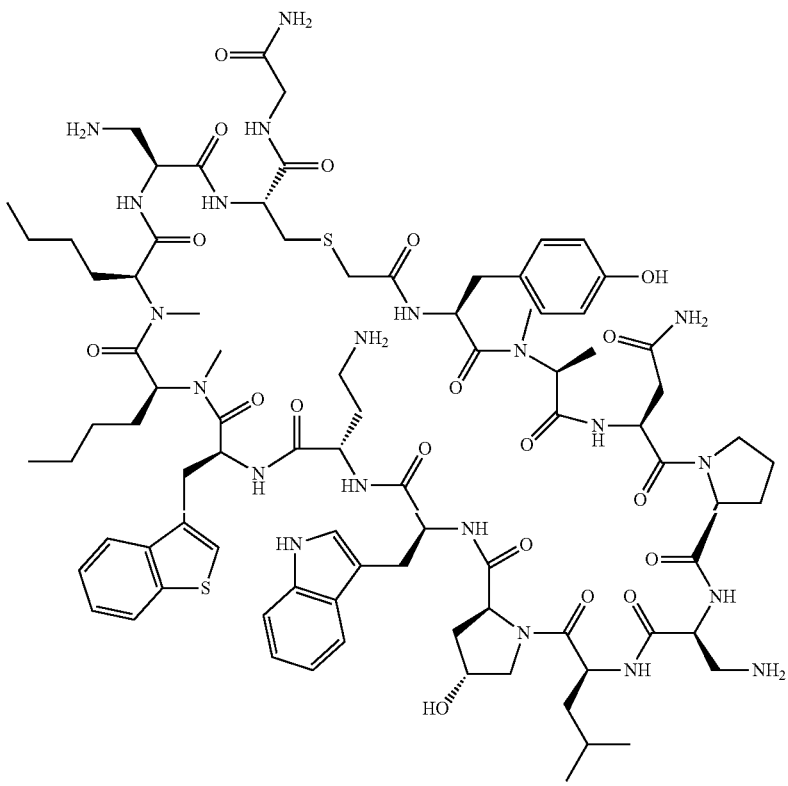

Molecular Weight: 1819.16

Example 1180 was prepared from Intermediate Resin C, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 100%.

Analysis LCMS Condition D: Retention time=1.50 min; ESI-MS(+) m/z 910.4 (M+2H).

Analysis LCMS Condition E: Retention time=1.45 min; ESI-MS(+) m/z 910.1 (M+2H).

Preparation of Example 1181

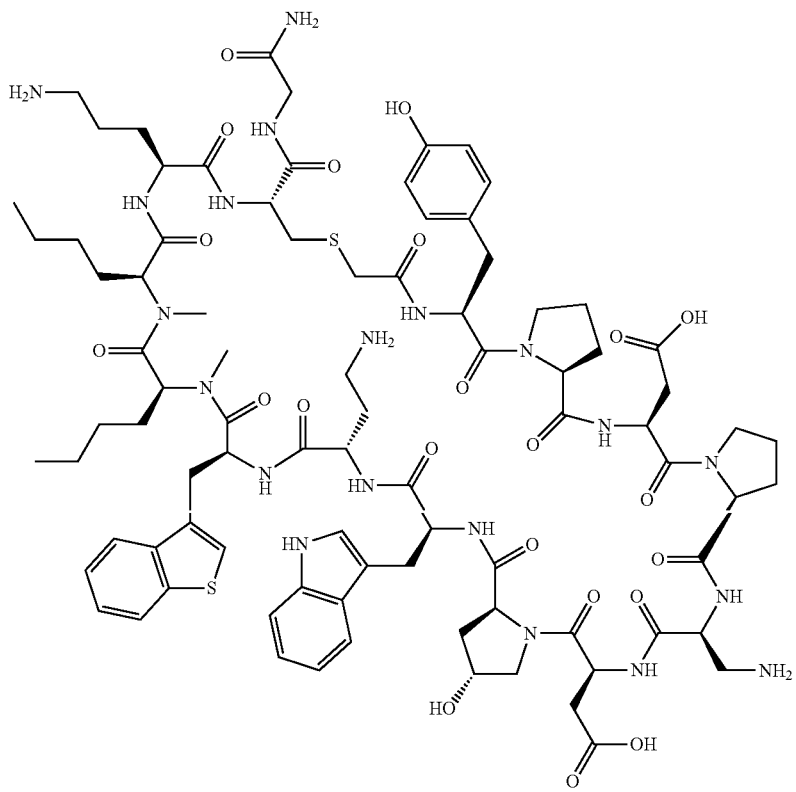

Molecular Weight: 1862.13

Example 1181 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 99%.

Analysis LCMS Condition D: Retention time=1.34 min; ESI-MS(+) m/z 931.9 (M+2H).

Analysis LCMS Condition E: Retention time=1.28 min; ESI-MS(+) m/z 932.0 (M+2H).

ESI-HRMS(+) m/z:
Calculated: 931.4236 (M+2H).
Found: 931.4212 (M+2H).

Preparation of Example 1182

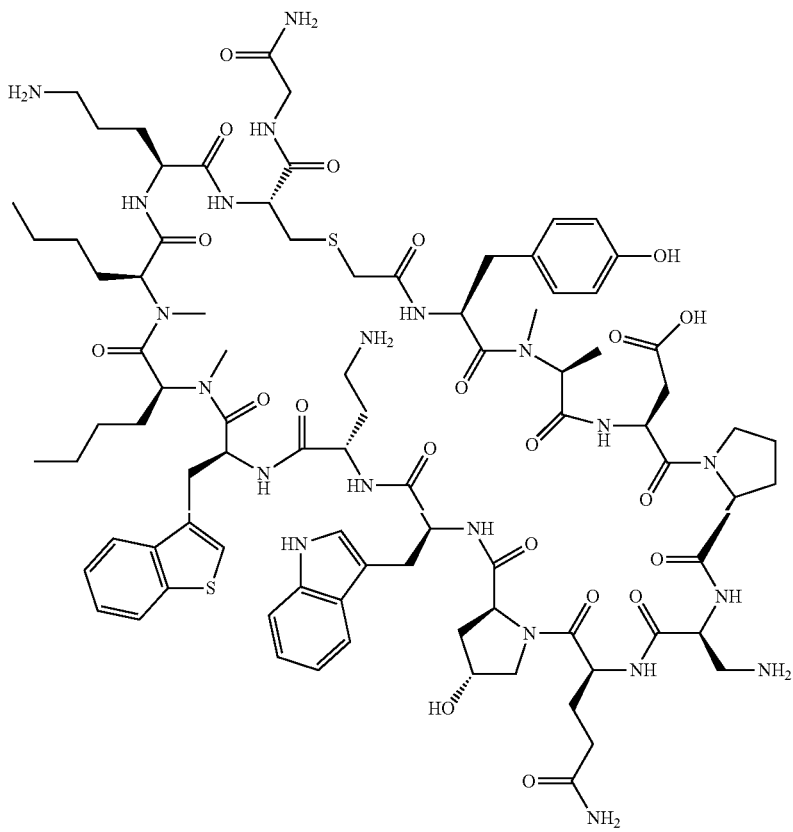

Molecular Weight: 1863.17

Example 1182 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 16.7 mg, and its estimated purity by LCMS analysis was 99%.

Analysis LCMS Condition D: Retention time=1.41 min; ESI-MS(+) m/z 932.1 (M+2H).

Analysis LCMS Condition E: Retention time=1.38 min; ESI-MS(+) m/z 932.5 (M+2H).

ESI-HRMS(+) m/z:

Calculated: 931.9395 (M+2H).

Found: 931.9369 (M+2H).

Preparation of Example 1183

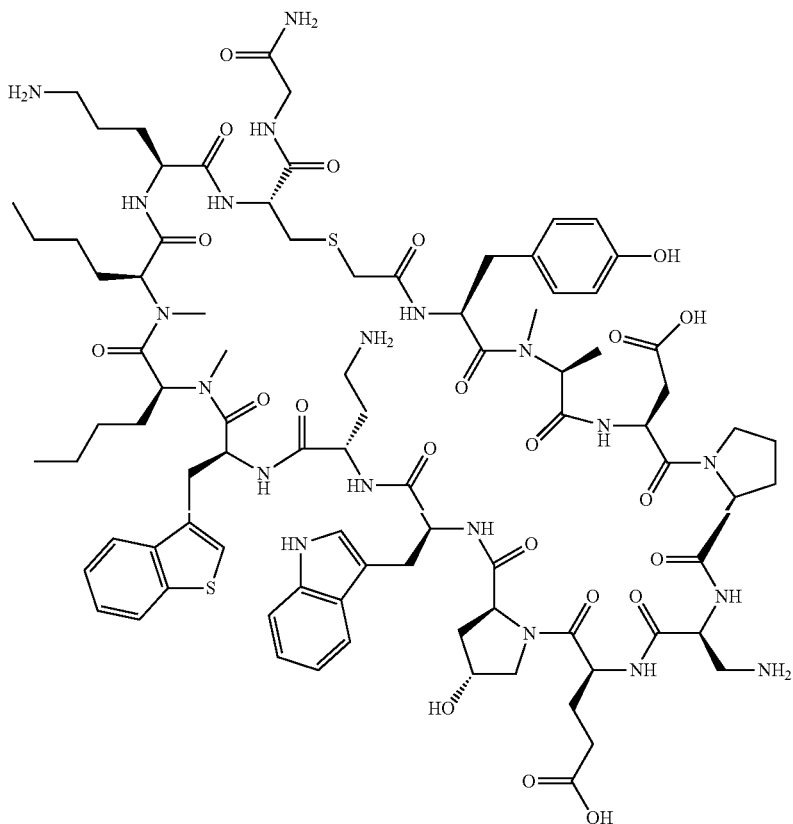

Molecular Weight: 1864.15

Example 1183 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 15.3 mg, and its estimated purity by LCMS analysis was 91%.

Analysis LCMS Condition D: Retention time=1.44 min; ESI-MS(+) m/z 932.6 (M+2H).

Analysis LCMS Condition E: Retention time=1.41 min; ESI-MS(+) m/z 932.7 (M+2H).

ESI-HRMS(+) m/z:

Calculated: 932.4315 (M+2H).

Found: 932.4284 (M+2H).

Preparation of Example 1184

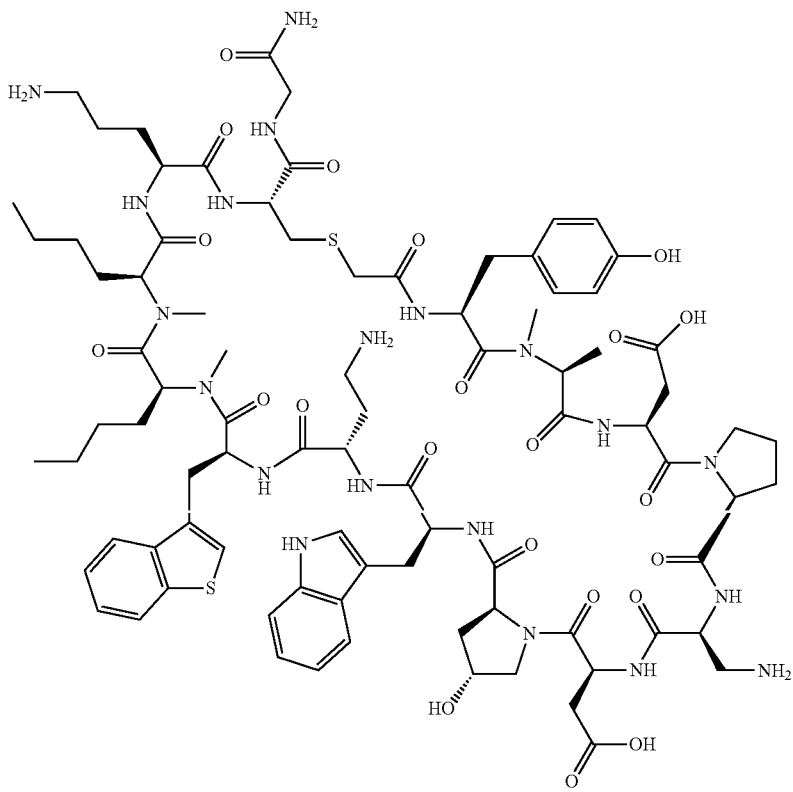

Molecular Weight: 1850.12

Example 1184 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 97%.

Analysis LCMS Condition D: Retention time=1.36 min; ESI-MS(+) m/z 926.3 (M+2H).

Analysis LCMS Condition E: Retention time=1.39 min; ESI-MS(+) m/z 926.9 (M+2H).

ESI-HRMS(+) m/z:
Calculated: 925.4236 (M+2H).
Found: 925.4208 (M+2H).

Preparation of Example 1185

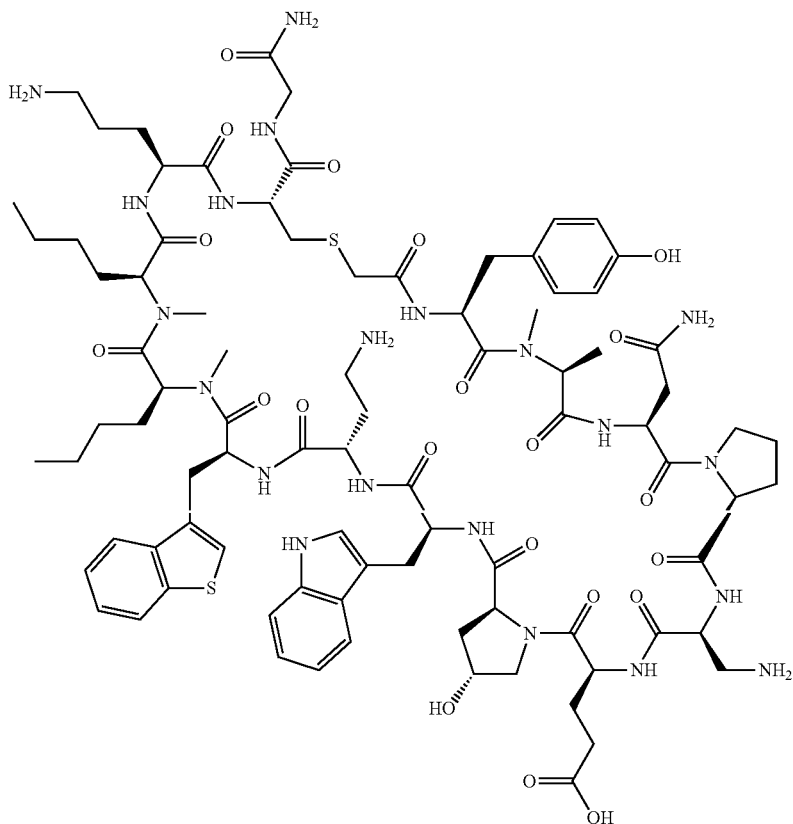 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](CC(=O)O)C(=O)N2C[C@H](O)C[C@H]2C(=O)N[C@@H](Cc2c[nH]c3ccccc23)C(=O)N[C@@H](CCN)C(=O)N[C@@H](Cc2csc3ccccc23)C(=O)N1C]

Molecular Weight: 1863.17

Example 1185 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 99%.

Analysis LCMS Condition D: Retention time=1.36 min; ESI-MS(+) m/z 932.6 (M+2H).

Analysis LCMS Condition E: Retention time=1.41 min; ESI-MS(+) m/z 932.3 (M+2H).

ESI-HRMS(+) m/z:
Calculated: 931.9395 (M+2H).
Found: 931.9371 (M+2H).

Preparation of Example 1186

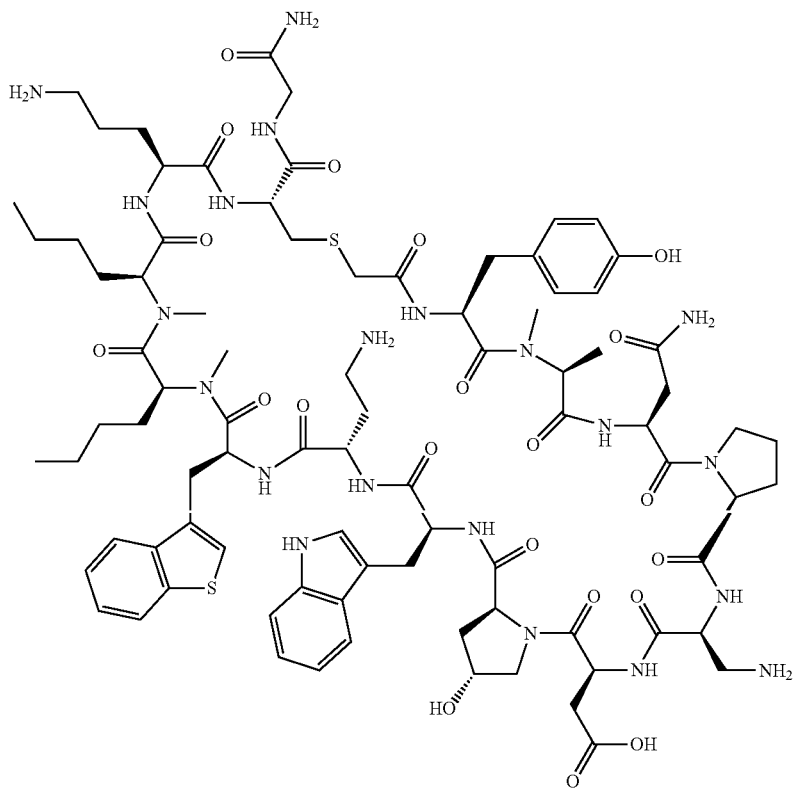

Molecular Weight: 1849.14

Example 1186 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 11.8 mg, and its estimated purity by LCMS analysis was 98%.

Analysis LCMS Condition D: Retention time=1.31 min; ESI-MS(+) m/z 925.0 (M+2H).

Analysis LCMS Condition E: Retention time=1.42 min; ESI-MS(+) m/z 925.3 (M+2H).

ESI-HRMS(+) m/z:
Calculated: 924.9316 (M+2H).
Found: 924.9286 (M+2H).

Preparation of Example 1187

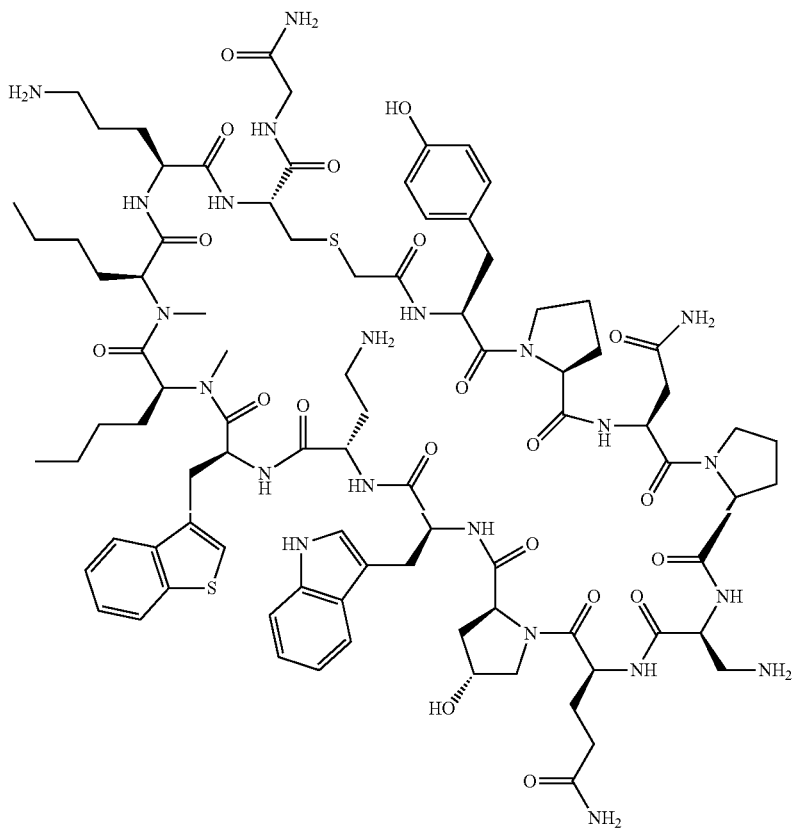

Molecular Weight: 1875.18

Example 1187 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-60% B over 25 minutes, then a 5-minute hold at 100% B; Flow: 20 mL/min. Fractions containing the desired product were combined and dried via centrifugal evaporation. The yield of the product was 29.0 mg, and its estimated purity by LCMS analysis was 97%.

Analysis LCMS Condition D: Retention time=1.27 min; ESI-MS(+) m/z 937.5 (M+2H).

Analysis LCMS Condition E: Retention time=1.29 min; ESI-MS(+) m/z 938.0 (M+2H).

Preparation of Example 1188

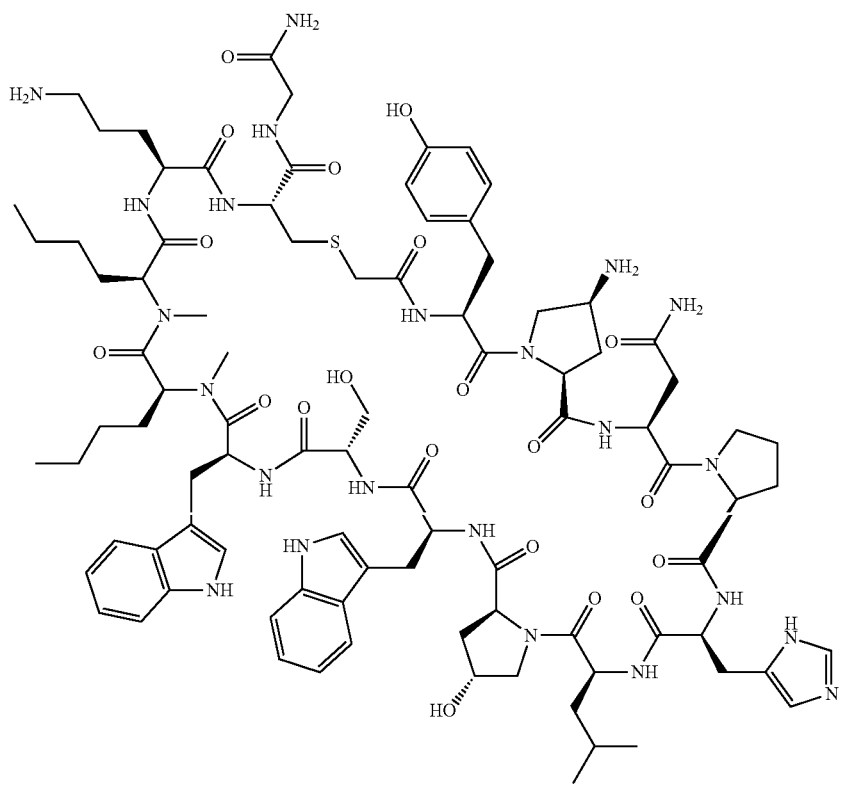

Molecular Weight: 1895.19

Example 1188 was prepared from Intermediate Resin E, following the general synthetic sequence described for the preparation of Example 0001, composed of the following general procedures: "Symphony Method A: Standard-coupling procedure", "Symphony Method B: Secondary amine-coupling procedure "Symphony Method B: Final capping procedure", "Global Deprotection Method F", and "Cyclization Method D". (2S,4S)-1-(((9H-fluoren-9-yl)methoxy)carbonyl)-4-((tert-butoxycarbonyl)amino)pyrrolidine-2-carboxylic acid was used in the first amino acid coupling step onto intermediate Resin E.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-55% B over 25 minutes, then a 5-minute hold at 100% B; Flow: 20 mL/min. Fractions containing the desired product were combined and dried via centrifugal evaporation. The yield of the product was 27.6 mg, and its estimated purity by LCMS analysis was 100%.

Analysis LCMS Condition D: Retention time=1.21 min; ESI-MS(+) m/z 948.1 (M+2H).

Analysis LCMS Condition E: Retention time=1.18 min; ESI-MS(+) m/z 948.2 (M+2H).

ESI-HRMS(+) m/z:
Calculated: 947.9747 (M+2H).
Found: 947.9706 (M+2H).

Preparation of Example 1189

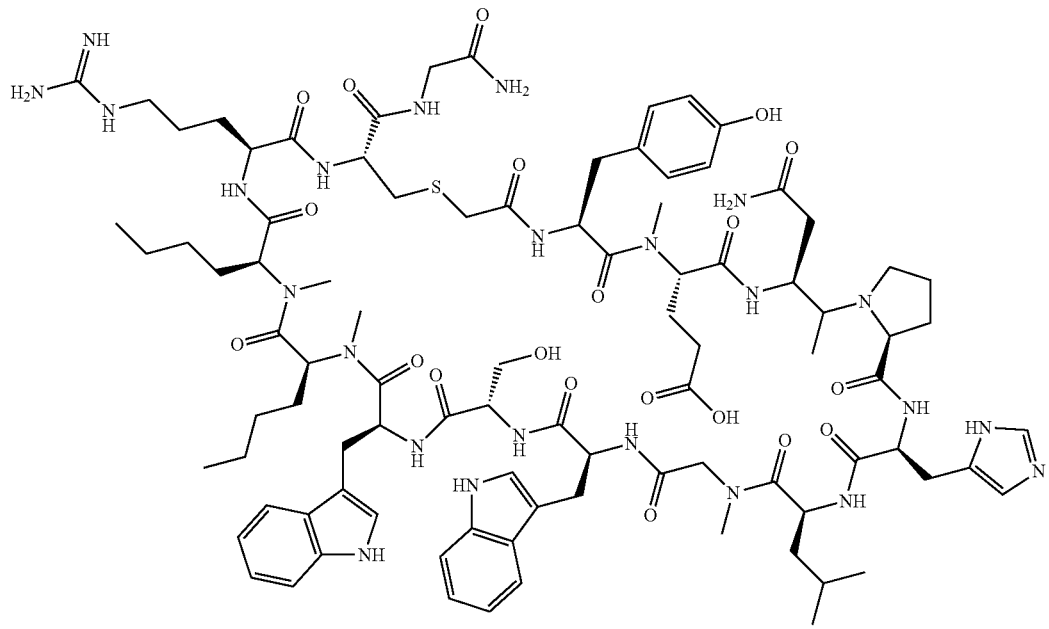

Molecular Weight: 1926.20

Example 1189 was prepared from Intermediate Resin B, following the general synthetic sequence described for the preparation of Example 0001, composed of the following general procedures: "Symphony Method A: Custom amino acids-coupling procedure", "Symphony Method B: Secondary amine-coupling procedure "Symphony Method B: Final capping procedure", "Global Deprotection Method F", and "Cyclization Method D". Fmoc-N-Me-Glu(tBu)-OH was used in the first amino acid coupling step onto Intermediate Resin B.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 100%.

Analysis LCMS Condition D: Retention time=1.33 min; ESI-MS(+) m/z 963.7 (M+2H).

Analysis LCMS Condition E: Retention time=1.35 min; ESI-MS(+) m/z 963.6 (M+2H).

ESI-HRMS(+) m/z:
Calculated: 963.4776 (M+2H).
Found: 963.4749 (M+2H).

Preparation of Example 1190

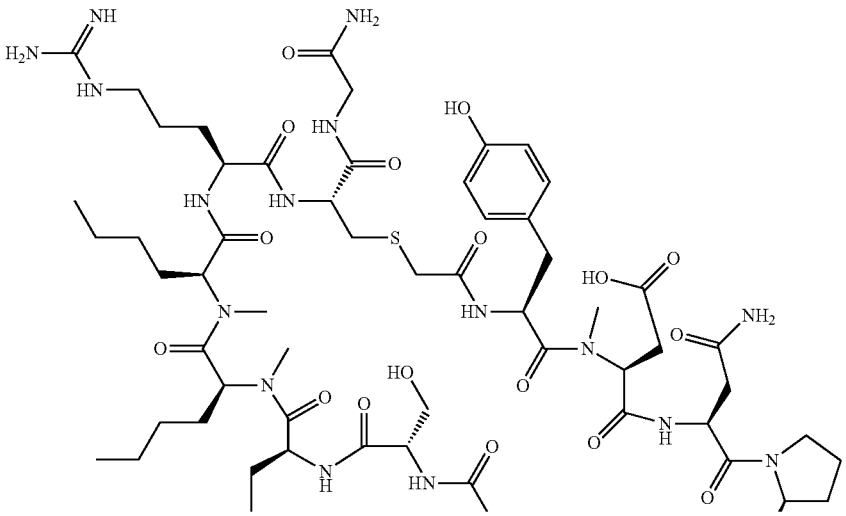

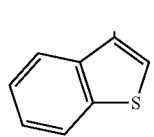
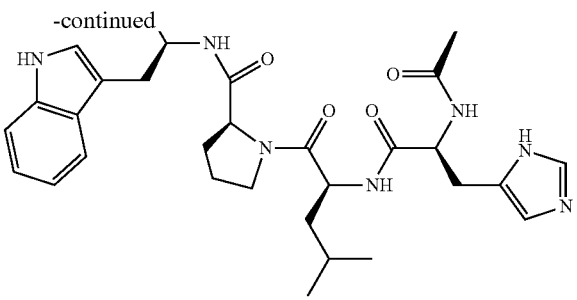

Molecular Weight: 1955.26

Example 1190 was prepared from Intermediate Resin F, following the general synthetic sequence described for the preparation of Example 0001, composed of the following general procedures: "Symphony Method A: Custom amino acids-coupling procedure", "Symphony Method B: Secondary amine-coupling procedure "Symphony Method B: Final capping procedure", "Global Deprotection Method F", and "Cyclization Method D". Fmoc-N-Me-Asp(tBu)-OH was used in the first amino acid coupling step onto intermediate Resin F.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 97%.

Analysis LCMS Condition D: Retention time=1.50 min; ESI-MS(+) m/z 978.5 (M+2H).

Analysis LCMS Condition E: Retention time=1.49 min; ESI-MS(+) m/z 978.8 (M+2H).

ESI-HRMS(+) m/z:
Calculated: 977.9582 (M+2H).
Found: 977.9561 (M+2H).

Preparation of Example 1191

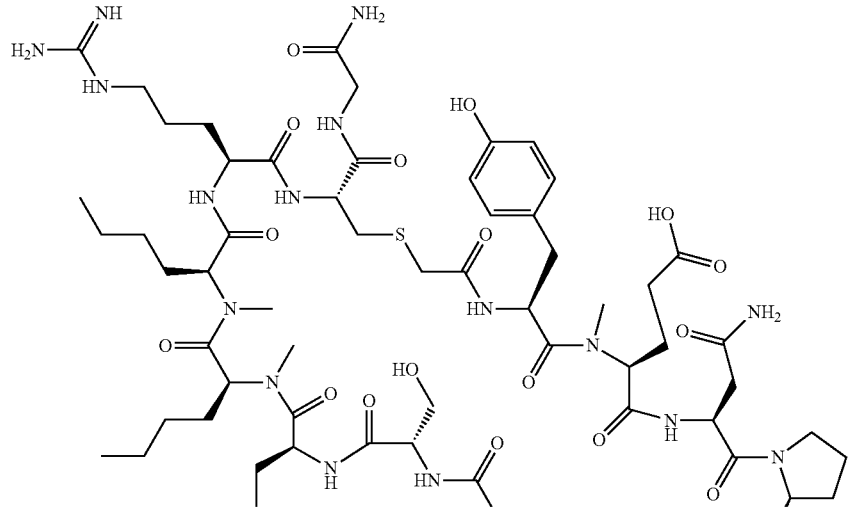
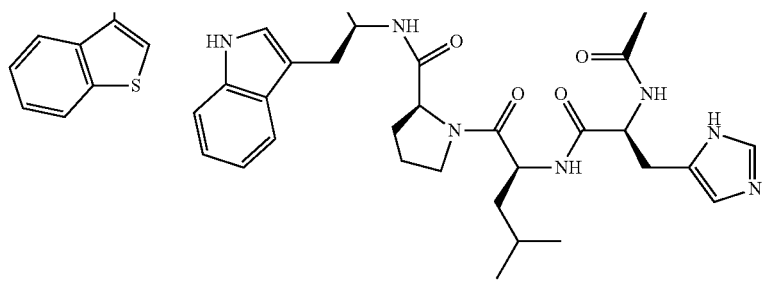

Molecular Weight: 1969.29

Example 1191 was prepared from Intermediate Resin F, following the general synthetic sequence described for the preparation of Example 0001, composed of the following general procedures: "Symphony Method A: Custom amino acids-coupling procedure", "Symphony Method B: Secondary amine-coupling procedure "Symphony Method B: Final capping procedure", "Global Deprotection Method F", and "Cyclization Method D". Fmoc-N-Me-Glu(tBu)-OH was used in the first amino acid coupling step onto intermediate Resin F.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 12.3 mg, and its estimated purity by LCMS analysis was 92%.

Analysis LCMS Condition D: Retention time=1.48 min; ESI-MS(+) m/z 985.3 (M+2H).

Analysis LCMS Condition E: Retention time=1.46 min; ESI-MS(+) m/z 985.1 (M+2H).

ESI-HRMS(+) m/z:
Calculated: 984.9660 (M+2H).
Found: 984.9631 (M+2H).

Preparation of Example 1192

Example 1192 was prepared from Intermediate Resin E, following the general synthetic sequence described for the preparation of Example 0001, composed of the following general procedures: "Symphony Method A: Standard-coupling procedure", "Symphony Method B: Secondary amine-coupling procedure "Symphony Method B: Final capping procedure", "Global Deprotection Method F", and "Cyclization Method D". (2S,4R)-1-(((9H-fluoren-9-yl)methoxy)carbonyl)-4-((tert-butoxycarbonyl)amino)pyrrolidine-2-carboxylic acid was used in the first amino acid coupling step onto intermediate Resin E.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-55% B over 25 minutes, then a 5-minute hold at 100% B; Flow: 20 mL/min. Fractions containing the desired product were combined and dried via centrifugal evaporation. The yield of the product was 29.4 mg, and its estimated purity by LCMS analysis was 98%.

Analysis LCMS Condition D: Retention time=1.14 min; ESI-MS(+) m/z 948.0 (M+2H).

Analysis LCMS Condition E: Retention time=1.19 min; ESI-MS(+) m/z 948.1 (M+2H).

ESI-HRMS(+) m/z:
Calculated: 947.9747 (M+2H).
Found: 947.9710 (M+2H).

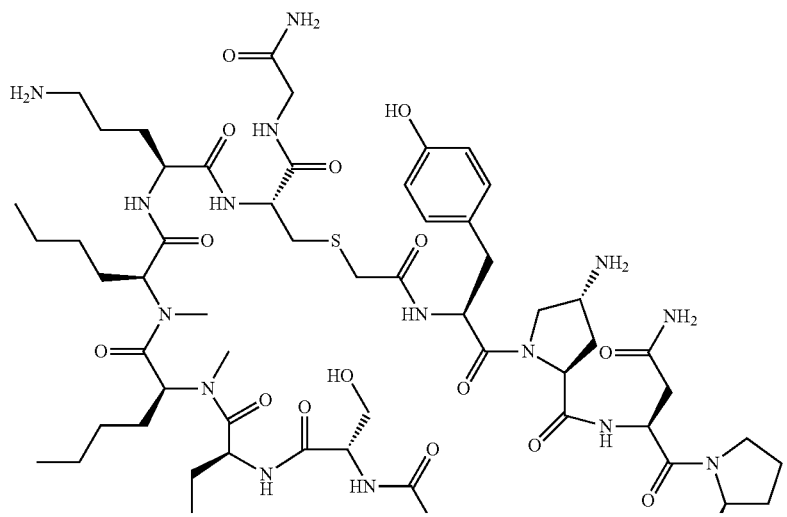

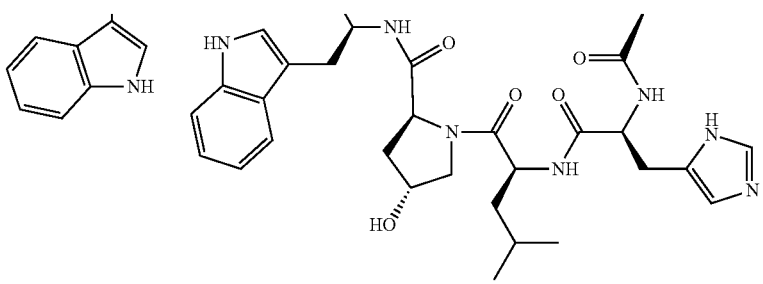

Molecular Weight: 1895.19

Preparation of Example 1193

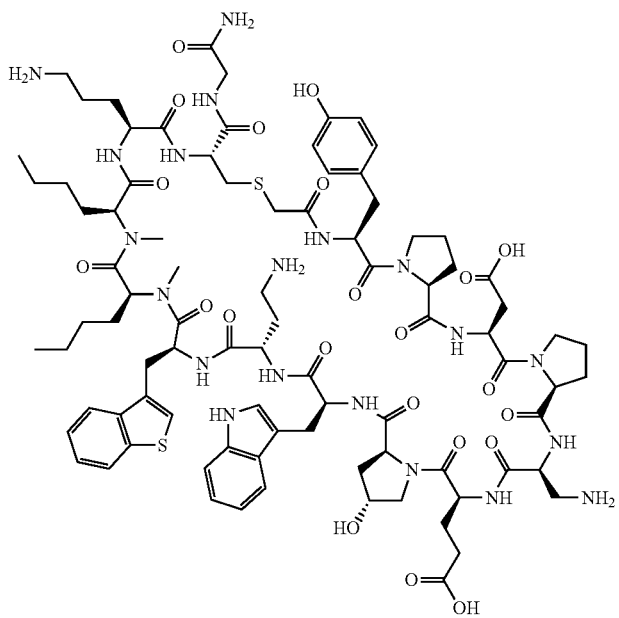

Molecular Weight: 1876.16

Example 1193 was prepared from Intermediate Resin D, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-55% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 18.6 mg, and its estimated purity by LCMS analysis was 100%.

Analysis LCMS Condition D: Retention time=1.38 min; ESI-MS(+) m/z 938.9 (M+2H).

Analysis LCMS Condition E: Retention time=1.28 min; ESI-MS(+) m/z 938.8 (M+2H).

ESI-HRMS(+) m/z:

Calculated: 938.4315 (M+2H).

Found: 938.4283 (M+2H).

Preparation of Example 1194

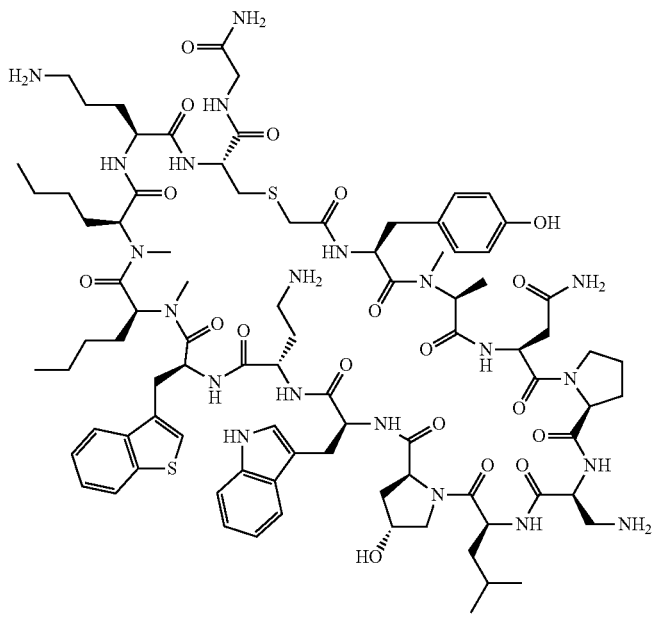

Molecular Weight: 1847.21

Example 1194 was prepared from Intermediate Resin D, following the general synthetic sequence described for the preparation of Example 0001, composed of the following general procedures: "Symphony Method B: Resin-swelling procedure", "Symphony Method A: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 12.9 mg, and its estimated purity by LCMS analysis was 97%.

Analysis LCMS Condition D: Retention time=1.38 min; ESI-MS(+) m/z 924.4 (M+2H).

Analysis LCMS Condition E: Retention time=1.44 min; ESI-MS(+) m/z 924.2 (M+2H).

ESI-HRMS(+) m/z:

Calculated: 923.9602 (M+2H).

Found: 923.9567 (M+2H).

Preparation of Example 1195

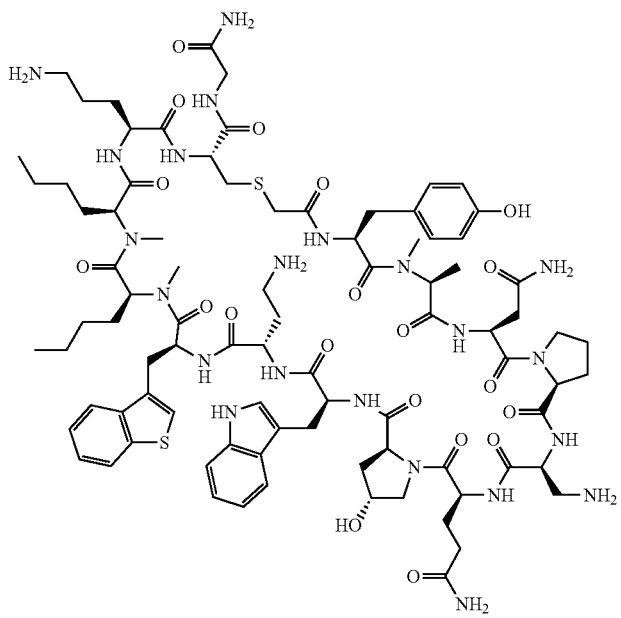

Molecular Weight: 1862.18

Example 1195 was prepared from Intermediate Resin D, following the general synthetic sequence described for the preparation of Example 0001, composed of the following general procedures: "Symphony Method B: Resin-swelling procedure", "Symphony Method A: Standard-coupling procedure", "Symphony Method B: Secondary amine-coupling procedure "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 10.0 mg, and its estimated purity by LCMS analysis was 100%.

Analysis LCMS Condition D: Retention time=1.36 min; ESI-MS(+) m/z 932.0 (M+2H).

Analysis LCMS Condition E: Retention time=1.39 min; ESI-MS(+) m/z 931.9 (M+2H).

ESI-HRMS(+) m/z:

Calculated: 931.4475 (M+2H).

Found: 931.4443 (M+2H).

Preparation of Example 1196

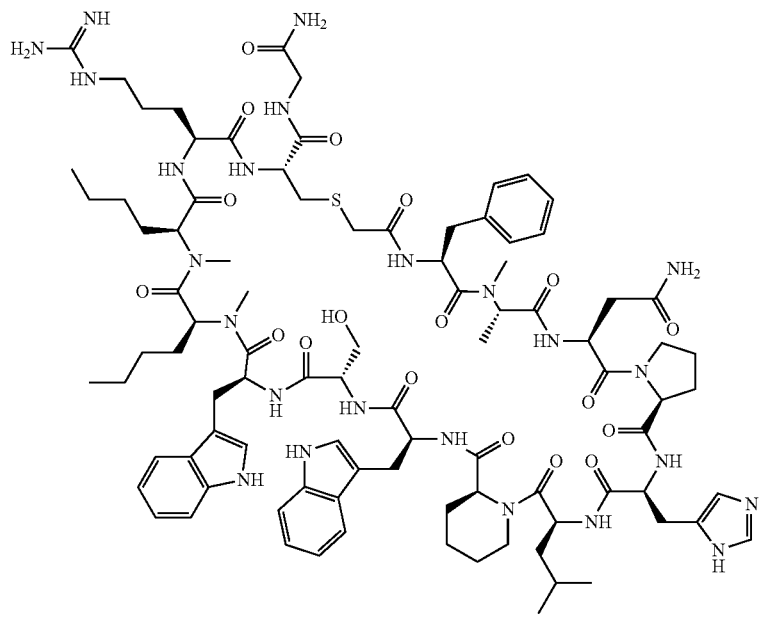

Molecular Weight: 1892.23

Example 1196 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-72% B over 25 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 99%.

Analysis LCMS Condition D: Retention time=1.75 min; ESI-MS(+) m/z 947.0 (M+2H).

Analysis LCMS Condition E: Retention time=1.71 min; ESI-MS(+) m/z 947.3 (M+2H).

Preparation of Example 1197

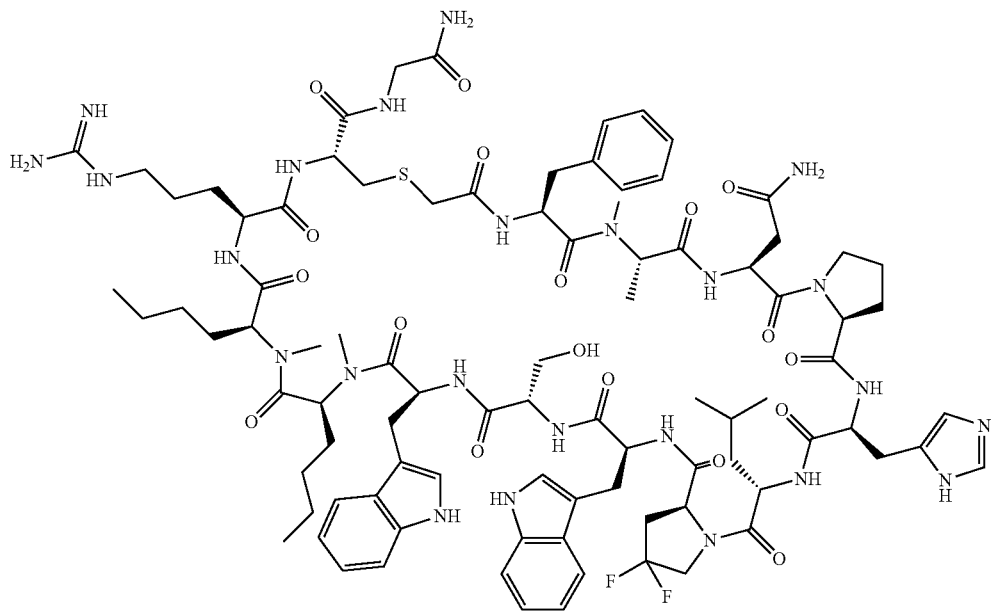

Molecular Weight: 1914.19

Example 1197 was prepared following the general synthetic sequence described for the preparation of Example 0001, composed of the following general procedures: "Prelude Method C: Resin-swelling procedure", "Prelude Method C: Single-coupling procedure", "Prelude Method C: Secondary amine-coupling procedure", "Prelude Method C: Final Wash procedure", Chloroacetic acid coupling procedure B "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-72% B over 25 minutes, then a 5-minute hold at 100% B; Flow: 20 mL/min. Fractions containing the desired product were combined and dried via centrifugal evaporation. The yield of the product was 5.1 mg, and its estimated purity by LCMS analysis was 98%.

Analysis LCMS Condition D: Retention time=1.80 min; ESI-MS(+) m/z 957.5 (M+2H).

Analysis LCMS Condition E: Retention time=1.76 min; ESI-MS(+) m/z 958.1 (M+2H).

Preparation of Example 1198

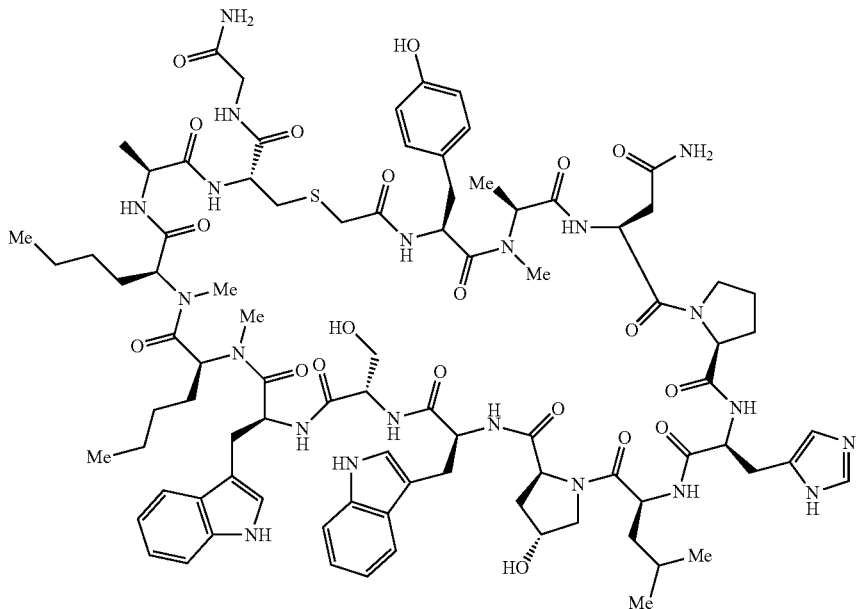

Molecular Weight: 1825.10

Example 1198 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 97%.

Analysis LCMS Condition D: Retention time=1.50 min; ESI-MS(+) m/z 913.4 (M+2H).

Analysis LCMS Condition E: Retention time=1.46 min; ESI-MS(+) m/z 913.1 (M+2H).

Preparation of Example 1199

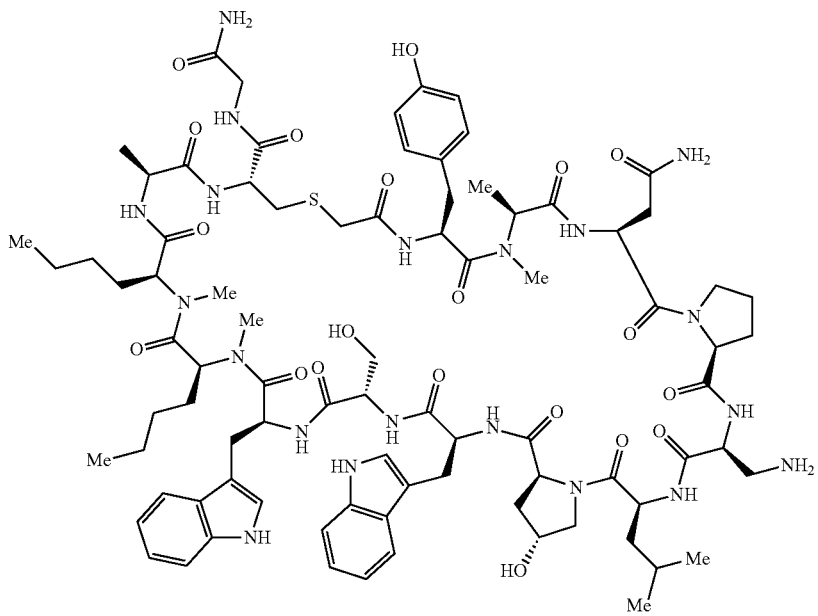 [SMILES: CCCC[C@H]1C(=O)N(C)[C@@H](CCCC)C(=O)N[C@@H](CCCN)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](CN)C(=O)N[C@@H](C)C(=O)N2C[C@H](O)C[C@H]2C(=O)N[C@@H](Cc2c[nH]c3ccccc23)C(=O)N[C@@H](CO)C(=O)N[C@@H](Cc2csc3ccccc23)C(=O)N1C]

Molecular Weight: 1774.05

Example 1199 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 9.8 mg, and its estimated purity by LCMS analysis was 96%.

Analysis LCMS Condition D: Retention time=1.47 min; ESI-MS(+) m/z 887.8 (M+2H).

Analysis LCMS Condition E: Retention time=1.48 min; ESI-MS(+) m/z 887.8 (M+2H).

Preparation of Example 1200

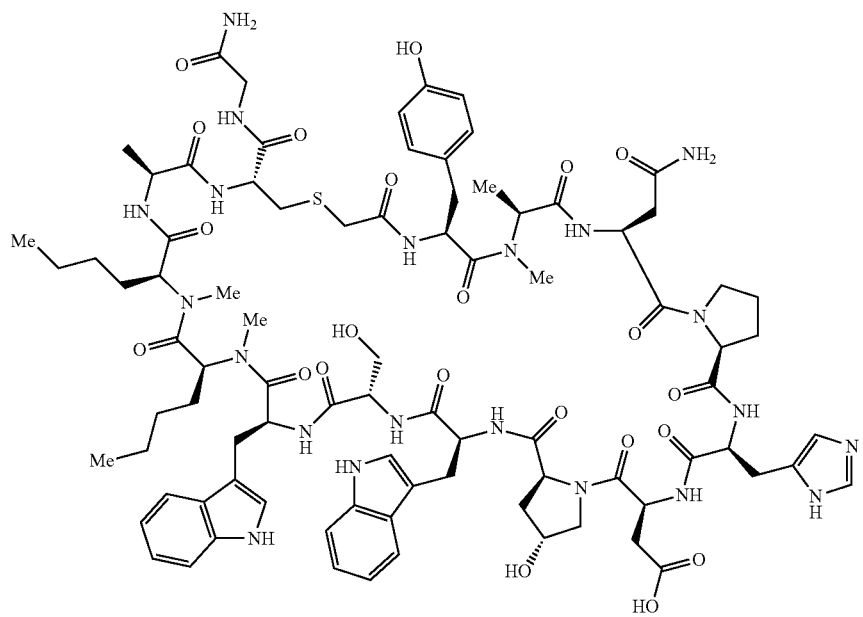

Molecular Weight: 1827.03

Example 1200 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 100%.

Analysis LCMS Condition D: Retention time=1.34 min; ESI-MS(+) m/z 914.8 (M+2H).

Analysis LCMS Condition E: Retention time=1.43 min; ESI-MS(+) m/z 914.4 (M+2H).

Preparation of Example 1201

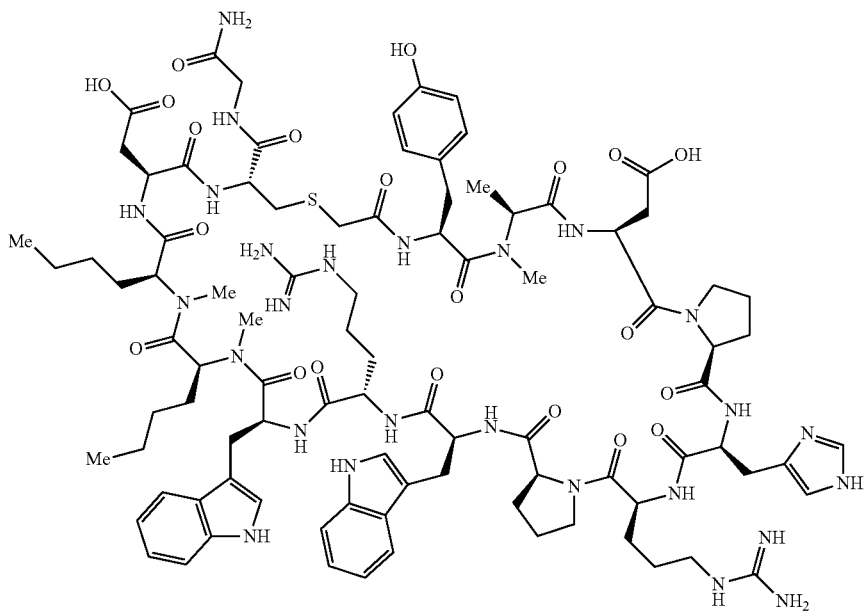

Molecular Weight: 1966.23

Example 1201 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 9.7 mg, and its estimated purity by LCMS analysis was 91%.

Analysis LCMS Condition D: Retention time=1.41 min; ESI-MS(+) m/z 984.3 (M+2H).

Analysis LCMS Condition E: Retention time=1.30 min; ESI-MS(+) m/z 983.8 (M+2H).

Preparation of Example 1202

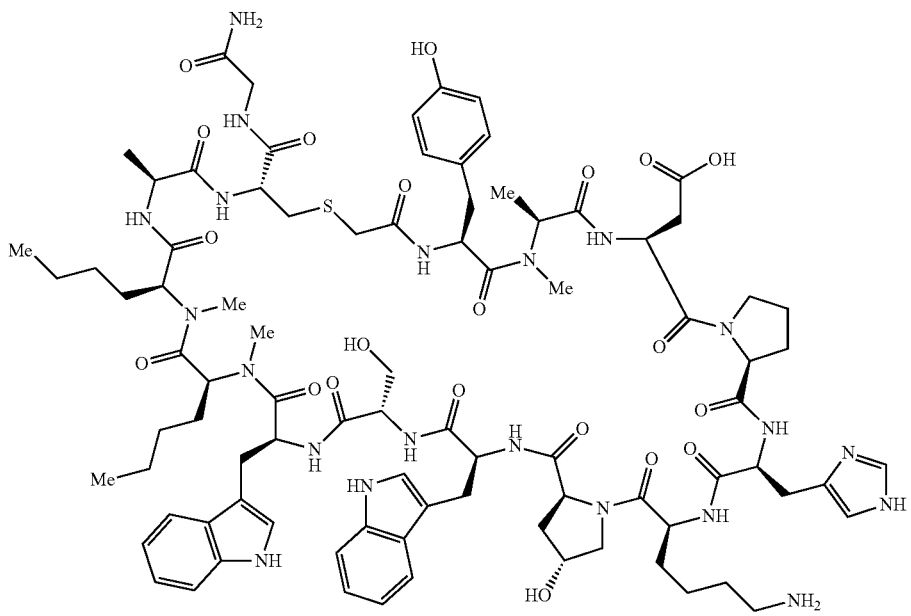

Molecular Weight: 1841.10

Example 1202 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 93%.

Analysis LCMS Condition D: Retention time=1.44 min; ESI-MS(+) m/z 921.1 (M+2H).

Analysis LCMS Condition E: Retention time=1.38 min; ESI-MS(+) m/z 921.4 (M+2H).

Preparation of Example 1203

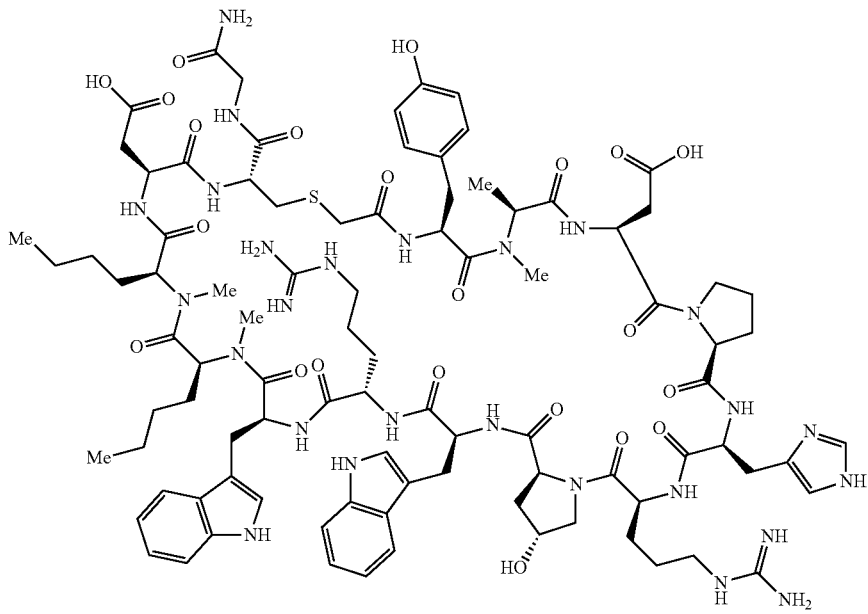

Molecular Weight: 1982.23

Example 1203 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 6.8 mg, and its estimated purity by LCMS analysis was 98%.

Analysis LCMS Condition D: Retention time=1.38 min; ESI-MS(+) m/z 992.1 (M+2H).

Analysis LCMS Condition E: Retention time=1.38 min; ESI-MS(+) m/z 991.8 (M+2H).

Preparation of Example 1204

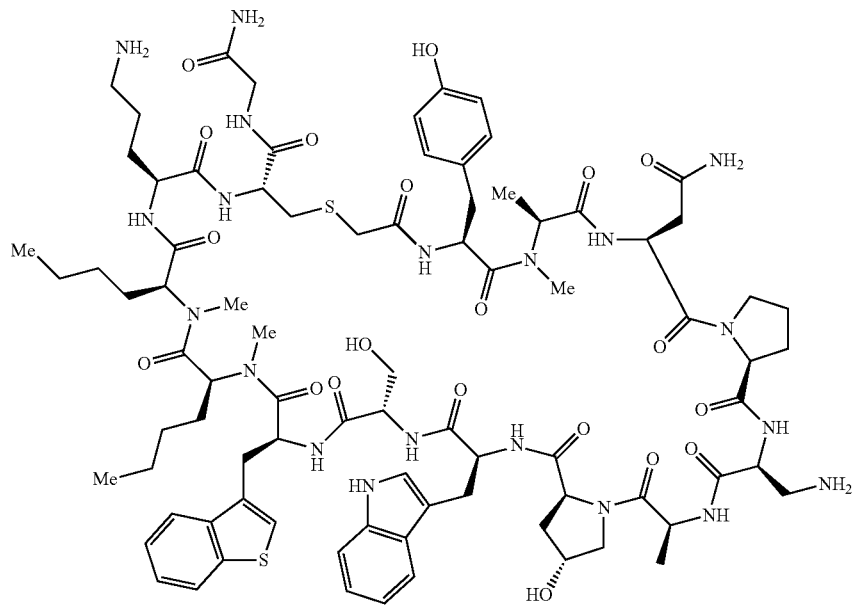

Molecular Weight: 1792.09

Example 1204 was prepared following the general synthetic sequence described for the preparation of Example 0001, composed of the following general procedures: "Symphony Method A: Resin-swelling procedure", "Symphony Method A: Standard-coupling procedure", "Symphony Method A: Secondary amine-coupling procedure B", "Custom amino acids-coupling procedure", "Chloroacetic acid coupling procedure B", "Global Deprotection Method C", and "Cyclization Method D".

The crude material was purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 100%.

Analysis LCMS Condition D: Retention time=1.49 min; ESI-MS(+) m/z 897.0 (M+2H).

Analysis LCMS Condition E: Retention time=1.50 min; ESI-MS(+) m/z 896.7 (M+2H).

Preparation of Example 1205

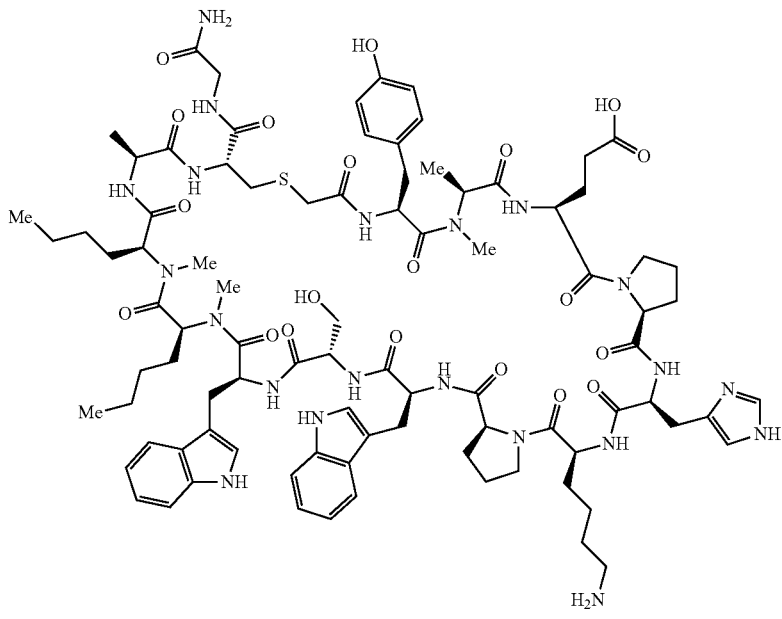

Molecular Weight: 1839.12

Example 1205 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 25 minutes, then a 5-minute hold at 100% B; Flow: 20 mL/min. Fractions containing the desired product were combined and dried via centrifugal evaporation. The yield of the product was 1.2 mg, and its estimated purity by LCMS analysis was 99%.

Analysis LCMS Condition D: Retention time=1.44 min; ESI-MS(+) m/z 920.2 (M+2H).

Analysis LCMS Condition E: Retention time=1.35 min; ESI-MS(+) m/z 920.2 (M+2H).

Preparation of Example 1206

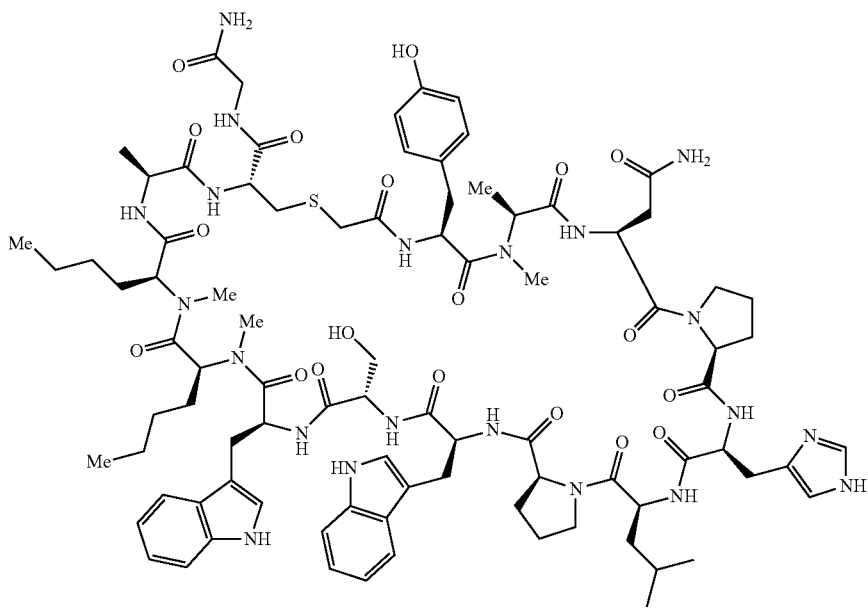

Molecular Weight: 1809.10

Example 1206 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 2.5 mg, and its estimated purity by LCMS analysis was 100%.

Analysis LCMS Condition D: Retention time=1.55 min; ESI-MS(+) m/z 905.2 (M+2H).
Analysis LCMS Condition E: Retention time=1.52 min; ESI-MS(+) m/z 905.4 (M+2H).

Preparation of Example 1207

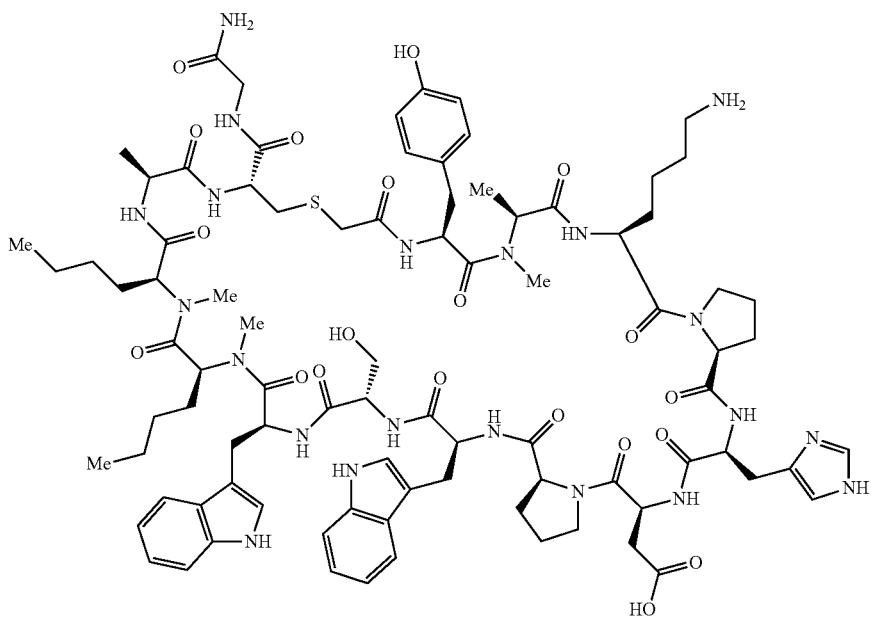

Molecular Weight: 1825.10

Example 1207 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 7.1 mg, and its estimated purity by LCMS analysis was 97%.

Analysis LCMS Condition D: Retention time=1.38 min; ESI-MS(+) m/z 913.0 (M+2H).

Analysis LCMS Condition E: Retention time=1.36 min; ESI-MS(+) m/z 913.5 (M+2H).

Preparation of Example 1208

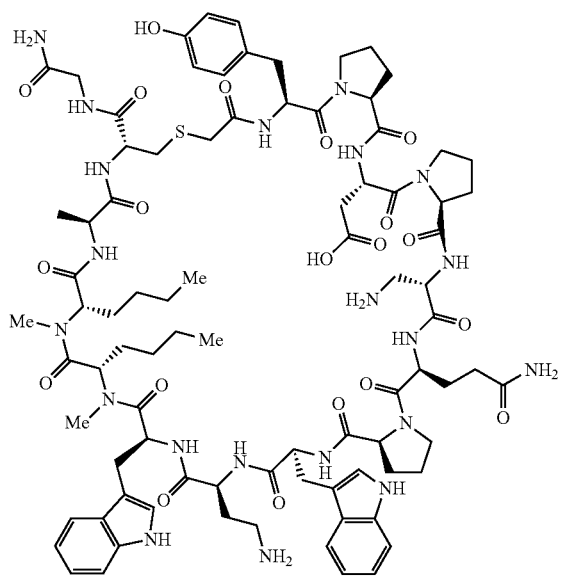

Molecular Weight: 1799.06

Example 1208 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 100%.

Analysis LCMS Condition D: Retention time=1.40 min; ESI-MS(+) m/z 900.1 (M+2H).

Analysis LCMS Condition E: Retention time=1.35 min; ESI-MS(+) m/z 900.1 (M+2H).

Preparation of Example 1209

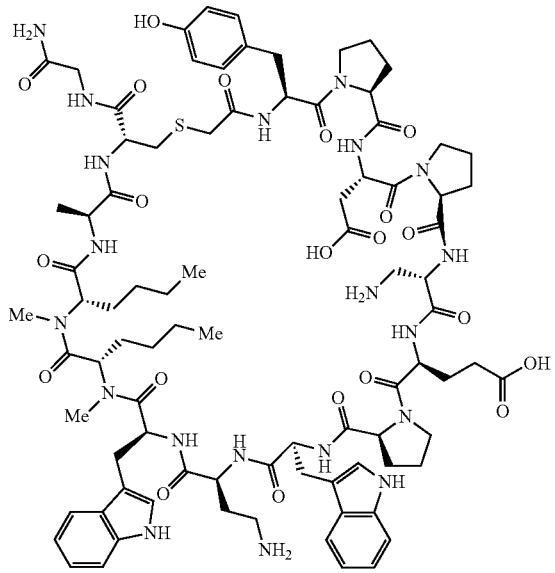

Molecular Weight: 1800.04

Example 1209 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 1.9 mg, and its estimated purity by LCMS analysis was 99%.

Analysis LCMS Condition D: Retention time=1.43 min; ESI-MS(+) m/z 900.5 (M+2H).

Analysis LCMS Condition E: Retention time=1.35 min; ESI-MS(+) m/z 900.7 (M+2H).

Preparation of Example 1210

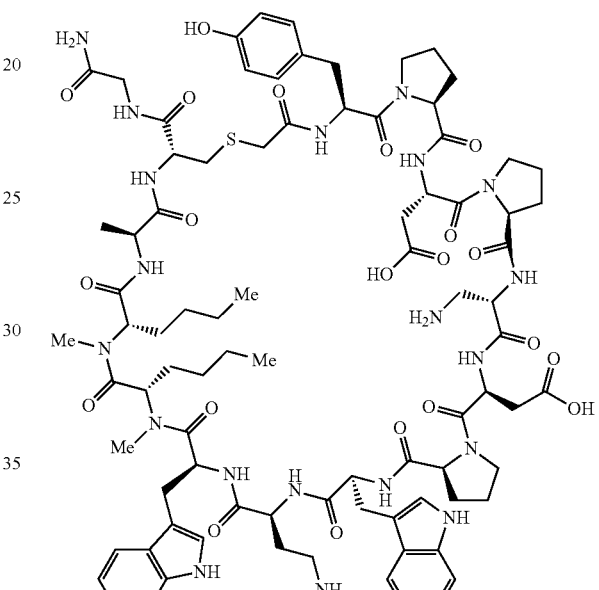

Molecular Weight: 1786.02

Example 1210 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 7.8 mg, and its estimated purity by LCMS analysis was 96%.

Analysis LCMS Condition D: Retention time=1.43 min; ESI-MS(+) m/z 893.6 (M+2H).

Analysis LCMS Condition E: Retention time=1.38 min; ESI-MS(+) m/z 893.6 (M+2H).

Preparation of Example 1211

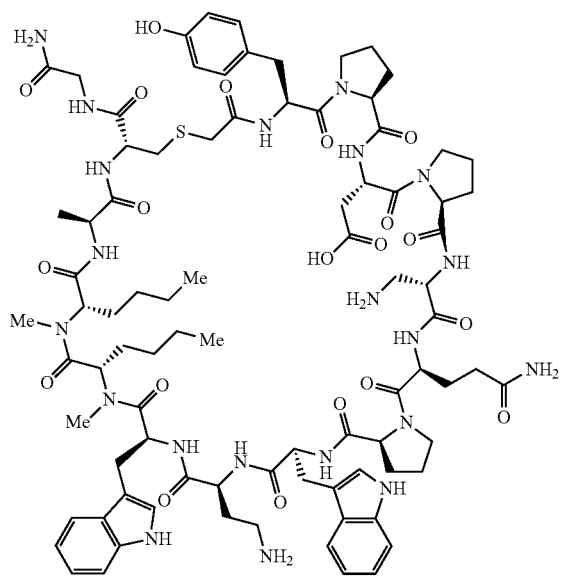

Molecular Weight: 1798.07

Example 1211 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 99%.

Analysis LCMS Condition D: Retention time=1.33 min; ESI-MS(+) m/z 899.7 (M+2H).

Analysis LCMS Condition E: Retention time=1.35 min; ESI-MS(+) m/z 899.6 (M+2H).

Preparation of Example 1212

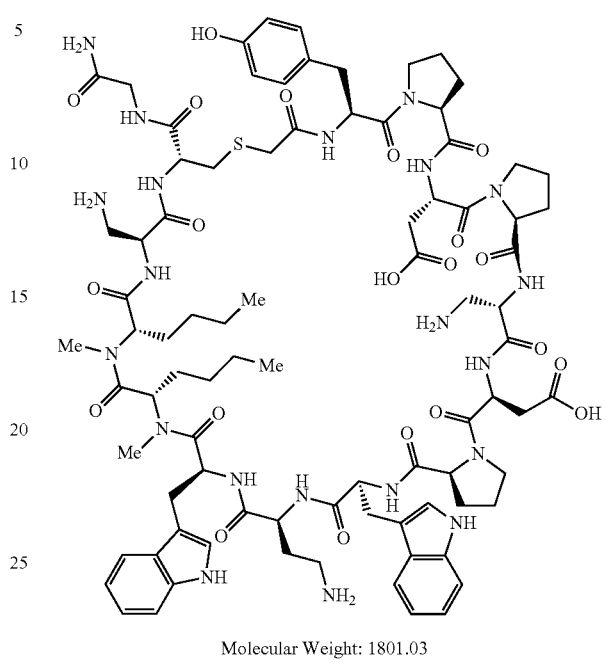

Molecular Weight: 1801.03

Example 1212 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-55% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 3.6 mg, and its estimated purity by LCMS analysis was 92%.

Analysis LCMS Condition D: Retention time=1.37 min; ESI-MS(+) m/z 901.1 (M+2H).

Analysis LCMS Condition E: Retention time=1.25 min; ESI-MS(+) m/z 901.4 (M+2H).

Preparation of Example 1213

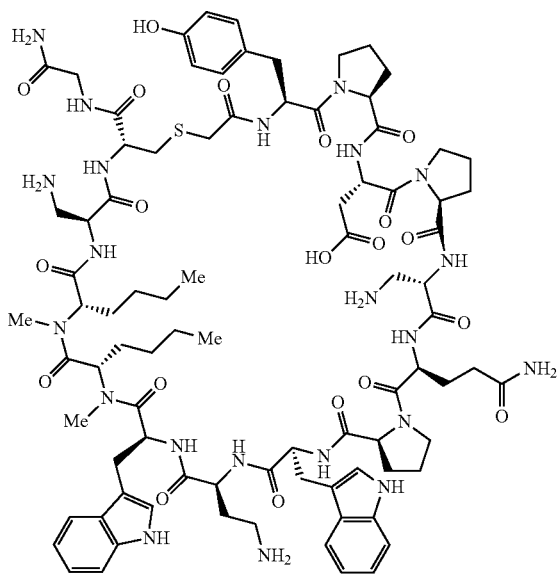

Molecular Weight: 1814.07

Preparation of Example 1214

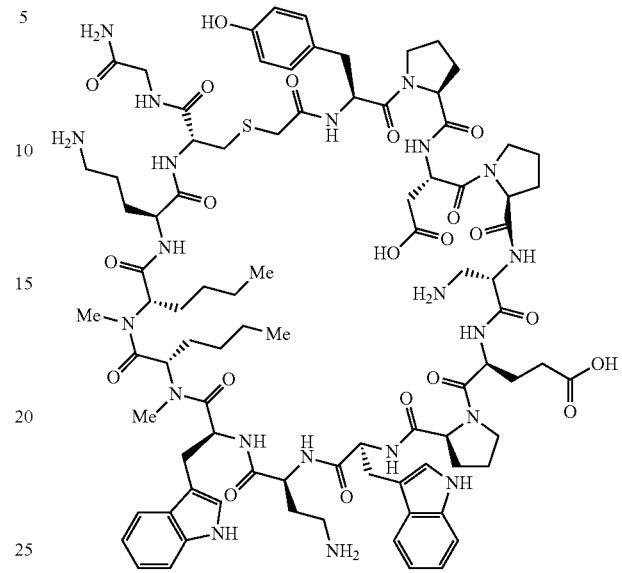

Molecular Weight: 1843.11

Example 1213 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-55% B over 25 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 99%.

Analysis LCMS Condition D: Retention time=1.33 min; ESI-MS(+) m/z 907.4 (M+2H).

Analysis LCMS Condition E: Retention time=1.23 min; ESI-MS(+) m/z 907.9 (M+2H).

Example 1214 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 92%.

Analysis LCMS Condition D: Retention time=1.33 min; ESI-MS(+) m/z 922.2 (M+2H).

Analysis LCMS Condition E: Retention time=1.22 min; ESI-MS(+) m/z 922.7 (M+2H).

Preparation of Example 1215

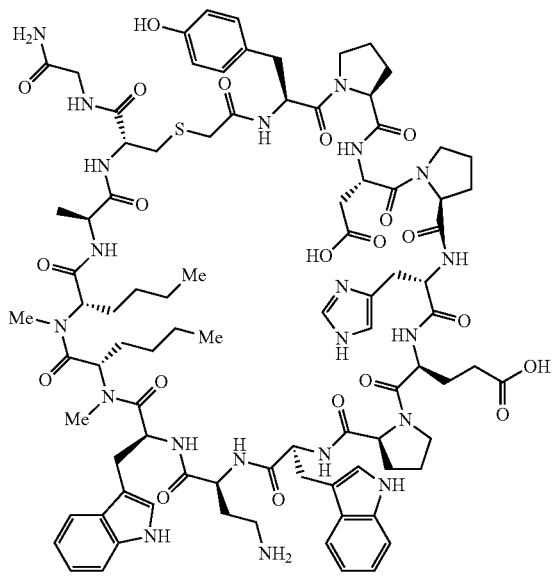

Molecular Weight: 1851.09

Preparation of Example 1216

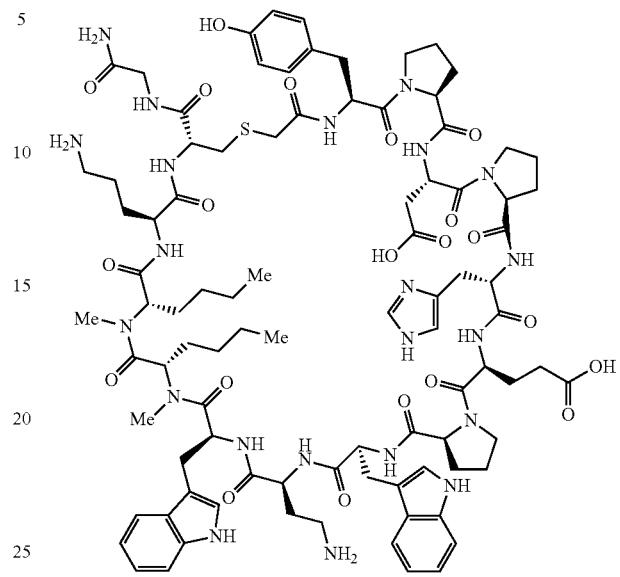

Molecular Weight: 1894.16

Example 1215 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 99%.

Analysis LCMS Condition D: Retention time=1.40 min; ESI-MS(+) m/z 926.5 (M+2H).

Analysis LCMS Condition E: Retention time=1.35 min; ESI-MS(+) m/z 926.2 (M+2H).

Example 1216 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 93%.

Analysis LCMS Condition D: Retention time=1.32 min; ESI-MS(+) m/z 948.1 (M+2H).

Analysis LCMS Condition E: Retention time=1.23 min; ESI-MS(+) m/z 948.0 (M+2H).

Preparation of Example 1217

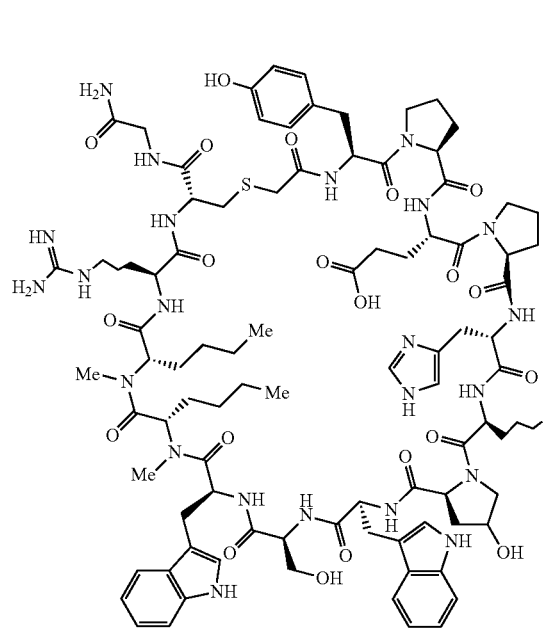

Molecular Weight: 1952.24

Example 1217 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 100%.

Analysis LCMS Condition D: Retention time=1.37 min; ESI-MS(+) m/z 977.6 (M+2H).

Analysis LCMS Condition E: Retention time=1.31 min; ESI-MS(+) m/z 976.7 (M+2H).

Preparation of Example 1218

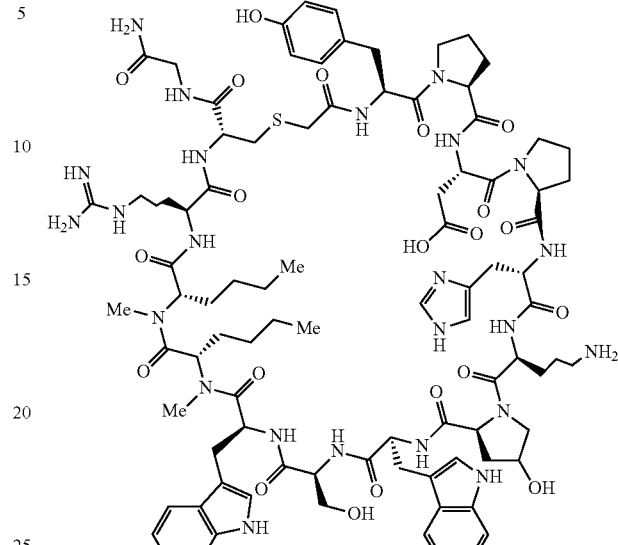

Molecular Weight: 1938.21

Example 1218 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-55% B over 25 minutes, then a 5-minute hold at 100% B; Flow: 20 mL/min. Fractions containing the desired product were combined and dried via centrifugal evaporation. The yield of the product was 1.9 mg, and its estimated purity by LCMS analysis was 99%.

Analysis LCMS Condition D: Retention time=1.43 min; ESI-MS(+) m/z 969.7 (M+2H).

Analysis LCMS Condition E: Retention time=1.40 min; ESI-MS(+) m/z 969.7 (M+2H).

Preparation of Example 1219

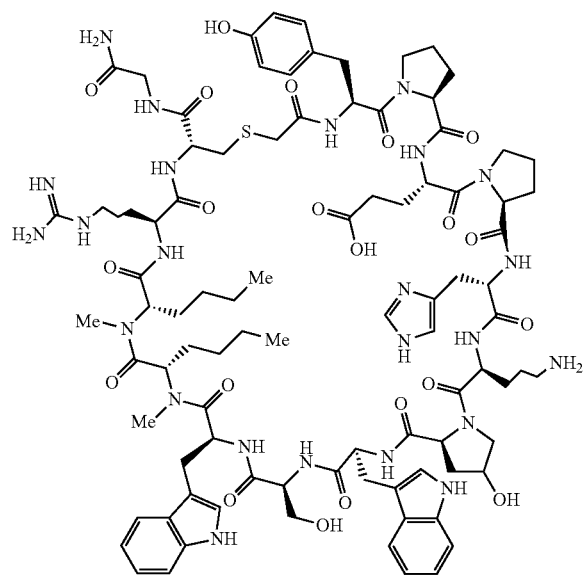

Molecular Weight: 1911.14

Example 1219 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 1.6 mg, and its estimated purity by LCMS analysis was 99%.

Analysis LCMS Condition D: Retention time=1.40 min; ESI-MS(+) m/z 956.7 (M+2H).

Analysis LCMS Condition E: Retention time=1.43 min; ESI-MS(+) m/z 956.7 (M+2H).

Preparation of Example 1220

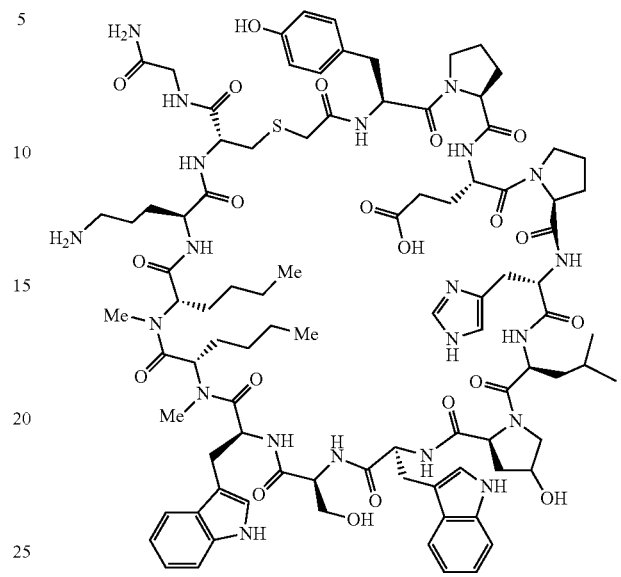

Molecular Weight: 1895.19

Example 1220 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-50% B over 25 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis LCMS Condition D: Retention time=1.32 min; ESI-MS(+) m/z 948.5 (M+2H).

Analysis LCMS Condition E: Retention time=1.21 min; ESI-MS(+) m/z 948.7 (M+2H).

Preparation of Example 1221

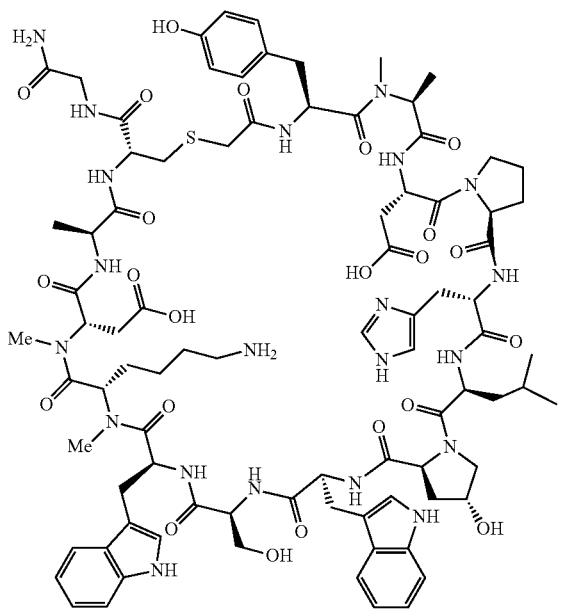

Molecular Weight: 1842.04

Example 1221 was prepared following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-50% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-45% B over 25 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 95%.

Analysis LCMS Condition D: Retention time=0.94 min; ESI-MS(+) m/z 922.1 (M+2H).

Analysis LCMS Condition E: Retention time=0.97 min; ESI-MS(+) m/z 921.5 (M+2H).

Preparation of Example 1222

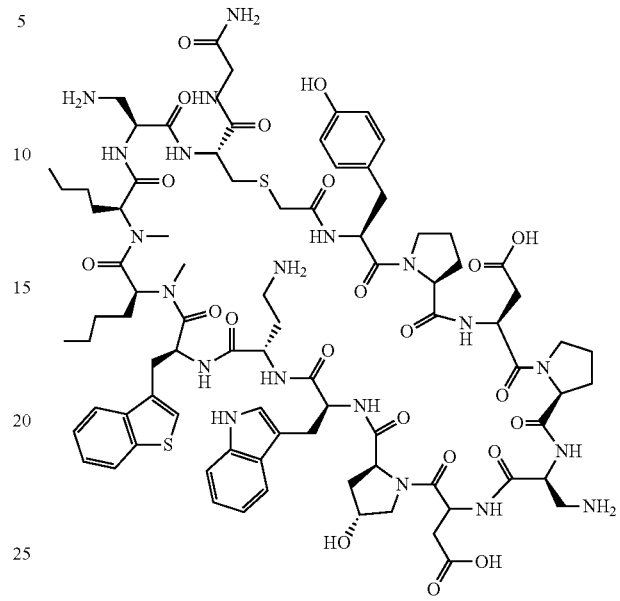

Molecular Weight: 1834.08

Example 1222 was prepared starting from Intermediate Resin C following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 95%.

Analysis LCMS Condition D: Retention time=1.37 min; ESI-MS(+) m/z 917.7 (M+2H).

Analysis LCMS Condition E: Retention time=1.31 min; ESI-MS(+) m/z 918.0 (M+2H).

ESI-HRMS(+) m/z:

Calculated: 917.4080 (M+2H).

Found: 917.4042 (M+2H).

Preparation of Example 1223

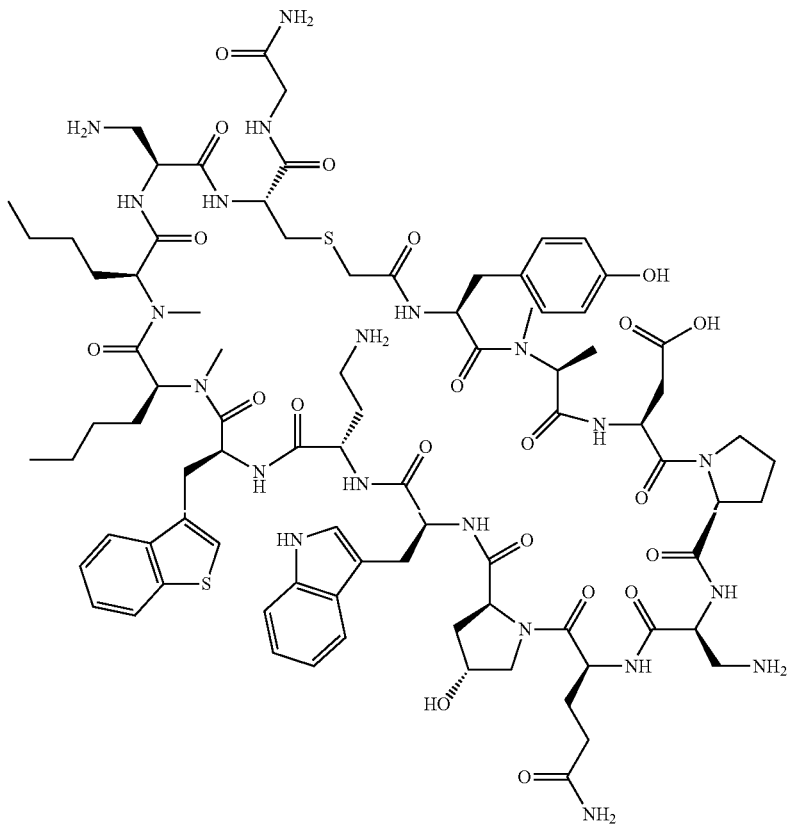

Molecular Weight: 1835.11

Example 1223 was prepared starting from Intermediate Resin C, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 95%.

Analysis LCMS Condition D: Retention time=1.52 min; ESI-MS(+) m/z 918.6 (M+2H).

Analysis LCMS Condition E: Retention time=1.38 min; ESI-MS(+) m/z 918.7 (M+2H).

ESI-HRMS(+) m/z:

Calculated: 917.9238 (M+2H).

Found: 917.9207 (M+2H).

Preparation of Example 1224

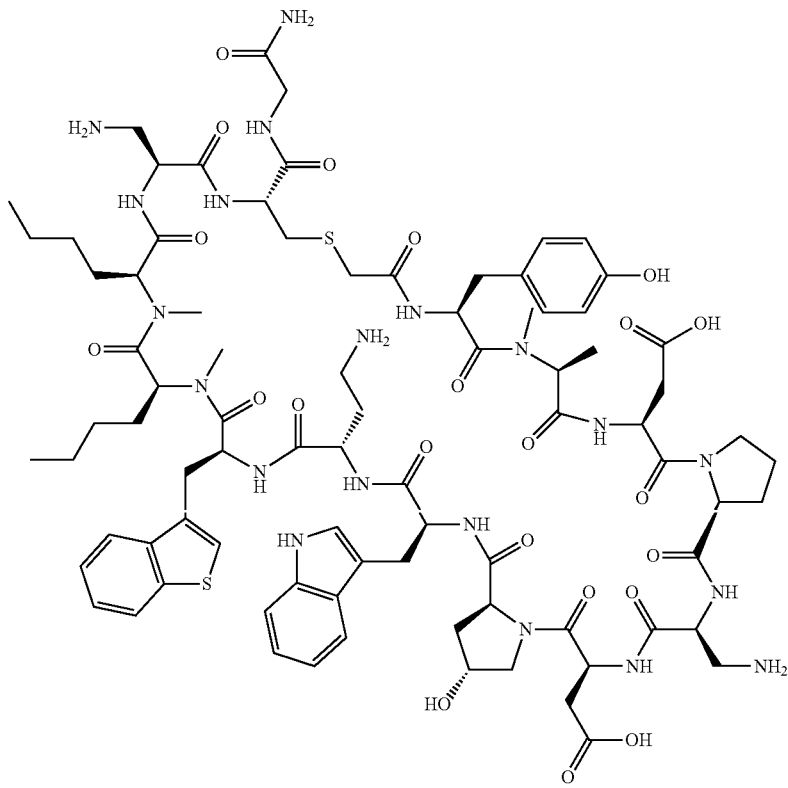

Molecular Weight: 1822.07

Example 1224 was prepared starting from Intermediate Resin C, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 95%.

Analysis LCMS Condition D: Retention time=1.39 min; ESI-MS(+) m/z 911.8 (M+2H).

Analysis LCMS Condition E: Retention time=1.40 min; ESI-MS(+) m/z 911.5 (M+2H).

ESI-HRMS(+) m/z:
Calculated: 911.4080 (M+2H).
Found: 911.4052 (M+2H).

Preparation of Example 1225

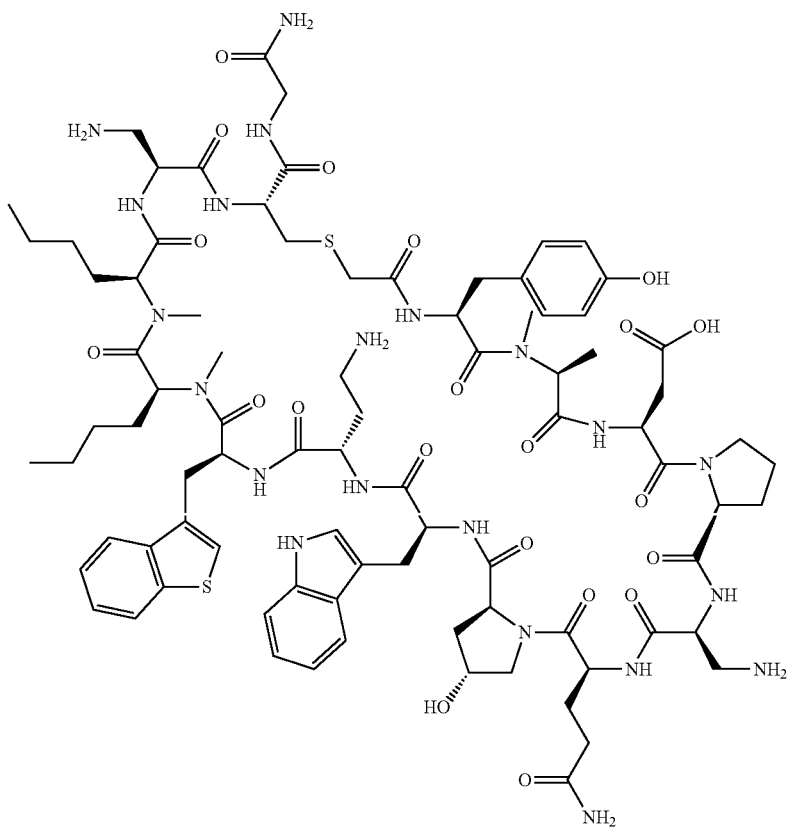

Molecular Weight: 1834.13

Example 1225 was prepared starting from Intermediate Resin C, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 minutes, then a 5-minute hold at 100% B; Flow: 20 mL/min. Fractions containing the desired product were combined and dried via centrifugal evaporation. The yield of the product was 1.8 mg, and its estimated purity by LCMS analysis was 98%.

Analysis LCMS Condition D: Retention time=1.45 min; ESI-MS(+) m/z 917.7 (M+2H).
Analysis LCMS Condition E: Retention time=1.41 min; ESI-MS(+) m/z 917.9 (M+2H).
ESI-HRMS(+) m/z:
Calculated: 917.4318 (M+2H).
Found: 917.4290 (M+2H).

Preparation of Example 1226

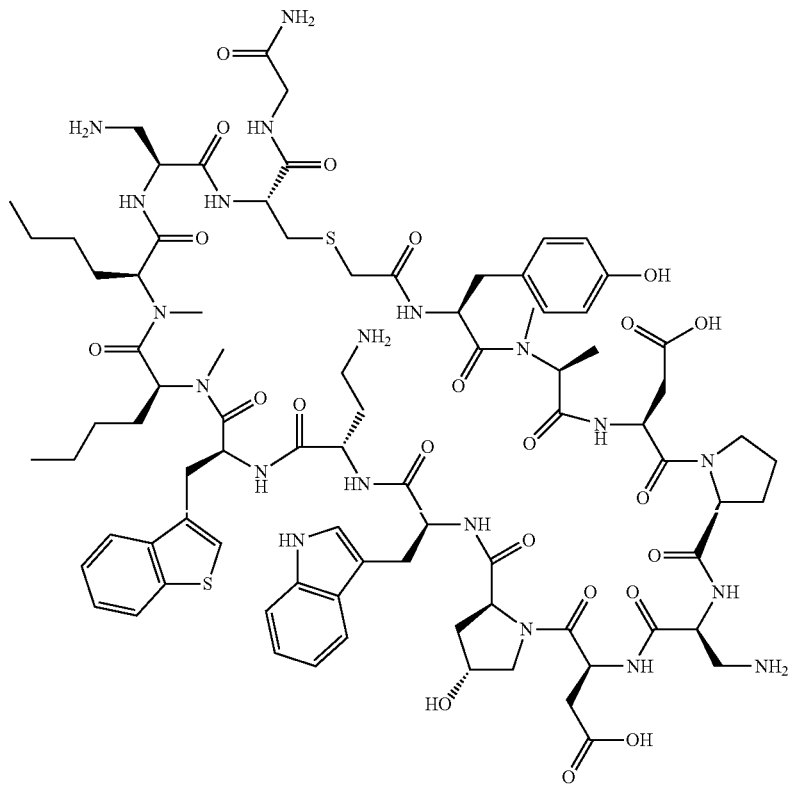

Molecular Weight: 1821.09

Example 1226 was prepared starting from Intermediate Resin C, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 5.1 mg, and its estimated purity by LCMS analysis was 95%.

Analysis LCMS Condition D: Retention time=1.38 min; ESI-MS(+) m/z 911.2 (M+2H).

Analysis LCMS Condition E: Retention time=1.40 min; ESI-MS(+) m/z 911.3 (M+2H).

ESI-HRMS(+) m/z:
Calculated: 910.9160 (M+2H).
Found: 910.9128 (M+2H).

Preparation of Example 1227

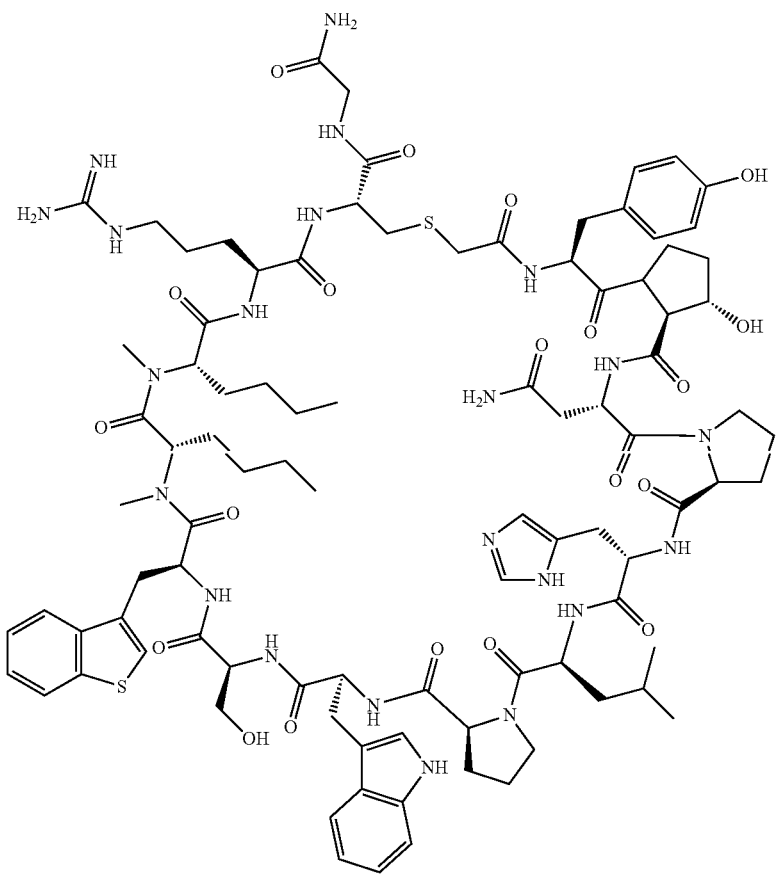

Molecular Weight: 1939.26

Example 1227 was prepared starting from Intermediate Resin F, following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 1.6 mg, and its estimated purity by LCMS analysis was 97%.

Analysis LCMS Condition D: Retention time=1.49 min; ESI-MS(+) m/z 970.1 (M+2H).

Analysis LCMS Condition E: Retention time=1.47 min; ESI-MS(+) m/z 970.2 (M+2H).

ESI-HRMS(+) m/z:

Calculated: 969.9607 (M+2H).

Found: 969.9592 (M+2H).

Preparation of Example 1228

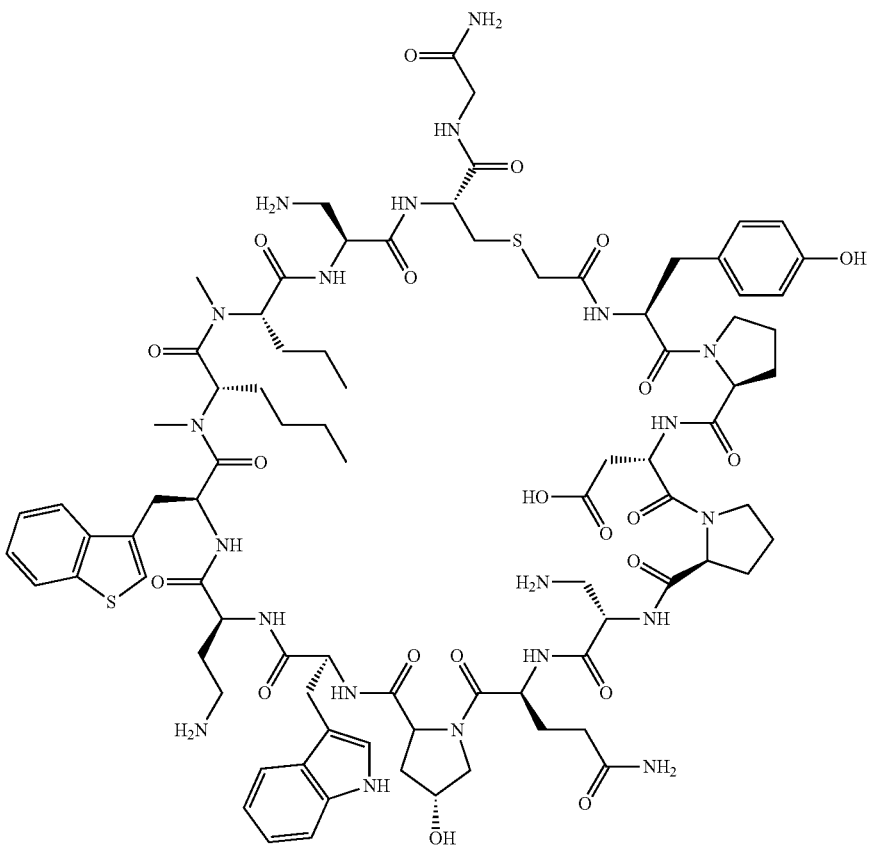

Molecular Weight: 1847.12

Example 1228 was prepared starting from Intermediate Resin C following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-60% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 2.8 mg, and its estimated purity by LCMS analysis was 98%.

Analysis LCMS Condition D: Retention time=1.45 min; ESI-MS(+) m/z 924.5 (M+2H).

Analysis LCMS Condition E: Retention time=1.34 min; ESI-MS(+) m/z 924.6 (M+2H).

ESI-HRMS(+) m/z:
Calculated: 923.9238 (M+2H).
Found: 923.9242 (M+2H).

Preparation of Example 1229

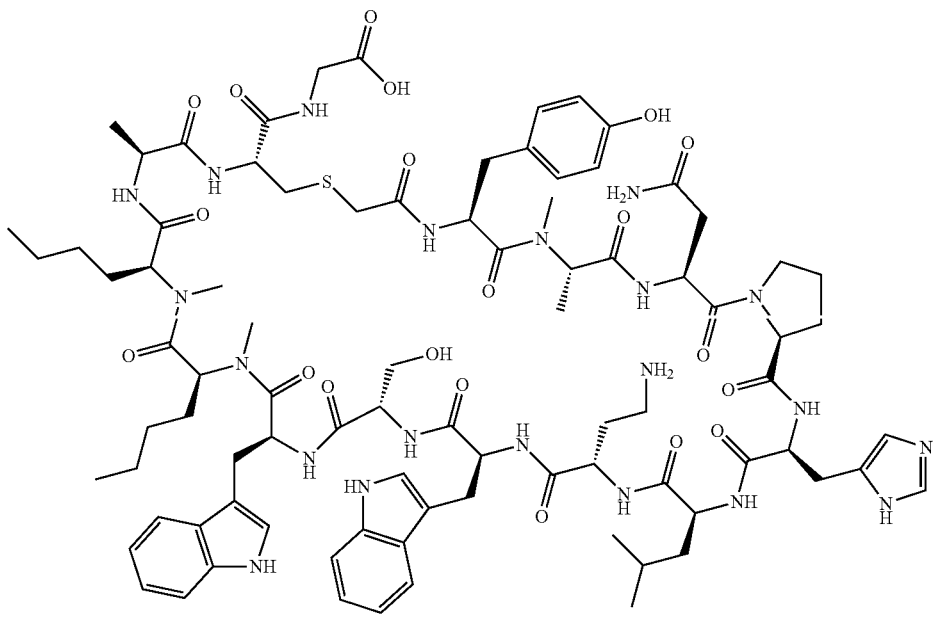

Molecular Weight: 1813.09

Example 1229 was prepared on Fmoc-Gly-Chlortrityl Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure "Symphony Method B: Final capping procedure", "Global Deprotection Method E", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 91%.

Analysis LCMS Condition D: Retention time=1.48 min; ESI-MS(+) m/z 907.3 (M+2H).

Analysis LCMS Condition E: Retention time=1.43 min; ESI-MS(+) m/z 907.2 (M+2H).

Preparation of Example 1230

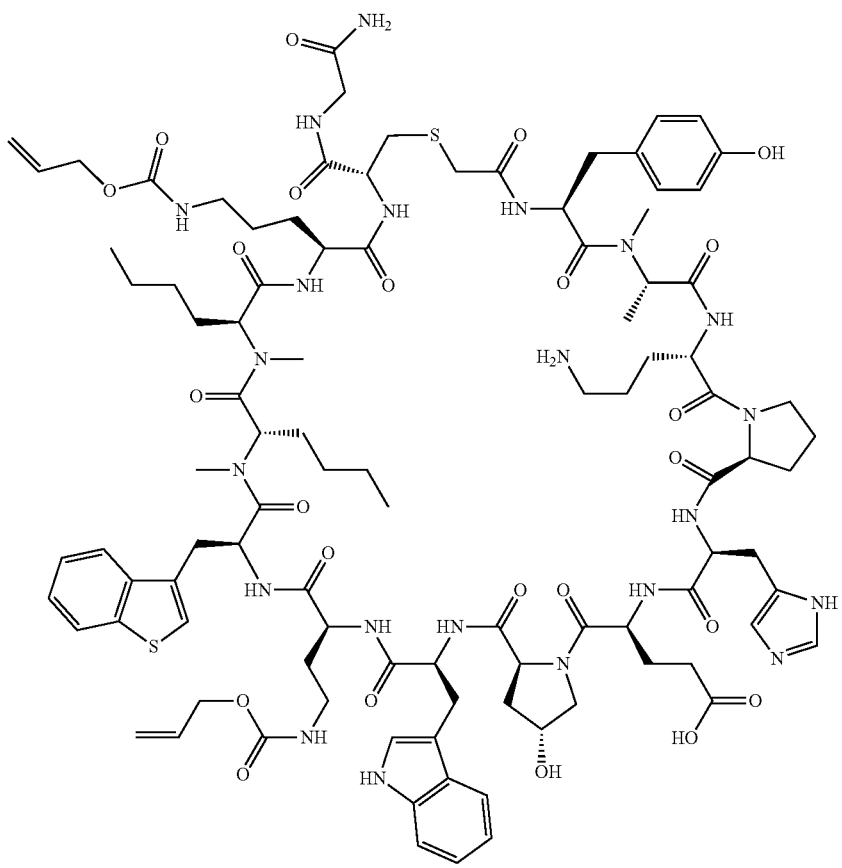

Molecular Weight: 2082.40

Example 1230 was prepared starting from Intermediate Resin H following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-65% B over 25 minutes, then a 5-minute hold at 100% B; Flow: 20 mL/min. Fractions containing the desired product were combined and dried via centrifugal evaporation. The yield of the product was 16.9 mg, and its estimated purity by LCMS analysis was 99%.

Analysis LCMS Condition D: Retention time=1.66 min; ESI-MS(+) m/z 1041.4 (M+2H).

Preparation of Example 1231

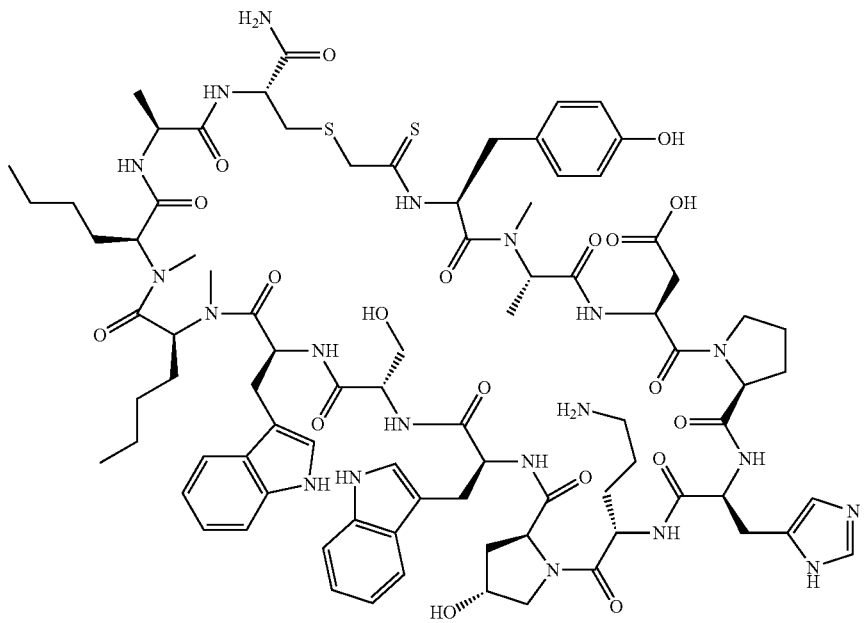

Molecular Weight: 1770.02

Example 1231 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 12.3 mg, and its estimated purity by LCMS analysis was 100%.

Analysis LCMS Condition D: Retention time=1.45 min; ESI-MS(+) m/z 886.4 (M+2H).

Analysis LCMS Condition E: Retention time=1.40 min; ESI-MS(+) m/z 886.0 (M+2H).

Preparation of Example 1232

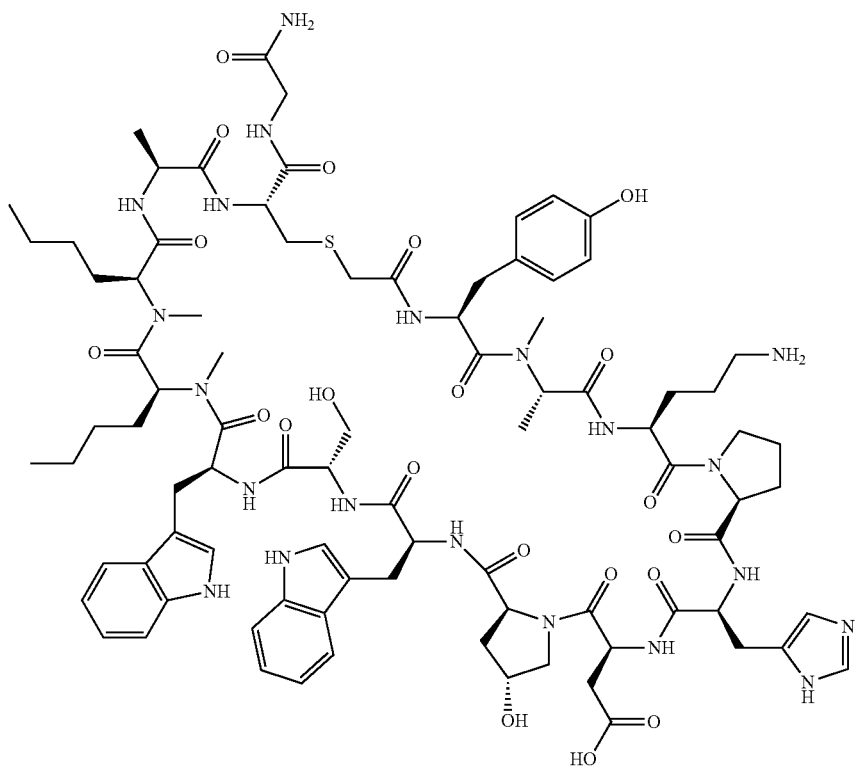

Molecular Weight: 1827.07

Example 1232 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 minutes, then a 5-minute hold at 100% B; Flow: 20 mL/min. Fractions containing the desired product were combined and dried via centrifugal evaporation. The yield of the product was 15.3 mg, and its estimated purity by LCMS analysis was 92%.

Analysis LCMS Condition D: Retention time=1.47 min; ESI-MS(+) m/z 914.6 (M+2H).

Preparation of Example 1233

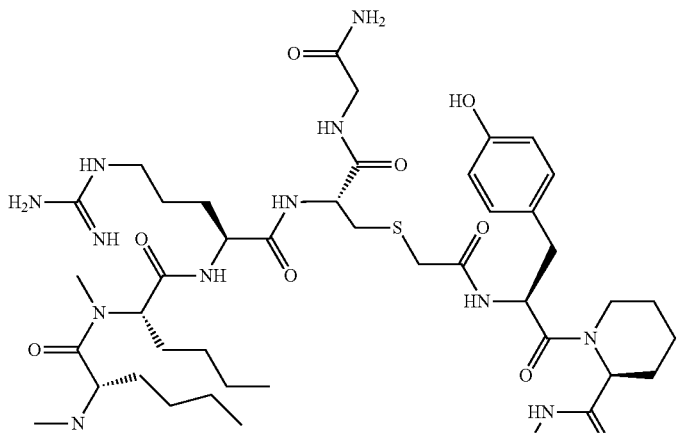

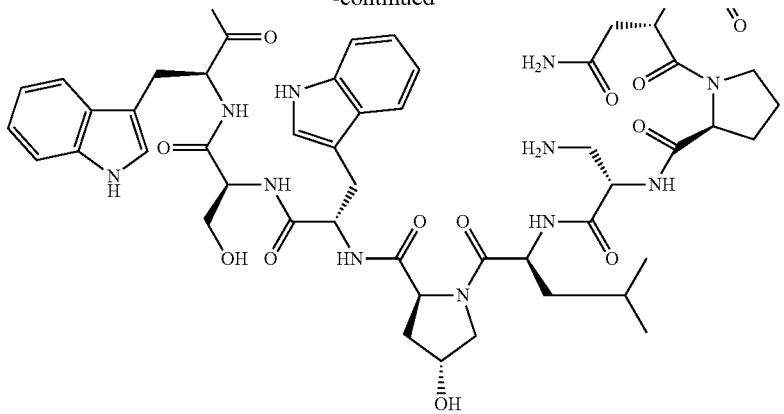

Molecular Weight: 1886.18

Example 1233 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 98%.

Analysis LCMS Condition D: Retention time=1.57 min; ESI-MS(+) m/z 944.1 (M+2H).

Analysis LCMS Condition E: Retention time=1.56 min; ESI-MS(+) m/z 944.0 (M+2H).

Preparation of Example 1234

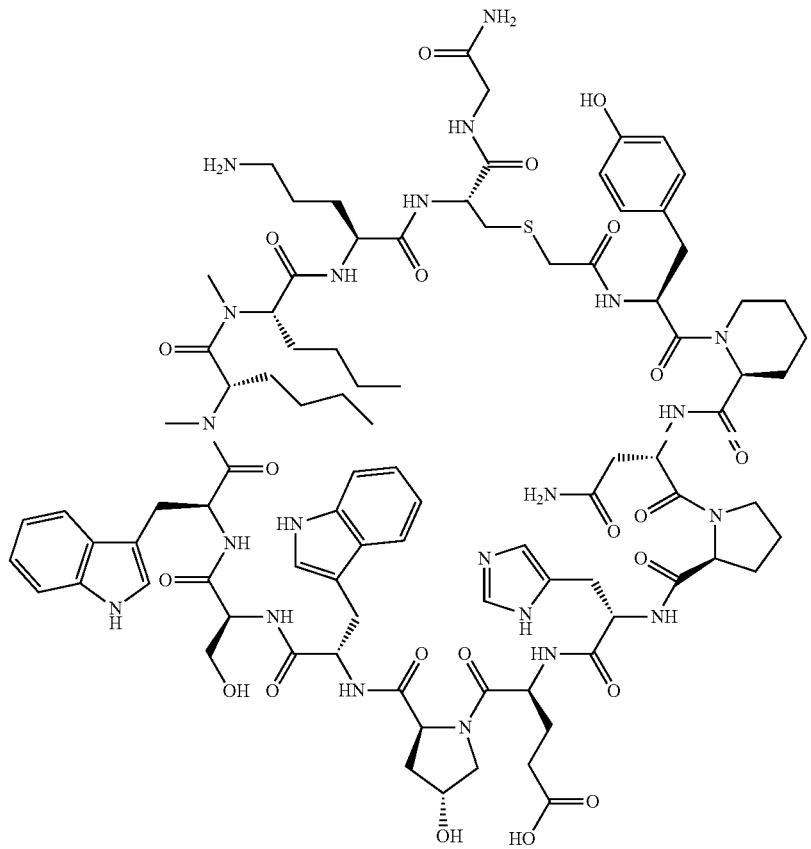

Molecular Weight: 1910.16

Example 1234 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 98%.

Analysis LCMS Condition D: Retention time=1.52 min; ESI-MS(+) m/z 956.3 (M+2H).

Analysis LCMS Condition E: Retention time=1.50 min; ESI-MS(+) m/z 956.0 (M+2H).

Preparation of Example 1235

Example 1235 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 6.5 mg, and its estimated purity by LCMS analysis was 100%.

Analysis LCMS Condition D: Retention time=1.54 min; ESI-MS(+) m/z 923.0 (M+2H).

Analysis LCMS Condition E: Retention time=1.52 min; ESI-MS(+) m/z 923.2 (M+2H).

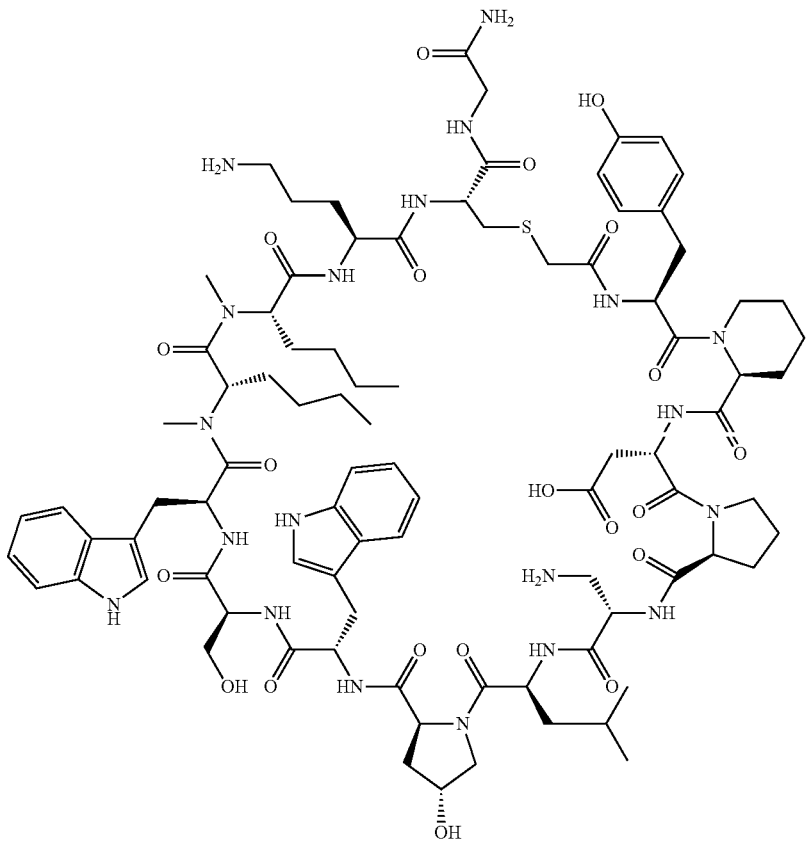

Molecular Weight: 1844.14

Preparation of Example 1236

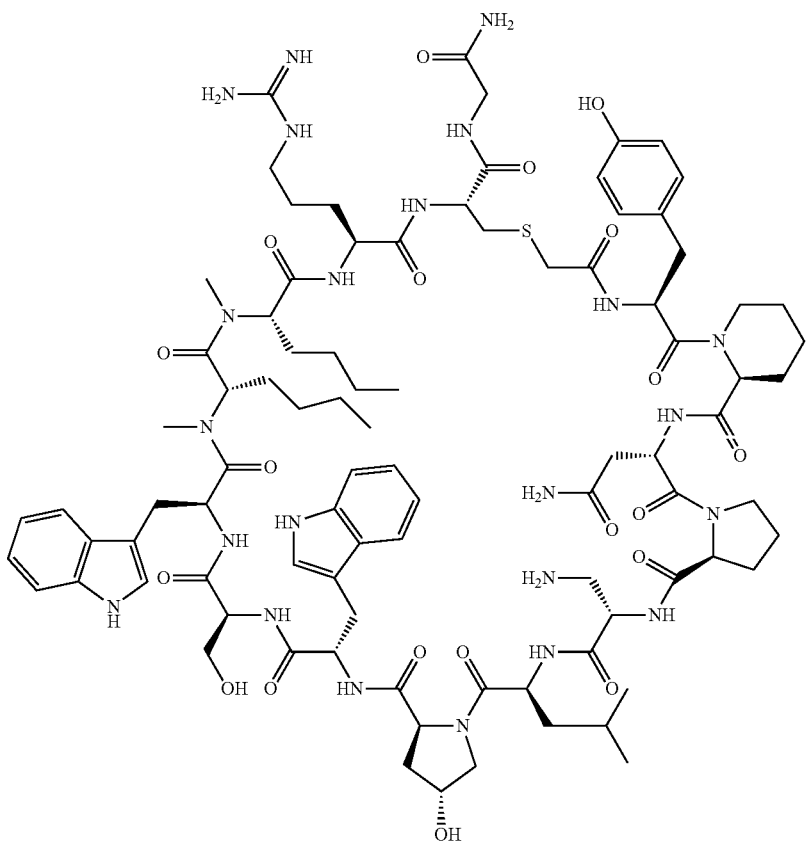

Molecular Weight: 1885.19

Example 1236 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 82%.

Analysis LCMS Condition D: Retention time=1.58 min; ESI-MS(+) m/z 943.7 (M+2H).

Analysis LCMS Condition E: Retention time=1.55 min; ESI-MS(+) m/z 943.8 (M+2H).

Preparation of Example 1237

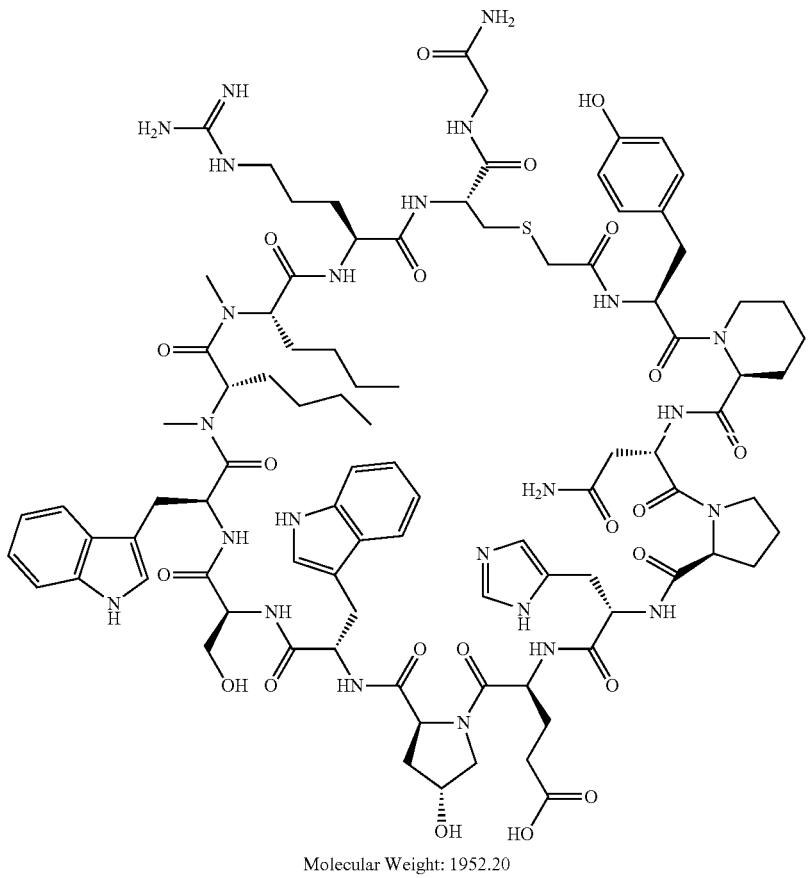 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N2CCCC[C@H]2C(=O)N[C@@H](CC(N)=O)C(=O)N2CCC[C@H]2C(=O)N[C@@H](Cc2cnc[nH]2)C(=O)N[C@@H](CCC(=O)O)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

Molecular Weight: 1952.20

Example 1237 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 97%.

Analysis LCMS Condition D: Retention time=1.54 min; ESI-MS(+) m/z 977.0 (M+2H).

Analysis LCMS Condition E: Retention time=1.51 min; ESI-MS(+) m/z 977.0 (M+2H).

Preparation of Example 1238

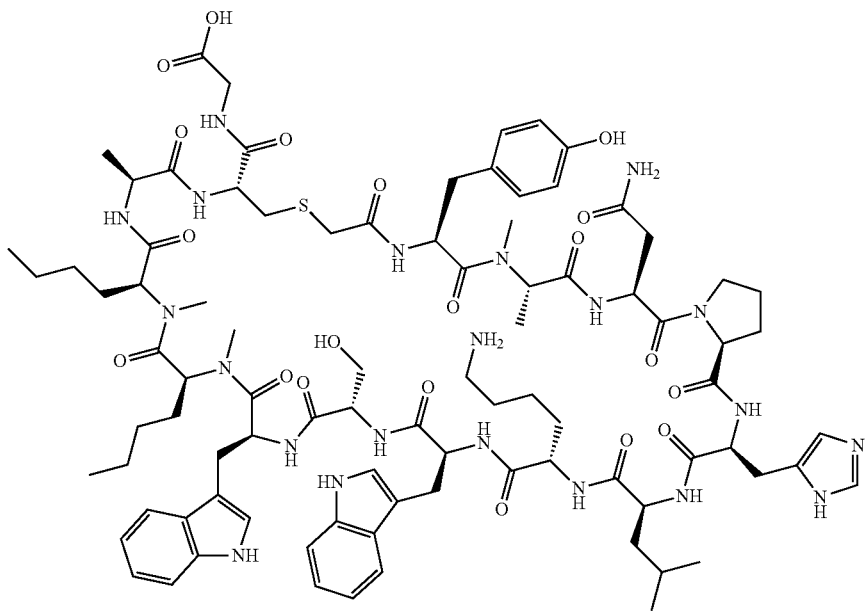

Molecular Weight: 1841.14

Example 1238 was prepared on Gly-Chlortrityl Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method E", and "Cyclization Method D".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 88%.

Analysis LCMS Condition D: Retention time=1.47 min; ESI-MS(+) m/z 921.4 (M+2H).

Analysis LCMS Condition E: Retention time=1.42 min; ESI-MS(+) m/z 921.3 (M+2H).

ESI-HRMS(+) m/z:
Calculated: 920.9638 (M+2H).
Found: 920.9628 (M+2H).

Preparation of Example 1239

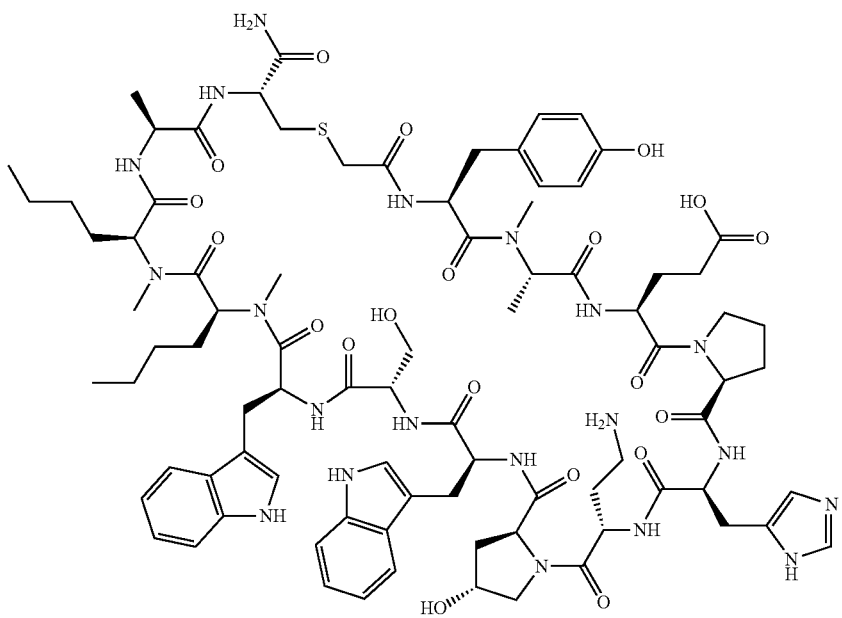

Molecular Weight: 1770.02

Example 1239 was prepared on Rink Resin following the general synthetic sequence described for the preparation of Example 0001, composed of the following general procedures: "Symphony Method B: Resin-swelling procedure", "Symphony Method B: Standard-coupling procedure", "Symphony Method B: Secondary amine-coupling procedure", "Symphony Method B: Final capping procedure", "Global Deprotection Method F", and "Cyclization Method D".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 93%.

Analysis LCMS Condition D: Retention time=1.42 min; ESI-MS(+) m/z 885.7 (M+2H).

Analysis LCMS Condition E: Retention time=1.36 min; ESI-MS(+) m/z 885.8 (M+2H).

ESI-HRMS(+) m/z:
Calculated: 885.4270 (M+2H).
Found: 885.4269 (M+2H).

Analytical Data:
Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis LCMS Condition A:
Column: BEH C18, 2.1×50 mm, 1.7-μm particles; Mobile Phase A: water with 0.05% TFA; Mobile Phase B:Acetonitrile with 0.05% TFA; Temperature: 50° C.; Gradient: 2% B to 98% B over 2 min., then a 0.5 min. hold at 98% B; Flow: 0.8 mL/min; Detection: UV at 220 nm.

Analysis LCMS Condition C:
Column: BEH C18, 2.1×50 mm, 1.7-μm particles; Mobile Phase A: water with 0.2% Formic Acid and 0.01% TFA; Mobile Phase B: Acetonitrile with 0.2% Formic acid an 0.01% TFA; Temperature: 50° C.; Gradient: 2% B to 80% B over 2 min., 80% B to 98% B over 0.1 minute then a 0.5 min. hold at 98% B; Flow: 0.8 mL/min; Detection: UV at 220 nm.

Analysis LCMS Condition D:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 min., then a 0.75-minute hold at 100% B; Flow: 1.11 mL/min; Detection: UV at 220 nm.

Analysis LCMS Condition E:
Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; temperature: 50° C.; Gradient: 0-100% B over 3 min., then a 0.75-minute hold at 100% B; Flow: 1.11 mL/min; Detection: UV at 220 nm.

Analysis LCMS Condition F:
Column: Waters Xbridge C18, 2.1×50 mm; Mobile Phase A: 5:95 acetonitrile:water with 10 mM ammonium acetate; Mobile Phase B: 95:5 acetonitrile:water with 10 mM ammonium acetate; Temperature: 35° C.; Gradient: 0-100% B over 4 min., then a 1-minute hold at 100% B; Flow: 4 mL/min; Detection: UV at 220 nm.

Analysis HPLC Condition B:
Column: YMC Pack ODS-AQ 3 um 150×4.6 mm Mobile Phase A: water with 0.1% TFA; Mobile Phase B: Acetonitrile with 0.1% TFA; Temperature: 40° C.; Gradient: from 10% B to 100% B over 10 to 40 min.; Flow: 1 mL/min; Detection: UV at 220 nm.

General Procedures:
Prelude Method A:
All manipulations were performed under automation on a Prelude peptide synthesizer (Protein Technologies). All procedures unless noted were performed in a 10 or 45 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed below.

Resin-Swelling Procedure:
To a 40 mL polypropylene solid-phase reaction vessel was added Merrifield:Sieber resin (140 mg, 0.100 mmol). The resin was washed (swelled) three times as follows: to the reaction vessel was added DMF (5.0 mL) and DCM (5.0 mL), upon which the mixture was periodically agitated with N2 bubbling from the bottom of the reaction vessel for 10 min. before the solvent was drained through the frit.

Single-Coupling Procedure:
To the reaction vessel containing resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 60 seconds before the solution was drained through the frit. To the reaction vessel was added the amino acid (0.2M in DMF, 5.0 mL, 10 eq), then HATU (0.2M in DMF, 5.0 mL, 10 eq), and finally DIPEA (0.8M in DMF, 2.5 mL, 20 eq). The mixture was periodically agitated for 60 min., then the reaction solution was drained through the frit. The resin was washed successively four times as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Secondary Amine-Coupling Procedure:
To the reaction vessel containing resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2M in DMF, 2.5 mL, eq), then HATU (0.2M in DMF, 2.5 mL, 5 eq), and finally DIPEA (0.8M in DMF, 1.5 mL, 12 eq). The mixture was periodically agitated for 300 min., then the reaction solution was drained through the frit. The resin was twice washed as follows: for each wash, DMF (4.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Custom Amino Acids-Coupling Procedure:

To the reaction vessel containing resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added the amino acid (0.2 M in DMF, 0.5 to 2.5 mL, 1 to 5 eq), then HATU (0.2 M in DMF, 0.5 to 2.5 mL, 1 to 5 eq), and finally DIPEA (0.8 M in DMF, 0.5 to 1.5 mL, 4 to 12 eq). The mixture was periodically agitated for 60 min. to 600 min., then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added a solution of acetic anhydride:DIEA:DMF (10:1:89 v/v/v, 5.0 mL). The mixture was periodically agitated for 10 min., then the solution was drained through the frit. The resin was washed successively four times as follows: for each wash, DMF (4.0 mL) was added through the top of the vessel and the resulting mixture was periodically agitated for 90 seconds before the solution was drained through the frit. The resulting resin was used directly in the next step.

Chloroacetyl Chloride Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added 3.0 mL of a solution of DIPEA (4.0 mmol, 0.699 mL, 40 eq), and chloroacetyl chloride (2.0 mmol, 0.160 mL, 20 eq) in DMF. The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

Chloroacetic Acid Coupling Procedure A:

To the reaction vessel containing the resin from the previous step was added piperidine:DMF (20:80 v/v, 5.0 mL). The mixture was periodically agitated for 3 min. and then the solution was drained through the frit. To the reaction vessel was added piperidine:DMF (20:80 v/v, 5.0 mL). The mixture was periodically agitated for 3 min. and then the solution was drained through the frit. The resin was washed successively five times as follows: for each wash, DMF (4.0 mL) was added through the top of the vessel and the resulting mixture was periodically agitated for 30 seconds before the solution was drained through the frit. To the reaction vessel was added DMF (2.0 mL), chloroacetic acid (1.2 mmol, 113 mg, 12 eq), and N,N'-Diisopropylcarbodiimide (1.2 mmol, 0.187 mL, 12 eq). The mixture was periodically agitated for 12 to 18 hours, then the solution was drained through the frit. The resin was washed successively three times as follows: for each wash, DMF (4.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit.

CEM Method A:

All manipulations were performed under automation on a CEM Liberty microwave peptide synthesizer (CEM Corporation, Matthews, N.C.). All procedures unless noted were performed in a 30 or 125 mL polypropylene tube fitted with a bottom frit to a CEM Discovery microwave unit. The tube connects to a the CEM Liberty synthesizer through both the bottom and the top of the tube. DMF and DCM can be added through the top and bottom of the tube, which washes down the sides of the tube equally. All solutions are removed through the bottom of the tube except while transferring resin from the top. "Periodic bubbling" describes a brief bubbling of N2 gas through the bottom frit. Amino acid solutions were generally not used beyond three weeks from preparation. HATU solution was used within 5 days of preparation. DMF=dimethylformamide; HCTU=2-(6-Chloro-1-H-benzotriazol-1-yl)-1,1,3,3-tetramethyluronium; HATU=1-[Bis(dimethylamino)methylene]-1H-1,2,3-triazolo[4,5-b]pyridinium 3-oxid hexafluorophosphate; DIPEA=diisopropylethylamine; Sieber=Fmoc-amino-xanthen-3-yloxy, where "3-yloxy" describes the position and type of connectivity to the polystyrene resin. The resin used is Merrifield polymer (polystyrene) with a Sieber linker (Fmoc-protected at nitrogen); 100-200 mesh, 1% DVB, 0.71 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "CEM Method A" describe an experiment performed on a 0.100 mmol scale, where the scale is determined by the amount of Sieber linker bound to the resin. This scale corresponds to approximately 140 mg of the Sieber-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Secondary amine-coupling procedure" described below. Coupling of chloroacetyl group to the N-terminus of the peptide is described by the "Chloroacetyl chloride coupling procedure" or "Chloroacetic acid coupling procedure" detailed above.

Resin-Swelling Procedure:

To 50 ml, polypropylene conical tube was added Merrifield:Sieber resin (140 mg, 0.100 mmol). Then DMF (7 mL) was added to the tube followed by DCM (7 mL). The resin was then transferred to the reaction vessel from top of the vessel. The procedure is repeated additionally two times.

DMF (7 mL) was added followed by DCM (7 mL). The resin was allowed to swell with N2 bubbling from the bottom of the reaction vessel for 15 min. before the solvent was drained through the frit.

Standard Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH, which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Double-Couple Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added the amino acid (0.2M in DMF, 2.5 mL, 5 eq), HATU (0.5M in DMF, 1.0 mL, 5 eq), and DIPEA (2M in NMP, 0.5 mL, 10 eq). The mixture was mixed by N2 bubbling for 5 min. at 75° C. for all amino acids, except Fmoc-Cys(Trt)-OH and Fmoc-His(Trt)-OH which are coupled at 50° C., the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

Custom Amino Acids-Coupling Procedure:

To the reaction vessel containing resin from the previous step was added a solution of piperidine:DMF (20:80 v/v, 5.0 mL). The mixture was periodically agitated for 3 min. and then the solution was drained through the frit. To the reaction vessel was added a solution of piperidine:DMF (20:80 v/v, 5.0 mL). The mixture was periodically agitated for 3 min. and then the solution was drained through the frit. The resin was washed successively three times as follows: DMF (7 mL) wash from top, followed by DMF (7 mL) wash from bottom and finally with DMF (7 mL) wash from top. To the reaction vessel was added the amino acid solution (1.25 mL to 5 mL, 2.5 eq to 10 eq) containing HATU (2.5 eq to 10 eq), and finally DIPEA (2M in NMP, 0.5 mL to 1 mL, 10 to 20 eq). The mixture was mixed by N2 bubbling for 5 min. to 2 hours at 25° C. to 75° C., then the reaction solution was drained through the frit. The resin was washed successively three times as follows: DMF (7 mL) wash from top, followed by DMF (7 mL) wash from bottom and finally with DMF (7 mL) wash from top. To the reaction vessel was added a solution of acetic anhydride:DIEA:DMF (10:1:89 v/v/v, 5.0 mL). The mixture was periodically bubbled for 2 min. at 65° C., then the solution was drained through the frit. The resin was washed successively three times as follows: DMF (7 mL) wash from top, followed by DMF (7 mL) wash from bottom and finally with DMF (7 mL) wash from top. The resulting resin was used directly in the next step.

N-methylation on-resin Method A (Turner, R. A.; Hauksson, N. E.; Gipe, J. H.; Lokey, R. S. *Org. Lett.* 2013, 15(19), 5012-5015):

All manipulations were performed manually unless noted. The procedure of "N-methylation on-resin Method A" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale.

The resin was transferred into a 25 mL fritted syringe. To the resin was added piperidine:DMF (20:80 v/v, 5.0 mL). The mixture was shaken for 3 min. and then the solution was drained through the frit. The resin was washed 3 times with DMF (4.0 mL). To the reaction vessel was added piperidine:DMF (20:80 v/v, 4.0 mL). The mixture was shaken for 3 min. and then the solution was drained through the frit. The resin was washed successively three times with DMF (4.0 mL) and three times with DCM (4.0 mL). The resin was suspended in DMF (2.0 mL) and ETHYL TRIFLUOROACETATE (0.119 ml, 1.00 mmol), 1,8-DIAZABICYCLO[5.4.0]UNDEC-7-ENE (0.181 ml, 1.20 mmol). The mixture was placed on a shaker for 60 min. The solution was drained through the frit. The resin was washed successively three times with DMF (4.0 mL) and three times with DCM (4.0 mL).

The resin was washed three times with dry THF (2.0 mL) to remove any residual water. In an oven dried 4.0 mL vial was added THF (1.0 mL) and TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit and the resin was washed with three times with dry THF (2.0 mL) to remove any residual water. In an oven dried 4.0 mL vial was added THF (1.0 mL), TRIPHENYLPHOSPHINE (131 mg, 0.500 mmol) on dry 4 Å molecular sieves (20 mg). The solution was transferred to the resin and diisopropyl azodicarboxylate (0.097 mL, 0.5 mmol) was added slowly. The resin was stirred for 15 min. The solution was drained through the frit. The resin was washed successively three times with DMF (4.0 mL) and three times with DCM (4.0 mL). The resin was suspended in Ethanol (1.0 mL) and THF (1.0 mL), and SODIUM BOROHYDRIDE (37.8 mg, 1.000 mmol) was added. The mixture was stirred for 30 min. and drained. The resin was washed successively three times with DMF (4.0 mL) and three times with DCM (4.0 mL).

Global Deprotection Method B:

All manipulations were performed manually unless noted. The procedure of "Global Deprotection Method B" describes an experiment performed on a 0.100 mmol scale, where the scale is determined by the amount of Sieber linker bound to the resin. The procedure can be scaled beyond 0.100 mmol scale by adjusting the described volumes by the multiple of the scale. A "deprotection solution" was prepared using trifluoroacetic acid:triisopropylsilane:dithiothreitol (94:3:3 v:v: w). The resin was removed from the reaction vessel and transferred to a 25 mL fritted syringe to which was added the "deprotection solution" (5.0 mL). The mixture was stirred for 5 min. The solution was filtered and the filtrate was dripped into diethyl ether (30 mL). The precipitated solid was centrifuged for 3 min. The supernatant solution was decanted and the solid was resuspended in diethyl ether (25 mL). The suspension was centrifuged for 3 min. The procedure was repeated once more and the remaining solid was dried under high vacuum to yield a white to off-white solid.

Cyclization Method C:

All manipulations were performed manually unless noted. The procedure of "Cyclization Method C" describes an experiment performed on a 0.100 mmol scale, where the scale is determined by the amount of Sieber linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in a solution of acetonitrile:aqueous 0.1M ammonium bicarbonate buffer (11 mL:24 mL or similar ratio), and the solution was then carefully adjusted to pH=8.5-9.0 using aq NaOH (1.0M). The solution was then stirred for 12 to 18 hours. The reaction solution was concentrated and the residue was then dissolved in acetonitrile:water. This solution was subjected to reverse-phase HPLC purification to afford the desired cyclic peptide.

Preparation of (S)-2-((((9H-fluoren-9-yl)methoxy) carbonyl)(methyl)amino)-3-(naphthalen-1-yl)propanoic acid (Freidinger, R. M.; Hinkle, J. S.; Perlow, D. S.; Arison, B. H. *J. Org. Chem.* 1983, 48(1), 77-81.)

Scheme:

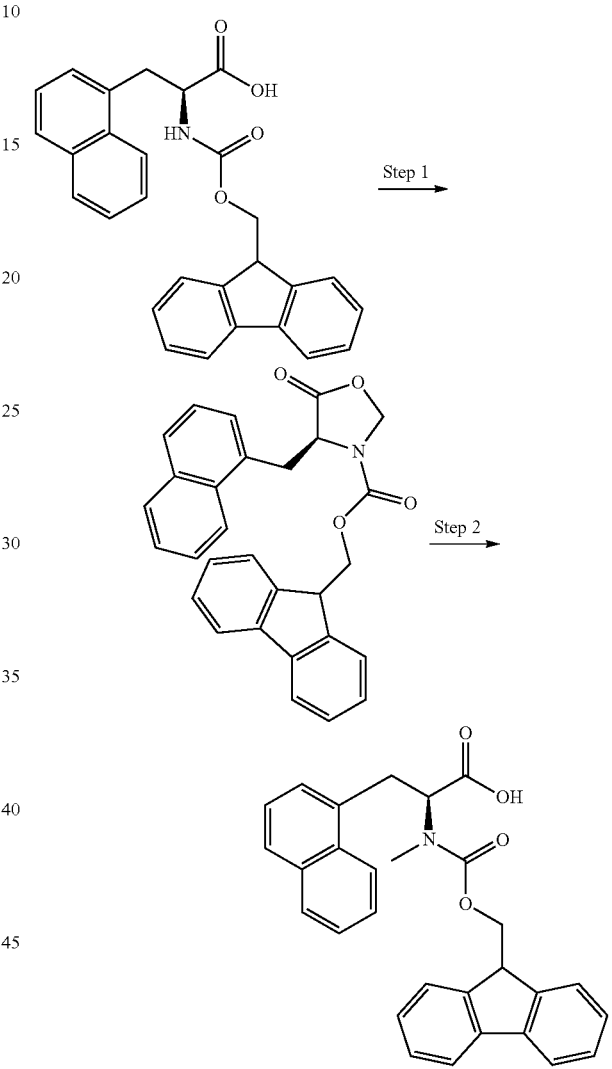

Step 1:

To a suspension of (S)-2-((((9H-fluoren-9-yl)methoxy) carbonyl)amino)-3-(naphthalen-1-yl)propanoic acid (1.00 g, 2.286 mmol) in Toluene (50 ml) was added the paraformaldehyde (0.500 g, 16.65 mmol) and p-toluenesulfonic acid monohydrate (0.435 g, 2.286 mmol). The reaction mixture was heated to reflux for 16 hours with azeotropic water removal using a Dean-Stark trap. The reaction was cooled to room temperature and diluted with 20 mL of EtOAc. The organic phase was washed with 2×50 mL of an aqueous solution of saturated NaHCO₃ and then dried over anhydrous sodium sulfate. After filtration and concentration a colorless oil was obtained. Purification by column chromatography on silica gel using 30% EtOAc/Hexanes lead to the desired product as a colorless oil. (S)-(9H-fluoren-9-yl)methyl 4-(naphthalen-1-ylmethyl)-5-oxooxazolidine-3-carboxylate 0.750 g (73%) $^1$H NMR (400 MHz, DMSO-d$_6$) δ 7.88 (d, J=7.5 Hz, 3H), 7.82 (d, J=8.1 Hz, 2H), 7.68-7.51 (m, 2H), 7.49-7.21 (m, 8H), 5.18 (d, J=4.0 Hz, 1H), 4.40 (br. s., 4H), 3.31 (br. s., 4H)

Step 2:

To a solution of (S)-(9H-fluoren-9-yl)methyl 4-(naphthalen-1-ylmethyl)-5-oxooxazolidine-3-carboxylate (0.750 g, 1.669 mmol) in DCM (8.0 ml) was added trifluoroacetic acid (8.0 mL, 104 mmol) followed by triethylsilane (0.799 ml, 5.01 mmol). The reaction mixture was allowed to stir at room temperature for 24 hours. Reaction mixture was dried on rotovap. The crude oil was dissolved in 15.0 mL of DCM and evaporated on rotovap twice. The crude product was obtained as an off-white gum and was purified by silica gel chromatography using dichloromethane and methanol as eluant. The desired product, (S)-2-((((9H-fluoren-9-yl)methoxy)carbonyl)(methyl)amino)-3-(naphthalen-1-yl)propanoic acid, was obtained as a colorless gum (0.692 g, 46%).

(S)-2-((((9H-fluoren-9-yl)methoxy)carbonyl)amino)-3-(3-chloro-4-fluorophenyl)propanoic acid (Ross, A. J.; Lang, H. L.; Jackson, R. F. W. *J. Org. Chem.*, 2010, 75, 245-248.)

Scheme:

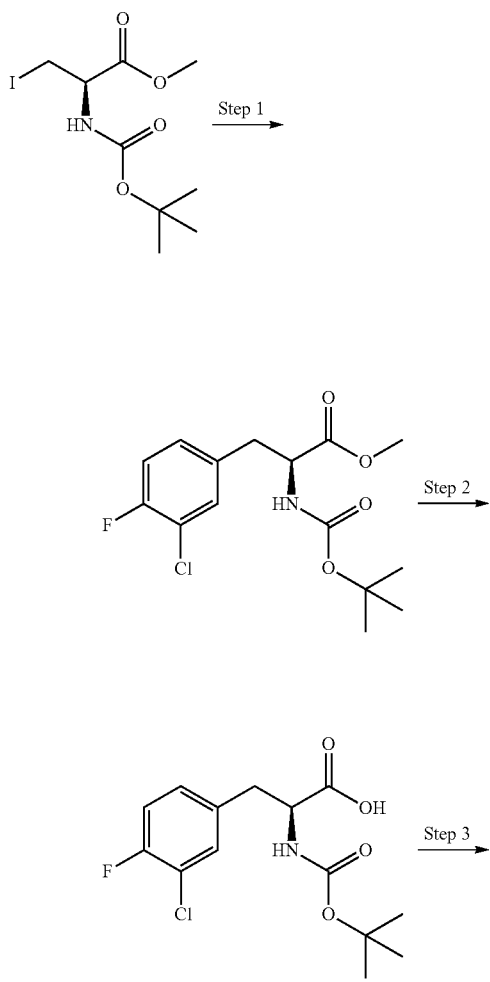

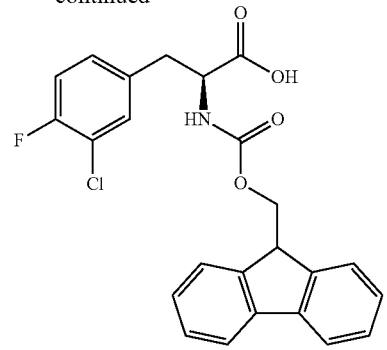

Step 1:

To an oven dried 8 mL vial with teflon cap purged with N$_2$ was added Zinc dust (298 mg, 4.56 mmol), DMF (1.5 mL), and iodine (57.8 mg, 0.228 mmol). To this mixture was added (R)-methyl 2-((tert-butoxycarbonyl)amino)-3-iodopropanoate (500 mg, 1.519 mmol), immediately followed by iodine (57.8 mg, 0.228 mmol). Pd$_2$(dba)$_3$ (69.6 mg, 0.076 mmol), 2-dicyclohexylphosphino-2'6-dimethoxybiphenyl (62.4 mg, 0.152 mmol) and 4-bromo-2-chloro-1-fluorobenzene (477 mg, 2.279 mmol) were then added and the reaction mixture was allowed to stir at 50° C. for 3 hours. The crude mixture was diluted in 30 mL of EtOAc and DMF was removed with 4 aqueous washes. The organic phase was dried over anhydrous sodium sulfate. The solution was filtered and concentrated, and the crude product was purified by silica gel chromatography using 100% hexanes to 30% EtOAc/Hexanes. The desired product was obtained as a pale yellow oil, (S)-methyl 2-((tert-butoxycarbonyl)amino)-3-(3-chloro-4-fluorophenyl)propanoate (0.174 g, 35%). $^1$H NMR (400 MHz, chloroform-d) δ 7.27 (s, 1H), 7.17 (dd, J=6.9, 1.4 Hz, 1H), 7.11-6.93 (m, 1H), 5.03 (d, J=6.8 Hz, 1H), 4.55 (d, J=6.4 Hz, 1H), 3.73 (s, 3H), 3.19-3.04 (m, 1H), 2.98 (dd, J=13.9, 5.9 Hz, 1H), 1.49-1.37 (m, 10H).

Step 2:

To a solution of (S)-methyl 2-((tert-butoxycarbonyl)amino)-3-(3-chloro-4-fluorophenyl)propanoate (174 mg, 0.524 mmol) in THF (1967 µl)/H$_2$O (656 µl) was added LiOH (37.7 mg, 1.573 mmol) and the reaction was allowed to stir for 2 h. THF was removed by rotovap before the solution was diluted in EtOAc (10 mL) and aqueous phase was acidified to pH 3 using a 1N aqueous HCl solution. The crude product was extracted with EtOAc. The organic fractions were combined and dried over anhydrous sodium sulfate. After filtration and concentration, the crude product, (S)-2-((tert-butoxycarbonyl)amino)-3-(3-chloro-4-fluorophenyl)propanoic acid, was obtained as a yellow gum (0.183 mg, 99%).

Step 3:

The (S)-2-((tert-butoxycarbonyl)amino)-3-(3-chloro-4-fluorophenyl)propanoic acid (183.0 mg, 0.576 mmol) was suspended in a 4M hydrochloric acid (1440 µl, 5.76 mmol) solution in dioxane at room temperature for 2 h. After solvent evaporation, the crude product was cooled to 0° C. using an ice bath before being dissolved in MeCN (288 µl) and a 2.0M aqueous solution of Na$_2$CO$_3$ (288 µl, 0.576 mmol). (9H-fluoren-9-yl)methyl (2,5-dioxopyrrolidin-1-yl) carbonate (194 mg, 0.576 mmol) was added to the solution and the reaction mixture was allowed to stir for 30 min. The mixture was diluted in 5.0 mL of EtOAc and the aqueous phase was neutralized with a few drops of an aqueous 1N HCl solution. The organic solvents were evaporated and the crude product was then partitioned between a saturated aqueous NH$_4$Cl solution and EtOAc. The crude product was extracted with EtOAc. The organic fractions were combined and dried over anhydrous sodium sulfate. After filtration and concentration, a yellow crystalline solid was obtained. Purification by silica gel chromatography using 100% hexanes to 30% EtOAc/Hexanes yielded the desired product as a white crystalline solid. A second purification on silica gel was performed using 100% DCM to 20% MeOH/DCM as eluant. The desired product, (S)-2-((((9H-fluoren-9-yl)methoxy)carbonyl)amino)-3-(3-chloro-4-fluorophenyl)propanoic acid, was obtained as a white solid (0.111 g, 44%). $^1$H NMR (400 MHz, methanol-$d_4$) δ 7.79 (d, J=7.5 Hz, 2H), 7.60 (t, J=6.8 Hz, 2H), 7.47-7.23 (m, 5H), 7.25-7.14 (m, 1H), 7.13 (d, J=9.0 Hz, 1H), 4.52-4.11 (m, 4H), 3.19 (dd, J=14.3, 4.6 Hz, 1H), 2.92 (dd, J=13.9, 9.7 Hz, 1H).

(R)-2-(((((9H-fluoren-9-yl)methoxy)carbonyl)(methyl)amino)-5-(tert-butoxy)-5-oxopentanoic acid (Ley, S. V.; Smith, S. C.; Woodward, P. R. *Tetrahedron* 1992, 48(6), 1145-1174.)

Scheme:

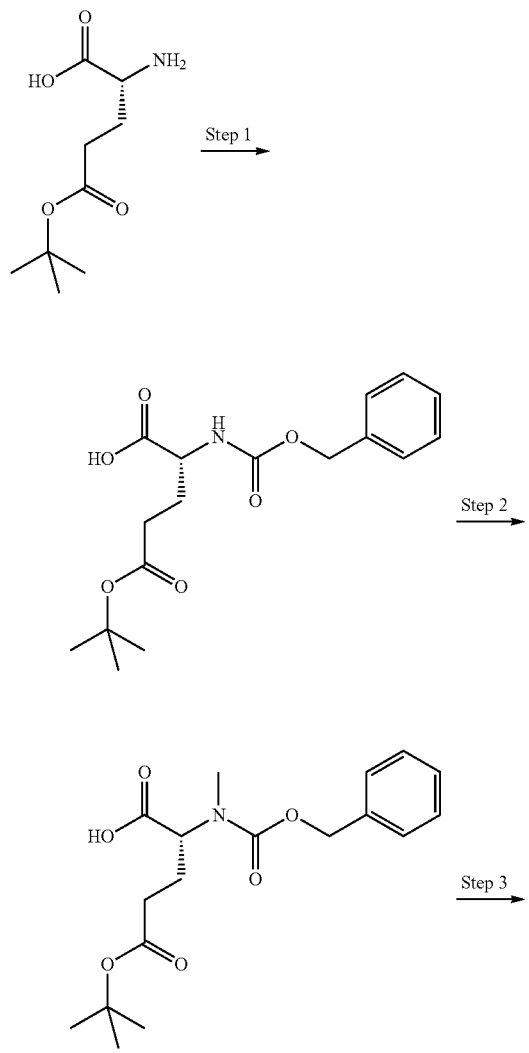

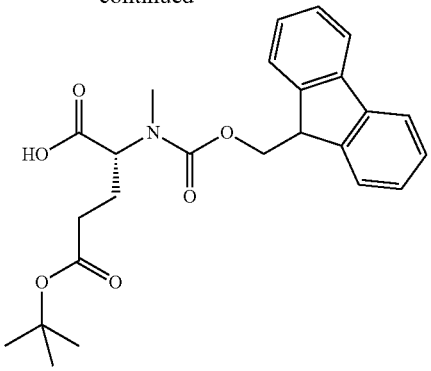

Step 1:
(R)-2-amino-5-(tert-butoxy)-5-oxopentanoic acid (1.00 g, 4.92 mmol) was suspended in THF (18.45 ml)/Water (6.15 ml) and cooled to 0° C. using an ice bath. To the cold slurry was slowly added benzyl chloroformate (0.773 mL, 5.41 mmol) and the reaction mixture was allowed to stir for 2.5 h. The slurry was diluted with 50 mL of EtOAc before being acidified to pH 3 using an aqueous 1N HCl solution. The crude product was extracted three times with EtOAc. The organic phases were combined, dried over anhydrous sodium sulfate, filtered and concentrated. The crude product was obtained as a clear oil and was subjected to silica gel chromatography using 100% Hexanes to 100% ethyl acetate as eluant. The product, (R)-2-(((benzyloxy)carbonyl)amino)-5-(tert-butoxy)-5-oxopentanoic acid, was obtained as a colorless oil (1.41 g, 71%). $^1$H NMR (400 MHz, chloroform-d) δ 7.44-7.29 (m, 5H), 5.53 (d, J=7.5 Hz, 1H), 5.13 (s, 2H), 4.41 (d, J=5.1 Hz, 1H), 2.56-2.30 (m, 2H), 2.21 (dd, J=13.5, 6.5 Hz, 1H), 2.06-1.88 (m, 2H), 1.45 (s, 9H).

Step 2:
To a solution of (R)-2-(((benzyloxy)carbonyl)amino)-5-(tert-butoxy)-5-oxopentanoic acid (1.41 g, 4.18 mmol) and MeI (2.091 mL, 33.4 mmol) in THF (12.66 ml) at 0° C. was slowly added NaH (0.501 g, 12.54 mmol) and the suspension was allowed to stir while warming up to room temperature for 24 hours. The reaction mixture was cooled to 0° C. before 10 mL of EtOAc were added along with 5 mL of water to quench the excess of NaH. The crude product was partitioned between a saturated NaHCO$_3$ aqueous solution and Et$_2$O. The two phases were separated and the organic phase was washed with a saturated NaHCO$_3$ solution and both aqueous extracts were combined. The aqueous solution was brought to pH 3 using a 6N HCl aqueous solution. The aqueous phase was extracted with EtOAc, the organic extracts were combined and dried over anhydrous sodium sulfate. After filtration and concentration, (R)-2-(((benzyloxy)carbonyl)(methyl)amino)-5-(tert-butoxy)-5-oxopentanoic acid was obtained as a yellow oil, 1.4 g (78%). LCMS showed the m/z of desired product, (M+Na)$^+$ 374.

Step 3:
To a solution of (R)-2-(((benzyloxy)carbonyl)(methyl)amino)-5-(tert-butoxy)-5-oxopentanoic acid (1.40 g, 3.98 mmol) in MeOH (18.79 ml) was added 10% Pd/C (0.424 g, 0.398 mmol) and the reaction mixture was placed under a hydrogen atmosphere using. The reaction was allowed to stir at room temperature for 18 h. The catalyst was removed by filtration on CELITE® and the filtrate was concentrated under reduced pressure to give a white solid. The crude material was dissolved in Acetonitrile (9.40 ml), Water (9.40 ml) and TEA (1.111 mL, 7.97 mmol). The solution was cooled to 0° C. using and icebath and the FMOC-OSU (1.344 g, 3.98 mmol) was added. The reaction mixture was allowed to stir while warming up to room temperature for 18 hours. The crude product was diluted in 200 mL EtOAc and washed with 1N HCl aqueous solution and brine. The organic phase was dried over anhydrous sodium sulfate. After filtration and concentration a clear oil was obtained, which was purified by silica gel chromatography using 100% hexanes to 100% EtOAc. (R)-2-((((9H-fluoren-9-yl)methoxy)carbonyl)(methyl)amino)-5-(tert-butoxy)-5-oxopentanoic acid was obtained as a colorless oil (0.481 g, 28%). $^1$H NMR (400 MHz, chloroform-d) δ 7.81-7.68 (m, 2H), 7.63-7.49 (m, 2H), 7.43-7.21 (m, 4H), 5.95 (br. s., 3H), 4.76 (dd, J=10.7, 4.5 Hz, 1H), 4.60-4.48 (m, 1H), 4.47-4.32 (m, 2H), 4.29-4.10 (m, 1H), 2.87 (s, 3H), 2.43-1.82 (m, 4H), 1.51-1.36 (m, 9H).

Step 1:

A solution of L-PHENYLALANINE BENZYL ESTER HYDROCHLORIDE (2 g, 6.85 mmol), Z-Phe-OH (2.257 g, 7.54 mmol), DIPEA (2.99 mL, 17.14 mmol) and DCM (100 mL) was treated with 1-HYDROXY-7-AZABENZOTRIAZOLE (1.120 g, 8.23 mmol) and EDC (1.577 g, 8.23 mmol) and stirred at rt for 15 h. The mixture was washed with saturated NaHCO$_3$ (2×100 mL), 1 M HCl (2×50 mL) and brine (50 mL), dried over sodium sulfate, and concentrated under reduced pressure to give (S)-benzyl 2-((S)-2-(((benzyloxy)carbonyl)amino)-3-phenylpropanamido)-3-phenylpropanoate (3.2 g, 5.96 mmol, 87% yield) as a white solid. $^1$H NMR (400 MHz, DMSO-d$_6$) δ 7.42-7.11 (m, 21H), 4.96 (d, J=2.0 Hz, 4H), 4.63-4.45 (m, 1H), 4.06-3.91 (m, 2H), 3.34-2.96 (m, 3H), 2.85 (br. s., 4H)

Step 2 (Schroeder, G. M.; Marshall, S.; Wan, H.; Purandare, A. V. *Tetrahedron Lett.* 2010, 51, 1404-1406.):

A pressure vial was charged with (S)-benzyl 2-((S)-2-(((benzyloxy)carbonyl)amino)-3-phenylpropanamido)-3-phenylpropanoate (1.0 g, 1.864 mmol) and DIPHENYL-2-PYRIDYLPHOSPHINE (3.17 g, 7.45 mmol) in THF (9.32 mL) under N$_2$. The solution was purged with N$_2$ before DIAD (1.449 mL, 7.45 mmol) was added dropwise. The reaction was allowed to stir for 5 min. DIPHENYLPHOSPHORYL AZIDE (1.606 mL, 7.45 mmol) was then added dropwise over 30 min. After the addition was completed and there was no more nitrogen formation, the sealed tube was closed and the reaction is allowed to stir at 55° C. for 4 h.

The reaction was cooled down to rt and poured into ethyl acetate (200 ml), washed with cold 1N HCl (100 mL), Sat. NaHCO$_3$ (100 mL) and brine (100 mL). The organic layer dried over anhydrous sodium sulfate, filtered and concentrated to give an orange oil. Purification by silical gel chromatography using 100% hexanes to 60% Ethyl acetate in hexanes as eluent afforded 660 mg of (S)-benzyl 2-(5-((S)-1-(((benzyloxy)carbonyl)amino)-2-phenylethyl)-1H-tetrazol-1-yl)-3-phenylpropanoate with low purity. Second purification by preparative HPLC using the following conditions: Column: PHENOMENEX® Luna 5 u C18(2) 100 A 250× 21.2 mm AXIA packed (10-100 mg)#520551-2. Mobile Phase A: 0.1 TFA in water; Mobile Phase B: 0.1% TFA in acetonitrile; Gradient: 50-80% B over 20 min., then a 10-minute gradient 95% B; Flow: 15 mL/min; Detection: UV at 220 nm. Fractions containing the desired product were combined and dried. (S)-benzyl 2-(5-((S)-1-(((benzyloxy)carbonyl)amino)-2-phenylethyl)-1H-tetrazol-1-yl)-3-phenylpropanoate was obtained as a beige hygroscopic solid in 60.0 mg yield in 70% purity by LC/MS analysis. Analysis LCMS condition A: Retention time=1.82 min; ESI-MS(+) m/z 562.5 (M+H).

Step 3:

A solution of (S)-benzyl 2-(5-((S)-1-(((benzyloxy)carbonyl)amino)-2-phenylethyl)-1H-tetrazol-1-yl)-3-phenylpropanoate (60 mg, 0.107 mmol) in MeOH (534 μl) was hydrogenated over 10% Pd/C (22.74 mg, 0.021 mmol) using hydrogen from a latex balloon for 2 h.

The catalyst was removed by filtration and the filtrate was concentrated under reduced pressure to give a white gummy solid. The product was dissolved in MeCN (2 mL) and water (2 mL) and Et$_3$N (100 μL) and treated with FMOC-OSU (36.0 mg, 0.107 mmol).

The mixture was stirred at rt for 15 h.

The reaction mixture was diluted with EtOAc (50 mL), washed with 1 M HCl (2×20 mL) and brine (20 mL), dried (Sodium sulfate) and concentrated under reduced pressure to give (S)-2-(5-((S)-1-((((9H-fluoren-9-yl)methoxy)carbonyl)amino)-2-phenylethyl)-1H-tetrazol-1-yl)-3-phenylpropanoic acid (42 mg, 0.075 mmol, 70.3% yield) as a yellow solid. Product is 64% pure by LC/MS analysis. Analysis condition A: Retention time=1.70 min; ESI-MS(+) m/z 560.5 (M+H).

(S)-2-((((9H-fluoren-9-yl)methoxy)carbonyl)amino)-3-(3,5-dichlorophenyl)propanoic acid (Ross, A. J.; Lang, H. L.; Jackson, R. F. W. *J. Org. Chem.*, 2010, 75, 245-248.)

Scheme:

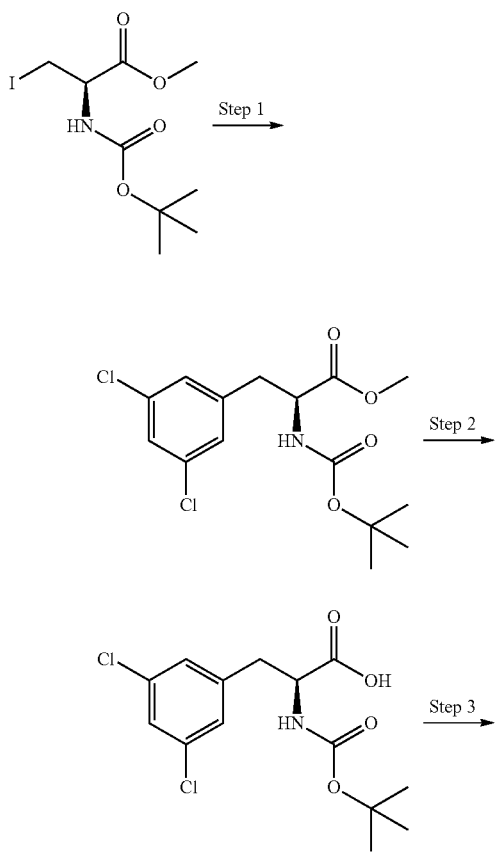

-continued

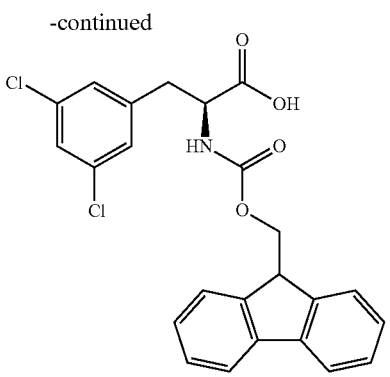

Step 1:

To an oven dried 8 mL vial with teflon cap purged with $N_2$ was added Zinc dust (298 mg, 4.56 mmol), DMF (1.5 mL), and iodine (57.8 mg, 0.228 mmol). To this mixture was added (R)-methyl 2-((tert-butoxycarbonyl)amino)-3-iodopropanoate (500 mg, 1.519 mmol), immediately followed by iodine (57.8 mg, 0.228 mmol). Pd2(dba)3 (69.6 mg, 0.076 mmol), 2-DICYCLOHEXYLPHOSPHINO-2',6'-DIMETHOXYBIPHENYL (62.4 mg, 0.152 mmol), 1,3-dichloro-5-iodobenzene (622 mg, 2.279 mmol) and the reaction mixture was allowed to stir at rt for 16 h. The crude mixture was diluted in EtOAc (30 mL) and DMF was removed with four aqueous washes. The organic phase was dried over anhydrous sodium sulfate. The solution was filtered and concentrated, and the crude was purified by silica gel chromatography using 100% hexanes to 30% EtOAc/Hexanes. The desired product was obtained as a pale yellow oil, (S)-methyl 2-((tert-butoxycarbonyl)amino)-3-(3,5-dichlorophenyl)propanoate, 0.160 g yield in 77% purity by LCMS analysis. Analysis LCMS condition F: Retention time=2.84 min; ESI-MS(+) m/z 348.1 (M+H).

Step 2:

To a solution of (S)-methyl 2-((tert-butoxycarbonyl) amino)-3-(3,5-dichlorophenyl)propanoate (160 mg, 0.459 mmol) in THF (2 mL)/$H_2O$ (0.667 mL) is added the LiOH (33.0 mg, 1.378 mmol) and the reaction was allowed to stir for 2 h. THF was evaporated before the solution was diluted in EtOAc (10 mL) and the aqueous phase was acidified to pH 3 using a 1N aqueous HCl solution. The crude product was extracted with EtOAc. The organic fractions were combined and dried over anhydrous sodium sulfate. After filtration and concentration, the crude product was obtained as a yellow gum. The solid were taken directly into step 3.

Step 3:

To the solids from the previous step was added 4M HCl in Dioxane (1.149 mL, 4.59 mmol) and the solution was allowed to stir for 2 h. After solvent evaporation, the crude product was cooled to 0° C. and dissolved in 5% aqueous $Na_2CO_3$/AcCN (2:1) (30 mL). (9H-fluoren-9-yl)methyl (2,5-dioxopyrrolidin-1-yl) carbonate (170 mg, 0.505 mmol) was added and the reaction mixture was allowed to stir for 16 hrs. The mixture was diluted in 15.0 mL of EtOAc and the aqueous phase was neutralized with a few drops of an aqueous 1N HCl solution. The organic solvents were evaporated and the crude product was then partitioned between a saturated aqueous $NH_4Cl$ solution and EtOAc. The crude product was extracted with EtOAc. The organic extracts were combined, dried over anhydrous sodium sulfate and concentrated. The crude product was purified by preparative LCMS using the following conditions: Column: PHENOMENEX® Luna 20×250, 5 u particles; Mobile Phase A: water with 0.05% TFA; Mobile Phase B: Acetonitrile with 0.05% TFA; Gradient: 35-100% B over 50 min., then a 10-minute hold at 100% B; Flow: 15 mL/min. Fractions containing the desired product were combined and dried. The yield of (S)-2-((((9H-fluoren-9-yl) methoxy)carbonyl)amino)-3-(3,5-dichlorophenyl)propanoic acid was 50 mg; purity, 87% by Analysis LCMS condition A: rt=1.73 min; ESI-MS(+) m/z 478.0 (M+Na)$^+$.

(S)-2-((((9H-fluoren-9-yl)methoxy)carbonyl)amino)-3-(3-chloro-4,5-difluorophenyl)propanoic acid (Ross, A. J.; Lang, H. L.; Jackson, R. F. W. J. Org. Chem., 2010, 75, 245-248)

Scheme:

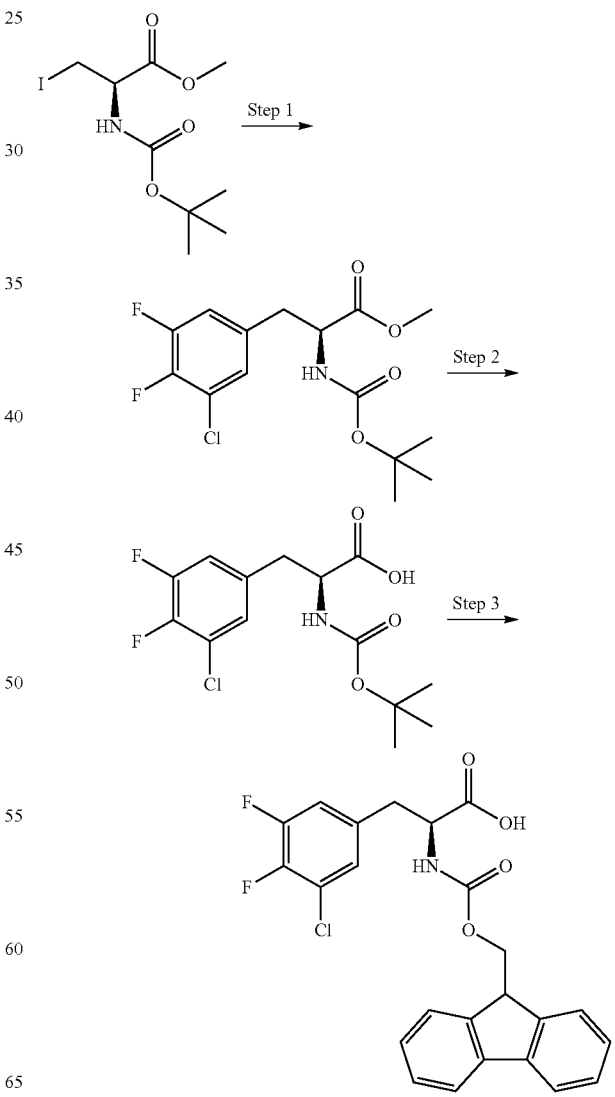

Step 1:

To an oven dried 8 mL vial with teflon cap purged with N₂ was added Zinc dust (298 mg, 4.56 mmol), DMF (1.5 mL), and iodine (57.8 mg, 0.228 mmol). To this mixture was added (R)-methyl 2-((tert-butoxycarbonyl)amino)-3-iodopropanoate (500 mg, 1.519 mmol), immediately followed by iodine (57.8 mg, 0.228 mmol). Pd2(dba)₃ (69.6 mg, 0.076 mmol), 2-dicyclohexylphosphino-2',6'-dimethoxybiphenyl (62.4 mg, 0.152 mmol), 5-bomo-1chloro-2,3-difluorobenzene (518 mg, 2.279 mmol) and the reaction mixture was allowed to stir at room temperature for 16 h. The crude mixture was diluted in 30 mL of EtOAc and DMF was removed with four aqueous washes. The organic phase was dried over anhydrous sodium sulfate. The solution was filtered and concentrated and the crude was purified by silica gel chromatography using 100% hexanes to 30% EtOAc/Hexanes. The desired product was obtained as a pale yellow oil, (S)-methyl 2-((tert-butoxycarbonyl)amino)-3-(3-chloro-4,5-difluorophenyl)propanoate, 0.165 g, which was taken directly into next step.

Step 2:

To a solution of (S)-methyl 2-((tert-butoxycarbonyl)amino)-3-(3-chloro-4,5-difluorophenyl)propanoate (165 mg, 0.472 mmol) in THF (2 ml)/H₂O (0.667 ml) is added LiOH (33.9 mg, 1.415 mmol) and the reaction was allowed to stir for 2 h. THF was removed before the solution was diluted in EtOAc (10 mL). The aqueous phase was acidified to pH 3 using a 1N aqueous HCl solution. The crude product was extracted with EtOAc. The organic fractions were combined and dried over anhydrous sodium sulfate. After filtration and concentration, the crude product was obtained as a yellow gum, which was taken directly into step 3.

Step 3:

To the solids was added 4M HCl in Dioxane (1.179 mL, 4.72 mmol) and the reaction mixture was allowed to stir for 2 h. After solvent evaporation, the crude product was cooled to 0° C. and dissolved in 5% aqueous Na₂CO₃/ACN (2:1) (30 mL). (9H-fluoren-9-yl)methyl (2,5-dioxopyrrolidin-1-yl) carbonate (175 mg, 0.519 mmol) was added to the solution and the reaction mixture was allowed to stir for 16 h. The mixture was diluted in 15.0 mL of EtOAc and the aqueous phase was neutralized with a few drops of aqueous 1N HCl. The organic solvents were evaporated and the crude product was then partitioned between a saturated aqueous NH₄Cl solution and EtOAc. The crude product was extracted with EtOAc. The organic extracts were combined, dried over anhydrous sodium sulfate and concentrated. The resulting product was then purified by preparative LCMS using the following conditions: Column: PHENOMENEX® Luna 20×250, 5 u particles; Mobile Phase A: water with 0.05% TFA; Mobile Phase B: Acetonitrile with 0.05% TFA; Gradient: 35-100% B over 50 min., then a 10-minute hold at 100% B; Flow: 15 mL/min. Fractions containing the desired product were combined and dried to yield 62 mg of (S)-2-((((9H-fluoren-9-yl)methoxy)carbonyl)amino)-3-(3-chloro-4,5-difluorophenyl)propanoic acid.

(S)-2-((((9H-fluoren-9-yl)methoxy)carbonyl)amino)-3-(3,5-dichloro-4-fluorophenyl)propanoic acid (Ross, A. J.; Lang, H. L.; Jackson, R. F. W. J. Org. Chem., 2010, 75, 245-248.)

Scheme:

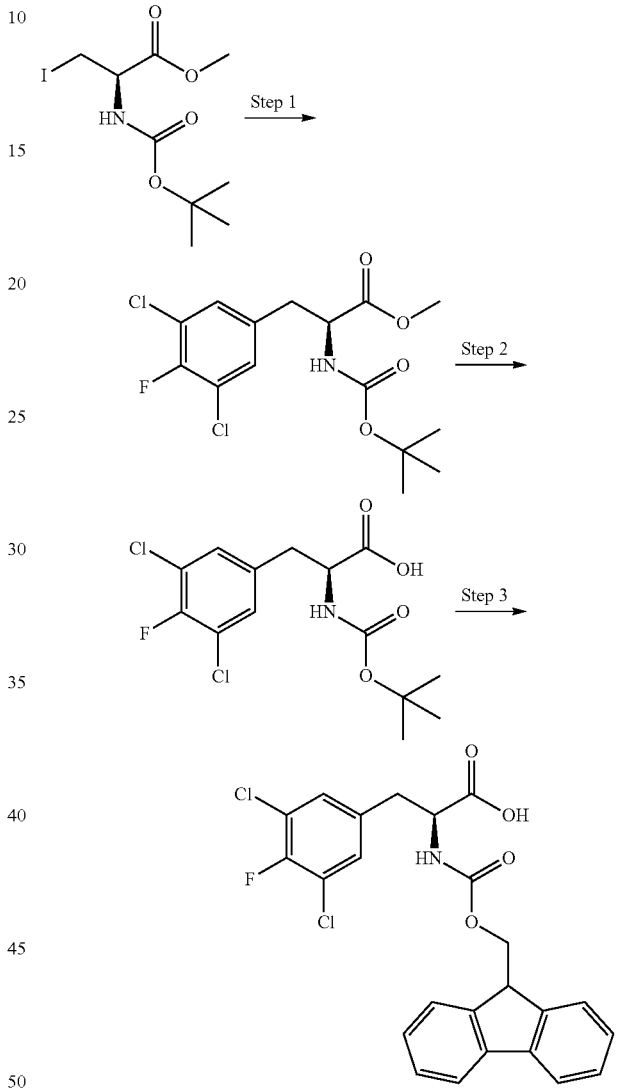

Step 1:

To an oven dried 8 mL vial with teflon cap purged with N₂ was added Zinc dust (298 mg, 4.56 mmol), DMF (1.5 mL), and iodine (57.8 mg, 0.228 mmol). To this mixture was added (R)-methyl 2-((tert-butoxycarbonyl)amino)-3-iodopropanoate (500 mg, 1.519 mmol), immediately followed by iodine (57.8 mg, 0.228 mmol). Pd₂(dba)₃ (69.6 mg, 0.076 mmol), 2-dicyclohexylphosphino-2',6'-dimethoxybiphenyl (62.4 mg, 0.152 mmol), 5-bromo-1,3-dichloro-2-fluorobenzene (556 mg, 2.279 mmol) and the reaction mixture was allowed to stir at rt for 16 h. The crude mixture was diluted in 30 mL of EtOAc and DMF was removed using four aqueous washes. The organic phase was dried over anhydrous sodium sulfate. The solution was filtered and concentrated and the crude product was purified by silica gel chromatography using 100% hexanes to 30% EtOAc/Hexanes. The desired product was obtained as a pale yellow oil, (S)-methyl 2-((tert-butoxycarbonyl)amino)-3-(3,5-dichloro-4-fluorophenyl)propanoate, 0.102 g which was taken into next step directly.

Step 2:

To a solution of (S)-methyl 2-((tert-butoxycarbonyl)amino)-3-(3,5-dichloro-4-fluorophenyl)propanoate (102 mg, 0.279 mmol) in THF (2 ml)/H$_2$O (0.667 ml) was added LiOH (20.01 mg, 0.836 mmol) and the reaction was stirred for 2 h. THF was removed and the solution was diluted in EtOAc (10 mL). The aqueous phase was acidified to pH 3 using a 1N aqueous HCl. The crude product was extracted with EtOAc. The organic extracts were combined and dried over anhydrous sodium sulfate. After filtration and concentration the crude product was obtained as a yellow gum, and was taken directly into step 3.

Step 3:

To the product from Step 2 was added 4M HCl in Dioxane (0.696 mL, 2.79 mmol) and the reaction mixture was allowed to stir for 2 h. After solvent evaporation, the crude product was cooled to 0° C. and dissolved in 5% aqueous Na$_2$CO$_3$/MeCN (2:1) (30 mL). (9H-fluoren-9-yl)methyl (2,5-dioxopyrrolidin-1-yl)carbonate (103 mg, 0.306 mmol) was added to the solution and the reaction mixture was stirred for 16 h. The mixture was diluted in 15.0 mL of EtOAc and the aqueous phase was neutralized with a few drops of an aqueous 1N HCl. The organic solvents were evaporated and the crude product was then partitioned between a saturated aqueous NH$_4$Cl solution and EtOAc. The crude product was extracted with EtOAc. The organic extracts were combined, dried over anhydrous sodium sulfate, concentrated and then purified by preparative LCMS using the following conditions: Column: PHENOMENEX® Luna 20×250 5 u particles; Mobile Phase A: water with 0.05% TFA; Mobile Phase B: Acetonitrile with 0.05% TFA; Gradient: 35-100% B over 50 min., then a 10-minute hold at 100% B; Flow: 15 mL/min. Fractions containing the desired product were combined and dried to yield 36 mg of (S)-2-((((9H-fluoren-9-yl)methoxy)carbonyl)amino)-3-(3,5-dichloro-4-fluorophenyl)propanoic acid.

(S)-2-((((9H-fluoren-9-yl)methoxy)carbonyl)amino)-3-(4-chloro-3-fluorophenyl)propanoic acid (Ross, A. J.; Lang, H. L.; Jackson, R. F. W. J. Org. Chem., 2010, 75, 245-248)

Scheme:

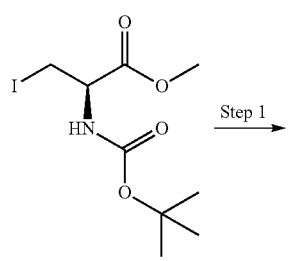

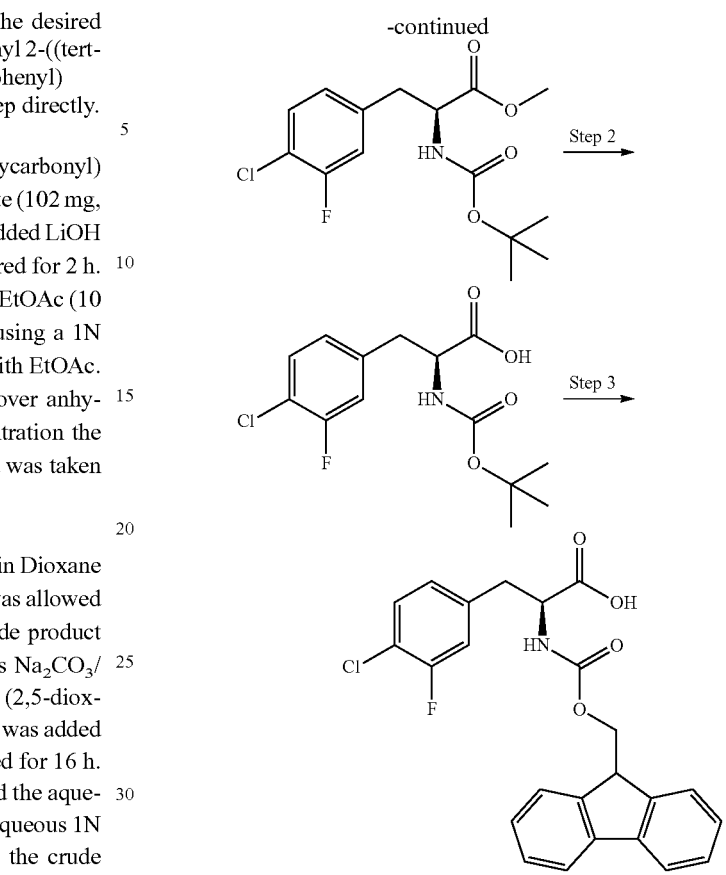

Step 1:

To an oven dried 8 mL vial with teflon cap purged with N$_2$ was added Zinc dust (298 mg, 4.56 mmol), DMF (1.5 mL), and iodine (57.8 mg, 0.228 mmol). To this mixture was added (R)-methyl 2-((tert-butoxycarbonyl)amino)-3-iodopropanoate (500 mg, 1.519 mmol), immediately followed by iodine (57.8 mg, 0.228 mmol). Pd$_2$(dba)$_3$ (69.6 mg, 0.076 mmol), 2-dicyclohexylphosphino-2',6'-dimethoxybiphenyl (62.4 mg, 0.152 mmol), 1-chloro-2-fluoro-4-iodobenzene (584 mg, 2.279 mmol), and the reaction mixture was stirred at room temperature for 16 h. The crude mixture was diluted in 30 mL of EtOAc and DMF was removed using four aqueous washes. The organic phase was dried over anhydrous sodium sulfate, filtered, concentrated and the crude product was purified by silica gel chromatography using 100% hexanes to 30% EtOAc/Hexanes. The desired product was obtained as a pale yellow oil, (S)-methyl 2-((tert-butoxycarbonyl)amino)-3-(4-chloro-3-fluorophenyl)propanoate, 0.220 g; purity, 93% by LCMS analysis. Analysis LCMS condition F: rt=2.59 min; ESI-MS(+) m/z 332.2 (M+H).

Step 2:

To a solution of (S)-methyl 2-((tert-butoxycarbonyl)amino)-3-(4-chloro-3-fluorophenyl)propanoate (220 mg, 0.663 mmol) in THF (2 mL)/Water (0.667 mL) was added LiOH (47.6 mg, 1.989 mmol) and the reaction was allowed to stir for 2 hours. THF was removed and the solution was diluted in EtOAc (10 mL). The aqueous phase was acidified to pH 3 using a 1N aqueous HCl. The crude product was extracted with EtOAc. The organic extracts were combined and dried over anhydrous sodium sulfate. After filtration and concentration the crude product was obtained as a yellow gum and taken directly into step 3.

Step 3:

To the solid from Step 2 was added 4M HCl in Dioxane (1.658 mL, 6.63 mmol) and the mixture was stirred for 2 h. After solvent evaporation, the crude product was cooled to 0° C. and dissolved in 5% aqueous $Na_2CO_3$/AcCN (2:1) (30 mL). (9H-fluoren-9-yl)methyl (2,5-dioxopyrrolidin-1-yl) carbonate (246 mg, 0.729 mmol) was added to the solution and the reaction mixture was stirred for 16 h. The mixture was diluted in 15.0 mL of EtOAc and the aqueous phase was neutralized with a few drops of an aqueous 1N HCl. The organic solvents were evaporated and the crude product was then partitioned between a saturated aqueous $NH_4Cl$ solution and EtOAc. The crude product was extracted with EtOAc. The organic extracts were combined, dried over anhydrous sodium sulfate, concentrated and then purified by preparative LCMS with the following conditions: Column: PHENOMENEX® Luna 20×250, 5 u particles; Mobile Phase A: water with 0.05% TFA; Mobile Phase B: Acetonitrile with 0.05% TFA; Gradient: 35-100% B over 50 min., then a 10-minute hold at 100% B; Flow: 15 mL/min. Fractions containing the desired product were combined and dried to yield 30 mg of (S)-2-((((9H-fluoren-9-yl)methoxy)carbonyl)amino)-3-(4-chloro-3-fluorophenyl)propanoic acid. Analysis LCMS condition A: rt=1.65 min, 85% purity; ESI-MS(+) m/z 462.0 (M+Na).

Preparation of Example 3052

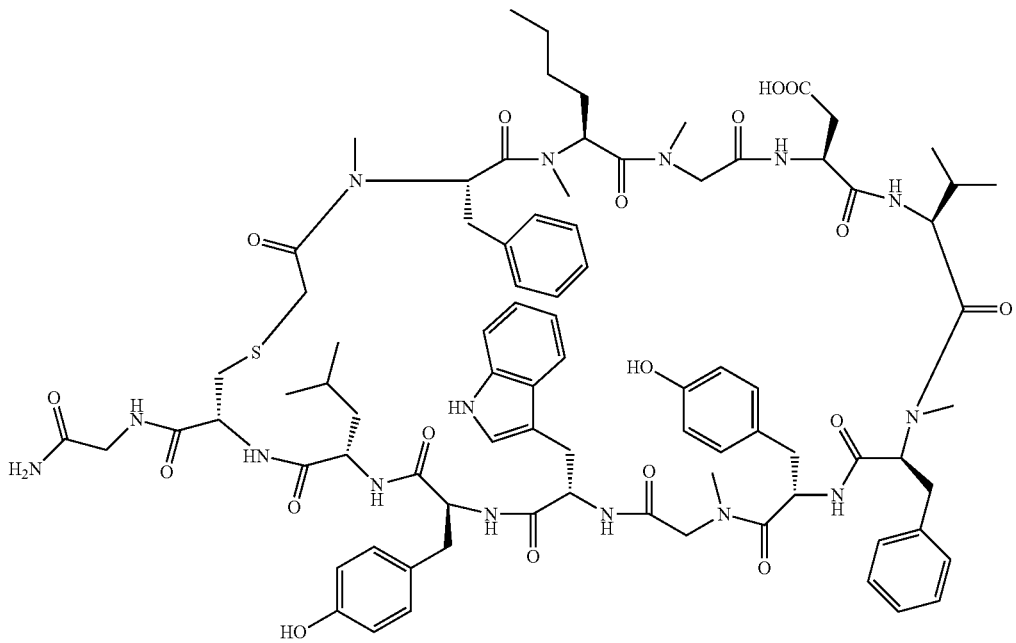

Example 3052

Example 3052 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250, 5 u particles; Mobile Phase A: water with 0.05% TFA; Mobile Phase B: Acetonitrile with 0.05% TFA; Gradient: 25-95% B in A over 50 min., then a 5-minute hold at 95% B; Flow: 15 mL/min. Fractions containing the desired product were combined and dried. The yield of product was 5 mg, and its estimated purity was 99% by HPLC "Analysis Condition B" using a gradient of 35% to 95% buffer B over 30 min.

Analysis LCMS condition A: Retention time=1.43 min; ESI-MS(+) m/z 825.2 (M+2H).

Preparation of Example 3053

Example 3053

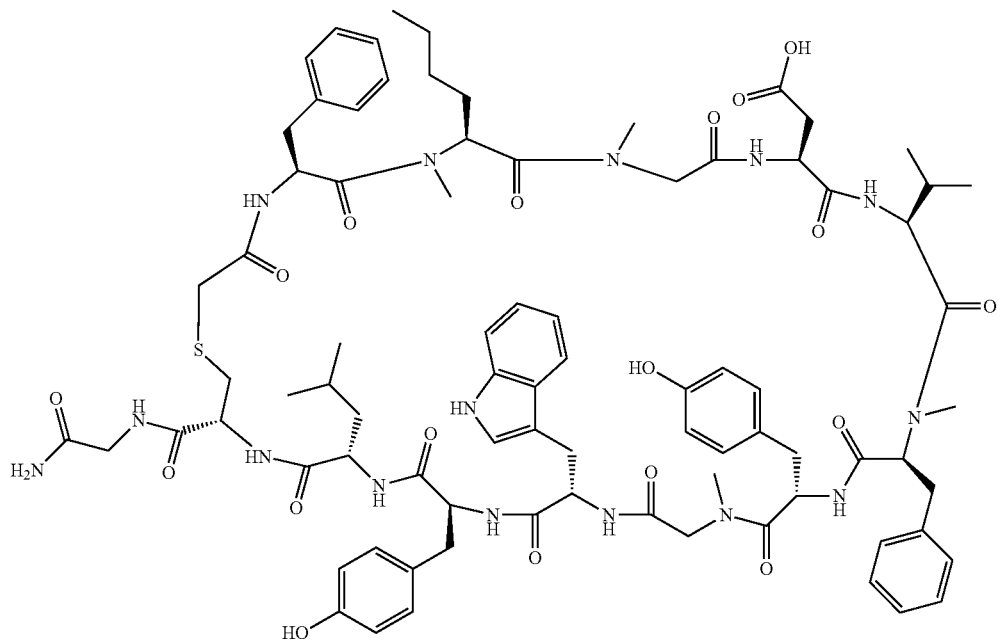

Example 3053 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 25-95% B in A over 50 min., then a 5-minute hold at 95% B; Flow: 15 mL/min. Fractions containing the desired product were combined and dried. The yield of product was 15 mg, and its estimated purity was 92% by "Analysis HPLC Condition B" using a gradient of 35% to 95% buffer B in A over 30 min.

Analysis LCMS condition A: Retention time=1.39 min; ESI-MS(+) m/z 818.2 (M+2H).

Preparation of Example 3054

Example 3054

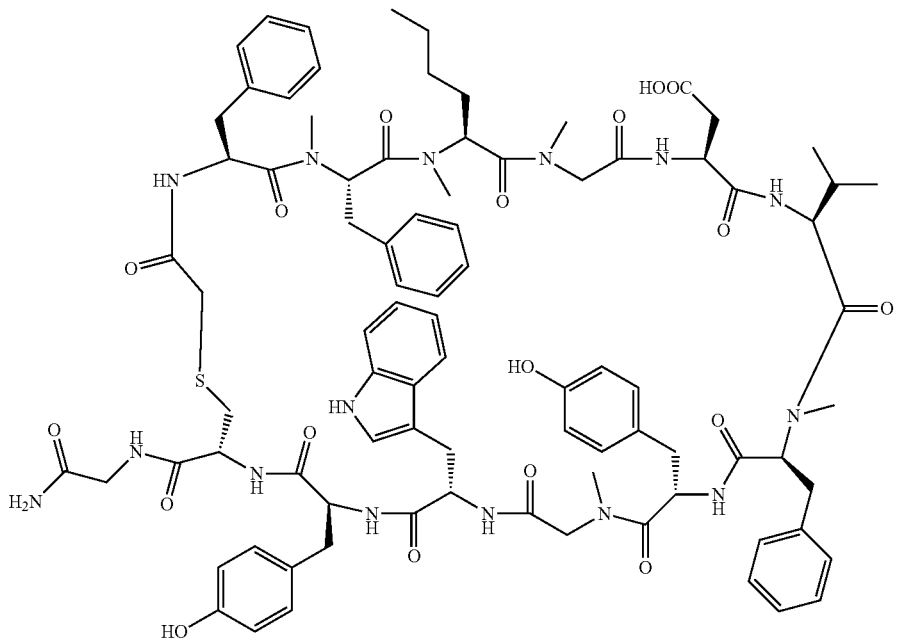

Example 3054 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 25-95% B in A over 50 min., then a 5-minute hold at 95% B; Flow: 15 mL/min. Fractions containing the desired product were combined and dried. The yield of product was 21 mg, and its estimated purity was 99% by "Analysis HPLC Condition B" using a gradient of 35% to 95% buffer B in A over 30 min.

Analysis LCMS condition A: Retention time=1.43 min; ESI-MS(+) m/z 842.2 (M+2H).

Preparation of Example 3055

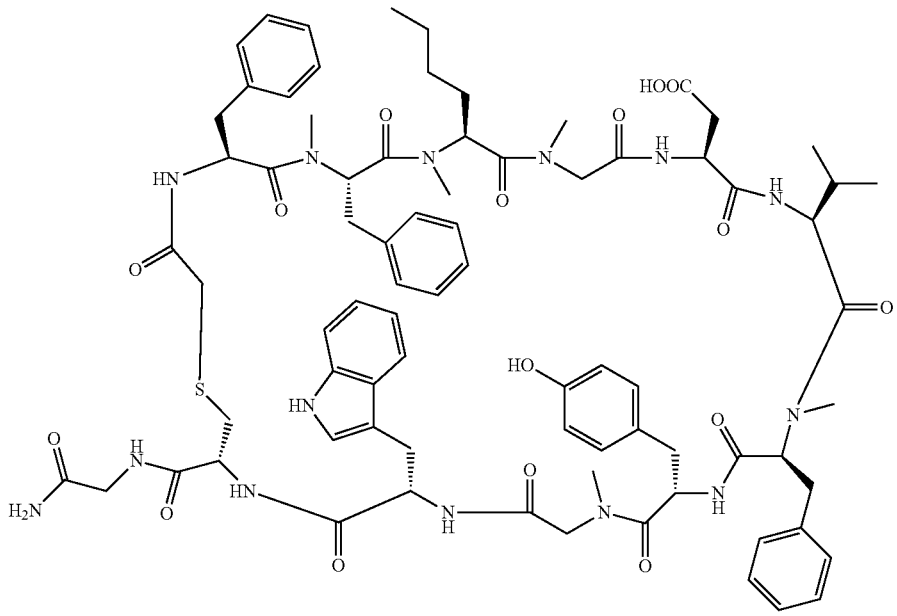

Example 3055

Example 3055 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 25-95% B in A over 50 min., then a 5-minute hold at 95% B; Flow: 15 mL/min. Fractions containing the desired product were combined and dried. The yield of product was 19 mg, and its estimated purity was 92% by "Analysis HPLC Condition B" using a gradient of 35% to 95% buffer B in A over 30 min.

Analysis LCMS condition A: Retention time=1.45 min; ESI-MS(+) m/z 760.6 (M+2H).

Preparation of Example 3056

Example 3056

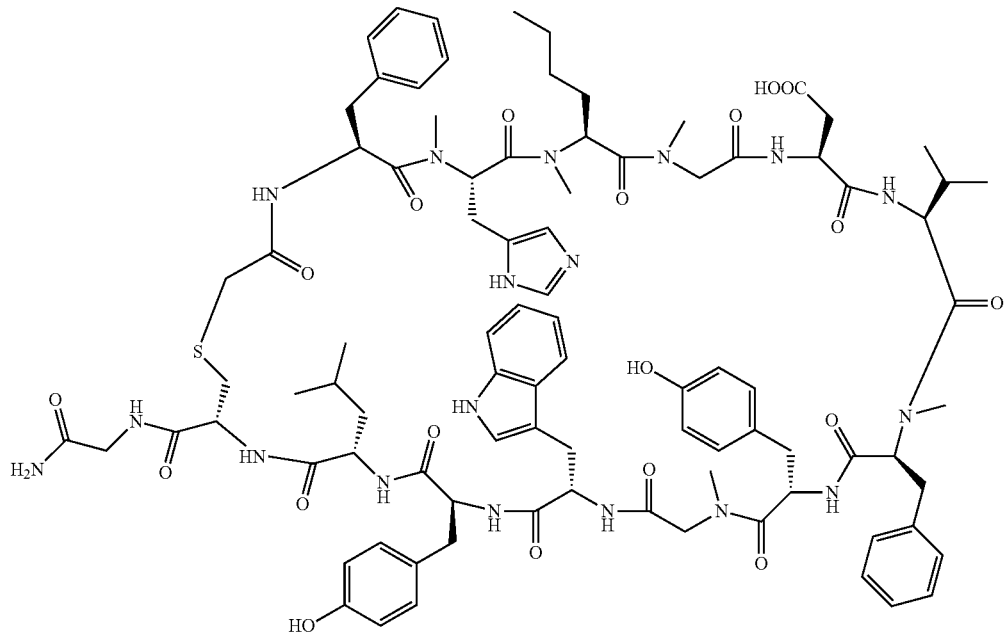

Example 3056 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 25-95% B over 50 min., then a 5-minute hold at 95% B; Flow: 15 mL/min. Fractions containing the desired product were combined and dried. Two isomers (isomer 3056-A and isomer 3056-B) were obtained. The yield of products isomer 3056-A and isomer 3056-B was 3.6 mg and 5.7 mg, respectively, and their estimated purity by "Analysis Condition B" using a gradient of 20% to 85% buffer B in A over 30 min. at 60° C. were 83% and 96%, respectively.

Analysis LCMS condition A: isomer 3056-A, Retention time=1.21 min; ESI-MS(+) m/z 894.2 (M+2H); isomer 3056-B, 1.31 min; ESI-MS(+) m/z 894.2 (M+2H).

Preparation of Example 3057

Example 3057

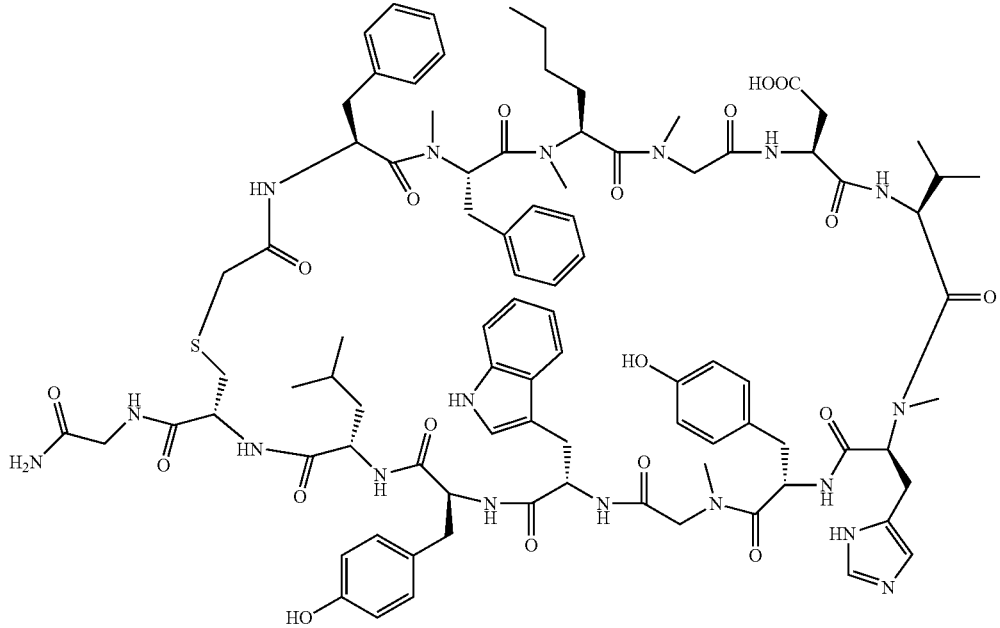

Example 3057 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250, 5 u particles; Mobile Phase A: water with 0.05% TFA; Mobile Phase B: Acetonitrile with 0.05% TFA; Gradient: 20-85% B in A over 50 min., then a 5-minute hold at 95% B; Flow: 15 mL/min. Fractions containing the desired product were combined and dried. The yield of product was 10.3 mg, and its estimated purity was 91% by "Analysis HPLC Condition B" using a gradient of 20% to 85% buffer B in A at 60° C. over 30 min.

Analysis LCMS condition A: Retention time=1.23 min; ESI-MS(+) m/z 894.1 (M+2H).

Preparation of Example 3058

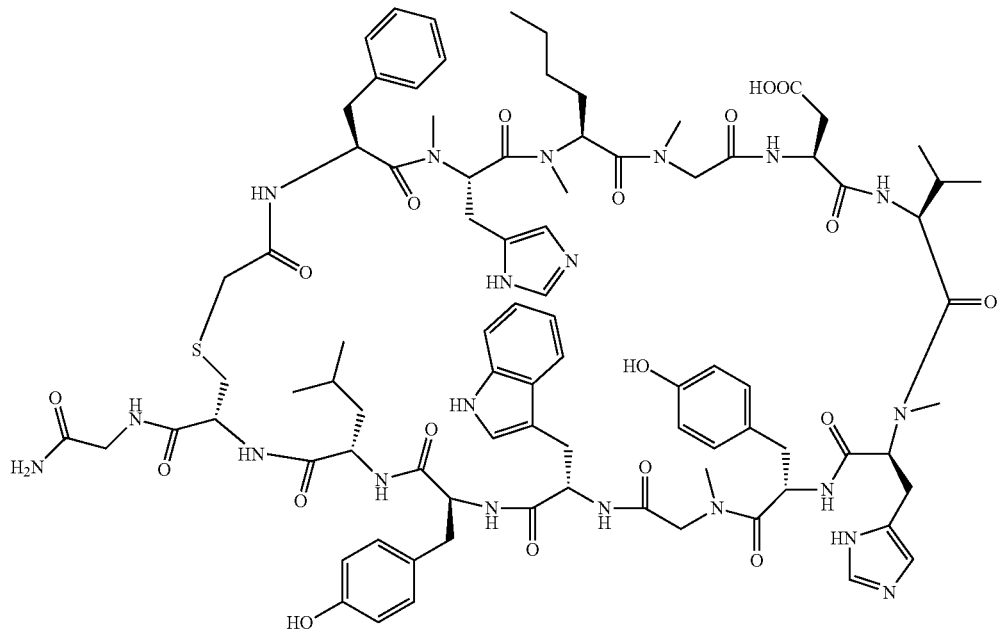

Example 3058

Example 3058 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250, 5 u particles; Mobile Phase A: water with 0.05% TFA; Mobile Phase B: Acetonitrile with 0.05% TFA; Gradient: 20-85% B in A over 50 min., then a 5-minute hold at 95% B; Flow: 15 mL/min. Fractions containing the desired product were combined and dried. Two isomers (isomer 3058-A and isomer 3058-B) were obtained. The yield of product isomer 3058-A and isomer 3058-B was 4.3 mg and 7.6 mg respectively, and their estimated purities by "Analysis HPLC Condition B" using a gradient of 20% to 85% buffer B in A over 30 min. at 60° C. were 93% and 92%, respectively.

Analysis LCMS condition A: isomer 3058-A, retention time=0.99 min; ESI-MS(+) m/z 889.1 (M+2H); isomer 3058-B, 1.10 min; ESI-MS(+) m/z 889.1 (M+2H).

Preparation of Example 3059

Example 3059

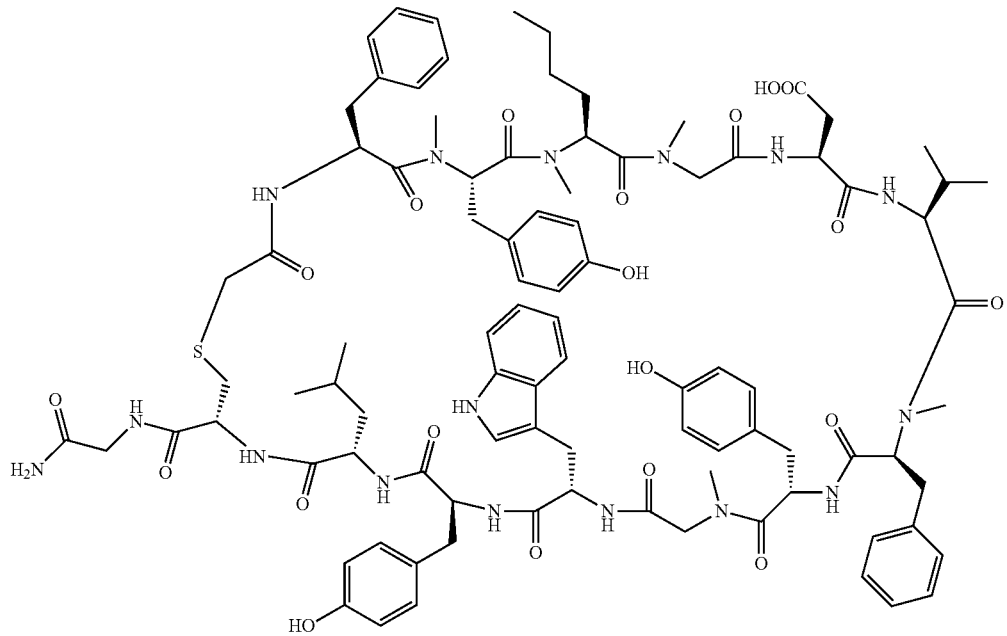

Example 3059 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile phase B: 95:5 acetonitrile:water with 0.1% trifluoroacetic acid; Gradient: 30-70% B in A over 25 min., then a 5-minute hold at 100% B; Flow: 20 mL/min. Fractions containing the desired product were combined and dried to obtain 9.2 mg of product in 96% purity.

Analysis LCMS condition D: Retention time=1.573 min; ESI-MS(+) m/z 1811.80 (M+H).

Analysis LCMS condition E: Retention time=1.711 min; ESI-MS(+) m/z 906.80 (M+2H), 1811.80 (M+H).

Preparation of Example 3060

Example 3060

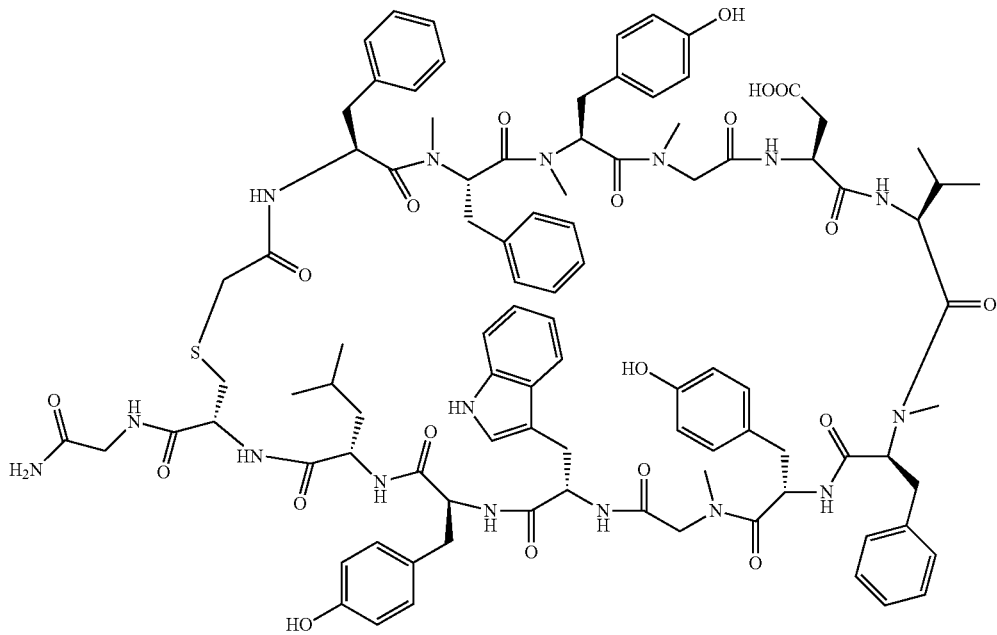

Example 3060 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile phase B: 95:5 acetonitrile:water with 0.1% trifluoroacetic acid; Gradient: 25-70% B in A over 25 min., then a 5-minute hold at 100% B; Flow: 20 mL/min. Fractions containing the desired product were combined and dried. Two isomers (isomer 3060-A and isomer 3060-B) were obtained.

The yields of product isomer 3060-A and isomer 3060-B were 5.5 mg and 1.7 mg respectively, and their estimated purities by "Analysis conditions D and E" were 95% and 86%, respectively.

Analysis condition D: isomer 3060-A: Retention time=1.455 min; ESI-MS(+) m/z 923.65 (M+2H).

Analysis condition D: isomer 3060-B: Retention time=1.570 min; ESI-MS(+) m/z 923.60 (M+2H).

Analysis condition E: isomer 3060-A: Retention time=1.549 min; ESI-MS(+) m/z 923.45 (M+2H).

Analysis condition E: isomer 3060-B: Retention time=1.666 min; ESI-MS(+) m/z 923.70 (M+2H).

Preparation of Example 3061

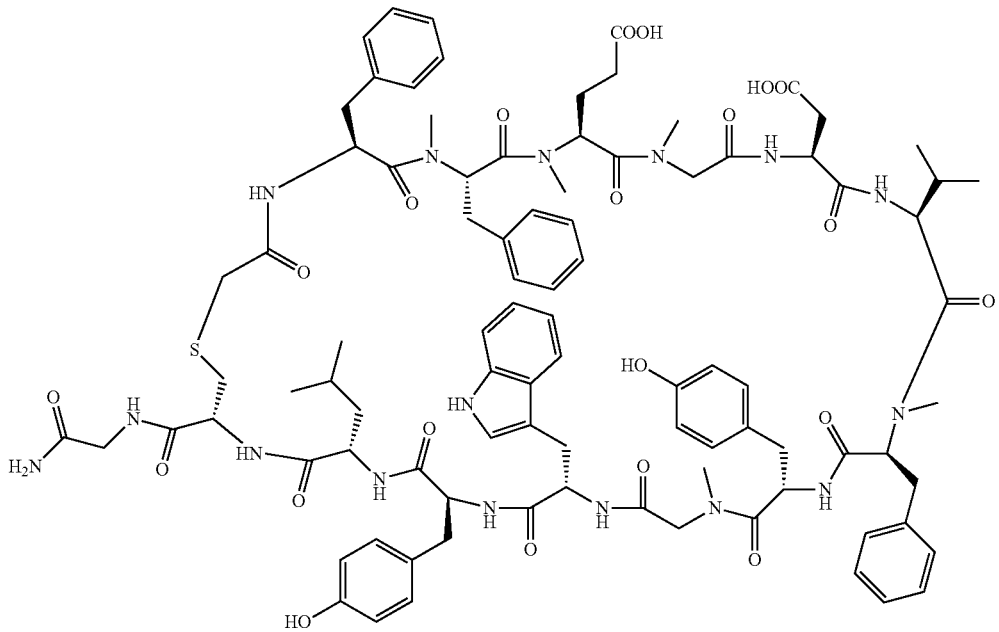

Example 3061

Example 3061 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 5-minute hold at 100% B; Flow: 20 mL/min. Fractions containing the desired product were combined and dried to yield 3.2 mg in 98% purity".

Analysis LCMS condition D: Retention time=1.573 min; ESI-MS(+) m/z 1811.80 (M+H).

Analysis LCMS condition E: Retention time=1.711 min; ESI-MS(+) m/z 906.80 (M+2H), 1811.80 (M+H).

Preparation of Example 3062

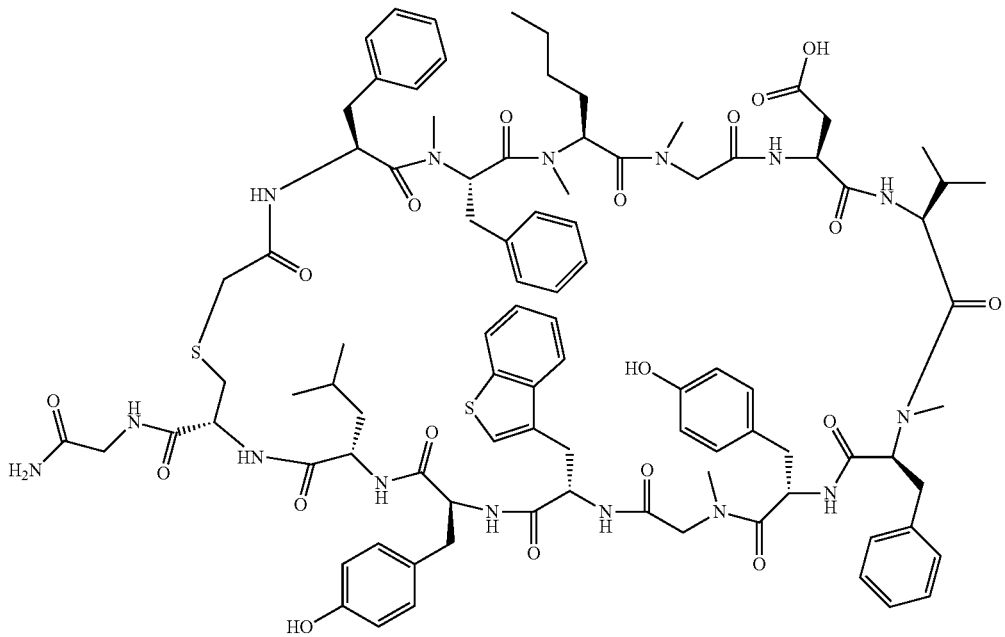

Example 3062

Example 3062 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 min., then a 5-minute hold at 100% B; Flow: 20 mL/min. Fractions containing the desired product were combined and dried to obtain 5.7 mg in 95% purity.

Analysis LCMS condition D: Retention time=1.698 min; ESI-MS(+) m/z 1813.70 (M+H).

Analysis LCMS condition E: Retention time=1.853 min; ESI-MS(+) m/z 1813.65 (M+H).

Preparation of Example 3063

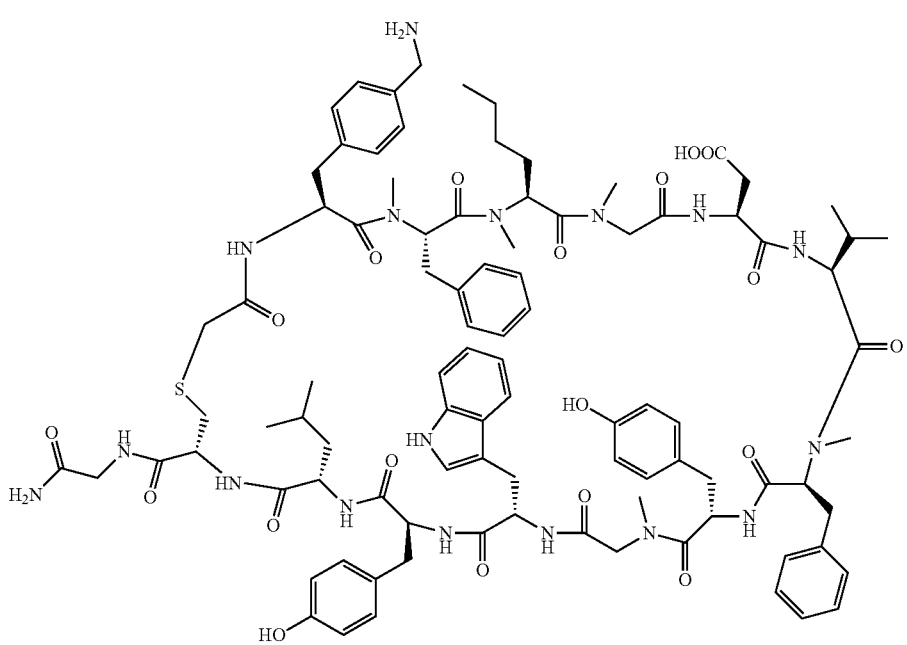

Example 3063

Example 3063 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 min., then a 5-minute hold at 100% B; Flow: 20 mL/min. Fractions containing the desired product were combined and dried. The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min., then a 5-minute hold at 100% B; Flow: 20 mL/min. Fractions containing the desired product were combined and dried. The yield of product was 4.4 mg, and its estimated purity by LCMS analysis was 99%.

Analysis LCMS condition D: Retention time=1.439 min; ESI-MS(+) m/z 1825.90 (M+H).

Analysis LCMS condition E: Retention time=1.490 min; ESI-MS(+) m/z 1825.85 (M+H).

Preparation of Example 3064

Example 3064 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The material was further purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min., then a 5-minute hold at 100% B; Flow: 20 mL/min. Fractions containing the desired product were combined and dried. The yield of product was 3.31 mg, and its estimated purity by LCMS analysis was 98%.

Analysis LCMS condition D: Retention time=1.468 min; ESI-MS(+) m/z 1777.95 (M+H).

Analysis LCMS condition E: Retention time=1.671 min; ESI-MS(+) m/z 1778.80 (M+H).

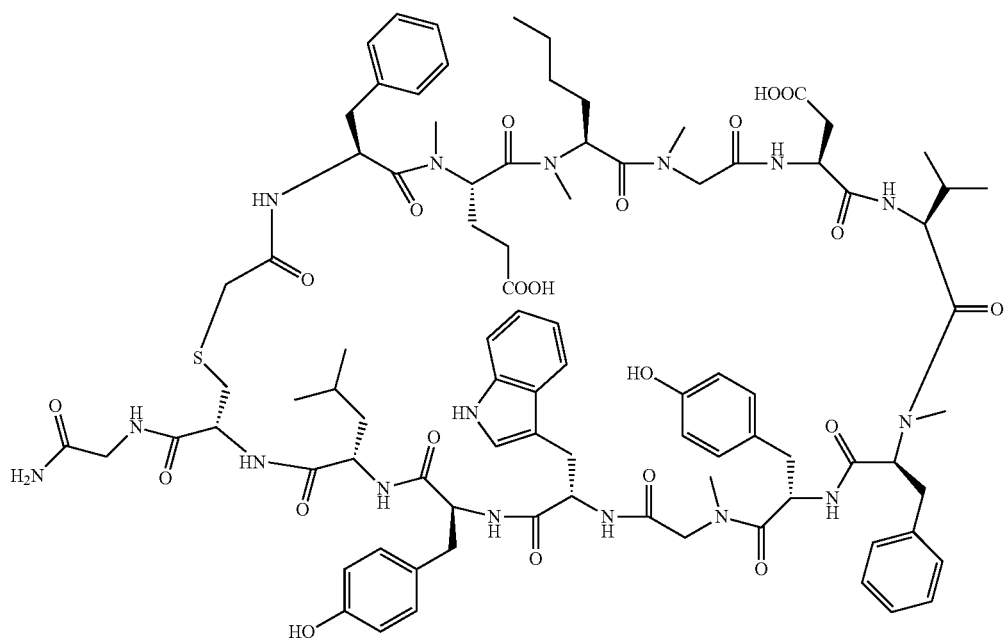

Example 3064

Preparation of Example 3065

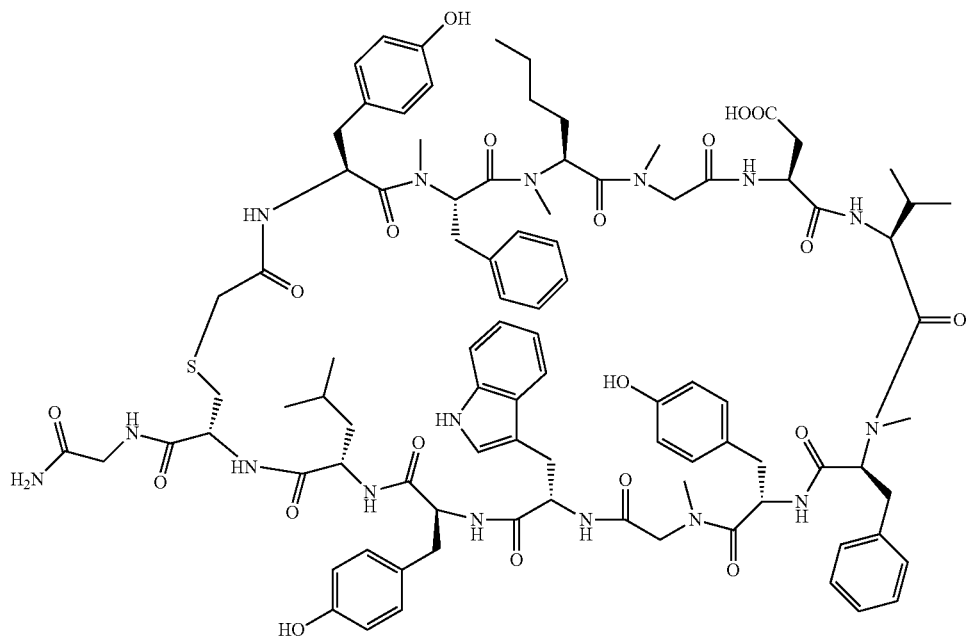

Example 3065

Example 3065 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-80% B over 50 min., then a 5-minute hold at 80% B; Flow: 15 mL/min. Fractions containing the desired product were combined and dried. The yield of product was 4.1 mg, and its estimated purity by HPLC "Analysis Condition B" using a gradient of 35% to 75% buffer B over 30 min giving 96% purity.

Analysis LCMS condition A: Retention time=1.37 min; ESI-MS(+) m/z 907.2 (M+2H).

Preparation of Example 3066

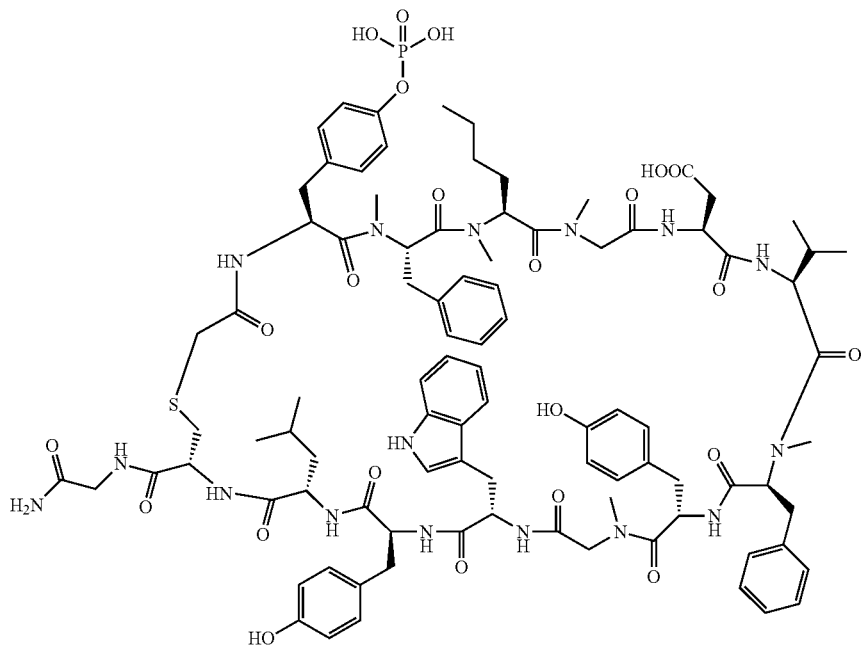

Example 3066

Example 3066 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-70% B over 50 min., then a 5-minute hold at 70% B; Flow: 15 mL/min. Fractions containing the desired product were combined and dried. The yield of product was 2.5 mg, and its estimated purity was 91% by HPLC "Analysis HPLC Condition B" using a gradient of 35% to 70% buffer B over 30 min.

Analysis LCMS condition A: Retention time=1.36 min; ESI-MS(+) m/z 947.1 (M+2H).

Preparation of Example 3067

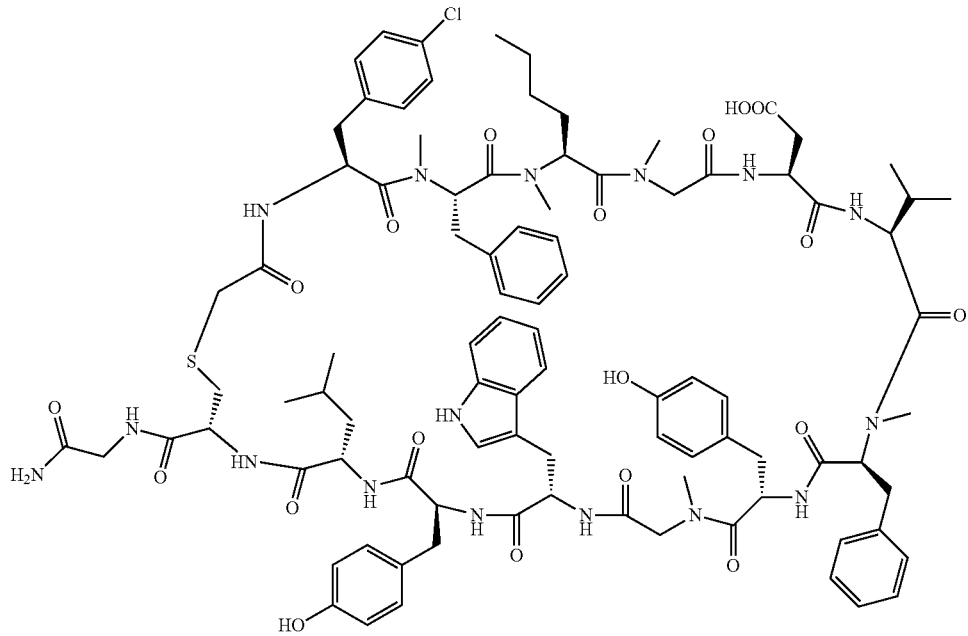

Example 3067

Example 3067 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-70% B over 50 min., then a 5-minute hold at 70% B; Flow: 15 mL/min. Fractions containing the desired product were combined and dried. The yield of product was 11.8 mg, and its estimated purity by HPLC was 99% "Analysis HPLC Condition B" using a gradient of 35% to 95% buffer B over 30 min.

Analysis LCMS condition A: Retention time=1.55 min; ESI-MS(+) m/z 916.5 (M+2H).

Preparation of Example 3068

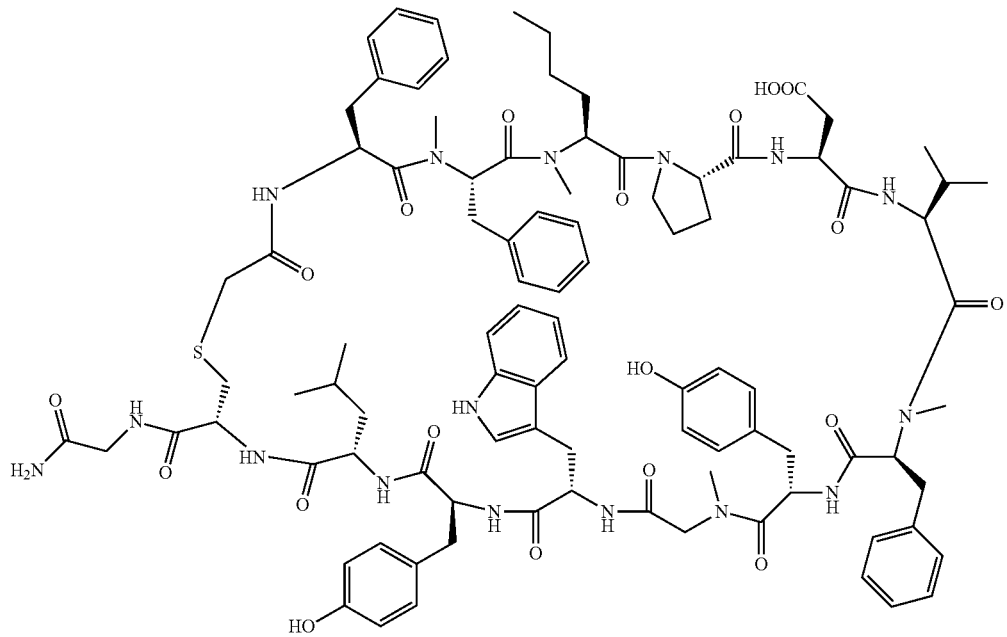

Example 3068

Example 3068 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 11.8 mg, and its estimated purity was 99% by "Analysis HPLC Condition B" using a gradient of 35% to 95% buffer B over 30 min.

Analysis LCMS condition A: Retention time=1.45 min; ESI-MS(+) m/z 912.3 (M+2H).

Preparation of Example 3069

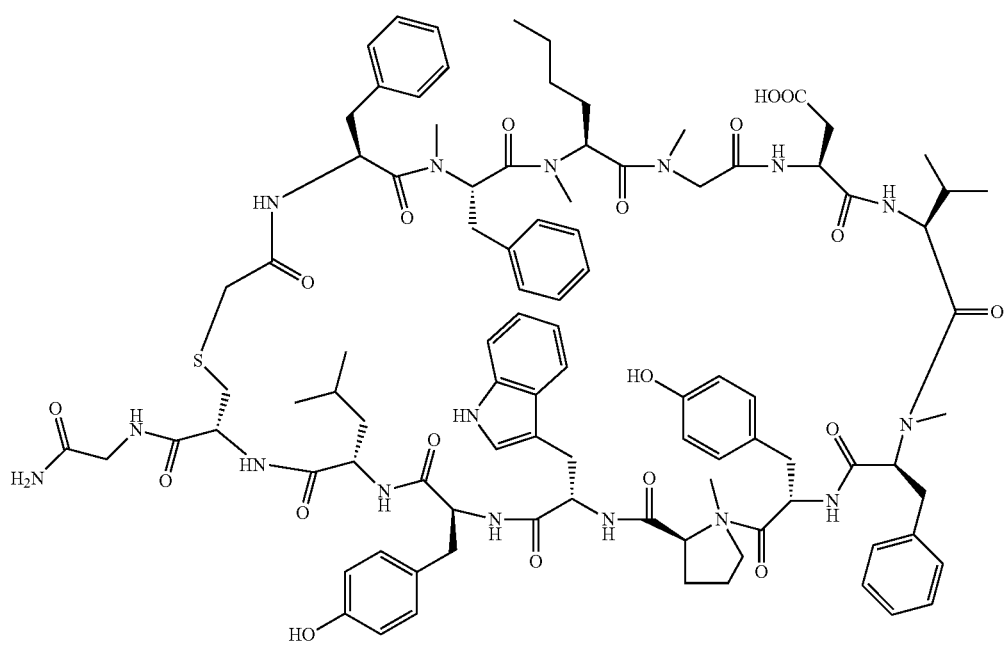

Example 3069

Example 3069 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 8.1 mg, and its estimated purity was 98% by "Analysis HPLC Condition B" using a gradient of 35% to 95% buffer B over 30 min.

Analysis LCMS condition A: Retention time=1.47 min; ESI-MS(+) m/z 912.3 (M+2H).

Preparation of Example 3070

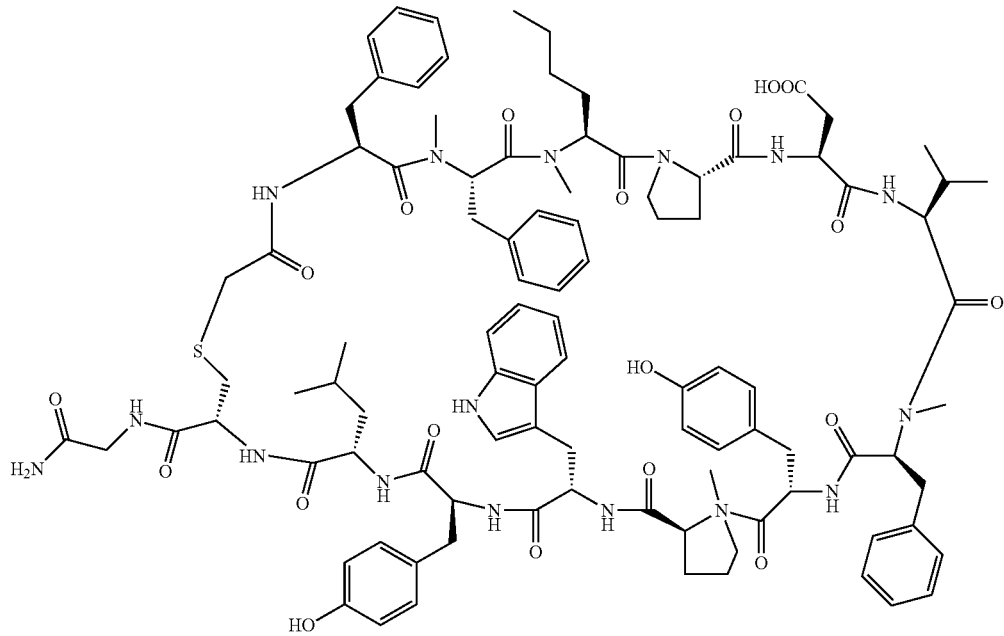

Example 3070

Example 3070 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 7.9 mg, and its estimated purity was 98% by "Analysis HPLC Condition B" using a gradient of 35% to 95% buffer B over 30 min.

Analysis LCMS condition A: Retention time=1.47 min; ESI-MS(+) m/z 925.5 (M+2H).

Preparation of Example 3071

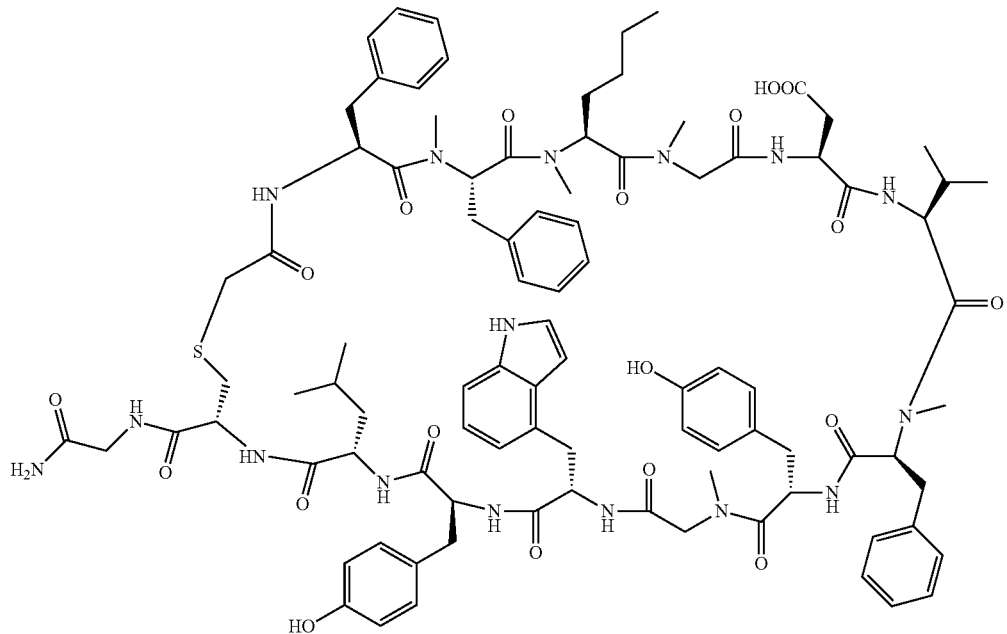

Example 3071

Example 3071 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 6.3 mg, and its estimated purity was 99% by "Analysis HPLC Condition B" using a gradient of 35% to 95% buffer B over 30 min.

Analysis LCMS condition A: Retention time=1.45 min; ESI-MS(+) m/z 899.3 (M+2H).

Preparation of Example 3072

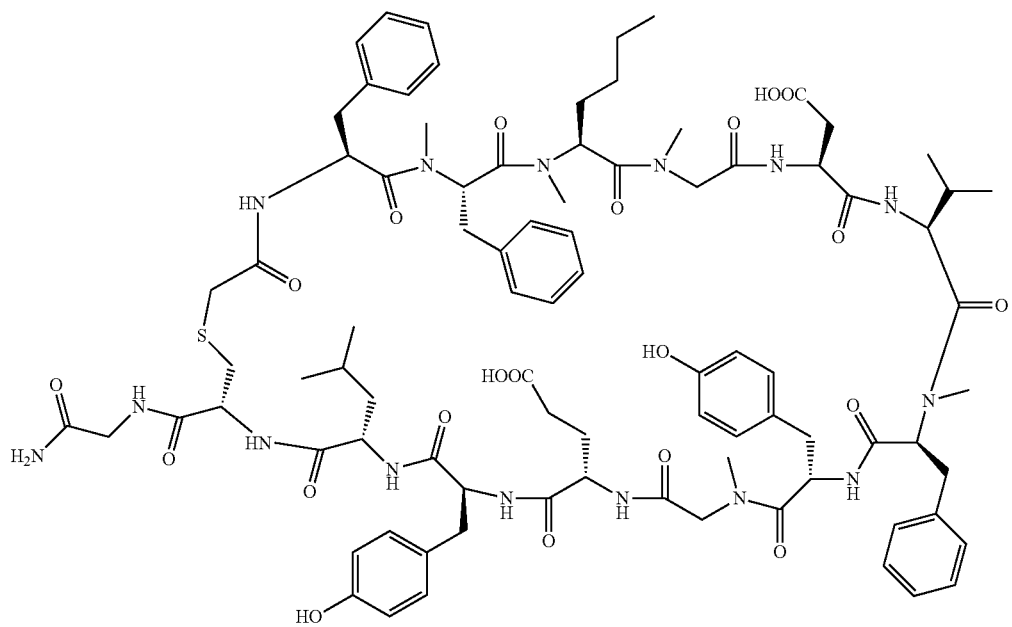

Example 3072

Example 3072 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 6.5 mg, and its estimated purity was 99% by "Analysis HPLC Condition B" using a gradient of 35% to 95% buffer B over 30 min.

Analysis LCMS condition A: Retention time=1.37 min; ESI-MS(+) m/z 870.7 (M+2H).

Preparation of Example 3073

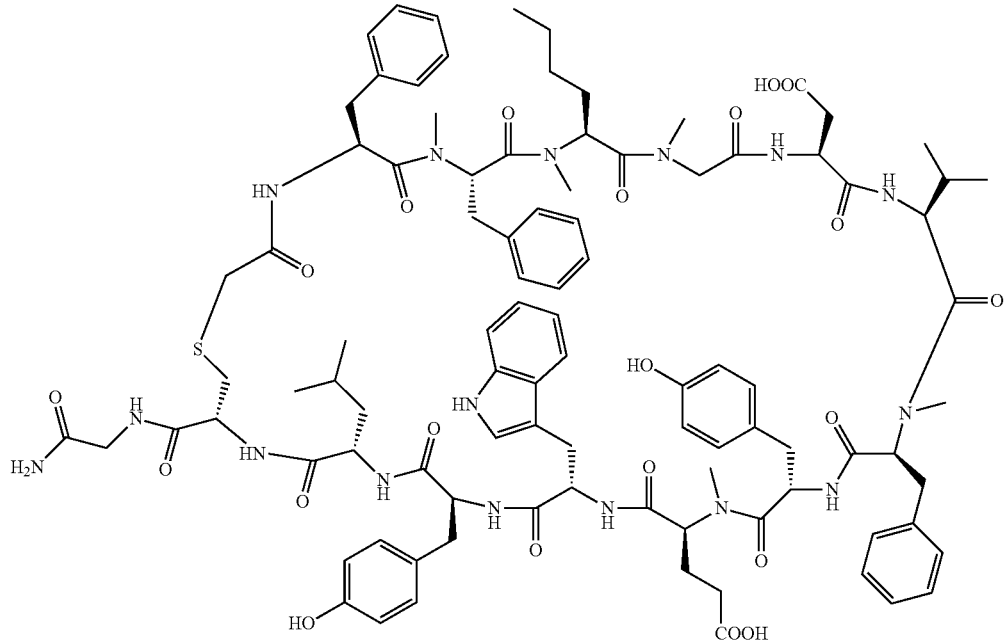

Example 3073

Example 3073 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.35-95% B over 50 min., then a 5-minute hold at 95% B; Flow: 15 mL/min. Fractions containing the desired product were combined and dried. The yield of product was 5.9 mg, and its estimated purity was 98% by "Analysis HPLC Condition B" using a gradient of 35% to 95% buffer B over 30 min.

Analysis LCMS condition A: Retention time=1.55 min; ESI-MS(+) m/z 943.9 (M+2H).

Preparation of Example 3074

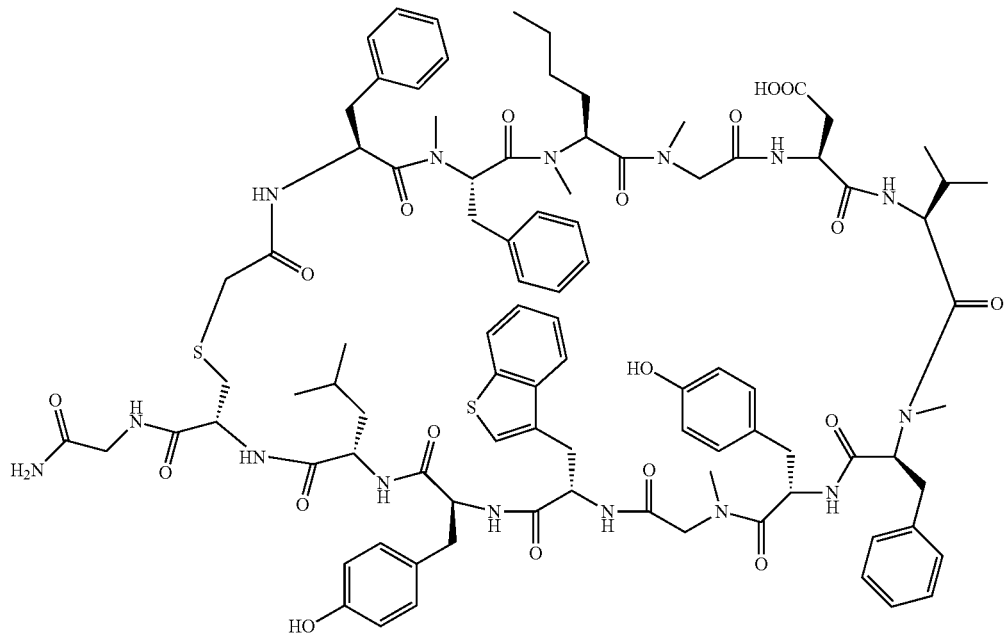

Example 3074

Example 3074 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 50 min., then a 5-minute hold at 90% B; Flow: 15 mL/min. Fractions containing the desired product were combined and dried. The yield of product was 4.8 mg, and its estimated purity was 99% by "Analysis HPLC Condition B" using a gradient of 30% to 90% buffer B over 30 min.

Analysis LCMS condition A: Retention time=1.49 min; ESI-MS(+) m/z 915.9 (M+2H).

Preparation of Example 3075

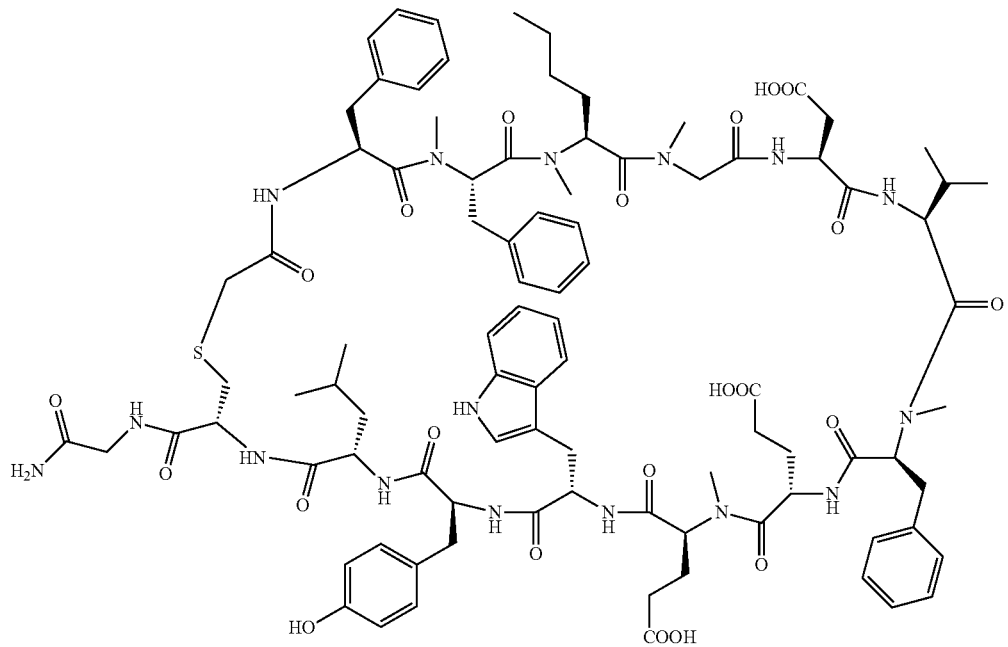

Example 3075

Example 3075 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.30-90% B over 60 min., then a 5-minute hold at 90% B; Flow: 15 mL/min. Fractions containing the desired product were combined and dried. The yield of product was 9.5 mg, and its estimated purity by HPLC "Analysis Condition B" using a gradient of 30% to 85% buffer B over 30 min. giving 97% purity.

Analysis LCMS condition A: Retention time=1.36 min; ESI-MS(+) m/z 926.3 (M+2H).

Preparation of Example 3076

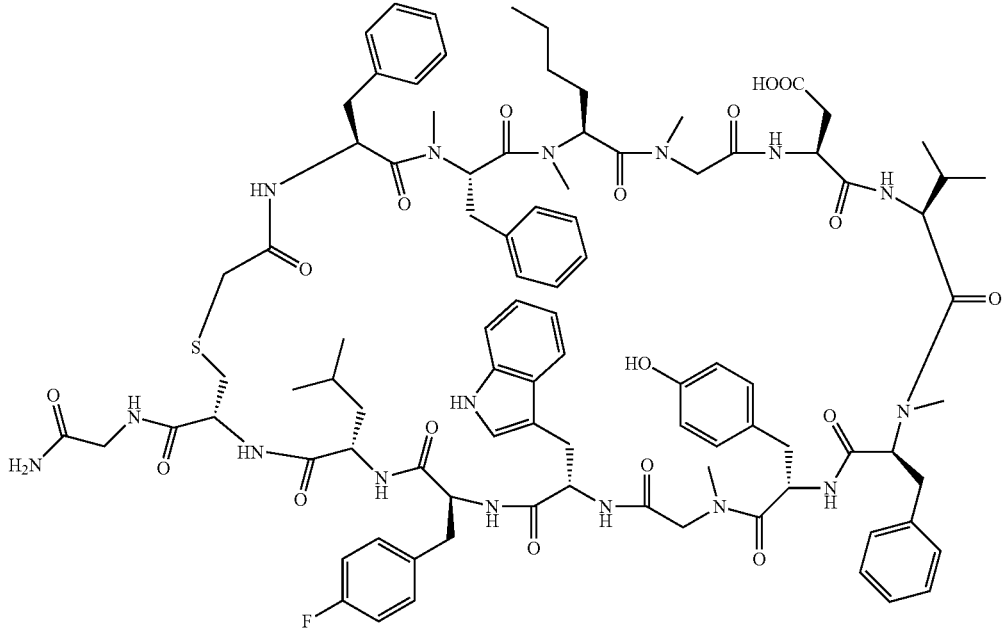

Example 3076

Example 3076 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.35-95% B over 60 min, then a 5-minute hold at 95% B; Flow: 15 mL/min. Fractions containing the desired product were combined and dried. The yield of product was 11.9 mg, and its estimated purity by HPLC "Analysis Condition B" using a gradient of 35% to 95% buffer B over 30 min giving 99% purity.

Analysis LCMS condition A: Retention time=1.59 min; ESI-MS(+) m/z 900.3 (M+2H).

Preparation of Example 3077

Example 3077

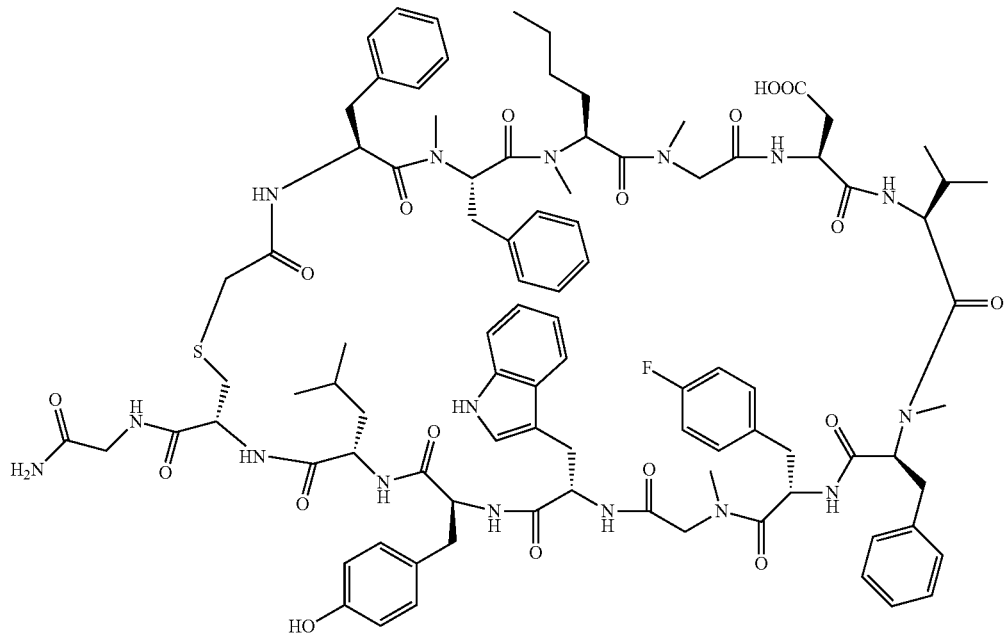

Example 3077 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.35-95% B over 60 min, then a 5-minute hold at 95% B; Flow: 15 mL/min. Fractions containing the desired product were combined and dried. The yield of product was 12.3 mg, and its estimated purity by HPLC "Analysis Condition B" using a gradient of 35% to 95% buffer B over 30 min giving 99% purity.

Analysis LCMS condition A: Retention time=1.60 min; ESI-MS(+) m/z 900.3 (M+2H).

Preparation of Example 3078

Example 3078

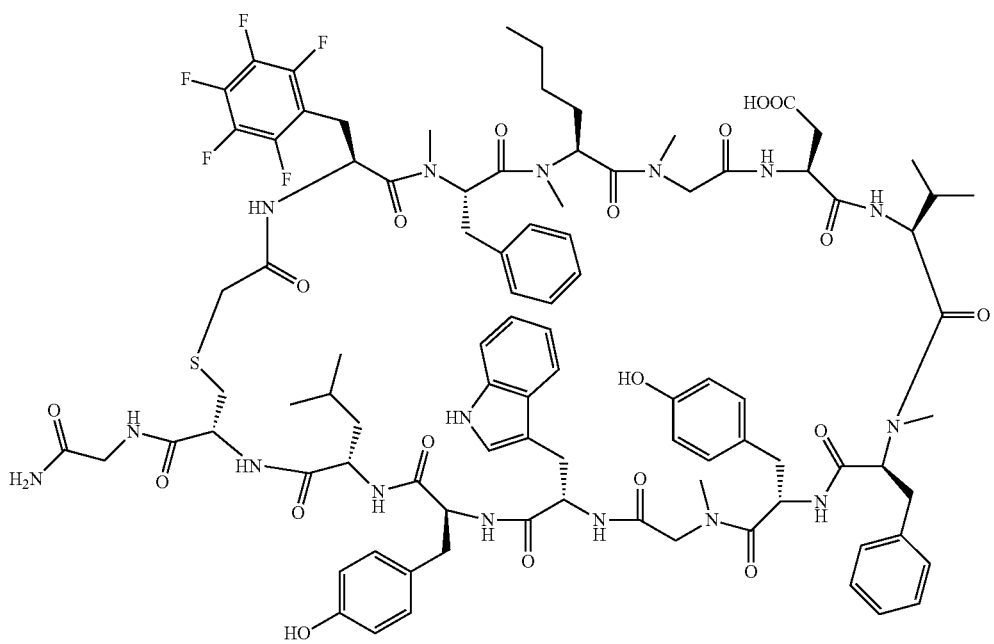

To a 50 mL polypropylene tube was added Sieber resin (140 mg, 0.100 mmol), and the tube was placed on the CEM Liberty microwave peptide synthesizer. The following procedures were then performed sequentially:
"CEM Method A: Resin-swelling procedure" was followed;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Leu-OH;
"CEM Method A: Standard coupling procedure" was followed with Fmoc-Tyr(tBu)-OH;
"CEM Method A: Standard coupling procedure" was followed with Fmoc-Trp(Boc)-OH;
"CEM Method A: Standard coupling procedure" was followed with Fmoc-Sar-OH;
"CEM Method A: Standard coupling procedure" was followed with Fmoc-Tyr(tBu)-OH;
"CEM Method A: Standard coupling procedure" was followed with Fmoc-[N-Me]Phe-OH;
"CEM Method A: Custom amino acids-coupling procedure" was followed with Fmoc-Val-OH using 10 eq for 2 hours at 75° C.;
"CEM Method A: Standard coupling procedure" was followed with Fmoc-Asp(OtBu)-OH;
"CEM Method A: Standard coupling procedure" was followed with Fmoc-Sar-OH;
"CEM Method A: Custom amino acids-coupling procedure" was followed with Fmoc-[N-Me]Nle-OH using 5 eq for 10 min;
"CEM Method A: Custom amino acids-coupling procedure" was followed with Fmoc-[N-Me]Phe-OH using 5 eq for 10 min;
"CEM Method A: Custom amino acids-coupling procedure" was followed with Fmoc-Phe(penta-F)—OH using 5 eq for 10 min;
"Prelude Method A: Chloroacetyl chloride coupling procedure A" was followed;
"Global Deprotection Method B" was followed;
"Cyclization Method C" was followed.

The crude material was purified via preparative LC/MS with the following conditions: Column: Waters XBridge C18, 19×250 mm, 5-μm particles; Mobile Phase A: 5:95 acetonitrile:water with 0.05% TFA; Mobile Phase B: 95:5 acetonitrile:water with 0.05% TFA; Gradient: 30-70% B over 25 min, then a 5-minute hold at 100% B; Flow: 20 mL/min. Fractions containing the desired product were combined and dried. The yield of product was 10.7 mg, and its estimated purity by LCMS analysis was 97%.

Analysis LCMS condition D: Retention time=1.79 min; ESI-MS(+) m/z 944.4 (M+2H).

Analysis LCMS condition E: Retention time=1.98 min; ESI-MS(+) m/z 944.3 (M+2H).

Preparation of Example 3079

Example 3079

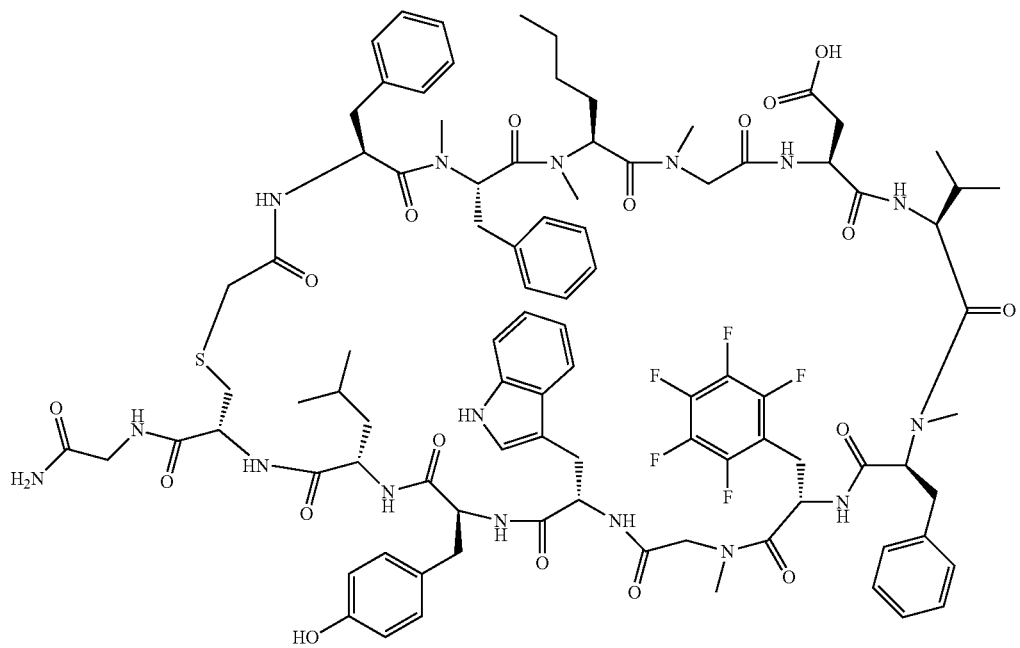

Example 3079 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 25 min., then a 5-minute hold at 100% B; Flow: 20 mL/min. Fractions containing the desired product were combined and dried. The yield of product was 10.3 mg, and its estimated purity by LCMS analysis was 99%

Analysis LCMS condition D: Retention time=1.87 min; ESI-MS(+) m/z 936.5 (M+2H).

Analysis LCMS condition E: Retention time=2.09 min; ESI-MS(+) m/z 935.8 (M+2H).

Preparation of Example 3080

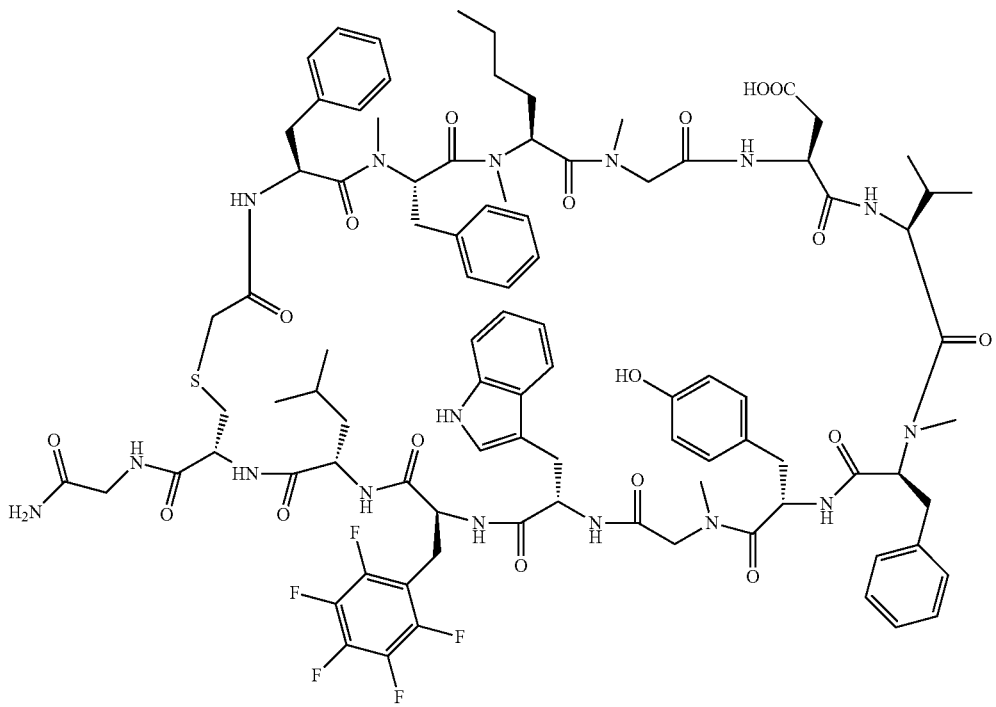

Example 3080

Example 3080 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 min, then a 5-minute hold at 100% B; Flow: 20 mL/min. Fractions containing the desired product were combined and dried. The yield of product was 8.71 mg, and its estimated purity by LCMS analysis was 98%.

Analysis LCMS condition D: Retention time=1.90 min; ESI-MS(+) m/z 935.9 (M+2H).

Analysis LCMS condition E: Retention time=2.11 min; ESI-MS(+) m/z 936.0 (M+2H).

Preparation of Example 3081

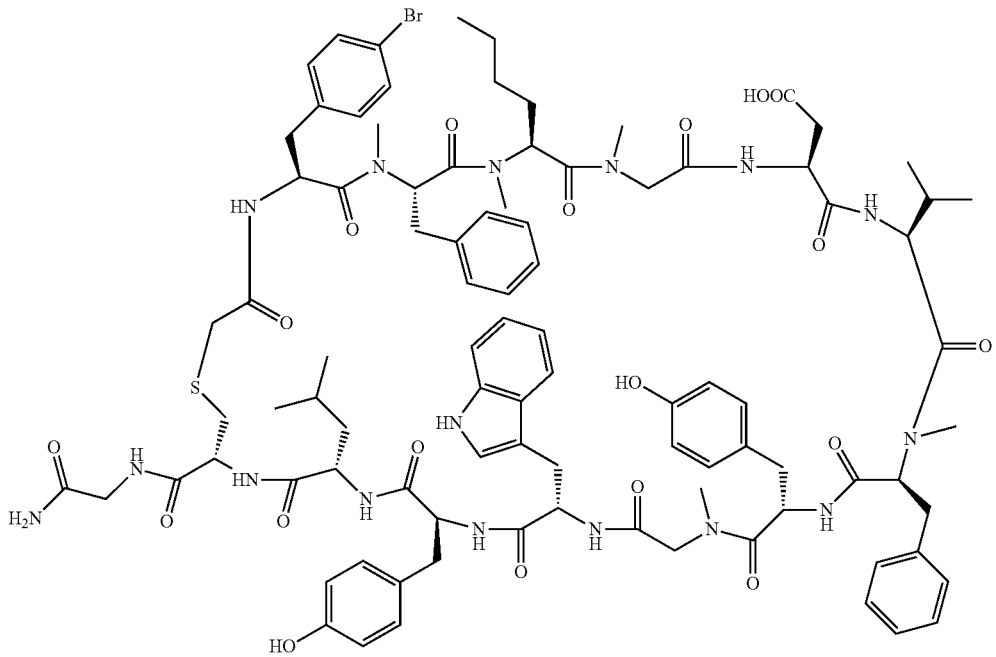

Example 3081

Example 3081 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min, then a 0-minute hold at 100% B; Flow: 20 mL/min. Fractions containing the desired product were combined and dried. The yield of product was 7.0 mg, and its estimated purity by LCMS analysis was 98%.

Analysis LCMS condition D: Retention time=1.72 min; ESI-MS(+) m/z 938.8 (M+2H).

Analysis LCMS condition E: Retention time=1.92 min; ESI-MS(+) m/z 938.9 (M+2H).

Preparation of Example 3082

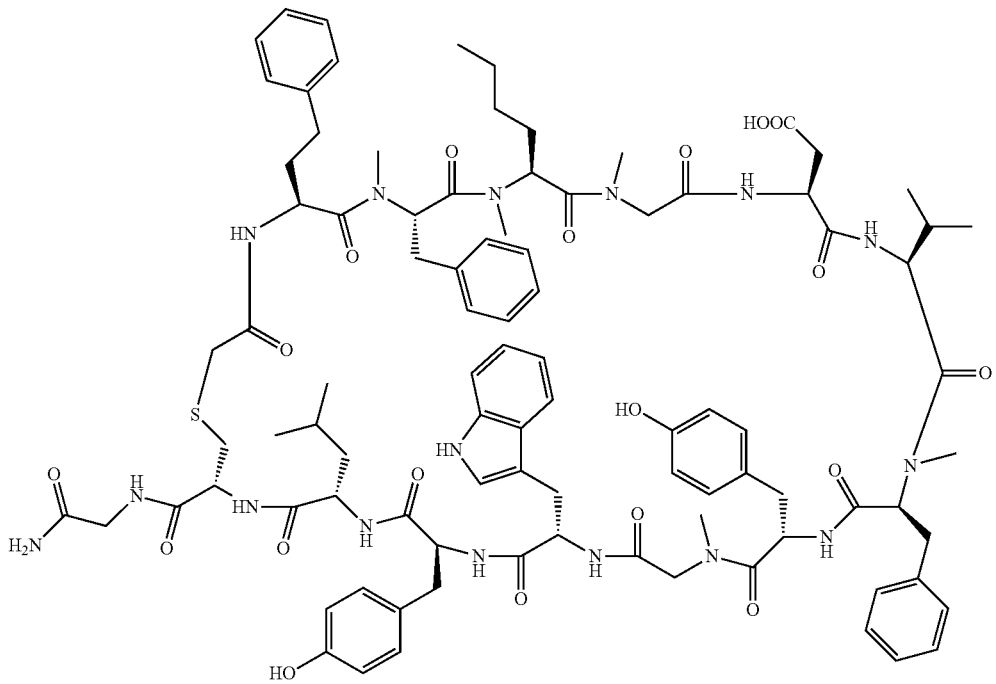

Example 3082

Example 3082 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min., then a 5-minute hold at 100% B; Flow: 20 mL/min. Fractions containing the desired product were combined and dried. The yield of product was 8.8 mg, and its estimated purity by LCMS analysis was 99%.

Analysis LCMS condition D: Retention time=1.68 min; ESI-MS(+) m/z 906.1 (M+2H).

Analysis LCMS condition E: Retention time=1.89 min; ESI-MS(+) m/z 906.2 (M+2H).

Preparation of Example 3083

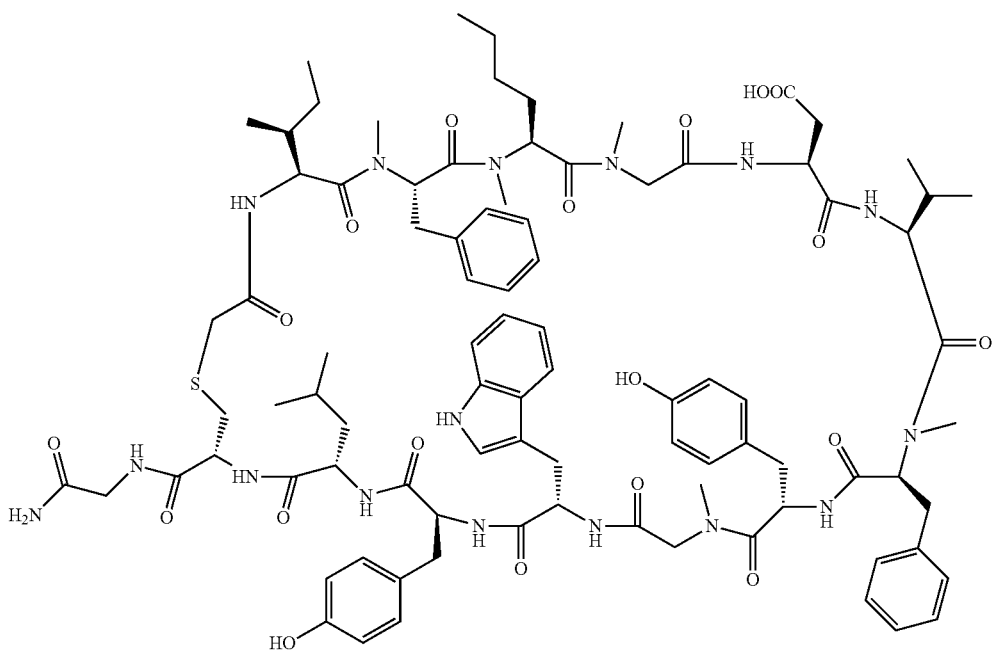

Example 3083

Example 3083 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 min., then a 5-minute hold at 100% B; Flow: 20 mL/min. Fractions containing the desired product were combined and dried. The yield of product was 9.4 mg, and its estimated purity by LCMS analysis was 95%.

Analysis LCMS condition D: Retention time=1.61 min; ESI-MS(+) m/z 882.0 (M+2H).

Analysis LCMS condition E: Retention time=1.81 min; ESI-MS(+) m/z 881.7 (M+2H).

Preparation of Example 3086

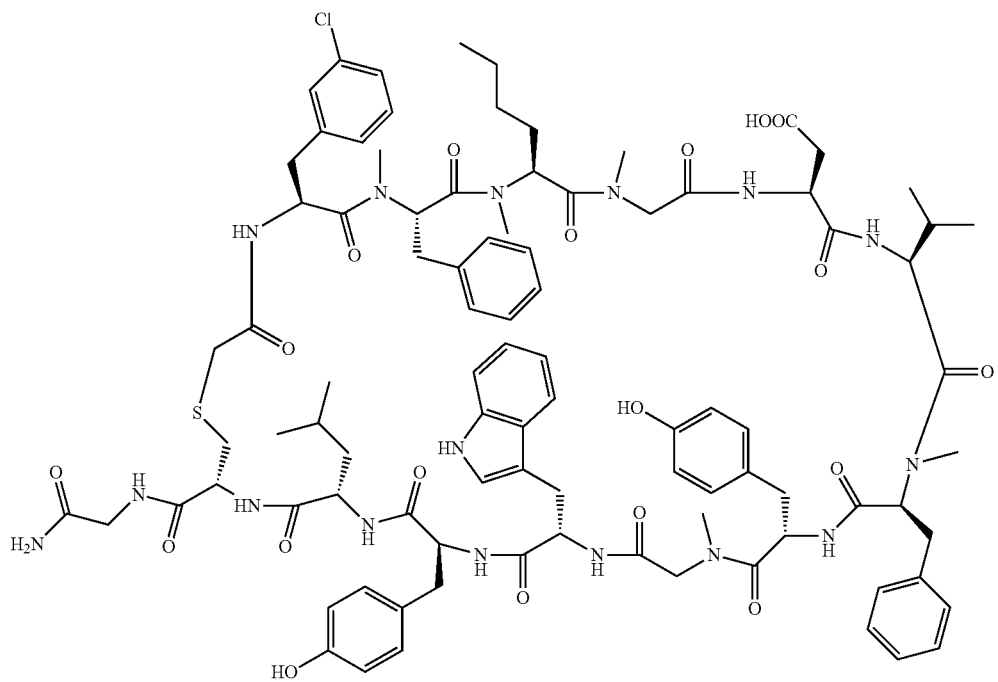

Example 3086

Example 3086 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 11.1 mg, and its estimated purity by LCMS analysis was 95%.

Analysis LCMS condition D: Retention time=1.68 min; ESI-MS(+) m/z 916.3 (M+2H).

Analysis LCMS condition E: Retention time=1.89 min; ESI-MS(+) m/z 916.5 (M+2H).

Preparation of Example 3087

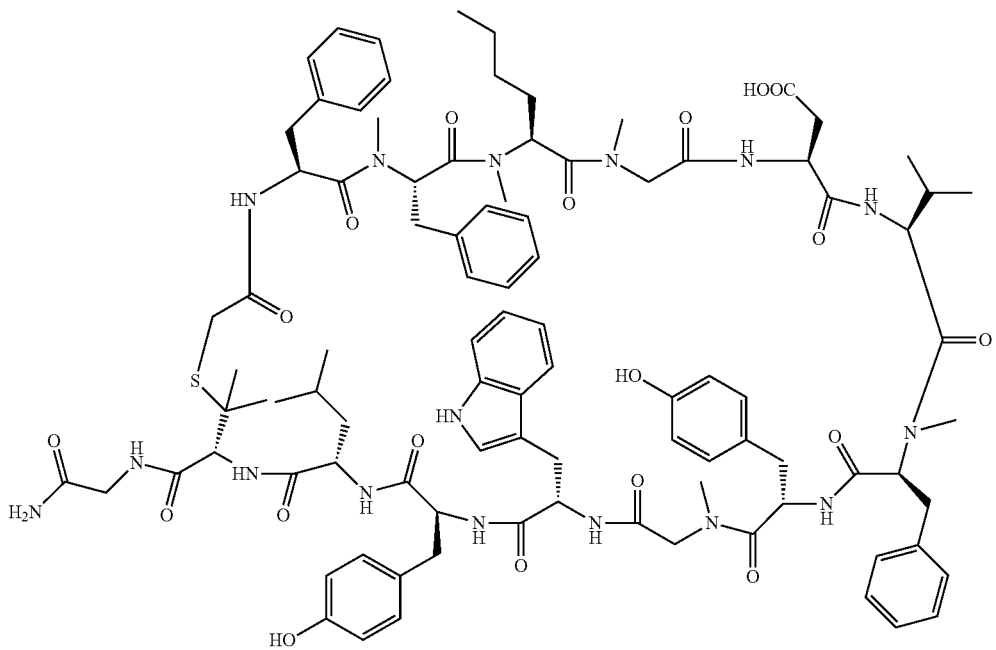

Example 3087

Example 3087 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: YMC AQ-ODS 250×20 mm column; Mobile Phase A: water with 0.05% TFA; Mobile Phase B: Acetonitrile with 0.05% TFA; Gradient: 30-90% B over 55 min., then a 5-minute hold at 90% B; Flow: 15 mL/min. Fractions containing the desired product were combined and dried. The peptide was not very clean and hence another preparative HPLC with the following conditions was performed: Column: YMC AQ-ODS 250×20 mm column; Mobile Phase A: water with 0.05% TFA; Mobile Phase B: Acetonitrile with 0.05% TFA; Gradient: 40-80% B over 50 min., then a 5-minute hold at 80% B; Flow: 15 mL/min. Fractions containing the desired product were combined and dried. The yield of product was 2.5 mg, and its estimated purity was 97% by HPLC "Analysis Condition B" using a gradient of 35% to 85% buffer B over 30 min.

Analysis LCMS condition A: Retention time=1.48 min; ESI-MS(+) m/z 913.5 (M+2H).

Preparation of Example 3088

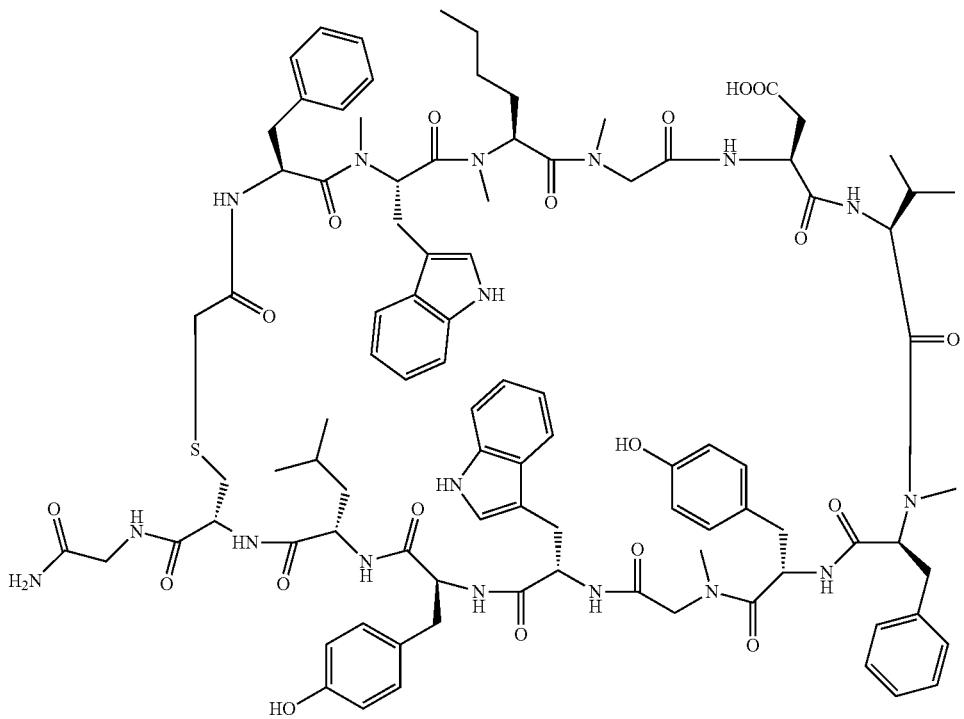

Example 3088

Example 3088 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative HPLC with the following conditions: Column: YMC AQ-ODS 250×20 mm column; Mobile Phase A: water with 0.05% TFA; Mobile Phase B: Acetonitrile with 0.05% TFA; Gradient: 30-90% B over 55 min., then a 5-minute hold at 90% B; Flow: 15 mL/min. Fractions containing the desired product were combined and dried. The peptide was not very clean and hence another preparative HPLC with the following conditions was performed: Column: YMC AQ-ODS 250×20 mm column; Mobile Phase A: water with 0.05% TFA; Mobile Phase B: Acetonitrile with 0.05% TFA; Gradient: 40-80% B over 50 min., then a 5-minute hold at 80% B; Flow: 15 mL/min. Fractions containing the desired product were combined and dried. Two isomers (isomer 3088-A and isomer 3088-B) were obtained. The yield of product s isomer 3088-A and isomer 3088-B was 1.1 mg and 0.81 mg respectively, and its estimated purity by HPLC "Analysis Condition B" using a gradient of 35% to 85% buffer B over 30 min. giving 99% and 93% purity for isomer 3088-A and isomer 3088-B, respectively. LC/MS confirmed product using LCMS "Analysis Condition A"

Isomer 3088-A: Analysis LCMS condition A: Retention time=1.45 min; ESI-MS(+) m/z 918.7 (M+2H).

Isomer 3088-B: Analysis LCMS condition A: Retention time=1.51 min; ESI-MS(+) m/z 918.8 (M+2H).

Preparation of Example 3089

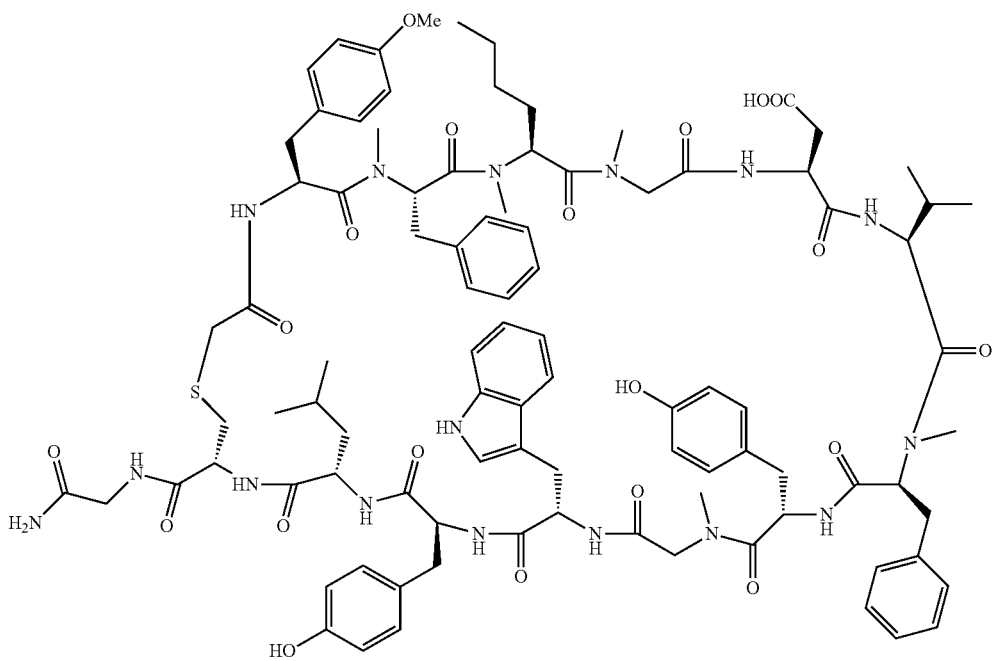

Example 3089

Example 3089 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 min., then a 5-minute hold at 100% B; Flow: 20 mL/min. Fractions containing the desired product were combined and dried. The yield of product was 9.0 mg, and its estimated purity by LCMS analysis was 95%.

Analysis LCMS condition D: Retention time=1.60 min; ESI-MS(+) m/z 914.1 (M+2H).

Analysis LCMS condition E: Retention time=1.81 min; ESI-MS(+) m/z 914.2 (M+2H).

Preparation of Example 3090

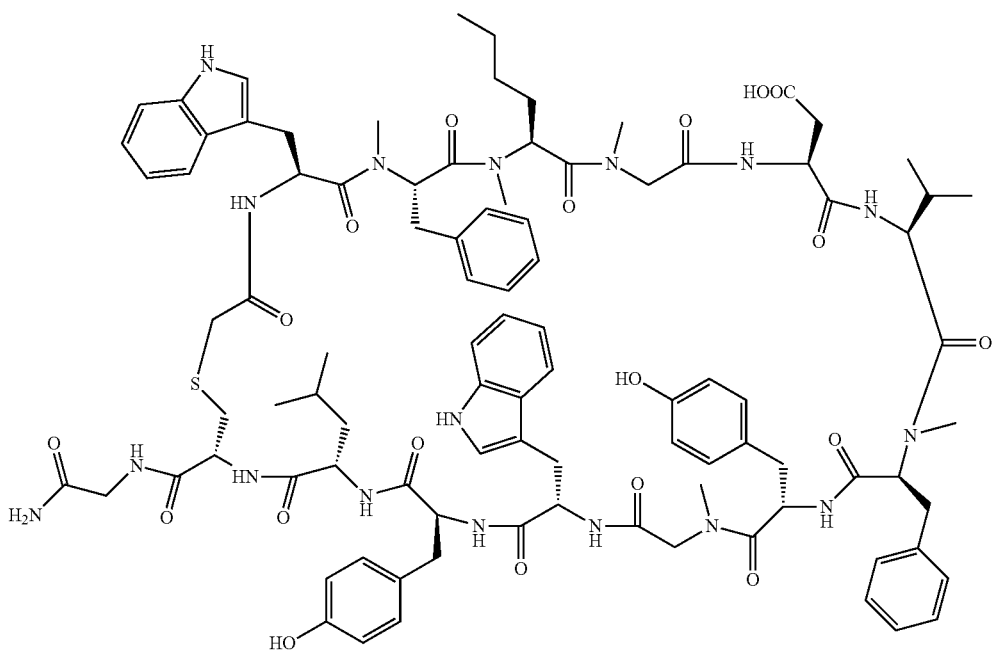

Example 3090

Example 3090 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 5.11 mg, and its estimated purity by LCMS analysis was 99%.

Analysis LCMS condition D: Retention time=1.61 min; ESI-MS(+) m/z 918.6 (M+2H).

Analysis LCMS condition E: Retention time=1.82 min; ESI-MS(+) m/z 918.9 (M+2H).

Preparation of Example 3091

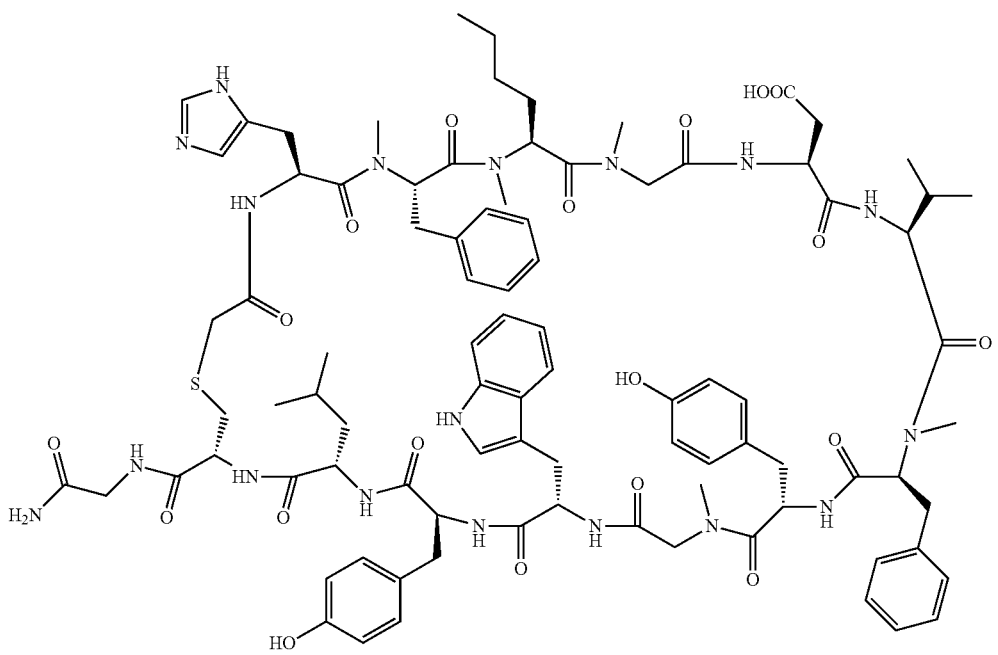

Example 3091

Example 3091 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 6.9 mg, and its estimated purity by LCMS analysis was 92%.

Analysis LCMS condition D: Retention time=1.40 min; ESI-MS(+) m/z 894.4 (M+2H).

Analysis LCMS condition E: Retention time=1.53 min; ESI-MS(+) m/z 893.9 (M+2H).

Preparation of Example 3092

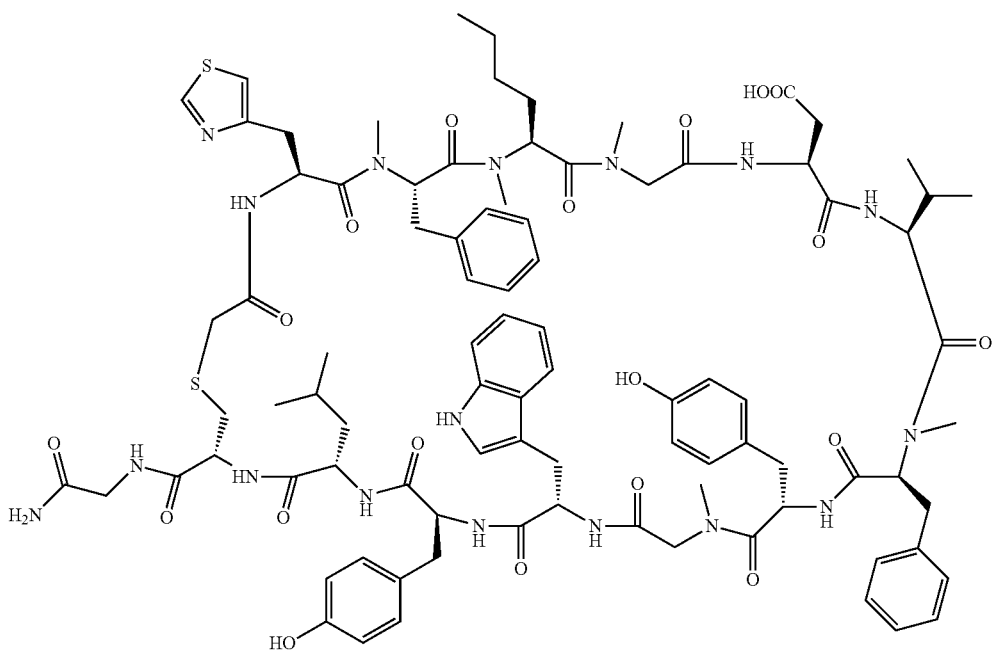

Example 3092

Example 3092 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 6.8 mg, and its estimated purity by LCMS analysis was 95%.

Analysis LCMS condition D: Retention time=1.49 min; ESI-MS(+) m/z 902.6 (M+2H).

Analysis LCMS condition E: Retention time=1.68 min; ESI-MS(+) m/z 902.6 (M+2H).

Preparation of Example 3093

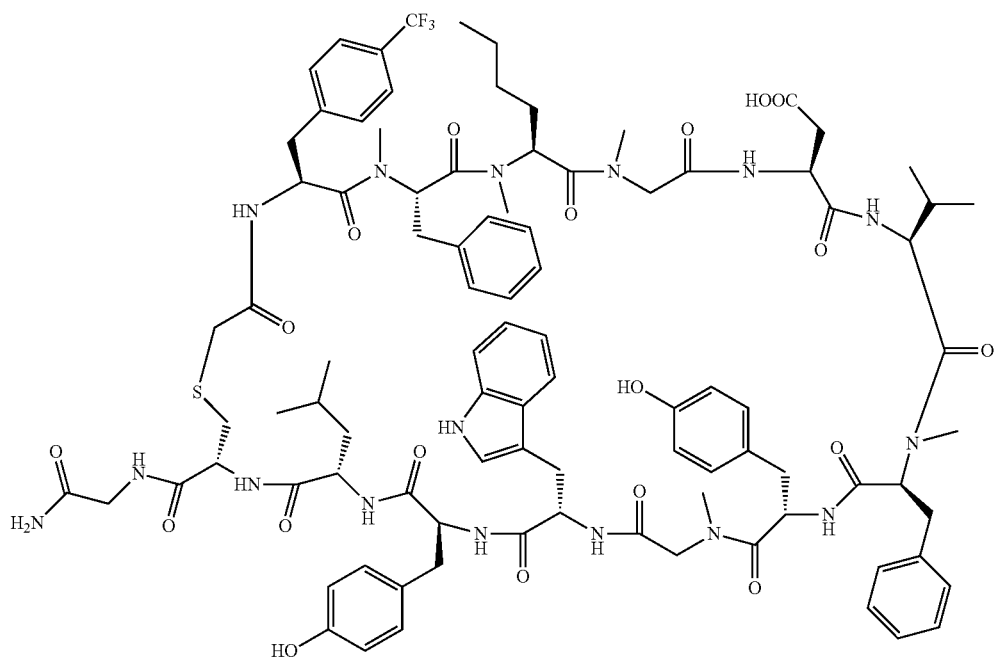

Example 3093

Example 3093 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min., then a 10-minute hold at 60% B; Flow: 20 mL/min. Fractions containing the desired product were combined and dried. The yield of product was 7.8 mg, and its estimated purity by LCMS analysis was 93%.

Analysis LCMS condition D: Retention time=1.71 min; ESI-MS(+) m/z 933.1 (M+2H).

Analysis LCMS condition E: Retention time=1.94 min; ESI-MS(+) m/z 933.4 (M+2H).

Preparation of Example 3094

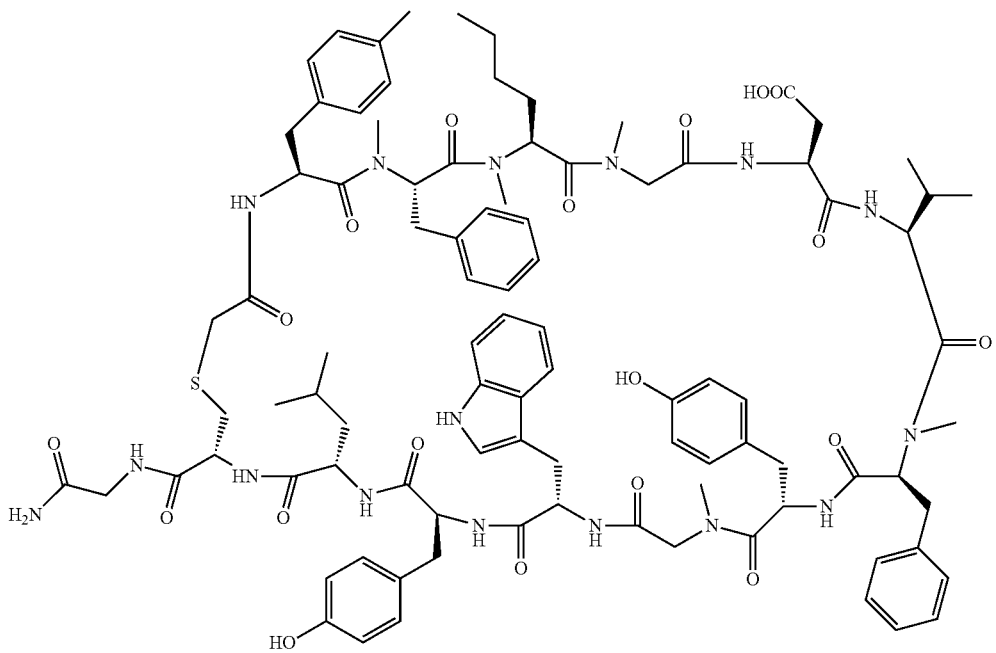

Example 3094

Example 3094 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 4.7 mg, and its estimated purity by LCMS analysis was 100%.

Analysis LCMS condition D: Retention time=1.67 min; ESI-MS(+) m/z 906.4 (M+2H).

Analysis LCMS condition E: Retention time=1.88 min; ESI-MS(+) m/z 906.8 (M+2H).

Preparation of Example 3095

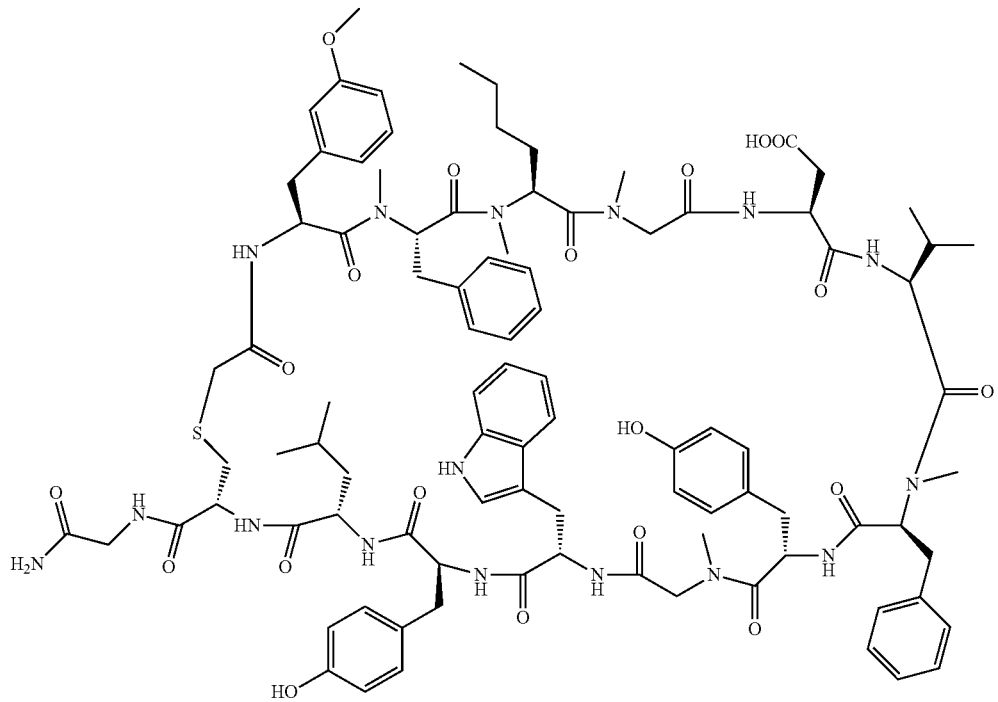

Example 3095

Example 3095 was prepared following the general synthetic sequence described for the preparation of Example 0072, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 4.6 mg, and its estimated purity by LCMS analysis was 100%.

Analysis LCMS condition D: Retention time=1.61 min; ESI-MS(+) m/z 914.5 (M+2H).
Analysis LCMS condition E: Retention time=1.80 min; ESI-MS(+) m/z 914.1 (M+2H).

Preparation of Example 3096

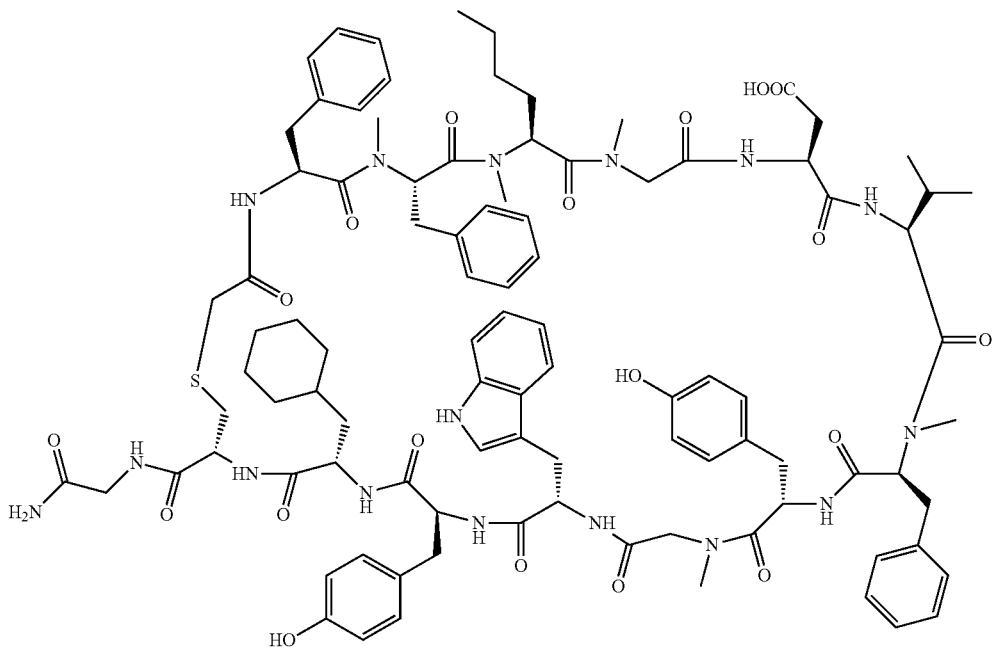

Example 3096

Example 3096 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 min., then a 10-minute hold at 65% B; Flow: 20 mL/min. Fractions containing the desired product were combined and dried. The yield of product was 6.8 mg, and its estimated purity by LCMS analysis was 100%.

Analysis LCMS condition D: Retention time=1.72 min; ESI-MS(+) m/z 919.3 (M+2H).

Analysis LCMS condition E: Retention time=1.93 min; ESI-MS(+) m/z 919.0 (M+2H).

Preparation of Example 3097

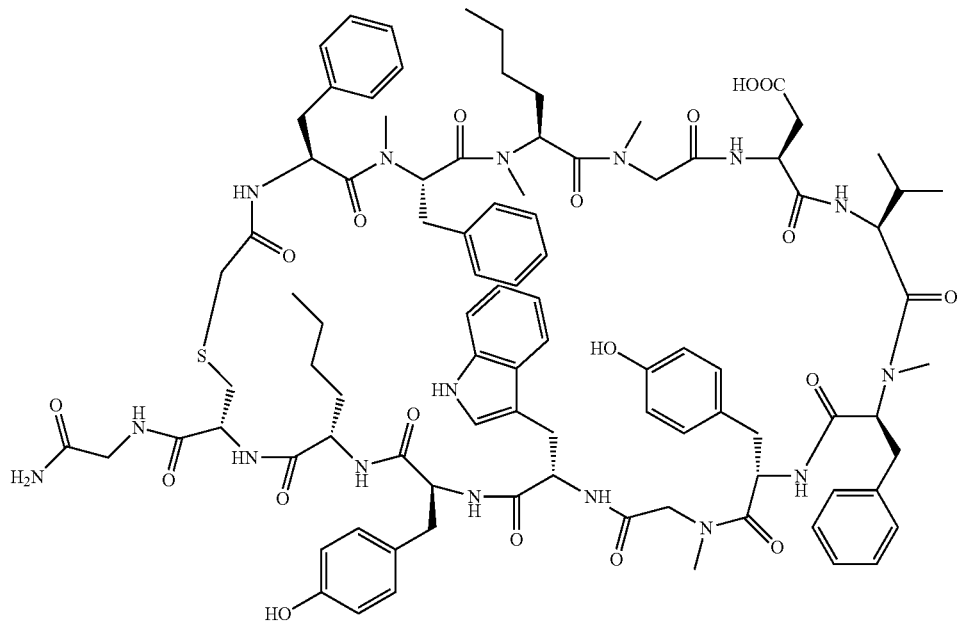

Example 3097

Example 3097 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-55% B over 25 min., then a 10-minute hold at 55% B; Flow: 20 mL/min. Fractions containing the desired product were combined and dried. The yield of product was 8.4 mg, and its estimated purity by LCMS analysis was 100%.

Analysis LCMS condition D: Retention time=1.62 min; ESI-MS(+) m/z 898.8 (M+2H).

Analysis LCMS condition E: Retention time=1.84 min; ESI-MS(+) m/z 898.9 (M+2H).

Preparation of Example 3098

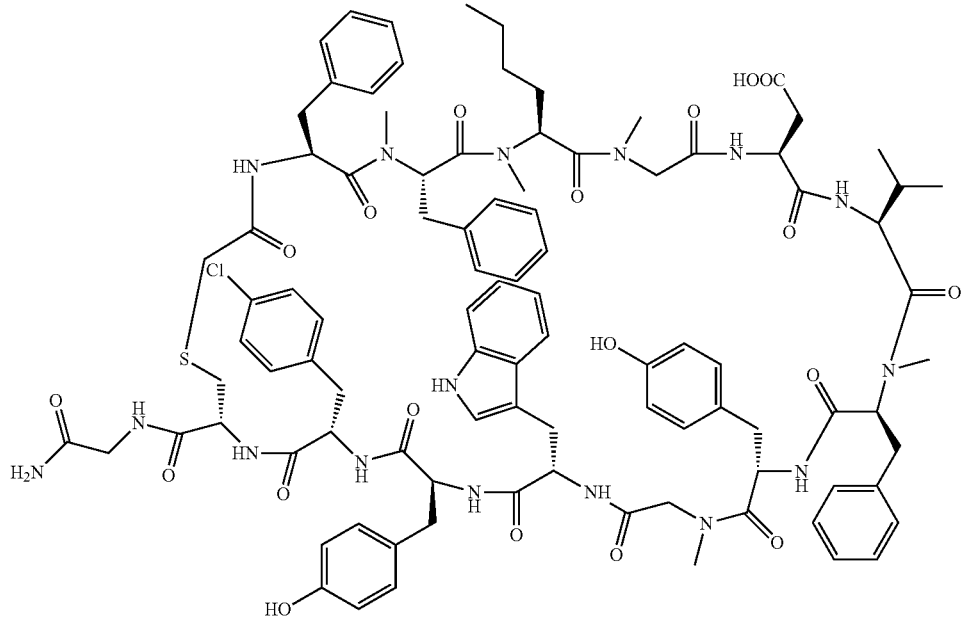

Example 3098

Example 3098 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 min., then a 10-minute hold at 65% B; Flow: 20 mL/min. Fractions containing the desired product were combined and dried. The yield of product was 8.2 mg, and its estimated purity by LCMS analysis was 100%.

Analysis LCMS condition D: Retention time=1.68 min; ESI-MS(+) m/z 934.0 (M+2H).

Analysis LCMS condition E: Retention time=1.91 min; ESI-MS(+) m/z 932.8 (M+2H).

Preparation of Example 3099

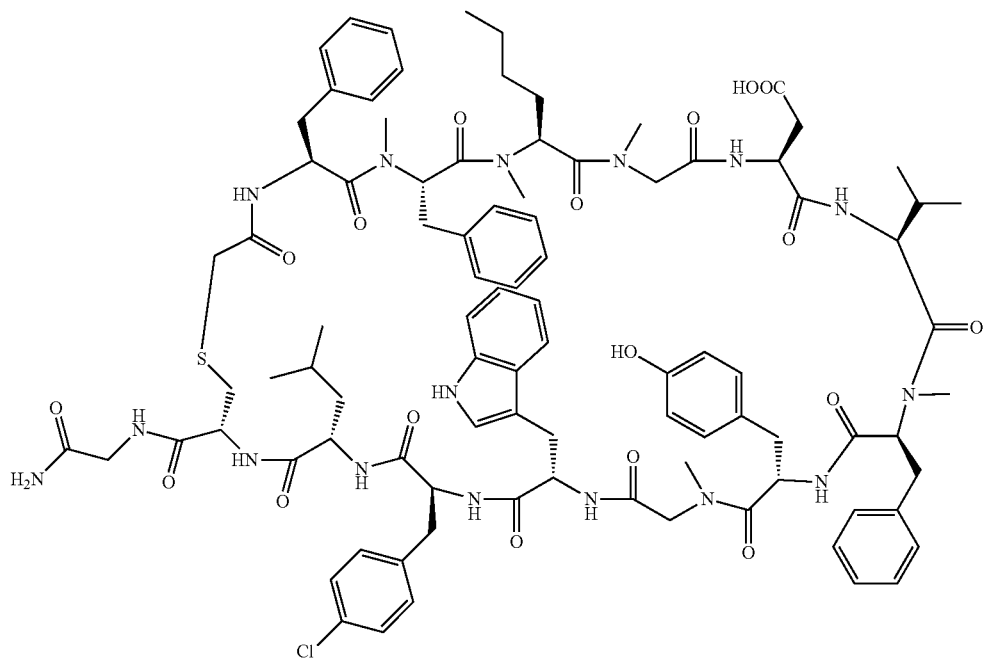

Example 3099

Example 3099 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 8.3 mg, and its estimated purity by LCMS analysis was 97%.

Analysis LCMS condition D: Retention time=1.78 min; ESI-MS(+) m/z 908.2 (M+2H).

Analysis LCMS condition E: Retention time=2.03 min; ESI-MS(+) m/z 908.0 (M+2H).

Preparation of Example 3100

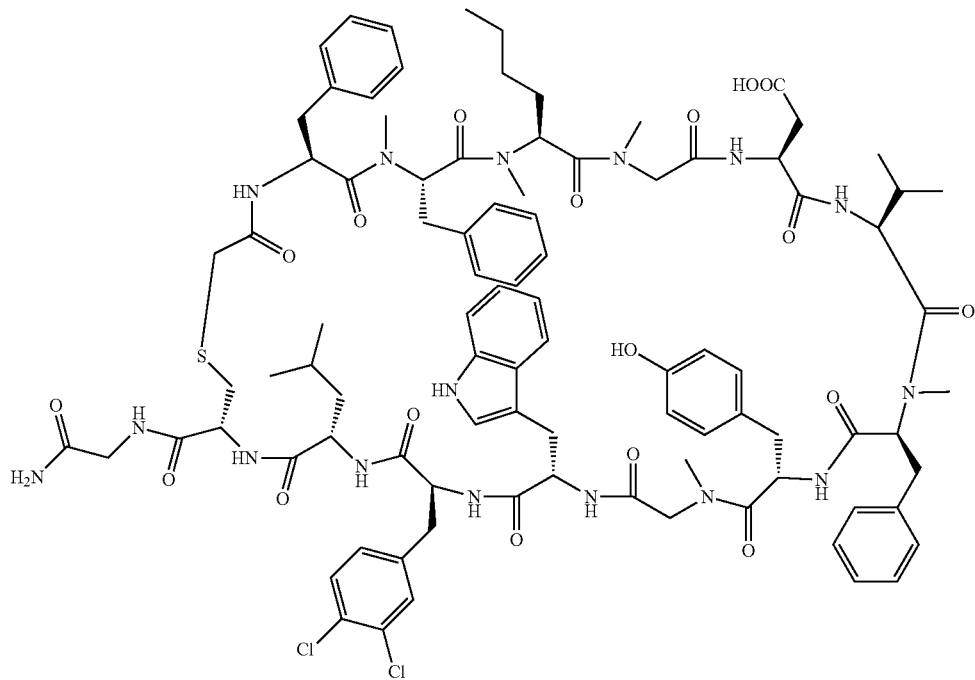

Example 3100

Example 3100 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 10.2 mg, and its estimated purity by LCMS analysis was 91%.

Analysis LCMS condition D: Retention time=1.85 min; ESI-MS(+) m/z 925.3 (M+2H).

Analysis LCMS condition E: Retention time=2.09 min; ESI-MS(+) m/z 925.6 (M+2H).

Preparation of Example 3101

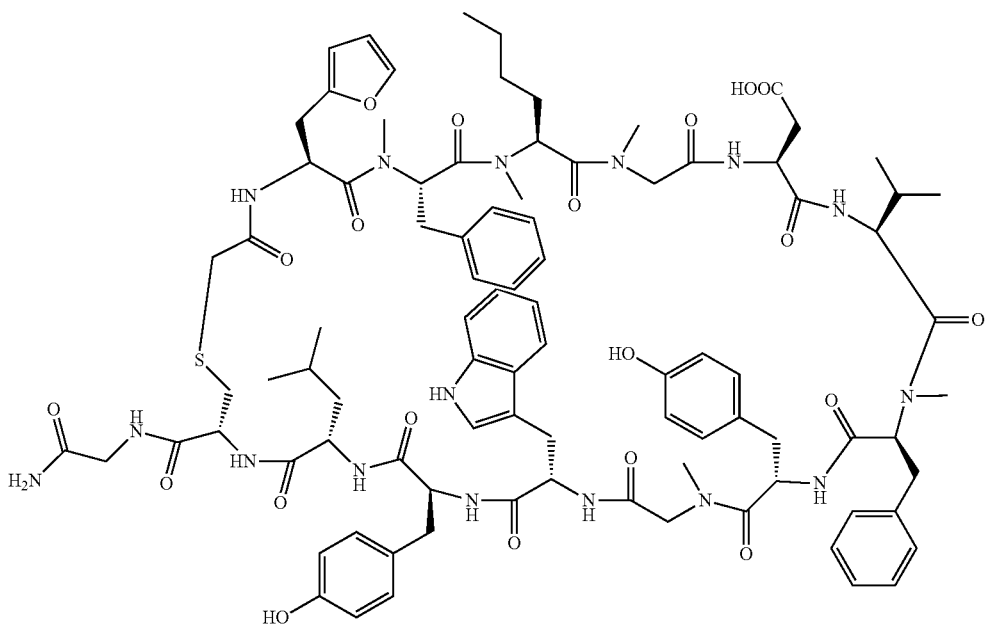

Example 3101

Example 3101 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 7.1 mg, and its estimated purity by LCMS analysis was 96%.

Analysis LCMS condition D: Retention time=1.56 min; ESI-MS(+) m/z 893.6 (M+2H).

Analysis LCMS condition E: Retention time=1.78 min; ESI-MS(+) m/z 893.8 (M+2H).

Preparation of Example 3102

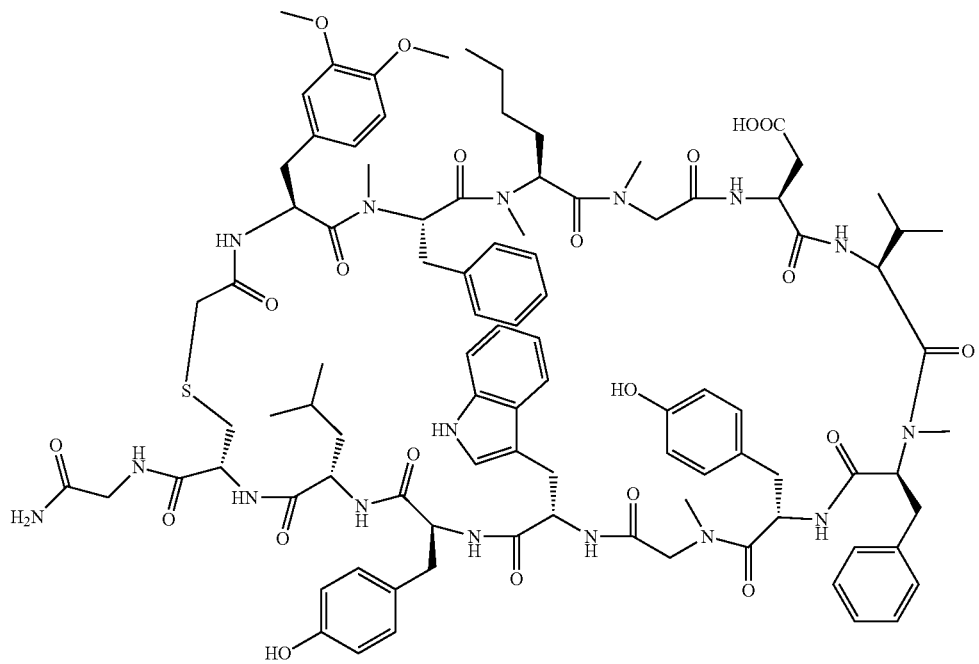

Example 3102

Example 3102 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.5 mg, and its estimated purity by LCMS analysis was 96%.

Analysis LCMS condition D: Retention time=1.52 min; ESI-MS(+) m/z 928.7 (M+2H).

Analysis LCMS condition E: Retention time=1.73 min; ESI-MS(+) m/z 928.6 (M+2H).

Preparation of Example 3103

Example 3103

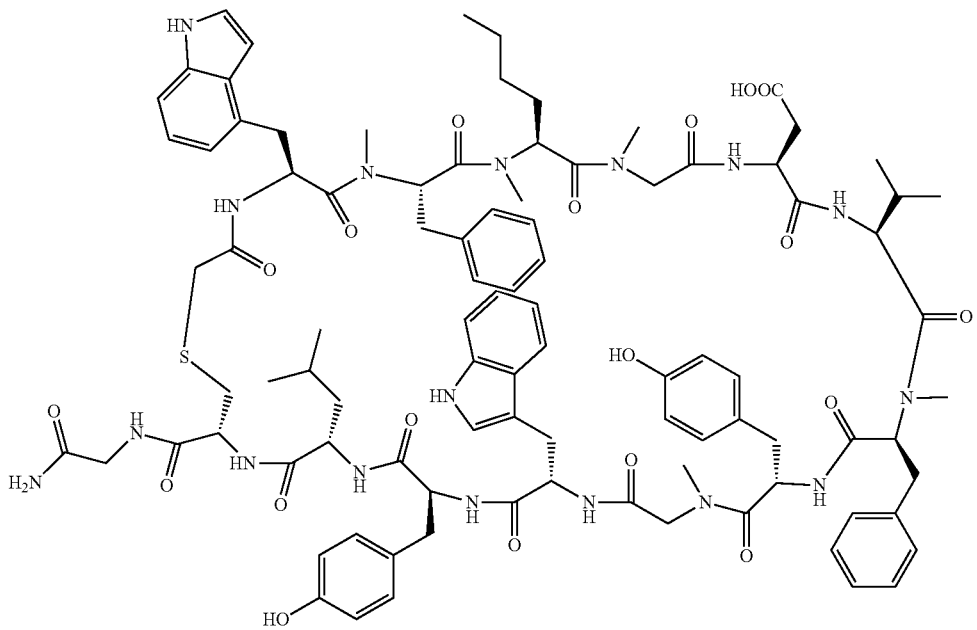

Example 3103 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 5.0 mg, and its estimated purity by LCMS analysis was 96%.

Analysis LCMS condition D: Retention time=1.51 min; ESI-MS(+) m/z 918.9 (M+2H).

Analysis LCMS condition E: Retention time=1.71 min; ESI-MS(+) m/z 918.1 (M+2H).

Preparation of Example 3104

Example 3104

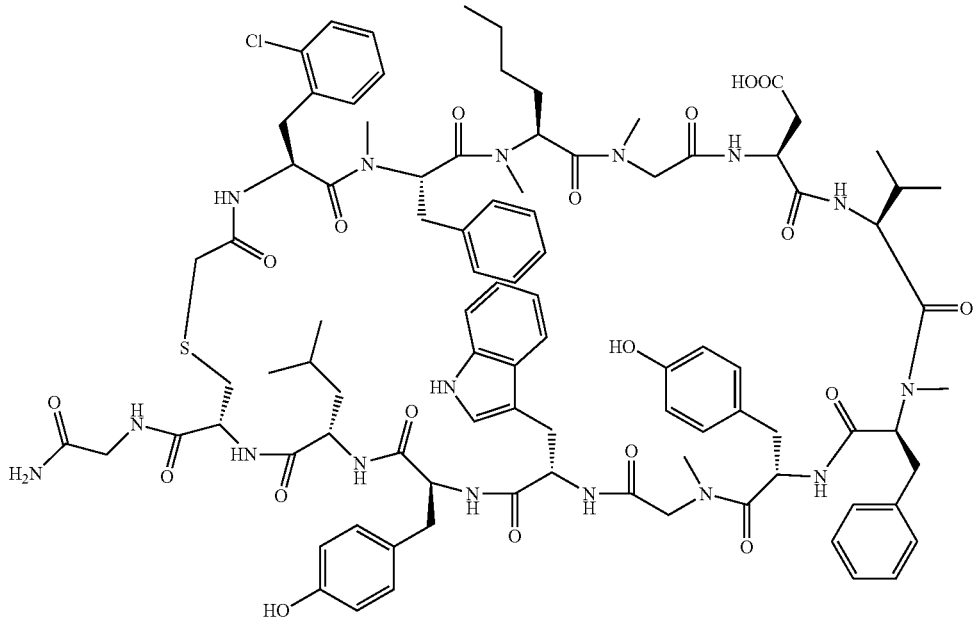

Example 3104 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The yield of product was 6.3 mg, and its estimated purity by LCMS analysis was 99%.

Analysis LCMS condition D: Retention time=1.65 min; ESI-MS(+) m/z 916.0 (M+2H).

Analysis LCMS condition E: Retention time=1.88 min; ESI-MS(+) m/z 916.0 (M+2H).

Preparation of Example 3105

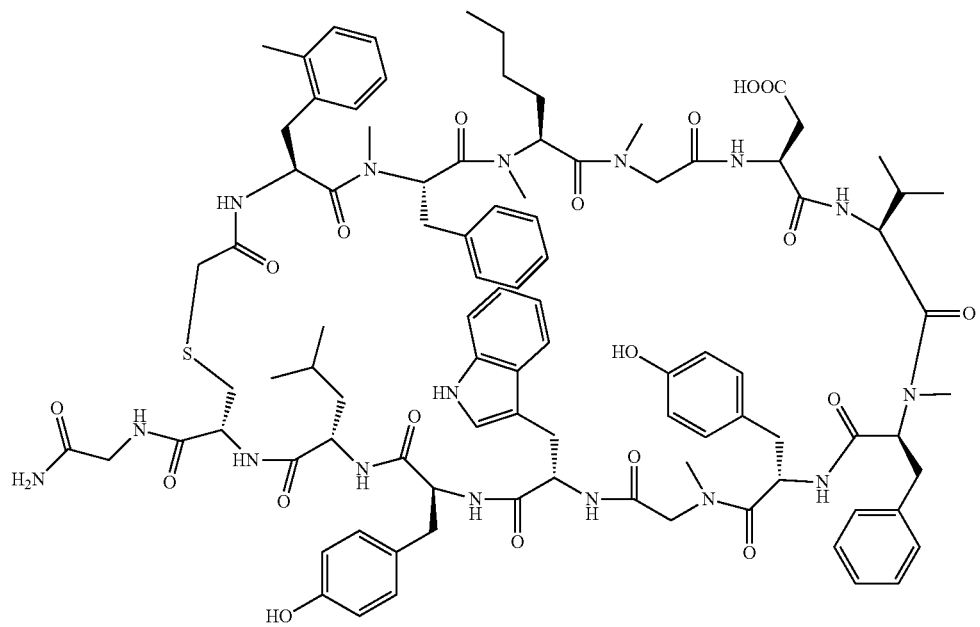

Example 3105

Example 3105 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The yield of product was 6.6 mg, and its estimated purity by LCMS analysis was 97%.

Analysis LCMS condition D: Retention time=1.65 min; ESI-MS(+) m/z 906.0 (M+2H).

Analysis LCMS condition E: Retention time=1.88 min; ESI-MS(+) m/z 905.6 (M+2H).

Preparation of Example 3106

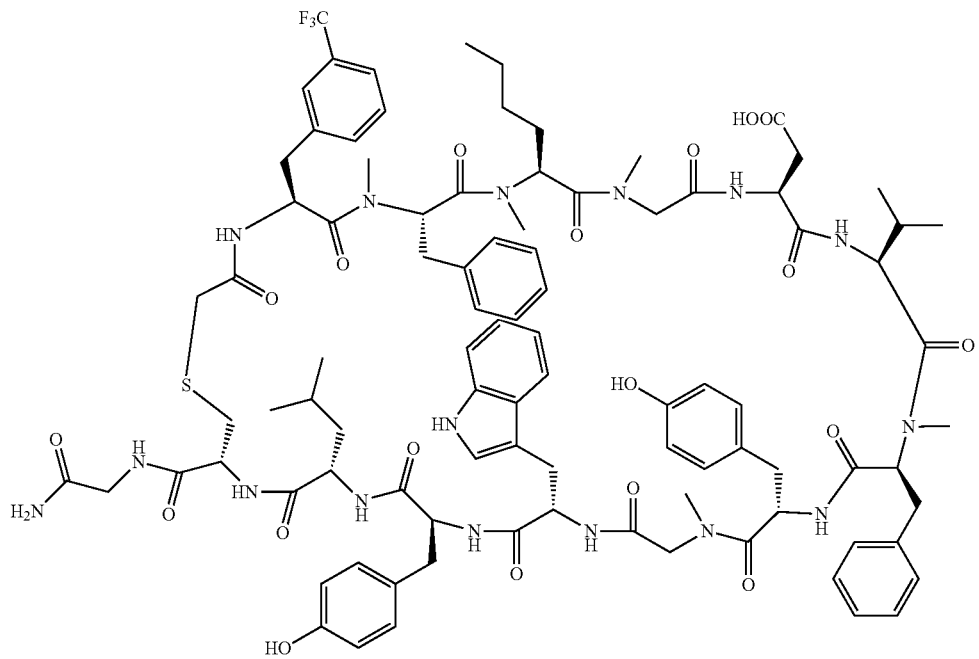

Example 3106

Example 3106 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 5.4 mg, and its estimated purity by LCMS analysis was 99%.

Analysis LCMS condition D: Retention time=1.71 min; ESI-MS(+) m/z 933.0 (M+2H).

Analysis LCMS condition E: Retention time=1.93 min; ESI-MS(+) m/z 932.9 (M+2H).

Preparation of Example 3107

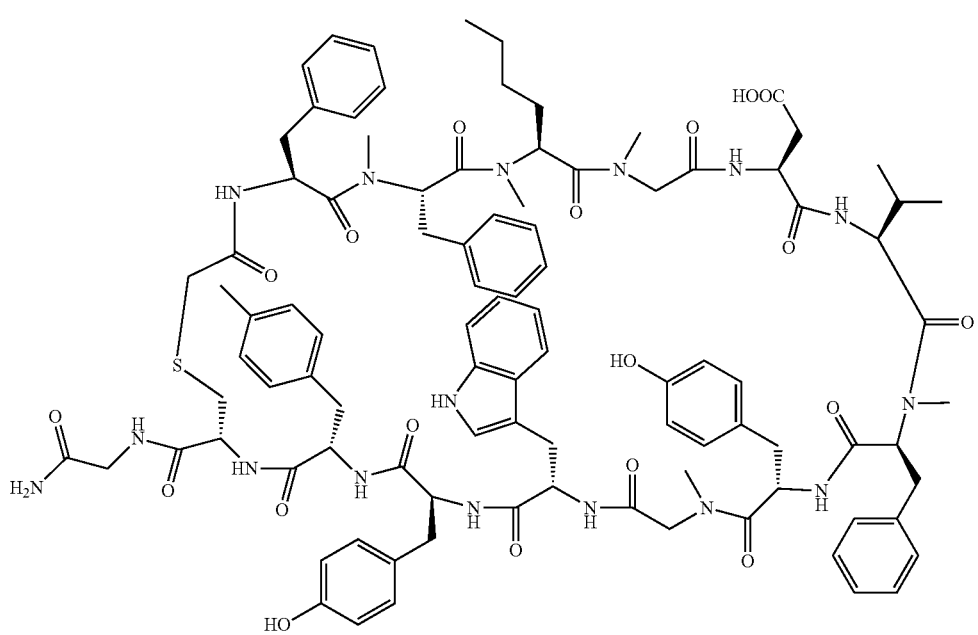

Example 3107

Example 3107 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-75% B over 25 min., then a 5-minute hold at 100% B; Flow: 20 mL/min. Fractions containing the desired product were combined and dried. The yield of product was 6.1 mg, and its estimated purity by LCMS analysis was 100%.

Analysis LCMS condition D: Retention time=1.65 min; ESI-MS(+) m/z 922.7 (M+2H).

Analysis LCMS condition E: Retention time=1.88 min; ESI-MS(+) m/z 922.8 (M+2H).

Preparation of Example 3109

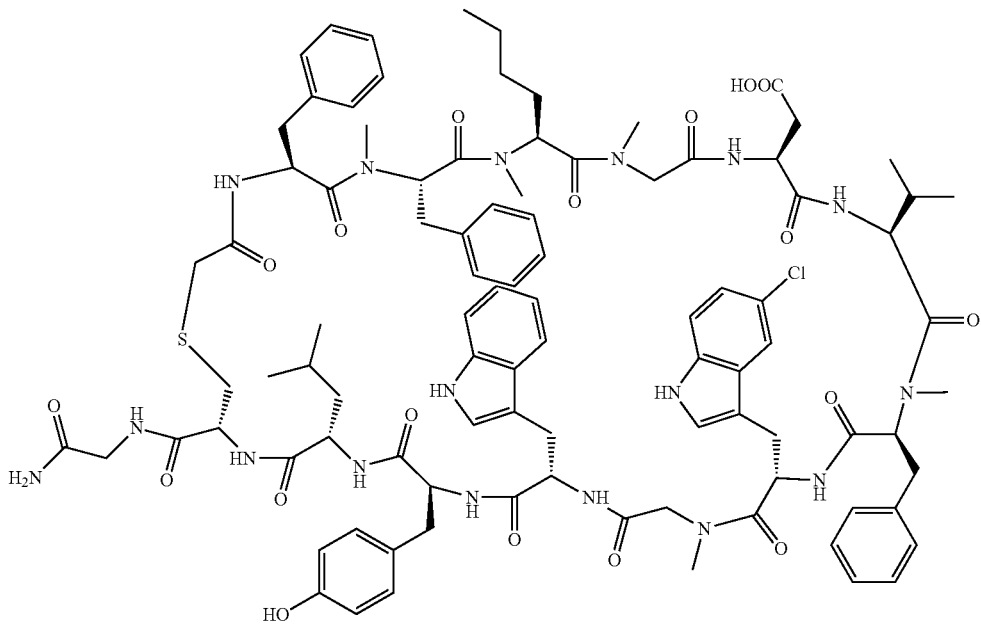

Example 3109

Example 3109 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 5.1 mg, and its estimated purity by LCMS analysis was 96%.

Analysis LCMS condition D: Retention time=1.77 min; ESI-MS(+) m/z 927.5 (M+2H).

Analysis LCMS condition E: Retention time=2.03 min; ESI-MS(+) m/z 927.9 (M+2H).

Preparation of Example 3110

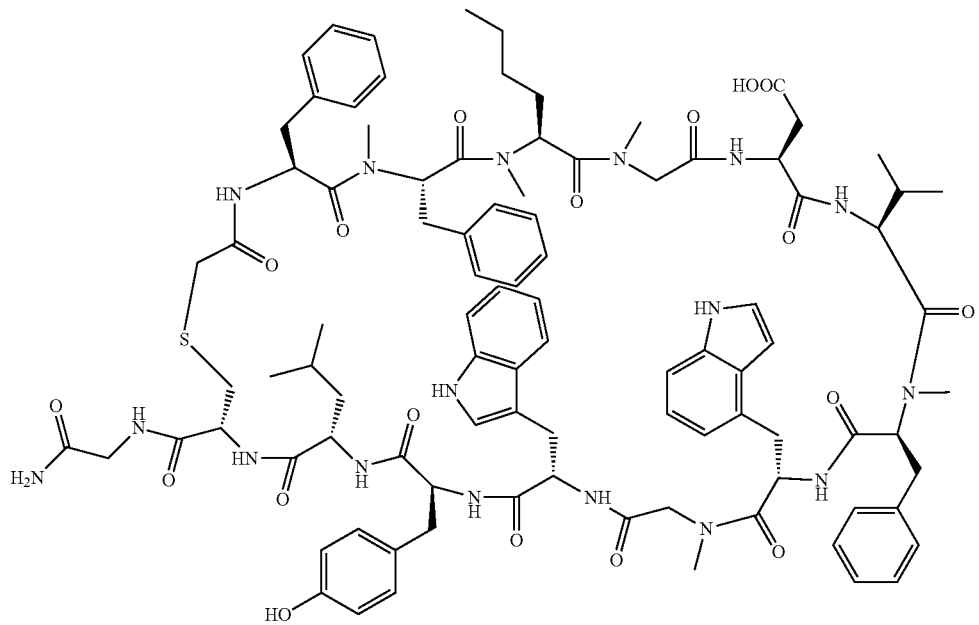

Example 3110

Example 3110 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-80% B over 25 min., then a 5-minute hold at 100% B; Flow: 20 mL/min. Fractions containing the desired product were combined and dried. The yield of product was 3.4 mg, and its estimated purity by LCMS analysis was 100%.

Analysis LCMS condition D: Retention time=1.69 min; ESI-MS(+) m/z 910.7 (M+2H).

Analysis LCMS condition E: Retention time=1.93 min; ESI-MS(+) m/z 910.8 (M+2H).

Preparation of Example 3111

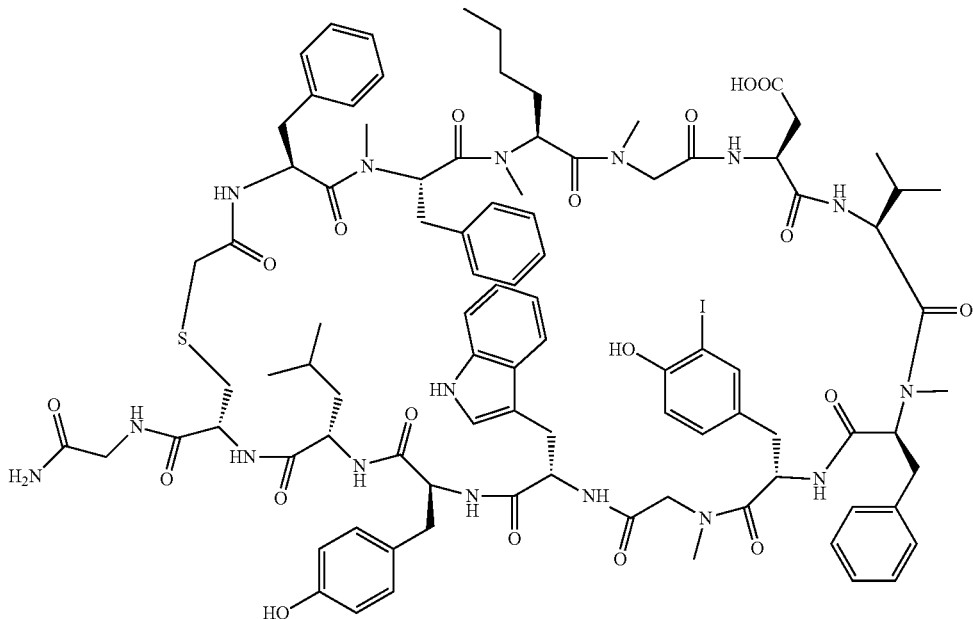

Example 3111

Example 3111 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 4.9 mg, and its estimated purity by LCMS analysis was 88%.

Analysis LCMS condition D: Retention time=1.70 min; ESI-MS(+) m/z 962.5 (M+2H).

Analysis LCMS condition E: Retention time=1.94 min; ESI-MS(+) m/z 962.2 (M+2H).

Preparation of Example 3112

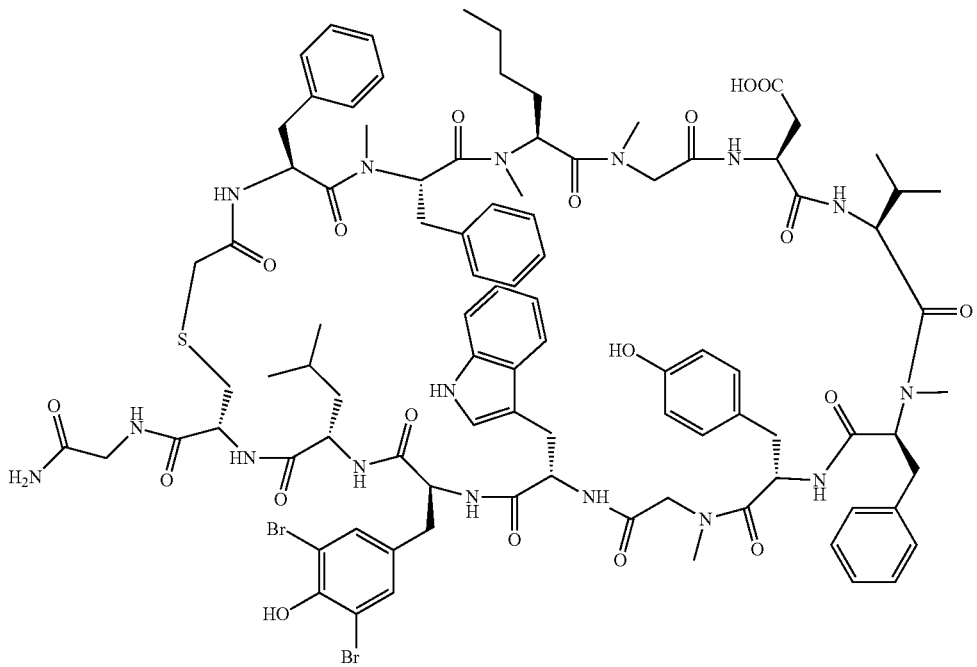

Example 3112

Example 3112 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-80% B over 25 min., then a 5-minute hold at 100% B; Flow: 20 mL/min. Fractions containing the desired product were combined and dried. The yield of product was 2.2 mg, and its estimated purity by LCMS analysis was 100%.

Analysis LCMS condition D: Retention time=1.72 min; ESI-MS(+) m/z 977.8 (M+2H).

Analysis LCMS condition E: Retention time=1.97 min; ESI-MS(+) m/z 978.1 (M+2H).

Preparation of Example 3113

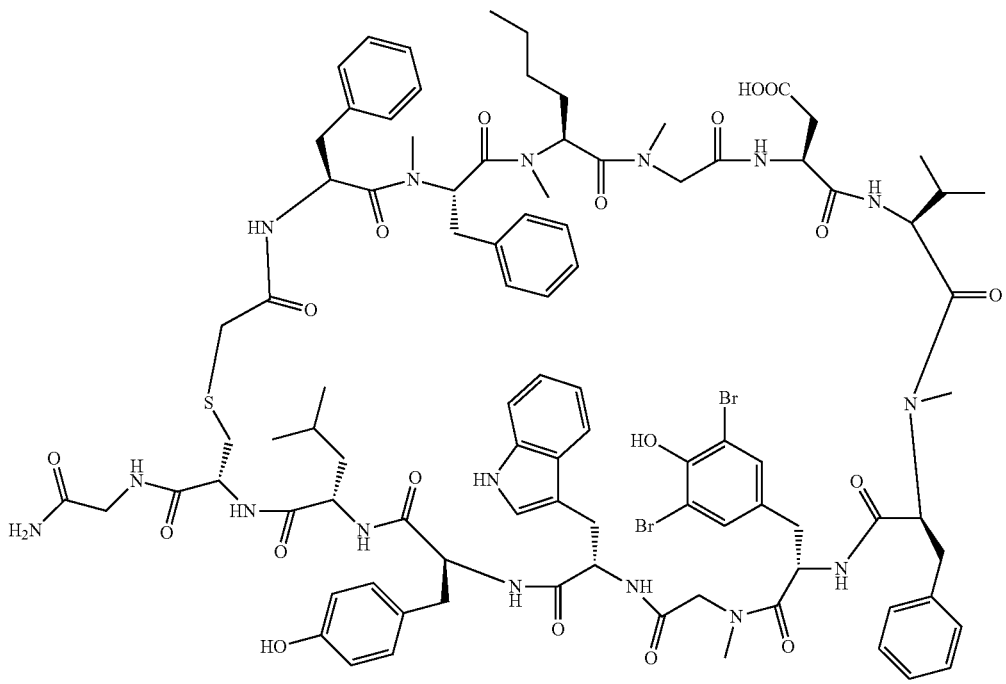

Example 3113

Example 3113 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 min., then a 10-minute hold at 65% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min., then a 5-minute hold at 100% B; Flow: 20 mL/min. Fractions containing the desired product were combined and dried. The yield of product was 2.6 mg, and its estimated purity by LCMS analysis was 97%.

Analysis LCMS condition D: Retention time=1.66 min; ESI-MS(+) m/z 977.9 (M+2H).

Analysis LCMS condition E: Retention time=1.89 min; ESI-MS(+) m/z 977.7 (M+2H).

Preparation of Example 3114

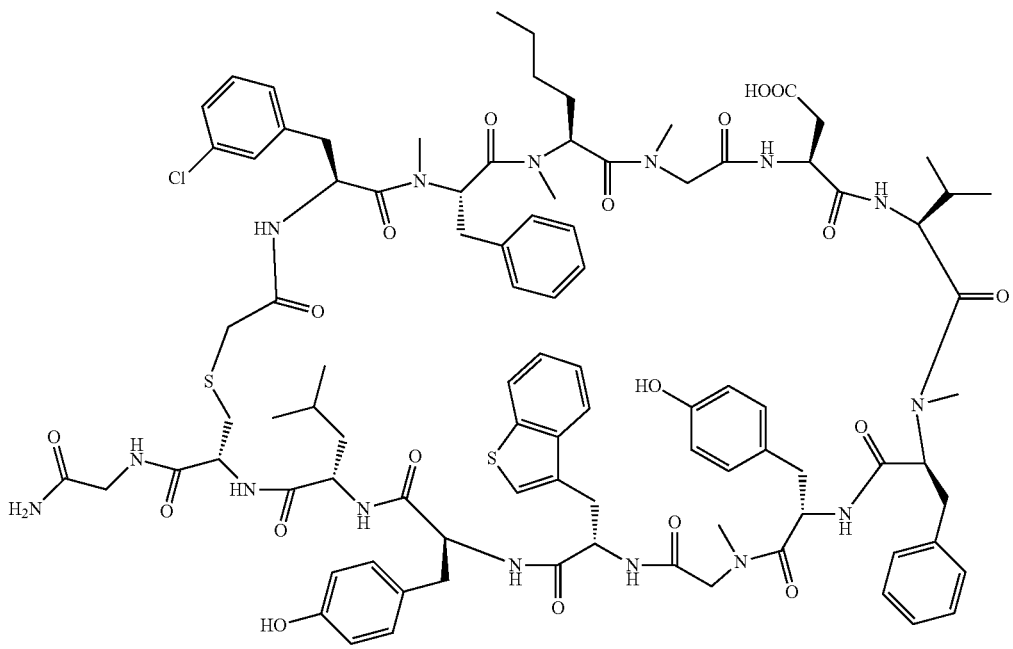

Example 3114

Example 3114 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 0-minute hold at 100% B; Flow: 20 mL/min. Fractions containing the desired product were combined and dried. The yield of product was 4.3 mg, and its estimated purity by LCMS analysis was 96%.

Analysis LCMS condition D: Retention time=1.80 min; ESI-MS(+) m/z 924.2 (M+2H).

Analysis LCMS condition E: Retention time=1.99 min; ESI-MS(+) m/z 925.4 (M+2H).

Preparation of Example 3115

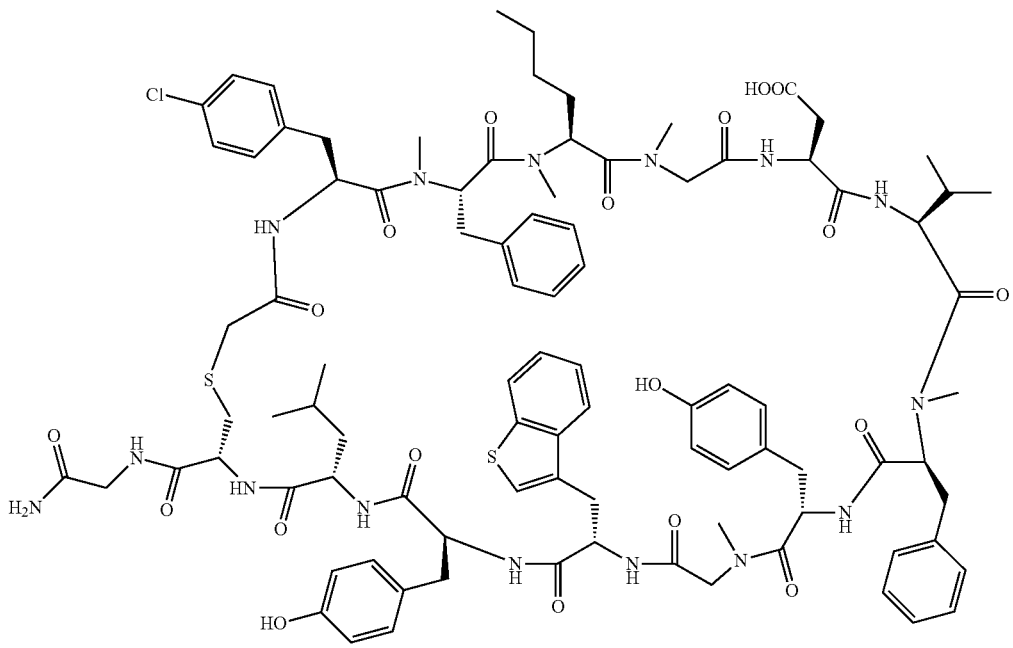

Example 3115

Example 3115 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 3.7 mg, and its estimated purity by LCMS analysis was 94%.

Analysis LCMS condition D: Retention time=1.81 min; ESI-MS(+) m/z 924.4 (M+2H).

Analysis LCMS condition E: Retention time=2.02 min; ESI-MS(+) m/z 924.6 (M+2H).

Preparation of Example 3116

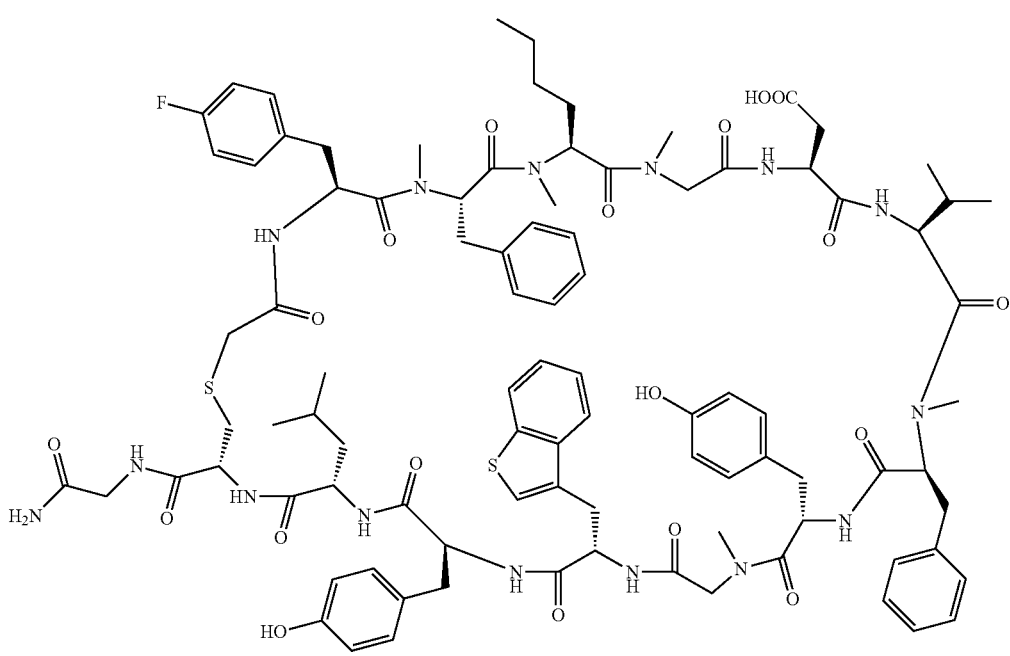

Example 3116

Example 3116 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 4.5 mg, and its estimated purity by LCMS analysis was 98%.

Analysis LCMS condition D: Retention time=1.72 min; ESI-MS(+) m/z 916.3 (M+2H).

Analysis LCMS condition E: Retention time=1.95 min; ESI-MS(+) m/z 916.3 (M+2H).

Preparation of Example 3117

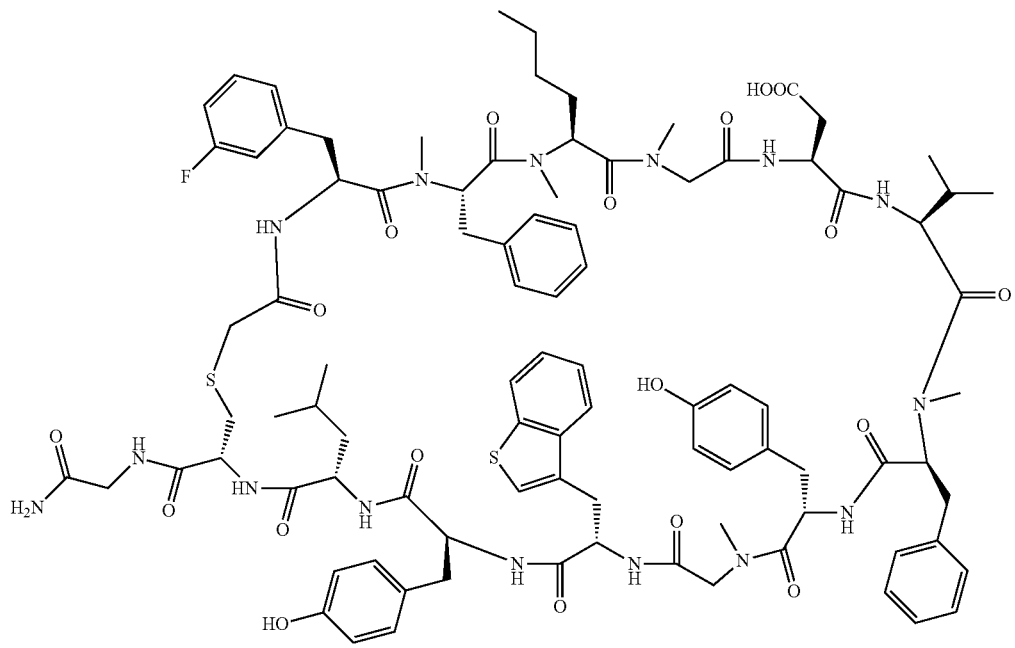

Example 3117

Example 3117 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 4.1 mg, and its estimated purity by LCMS analysis was 98%.

Analysis LCMS condition D: Retention time=1.71 min; ESI-MS(+) m/z 916.2 (M+2H).

Analysis LCMS condition E: Retention time=1.93 min; ESI-MS(+) m/z 916.7 (M+2H).

Preparation of Example 3118

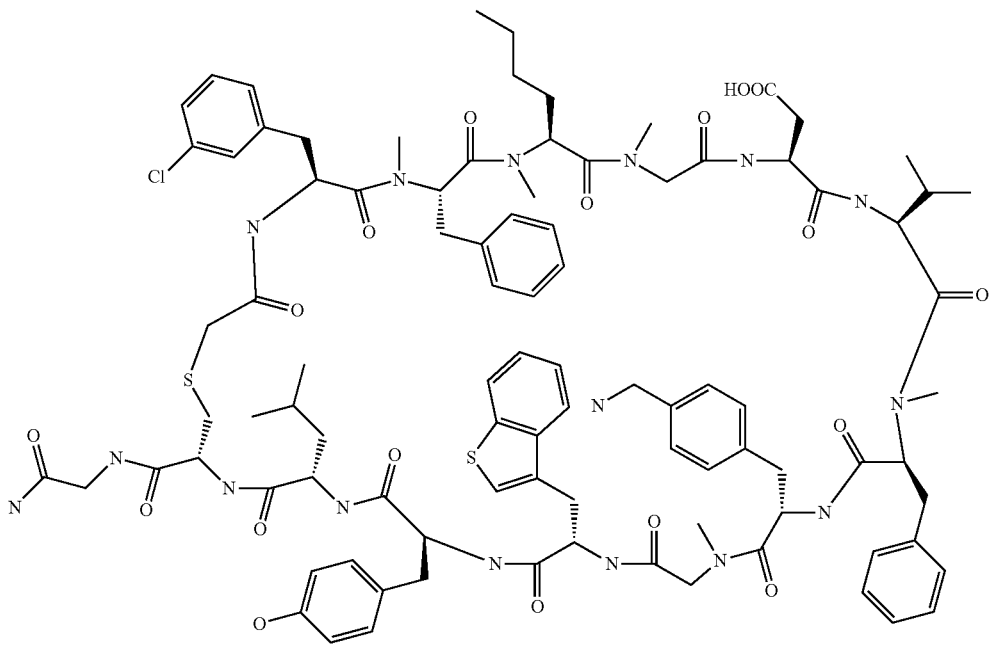

Example 3118

Example 3118 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.3 mg, and its estimated purity by LCMS analysis was 94%.

Analysis LCMS condition D: Retention time=1.82 min; ESI-MS(+) m/z 931.6 (M+2H).

Analysis LCMS condition E: Retention time=1.91 min; ESI-MS(+) m/z 931.3 (M+2H).

Preparation of Example 3119

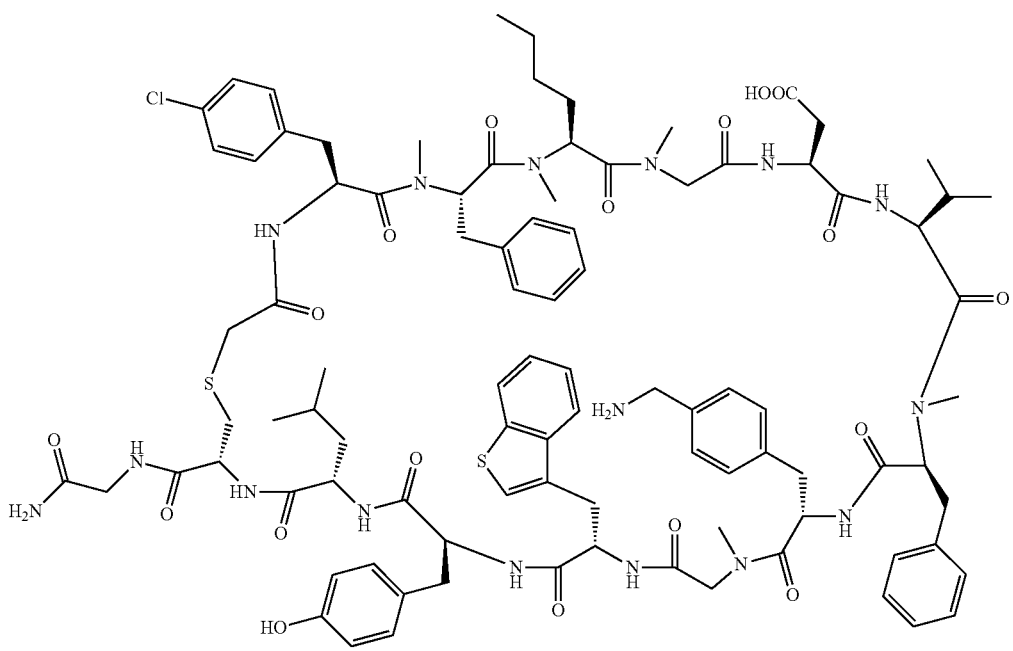

Example 3119

Example 3119 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.3 mg, and its estimated purity by LCMS analysis was 96%.

Analysis LCMS condition D: Retention time=1.83 min; ESI-MS(+) m/z 931.6 (M+2H).

Analysis LCMS condition E: Retention time=1.94 min; ESI-MS(+) m/z 931.3 (M+2H).

Preparation of Example 3120

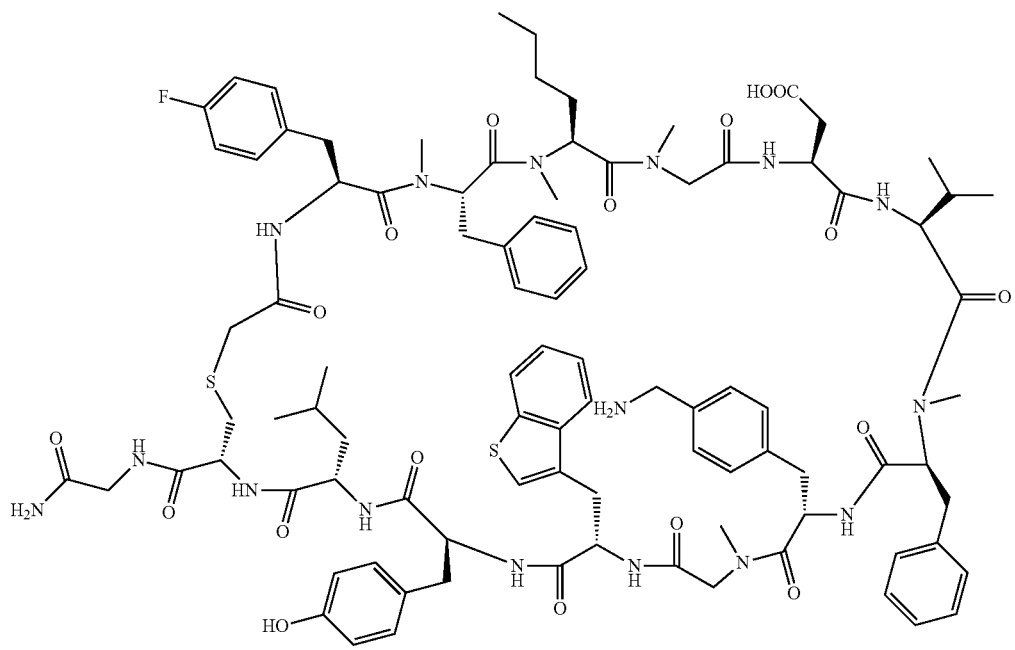

Example 3120

Example 3120 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.2 mg, and its estimated purity by LCMS analysis was 93%.

Analysis LCMS condition D: Retention time=1.77 min; ESI-MS(+) m/z 923.0 (M+2H).

Analysis LCMS condition E: Retention time=1.87 min; ESI-MS(+) m/z 923.1 (M+2H).

Preparation of Example 3121

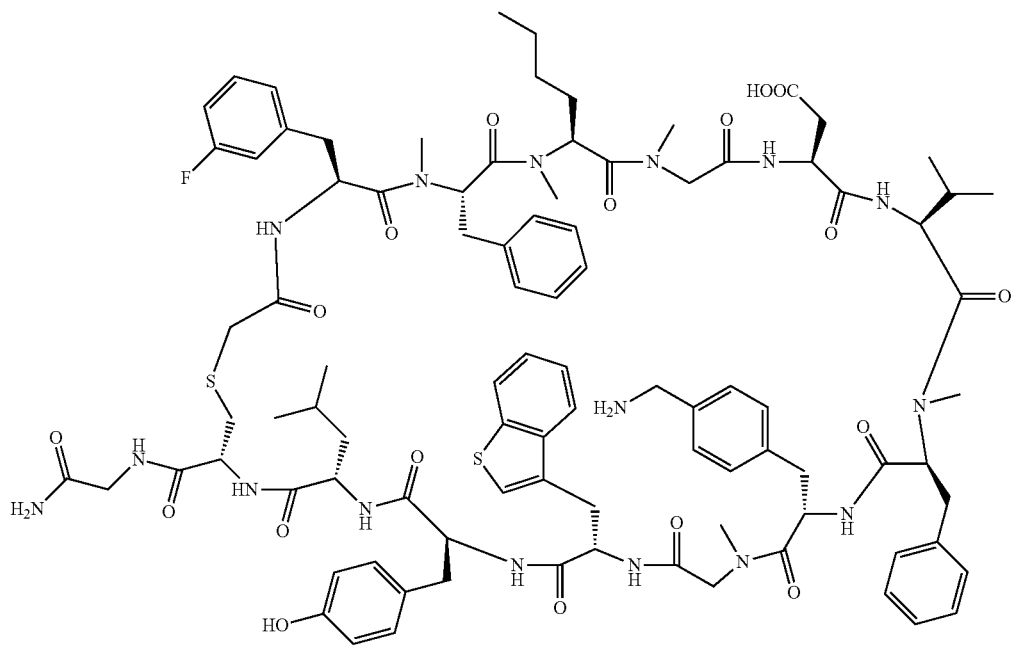

Example 3121

Example 3121 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.2 mg, and its estimated purity by LCMS analysis was 96%.

Analysis LCMS condition D: Retention time=1.76 min; ESI-MS(+) m/z 922.7 (M+2H).

Analysis LCMS condition E: Retention time=1.85 min; ESI-MS(+) m/z 923.0 (M+2H).

Preparation of Example 3122

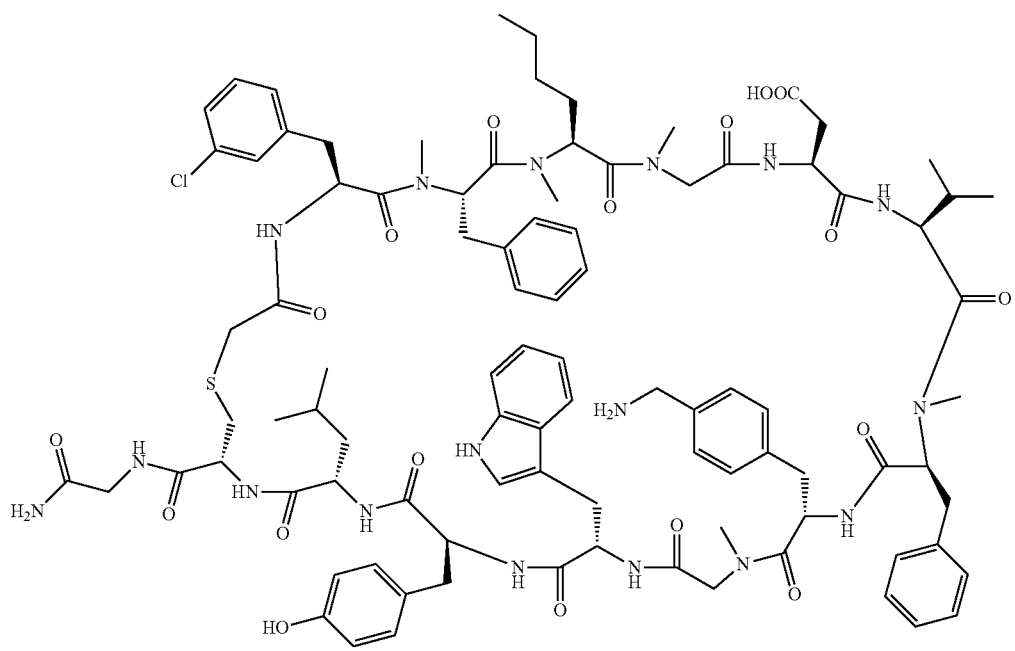

Example 3122

Example 3122 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.1 mg, and its estimated purity by LCMS analysis was 94%.

Analysis LCMS condition D: Retention time=1.71 min; ESI-MS(+) m/z 922.6 (M+2H).

Analysis LCMS condition E: Retention time=1.82 min; ESI-MS(+) m/z 922.6 (M+2H).

Preparation of Example 3123

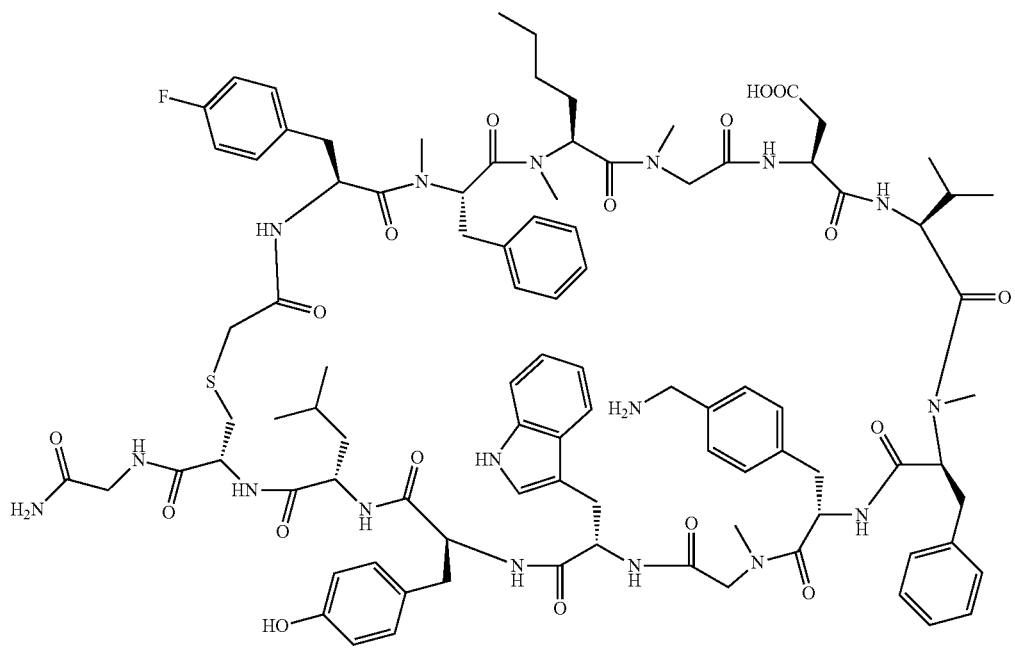

Example 3123

Example 3123 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.3 mg, and its estimated purity by LCMS analysis was 91%.

Analysis LCMS condition D: Retention time=1.66 min; ESI-MS(+) m/z 914.2 (M+2H).

Analysis LCMS condition E: Retention time=1.73 min; ESI-MS(+) m/z 914.4 (M+2H).

Preparation of Example 3124

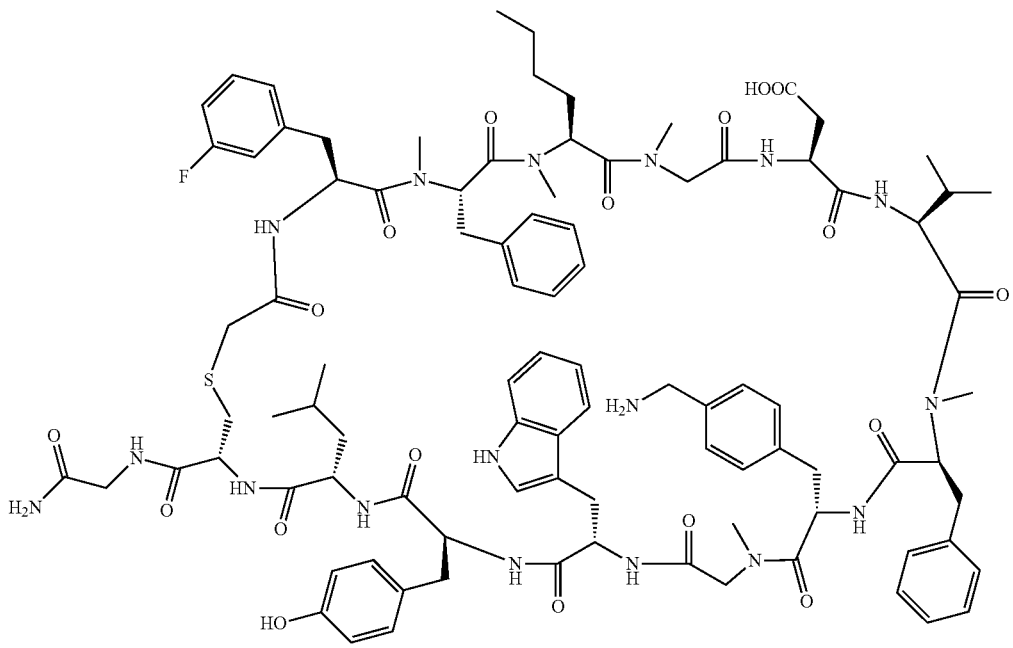

Example 3124

Example 3124 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 1.0 mg, and its estimated purity by LCMS analysis was 93%.

Analysis LCMS condition D: Retention time=1.66 min; ESI-MS(+) m/z 914.2 (M+2H).

Analysis LCMS condition E: Retention time=1.74 min; ESI-MS(+) m/z 914.3 (M+2H).

Preparation of Example 3125

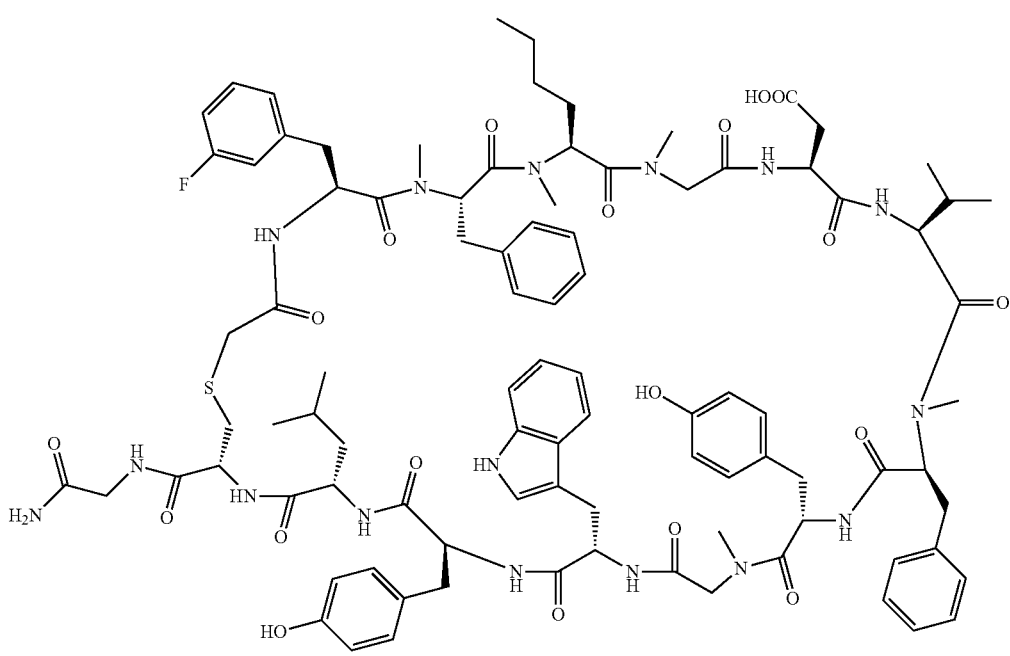

Example 3125

Example 3125 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 25 min., then a 5-minute hold at 100% B; Flow: 20 mL/min. Fractions containing the desired product were combined and dried. The yield of product was 3.8 mg, and its estimated purity by LCMS analysis was 96%.

Analysis LCMS condition D: Retention time=1.61 min; ESI-MS(+) m/z 908.0 (M+2H).

Analysis LCMS condition E: Retention time=1.82 min; ESI-MS(+) m/z 907.8 (M+2H).

Analysis LCMS condition D: Retention time=Analysis LCMS condition E: Retention time=

Analysis LCMS condition D: Retention time=Analysis LCMS condition E: Retention time=Analysis LCMS condition D: Retention time=Analysis LCMS condition E: Retention time=

Analysis LCMS condition D: Retention time=Analysis LCMS condition E: Retention time=

Preparation of Example 3130

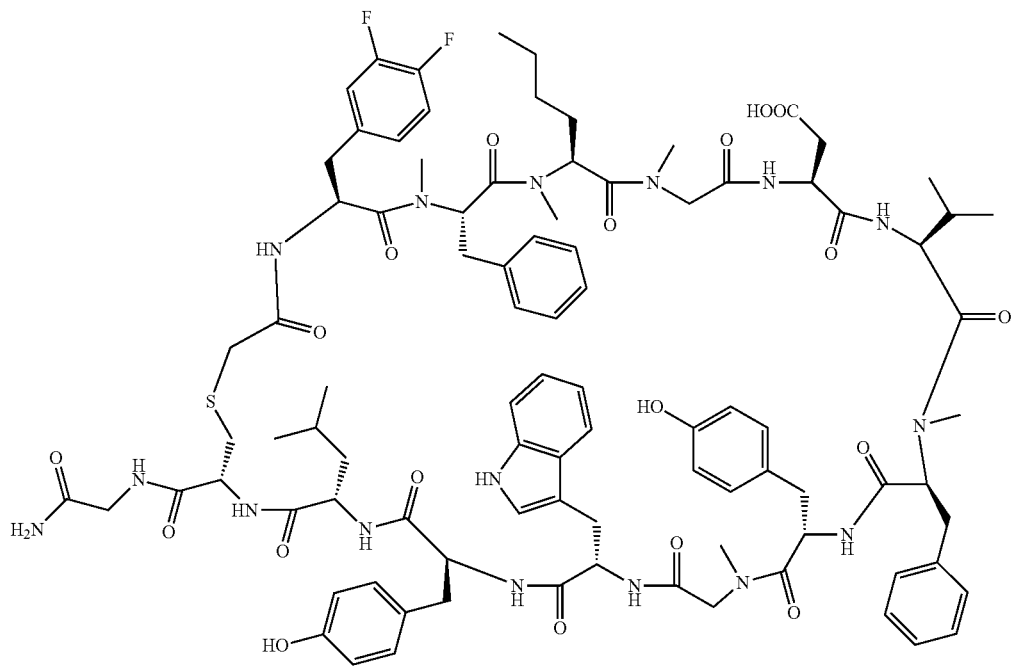

Example 3130

Example 3130 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 min., then a 10-minute hold at 65% B; Flow: 20 mL/min. Fractions containing the desired product were combined and dried. The yield of product was 4.8 mg, and its estimated purity by LCMS analysis was 99%.

Analysis LCMS condition D: Retention time=1.64 min; ESI-MS(+) m/z 917.4 (M+2H).

Analysis LCMS condition E: Retention time=1.86 min; ESI-MS(+) m/z 916.5 (M+2H).

Preparation of Example 3131

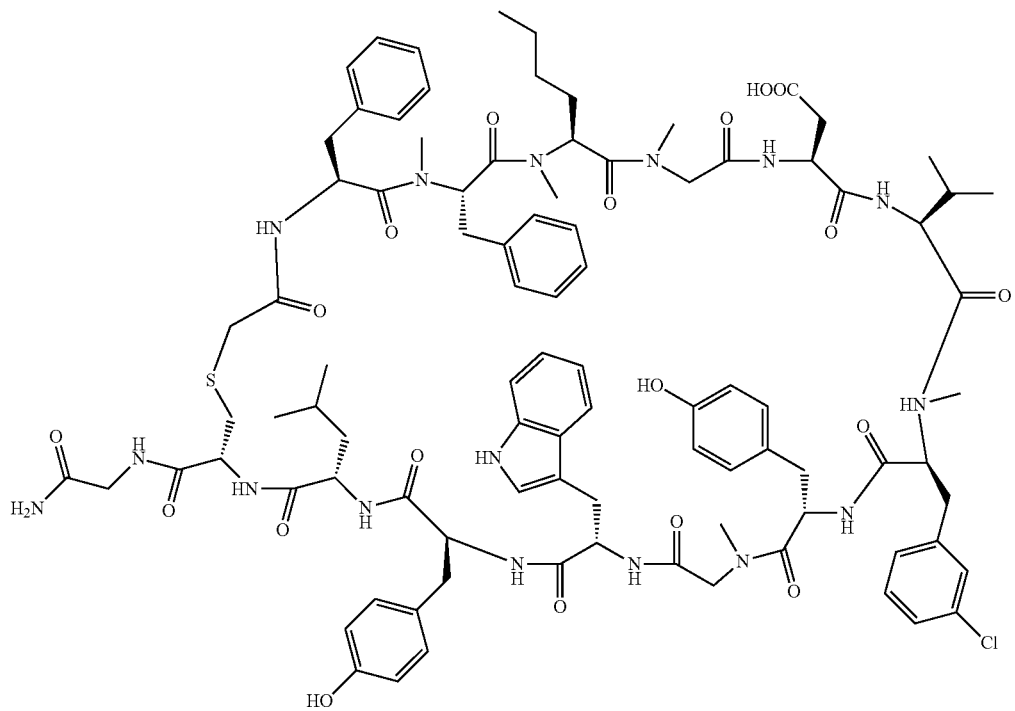

Example 3131

Example 3131 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 4.3 mg, and its estimated purity by LCMS analysis was 100%.

Analysis LCMS condition D: Retention time=1.60 min; ESI-MS(+) m/z 908.6 (M+2H).

Analysis LCMS condition E: Retention time=1.83 min; ESI-MS(+) m/z 909.3 (M+2H).

Preparation of Example 3132

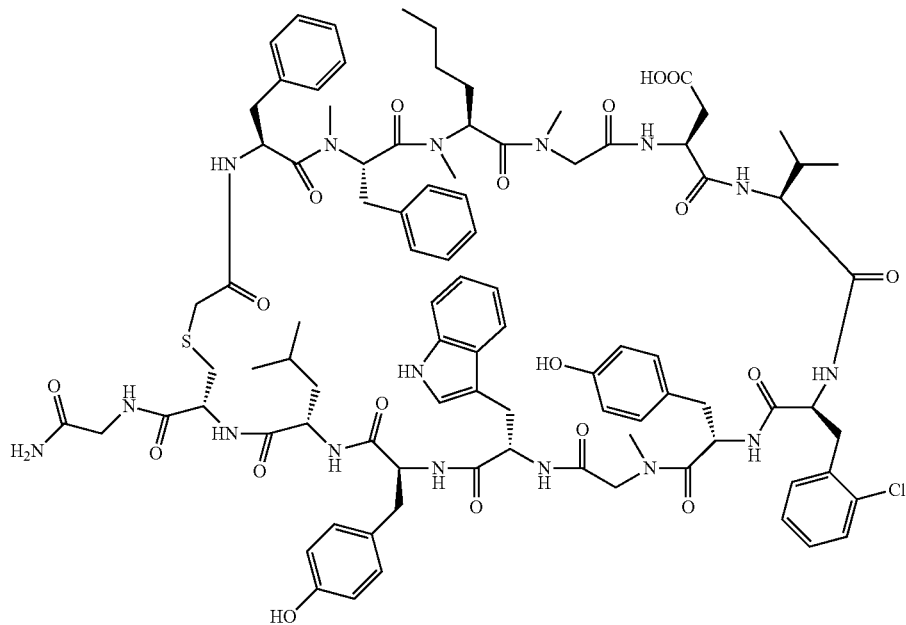

Example 3132

Example 3132 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 25 min., then a 10-minute hold at 65% B; Flow: 20 mL/min. Fractions containing the desired product were combined and dried. The yield of product was 3.5 mg, and its estimated purity by LCMS analysis was 99%.

Analysis LCMS condition D: Retention time=1.57 min; ESI-MS(+) m/z 909.0 (M+2H).

Analysis LCMS condition E: Retention time=1.77 min; ESI-MS(+) m/z 909.7 (M+2H).

Preparation of Example 3133

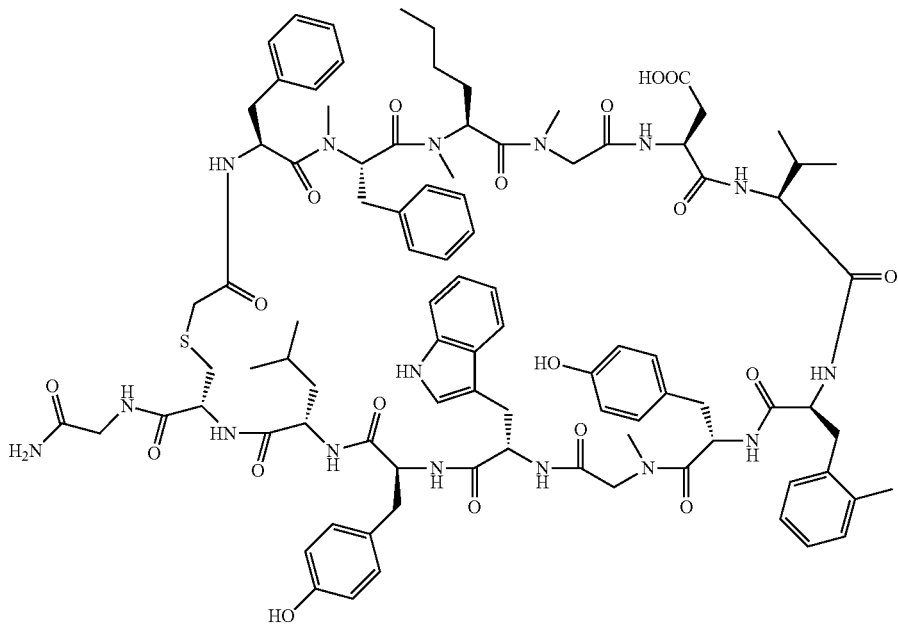

Example 3133

Example 3133 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 0.7 mg, and its estimated purity by LCMS analysis was 98%.

Analysis LCMS condition D: Retention time=1.59 min; ESI-MS(+) m/z 898.8 (M+2H).

Analysis LCMS condition E: Retention time=1.77 min; ESI-MS(+) m/z 898.8 (M+2H).

Preparation of Example 3134

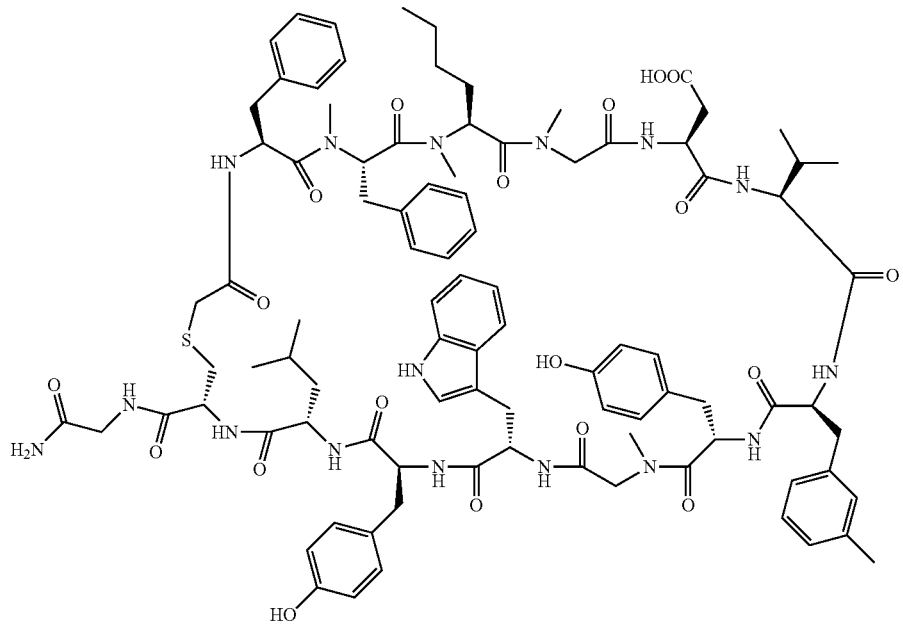

Example 3134

Example 3134 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 0.7 mg, and its estimated purity by LCMS analysis was 98%.

Analysis LCMS condition D: Retention time=1.59 min; ESI-MS(+) m/z 898.8 (M+2H).

Analysis LCMS condition E: Retention time=1.77 min; ESI-MS(+) m/z 898.8 (M+2H).

Preparation of Example 3135

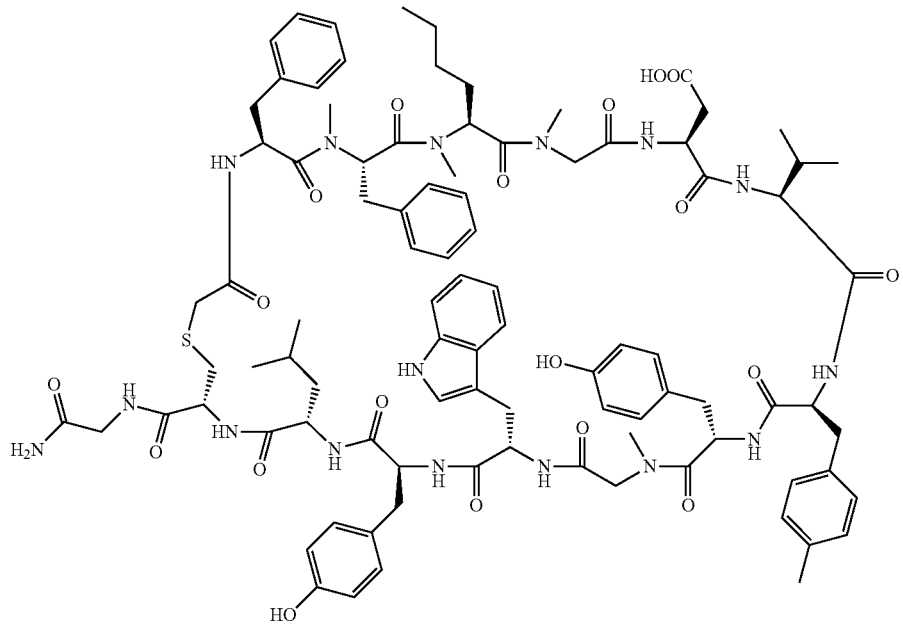

Example 3135

Example 3135 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 10-minute hold at 55% B; Flow: 20 mL/min. Fractions containing the desired product were combined and dried. The yield of product was 0.8 mg, and its estimated purity by LCMS analysis was 94%.

Analysis LCMS condition D: Retention time=1.60 min; ESI-MS(+) m/z 898.7 (M+2H).

Analysis LCMS condition E: Retention time=1.78 min; ESI-MS(+) m/z 898.8 (M+2H).

Preparation of Example 3136

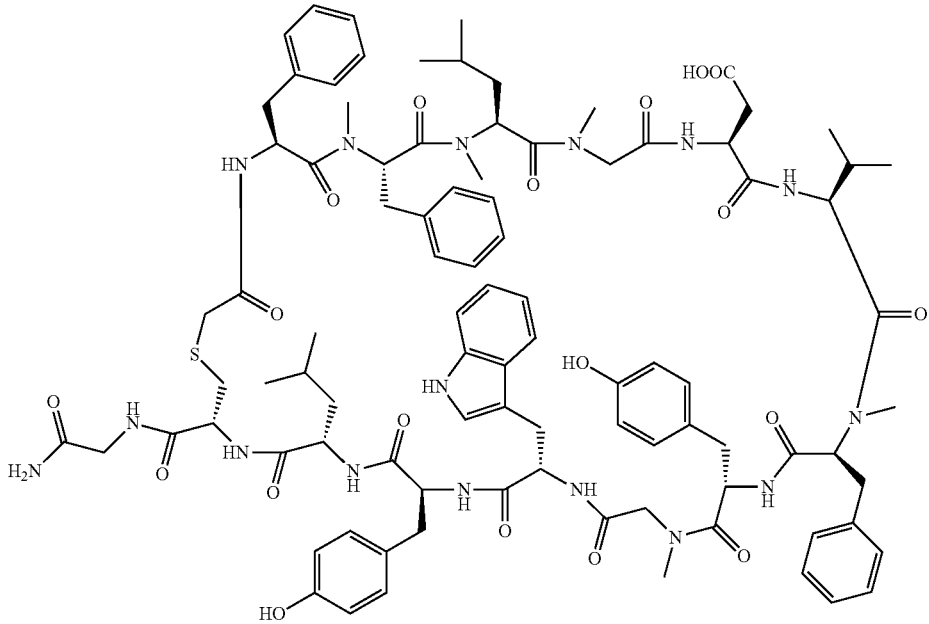

Example 3136

Example 3136 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 4.6 mg, and its estimated purity by LCMS analysis was 96%.

Analysis LCMS condition D: Retention time=1.56 min; ESI-MS(+) m/z 898.6 (M+2H).

Analysis LCMS condition E: Retention time=1.78 min; ESI-MS(+) m/z 899.0 (M+2H).

Preparation of Example 3138

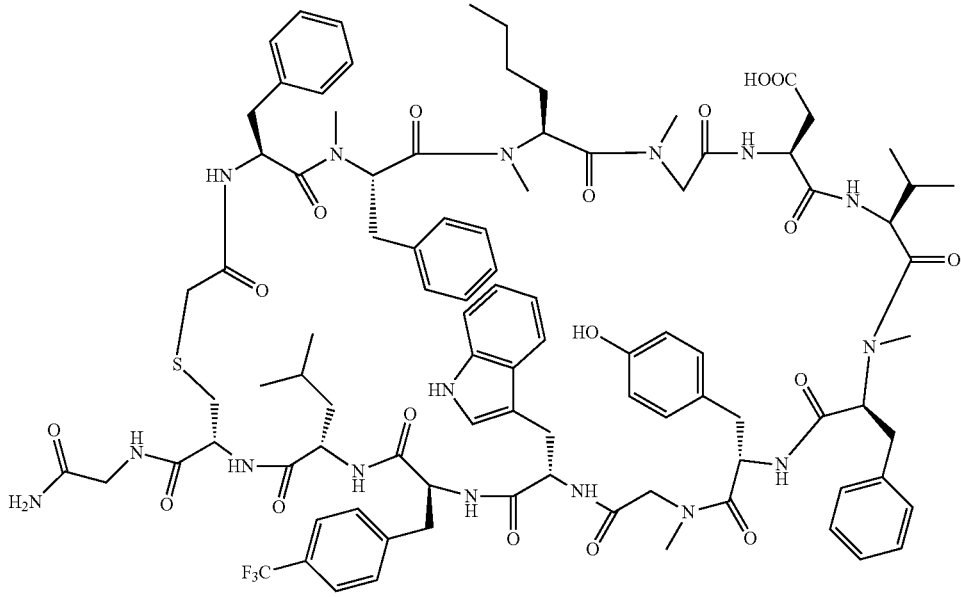

Example 3138

Example 3138 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 7.1 mg, and its estimated purity by LCMS analysis was 94%.

Analysis LCMS condition D: Retention time=1.80 min; ESI-MS(+) m/z 924.6 (M+2H).

Analysis LCMS condition E: Retention time=2.03 min; ESI-MS(+) m/z 924.8 (M+2H).

Preparation of Example 3139

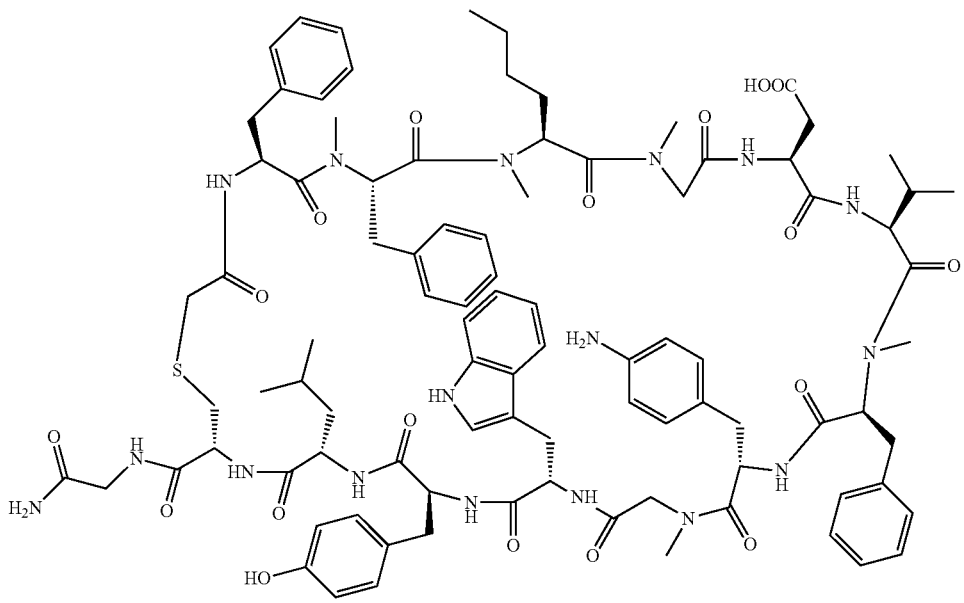

Example 3139

Example 3139 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 14.2 mg, and its estimated purity by LCMS analysis was 100%.

Analysis LCMS condition D: Retention time=1.57 min; ESI-MS(+) m/z 898.2 (M+2H).

Analysis LCMS condition E: Retention time=1.71 min; ESI-MS(+) m/z 898.3 (M+2H).

Preparation of Example 3140

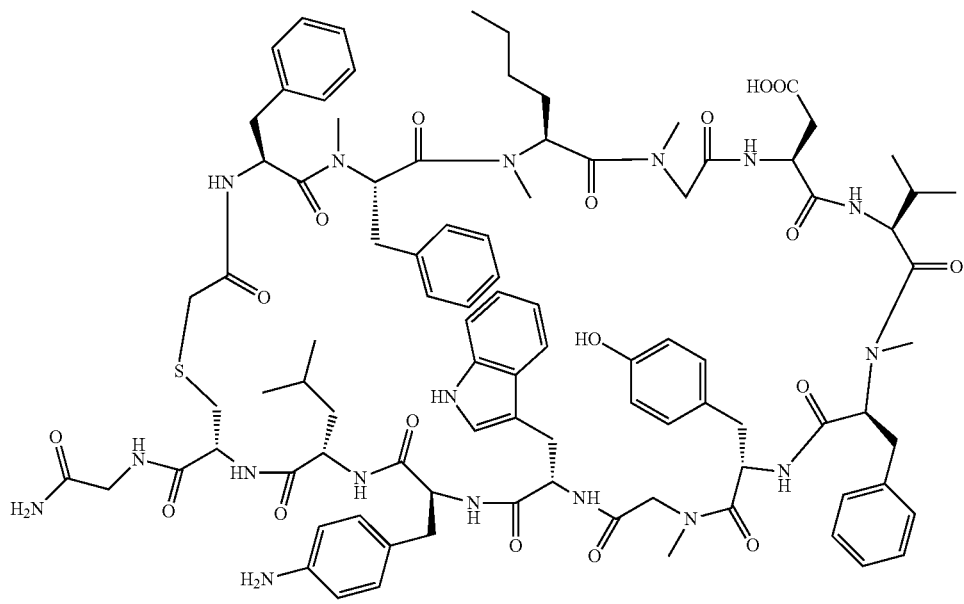

Example 3140

Example 3140 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 14.6 mg, and its estimated purity by LCMS analysis was 94%.

Analysis LCMS condition D: Retention time=1.56 min; ESI-MS(+) m/z 898.5 (M+2H).

Analysis LCMS condition E: Retention time=1.70 min; ESI-MS(+) m/z 898.2 (M+2H).

Preparation of Example 3141

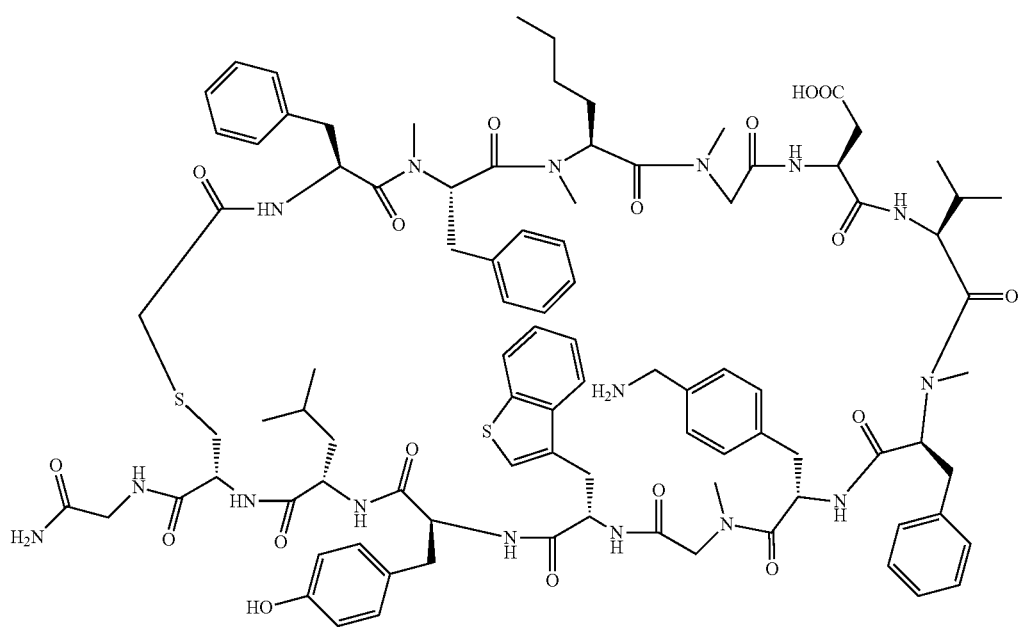

Example 3141

Example 3141 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The yield of product was 2.8 mg, and its estimated purity by LCMS analysis was 97%.

Analysis LCMS condition D: Retention time=1.71 min; ESI-MS(+) m/z 914.0 (M+2H).

Analysis LCMS condition E: Retention time=1.83 min; ESI-MS(+) m/z 913.7 (M+2H).

Preparation of Example 3142

Example 3142

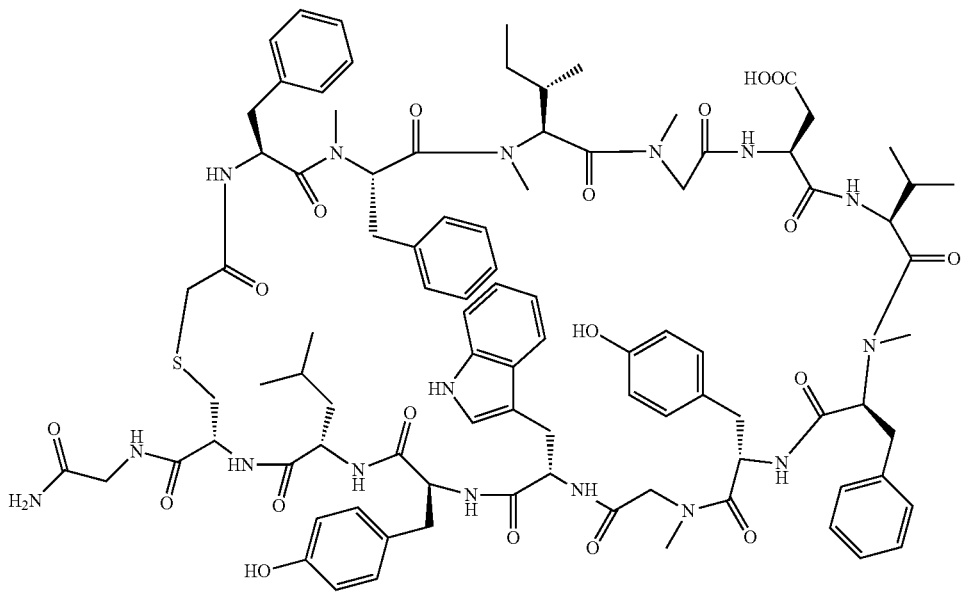

Example 3142 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 2.5 mg, and its estimated purity by LCMS analysis was 87%.

Analysis LCMS condition D: Retention time=1.56 min; ESI-MS(+) m/z 899.4 (M+2H).

Analysis LCMS condition E: Retention time=1.77 min; ESI-MS(+) m/z 899.0 (M+2H).

Preparation of Example 3143

Example 3143

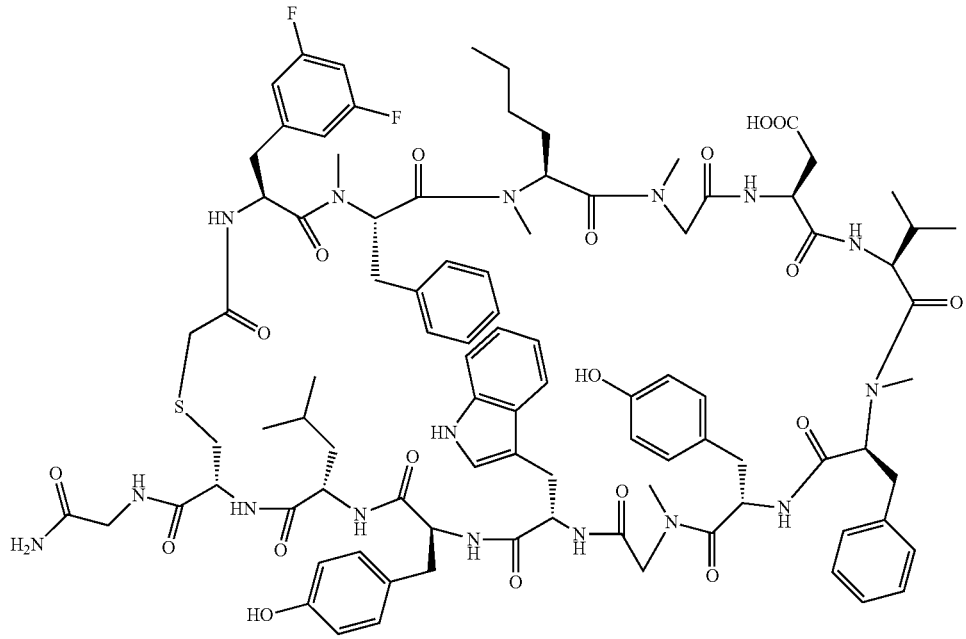

Example 3143 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.25-95% B over 50 min., then a 5-minute hold at 95% B; Flow: 15 mL/min. Fractions containing the desired product were combined and dried. The yield of product was 5.3 mg, and its estimated purity was 96% by HPLC "Analysis Condition B" using a gradient of 35% to 95% buffer B over 30 min.

Analysis LCMS condition A: Retention time=1.52 min; ESI-MS(+) m/z 916.9 (M+2H).

Preparation of Example 3144

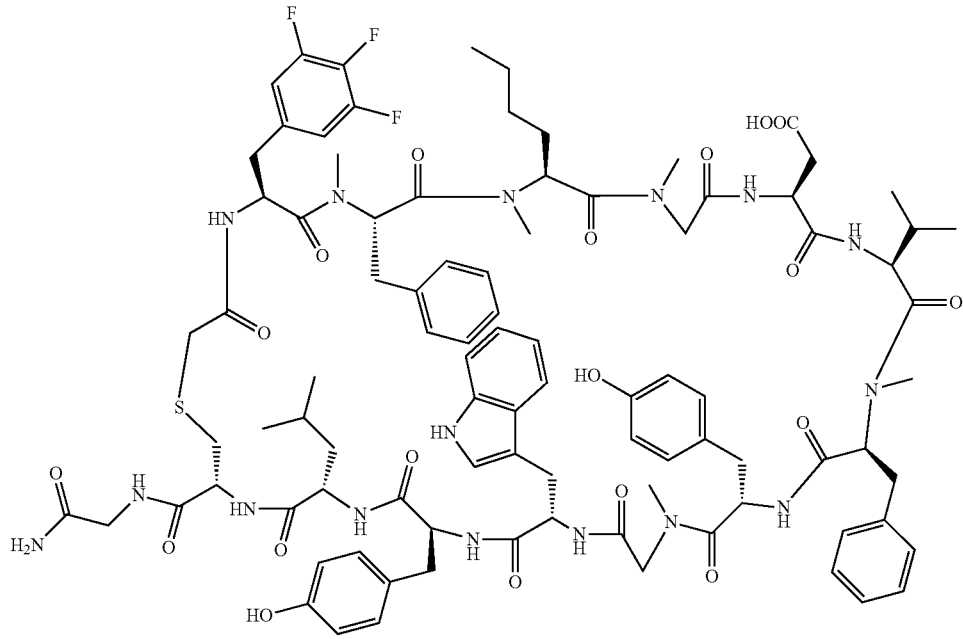

Example 3144

Example 3144 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.25-95% B over 50 min., then a 5-minute hold at 95% B; Flow: 15 mL/min. Fractions containing the desired product were combined and dried. The yield of product was 5.1 mg, and its estimated purity was 95% by HPLC "Analysis Condition B" using a gradient of 35% to 95% buffer B over 30 min.

Analysis LCMS condition A: Retention time=1.55 min; ESI-MS(+) m/z 925.8 (M+2H).

Preparation of Example 3145

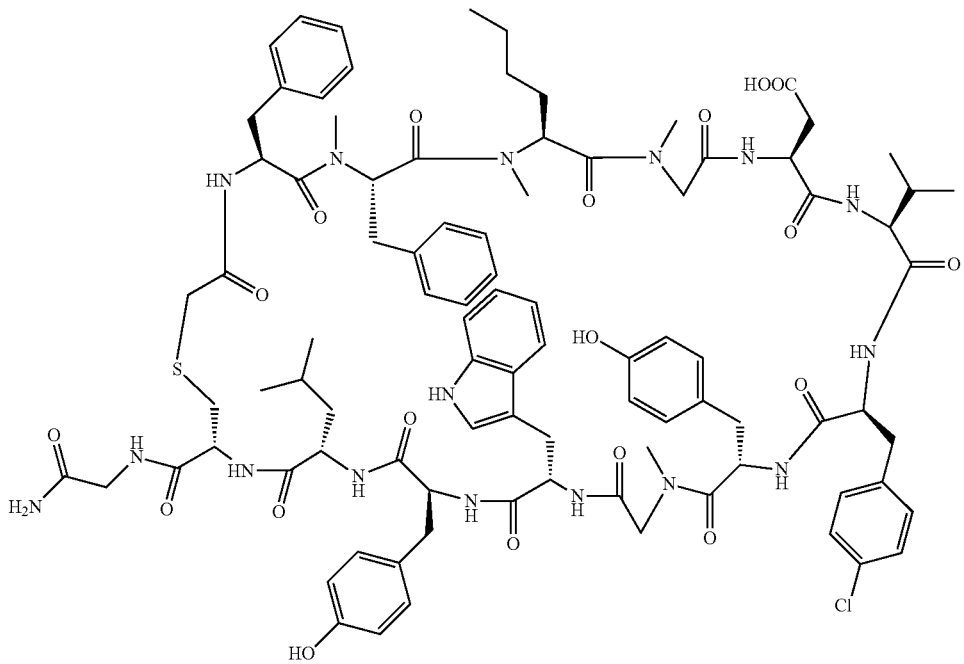

Example 3145

Example 3145 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 18.1 mg, and its estimated purity by LCMS analysis was 93%.

Analysis LCMS condition D: Retention time=1.63 min; ESI-MS(+) m/z 909.6 (M+2H).

Analysis LCMS condition E: Retention time=1.82 min; ESI-MS(+) m/z 908.6 (M+2H).

Preparation of Example 3146

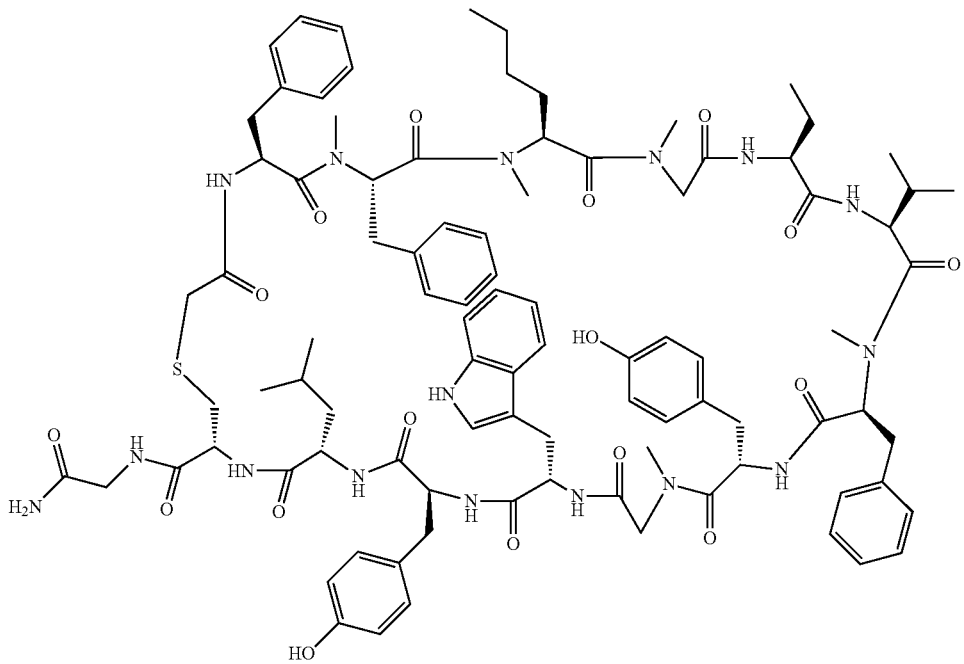

Example 3146

Example 3146 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 3.5 mg, and its estimated purity by LCMS analysis was 91%.

Analysis LCMS condition D: Retention time=1.90 min; ESI-MS(+) m/z 883.8 (M+2H).

Analysis LCMS condition E: Retention time=1.89 min; ESI-MS(+) m/z 883.8 (M+2H).

Preparation of Example 3147

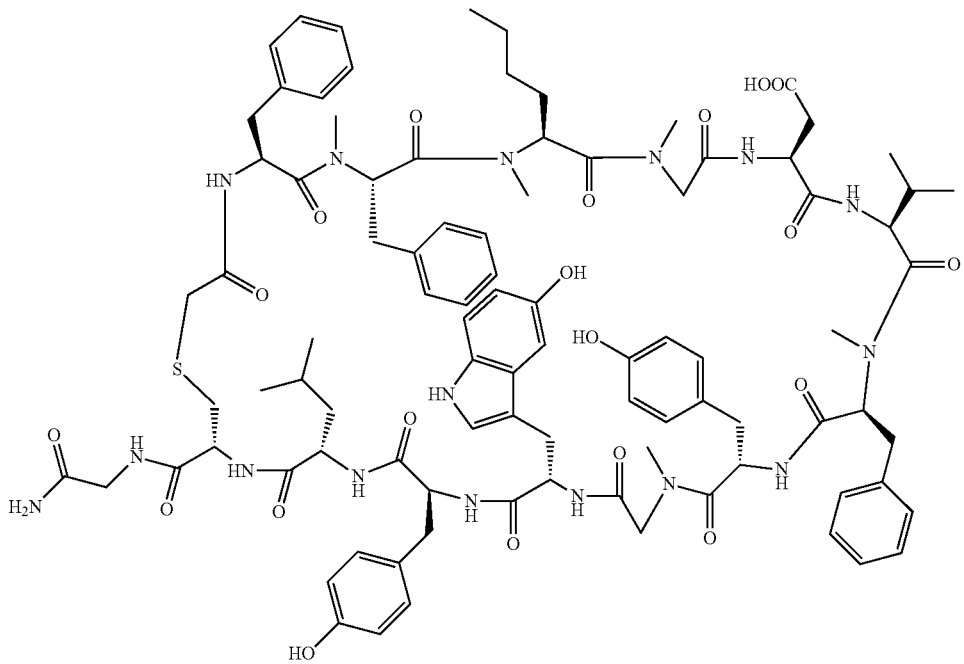

Example 3147

Example 3147 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 3.9 mg, and its estimated purity by LCMS analysis was 94%.

Analysis LCMS condition D: Retention time=1.49 min; ESI-MS(+) m/z 906.9 (M+2H).
Analysis LCMS condition E: Retention time=1.69 min; ESI-MS(+) m/z 907.2 (M+2H).

Preparation of Example 3148

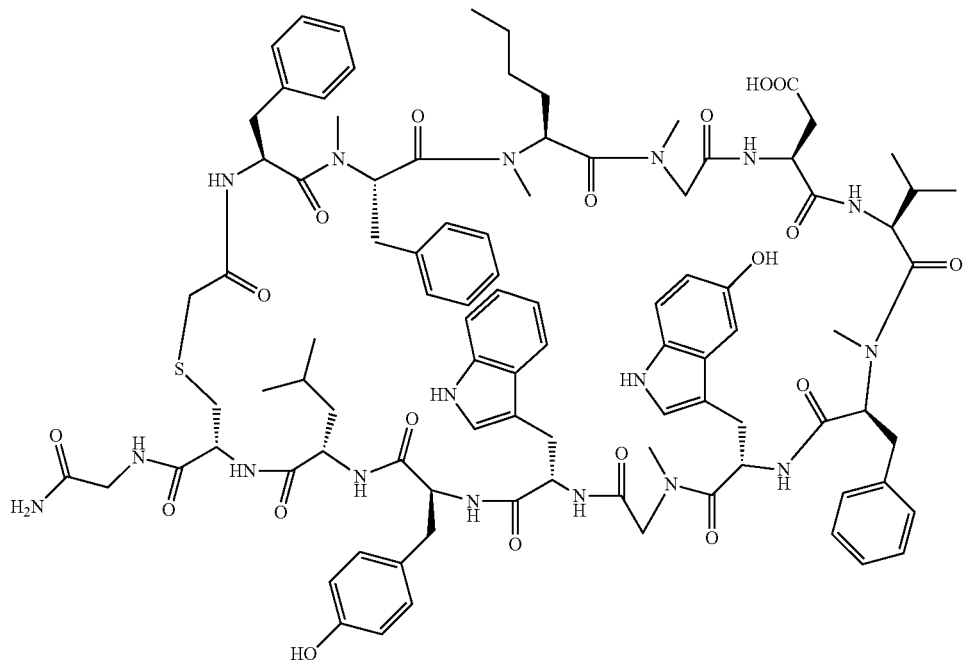

Example 3148

Example 3148 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The yield of product was 3.5 mg, and its estimated purity by LCMS analysis was 90%.

Analysis LCMS condition D: Retention time=1.60 min; ESI-MS(+) m/z 918.7 (M+2H).

Analysis LCMS condition E: Retention time=1.81 min; ESI-MS(+) m/z 918.4 (M+2H).

Preparation of Example 3149

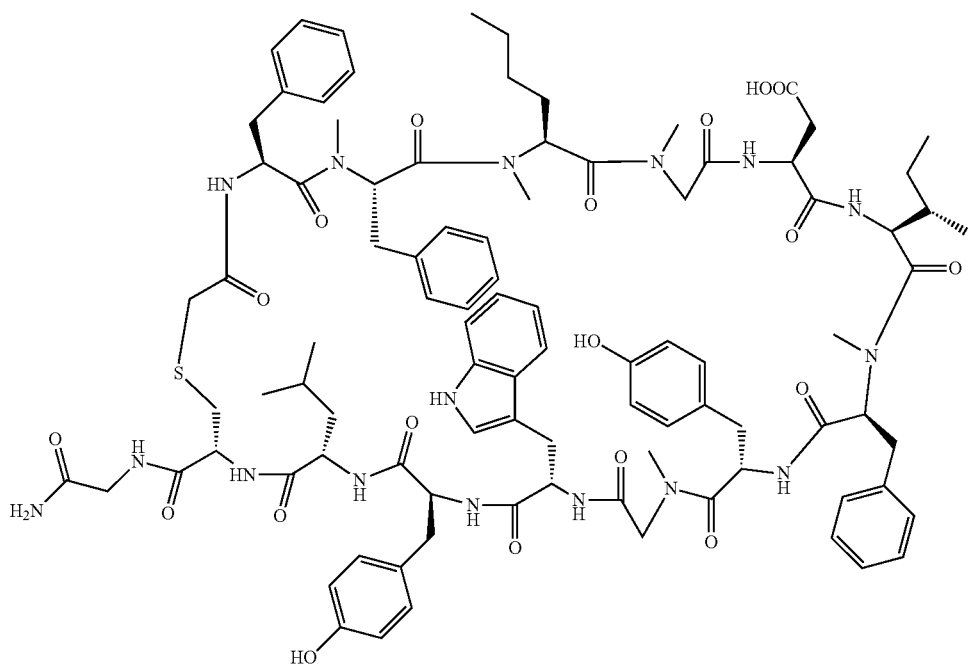

Example 3149

Example 3149 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 6.6 mg, and its estimated purity by LCMS analysis was 96%.

Analysis LCMS condition D: Retention time=1.68 min; ESI-MS(+) m/z 905.8 (M+2H).

Analysis LCMS condition E: Retention time=1.88 min; ESI-MS(+) m/z 905.8 (M+2H).

Preparation of Example 3150

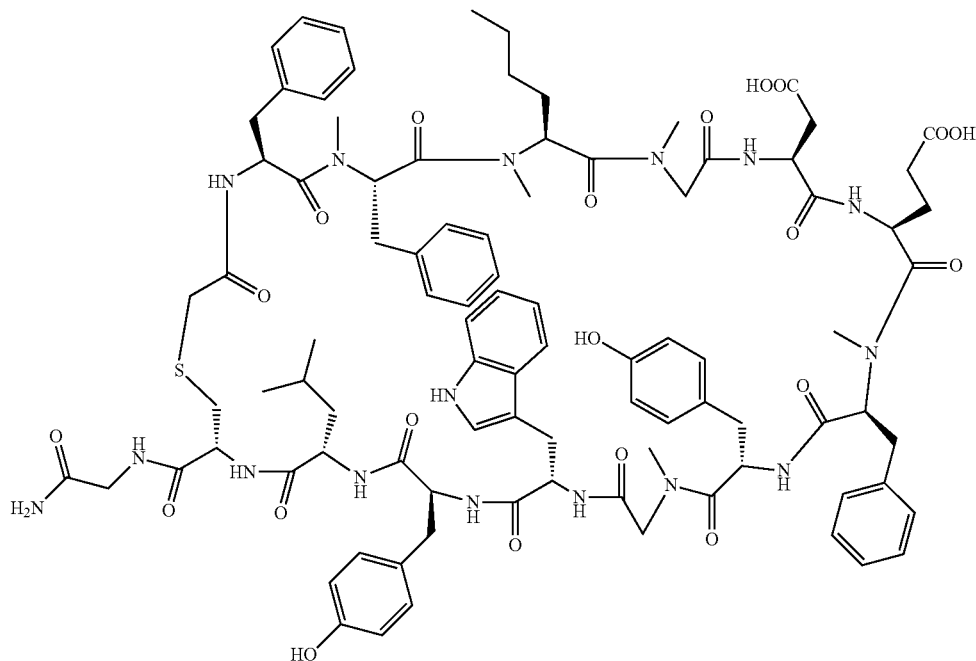

Example 3150

Example 3150 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 12.6 mg, and its estimated purity by LCMS analysis was 98%.

Analysis LCMS condition D: Retention time=1.35 min; ESI-MS(+) m/z 913.8 (M+2H).

Analysis LCMS condition E: Retention time=1.60 min; ESI-MS(+) m/z 913.9 (M+2H).

Preparation of Example 3151

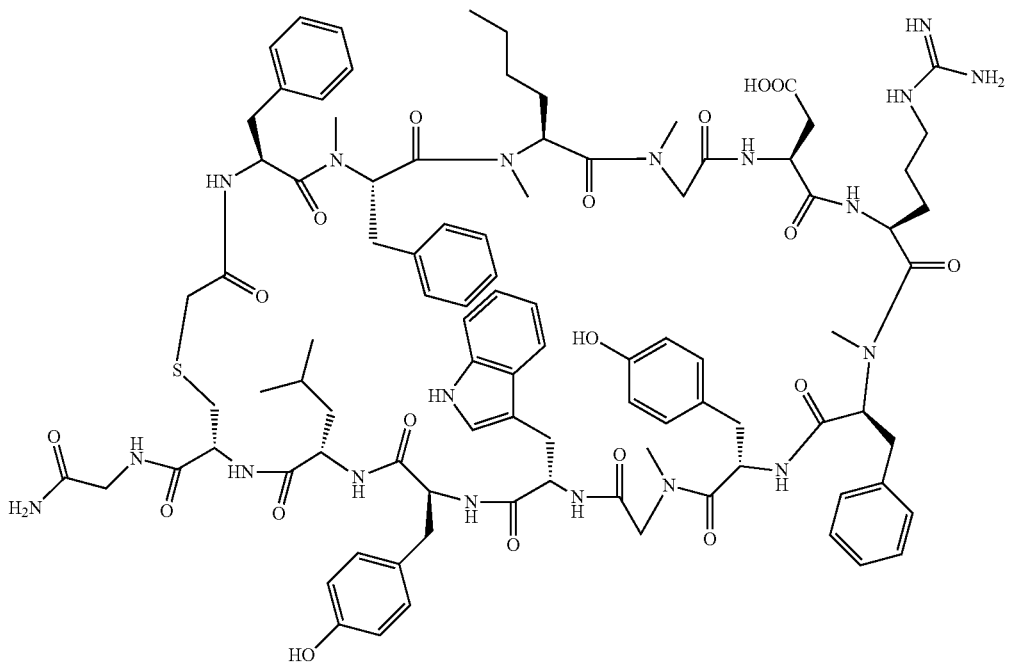

Example 3151

Example 3151 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 min., then a 5-minute hold at 100% B; Flow: 20 mL/min. Fractions containing the desired product were combined and dried. The material was further purified via preparative LC/MS with the following conditions: Column: Waters XBridge Phenyl, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-55% B over 20 min., then a 10-minute hold at 100% B; Flow: 20 mL/min. Fractions containing the desired product were combined and dried. The yield of product was 5.1 mg, and its estimated purity by LCMS analysis was 96%.

Analysis LCMS condition D: Retention time=1.45 min; ESI-MS(+) m/z 927.0 (M+2H).

Analysis LCMS condition E: Retention time=1.49 min; ESI-MS(+) m/z 927.3 (M+2H).

Preparation of Example 3152

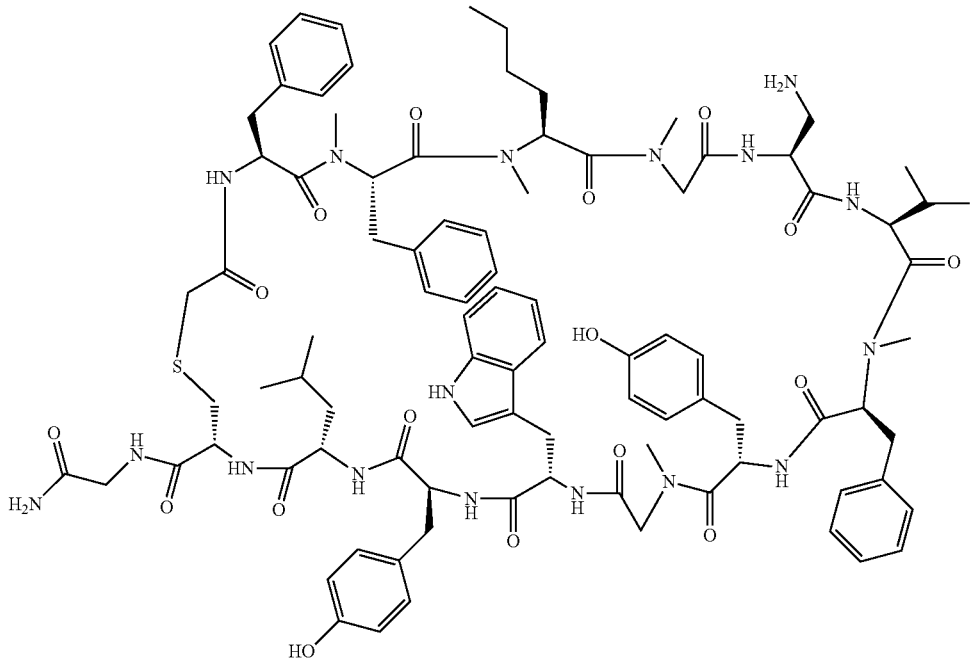

Example 3152

Example 3152 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 9.1 mg, and its estimated purity by LCMS analysis was 93% purity.

Analysis LCMS condition D: Retention time=1.67 min; ESI-MS(+) m/z 884.3 (M+2H).

Analysis LCMS condition E: Retention time=1.66 min; ESI-MS(+) m/z 884.3 (M+2H).

Preparation of Example 3153

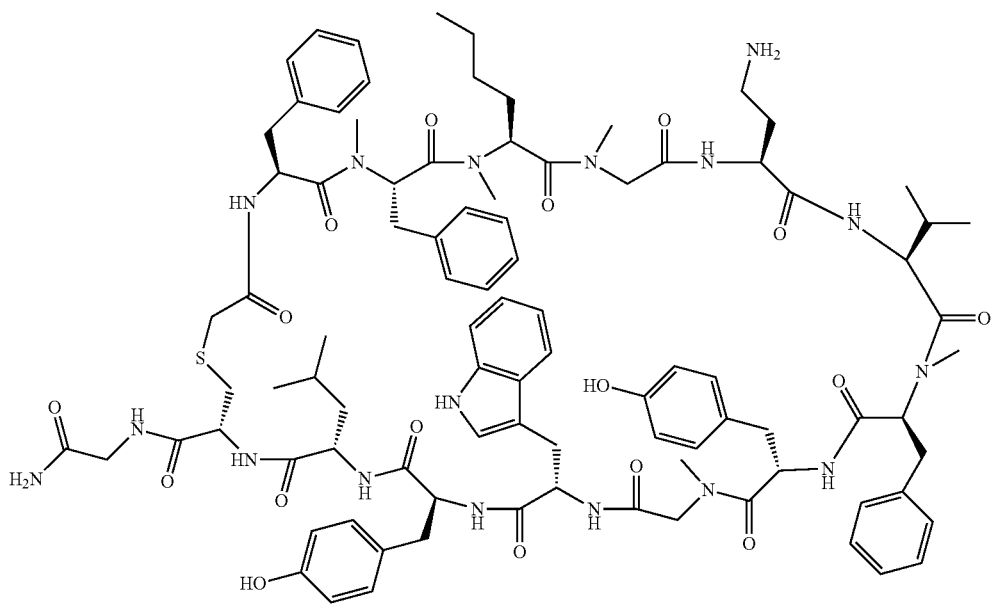

Example 3153

Example 3153 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The yield of product was 2.3 mg, and its estimated purity by LCMS analysis was 95% purity.

Analysis LCMS condition D: Retention time=1.61 min; ESI-MS(+) m/z 891.3 (M+2H).

Analysis LCMS condition E: Retention time=1.64 min; ESI-MS(+) m/z 891.4 (M+2H).

Preparation of Example 3154

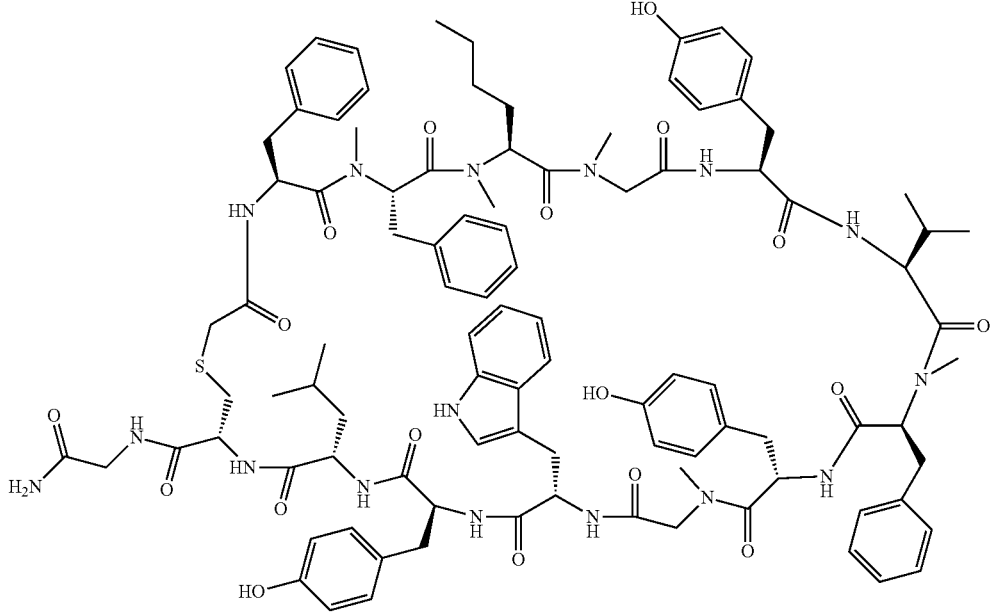

Example 3154

Example 3154 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 25 min., then a 5-minute hold at 100% B; Flow: 20 mL/min. Fractions containing the desired product were combined and dried. The yield of product was 7.4 mg, and its estimated purity by LCMS analysis was 94% purity.

Analysis LCMS condition D: Retention time=1.87 min; ESI-MS(+) m/z 922.8 (M+2H).

Analysis LCMS condition E: Retention time=1.87 min; ESI-MS(+) m/z 923.1 (M+2H).

Preparation of Example 3155

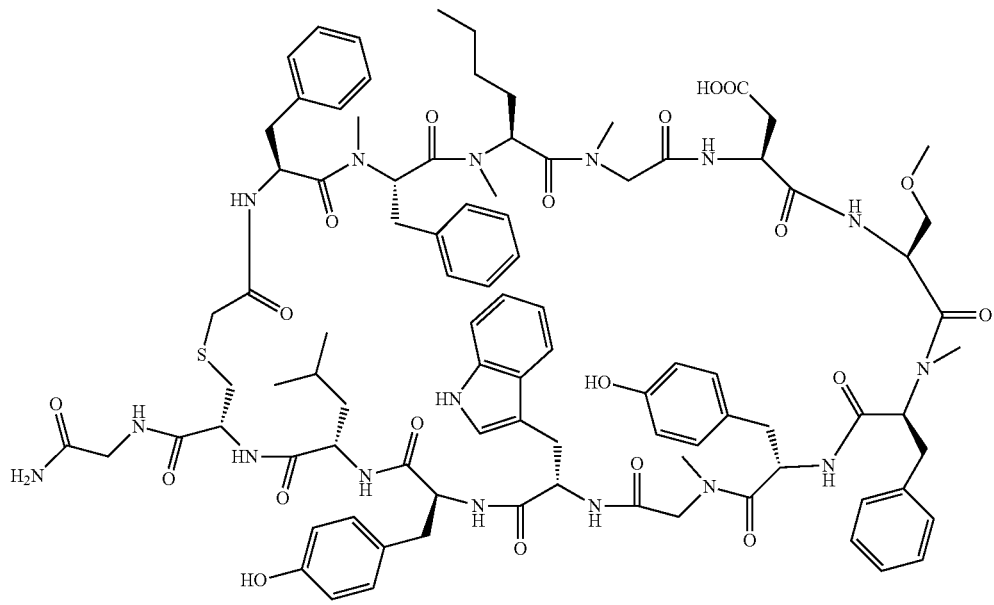

Example 3155

Example 3155 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 min., then a 5-minute hold at 100% B; Flow: 20 mL/min. Fractions containing the desired product were combined and dried. The yield of product was 15.3 mg, and its estimated purity by LCMS analysis was 98% purity.

Analysis LCMS condition D: Retention time=1.52 min; ESI-MS(+) m/z 900.3 (M+2H).

Analysis LCMS condition E: Retention time=1.71 min; ESI-MS(+) m/z 899.7 (M+2H).

Preparation of Example 3156

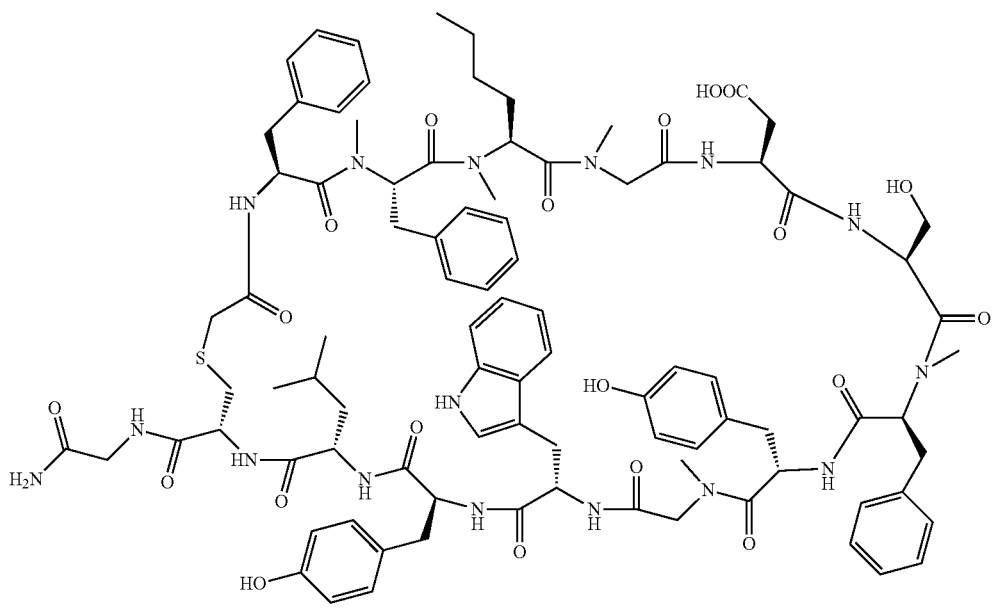

Example 3156

Example 3156 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-60% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min., then a 5-minute hold at 100% B; Flow: 20 mL/min. Fractions containing the desired product were combined and dried. The yield of product was 2.3 mg, and its estimated purity by LCMS analysis was 99% purity.

Analysis LCMS condition D: Retention time=1.47 min; ESI-MS(+) m/z 893.1 (M+2H).

Analysis LCMS condition E: Retention time=1.61 min; ESI-MS(+) m/z 892.8 (M+2H).

Preparation of Example 3157

Example 3157 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.1 mg, and its estimated purity by LCMS analysis was 94% purity.

Analysis LCMS condition D: Retention time=1.55 min; ESI-MS(+) m/z 906.9 (M+2H).

Analysis LCMS condition E: Retention time=1.74 min; ESI-MS(+) m/z 907.1 (M+2H).

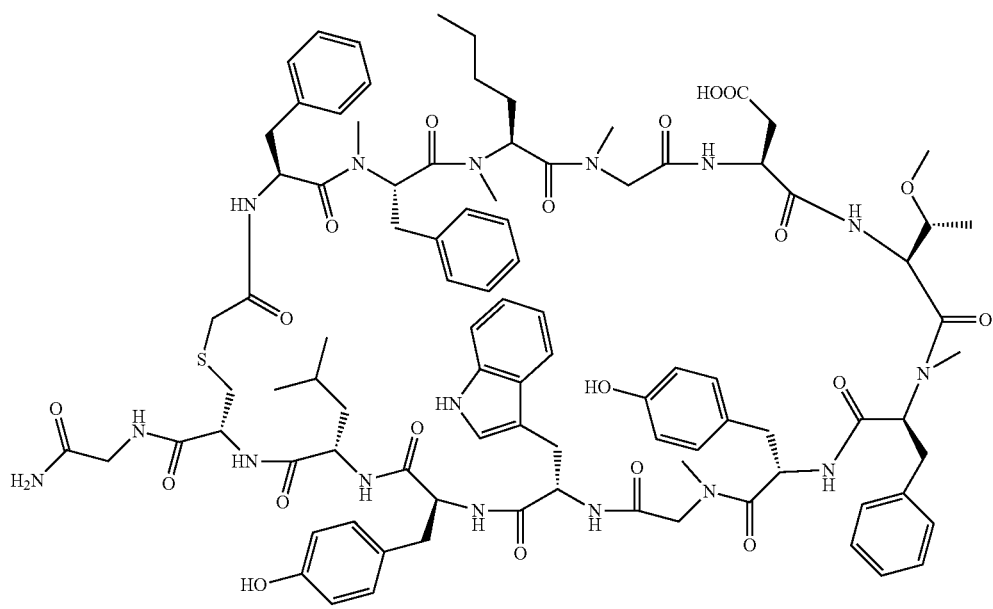

Example 3157

Preparation of Example 3158

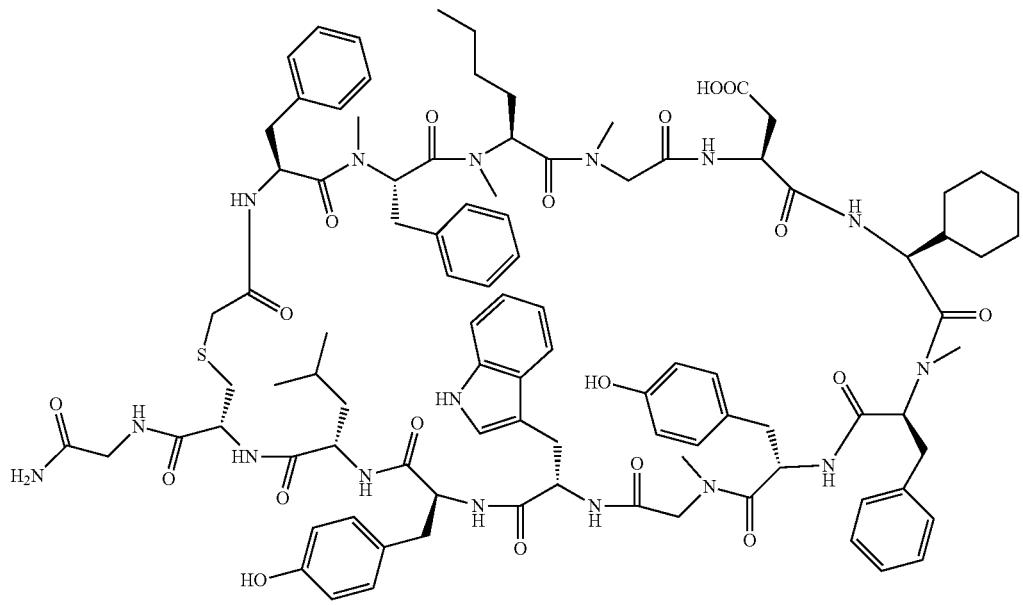

Example 3158

Example 3158 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 9.9 mg, and its estimated purity by LCMS analysis was 93% purity.

Analysis LCMS condition D: Retention time=1.74 min; ESI-MS(+) m/z 919.3 (M+2H).

Analysis LCMS condition E: Retention time=1.97 min; ESI-MS(+) m/z 919.2 (M+2H).

Preparation of Example 3159

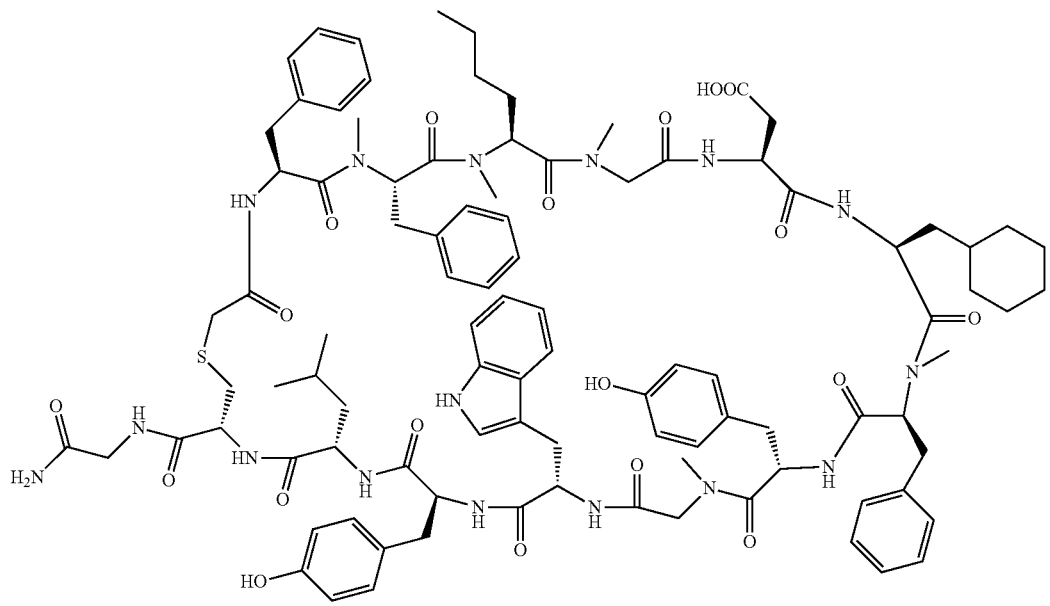

Example 3159

Example 3159 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 13.7 mg, and its estimated purity by LCMS analysis was 97% purity.

Analysis LCMS condition D: Retention time=1.85 min; ESI-MS(+) m/z 926.3 (M+2H).

Analysis LCMS condition E: Retention time=2.09 min; ESI-MS(+) m/z 926.1 (M+2H).

Preparation of Example 3160

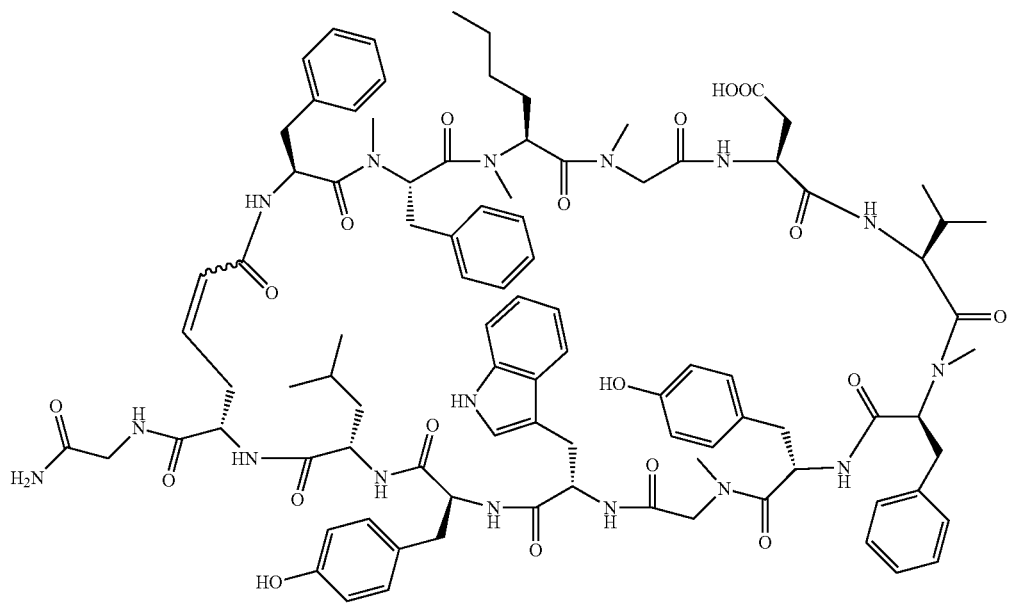

Example 3160

Example 3160 was prepared following the general synthetic sequence described for the preparation of Example 3078, composed of the following general procedures: "CEM Method A: Resin-swelling procedure", "CEM Method A: Standard-coupling procedure" and "Custom amino acids-coupling procedure".

The above peptidyl-resin (0.033 mmol) was purged with N2 and was put in 15 mL conical vial (equipped with stirrer) for microwave reactor. Then 0.033 mmol of Hoveyda-Grubb's 2nd generation catalyst dissolved in 5 mL 1,2-Dichloroethane was added. The mixture was then heated in microwave at 120° C. for 1 h. After the reaction was done, the resin was filtered and washed with DMF 2×5 mL followed by DCM 3×5 mL in a syringe equipped with a filter. The procedure for global deprotection and cyclization was repeated as in performed in example 3078 "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.35-95% B over 50 min., then a 5-minute hold at 95% B; Flow: 15 mL/min. Fractions containing the desired product were combined and dried. The yield of product was 0.77 mg, and its estimated purity was 86% by HPLC "Analysis Condition B" using a gradient of 35% to 85% buffer B over 30 min.

Analysis LCMS condition A: Retention time=1.78 min; ESI-MS(+) m/z 888.9 (M+2H).

Preparation of Example 3161

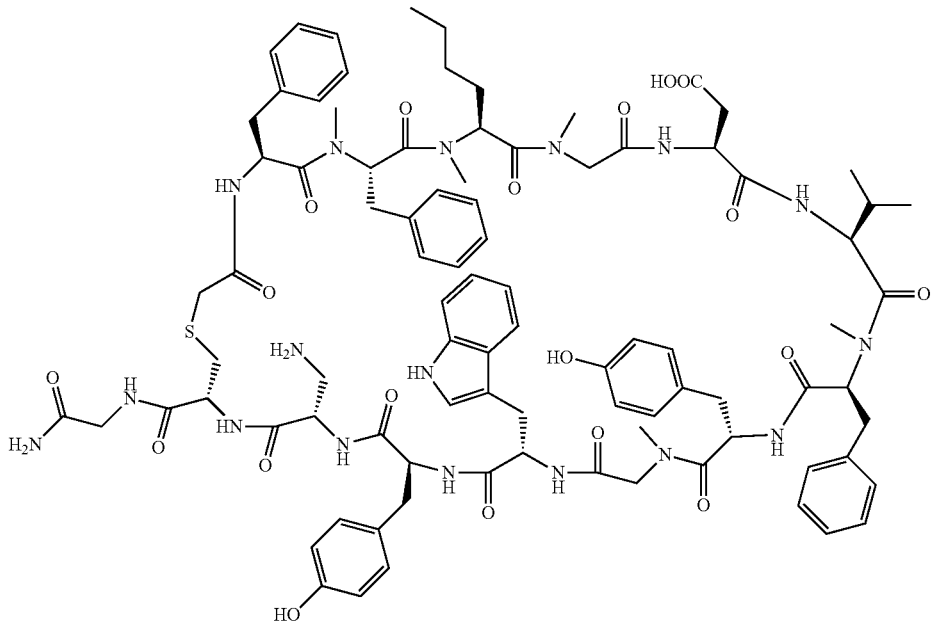

Example 3161

Example 3161 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.2 mg, and its estimated purity by LCMS analysis was 96%.

Analysis LCMS condition D: Retention time=1.58 min; ESI-MS(+) m/z 885.3 (M+2H).

Analysis LCMS condition E: Retention time=1.71 min; ESI-MS(+) m/z 885.3 (M+2H).

Preparation of Example 3162

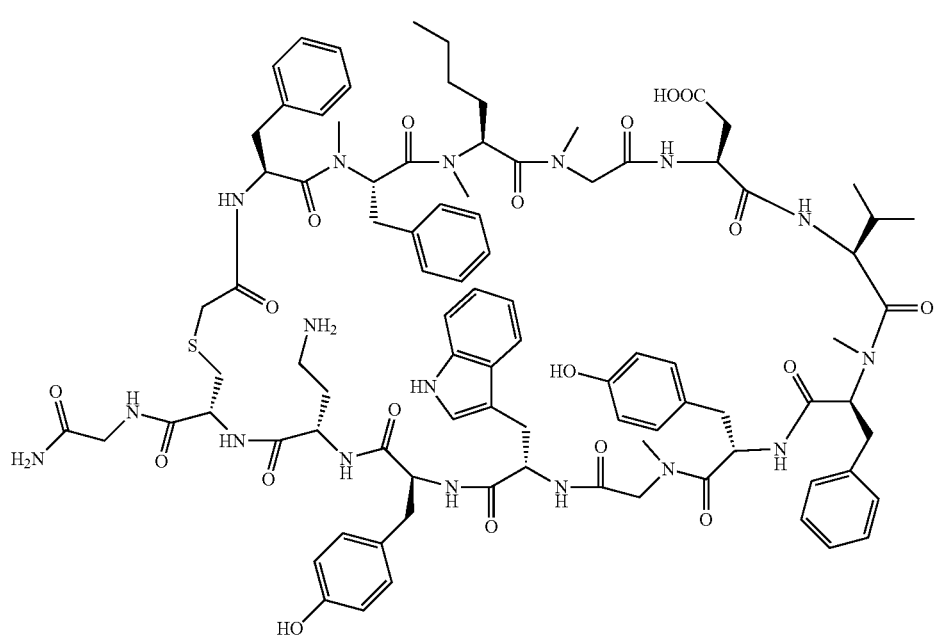

Example 3162

Example 3162 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.3 mg, and its estimated purity by LCMS analysis was 95%.

Analysis LCMS condition D: Retention time=1.59 min; ESI-MS(+) m/z 892.7 (M+2H).

Analysis LCMS condition E: Retention time=1.70 min; ESI-MS(+) m/z 892.3 (M+2H).

Preparation of Example 3163

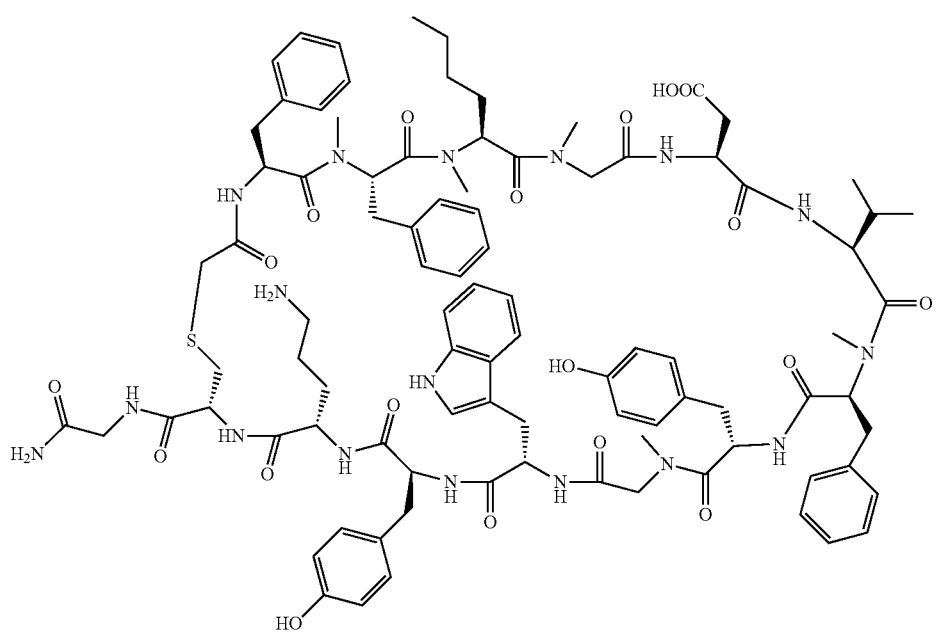

Example 3163

Example 3163 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.3 mg, and its estimated purity by LCMS analysis was 94%.

Analysis LCMS condition D: Retention time=1.58 min; ESI-MS(+) m/z 899.7 (M+2H).

Analysis LCMS condition E: Retention time=1.70 min; ESI-MS(+) m/z 899.5 (M+2H).

Preparation of Example 3164

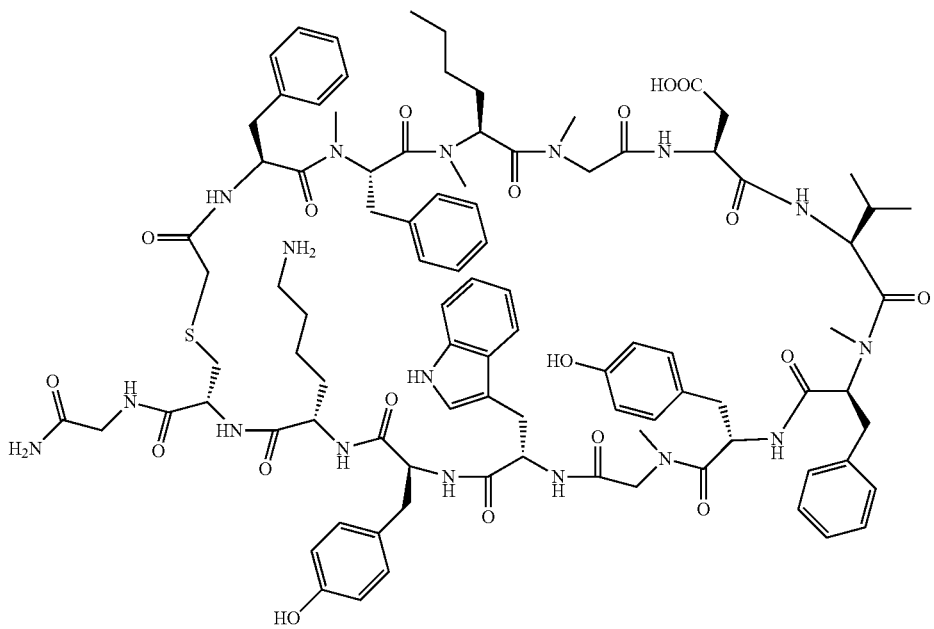

Example 3164

Example 3164 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 9.9 mg, and its estimated purity by LCMS analysis was 98%.

Analysis LCMS condition D: Retention time=1.58 min; ESI-MS(+) m/z 906.8 (M+2H).

Analysis LCMS condition E: Retention time=1.69 min; ESI-MS(+) m/z 906.4 (M+2H).

Preparation of Example 3165

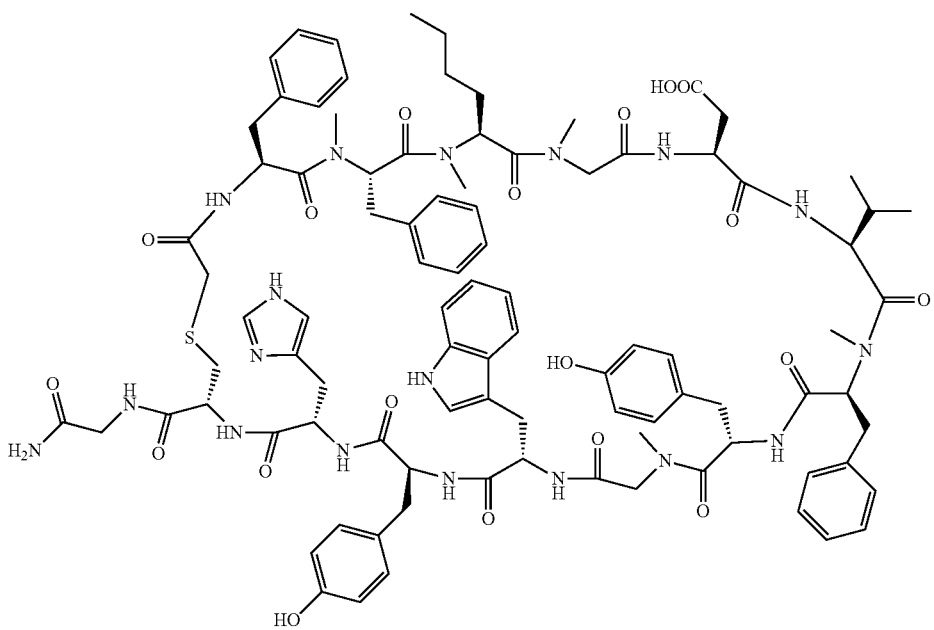

Example 3165

Example 3165 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 6.7 mg, and its estimated purity by LCMS analysis was 94%.

Analysis LCMS condition D: Retention time=1.57 min; ESI-MS(+) m/z 910.8 (M+2H).

Analysis LCMS condition E: Retention time=1.71 min; ESI-MS(+) m/z 910.9 (M+2H).

Preparation of Example 3166

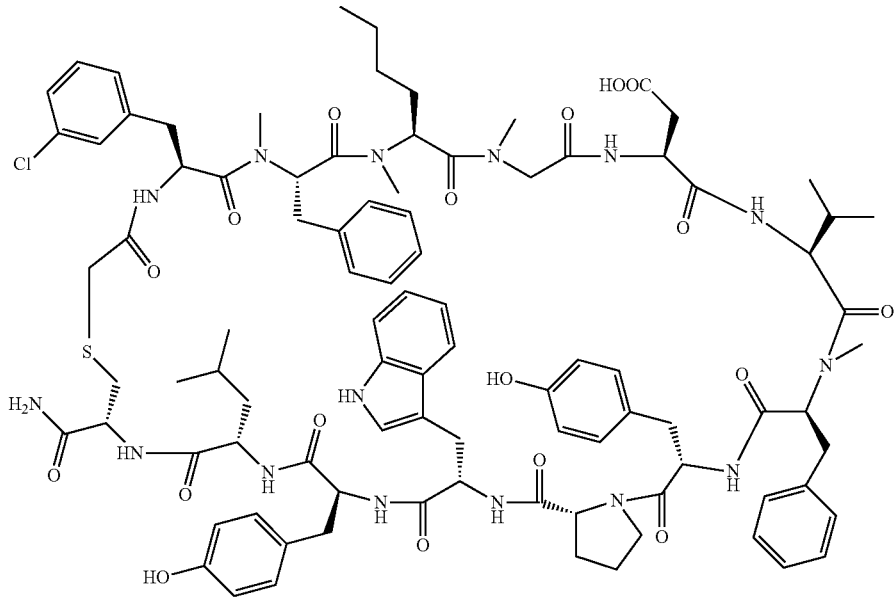

Example 3166

Example 3166 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 18.2 mg, and its estimated purity by LCMS analysis was 97%.

Analysis LCMS condition D: Retention time=1.85 min; ESI-MS(+) m/z 901.2 (M+2H).

Analysis LCMS condition E: Retention time=2.03 min; ESI-MS(+) m/z 900.9 (M+2H).

Preparation of Example 3167

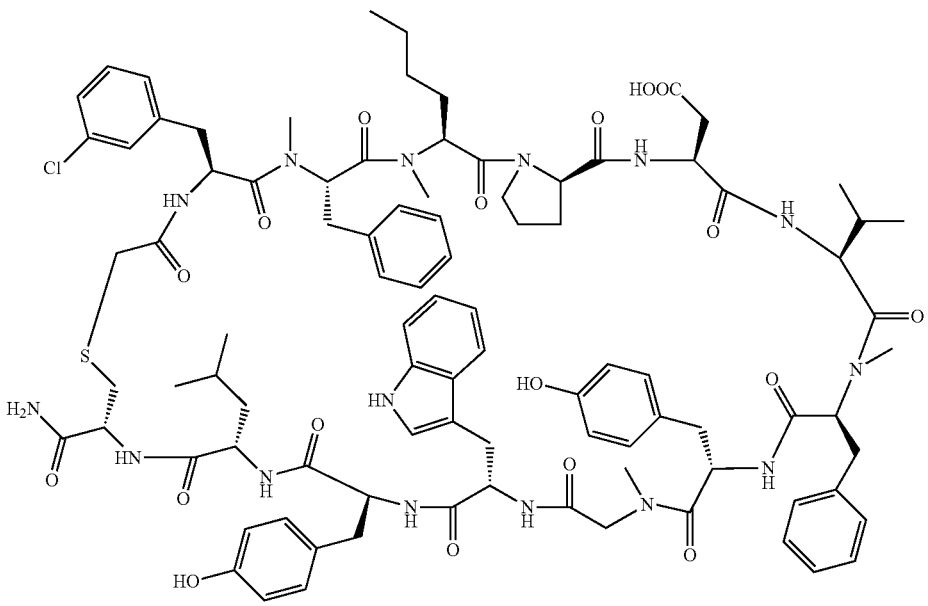

Example 3167

Example 3167 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 10.2 mg, and its estimated purity by LCMS analysis was 97%.

Analysis LCMS condition D: Retention time=1.93 min; ESI-MS(+) m/z 900.7 (M+2H).

Analysis LCMS condition E: Retention time=2.14 min; ESI-MS(+) m/z 900.8 (M+2H).

Preparation of Example 3168

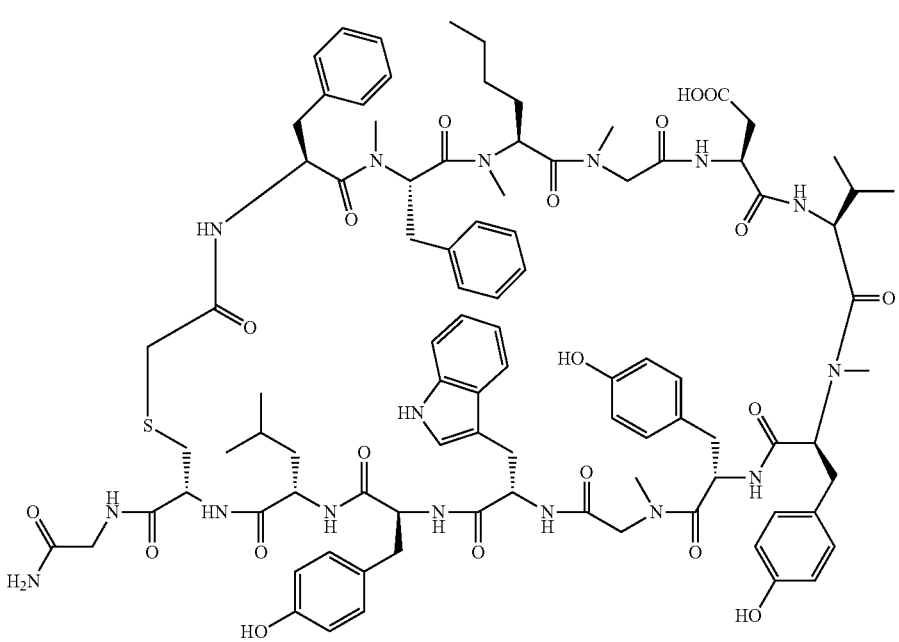

Example 3168

Example 3168 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 17.7 mg, and its estimated purity by LCMS analysis was 96%.

Analysis LCMS condition D: Retention time=1.52 min; ESI-MS(+) m/z 907.3 (M+2H).

Analysis LCMS condition E: Retention time=1.69 min; ESI-MS(+) m/z 907.2 (M+2H).

Preparation of Example 3171

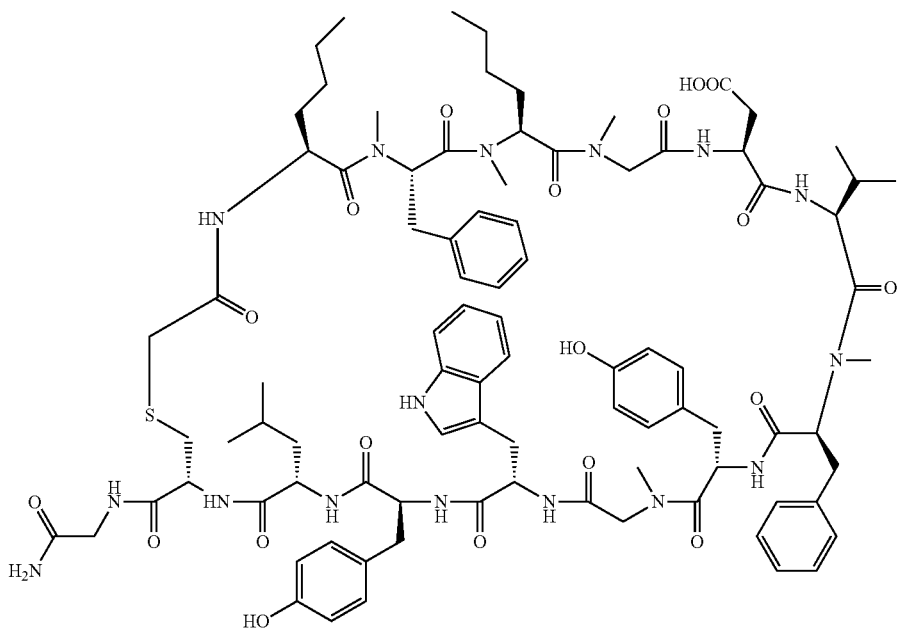

Example 3171

Example 3171 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-70% B over 25 min., then a 5-minute hold at 100% B; Flow: 20 mL/min. Fractions containing the desired product were combined and dried. The yield of product was 5.1 mg, and its estimated purity by LCMS analysis was 95%.

Analysis LCMS condition D: Retention time=1.64 min; ESI-MS(+) m/z 881.9 (M+2H).

Analysis LCMS condition E: Retention time=1.85 min; ESI-MS(+) m/z 881.9 (M+2H).

Preparation of Example 3172

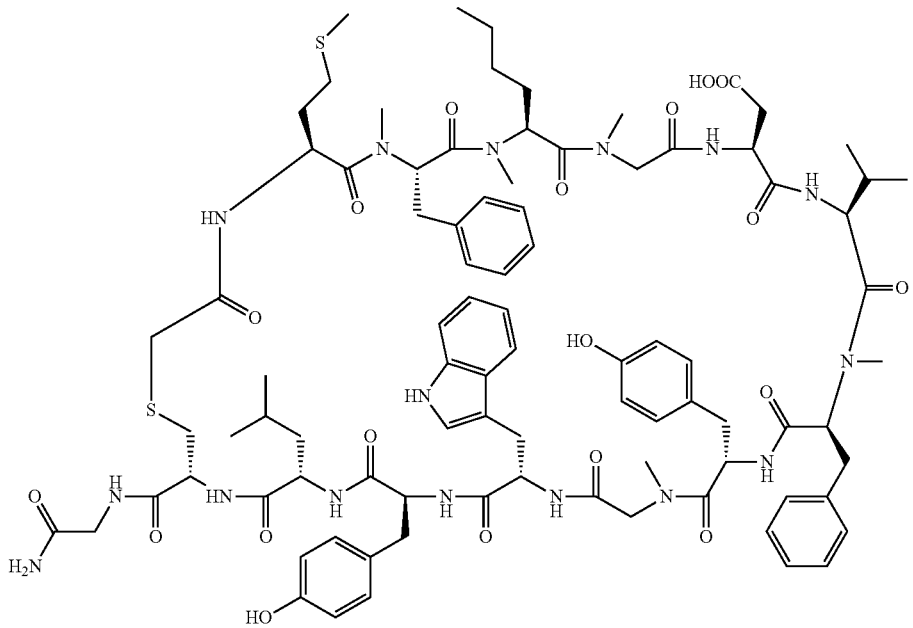

Example 3172

Example 3172 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 6.5 mg, and its estimated purity by LCMS analysis was 97%.

Analysis LCMS condition D: Retention time=1.61 min; ESI-MS(+) m/z 891.1 (M+2H).

Analysis LCMS condition E: Retention time=1.81 min; ESI-MS(+) m/z 891.1 (M+2H).

Preparation of Example 3173

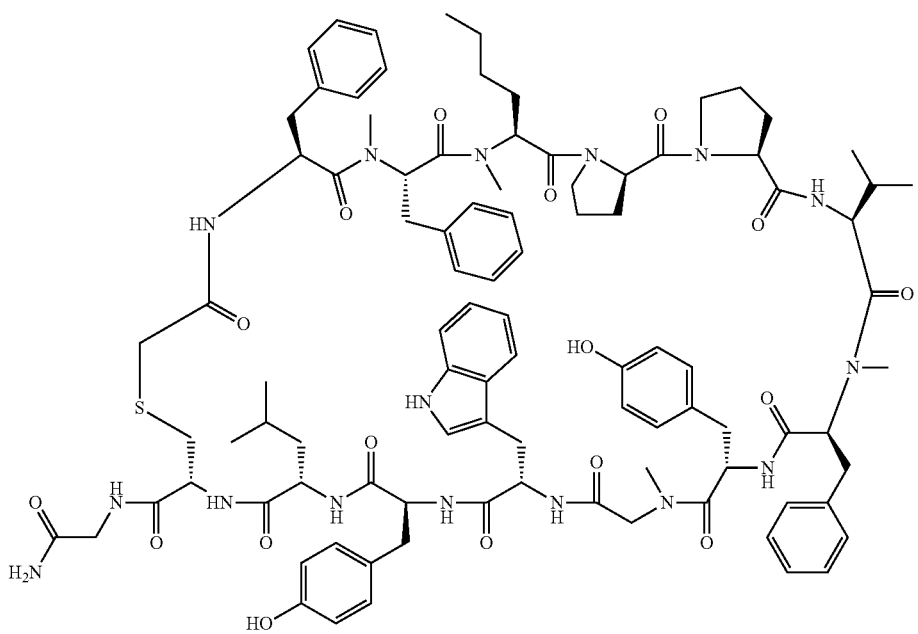

Example 3173

Example 3173 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge c-18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-80% B over 25 min., then a 5-minute hold at 100% B; Flow: 20 mL/min. Fractions containing the desired product were combined and dried. The yield of product was 6.5 mg, and its estimated purity by LCMS analysis was 97%.

Analysis LCMS condition D: Retention time=2.26 min; ESI-MS(+) m/z 903.3 (M+2H).

Analysis LCMS condition E: Retention time=2.25 min; ESI-MS(+) m/z 903.2 (M+2H).

Preparation of Example 3174

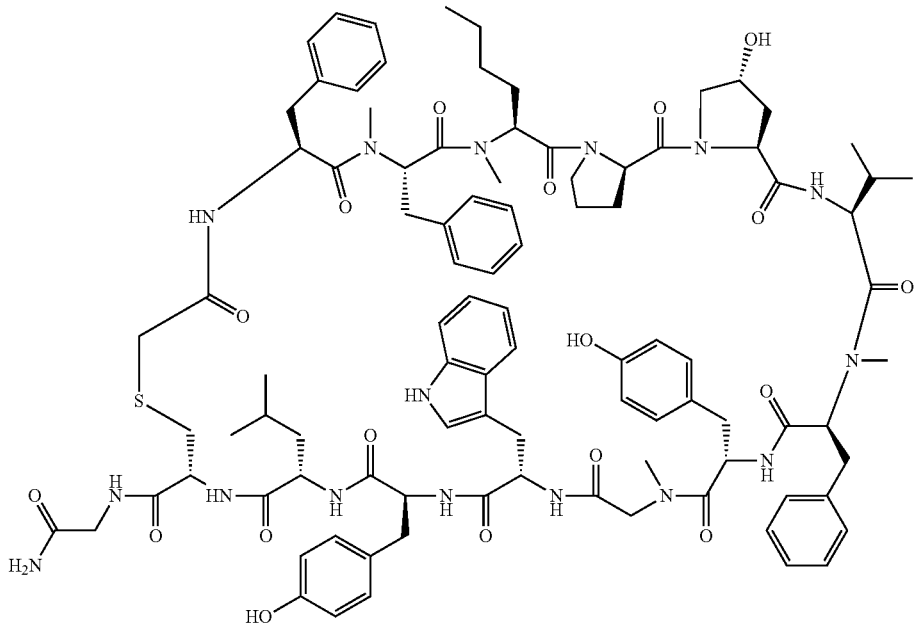

Example 3174

Example 3174 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge c-18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-70% B over 25 min., then a 5-minute hold at 100% B; Flow: 20 mL/min. Fractions containing the desired product were combined and dried. The yield of product was 7.3 mg, and its estimated purity by LCMS analysis was 100%.

Analysis LCMS condition D: Retention time=1.94 min; ESI-MS(+) m/z 911.0 (M+2H).

Analysis LCMS condition E: Retention time=1.94 min; ESI-MS(+) m/z 911.2 (M+2H).

Preparation of Example 3175

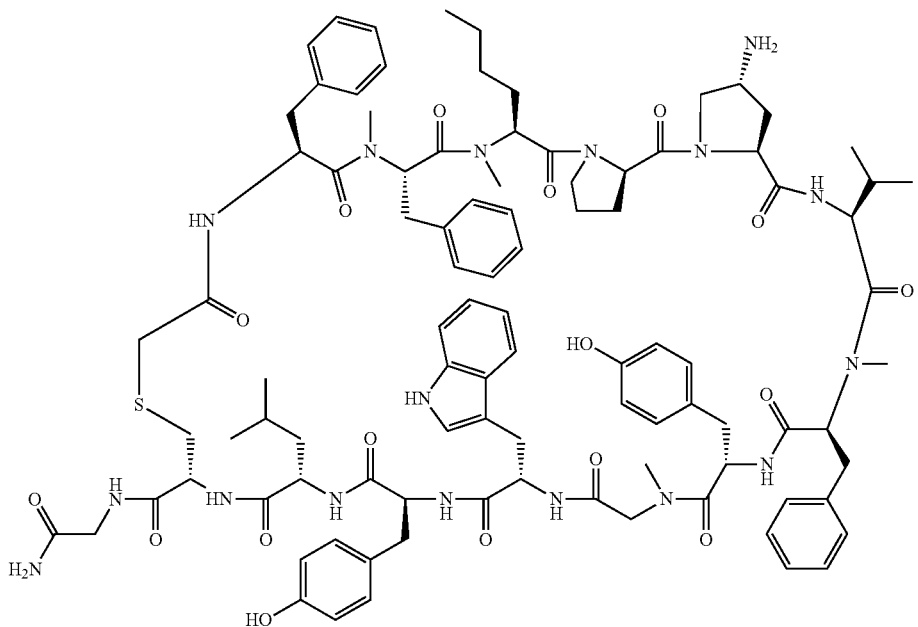

Example 3175

Example 3175 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge c-18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 9.8 mg, and its estimated purity by LCMS analysis was 95%.

Analysis LCMS condition D: Retention time=1.85 min; ESI-MS(+) m/z 910.3 (M+2H).

Analysis LCMS condition E: Retention time=1.68 min; ESI-MS(+) m/z 910.8 (M+2H).

Preparation of Example 3176

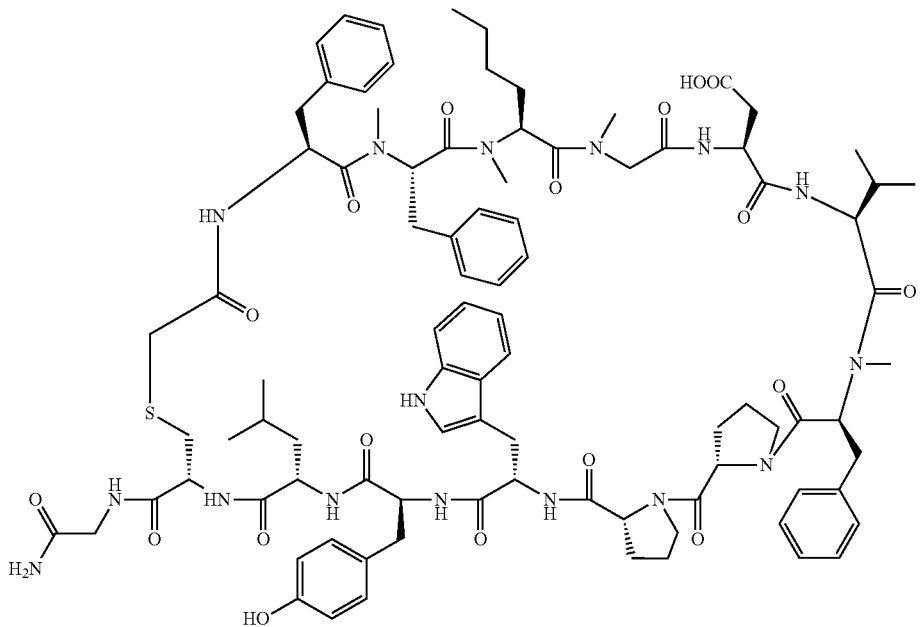

Example 3176

Example 3176 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 min., then a 5-minute hold at 100% B; Flow: 20 mL/min. Fractions containing the desired product were combined and dried. The yield of product was 4.2 mg, and its estimated purity by LCMS analysis was 100%.

Analysis LCMS condition D: Retention time=1.56 min; ESI-MS(+) m/z 879.1 (M+2H).

Analysis LCMS condition E: Retention time=1.78 min; ESI-MS(+) m/z 878.8 (M+2H).

Preparation of Example 3177

Example 3177 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-65% B over 25 min., then a 5-minute hold at 100% B; Flow: 20 mL/min. Fractions containing the desired product were combined and dried. The yield of product was 2.0 mg, and its estimated purity by LCMS analysis was 100%.

Analysis LCMS condition D: Retention time=1.52 min; ESI-MS(+) m/z 887.2 (M+2H).

Analysis LCMS condition E: Retention time=1.70 min; ESI-MS(+) m/z 886.6 (M+2H).

Example 3177

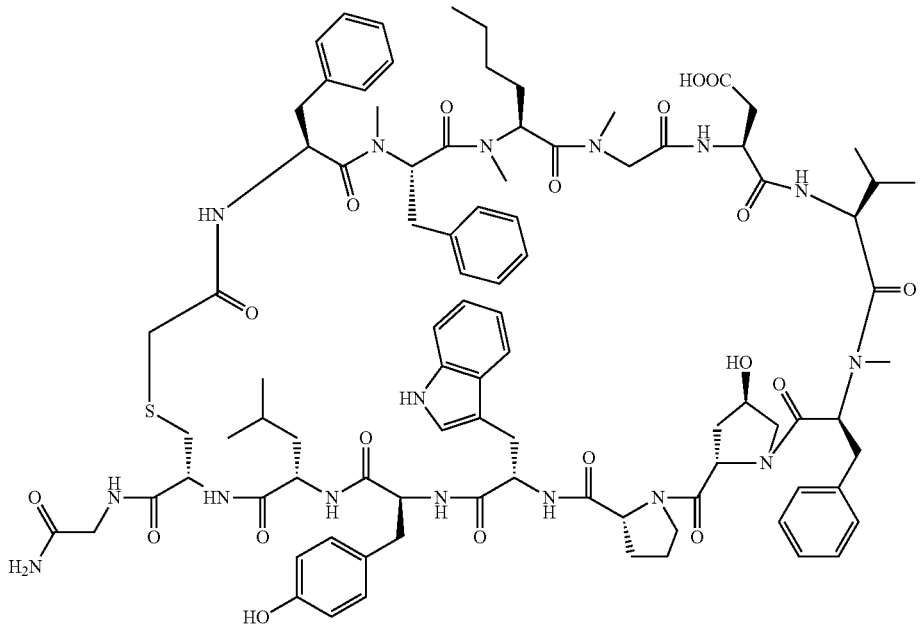

Preparation of Example 3178

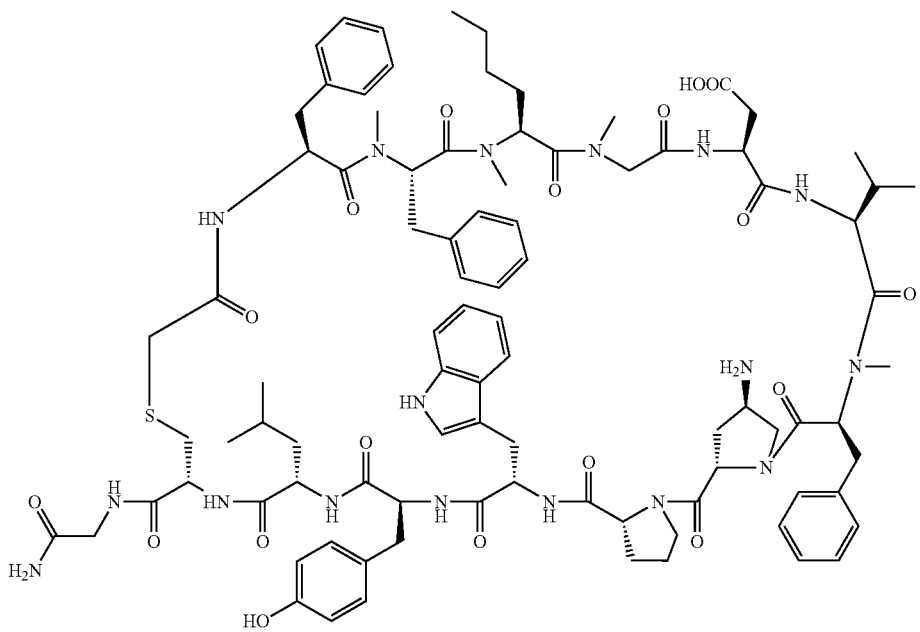

Example 3178

Example 3178 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 9.8 mg, and its estimated purity by LCMS analysis was 93%.

Analysis LCMS condition D: Retention time=1.68 min; ESI-MS(+) m/z 887.0 (M+2H).

Analysis LCMS condition E: Retention time=1.69 min; ESI-MS(+) m/z 886.2 (M+2H).

Preparation of Example 3179

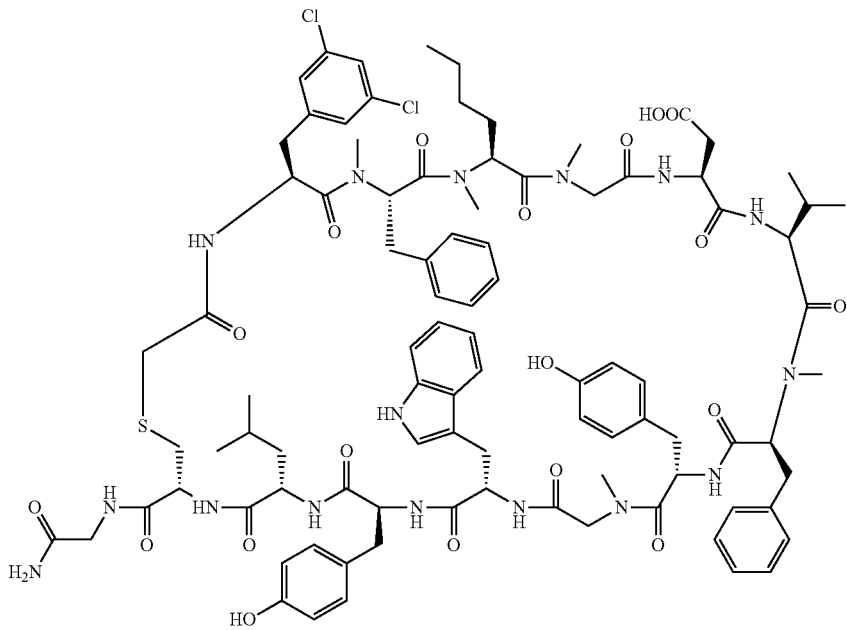

Example 3179

Example 3179 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". (S)-2-((((9H-fluoren-9-yl)methoxy)carbonyl)amino)-3-(3,5-dichlorophenyl)propanoic acid was used.

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 5.2 mg, and its estimated purity by LCMS analysis was 99%.

Analysis LCMS condition D: Retention time=1.75 min; ESI-MS(+) m/z 933.3 (M+2H).

Analysis LCMS condition E: Retention time=1.97 min; ESI-MS(+) m/z 933.6 (M+2H).

Preparation of Example 3180

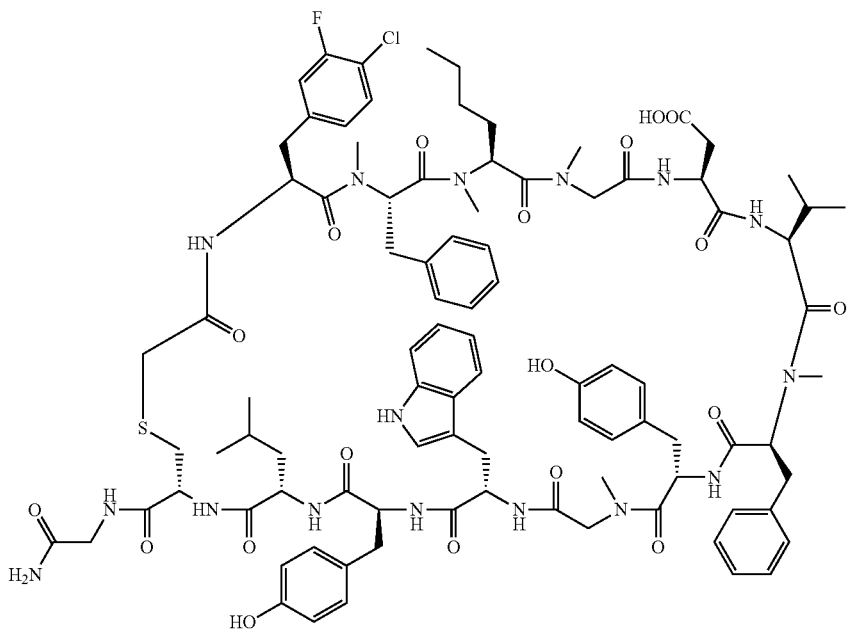

Example 3180

Example 3180 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". (S)-2-((((9H-fluoren-9-yl)methoxy)carbonyl)amino)-3-(4-chloro-3-fluorophenyl)propanoic acid was used.

The crude material was purified via preparative LC/MS with the following conditions: Column: Waters XBridge C18, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-75% B over 25 min., then a 5-minute hold at 100% B; Flow: 20 mL/min. Fractions containing the desired product were combined and dried. The yield of product was 4.4 mg, and its estimated purity by LCMS analysis was 94%.

Analysis LCMS condition D: Retention time=1.69 min; ESI-MS(+) m/z 924.8 (M+2H).

Analysis LCMS condition E: Retention time=1.91 min; ESI-MS(+) m/z 925.3 (M+2H).

Preparation of Example 3181

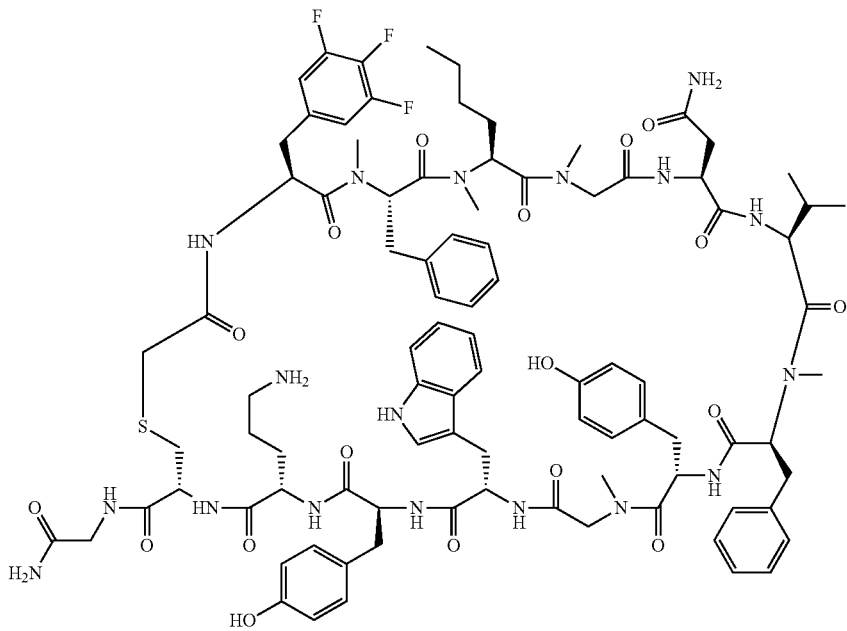

Example 3181

Example 3181 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.3 mg, and its estimated purity by LCMS analysis was 97%.

Analysis LCMS condition D: Retention time=1.65 min; ESI-MS(+) m/z 925.6 (M+2H).

Analysis LCMS condition E: Retention time=1.71 min; ESI-MS(+) m/z 925.7 (M+2H).

Preparation of Example 3182

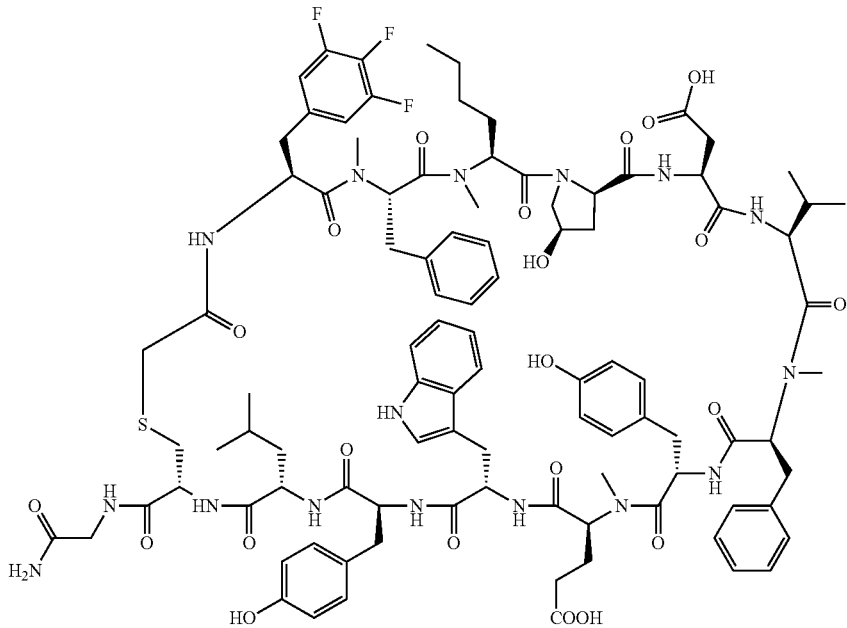

Example 3182

Example 3182 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge c-18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-75% B over 25 min., then a 5-minute hold at 100% B; Flow: 20 mL/min. Fractions containing the desired product were combined and dried. The yield of product was 6.9 mg, and its estimated purity by LCMS analysis was 100%.

Analysis LCMS condition D: Retention time=1.58 min; ESI-MS(+) m/z 982.9 (M+2H).

Analysis LCMS condition E: Retention time=1.85 min; ESI-MS(+) m/z 982.8 (M+2H).

ESI-HRMS(+) m/z:
Calculated: 982.4330 (M+2H).
Found: 982.4307 (M+2H).

Preparation of Example 3183

Example 3183 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge c-18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-75% B over 25 min., then a 5-minute hold at 100% B; Flow: 20 mL/min. Fractions containing the desired product were combined and dried. The yield of product was 2.0 mg, and its estimated purity by LCMS analysis was 100%.

Analysis LCMS condition D: Retention time=1.66 min; ESI-MS(+) m/z 960.2 (M+2H).

Analysis LCMS condition E: Retention time=1.87 min; ESI-MS(+) m/z 960.2 (M+2H).

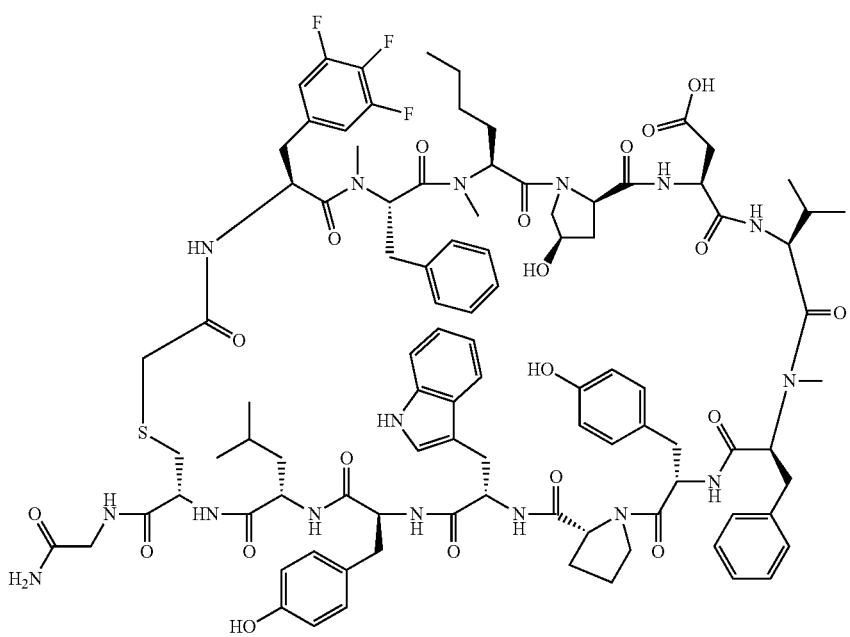

Example 3183

Preparation of Example 3184

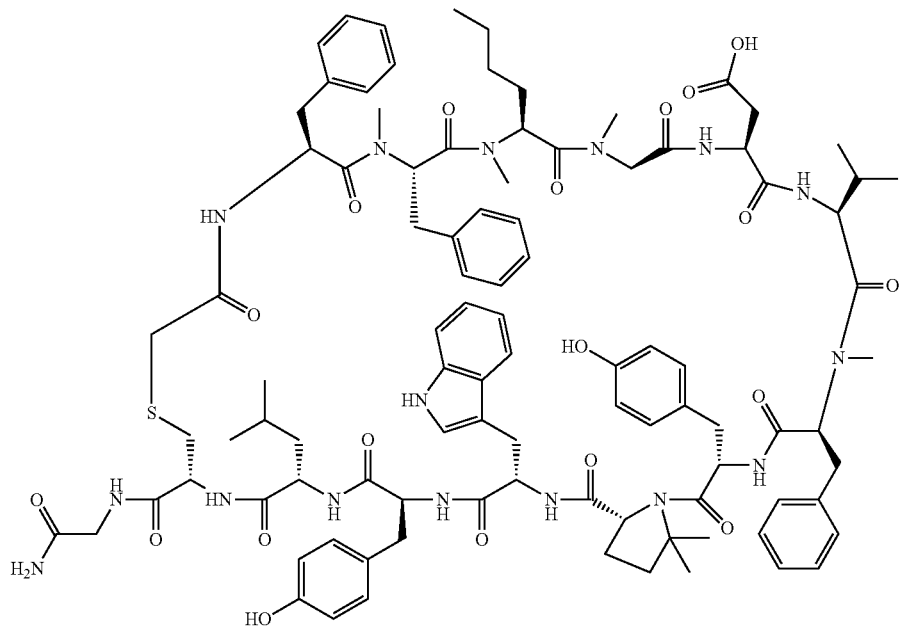

Example 3184

Example 3184 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-75% B over 25 min., then a 5-minute hold at 100% B; Flow: 20 mL/min. Fractions containing the desired product were combined and dried. The yield of product was 21.8 mg, and its estimated purity by LCMS analysis was 97%.

Analysis LCMS condition D: Retention time=1.71 min; ESI-MS(+) m/z 925.9 (M+2H).

Analysis LCMS condition E: Retention time=1.95 min; ESI-MS(+) m/z 926.0 (M+2H).

Preparation of Example 3185

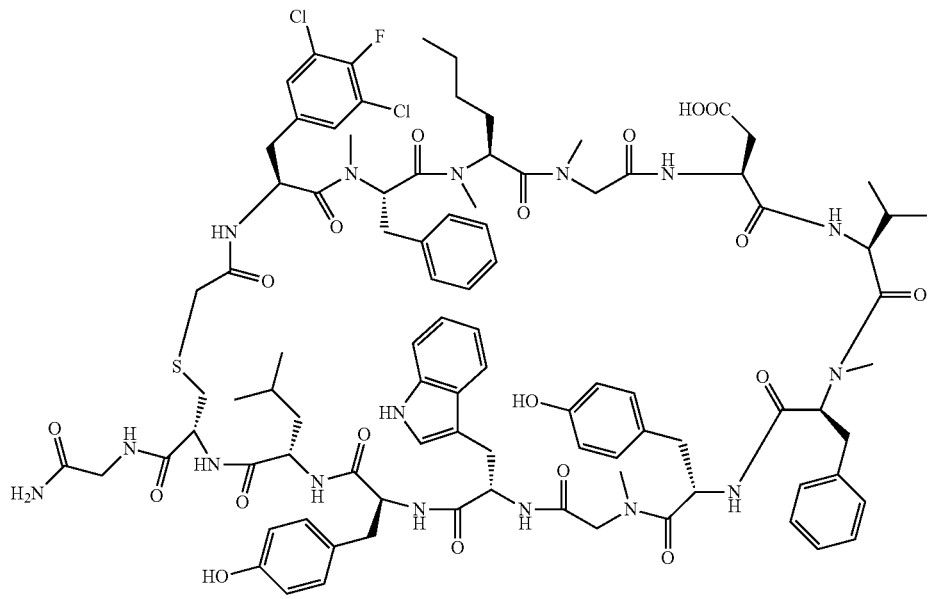

Example 3185

Example 3185 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". (S)-2-((((9H-fluoren-9-yl)methoxy)carbonyl)amino)-3-(3,5-dichloro-4-fluorophenyl)propanoic acid was used.

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 6-minute hold at 100% B; Flow: 20 mL/min. Fractions containing the desired product were combined and dried. The yield of product was 3.6 mg, and its estimated purity by LCMS analysis was 98%.

Analysis LCMS condition D: Retention time=1.76 min; ESI-MS(+) m/z 942.0 (M+2H).

Analysis LCMS condition E: Retention time=1.96 min; ESI-MS(+) m/z 942.2 (M+2H).

Preparation of Example 3186

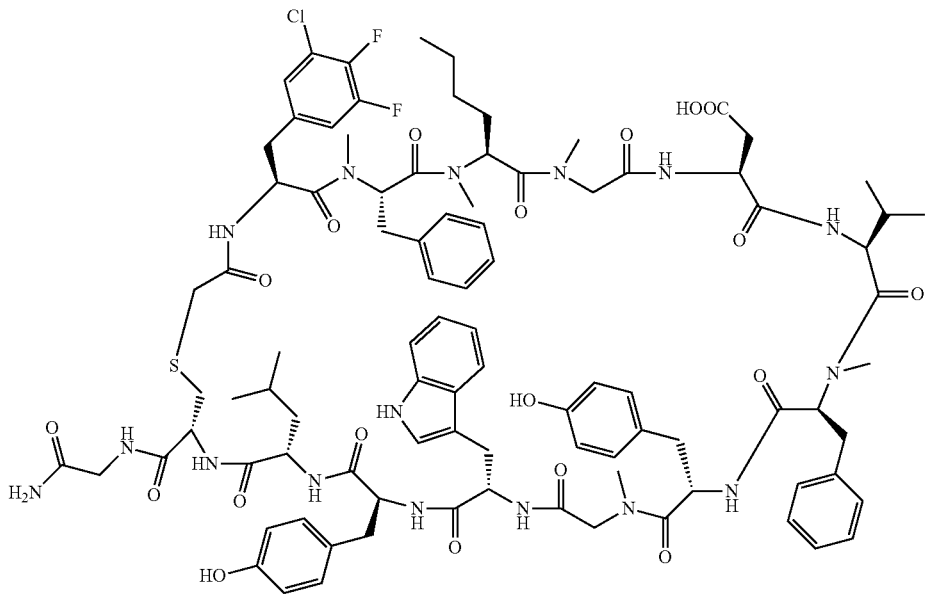

Example 3186

Example 3186 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". (S)-2-((((9H-fluoren-9-yl)methoxy)carbonyl)amino)-3-(3-chloro-4,5-difluorophenyl)propanoic acid was used.

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 0.35-85% B over 50 min., then a 5-minute hold at 85% B; Flow: 15 mL/min. Fractions containing the desired product were combined and dried. The yield of product was 6.3 mg, and its estimated purity was 99% by HPLC "Analysis Condition B" using a gradient of 30% to 85% buffer B over 20 min.

Analysis LCMS condition A: Retention time=1.37 min; ESI-MS(+) m/z 933.9 (M+2H).

Preparation of Example 3187

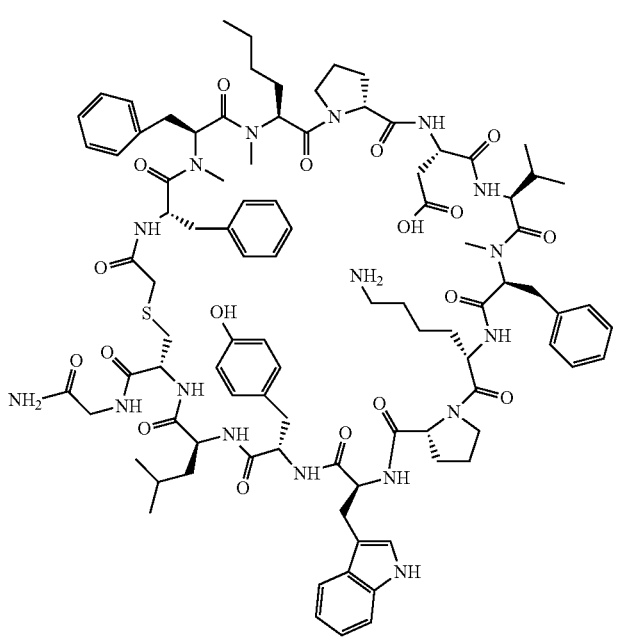

Example 3187

Example 3187 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 5.4 mg and its estimated purity by LCMS analysis was 100%.

Analysis LCMS condition D: Retention time=1.75 min; ESI-MS(+) m/z 907.3 (M+2H).

Analysis LCMS condition E: Retention time=1.79 min; ESI-MS(+) m/z 907.5 (M+2H).

Preparation of Example 3188

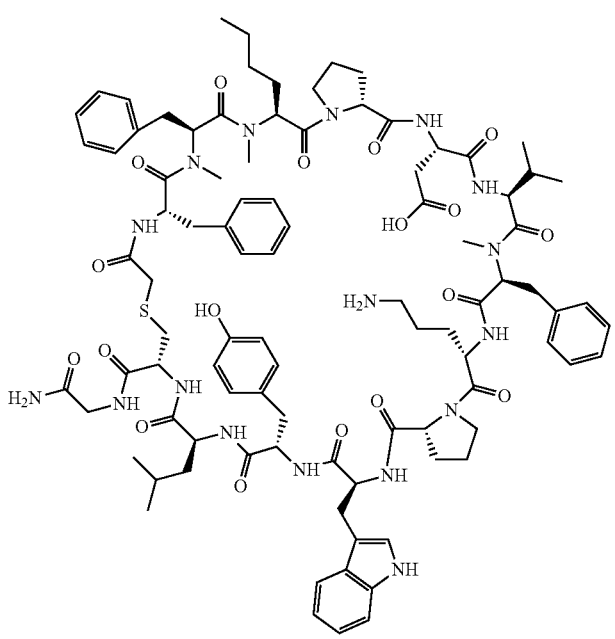

Example 3188

Example 3188 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 7 mg and its estimated purity by LCMS analysis was 95%.

Analysis LCMS condition D: Retention time=1.74 min; ESI-MS(+) m/z 900.3 (M+2H).

Analysis LCMS condition E: Retention time=1.79 min; ESI-MS(+) m/z 900.6 (M+2H).

Preparation of Example 3189

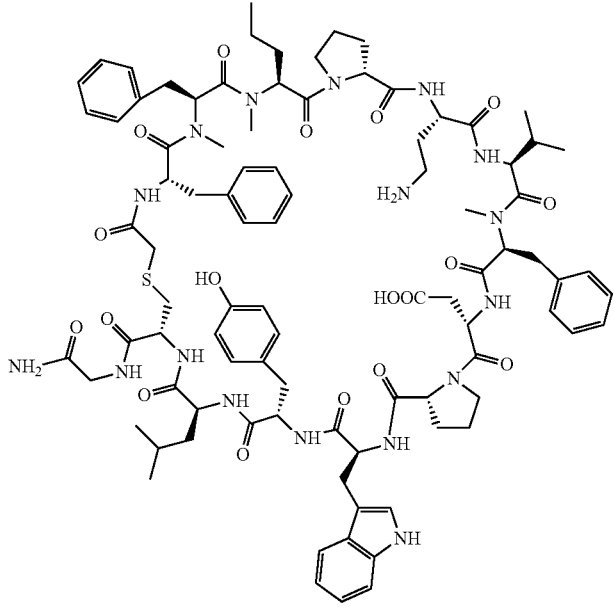

Example 3189

Example 3189 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 8.6 mg and its estimated purity by LCMS analysis was 92%.

Analysis LCMS condition D: Retention time=1.70 min; ESI-MS(+) m/z 893.4 (M+2H).

Analysis LCMS condition E: Retention time=1.68 min; ESI-MS(+) m/z 893.2 (M+2H).

Preparation of Example 3190

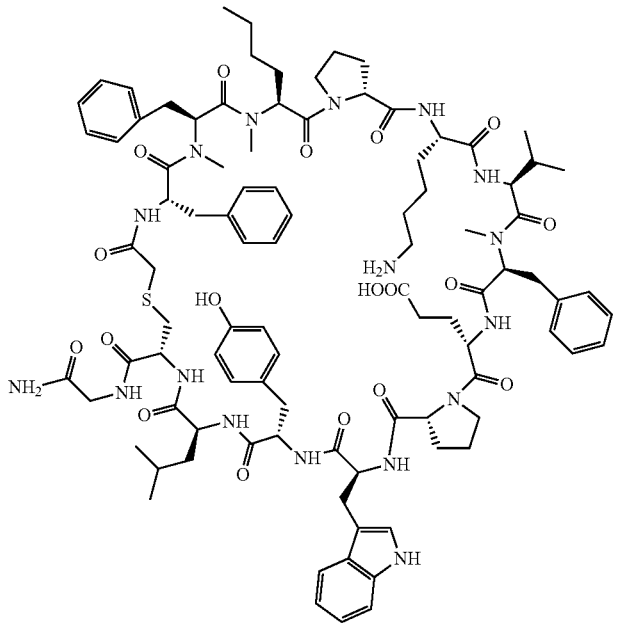

Example3190

Example 3190 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 5.8 mg and its estimated purity by LCMS analysis was 94%.

Analysis LCMS condition D: Retention time=1.74 min; ESI-MS(+) m/z 914.8 (M+2H).

Analysis LCMS condition E: Retention time=1.71 min; ESI-MS(+) m/z 914.4 (M+2H).

Preparation of Example 3191

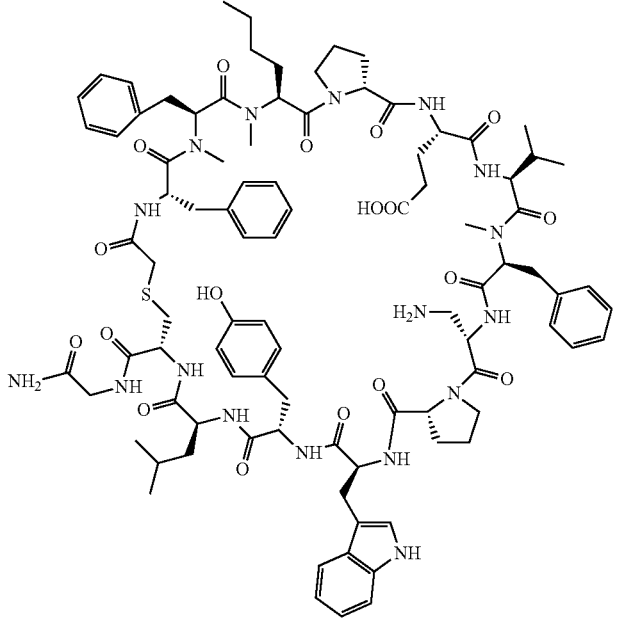

Example 3191

Example 3191 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 min., then a 5-minute hold at 100% B; Flow: 20 mL/min. Fractions containing the desired product were combined and dried. The yield of product was 5.4 mg, and its estimated purity by LCMS analysis was 92%.

Analysis LCMS condition D: Retention time=1.72 min; ESI-MS(+) m/z 893.4 (M+2H).

Analysis LCMS condition E: Retention time=1.82 min; ESI-MS(+) m/z 893.6 (M+2H).

Preparation of Example 3192

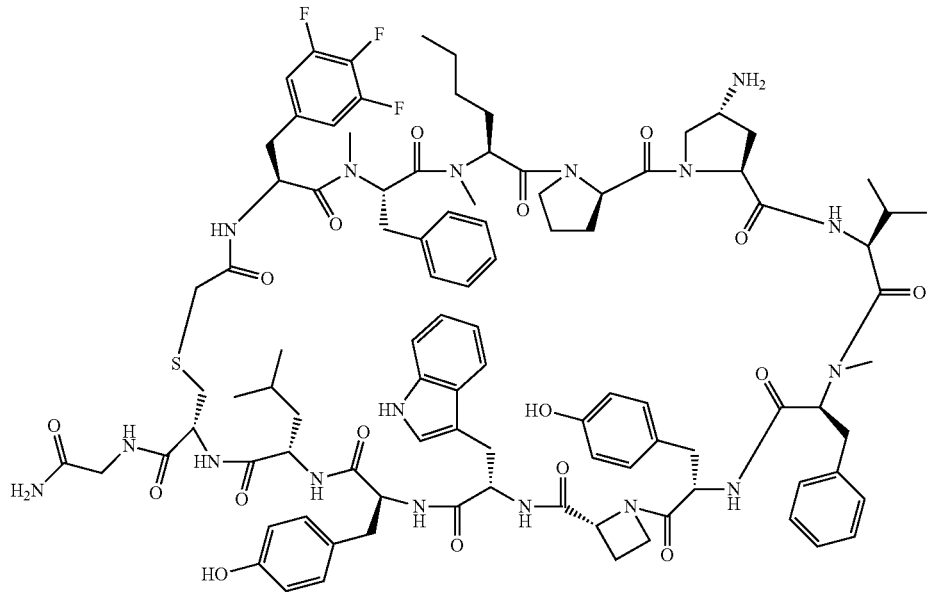

Example 3192

Example 3192 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 min., then a 0-minute hold at 100% B; Flow: 20 mL/min. Fractions containing the desired product were combined and dried. The yield of product was 9.4 mg, and its estimated purity by LCMS analysis was 94%.

Analysis LCMS condition D: Retention time=1.89 min; ESI-MS(+) m/z 943.4 (M+2H).

Analysis LCMS condition E: Retention time=1.71 min; ESI-MS(+) m/z 943.2 (M+2H).

Preparation of Example 3193

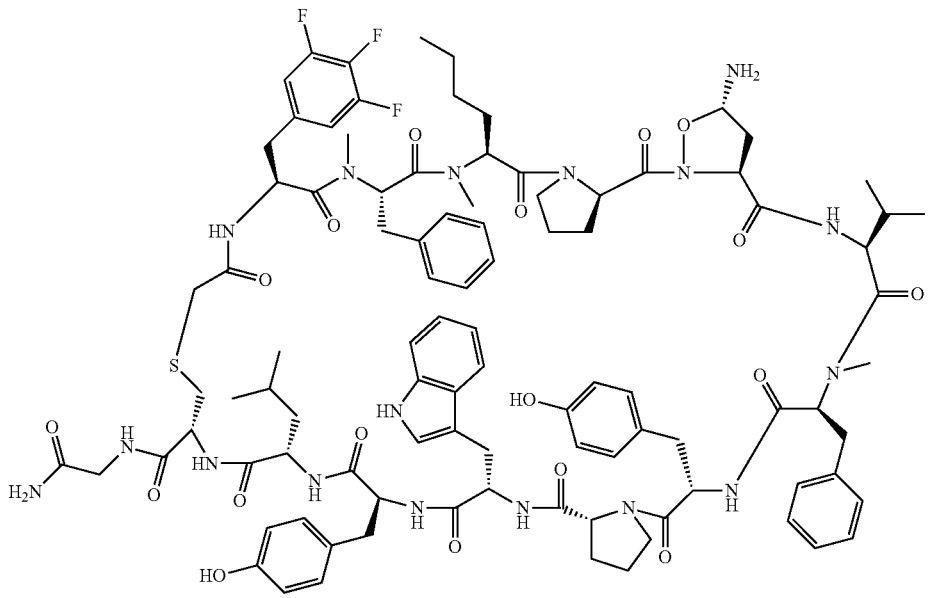

Example 3193

Example 3193 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-75% B over 25 min., then a 0-minute hold at 100% B; Flow: 20 mL/min. Fractions containing the desired product were combined and dried. The yield of product was 8.9 mg, and its estimated purity by LCMS analysis was 91%.

Analysis LCMS condition D: Retention time=1.90 min; ESI-MS(+) m/z 950.6 (M+2H).

Analysis LCMS condition E: Retention time=1.72 min; ESI-MS(+) m/z 950.4 (M+2H).

Preparation of Example 3194

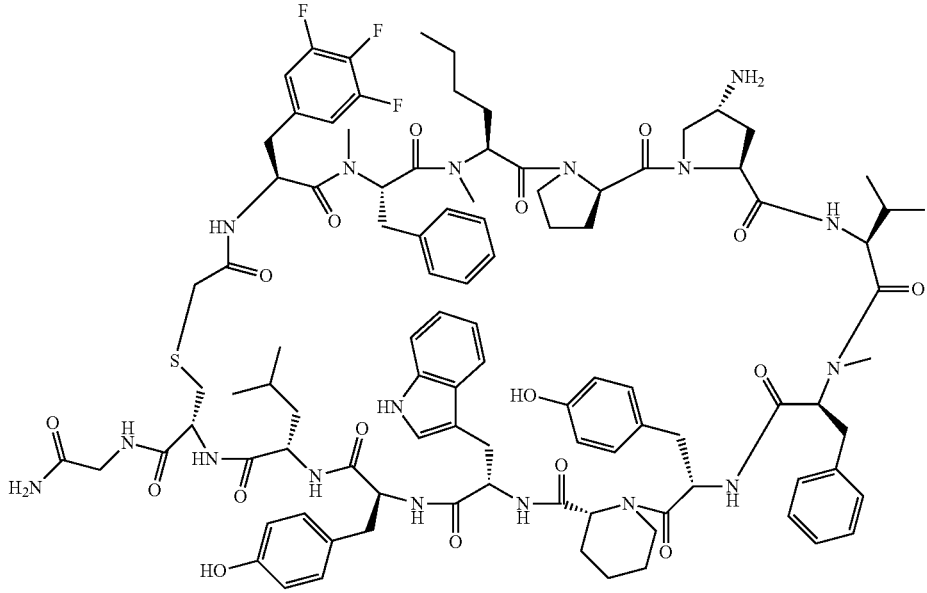

Example 3194

Example 3194 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 min., then a 0-minute hold at 100% B; Flow: 20 mL/min. Fractions containing the desired product were combined and dried. The yield of product was 9.6 mg, and its estimated purity by LCMS analysis was 95%.

Analysis LCMS condition D: Retention time=1.99 min; ESI-MS(+) m/z 957.3 (M+2H).

Analysis LCMS condition E: Retention time=1.77 min; ESI-MS(+) m/z 957.3 (M+2H).

Preparation of Example 3195

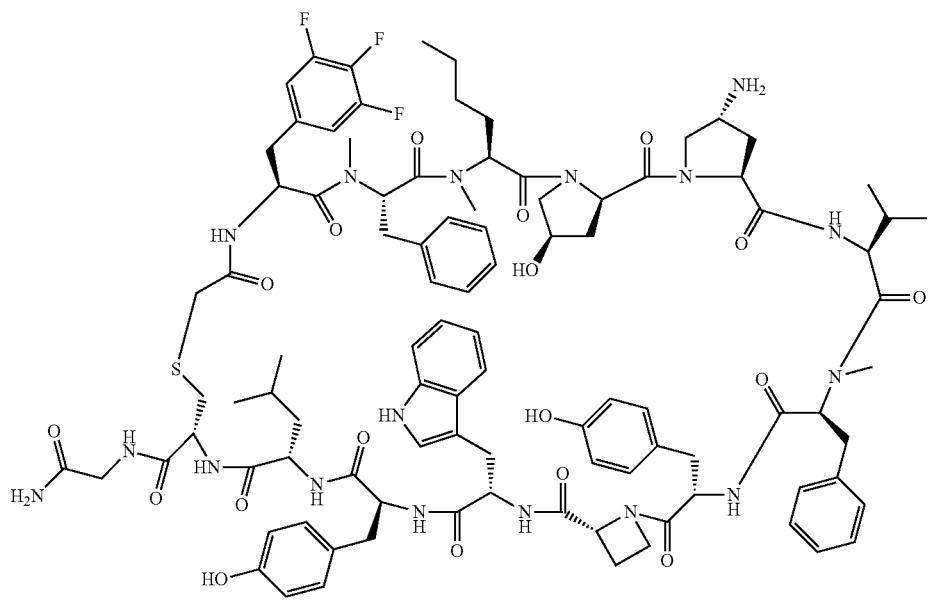

Example 3195

Example 3195 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min., then a 0-minute hold at 100% B; Flow: 20 mL/min. Fractions containing the desired product were combined and dried. The yield of product was 6.4 mg, and its estimated purity by LCMS analysis was 90%.

Analysis LCMS condition D: Retention time=1.78 min; ESI-MS(+) m/z 951.2 (M+2H).

Analysis LCMS condition E: Retention time=1.64 min; ESI-MS(+) m/z 951.2 (M+2H).

Preparation of Example 3196

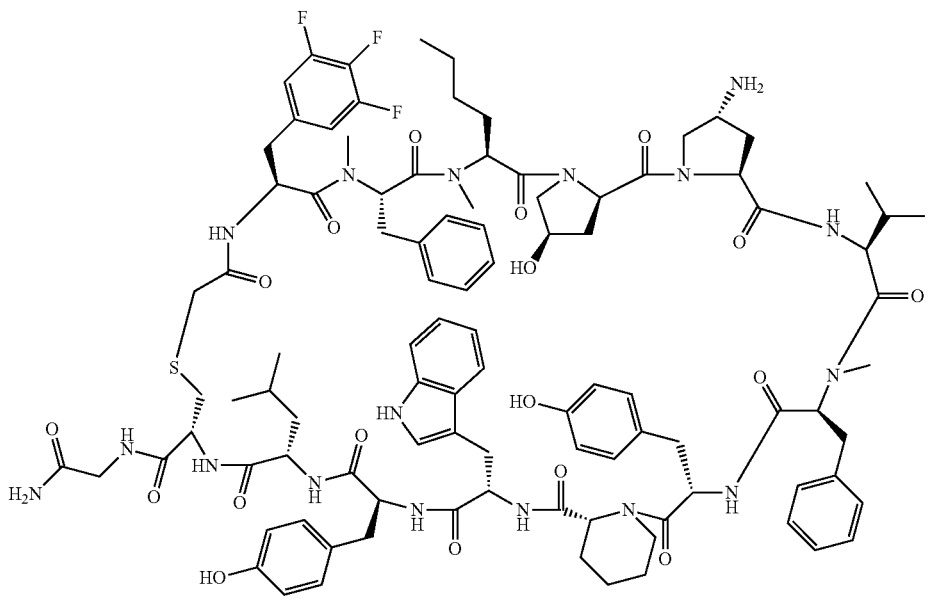

Example 3196

Example 3196 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 min., then a 0-minute hold at 100% B; Flow: 20 mL/min. Fractions containing the desired product were combined and dried. The yield of product was 5.2 mg, and its estimated purity by LCMS analysis was 98%.

Analysis LCMS condition D: Retention time=1.86 min; ESI-MS(+) m/z 965.4 (M+2H).

Analysis LCMS condition E: Retention time=1.70 min; ESI-MS(+) m/z 965.3 (M+2H).

Preparation of Example 3197

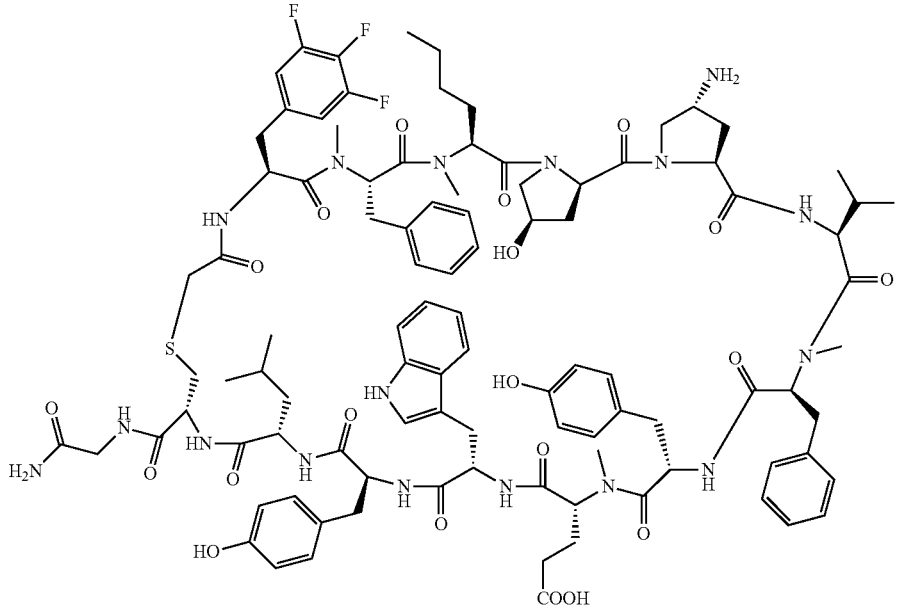

Example 3197

Example 3197 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 25 min., then a 0-minute hold at 100% B; Flow: 20 mL/min. Fractions containing the desired product were combined and dried. The yield of product was 4.7 mg, and its estimated purity by LCMS analysis was 95%.

Analysis LCMS condition D: Retention time=1.71 min; ESI-MS(+) m/z 981.3 (M+2H).

Analysis LCMS condition E: Retention time=1.65 min; ESI-MS(+) m/z 981.4 (M+2H).

Preparation of Example 3198

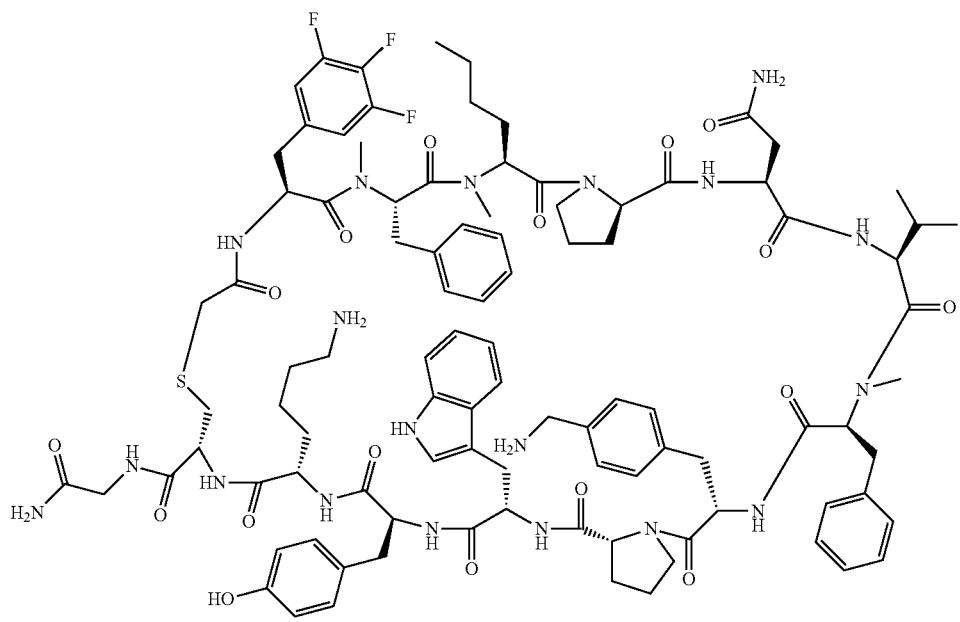

Example 3198

Example 3198 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 min., then a 0-minute hold at 100% B; Flow: 20 mL/min. Fractions containing the desired product were combined and dried. The yield of product was 3.4 mg, and its estimated purity by LCMS analysis was 99%.

Analysis LCMS condition D: Retention time=1.81 min; ESI-MS(+) m/z 965.6 (M+2H).

Analysis LCMS condition E: Retention time=1.82 min; ESI-MS(+) m/z 965.5 (M+2H).

Preparation of Example 3199

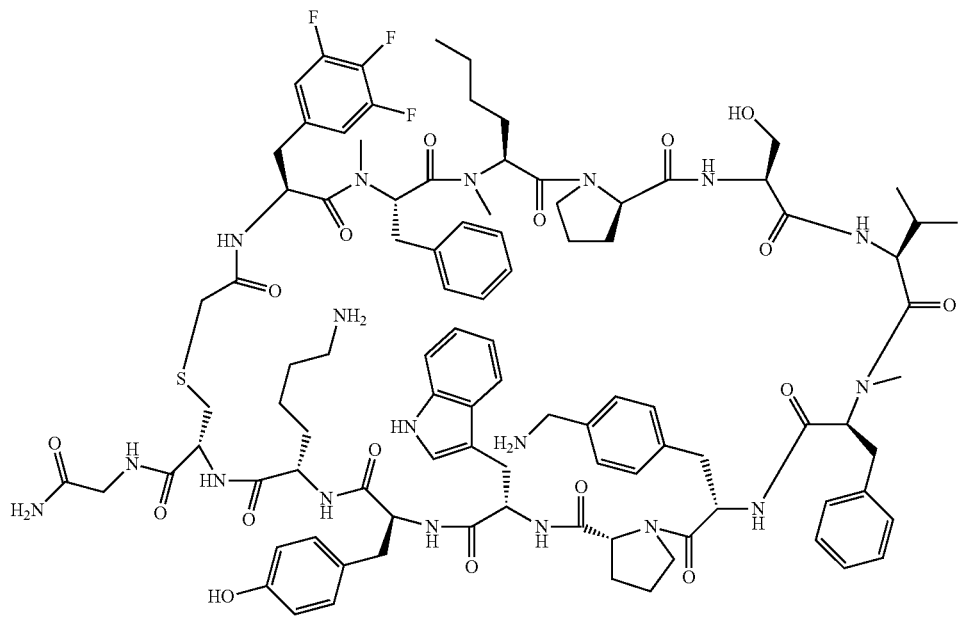

Example 3199

Example 3199 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-75% B over 25 min., then a 0-minute hold at 100% B; Flow: 20 mL/min. Fractions containing the desired product were combined and dried. The yield of product was 3.3 mg, and its estimated purity by LCMS analysis was 92%.

Analysis LCMS condition D: Retention time=1.82 min; ESI-MS(+) m/z 951.8 (M+2H).

Analysis LCMS condition E: Retention time=1.79 min; ESI-MS(+) m/z 951.7 (M+2H).

Preparation of Example 3200

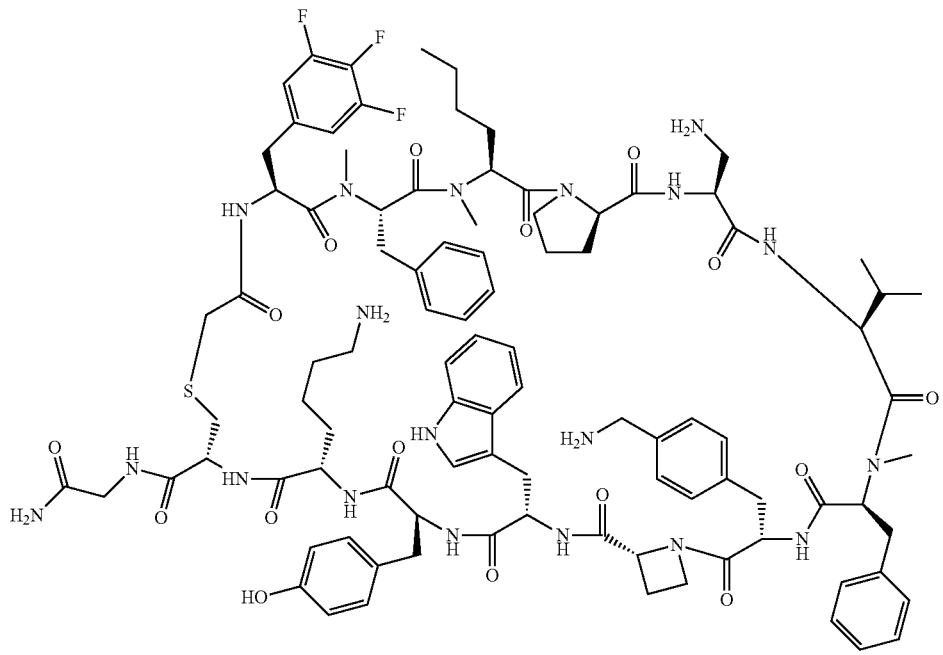

Example 3200

Example 3200 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 0-minute hold at 100% B; Flow: 20 mL/min. Fractions containing the desired product were combined and dried. The yield of product was 5.1 mg, and its estimated purity by LCMS analysis was 94%.

Analysis LCMS condition D: Retention time=1.82 min; ESI-MS(+) m/z 944.7 (M+2H).

Analysis LCMS condition E: Retention time=1.57 min; ESI-MS(+) m/z 944.6 (M+2H).

Preparation of Example 3201

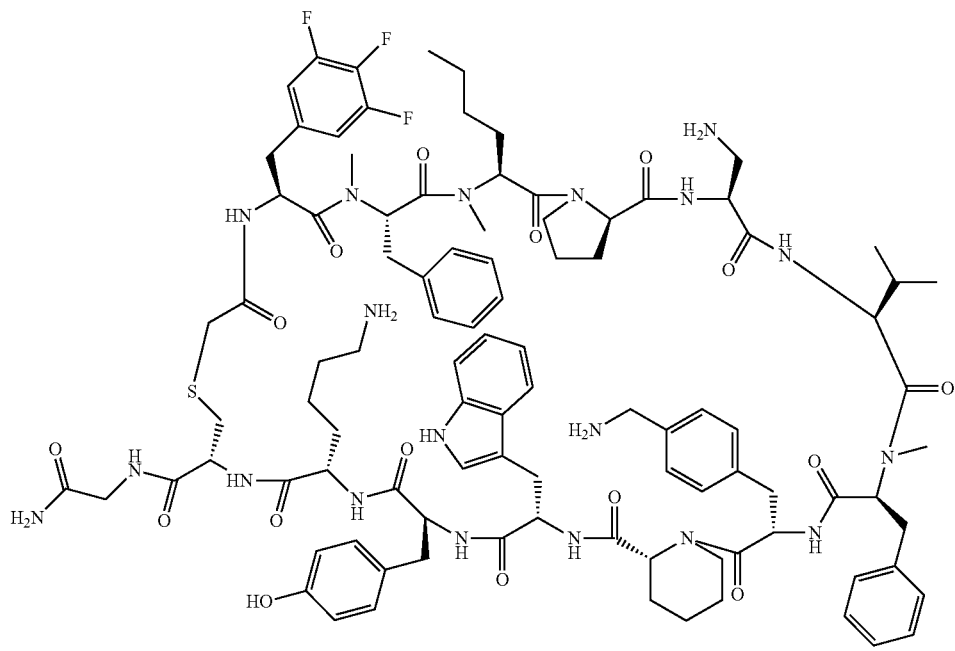

Example 3201

Example 3201 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 25 min., then a 0-minute hold at 100% B; Flow: 20 mL/min. Fractions containing the desired product were combined and dried. The yield of product was 7.1 mg, and its estimated purity by LCMS analysis was 100%.

Analysis LCMS condition D: Retention time=1.90 min; ESI-MS(+) m/z 958.6 (M+2H).

Analysis LCMS condition E: Retention time=1.63 min; ESI-MS(+) m/z 958.5 (M+2H).

Preparation of Example 3202

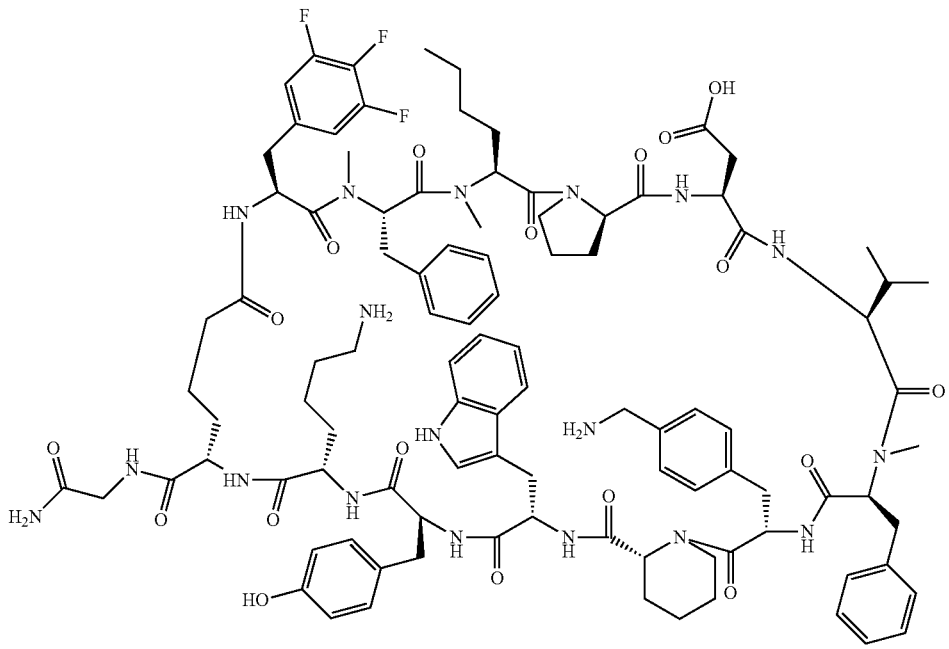

Example 3202

Example 3202 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 3.1 mg, and its estimated purity by LCMS analysis was 97%.

Analysis LCMS condition D: Retention time=1.75 min; ESI-MS(+) m/z 966.8 (M+2H).
Analysis LCMS condition E: Retention time=1.82 min; ESI-MS(+) m/z 966.1 (M+2H).

Preparation of Example 3203

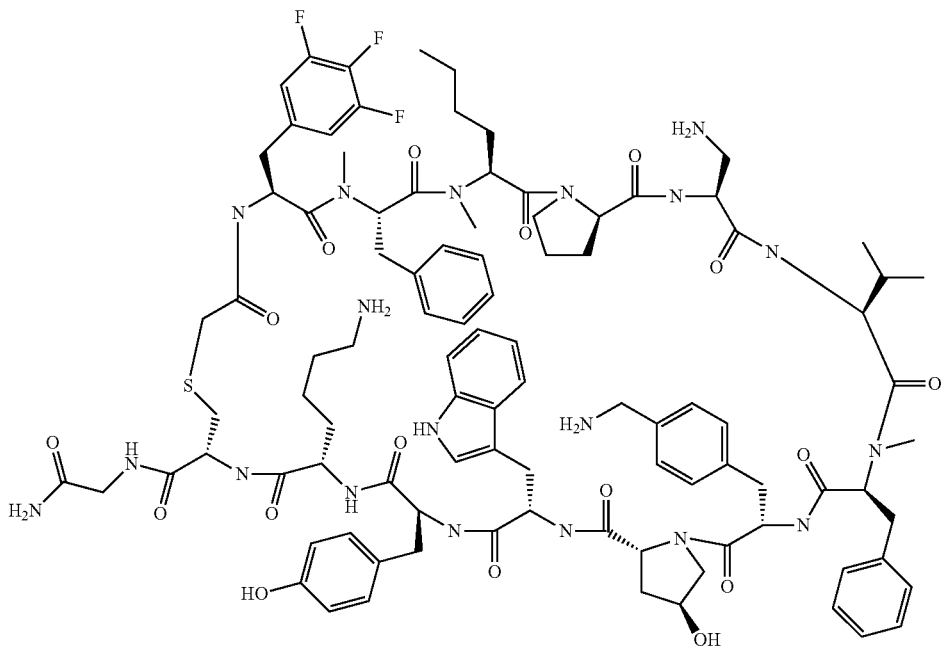

Example 3203

Example 3203 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-65% B over 25 min., then a 5-minute hold at 100% B; Flow: 20 mL/min. Fractions containing the desired product were combined and dried. The yield of product was 3.6 mg, and its estimated purity by LCMS analysis was 99%.

Analysis LCMS condition D: Retention time=1.64 min; ESI-MS(+) m/z 959.3 (M+2H).

Analysis LCMS condition E: Retention time=1.50 min; ESI-MS(+) m/z 959.3 (M+2H).

Preparation of Example 3204

Example 3204

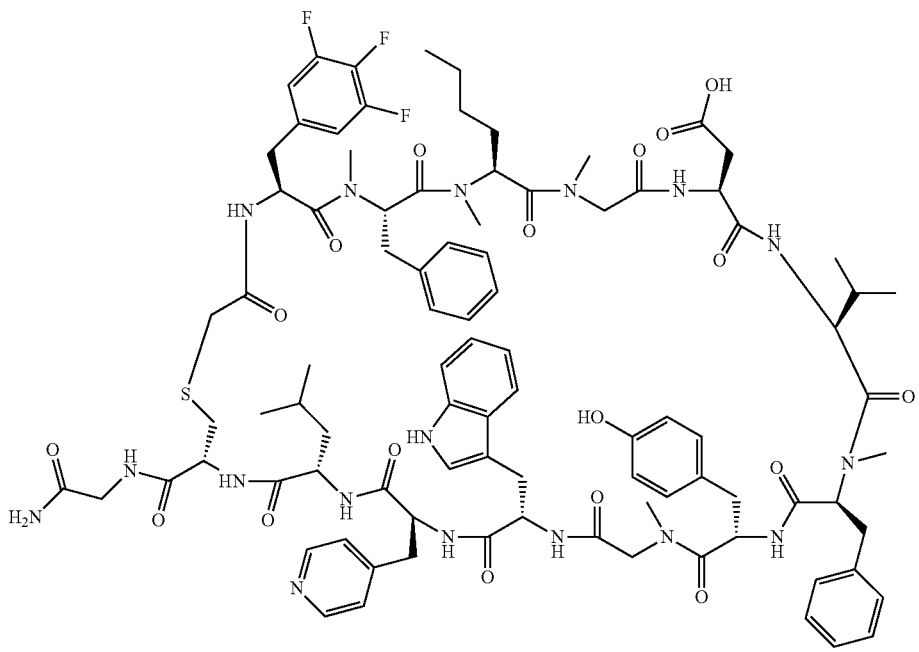

Example 3204 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 5.1 mg, and its estimated purity by LCMS analysis was 95%.

Analysis LCMS condition D: Retention time=1.64 min; ESI-MS(+) m/z 918.4 (M+2H).

Analysis LCMS condition E: Retention time=1.76 min; ESI-MS(+) m/z 918.1 (M+2H).

Preparation of Example 3205

Example 3205

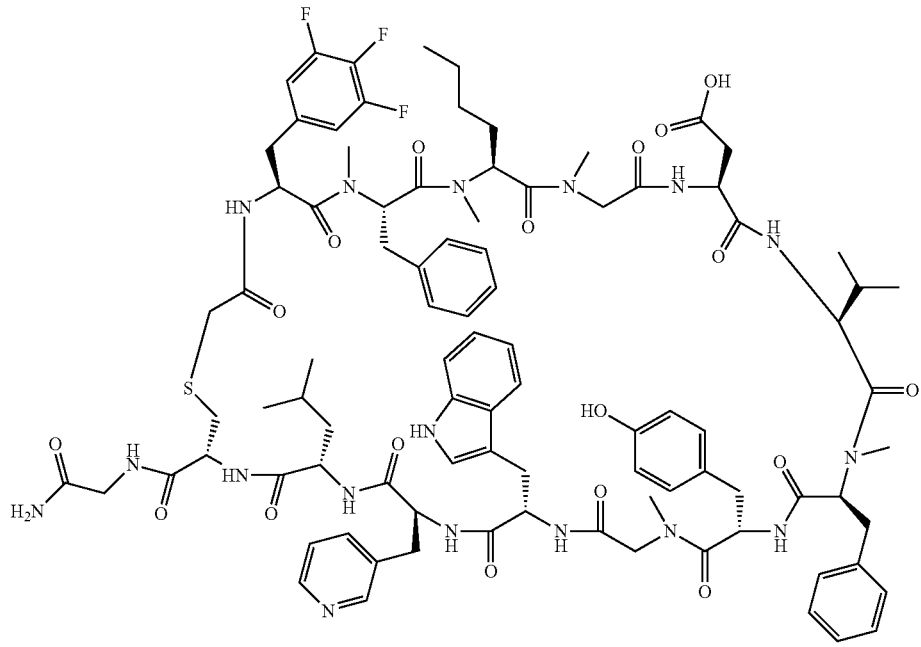

Example 3205 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The material was further purified via preparative LC/MS with the following conditions: Column: XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-70% B over 25 min., then a 5-minute hold at 100% B; Flow: 20 mL/min. Fractions containing the desired product were combined and dried. The yield of product was 0.7 mg, and its estimated purity by LCMS analysis was 99%.

Analysis LCMS condition D: Retention time=1.66 min; ESI-MS(+) m/z 918.4 (M+2H).
Analysis LCMS condition E: Retention time=1.77 min; ESI-MS(+) m/z 918.5 (M+2H).
ESI-HRMS(+) m/z:
Calculated: 917.9173 (M+2H).
Found: 917.9147 (M+2H).

Preparation of Example 3206

Example 3206 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". The eighth coupling of Fmoc-N-Me-Phe(3-F)—OH was performed using "N-Methylation on-resin Method A" procedure.

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-70% B over 25 min., then a 5-minute hold at 100% B; Flow: 20 mL/min. Fractions containing the desired product were combined and dried. The yield of product was 11.6 mg, and its estimated purity by LCMS analysis was 96%.

Analysis LCMS condition D: Retention time=1.66 min; ESI-MS(+) m/z 907.6 (M+2H).

Analysis LCMS condition E: Retention time=1.81 min; ESI-MS(+) m/z 908.0 (M+2H).

ESI-HRMS(+) m/z:
Calculated: 907.4266 (M+2H).
Found: 907.4237 (M+2H).

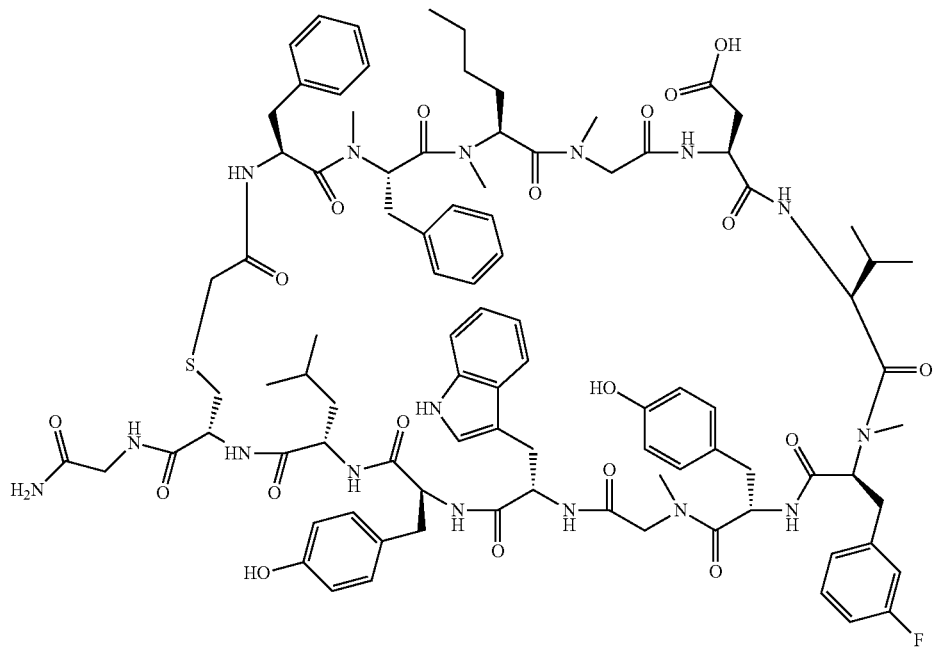

Example 3206

Preparation of Example 3207

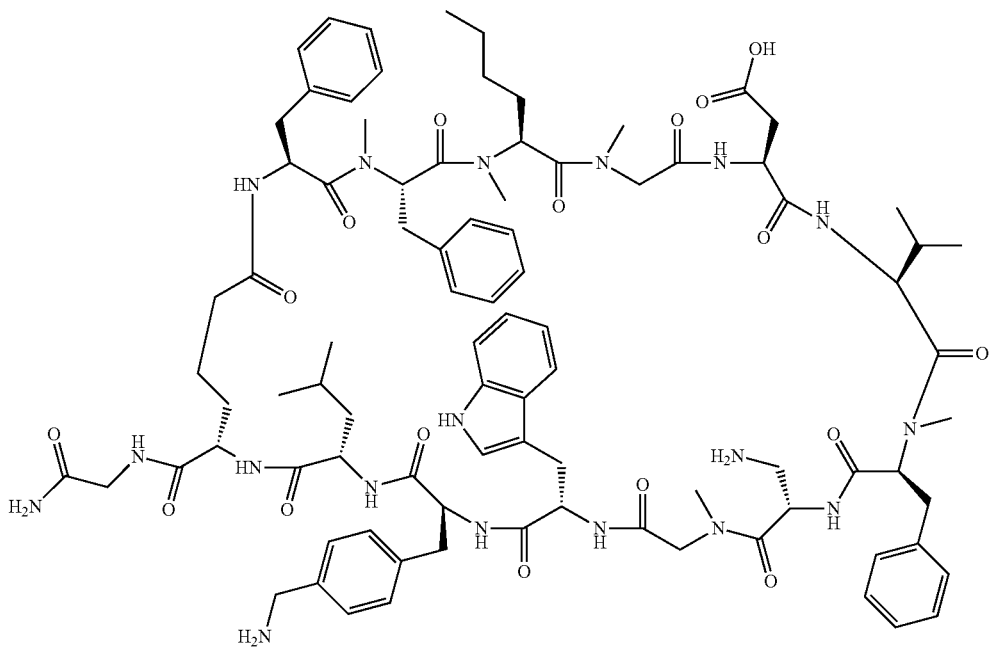

Example 3207

Example 3207 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-65% B over 25 min., then a 5-minute hold at 100% B; Flow: 20 mL/min. Fractions containing the desired product were combined and dried. The yield of product was 16.3 mg, and its estimated purity by LCMS analysis was 95%.

Analysis LCMS condition D: Retention time=1.70 min; ESI-MS(+) m/z 867.1 (M+2H).

Analysis LCMS condition E: Retention time=1.68 min; ESI-MS(+) m/z 867.2 (M+2H).

ESI-HRMS(+) m/z:

Calculated: 866.4394 (M+2H).

Found: 866.4367 (M+2H).

Preparation of Example 3208

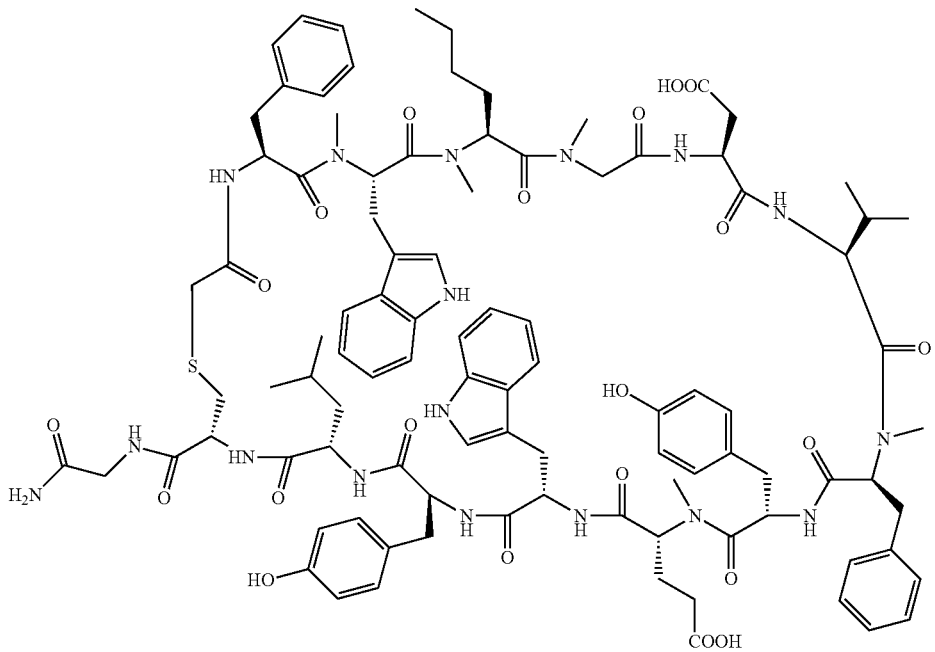

Example 3208

Example 3208 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 40-95% B over 50 min., then a 5-minute hold at 95% B; Flow: 15 mL/min. Fractions containing the desired product were combined and dried. Two isomers (isomer 3208-A and isomer 3208-B) were obtained. The yield of products isomer 3208-A and isomer 3208-B was 1.68 mg and 1.47 mg respectively, and their estimated purities were 97% and 99%, respectively, by HPLC "Analysis Condition B" using a gradient of 35% to 85% buffer B over 25 min.

Analysis LCMS condition A: Retention time=1.43 min; ESI-MS(+) m/z 954.7 (M+2H) for isomer 3208-A and 1.50 min; ESI-MS(+) m/z 954.3 (M+2H) for isomer 3208-B.

ESI-HRMS(+) m/z for isomer 3208-A:

Calculated: 953.9473 (M+2H).

Found: 953.9456 (M+2H).

Preparation of Example 3209

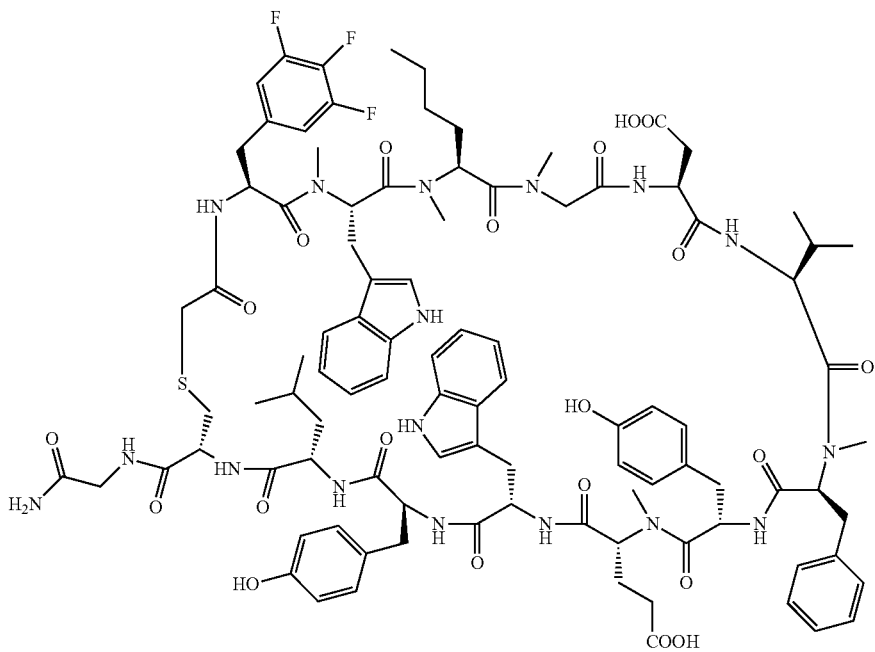

Example 3209

Example 3209 was prepared following the general synthetic sequence described for the preparation of Example 3078, composed of the following general procedures: "CEM Method A: Resin-swelling procedure", "CEM Method A: Standard-coupling procedure", "Custom amino acids-coupling procedure", "CEM Method A: Chloroacetyl chloride coupling procedure A", "Global Deprotection Method B", and "Cyclization Method C".

The crude material was purified via preparative LC/MS with the following conditions: Column: PHENOMENEX® Luna 20×250 5 u particles; Mobile Phase A: water with 0.05% TFA; Mobile Phase B: Acetonitrile with 0.05% TFA; Gradient: 40-95% B over 50 min., then a 5-minute hold at 95% B; Flow: 15 mL/min. Fractions containing the desired product were combined and dried. Two isomers (isomer 3209-A and isomer 3209-B) were obtained. The yield of products isomer 3209-A and isomer 3209-B was 2.35 mg and 3.2 mg respectively, and their estimated purities were 96% and 99%, respectively, by HPLC "Analysis Condition B" using a gradient of 35% to 85% buffer B over 25 min.

Analysis LCMS condition A: Retention time=1.48 min; ESI-MS(+) m/z 981.7 (M+2H) for isomer 3209-A and 1.54 min; ESI-MS(+) m/z 981.4 (M+2H) for isomer 3209-B.

ESI-HRMS(+) m/z for isomer 3209-A:

Calculated: 980.9332 (M+2H).

Found: 980.9318 (M+2H).

Preparation of Example 3500

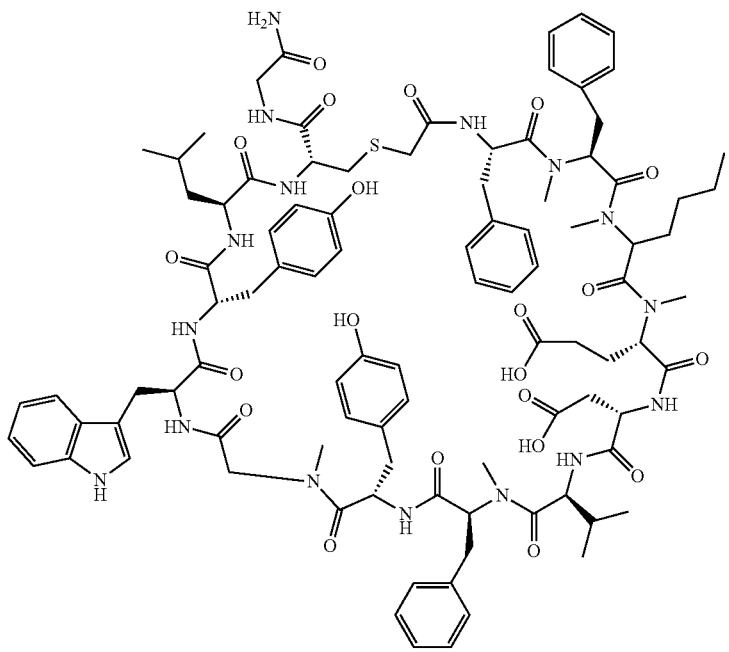

Example 3500

Example 3500 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 23.2 mg, and its estimated purity by HPLC analysis was 100% using the general "analysis conditions B" 35-95% over 30 min.

Analysis LCMS condition C: Retention time=1.64 min; ESI-MS(+) m/z 1855.5 (M+H).

Preparation of Example 3501

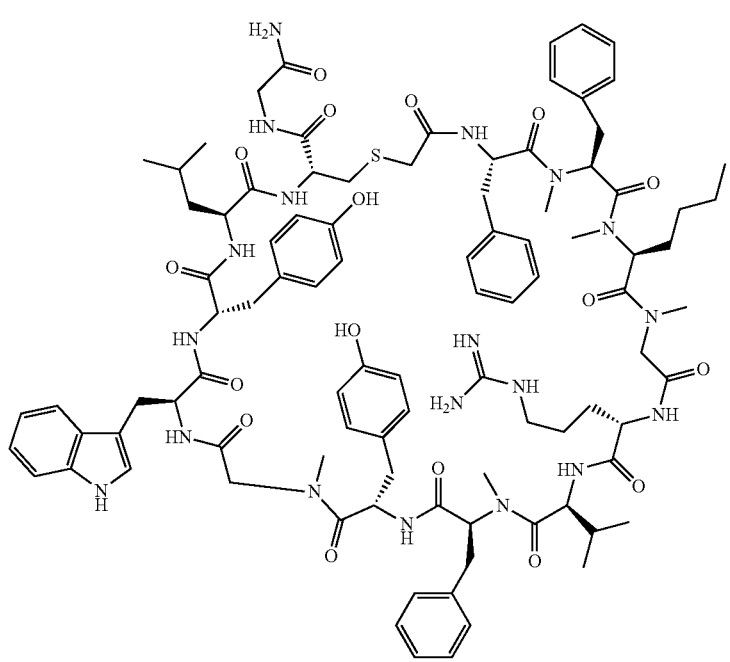

Example 3501

Example 3501 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 22.3 mg, and its estimated purity by HPLC analysis was 97.6% using the general "analysis conditions B" 35-95% over 30 min.

Analysis LCMS condition C: Retention time=1.35 min; ESI-MS(+) m/z 1838.7 (M+H).

Preparation of Example 3502

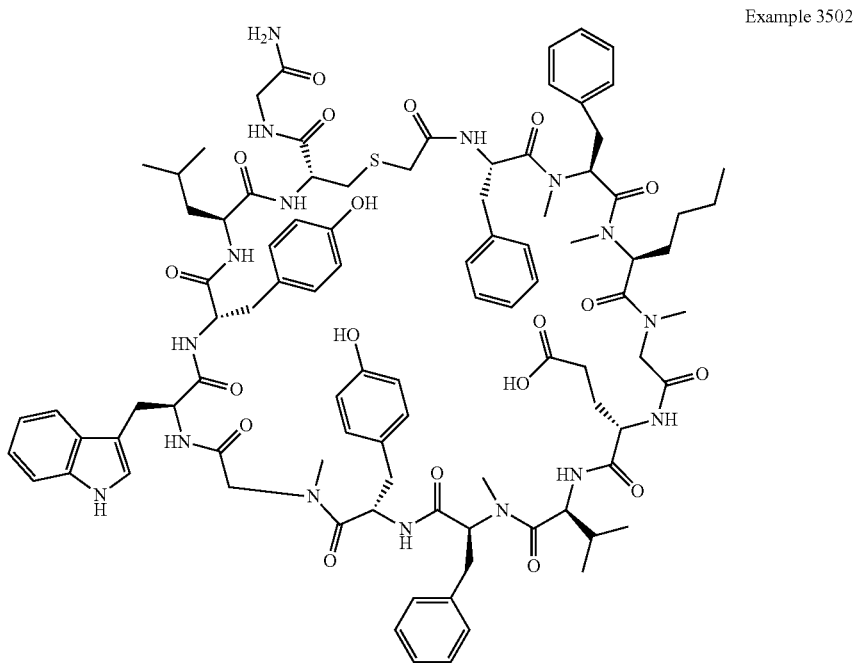 [SMILES: CCCC[C@H]1C(=O)N(C)CC(=O)N[C@@H](CCC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3502

Example 3502 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 33.4 mg, and its estimated purity by HPLC analysis was 96.6% using the general "analysis conditions B" 35-95% over 30 min.

Analysis LCMS condition C: Retention time=1.67 min; ESI-MS(+) m/z 1811.7 (M+H).

Preparation of Example 3503

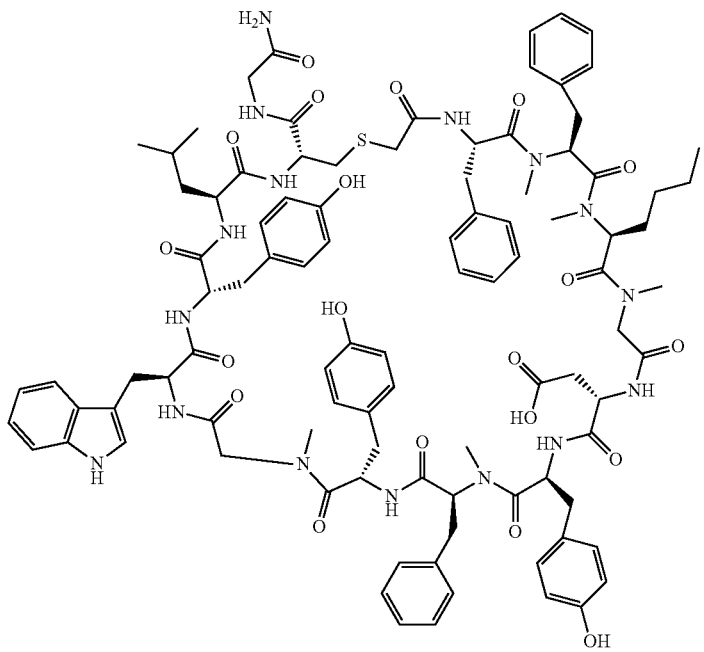

Example 3503

Example 3503 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 19.4 mg, and its estimated purity by HPLC analysis was 96.6% using the general "analysis conditions B" 35-95% over 30 min.

Analysis LCMS condition C: Retention time=1.62 min; ESI-MS(+) m/z 1861.9 (M+H).

Preparation of Example 3504

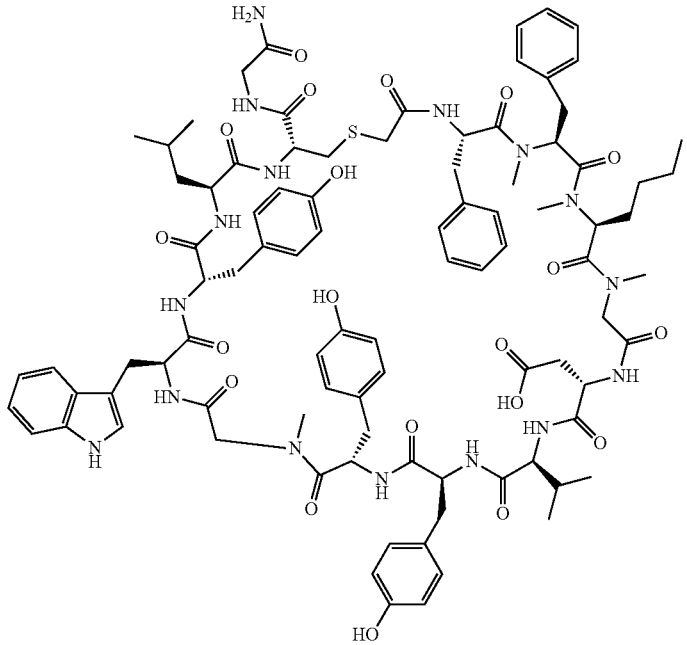

Example 3504

Example 3504 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 13.6 mg, and its estimated purity by HPLC analysis was 98.9% using the following conditions: Column: Phenom Jupiter 5 u C18 300 A 150×4.6 mm (575289-17); Mobile Phase A: 0.1% TFA in water; Mobile Phase B: 0.1% TFA in Acetonitrile; Gradient: 30-95% B over 30 min.; Flow: 1 mL/min. Detection UV: 217 nM.

Analysis LCMS condition C: Retention time=1.53 min; ESI-MS(+) m/z 1798.6 (M+H).

Preparation of Example 3505

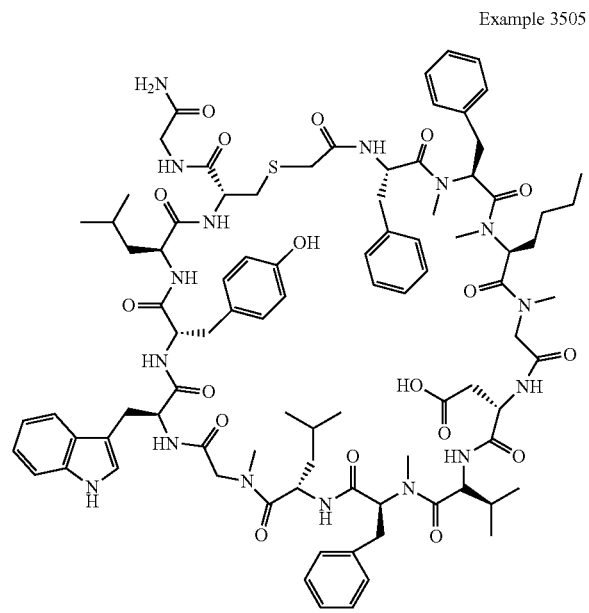

Example 3505

Example 3505 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-55% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 18.4 mg, and its estimated purity by HPLC analysis was 97.2% using the general "analysis conditions B" 35-95% over 30 min.

Analysis LCMS condition C: Retention time=1.77 min; ESI-MS(+) m/z 1748.0 (M+H).

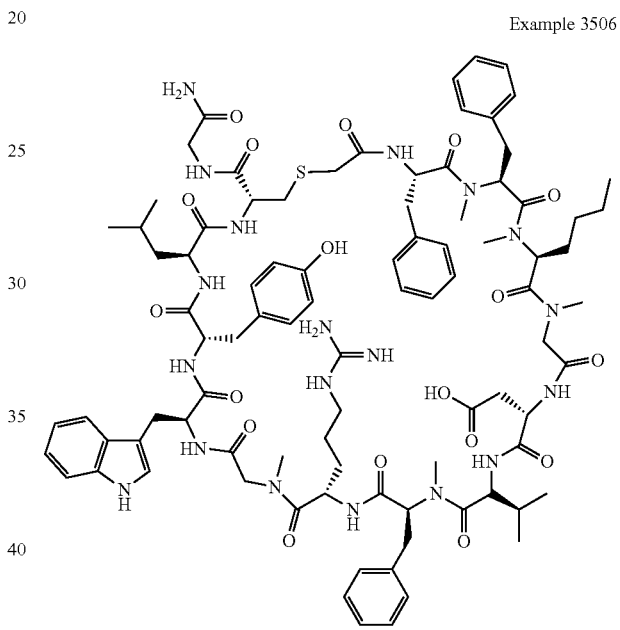

Example 3506

Example 3506 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 3.4 mg, and its estimated purity by HPLC analysis was 99.6% using the general "analysis conditions B" 35-95% over 30 min.

Analysis LCMS condition C: Retention time=1.38 min; ESI-MS(+) m/z 1790.9 (M+H).

Preparation of Example 3507

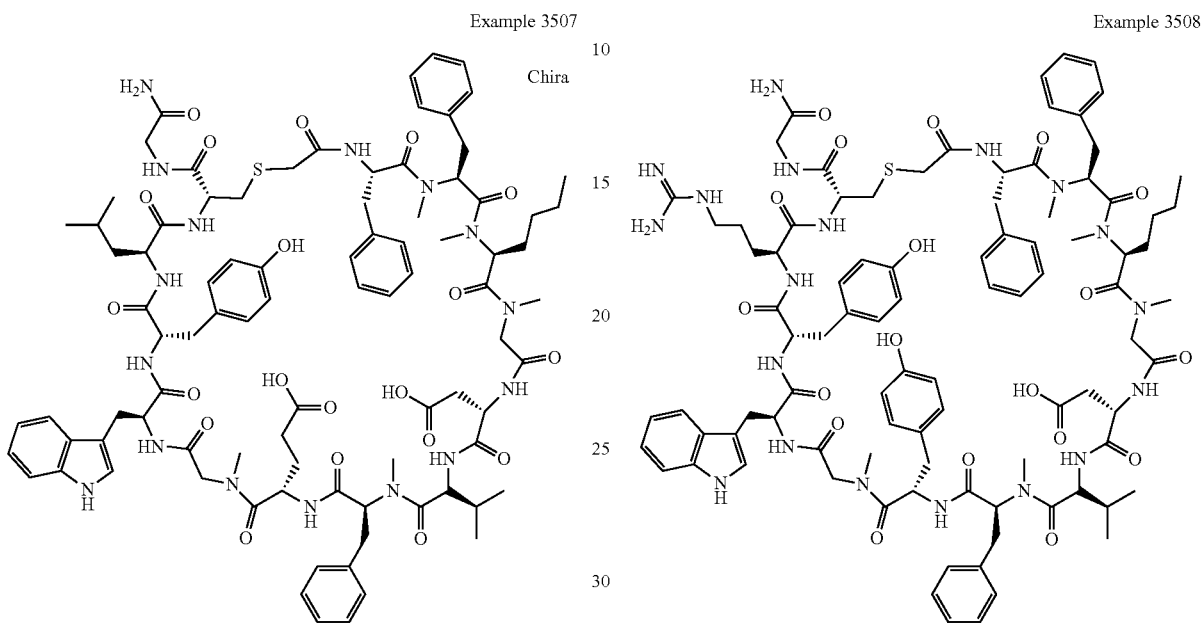

Example 3507

Example 3507 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 45 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 14.3 mg, and its estimated purity by HPLC analysis was 100% using the general "analysis conditions B" 35-95% over 30 min.

Analysis LCMS condition C: Retention time=1.38 min; ESI-MS(+) m/z 1764.0 (M+H).

Preparation of Example 3508

Example 3508

Example 3508 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 8.7 mg, and its estimated purity by HPLC analysis was 93% using the general "analysis conditions B" 35-95% over 30 min.

Analysis LCMS condition C: Retention time=1.36 min; ESI-MS(+) m/z 1841.1 (M+H).

Preparation of Example 3509

Preparation of Example 3510

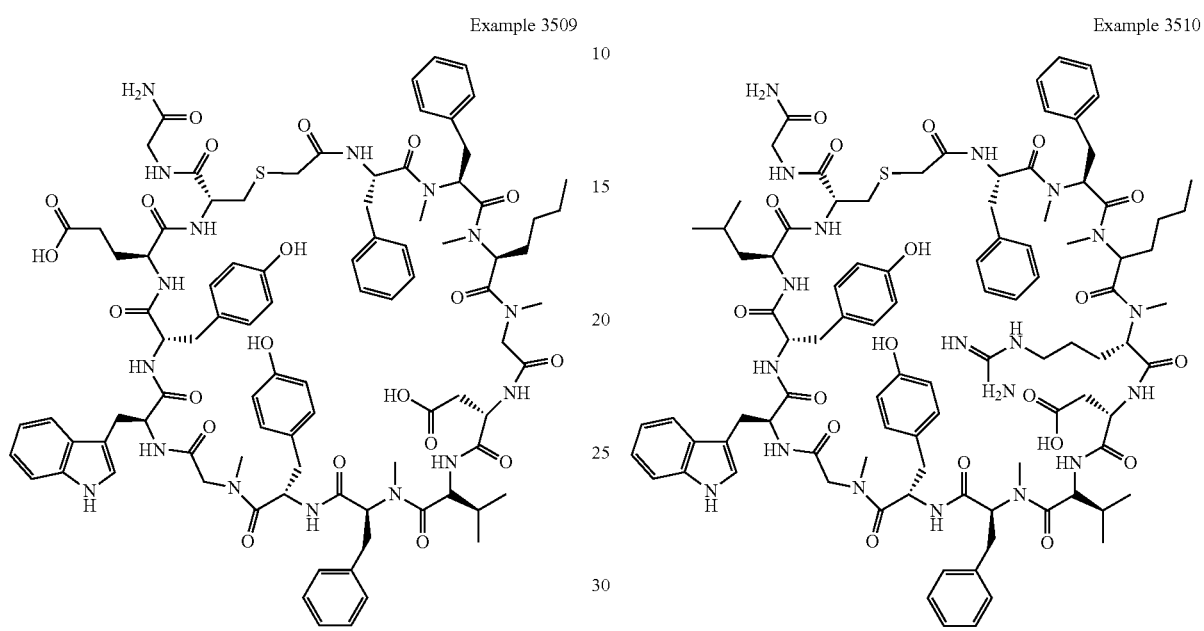

Example 3509

Example 3510

Example 3509 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 45 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 9.5 mg, and its estimated purity by HPLC analysis was 98.6% using the general "analysis conditions B" 35-95% over 30 min.

Analysis LCMS condition C: Retention time=1.61 min; ESI-MS(+) m/z 1813.8 (M+H).

Example 3510 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 7.1 mg, and its estimated purity by HPLC analysis was 99.6% using the general "analysis conditions B" 35-95% over 30 min.

Analysis condition A: Retention time=1.29 min; ESI-MS (+) m/z 941.9 (M+2H).

Preparation of Example 3511

Preparation of Example 3512

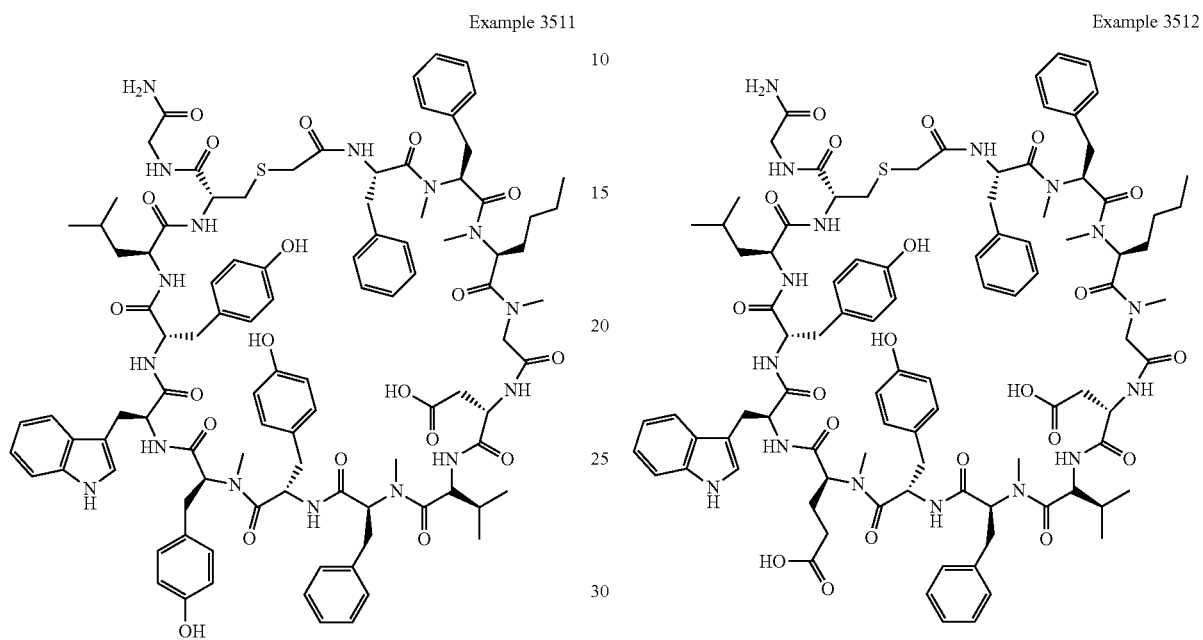

Example 3511

Example 3512

Example 3511 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 5.0 mg, and its estimated purity by HPLC analysis was 83% using the general "analysis conditions B" 35-95% over 30 min.

Analysis condition A: Retention time=1.38 min; ESI-MS (+) m/z 952.4 (M+2H).

Example 3512 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 45 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 29.7 mg, and its estimated purity by HPLC analysis was 99.2% using the general "analysis conditions B" 35-80% over 30 min.

Analysis LCMS condition C: Retention time=1.72 min; ESI-MS(+) m/z 1869.9 (M+H).

Analysis LCMS condition A: Retention time=1.45 min; ESI-MS(+) m/z 935.3 (M+2H).

Preparation of Example 3513

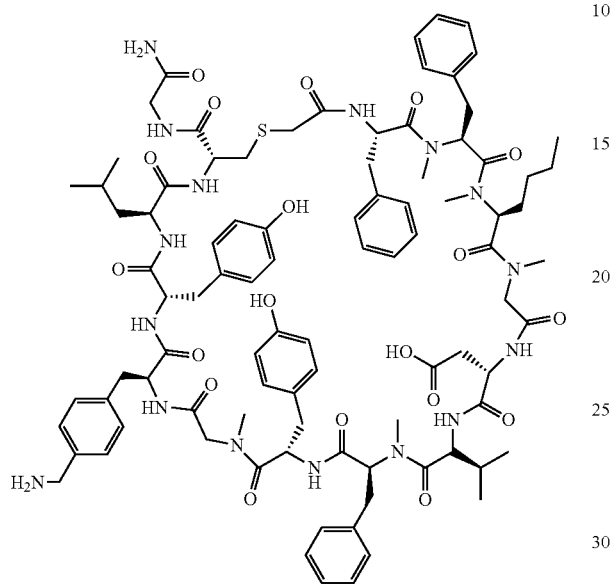

Example 3513

Preparation of Example 3514

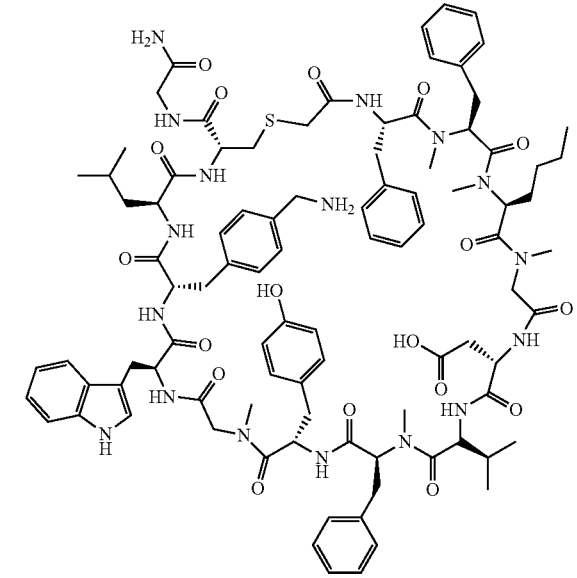

Example 3514

Example 3513 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 7.1 mg, and its estimated purity by HPLC analysis was 87% using the general "analysis conditions B" 35-80% over 30 min.

Analysis condition A: Retention time=1.27 min; ESI-MS (+) m/z 894.2 (M+2H).

Example 3514 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 5.0 mg, and its estimated purity by HPLC analysis was 90% using the general "analysis conditions B" 35-80% over 30 min.

Analysis condition A: Retention time=1.34 min; ESI-MS (+) m/z 905.8 (M+2H).

Example 3515

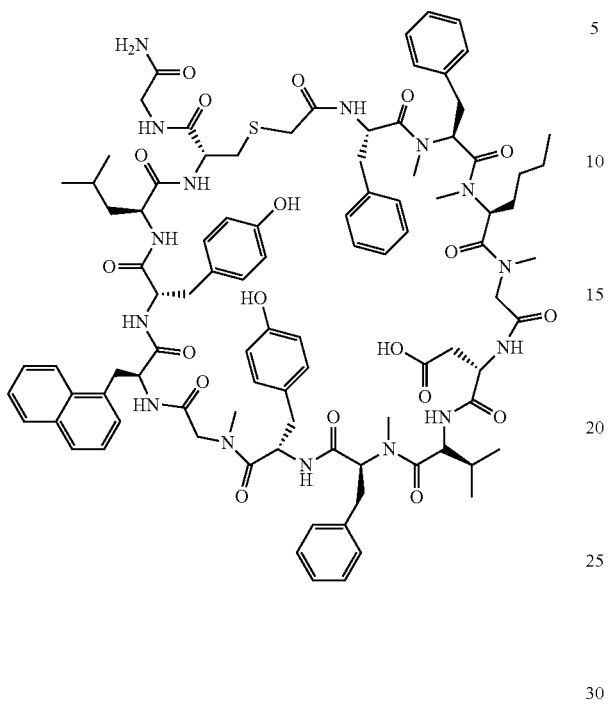

Preparation of Example 3516

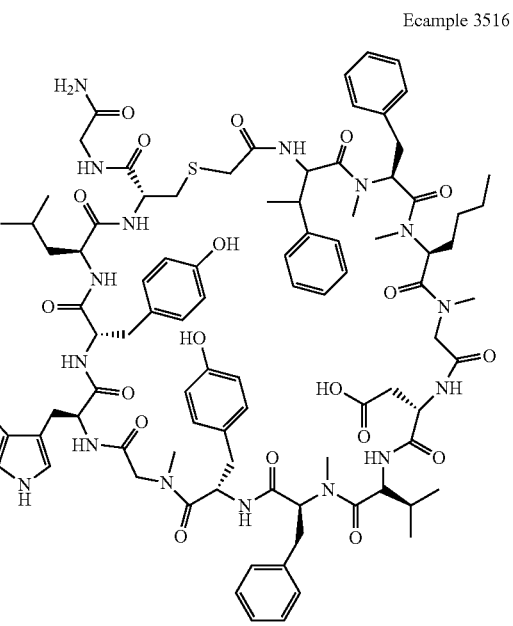

Example 3515 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 5.6 mg, and its estimated purity by HPLC analysis was 99% using the general "analysis conditions B" 35-95% over 30 min.

Analysis condition A: Retention time=1.54 min; ESI-MS (+) m/z 904.8 (M+2H).

Example 3516 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 1.8 mg, and its estimated purity by HPLC analysis was 89% using the following conditions: Column: Phenom Kinetex 2.6 u C18(2) 2.1×50 mm Ser.#515561-57; Mobile Phase A: 0.025% Ammonium Acetate in 5% methanol/water; Mobile Phase B: Acetonitrile/water (4:1); Gradient: 30-95% B over 20 min.; Flow: 1 mL/min. Detection UV: 217 nM, Oven: 60° C.

Analysis LCMS condition C: Retention time=1.87 min; ESI-MS(+) m/z 1812.1 (M+H).

Preparation of Example 3517

Example 3517

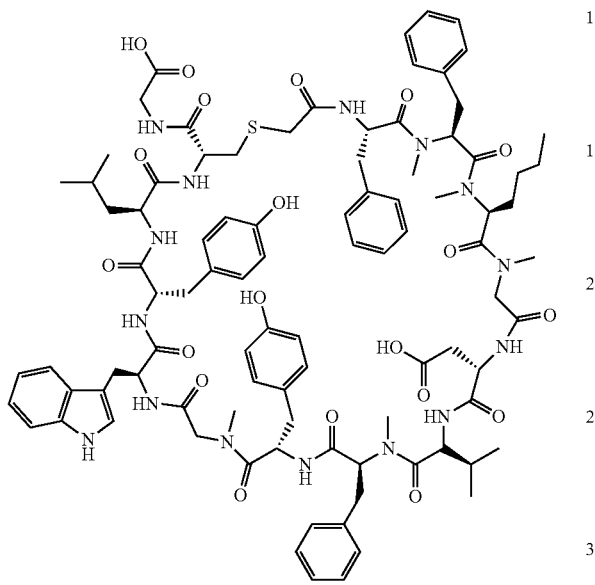

Example 3517 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C". Preloaded Fmoc-Gly-Trityl Resin was used instead of Seiber resin.

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 5.6 mg, and its estimated purity by HPLC analysis was 95% using the general "analysis conditions B" 30-80% over 30 min.

Analysis condition A: Retention time=1.49 min; ESI-MS (+) m/z 899.8 (M+2H).

Preparation of Example 3518

Example 3518

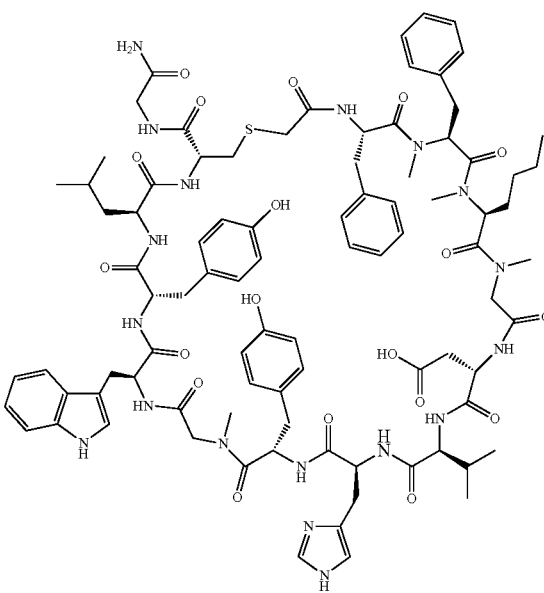

Example 3518 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 2.8 mg, and its estimated purity by HPLC analysis was 82% using the general "analysis conditions B" 35-95% over 30 min.

Analysis LCMS condition C: Retention time=1.53 min; ESI-MS(+) m/z 1772.7 (M+H).

Preparation of Example 3519

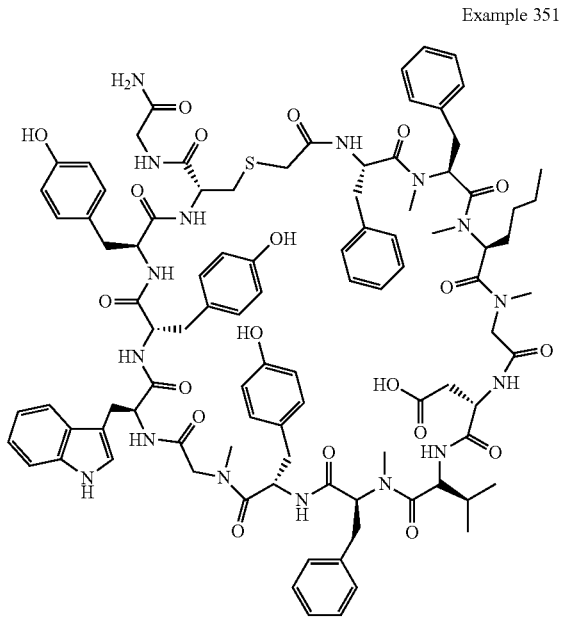

Example 3519

Example 3519 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 15.7 mg, and its estimated purity by HPLC analysis was 96% using the general "analysis conditions B" 35-95% over 30 min. Analysis LCMS condition C: Retention time=1.68 min; ESI-MS(+) m/z 1847.4 (M+H).

Preparation of Example 3520

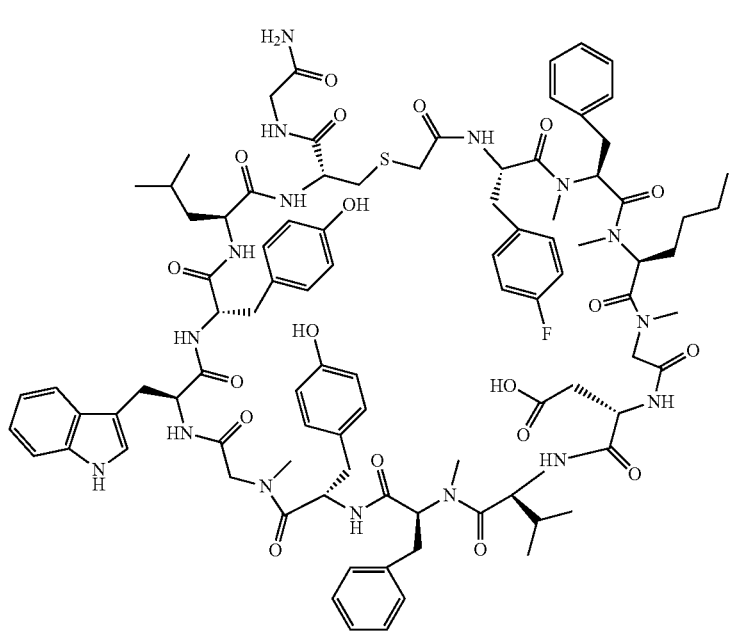

Example 3520

Example 3520 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 10.9 mg, and its estimated purity by LCMS analysis was 100%.

Analysis LCMS condition E: Retention time=1.89 min; ESI-MS(+) m/z 907.9 (M+2H).

Preparation of Example 3522

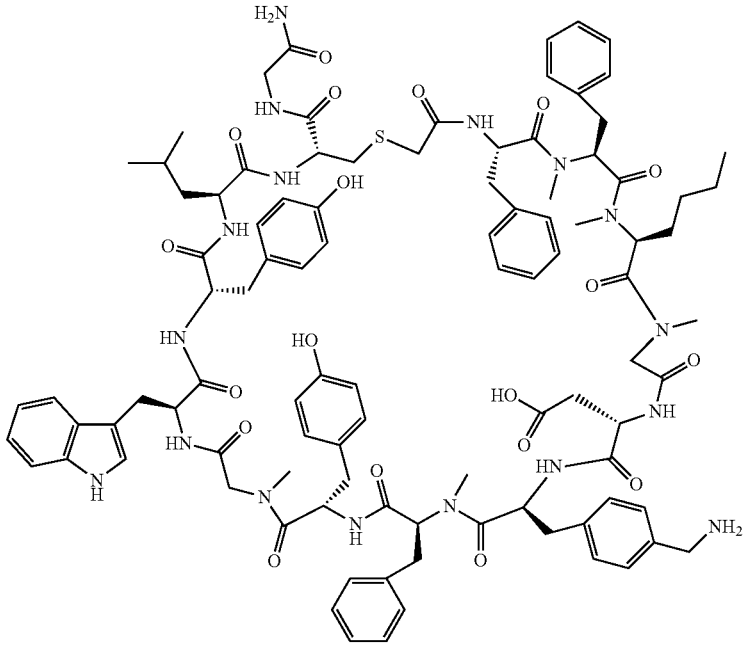

Example 3522

Example 3522 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 13.2 mg, and its estimated purity by LCMS analysis was 93.5%.

Analysis LCMS condition E: Retention time=1.61 min; ESI-MS(+) m/z 937.8 (M+2H).

Preparation of Example 3523

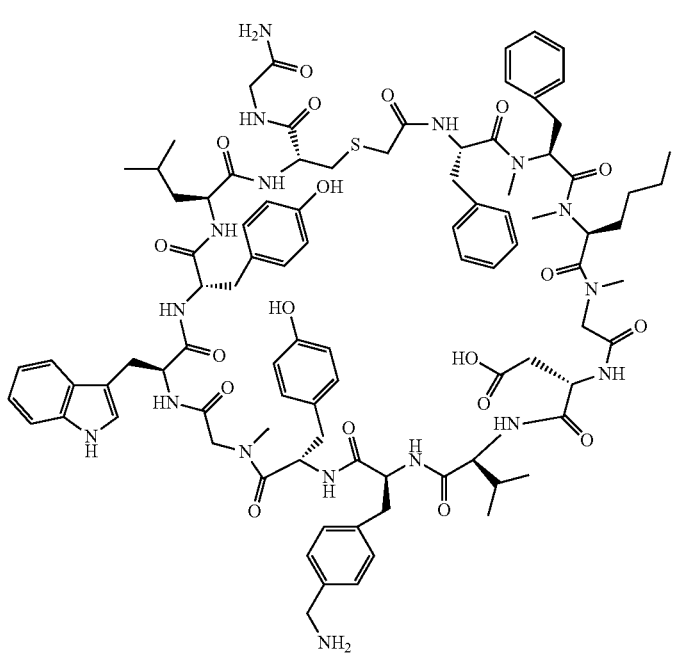

Example 3523

Example 3523 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 14.4 mg, and its estimated purity by LCMS analysis was 99.5%.

Analysis LCMS condition E: Retention time=1.58 min; ESI-MS(+) m/z 906.4 (M+2H).

Preparation of Example 3524

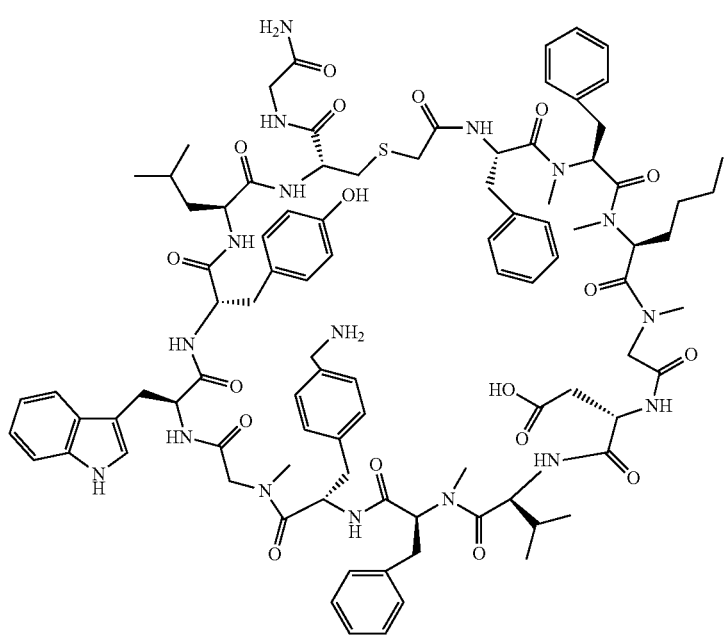

Example 3524

Example 3524 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 12.7 mg, and its estimated purity by LCMS analysis was 100.0%.

Analysis LCMS condition E: Retention time=1.81 min; ESI-MS(+) m/z 905.4 (M+2H).

Preparation of Example 3525

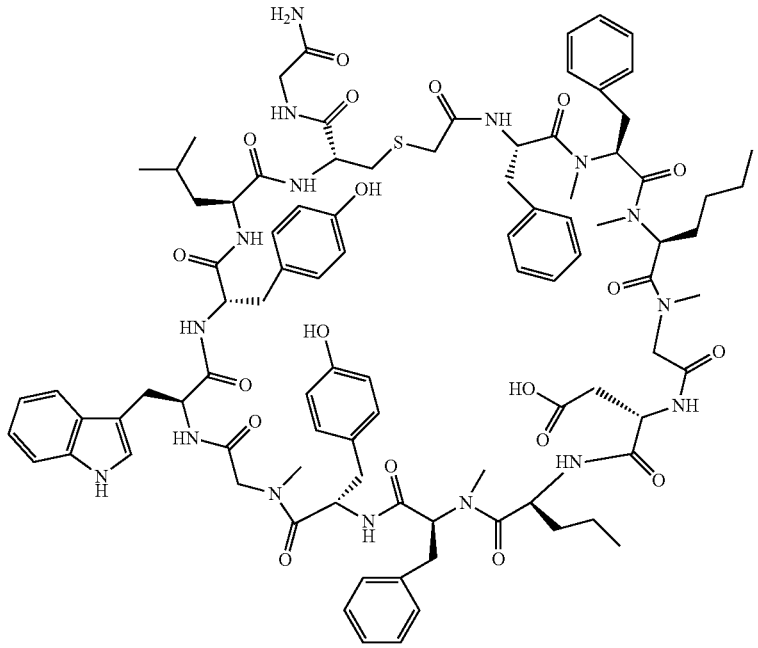

Example 3525

Example 3525 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 9.3 mg, and its estimated purity by LCMS analysis was 96.4%.

Analysis LCMS condition E: Retention time=1.92 min; ESI-MS(+) m/z 899.0 (M+2H).

Preparation of Example 3526

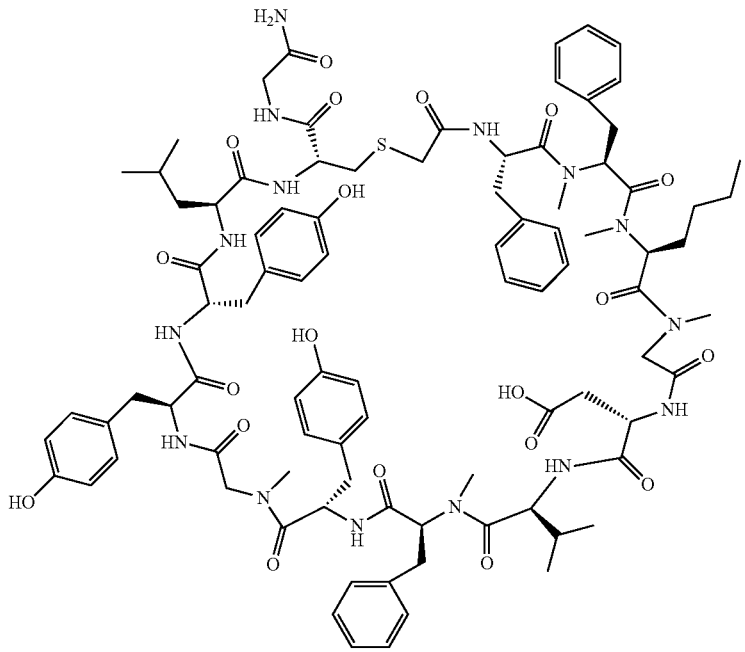

Example 3526

Example 3526 was prepared following the general synthetic sequence described below. To a 50 mL polypropylene tube was added Sieber resin (140 mg, 0.100 mmol), and the tube was placed on the CEM Liberty microwave peptide synthesizer. The following procedures were then performed sequentially:

"CEM Method A: Resin-swelling procedure" was followed;
"CEM Method A: Standard coupling procedure" was followed with Fmoc-Gly-OH;
"CEM Method A: Standard coupling procedure" was followed with Fmoc-Cys(Trt)-OH;
"CEM Method A: Standard coupling procedure" was followed with Fmoc-Leu-OH;
"CEM Method A: Standard coupling procedure" was followed with Fmoc-Tyr(tBu)-OH;
"CEM Method A: Standard coupling procedure" was followed with Fmoc-Tyr(tBu)-OH;
"CEM Method A: Standard coupling procedure" was followed with Fmoc-Sar-OH;
"CEM Method A: Standard coupling procedure" was followed with Fmoc-Tyr(tBu)-OH;
"CEM Method A: Standard coupling procedure" was followed with Fmoc-[N-Me]Phe-OH;
"CEM Method A: Custom amino acids-coupling procedure" was followed with Fmoc-Val-OH using 10 eq for 2 hours at 75° C.;
"CEM Method A: Standard coupling procedure" was followed with Fmoc-Asp(OtBu)-OH;
"CEM Method A: Standard coupling procedure" was followed with Fmoc-Sar-OH;
"CEM Method A: Custom amino acids-coupling procedure" was followed with Fmoc-[N-Me]Nle-OH using 5 eq for 10 min;
"CEM Method A: Custom amino acids-coupling procedure" was followed with Fmoc-[N-Me]Phe-OH using 5 eq for 10 min;
"CEM Method A: Standard coupling procedure" was followed with Fmoc-Phe-OH using 5 eq for 10 mins;

"Prelude Method A: Chloroacetyl chloride coupling procedure A" was followed, "Global Deprotection Method B" was followed and "Cyclization Method C" was followed.

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 12.9 mg, and its estimated purity by LCMS analysis was 97.8%.

Analysis LCMS condition E: Retention time=1.77 min; ESI-MS(+) m/z 887.5 (M+2H).

Preparation of Example 3527

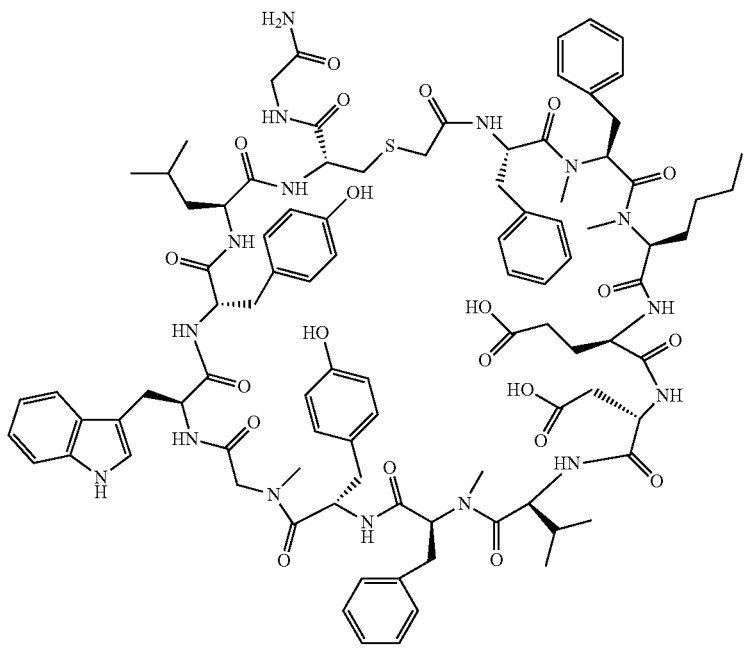

Example 3527

Example 3527 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 3.8 mg, and its estimated purity by LCMS analysis was 95.0%.

Analysis LCMS condition D: Retention time=1.50 min; ESI-MS(+) m/z 928.0 (M+2H).

Analysis LCMS condition E: Retention time=1.75 min; ESI-MS(+) m/z 928.2 (M+2H).

Preparation of Example 3528

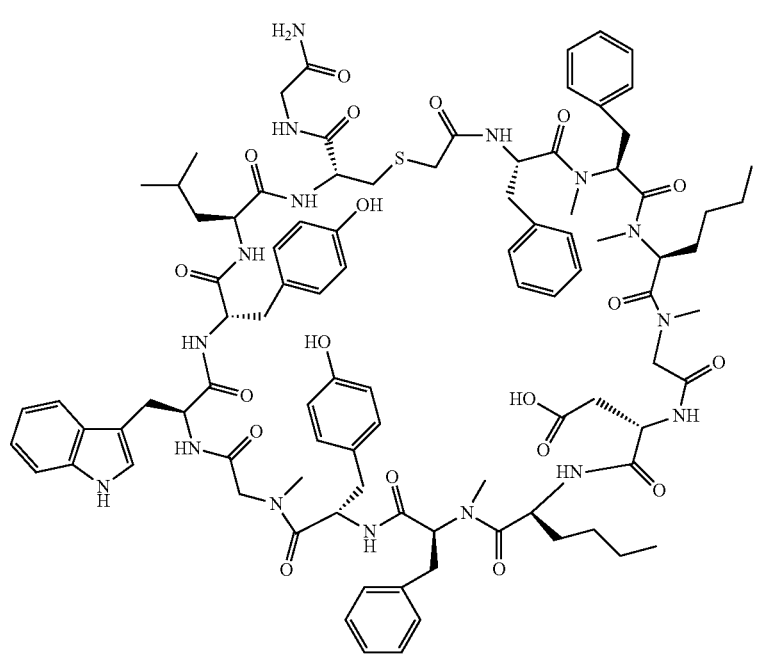

Example 3528

Example 3528 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.3 mg, and its estimated purity by LCMS analysis was 100.0%.

Analysis LCMS condition D: Retention time=1.74 min; ESI-MS(+) m/z 906.3 (M+2H).

Analysis LCMS condition E: Retention time=1.95 min; ESI-MS(+) m/z 906.0 (M+2H).

Preparation of Example 3529

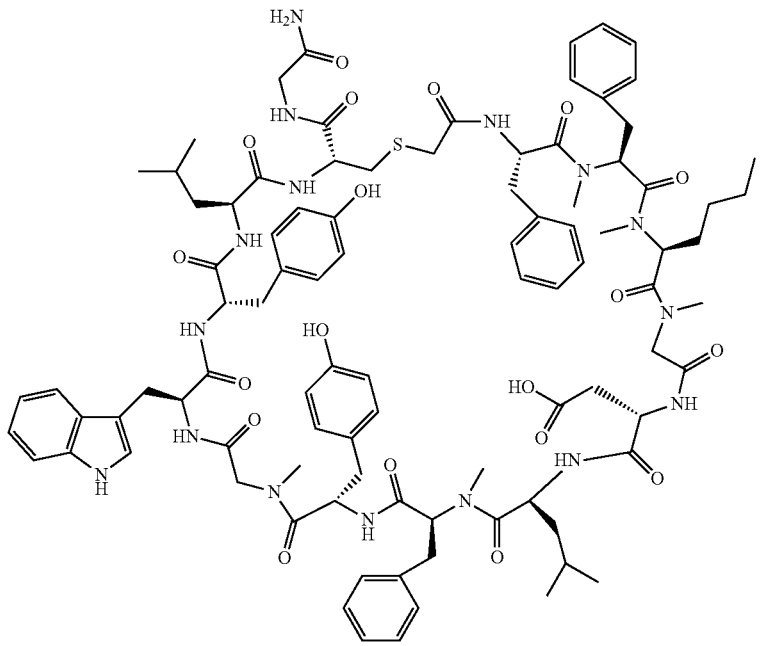

Example 3529

Example 3529 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 9.7 mg, and its estimated purity by LCMS analysis was 100.0%.

Analysis LCMS condition D: Retention time=1.75 min; ESI-MS(+) m/z 906.5 (M+2H).

Analysis LCMS condition E: Retention time=1.96 min; ESI-MS(+) m/z 906.0 (M+2H).

Preparation of Example 3531

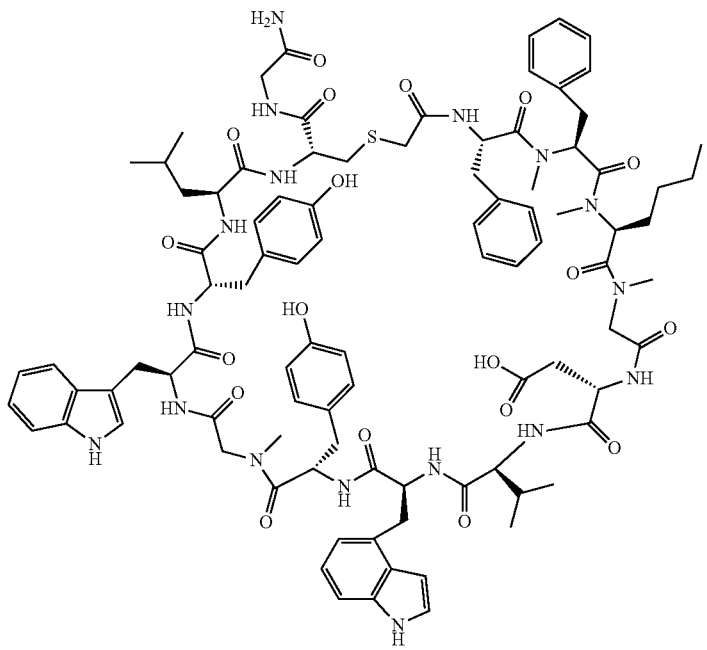

Example 3531

Example 3531 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.6 mg, and its estimated purity by LCMS analysis was 95.7%.

Analysis LCMS condition D: Retention time=1.50 min; ESI-MS(+) m/z 911.6 (M+2H).

Analysis LCMS condition E: Retention time=1.68 min; ESI-MS(+) m/z 911.4 (M+2H).

Preparation of Example 3532

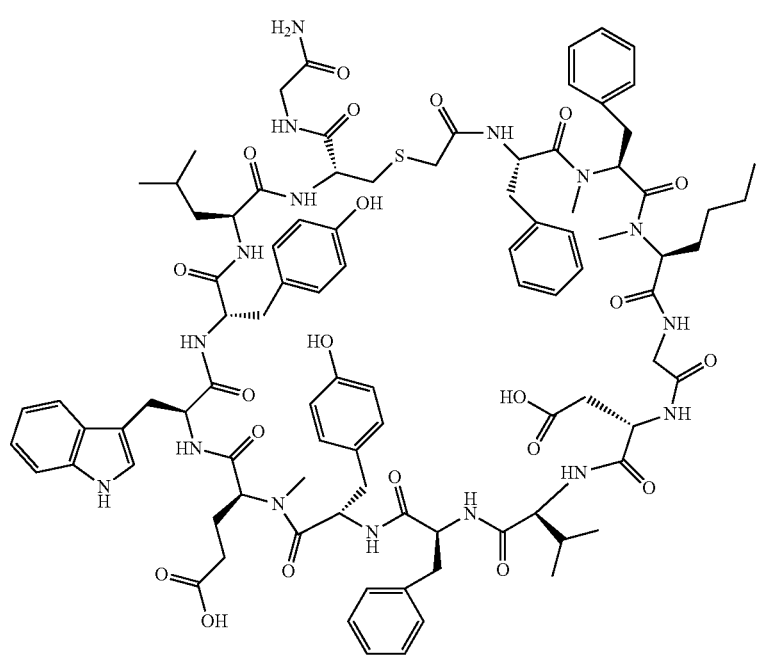

Example 3532

Example 3532 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 9.9 mg, and its estimated purity by LCMS analysis was 95.7%.

Analysis LCMS condition D: Retention time=1.47 min; ESI-MS(+) m/z 921.3 (M+2H).

Analysis LCMS condition E: Retention time=1.73 min; ESI-MS(+) m/z 920.9 (M+2H).

Preparation of Example 3533

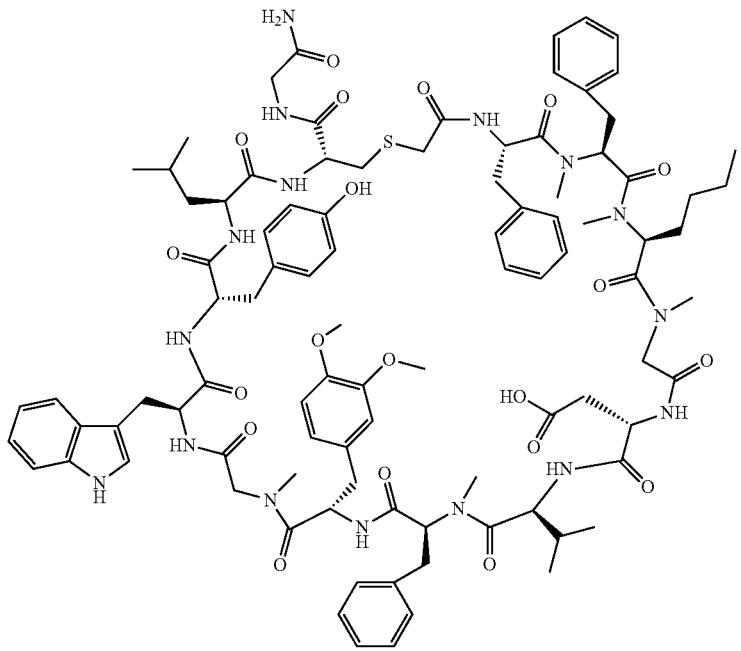

Example 3533

Example 3533 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 5.41 mg, and its estimated purity by LCMS analysis was 100.0%.

Analysis LCMS condition D: Retention time=1.65 min; ESI-MS(+) m/z 920.7 (M+2H).

Analysis LCMS condition E: Retention time=1.89 min; ESI-MS(+) m/z 920.7 (M+2H).

Preparation of Example 3534

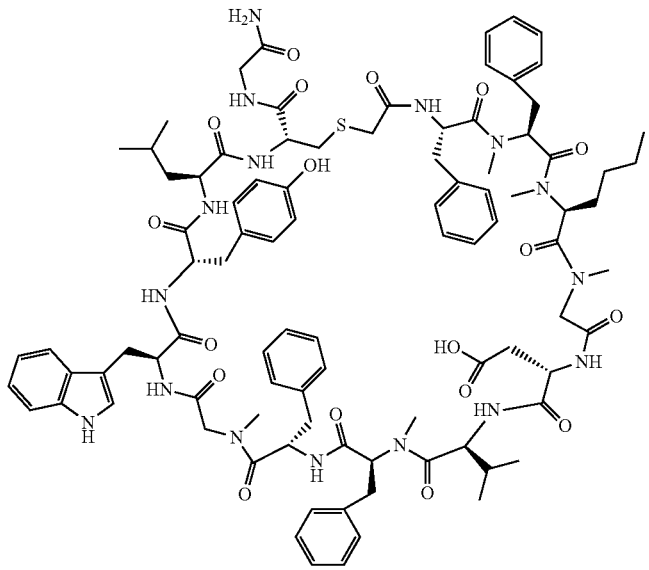

Example 3534

Example 3534 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 2.72 mg, and its estimated purity by LCMS analysis was 100.0%.

Analysis LCMS condition D: Retention time=1.70 min; ESI-MS(+) m/z 890.7 (M+2H).

Analysis LCMS condition E: Retention time=1.94 min; ESI-MS(+) m/z 890.5 (M+2H).

Preparation of Example 3535

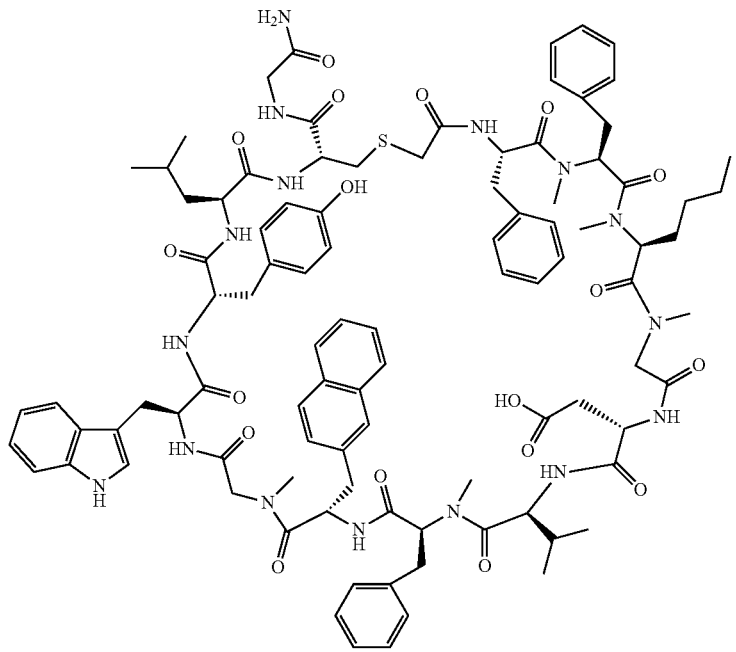

Example 3535

Example 3535 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 1.81 mg, and its estimated purity by LCMS analysis was 99.3%.

Analysis LCMS condition E: Retention time=2.03 min; ESI-MS(+) m/z 916.1 (M+2H).

Preparation of Example 3536

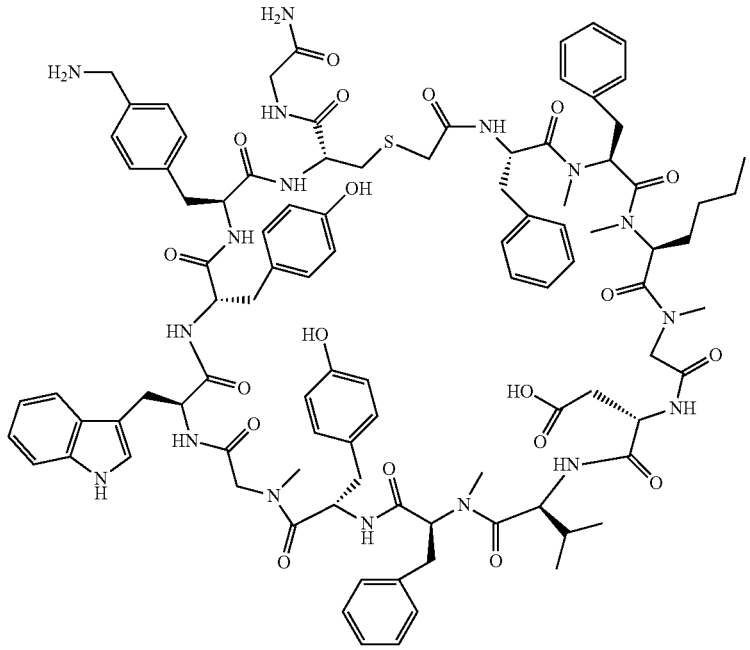

Example 3536

Example 3536 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.61 mg, and its estimated purity by LCMS analysis was 94.2%.

Analysis LCMS condition D: Retention time=1.57 min; ESI-MS(+) m/z 930.1 (M+2H).

Analysis LCMS condition E: Retention time=1.71 min; ESI-MS(+) m/z 930.2 (M+2H).

Preparation of Example 3537

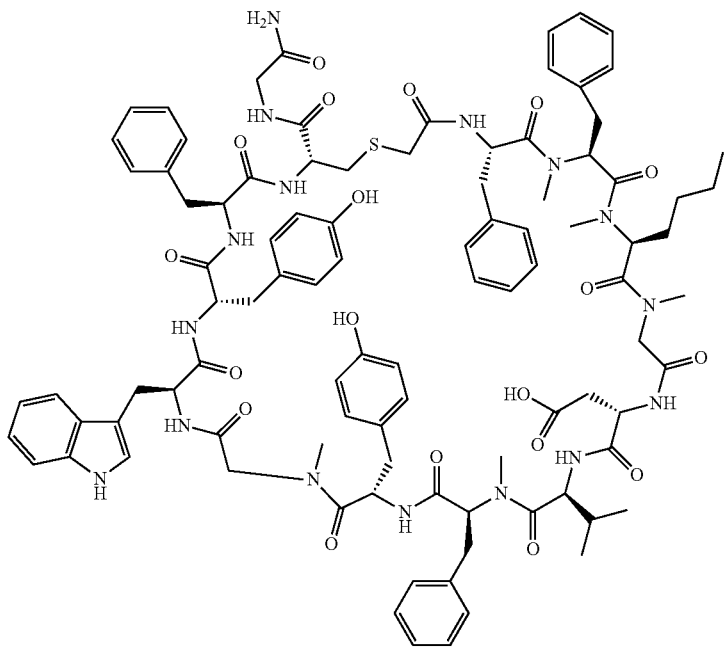

Example 3537

Example 3537 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.81 mg, and its estimated purity by LCMS analysis was 91.1%.

Analysis LCMS condition D: Retention time=1.64 min; ESI-MS(+) m/z 915.7 (M+2H).

Analysis LCMS condition E: Retention time=1.84 min; ESI-MS(+) m/z 915.8 (M+2H).

Preparation of Example 3538

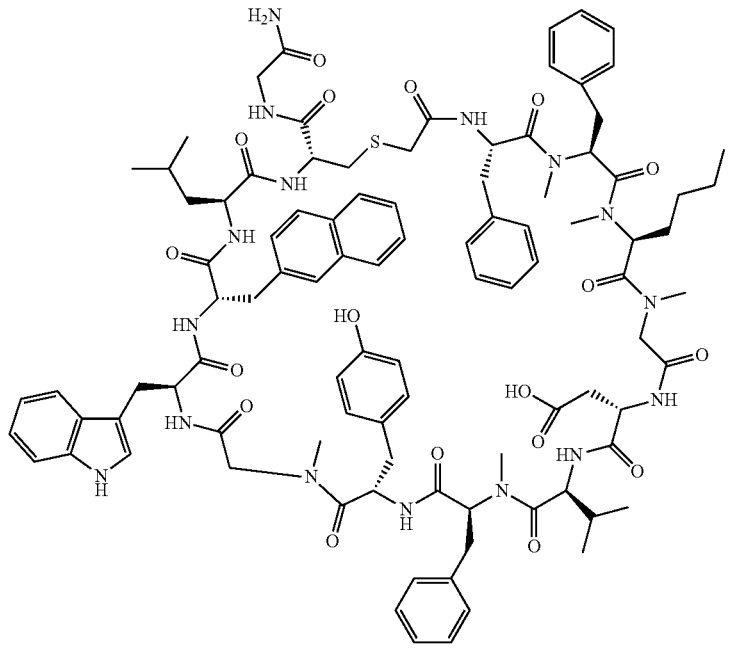

Example 3538

Example 3538 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 0.91 mg, and its estimated purity by LCMS analysis was 95.8%.

Analysis LCMS condition D: Retention time=1.82 min; ESI-MS(+) m/z 916.0 (M+2H).

Analysis LCMS condition E: Retention time=2.05 min; ESI-MS(+) m/z 915.9 (M+2H).

Preparation of Example 3539

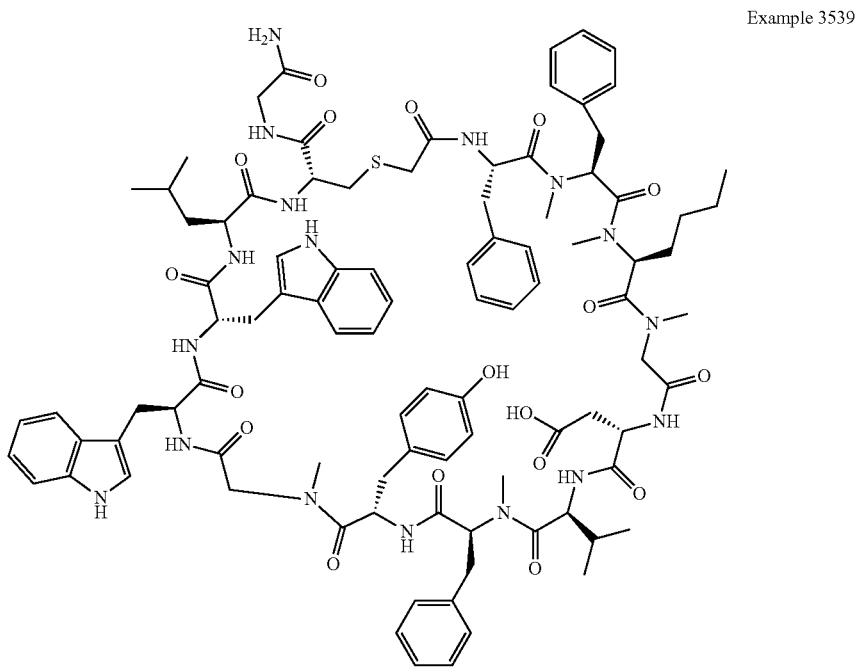 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2c[nH]c3ccccc23)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3539

Example 3539 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.52 mg, and its estimated purity by LCMS analysis was 91.2%.

Analysis LCMS condition D: Retention time=1.68 min; ESI-MS(+) m/z 910.5 (M+2H).

Analysis LCMS condition E: Retention time=1.90 min; ESI-MS(+) m/z 910.4 (M+2H).

Preparation of Example 3540

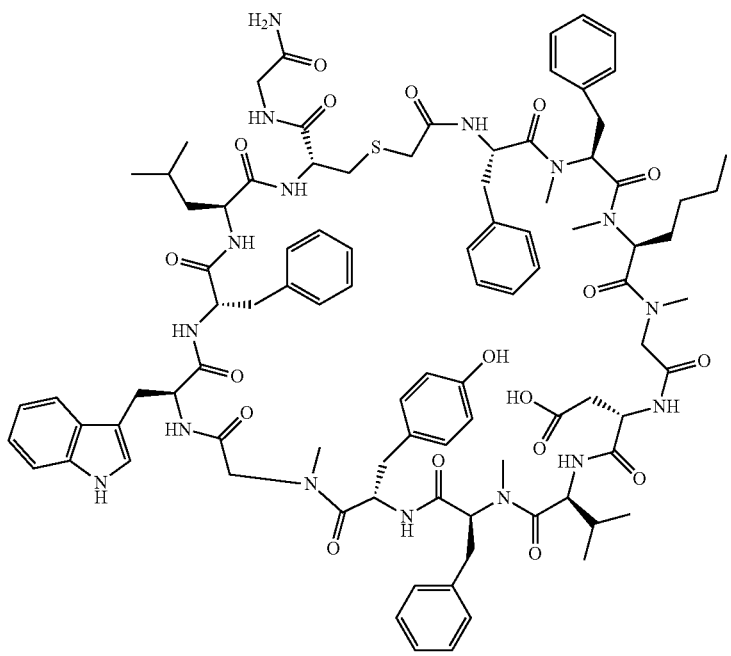

Example 3540

Example 3540 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 9.52 mg, and its estimated purity by LCMS analysis was 93.2%.

Analysis LCMS condition D: Retention time=1.72 min; ESI-MS(+) m/z 890.7 (M+2H).

Analysis LCMS condition E: Retention time=1.95 min; ESI-MS(+) m/z 890.8 (M+2H).

Preparation of Example 3541

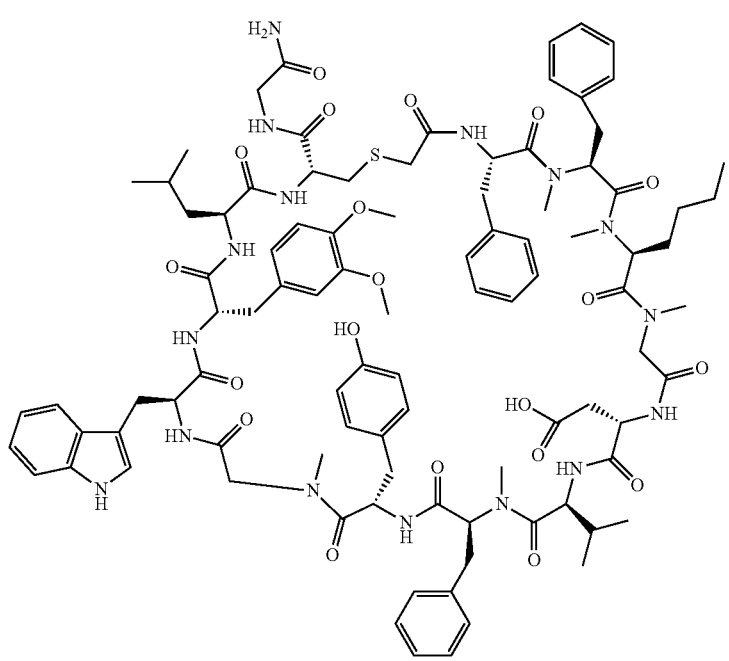

Example 3541

Example 3541 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 10.41 mg, and its estimated purity by LCMS analysis was 91.7%.

Analysis LCMS condition D: Retention time=1.68 min; ESI-MS(+) m/z 921.2 (M+2H).

Analysis LCMS condition E: Retention time=1.89 min; ESI-MS(+) m/z 921.2 (M+2H).

Preparation of Example 3542

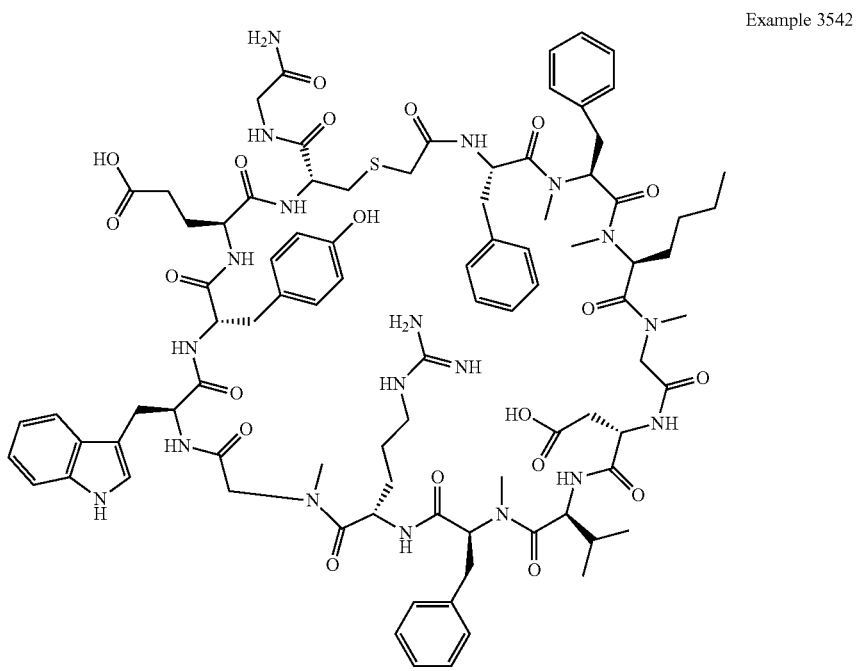 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](CCCNC(=N)N)C(=O)N(C)CC(=O)N[C@@H](Cc2c[nH]c3ccccc23)C(=O)N[C@@H](Cc2ccc(O)cc2)C(=O)N[C@@H](CCC(=O)O)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3542

Example 3542 was prepared following the general synthetic sequence described for the preparation of Example 3026, composed of the following general procedures: "CEM Method A: Resin-swelling procedure", "CEM Method A: Standard coupling procedure", "CEM Method A: Double-couple coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 8.3 mg, and its estimated purity by LCMS analysis was 93.2%.

Analysis LCMS condition D: Retention time=1.51 min; ESI-MS(+) m/z 903.2 (M+2H).

Analysis LCMS condition E: Retention time=1.64 min; ESI-MS(+) m/z 903.1 (M+2H).

Preparation of Example 3543

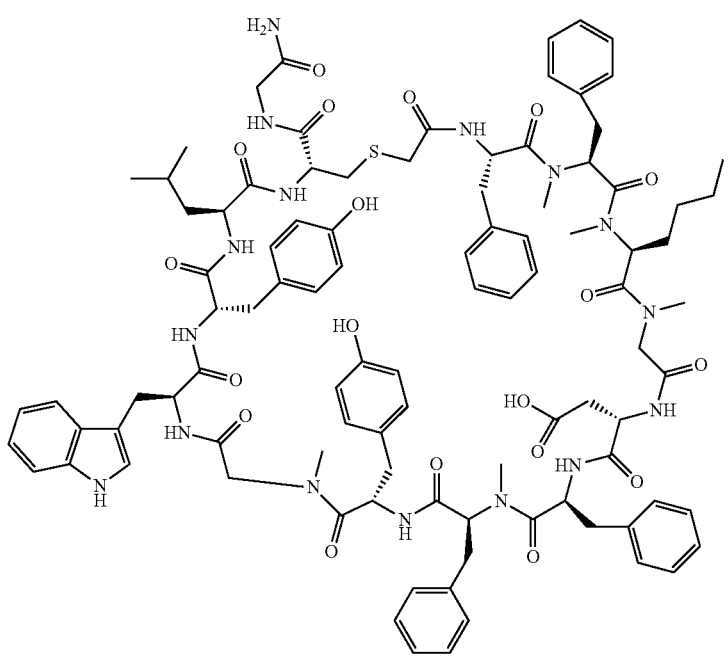

Example 3543

Example 3543 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 8.71 mg, and its estimated purity by LCMS analysis was 100.0%.

Analysis LCMS condition D: Retention time=1.71 min; ESI-MS(+) m/z 923.3 (M+2H).

Analysis LCMS condition E: Retention time=1.95 min; ESI-MS(+) m/z 923.0 (M+2H).

Preparation of Example 3544

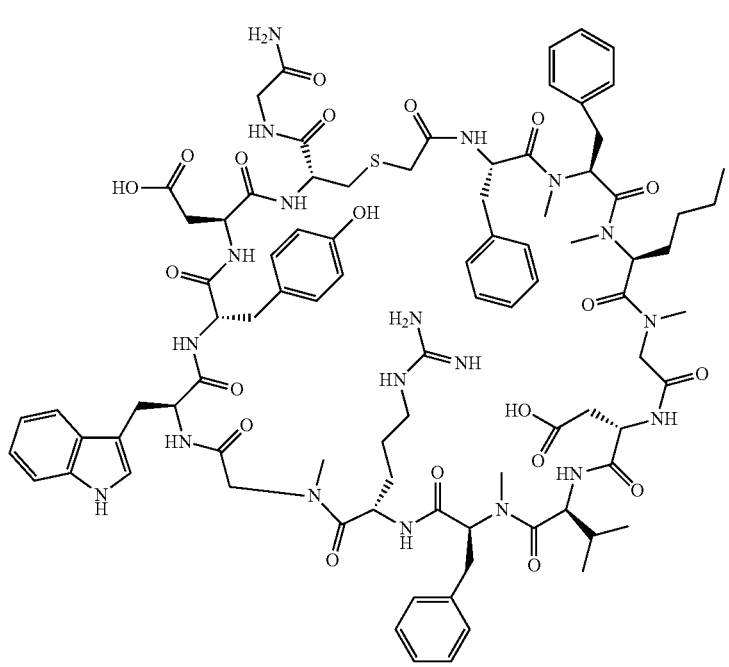

Example 3544

Example 3544 was prepared following the general synthetic sequence described for the preparation of Example 3026, composed of the following general procedures: "CEM Method A: Resin-swelling procedure", "CEM Method A: Standard coupling procedure", "CEM Method A: Double-couple coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 2.3 mg, and its estimated purity by LCMS analysis was 98.9%.

Analysis LCMS condition D: Retention time=1.51 min; ESI-MS(+) m/z 896.4 (M+2H).

Analysis LCMS condition E: Retention time=1.64 min; ESI-MS(+) m/z 896.3 (M+2H).

Preparation of Example 3545

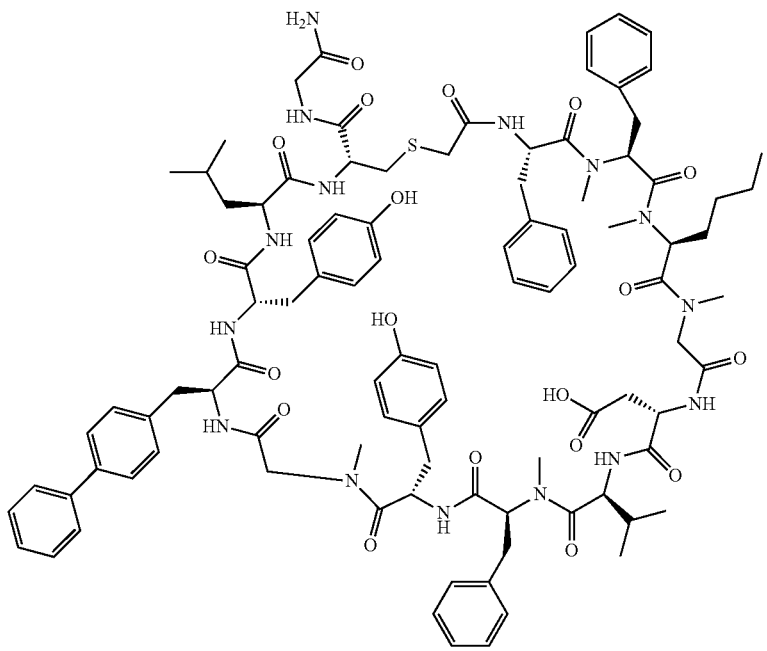

Example 3545

Example 3545 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 11.4 mg, and its estimated purity by LCMS analysis was 96.5%.

Analysis LCMS condition D: Retention time=1.80 min; ESI-MS(+) m/z 917.4 (M+2H).

Analysis LCMS condition E: Retention time=2.01 min; ESI-MS(+) m/z 917.4 (M+2H).

Preparation of Example 3546

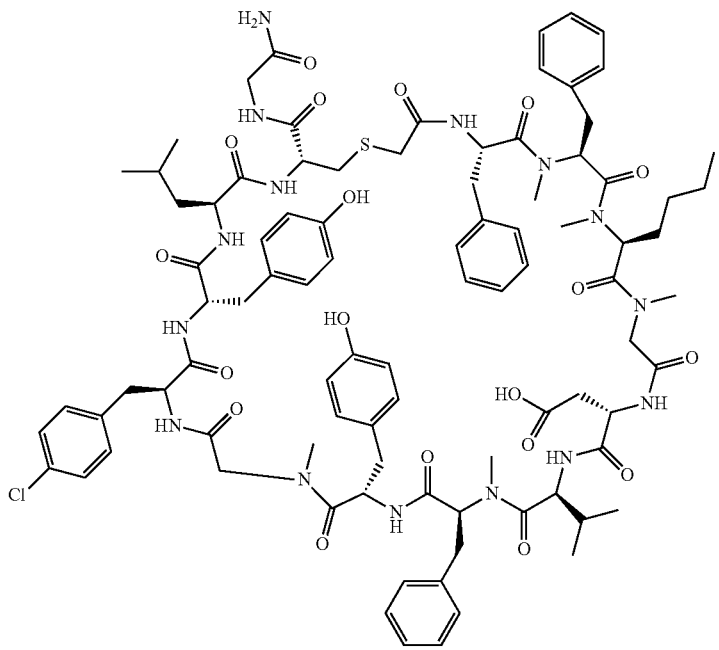

Example 3546

Example 3546 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 12.5 mg, and its estimated purity by LCMS analysis was 98.4%.

Analysis LCMS condition D: Retention time=1.69 min; ESI-MS(+) m/z 896.7 (M+2H).

Analysis LCMS condition E: Retention time=1.92 min; ESI-MS(+) m/z 897.2 (M+2H).

Preparation of Example 3547

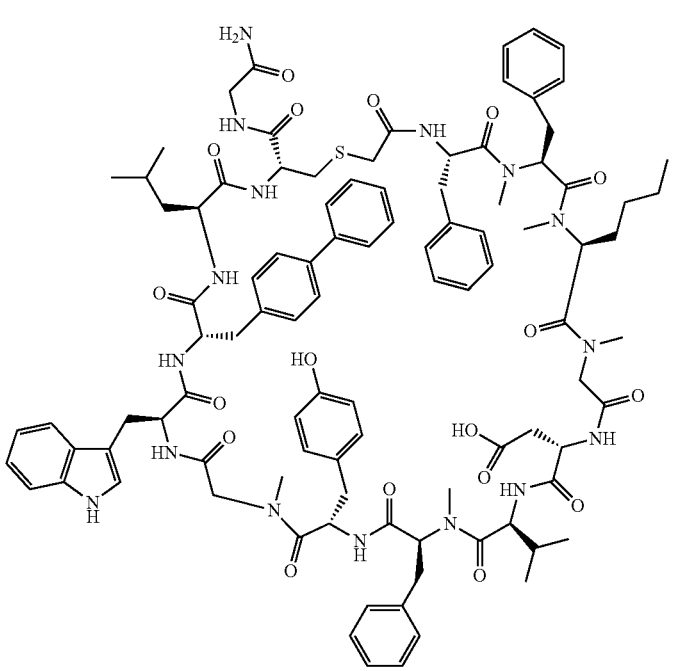

Example 3547

Example 3547 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 12.5 mg, and its estimated purity by LCMS analysis was 95.5%.

Analysis LCMS condition D: Retention time=1.88 min; ESI-MS(+) m/z 928.9 (M+2H).

Analysis LCMS condition E: Retention time=2.12 min; ESI-MS(+) m/z 928.9 (M+2H).

Preparation of Example 3548

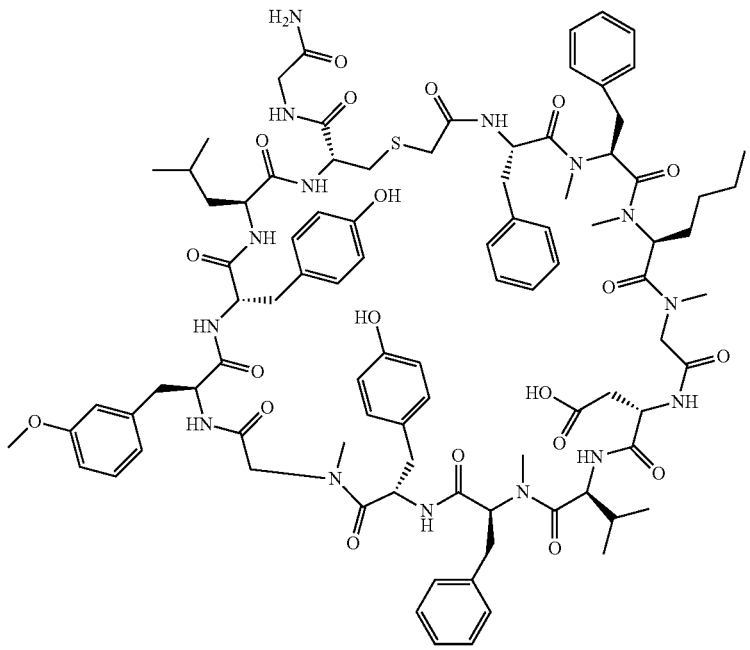

Example 3548

Example 3548 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 11.7 mg, and its estimated purity by LCMS analysis was 99.1%.

Analysis LCMS condition D: Retention time=1.62 min; ESI-MS(+) m/z 894.2 (M+2H).

Analysis LCMS condition E: Retention time=1.85 min; ESI-MS(+) m/z 894.2 (M+2H).

Preparation of Example 3549

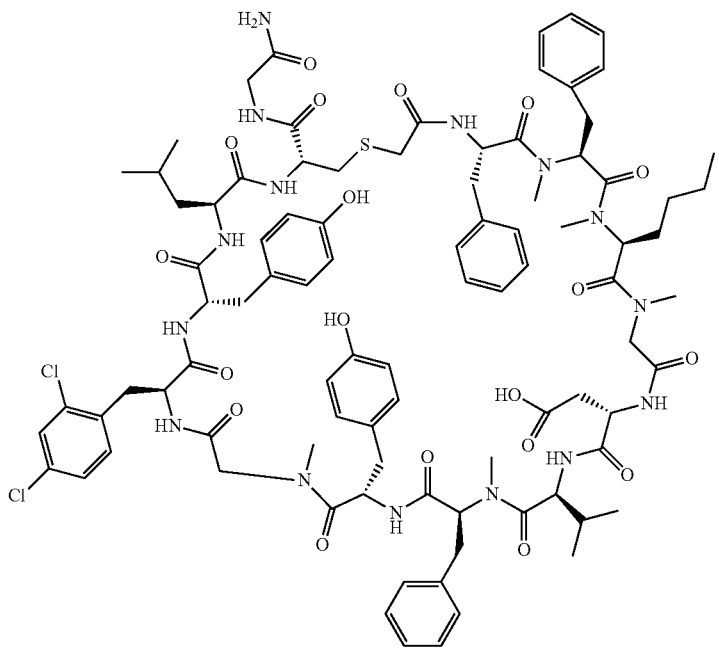

Example 3549

Example 3549 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 8.41 mg, and its estimated purity by LCMS analysis was 99.2%.

Analysis LCMS condition D: Retention time=1.75 min; ESI-MS(+) m/z 913.5 (M+2H).

Analysis LCMS condition E: Retention time=1.99 min; ESI-MS(+) m/z 913.6 (M+2H).

Preparation of Example 3550

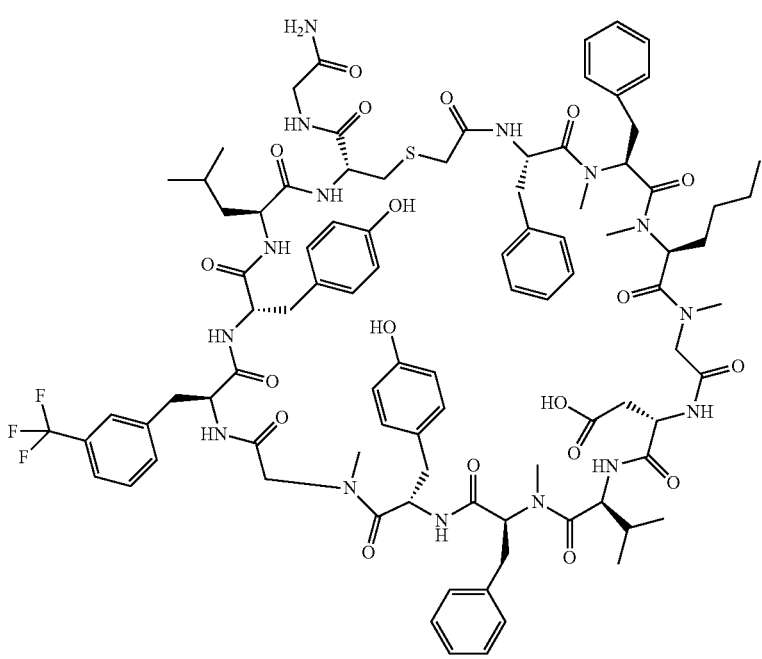

Example 3550

Example 3550 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 13.72 mg, and its estimated purity by LCMS analysis was 97.6%.

Analysis LCMS condition D: Retention time=1.72 min; ESI-MS(+) m/z 913.3 (M+2H).

Analysis LCMS condition E: Retention time=1.95 min; ESI-MS(+) m/z 913.5 (M+2H).

Preparation of Example 3551

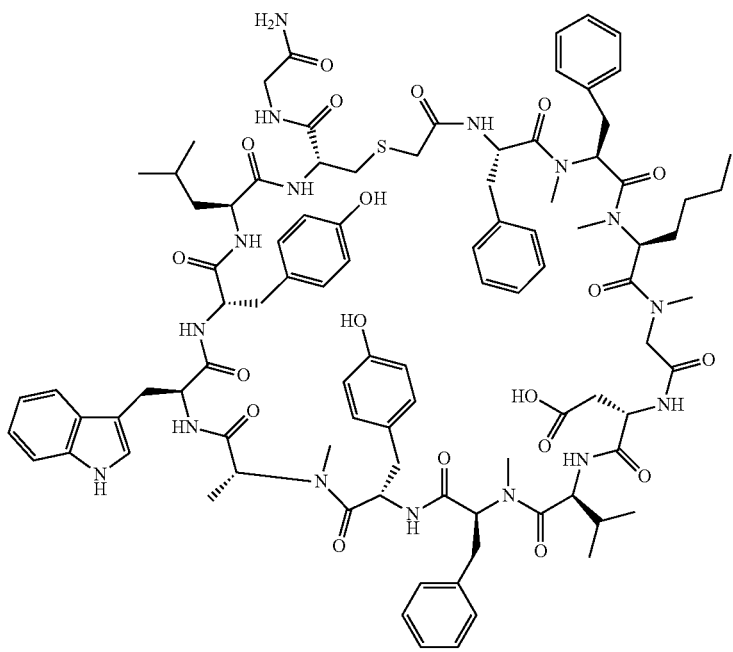

Example 3551

Example 3551 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.82 mg, and its estimated purity by LCMS analysis was 93.7%.

Analysis LCMS condition D: Retention time=1.65 min; ESI-MS(+) m/z 905.6 (M+2H).

Analysis LCMS condition E: Retention time=1.87 min; ESI-MS(+) m/z 905.9 (M+2H).

Preparation of Example 3552

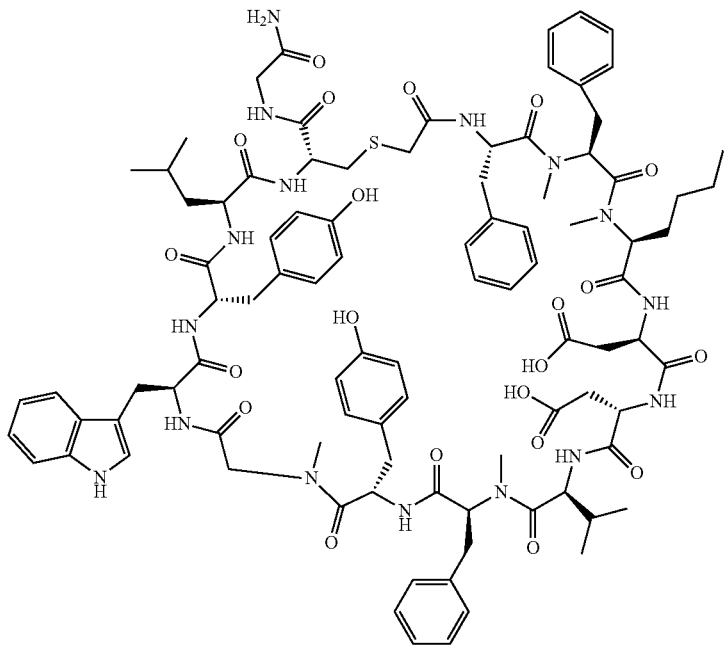

Example 3552

Example 3552 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.61 mg, and its estimated purity by LCMS analysis was 95.2%.

Analysis LCMS condition D: Retention time=1.40 min; ESI-MS(+) m/z 920.7 (M+2H).

Analysis LCMS condition E: Retention time=1.73 min; ESI-MS(+) m/z 920.8 (M+2H).

Preparation of Example 3553

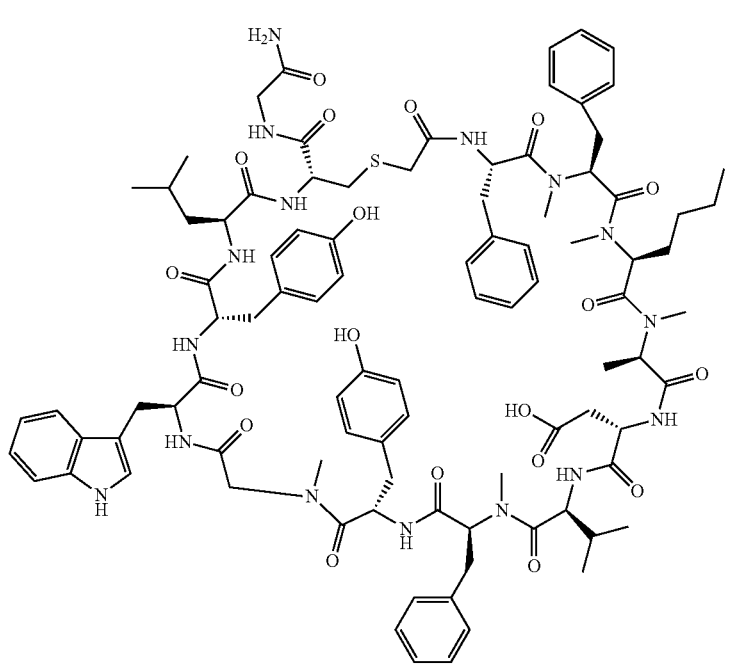

Example 3553

Example 3553 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.22 mg, and its estimated purity by LCMS analysis was 97.7%.

Analysis LCMS condition D: Retention time=1.61 min; ESI-MS(+) m/z 906.3 (M+2H).

Analysis LCMS condition E: Retention time=1.89 min; ESI-MS(+) m/z 905.7 (M+2H).

Preparation of Example 3555

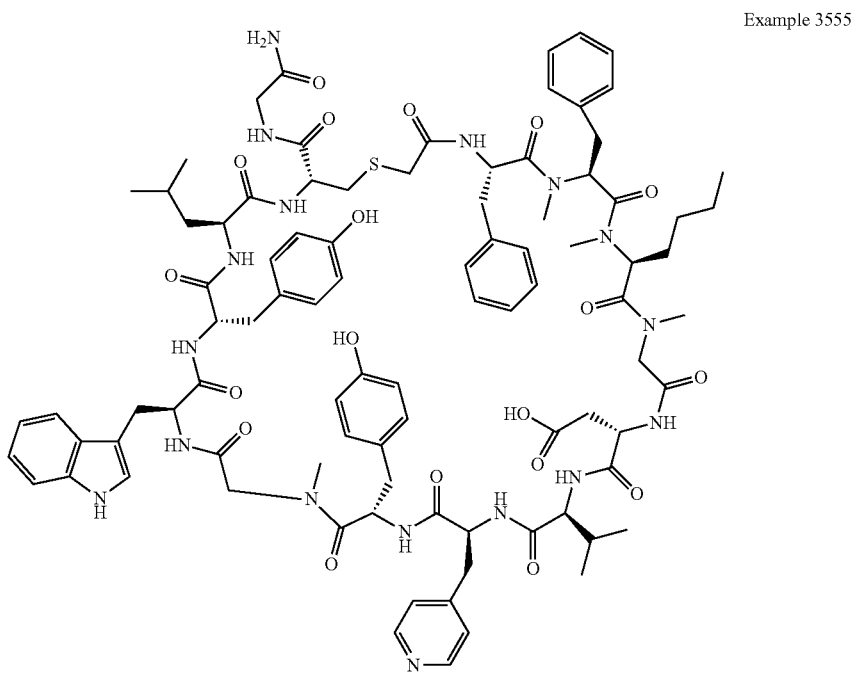 [SMILES: CCCC[C@H]1C(=O)N(C)CC(=O)N[C@@H](CC(=O)O)C(=O)N[C@@H](C(C)C)C(=O)N[C@@H](Cc2ccncc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3555

Example 3555 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 3.82 mg, and its estimated purity by LCMS analysis was 93.2%.

Analysis LCMS condition D: Retention time=1.38 min; ESI-MS(+) m/z 892.4 (M+2H).

Analysis LCMS condition E: Retention time=1.51 min; ESI-MS(+) m/z 892.6 (M+2H).

Preparation of Example 3556

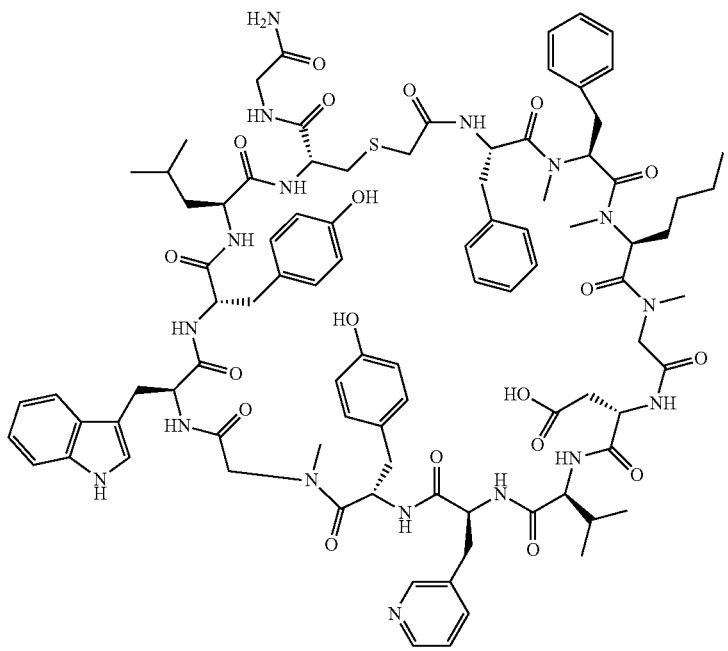

Example 3556

Example 3556 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 4.02 mg, and its estimated purity by LCMS analysis was 91.0%.

Analysis LCMS condition D: Retention time=1.41 min; ESI-MS(+) m/z 892.3 (M+2H).

Analysis LCMS condition E: Retention time=1.50 min; ESI-MS(+) m/z 892.1 (M+2H).

Preparation of Example 3557

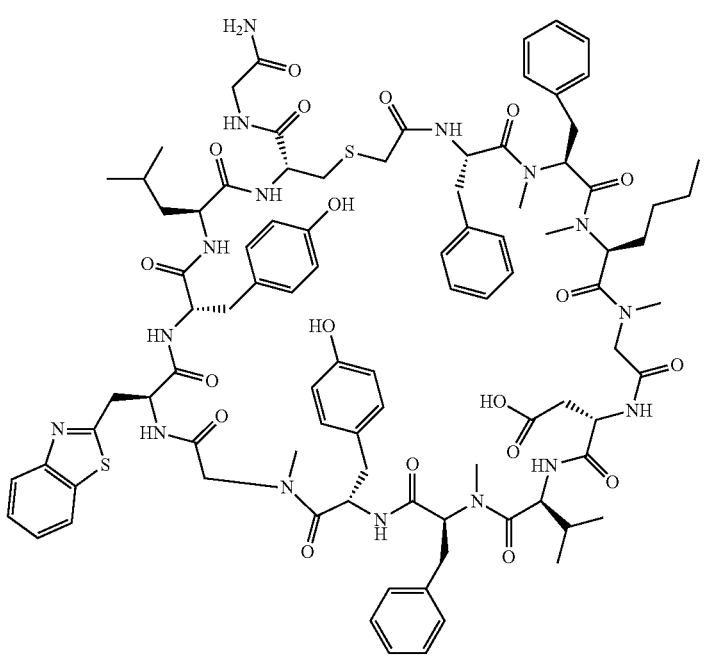

Example 3557

Example 3557 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 5.3 mg, and its estimated purity by HPLC analysis was 83% using the following conditions: Column: Phenom Kinetex 2.6 u C18(2) 2.1×50 mm Ser.#515561-57; Mobile Phase A: 0.025% Ammonium Acetate in 5% methanol/water; Mobile Phase B: Acetonitrile/water (4:1); Gradient: 25-75% B over 20 min.; Flow: 1 mL/min. Detection UV: 217 nM, Oven: 60° C.

Analysis condition A: Retention time=1.52 min; ESI-MS (+) m/z 907.9 (M+2H).

Analysis LCMS condition C: Retention time=1.73 min; ESI-MS(+) m/z 1815.0 (M+H).

Preparation of Example 3558

Example 3558 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 1.8 mg, and its estimated purity by HPLC analysis was 96% using the following conditions: Column: Phenom Kinetex 2.6 u C18(2) 2.1×50 mm Ser.#515561-57; Mobile Phase A: 0.025% Ammonium Acetate in 5% methanol/water; Mobile Phase B: Acetonitrile/water (4:1); Gradient: 25-75% B over 20 min.; Flow: 1 mL/min. Detection UV: 217 nM, Oven: 60° C.

Analysis condition A: Retention time=1.61 min; ESI-MS (+) m/z 919.5 (M+2H).

Analysis LCMS condition C: Retention time=1.88 min; ESI-MS(+) m/z 1837.1 (M+H).

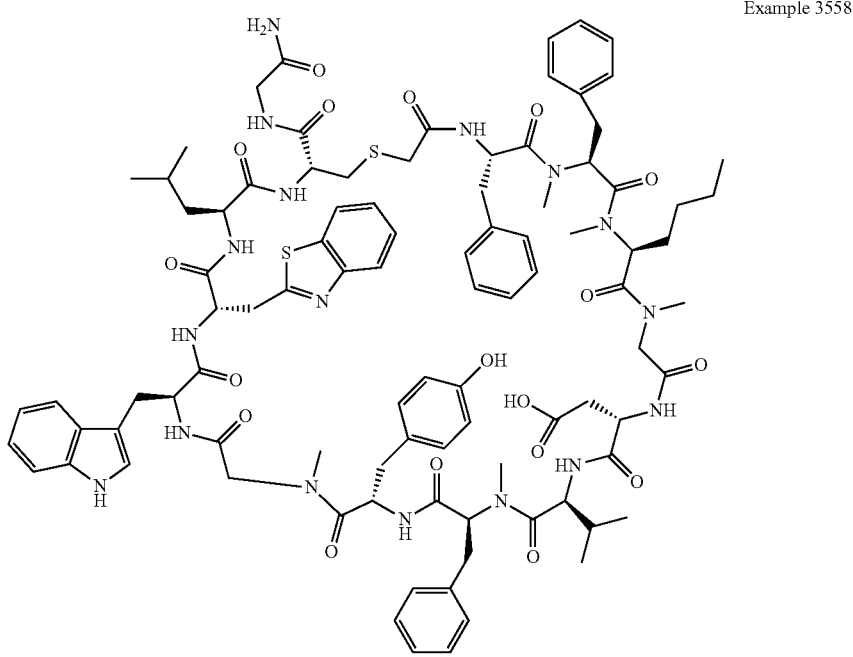 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2nc3ccccc3s2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3558

Preparation of Example 3559

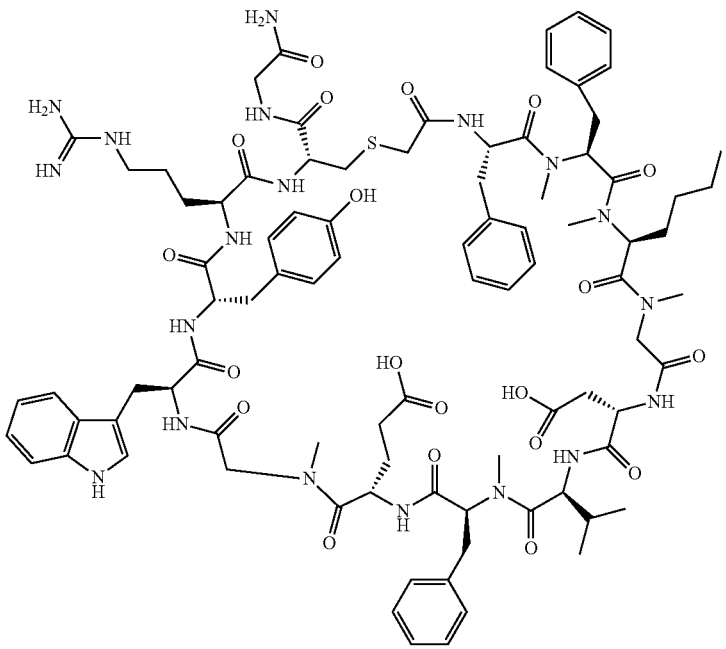

Example 3559

Example 3559 was prepared following the general synthetic sequence described for the preparation of Example 3026, composed of the following general procedures: "CEM Method A: Resin-swelling procedure", "CEM Method A: Standard coupling procedure", "CEM Method A: Double-couple coupling procedure", "CEM Method A: Custom amino acids-coupling procedure", "Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 3.5 mg, and its estimated purity by HPLC analysis is 89% using the following conditions: Column: Phenom Kinetex 2.6 u C18(2) 2.1×50 mm Ser.#515561-57; Mobile Phase A: 0.1% TFA in water; Mobile Phase B: 0.1% TFA in acetonitrile; Gradient: 25-55% B over 20 min.; Flow: 1 mL/min. Detection UV: 217 nM, Oven: 60° C.

Analysis LCMS condition A: Retention time=1.61 min; ESI-MS(+) m/z 919.5 (M+2H).
Analysis LCMS condition C: Retention time=1.88 min; ESI-MS(+) m/z 1837.1 (M+H).

Preparation of Example 3560

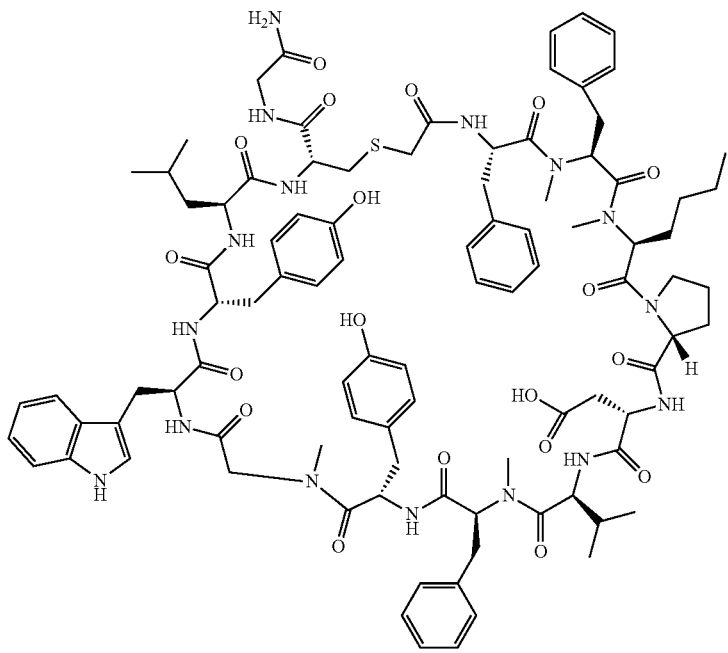

Example 3560

Example 3560 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 20.72 mg, and its estimated purity by LCMS analysis was 99.0%.

Analysis LCMS condition D: Retention time=1.78 min; ESI-MS(+) m/z 912.2 (M+2H).

Analysis LCMS condition E: Retention time=2.01 min; ESI-MS(+) m/z 912.2 (M+2H).

Preparation of Example 3561

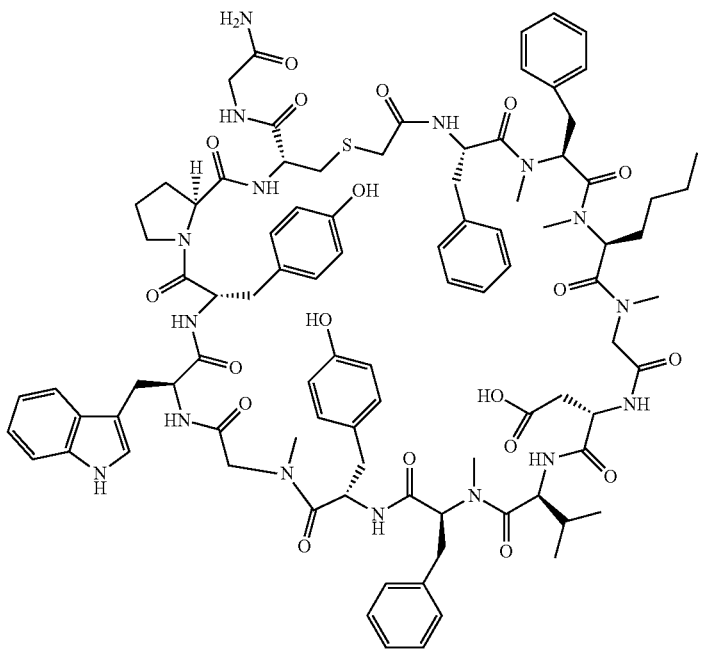

Example 3561

Example 3561 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 16.3 mg, and its estimated purity by LCMS analysis was 94%.

Analysis LCMS condition D: Retention time=1.50 min; ESI-MS(+) m/z 890.8 (M+2H).

Analysis LCMS condition E: Retention time=1.72 min; ESI-MS(+) m/z 890.7 (M+2H).

Preparation of Example 3562

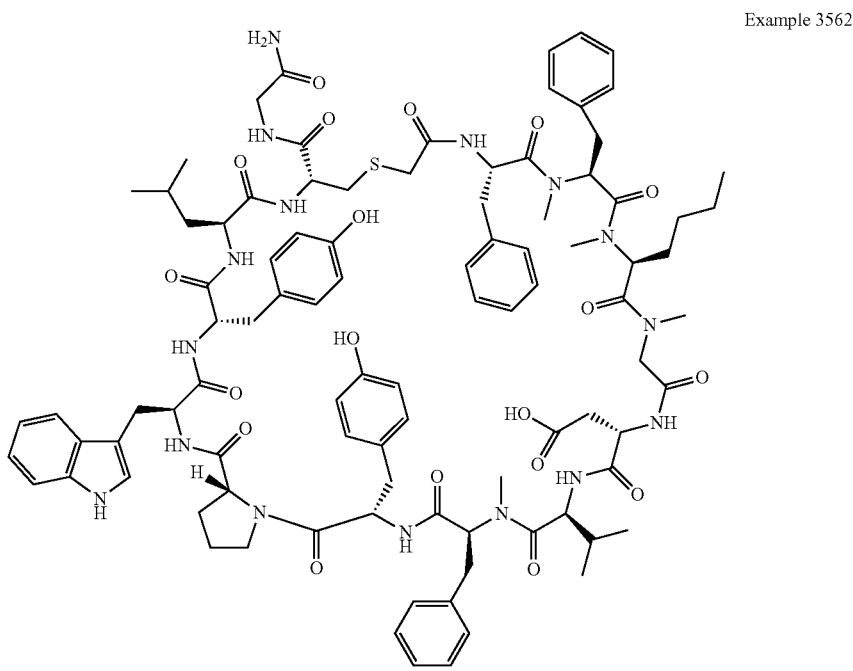 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N2CCC[C@@H]2C(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3562

Example 3562 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 11.6 mg, and its estimated purity by LCMS analysis was 94.9%.

Analysis LCMS condition D: Retention time=1.58 min; ESI-MS(+) m/z 911.8 (M+2H).

Analysis LCMS condition E: Retention time=1.81 min; ESI-MS(+) m/z 912.0 (M+2H).

Preparation of Example 3563

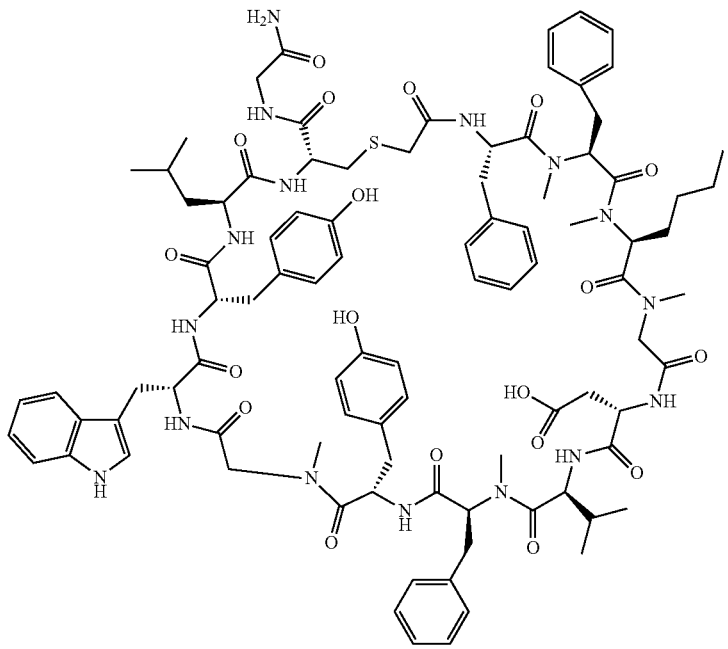

Example 3563

Example 3563 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 11.6 mg, and its estimated purity by LCMS analysis was 95.9%.

Analysis LCMS condition D: Retention time=1.54 min; ESI-MS(+) m/z 899.1 (M+2H).

Analysis LCMS condition E: Retention time=1.76 min; ESI-MS(+) m/z 898.8 (M+2H).

Preparation of Example 3564

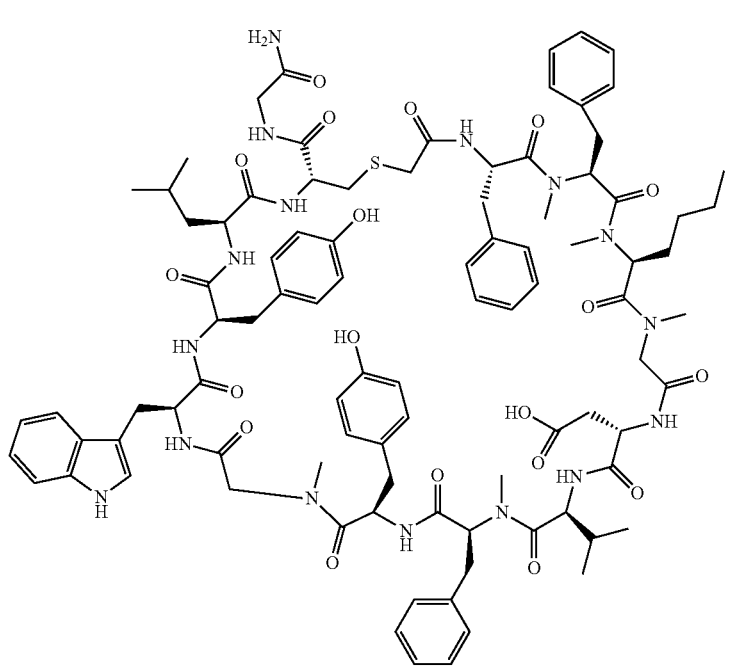

Example 3564

Example 3564 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 18.3 mg, and its estimated purity by LCMS analysis was 95.4%.

Analysis LCMS condition D: Retention time=1.60 min; ESI-MS(+) m/z 898.9 (M+2H).

Analysis LCMS condition E: Retention time=1.82 min; ESI-MS(+) m/z 898.8 (M+2H).

Preparation of Example 3565

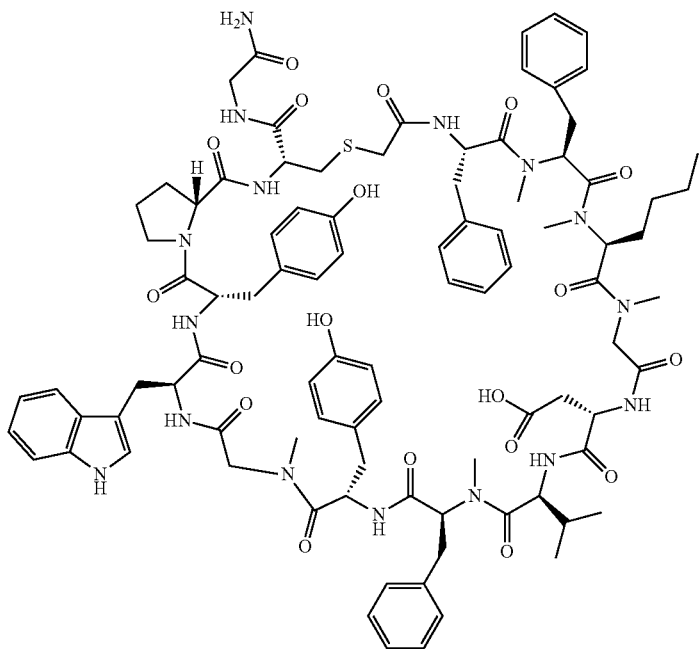

Example 3565

Example 3565 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 15.2 mg, and its estimated purity by LCMS analysis was 95.8%.

Analysis LCMS condition D: Retention time=1.50 min; ESI-MS(+) m/z 890.8 (M+2H).

Analysis LCMS condition E: Retention time=1.73 min; ESI-MS(+) m/z 891.2 (M+2H).

Preparation of Example 3566

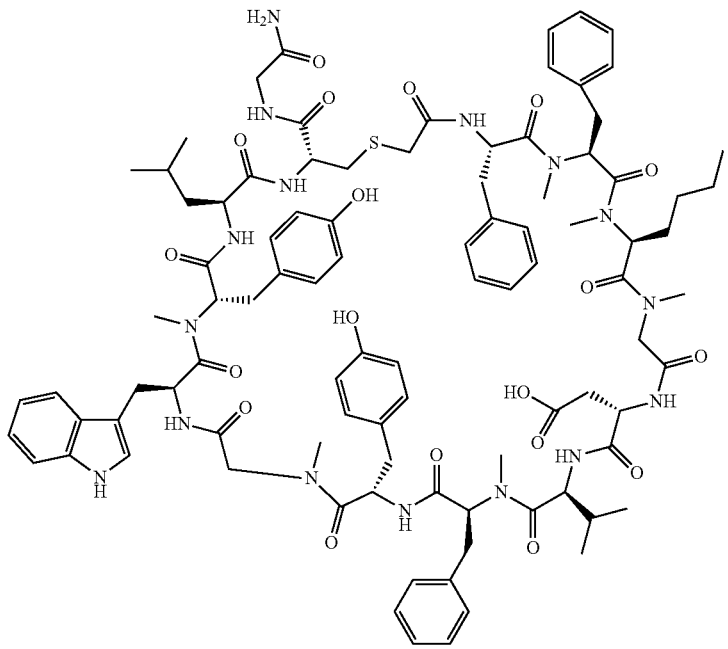

Example 3566

Example 3566 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 1.56 mg, and its estimated purity by LCMS analysis was 100.0%.

Analysis LCMS condition D: Retention time=1.70 min; ESI-MS(+) m/z 906.2 (M+2H).

Analysis LCMS condition E: Retention time=1.92 min; ESI-MS(+) m/z 906.2 (M+2H).

Preparation of Example 3567

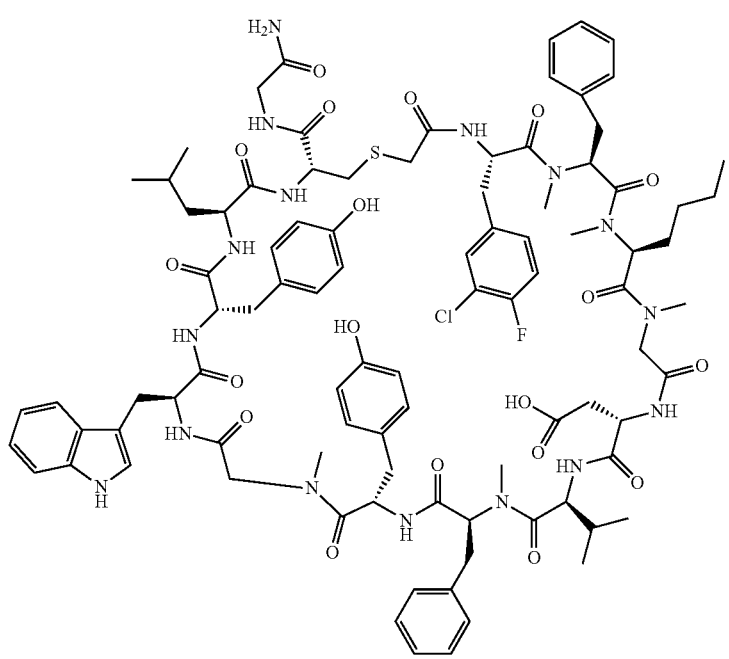

Example 3567

Example 3567 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".
(S)-2-((((9H-fluoren-9-yl)methoxy)carbonyl)amino)-3-(3-chloro-4-fluorophenyl)propanoic acid was used.

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 40-85% B over 35 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 9.82 mg, and its estimated purity by HPLC analysis is 98.8% using the following conditions: Column: Phenom Kinetex 2.6 u C18(2) 2.1×50 mm Ser.#515561-57; Mobile Phase A: 0.1% TFA in water; Mobile Phase B: 0.1% TFA in acetonitrile; Gradient: 25-55% B over 20 min.; Flow: 1 mL/min. Detection UV: 217 nM, Oven: 40° C.

Analysis LCMS condition C: Retention time=1.88 min; ESI-MS(+) m/z 1849.9 (M+H).

Preparation of Example 3568

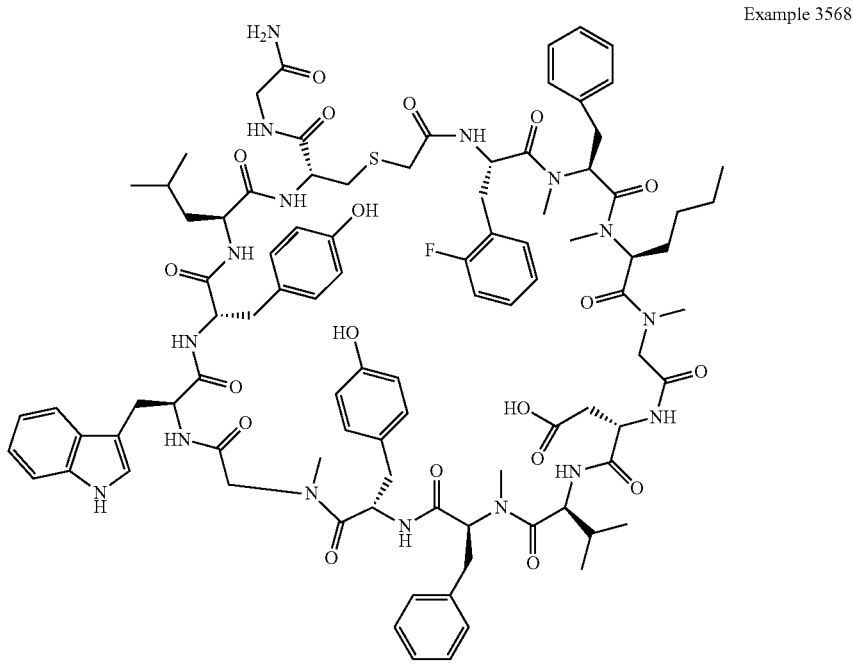 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2F)C(=O)N(C)[C@@H](Cc2ccccc2)C(=O)N1C]

Example 3568

Example 3568 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 40-85% B over 35 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 8.08 mg, and its estimated purity by HPLC analysis is 98.8% using the following conditions: Column: Phenom Kinetex 2.6 u C18(2) 2.1×50 mm Ser.#515561-57; Mobile Phase A: 0.1% TFA in water; Mobile Phase B: 0.1% TFA in acetonitrile; Gradient: 25-55% B over 20 min.; Flow: 1 mL/min. Detection UV: 217 nM, Oven: 40° C.

Analysis LCMS condition C: Retention time=1.81 min; ESI-MS(+) m/z 1815.0 (M+H).

Preparation of Example 3569

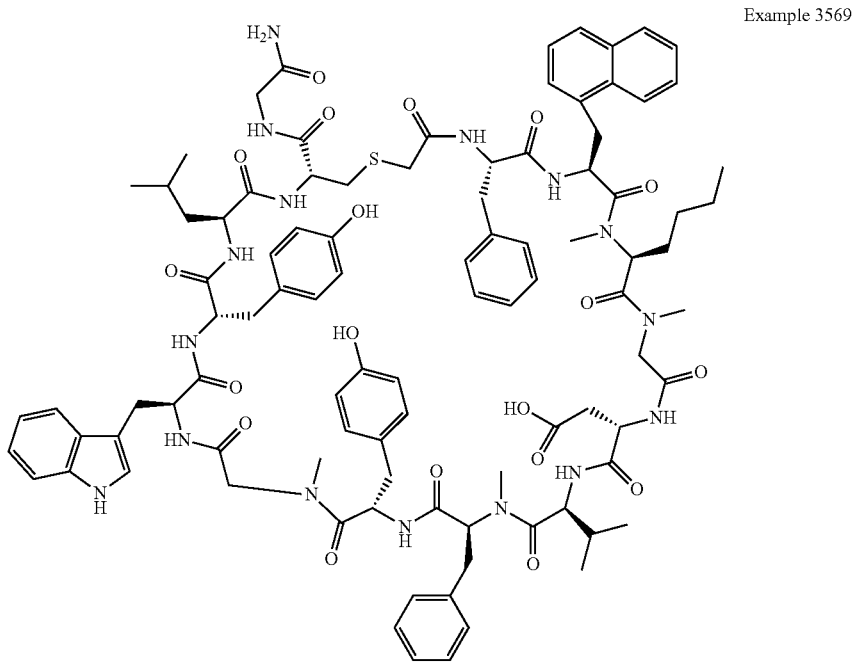 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N[C@@H](Cc2cccc3ccccc23)C(=O)N1C]

Example 3569

Example 3569 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 16.3 mg, and its estimated purity by LCMS analysis was 96%.

Analysis LCMS condition D: Retention time=1.83 min; ESI-MS(+) m/z 916.9 (M+2H).

Analysis LCMS condition E: Retention time=1.86 min; ESI-MS(+) m/z 917.3 (M+2H).

Preparation of Example 3570

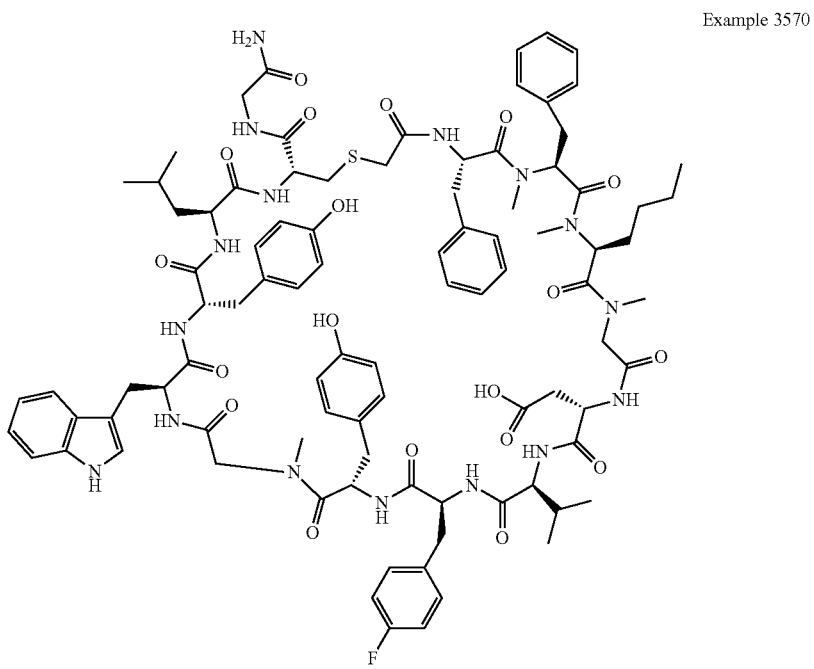 [SMILES: CCCC[C@H]1C(=O)N(C)CC(=O)N[C@@H](CC(=O)O)C(=O)N[C@@H](C(C)C)C(=O)N[C@@H](Cc2ccc(F)cc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3570

Example 3570 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 27.0 mg, and its estimated purity by LCMS analysis was 97%.

Analysis LCMS condition D: Retention time=1.60 min; ESI-MS(+) m/z 900.8 (M+2H).

Analysis LCMS condition E: Retention time=1.78 min; ESI-MS(+) m/z 900.8 (M+2H).

Preparation of Example 3571

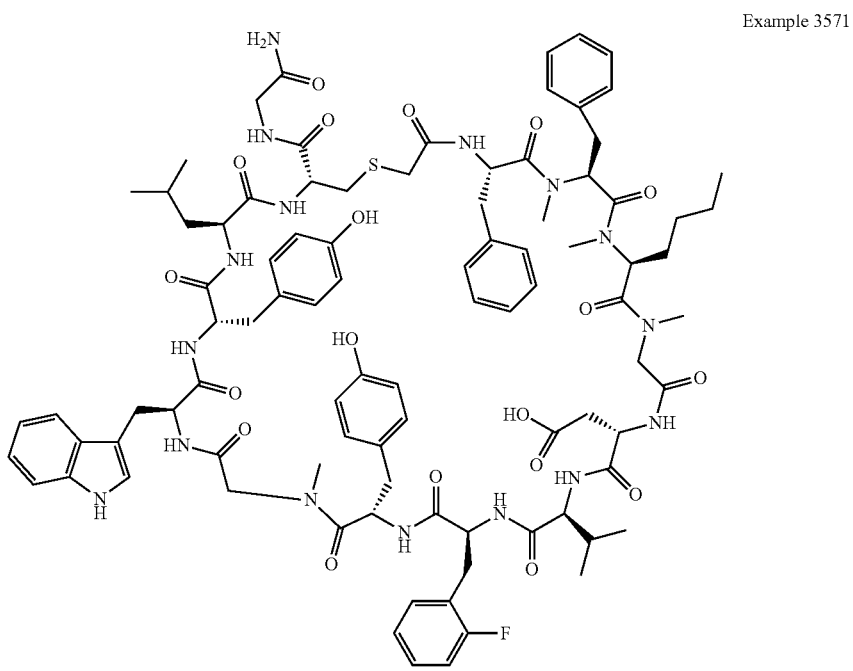 [SMILES: CCCC[C@H]1C(=O)N(C)CC(=O)N[C@@H](CC(=O)O)C(=O)N[C@@H](C(C)C)C(=O)N[C@@H](Cc2ccccc2F)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

Example 3571

Example 3571 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 25.0 mg, and its estimated purity by LCMS analysis was 95%.

Analysis LCMS condition D: Retention time=1.58 min; ESI-MS(+) m/z 900.7 (M+2H).

Analysis LCMS condition E: Retention time=1.76 min; ESI-MS(+) m/z 900.9 (M+2H).

Preparation of Example 3572

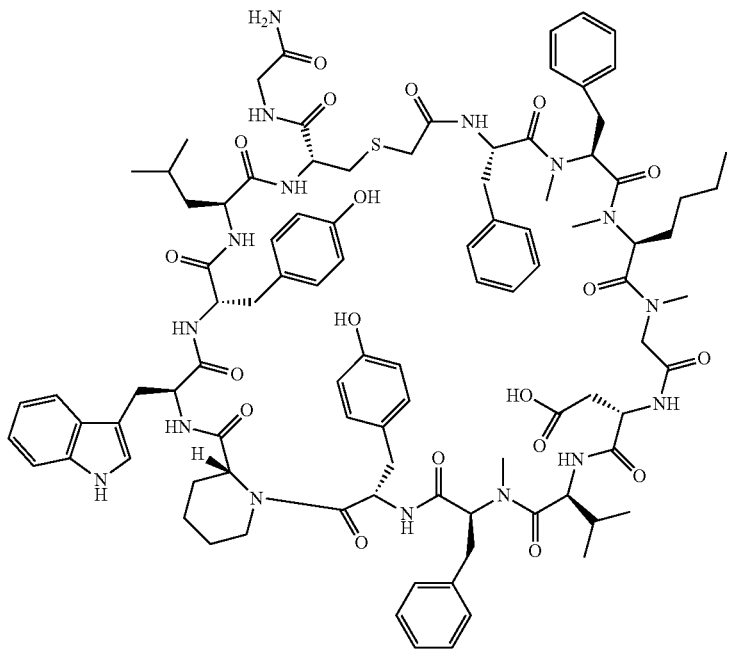

Example 3572

Example 3572 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 16.01 mg, and its estimated purity by LCMS analysis was 90.8%.

Analysis LCMS condition D: Retention time=1.68 min; ESI-MS(+) m/z 919.4 (M+2H).

Analysis LCMS condition E: Retention time=1.90 min; ESI-MS(+) m/z 918.9 (M+2H).

Preparation of Example 3573

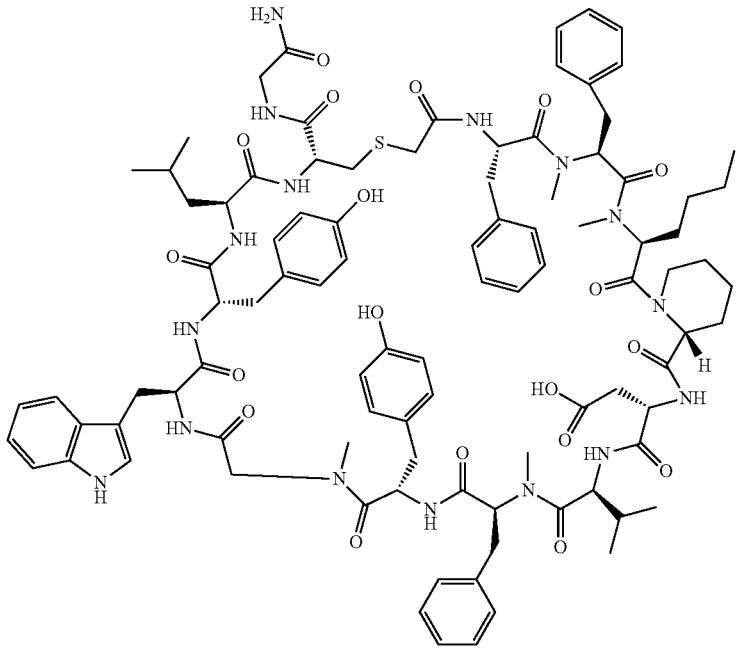

Example 3573

Example 3573 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 9.71 mg, and its estimated purity by LCMS analysis was 92.4%.

Analysis LCMS condition D: Retention time=1.76 min; ESI-MS(+) m/z 919.0 (M+2H).

Analysis LCMS condition E: Retention time=1.96 min; ESI-MS(+) m/z 919.3 (M+2H).

Preparation of Example 3574

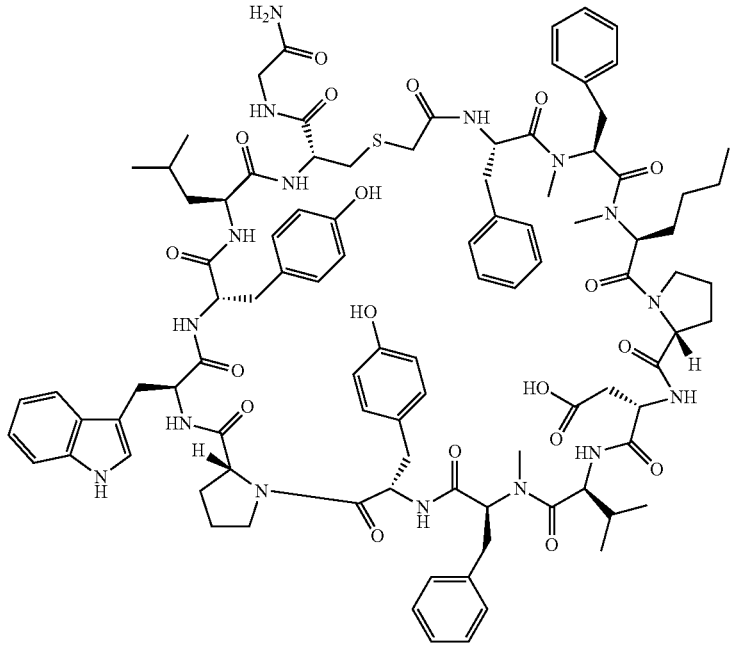

Example 3574

Example 3574 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 16.8 mg, and its estimated purity by HPLC analysis is 94.1% using the following conditions: Column: Phenom Kinetex 2.6 u C18(2) 2.1×50 mm Ser.#515561-57; Mobile Phase A: 0.025% Ammonium Acetate in 5% methanol/water; Mobile Phase B: Acetonitrile/water (4:1); Gradient: 25-55% B over 20 min.; Flow: 1 mL/min. Detection UV: 217 nM, Oven: 60° C.

Analysis condition A: Retention time=1.65 min; ESI-MS (+) m/z 925.0 (M+2H).

Analysis LCMS condition C: Retention time=1.89 min; ESI-MS(+) m/z 1848.5 (M+H).

Preparation of Example 3575

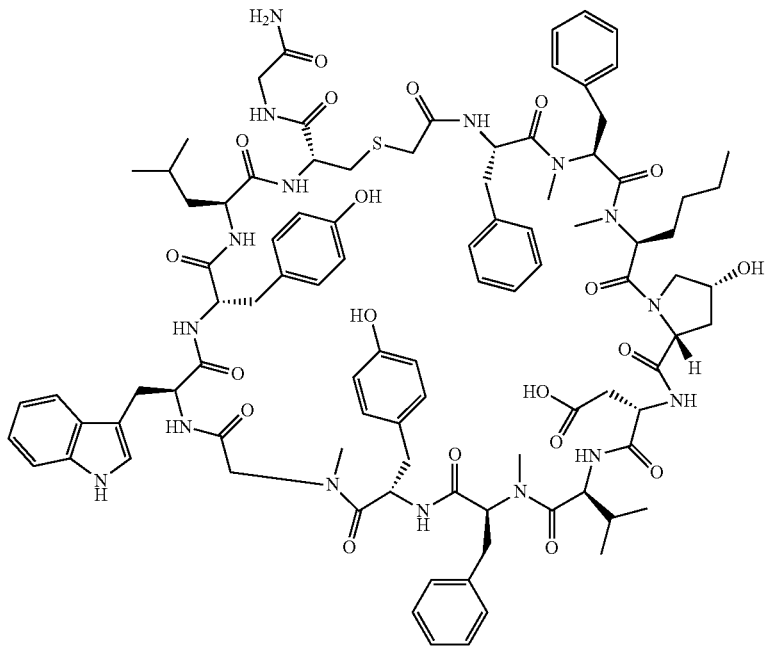

Example 3575

Example 3575 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The dissolved in a minimum if acetonitrile and water, frozen and lyophilized to give a white amorphous solid. The yield of product was 19.7 mg, and its estimated purity by HPLC analysis is 94.1% using the "Analysis condition B"; Gradient: 30-75% B over 30 min.; Flow: 1 mL/min. Detection UV: 217 nM, Oven: 60° C.

Analysis condition A: Retention time=1.57 min; ESI-MS (+) m/z 920.0 (M+2H).

Analysis LCMS condition C: Retention time=1.76 min; ESI-MS(+) m/z 1839.3 (M+H).

Preparation of Example 3576

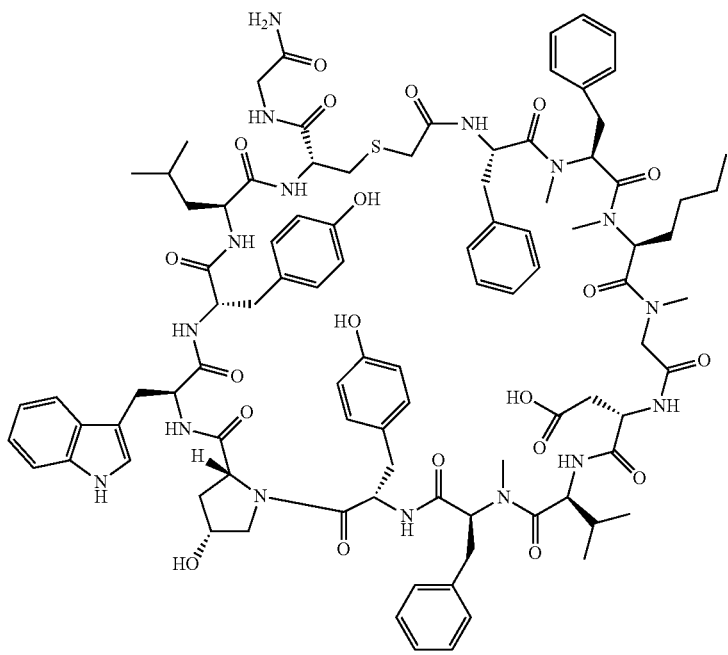

Example 3576

Example 3576 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: "Chloroacetic acid coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 1.70 mg, and its estimated purity by LCMS analysis was 97.0%.

Analysis LCMS condition D: Retention time=1.61 min; ESI-MS(+) m/z 919.8 (M+2H).

Analysis LCMS condition E: Retention time=1.77 min; ESI-MS(+) m/z 919.8 (M+2H).

Preparation of Example 3577

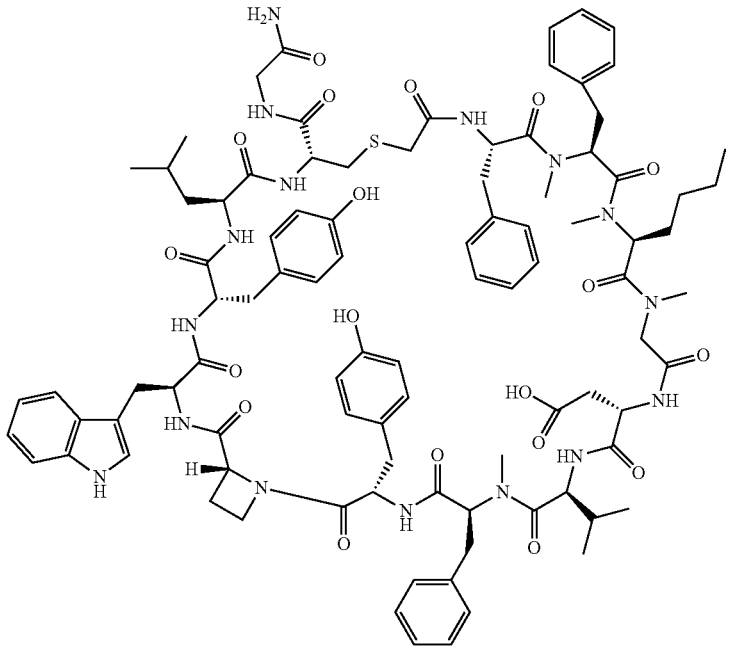

Example 3577

Example 3577 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.92 mg, and its estimated purity by LCMS analysis was 91.3%.

Analysis LCMS condition D: Retention time=1.66 min; ESI-MS(+) m/z 905.2 (M+2H).

Analysis LCMS condition E: Retention time=1.84 min; ESI-MS(+) m/z 904.8 (M+2H).

Preparation of Example 3578

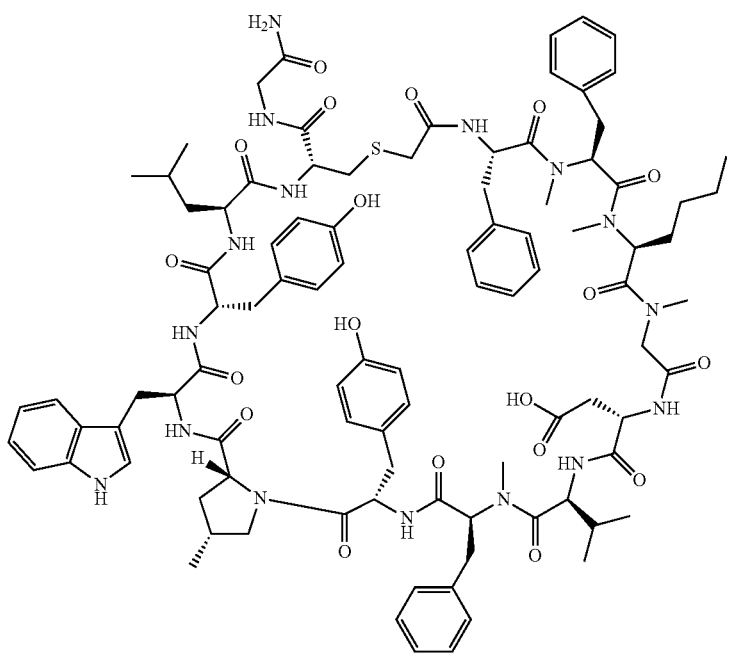

Example 3578

Example 3578 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 4.21 mg, and its estimated purity by LCMS analysis was 100.0%.

Analysis LCMS condition D: Retention time=1.65 min; ESI-MS(+) m/z 919.1 (M+2H).

Analysis LCMS condition E: Retention time=1.87 min; ESI-MS(+) m/z 919.0 (M+2H).

Preparation of Example 3579

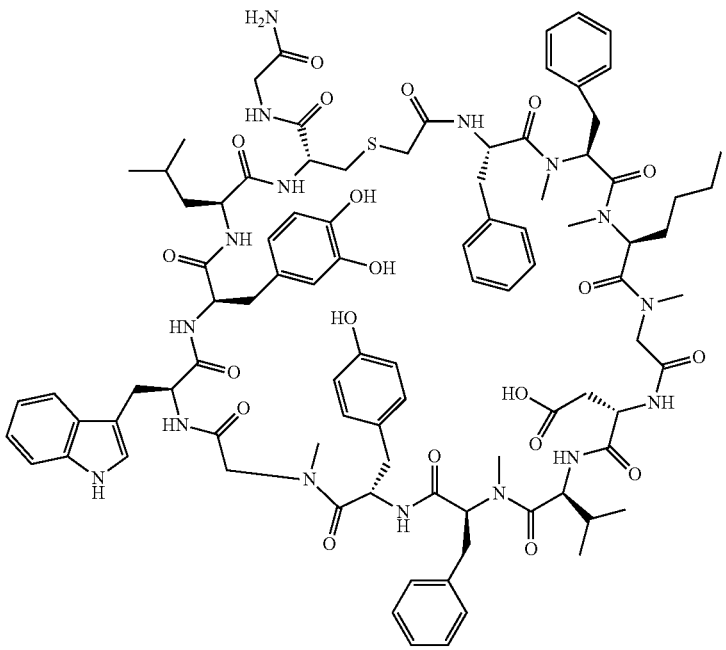

Example 3579

Example 3579 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 1.52 mg, and its estimated purity by LCMS analysis was 99.1%.

Analysis LCMS condition D: Retention time=1.64 min; ESI-MS(+) m/z 906.8 (M+2H).

Analysis LCMS condition E: Retention time=1.82 min; ESI-MS(+) m/z 907.3 (M+2H).

Preparation of Example 3580

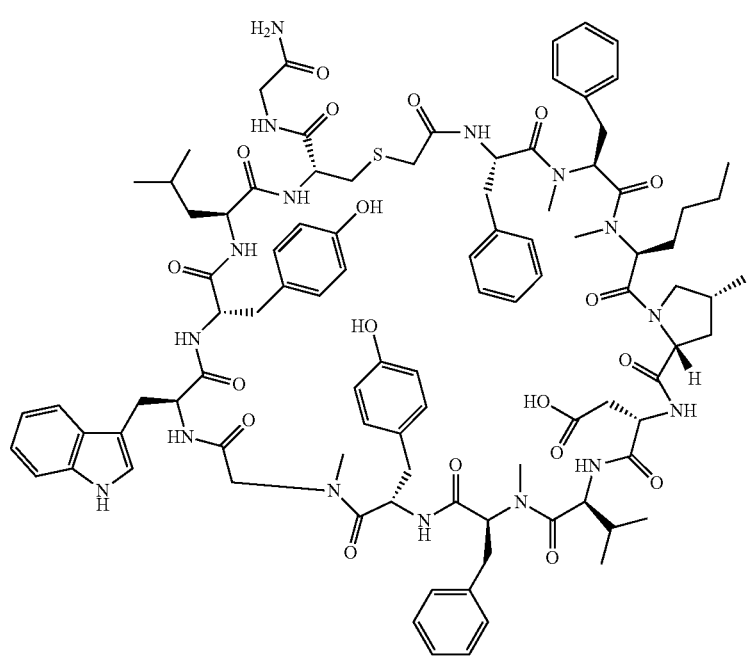

Example 3580

Example 3580 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 5.81 mg, and its estimated purity by LCMS analysis was 96.1%.

Analysis LCMS condition D: Retention time=1.84 min; ESI-MS(+) m/z 919.2 (M+2H).

Analysis LCMS condition E: Retention time=2.06 min; ESI-MS(+) m/z 919.4 (M+2H).

Preparation of Example 3581

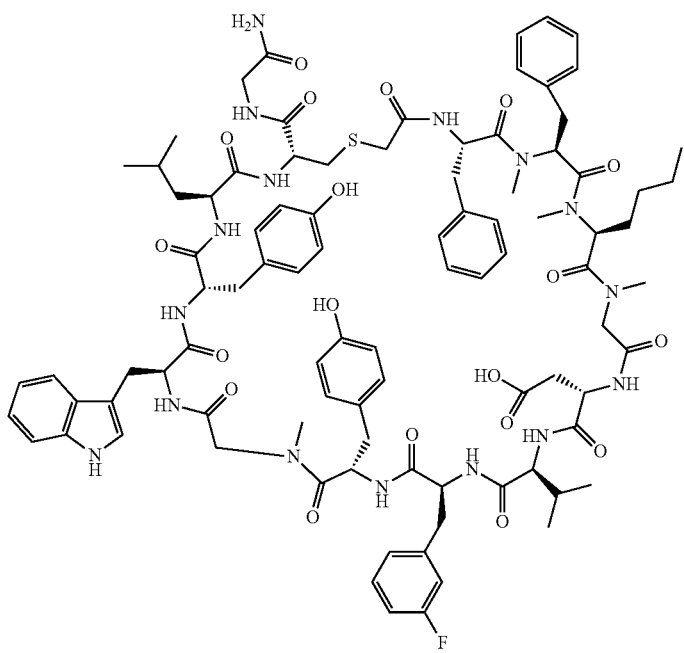

Example 3581

Example 3581 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 28.22 mg, and its estimated purity by LCMS analysis was 94.4%.

Analysis LCMS condition D: Retention time=1.66 min; ESI-MS(+) m/z 901.2 (M+2H).

Analysis LCMS condition E: Retention time=1.85 min; ESI-MS(+) m/z 901.3 (M+2H).

Preparation of Example 3582

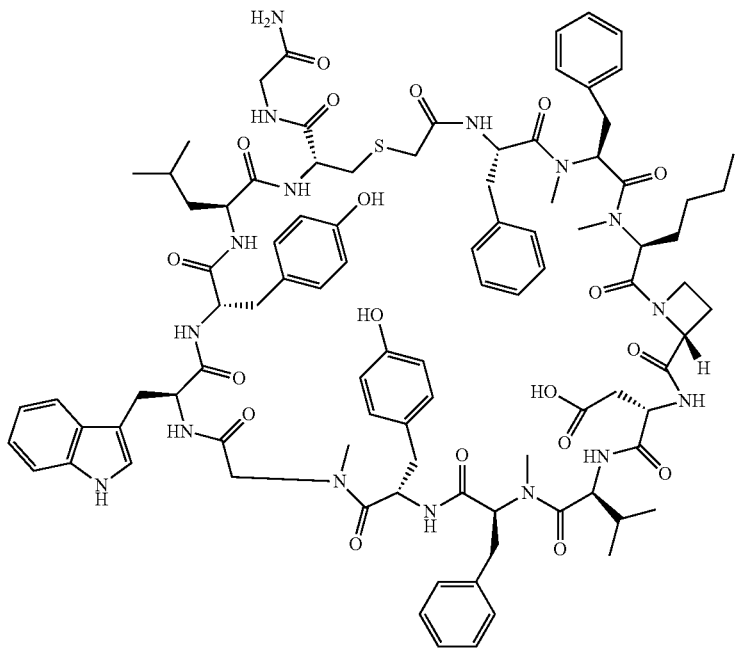

Example 3582

Example 3582 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetyl chloride coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 26.6 mg, and its estimated purity by LCMS analysis was 96.8%.

Analysis LCMS condition D: Retention time=1.58 min; ESI-MS(+) m/z 904.7 (M+2H).

Analysis LCMS condition E: Retention time=1.80 min; ESI-MS(+) m/z 904.8 (M+2H).

Preparation of Example 3583

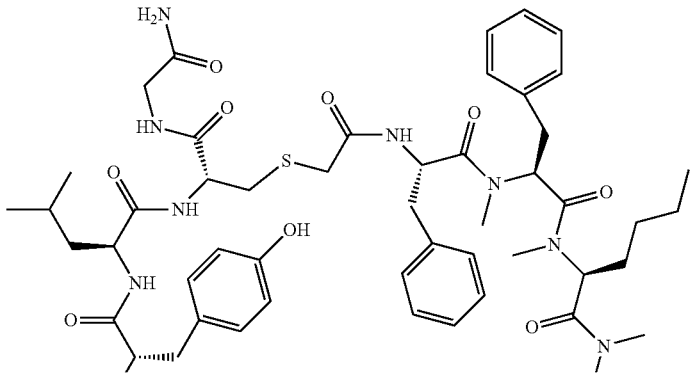

Example 3583

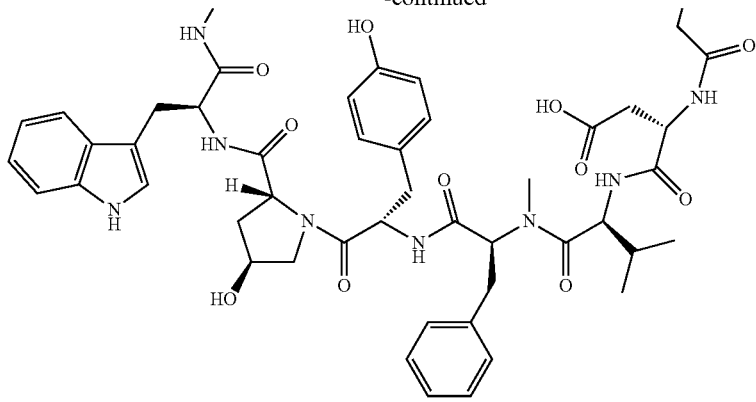

Example 3583 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B;

Flow: 20 mL/min. Fractions containing the desired product were combined and dried. The yield of product was 14.60 mg, and its estimated purity by LCMS analysis was 98.8%.

Analysis LCMS condition D: Retention time=1.57 min; ESI-MS(+) m/z 919.8 (M+2H).

Preparation of Example 3584

Example 3584

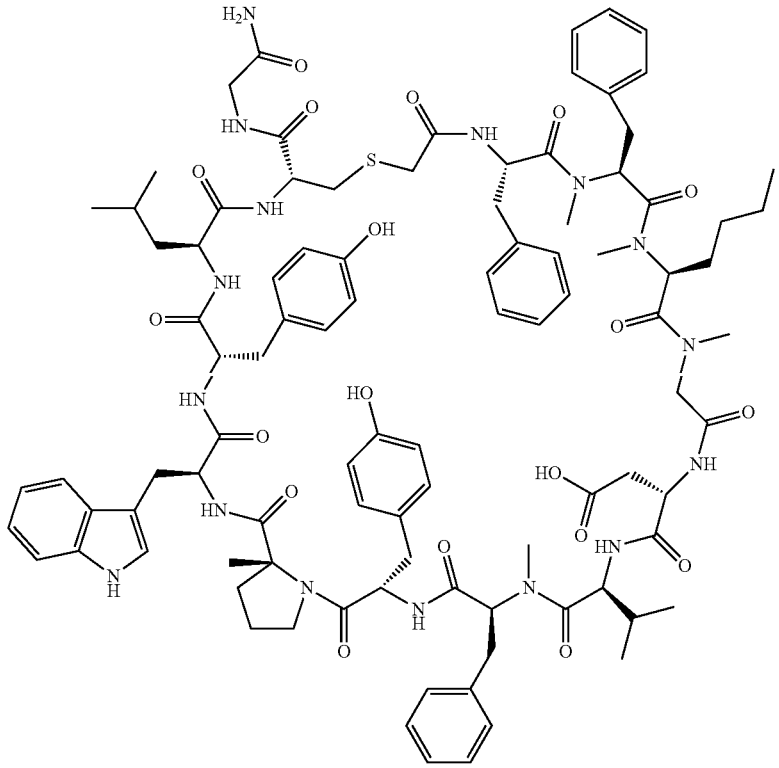

Example 3584 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 50 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 3.06 mg, and its estimated purity by HPLC analysis is 95.4% using the following conditions: Column: Phenom Kinetex 2.6 u C18(2) 2.1×50 mm Ser.#515561-57; Mobile Phase A: 0.025% Ammonium Acetate in 5% methanol/water; Mobile Phase B: Acetonitrile/water (4:1); Gradient: 25-55% B over 20 min.; Flow: 1 mL/min. Detection UV: 217 nM, Oven: 60° C.

Analysis condition A: Retention time=1.47 min; ESI-MS (+) m/z 919.0 (M+2H).

Analysis LCMS condition C: Retention time=1.71 min; ESI-MS(+) m/z 1837.1 (M+H).

Preparation of Example 3585

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. Two isomeric products were isolated: Isomer A and B.

The yield of the isomer A was 1.70 mg, and its estimated purity by HPLC analysis is 100.0% using the following conditions: Column: Phenom Jupiter 5 u C18 150×4.6 mm 300 A.; Mobile Phase A: 0.1% TFA in water; Mobile Phase B: 0.1% TFA in acetonitrile: 30-60% B over 15 min.; Flow: 1 mL/min. Detection UV: 217 nM, Oven: 40° C.

Analysis condition A: Retention time=1.49 min; ESI-MS (+) m/z 923.0 (M+2H).

Analysis LCMS condition C: Retention time=1.75 min; ESI-MS(+) m/z 1845.1 (M+H).

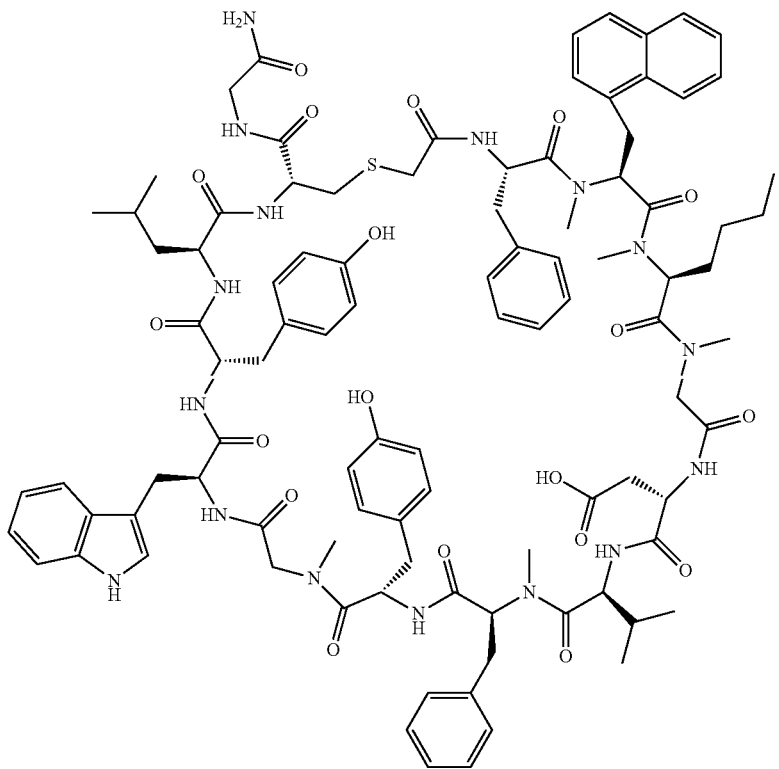

Example 3585

Example 3585 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The yield of the isomer B was 2.18 mg, and its estimated purity by HPLC analysis is 92.8% using the following conditions: Column: Phenom Jupiter 5 u C18 150×4.6 mm 300 A.; Mobile Phase A: 0.1% TFA in water; Mobile Phase B: 0.1% TFA in acetonitrile: 35-60% B over 15 min.; Flow: 1 mL/min. Detection UV: 217 nM, Oven: 40° C.

Analysis condition A: Retention time=1.50 min; ESI-MS (+) m/z 923.9 (M+2H).

Analysis LCMS condition C: Retention time=1.77 min; ESI-MS(+) m/z 1847.9 (M+H).

Preparation of Example 3586

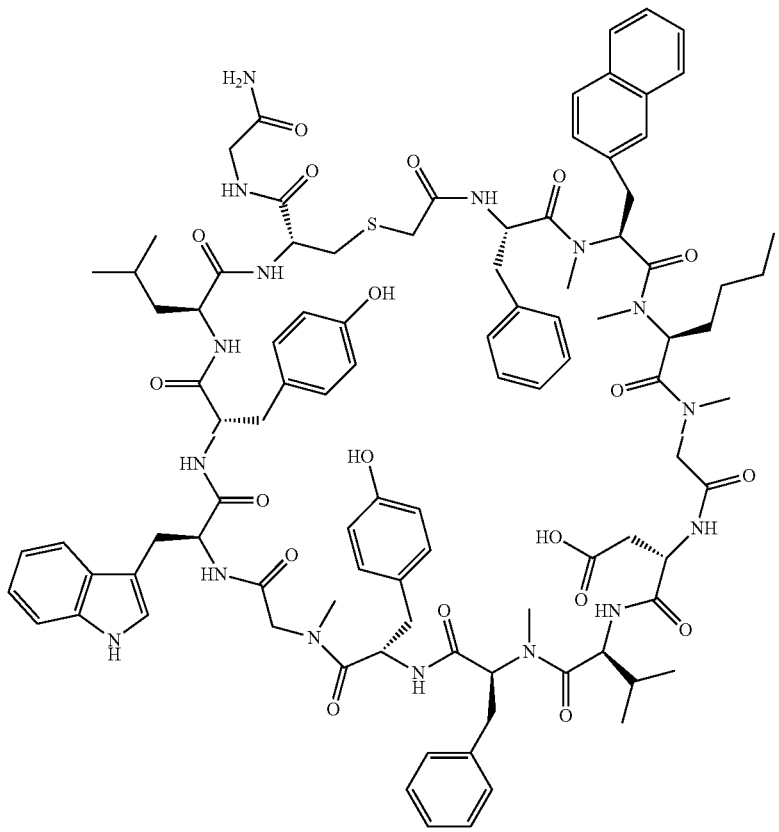

Example 3586

Example 3586 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetyl chloride coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 4.79 mg, and its estimated purity by HPLC analysis is 96.6% using the following conditions: Column: Phenom Jupiter 5 u C18 150×4.6 mm 300 A.; Mobile Phase A: 0.1% TFA in water; Mobile Phase B: 0.1% TFA in acetonitrile: 35-60% B over 15 min.; Flow: 1 mL/min. Detection UV: 217 nM, Oven: 40° C.

Analysis condition A: Retention time=1.47 min; ESI-MS (+) m/z 916.9 (M+2H).

Analysis LCMS condition C: Retention time=1.71 min; ESI-MS(+) m/z 1832.9 (M+H).

Preparation of Example 3588

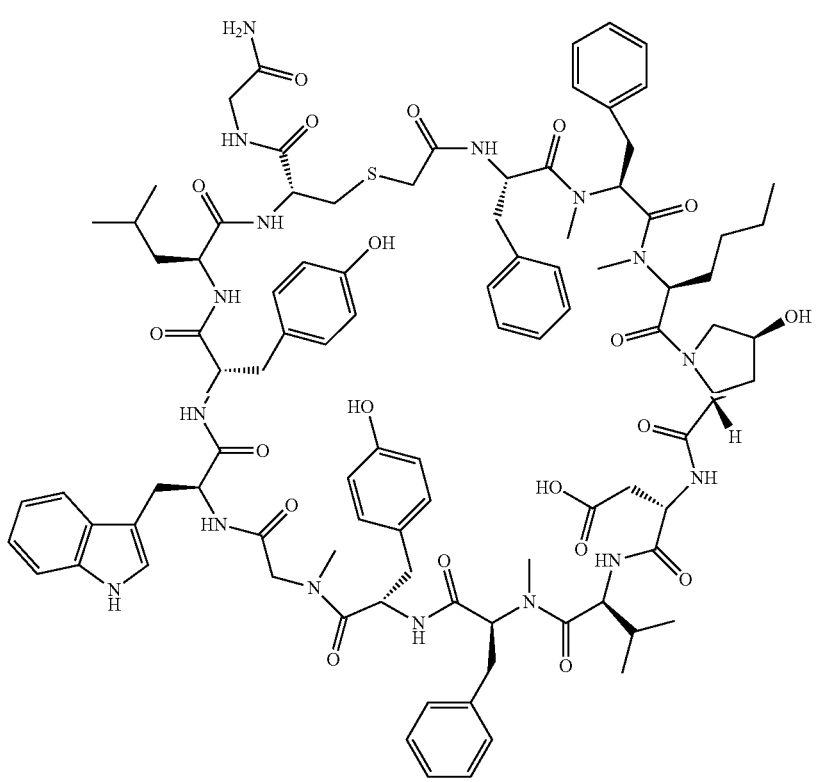

Example 3588

Example 3588 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 95% B; Flow: 15 mL/min. Fractions containing the desired product were combined and dried. The product was dissolved in a minimum if acetonitrile and water, frozen and lyophilized to give a white amorphous solid. The yield of product was 3.19 mg, and its estimated purity by HPLC analysis is 91.9% using the following conditions: Column: Phenom Jupiter 5 u C18 150×4.6 mm 300 A.; Mobile Phase A: 0.025% Ammonium Acetate in 5% methanol/water; Mobile Phase B: Acetonitrile/water (4:1): 30-60% B over 15 min.; Flow: 1 mL/min. Detection UV: 217 nM, Oven: 40° C.

Analysis condition A: Retention time=1.43 min; ESI-MS (+) m/z 920.0 (M+2H).

Analysis LCMS condition C: Retention time=1.65 min; ESI-MS(+) m/z 1838.3 (M+H).

Preparation of Example 3589

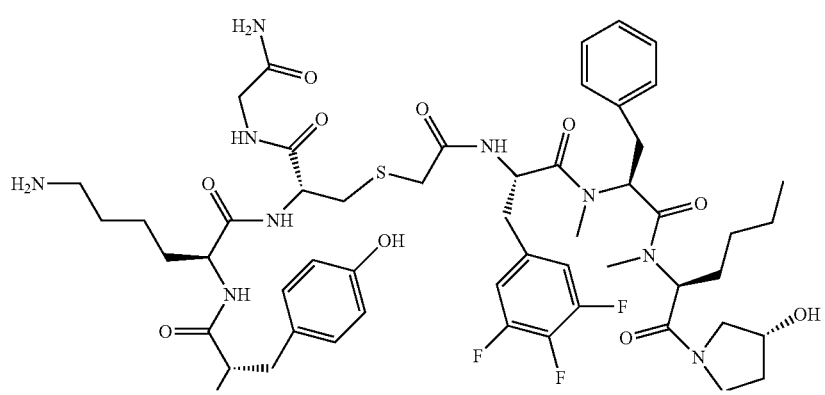

Example 3589

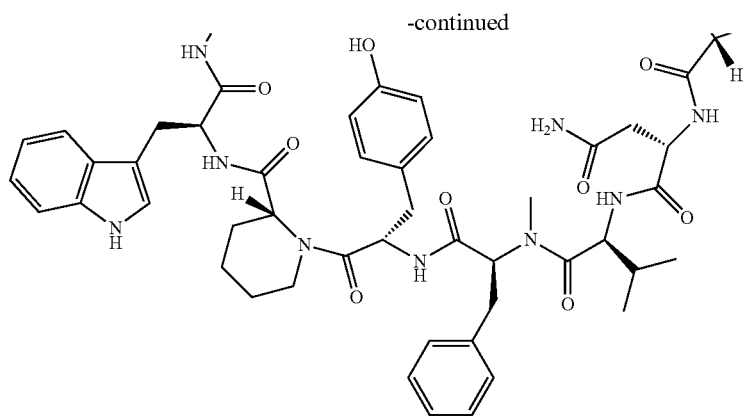

Example 3589 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.31 mg, and its estimated purity by LCMS analysis was 98.3%.

Analysis LCMS condition D: Retention time=1.69 min; ESI-MS(+) m/z 974.4 (M+2H).

Analysis LCMS condition E: Retention time=1.74 min; ESI-MS(+) m/z 973.7 (M+2H).

Preparation of Example 3590

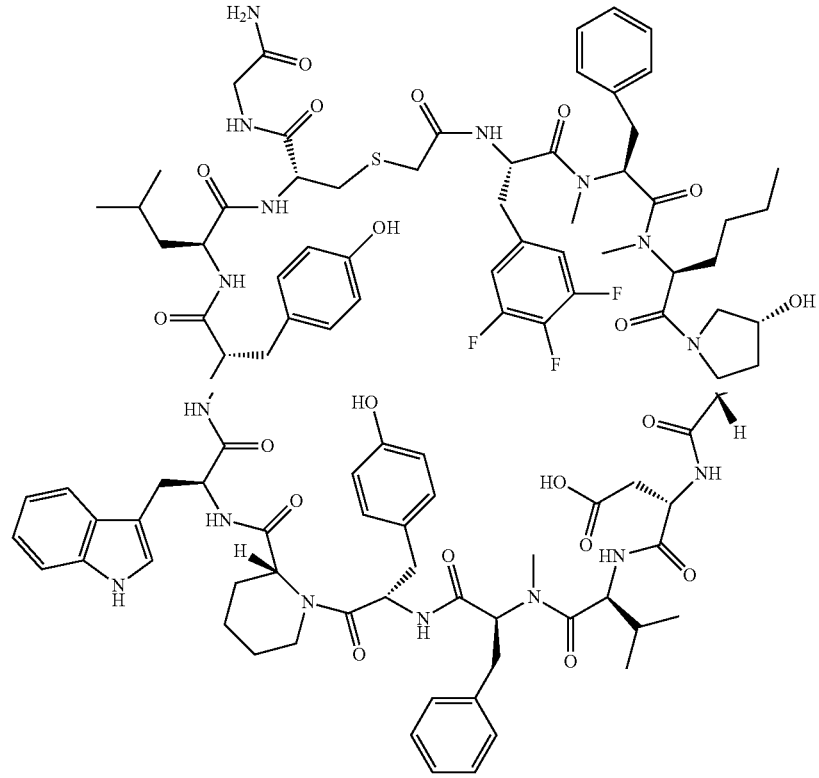

Example 3590

Example 3590 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.60 mg, and its estimated purity by LCMS analysis was 95.7%.

Analysis LCMS condition D: Retention time=1.74 min; ESI-MS(+) m/z 967.3 (M+2H).
Analysis LCMS condition E: Retention time=1.92 min; ESI-MS(+) m/z 966.7 (M+2H).

Preparation of Example 35901

Example 3591 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 10.21 mg, and its estimated purity by LCMS analysis was 100.0%.

Analysis LCMS condition D: Retention time=1.69 min; ESI-MS(+) m/z 973.8 (M+2H).
Analysis LCMS condition E: Retention time=1.74 min; ESI-MS(+) m/z 973.9 (M+2H).

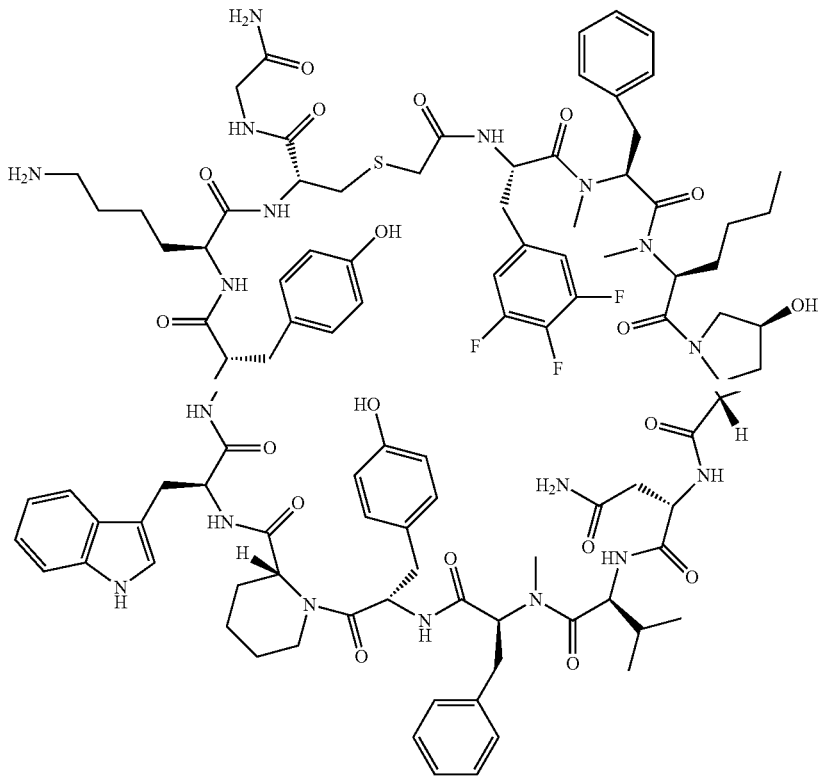

Example 3591

Preparation of Example 3592

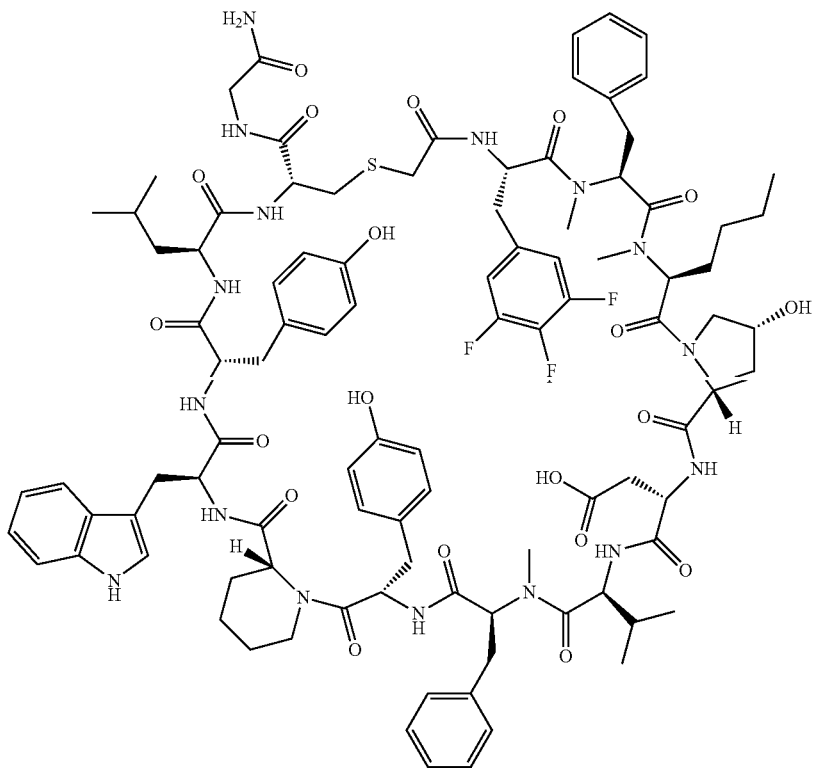

Example 3592

Example 3592 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.40 mg, and its estimated purity by LCMS analysis was 93.2%.

Analysis LCMS condition D: Retention time=1.73 min; ESI-MS(+) m/z 966.8 (M+2H).

Analysis LCMS condition E: Retention time=1.92 min; ESI-MS(+) m/z 966.9 (M+2H).

Preparation of Example 3593

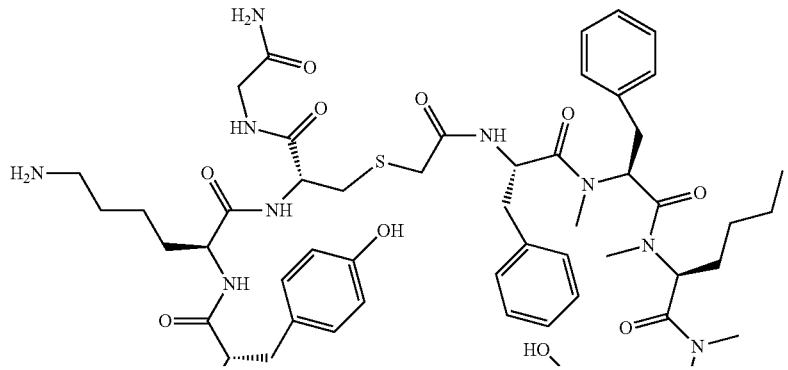

Example 3593

-continued

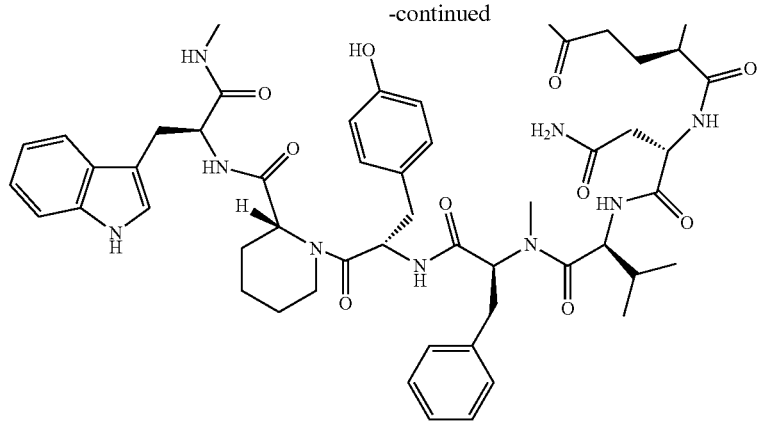

Example 3593 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 7.80 mg, and its estimated purity by LCMS analysis was 98.0%.

Analysis LCMS condition D: Retention time=1.49 min; ESI-MS(+) m/z 962.2 (M+2H).

Analysis LCMS condition E: Retention time=1.59 min; ESI-MS(+) m/z 962.2 (M+2H).

Preparation of Example 3594

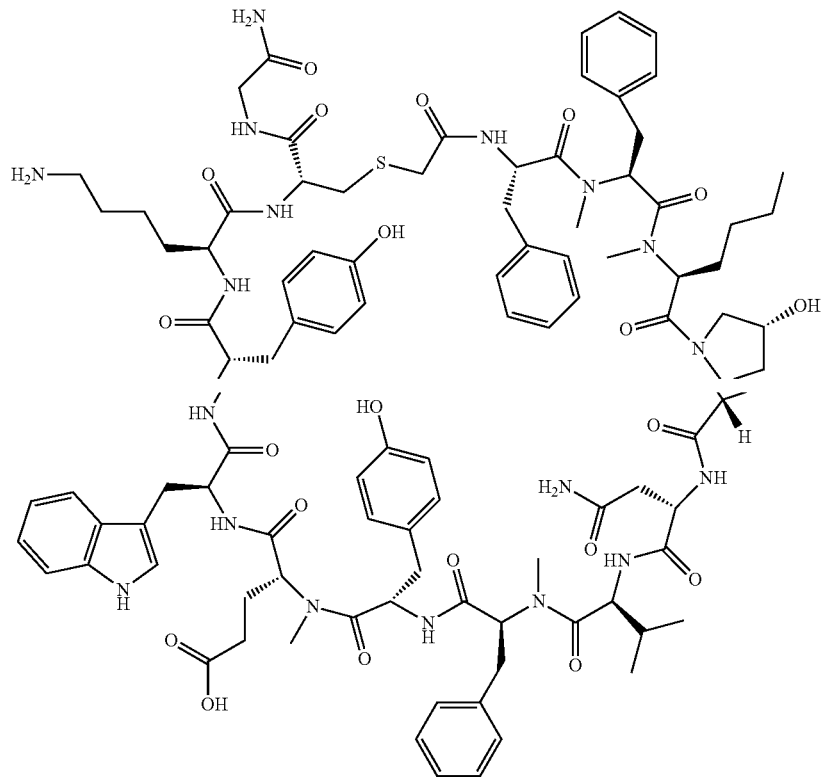

Example 3594

Example 3594 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 2.08 mg, and its estimated purity by HPLC analysis is 89.3% using the "Analysis conditions B"; 30-60% B over 15 min.; Flow: 1 mL/min. Detection UV: 217 nM, Oven: 40° C.

Analysis condition A: Retention time=1.29 min; ESI-MS (+) m/z 1925.6 (M+H).

Analysis LCMS condition C: Retention time=1.32 min; ESI-MS(+) m/z 1924.4 (M+H).

ESI-HRMS(+) m/z:
Calculated: 962.4605 (M+2H).
Found: 962.45821 (M+2H).

Example 3595 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 3.39 mg, and its estimated purity by HPLC analysis is 100% using the "Analysis conditions B"; 35-75% B over 15 min.; Flow: 1 mL/min. Detection UV: 217 nM, Oven: 40° C.

Analysis condition A: Retention time=1.67 min; ESI-MS (+) m/z 1925.4 (M(−Trt)+H).

Analysis LCMS condition C: Retention time=1.69 min; ESI-MS(+) m/z 1927.6 (M(−Trt)+H).

ESI-HRMS(+) m/z:
Calculated: 1083.5153 (M+2H).
Found: 1083.51169 (M+2H).

Preparation of Example 3595

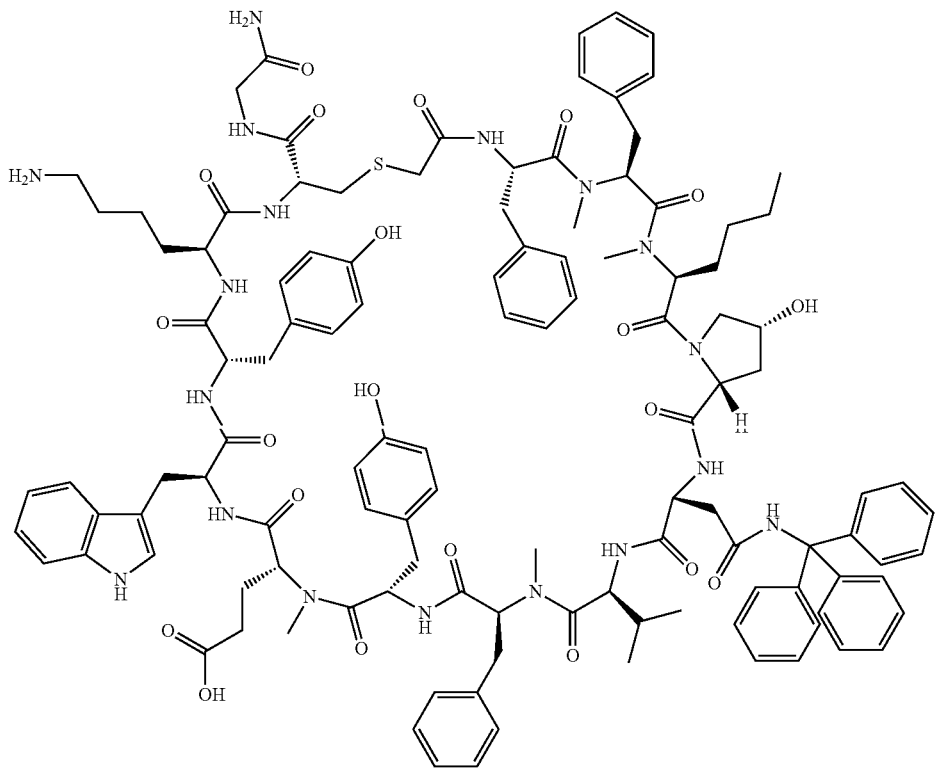

Example 3595

Preparation of Example 3596

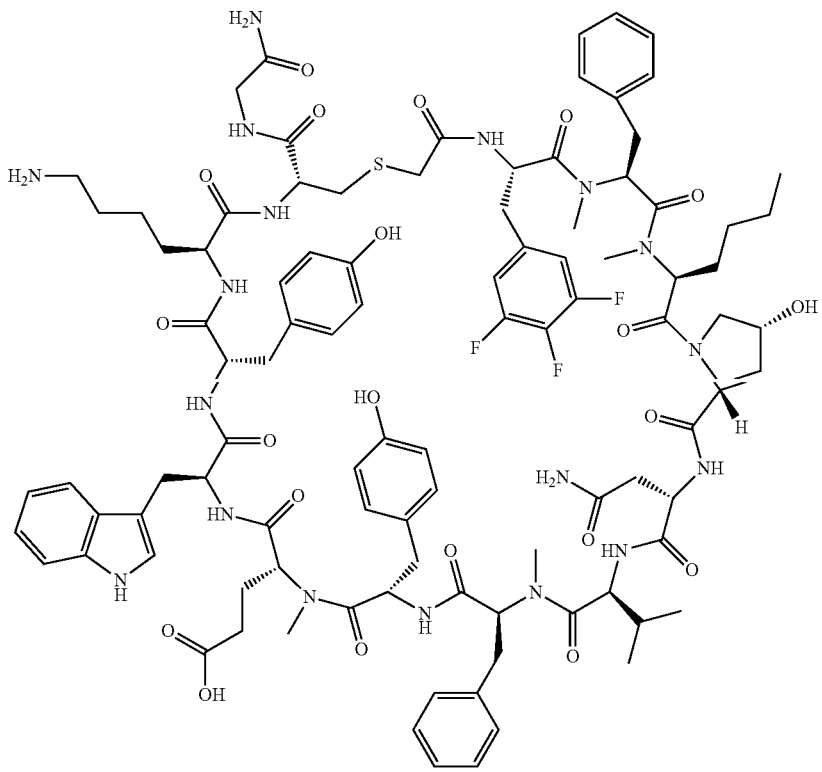

Example 3596

Example 3596 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative HPLC with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 2.52 mg, and its estimated purity by HPLC analysis is 90.6% using the following conditions: Column: Phenom Jupiter 5 u C18 150×4.6 mm 300 A.; Mobile Phase A: 0.1% TFA in water; Mobile Phase B: 0.1% TFA in acetonitrile: 35-60% B over 25 min.; Flow: 1 mL/min. Detection UV: 217 nM.

Analysis condition A: Retention time=1.35 min; ESI-MS (+) m/z 1978.3 (M+H).

Analysis LCMS condition C: Retention time=1.39 min; ESI-MS(+) m/z 1979.4 (M+H).

Preparation of Example 3597

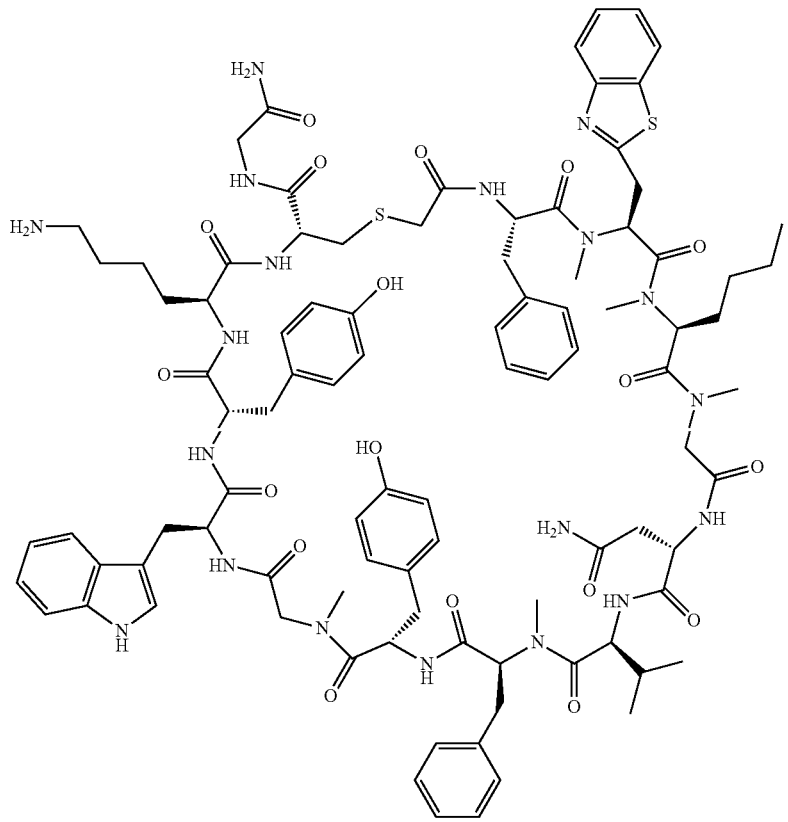

Example 3597

Example 3597 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. Two isomeric products were isolated. The yield of isomer A was 3.40 mg, and its estimated purity by LCMS analysis was 98.9%.

Analysis LCMS condition D: Retention time=1.53 min; ESI-MS(+) m/z 920.0 (M+2H).

Analysis LCMS condition E: Retention time=1.54 min; ESI-MS(+) m/z 920.4 (M+2H).

The yield of isomer B was 4.50 mg, and its estimated purity by LCMS analysis was 98.4%.

Analysis LCMS condition D: Retention time=1.72 min; ESI-MS(+) m/z 920.5 (M+2H).

Analysis LCMS condition E: Retention time=1.74 min; ESI-MS(+) m/z 920.2 (M+2H).

Preparation of Example 3598

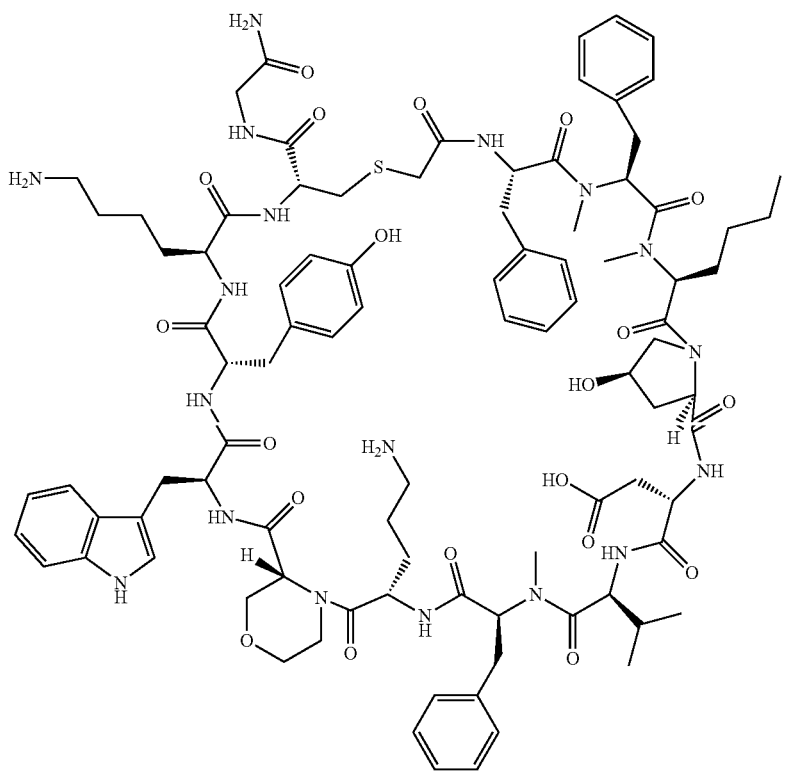

Example 3598

Example 3598 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 4.45 mg, and its estimated purity by LCMS analysis was 95.7%.

Analysis LCMS condition D: Retention time=1.67 min; ESI-MS(+) m/z 944.0 (M+2H).

Analysis LCMS condition E: Retention time=1.65 min; ESI-MS(+) m/z 943.7 (M+2H).

Preparation of Example 3599

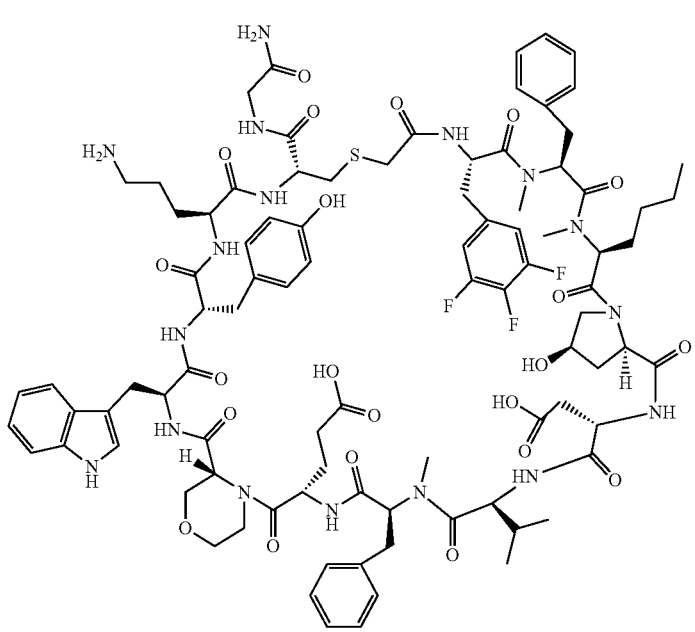

Example 3599

Example 3599 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 3.01 mg, and its estimated purity by LCMS analysis was 92.7%.

Analysis LCMS condition D: Retention time=1.63 min; ESI-MS(+) m/z 951.7 (M+2H).

Analysis LCMS condition E: Retention time=1.75 min; ESI-MS(+) m/z 951.7 (M+2H).

Preparation of Example 3600

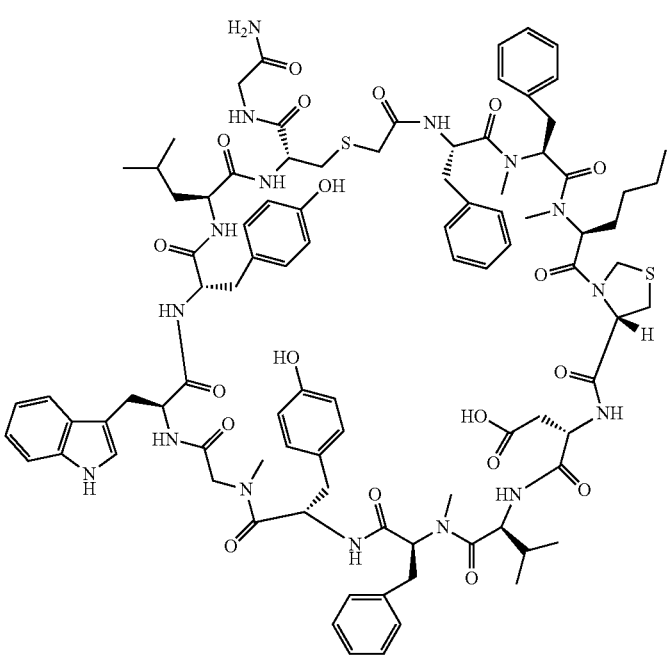

Example 3600

Example 3600 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 5.40 mg, and its estimated purity by LCMS analysis was 95.4%.

Analysis LCMS condition D: Retention time=1.73 min; ESI-MS(+) m/z 921.2 (M+2H).

Analysis LCMS condition E: Retention time=1.75 min; ESI-MS(+) m/z 920.6 (M+2H).

Preparation of Example 3601

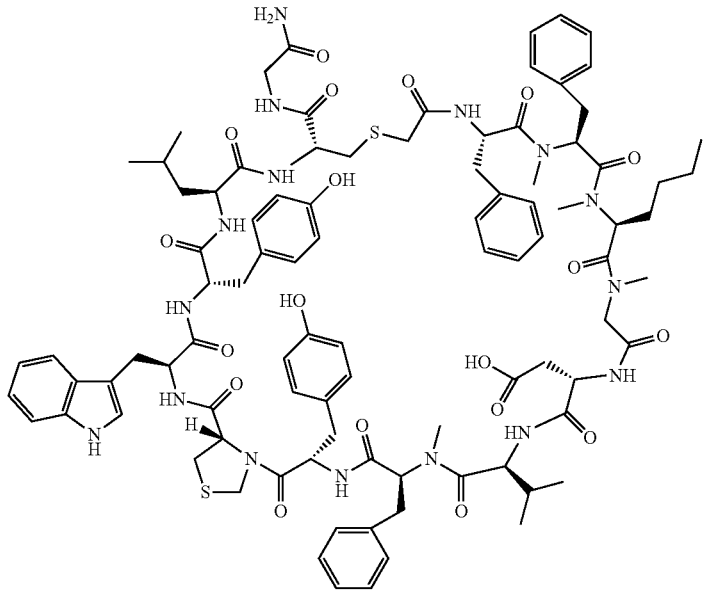

Example 3601

Example 3601 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 5.30 mg, and its estimated purity by LCMS analysis was 96.0%.

Analysis LCMS condition D: Retention time=1.66 min; ESI-MS(+) m/z 920.8 (M+2H).

Analysis LCMS condition E: Retention time=1.87 min; ESI-MS(+) m/z 920.9 (M+2H).

Preparation of Example 3602

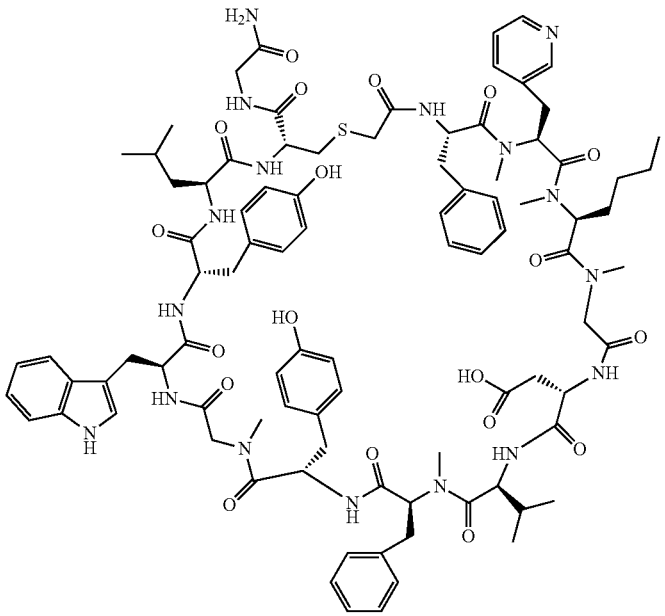

Example 3602

Example 3602 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 35 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 0.99 mg, and its estimated purity by HPLC analysis is 96% using the following conditions: Column: YMC Pack ODS-AQ 3 um 150×; Mobile Phase A: 0.025 Ammonium Acetate/acetonitrile (8:2); Mobile Phase B: 0.025% Ammonium Acetate/acetonitrile (2:8): 30-60% B over 15 min.; Flow: 1 mL/min. Detection UV: 217 nM. Oven 40° C.

Analysis LCMS condition C: Retention time=1.35 min; ESI-MS(+) m/z 1783.0 (M+H).

Analysis condition A: Retention time=1.27 min; ESI-MS (+) m/z 1783.8 (M+H).

Preparation of Example 3603

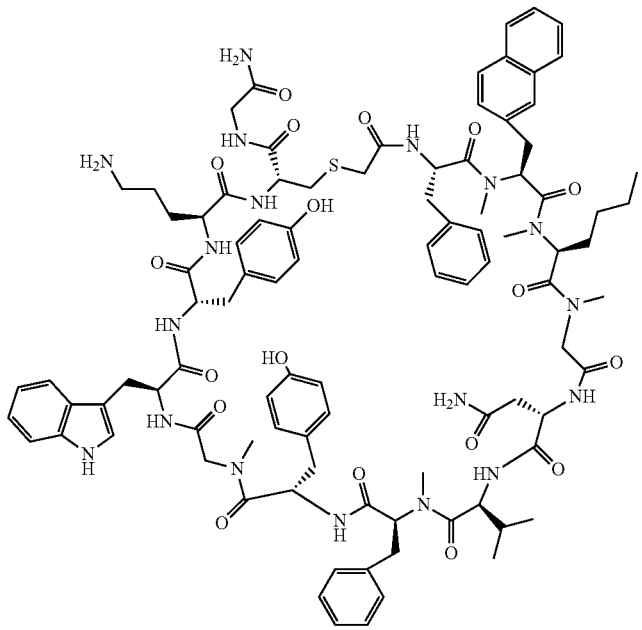

Example 3603

Example 3603 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "N-Methylation on-resin procedure" for the N-methylation of the Fmoc-2-Nal-OH, "Chloroacetic acid coupling procedure A", "Global Deprotection Method B", and "Cyclization Method C".

The crude material was purified via preparative LC/MS with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 0.89 mg, and its estimated purity by HPLC analysis is 100% using the "Analysis conditions C": 30-60% B over 15 min.; Flow: 1 mL/min. Detection UV: 217 nM. Oven 40° C.

Analysis LCMS condition C: Retention time=1.36 min; ESI-MS(+) m/z 1845.8 (M+H).

Analysis condition A: Retention time=1.33 min; ESI-MS (+) m/z 1847.5 (M+H).

Preparation of Example 3604

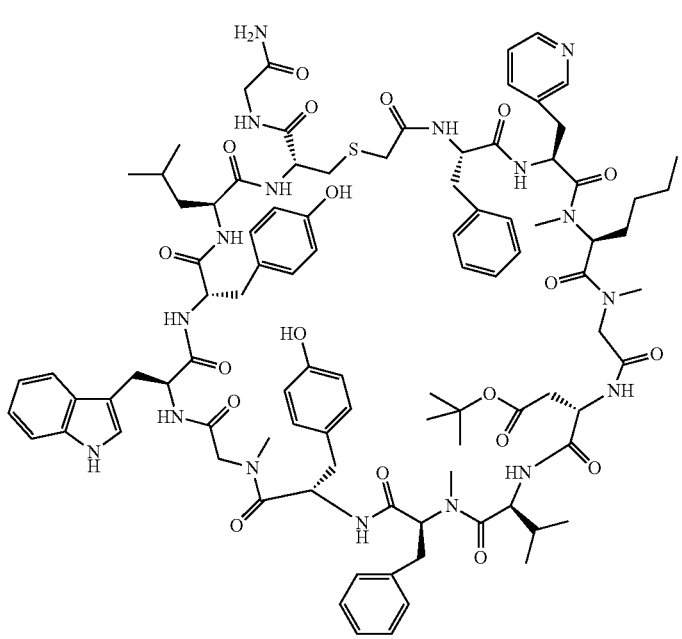

Example 3604

Example 3604 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: PHENOMENEX® Luna 5 u C18(2) 250×21.2 AXIA, 100 A Ser.#520221-1; Mobile Phase A: 0.1% TFA in water; Mobile Phase B: 0.1% TFA in acetonitrile; Gradient: 35-75% B over 40 min., then a 5-minute gradient up to 85% B; Flow: 15 mL/min. Fractions containing the desired product were combined and dried. The product was dissolved in a minimum if acetonitrile and water, frozen and lyophilized to give a white amorphous solid. The yield of product was 1.10 mg, and its estimated purity by HPLC analysis is 96% using the following conditions: Column: Phenom Jupiter 5 u C18 150×4.6 mm 300 A.; Mobile Phase A: 0.1% TFA in water; Mobile Phase B: 0.1% TFA in acetonitrile: 35-60% B over 25 min.; Flow: 1 mL/min. Detection UV: 217 nM. Oven 40° C.

Analysis LCMS condition C: Retention time=1.51 min; ESI-MS(+) m/z 1839.9 (M+H).

Preparation of Example 3605

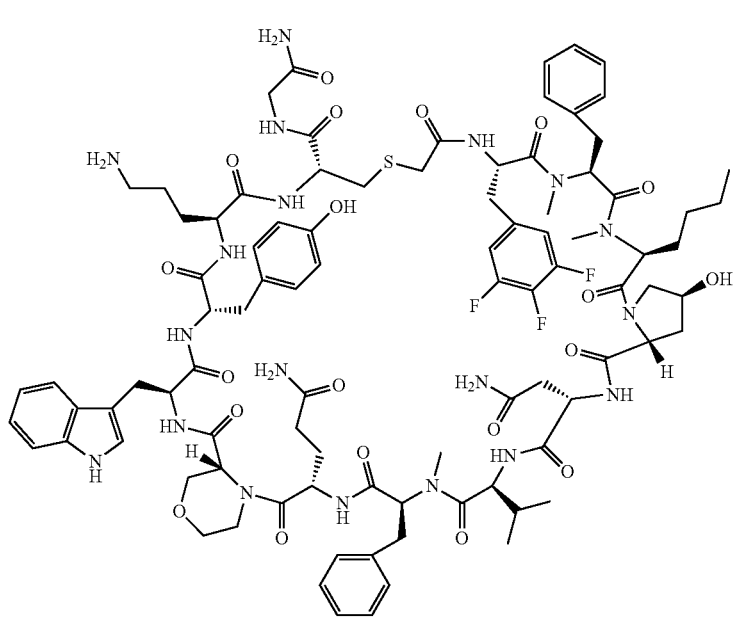

Example 3605

Example 3605 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 6.50 mg, and its estimated purity by LCMS analysis was 93.8%.

Analysis LCMS condition D: Retention time=1.75 min; ESI-MS(+) m/z 950.5 (M+2H).

Analysis LCMS condition E: Retention time=1.77 min; ESI-MS(+) m/z 950.5 (M+2H).

Preparation of Example 3606

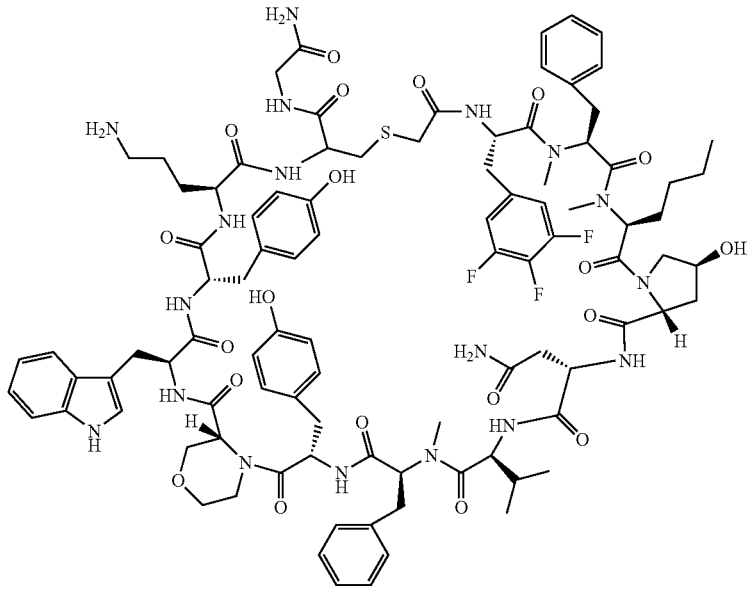

Example 3606

Example 3606 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 4.07 mg, and its estimated purity by LCMS analysis was 92.5%.

Analysis LCMS condition D: Retention time=1.73 min; ESI-MS(+) m/z 967.4 (M+2H).

Analysis LCMS condition E: Retention time=1.75 min; ESI-MS(+) m/z 967.5 (M+2H).

Preparation of Example 3607

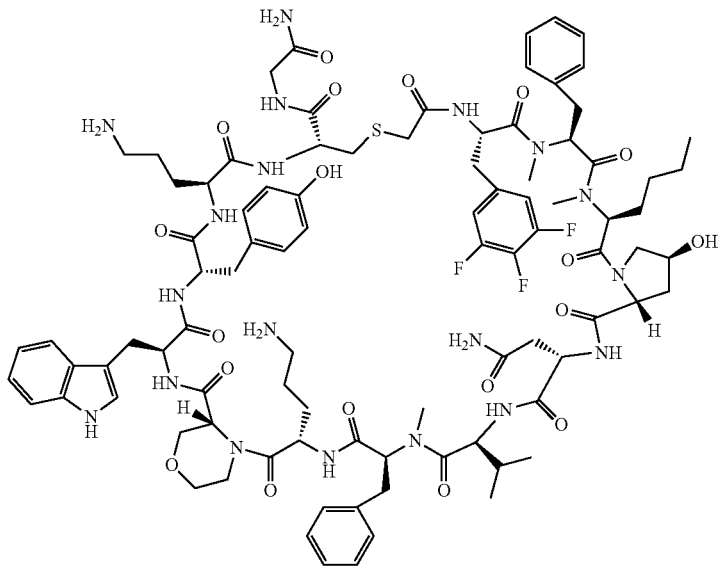

Example 3607

Example 3607 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 3.8 mg, and its estimated purity by LCMS analysis was 96.2%.

Analysis LCMS condition D: Retention time=1.56 min; ESI-MS(+) m/z 943.3 (M+2H).

Analysis LCMS condition E: Retention time=1.61 min; ESI-MS(+) m/z 943.2 (M+2H).

Preparation of Example 3608

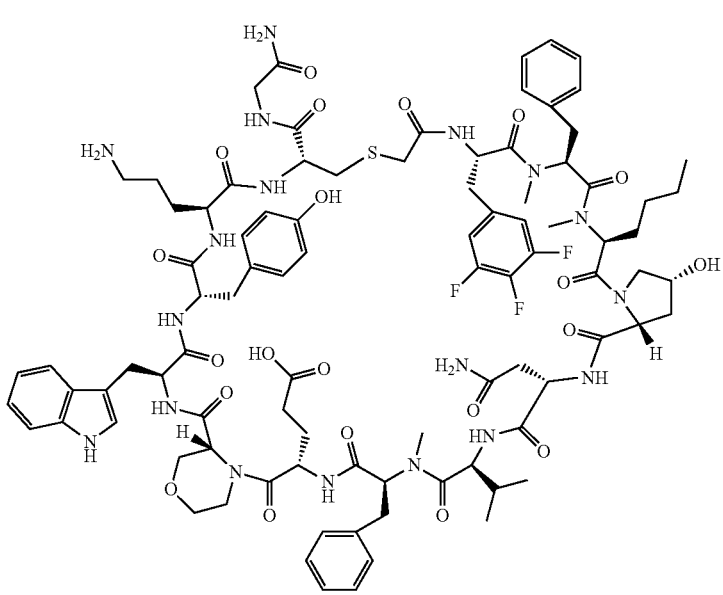

Example 3608

Example 3608 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 1.49 mg, and its estimated purity by LCMS analysis was 91.1%.

Analysis LCMS condition D: Retention time=1.69 min; ESI-MS(+) m/z 950.6 (M+2H).

Analysis LCMS condition E: Retention time=1.70 min; ESI-MS(+) m/z 950.7 (M+2H).

ESI-HRMS(+) m/z:
Calculated: 950.4230 (M+2H).
Found: 950.4200 (M+2H).

Preparation of Example 3609

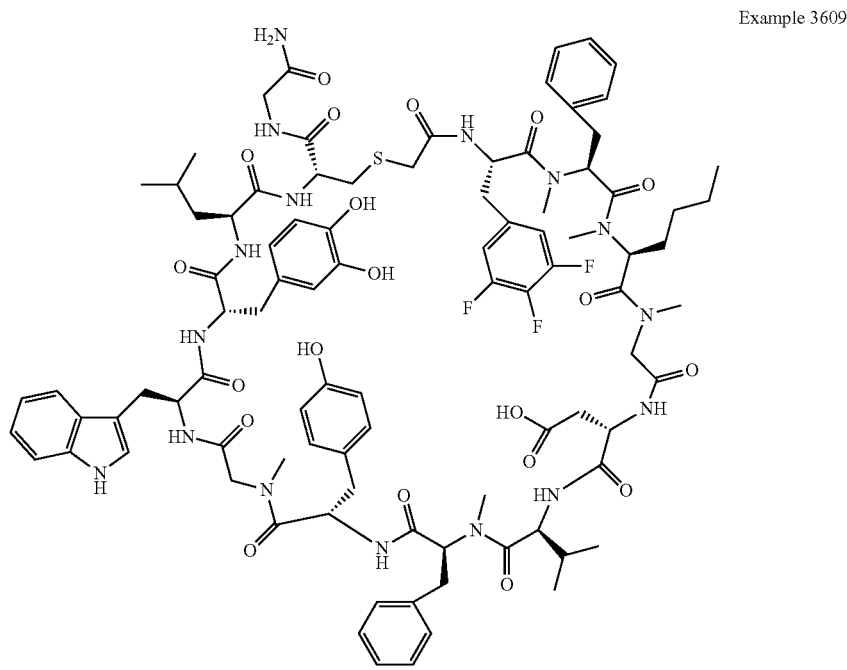 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)c(O)c2)C(=O)N[C@@H](CC(C)C)C(=O)N[C@H](C(=O)NCC(N)=O)CSCC(=O)N[C@@H](Cc2cc(F)c(F)c(F)c2)C(=O)N(C)[C@@H](Cc2ccccc2)C(=O)N1C]

Example 3609

Example 3609 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 0.39 mg, and its estimated purity by LCMS analysis was 91.5%.

Analysis LCMS condition D: Retention time=1.67 min; ESI-MS(+) m/z 934.1 (M+2H).

Analysis LCMS condition E: Retention time=1.86 min; ESI-MS(+) m/z 934.0 (M+2H).

ESI-HRMS(+) m/z:
Calculated: 933.4146 (M+2H).
Found: 933.4126 (M+2H).

Preparation of Example 3610

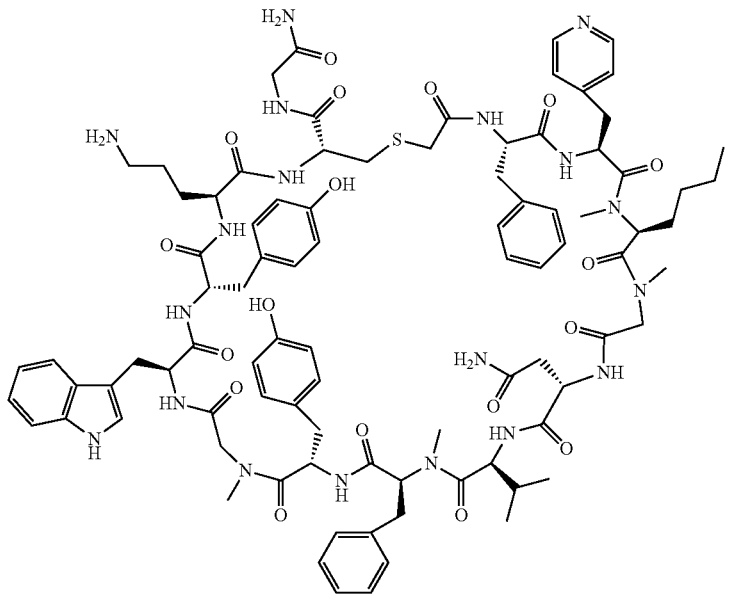

Example 3610

Example 3610 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 14.79 mg, and its estimated purity by LCMS analysis was 96.0%.

Analysis LCMS condition D: Retention time=1.46 min; ESI-MS(+) m/z 892.0 (M+2H).

Analysis LCMS condition E: Retention time=1.40 min; ESI-MS(+) m/z 892.0 (M+2H).

ESI-HRMS(+) m/z:

Calculated: 891.9267 (M+2H).

Found: 891.9229 (M+2H).

Preparation of Example 3611

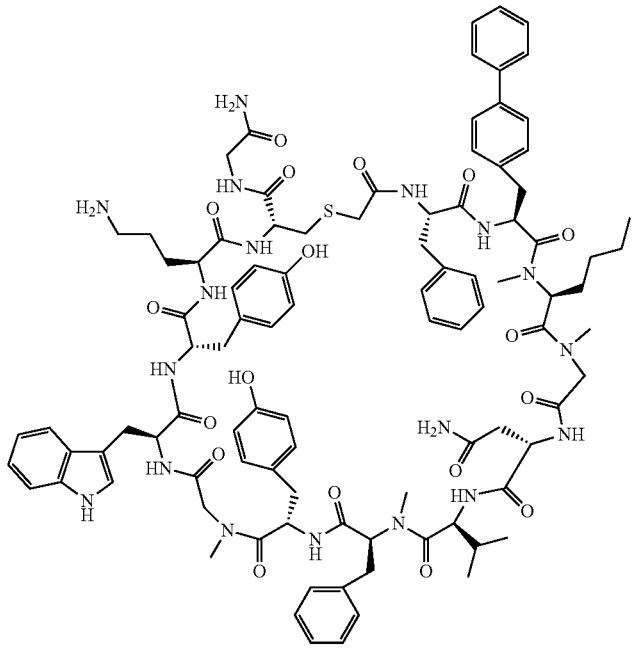

Example 3611

Example 3611 was prepared following the general synthetic sequence described for the preparation of Example 3026, composed of the following general procedures: "CEM Method A: Resin-swelling procedure", "CEM Method A: Standard coupling procedure", "CEM Method A: Custom amino acids-coupling procedure", "Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 25.53 mg, and its estimated purity by LCMS analysis was 100.0%.

Analysis LCMS condition D: Retention time=1.68 min; ESI-MS(+) m/z 929.7 (M+2H).

Analysis LCMS condition E: Retention time=1.70 min; ESI-MS(+) m/z 929.7 (M+2H).

ESI-HRMS(+) m/z:

Calculated: 929.4447 (M+2H).

Found: 929.4428 (M+2H).

Preparation of Example 3613

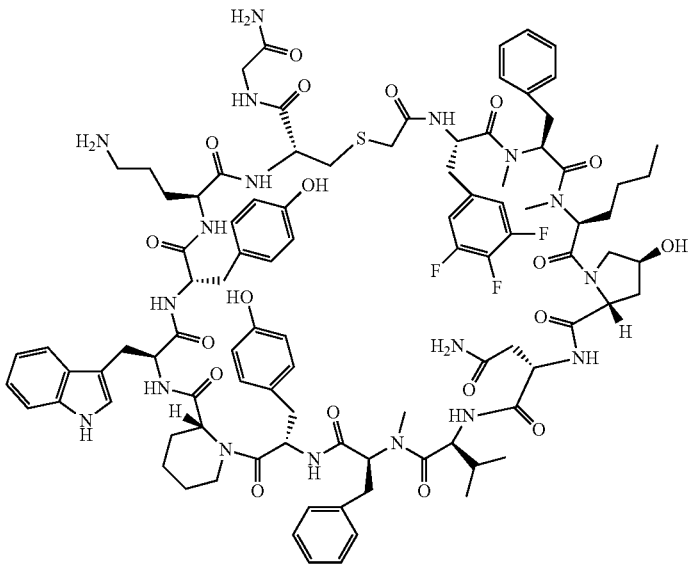

Example 3613

Example 3613 was prepared following the general synthetic sequence described for the preparation of Example 72, composed of the following general procedures: "Prelude Method A: Resin-swelling procedure", "Prelude Method A: Single-coupling procedure", "Prelude Method A: Secondary amine-coupling procedure", "Prelude Method A: Chloroacetic acid coupling procedure A", "Global Deprotection Method B", and "Cyclization Method C".

The crude material was purified via preparative LC/MS with the following conditions: Column: XBridge C18 300, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 25 min., then a 5-minute hold at 100% B; Flow: 20 mL/min. Fractions containing the desired product were combined and dried. The yield of product was 4.93 mg, and its estimated purity by LCMS analysis was 95.5%.

Analysis LCMS condition D: Retention time=1.74 min; ESI-MS(+) m/z 966.9 (M+2H).

Analysis LCMS condition E: Retention time=1.76 min; ESI-MS(+) m/z 966.8 (M+2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:

Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:

Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis Condition C:

Column: Waters AQUITY® BEH C18 2.1×50 mm 1.7 μm particles; Mobile Phase A: water with 0.05% TFA; Mobile Phase B: acetonitrile with 0.05% TFA; Temperature: 40° C.; Gradient: 0% B, 0-100% B over 1.5 minutes, then a 0.5-minute hold at 100% B; Flow: 0.8 mL/min; Detection: UV at 220 nm.

General Procedures:

Prelude Method A:

All manipulations were performed under automation on a Prelude peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisoprop- ylethylamine; Rink=(2,4-dimethoxyphenyl)(4-alkoxyphenyl)methanamine, where "4-alkoxy" describes the position and type of connectivity to the polystyrene resin. The resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis.

Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures of "Prelude Method A" describe an experiment performed on a 0.100 mmol scale, where the scale is determined by the amount of Rink linker bound to the resin. This scale corresponds to approximately 178 mg of the Rink-Merrifield resin described above. All procedures can be scaled beyond 0.100 mmol scale by adjusting the described volumes by the multiple of the scale. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

To a 10 mL polypropylene solid-phase reaction vessel was added Merrifield:Rink resin (178 mg, 0.100 mmol). The resin washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin washed successively four times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin washed successively six times as follows: for each wash, DMF (2.0 mL) was added through the top of the vessel and the resulting mixture was periodically agitated for 30 seconds before the solution was drained through the frit. To the reaction vessel was added DIPEA (0.8M in DMF, 3.0 mL, 24 eq), then chloroacetyl chloride (0.8M in DMF, 1.65 mL, 13.2 eq). The mixture was periodically agitated for 30 minutes, then the solution was drained through the frit. The resin washed successively three times as follows: for each wash, DMF (2.0 mL) was added to top of the vessel and the resulting mixture was periodically agitated for 90 seconds before the solution was drained through the frit. The resin washed successively four times as follows: for each wash, $CH_2Cl_2$ (2.0 mL) was added to top of the vessel and the resulting mixture was periodically agitated for 90 seconds before the solution was drained through the frit. The resulting resin was placed under a $N_2$ stream for 15 minutes.

Symphony Method A:

This collection of procedures is identical that of "Prelude Method A" except as noted. For all procedures a Symphony X peptide synthesizer (Protein Technologies) was used instead of a Prelude peptide synthesizer and all reagents were added through the top of the reaction vessel.

Resin-Swelling Procedure:

This procedure is identical to "Prelude Method A: Resin-swelling procedure".

Single-Coupling Procedure:

This procedure is identical to "Prelude Method A: Single-coupling procedure" except that the concentration of DIPEA solution was 0.4M and 1.0 mL of this solution was delivered to the reaction.

Double-Coupling Procedure:

This procedure is identical to "Prelude Method A: Double-coupling procedure" except that the concentration of DIPEA solution was 0.4M and 1.0 mL of this solution was delivered to the reaction.

Chloroacetyl Chloride Coupling Procedure:

This procedure is identical to "Prelude Method A: Chloroacetyl chloride coupling procedure".

Global Deprotection Method A:

All manipulations were performed manually unless noted. The procedure of "Global Deprotection Method A" describes an experiment performed on a 0.100 mmol scale, where the scale is determined by the amount of Rink linker bound to the resin. The procedure can be scaled beyond 0.100 mmol scale by adjusting the described volumes by the multiple of the scale. A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 1-2 h). The mixture was filtered through a 0.2 micron syringe filter and the solids were extracted with the "deprotection solution" (1.0 mL) or TFA (1.0 mL). To a 24 mL test tube charged with the combined filtrates was added Et$_2$O (15 mL). The mixture was vigorously mixed upon which a significant amount of a white solid precipitated. The mixture was centrifuged for 5 minutes, then the solution was decanted away from the solids and discarded. The solids were suspended in Et$_2$O (20 mL); then the mixture was centrifuged for 5 minutes; and the solution was decanted away from the solids and discarded. For a final time, the solids were suspended in Et$_2$O (20 mL); the mixture was centrifuged for 5 minutes; and the solution was decanted away from the solids and discarded to afford the crude peptide as a white to off-white solid.

Cyclization Method A:

All manipulations were performed manually unless noted. The procedure of "Cyclization Method A" describes an experiment performed on a 0.100 mmol scale, where the scale is determined by the amount of Rink linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in MeCN: aq. 0.1M NH$_4$OAc (30 mL:30 mL), and the solution was then carefully adjusted to pH=8.5-9.0 using aq NaOH (1.0M). The solution was then allowed to stand without stirring for 12-18 h. The reaction solution was concentrated and the residue was then dissolved in DMSO:MeOH. This solution was subjected to reverse-phase HPLC purification to afford the desired cyclic peptide.

Cyclization Method B:

All manipulations were performed manually unless noted. The procedure of "Cyclization Method B" describes an experiment performed on a 0.100 mmol scale, where the scale is determined by the amount of Rink linker bound to the resin that was used to generate the peptide. This scale is not based on a direct determination of the quantity of peptide used in the procedure. The procedure can be scaled beyond 0.100 mmol scale by adjusting the described volumes by the multiple of the scale. The crude peptide solids were dissolved in MeCN: aq. 0.1M NH$_4$OAc (1:1) to a total volume of 18-22 mL, and the solution was carefully then adjusted to pH=8.5-9.0 using aq NaOH (1.0M). The solution was then allowed to stand without stirring for 12-18 h. The reaction solution was concentrated and the residue was then dissolved in DMSO: MeOH. This solution was subjected to reverse-phase HPLC purification to afford the desired cyclic peptide.

General Synthetic Sequence A:

"General Synthetic Sequence A" describes a general sequence of procedures that were used to afford the cyclic peptides described herein. For the purposes of this general procedure, the procedures of "Symphony Method A" are interchangeable with those of "Prelude Method A". To a 10 mL polypropylene solid-phase reaction vessel was added Rink-Merrifield resin (178 mg, 0.100 mmol), and the reaction vessel was placed on the Prelude peptide synthesizer. "Prelude Method A: Resin-swelling procedure" was followed. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine. "Prelude Method A: Chloroacetyl chloride coupling procedure" was followed; then "Global Deprotection Method A" was followed; then "Cyclization Method A" was followed.

Preparation of (S)-2-((((9H-fluoren-9-yl)methoxy)carbonyl)([$^{13}$C]methyl)amino)hexanoic acid Scheme:

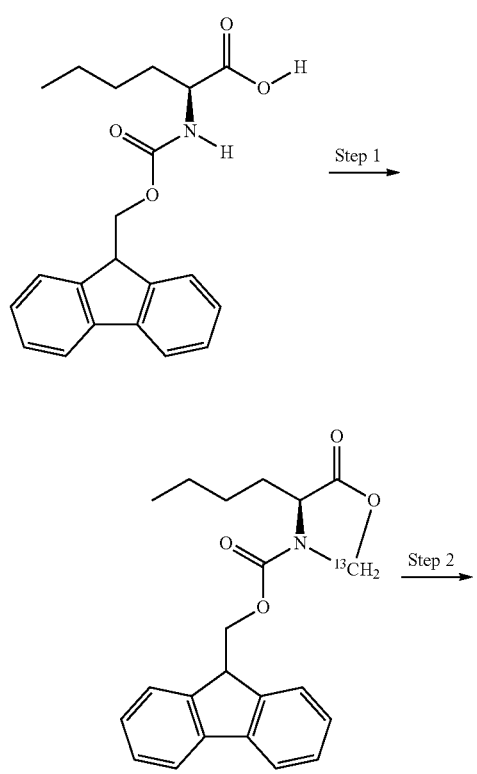

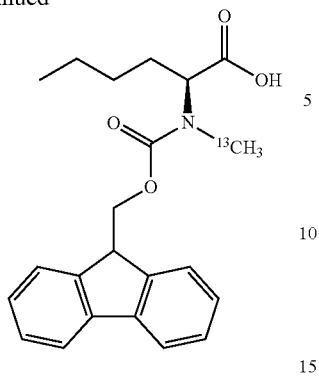

Step 1:

A mixture containing paraformaldehyde($^{13}$C labeled) (500 mg, 16.65 mmol), (S)-2-((((9H-fluoren-9-yl)methoxy)carbonyl)amino)hexanoic acid (4527 mg, 12.81 mmol), and p-toluenesulfonic acid (221 mg, 1.281 mmol) was refluxed in toluene (100 mL) for 2 hrs. The reaction was then cooled to RT, washed with sat. sodium bicarbonate solution, followed by brine, dried with MgSO$_4$, filtered and evaporated to get the product from step 1 (4.694 g, 12.81 mmol) as a yellow oil. Yield was assumed to be 100%. ESI-MS(+) m/z=389.2 (M+Na)

Step 2:

The entirety of the product from step 1 (4.694 g, 12.83 mmol) was dissolved in CHCl$_3$ (40 mL) and to the solution was added triethylsilane (10.24 mL, 64.1 mmol) followed by TFA (10 mL, 130 mmol). The solution was stirred at RT under positive pressure of N$_2$ for 18 hrs. Volatiles were removed in vacuo to afford a sticky oil. The oil was dissolved in EtOAc and then extracted with sat. sodium bicarbonate (2×100 mL). Solids at the phase interface were collected with the aqueous phase. The aqueous phase was adjusted with aq. HCl to pH 4-5. A white solid precipitated near the end point of pH adjustment. The mixture was extracted with EtOAc (200 mL) and the organic phase washed with brine, dried over MgSO$_4$, filtered and concentrated to afford the pure product (S)-2-((((9H-fluoren-9-yl)methoxy)carbonyl)([$^{13}$C]methyl)amino)hexanoic acid (3 g, 8.14 mmol, 63.5% yield) as a white solid. $^1$H NMR (400 MHz, CDCl$_3$) d 7.78 (d, J=7.1 Hz, 2H), 7.66-7.52 (m, 2H), 7.41 (d, J=6.8 Hz, 2H), 7.33 (d, J=6.1 Hz, 2H), 4.84-4.59 (m, 1H), 4.55-4.40 (m, 2H), 4.34-4.17 (m, 1H), 3.16-2.98 (m, 1H), 2.71 (br. s., 1H), 1.77 (br. s., 1H), 1.44-1.14 (m, 5H), 0.91 (d, J=7.3 Hz, 3H). ESI-MS(+) m/z=369.4 (M+H)

Preparation of (S)-2-((((9H-fluoren-9-yl)methoxy)carbonyl)([$^{13}$C]methyl)amino)propanoic acid Scheme:

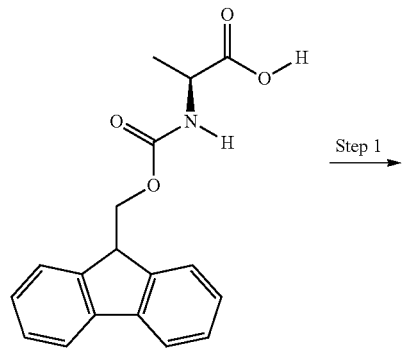

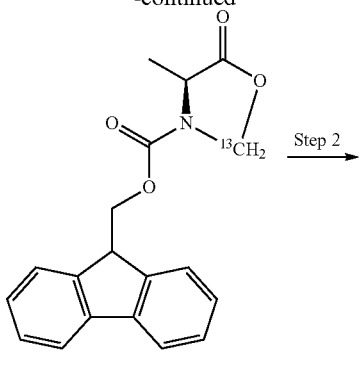

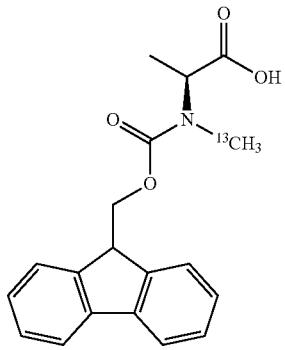

Step 1:

A mixture containing paraformaldehyde(C13 labeled) (250 mg, 8.33 mmol), (S)-2-((((9H-fluoren-9-yl)methoxy)carbonyl)amino)propanoic acid (1994 mg, 6.40 mmol), and p-toluene sulfonic acid (110 mg, 0.640 mmol) was refluxed in toluene (50 mL) for 2 hrs. The reaction was then cooled to RT, washed with sat. sodium bicarbonate solution, followed by brine, dried with MgSO$_4$, filtered and evaporated to get the product from step 1 (2.08 g, 6.41 mmol) as a yellow oil. The yield assumed to be 100%. ESI-MS(+) m/z=348.1 (M+Na)

Step 2:

The entirety of the product from step 1 (2.08 g, 6.41 mmol) was dissolved in CHCl$_3$ (20 mL) and to the solution was added triethylsilane (5.12 mL, 32.1 mmol) followed by TFA (4.94 mL, 64.1 mmol). The solution was stirred at RT under positive pressure of N$_2$ for 18 hrs. The volatiles were removed to afford a sticky oil. The oil was dissolved in EtOAc and then extracted with sat. sodium bicarbonate (2×100 mL). Solids at the phase interface were collected with the aqueous phase. The aqueous phase was adjusted to pH 4-5 using aq. HCl. A white solid precipitated near the end point of the pH adjustment. The mixture was extracted with EtOAc (200 mL) and the organic phase washed with brine, dried over MgSO$_4$, filtered and concentrated to afford the pure product (S)-2-((((9H-fluoren-9-yl)methoxy)carbonyl)([$^{13}$C]methyl)amino)propanoic acid (1 g, 3.06 mmol, 47.8% yield) as a white solid. $^1$H NMR (400 MHz, chloroform-d) d 7.79 (d, J=7.3 Hz, 2H), 7.62 (br. s., 2H), 7.43 (t, J=7.2 Hz, 2H), 7.34 (t, J=7.3 Hz, 2H), 4.88 (br. s., 1H), 4.52-4.37 (m, 2H), 4.29 (d, J=6.1 Hz, 1H), 3.11 (s, 1H), 2.76 (s, 2H), 1.49 (d, J=6.8 Hz, 2H), 1.39 (br. s., 1H). ESI-MS(+) m/z=349.2 (M+H)

Preparation of (2S,5S)-1-(((9H-fluoren-9-yl)methoxy)carbonyl)-5-hydroxypiperidine-2-carboxylic acid Scheme:

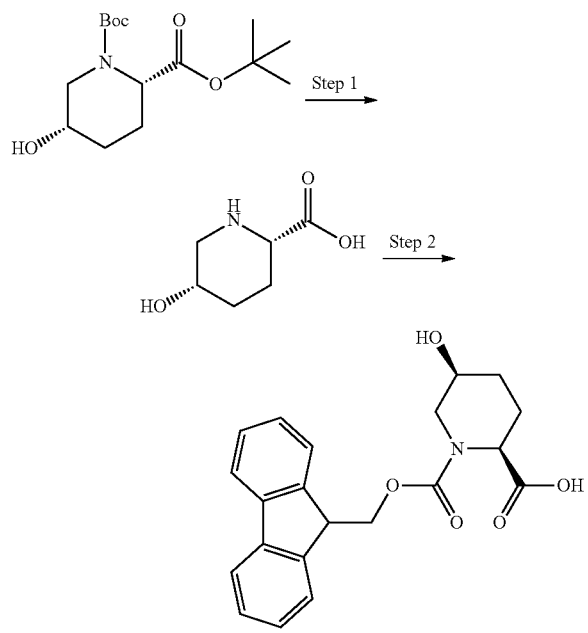

Step 1:

TFA (5 mL, 64.9 mmol) was added to a solution of (2S, 5S)-di-tert-butyl 5-hydroxypiperidine-1,2-dicarboxylate (1 g, 3.32 mmol) in DCM (5 mL) at RT, and the solution was stirred for 1 h upon which LCMS analysis indicated complete conversion (removal of Boc). The solution was concentrated in vacuo and the residue was then treated with 3 mL of aq. conc. HCl. The solution was stirred for 5 min upon which LCMS analysis indicated complete conversion (removal of tBu). The solution was concentrated in vacuo to afford (2S, 5S)-5-hydroxypiperidine-2-carboxylic acid, HCl (0.6 g) as an oil. The yield was assumed to be 100%. ESI-MS(+) m/z=146.2 (M+H)

Step 2:

To a solution of (2S,5S)-5-hydroxypiperidine-2-carboxylic acid, HCl (0.603 g, 3.32 mmol) in 1,4-dioxane (4 mL) and water (16 mL) was added potassium carbonate (1.835 g, 13.28 mmol) followed by (9H-fluoren-9-yl)methyl carbonochloridate (0.859 g, 3.32 mmol) at 0° C. The mixture was stirred at RT for 18 hrs and then treated with water (10 ml). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product (2S,5S)-1-(((9H-fluoren-9-yl)methoxy)carbonyl)-5-hydroxypiperidine-2-carboxylic acid (800 mg, 65.6% yield) as a white solid. $^1$H NMR (500 MHz, methanol-d$_4$) d 7.86-7.78 (m, 2H), 7.69-7.57 (m, 2H), 7.48-7.37 (m, 2H), 7.37-7.20 (m, 2H), 4.81-4.77 (m, 1H), 4.59-4.36 (m, 2H), 4.32-4.20 (m, 1H), 4.18-4.08 (m, 1H), 3.75-3.64 (m, 2H), 3.58-3.43 (m, 1H), 2.01-1.89 (m, 1H), 1.81-1.57 (m, 1H), 1.30-1.17 (m, 1H). ESI-MS(+) m/z=368.2 (M+Na)

Preparation of (S)-2-((((9H-fluoren-9-yl)methoxy)carbonyl)amino)-3-(4-((((9H-fluoren-9-yl)methoxy)carbonyl)oxy)-3-bromophenyl)propanoic acid Scheme:

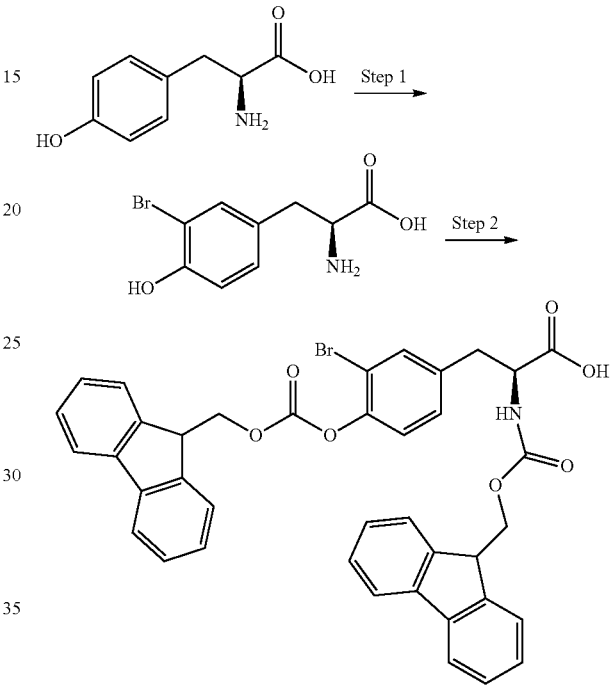

Step 1:

To a 250 mL r.b. flask equipped with a stir bar was added acetic acid (50 mL) and hydrobromic acid in AcOH (27 mL, 149 mmol), then (S)-2-amino-3-(4-hydroxyphenyl)propanoic acid (13.47 g, 74.3 mmol). To the stirred solution was added dropwise over 3 hr via an addition funnel bromine (4.14 mL, 80 mmol) in AcOH (20 mL). The solution was stirred at room temperature. After 9 days, stirring was stopped and the mixture was filtered (reaction time not optimized). The filter cake washed with AcOH (100 mL) and then Et$_2$O (150 mL). The isolated off-white solids were dried under vacuum to afford the product (S)-2-amino-3-(3-bromo-4-hydroxyphenyl)propanoic acid, hydrobromide (23.9 g, 85% yield) as a pale yellow powder. $^1$H NMR (500 MHz, methanol-d$_4$) d 7.47-7.41 (m, 1H), 7.12 (dd, J=8.2, 2.2 Hz, 1H), 6.92 (d, J=8.4 Hz, 1H), 4.22 (dd, J=7.6, 5.4 Hz, 1H), 3.23 (dd, J=14.8, 5.4 Hz, 1H), 3.08 (dd, J=14.7, 7.7 Hz, 1H).

Step 2:

To a solution of (S)-2-amino-3-(3-bromo-4-hydroxyphenyl)propanoic acid, hydrobromide (3 g, 8.80 mmol) in 1,4-Dioxane (12 mL) and Water (48 mL) was added potassium carbonate (4.86 g, 35.2 mmol) followed by (9H-fluoren-9-yl)methyl carbonochloridate (2.276 g, 8.80 mmol) at 0° C. The mixture was stirred at RT for 18 hrs and then treated with water (50 mL). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product. The crude product was purified via silica gel chromatography (120 g column, 30-90% EtOAc:Hexanes, 20 column volumes) to give the product (S)-2-((((9H-fluoren-9-yl)methoxy)carbonyl)amino)-3-(4-((((9H-fluoren-9-yl)methoxy)carbonyl)oxy)-3-bromophenyl)propanoic acid (3.42 g, 55.2% yield) as a light yellow solid. ¹H NMR (400 MHz, chloroform-d) d 7.80 (t, J=7.9 Hz, 4H), 7.68 (d, J=7.6 Hz, 2H), 7.60 (d, J=7.3 Hz, 2H), 7.49-7.32 (m, 9H), 7.16 (br. s., 2H), 5.32 (s, 1H), 4.73 (br. s., 1H), 4.58 (d, J=7.3 Hz, 2H), 4.54-4.34 (m, 2H), 4.24 (t, J=6.6 Hz, 1H), 3.31-3.03 (m, 2H). ESI-MS (+) m/z=721 (M+H₂O).

Preparation of (S)-2-((((9H-fluoren-9-yl)methoxy)carbonyl)amino)-3-(1-(2-(tert-butoxy)-2-oxoethyl)-1H-indol-3-yl)propanoic acid Scheme:

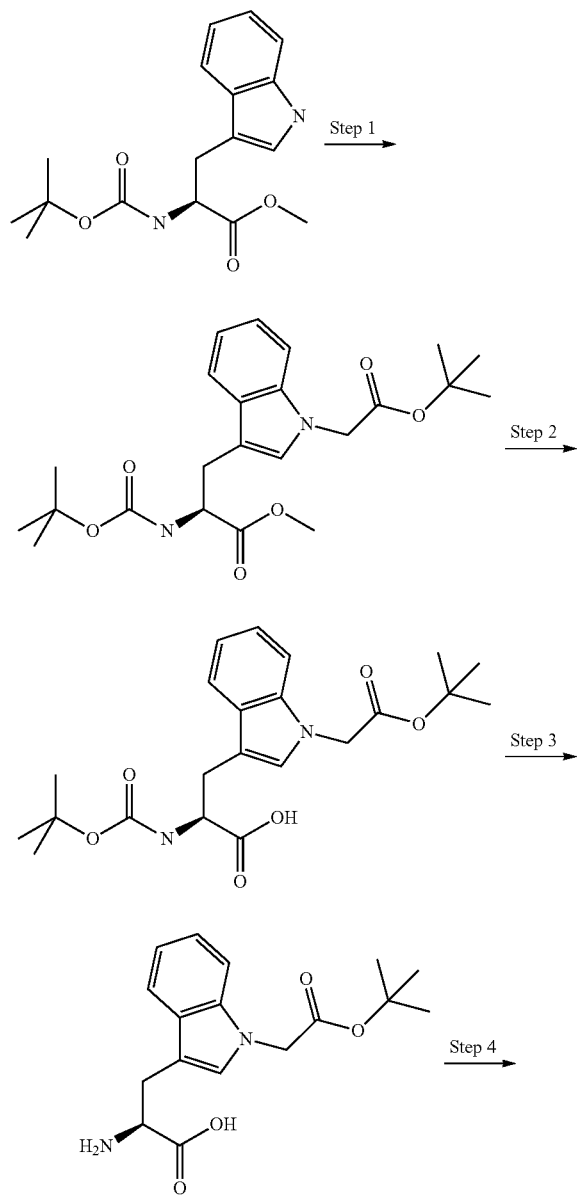

-continued

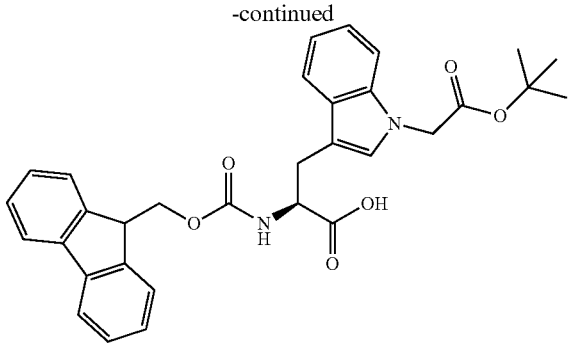

Step 1:

To a 0° C. solution of (S)-methyl 2-((tert-butoxycarbonyl)amino)-3-(1H-indol-3-yl)propanoate (4 g, 12.56 mmol) and cesium carbonate (4.50 g, 13.82 mmol) in DMF (40 mL) was added tert-butyl 2-bromoacetate (2.015 mL, 13.82 mmol) and was allowed to warm up to RT by removing from ice bath and stirred for 18 hrs. The reaction was poured into 1:1 ice water:1N HCl and extracted with EtOAc. The organic layer washed with brine, collected, dried over MgSO₄, filtered and evaporated to give the crude product. The crude product was purified via silica gel chromatography (80 g column, 0-50% EtOAc:Hexanes over 20 CV) to get the product (S)-methyl 3-(1-(2-(tert-butoxy)-2-oxoethyl)-1H-indol-3-yl)-2-((tert-butoxycarbonyl)amino)propanoate (4.69 g, 86% yield). ¹H NMR (400 MHz, chloroform-d) d 7.56 (d, J=7.8 Hz, 1H), 7.26-7.18 (m, 2H), 7.17-7.12 (m, 1H), 6.92 (s, 1H), 5.09 (d, J=7.6 Hz, 1H), 4.71 (s, 2H), 3.73-3.59 (m, 3H), 3.30 (d, J=5.1 Hz, 2H), 1.45 (s, 18H). ESI-MS(+) m/z=433 (M+H).

Step 2:

Lithium hydroxide monohydrate (0.455 g, 10.84 mmol) was added to a solution of (S)-methyl 3-(1-(2-(tert-butoxy)-2-oxoethyl)-1H-indol-3-yl)-2-((tert-butoxycarbonyl)amino)propanoate (4.69 g, 10.84 mmol) in dioxane (50 mL) and water (16.67 mL) and stirred at RT for 1 hr. The reaction was neutralized with 1M HCl and extracted with EtOAc. The organic layer washed with brine, collected, dried over MgSO₄, filtered and evaporated to give the crude material. The crude material was purified via silica gel chromatography (120 g column, 0-50% EtOAc:Hex over 20 CV) to get the product (S)-3-(1-(2-(tert-butoxy)-2-oxoethyl)-1H-indol-3-yl)-2-((tert-butoxycarbonyl)amino)propanoic acid (3.54 g, 78% yield). ¹H NMR (400 MHz, chloroform-d) d 7.62 (d, J=7.8 Hz, 1H), 7.26-7.21 (m, 2H), 7.15 (ddd, J=7.9, 5.6, 2.3 Hz, 1H), 6.99 (s, 1H), 5.08 (d, J=7.8 Hz, 1H), 4.71 (s, 2H), 4.65 (br. s., 1H), 3.42-3.31 (m, 2H), 1.46 (s, 18H). ESI-MS(+) m/z=441 (M+Na).

Step 3:

HCl (4M in dioxane, 10 ml, 40.0 mmol) was cooled in an ice bath under N2 atm. (S)-3-(1-(2-(tert-butoxy)-2-oxoethyl)-1H-indol-3-yl)-2-((tert-butoxycarbonyl)amino)propanoic acid (1 g, 2.390 mmol) was added to the HCl solution. The ice bath was removed and the reaction was stirred for 30 minutes. The solution was concentrated (bath temp=RT) to afford the product (S)-2-amino-3-(1-(2-(tert-butoxy)-2-oxoethyl)-1H-indol-3-yl)propanoic acid, HCl (848 mg, 100% yield) as a sticky oil. ESI-MS(+) m/z=319.2 (M+Na).

Step 4:

To a solution of (S)-2-amino-3-(1-(2-(tert-butoxy)-2-oxoethyl)-1H-indol-3-yl)propanoic acid, HCl (848 mg, 2.390 mmol) in 1,4-dioxane (5 mL) and water (20 mL) was added potassium carbonate (1321 mg, 9.56 mmol) followed by (9H-fluoren-9-yl)methyl carbonochloridate (618 mg, 2.390 mmol) at 0° C. The mixture was stirred at RT for 18 hrs and treated with water (10 ml). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product. The crude product was purified via prep HPLC(10-100% CH3CN:Water with 0.1% TFA buffer) to get the product (S)-2-((((9H-fluoren-9-yl)methoxy)carbonyl)amino)-3-(1-(2-(tert-butoxy)-2-oxoethyl)-1H-indol-3-yl)propanoic acid (405 mg, 0.749 mmol, 31.3% yield) as a white solid. $^1$H NMR (500 MHz, methanol-d$_4$) d 7.80 (d, J=7.6 Hz, 2H), 7.67-7.60 (m, 2H), 7.39 (t, J=7.5 Hz, 2H), 7.32-7.22 (m, 3H), 7.18 (td, J=7.6, 0.9 Hz, 1H), 7.08 (td, J=7.5, 0.9 Hz, 1H), 7.04 (s, 1H), 4.54 (dd, J=8.4, 4.9 Hz, 1H), 4.36-4.23 (m, 2H), 4.23-4.14 (m, 1H), 3.43-3.35 (m, 2H), 3.25-3.09 (m, 1H), 1.55-1.38 (m, 9H). ESI-MS(+) m/z=541.3 (M+H).

Preparation of (2S,4R)-1-(((9H-fluoren-9-yl)methoxy)carbonyl)-4-((6-methoxyisoquinolin-1-yl)oxy)pyrrolidine-2-carboxylic acid Scheme:

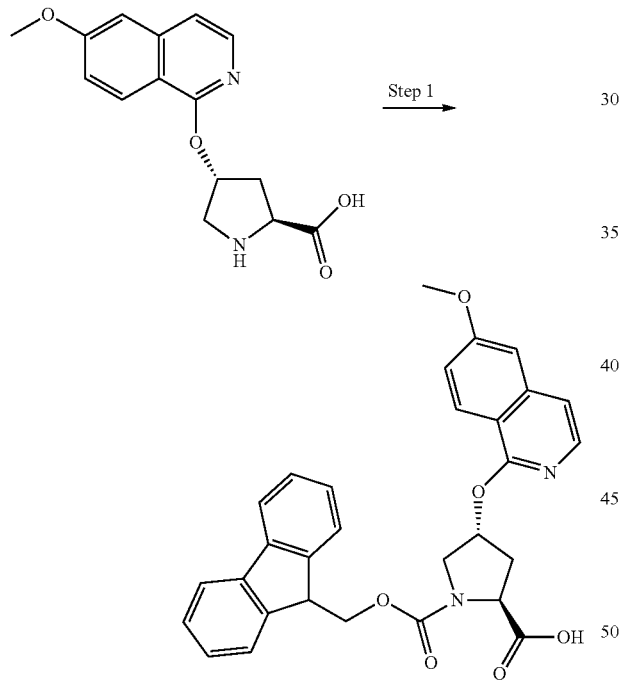

Step 1:
To a solution of (2S,4R)-4-((6-methoxyisoquinolin-1-yl)oxy)pyrrolidine-2-carboxylic acid, HCl (750 mg, 2.309 mmol) in 1,4-dioxane (5 mL) and water (20 mL) was added potassium carbonate (1277 mg, 9.24 mmol) followed by (9H-fluoren-9-yl)methyl carbonochloridate (597 mg, 2.309 mmol) at 0° C. The mixture was stirred at RT for 18 hrs and treated with water (10 ml). The resulting mixture was acidified with aq. HCl (1M) to pH 2-3, and extracted with DCM (3×20 ml). The combined organic layers were dried over MgSO$_4$ and concentrated to give the crude product. The crude product was purified via silica gel chromatography (40 g column, MeOH in DCM 0-10% over 20 CV) to afford the product (2S,4R)-1-(((9H-fluoren-9-yl)methoxy)carbonyl)-4-((6-methoxyisoquinolin-1-yl)oxy)pyrrolidine-2-carboxylic acid as a white solid. $^1$H NMR (400 MHz, chloroform-d) d 8.09 (d, J=9.3 Hz, 1H), 8.00-7.88 (m, 1H), 7.80-7.65 (m, 2H), 7.65-7.47 (m, 2H), 7.37 (t, J=7.2 Hz, 2H), 7.34-7.29 (m, 2H), 7.25-7.12 (m, 2H), 7.09-7.04 (m, 1H), 5.83 (br. s., 1H), 4.76 (t, J=7.9 Hz, 1H), 4.61-4.39 (m, 3H), 4.30-4.19 (m, 2H), 4.06-3.94 (m, 3H), 2.70 (dd, J=7.9, 3.3 Hz, 2H). ESI-MS(+) m/z=511 (M+H).

Preparation of (2S,4R)-1-(((9H-fluoren-9-yl)methoxy)carbonyl)-4-((3-bromoquinolin-2-yl)oxy)pyrrolidine-2-carboxylic acid Scheme:

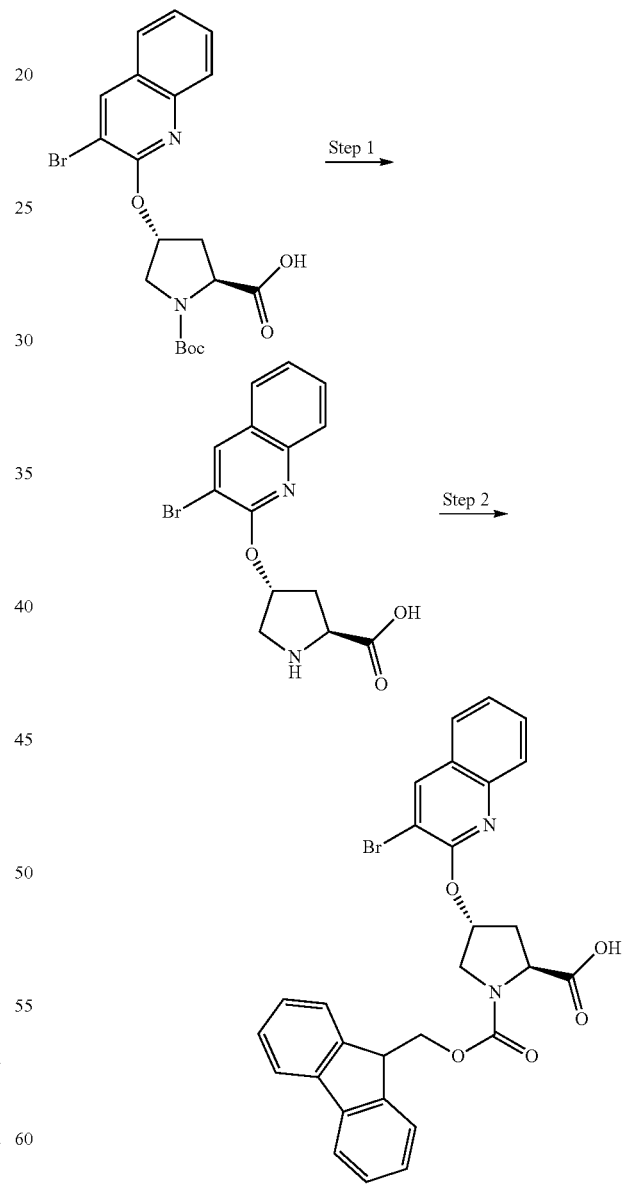

Step 1:
TFA (5.0 ml, 65 mmol) was added to a solution of (2S,4R)-4-((3-bromoquinolin-2-yl)oxy)-1-(tert-butoxycarbonyl)pyrrolidine-2-carboxylic acid (300 mg, 0.686 mmol) in DCM (5 mL) and stirred at RT until LCMS analysis indicated complete conversion. The solution was concentrated to afford the product (2S,4R)-4-((3-bromoquinolin-2-yl)oxy)pyrrolidine-2-carboxylic acid, TFA (310 mg) as a sticky oil. Yield was assumed to be 100%. ESI-MS(+) m/z=337 (M+H).

Step 2:

To a solution of (2S,4R)-4-((3-bromoquinolin-2-yl)oxy)pyrrolidine-2-carboxylic acid, TFA (310 mg, 0.687 mmol) in 1,4-dioxane (3 mL) and water (12 mL) was added potassium carbonate (380 mg, 2.75 mmol) followed by (9H-fluoren-9-yl)methyl carbonochloridate (178 mg, 0.687 mmol) at 0° C. The mixture was stirred at RT for 18 hrs and treated with water (10 ml). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product. The crude product was purified via prep HPLC (10-100% CH$_3$CN:Water, 0.1% TFA buffer) to afford the product (2S,4R)-1-(((9H-fluoren-9-yl)methoxy)carbonyl)-4-((3-bromoquinolin-2-yl)oxy)pyrrolidine-2-carboxylic acid (250 mg, 65% yield) as a white solid. $^1$H NMR (500 MHz, methanol-d$_4$) d 7.90-7.75 (m, 2H), 7.73-7.63 (m, 2H), 7.58-7.49 (m, 2H), 7.49-7.39 (m, 2H), 7.37-7.31 (m, 1H), 7.26 (t, J=7.5 Hz, 1H), 7.20-7.14 (m, 1H), 7.12 (t, J=7.4 Hz, 1H), 7.04 (td, J=7.4, 1.0 Hz, 1H), 4.68-4.56 (m, 2H), 4.51 (t, J=8.3 Hz, 1H), 4.44-4.33 (m, 2H), 4.27-4.16 (m, 2H), 3.99-3.92 (m, 1H), 3.81-3.73 (m, 1H), 3.73-3.64 (m, 1H). ESI-MS(+) m/z=337 (M+H).

Preparation of (2S,4R)-1-(((9H-fluoren-9-yl)methoxy)carbonyl)-4-(benzyloxy)pyrrolidine-2-carboxylic acid Scheme:

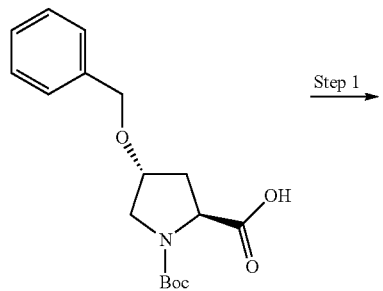

Step 1

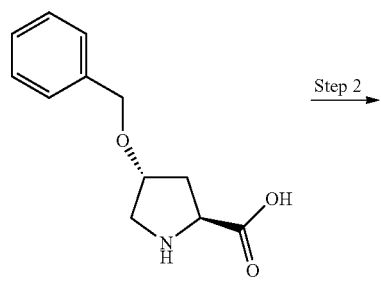

Step 2

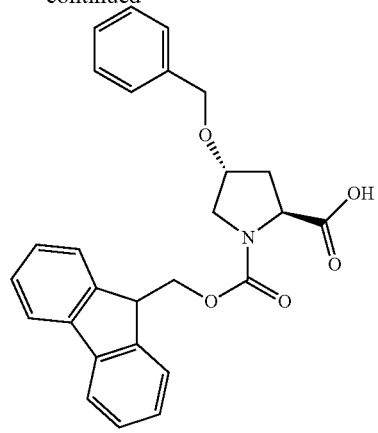

Step 1:

TFA (5 ml, 64.9 mmol) was added to a solution of (2S,4R)-4-(benzyloxy)-1-(tert-butoxycarbonyl)pyrrolidine-2-carboxylic acid (500 mg, 1.556 mmol) in DCM (5 mL) and stirred at RT until LCMS analysis indicated complete conversion. The solution was concentrated to afford the product. Yield was assumed to be 100%. ESI-MS(+) m/z=222 (M+H).

Step 2:

To a solution of (2S,4R)-4-(benzyloxy)pyrrolidine-2-carboxylic acid, TFA (522 mg, 1.557 mmol) in 1,4-dioxane (4 mL) and water (16 mL) was added potassium carbonate (861 mg, 6.23 mmol) followed by (9H-fluoren-9-yl)methyl carbonochloridate (403 mg, 1.557 mmol) at 0° C. The mixture was stirred at RT for 18 hrs and treated with water (10 ml). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product. The crude product was purified via prep HPLC (10-100% CH$_3$CN:Water 0.1% TFA buffer) to afford the pure product (2S,4R)-1-(((9H-fluoren-9-yl)methoxy)carbonyl)-4-(benzyloxy)pyrrolidine-2-carboxylic acid (430 mg, 62.3% yield) as a white solid. $^1$H NMR (500 MHz, methanol-d$_4$) d 7.86-7.76 (m, 2H), 7.71-7.57 (m, 2H), 7.44-7.27 (m, 9H), 4.58-4.50 (m, 2H), 4.49-4.33 (m, 3H), 4.29-4.19 (m, 2H), 3.72-3.49 (m, 2H), 2.49 (br. s., 1H), 2.10 (ddd, J=13.4, 8.2, 4.8 Hz, 1H). ESI-MS (+) m/z=444 (M+H).

Preparation of (S)-1-(((9H-fluoren-9-yl)methoxy)carbonyl)-4-(tert-butoxycarbonyl)piperazine-2-carboxylic acid Scheme:

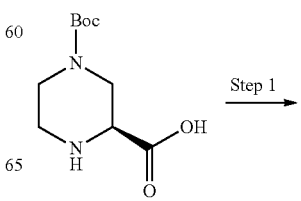

Step 1

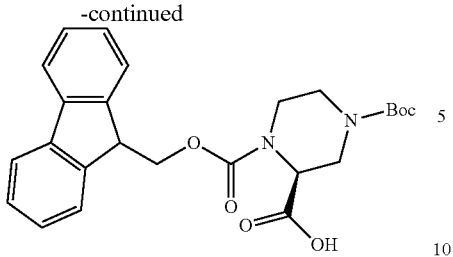

Step 1:

To a solution of (S)-4-(tert-butoxycarbonyl)piperazine-2-carboxylic acid (500 mg, 2.171 mmol) in 1,4-dioxane (5 mL) and water (20 mL) was added potassium carbonate (1200 mg, 8.69 mmol) followed by (9H-fluoren-9-yl)methyl carbonochloridate (562 mg, 2.171 mmol) at 0° C. The mixture was stirred at RT for 18 hrs and then treated with water (10 ml). The resulting mixture was extracted with diethyl ether (2×15 ml). The aqueous phase was acidified with aq. HCl (1M) to pH 2-3, and extracted with DCM (3×20 ml). The combined organic layers were dried over MgSO$_4$ and concentrated to give the crude product. The crude product was purified via prep HPLC (10-100% CH$_3$CN:Water with 0.1% TFA buffer) to afford the product (S)-1-(((9H-fluoren-9-yl)methoxy)carbonyl)-4-(tert-butoxycarbonyl)piperazine-2-carboxylic acid (294 mg, 30% yield) as a white solid. $^1$H NMR (500 MHz, methanol-d$_4$) d 7.83 (t, J=6.6 Hz, 2H), 7.68-7.58 (m, 2H), 7.45-7.38 (m, 2H), 7.38-7.30 (m, 2H), 4.65 (br. s., 1H), 4.58 (d, J=13.7 Hz, 1H), 4.55-4.39 (m, 3H), 4.33-4.18 (m, 1H), 2.91-2.85 (m, 4H), 1.47 (s, 9H). ESI-MS(+) m/z=475 (M+Na).

Preparation of (S)-2-(((((9H-fluoren-9-yl)methoxy)carbonyl)(methyl)amino)-3-(m-tolyloxy)propanoic acid Scheme:

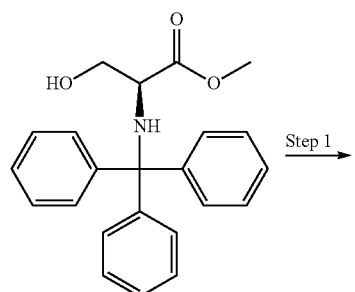

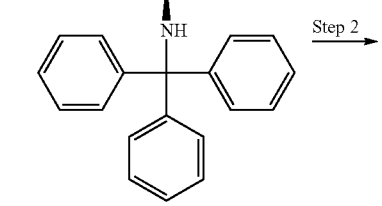

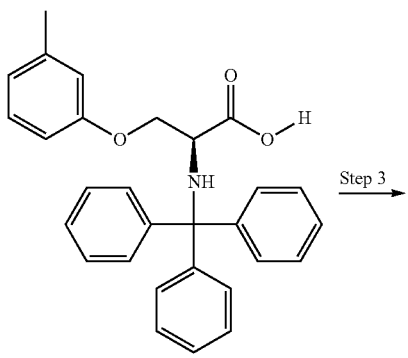

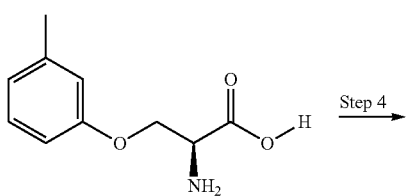

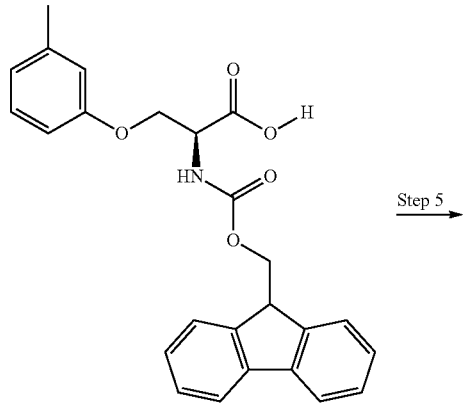

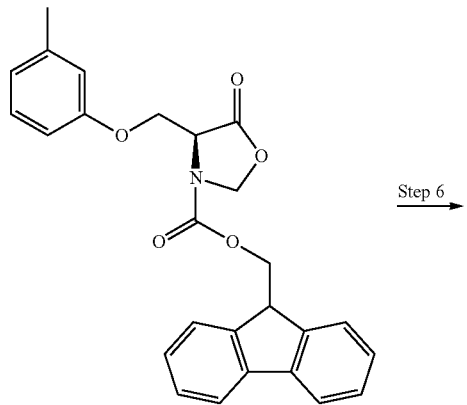

-continued

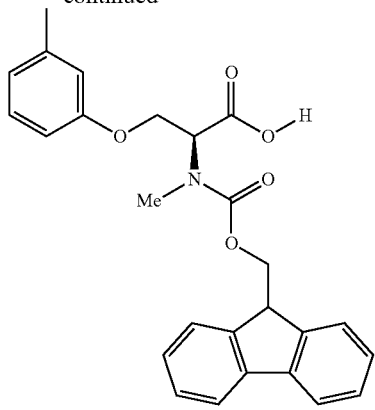

Step 1:

To a round-bottom flask equipped with a stir bar was added (S)-methyl 3-hydroxy-2-(tritylamino)propanoate (10.0 g, 27.7 mmol), triphenylphosphine (7.98 g, 30.4 mmol) and toluene (100 mL). The solution was stirred at room temperature for 30 min., then to the solution was added m-cresol (3.78 mL, 36.0 mmol) and diisopropylazodicarboxylate ("DIAD", 5.92 mL, 30.4 mmol). The solution was heated at 80° C. with stirring for 18 h. The solution was cooled to room temperature and concentrated and the resulting residue was subjected to silica gel chromatography (hexanes:EtOAc) to afford (S)-methyl 3-(m-tolyloxy)-2-(tritylamino)propanoate, 8.28 g (66%). $^1$H-NMR (400 MHz, CDCl$_3$) δ 7.53 (d, J=7.6 Hz, 6H), 7.29-7.23 (m, 5H), 7.21-7.11 (m, 4H), 6.77 (d, J=7.3 Hz, 1H), 6.73-6.64 (m, 2H), 5.30 (s, 2H), 4.25 (dd, J=9.3, 4.9 Hz, 1H), 4.01 (dd, J=9.2, 6.7 Hz, 1H), 3.76-3.68 (m, 1H), 3.22 (s, 3H), 2.88 (d, J=10.5 Hz, 1H), 2.32 (s, 3H).

Step 2:

To a round bottom flask equipped with a stir bar and charged with (S)-methyl 3-(m-tolyloxy)-2-(tritylamino)propanoate (8.28 g, 18.34 mmol) in MeOH (30 mL) and THF (30 mL) was added lithium hydroxide in water (55.0 mmol, 27.5 mL). The mixture was stirred at room temperature for 1 h. The reaction mixture was neutralized with aq. 2N HCl. The mixture was diluted with EtOAc and the organic phase was isolated and washed with brine; dried over MgSO$_4$; filtered; then concentrated in vacuo. The resulting residue was purified via silica gel chromatography to afford (S)-3-(m-tolyloxy)-2-(tritylamino)propanoic acid, 1.47 g (18%). $^1$H-NMR (400 MHz, CDCl$_3$) δ 7.44 (d, J=7.1 Hz, 6H), 7.35-7.24 (m, 8H), 7.09 (t, J=7.8 Hz, 1H), 6.76 (d, J=7.6 Hz, 1H), 6.52 (s, 1H), 6.46 (d, J=8.1 Hz, 1H), 4.07 (dd, J=9.2, 2.3 Hz, 1H), 3.71 (t, J=3.2 Hz, 1H), 2.79 (dd, J=9.2, 4.0 Hz, 1H), 2.28 (s, 3H).

Step 3:

To a round-bottom flask equipped with a stir bar and charged with (S)-3-(m-tolyloxy)-2-(tritylamino)propanoic acid (1.47 g, 3.36 mmol) cooled to 0° C. was added trifluoroacetic acid (6.0 ml, 78 mmol). The solution was stirred for 1 h. The volatiles were removed in vacuo and the residue was then dissolved in MeOH (5 mL) and again concentrated in vacuo. The resulting crude (S)-2-amino-3-(m-tolyloxy)propanoic acid TFA salt was carried directly into Step 4.

Step 4:

To a round-bottom flask equipped with a stir bar and charged with the entirety of (S)-2-amino-3-(m-tolyloxy)propanoic acid TFA salt afforded in Step 3 (assumed 3.36 mmol) was added 1,4-Dioxane (4 mL) and water (16 mL), then K$_2$CO$_3$ (1.17 g, 8.49 mmol). The mixture was cooled to 0° C., then to the mixture was added (9H-fluoren-9-yl)methyl carbonochloridate (549 mg, 2.12 mmol). The mixture was allowed to warm to room temperature with stirring for 18 h. The mixture was diluted with water (10 mL) and then washed with diethyl ether (2×15 mL). The aqueous phase was acidified with aq. HCl (1M) to pH 2-3, and then was extracted with CH$_2$Cl$_2$ (3×20 ml). The combined CH$_2$Cl$_2$ solutions were dried over MgSO$_4$; filtered; then concentrated in vacuo to afford (S)-2-(((((9H-fluoren-9-yl)methoxy)carbonyl)amino)-3-(m-tolyloxy)propanoic acid as a white solid, 430 mg (31% over two steps).

Step 5:

Using a Dean-Stark setup, a mixture containing paraformaldehyde (340 mg, 11.34 mmol), (S)-2-(((((9H-fluoren-9-yl)methoxy)carbonyl)amino)-3-(m-tolyloxy)propanoic acid (789 mg, 1.890 mmol), and p-toluenesulfonic acid (32.5 mg, 0.189 mmol) was refluxed in Toluene (15 mL) for 2 hrs. The reaction was then cooled to RT, washed with sat. sodium bicarbonate solution, followed by brine, dried with MgSO$_4$, filtered and concentrated to get the product (S)-(9H-fluoren-9-yl)methyl 5-oxo-4-((m-tolyloxy)methyl)oxazolidine-3-carboxylate (812 mg, 1.891 mmol, 100% yield) as a yellow oil. ESI-MS(+) m/z=430 (M+H).

Step 6:

(S)-(9H-fluoren-9-yl)methyl 5-oxo-4-((m-tolyloxy)methyl)oxazolidine-3-carboxylate (825 mg, 1.921 mmol) was dissolved in CHCl$_3$ (10 mL) and added triethylsilane (1.534 ml, 9.60 mmol) followed by TFA (10 ml, 130 mmol) and stirred at RT under positive pressure of N2 for 18 hrs. The reaction was then evaporated on rotovap until a sticky oil was left behind. The oil was dissolved in EtOAc and then extracted with sat. sodium bicarbonate (10 ml×2). There was a middle layer between the aqueous layer and organic layer that appeared to be the deprotonated product. The aqueous layer and middle layer were separated and collected and then acidified until pH 4-5. The solution formed a precipitate once acidic. EtOAc (200 ml) was used to extract the precipitate. The organic layer washed with brine, collected, dried over MgSO$_4$, filtered and evaporated to get the pure product (S)-2-(((((9H-fluoren-9-yl)methoxy)carbonyl)(methyl)amino)-3-(m-tolyloxy)propanoic acid (506 mg, 1.173 mmol, 61.0% yield) as a white solid. ESI-MS (+) m/z=454 (M+Na)

Preparation of Example 5001

Example 5001

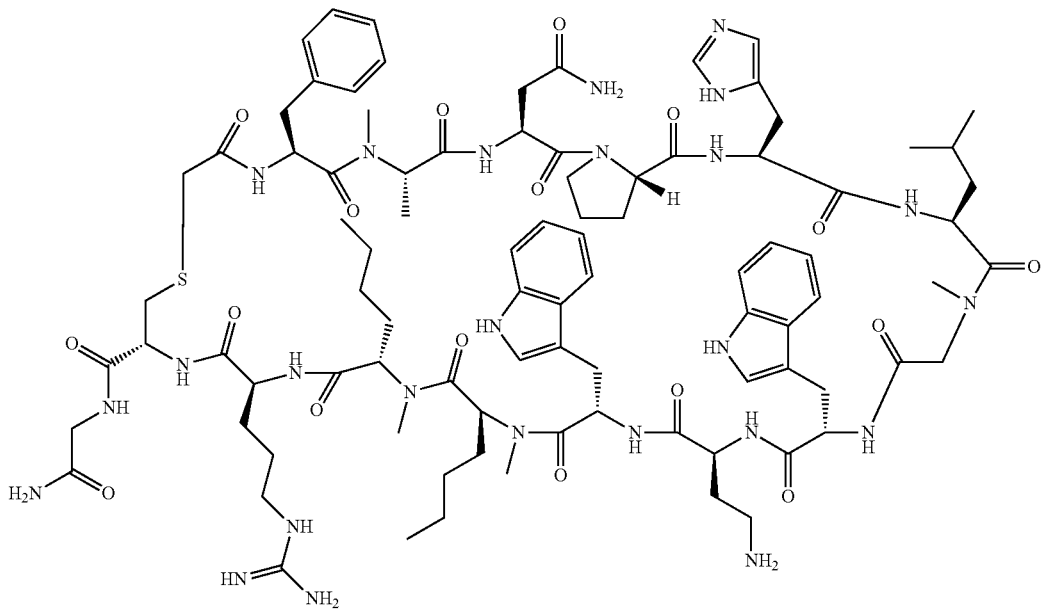

Example 5001 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 32.2 mg, and its estimated purity by LCMS analysis was 100%.

Analysis condition A: Retention time=1.81 min; ESI-MS (+) m/z 933.0 (M+2H)

Analysis condition B: Retention time=2.93 min; ESI-MS (+) m/z 933.8 (M+2H)

Preparation of Example 5002

Example 5002

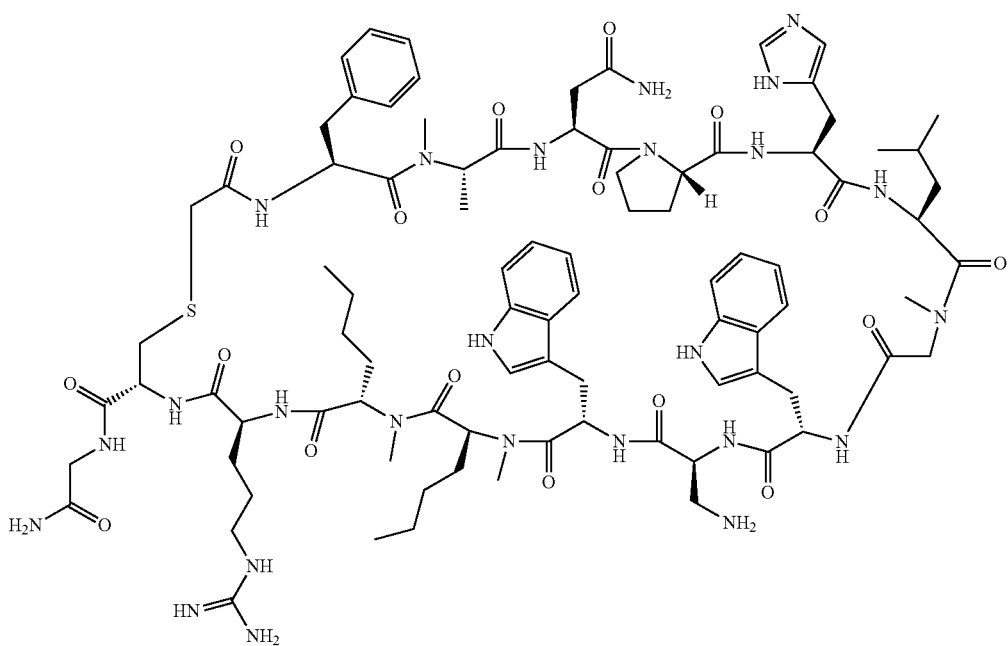

Example 5002 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 4-minute hold at 100% B; Flow: 20 mL/min. Fractions containing the desired product were combined and dried via centrifugal evaporation. The yield of the product was 11.0 mg, and its estimated purity by LCMS analysis was 97%.

Analysis condition A: Retention time=1.64 min; ESI-MS (+) m/z 926.0 (M+2H)

Analysis condition B: Retention time=2.68 min; ESI-MS (+) m/z 617.6 (M+2H)

Preparation of Example 5003

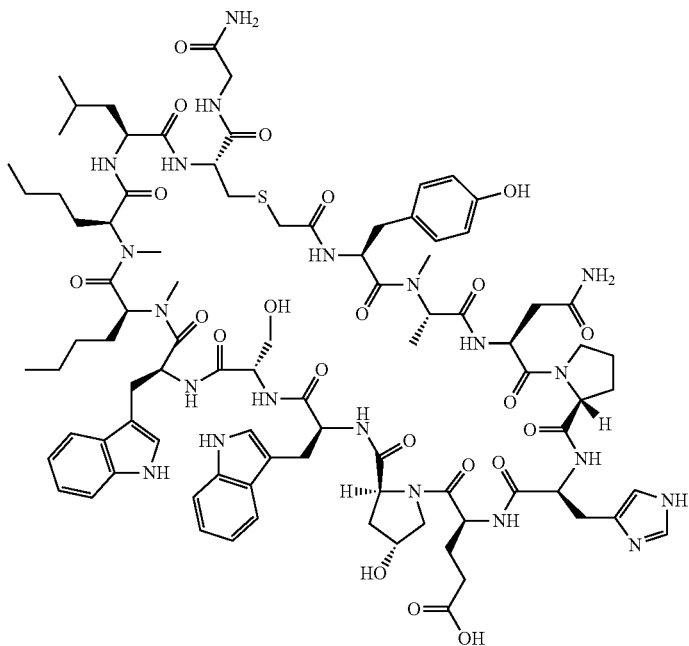

Example 5003

Example 5003 was prepared following "General Synthetic Sequence A" substituting "Cyclization Method B" for "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 40 minutes, then a 5-minute hold at 100% B; Flow: 20 mL/min. Fractions containing the desired product were combined and dried via centrifugal evaporation. The yield of the product was 25.3 mg, and its estimated purity by LCMS analysis was 100%.

Analysis condition A: Retention time=1.55 min; ESI-MS (+) m/z 942.7 (M+2H)

Analysis condition B: Retention time=2.66 min; ESI-MS (+) m/z 942.7 (M+2H)

Preparation of Example 5004

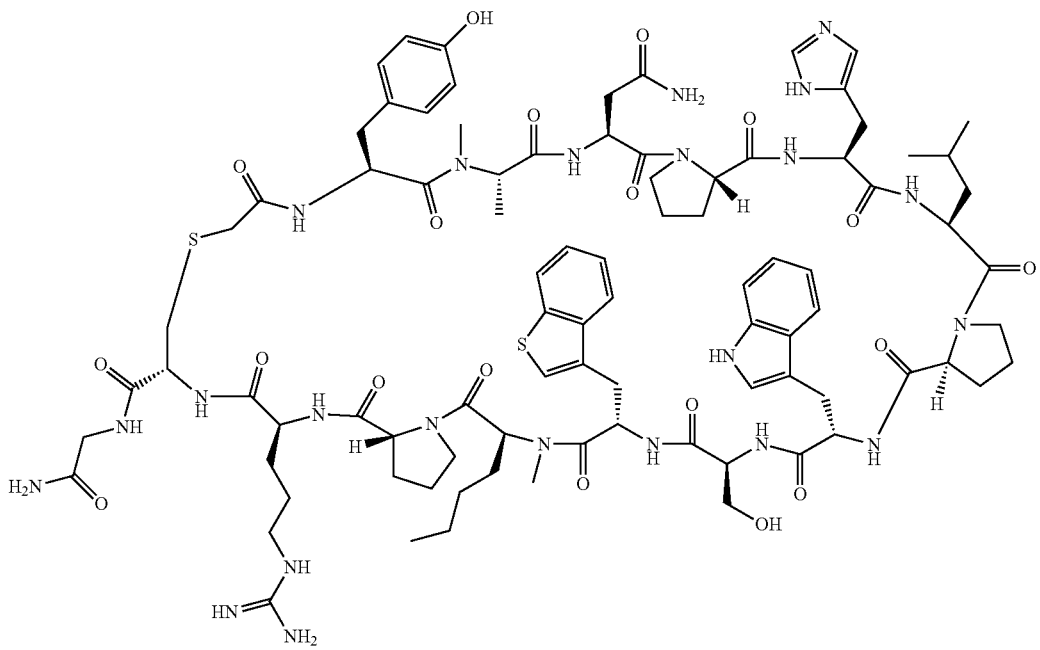

Example 5004

Example 5004 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The yield of the product was 40.8 mg, and its estimated purity by LCMS analysis was 99%.

Analysis condition A: Retention time=1.63 min; ESI-MS (+) m/z 940.8 (M+2H)

Analysis condition B: Retention time=2.66 min; ESI-MS (+) m/z 941.0 (M+2H)

ESI-HRMS(+) m/z: Calculated: 940.9398 (M+2H). Found: 940.9378 (M+2H).

Preparation of Example 5005

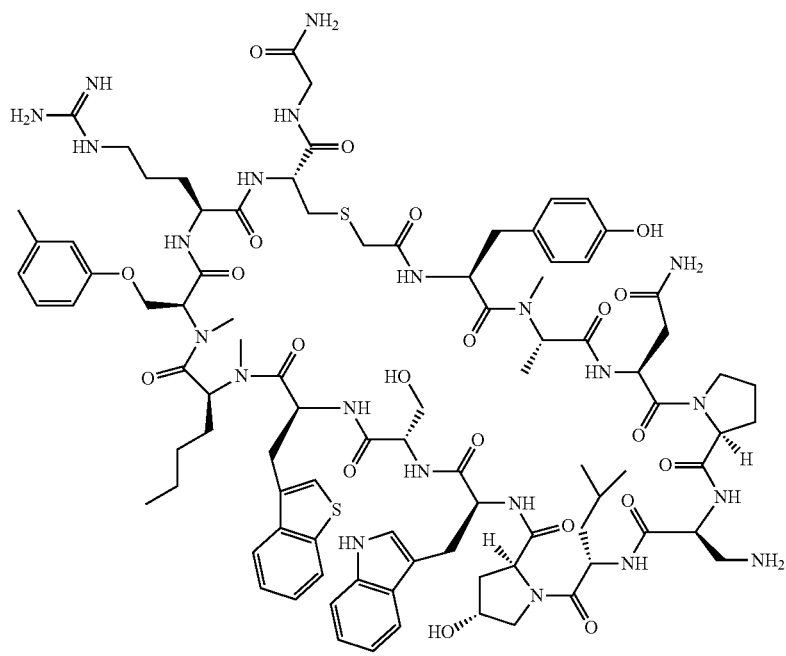

Example 5005

Example 5005 was prepared following "General Synthetic Sequence A". (S)-2-((((9H-fluoren-9-yl)methoxy)carbonyl)amino)-3-(m-tolyloxy)propanoic acid was used in the fourth amino acid coupling step. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 21.3 mg, and its estimated purity by LCMS analysis was 100%.

Analysis condition A: Retention time=1.78 min; ESI-MS (+) m/z 971.2 (M+2H)

Analysis condition B: Retention time=2.94 min; ESI-MS (+) m/z 971.2 (M+2H)

Preparation of Example 5006

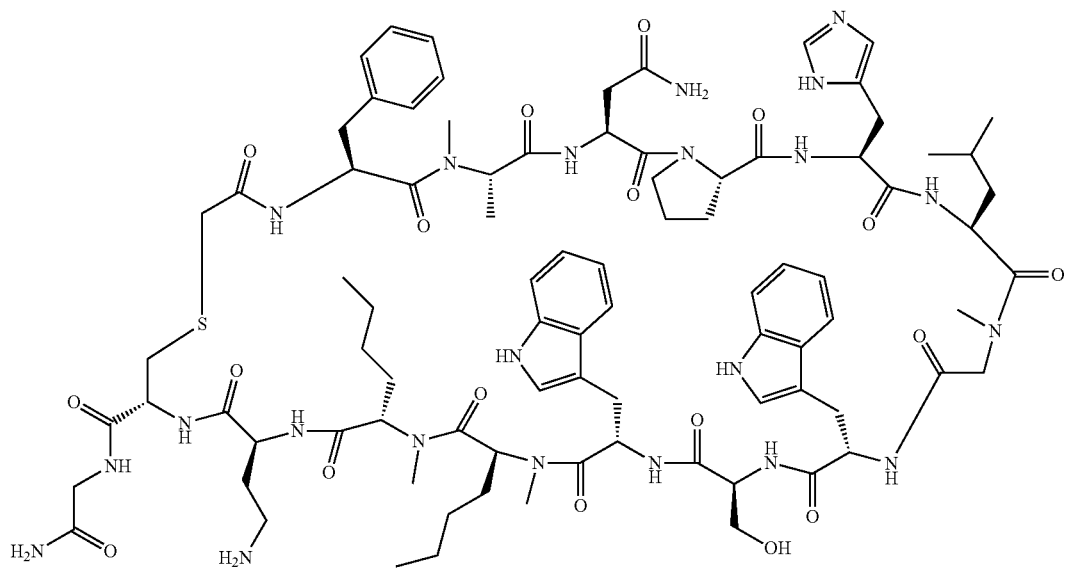

Example 5006

Example 5006 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 42.3 mg, and its estimated purity by LCMS analysis was 99%.

Analysis condition A: Retention time=1.88 min; ESI-MS (+) m/z 898.4 (M+2H)

Analysis condition B: Retention time=2.97 min; ESI-MS (+) m/z 898.9 (M+2H)

Preparation of Example 5007

Example 5007

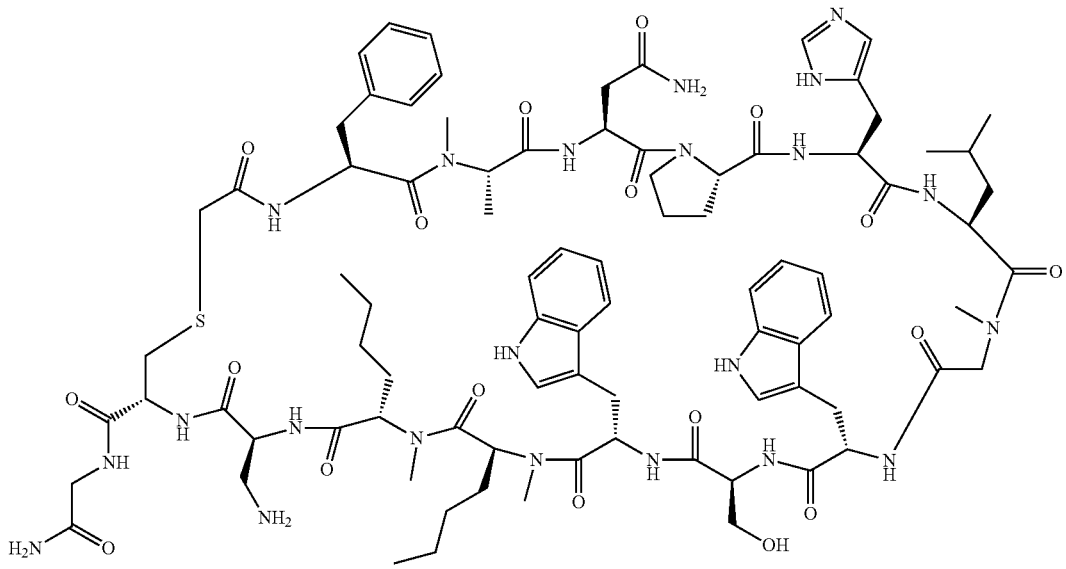

Example 5007 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 44.0 mg, and its estimated purity by LCMS analysis was 100%.

Analysis condition A: Retention time=1.97 min; ESI-MS (+) m/z 892.1 (M+2H)

Analysis condition B: Retention time=3.02 min; ESI-MS (+) m/z 892.0 (M+2H)

Preparation of Example 5008

Example 5008

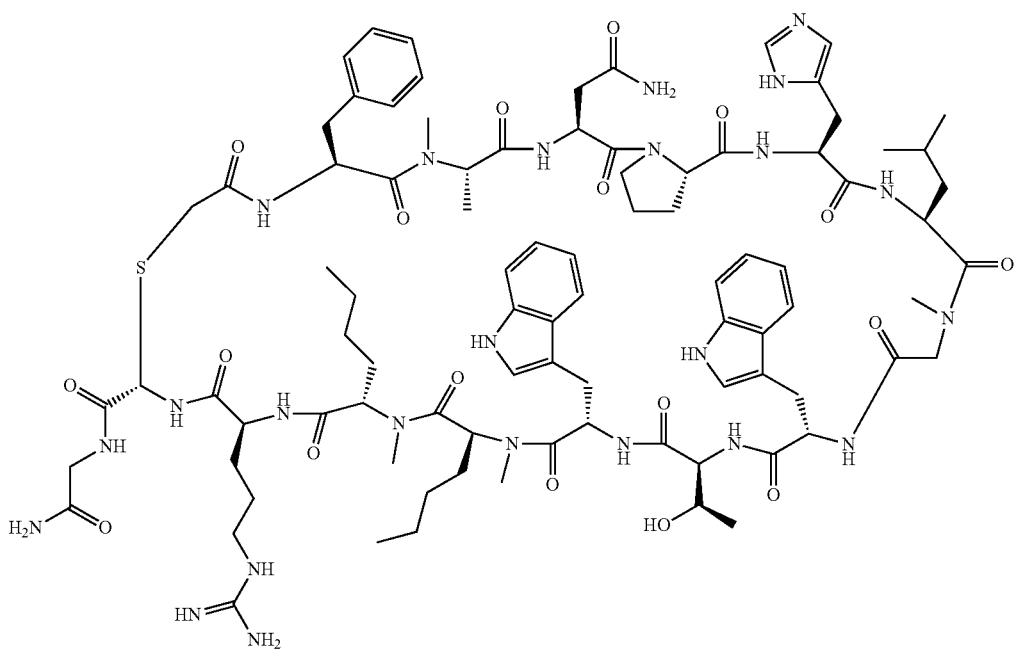

Example 5008 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 70-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 30.6 mg, and its estimated purity by LCMS analysis was 100%.

Analysis condition A: Retention time=1.78 min; ESI-MS (+) m/z 933.8 (M+2H)

Analysis condition B: Retention time=3.00 min; ESI-MS (+) m/z 933.4 (M+2H)

Preparation of Example 5009

Example 5009

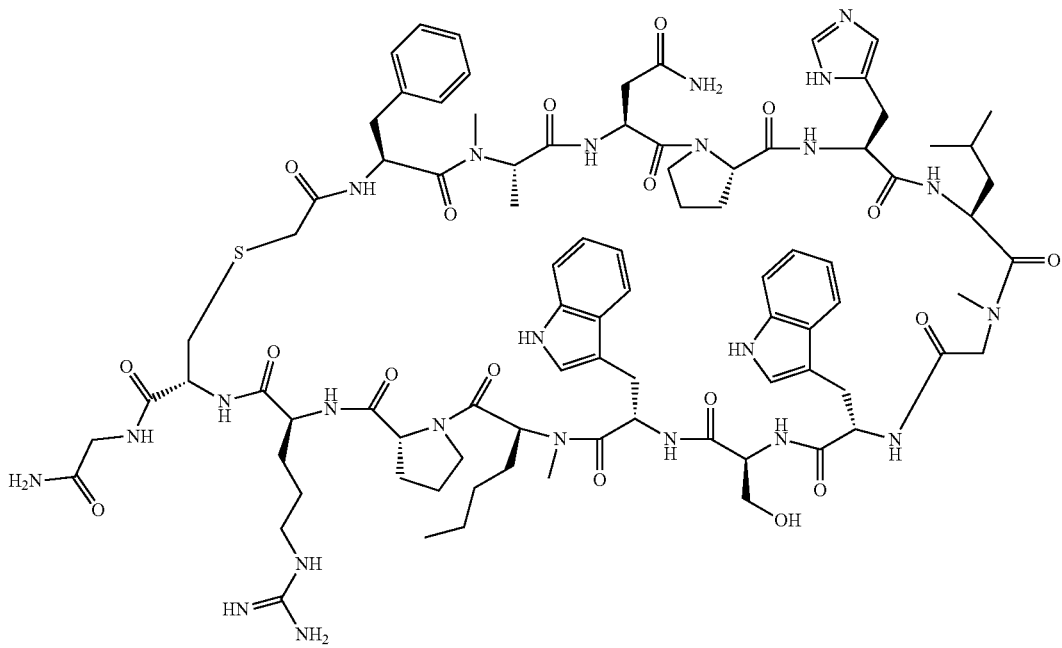

Example 5009 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 35.5 mg, and its estimated purity by LCMS analysis was 100%.

Analysis condition A: Retention time=1.66 min; ESI-MS (+) m/z 911.5 (M+2H)

Analysis condition B: Retention time=2.69 min; ESI-MS (+) m/z 911.9 (M+2H)

Preparation of Example 5010

Example 5010

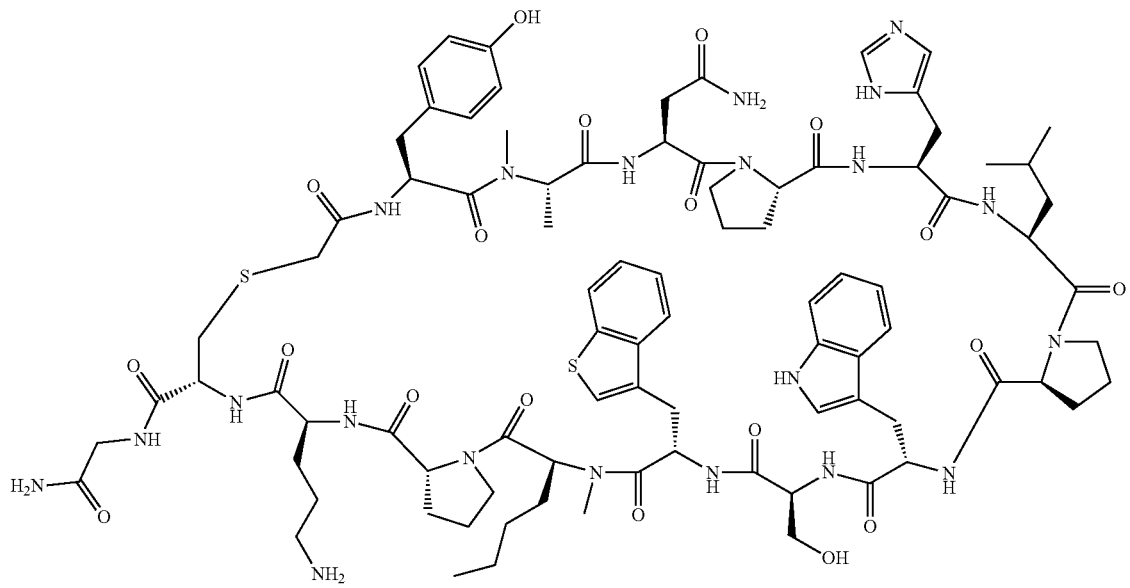

Example 5010 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 31.2 mg, and its estimated purity by LCMS analysis was 100%.

Analysis condition A: Retention time=1.68 min; ESI-MS (+) m/z 920.1 (M+2H)

Analysis condition B: Retention time=2.64 min; ESI-MS (+) m/z 919.8 (M+2H)

Preparation of Example 5011

Example 5011

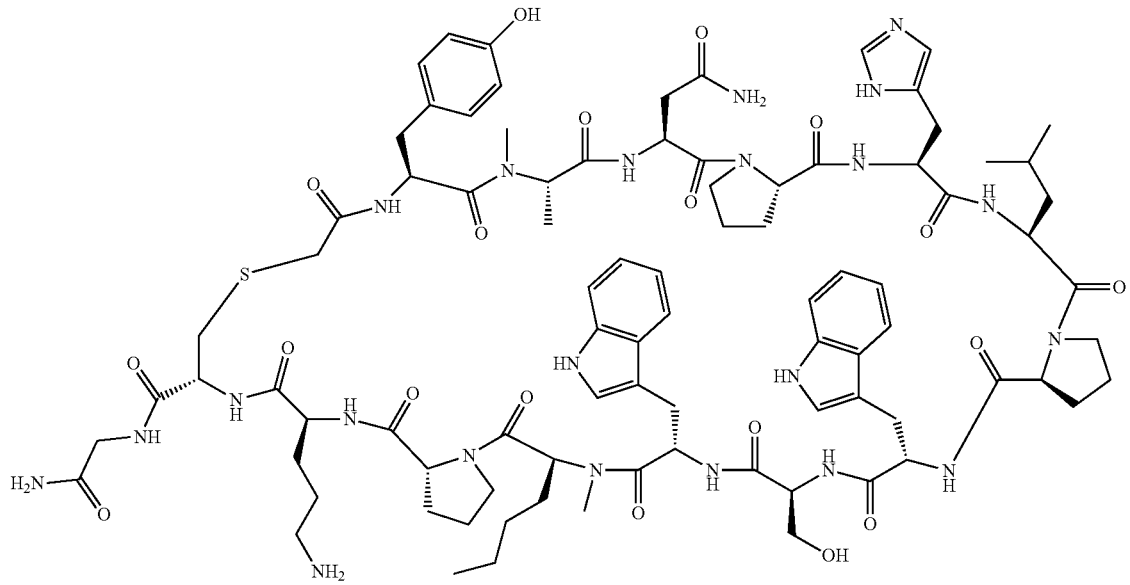

Example 5011 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 24.0 mg, and its estimated purity by LCMS analysis was 99%.

Analysis condition A: Retention time=1.49 min; ESI-MS (+) m/z 911.5 (M+2H)

Analysis condition B: Retention time=2.45 min; ESI-MS (+) m/z 911.4 (M+2H)

Preparation of Example 5012

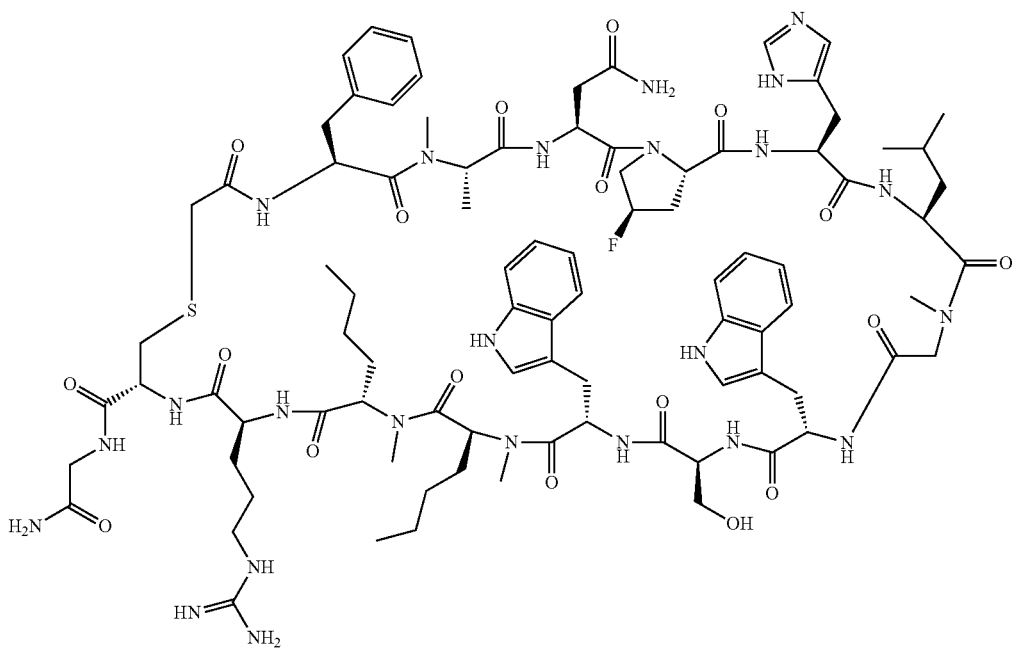

Example 5012

Example 5012 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 21.0 mg, and its estimated purity by LCMS analysis was 99%.

Analysis condition A: Retention time=1.77 min; ESI-MS (+) m/z 935.8 (M+2H)

Preparation of Example 5013

Example 5013

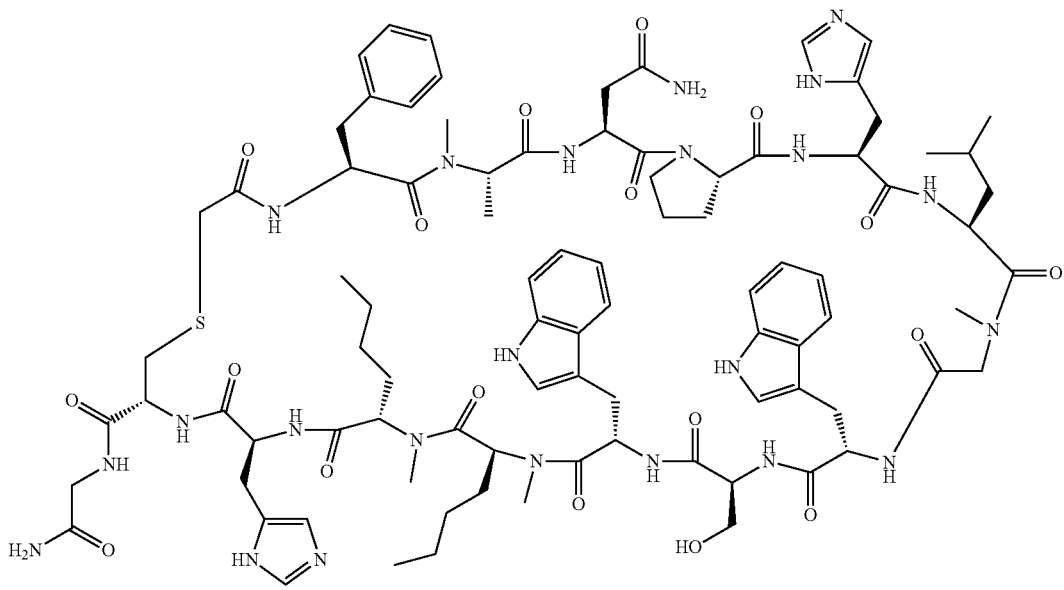

Example 5013 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 100%.

Analysis condition A: Retention time=1.79 min; ESI-MS (+) m/z 916.9 (M+2H)

Analysis condition B: Retention time=2.94 min; ESI-MS (+) m/z 917.5 (M+2H)

Preparation of Example 5014

Example 5014

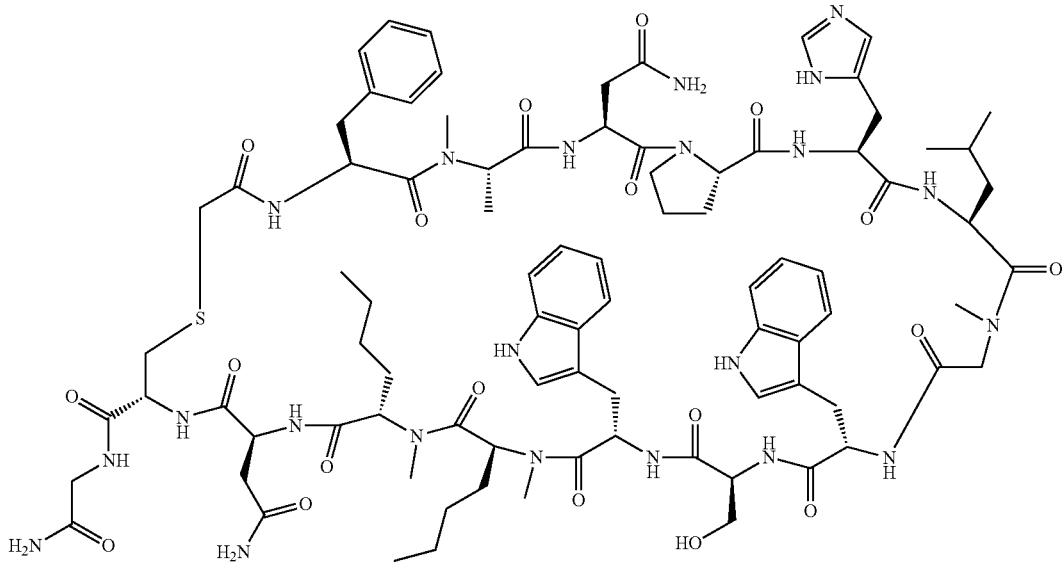

Example 5014 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 10.3 mg, and its estimated purity by LCMS analysis was 100%.

Analysis condition A: Retention time=1.77 min; ESI-MS (+) m/z 905.5 (M+2H)

Analysis condition B: Retention time=2.83 min; ESI-MS (+) m/z 905.5 (M+2H)

Preparation of Example 5015

Example 5015

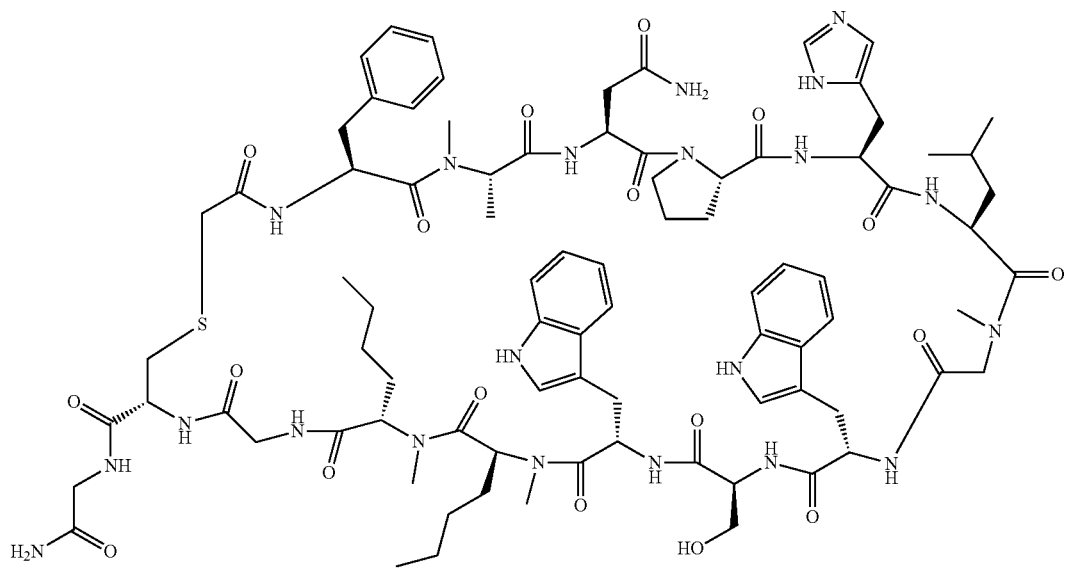

Example 5015 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 21.3 mg, and its estimated purity by LCMS analysis was 99%.

Analysis condition A: Retention time=1.89 min; ESI-MS (+) m/z 876.7 (M+2H)

Analysis condition B: Retention time=2.99 min; ESI-MS (+) m/z 877.0 (M+2H)

Preparation of Example 5016

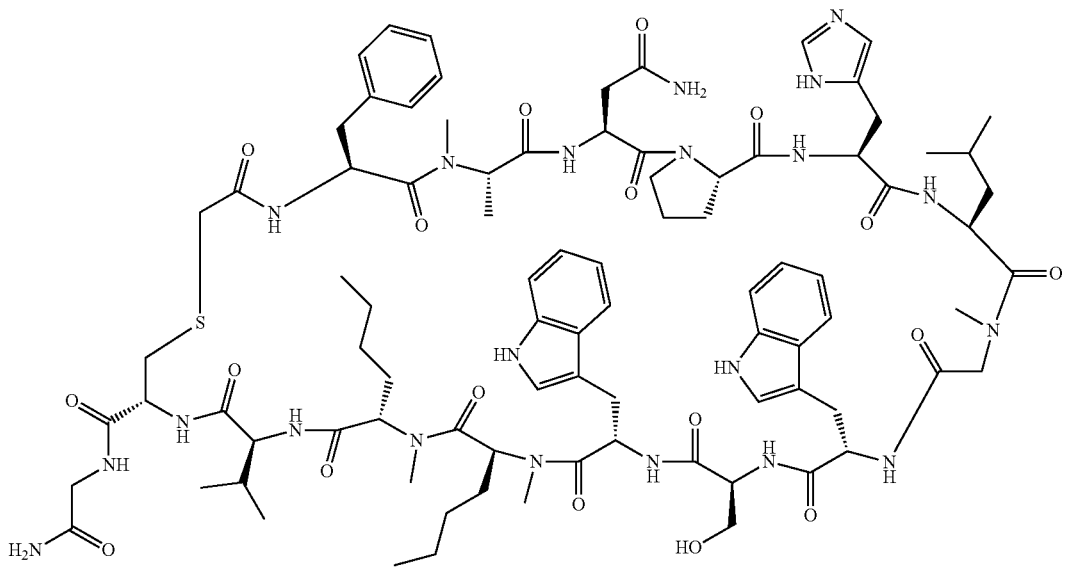

Example 5016

Example 5016 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 97%.

Analysis condition A: Retention time=1.91 min; ESI-MS (+) m/z 898.0 (M+2H)

Analysis condition B: Retention time=2.98 min; ESI-MS (+) m/z 898.5 (M+2H)

Preparation of Example 5017

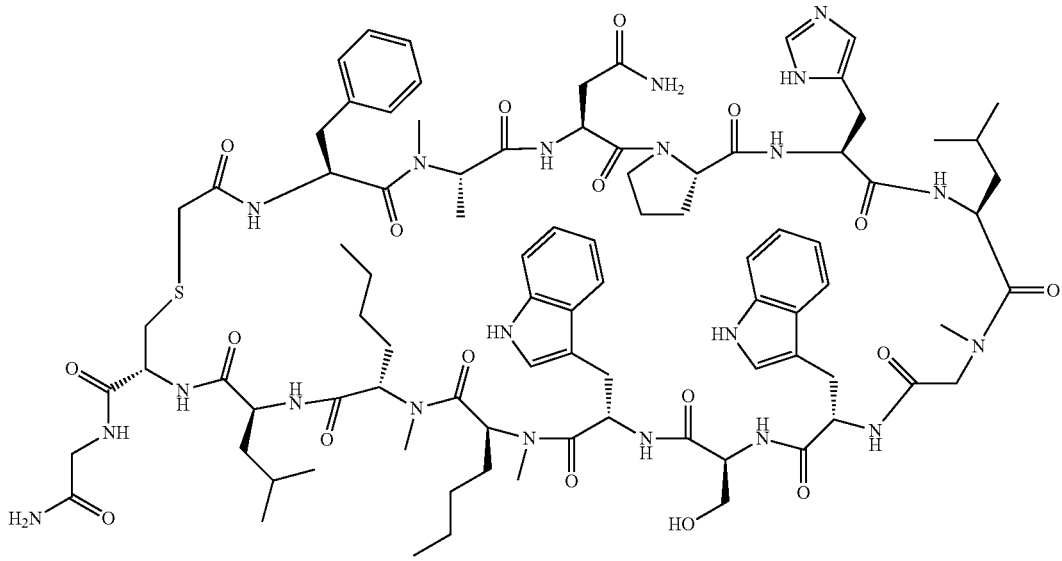

Example 5017

Example 5017 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 98%.

Analysis condition A: Retention time=1.97 min; ESI-MS (+) m/z 905.0 (M+2H)

Analysis condition B: Retention time=3.01 min; ESI-MS (+) m/z 905.3 (M+2H)

Preparation of Example 5018

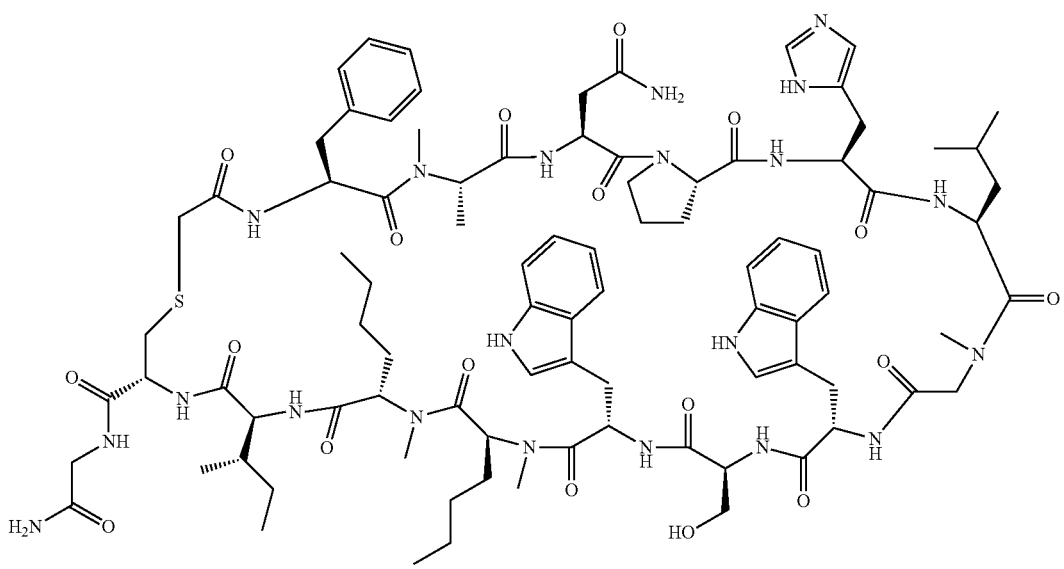

Example 5018

Example 5018 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 97%.

Analysis condition A: Retention time=1.95 min; ESI-MS (+) m/z 904.9 (M+2H)

Analysis condition B: Retention time=3.00 min; ESI-MS (+) m/z 905.0 (M+2H)

Preparation of Example 5019

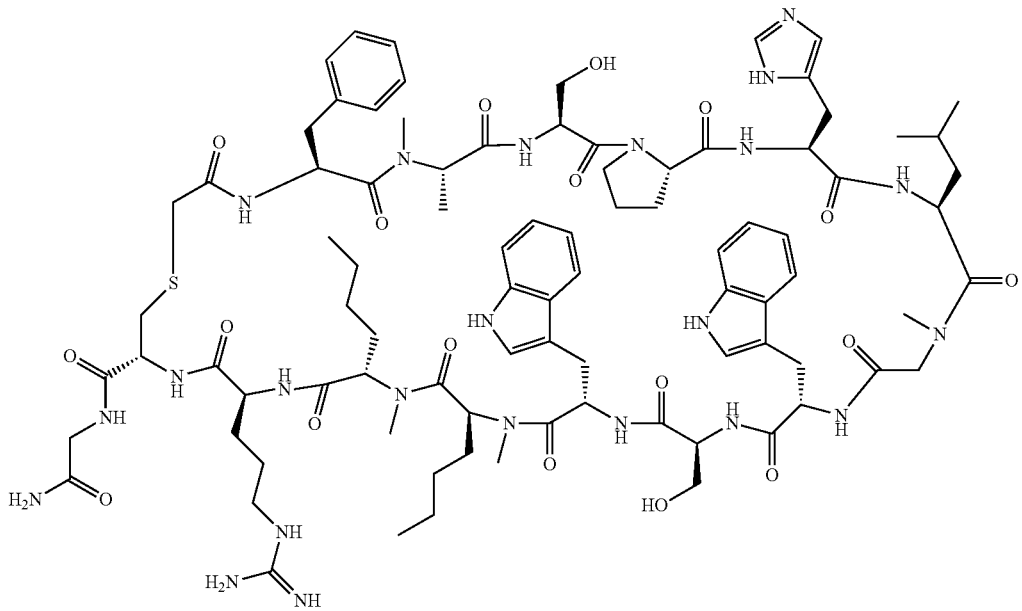

Example 5019

Example 5019 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 36.1 mg, and its estimated purity by LCMS analysis was 99%.

Analysis condition A: Retention time=1.88 min; ESI-MS (+) m/z 912.8 (M+2H)

Analysis condition B: Retention time=2.92 min; ESI-MS (+) m/z 913.0 (M+2H)

Preparation of Example 5020

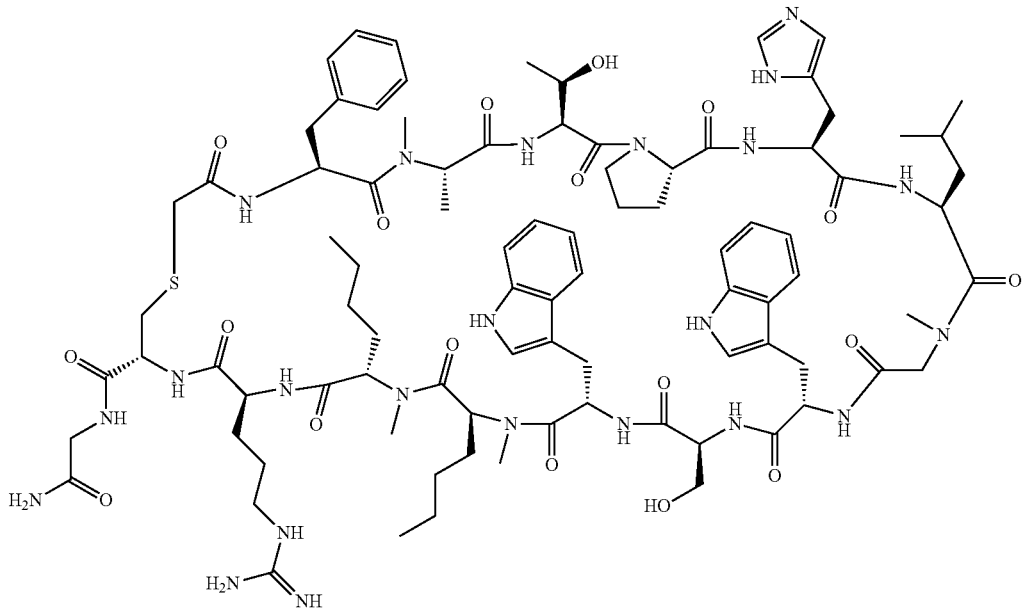

Example 5020

Example 5020 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 36.1 mg, and its estimated purity by LCMS analysis was 99%.

Analysis condition A: Retention time=1.88 min; ESI-MS (+) m/z 919.4 (M+2H)

Analysis condition B: Retention time=2.90 min; ESI-MS (+) m/z 920.0 (M+2H)

Preparation of Example 5021

Example 5021

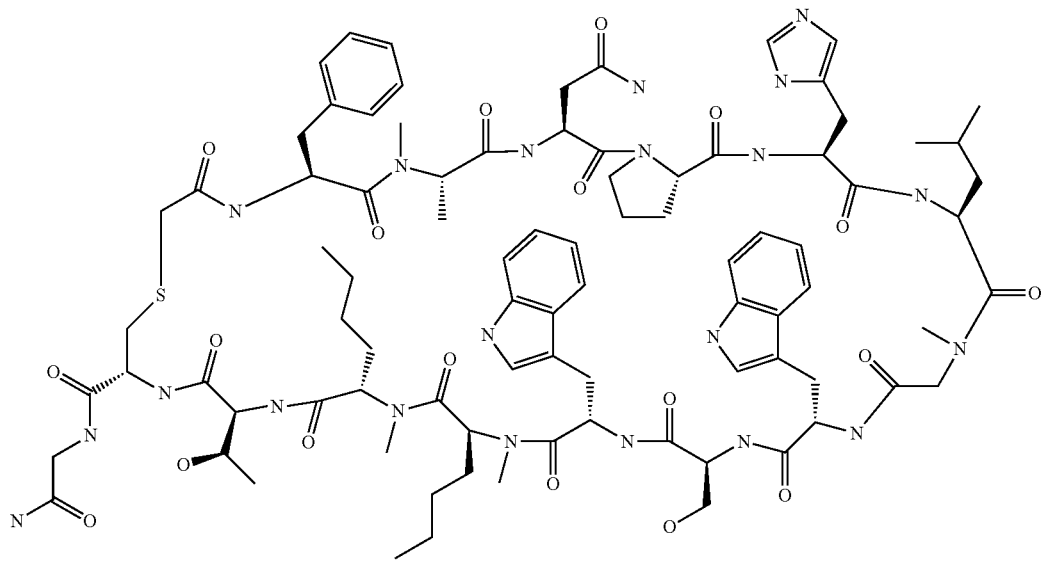

Example 5021 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 5.3 mg, and its estimated purity by LCMS analysis was 100%.

Analysis condition A: Retention time=2.14 min; ESI-MS (+) m/z 899.6 (M+2H)

Analysis condition B: Retention time=2.93 min; ESI-MS (+) m/z 899.8 (M+2H)

Preparation of Example 5022

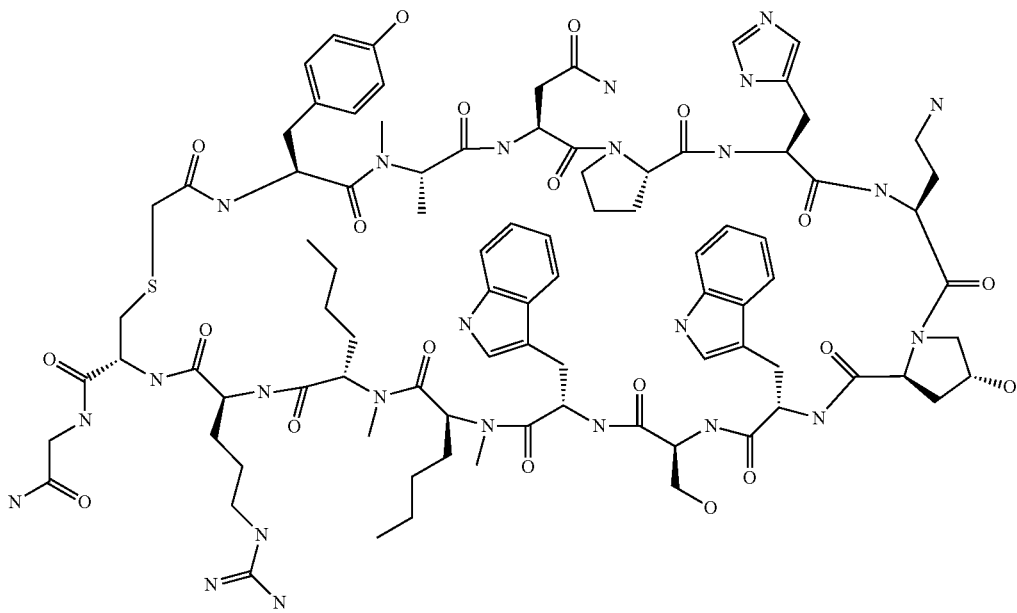

Example 5022

Example 5022 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 98%.

Analysis condition A: Retention time=1.58 min; ESI-MS (+) m/z 950.0 (M+2H)

Analysis condition B: Retention time=2.56 min; ESI-MS (+) m/z 950.2 (M+2H)

Preparation of Example 5023

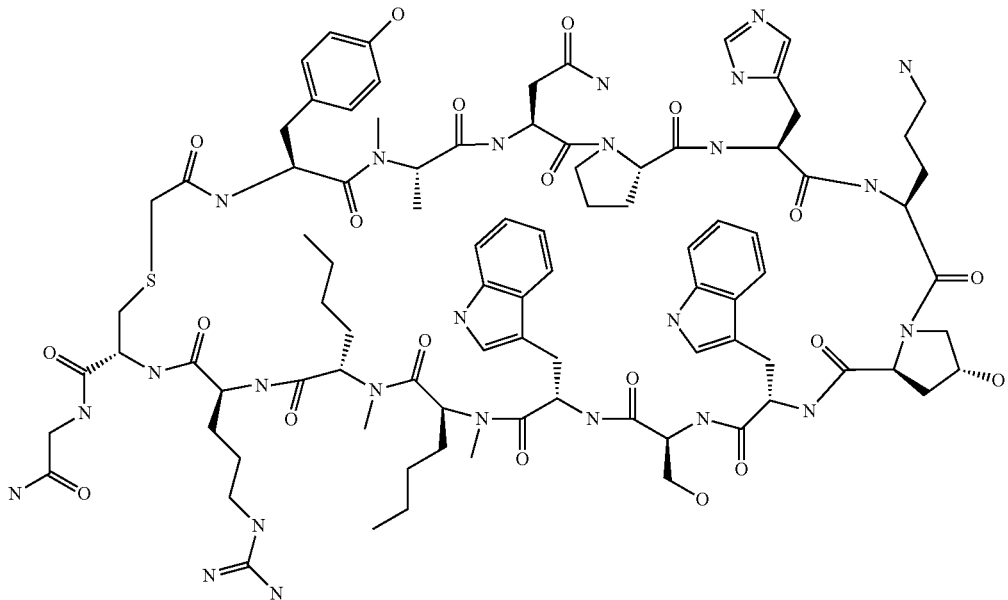

Example 5023

Example 5023 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.1 mg, and its estimated purity by LCMS analysis was 100%.

Analysis condition A: Retention time=1.59 min; ESI-MS (+) m/z 957.1 (M+2H)

Analysis condition B: Retention time=2.55 min; ESI-MS (+) m/z 957.2 (M+2H)

Preparation of Example 5024

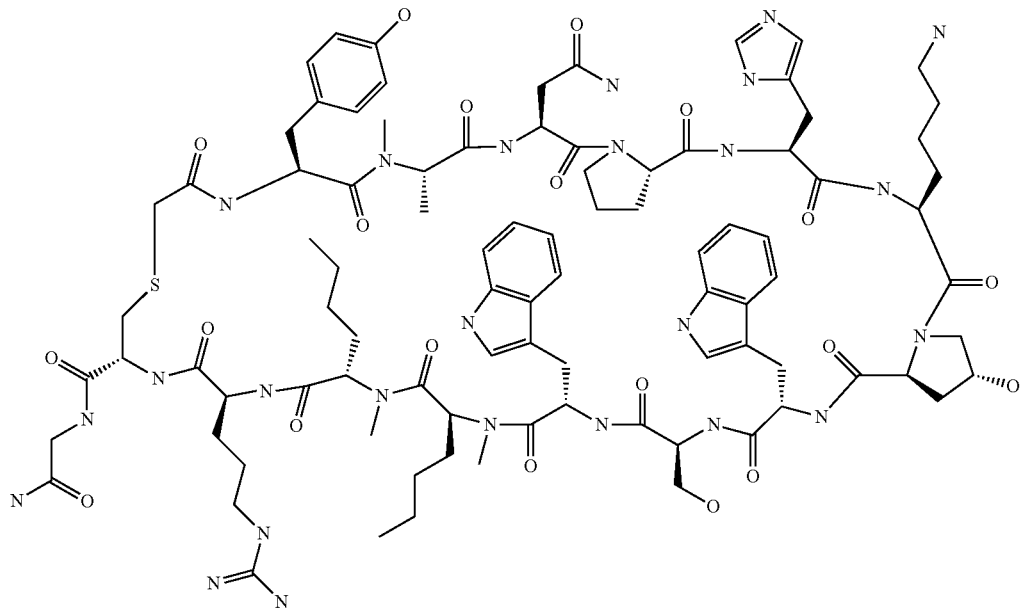

Example 5024

Example 5024 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 27.5 mg, and its estimated purity by LCMS analysis was 100%.

Analysis condition A: Retention time=2.07 min; ESI-MS (+) m/z 963.4 (M+2H)

Analysis condition B: Retention time=2.61 min; ESI-MS (+) m/z 963.3 (M+2H)

Preparation of Example 5025

Example 5025

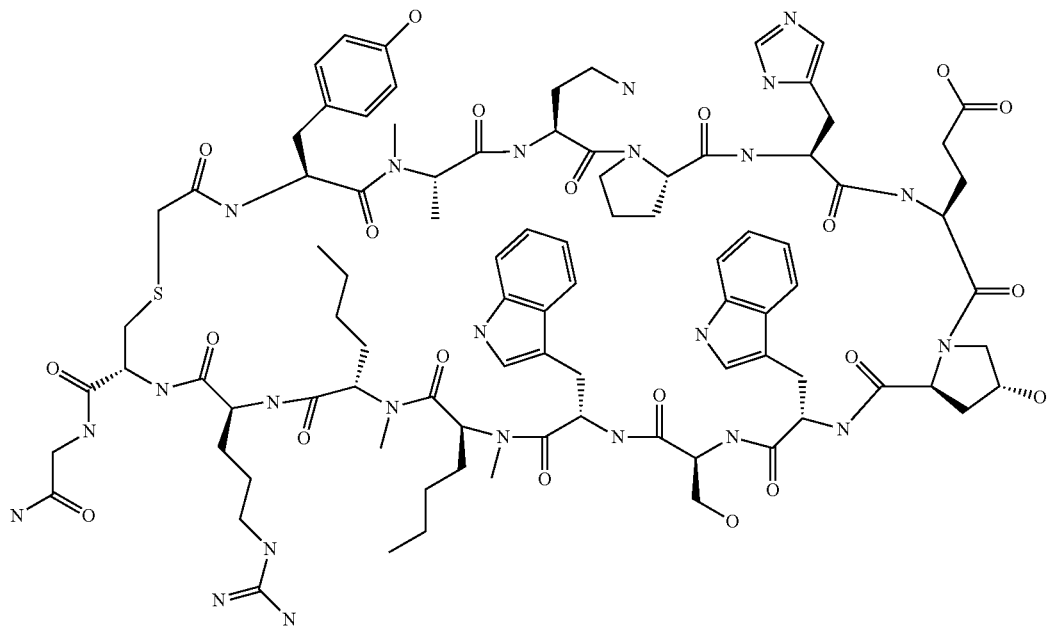

Example 5025 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 36.8 mg, and its estimated purity by LCMS analysis was 98%.

Analysis condition B: Retention time=2.55 min; ESI-MS (+) m/z 957.2 (M+2H)

Preparation of Example 5026

Example 5026

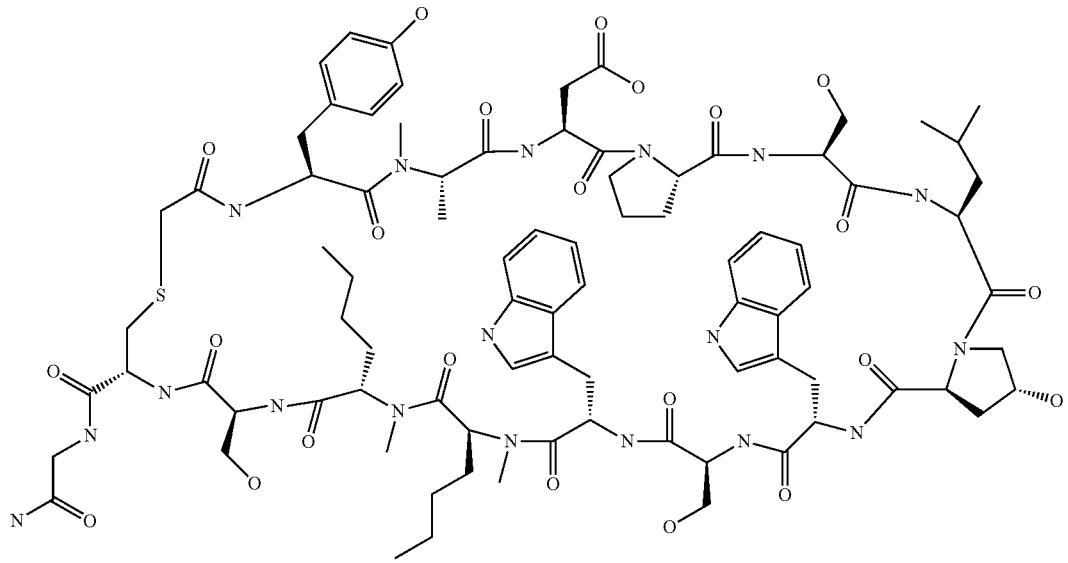

Example 5026 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Mobile Phase A: water with 20-mM ammonium acetate; Mobile Phase B: 95:5 methanol:water with 20-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 100%.

Analysis condition A: Retention time=1.70 min; ESI-MS (+) m/z 896.0 (M+2H)

Analysis condition B: Retention time=2.68 min; ESI-MS (+) m/z 895.9 (M+2H)

Preparation of Example 5027

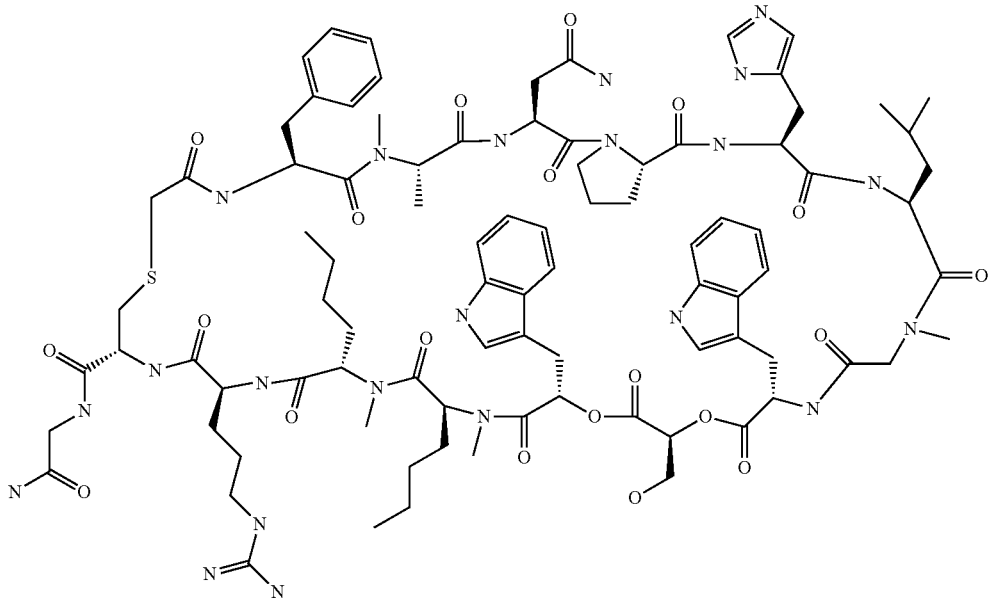

Example 5027

Example 5027 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.3 mg, and its estimated purity by LCMS analysis was 100%.

Analysis condition A: Retention time=1.62 min; ESI-MS (+) m/z 898.5 (M+2H)

Analysis condition B: Retention time=2.57 min; ESI-MS (+) m/z 898.5 (M+2H)

Preparation of Example 5028

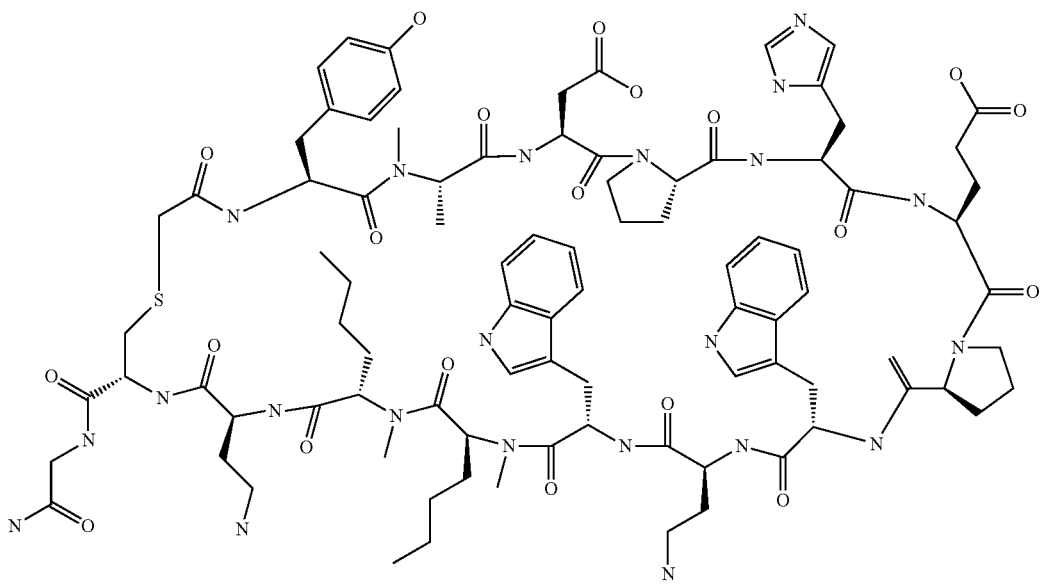

Example 5028

Example 5028 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.1 mg, and its estimated purity by LCMS analysis was 100%.

Analysis condition A: Retention time=1.53 min; ESI-MS (+) m/z 941.9 (M+2H)

Analysis condition B: Retention time=2.52 min; ESI-MS (+) m/z 941.9 (M+2H)

Preparation of Example 5029

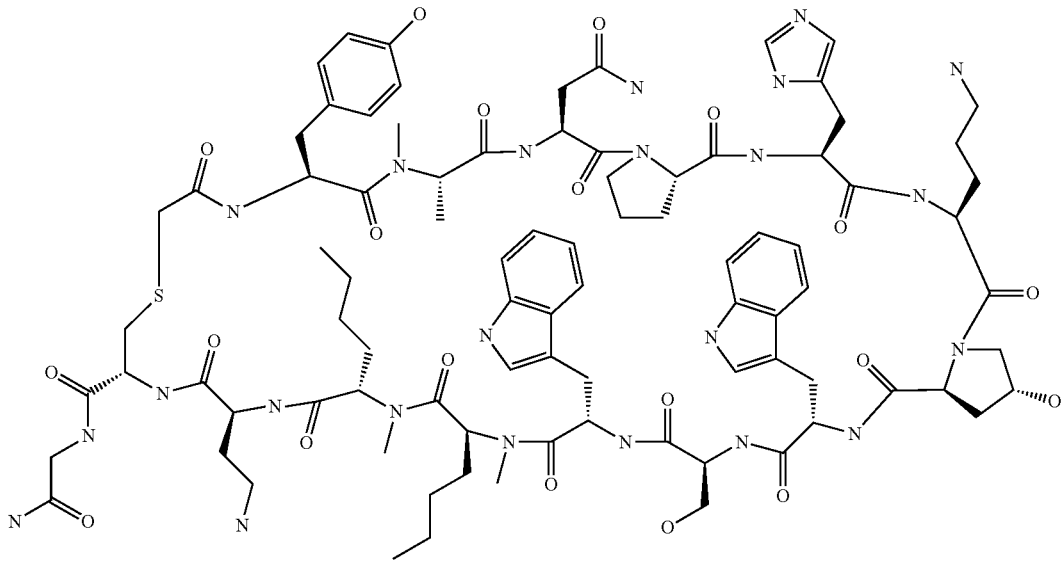

Example 5029

Example 5029 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 100%.

Analysis condition A: Retention time=1.55 min; ESI-MS (+) m/z 935.9 (M+2H)

Analysis condition B: Retention time=2.54 min; ESI-MS (+) m/z 935.9 (M+2H)

Preparation of Example 5030

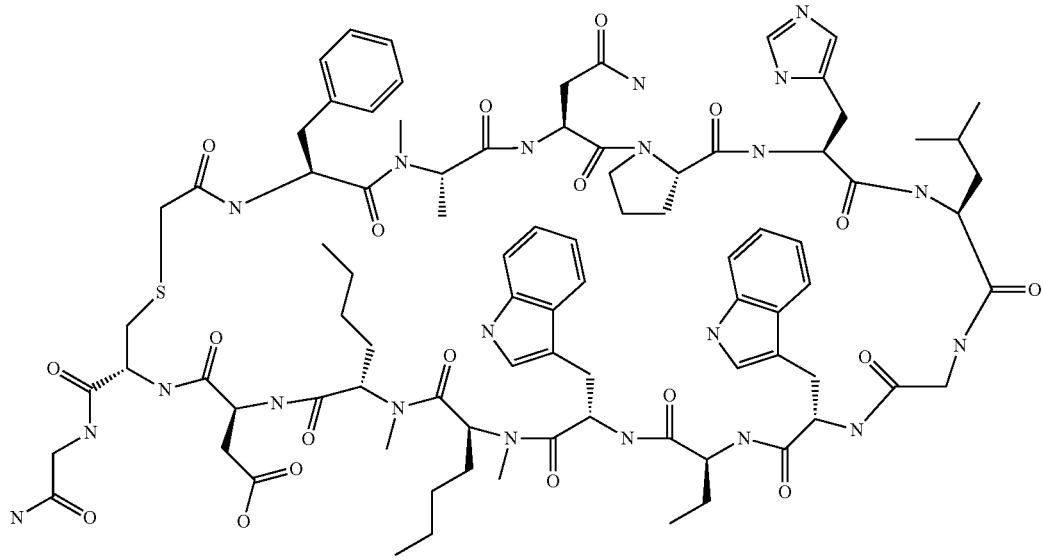

Example 5030

Example 5030 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 40 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 100%.

Analysis condition A: Retention time=1.72 min; ESI-MS (+) m/z 905.5 (M+2H)

Analysis condition B: Retention time=2.89 min; ESI-MS (+) m/z 905.5 (M+2H)

Preparation of Example 5031

Example 5031

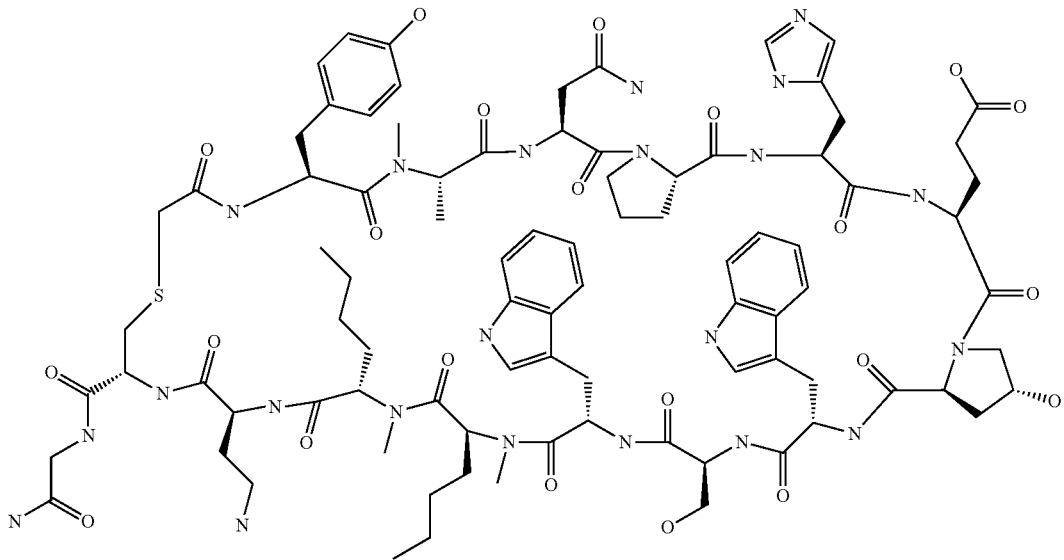

Example 5031 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 100%.

Analysis condition A: Retention time=1.56 min; ESI-MS (+) m/z 935.4 (M+2H)

Analysis condition B: Retention time=2.57 min; ESI-MS (+) m/z 935.5 (M+2H)

Preparation of Example 5032

Example 5032

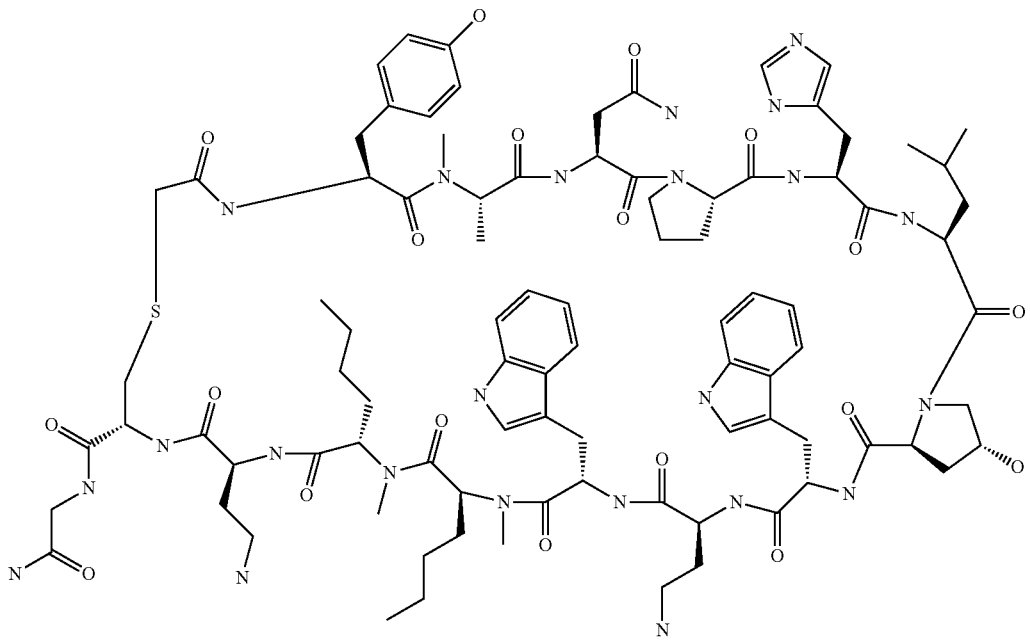

Example 5032 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 27.1 mg, and its estimated purity by LCMS analysis was 98%.

Analysis condition A: Retention time=1.58 min; ESI-MS (+) m/z 934.0 (M+2H)

Analysis condition B: Retention time=2.55 min; ESI-MS (−) m/z 932.0 (M−2H)

Preparation of Example 5033

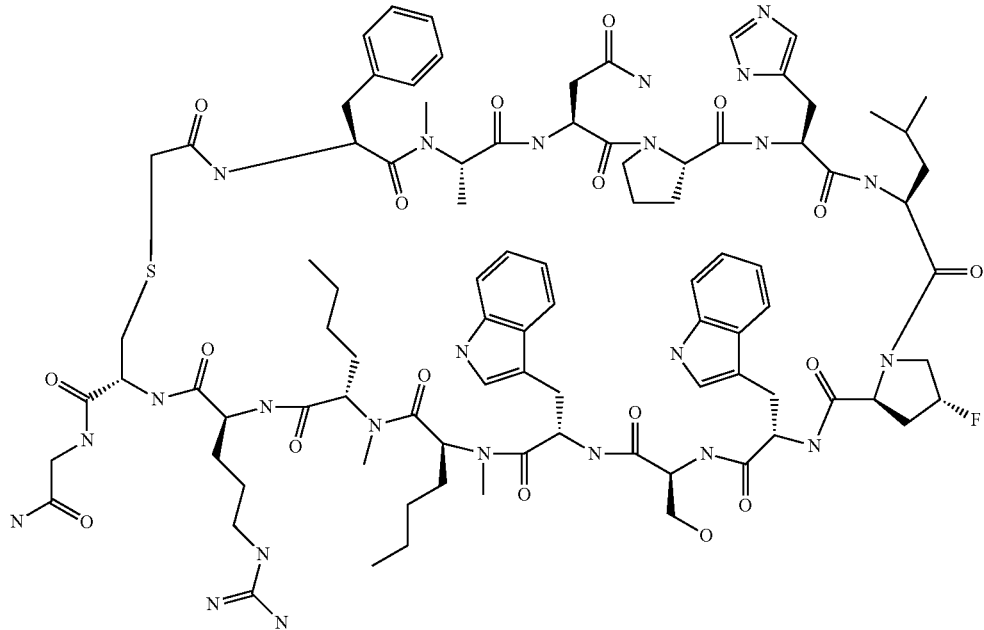

Example 5033

Example 5033 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 100%.

Analysis condition A: Retention time=1.93 min; ESI-MS (+) m/z 948.5 (M+2H)

Analysis condition B: Retention time=2.97 min; ESI-MS (+) m/z 949.1 (M+2H)

Preparation of Example 5034

Example 5034

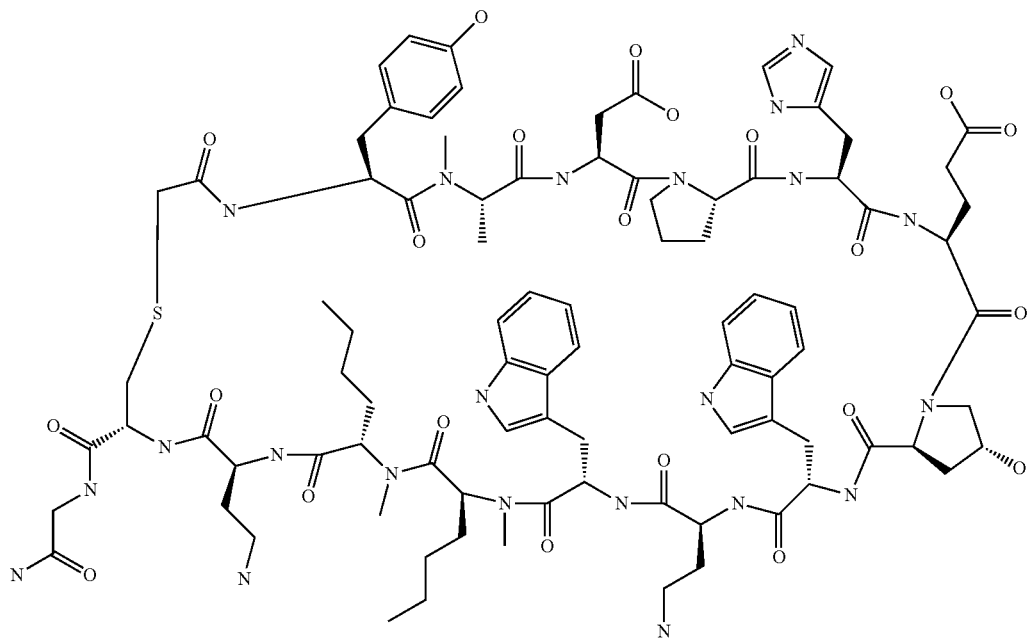

Example 5034 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 32.4 mg, and its estimated purity by LCMS analysis was 95%.

Analysis condition A: Retention time=1.49 min; ESI-MS (+) m/z 943.0 (M+2H)

Analysis condition B: Retention time=2.50 min; ESI-MS (+) m/z 943.1 (M+2H)

Preparation of Example 5035

Example 5035

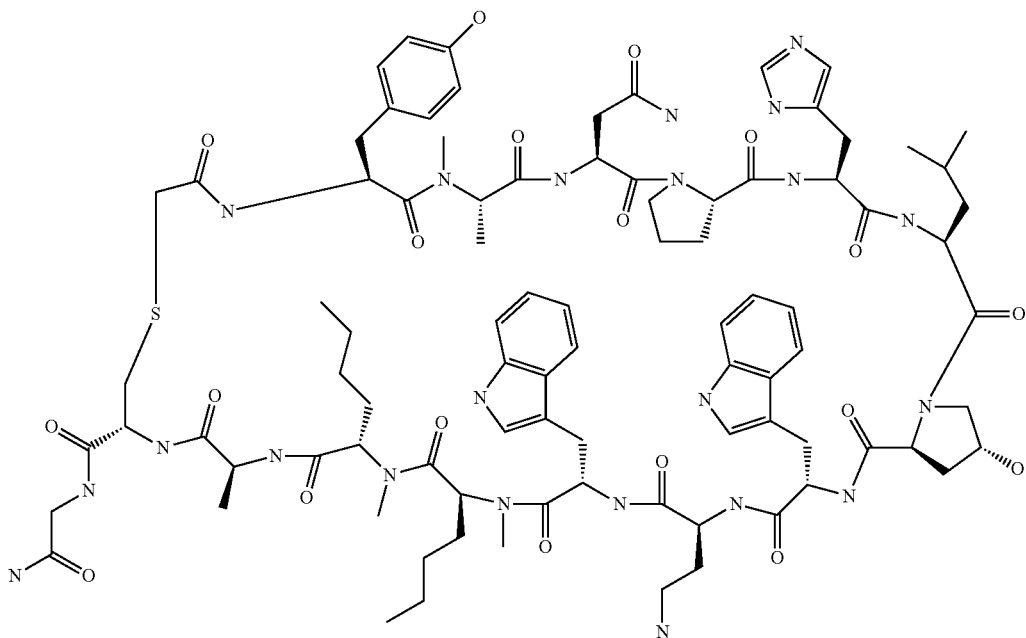

Example 5035 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 26.9 mg, and its estimated purity by LCMS analysis was 100%.

Analysis condition A: Retention time=1.57 min; ESI-MS (+) m/z 919.6 (M+2H)

Analysis condition B: Retention time=2.61 min; ESI-MS (+) m/z 919.5 (M+2H)

Preparation of Example 5026

Example 5036

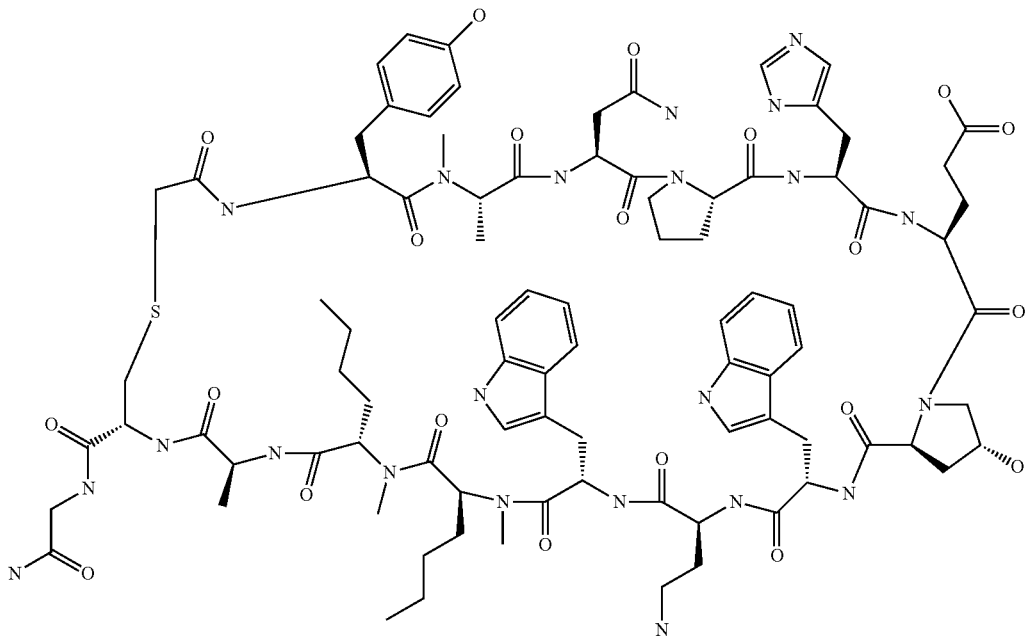

Example 5036 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 100%.

Analysis condition A: Retention time=1.51 min; ESI-MS (+) m/z 927.6 (M+2H)

Analysis condition B: Retention time=2.64 min; ESI-MS (+) m/z 927.6 (M+2H)

Preparation of Example 5037

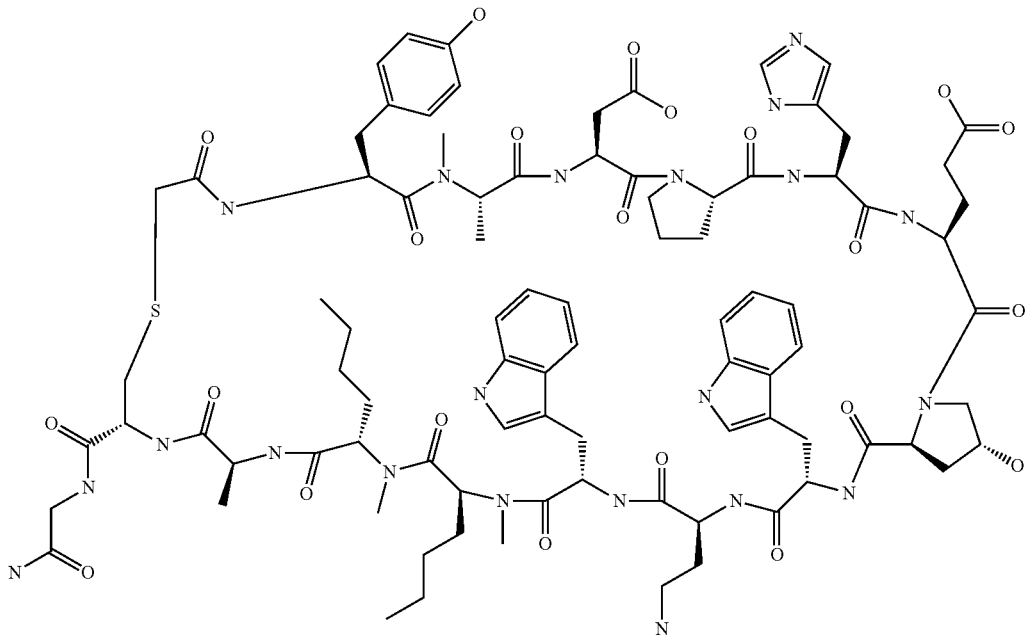

Example 5037

Example 5037 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 100%.

Analysis condition A: Retention time=1.48 min; ESI-MS (+) m/z 928.0 (M+2H)

Analysis condition B: Retention time=2.55 min; ESI-MS (+) m/z 927.9 (M+2H)

Preparation of Example 5038

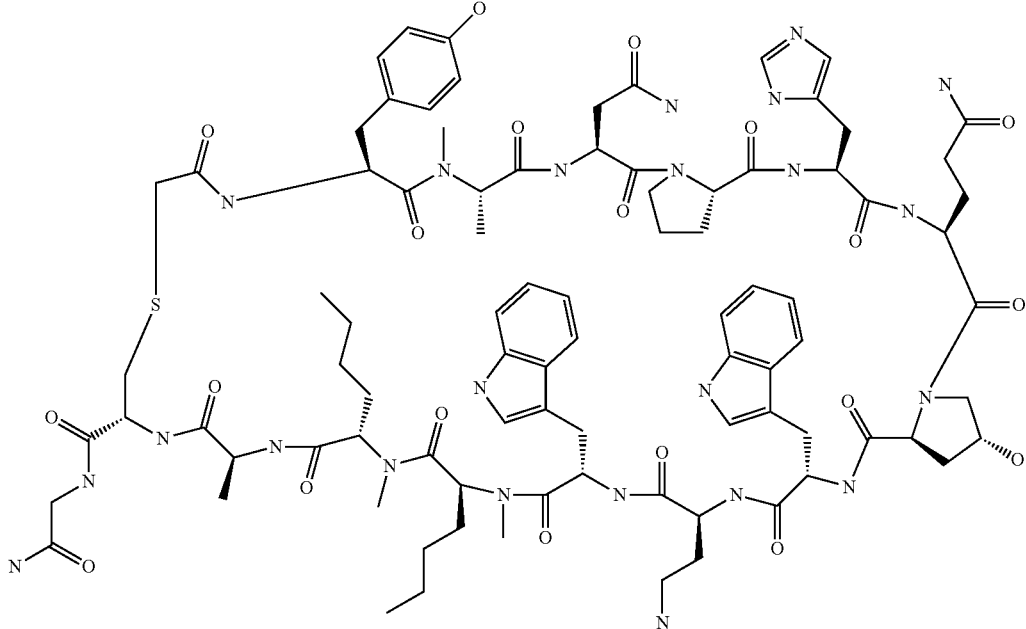

Example 5038

Example 5038 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 99%.

Analysis condition A: Retention time=1.57 min; ESI-MS (+) m/z 927.2 (M+2H)

Analysis condition B: Retention time=2.59 min; ESI-MS (+) m/z 927.0 (M+2H)

Preparation of Example 5039

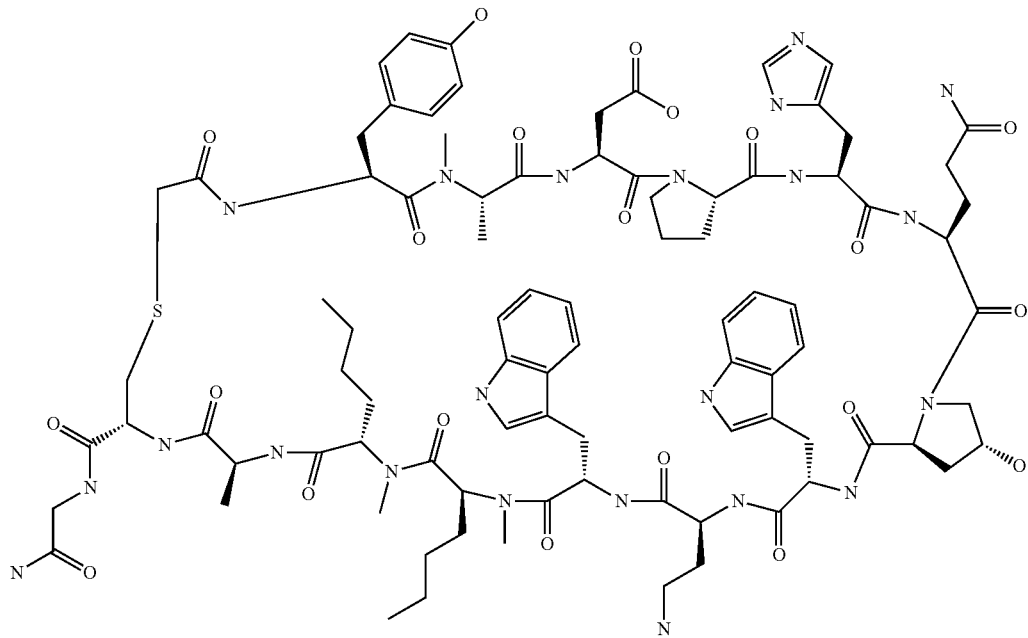

Example 5039

Example 5039 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 99%.

Analysis condition A: Retention time=1.43 min; ESI-MS (+) m/z 928.0 (M+2H)

Analysis condition B: Retention time=2.60 min; ESI-MS (+) m/z 928.0 (M+2H)

Preparation of Example 5040

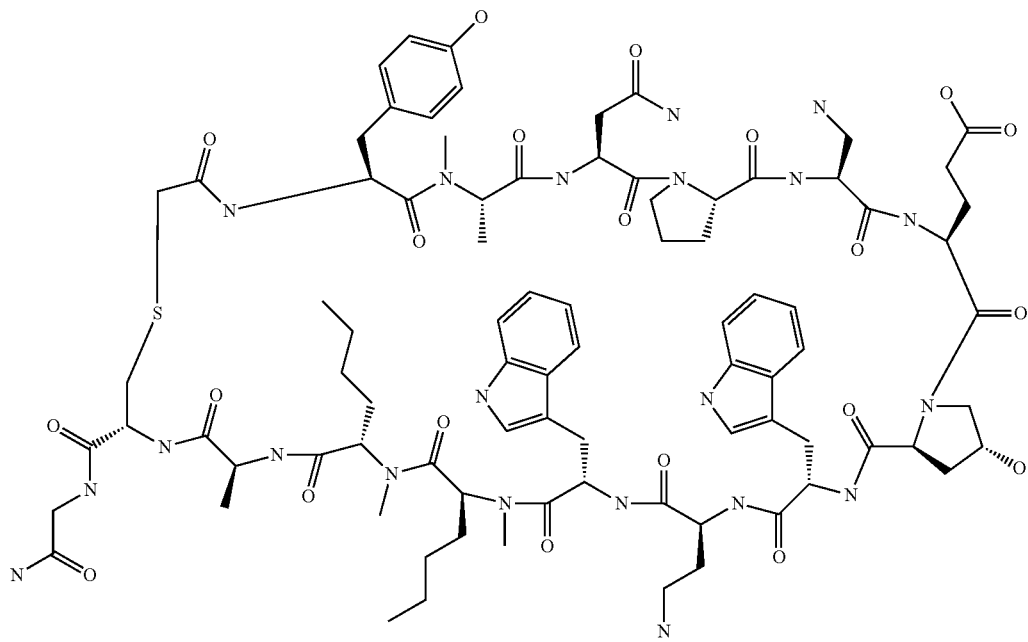

Example 5040

Example 5040 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 99%.

Analysis condition A: Retention time=1.42 min; ESI-MS (+) m/z 901.6 (M+2H)

Analysis condition B: Retention time=2.59 min; ESI-MS (+) m/z 901.7 (M+2H)

Preparation of Example 5041

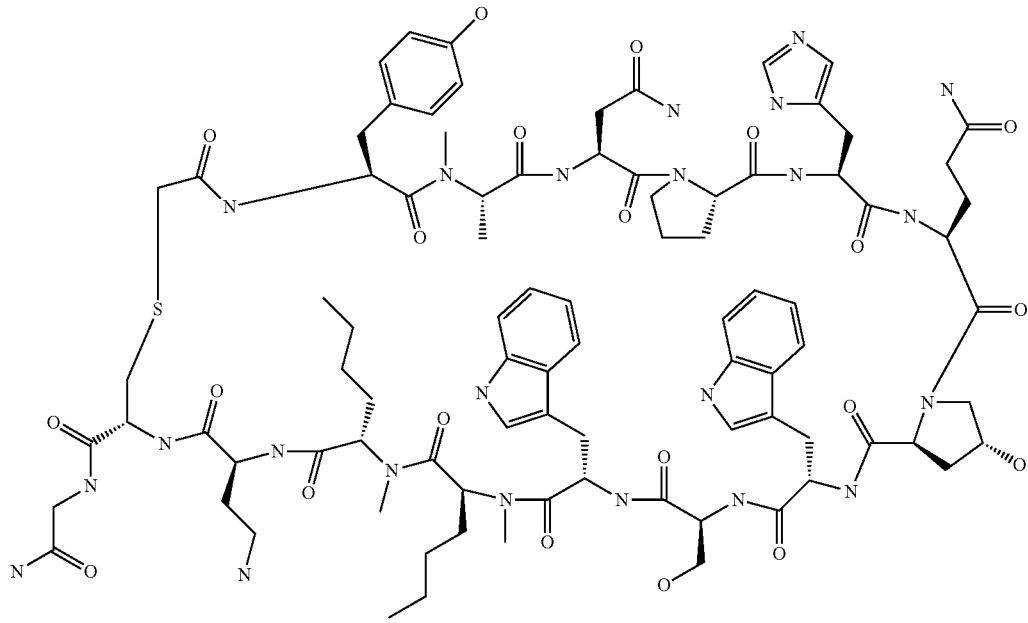

Example 5041

Example 5041 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-50% B over 15 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 100%.

Analysis condition A: Retention time=1.44 min; ESI-MS (+) m/z 935.8 (M+2H)

Analysis condition B: Retention time=2.56 min; ESI-MS (+) m/z 935.5 (M+2H)

Preparation of Example 5042

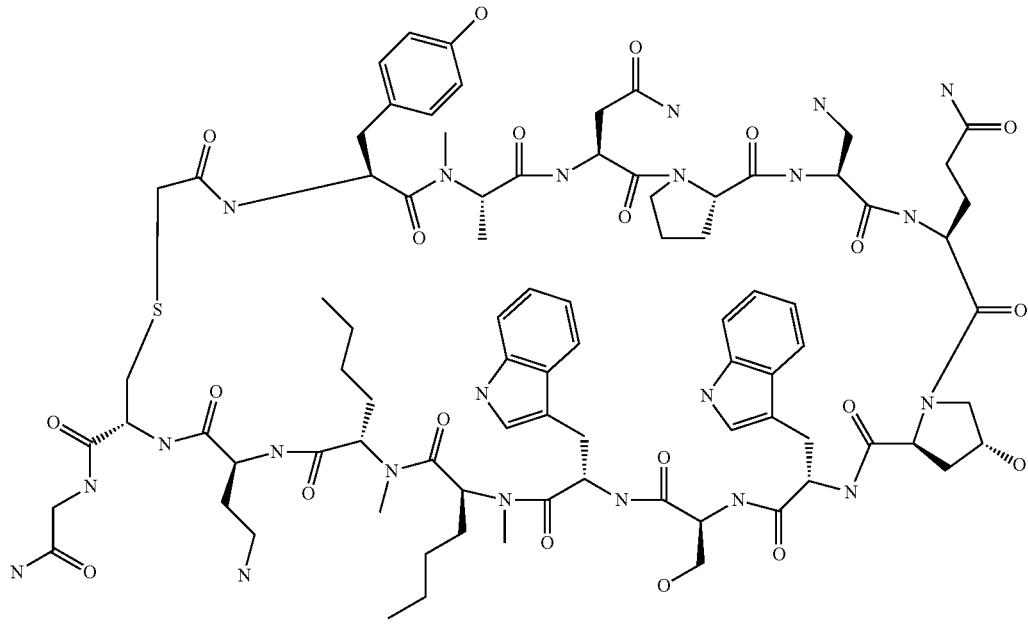

Example 5042

Example 5042 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 25.8 mg, and its estimated purity by LCMS analysis was 99%.

Analysis condition A: Retention time=1.41 min; ESI-MS (+) m/z 910.2 (M+2H)

Analysis condition B: Retention time=2.56 min; ESI-MS (+) m/z 910.1 (M+2H)

Preparation of Example 5043

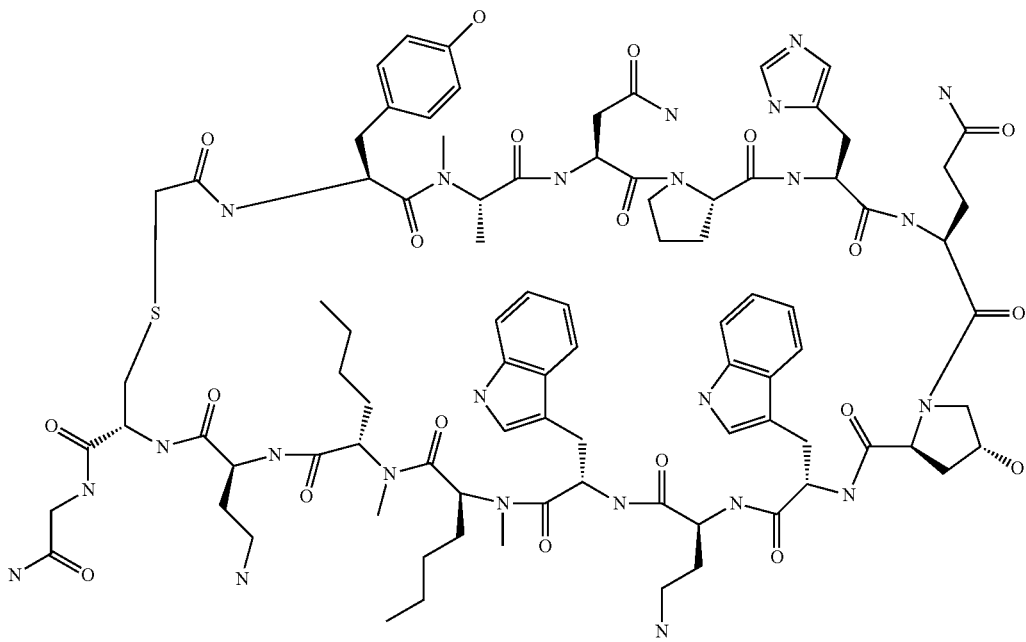

Example 5043

Example 5043 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-50% B over 15 minutes, then a 5-minute hold at 100% B; Flow: 20 mL/min. Fractions containing the desired product were combined and dried via centrifugal evaporation. The yield of the product was 32.9 mg, and its estimated purity by LCMS analysis was 99%.

Analysis condition A: Retention time=1.36 min; ESI-MS (+) m/z 942.3 (M+2H)

Analysis condition B: Retention time=2.50 min; ESI-MS (+) m/z 942.1 (M+2H)

Preparation of Example 5044

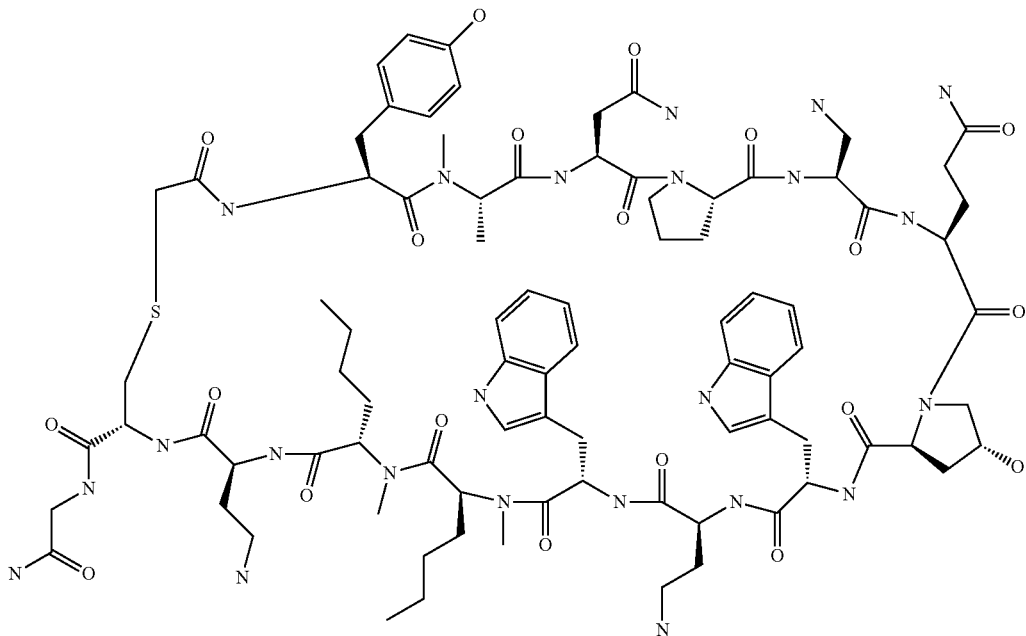

Example 5044

Example 5044 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 98%.

Analysis condition A: Retention time=1.36 min; ESI-MS (+) m/z 916.7 (M+2H)

Analysis condition B: Retention time=2.52 min; ESI-MS (+) m/z 916.4 (M+2H)

Preparation of Example 5045

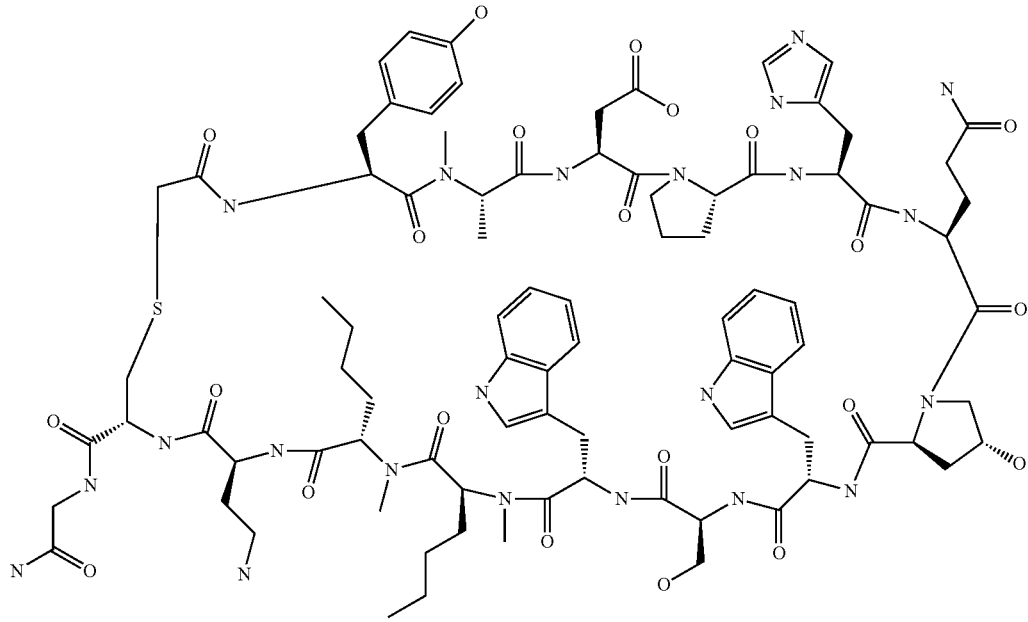

Example 5045

Example 5045 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 20 minutes, then a 5-minute hold at 100% B; Flow: 20 mL/min. Fractions containing the desired product were combined and dried via centrifugal evaporation. The yield of the product was 18.0 mg, and its estimated purity by LCMS analysis was 100%.

Analysis condition A: Retention time=1.44 min; ESI-MS (+) m/z 936.5 (M+2H)

Analysis condition B: Retention time=2.56 min; ESI-MS (+) m/z 936.4 (M+2H)

Preparation of Example 5046

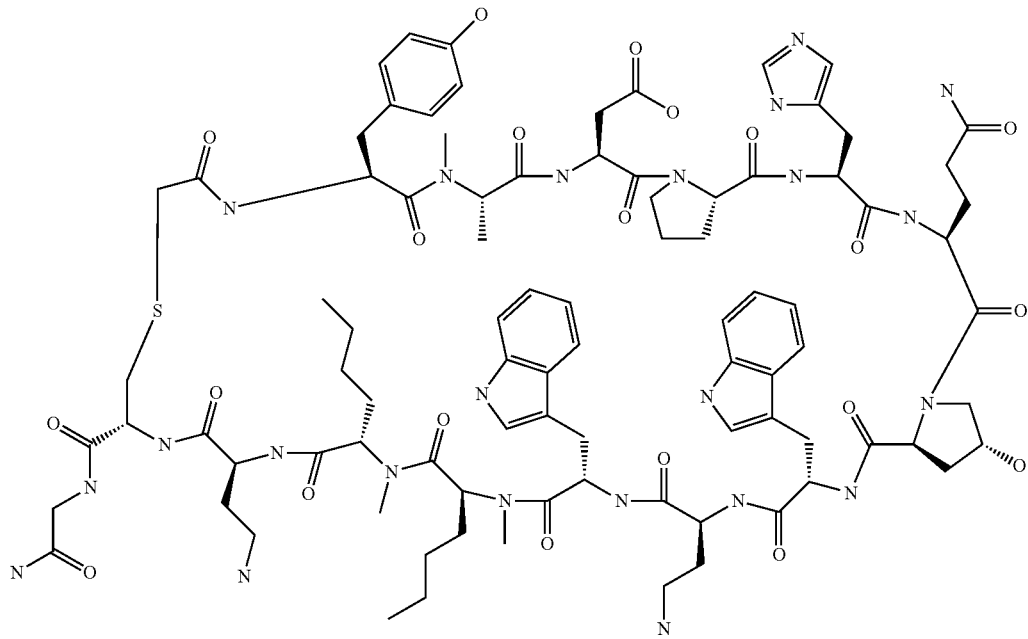

Example 5046

Example 5046 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-50% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 19.9 mg, and its estimated purity by LCMS analysis was 98%.

Analysis condition A: Retention time=1.37 min; ESI-MS (+) m/z 942.9 (M+2H)

Analysis condition B: Retention time=2.50 min; ESI-MS (+) m/z 942.9 (M+2H)

Preparation of Example 5047

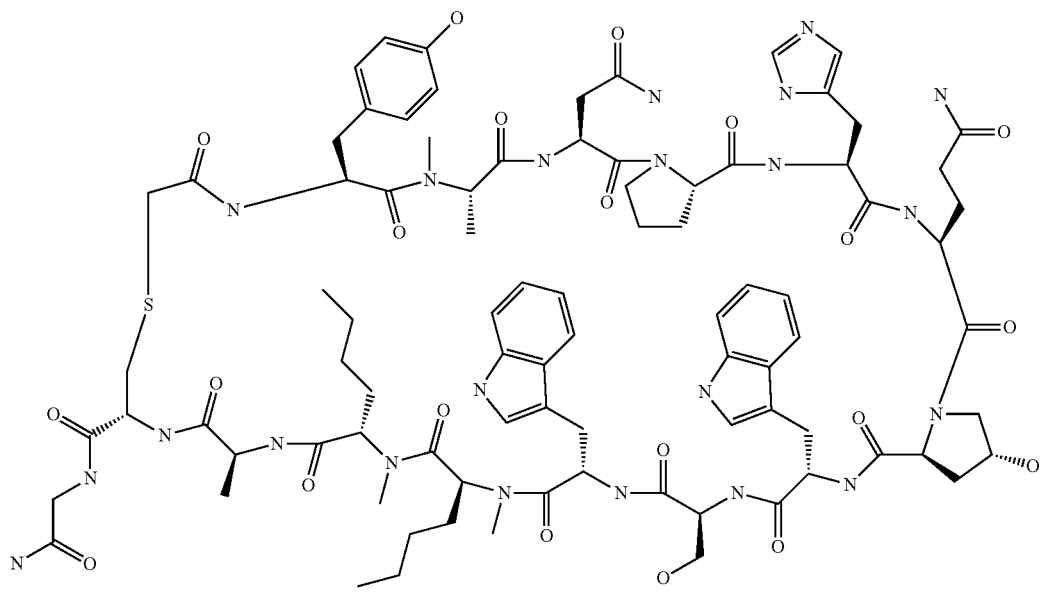

Example 5047

Example 5047 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-50% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 98%.

Analysis condition A: Retention time=1.53 min; ESI-MS (+) m/z 921.2 (M+2H)

Analysis condition B: Retention time=2.63 min; ESI-MS (+) m/z 921.4 (M+2H)

Preparation of Example 5048

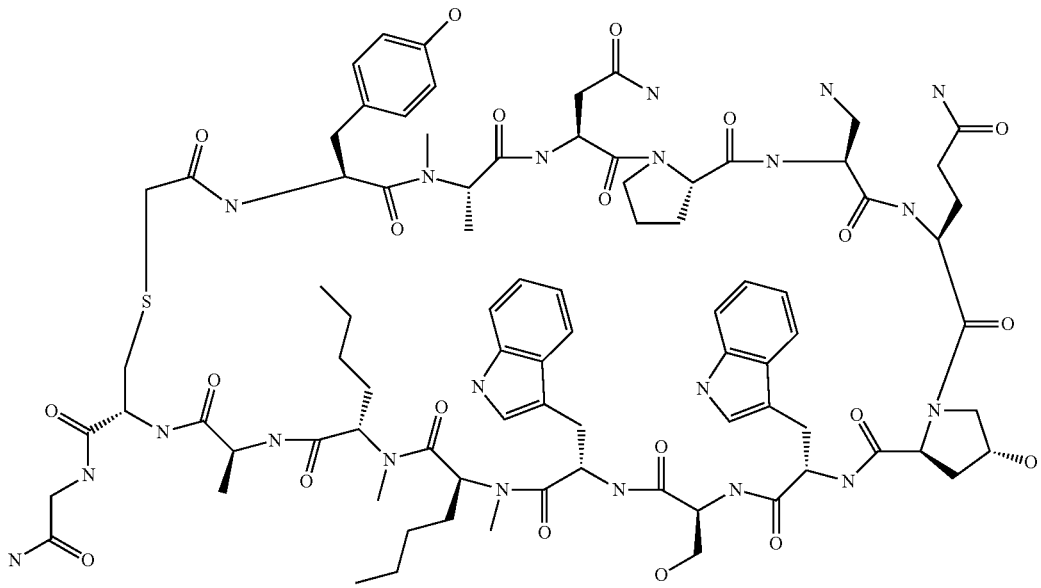

Example 5048

Example 5048 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.5 mg, and its estimated purity by LCMS analysis was 99%.

Analysis condition A: Retention time=1.47 min; ESI-MS (+) m/z 895.6 (M+2H)

Analysis condition B: Retention time=2.63 min; ESI-MS (+) m/z 895.7 (M+2H)

Preparation of Example 5049

Example 5049

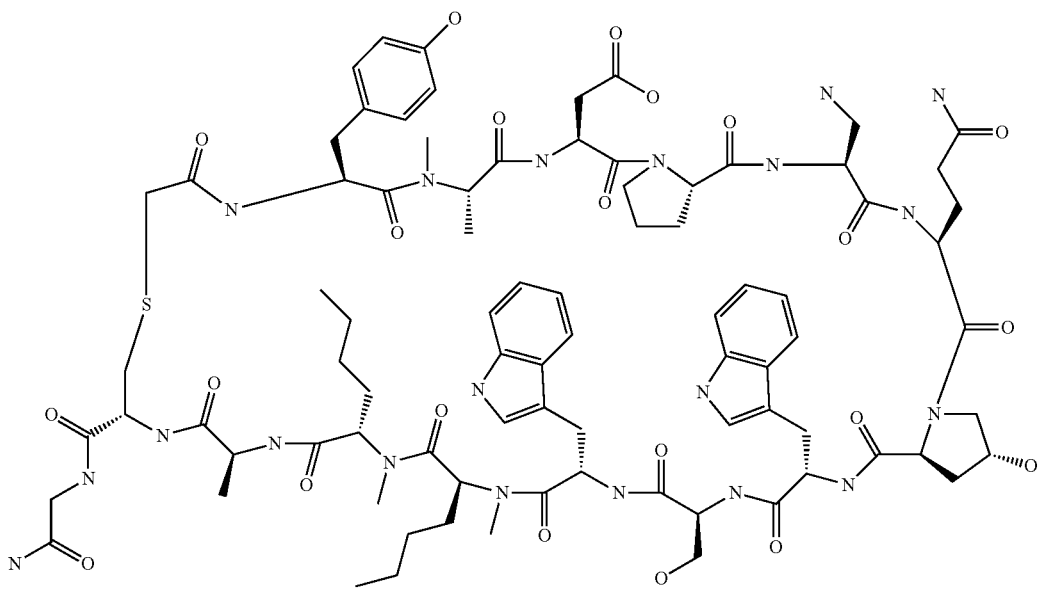

Example 5049 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 97%.

Analysis condition A: Retention time=1.53 min; ESI-MS (+) m/z 895.9 (M+2H)

Analysis condition B: Retention time=2.65 min; ESI-MS (+) m/z 896.2 (M+2H)

Preparation of Example 5050

Example 5050

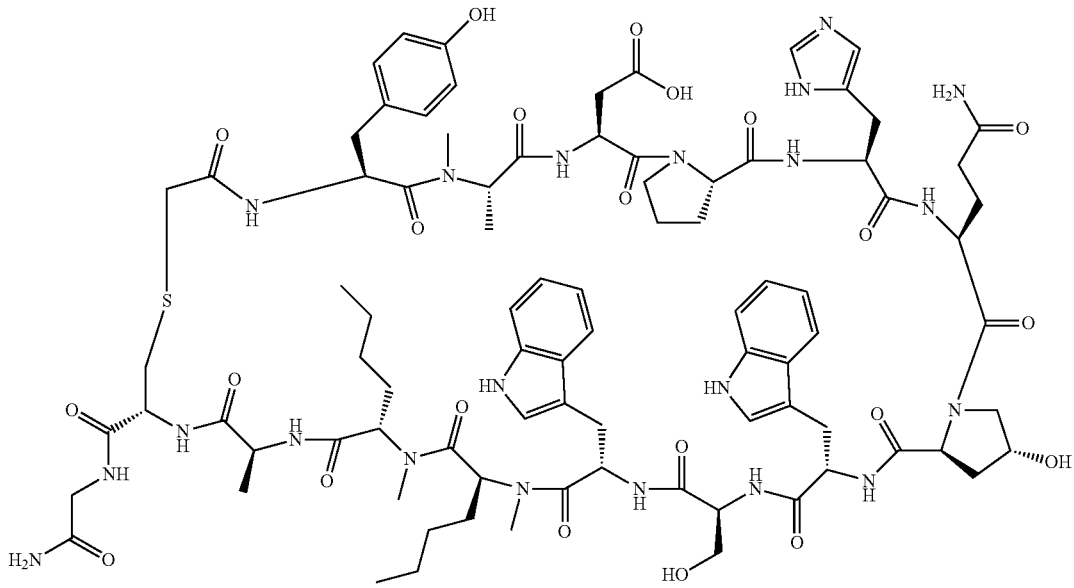

Example 5050 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-50% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 40 minutes, then a 5-minute hold at 100% B; Flow: 20 mL/min. Fractions containing the desired product were combined and dried via centrifugal evaporation. The yield of the product was 5.2 mg, and its estimated purity by LCMS analysis was 100%.

Analysis condition A: Retention time=1.47 min; ESI-MS (+) m/z 921.7 (M+2H)

Analysis condition B: Retention time=2.63 min; ESI-MS (+) m/z 921.8 (M+2H)

Preparation of Example 5051

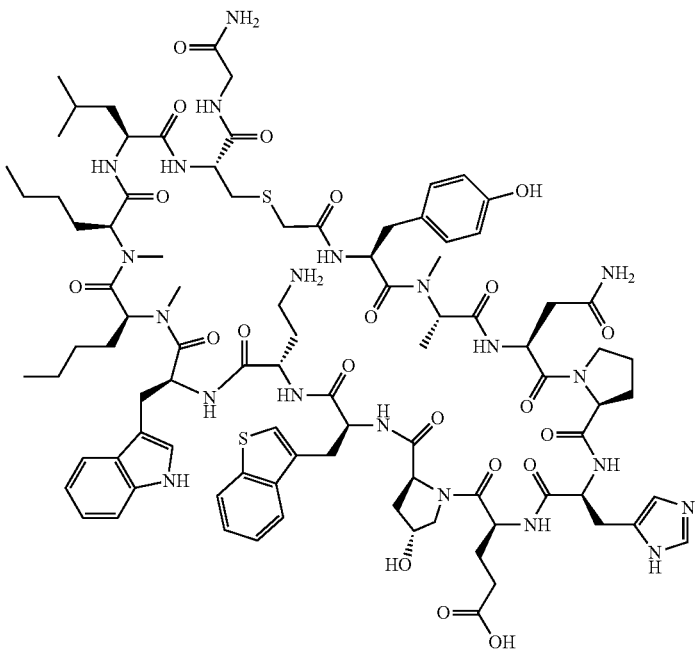

Example 5051

Example 5051 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 97%.

Analysis condition A: Retention time=1.65 min; ESI-MS (+) m/z 957.3 (M+2H)

Analysis condition B: Retention time=2.93 min; ESI-MS (+) m/z 957.5 (M+2H)

Preparation of Example 5052

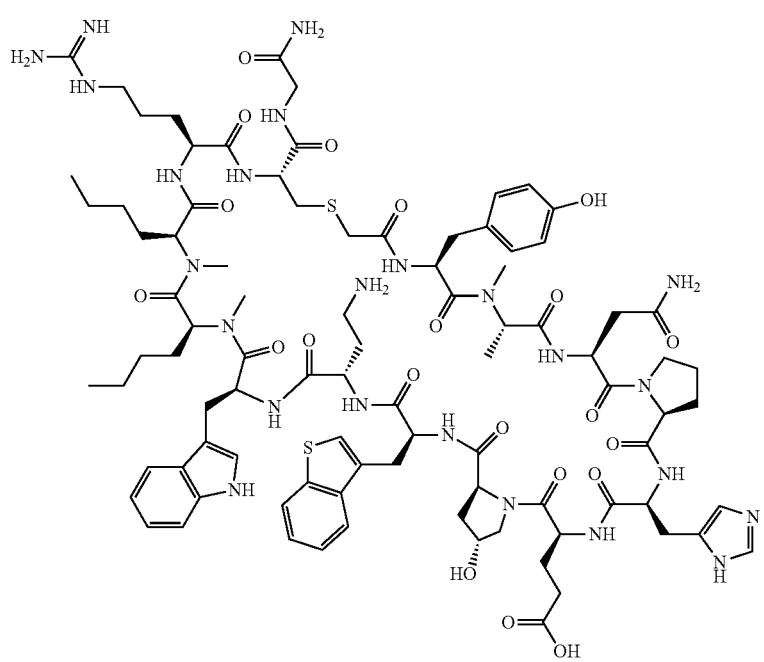

Example 5052

Example 5052 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 5.4 mg, and its estimated purity by LCMS analysis was 100%.

Analysis condition A: Retention time=1.41 min; ESI-MS (+) m/z 978.9 (M+2H)

Analysis condition B: Retention time=2.68 min; ESI-MS (−) m/z 977.3 (M−2H)

Preparation of Example 5053

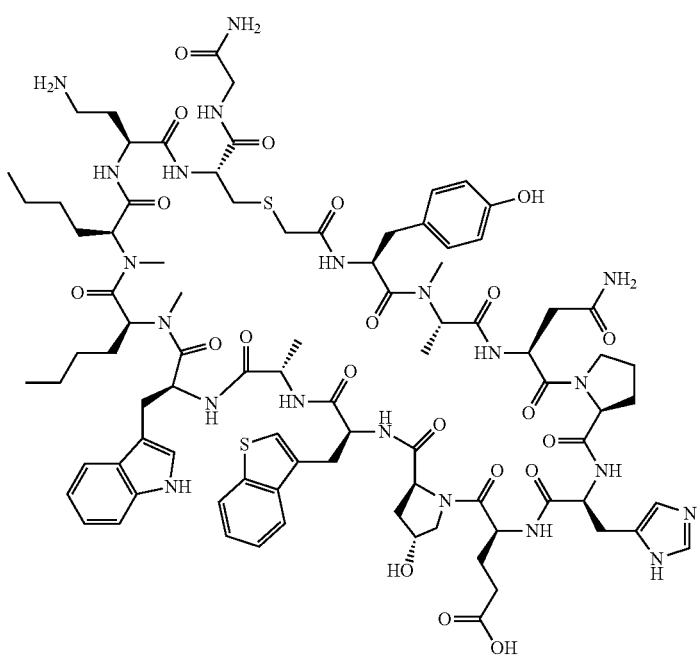

Example 5053

Example 5053 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 99%.

Analysis condition A: Retention time=1.45 min; ESI-MS (+) m/z 936.1 (M+2H)

Analysis condition B: Retention time=2.73 min; ESI-MS (+) m/z 936.5 (M+2H)

Preparation of Example 5054

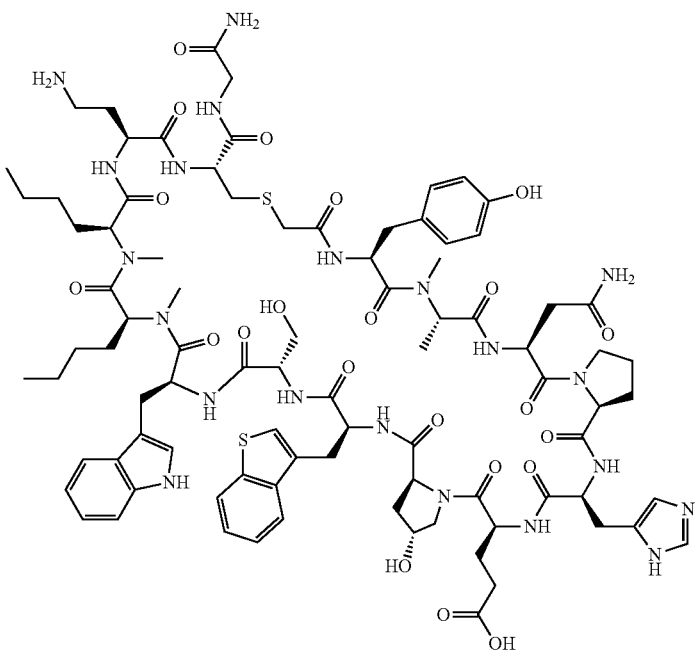

Example 5054

Example 5054 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 100%.

Analysis condition A: Retention time=1.46 min; ESI-MS (+) m/z 944.2 (M+2H)

Analysis condition B: Retention time=2.72 min; ESI-MS (+) m/z 944.4 (M+2H)

Preparation of Example 5055

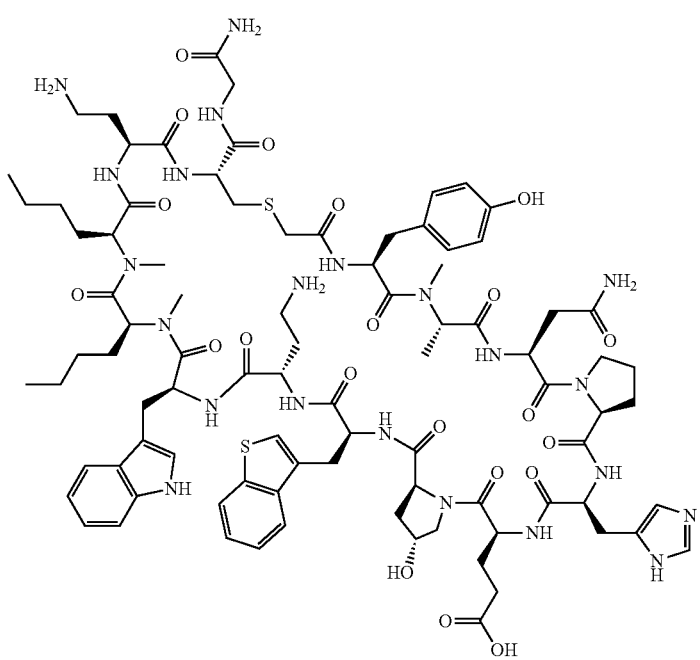

Example 5055

Example 5055 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 19.8 mg, and its estimated purity by LCMS analysis was 99%.

Analysis condition A: Retention time=1.39 min; ESI-MS (+) m/z 950.6 (M+2H)

Analysis condition B: Retention time=2.69 min; ESI-MS (−) m/z 949.2 (M−2H)

Preparation of Example 5056

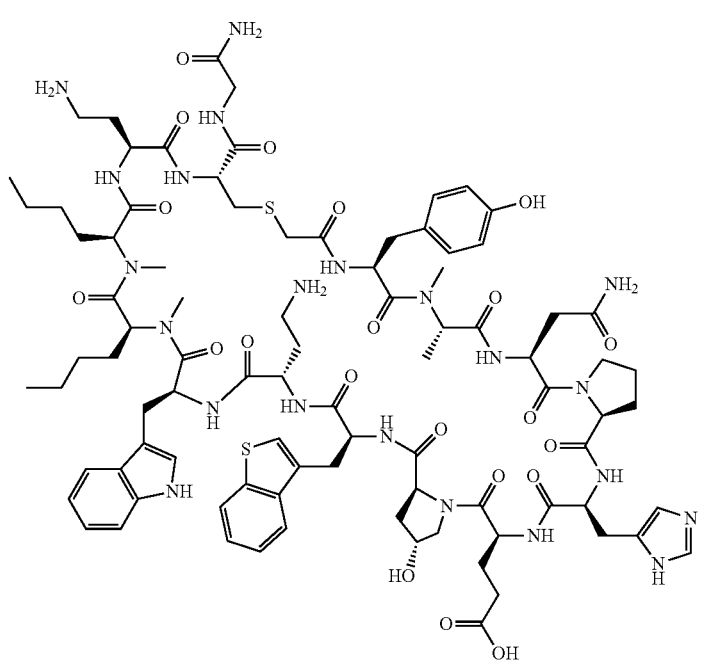

Example 5056

Example 5056 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.4 mg, and its estimated purity by LCMS analysis was 98%.

Analysis condition A: Retention time=1.41 min; ESI-MS (+) m/z 950.4 (M+2H)

Analysis condition B: Retention time=2.63 min; ESI-MS (+) m/z 950.9 (M+2H)

Preparation of Example 5057

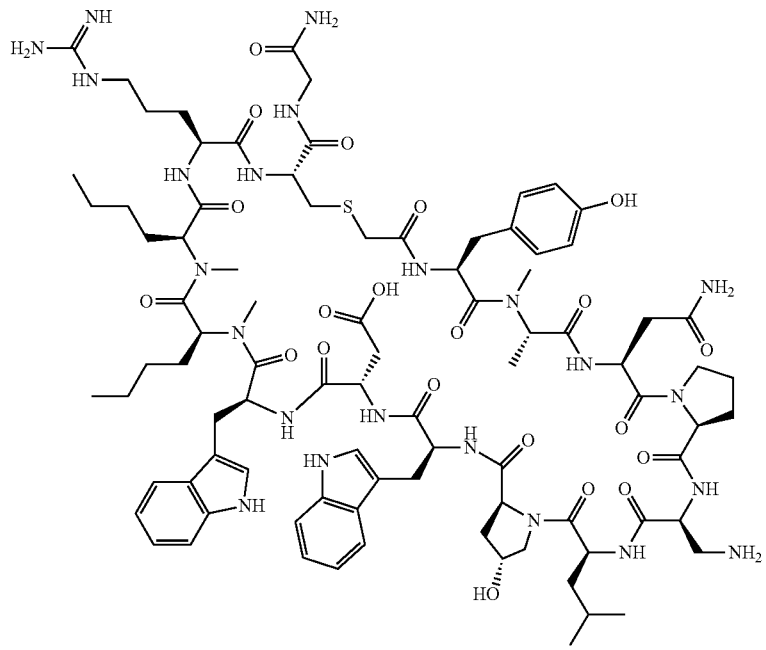

Example 5057

Example 5057 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 100%.

Analysis condition A: Retention time=1.48 min; ESI-MS (+) m/z 944.7 (M+2H)

Analysis condition B: Retention time=2.63 min; ESI-MS (+) m/z 944.8 (M+2H)

Preparation of Example 5058

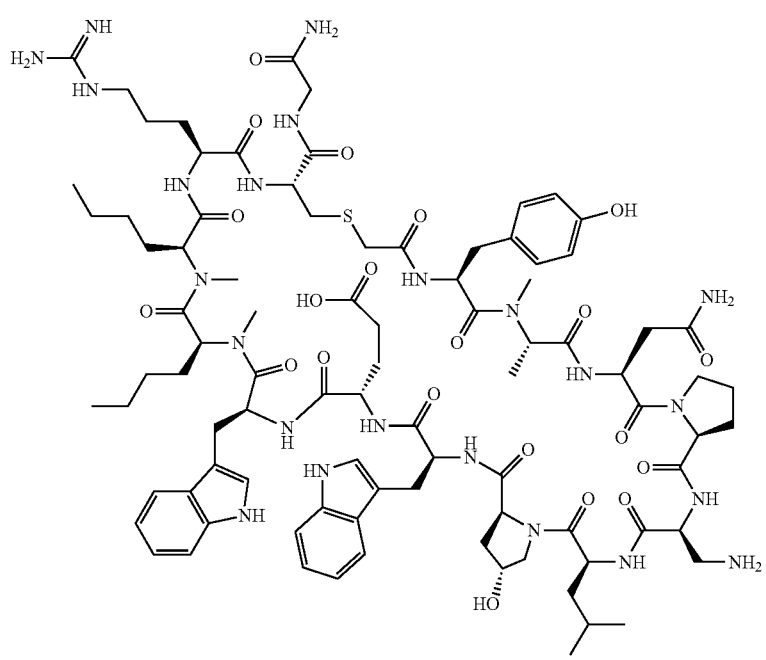

Example 5058

Example 5058 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 98%.

Analysis condition A: Retention time=1.50 min; ESI-MS (+) m/z 951.7 (M+2H)

Analysis condition B: Retention time=2.62 min; ESI-MS (+) m/z 951.7 (M+2H)

Preparation of Example 5059

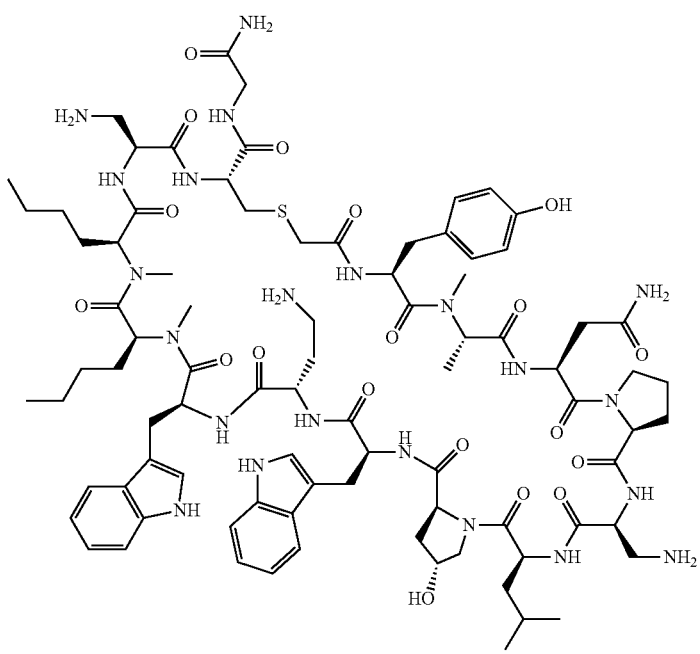

Example 5059

Example 5059 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 17.5 mg, and its estimated purity by LCMS analysis was 99%.

Analysis condition A: Retention time=1.46 min; ESI-MS (+) m/z 902.2 (M+2H)

Analysis condition B: Retention time=2.60 min; ESI-MS (+) m/z 902.3 (M+2H)

Preparation of Example 5060

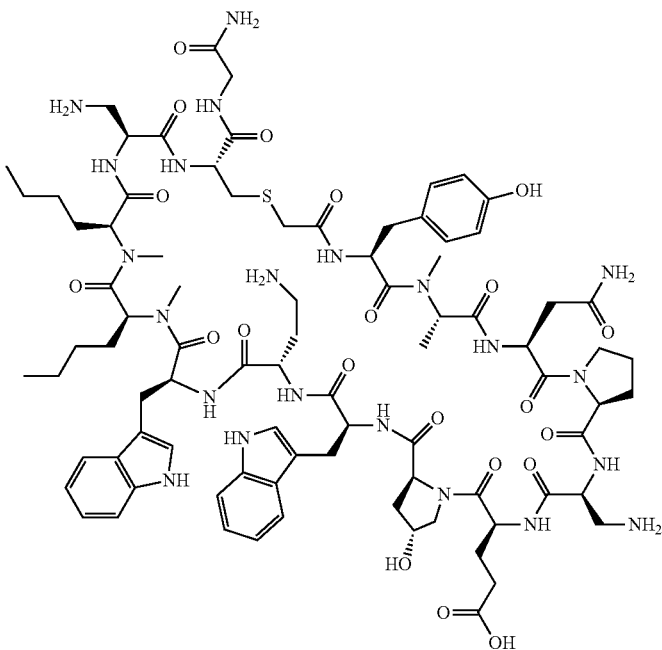

Example 5060

Example 5060 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.4 mg, and its estimated purity by LCMS analysis was 98%.

Analysis condition A: Retention time=1.40 min; ESI-MS (+) m/z 910.2 (M+2H)

Analysis condition B: Retention time=2.58 min; ESI-MS (+) m/z 910.2 (M+2H)

Preparation of Example 5061

Example 5061

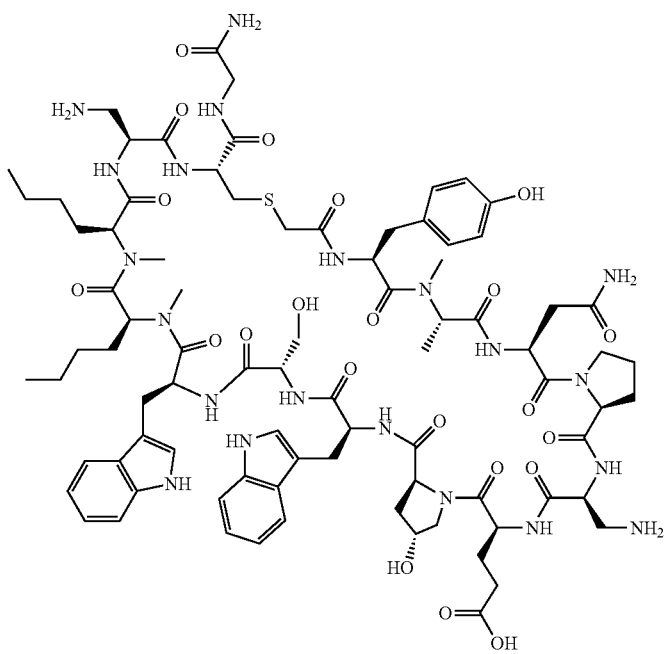

Example 5061 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 18.5 mg, and its estimated purity by LCMS analysis was 100%.

Analysis condition A: Retention time=1.46 min; ESI-MS (+) m/z 903.4 (M+2H)

Analysis condition B: Retention time=2.62 min; ESI-MS (−) m/z 901.6 (M−2H)

Preparation of Example 5062

Example 5062

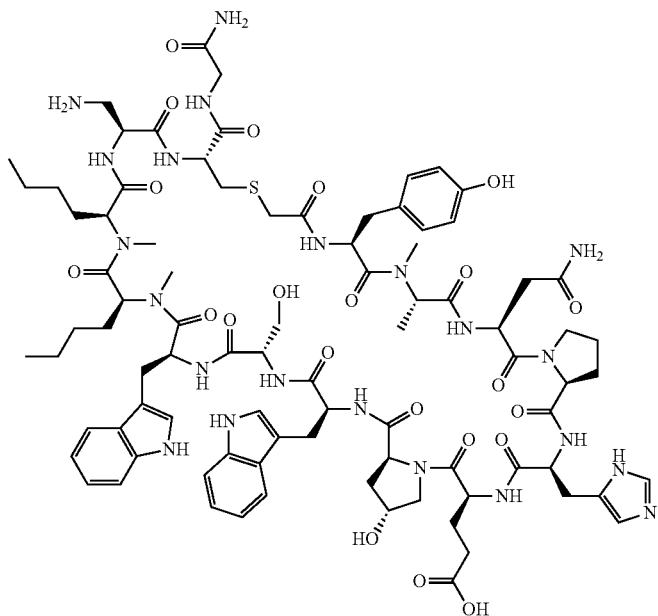

Example 5062 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.6 mg, and its estimated purity by LCMS analysis was 98%.

Analysis condition A: Retention time=1.49 min; ESI-MS (+) m/z 929.2 (M+2H)

Analysis condition B: Retention time=2.59 min; ESI-MS (−) m/z 926.8 (M−2H)

Preparation of Example 5063

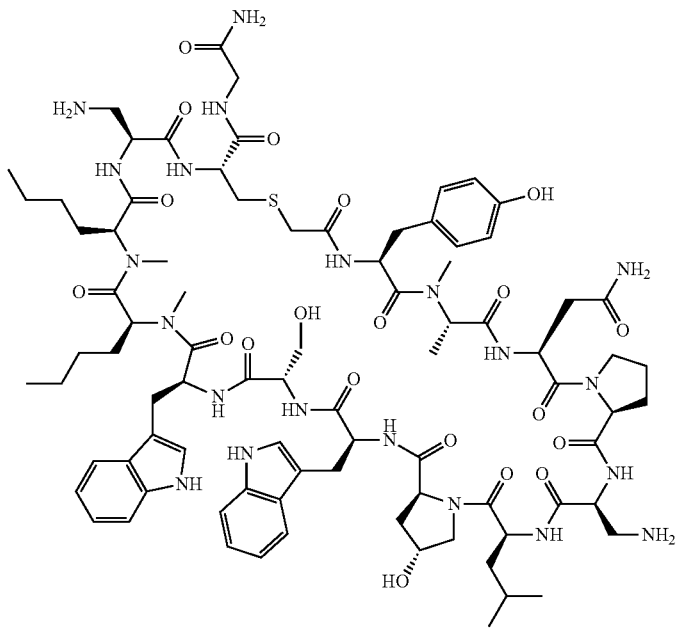

Example 5063

Example 5063 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 37.2 mg, and its estimated purity by LCMS analysis was 99%.

Analysis condition A: Retention time=1.51 min; ESI-MS (+) m/z 895.7 (M+2H)

Analysis condition B: Retention time=2.65 min; ESI-MS (−) m/z 893.8 (M−2H)

Preparation of Example 5064

Example 5064

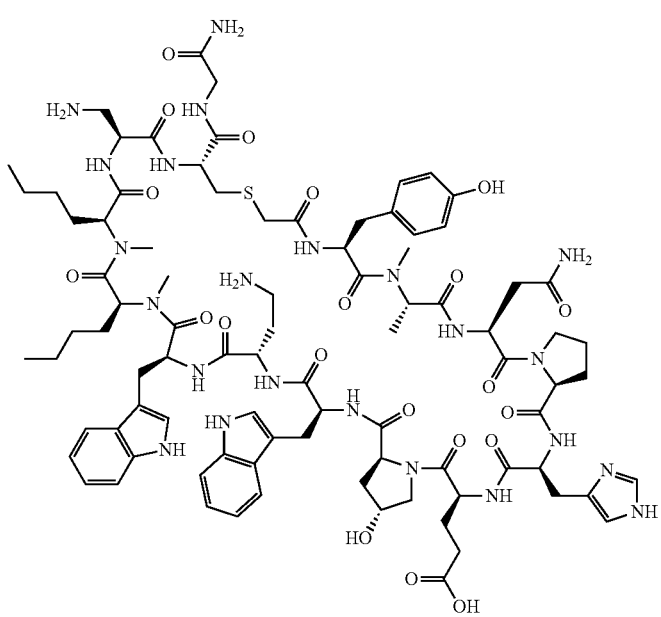

Example 5064 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 26.1 mg, and its estimated purity by LCMS analysis was 96%.

Analysis condition A: Retention time=1.42 min; ESI-MS (+) m/z 935.8 (M+2H)

Analysis condition B: Retention time=2.57 min; ESI-MS (−) m/z 933.2 (M−2H)

Preparation of Example 5065

Example 5065

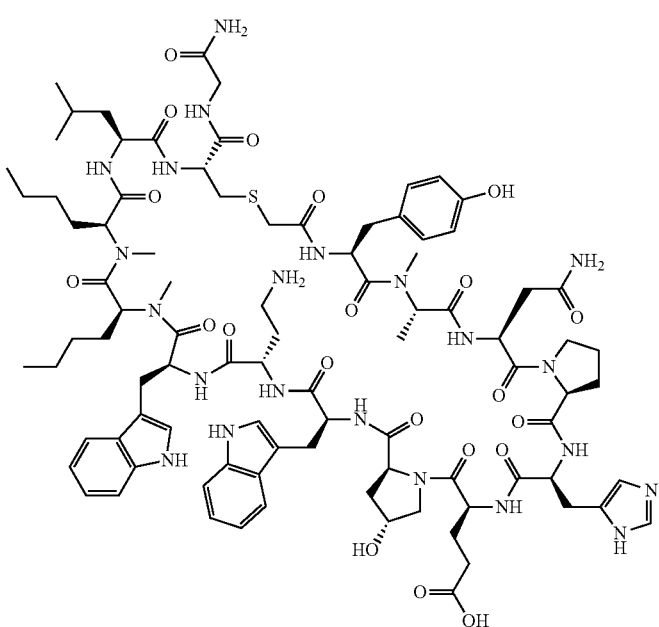

Example 5065 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 95%.

Analysis condition A: Retention time=1.56 min; ESI-MS (+) m/z 949.3 (M+2H)

Analysis condition B: Retention time=2.75 min; ESI-MS (+) m/z 949.3 (M+2H)

Preparation of Example 5066

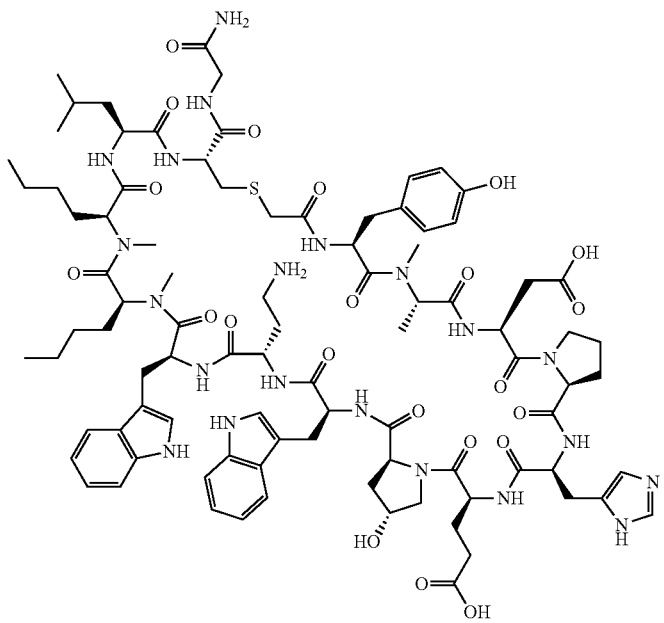

Example 5066

Example 5066 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 33.4 mg, and its estimated purity by LCMS analysis was 100%.

Analysis condition A: Retention time=1.56 min; ESI-MS (+) m/z 949.7 (M+2H)

Analysis condition B: Retention time=2.72 min; ESI-MS (+) m/z 949.8 (M+2H)

Preparation of Example 5067

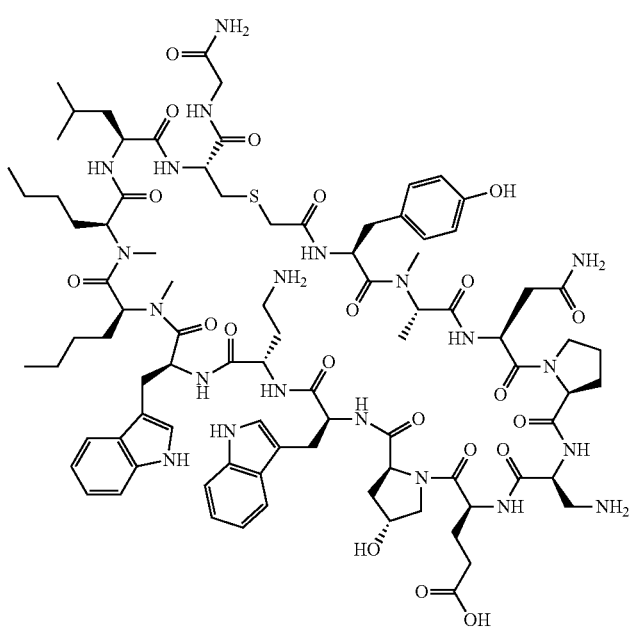

Example 5067

Example 5067 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 34.5 mg, and its estimated purity by LCMS analysis was 96%.

Analysis condition A: Retention time=1.58 min; ESI-MS (+) m/z 923.7 (M+2H)

Analysis condition B: Retention time=2.74 min; ESI-MS (+) m/z 923.7 (M+2H)

Preparation of Example 5068

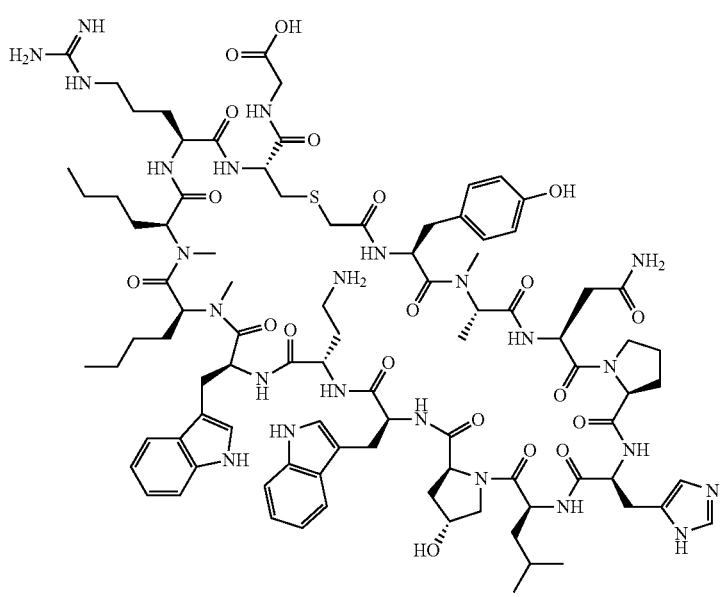

Example 5068

Example 5068 was prepared following "General Synthetic Sequence A" but with the following modification: "Cyclization Method B" was used instead of "Cyclization Method A", the scale was 0.600 mmol and all reagent portions were adjusted accordingly, and the resin was 2-chlorotrityl resin with Fmoc-Gly pre-loaded onto the resin. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold. Fractions containing the desired product were combined and dried via centrifugal evaporation. The yield of the product was 8.7 mg, and its estimated purity by LCMS analysis was 100%.

Analysis condition A: Retention time=1.52 min; ESI-MS (+) m/z 956.8 (M+2H)

Analysis condition B: Retention time=2.62 min; ESI-MS (+) m/z 956.8 (M+2H)

Preparation of Example 5069

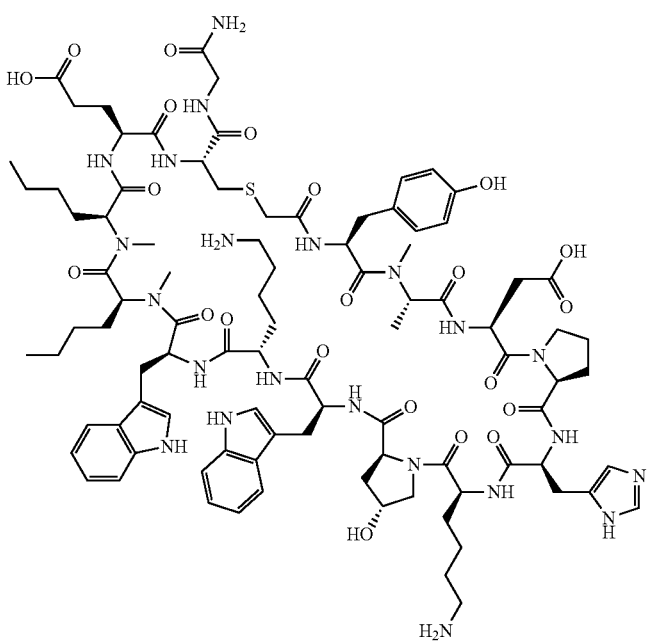

Esample 5069

Example 5069 was prepared following "General Synthetic Sequence A" but using "Cyclization Method B" instead of "Cyclization Method A" and run on a 0.300 mmol scale and all reagent portions were adjusted accordingly. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 40 minutes, then a 5-minute hold at 100% B; Flow: 20 mL/min. Fractions containing the desired product were combined and dried via centrifugal evaporation. The yield of the product was 112.8 mg, and its estimated purity by LCMS analysis was 93%.

Analysis condition A: Retention time=1.37 min; ESI-MS (+) m/z 971.2 (M+2H)

Analysis condition B: Retention time=2.58 min; ESI-MS (+) m/z 971.3 (M+2H) ESI-HRMS(+) m/z: Calculated: 970.4798 (M+2H). Found: 970.4764 (M+2H).

Preparation of Example 5070

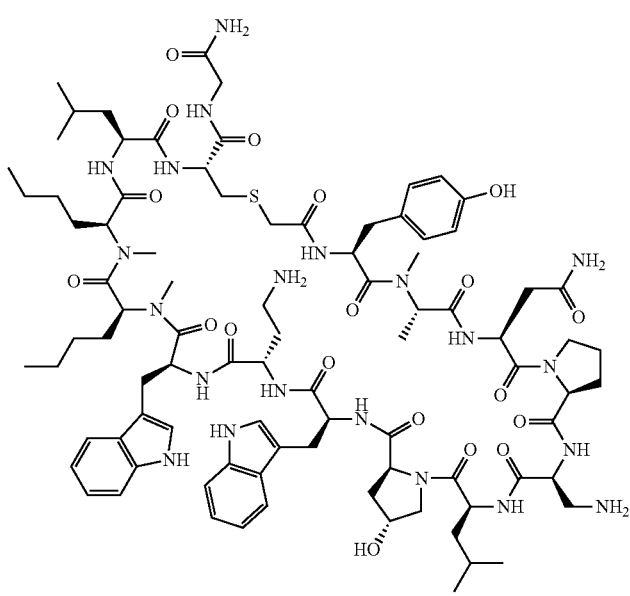

Example 5070

Example 5070 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 100%.

Analysis condition A: Retention time=1.66 min; ESI-MS (+) m/z 909.6 (M+2H)

Analysis condition B: Retention time=2.77 min; ESI-MS (+) m/z 909.1 (M+2H)

Preparation of Example 5071

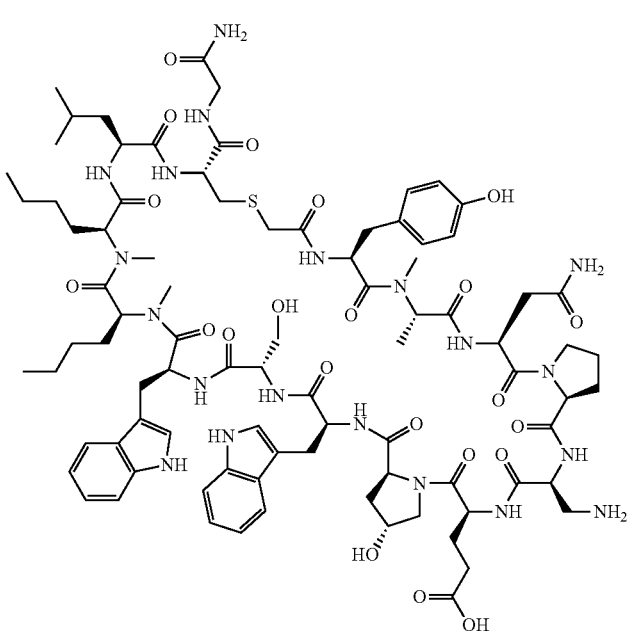

Example 5071

Example 5071 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 95%.

Analysis condition A: Retention time=1.60 min; ESI-MS (+) m/z 917.1 (M+2H)

Analysis condition B: Retention time=2.72 min; ESI-MS (+) m/z 917.2 (M+2H)

Preparation of Example 5072

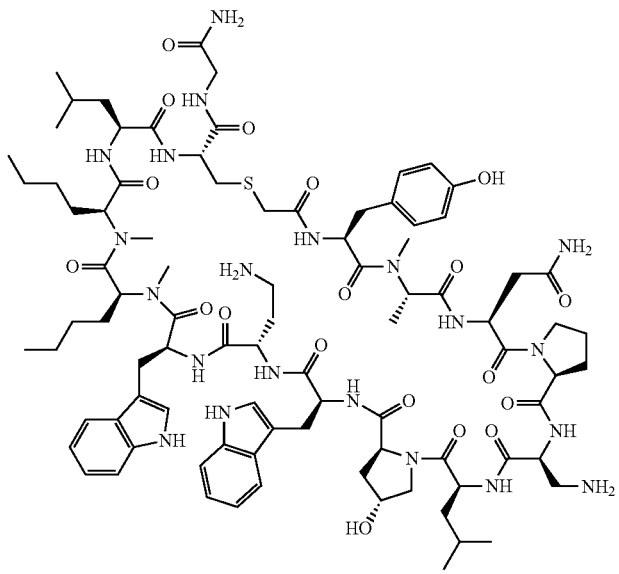

Example 5072

Example 5072 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 100%.

Analysis condition A: Retention time=1.57 min; ESI-MS (+) m/z 915.1 (M+2H)

Analysis condition B: Retention time=2.72 min; ESI-MS (+) m/z 915.1 (M+2H)

Preparation of Example 5073

Example 5073

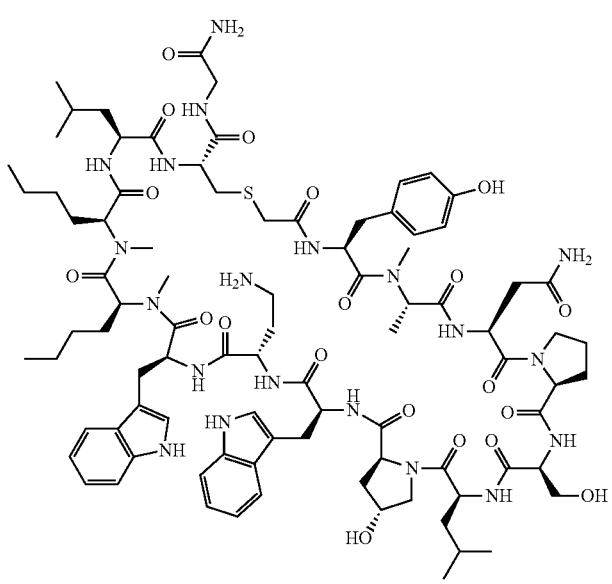

Example 5073 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 22.8 mg, and its estimated purity by LCMS analysis was 98%.

Analysis condition A: Retention time=1.61 min; ESI-MS (+) m/z 915.9 (M+2H)

Analysis condition B: Retention time=2.73 min; ESI-MS (+) m/z 915.9 (M+2H)

Preparation of Example 5074

Example 5074

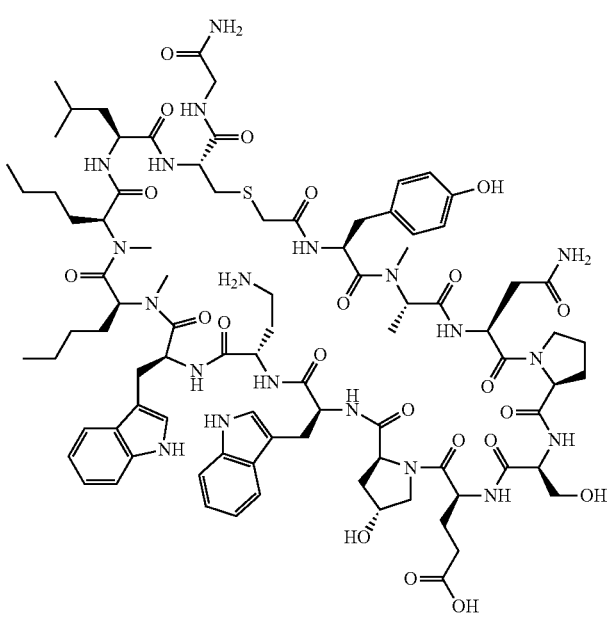

Example 5074 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.9 mg, and its estimated purity by LCMS analysis was 98%.

Analysis condition A: Retention time=1.60 min; ESI-MS (+) m/z 924.3 (M+2H)

Analysis condition B: Retention time=2.76 min; ESI-MS (+) m/z 923.8 (M+2H)

Preparation of Example 5075

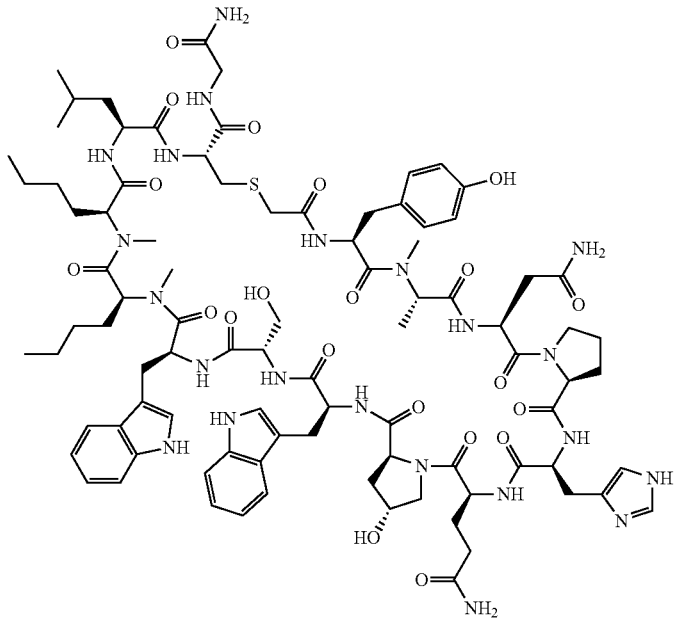

Example 5075

Example 5075 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.4 mg, and its estimated purity by LCMS analysis was 97%.

Analysis condition A: Retention time=1.60 min

Analysis condition B: Retention time=2.74 min; ESI-MS (+) m/z 941.8 (M+2H); ESI-MS (−) m/z 940.3 (M−2H)

ESI-HRMS(+) m/z: Calculated: 941.4589 (M+2H). Found: 941.4568 (M+2H).

Preparation of Example 5076

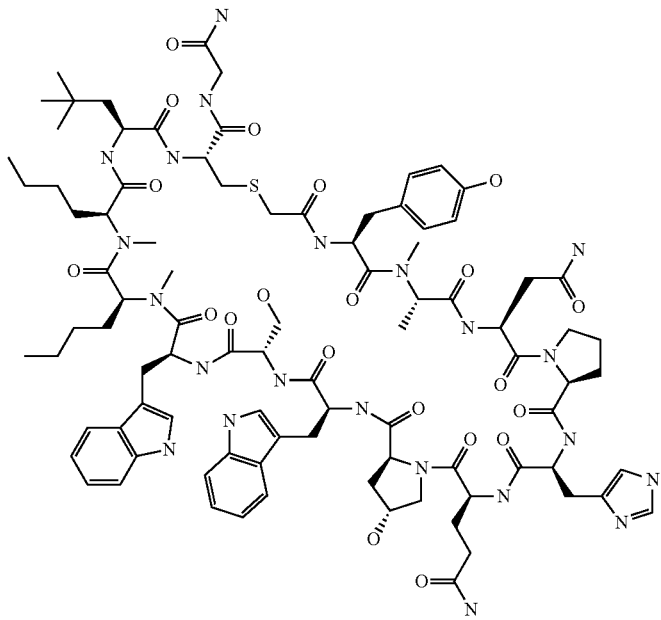

Example 5076

Example 5076 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 100%.

Analysis condition A: Retention time=1.65 min

Analysis condition B: Retention time=2.79 min; ESI-MS (+) m/z 949.1 (M+2H); ESI-MS (−) m/z 947.7 (M−2H)

Preparation of Example 5077

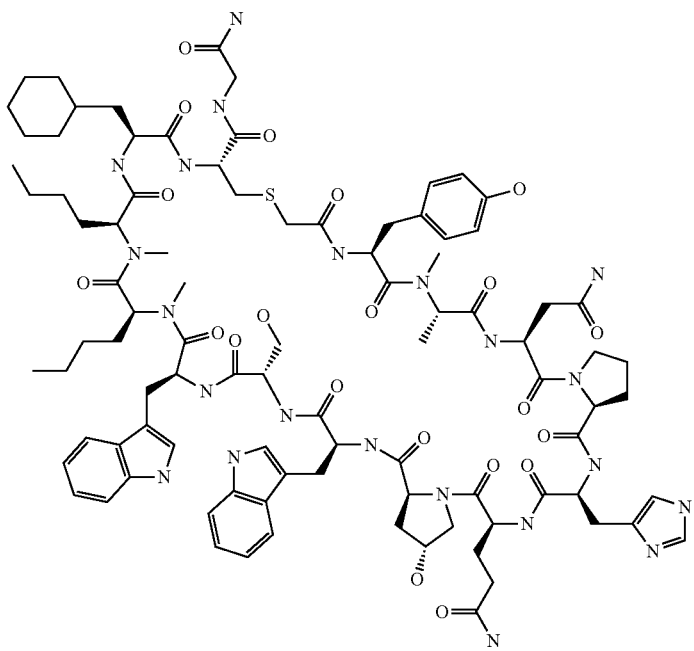

Example 5077

Example 5077 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 98%.

Analysis condition A: Retention time=1.76 min

Analysis condition B: Retention time=2.90 min; ESI-MS (−) m/z 960.3 (M−2H)

ESI-HRMS(+) m/z: Calculated: 961.4745 (M+2H). Found: 961.4715 (M+2H).

Preparation of Example 5078

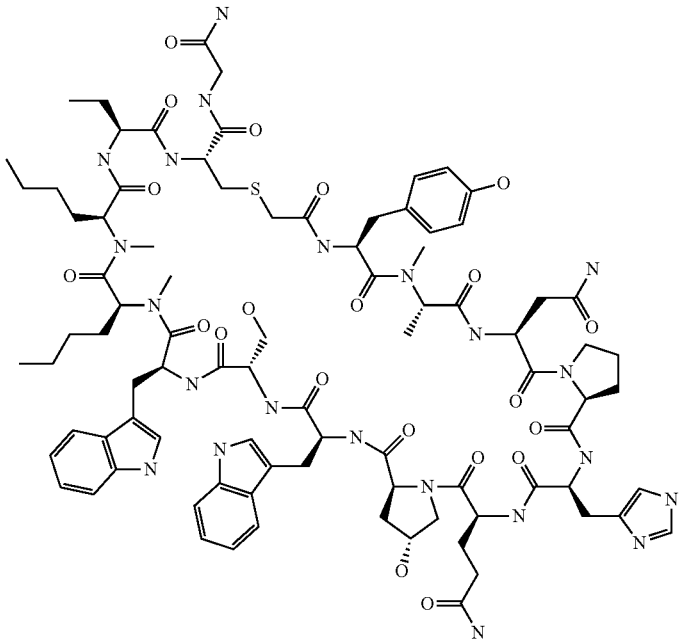

Example 5078

Example 5078 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 96%.

Analysis condition A: Retention time=1.51 min

Analysis condition B: Retention time=2.66 min; ESI-MS (+) m/z 927.7 (M+2H)

ESI-HRMS(+) m/z: Calculated: 927.4432 (M+2H). Found: 927.4402 (M+2H).

Preparation of Example 5079

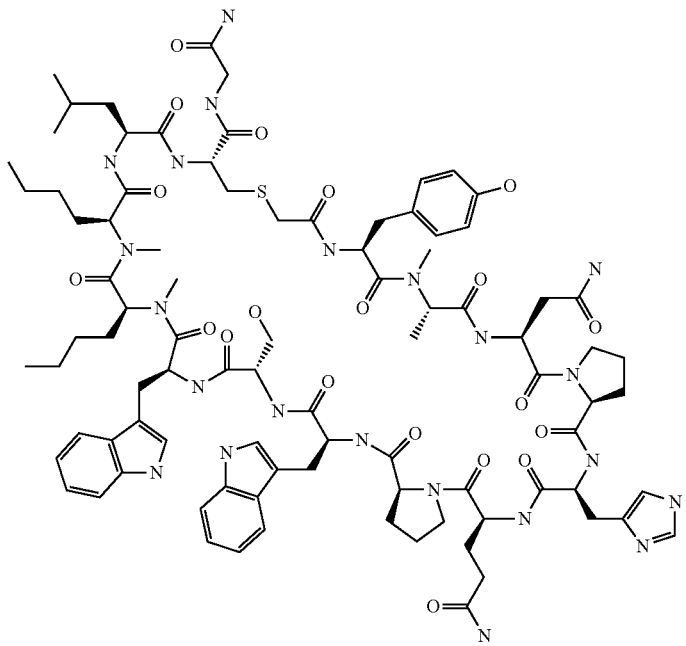

Example 5079

Example 5079 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 100%.

Analysis condition A: Retention time=1.63 min
Analysis condition B: Retention time=2.77 min
Analysis condition C: Retention time=1.024 min; ESI-MS (+) m/z 935.35 (M+2H)
ESI-HRMS(+) m/z: Calculated: 933.4614 (M+2H). Found: 933.4583 (M+2H).

Preparation of Example 5080

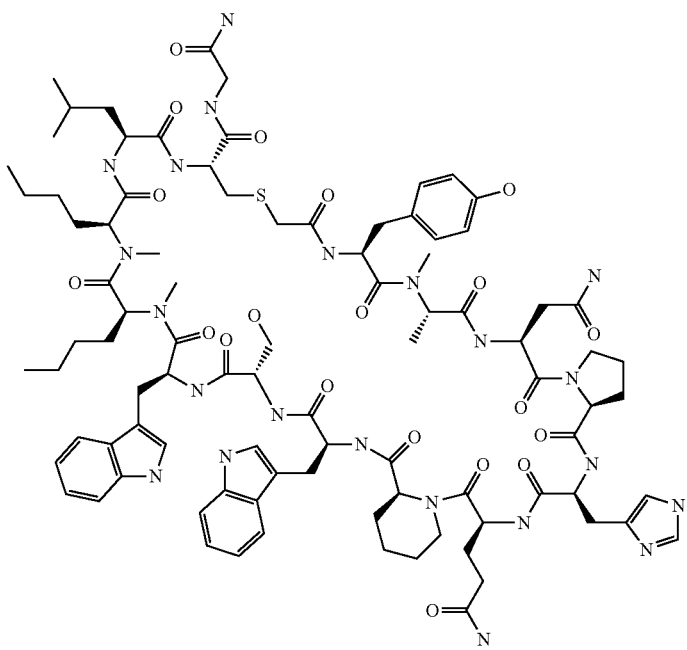

Example 5080

Example 5080 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 100%.

Analysis condition A: Retention time=1.64 min
Analysis condition B: Retention time=2.79 min; ESI-MS (+) m/z 941.2 (M+2H)
ESI-HRMS(+) m/z: Calculated: 940.4692 (M+2H). Found: 940.4675 (M+2H).

Preparation of Example 5081

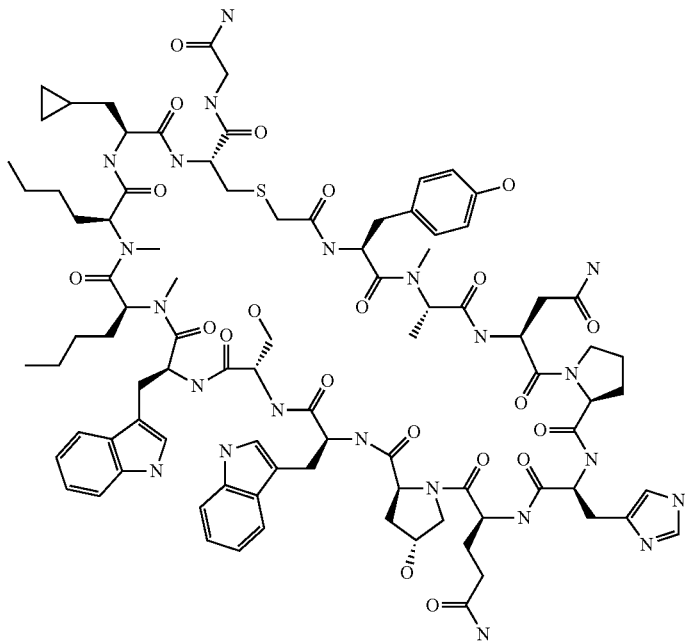

Example 5081

Example 5081 was prepared following "General Synthetic Sequence A" but using "Cyclization Method B" instead of "Cyclization Method A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 22.1 mg, and its estimated purity by LCMS analysis was 100%.

Analysis condition A: Retention time=1.56 min
Analysis condition B: Retention time=2.71 min
Analysis condition C: Retention time=0.997 min; ESI-MS (+) m/z 941.5 (M+2H)
ESI-HRMS(+) m/z: Calculated: 940.4511 (M+2H). Found: 940.4484 (M+2H).

Preparation of Example 5082

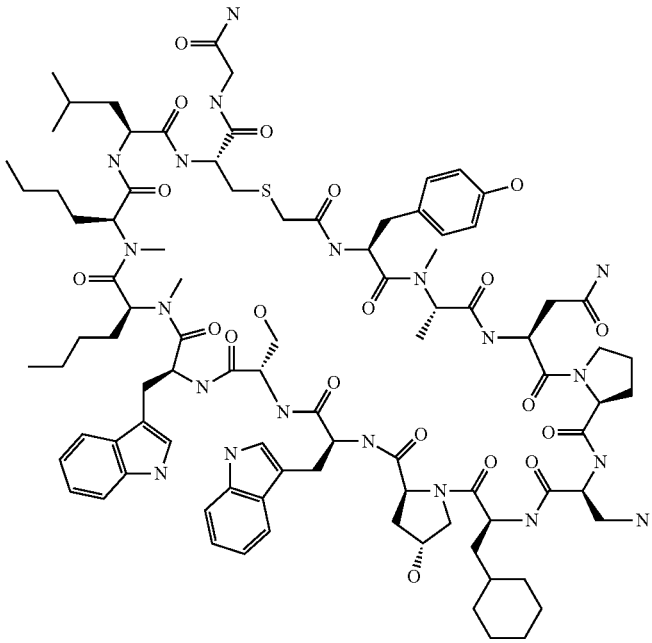

Example 5082

Example 5082 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.7 mg, and its estimated purity by LCMS analysis was 99%.

Analysis condition A: Retention time=1.71 min

Analysis condition B: Retention time=2.77 min; ESI-MS (+) m/z 928.9 (M+2H)

ESI-HRMS(+) m/z: Calculated: 928.4818 (M+2H). Found: 928.4794 (M+2H).

Preparation of Example 5083

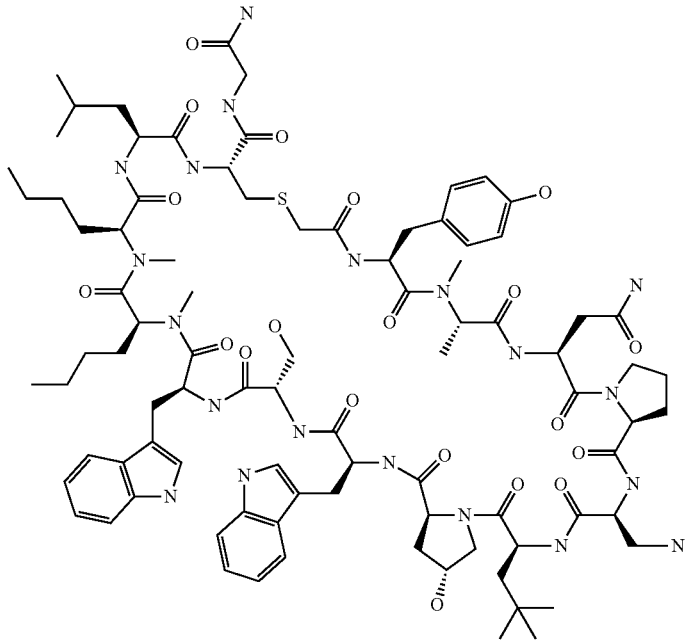

Example 5083

Example 5083 was prepared following "General Synthetic Sequence A" but using "Cyclization Method B" instead of "Cyclization Method A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.0 mg, and its estimated purity by LCMS analysis was 97%.

Analysis condition A: Retention time=1.68 min

Analysis condition B: Retention time=2.74 min

ESI-HRMS(+) m/z: Calculated: 915.4740 (M+2H). Found: 915.4709 (M+2H).

Preparation of Example 5084

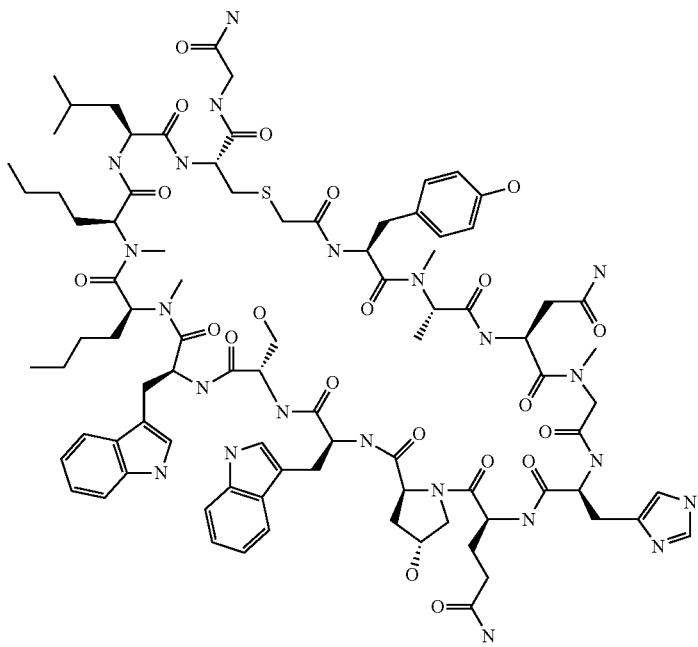

Example 5084

Example 5084 was prepared following "General Synthetic Sequence A" but using "Cyclization Method B" instead of "Cyclization Method A".

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 99%.

Analysis condition B: Retention time=2.71 min; ESI-MS (−) m/z 1855.3 (M−H)

ESI-HRMS(+) m/z: Calculated: 928.4511 (M+2H). Found: 928.4483 (M+2H).

Preparation of Example 5085

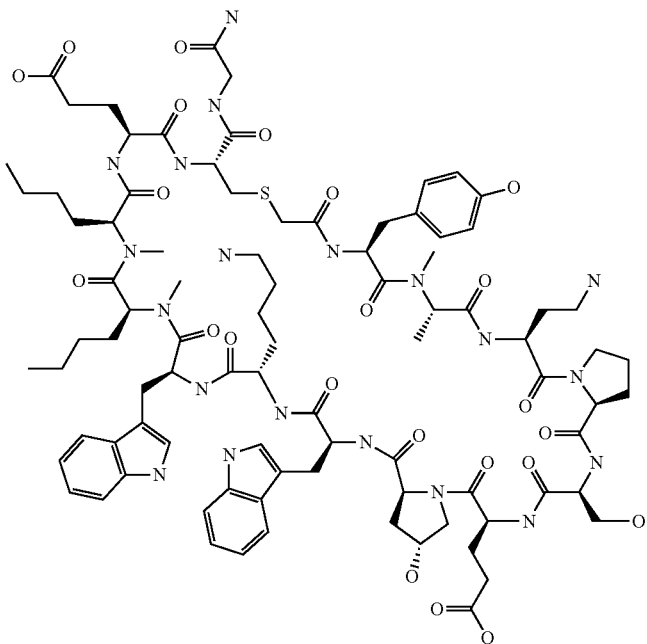

Example 5085

Example 5085 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 96%.

Analysis condition A: Retention time=1.36 min; ESI-MS (+) m/z 939.2 (M+2H)

Analysis condition B: Retention time=2.59 min; ESI-MS (+) m/z 939.3 (M+2H)

ESI-HRMS(+) m/z: Calculated: 938.4585 (M+2H). Found: 938.4562 (M+2H).

Preparation of Example 5086

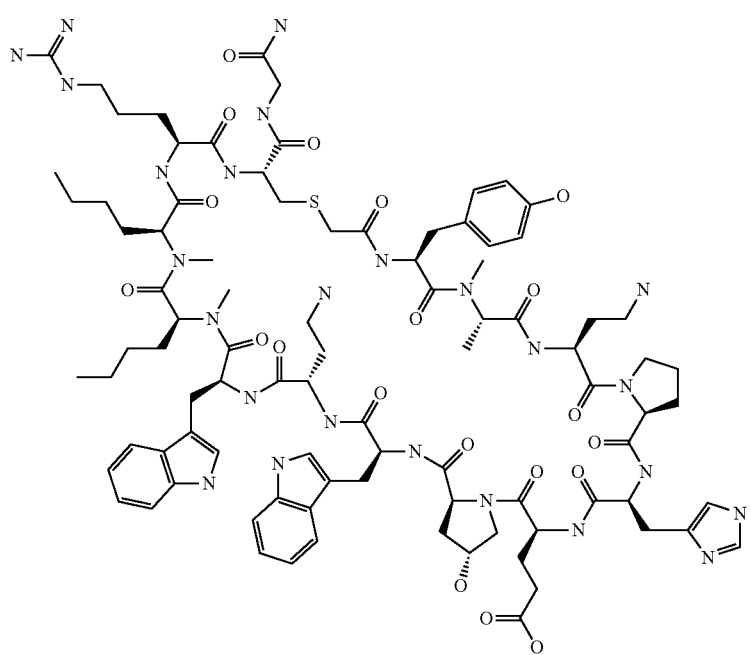

Example 5086

Example 5086 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 44.2 mg, and its estimated purity by LCMS analysis was 95%.

Analysis condition A: Retention time=1.37 min; ESI-MS (+) m/z 963.7 (M+2H)

Analysis condition B: Retention time=2.53 min; ESI-MS (−) m/z 961.8 (M−2H)

ESI-HRMS(+) m/z: Calculated: 962.9856 (M+2H). Found: 962.9827 (M+2H).

Preparation of Example 5087

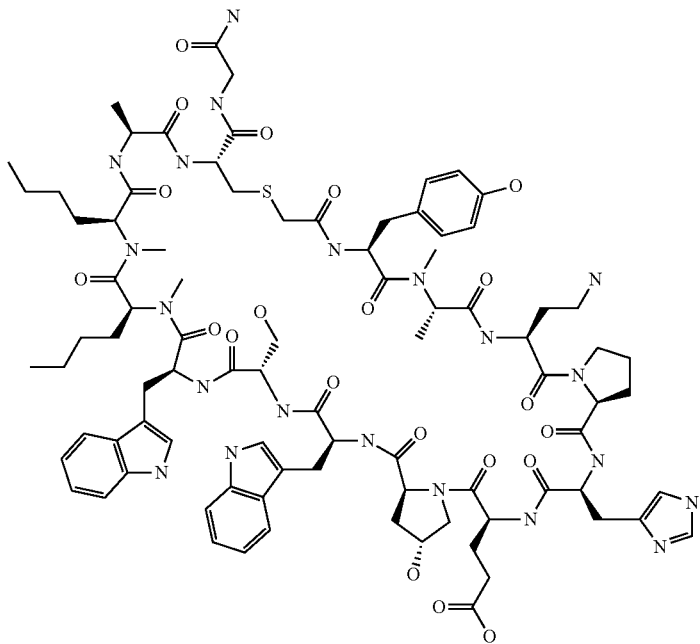

Example 5087

Example 5087 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 28.8 mg, and its estimated purity by LCMS analysis was 99%.

Analysis condition A: Retention time=1.50 min; ESI-MS (+) m/z 914.7 (M+2H)

Analysis condition B: Retention time=2.68 min; ESI-MS (−) m/z 912.7 (M−2H)

ESI-HRMS(+) m/z: Calculated: 913.9378 (M+2H). Found: 913.9353 (M+2H).

Preparation of Example 5088

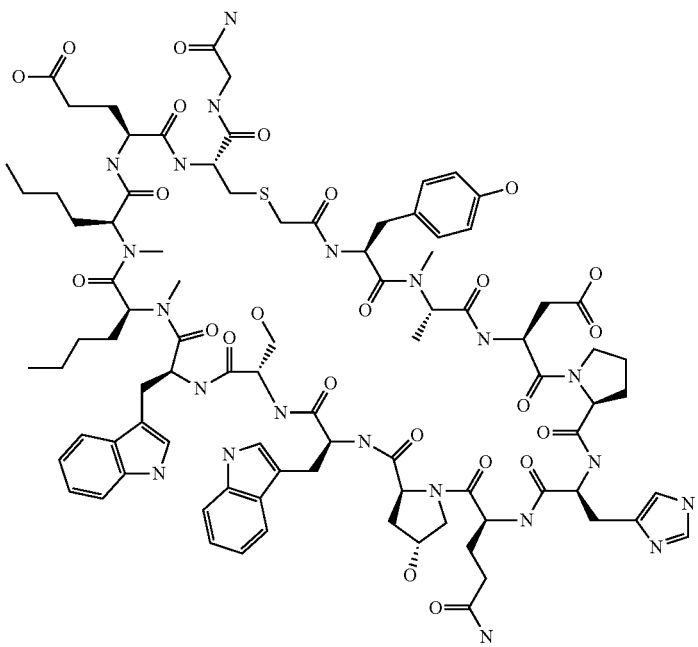

Example 5088

Example 5088 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 30.4 mg, and its estimated purity by LCMS analysis was 96%.

Analysis condition A: Retention time=1.36 min; ESI-MS (+) m/z 939.2 (M+2H)

Analysis condition B: Retention time=2.59 min; ESI-MS (+) m/z 939.3 (M+2H)

ESI-HRMS(+) m/z: Calculated: 938.4585 (M+2H). Found: 938.4562 (M+2H).

Preparation of Example 5089

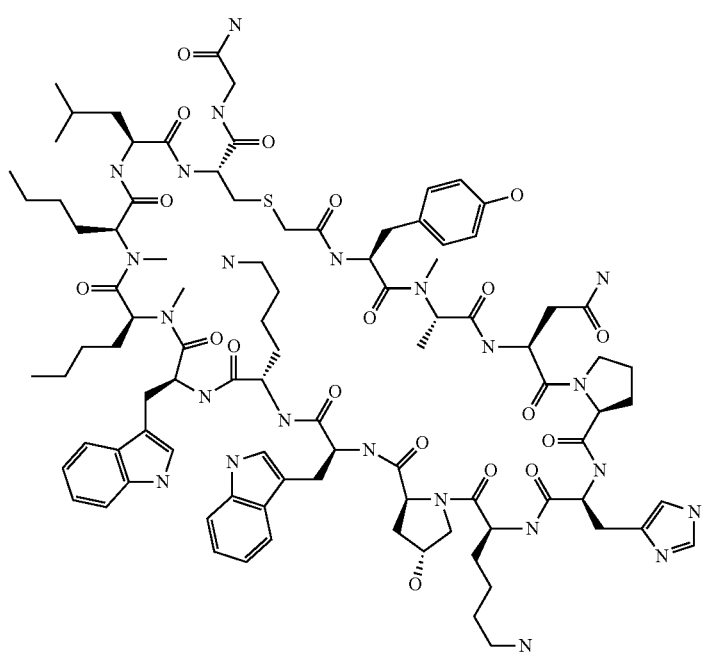

Example 5089

Example 5089 was prepared following "General Synthetic Sequence A" but using "Cyclization Method B" instead of "Cyclization Method A". The crude material was purified via preparative LC/MS with the following conditions: Column: Waters XBridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 23.2 mg, and its estimated purity by LCMS analysis was 97%.

Analysis condition A: Retention time=1.53 min; ESI-MS (+) m/z 962.4 (M+2H)

Analysis condition B: Retention time=2.70 min; ESI-MS (+) m/z 962.7 (M+2H)

ESI-HRMS(+) m/z: Calculated: 962.0085 (M+2H). Found: 962.0052 (M+2H).

Preparation of Example 5090

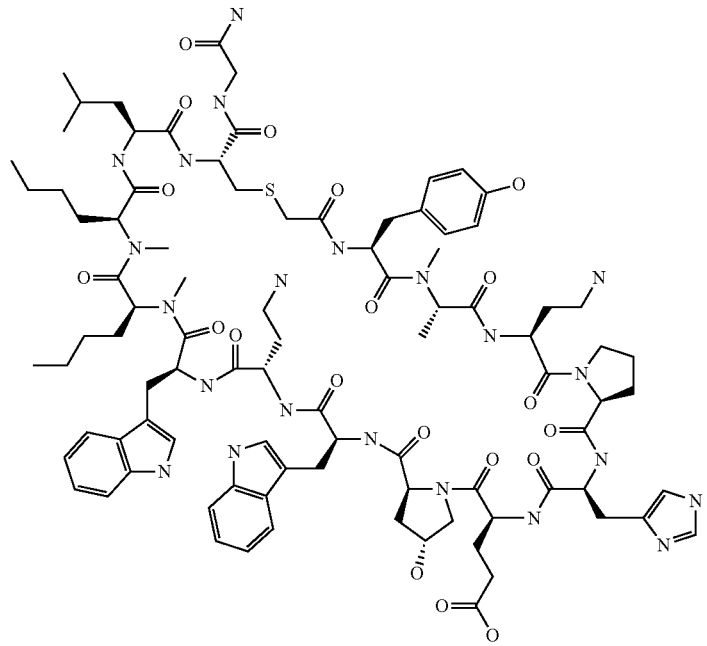

Example 5090

Example 5090 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 19.6 mg, and its estimated purity by LCMS analysis was 99%.

Analysis condition A: Retention time=1.58 min; ESI-MS (+) m/z 942.4 (M+2H)

Analysis condition B: Retention time=2.80 min; ESI-MS (+) m/z 942.3 (M+2H)

ESI-HRMS(+) m/z: Calculated: 941.4771 (M+2H). Found: 941.4739 (M+2H).

Preparation of Example 5091

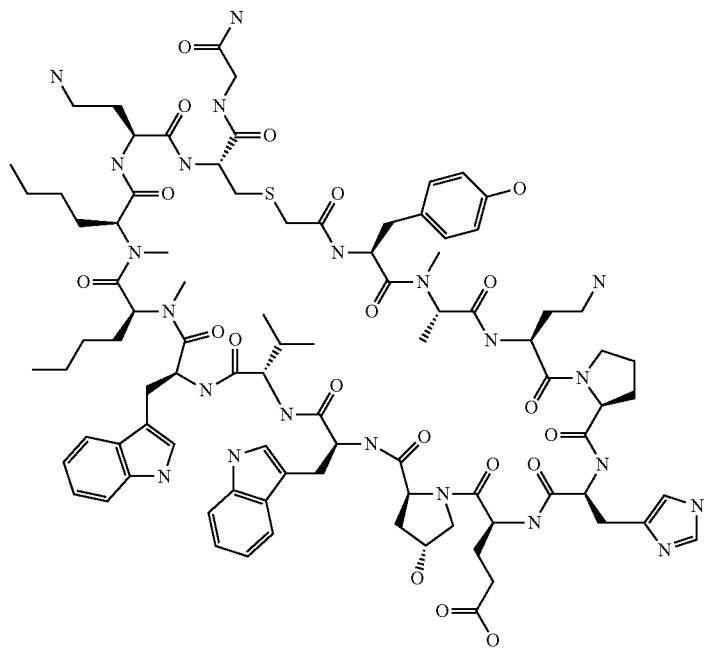

Example 5091

Example 5091 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.4 mg, and its estimated purity by LCMS analysis was 97%.

Analysis condition A: Retention time=1.46 min; ESI-MS (+) m/z 934.9 (M+2H)

Analysis condition B: Retention time=2.64 min

ESI-HRMS(+) m/z: Calculated: 934.4692 (M+2H). Found: 934.4662 (M+2H).

Preparation of Example 5092

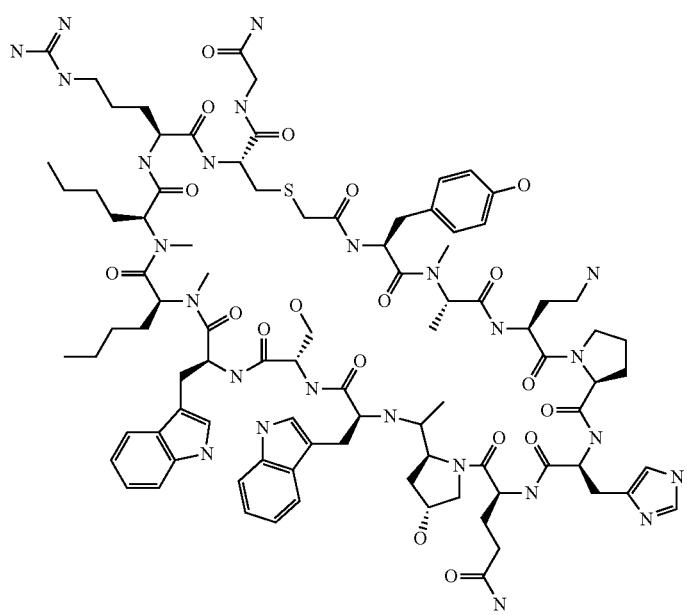

Example 5092

Example 5092 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 28.3 mg, and its estimated purity by LCMS analysis was 100%.

Analysis condition A: Retention time=1.46 min; ESI-MS (+) m/z 957.0 (M+2H)

Analysis condition B: Retention time=2.58 min; ESI-MS (+) m/z 956.9 (M+2H)

ESI-HRMS(+) m/z: Calculated: 955.9778 (M+2H). Found: 955.9749 (M+2H).

Preparation of Example 5093

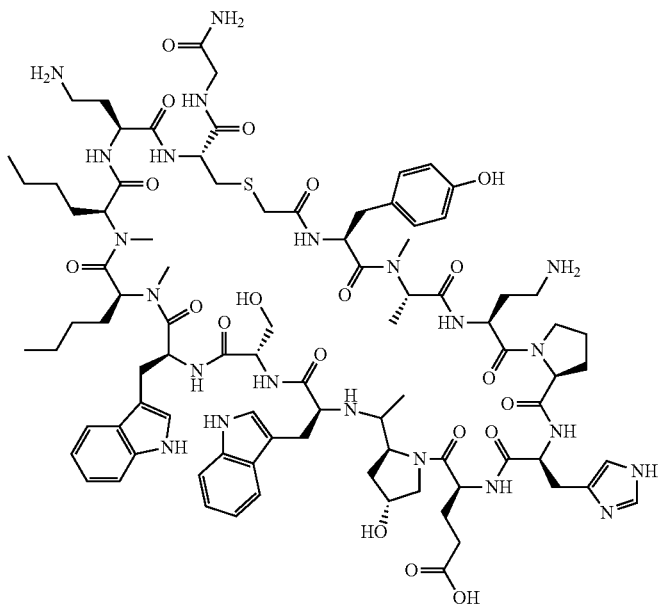

Example 5093

Example 5093 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 29.3 mg, and its estimated purity by LCMS analysis was 98%.

Analysis condition A: Retention time=1.48 min; ESI-MS (+) m/z 929.0 (M+2H)

Analysis condition B: Retention time=2.63 min; ESI-MS (+) m/z 929.3 (M+2H)

ESI-HRMS(+) m/z: Calculated: 928.9494 (M+2H). Found: 928.4476 (M+2H).

Preparation of Example 5094

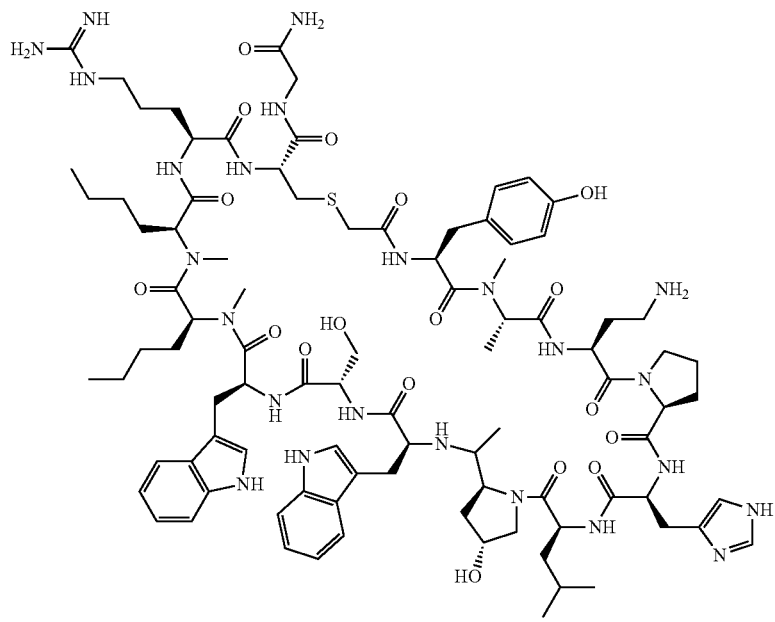

Example 5094

Example 5094 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 21.1 mg, and its estimated purity by LCMS analysis was 96%.

Analysis condition A: Retention time=1.47 min; ESI-MS (+) m/z 949.3 (M+2H)

Analysis condition B: Retention time=2.61 min; ESI-MS (+) m/z 949.3 (M+2H)

ESI-HRMS(+) m/z: Calculated: 948.4905 (M+2H). Found: 948.4872 (M+2H).

Preparation of Example 5095

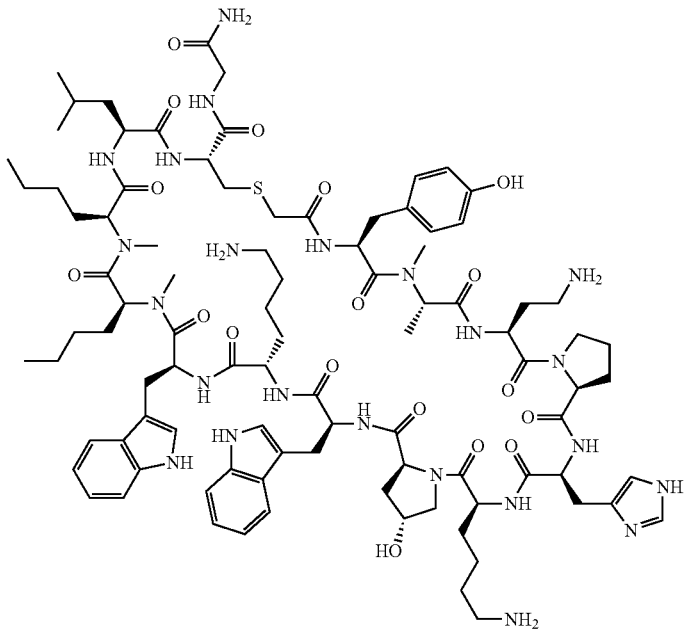

Example 5095

Example 5095 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 34.9 mg, and its estimated purity by LCMS analysis was 97%.

Analysis condition A: Retention time=1.56 min; ESI-MS (+) m/z 963.4 (M+2H)

Analysis condition B: Retention time=2.73 min; ESI-MS (+) m/z 963.4 (M+2H)

ESI-HRMS(+) m/z: Calculated: 962.5005 (M+2H). Found: 962.4969 (M+2H).

Preparation of Example 5096

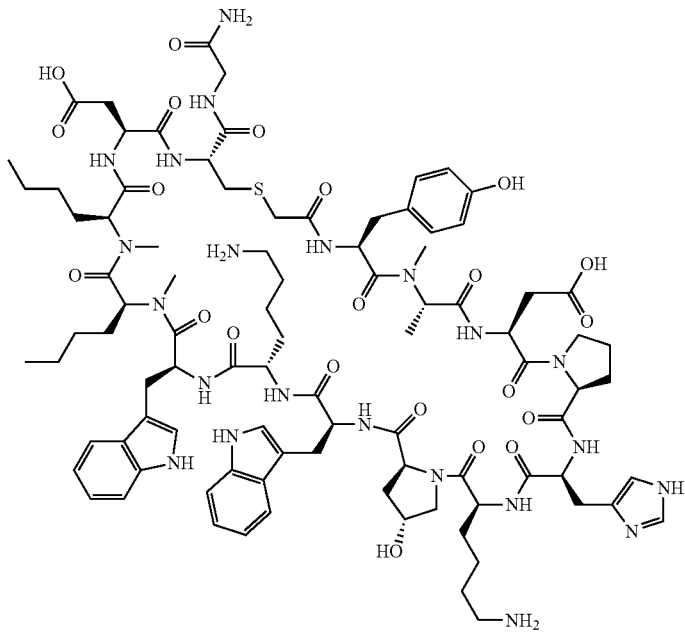

Example 5096

Example 5096 was prepared following "General Synthetic Sequence A" but using "Cyclization Method B" instead of "Cyclization Method A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 48.4 mg, and its estimated purity by LCMS analysis was 97%.

Analysis condition A: Retention time=1.48 min; ESI-MS (+) m/z 964.3 (M+2H)

Analysis condition B: Retention time=2.67 min; ESI-MS (+) m/z 964.4 (M+2H)

ESI-HRMS(+) m/z: Calculated: 963.4720 (M+2H). Found: 963.4685 (M+2H).

Preparation of Example 5097

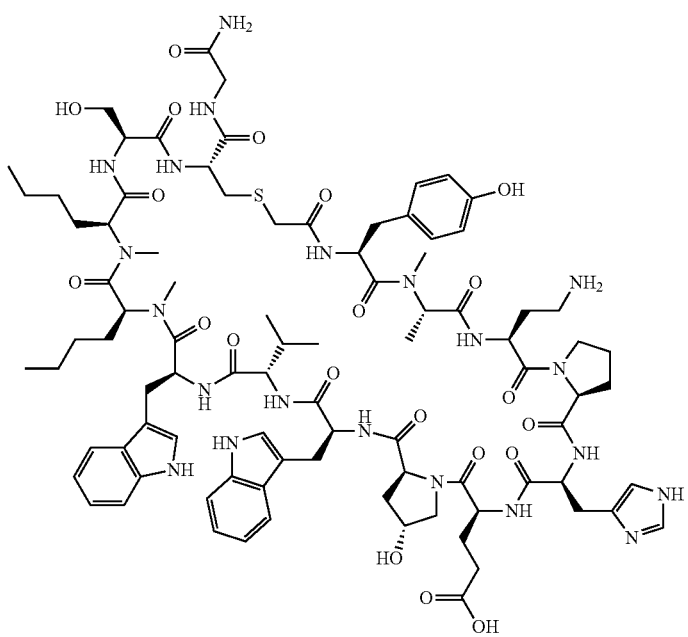

Example 5097

Example 5097 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 31.9 mg, and its estimated purity by LCMS analysis was 98%.

Analysis condition A: Retention time=1.50 min; ESI-MS (+) m/z 928.8 (M+2H)

Analysis condition B: Retention time=2.70 min; ESI-MS (+) m/z 928.8 (M+2H)

ESI-HRMS(+) m/z: Calculated: 927.9534 (M+2H). Found: 927.9498 (M+2H).

Preparation of Example 5098

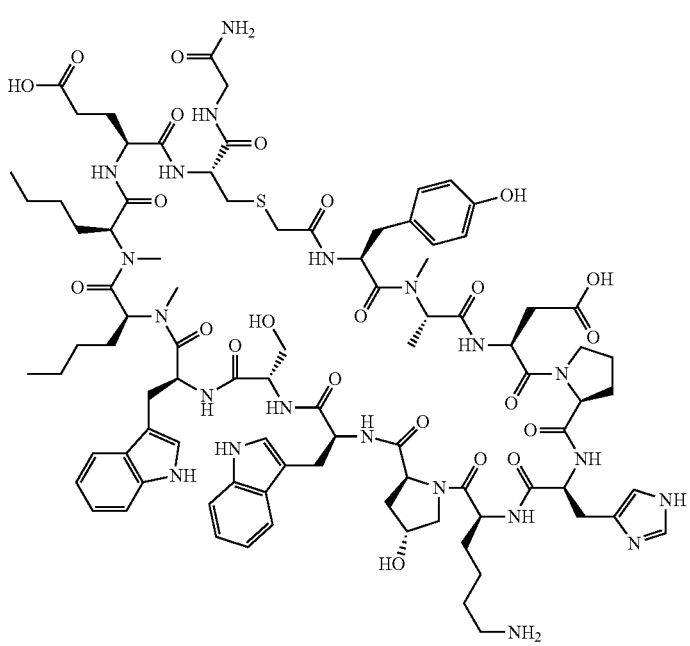

Example 5098

Example 5098 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 31.0 mg, and its estimated purity by LCMS analysis was 97%.

Analysis condition A: Retention time=1.36 min; ESI-MS (+) m/z 950.3 (M+2H)

Analysis condition B: Retention time=2.59 min; ESI-MS (+) m/z 950.9 (M+2H)
ESI-HRMS(+) m/z: Calculated: 949.9483 (M+2H). Found: 949.9460 (M+2H).

Preparation of Example 5099

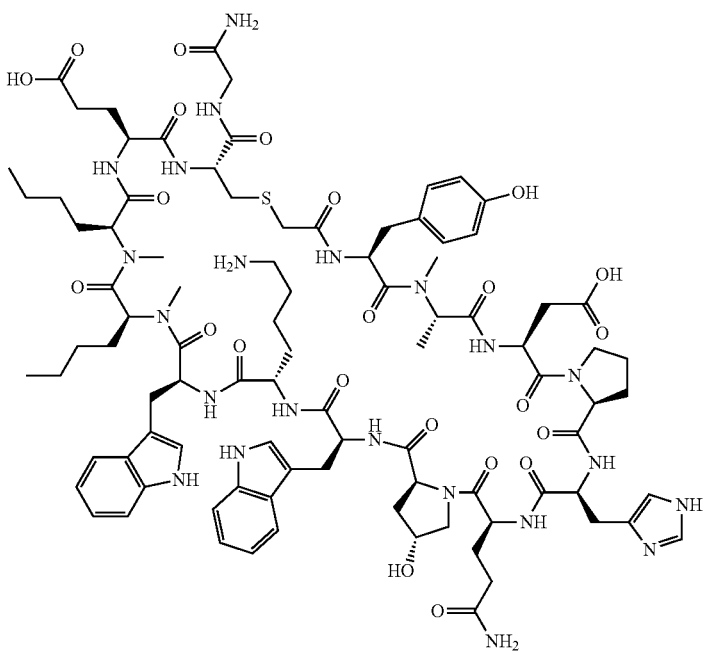

Example 5099

Example 5099 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The yield of the product was 15.4 mg, and its estimated purity by LCMS analysis was 100%.

Analysis condition A: Retention time=1.424 min; ESI-MS (+) m/z 971.00 (M+2H)
ESI-HRMS(+) m/z: Calculated: 970.4616 (M+2H). Found: 970.4595 (M+2H).

Preparation of Example 5100

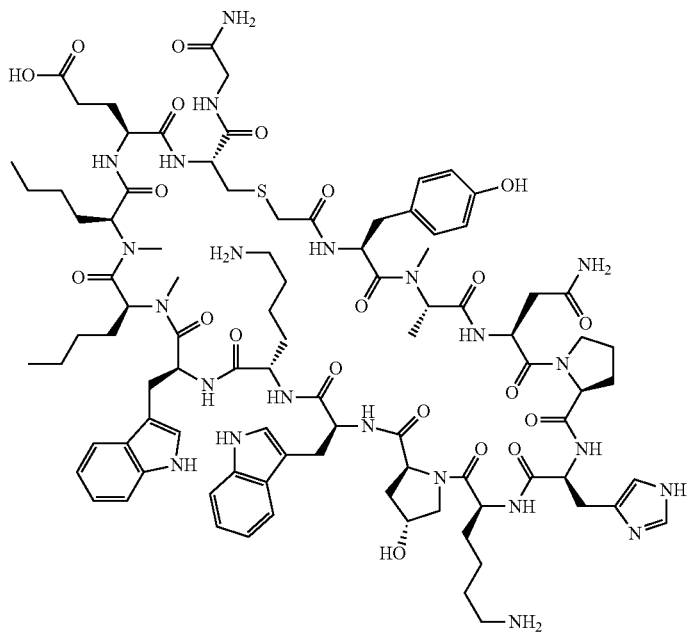

Example 5100

Example 5100 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 30 minutes, then a 5-minute hold at 100% B; Flow: 20 mL/min. Fractions containing the desired product were combined and dried via centrifugal evaporation. The yield of the product was 25.4 mg, and its estimated purity by LCMS analysis was 100%.

Analysis condition A: Retention time=1.44 min

Analysis condition B: Retention time=2.67 min; ESI-MS (+) m/z 971.1 (M+2H)

ESI-HRMS(+) m/z: Calculated: 969.9878 (M+2H). Found: 969.9850 (M+2H).

Preparation of Example 5101

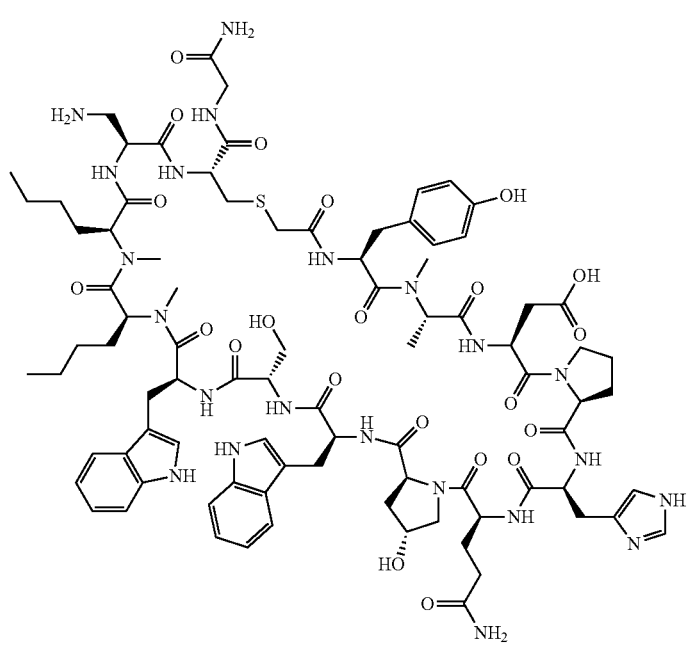

Example 5101

Example 5101 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.4 mg, and its estimated purity by LCMS analysis was 98%.

Analysis condition A: Retention time=1.51 min; ESI-MS (+) m/z 929.2 (M+2H)

Analysis condition B: Retention time=2.67 min; ESI-MS (+) m/z 929.3 (M+2H)

ESI-HRMS(+) m/z: Calculated: 928.4329 (M+2H). Found: 928.4301 (M+2H).

Preparation of Example 5102

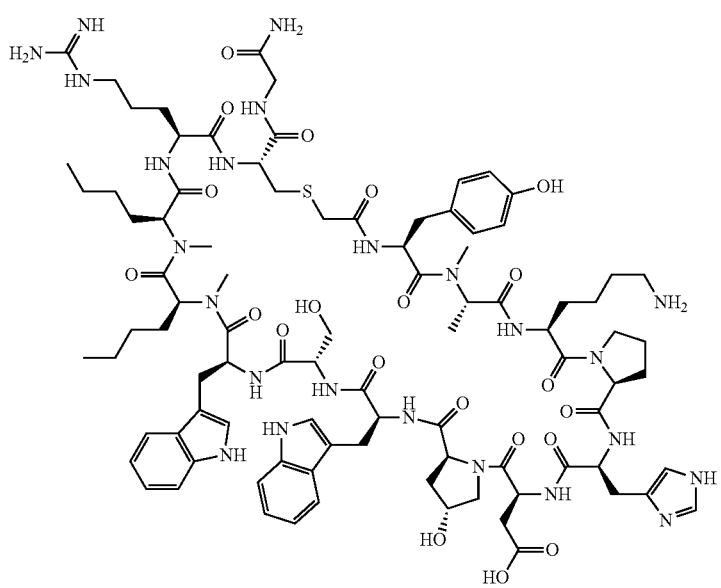

Example 5102

Example 5102 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 29.6 mg, and its estimated purity by LCMS analysis was 100%.

Analysis condition A: Retention time=1.35 min; ESI-MS (+) m/z 964.2 (M+2H)

Analysis condition B: Retention time=2.53 min; ESI-MS (+) m/z 964.3 (M+2H)

ESI-HRMS(+) m/z: Calculated: 963.4776 (M+2H). Found: 963.4740 (M+2H).

Preparation of Example 5103

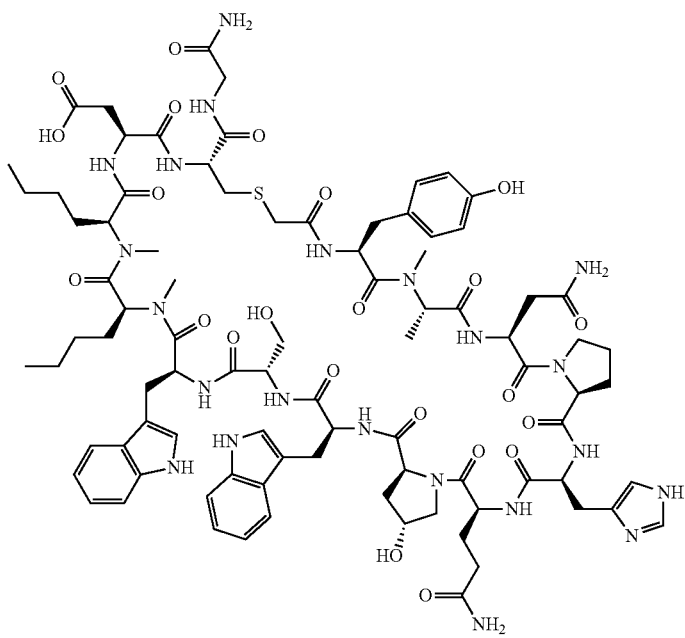

Example 5103

Example 5103 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 34.4 mg, and its estimated purity by LCMS analysis was 100%.

Analysis condition A: Retention time=1.35 min; ESI-MS (+) m/z 942.8 (M+2H)

Analysis condition B: Retention time=2.53 min; ESI-MS (+) m/z 943.2 (M+2H)

Preparation of Example 5104

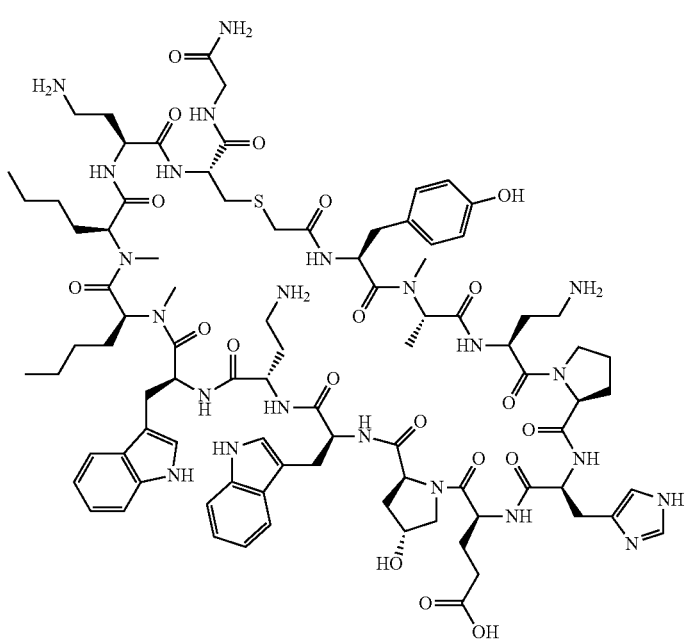

Example 5104

Example 5104 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 100%.

Analysis condition A: Retention time=1.38 min; ESI-MS (+) m/z 935.7 (M+2H)

Analysis condition B: Retention time=2.56 min; ESI-MS (+) m/z 935.7 (M+2H)

ESI-HRMS(+) m/z: Calculated: 934.9669 (M+2H). Found: 934.9637 (M+2H).

Preparation of Example 5105

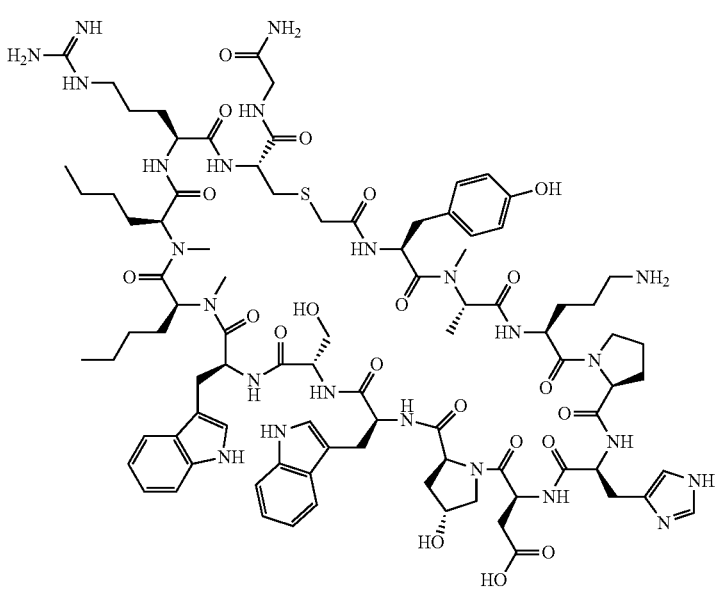

Example 5105

Example 5105 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 35.2 mg, and its estimated purity by LCMS analysis was 99%.

Analysis condition A: Retention time=1.42 min; ESI-MS (+) m/z 956.6 (M+2H)

Analysis condition B: Retention time=2.58 min; ESI-MS (+) m/z 957.0 (M+2H)

ESI-HRMS(+) m/z: Calculated: 956.4698 (M+2H). Found: 956.4670 (M+2H).

Preparation of Example 5106

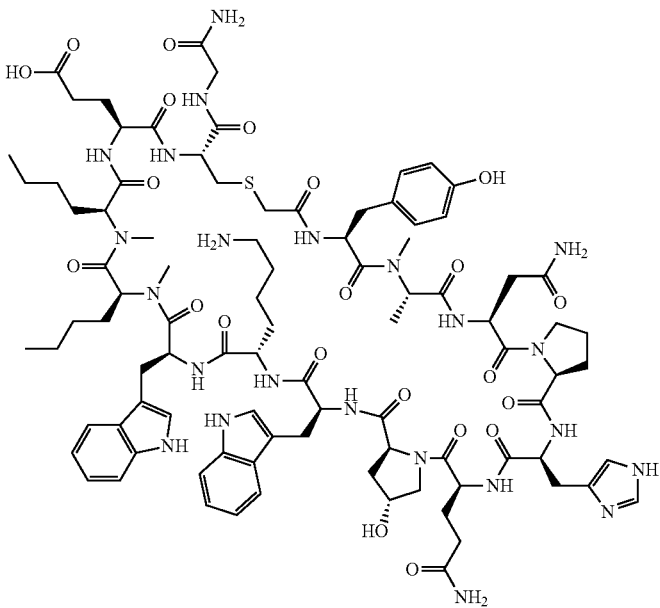

Example 5106

Example 5106 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 26.3 mg, and its estimated purity by LCMS analysis was 100%.

Analysis condition A: Retention time=1.43 min; ESI-MS (+) m/z 970.4 (M+2H)

Analysis condition B: Retention time=2.99 min; ESI-MS (+) m/z 970.3 (M+2H)

ESI-HRMS(+) m/z: Calculated: 969.9696 (M+2H). Found: 969.9662 (M+2H).

Preparation of Example 5107

Example 5107

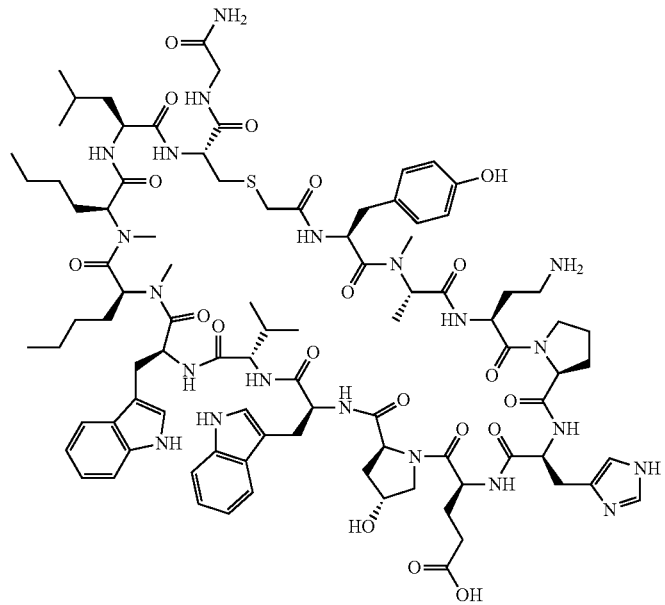

Example 5107 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 23.7 mg, and its estimated purity by LCMS analysis was 100%.

Analysis condition A: Retention time=1.65 min; ESI-MS (+) m/z 941.8 (M+2H)

Analysis condition B: Retention time=2.86 min; ESI-MS (+) m/z 941.4 (M+2H)

ESI-HRMS(+) m/z: Calculated: 940.9794 (M+2H). Found: 940.9762 (M+2H).

Preparation of Example 5108

Example 5108

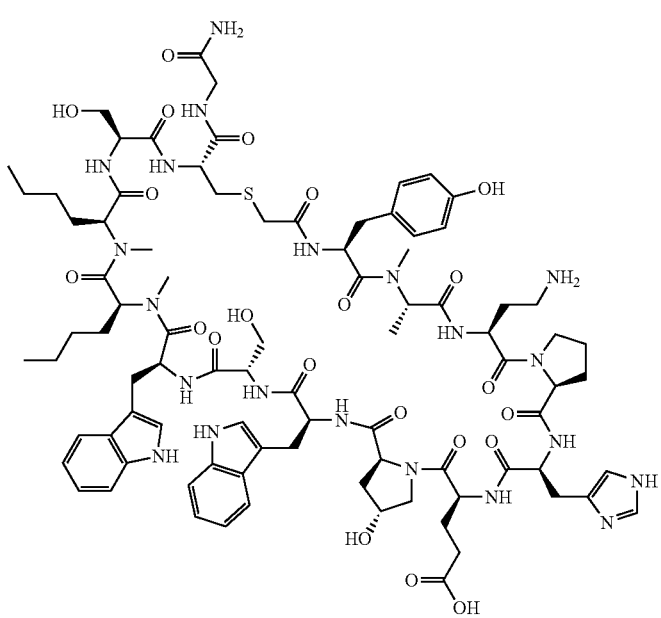

Example 5108 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 32.5 mg, and its estimated purity by LCMS analysis was 100%.

Analysis condition A: Retention time=1.48 min; ESI-MS (+) m/z 922.5 (M+2H)

Analysis condition B: Retention time=2.68 min; ESI-MS (+) m/z 922.7 (M+2H)

ESI-HRMS(+) m/z: Calculated: 921.9352 (M+2H). Found: 921.9318 (M+2H).

Preparation of Example 5109

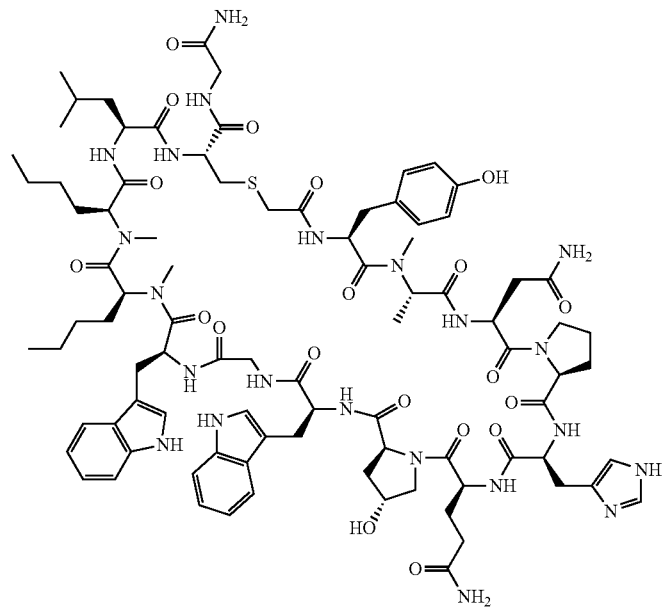

Example 5109

Example 5109 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.60 min; ESI-MS (+) m/z 927.3 (M+2H)

Analysis condition B: Retention time=2.80 min; ESI-MS (+) m/z 927.0 (M+2H)

ESI-HRMS(+) m/z: Calculated: 926.4536 (M+2H). Found: 926.4504 (M+2H).

Preparation of Example 5110

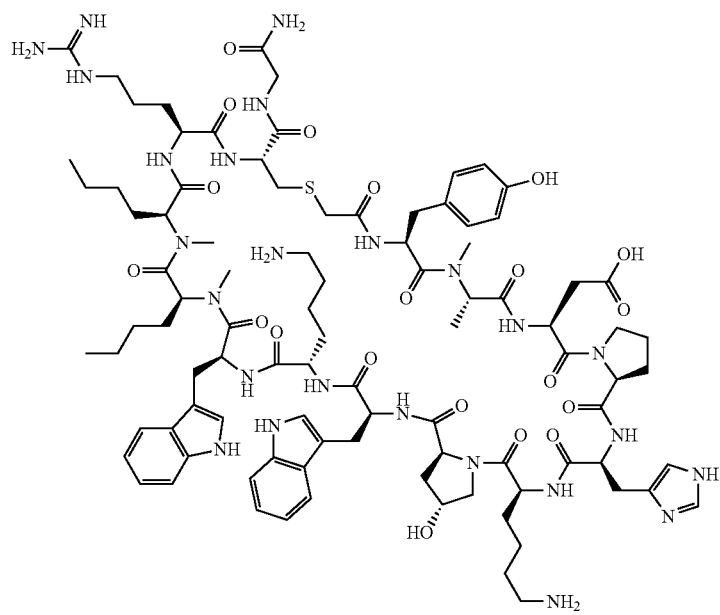

Example 5110

Example 5110 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 17.2 mg, and its estimated purity by LCMS analysis was 100%.

Analysis condition A: Retention time=1.40 min; ESI-MS (+) m/z 984.8 (M+2H)

Analysis condition B: Retention time=2.60 min; ESI-MS (+) m/z 984.9 (M+2H)

ESI-HRMS(+) m/z: Calculated: 984.0091 (M+2H). Found: 984.0061 (M+2H).

Preparation of Example 5111

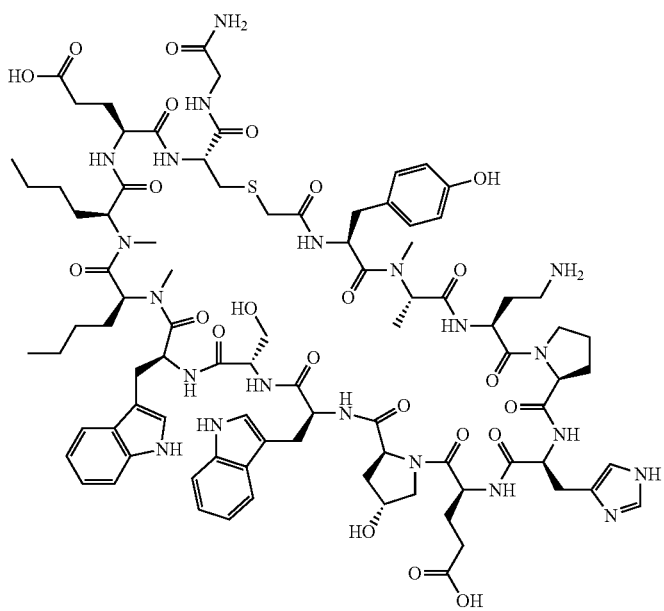

Example 5111

Example 5111 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 33.7 mg, and its estimated purity by LCMS analysis was 100%.

Analysis condition A: Retention time=1.28 min; ESI-MS (+) m/z 943.8 (M+2H)

Analysis condition B: Retention time=2.49 min; ESI-MS (+) m/z 943.8 (M+2H)

ESI-HRMS(+) m/z: Calculated: 942.9405 (M+2H). Found: 942.9380 (M+2H).

Preparation of Example 5112

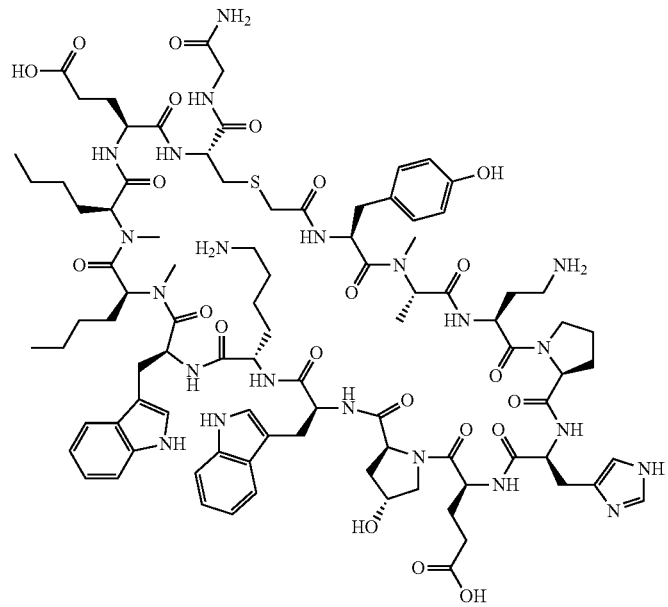

Example 5112

Example 5112 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 100%.

Analysis condition A: Retention time=1.38 min; ESI-MS (+) m/z 964.3 (M+2H)

Analysis condition B: Retention time=2.60 min; ESI-MS (+) m/z 964.2 (M+2H)

ESI-HRMS(+) m/z: Calculated: 963.4720 (M+2H). Found: 963.4688 (M+2H).

Preparation of Example 5113

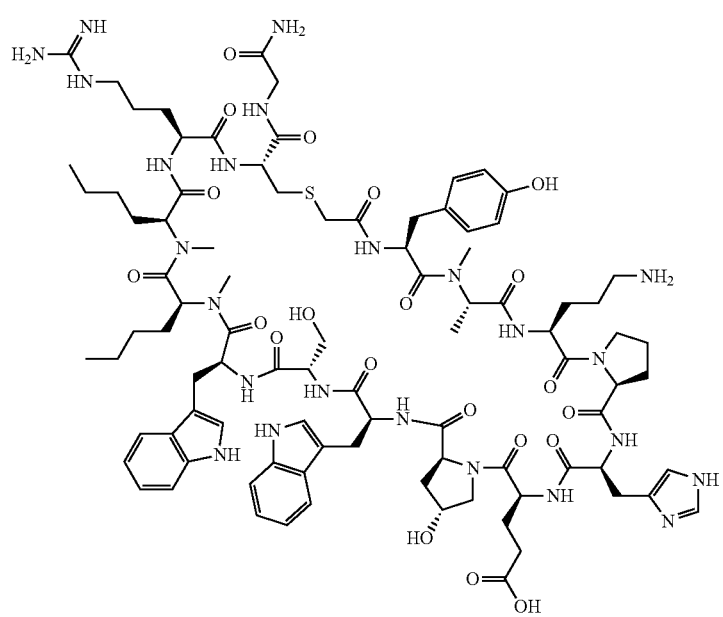

Example 5113

Example 5113 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 100%.

Analysis condition A: Retention time=1.45 min; ESI-MS (+) m/z 964.3 (M+2H)

Analysis condition B: Retention time=2.63 min; ESI-MS (+) m/z 964.3 (M+2H)

ESI-HRMS(+) m/z: Calculated: 963.4476 (M+2H). Found: 963.4742 (M+2H).

Preparation of Example 5114

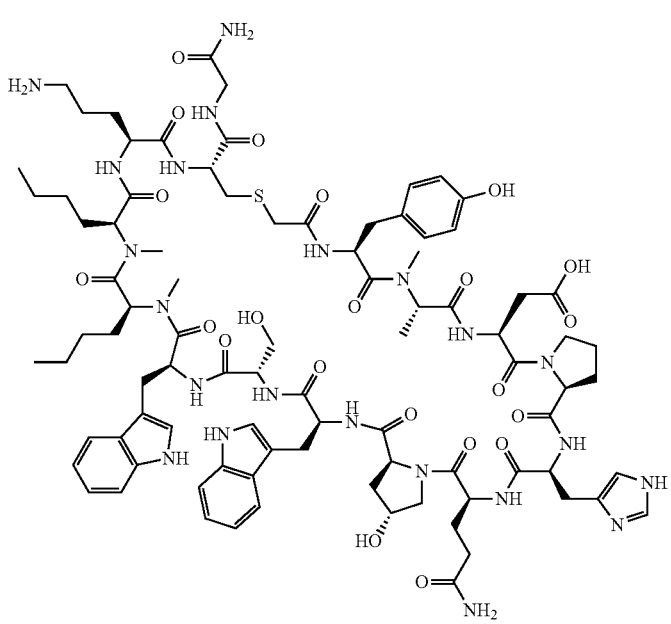

Example 5113

Example 5114 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 100%.

Analysis condition A: Retention time=1.45 min; ESI-MS (+) m/z 943.3 (M+2H)

Analysis condition B: Retention time=2.66 min; ESI-MS (+) m/z 943.3 (M+2H)

ESI-HRMS(+) m/z: Calculated: 942.4461 (M+2H). Found: 942.4485 (M+2H).

Preparation of Example 5115

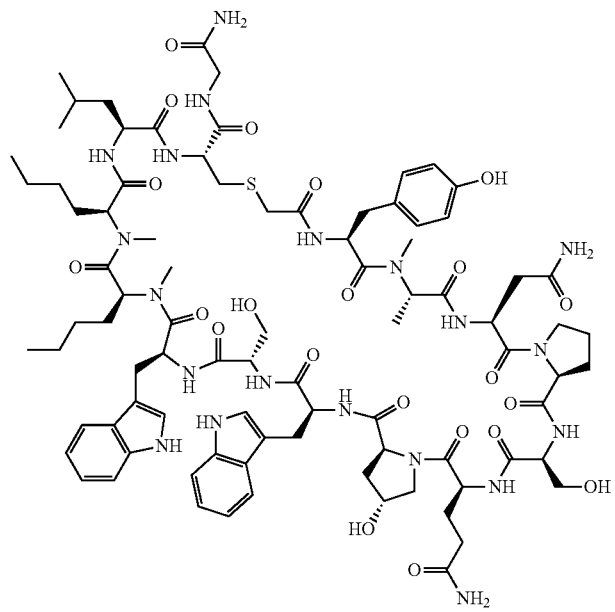

Example 5115

Example 5115 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-95% B over 30 minutes, then a 5-minute hold at 100% B; Flow: 20 mL/min. Fractions containing the desired product were combined and dried via centrifugal evaporation. The yield of the product was 8.3 mg, and its estimated purity by LCMS analysis was 100%.

Analysis condition A: Retention time=1.66 min; ESI-MS (+) m/z 916.6 (M+2H)

Analysis condition B: Retention time=2.82 min; ESI-MS (+) m/z 917.1 (M+2H)

ESI-HRMS(+) m/z: Calculated: 916.4454 (M+2H). Found: 916.4431 (M+2H).

Preparation of Example 5116

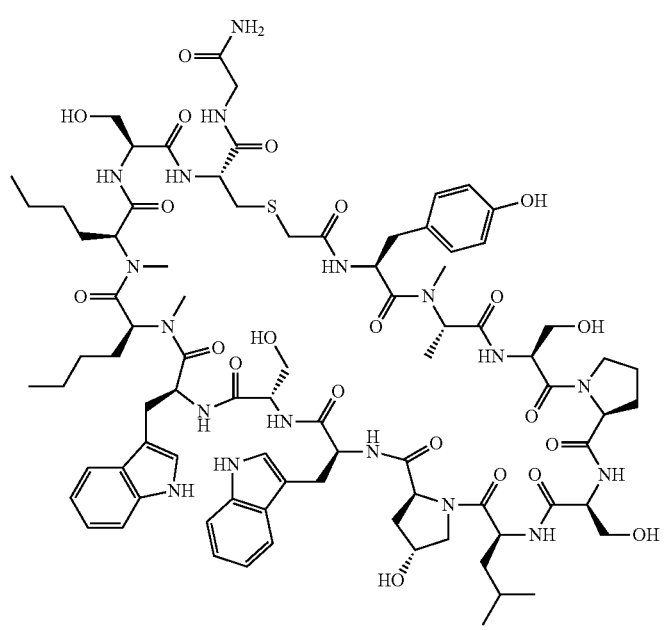

Example 5116

Example 5116 was prepared following "General Synthetic Sequence A" but using "Cyclization Method B" instead of "Cyclization Method A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.2 mg, and its estimated purity by LCMS analysis was 100%.

Analysis condition A: Retention time=1.67 min; ESI-MS (+) m/z 881.9 (M+2H)

Analysis condition B: Retention time=2.66 min; ESI-MS (−) m/z 880.5 (M−2H)

ESI-HRMS(+) m/z: Calculated: 882.4267 (M+2H). Found: 882.4241 (M+2H).

Preparation of Example 5117

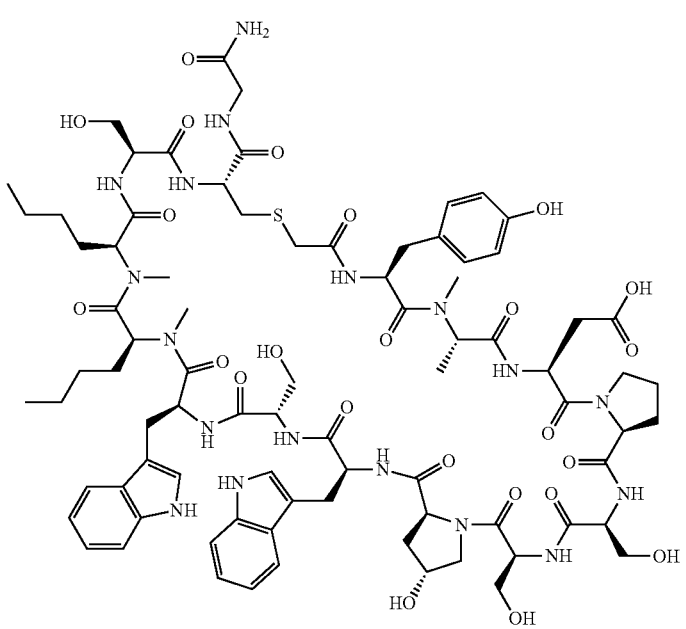

Example 5117

Example 5117 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 100%.

Analysis condition A: Retention time=1.55 min; ESI-MS (+) m/z 883.5 (M+2H)

Analysis condition B: Retention time=2.55 min; ESI-MS (−) m/z 881.8 (M−2H)

ESI-HRMS(+) m/z: Calculated: 883.3982 (M+2H). Found: 883.3956 (M+2H).

Preparation of Example 5118

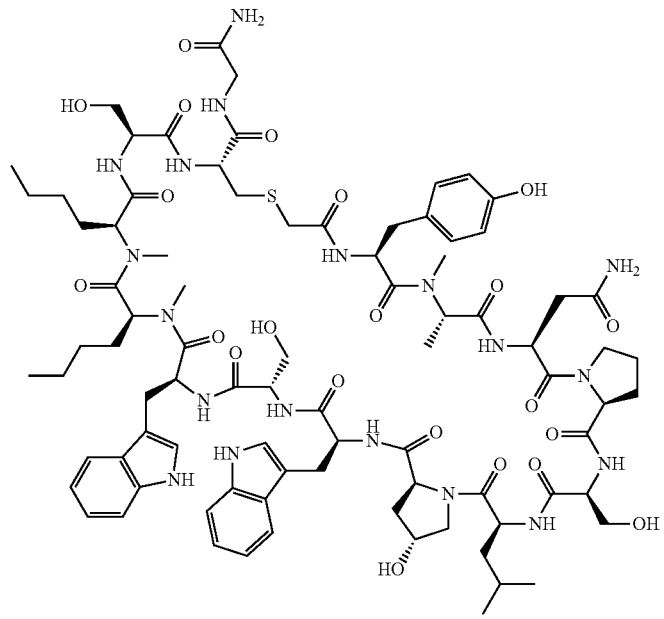

Example 5118

Example 5118 was prepared following "General Synthetic Sequence A" but using "Cyclization Method B" instead of "Cyclization Method A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 99%.

Analysis condition A: Retention time=1.70 min; ESI-MS (+) m/z 896.3 (M+2H)

Analysis condition B: Retention time=2.67 min; ESI-MS (−) m/z 894.2 (M−2H)

ESI-HRMS(+) m/z: Calculated: 895.9322 (M+2H). Found: 895.9297 (M+2H).

Preparation of Example 5119

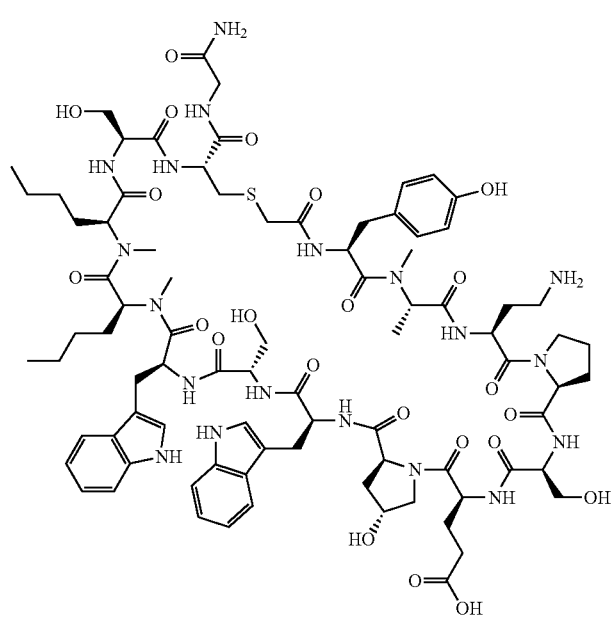

Example 5119

Example 5119 was prepared following "General Synthetic Sequence A" but using "Cyclization Method B" instead of "Cyclization Method A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 99%.

Analysis condition A: Retention time=1.44 min; ESI-MS (+) m/z 897.4 (M+2H)

Analysis condition B: Retention time=2.68 min; ESI-MS (+) m/z 897.6 (M+2H)

ESI-HRMS(+) m/z: Calculated: 896.9193 (M+2H). Found: 896.9218 (M+2H).

Preparation of Example 5120

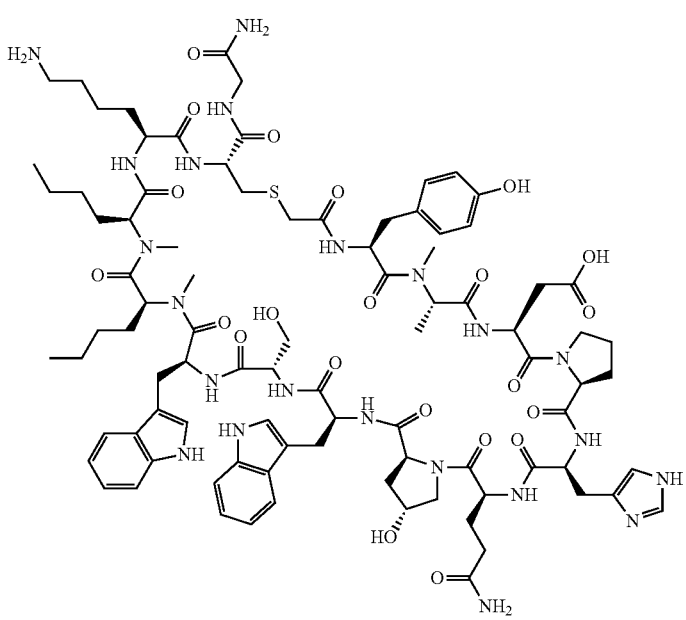

Example 5120

Example 5120 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 98%.

Analysis condition A: Retention time=1.48 min; ESI-MS (+) m/z 950.2 (M+2H)

Analysis condition B: Retention time=2.65 min; ESI-MS (+) m/z 950.2 (M+2H)

ESI-HRMS(+) m/z: Calculated: 949.4563 (M+2H). Found: 949.4537 (M+2H).

Preparation of Example 5121

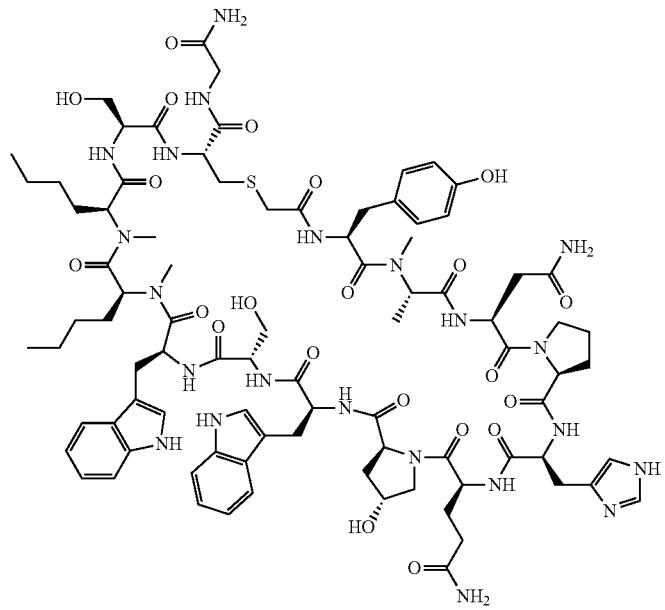

Example 5121

Example 5121 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 35.3 mg, and its estimated purity by LCMS analysis was 100%.

Analysis condition A: Retention time=1.54 min; ESI-MS (+) m/z 929.2 (M+2H)

Analysis condition B: Retention time=2.72 min; ESI-MS (+) m/z 928.8 (M+2H)

ESI-HRMS(+) m/z: Calculated: 928.4329 (M+2H). Found: 928.4301 (M+2H).

Preparation of Example 5122

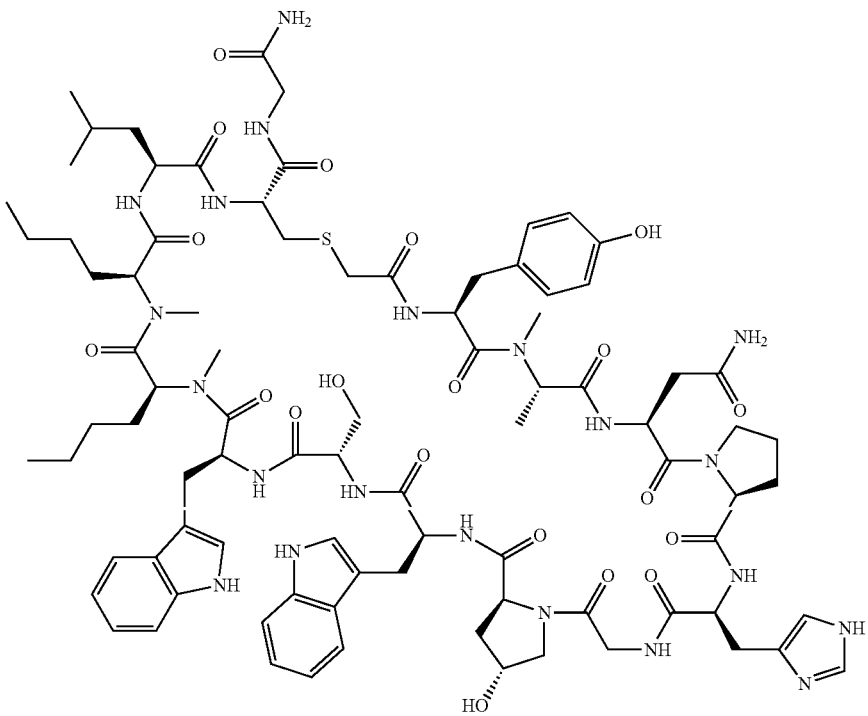

Example 5122

Example 5122 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 10.6 mg, and its estimated purity by LCMS analysis was 100%.

Analysis condition A: Retention time=1.66 min; ESI-MS (+) m/z 906.6 (M+2H)

Analysis condition B: Retention time=2.85 min; ESI-MS (+) m/z 906.3 (M+2H)

ESI-HRMS(+) m/z: Calculated: 905.9403 (M+2H). Found: 905.9375 (M+2H).

Preparation of Example 5123

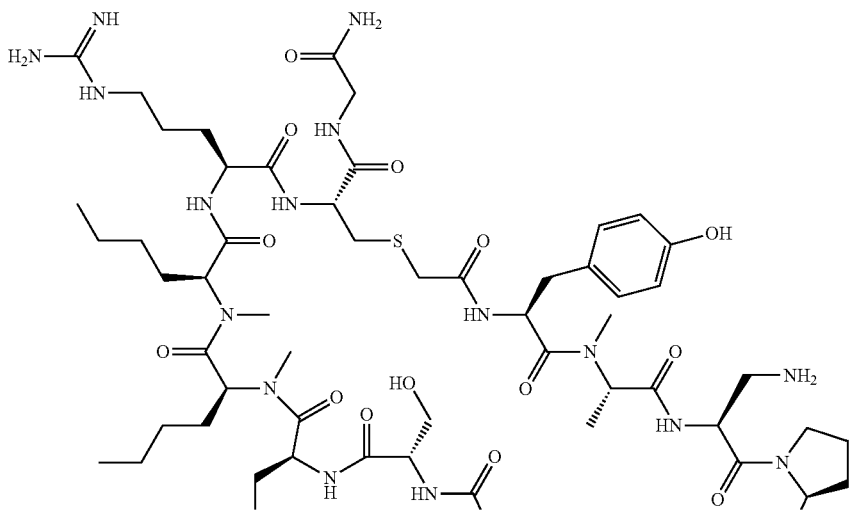

Example 5123

1263

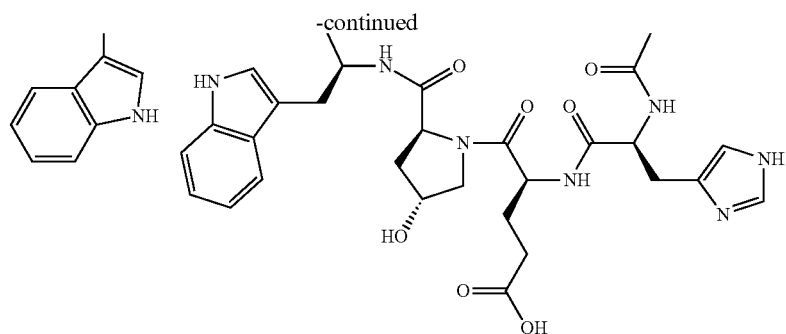

-continued

1264

Example 5123 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 29.2 mg, and its estimated purity by LCMS analysis was 99%.

Analysis condition A: Retention time=1.46 min; ESI-MS (+) m/z 950.1 (M+2H)

Analysis condition B: Retention time=2.63 min; ESI-MS (+) m/z 950.2 (M+2H)

ESI-HRMS(+) m/z: Calculated: 949.4620 (M+2H). Found: 949.4589 (M+2H).

Preparation of Example 5124

Example 5124

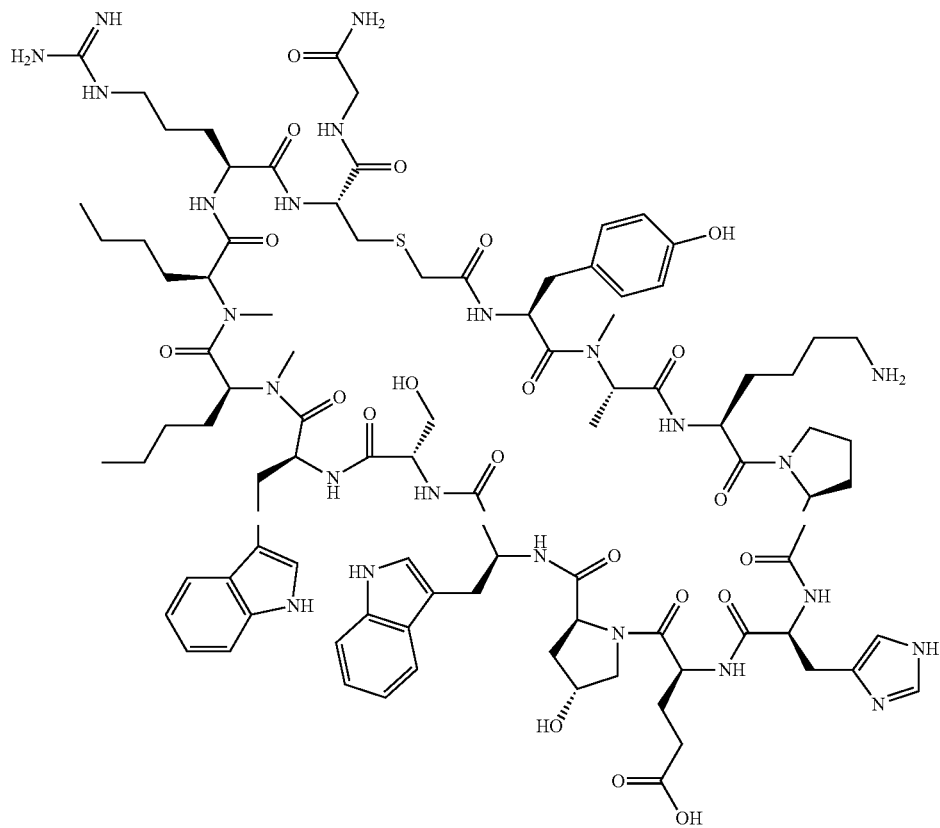

Example 5124 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 99%.

Analysis condition A: Retention time=1.46 min; ESI-MS (+) m/z 970.9 (M+2H)

Analysis condition B: Retention time=2.64 min; ESI-MS (+) m/z 971.2 (M+2H)

ESI-HRMS(+) m/z: Calculated: 970.4854 (M+2H). Found: 970.4820 (M+2H).

Preparation of Example 5125

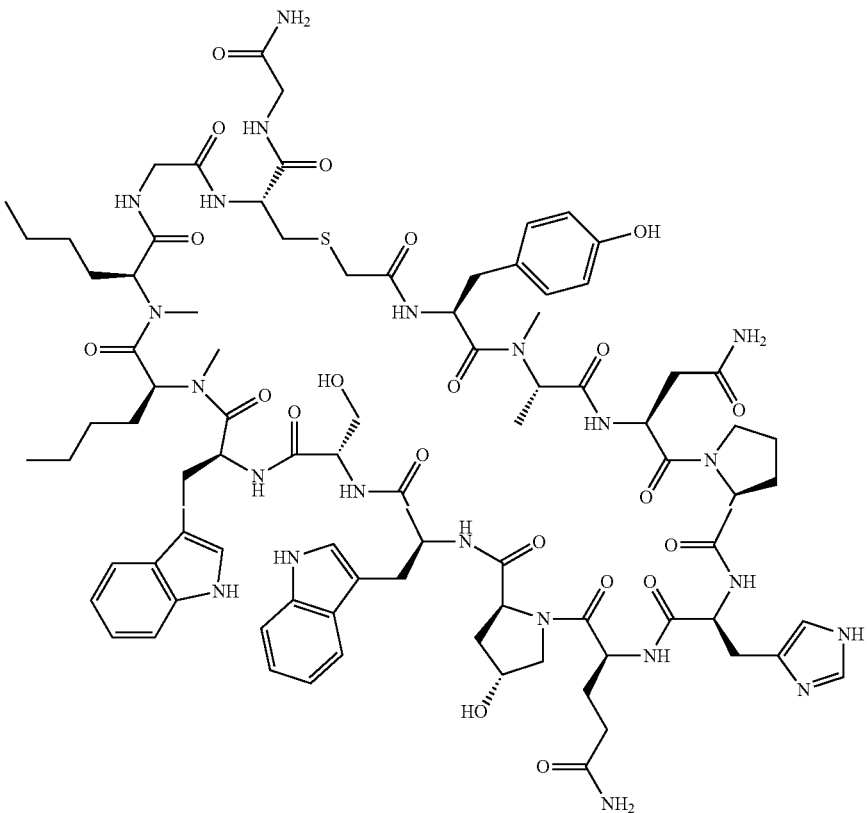

Example 5125

Example 5125 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 40.6 mg, and its estimated purity by LCMS analysis was 100%.

Analysis condition A: Retention time=1.49 min; ESI-MS (+) m/z 914.0 (M+2H)

Analysis condition B: Retention time=2.69 min; ESI-MS (+) m/z 914.1 (M+2H)

ESI-HRMS(+) m/z: Calculated: 913.4276 (M+2H). Found: 913.4242 (M+2H).

Preparation of Example 5126

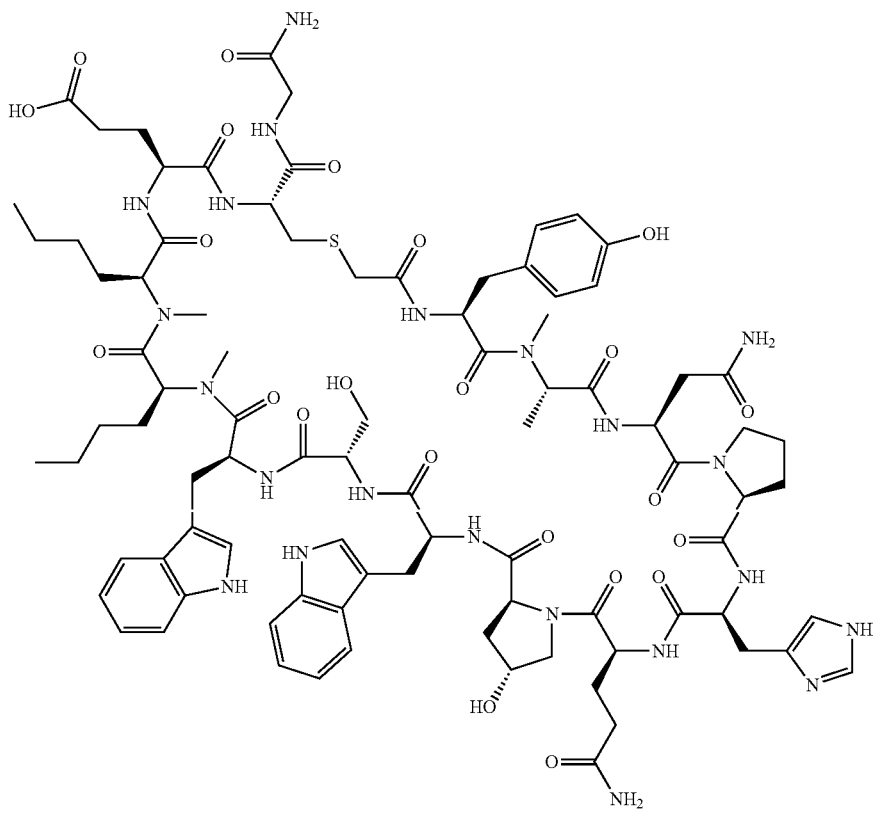

Example 5126

Example 5126 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 34.7 mg, and its estimated purity by LCMS analysis was 100%.

Analysis condition A: Retention time=1.38 min; ESI-MS (+) m/z 950.2 (M+2H)

Analysis condition B: Retention time=2.53 min; ESI-MS (+) m/z 950.2 (M+2H)

ESI-HRMS(+) m/z: Calculated: 949.4381 (M+2H). Found: 949.4355 (M+2H).

Preparation of Example 5127

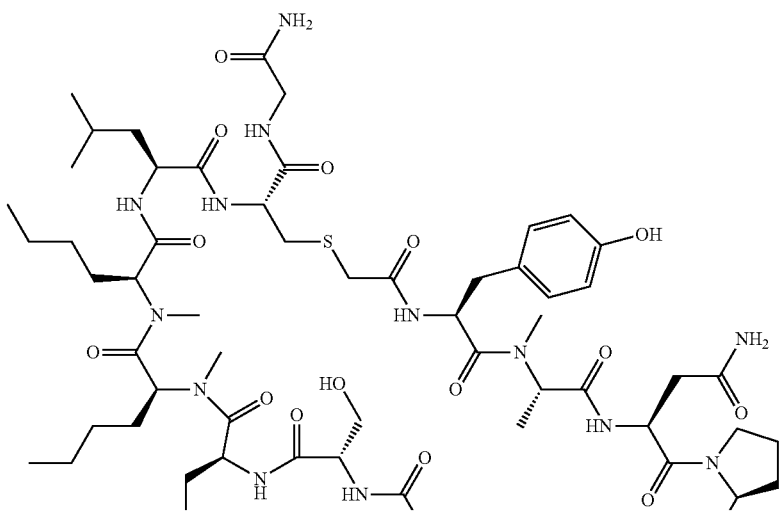

Example 5127

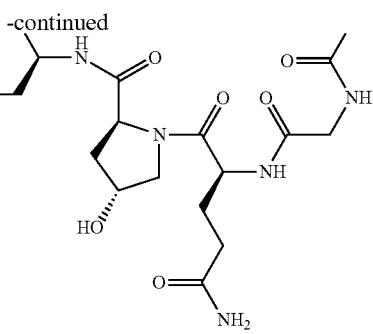

Example 5127 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 22.2 mg, and its estimated purity by LCMS analysis was 100%.

Analysis condition A: Retention time=1.63 min; ESI-MS (+) m/z 902.0 (M+2H)

Analysis condition B: Retention time=2.82 min; ESI-MS (+) m/z 902.2 (M+2H)

ESI-HRMS(+) m/z: Calculated: 901.4402 (M+2H). Found: 901.4375 (M+2H).

Preparation of Example 5128

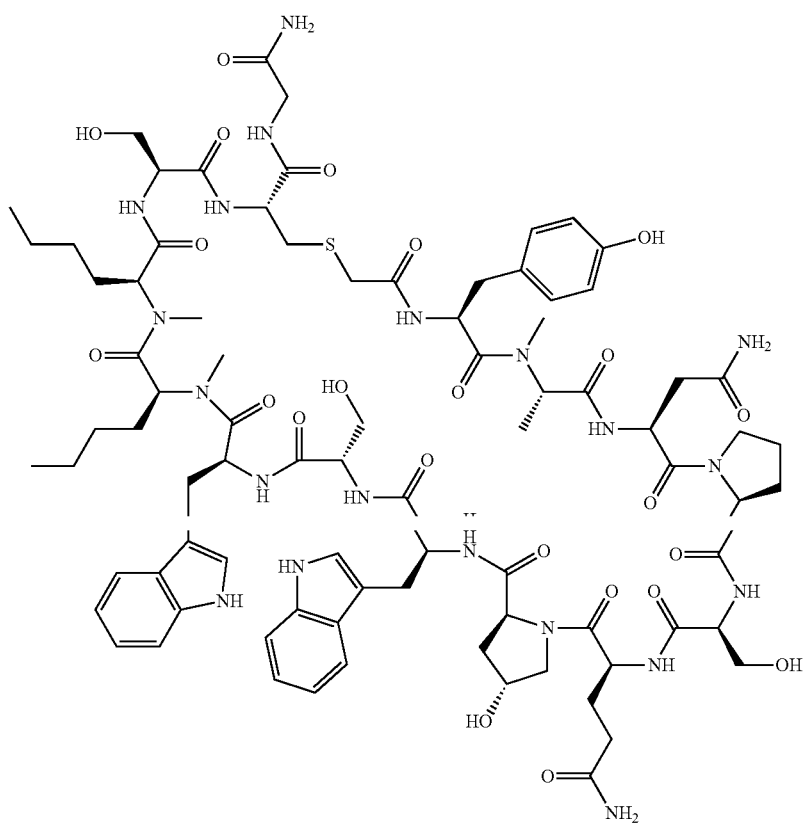

Example 5128

Example 5128 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.1 mg, and its estimated purity by LCMS analysis was 99%.

Analysis condition A: Retention time=1.53 min; ESI-MS (+) m/z 904.0 (M+2H)

Analysis condition B: Retention time=2.73 min; ESI-MS (+) m/z 904.1 (M+2H)

ESI-HRMS(+) m/z: Calculated: 903.4194 (M+2H). Found: 903.4167 (M+2H).

Preparation of Example 5129

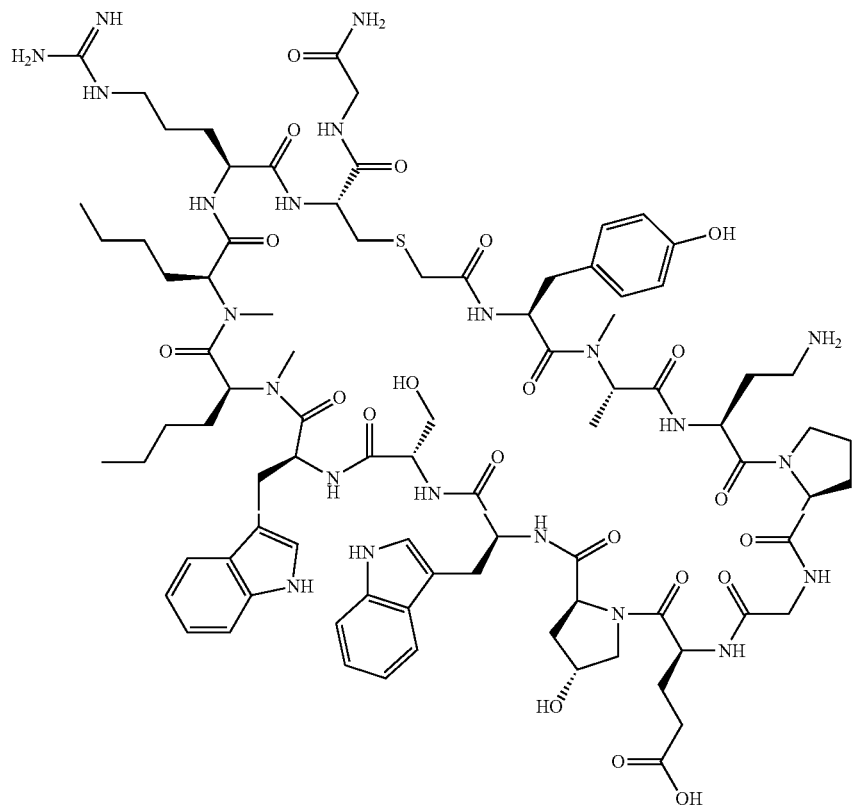

Example 5129

Example 5129 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 24.3 mg, and its estimated purity by LCMS analysis was 99%.

Analysis condition A: Retention time=1.47 min; ESI-MS (+) m/z 917.1 (M+2H)

Analysis condition B: Retention time=2.65 min; ESI-MS (+) m/z 917.2 (M+2H)

ESI-HRMS(+) m/z: Calculated: 916.4511 (M+2H). Found: 916.4482 (M+2H).

Preparation of Example 5130

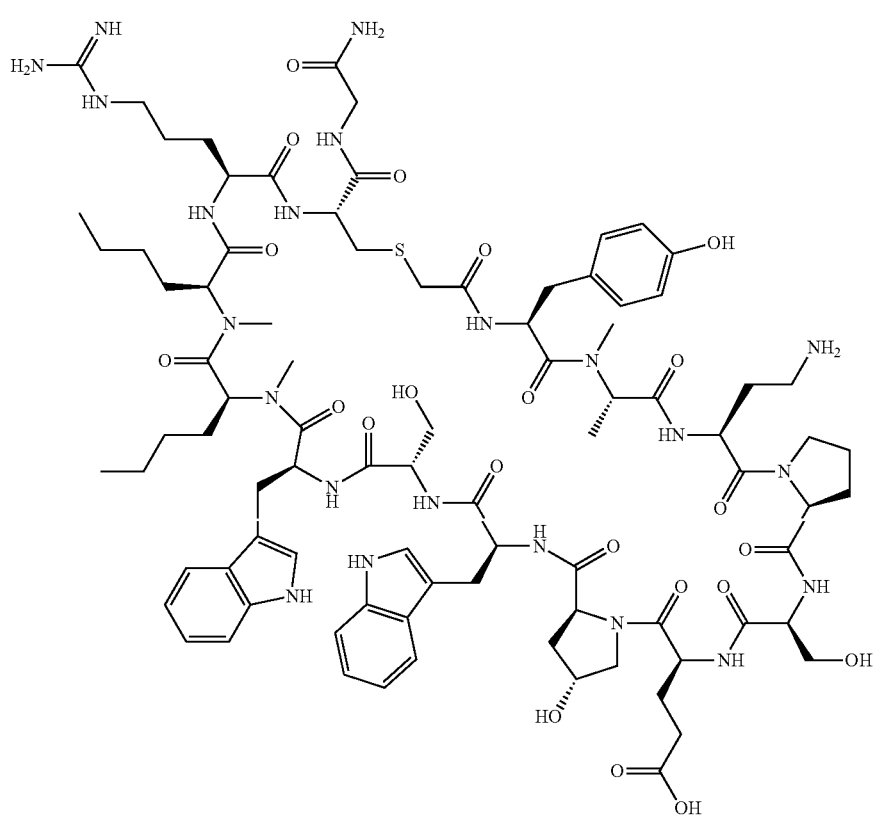

Example 5130

Example 5130 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 34.6 mg, and its estimated purity by LCMS analysis was 97%.

Analysis condition A: Retention time=1.46 min; ESI-MS (+) m/z 932.1 (M+2H)

Analysis condition B: Retention time=2.63 min; ESI-MS (+) m/z 932.2 (M+2H)

ESI-HRMS(+) m/z: Calculated: 931.4563 (M+2H). Found: 931.4534 (M+2H).

Preparation of Example 5131

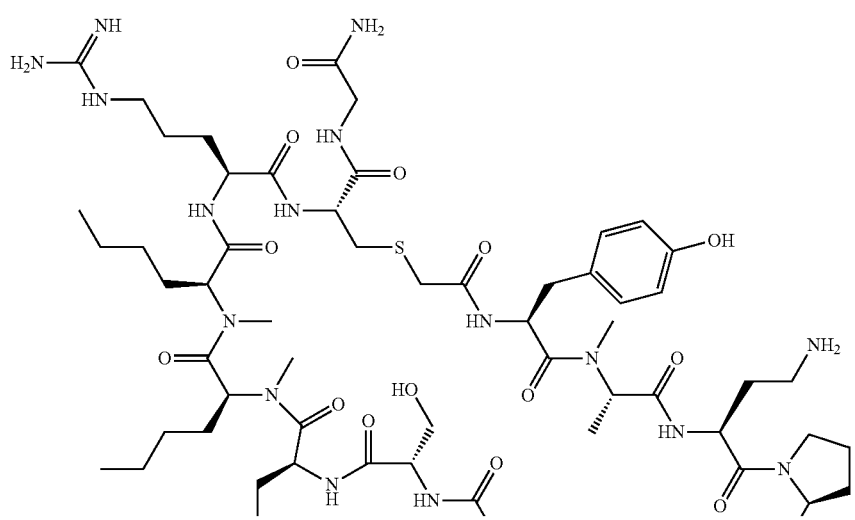

Example 5131

-continued

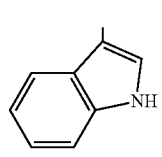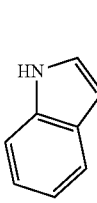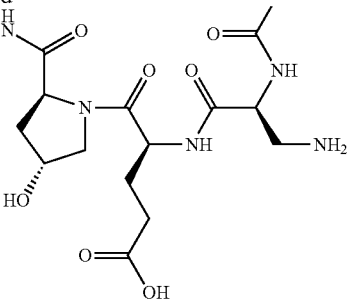

Example 5131 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 37.3 mg, and its estimated purity by LCMS analysis was 100%.

Analysis condition A: Retention time=1.44 min; ESI-MS (+) m/z 931.8 (M+2H)

Analysis condition B: Retention time=2.57 min; ESI-MS (+) m/z 931.6 (M+2H)

ESI-HRMS(+) m/z: Calculated: 930.9643 (M+2H). Found: 930.9617 (M+2H).

Preparation of Example 5132

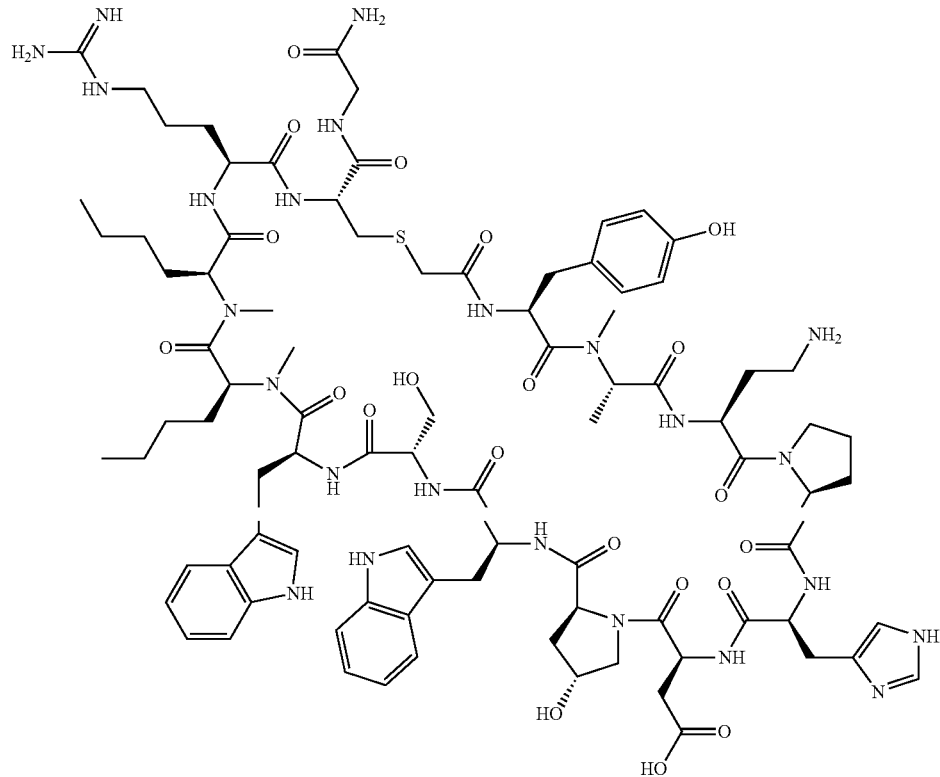

Example 5132

Example 5132 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 44.8 mg, and its estimated purity by LCMS analysis was 100%.

Analysis condition A: Retention time=1.39 min; ESI-MS (+) m/z 950.2 (M+2H)

Analysis condition B: Retention time=2.52 min; ESI-MS (+) m/z 950.4 (M+2H)

ESI-HRMS(+) m/z: Calculated: 949.4620 (M+2H). Found: 949.4587 (M+2H).

Preparation of Example 5133

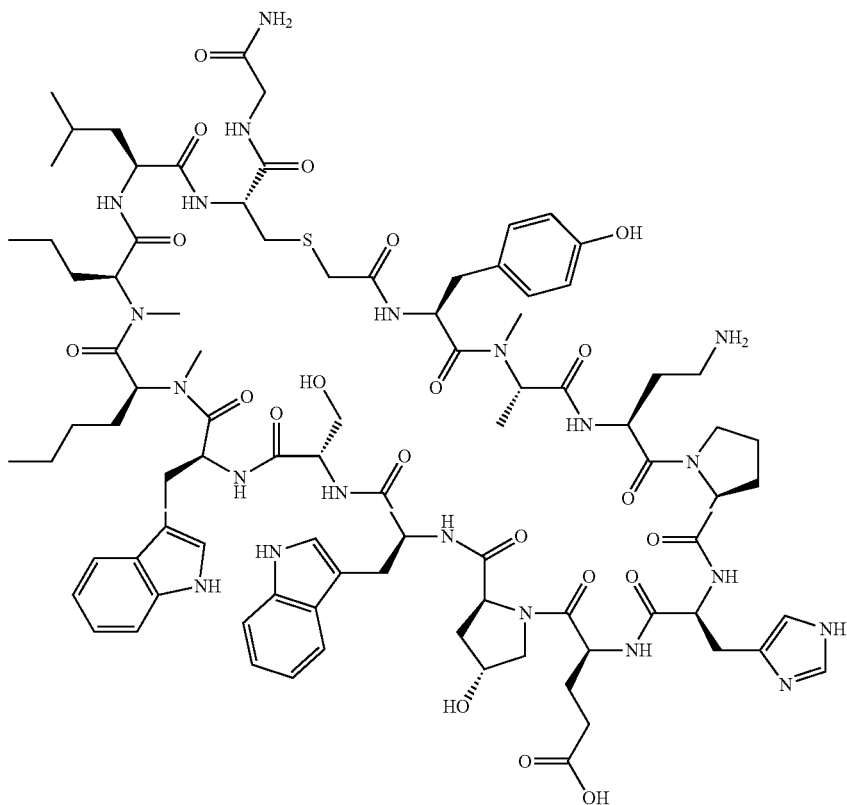

Example 5133

Example 5133 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 32.5 mg, and its estimated purity by LCMS analysis was 100%.

Analysis condition A: Retention time=1.48 min; ESI-MS (+) m/z 922.5 (M+2H)

Analysis condition B: Retention time=2.68 min; ESI-MS (+) m/z 922.7 (M+2H)

ESI-HRMS(+) m/z: Calculated: 921.9352 (M+2H). Found: 921.9318 (M+2H).

Preparation of Example 5134

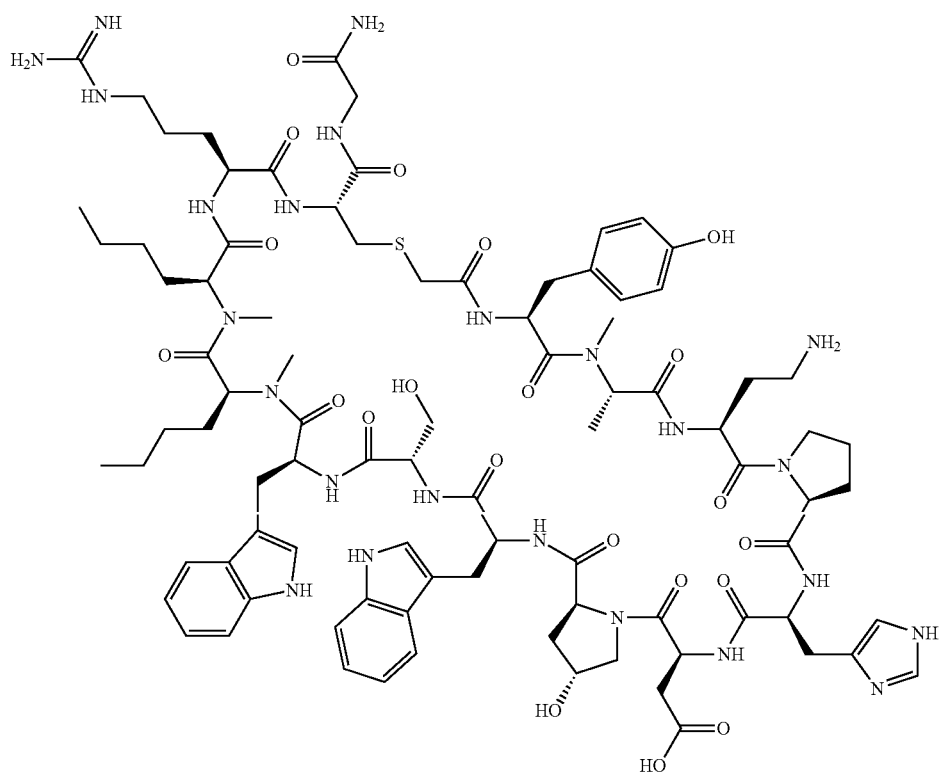

Example 5134

Example 5134 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-45% B over 30 minutes, then a 5-minute hold at 100% B; Flow: 20 mL/min. Fractions containing the desired product were combined and dried via centrifugal evaporation. The yield of the product was 12.8 mg, and its estimated purity by LCMS analysis was 100%.

Analysis condition A: Retention time=1.39 min; ESI-MS (+) m/z 943.2 (M+2H)

Analysis condition B: Retention time=2.54 min; ESI-MS (+) m/z 943.1 (M+2H)

ESI-HRMS(+) m/z: Calculated: 942.4541 (M+2H). Found: 942.4513 (M+2H).

Preparation of Example 5135

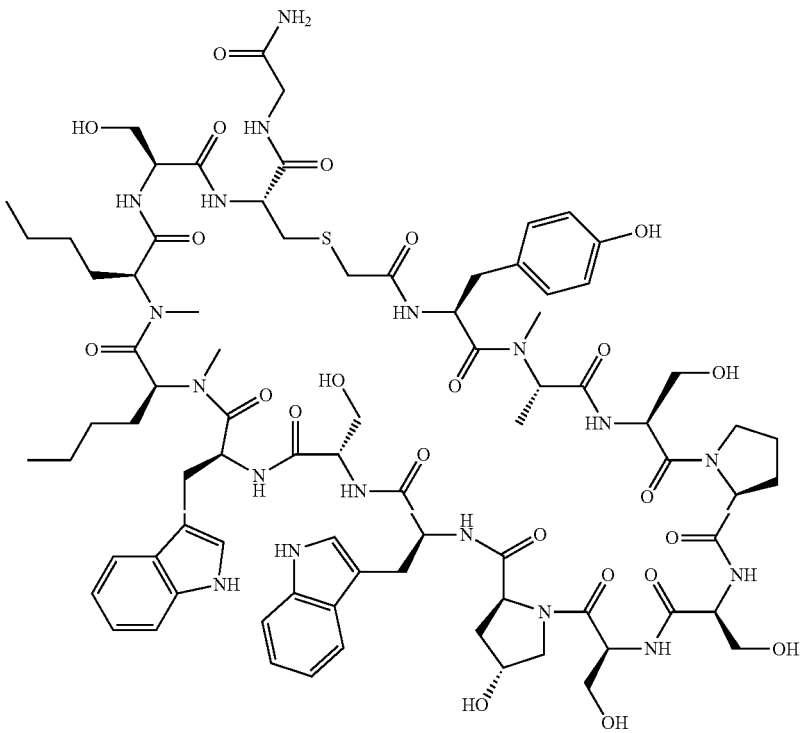

Example 5135

Example 5135 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-45% B over 30 minutes, then a 5-minute hold at 100% B; Flow: 20 mL/min. Fractions containing the desired product were combined and dried via centrifugal evaporation. The yield of the product was 19.8 mg, and its estimated purity by LCMS analysis was 100%.

Analysis condition A: Retention time=1.52 min; ESI-MS (+) m/z 869.4 (M+2H)

Analysis condition B: Retention time=2.66 min; ESI-MS (+) m/z 870.0 (M+2H)

ESI-HRMS(+) m/z: Calculated: 869.4007 (M+2H). Found: 869.3986 (M+2H).

Preparation of Example 5137

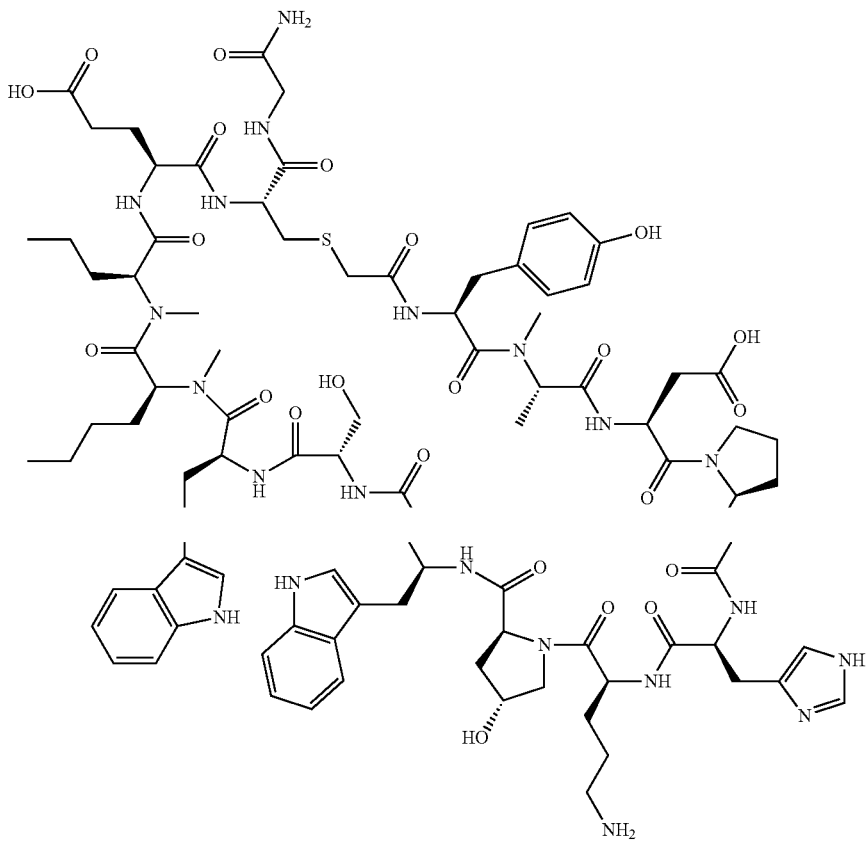

Example 5137

Example 5137 was prepared following "General Synthetic Sequence A" but using "Cyclization Method B" instead of "Cyclization Method A", and was prepared on a 0.300 mmol scale where the reagent amounts were scale appropriately. The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 102.2 mg, and its estimated purity by LCMS analysis was 98%.

Analysis condition A: Retention time=1.41 min; ESI-MS (+) m/z 964.3 (M+2H)

Analysis condition B: Retention time=2.62 min; ESI-MS (+) m/z 964.1 (M+2H)

ESI-HRMS(+) m/z: Calculated: 963.4720 (M+2H). Found: 963.4687 (M+2H).

Preparation of Example 5138

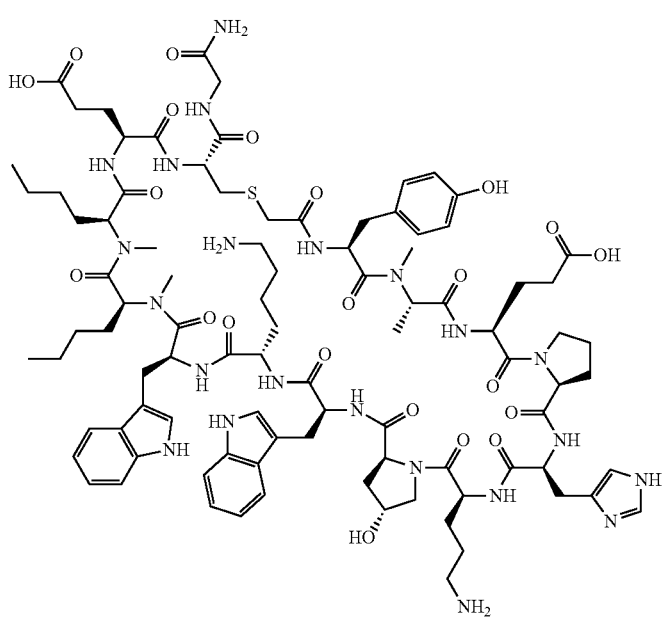

Example 5138

Example 5138 was prepared following "General Synthetic Sequence A" but using "Cyclization Method B" instead of "Cyclization Method A", and was prepared on a 0.300 mmol scale where the reagent amounts were scaled accordingly. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 57.8 mg, and its estimated purity by LCMS analysis was 100%.

Analysis condition A: Retention time=1.41 min; ESI-MS (+) m/z 971.2 (M+2H)

Analysis condition B: Retention time=2.60 min; ESI-MS (+) m/z 971.2 (M+2H)

Preparation of Example 5139

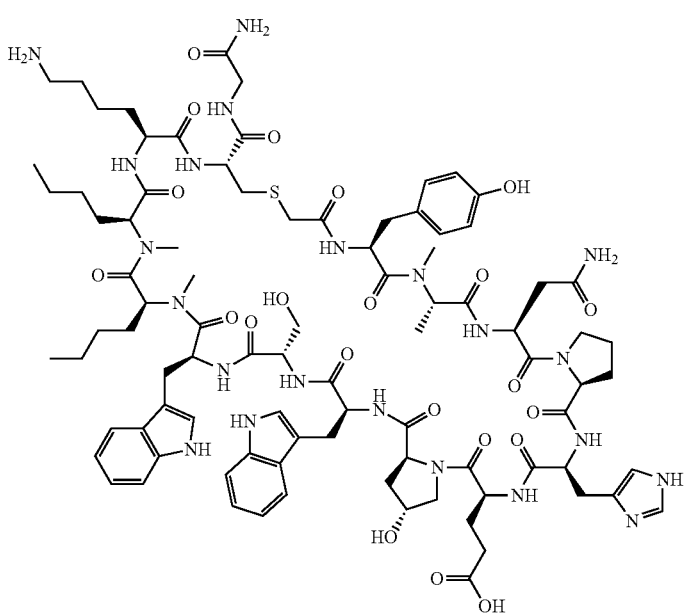

Example 5139

Example 5139 was prepared following "General Synthetic Sequence A" but using "Cyclization Method B" instead of "Cyclization Method A", and was prepared on a 0.300 mmol scale where the reagents amounts were scaled accordingly. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 27.7 mg, and its estimated purity by LCMS analysis was 100%.

Analysis condition A: Retention time=1.45 min; ESI-MS (+) m/z 950.1 (M+2H)

Analysis condition B: Retention time=2.63 min; ESI-MS (+) m/z 950.1 (M+2H)

ESI-HRMS(+) m/z: Calculated: 949.4563 (M+2H). Found: 949.4541 (M+2H).

Preparation on Example 5140

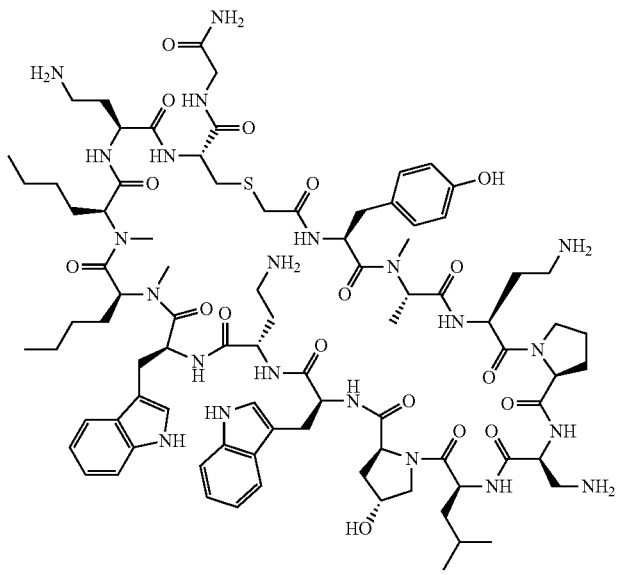

Example 5140

Example 5140 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 36.5 mg, and its estimated purity by LCMS analysis was 98%.

Analysis condition A: Retention time=1.34 min; ESI-MS (+) m/z 901.8 (M+2H)

Analysis condition B: Retention time=2.51 min; ESI-MS (+) m/z 902.1 (M+2H)

ESI-HRMS(+) m/z: Calculated: 901.4822 (M+2H). Found: 901.4800 (M+2H).

Preparation of Example 5141

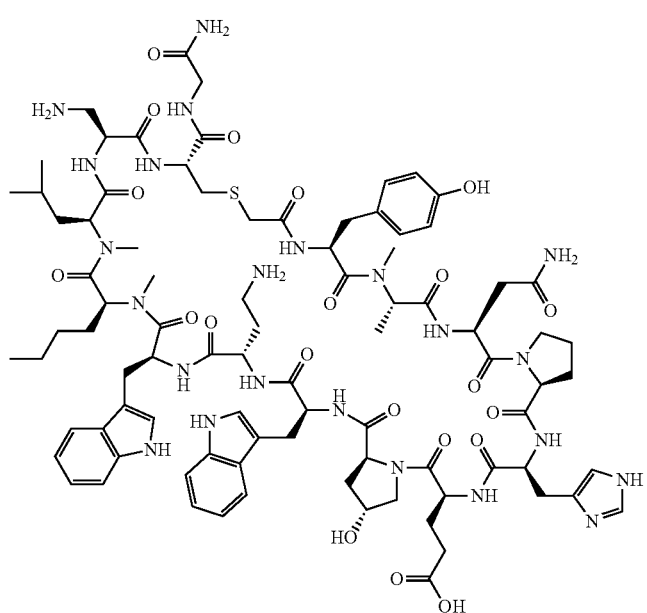

Example 5141

Example 5141 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 33.0 mg, and its estimated purity by LCMS analysis was 100%.

Analysis condition A: Retention time=1.40 min; ESI-MS (+) m/z 935.8 (M+2H)

Analysis condition B: Retention time=2.56 min; ESI-MS (+) m/z 935.5 (M+2H)

ESI-HRMS(+) m/z: Calculated: 934.9487 (M+2H). Found: 934.9471 (M+2H).

Preparation of Example 5142

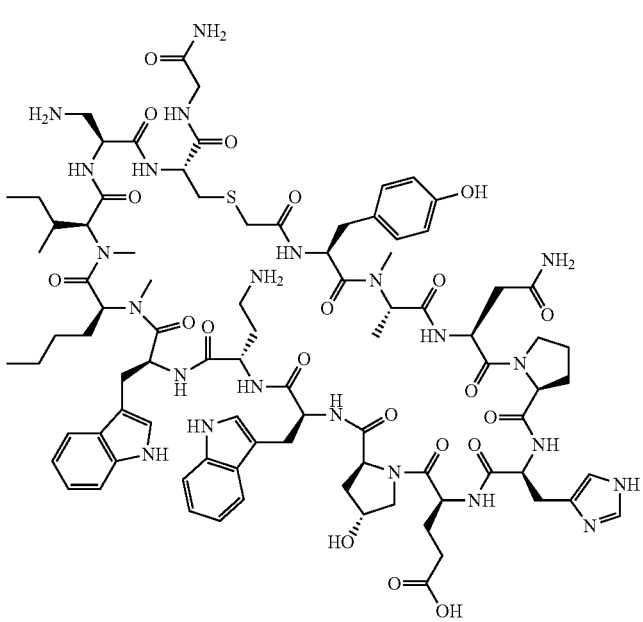

Example 5142

Example 5142 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.31 min; ESI-MS (+) m/z 935.1 (M+2H)

Analysis condition B: Retention time=2.49 min; ESI-MS (+) m/z 935.6 (M+2H)

ESI-HRMS(+) m/z: Calculated: 934.9487 (M+2H). Found: 934.9467 (M+2H).

Preparation of Example 5143

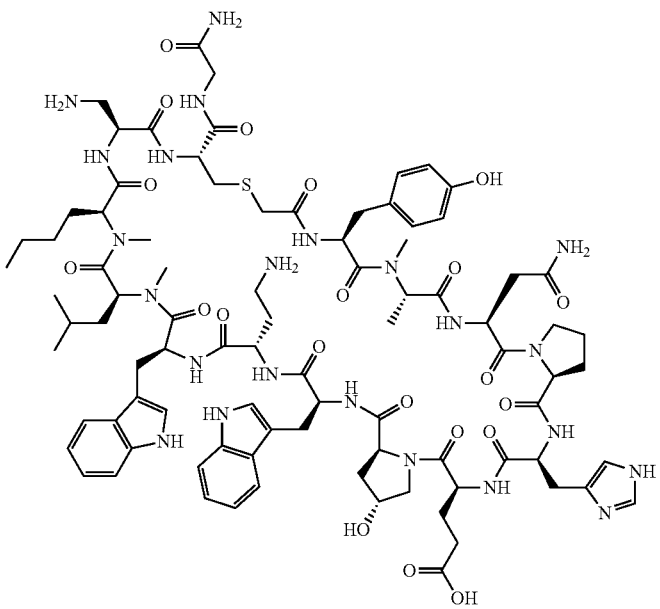

Example 5143

Example 5143 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 22.4 mg, and its estimated purity by LCMS analysis was 100%.

Analysis condition A: Retention time=1.34 min; ESI-MS (+) m/z 935.3 (M+2H)

Analysis condition B: Retention time=2.53 min; ESI-MS (+) m/z 935.4 (M+2H)

ESI-HRMS(+) m/z: Calculated: 934.9487 (M+2H). Found: 934.9464 (M+2H).

Preparation of Example 5144

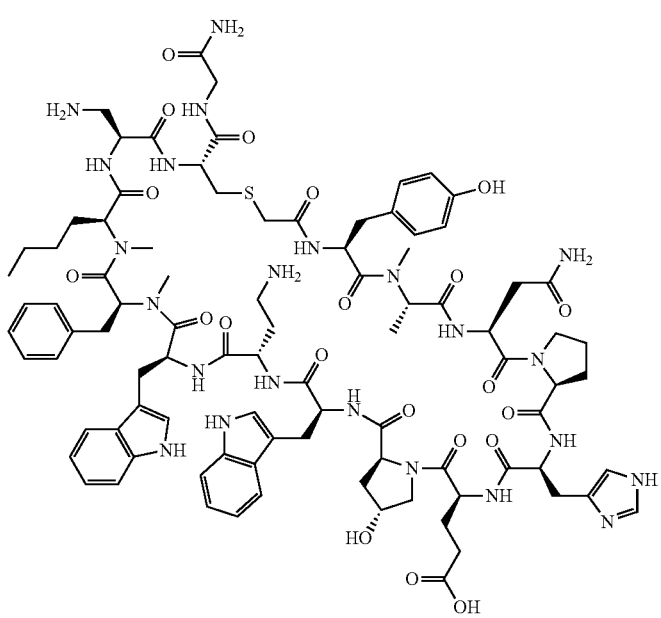

Example 5144

Example 5144 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 100%.

Analysis condition A: Retention time=1.41 min; ESI-MS (+) m/z 952.7 (M+2H)

Analysis condition B: Retention time=2.57 min; ESI-MS (+) m/z 952.7 (M+2H)

ESI-HRMS(+) m/z: Calculated: 951.9409 (M+2H). Found: 951.9385 (M+2H).

Preparation of Example 5145

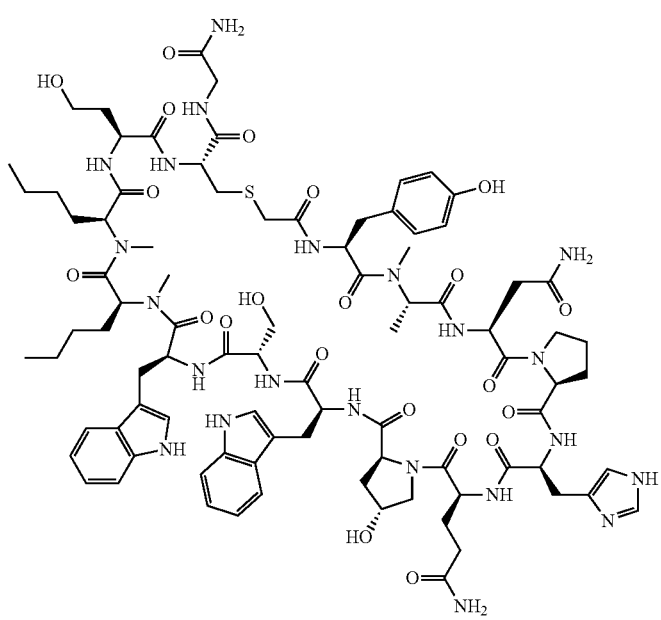

Example 5145

Example 5145 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 2.0 mg, and its estimated purity by LCMS analysis was 100%.

Analysis condition A: Retention time=1.48 min; ESI-MS (+) m/z 935.9 (M+2H)

Analysis condition B: Retention time=2.60 min; ESI-MS (−) m/z 934.2 (M−2H)

ESI-HRMS(+) m/z: Calculated: 935.4407 (M+2H). Found: 935.4385 (M+2H).

Preparation of Example 5146

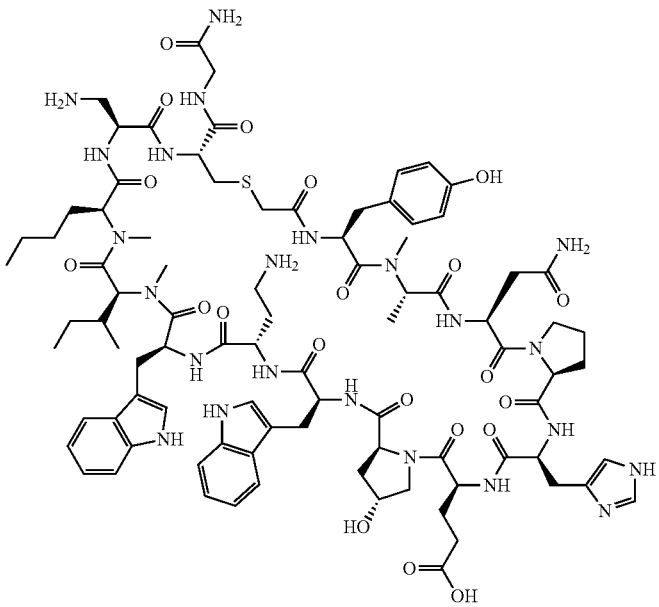

Example 5146

Example 5146 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 0.5 mg, and its estimated purity by LCMS analysis was 100%.

Analysis condition A: Retention time=1.33 min; ESI-MS (+) m/z 935.5 (M+2H)

Analysis condition B: Retention time=2.53 min; ESI-MS (−) m/z 933.2 (M−2H)

ESI-HRMS(+) m/z: Calculated: 934.9487 (M+2H). Found: 934.9464 (M+2H).

Preparation of Example 5147

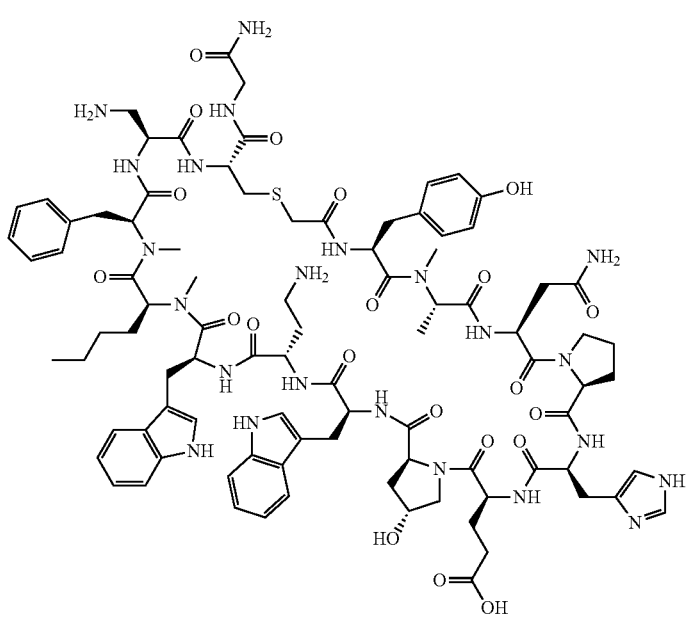

Example 5147

Example 5147 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 33.9 mg, and its estimated purity by LCMS analysis was 100%.

Analysis condition A: Retention time=1.45 min; ESI-MS (+) m/z 952.6 (M+2H)

Analysis condition B: Retention time=2.59 min; ESI-MS (+) m/z 952.7 (M+2H)

ESI-HRMS(+) m/z: Calculated: 951.9409 (M+2H). Found: 951.9377 (M+2H).

Preparation of Example 6001

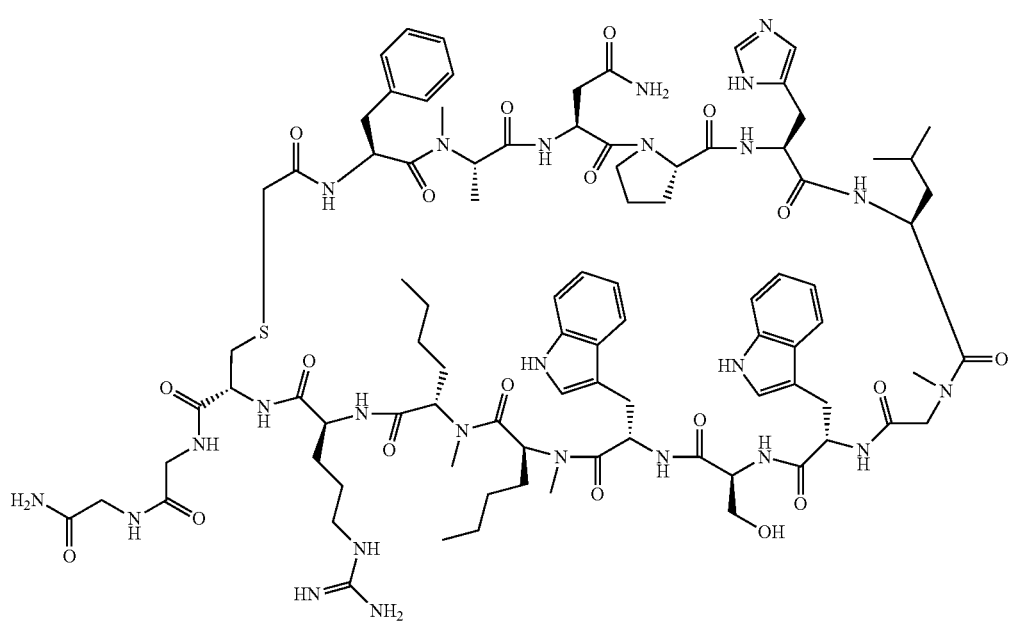

Example 6001

Example 6001 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 0-minute hold at 100% B; Flow: 20 mL/min. Fractions containing the desired product were combined and dried via centrifugal evaporation. The yield of the product was 5.2 mg, and its estimated purity by LCMS analysis was 99%.

Analysis condition A: Retention time=1.778 min; ESI-MS (+) m/z 955.25 (M+2H)

Preparation of Example 6002

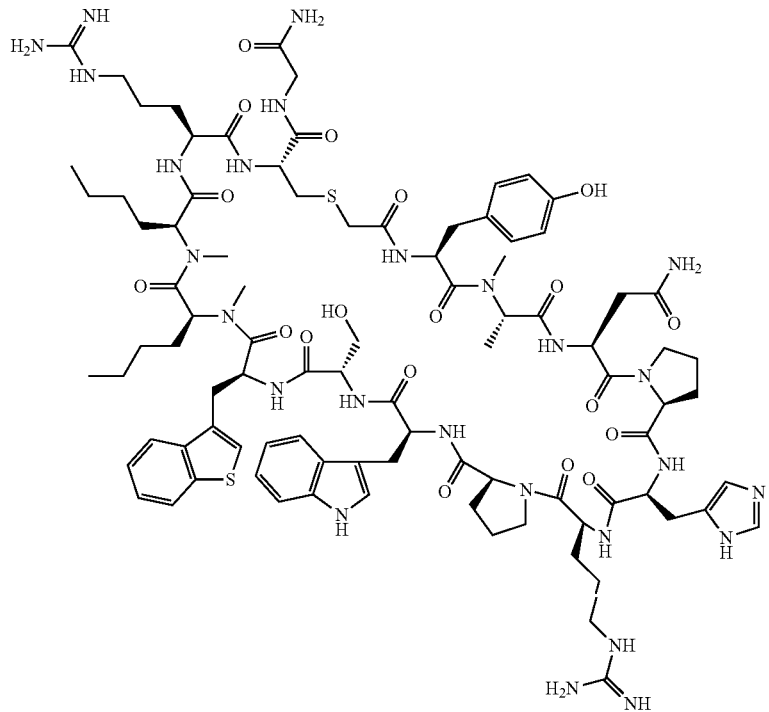

Example 6002

Example 6002 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 100%.

Analysis condition A: Retention time=1.55 min; ESI-MS (+) m/z 978.2 (M+2H)

Analysis condition B: Retention time=2.63 min; ESI-MS (+) m/z 977.8 (M+2H)

Preparation of Example 6003

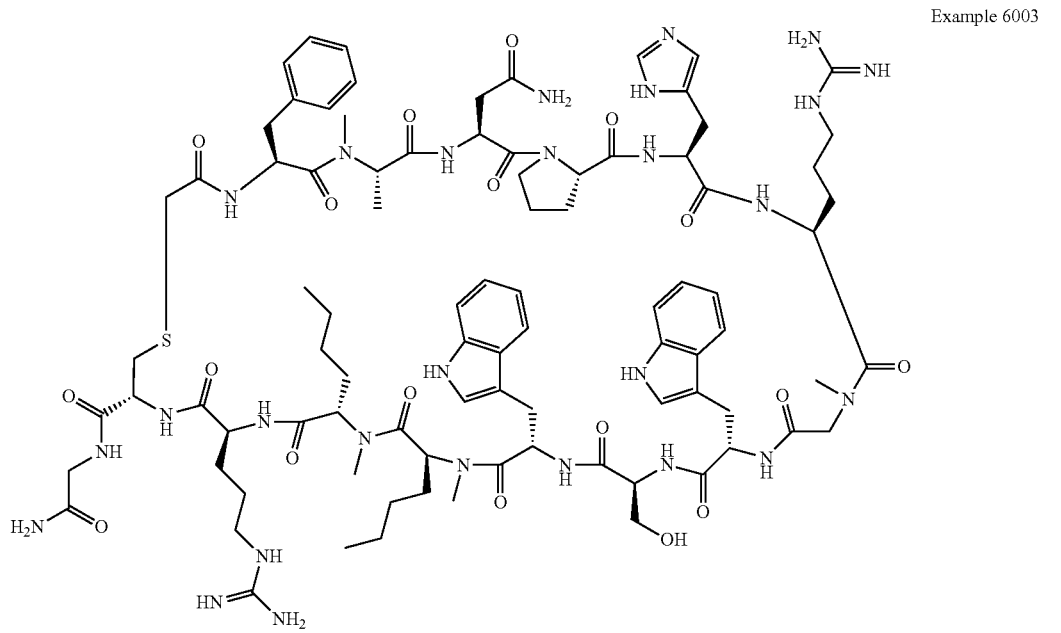 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccccc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCNC(=N)N)C(=O)N(C)CC(=O)N[C@@H](Cc2c[nH]c3ccccc23)C(=O)N[C@@H](CO)C(=O)N[C@@H](Cc2c[nH]c3ccccc23)C(=O)N1C]

Example 6003

Example 6003 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 32.2 mg, and its estimated purity by LCMS analysis was 100%.

Analysis condition A: Retention time=1.68 min; ESI-MS (+) m/z 948.1 (M+2H)

Analysis condition B: Retention time=2.64 min; ESI-MS (+) m/z 948.1 (M+2H)

Preparation of Example 6004

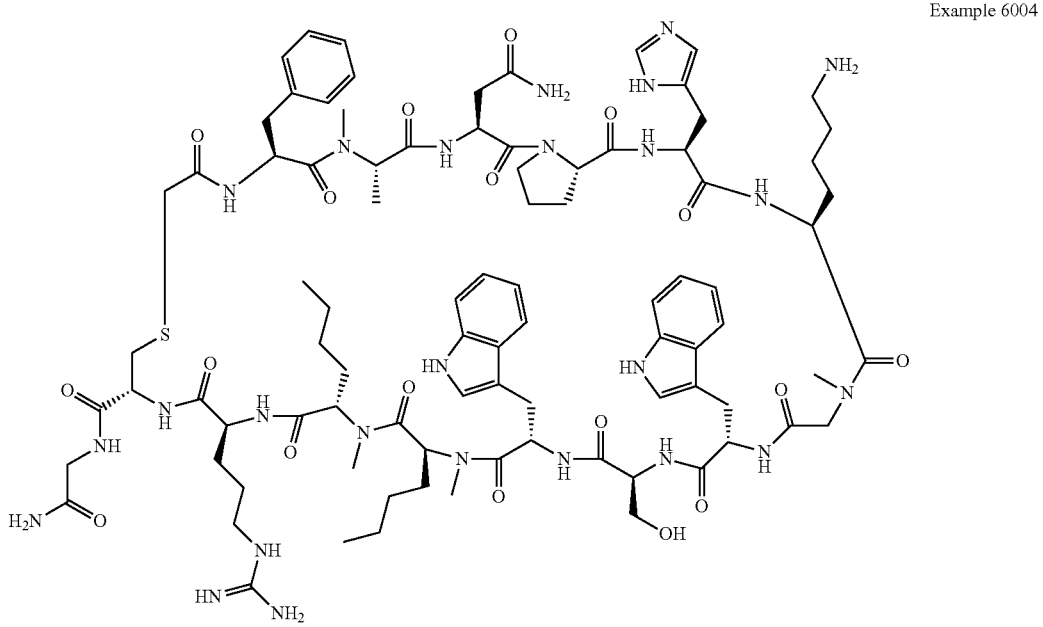 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccccc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CCCCN)C(=O)N(C)CC(=O)N[C@@H](Cc2c[nH]c3ccccc23)C(=O)N[C@@H](CO)C(=O)N[C@@H](Cc2c[nH]c3ccccc23)C(=O)N1C]

Example 6004

Example 6004 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 33.7 mg, and its estimated purity by LCMS analysis was 100%.

Analysis condition A: Retention time=1.69 min; ESI-MS (+) m/z 934.3 (M+2H)

Analysis condition B: Retention time=2.83 min; ESI-MS (+) m/z 934.0 (M+2H)

Preparation of Example 6005

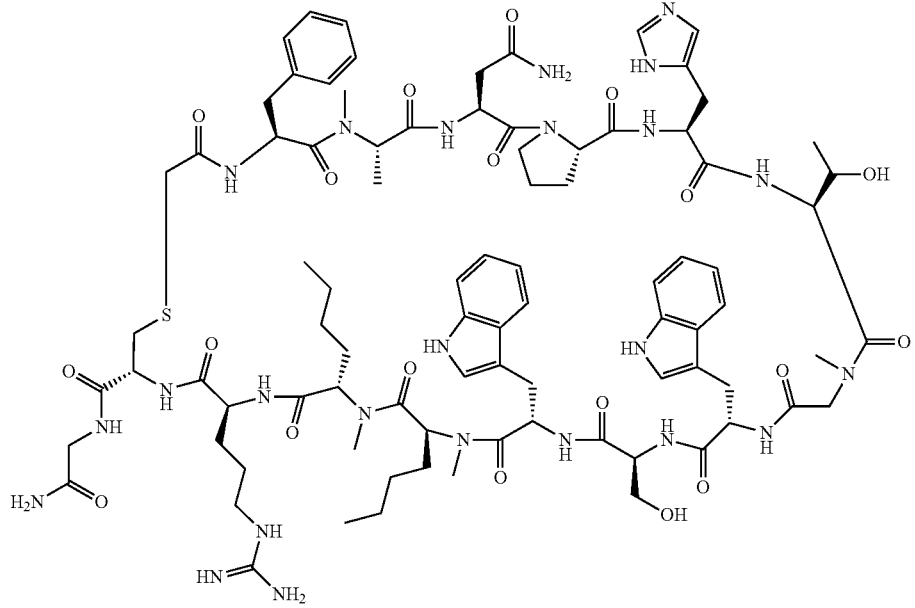

Example 6005

Example 6005 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 37.1 mg, and its estimated purity by LCMS analysis was 98%.

Analysis condition A: Retention time=1.63 min; ESI-MS (+) m/z 920.4 (M+2H)

Analysis condition B: Retention time=2.82 min; ESI-MS (+) m/z 920.5 (M+2H)

Preparation of Example 6006

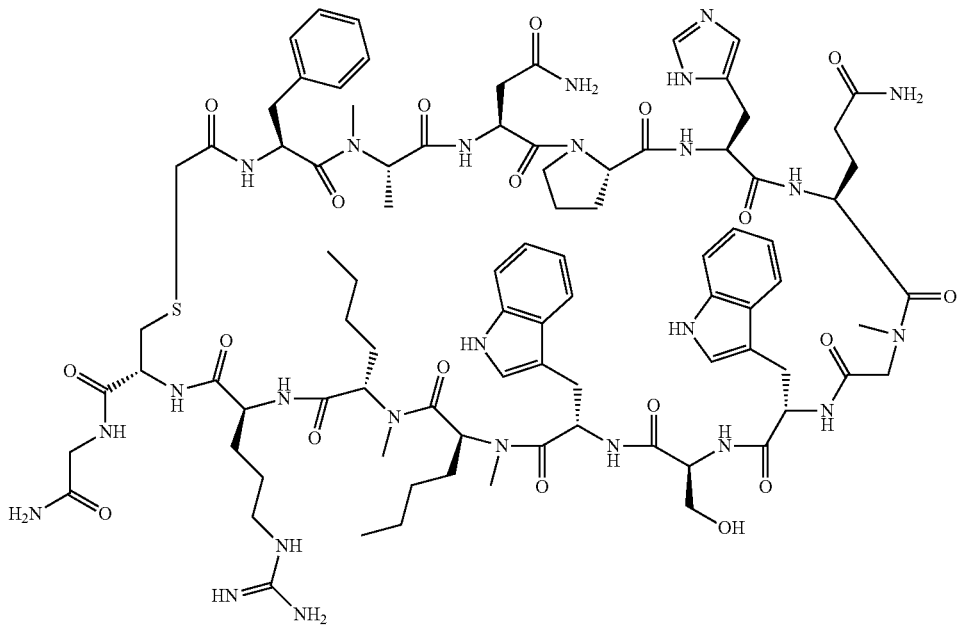

Example 6006

Example 6006 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 100%.

Analysis condition A: Retention time=1.71 min; ESI-MS (+) m/z 934.8 (M+2H)

Preparation of Example 6007

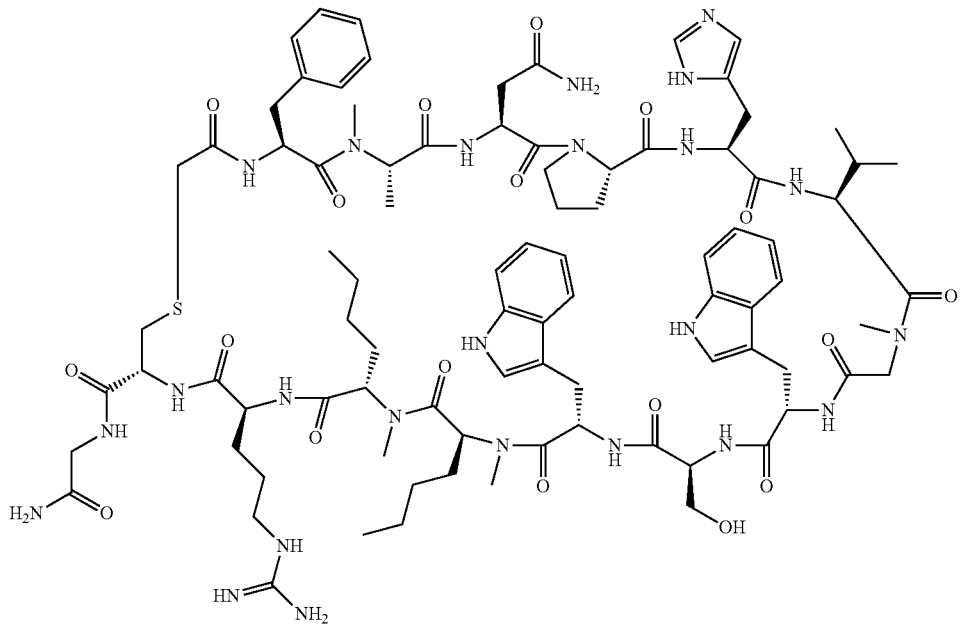

Example 6007

Example 6007 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 98%.

Analysis condition A: Retention time=1.72 min; ESI-MS (+) m/z 919.2 (M+2H)

Analysis condition B: Retention time=2.76 min; ESI-MS (+) m/z 919.4 (M+2H)

Preparation of Example 6008

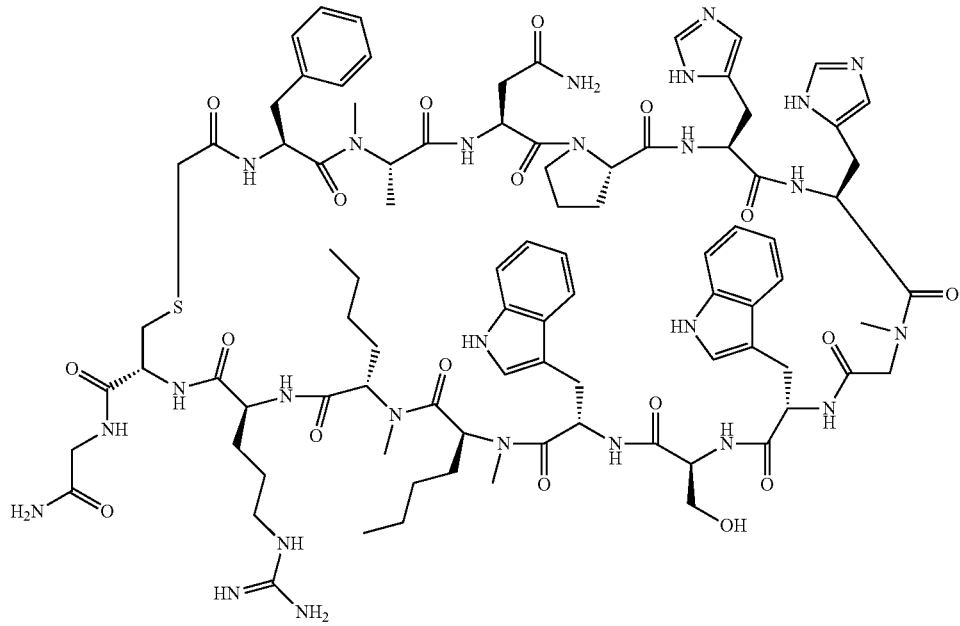

Example 6008

Example 6008 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 100%.

Analysis condition A: Retention time=1.93 min; ESI-MS (+) m/z 938.5 (M+2H)

Analysis condition B: Retention time=2.99 min; ESI-MS (+) m/z 938.6 (M+2H)

Preparation of Example 6009

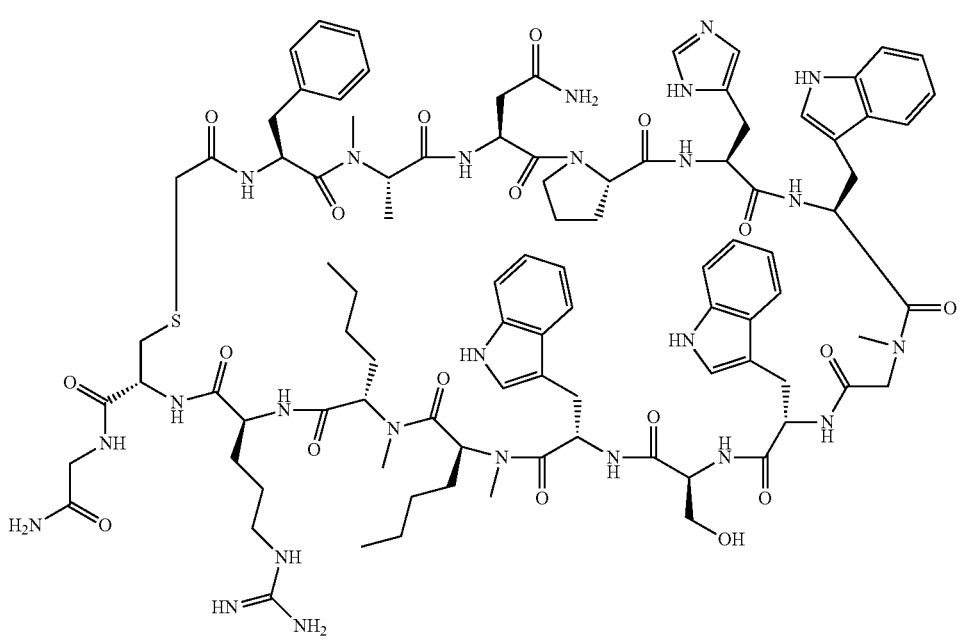

Example 6009

Example 6009 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 17.0 mg, and its estimated purity by LCMS analysis was 100%.

Analysis condition A: Retention time=1.87 min; ESI-MS (+) m/z 963.2 (M+2H)

Analysis condition B: Retention time=2.97 min; ESI-MS (+) m/z 963.0 (M+2H)

Preparation of Example 6010

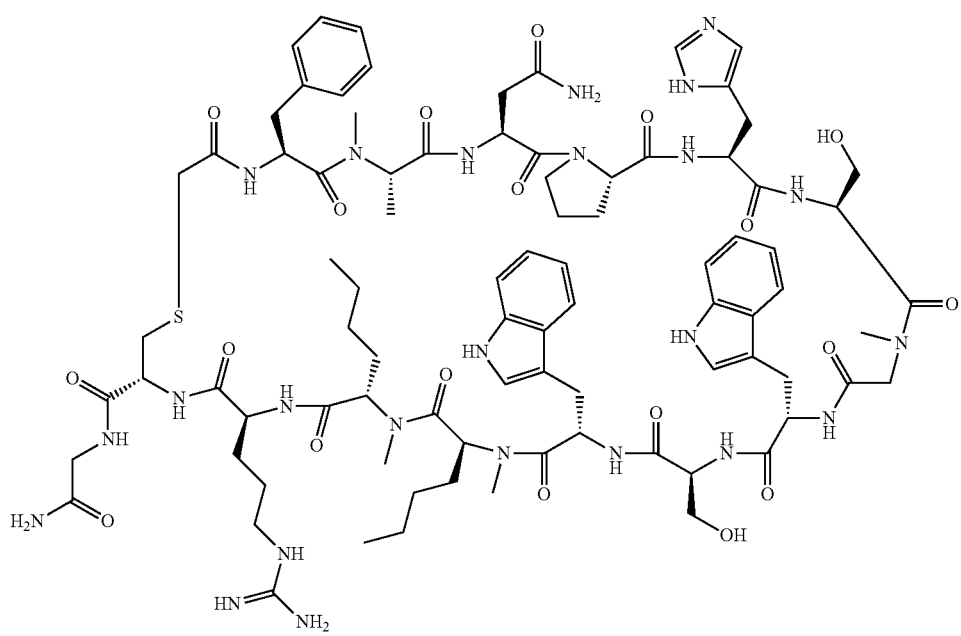

Example 6010

Example 6010 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 19.0 mg, and its estimated purity by LCMS analysis was 98%.

Analysis condition A: Retention time=1.66 min; ESI-MS (+) m/z 913.5 (M+2H)

Analysis condition B: Retention time=2.83 min; ESI-MS (+) m/z 913.4 (M+2H)

Preparation of Example 6011

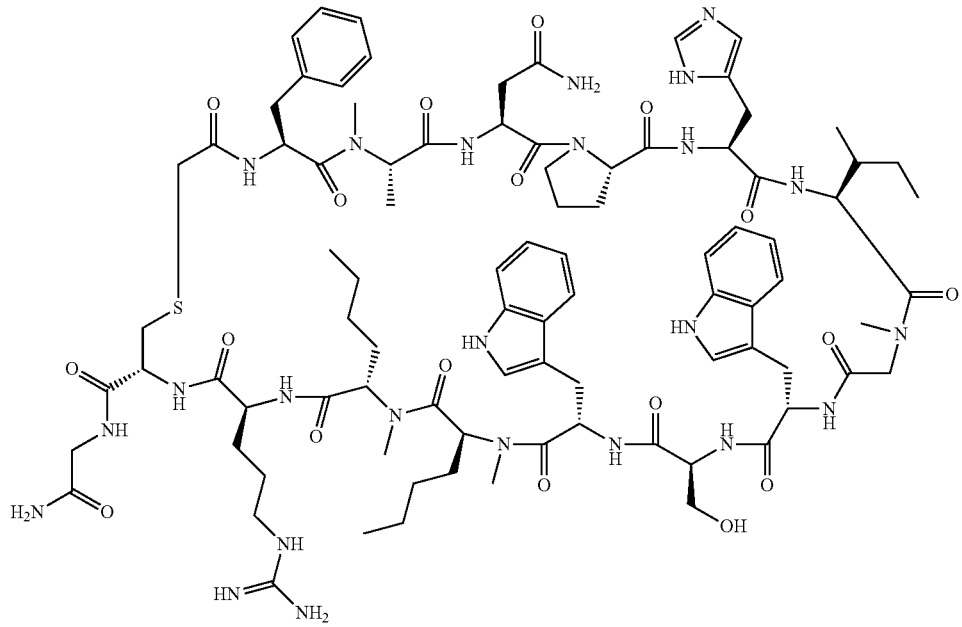

Example 6011

Example 6011 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.70 min; ESI-MS (+) m/z 926.4 (M+2H)

Analysis condition B: Retention time=2.87 min; ESI-MS (+) m/z 926.5 (M+2H)

Preparation of Example 6012

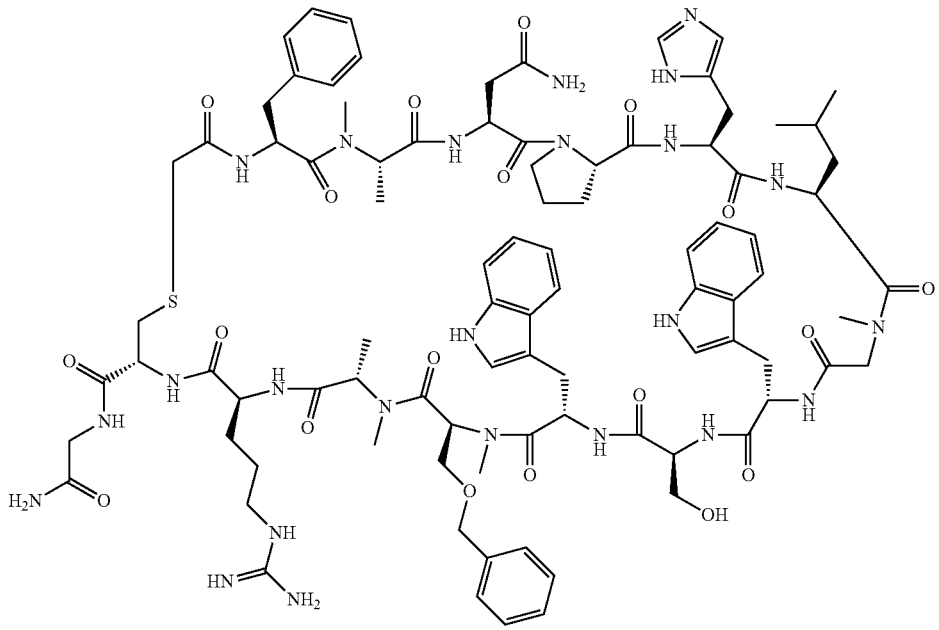

Example 6012

Example 6012 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 99%.

Analysis condition A: Retention time=1.71 min; ESI-MS (+) m/z 937.6 (M+2H)

Analysis condition B: Retention time=2.90 min; ESI-MS (+) m/z 937.4 (M+2H)

Preparation of Example 6013

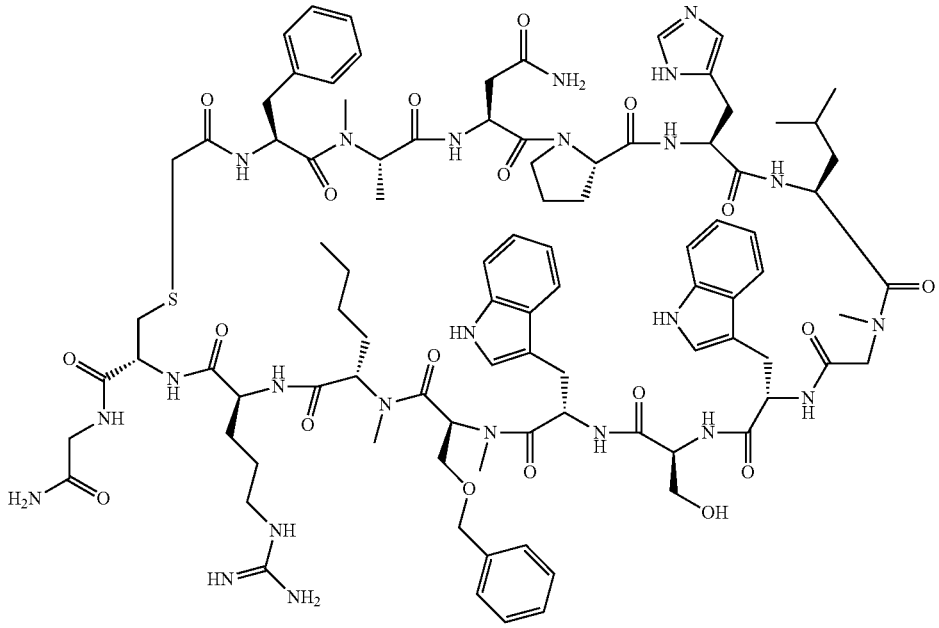

Example 6013

Example 6013 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 100%.

Analysis condition A: Retention time=1.96 min; ESI-MS (+) m/z 258.6 (M+2H)

Analysis condition B: Retention time=3.08 min; ESI-MS (−) m/z 956.5 (M−2H)

Preparation of Example 6014

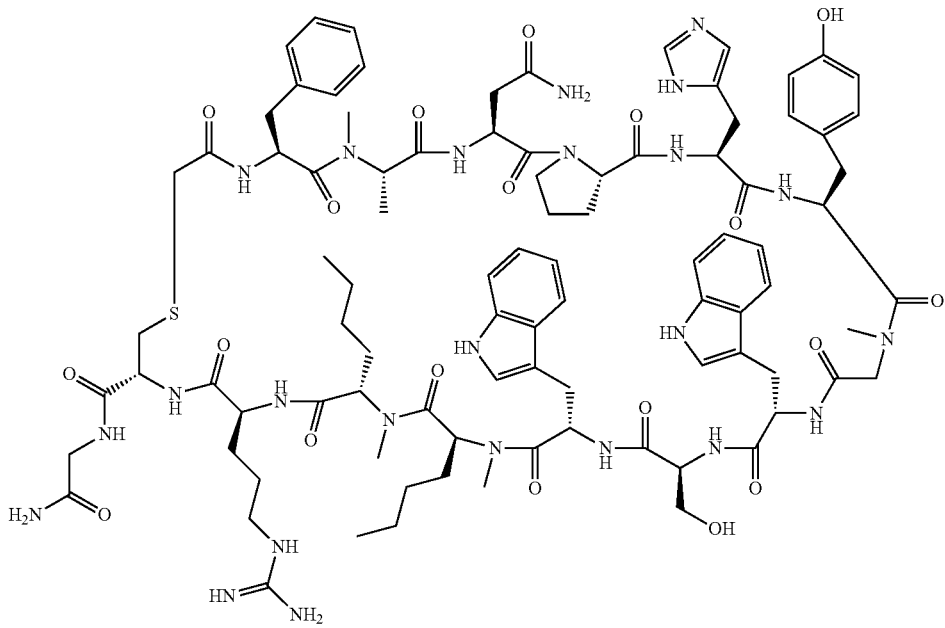

Example 6014

Example 6014 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 20 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 100%.

Analysis condition A: Retention time=1.83 min; ESI-MS (+) m/z 951.5 (M+2H)

Analysis condition B: Retention time=2.85 min; ESI-MS (+) m/z 951.4 (M+2H)

Preparation of Example 6015

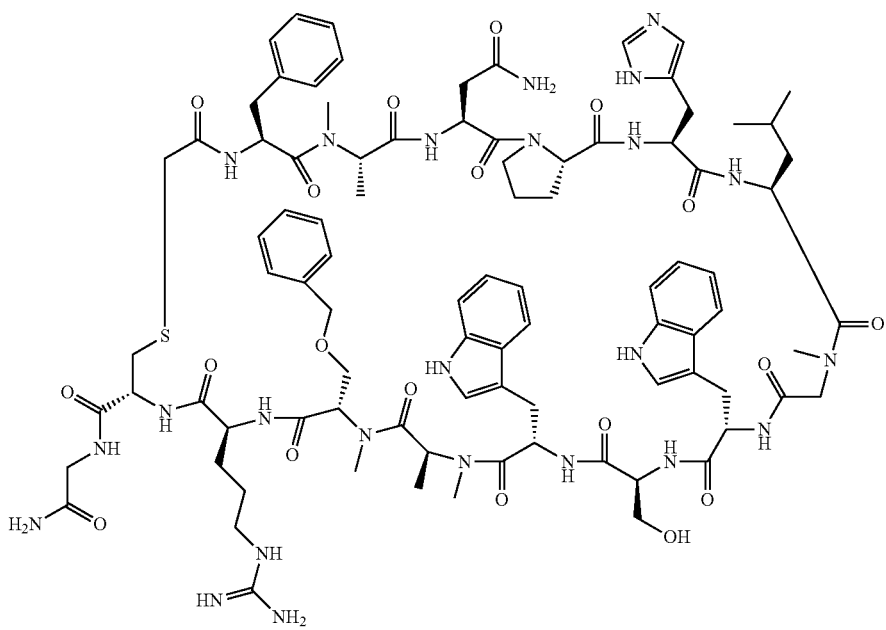

Example 6015

Example 6015 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 98%.

Analysis condition A: Retention time=1.73 min; ESI-MS (+) m/z 937.5 (M+2H)

Analysis condition B: Retention time=2.75 min; ESI-MS (+) m/z 937.5 (M+2H)

Preparation of Example 6016

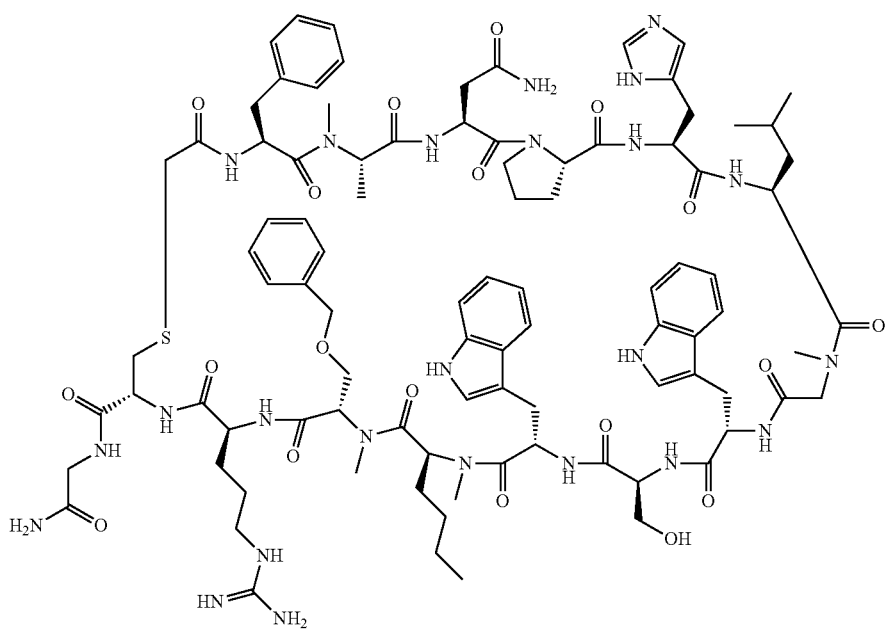

Example 6016

Example 6016 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 19.4 mg, and its estimated purity by LCMS analysis was 98%.

Analysis condition A: Retention time=1.97 min; ESI-MS (+) m/z 958.5 (M+2H)

Analysis condition B: Retention time=3.03 min; ESI-MS (+) m/z 958.4 (M+2H)

Preparation of Example 6017

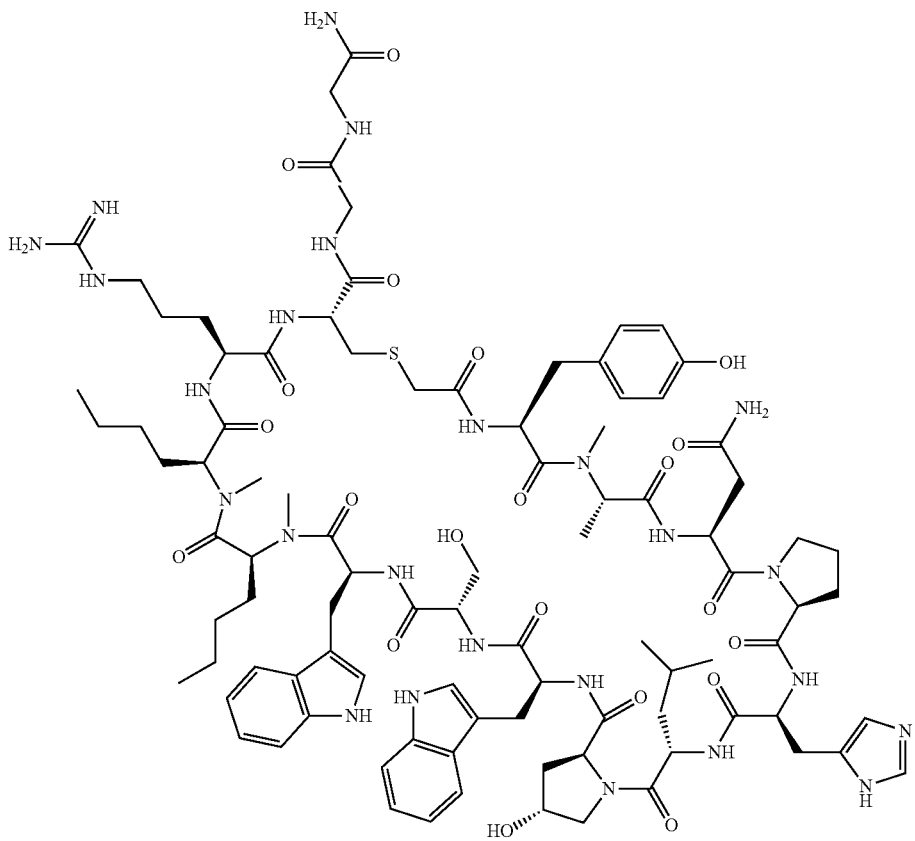

Example 6017

Example 6017 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 100%.

Analysis condition A: Retention time=1.52 min; ESI-MS (+) m/z 984.4 (M+2H)

Analysis condition B: Retention time=2.56 min; ESI-MS (−) m/z 983.1 (M−2H)

Preparation of Example 6018

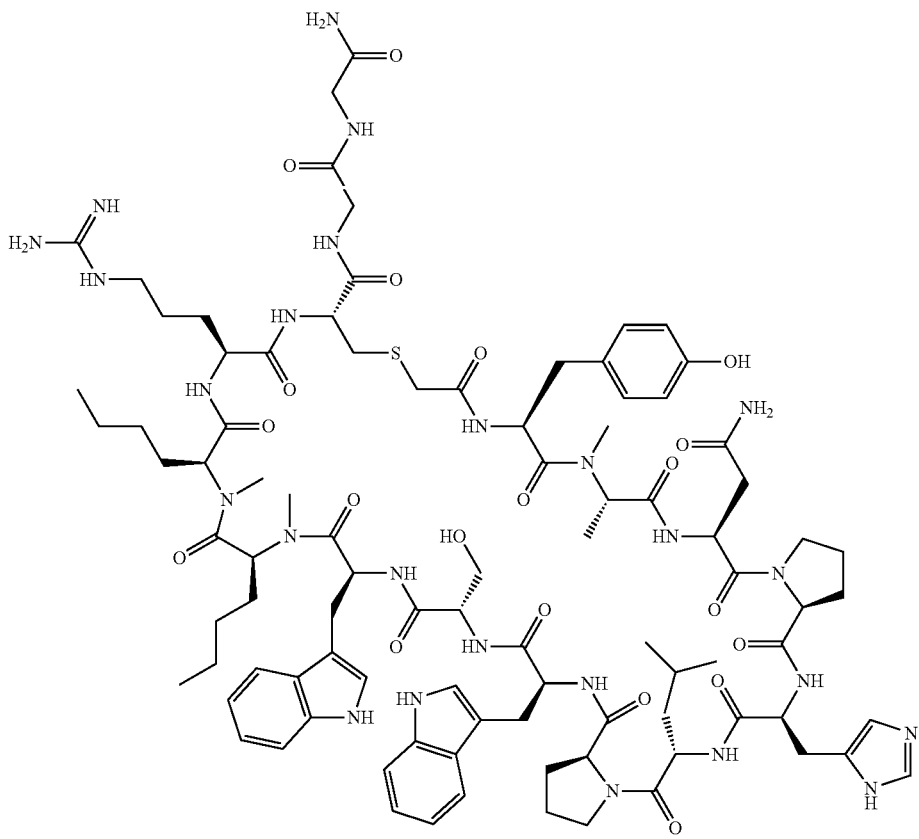

Example 6018

Example 6018 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 99%.

Analysis condition A: Retention time=1.64 min; ESI-MS (+) m/z 976.0 (M+2H)

Analysis condition B: Retention time=2.62 min; ESI-MS (+) m/z 976.7 (M+2H)

Preparation of Example 6019

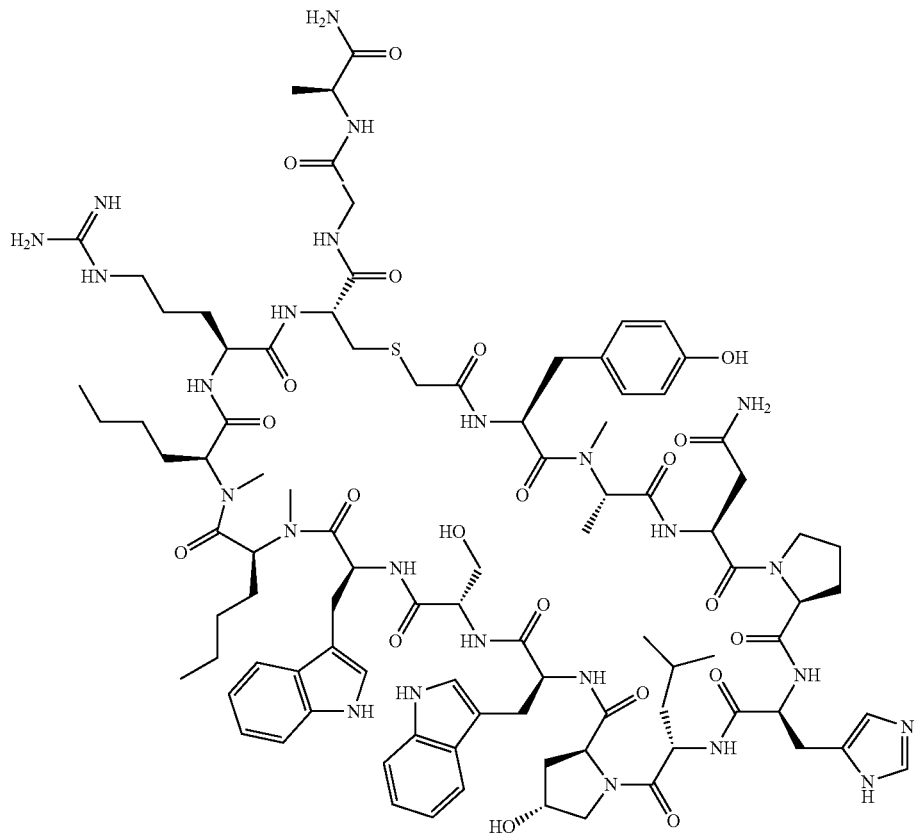

Example 6019

Example 6019 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 20 minutes, then a 5-minute hold at 100% B; Flow: 20 mL/min. Fractions containing the desired product were combined and dried via centrifugal evaporation. The yield of the product was 24.4 mg, and its estimated purity by LCMS analysis was 100%.

Analysis condition A: Retention time=1.62 min; ESI-MS (+) m/z 990.9 (M+2H)

Analysis condition B: Retention time=2.58 min; ESI-MS (+) m/z 991.2 (M+2H)

Preparation of Example 6020

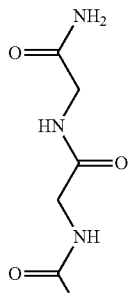

Example 6020

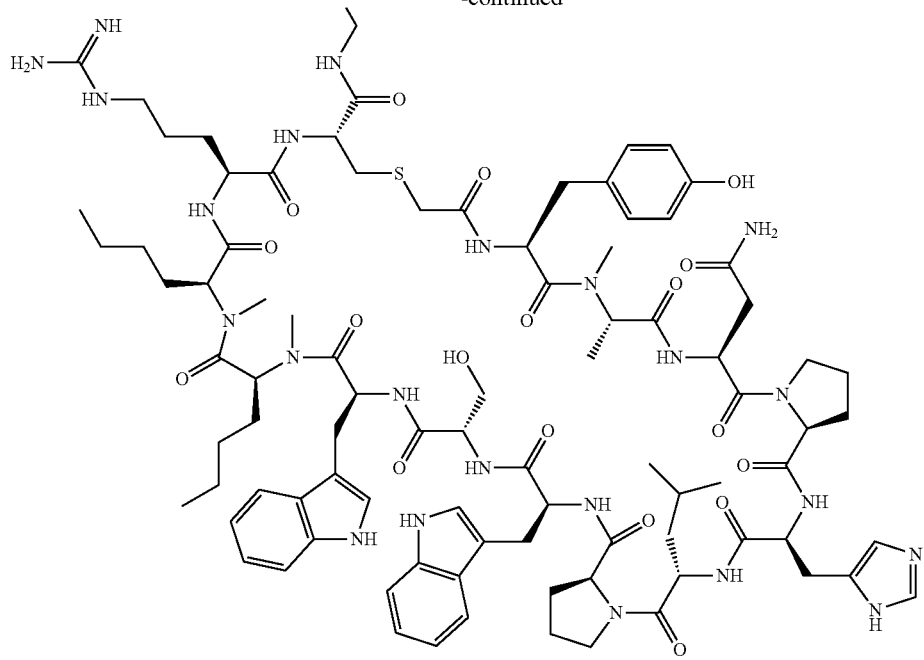

Example 6020 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 32.3 mg, and its estimated purity by LCMS analysis was 99%.

Analysis condition A: Retention time=1.62 min; ESI-MS (+) m/z 1004.6 (M+2H)

Analysis condition B: Retention time=2.59 min; ESI-MS (+) m/z 1004.6 (M+2H)

Preparation of Example 6021

Example 6021

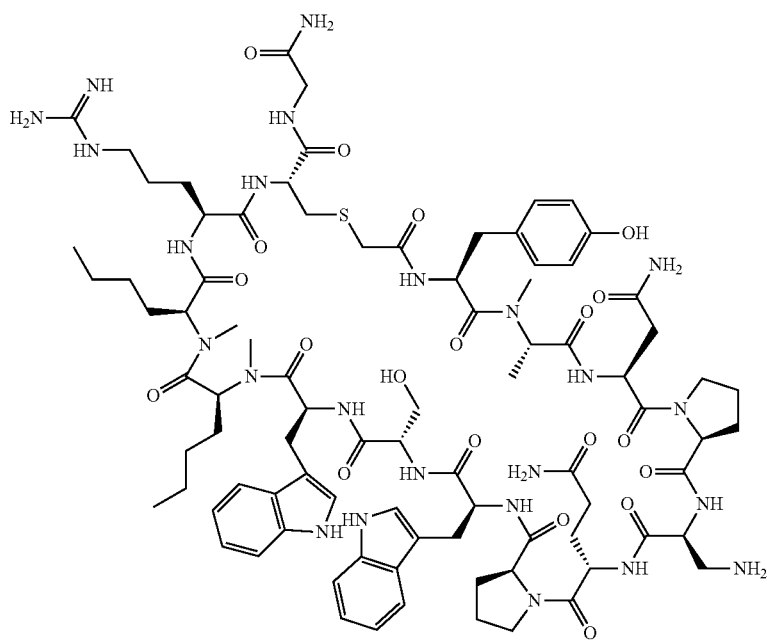

Example 6021 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-50% B over 15 minutes, then a 5-minute hold at 100% B; Flow: 20 mL/min. Fractions containing the desired product were combined and dried via centrifugal evaporation. The yield of the product was 28.2 mg, and its estimated purity by LCMS analysis was 100%.

Analysis condition A: Retention time=1.46 min; ESI-MS (+) m/z 929.8 (M+2H)

Analysis condition B: Retention time=2.58 min; ESI-MS (+) m/z 930.4 (M+2H)

Preparation of Example 6022

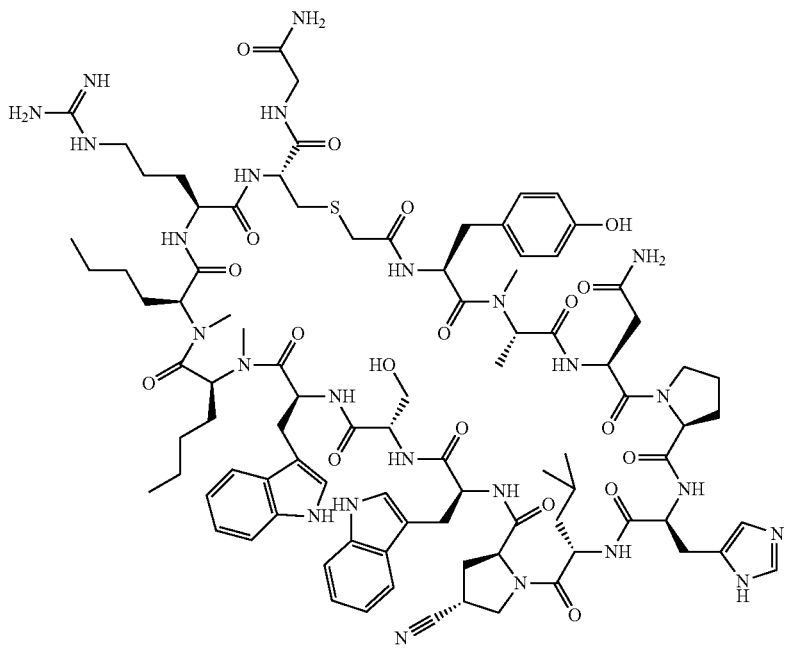

Example 6022

Example 6022 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 20 minutes, then a 5-minute hold at 100% B; Flow: 20 mL/min. Fractions containing the desired product were combined and dried via centrifugal evaporation. The yield of the product was 19.5 mg, and its estimated purity by LCMS analysis was 100%.

Analysis condition A: Retention time=1.52 min; ESI-MS (+) m/z 960.9 (M+2H)

Analysis condition B: Retention time=2.59 min; ESI-MS (+) m/z 960.9 (M+2H)

Preparation of Example 6023

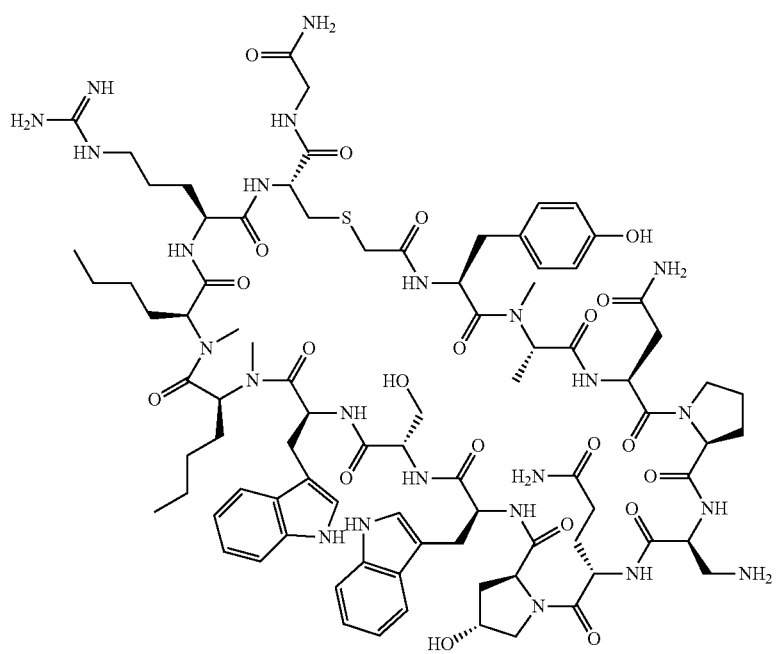

Example 6023

Example 6023 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-60% B over 15 minutes, then a 5-minute hold at 100% B; Flow: 20 mL/min. Fractions containing the desired product were combined and dried via centrifugal evaporation. The yield of the product was 20.2 mg, and its estimated purity by LCMS analysis was 96%.

Analysis condition B: Retention time=2.61 min; ESI-MS (+) m/z 946.8 (M+2H)

Preparation of Example 6024

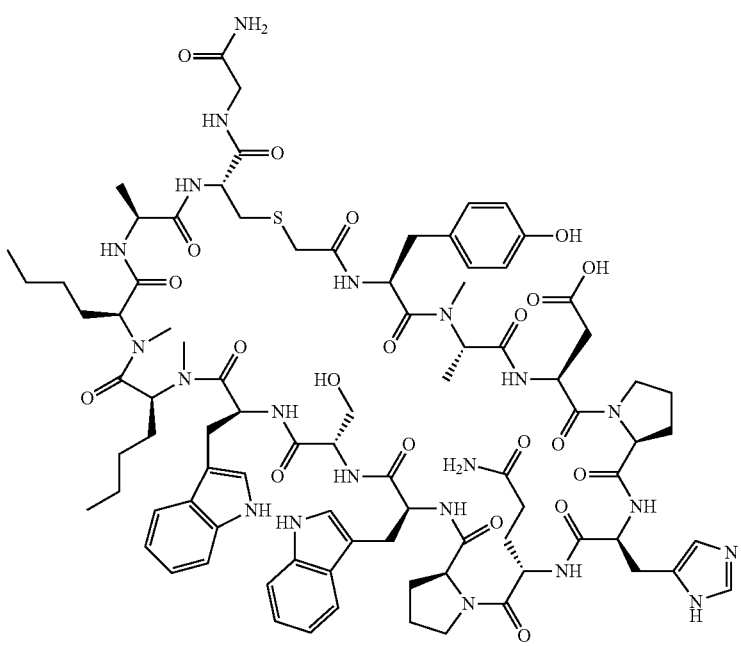

Example 6024

Example 6024 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 100%.

Analysis condition A: Retention time=1.51 min; ESI-MS (+) m/z 913.8 (M+2H)

Analysis condition B: Retention time=2.61 min; ESI-MS (−) m/z 911.9 (M−2H)

Preparation of Example 6025

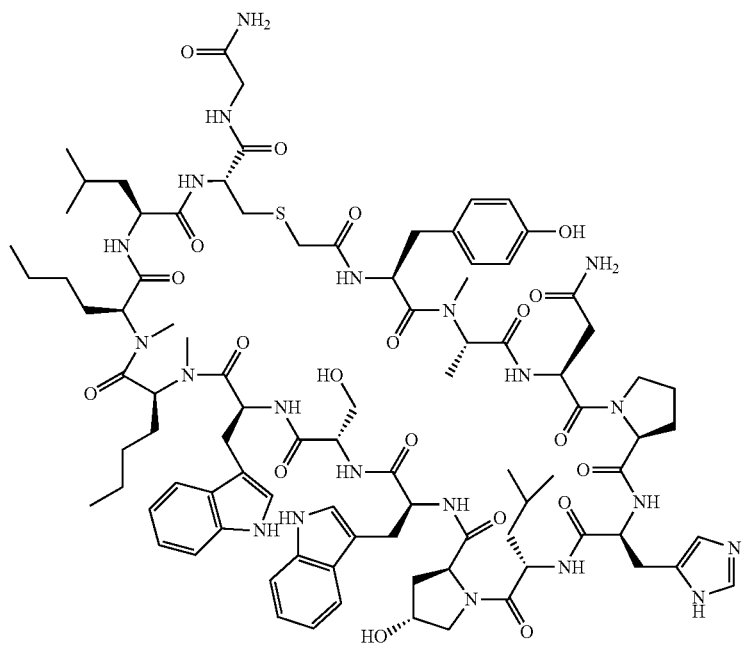

Example 6025

Example 6025 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 16.7 mg, and its estimated purity by LCMS analysis was 94%.

Analysis condition A: Retention time=1.65 min; ESI-MS (+) m/z 934.7 (M+2H)

Analysis condition B: Retention time=2.79 min; ESI-MS (+) m/z 934.4 (M+2H)

Preparation of Example 6026

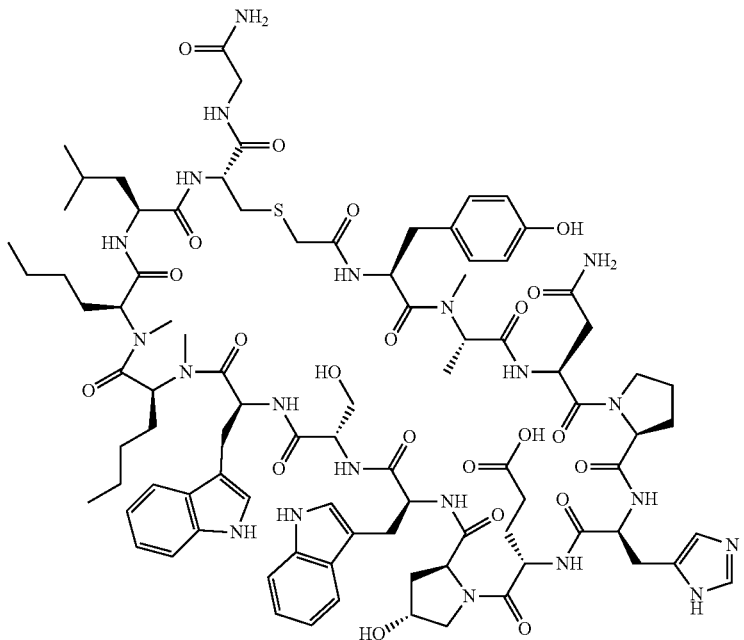

Example 6026

Example 6026 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 99%.

Analysis condition A: Retention time=1.48 min; ESI-MS (−) m/z 940.9 (M−2H)

Analysis condition B: Retention time=2.62 min; ESI-MS (−) m/z 940.7 (M−2H)

Preparation of Example 6027

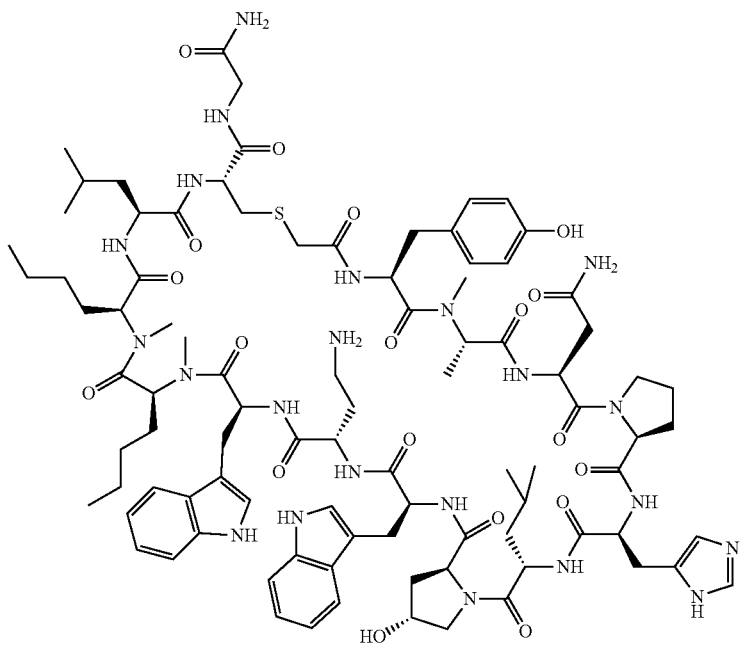

Example 6027

Example 6027 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 23.2 mg, and its estimated purity by LCMS analysis was 100%.

Analysis condition A: Retention time=1.59 min; ESI-MS (+) m/z 941.3 (M+2H)

Analysis condition B: Retention time=2.72 min; ESI-MS (+) m/z 941.3 (M+2H)

Preparation of Example 6028

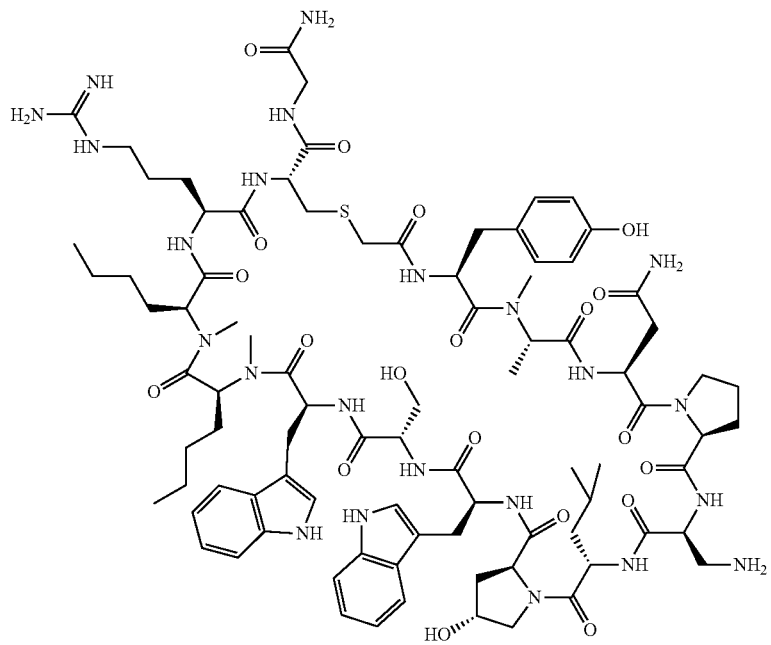

Example 6028

Example 6028 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 99%.

Analysis condition A: Retention time=1.53 min; ESI-MS (+) m/z 939.6 (M+2H)

Analysis condition B: Retention time=2.73 min; ESI-MS (−) m/z 937.8 (M−2H)

Preparation of Example 6029

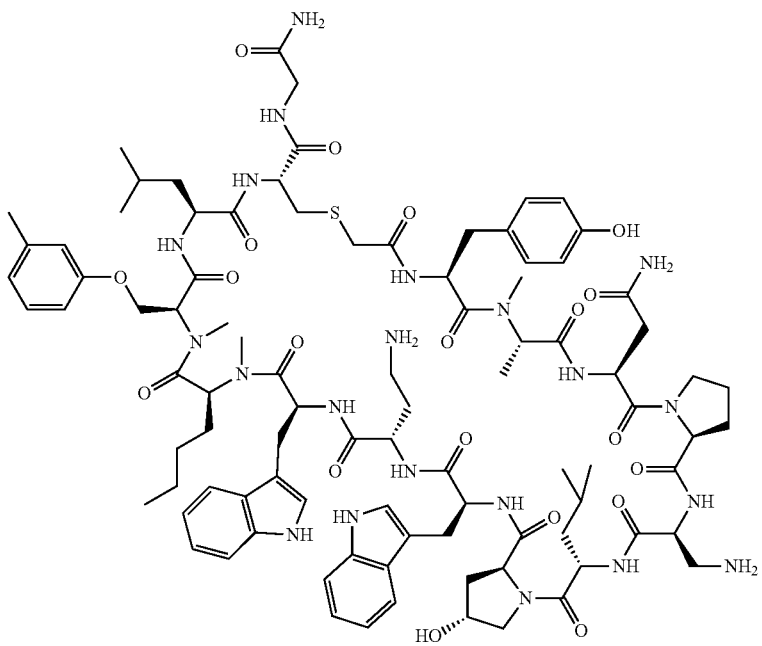

Example 6029

Example 6029 was prepared following "General Synthetic Sequence A". Amino acid (5)-2-(((((9H-fluoren-9-yl)methoxy)carbonyl)(methyl)amino)-3-(m-tolyloxy)propanoic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 16.9 mg, and its estimated purity by LCMS analysis was 96%.

Analysis condition A: Retention time=1.72 min; ESI-MS (+) m/z 947.8 (M+2H)

Analysis condition B: Retention time=2.82 min; ESI-MS (+) m/z 947.8 (M+2H)

Preparation of Example 6030

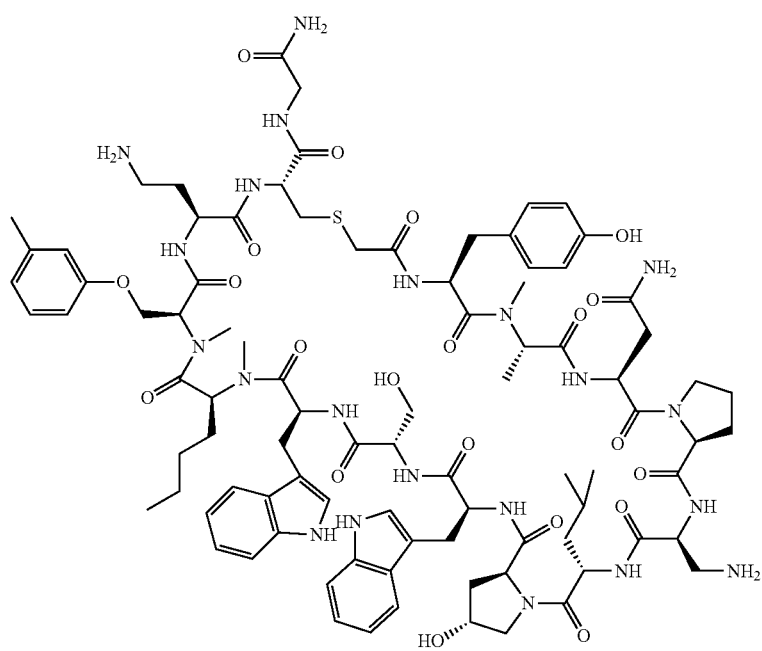

Example 6030

Example 6030 was prepared following "General Synthetic Sequence A". Amino acid (S)-2-((((9H-fluoren-9-yl)methoxy)carbonyl)(methyl)amino)-3-(m-tolyloxy)propanoic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 25.5 mg, and its estimated purity by LCMS analysis was 98%.

Analysis condition A: Retention time=1.57 min; ESI-MS (+) m/z 942.7 (M+2H)

Analysis condition B: Retention time=2.68 min; ESI-MS (+) m/z 942.7 (M+2H)

Preparation of Example 6031

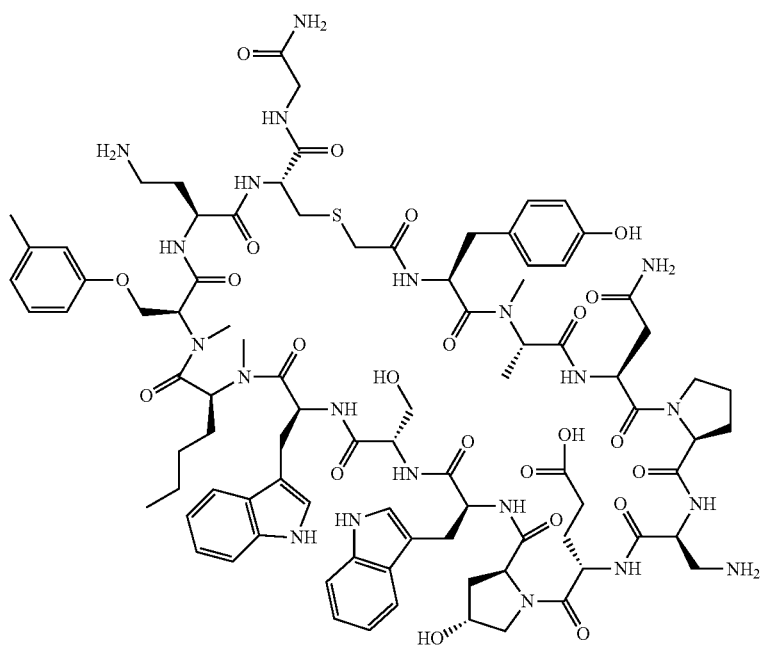

Example 6031

Example 6031 was prepared following "General Synthetic Sequence A". Amino acid (S)-2-((((9H-fluoren-9-yl)methoxy)carbonyl)(methyl)amino)-3-(m-tolyloxy)propanoic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 98%.

Analysis condition A: Retention time=1.59 min; ESI-MS (+) m/z 942.6 (M+2H)

Analysis condition B: Retention time=2.70 min; ESI-MS (+) m/z 943.2 (M+2H)

Preparation of Example 6032

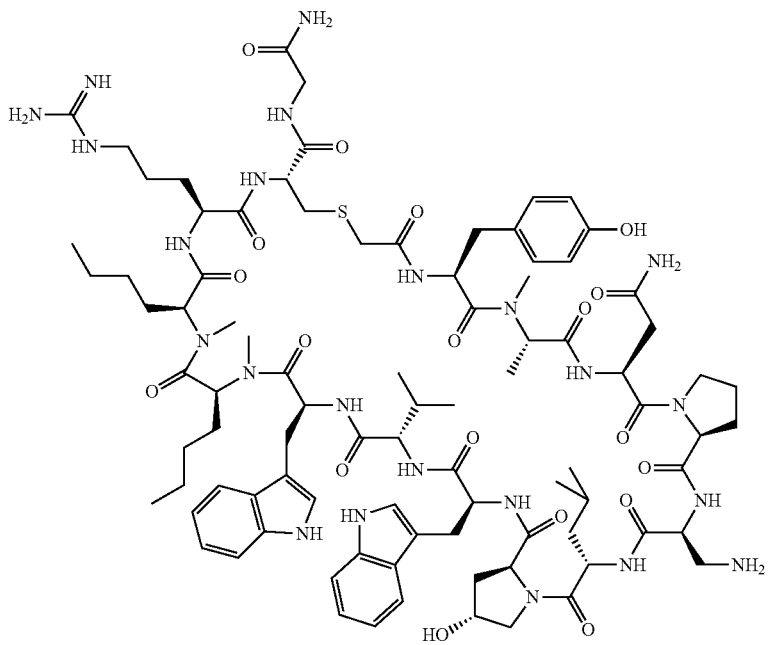

Example 6032

Example 6032 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 96%.

Analysis condition A: Retention time=1.46 min; ESI-MS (+) m/z 937.0 (M+2H)

Analysis condition B: Retention time=2.57 min; ESI-MS (+) m/z 936.9 (M+2H)

Preparation of Example 6033

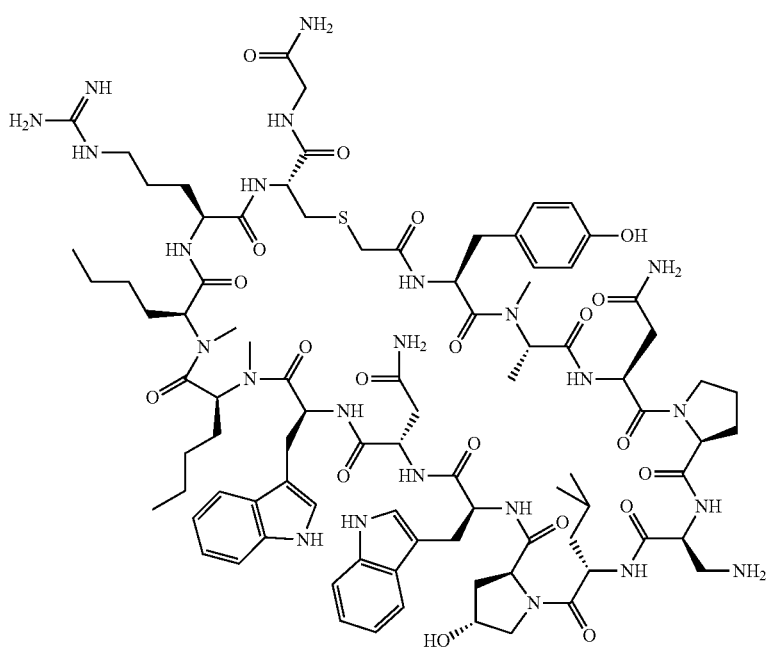

Example 6033

Example 6033 was prepared following "General Synthetic Sequence A". The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 97%.

Analysis condition A: Retention time=1.38 min; ESI-MS (+) m/z 944.1 (M+2H)

Analysis condition B: Retention time=2.53 min; ESI-MS (+) m/z 944.4 (M+2H)

Preparation of Example 6034

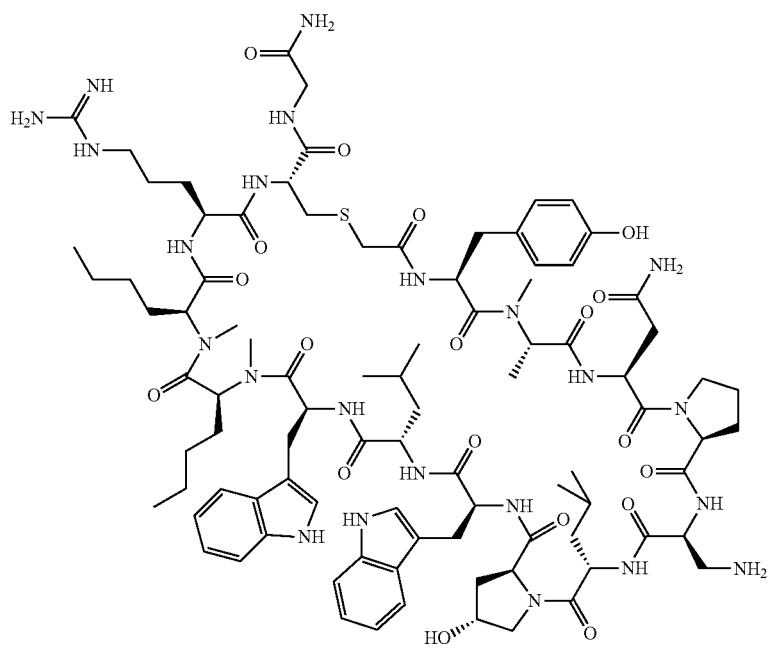

Example 6034

Example 6034 was prepared following "General Synthetic Sequence A". The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 30-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 97%.

Analysis condition A: Retention time=1.50 min; ESI-MS (+) m/z 943.5 (M+2H)

Analysis condition B: Retention time=2.63 min; ESI-MS (−) m/z 941.8 (M−2H)

Preparation of Example 6035

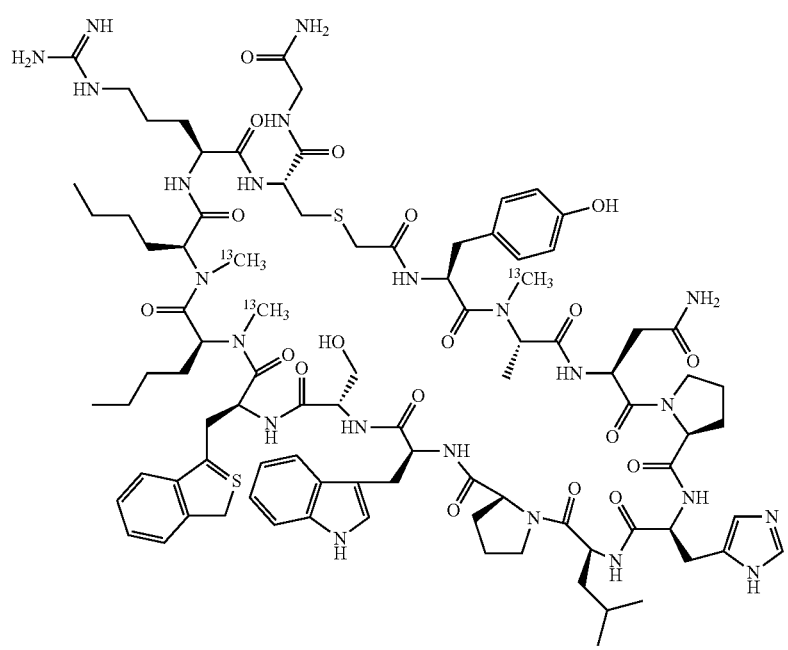

Example 6035

Example 6035 was prepared following "General Synthetic Sequence A". Amino acids (S)-2-((((9H-fluoren-9-yl)methoxy)carbonyl)([$^{13}$C]methyl)amino)propanoic acid and of (S)-2-((((9H-fluoren-9-yl)methoxy)carbonyl)([$^{13}$C]methyl)amino)hexanoic acid were used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 26.1 mg, and its estimated purity by LCMS analysis was 96%.

Analysis condition A: Retention time=1.65 min; ESI-MS (+) m/z 958.2 (M+2H)

Analysis condition B: Retention time=2.83 min; ESI-MS (−) m/z 955.7 (M−2H)

Preparation of Example 6036

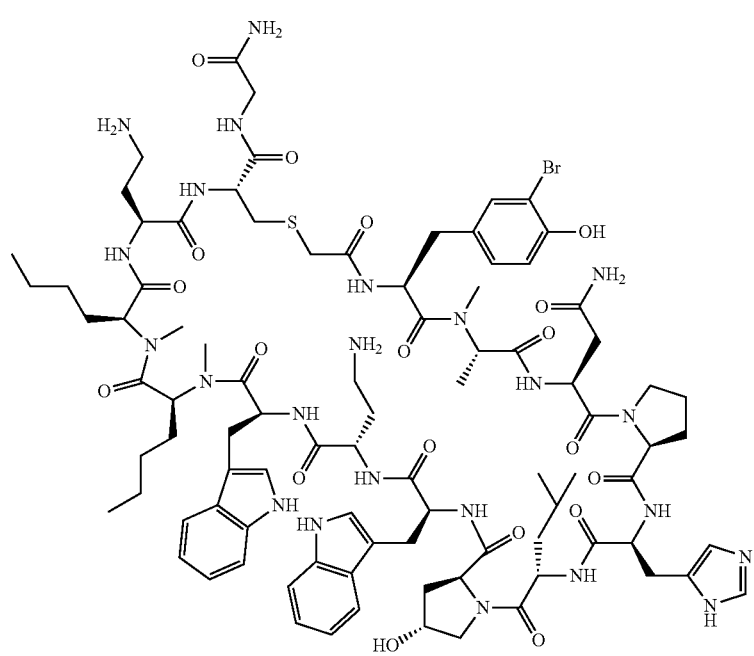

Example 6036

Example 6036 was prepared following "General Synthetic Sequence A". Amino acid (S)-2-((((9H-fluoren-9-yl)methoxy)carbonyl)amino)-3-(4-((((9H-fluoren-9-yl)methoxy)carbonyl)oxy)-3-bromophenyl)propanoic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 95%.

Analysis condition A: Retention time=1.57 min; ESI-MS (+) m/z 974.4 (M+2H)

Analysis condition B: Retention time=2.64 min; ESI-MS (+) m/z 973.6 (M+2H)

Preparation of Example 6037

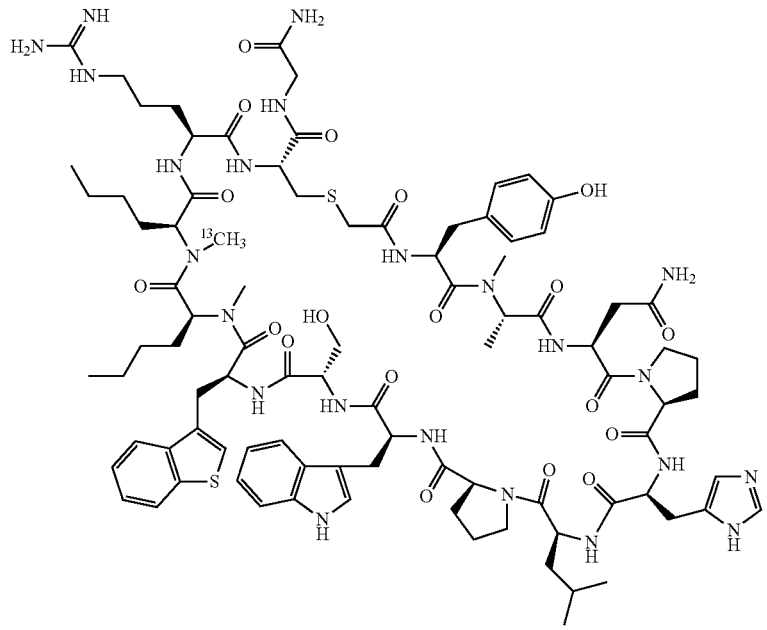

Example 6037

Example 6037 was prepared following "General Synthetic Sequence A". Amino acid (S)-2-((((9H-fluoren-9-yl)methoxy)carbonyl)([$^{13}$C]methyl)amino)hexanoic acid was used.

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 26.5 mg, and its estimated purity by LCMS analysis was 99%.

Analysis condition A: Retention time=1.68 min; ESI-MS (+) m/z 957.3 (M+2H)

Analysis condition B: Retention time=2.83 min; ESI-MS (+) m/z 957.4 (M+2H)

Preparation of Example 6038

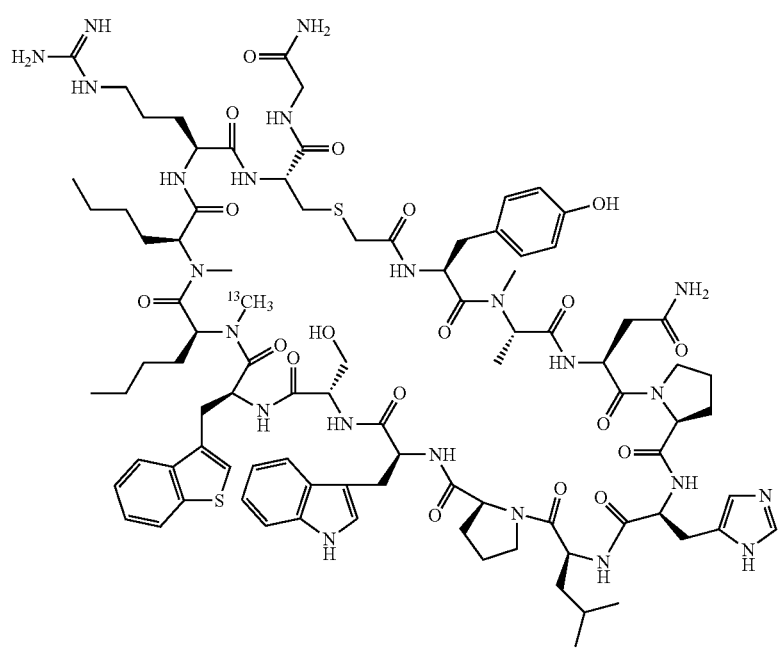

Example 6038

Example 6038 was prepared following "General Synthetic Sequence A". Amino acid (S)-2-((((9H-fluoren-9-yl)methoxy)carbonyl)([$^{13}$C]methyl)amino)hexanoic acid was used.

The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 23.0 mg, and its estimated purity by LCMS analysis was 99%.

Analysis condition A: Retention time=1.65 min; ESI-MS (+) m/z 957.3 (M+2H)

Analysis condition B: Retention time=2.83 min; ESI-MS (+) m/z 957.4 (M+2H)

Preparation of Example 6039

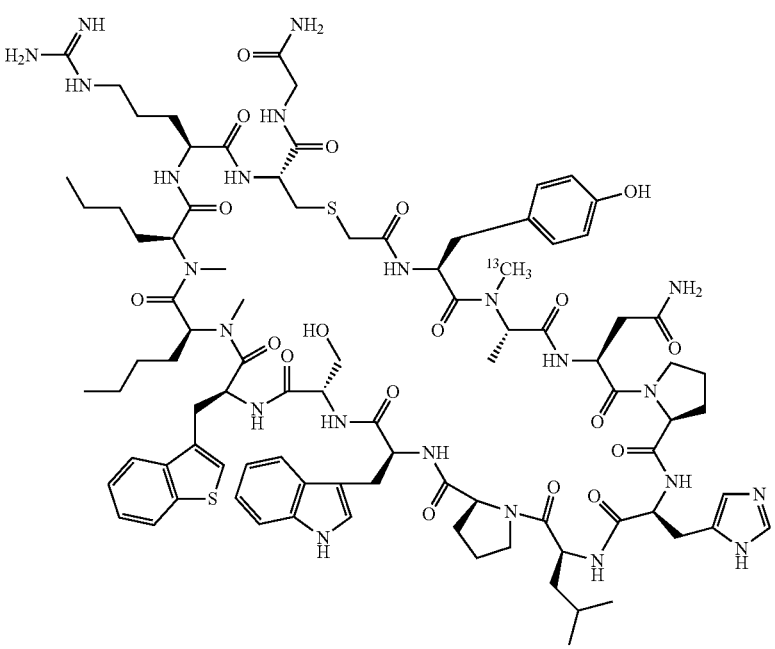

Example 6039

Example 6039 was prepared following "General Synthetic Sequence A". Amino acid (5)-2-((((9H-fluoren-9-yl)methoxy)carbonyl)([$^{13}$C]methyl)amino)propanoic acid was used.

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 18.8 mg, and its estimated purity by LCMS analysis was 95%.

Analysis condition A: Retention time=1.66 min; ESI-MS (+) m/z 957.3 (M+2H)

Analysis condition B: Retention time=2.83 min; ESI-MS (+) m/z 957.3 (M+2H)

Preparation of Example 6040

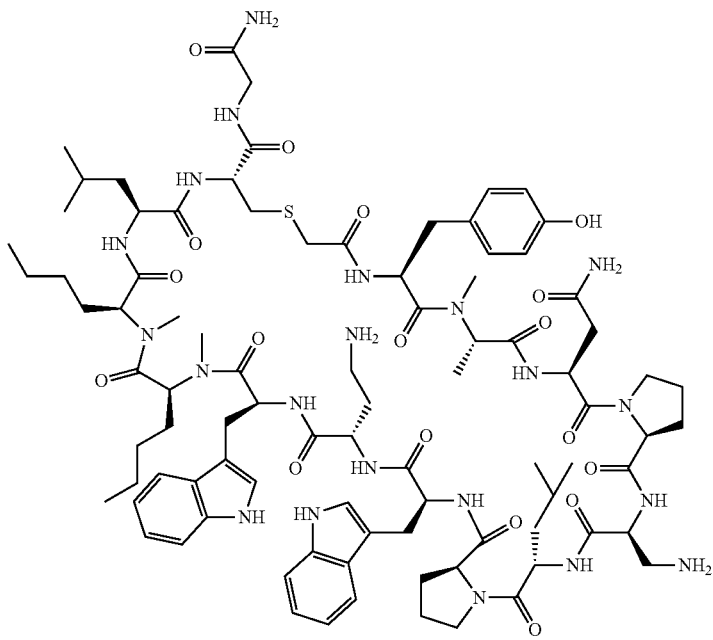

Example 6040

Example 6040 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 25.8 mg, and its estimated purity by LCMS analysis was 100%.

Analysis condition A: Retention time=1.64 min

Analysis condition B: Retention time=2.75 min

Preparation of Example 6041

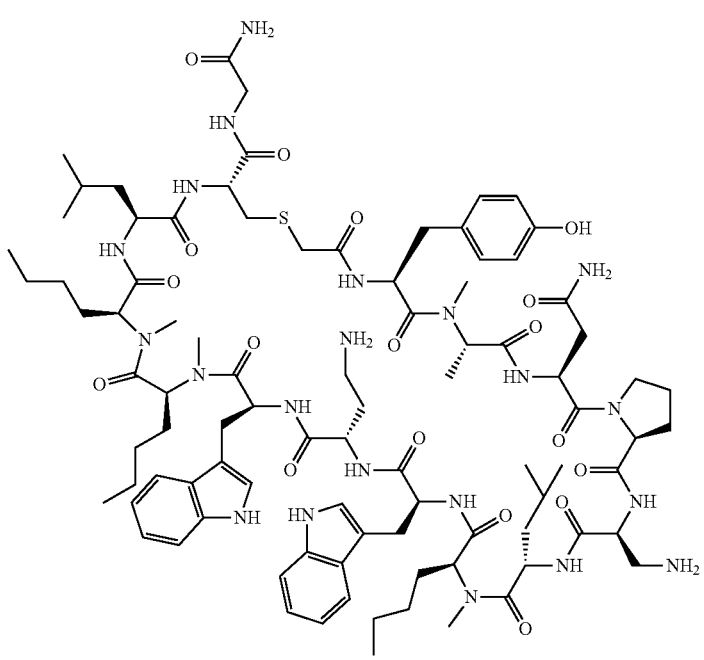

Example 6041

Example 6041 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 22.5 mg, and its estimated purity by LCMS analysis was 95%.

Analysis condition A: Retention time=1.80 min; ESI-MS (+) m/z 922.8 (M+2H)

Analysis condition B: Retention time=2.96 min; ESI-MS (+) m/z 922.9 (M+2H)

Preparation of Example 6042

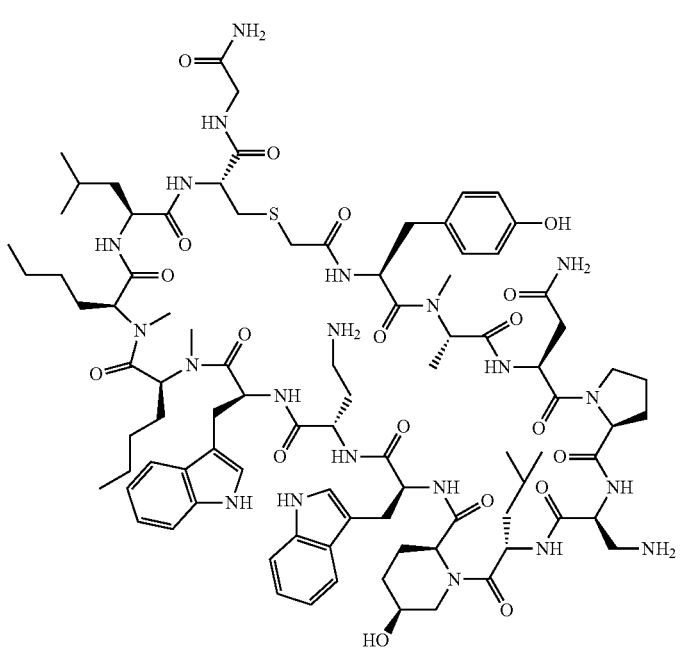

Example 6042

Example 6042 was prepared following "General Synthetic Sequence A". Amino acid (2S,5S)-1-(((9H-fluoren-9-yl)methoxy)carbonyl)-5-hydroxypiperidine-2-carboxylic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 17.3 mg, and its estimated purity by LCMS analysis was 100%.

Analysis condition A: Retention time=1.60 min; ESI-MS (+) m/z 922.8 (M+2H)

Analysis condition B: Retention time=2.78 min; ESI-MS (+) m/z 922.8 (M+2H)

Preparation of Example 6043

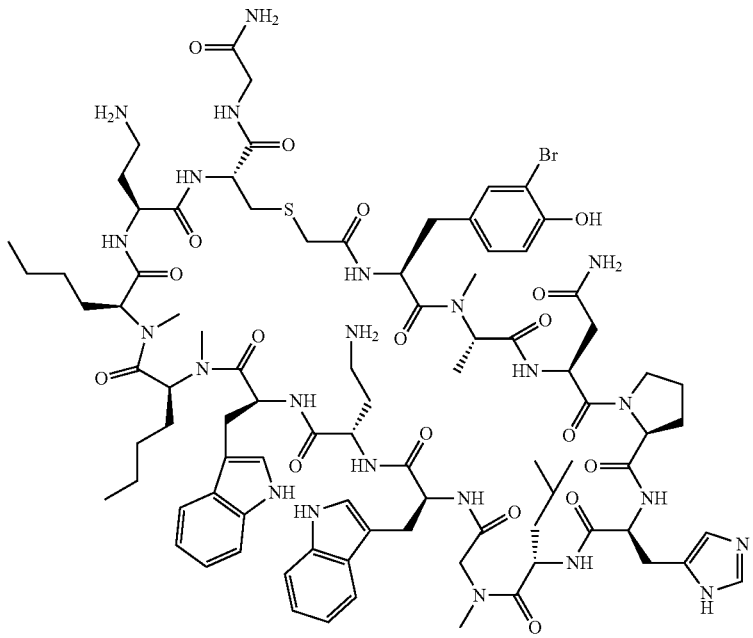

Example 6043

Example 6043 was prepared following "General Synthetic Sequence A". Amino acid (S)-2-(((((9H-fluoren-9-yl)methoxy)carbonyl)amino)-3-(4-((((9H-fluoren-9-yl)methoxy)carbonyl)oxy)-3-bromophenyl)propanoic acid was used. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 97%.

Analysis condition A: Retention time=1.40 min; ESI-MS (+) m/z 953.0 (M+2H)

Analysis condition B: Retention time=2.71 min; ESI-MS (−) m/z 950.6 (M−2H)

Preparation of Example 6044

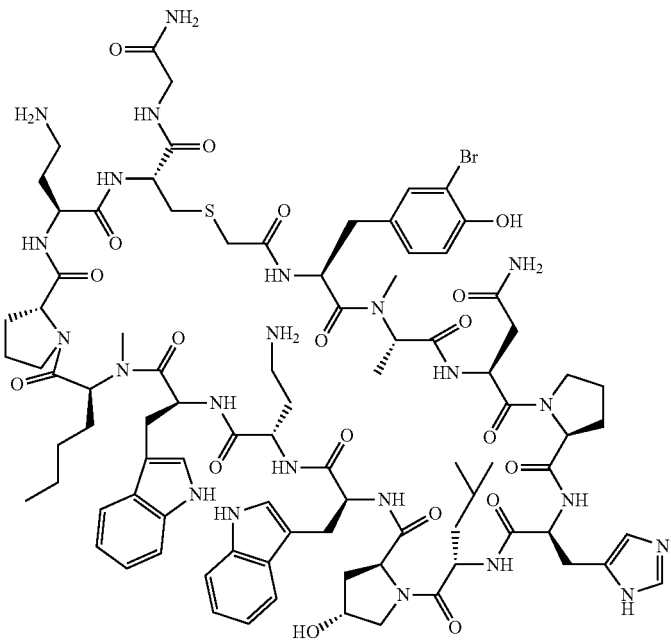

Example 6044

Example 6044 was prepared following "General Synthetic Sequence A". Amino acid (S)-2-((((9H-fluoren-9-yl)methoxy)carbonyl)amino)-3-(4-((((9H-fluoren-9-yl)methoxy)carbonyl)oxy)-3-bromophenyl)propanoic acid was used. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 97%.

Analysis condition A: Retention time=1.38 min; ESI-MS (+) m/z 958.5 (M+2H)

Analysis condition B: Retention time=2.50 min; ESI-MS (−) m/z 957.7 (M−2H)

Preparation of Example 6045

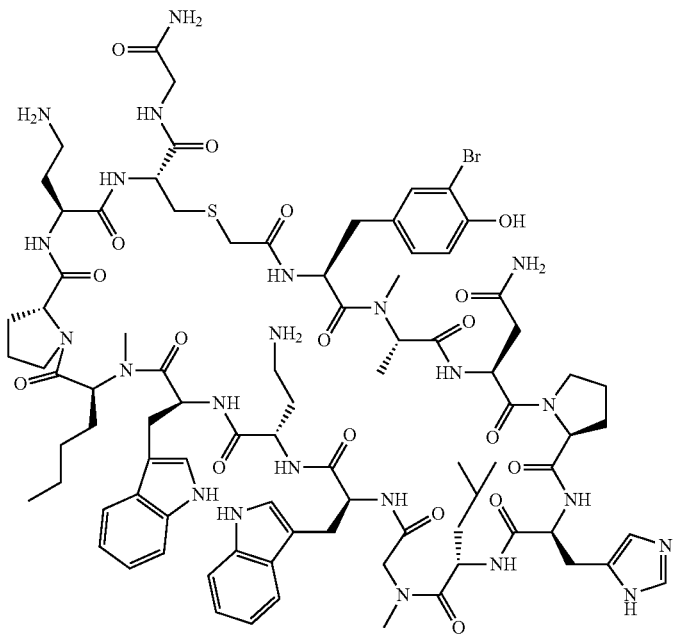

Example 6045

Example 6045 was prepared following "General Synthetic Sequence A". Amino acid (S)-2-((((9H-fluoren-9-yl)methoxy)carbonyl)amino)-3-(4-((((9H-fluoren-9-yl)methoxy)carbonyl)oxy)-3-bromophenyl)propanoic acid was used. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 0-minute hold at 100% B; Flow: 20 mL/min. Fractions containing the desired product were combined and dried via centrifugal evaporation. The yield of the product was 18.3 mg, and its estimated purity by LCMS analysis was 96%.

Analysis condition A: Retention time=1.42 min; ESI-MS (+) m/z 938.7 (M+2H)

Analysis condition B: Retention time=2.50 min; ESI-MS (−) m/z 935.5 (M−2H)

Preparation of Example 6046

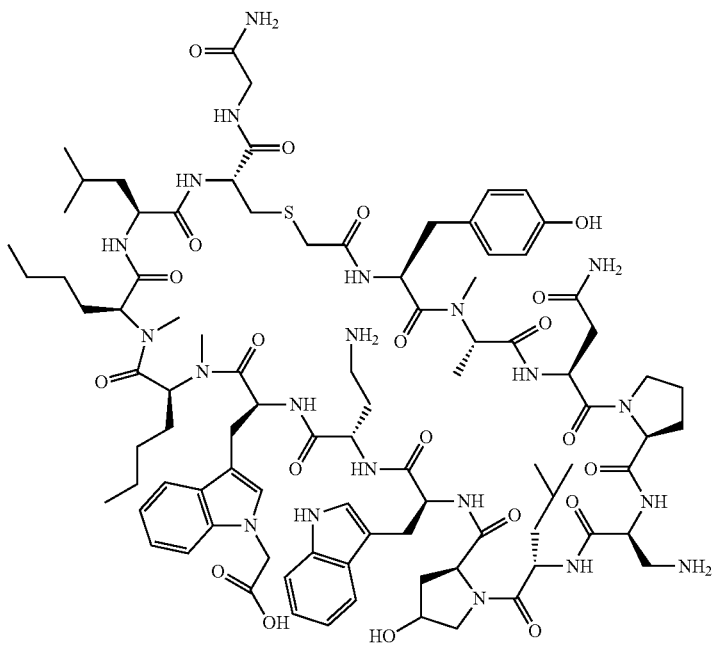

Example 6046

Example 6046 was prepared following "General Synthetic Sequence A". Amino acid (S)-2-((((9H-fluoren-9-yl)methoxy)carbonyl)amino)-3-(1-(2-(tert-butoxy)-2-oxoethyl)-1H-indol-3-yl)propanoic acid was used. The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 25.1 mg, and its estimated purity by LCMS analysis was 97%.

Analysis condition A: Retention time=1.51 min; ESI-MS (+) m/z 944.7 (M+2H)

Analysis condition B: Retention time=2.82 min; ESI-MS (+) m/z 944.3 (M+2H)

Preparation of Example 6047

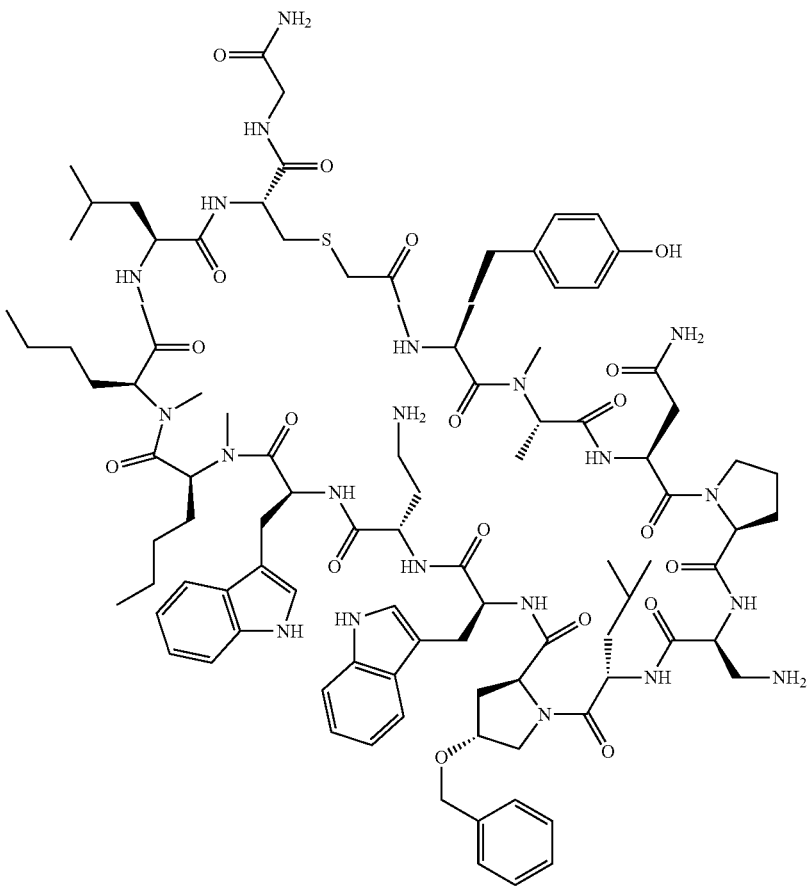

Example 6047

Example 6047 was prepared following "General Synthetic Sequence A". Amino acid (2S,4R)-1-(((9H-fluoren-9-yl)methoxy)carbonyl)-4-(benzyloxy)pyrrolidine-2-carboxylic acid was used. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 29.7 mg, and its estimated purity by LCMS analysis was 100%.

Analysis condition A: Retention time=1.80 min; ESI-MS (+) m/z 960.7 (M+2H)

Analysis condition B: Retention time=2.94 min; ESI-MS (+) m/z 960.3 (M+2H)

Preparation of Example 6048

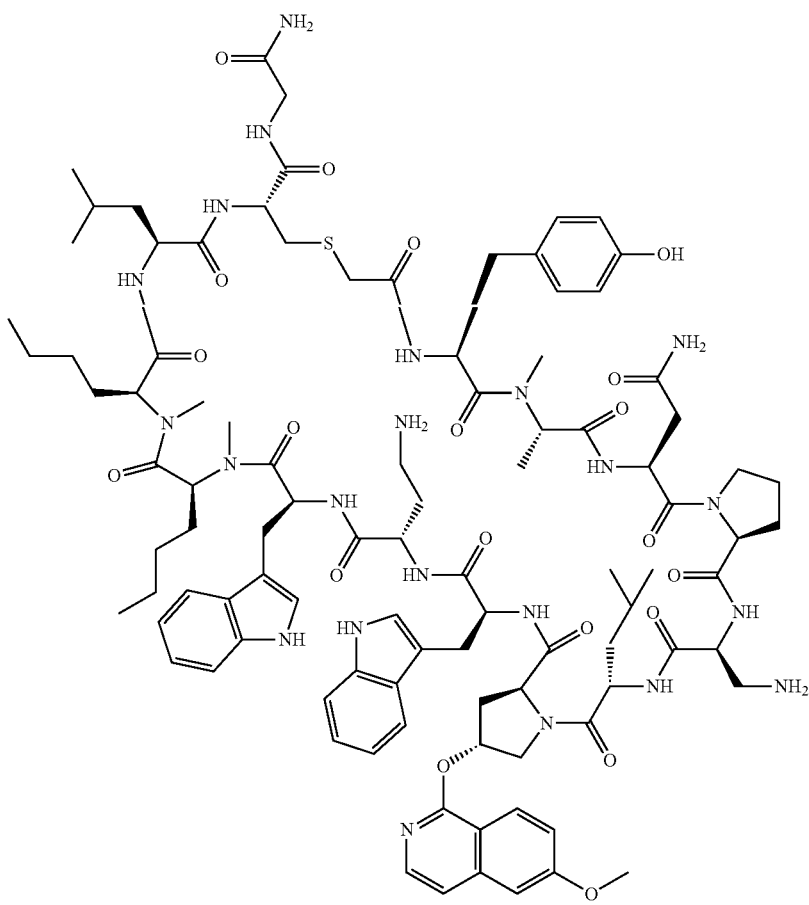

Example 6048

Example 6048 was prepared following "General Synthetic Sequence A". Amino acid (2S,4R)-1-(((9H-fluoren-9-yl)methoxy)carbonyl)-4-((6-methoxyisoquinolin-1-yl)oxy) pyrrolidine-2-carboxylic acid was used. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 100%.

Analysis condition A: Retention time=1.87 min; ESI-MS (+) m/z 993.8 (M+2H)

Analysis condition B: Retention time=2.98 min; ESI-MS (+) m/z 994.2 (M+2H)

Preparation of Example 6049

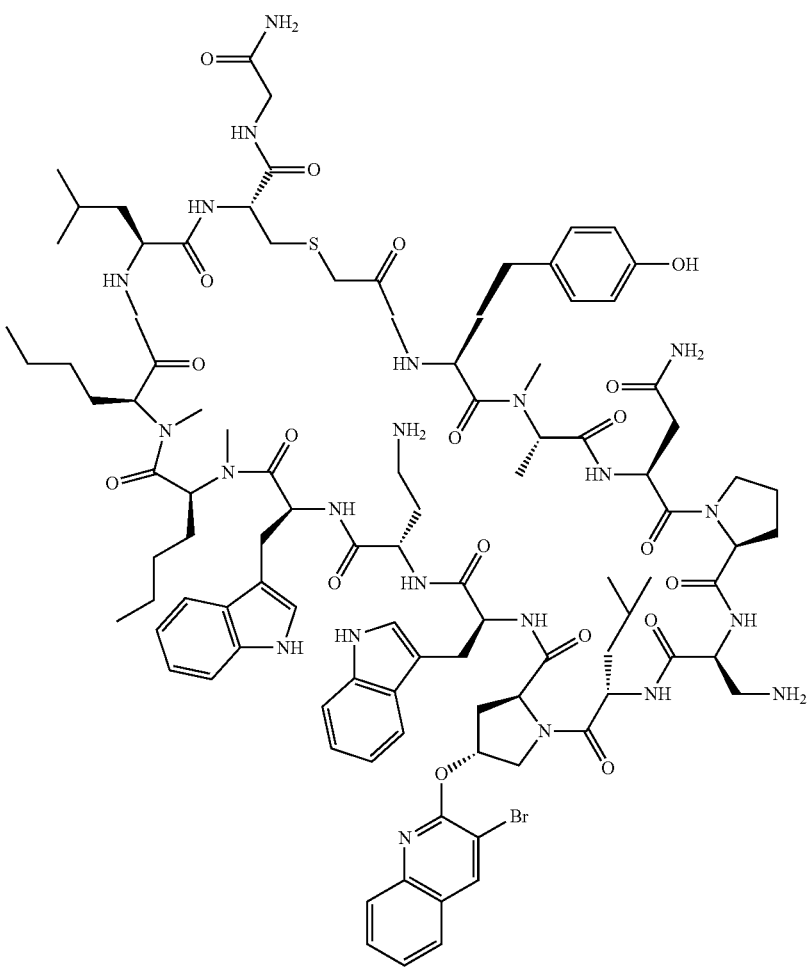

Example 6049

Example 6049 was prepared following "General Synthetic Sequence A". Amino acid (2S,4R)-1-(((9H-fluoren-9-yl)methoxy)carbonyl)-4-(((3-bromoquinolin-2-yl)oxy)pyrrolidine-2-carboxylic acid was used. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.96 min; ESI-MS (+) m/z 1018.1 (M+2H)

Analysis condition B: Retention time=3.07 min; ESI-MS (+) m/z 1018.1 (M+2H)

Preparation of Example 6050

Example 6050

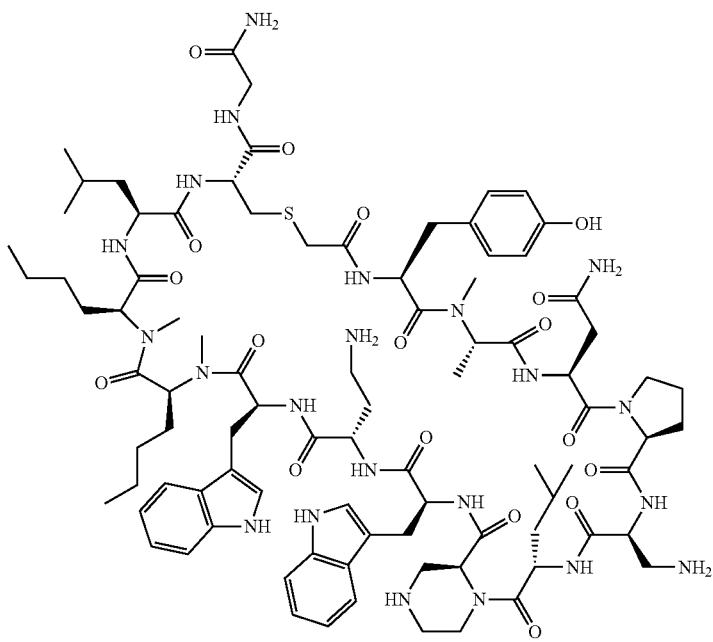

Example 6050 was prepared following "General Synthetic Sequence A". Amino acid (S)-1-(9H-fluoren-9-yl)methoxy)carbonyl)-4-(tert-butoxycarbonyl)piperazine-2-carboxylic acid was used. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-95% B over 30 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 97%.

Analysis condition A: Retention time=1.61 min; ESI-MS (+) m/z 914.8 (M+2H)

Analysis condition B: Retention time=2.77 min; ESI-MS (+) m/z 915.0 (M+2H)

Preparation of (S)-2-(((((9H-fluoren-9-yl)methoxy)carbonyl)amino)-3-(2-phenyl-1H-indol-3-yl)propanoic acid

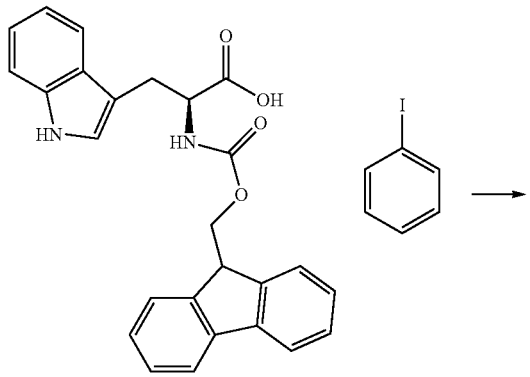

-continued

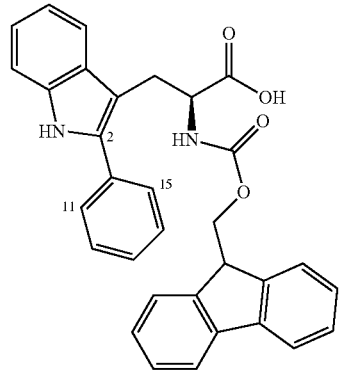

To a mixture of (S)-2-((((9H-fluoren-9-yl)methoxy)carbonyl)amino)-3-(1H-indol-3-yl)propanoic acid (500 mg, 1.172 mmol) and silver(I) tetrafluoroborate (456 mg, 2.345 mmol) in a 150 mL re-usable sealed round bottom flask at r.t. under $N_2$ was added a mixture of iodobenzene (478 mg, 2.345 mmol) in DMF (3 mL), followed by a mixture of trifluoroacetic acid (0.090 mL, 1.172 mmol) in DMF (3 mL) and then a mixture of diacetoxypalladium (13.16 mg, 0.059 mmol) in DMF (4 mL). The flask was tightly capped and stirred at 95° C. in an oil bath for 17 hr. The mixture was diluted with EtOAc (150 mL), and filtered. The filtrate was evaporated, and the residue was dissolved in MeOH and purified by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=50, Final % B=100, Gradient time=10 min, Stop time=12 min, Flow Rate=30 mL/min, Column: Sunfire Prep C18 19×100 5 um, (UV detection at 220 nm). The combined desired fractions at retention time=8.513 min were evaporated to give an off white solid of the product (247 mg).

$^1$H NMR (400 MHz, DMSO-$d_6$) δ 12.70 (br s, 1H), 11.23 (s, 1H), 7.88 (d, J=7.3, 2H), 7.80 (d, J=8.1, 1H), 7.73 (d,

J=7.8, 1H), 7.70-7.62 (m, 4H), 7.49 (t, J=7.6, 2H), 7.43-7.34 (m, 4H), 7.30 (m, 1H), 7.25 (m, 1H), 7.10 (t, J=7.5, 1H), 7.00 (m, 1H), 4.35-4.30 (m, 1H), 4.16-4.09 (m, 3H), 3.41 (m, 1H), 3.20 (dd, J=14.4, 8.6, 1H). The position of the phenyl ring at the indole C2 was indicated by the observation of the C—H long-range correlation between the phenyl protons H11/H15 and the indole carbon C2. Optical rotation $[\alpha]^{20}_D$ −9.83° (1.75 mg/mL, MeOH). LCMS (ES+) m/z=503.1 (M+H), retention time=2.250 min. LCMS were performed by using Shimadzu-VP instrument with UV detection at 220 nm and Waters MICROMASS®. HPLC method: Solvent A=10% MeOH90% $H_2O$0.1% TFA, Solvent B=90% MeOH10% $H_2O$0.1% TFA, Start % B=0, Final % B=100, Gradient time=2 min, Stop time at 3 min, Flow Rate=1 ml/min, Column: PHENOMENEX®-Luna, 2.0×30 mm, 3 um.

Preparation of (S)-2-((((9H-fluoren-9-yl)methoxy)carbonyl)amino)-3-(2-(4-fluorophenyl)-1H-indol-3-yl)propanoic acid

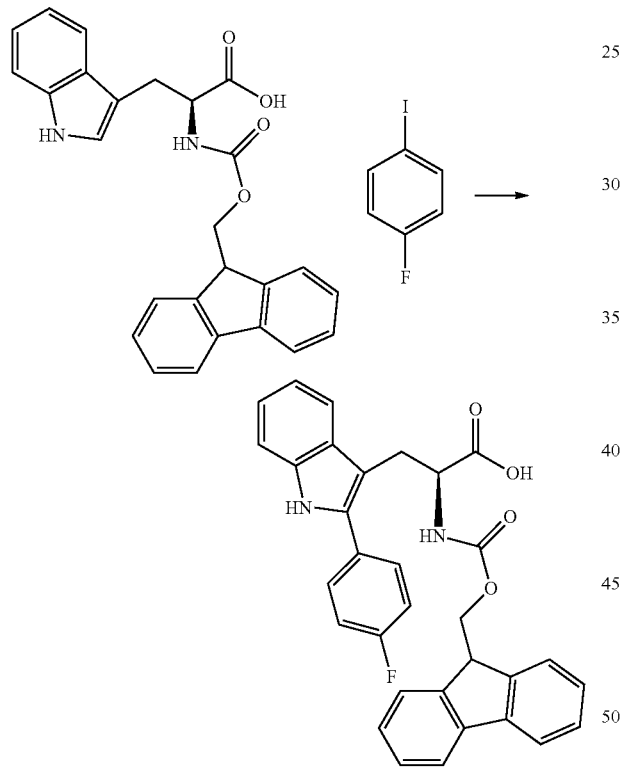

To a mixture of (S)-2-((((9H-fluoren-9-yl)methoxy)carbonyl)amino)-3-(1H-indol-3-yl)propanoic acid (1 g, 2.345 mmol) and silver(I) tetrafluoroborate (0.913 g, 4.69 mmol) in a 150 mL re-usable sealed round bottom flask at r.t. under $N_2$ was added a mixture of 1-fluoro-4-iodobenzene (1.041 g, 4.69 mmol) in DMF (5 mL), followed by a mixture of trifluoroacetic acid (0.181 mL, 2.345 mmol) in DMF (5 mL) and then a mixture of diacetoxypalladium (0.026 g, 0.117 mmol) in DMF (5 mL). Another 5 mL of DMF was added to the reaction mixture. The flask was tightly capped and the reaction mixture stirred at 95° C. in an oil bath for 18 hr. The mixture was diluted with 300 mL EtOAc, filtered, and the filtrate washed with brine (2×100 mL). The organic solution was evaporated. The residue was dissolved in MeOH and purified by Shimadzu-VP preparative reverse phase HPLC using the separation method: Solvent A=10% MeOH-90% $H_2O$-0.1% TFA, Solvent B=90% MeOH-10% $H_2O$-0.1% TFA, Start % B=50, Final % B=100, Gradient time=10 min, Stop time=12 min, Flow Rate=30 mL/min, Column: Sunfire Prep C18 19×100 5 um, (UV detection at 220 nm). The combined desired fractions at retention time=8.679 min were evaporated to give an off white solid of the product (586.8 mg).

$^1$H NMR (400 MHz, DMSO-$d_6$) δ 12.68 (br s, 1H), 11.24 (s, 1H), 7.88 (d, J=7.6, 2H), 7.79 (d, J=8.3, 1H), 7.72-7.63 (m, 5H), 7.43-7.38 (m, 2H), 7.35-7.23 (m, 5H), 7.10 (t, J=7.6, 1H), 7.00 (m, 1H), 4.33-4.28 (m, 1H), 4.15-4.09 (m, 3H), 3.36 (m, 1H), 3.18 (dd, J=14.4, 8.8, 1H). $[\alpha]^{20}_D$ −10.07° (1.35 mg/mL, solvent). LCMS (ES+) m/z=521.0 (M+H), retention time=2.262 min. LCMS were performed by using Shimadzu-VP instrument with UV detection at 220 nm and Waters MICROMASS®. HPLC method: Solvent A=10% MeOH90% $H_2O$0.1% TFA, Solvent B=90% MeOH10% $H_2O$0.1% TFA, Start % B=0, Final % B=100, Gradient time=2 min, Stop time at 3 min, Flow Rate=1 ml/min, Column: PHENOMENEX®-Luna, 2.0×30 mm, 3 um.

Preparation of (S)-2-((((9H-fluoren-9-yl)methoxy)carbonyl)amino)-3-(2-(3-methoxyphenyl)-1H-indol-3-yl)propanoic acid

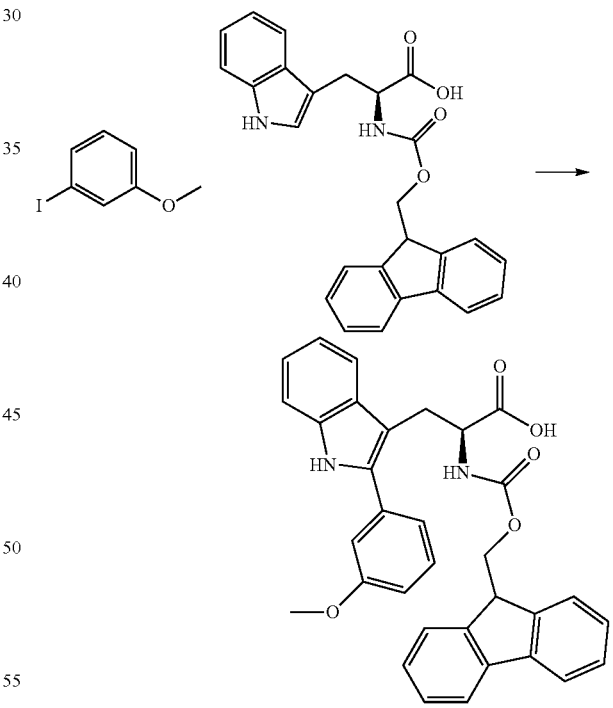

To a 150 mL sealed round bottom flask were added (S)-2-((((9H-fluoren-9-yl)methoxy)carbonyl)amino)-3-(1H-indol-3-yl)propanoic acid (1 g, 2.345 mmol), silver(I) tetrafluoroborate (0.913 g, 4.69 mmol), DMF (20 mL), 3-iodoanisole (1.098 g, 4.69 mmol), 2,2,2-trifluoroacetic acid (0.181 mL, 2.345 mmol) and diacetoxypalladium (0.026 g, 0.117 mmol). The mixture was flushed/degassed with nitrogen for 5 min. The flask was tightly capped and the mixture stirred at 95° C. for 18 hrs. The reaction mixture was diluted with EtOAc (300 mL), filtered, and the filtrate washed with brine (2×100 mL).

The organic solution was evaporated. The residue was purified by column chromatography (BIOTAGE® silica gel column 25 m, EtOAc/Hexane=0 to 100%) to give the product (560 mg, 42%) as a light brown solid. ¹H NMR (400 MHz, chloroform-d) δ 8.19 (s, 1H), 7.81-7.68 (m, 3H), 7.53-7.04 (m, 13H), 6.92 (dd, J=8.3, 2.0 Hz, 1H), 5.20 (d, J=8.0 Hz, 1H), 4.72-4.62 (m, 1H), 4.26-4.19 (m, 2H), 3.80 (s, 3H), 3.65-3.45 (m, 2H); [α]$^{20}_D$ –10.35° (2.88 mg/mL, MeOH). LCMS retention time=1.862 min., m/z=533 (M+H), 95.0% purity. The LCMS data was obtained on a Shimadzu analytical LC/MICROMASS® Platform LC (ESI+) at 220 nm using the following set of conditions: PHENOMENEX® Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a flow rate of 1 mL/minute.

Preparation of (S)-2-((((9H-fluoren-9-yl)methoxy)carbonyl)amino)-3-(2-(4-methoxyphenyl)-1H-indol-3-yl)propanoic acid

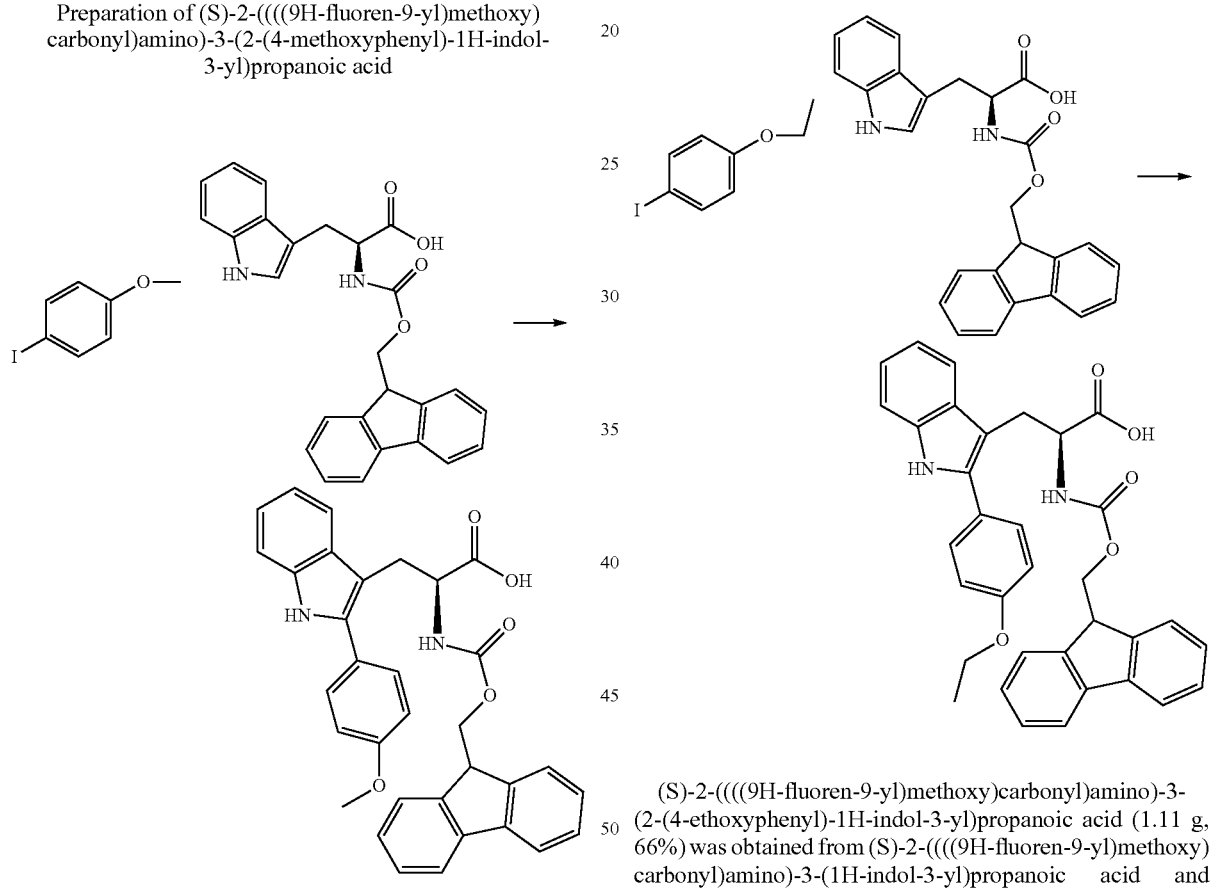

(S)-2-((((9H-fluoren-9-yl)methoxy)carbonyl)amino)-3-(2-(4-methoxyphenyl)-1H-indol-3-yl)propanoic acid (1.12 g, 85%) was obtained from (S)-2-((((9H-fluoren-9-yl)methoxy)carbonyl)amino)-3-(1H-indol-3-yl)propanoic acid and 1-iodo-4-methoxybenzene using the procedure described for (S)-2-((((9H-fluoren-9-yl)methoxy)carbonyl)amino)-3-(2-(3-methoxyphenyl)-1H-indol-3-yl)propanoic acid. ¹H NMR (400 MHz, DMSO-d₆) δ 12.89-12.48 (m, 1H), 11.14 (s, 1H), 7.93-7.77 (m, 2H), 7.72-7.58 (m, 5H), 7.46-7.22 (m, 6H), 7.11-6.94 (m, 4H), 4.30 (dd, J=8.5, 6.0 Hz, 1H), 4.18-4.07 (m, 3H), 3.84-3.77 (s, 3H), 3.35 (m, 1H), 3.23-3.14 (m, 1H); [α]$^{20}_D$ –9.44° (3.05 mg/mL, MeOH). LCMS retention time=1.810 min., m/z=533 (M+H), 97.3% purity. The LCMS data was obtained on a Shimadzu analytical LC/MICROMASS® Platform LC (ESI+) at 220 nm using The following set of conditions: PHENOMENEX® Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a flow rate of 1 mL/minute.

Preparation of (S)-2-((((9H-fluoren-9-yl)methoxy)carbonyl)amino)-3-(2-(4-ethoxyphenyl)-1H-indol-3-yl)propanoic acid

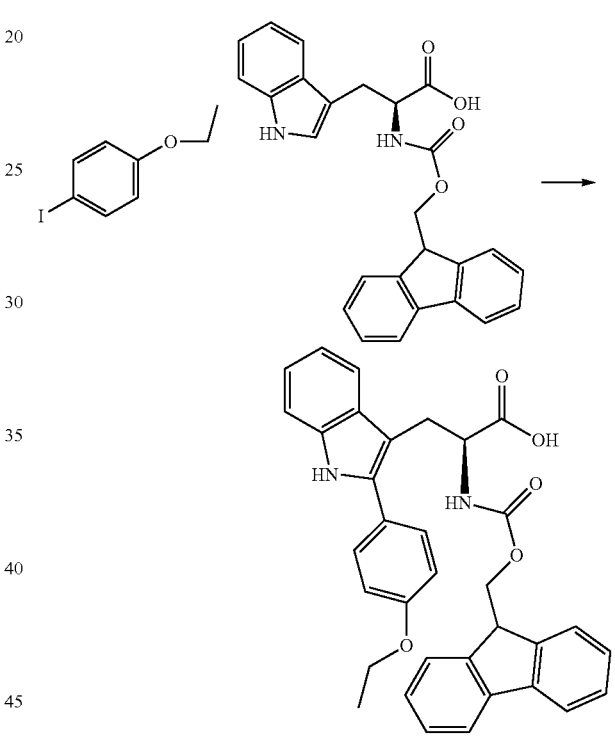

(S)-2-((((9H-fluoren-9-yl)methoxy)carbonyl)amino)-3-(2-(4-ethoxyphenyl)-1H-indol-3-yl)propanoic acid (1.11 g, 66%) was obtained from (S)-2-((((9H-fluoren-9-yl)methoxy)carbonyl)amino)-3-(1H-indol-3-yl)propanoic acid and 1-iodo-4-ethoxybenzene using the procedure described for (S)-2-((((9H-fluoren-9-yl)methoxy)carbonyl)amino)-3-(2-(3-methoxyphenyl)-1H-indol-3-yl)propanoic acid. ¹H NMR (400 MHz, chloroform-d) δ 8.12 (s, 1H), 7.77 (d, J=7.5 Hz, 2H), 7.69 (d, J=7.8 Hz, 1H), 7.54-7.34 (m, 8H), 7.33-7.12 (m, 4H), 6.97-6.90 (m, 2H), 5.16 (d, J=7.8 Hz, 1H), 4.64 (d, J=6.3 Hz, 1H), 4.28-4.06 (m, 4H), 3.62-3.42 (m, 2H), 1.44-1.36 (t, J=8.0 Hz, 3H); [α]$^{20}_D$ –10.68° (4.01 mg/mL, MeOH). LCMS retention time=1.898 min., m/z 547=(M+H), 98.2% purity. The LCMS data was obtained on a Shimadzu analytical LC/MICROMASS® Platform LC (ESI+) at 220 nm using The following set of conditions: PHENOMENEX® Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a flow rate of 1 mL/minute.

Preparation of (S)-2-((((9H-fluoren-9-yl)methoxy)carbonyl)amino)-3-(2-(4-propoxyphenyl)-1H-indol-3-yl)propanoic acid

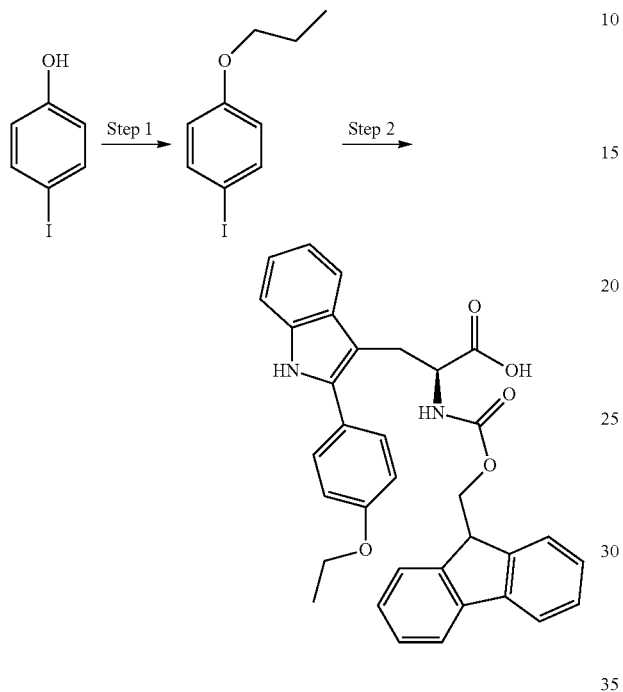

Step 1: 1-iodo-4-propoxybenzene

A suspension of 4-iodophenol (3 g, 13.64 mmol), 1-bromopropane (1.845 g, 15.00 mmol), and sodium carbonate (7.54 g, 54.5 mmol) in DMF (30 mL) was stirred at 80° C. for 4 hrs. The reaction mixture was diluted with water (250 mL) and extracted with EtOAc (3×75 mL). The combined organic extracts were washed with 0.5M NaOH (2×50 mL), and water (2×50 mL), and then dried over MgSO$_4$. The solvent was removed. The crude product (3.11 g) was obtained, which was directly used for the next reaction without further purification. $^1$H NMR (400 MHz, chloroform-d) δ 7.61-7.53 (m, 2H), 6.74-6.67 (m, 2H), 3.90 (t, J=6.5 Hz, 2H), 1.88-1.76 (m, 2H), 1.05 (t, J=7.4 Hz, 3H).

Step 2: (S)-2-((((9H-fluoren-9-yl)methoxy)carbonyl)amino)-3-(2-(4-propoxyphenyl)-1H-indol-3-yl)propanoic acid (830 mg, 57%) was obtained from (S)-2-((((9H-fluoren-9-yl)methoxy)carbonyl)amino)-3-(1H-indol-3-yl)propanoic acid and 1-iodo-4-propoxybenzene using the procedure described for (S)-2-((((9H-fluoren-9-yl)methoxy)carbonyl)amino)-3-(2-(3-methoxyphenyl)-1H-indol-3-yl)propanoic acid. $^1$H NMR (400 MHz, chloroform-d) δ 8.14 (s, 1H), 7.83-7.59 (m, 3H), 7.54-7.12 (m, 11H), 6.93 (d, J=8.5 Hz, 2H), 5.43-5.12 (m, 1H), 4.71-4.53 (m, 1H), 4.29-4.05 (m, 3H), 3.88 (t, J=6.4 Hz, 2H), 3.63-3.41 (m, 2H), 1.79 (sxt, J=7.0 Hz, 2H), 1.09-0.98 (m, 3H); [α]$^{20}_D$ −7.54° (3.05 mg/mL, MeOH). LCMS retention time=1.952 min., m/z=561 (M+H), 99.1% purity. The LCMS data was obtained on a Shimadzu analytical LC/MICROMASS® Platform LC (ESI+) at 220 nm using The following set of conditions: PHENOMENEX® Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a flow rate of 1 mL/minute.

Preparation of (S)-2-((((9H-fluoren-9-yl)methoxy)carbonyl)amino)-3-(2-(3-propoxyphenyl)-1H-indol-3-yl)propanoic acid

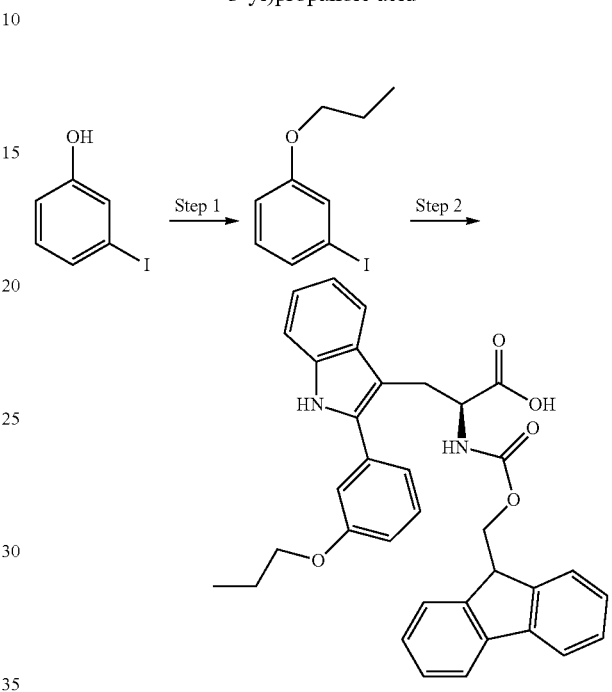

Step 1: Iodo-3-propoxybenzene (3.53 g, 98%) was obtained from 3-iodophenol and 1-bromopropane using the procedure described for 1-iodo-4-propoxybenzene. $^1$H NMR (400 MHz, chloroform-d) δ 7.33-7.25 (m, 2H), 7.05-6.97 (m, 1H), 6.92-6.85 (m, 1H), 3.91 (t, J=6.5 Hz, 2H), 1.82 (sxt, J=7.0 Hz, 2H), 1.05 (t, J=7.4 Hz, 3H).

Step 2: (S)-2-((((9H-fluoren-9-yl)methoxy)carbonyl)amino)-3-(2-(3-propoxyphenyl)-1H-indol-3-yl)propanoic acid (1.25 g, 83%) was obtained from (S)-2-((((9H-fluoren-9-yl)methoxy)carbonyl)amino)-3-(1H-indol-3-yl)propanoic acid and 1-iodo-3-propoxybenzene using the procedure described for (S)-2-((((9H-fluoren-9-yl)methoxy)carbonyl)amino)-3-(2-(3-methoxyphenyl)-1H-indol-3-yl)propanoic acid. $^1$H NMR (400 MHz, chloroform-d) δ 8.28 (s, 1H), 7.80-7.70 (m, 3H), 7.53-7.09 (m, 13H), 6.94-6.87 (m, 1H), 5.23 (d, J=8.0 Hz, 1H), 4.68 (d, J=6.0 Hz, 1H), 4.22-4.15 (m, 2H), 3.93 (t, J=6.7 Hz, 2H), 3.60 (d, J=5.3 Hz, 1H), 3.52 (d, J=7.0 Hz, 1H), 1.85-1.72 (m, 2H), 1.01 (t, J=7.4 Hz, 3H); [α]$^{20}_D$ −11.34° (4.25 mg/mL, MeOH). LCMS retention time=1.972 min., m/z=561 (M+H), 99.0% purity. The LCMS data was obtained on a Shimadzu analytical LC/MICROMASS® Platform LC (ESI+) at 220 nm using The following set of conditions: PHENOMENEX® Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 2 minutes with a 1 minute hold at a rate of 1 mL/minute.

Preparation of Example 7001

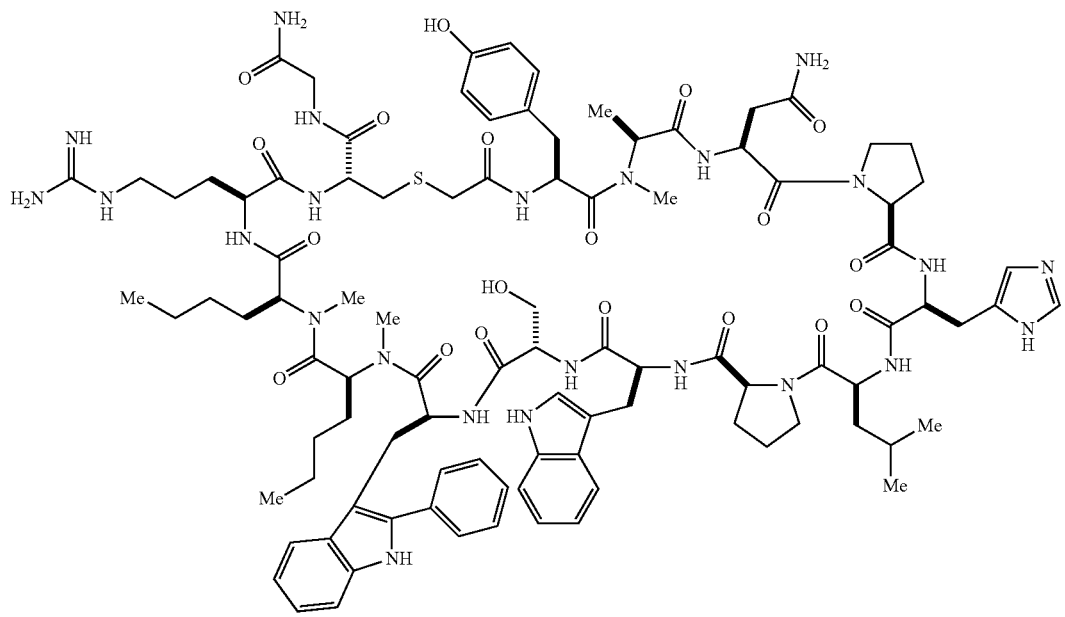

Example 7001 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-phenyl-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 96%.

Analysis condition A: Retention time=1.63 min; ESI-MS (+) m/z=986.4 (M+2H)

Analysis condition B: Retention time=2.66 min; ESI-MS (+) m/z=986.4 (M+2H)

ESI-HRMS(+) m/z Calculated 1969.9894. Found 1969.9865 (M+H); Calculated 985.4983. Found 985.4964 (M+2H); Calculated 657.3347. Found 657.3327 (M+3H).

Preparation of Example 7002

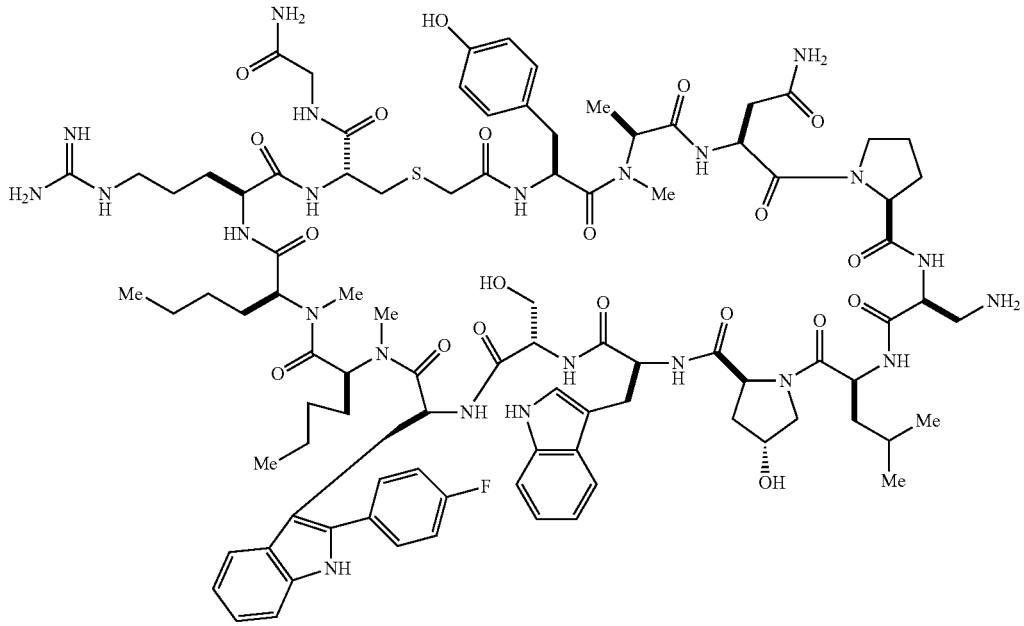

Example 7002 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-fluorophenyl)-1H-indol-3-yl)propanoic acid was used in the sixth amino acid coupling step.

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 14.1 mg, and its estimated purity by LCMS analysis was 98%.

Analysis condition A: Retention time=1.59 min; ESI-MS (+) m/z=977.4 (M+2H)

Analysis condition B: Retention time=2.68 min; ESI-MS (+) m/z=977.9 (M+2H)

ESI-HRMS(+) m/z Calculated 976.9856. Found 976.9838 (M+2H).

Preparation of Example 7003

Example 7003 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(3-methoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 98%.

Analysis condition A: Retention time=1.59 min; ESI-MS (+) m/z=983.9 (M+2H)

Analysis condition B: Retention time=2.60 min; ESI-MS (+) m/z=983.1 (M+2H)

ESI-HRMS(+) m/z Calculated 982.9956. Found 982.9936 (M+2H).

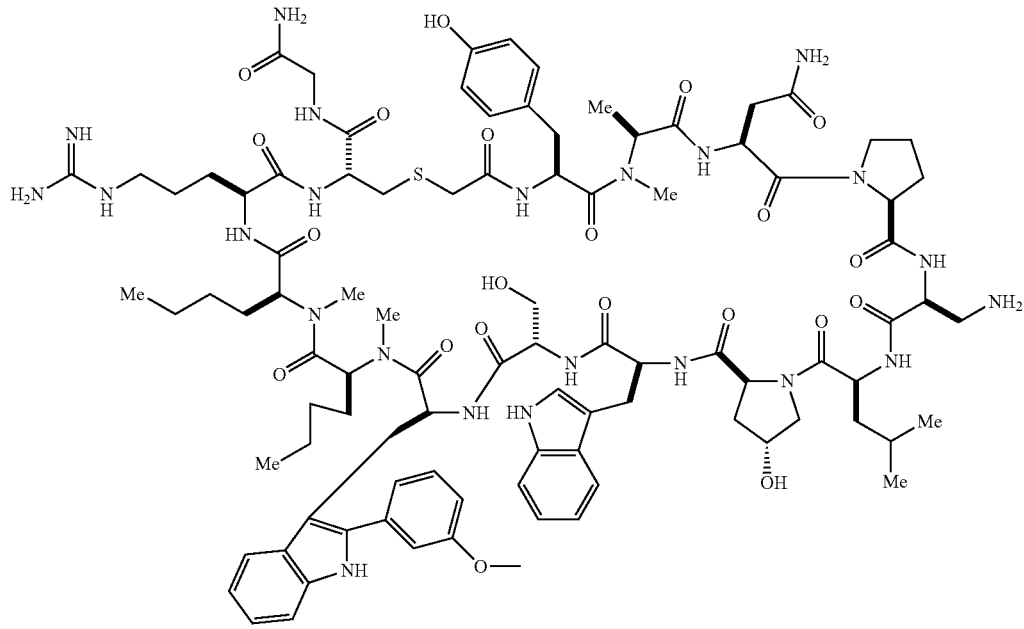

Preparation of Example 7004

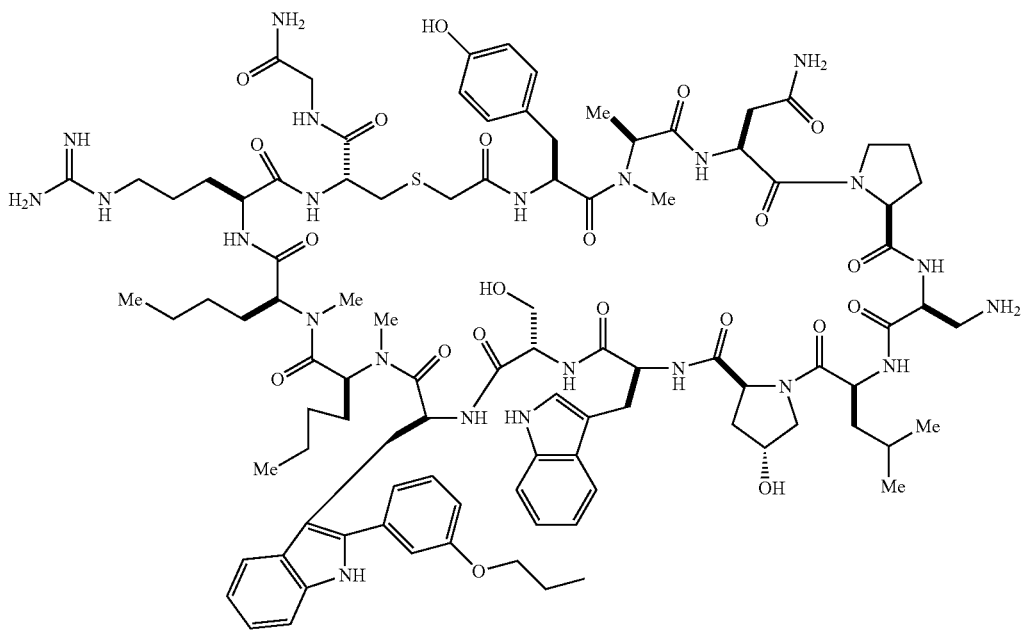

Example 7004 was prepared following the general synthetic sequence described for the preparation of Example 7001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(3-propoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 97%.

Analysis condition A: Retention time=1.59 min; ESI-MS (+) m/z=996.7 (M+2H)

Analysis condition B: Retention time=2.70 min; ESI-MS (+) m/z=997.3 (M+2H)

ESI-HRMS(+) m/z Calculated 997.0113. Found 997.0088 (M+2H).

Preparation of Example 7005

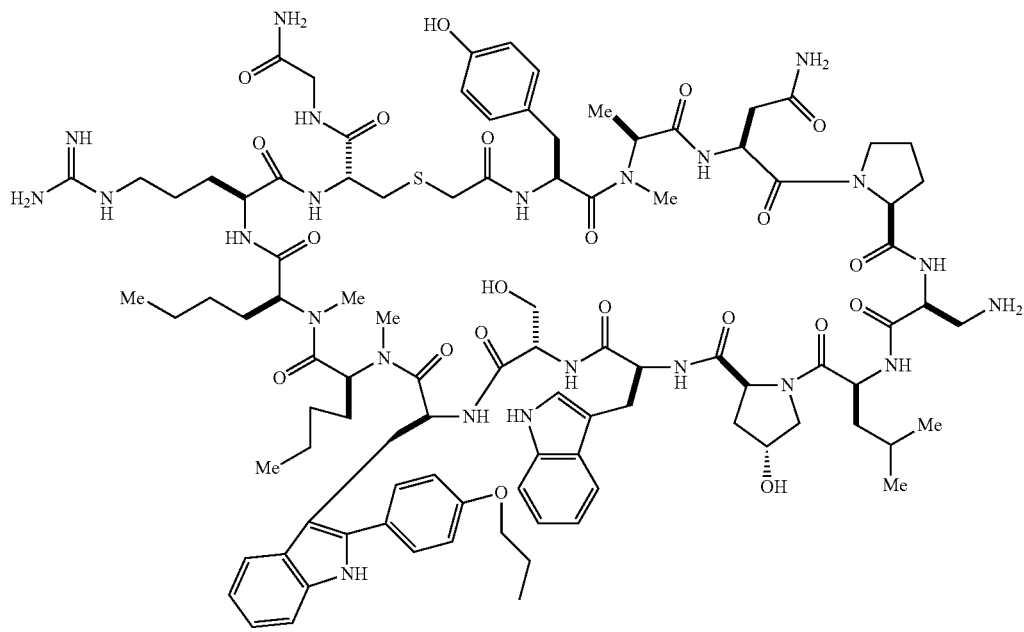

Example 7005 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-propoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 31.6 mg, and its estimated purity by LCMS analysis was 98%.

Analysis condition A: Retention time=1.84 min; ESI-MS (+) m/z=996.7 (M+2H)

Analysis condition B: Retention time=2.74 min; ESI-MS (+) m/z=997.5 (M+2H)

ESI-HRMS(+) m/z Calculated 997.0113. Found 997.0086 (M+2H).

Preparation of Example 7006

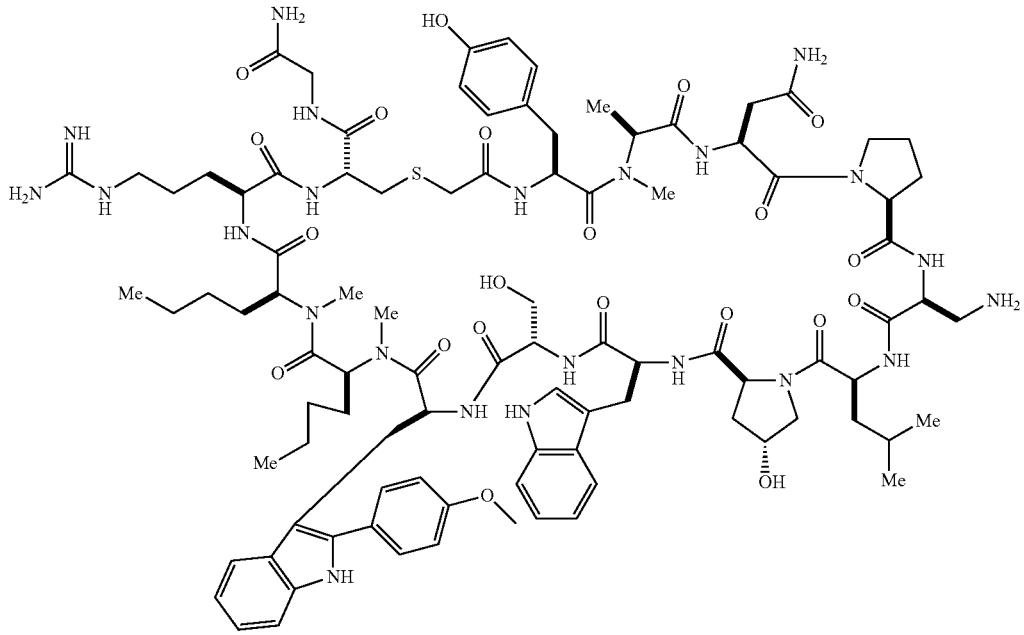

Example 7006 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-methoxyphenyl)-1H-indol-3-yl)propanoic acid was used in the sixth amino acid coupling step.

The crude material was purified via preparative LC/MS with the following conditions: Column: Waters XBridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 6.8 mg, and its estimated purity by LCMS analysis was 100%.

Analysis condition A: Retention time=1.84 min; ESI-MS (+) m/z=983.6 (M+2H)

Analysis condition B: Retention time=2.74 min; ESI-MS (+) m/z=983.6 (M+2H)

ESI-HRMS(+) m/z Calculated 982.9956. Found 982.9930 (M+2H).

Preparation of Example 7007

Example 7007 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-methoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 97%.

Analysis condition A: Retention time=1.60 min; ESI-MS (+) m/z 990.3 (M+2H)

Analysis condition B: Retention time=2.69 min; ESI-MS (+) m/z 990.6 (M+2H)

ESI-HRMS(+) m/z Calculated 990.0035. Found 990.0008 (M+2H).

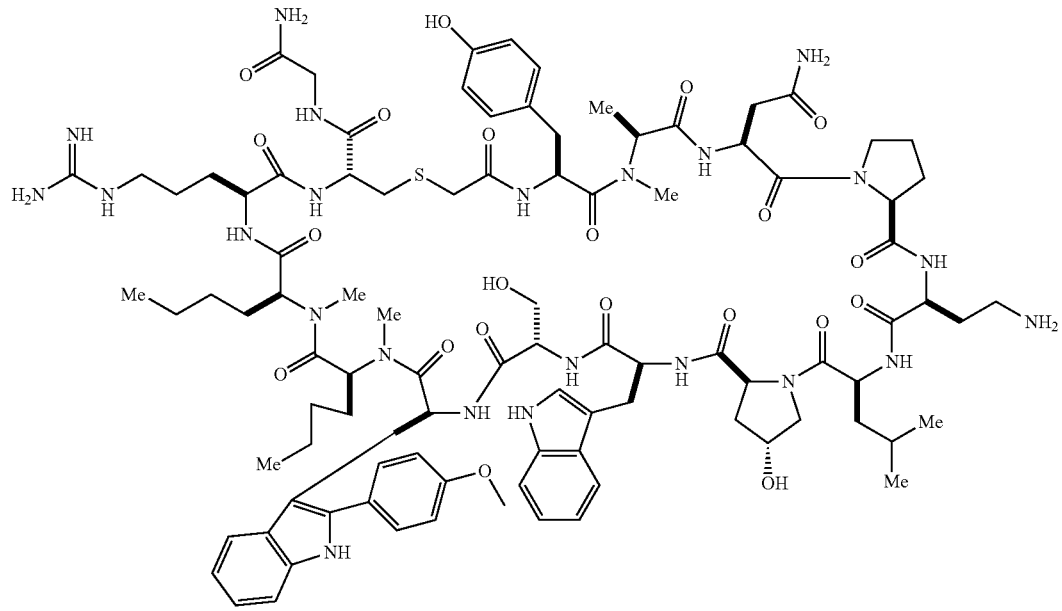

Preparation of Example 7008

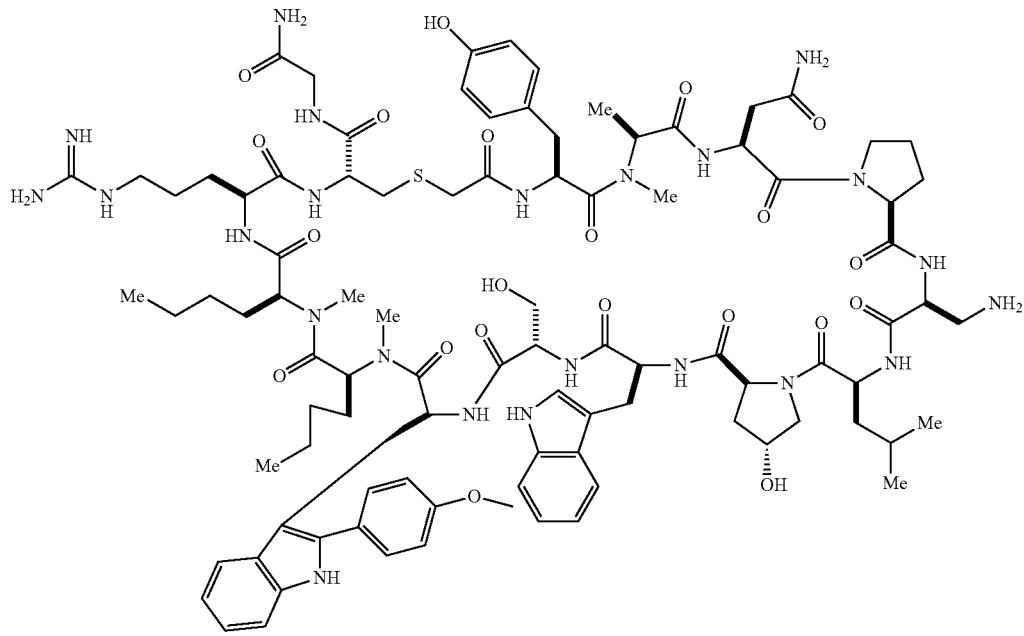

Example 7008 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-methoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 16.5 mg, and its estimated purity by LCMS analysis was 96%.

Analysis condition A: Retention time=1.68 min; ESI-MS (+) m/z=975.6 (M+2H)

Analysis condition B: Retention time=2.77 min; ESI-MS (+) m/z=975.3 (M+2H)

ESI-HRMS(+) m/z Calculated 974.9982. Found 974.9949 (M+2H).

Preparation of Example 7009

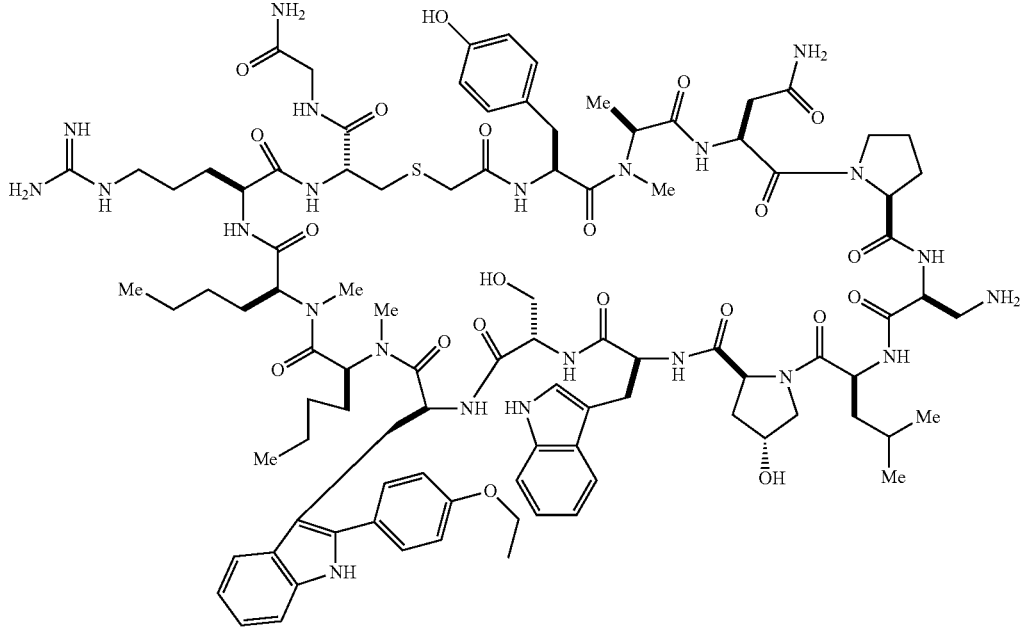

Example 7009 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-ethoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.9 mg, and its estimated purity by LCMS analysis was 99%.

Analysis condition A: Retention time=1.69 min; ESI-MS (+) m/z 990.7 (M+2H)

Analysis condition B: Retention time=2.79 min; ESI-MS (+) m/z 990.7 (M+2H)

ESI-HRMS(+) m/z Calculated 990.0035. Found 990.0014 (M+2H).

Preparation of Example 7010

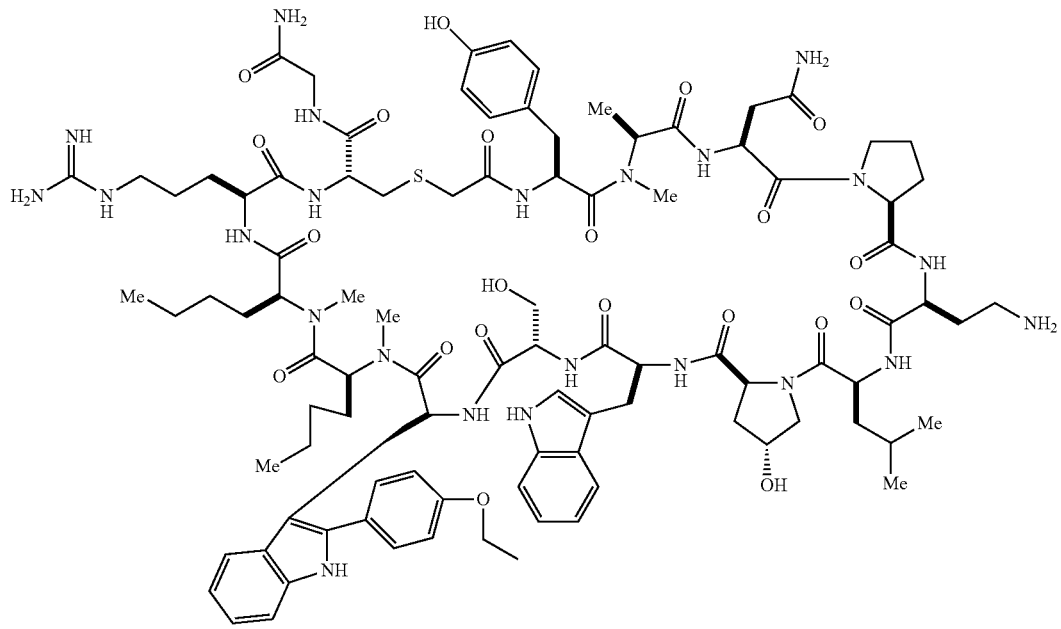

Example 7010 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-ethoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.9 mg, and its estimated purity by LCMS analysis was 92%.

Analysis condition A: Retention time=1.65 min; ESI-MS (+) m/z=997.4 (M+2H)

Analysis condition B: Retention time=2.79 min; ESI-MS (+) m/z=997.4 (M+2H)

Preparation of Example 7011

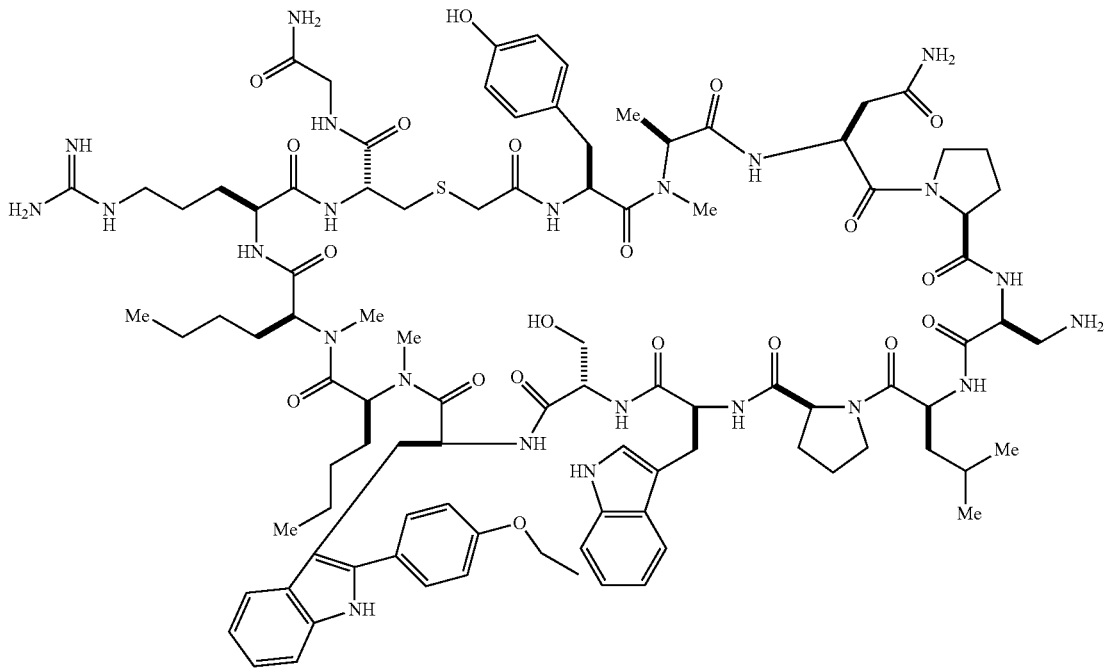

Example 7011 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A". (S)-2-((((9H-fluoren-9-yl)methoxy)carbonyl)amino)-3-(2-(4-ethoxyphenyl)-1H-indol-3-yl)propanoic acid was used in the sixth amino acid coupling step.

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 100%.

Analysis condition A: Retention time=1.73 min; ESI-MS (+) m/z 982.7 (M+2H)

Analysis condition B: Retention time=2.82 min; ESI-MS (+) m/z 982.6 (M+2H)
ESI-HRMS(+) m/z Calculated 982.0060. Found 982.0035 (M+2H).

Preparation of Example 7012

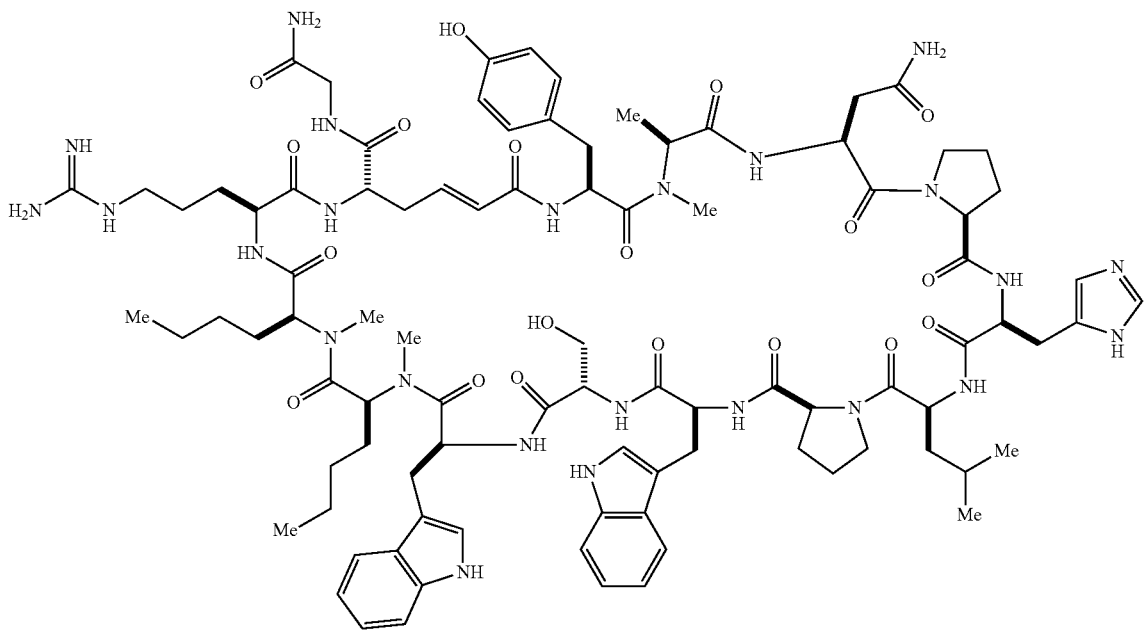

Example 7012 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure". A "Prelude Method A: Single-coupling procedure" was used to cap the amino terminal of Tyr1 with acrylic acid as the last amino acid coupling step. The resin bounded peptide obtained was then subjected to a "ring-closing olefin metathesis (RCM) reaction" as described below and then followed by the "Global Deprotection Method A".

Ring-closing olefin metathesis (RCM) reaction: The resin bounded peptide (0.044 mmol) was added into a 20 mL connical vial for microwave reactor. Hoveyda-Grubb's 2nd generation catalyst ((1,3-Bis-(2,4,6-trimethylphenyl)-2-imidazolidinylidene)dichloro(o-isopropoxyphenylmethylene) ruthenium) (27.5 mg, 0.033 mmol) and 1,2,-dichloroethane (10 mL) were added. The mixture was degassed, and heated in microwave reactor at 120° for 1 hr. After the reaction was done, the resin was filtered, and washed with DMF (2×5 mL), followed by DCM (3×5 mL) and then dried. The crude material was deprotected by using "Global Deprotection Method A".

The crude product was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 2.9 mg, and its estimated purity by LCMS analysis was 98%.

Analysis condition A: Retention time=1.52 min; ESI-MS (+) m/z=938.5 (M+2H)

Analysis condition B: Retention time=2.65 min; ESI-MS (+) m/z=938.3 (M+2H)

Preparation of Example 7013

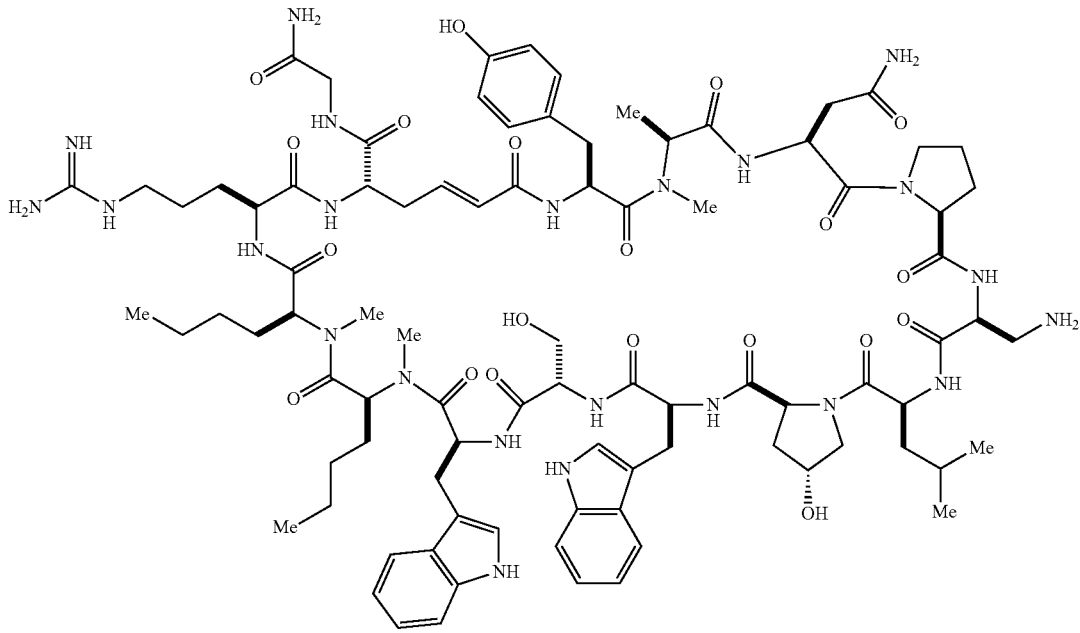

Example 7013 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure". A "Prelude Method A: Single-coupling procedure" was used to cap the amino terminal of Tyr1 with acrylic acid as the last amino acid coupling step. The resin bounded peptide obtained was then subjected to a "ring-closing olefin metathesis (RCM) reaction" as described below and then followed by the "Global Deprotection Method A".

Ring-closing olefin metathesis (RCM) reaction: The resin bounded peptide (0.262 mmol) was divided into six batches. Each batch (0.044 mmol) was added into a 20 mL conical vial for microwave reactor. Hoveyda-Grubb's 2nd generation catalyst (27.5 mg, 0.033 mmol) and 1,2,-dichloroethane (10 mL) were added. The mixture was degassed, and was heated in microwave reactor at 120° for 1 hr. After the reaction was done, the resin was filtered, and washed with DMF (2×5 mL), followed by DCM (3×5 mL) and then dried. The six batches were combined and the crude material was deprotected by using "Global Deprotection Method A".

The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-100% B over 30 minutes, then a 5-minute hold at 100% B; Flow: 20 mL/min. Fractions containing the desired product were combined and dried via centrifugal evaporation.

The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 100%.

Analysis condition A: Retention time=1.49 min; ESI-MS (+) m/z=920.5 (M+2H)

Analysis condition B: Retention time=2.61 min; ESI-MS (+) m/z=920.9 (M+2H)

Examples 7014 to 7064 were prepared by following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure". The "Global Deprotection Method A" and "Cyclization Method A" used for the preparation of Examples 7014 to 7064 were modified as described in the following. Global Deprotection Method A: The procedure of "Global Deprotection Method A" describes an experiment performed on a 0.100 mmol scale, where the scale is determined by the amount of Rink linker bound to the resin. A "deprotection solution" was prepared by combining in a 40 mL glass jar trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was mixed on an orbital shaker (175 RPM for 2 h). The mixture was filtered through a funnel, the solids washed with additional "de-protection solution" (1.0 mL) and collected into a 40 mL screw capped vial. To the combined filtrates was added $Et_2O$ (15 mL). The mixture was vigorously mixed upon which a significant amount of a white solid precipitated. The mixture was centrifuged for 3 minutes at 2000 RPM, the solution decanted away from the solids and discarded. The process was repeated ×3, the solids were then allowed to sit on the bench and air dry for 1-2 hrs before carrying on affording the crude peptide as an off-white solid. Cyclization Method A: The procedure of "Cyclization Method A" describes an experiment performed on a 0.100 mmol scale. The crude peptide solids were dissolved in MeCN:aq. 0.1M $NH_4OAc$ (15 mL:15 mL), and the solution was then carefully adjusted to pH=9.0 using aq NaOH (1.0M). The vials were capped and the solution was then mixed at 175 RPM on an orbital shaker overnight (~18 h). The reaction solution was concentrated and the residue was then dissolved in MeOH. This solution was subjected to reverse-phase HPLC purification to afford the desired cyclic peptide.

Preparation of Example 7014

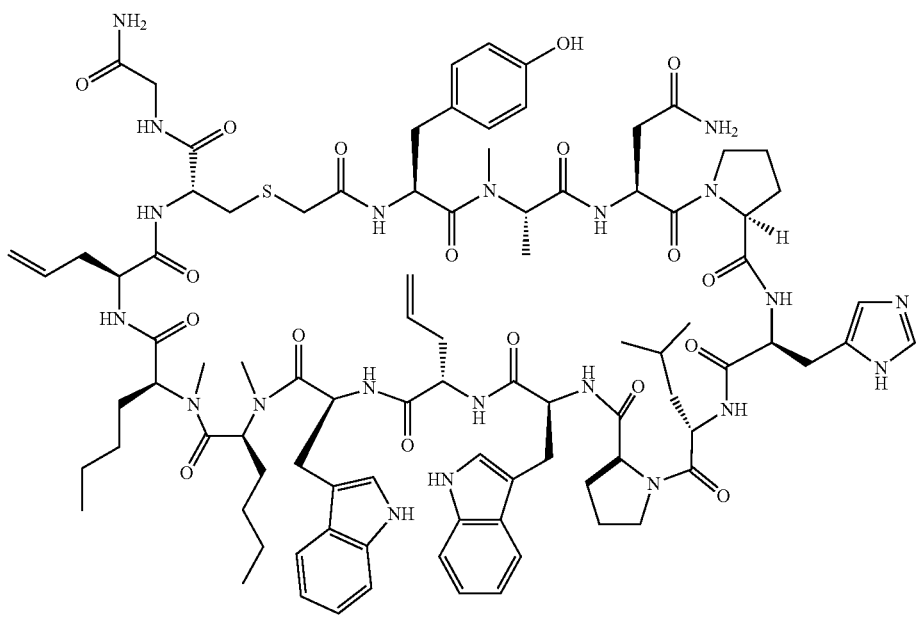 [SMILES: C=CC[C@@H]1NC(=O)[C@H](Cc2c[nH]c3ccccc23)NC(=O)[C@@H]2CCCN2C(=O)[C@H](CC(C)C)NC(=O)[C@H](Cc2cnc[nH]2)NC(=O)[C@@H]2CCCN2C(=O)[C@H](CC(N)=O)NC(=O)[C@H](C)N(C)C(=O)[C@H](Cc2ccc(O)cc2)NC(=O)CSC[C@@H](C(=O)NCC(N)=O)NC(=O)[C@H](CC=C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 33.2 mg, and its estimated purity by LCMS analysis was 96%.

Analysis condition A: Retention time=1.87 min; ESI-MS (+) m/z=923.6 (M+2H)

Analysis condition B: Retention time=2.83 min; ESI-MS (+) m/z=923.7 (M+2H)

Preparation of Example 7015

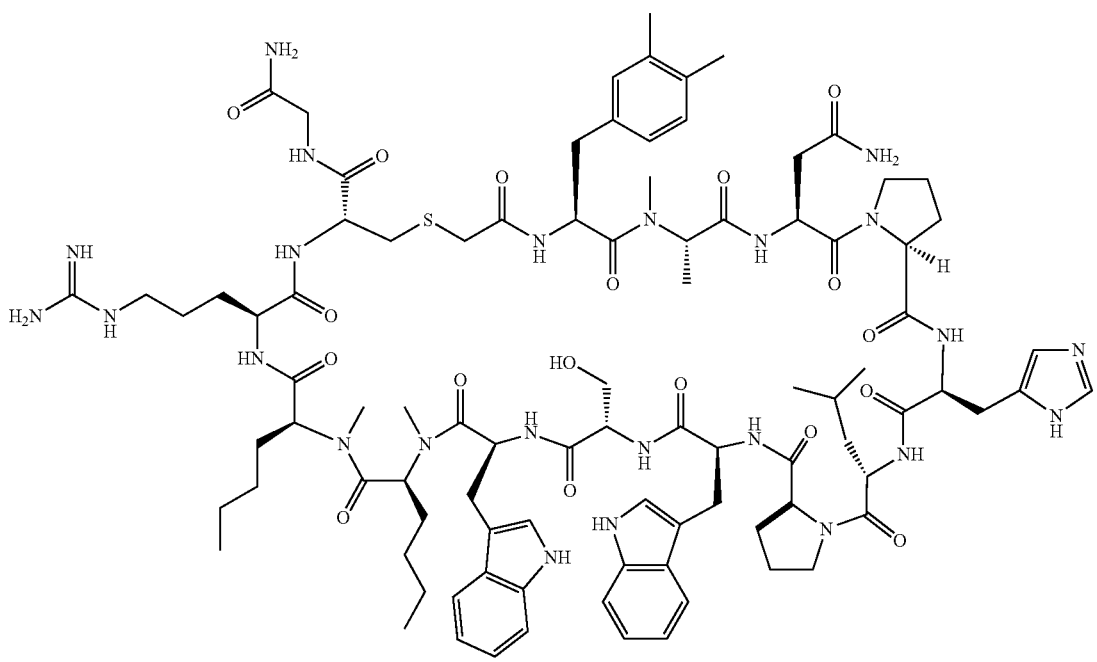 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C)c(C)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 40.4 mg, and its estimated purity by LCMS analysis was 100%.

Analysis condition A: Retention time=1.54 min; ESI-MS (+) m/z=955.3 (M+2H)

Analysis condition B: Retention time=3.06 min; ESI-MS (+) m/z=954.4 (M+2H)

Preparation of Example 7016

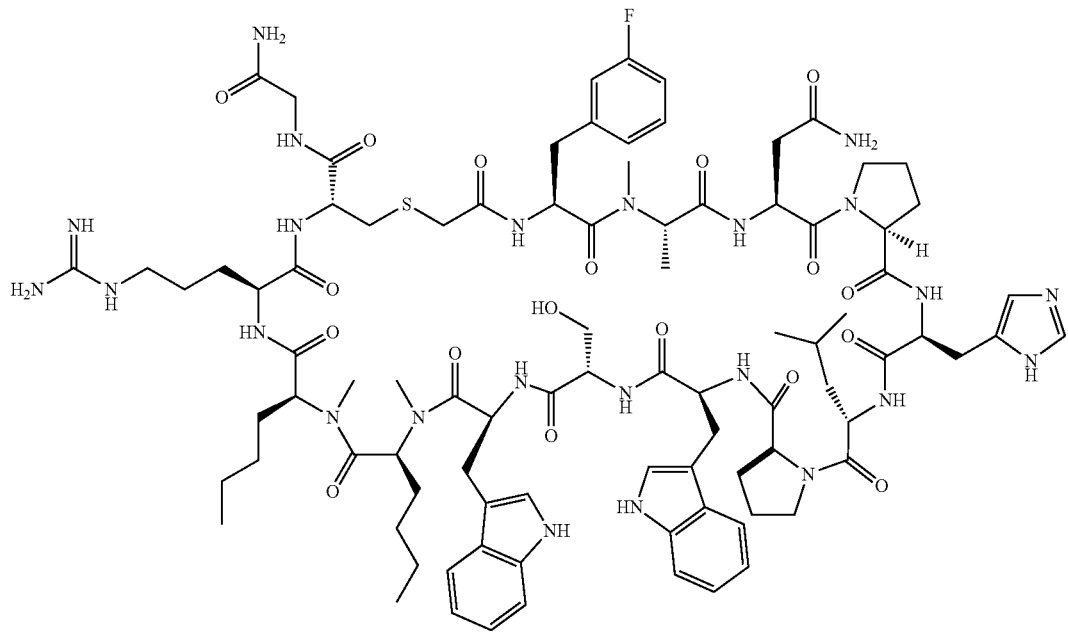 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(F)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 40-60% B over 15 minutes, then a 5-minute hold at 100% B; Flow: 20 mL/min. Fractions containing the desired product were combined and dried via centrifugal evaporation. The yield of the product was 42.5 mg, and its estimated purity by LCMS analysis was 95%.

Analysis condition A: Retention time=1.81 min; ESI-MS (+) m/z=949.6 (M+2H)

Analysis condition B: Retention time=2.96 min; ESI-MS (+) m/z=949.4 (M+2H)

Preparation of Example 7017

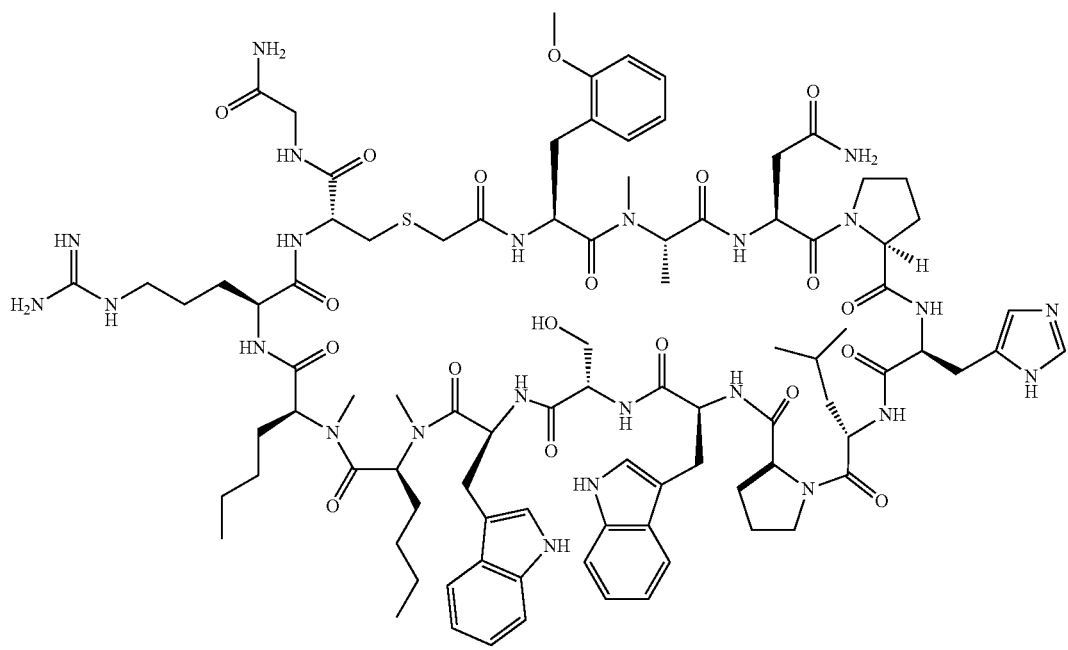 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccccc2OC)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 39.3 mg, and its estimated purity by LCMS analysis was 100%.

Analysis condition A: Retention time=1.75 min; ESI-MS (+) m/z=955.4 (M+2H)

Analysis condition B: Retention time=2.94 min; ESI-MS (+) m/z=955.6 (M+2H)

Preparation of Example 7018

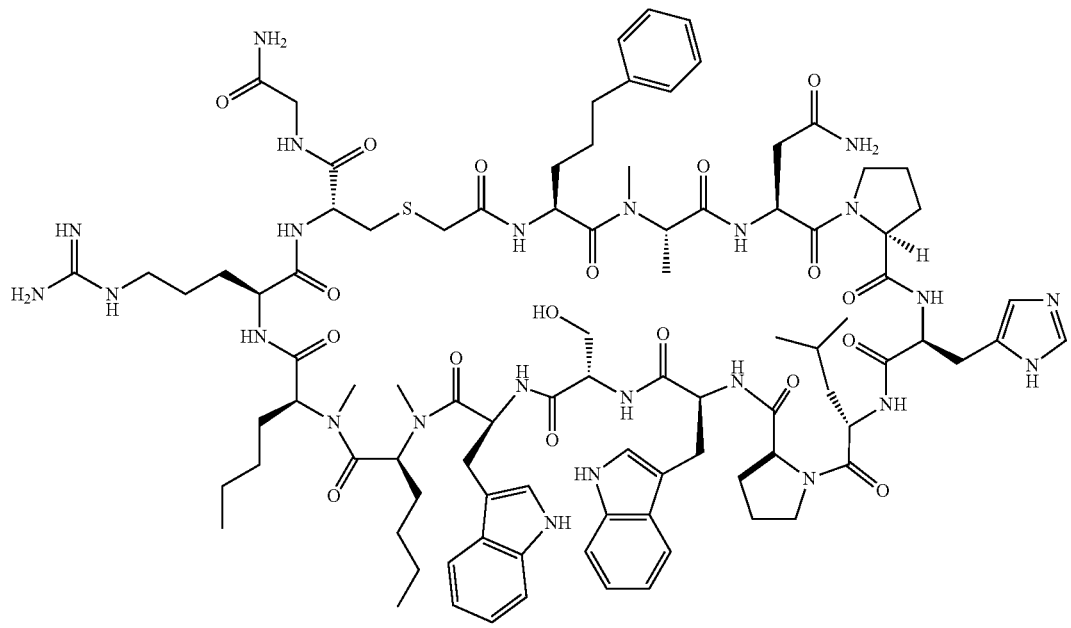 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](CCCc2ccccc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2CCC[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 30-70% B over 15 minutes, then a 5-minute hold at 100% B; Flow: 20 mL/min. Fractions containing the desired product were combined and dried via centrifugal evaporation. The yield of the product was 18.5 mg, and its estimated purity by LCMS analysis was 100%.

Analysis condition A: Retention time=1.77 min; ESI-MS (+) m/z=954.5 (M+2H)

Analysis condition B: Retention time=2.94 min; ESI-MS (+) m/z=954.8 (M+2H)

Preparation of Example 7019

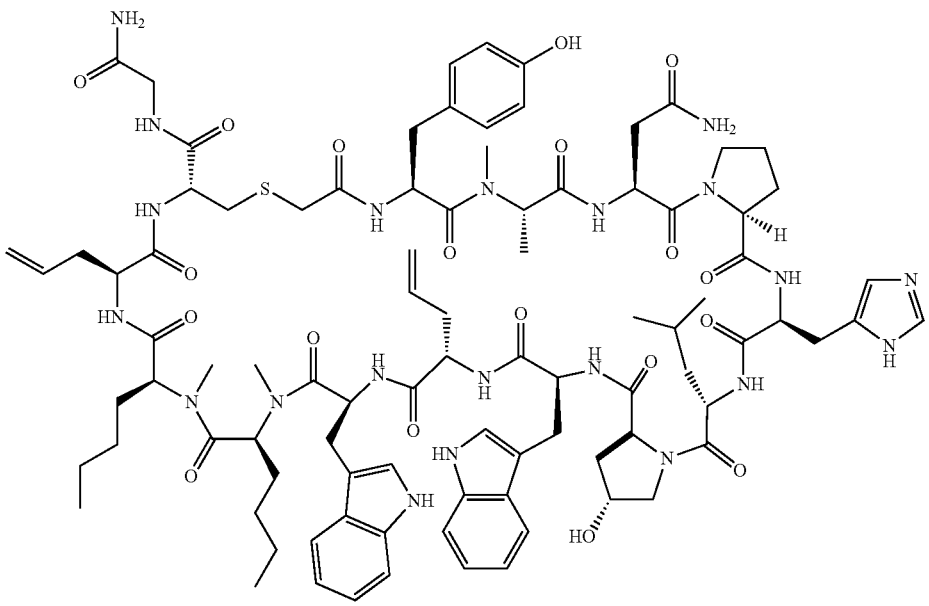 [SMILES: C=CC[C@@H]1NC(=O)[C@H](Cc2c[nH]c3ccccc23)NC(=O)[C@@H]2C[C@@H](O)CN2C(=O)[C@H](CC(C)C)NC(=O)[C@H](Cc2cnc[nH]2)NC(=O)[C@@H]2CCCN2C(=O)[C@H](CC(N)=O)NC(=O)[C@H](C)N(C)C(=O)[C@H](Cc2ccc(O)cc2)NC(=O)CSC[C@@H](C(=O)NCC(N)=O)NC(=O)[C@H](CC=C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min.

The material was further purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.4 mg, and its estimated purity by LCMS analysis was 98.6%.

Analysis condition A: Retention time=1.70 min; ESI-MS (+) m/z=931.7 (M+2H)

Analysis condition B: Retention time=2.77 min; ESI-MS (+) m/z=931.7 (M+2H)

Preparation of Example 7020

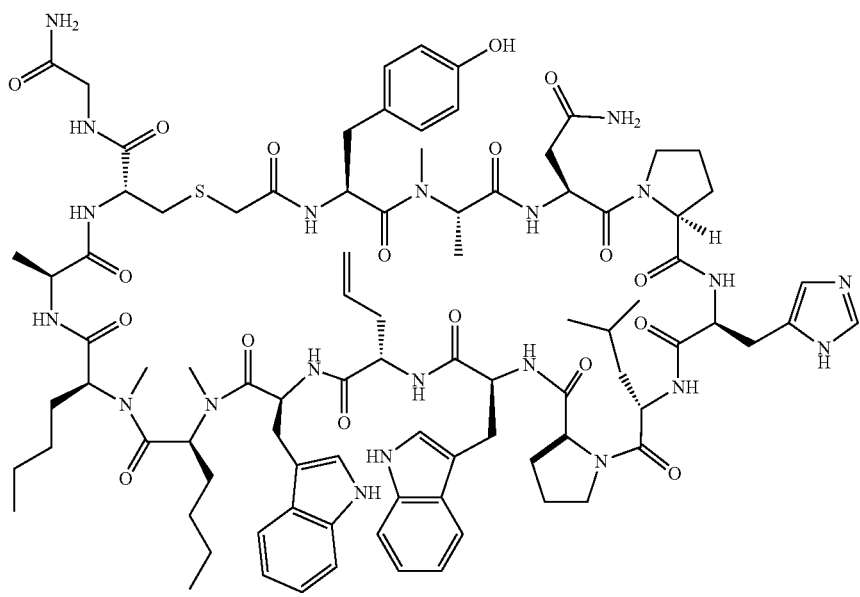 [SMILES: C=CC[C@@H]1NC(=O)[C@H](Cc2c[nH]c3ccccc23)NC(=O)[C@@H]2CCCN2C(=O)[C@H](CC(C)C)NC(=O)[C@H](Cc2cnc[nH]2)NC(=O)[C@@H]2CCCN2C(=O)[C@H](CC(N)=O)NC(=O)[C@H](C)N(C)C(=O)[C@H](Cc2ccc(O)cc2)NC(=O)CSC[C@@H](C(=O)NCC(N)=O)NC(=O)[C@H](C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 35.0 mg, and its estimated purity by LCMS analysis was 100%.

Analysis condition A: Retention time=1.68 min; ESI-MS (+) m/z=910.8 (M+2H)

Analysis condition B: Retention time=2.78 min; ESI-MS (+) m/z=910.7 (M+2H)

Preparation of Example 7021

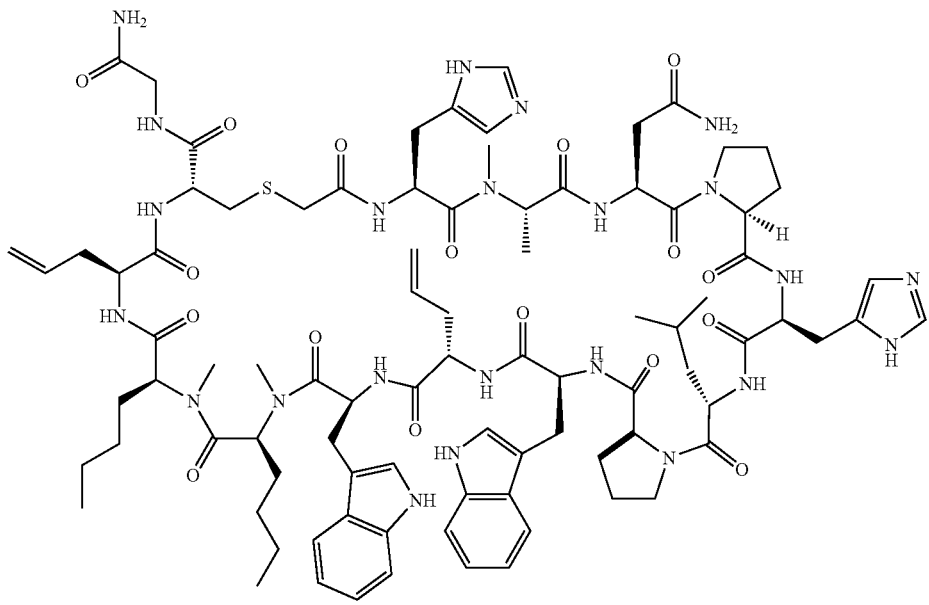 [SMILES: C=CC[C@@H]1NC(=O)[C@H](Cc2c[nH]c3ccccc23)NC(=O)[C@@H]2CCCN2C(=O)[C@H](CC(C)C)NC(=O)[C@H](Cc2cnc[nH]2)NC(=O)[C@@H]2CCCN2C(=O)[C@H](CC(N)=O)NC(=O)[C@H](C)N(C)C(=O)[C@H](Cc2cnc[nH]2)NC(=O)CSC[C@@H](C(=O)NCC(N)=O)NC(=O)[C@H](CC=C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 44.2 mg, and its estimated purity by LCMS analysis was 100%.

Analysis condition A: Retention time=1.73 min; ESI-MS (+) m/z=910.8 (M+2H)

Analysis condition B: Retention time=2.78 min; ESI-MS (+) m/z=910.7 (M+2H)

Preparation of Example 7022

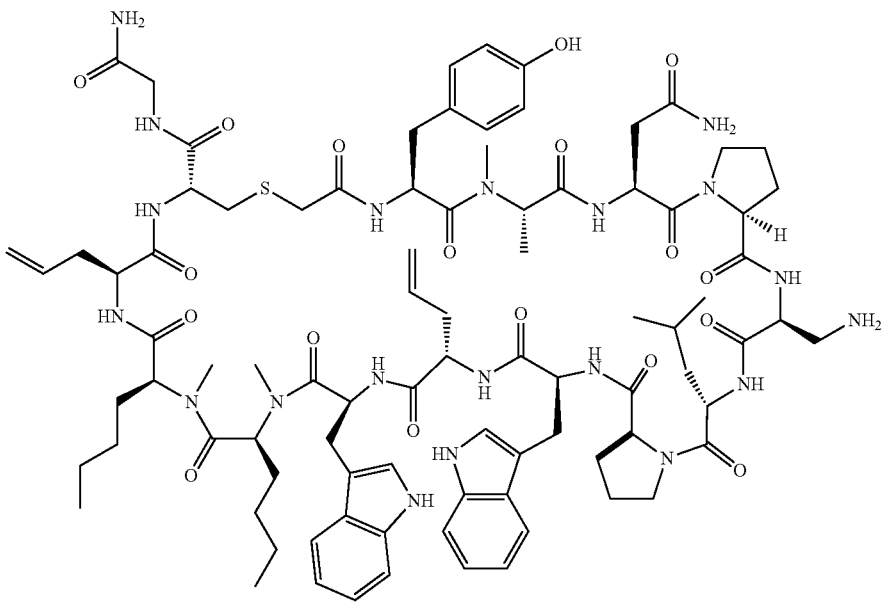 [SMILES: C=CC[C@@H]1NC(=O)[C@H](Cc2c[nH]c3ccccc23)NC(=O)[C@@H]2CCCN2C(=O)[C@H](CC(C)C)NC(=O)[C@H](CN)NC(=O)[C@@H]2CCCN2C(=O)[C@H](CC(N)=O)NC(=O)[C@H](C)N(C)C(=O)[C@H](Cc2ccc(O)cc2)NC(=O)CSC[C@@H](C(=O)NCC(N)=O)NC(=O)[C@H](CC=C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min.

The material was further purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 98%.

Analysis condition A: Retention time=1.73 min; ESI-MS (+) m/z=898.2 (M+2H)

Analysis condition B: Retention time=2.82 min; ESI-MS (+) m/z=898.3 (M+2H)

Preparation of Example 7023

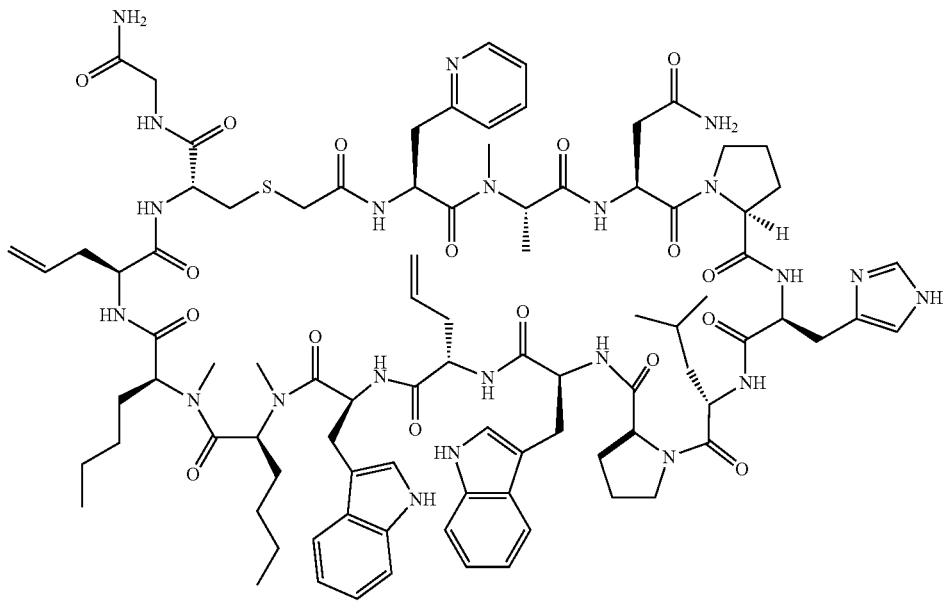 [SMILES: C=CC[C@@H]1NC(=O)[C@H](Cc2c[nH]c3ccccc23)NC(=O)[C@@H]2CCCN2C(=O)[C@H](CC(C)C)NC(=O)[C@H](Cc2c[nH]cn2)NC(=O)[C@@H]2CCCN2C(=O)[C@H](CC(N)=O)NC(=O)[C@H](C)N(C)C(=O)[C@H](Cc2ccccn2)NC(=O)CSC[C@@H](C(=O)NCC(N)=O)NC(=O)[C@H](CC=C)NC(=O)[C@H](CCCC)N(C)C(=O)[C@H](CCCC)N(C)C(=O)[C@H](Cc2c[nH]c3ccccc23)NC1=O]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 20-mM ammonium acetate; Mobile Phase B: 95:5 acetonitrile:water with 20-mM ammonium acetate; Gradient: 10-50% B over 40 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 80%.

Analysis condition A: Retention time=1.76 min; ESI-MS (+) m/z=916.2 (M+2H)

Analysis condition B: Retention time=2.92 min; ESI-MS (+) m/z=916.7 (M+2H)

Preparation of Example 7024

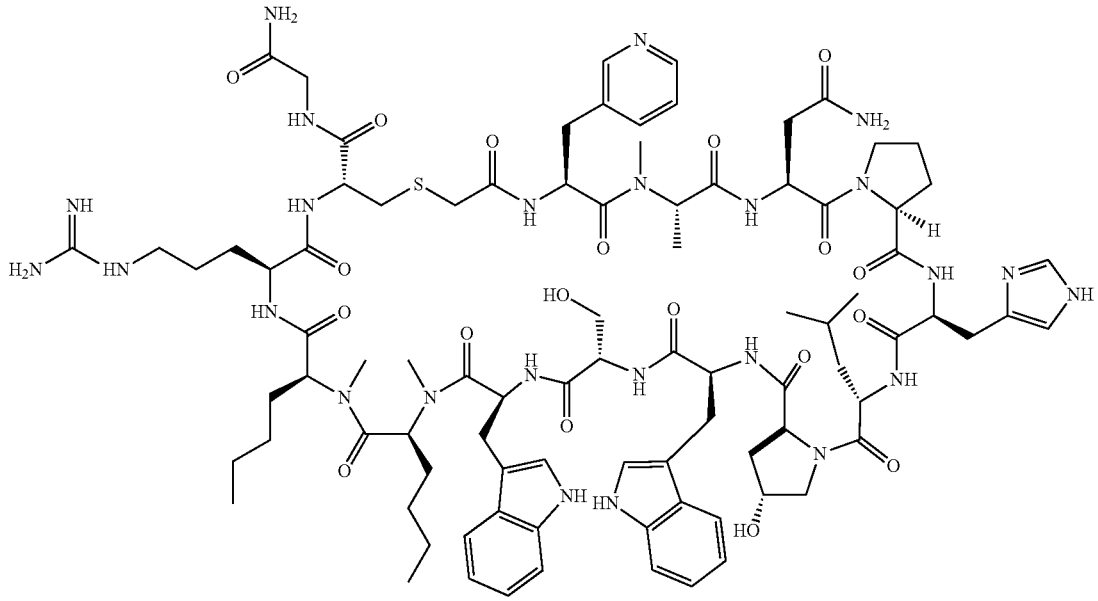 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccnc2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 33.4 mg, and its estimated purity by LCMS analysis was 98%.

Analysis condition A: Retention time=1.47 min; ESI-MS (+) m/z=948.9 (M+2H)

Analysis condition B: Retention time=2.65 min; ESI-MS (+) m/z=948.9 (M+2H)

Preparation of Example 7025

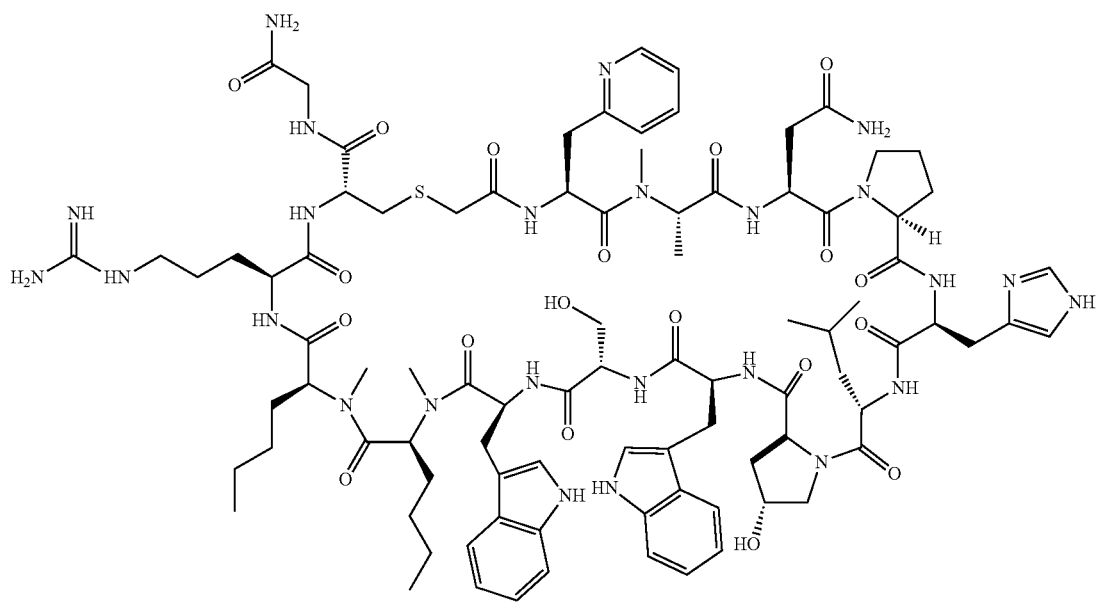 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccccn2)C(=O)N(C)[C@@H](C)C(=O)N[C@@H](CC(N)=O)C(=O)N2CCC[C@H]2C(=O)N[C@@H](Cc2c[nH]cn2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 2.2 mg, and its estimated purity by LCMS analysis was 95.4%.

Analysis condition A: Retention time=1.49 min; ESI-MS (+) m/z=948.7 (M+2H)

Analysis condition B: Retention time=2.70 min; ESI-MS (+) m/z=948.9 (M+2H)

Preparation of Example 7026

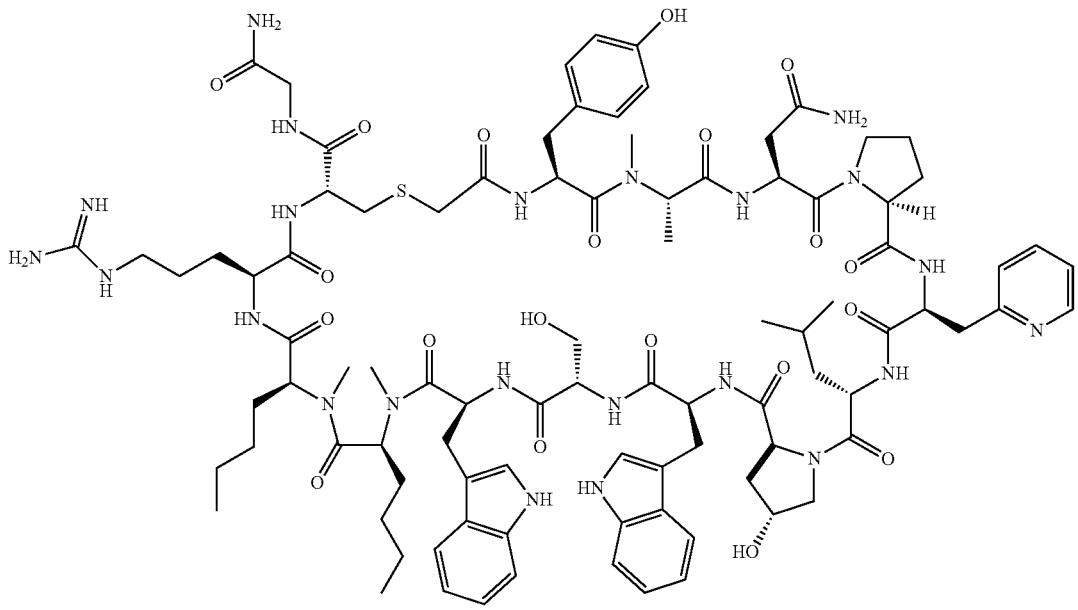 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2ccccn2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min.

The material was further purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 100%.

Analysis condition A: Retention time=1.63 min; ESI-MS (+) m/z=961.4 (M+2H)

Analysis condition B: Retention time=2.68 min; ESI-MS (+) m/z=961.7 (M+2H), 972.6 (M+H+Na)

Preparation of Example 7027

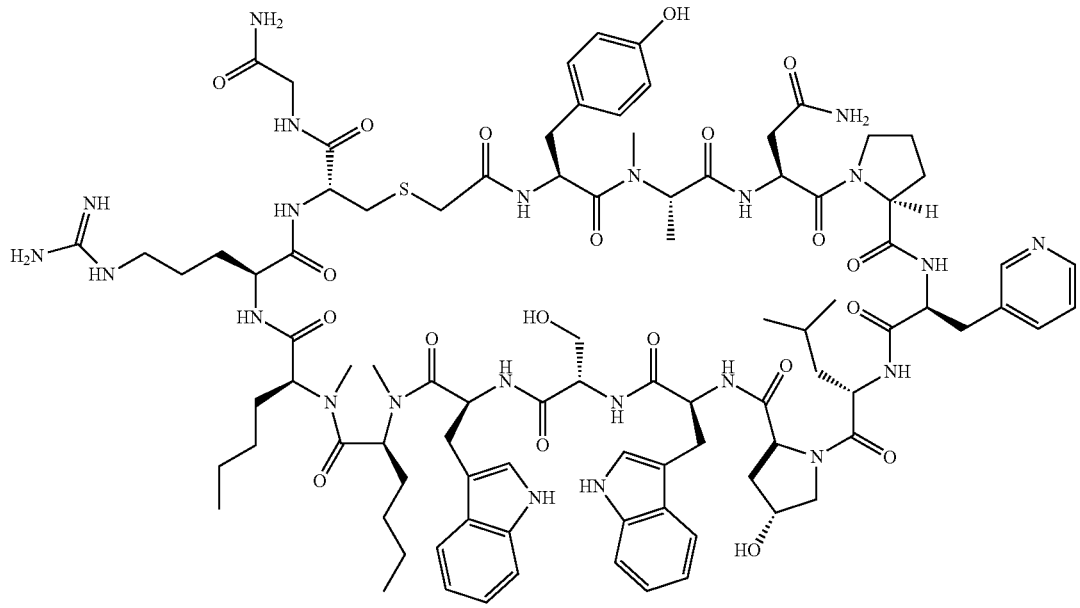 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cccnc2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 31.2 mg, and its estimated purity by LCMS analysis was 100%.

Analysis condition A: Retention time=1.62 min; ESI-MS (+) m/z=961.5 (M+2H)

Analysis condition B: Retention time=2.66 min; ESI-MS (+) m/z=961.9 (M+2H)

Preparation of Example 7028

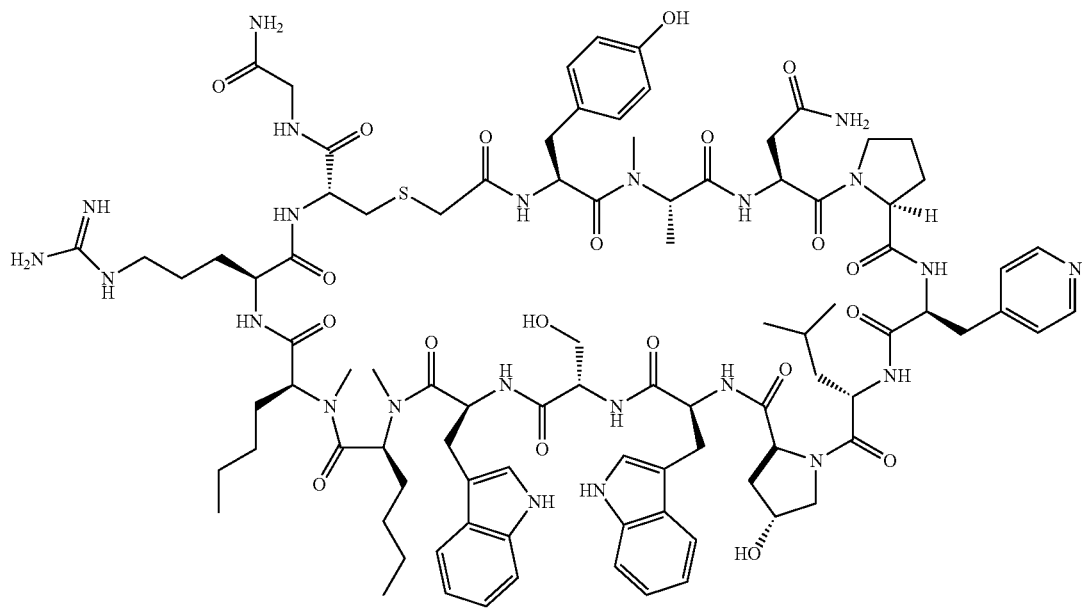 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2ccncc2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 13.1 mg, and its estimated purity by LCMS analysis was 98%.

Analysis condition A: Retention time=1.56 min; ESI-MS (+) m/z=961.4 (M+2H)

Analysis condition B: Retention time=2.62 min; ESI-MS (+) m/z=961.7 (M+2H)

Preparation of Example 7029

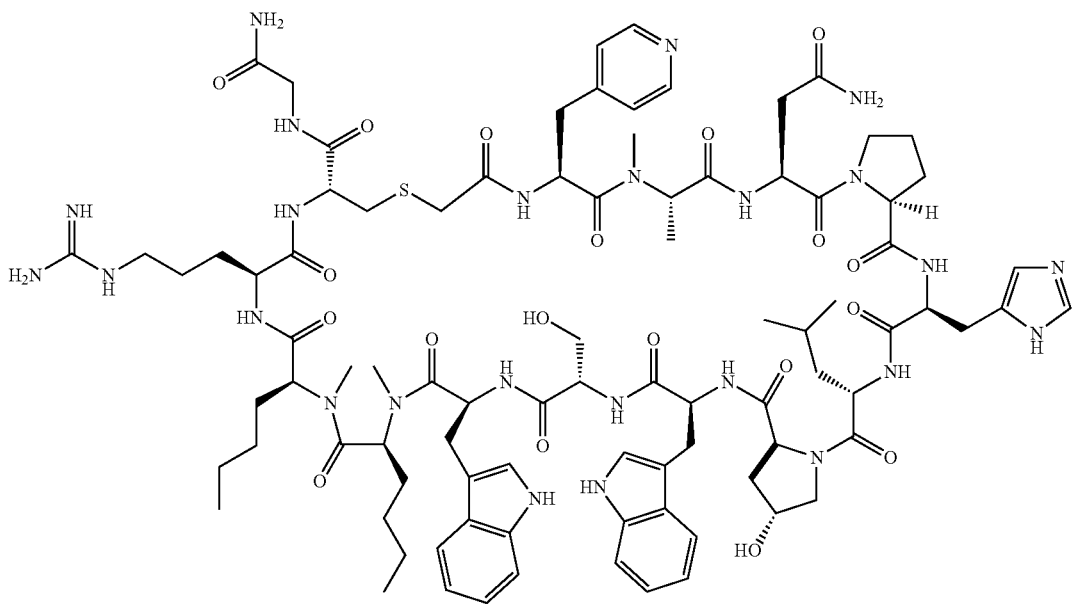 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccncc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 20-60% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-60% B over 30 minutes, then a 5-minute hold at 100% B; Flow: 20 mL/min. Fractions containing the desired product were combined and dried via centrifugal evaporation. The yield of the product was 53.2 mg, and its estimated purity by LCMS analysis was 98.7%.

Analysis condition A: Retention time=1.47 min; ESI-MS (+) m/z=948.8 (M+2H)

Analysis condition B: Retention time=2.63 min; ESI-MS (+) m/z=948.7 (M+2H)

Preparation of Example 7030

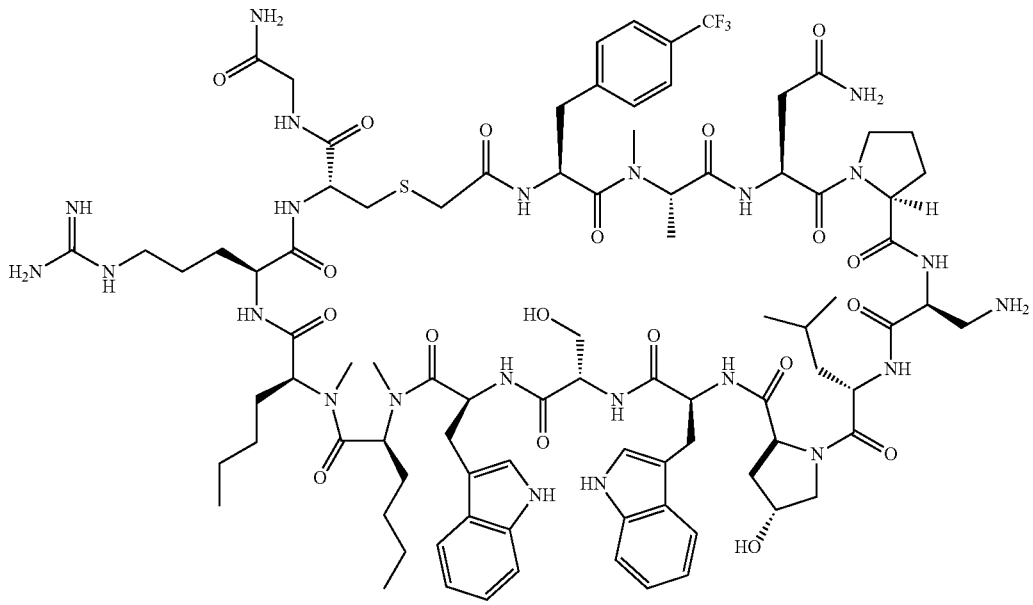 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C(F)(F)F)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 18.8 mg, and its estimated purity by LCMS analysis was 97.8%.

Analysis condition A: Retention time=2.05 min; ESI-MS (+) m/z=956.8 (M+2H)

Analysis condition B: Retention time=3.11 min; ESI-MS (+) m/z=956.8 (M+2H)

ESI-HRMS(+) m/z Calculated 955.9709. Found 955.9667 (M+2H).

Preparation of Example 7031

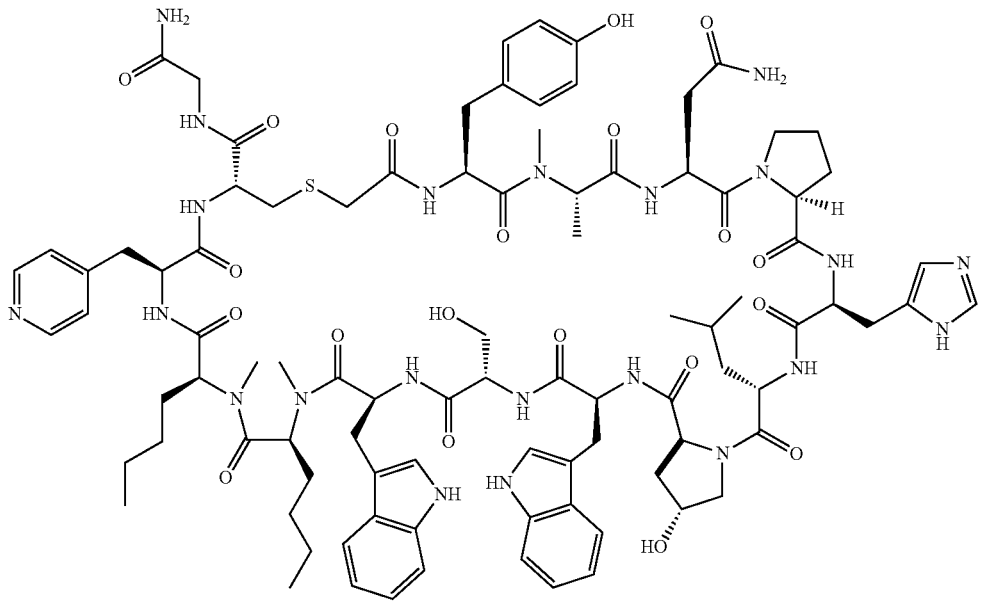

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 25.0 mg, and its estimated purity by LCMS analysis was 91.4%.

Analysis condition A: Retention time=1.59 min; ESI-MS (+) m/z=952.3 (M+2H)

Analysis condition B: Retention time=2.59 min; ESI-MS (+) m/z=952.1 (M+2H), 971.7 (M+MeCN+2H).

ESI-HRMS(+) m/z Calculated 951.4614. Found 951.4591 (M+2H).

Preparation of Example 7032

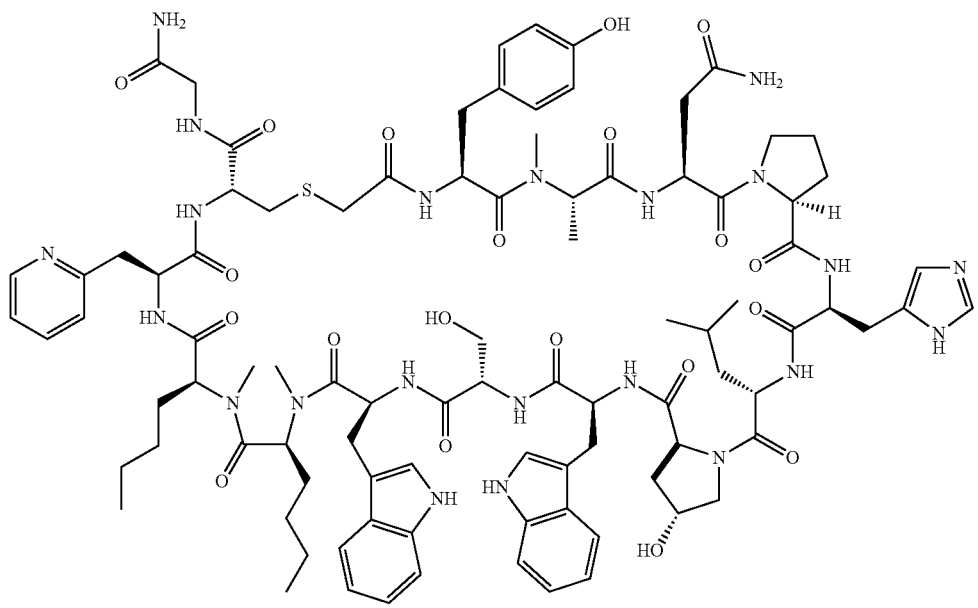 [SMILES: CCCC[C@H]1C(=O)N(C)[C@@H](CCCC)C(=O)N[C@@H](Cc2ccccn2)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min.

The material was further purified via preparative LC/MS with the following conditions: Column: XBridge C18, 5 µm, 19×200 mm, Mobile Phase A: 5:95 methanol:water with 20-mM ammonium acetate; Mobile Phase B: 95:5 methanol:water with 20-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.2 mg, and its estimated purity by LCMS analysis was 98.8%.

Analysis condition A: Retention time=1.61 min; ESI-MS (+) m/z=951.6 (M+2H)

Analysis condition B: Retention time=2.64 min; ESI-MS (+) m/z=951.8 (M+2H)

ESI-HRMS(+) m/z Calculated 951.4614. Found 951.4587 (M+2H).

Preparation of Example 7033

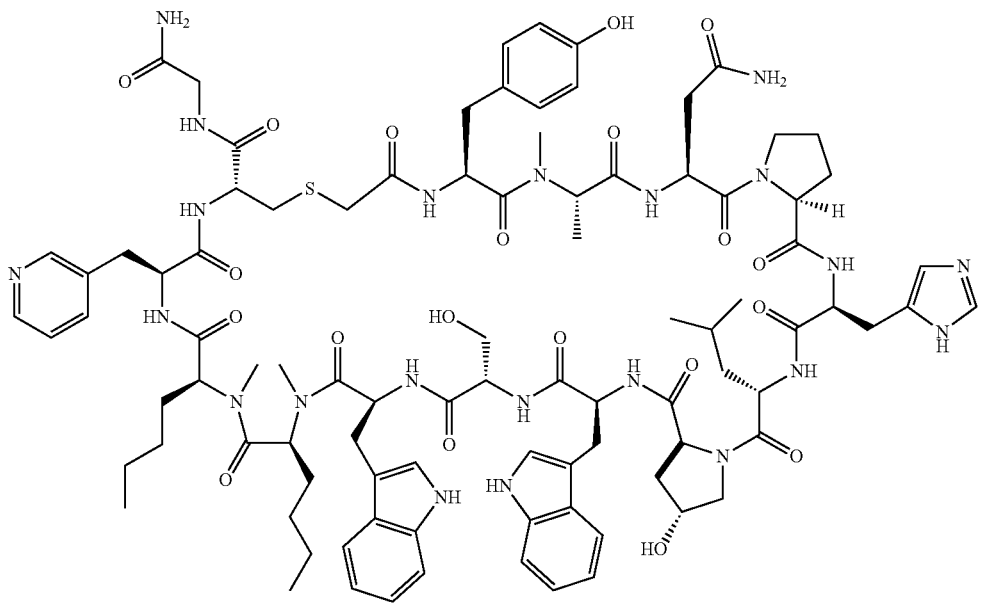 [SMILES: CCCC[C@H]1C(=O)N(C)[C@@H](CCCC)C(=O)N[C@@H](Cc2cccnc2)C(=O)N[C@H](C(=O)NCC(N)=O)CSCC(=O)N[C@@H](Cc2ccc(O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 methanol:water with 20-mM ammonium acetate; Mobile Phase B: 95:5 methanol:water with 20-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 98.5%.

Analysis condition A: Retention time=2.05 min; ESI-MS (+) m/z=952.3 (M+2H)

Analysis condition B: Retention time=3.11 min; ESI-MS (+) m/z=951.5 (M+2H), 972.0 (M+MeCN+2H).

ESI-HRMS(+) m/z Calculated 951.4614. Found 951.4590 (M+2H).

Preparation of Example 7034

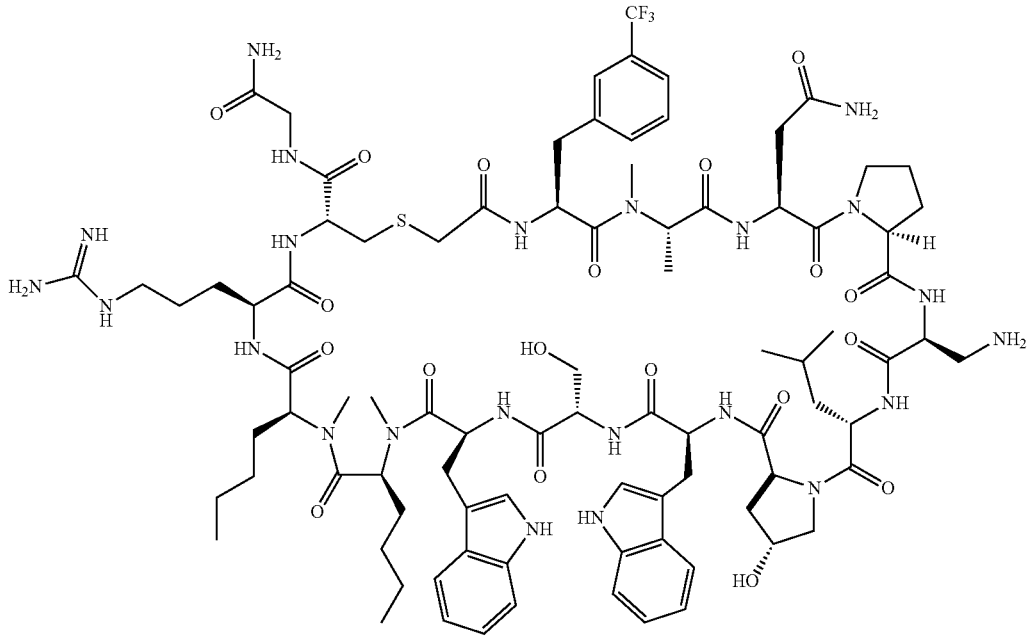 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(C(F)(F)F)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 38.1 mg, and its estimated purity by LCMS analysis was 100%.

Analysis condition A: Retention time=2.55 min; ESI-MS (+) m/z=955.7 (M+2H)

Analysis condition B: Retention time=3.02 min; ESI-MS (+) m/z=955.7 (M+2H) ESI-HRMS(+) m/z Calculated 955.9709. Found 955.9679 (M+2H).

Preparation of Example 7035

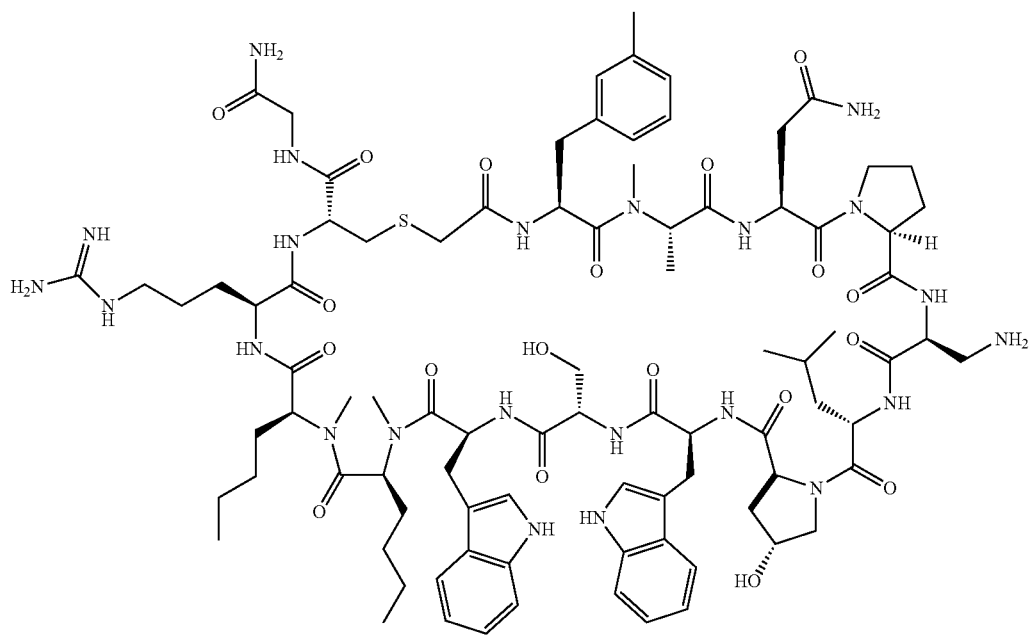 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(C)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 37.2 mg, and its estimated purity by LCMS analysis was 100%.

Analysis condition A: Retention time=2.02 min; ESI-MS (+) m/z=928.9 (M+2H)

Analysis condition B: Retention time=3.04 min; ESI-MS (+) m/z=928.7 (M+2H), 940.6 (M+H+Na)

ESI-HRMS(+) m/z Calculated 928.9851. Found 928.9822 (M+2H).

Preparation of Example 7036

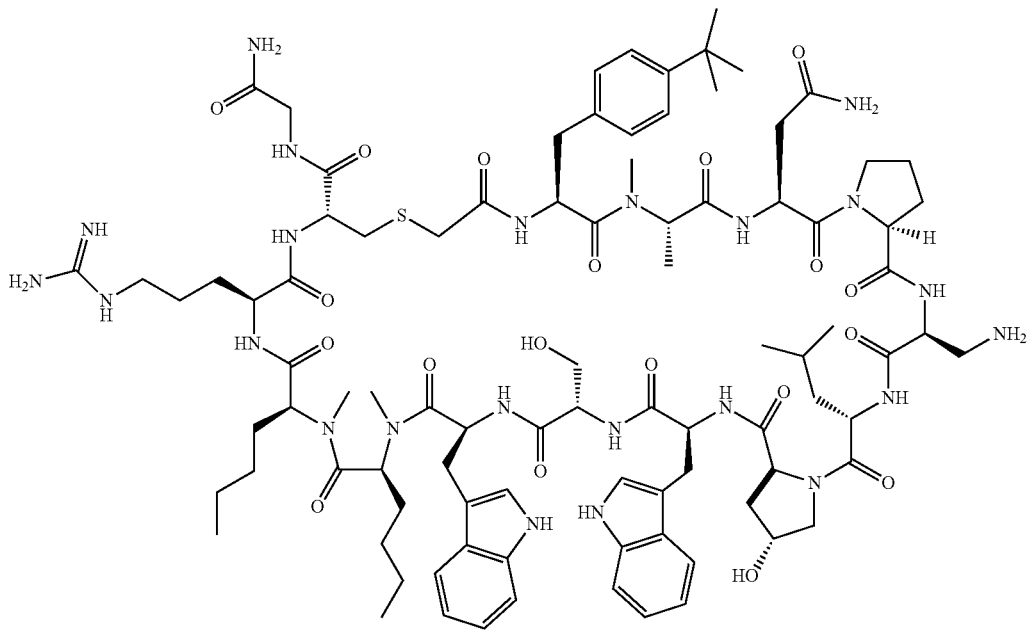 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C(C)(C)C)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 36.3 mg, and its estimated purity by LCMS analysis was 100%.

Analysis condition A: Retention time=2.21 min; ESI-MS (+) m/z=950.4 (M+2H)

Analysis condition B: Retention time=3.17 min; ESI-MS (+) m/z=950.5 (M+2H) ESI-HRMS(+) m/z Calculated 950.0085. Found 950.0054 (M+2H).

Preparation of Example 7037

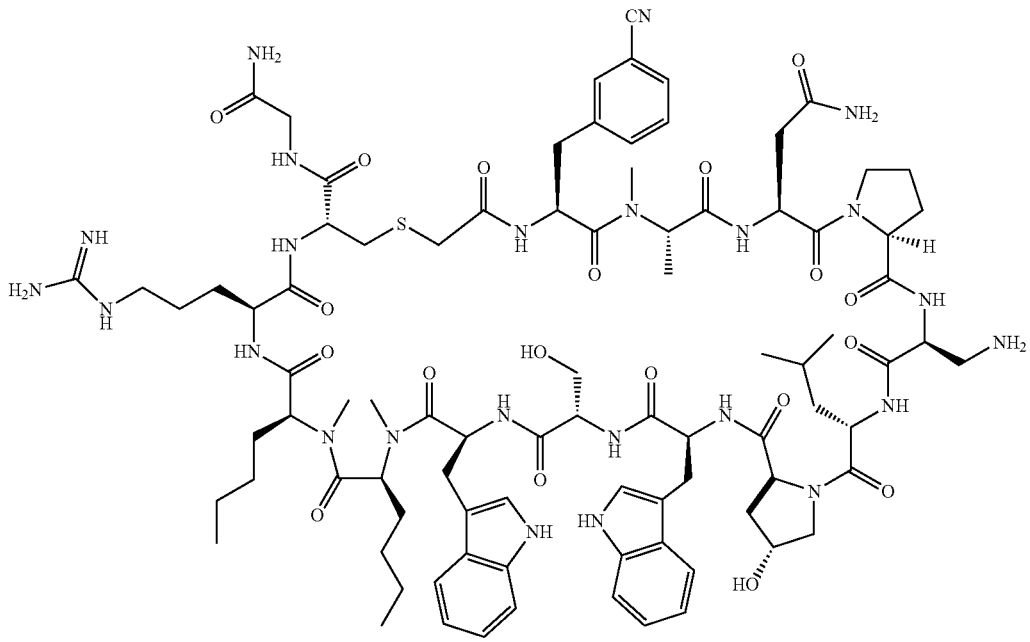

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 35.7 mg, and its estimated purity by LCMS analysis was 100%.

Analysis condition A: Retention time=1.76 min; ESI-MS (+) m/z=934.8 (M+2H)

Analysis condition B: Retention time=2.76 min; ESI-MS (+) m/z=935.2 (M+2H), 945.7 (M+H+Na).

ESI-HRMS(+) m/z Calculated 934.4749. Found 934.4719 (M+2H).

Preparation of Example 7038

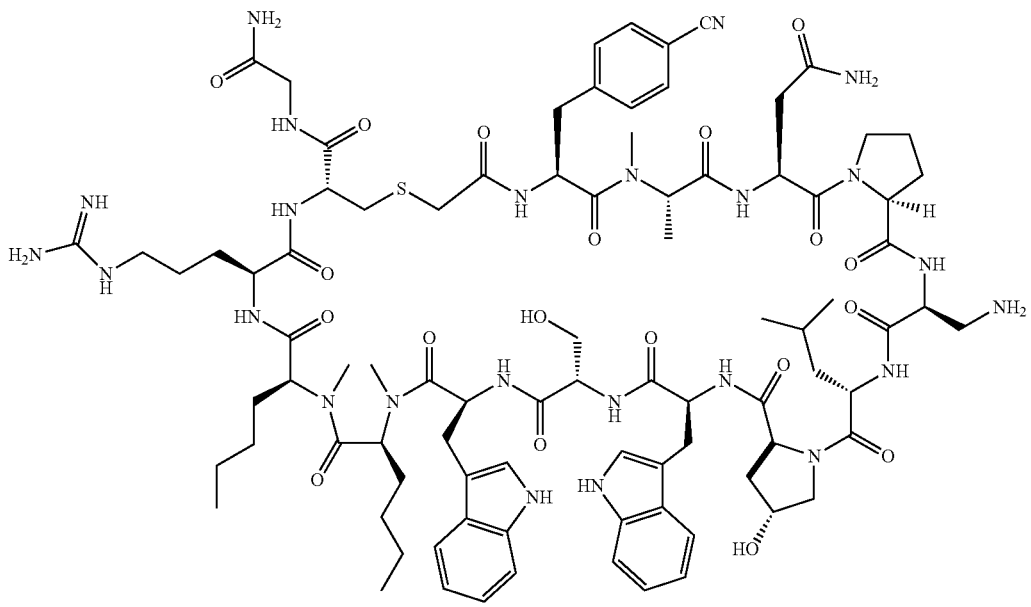 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C#N)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 40.2 mg, and its estimated purity by LCMS analysis was 100%.

Analysis condition A: Retention time=1.74 min; ESI-MS (+) m/z=934.8 (M+2H)

Analysis condition B: Retention time=2.76 min; ESI-MS (+) m/z=934.8 (M+2H) ESI-HRMS(+) m/z Calculated 934.4749. Found 934.4719 (M+2H).

Preparation of Example 7039

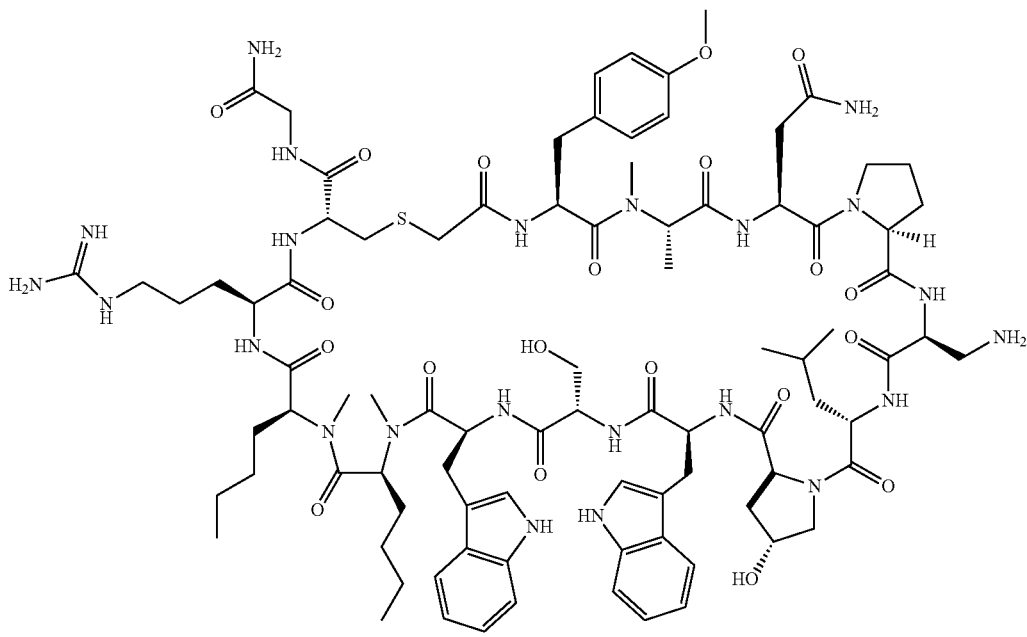 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 35.2 mg, and its estimated purity by LCMS analysis was 100%.

Analysis condition A: Retention time=1.89 min; ESI-MS (+) m/z=937.3 (M+2H)

Analysis condition B: Retention time=2.93 min; ESI-MS (+) m/z=937.3 (M+2H) ESI-HRMS(+) m/z Calculated 936.9825. Found 936.9799 (M+2H).

Preparation of Example 7040

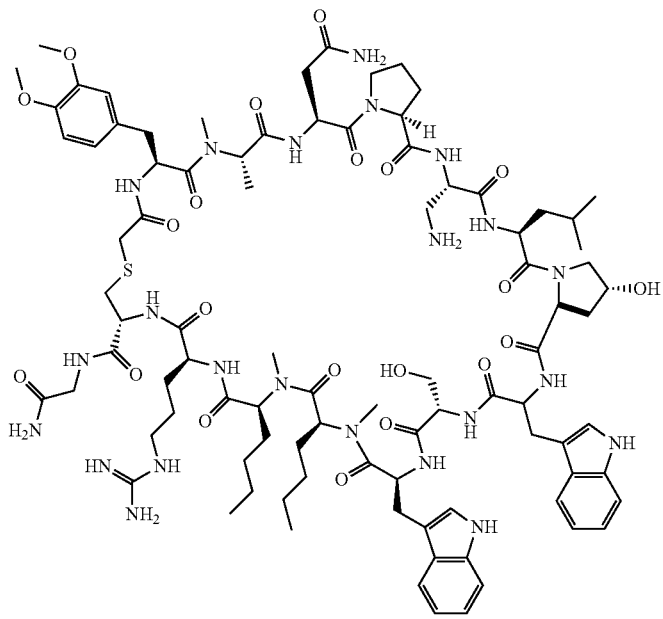 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)c(OC)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)NC(Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 100%.

Analysis condition A: Retention time=1.89 min; ESI-MS (+) m/z=951.7 (M+2H)

Analysis condition B: Retention time=2.79 min; ESI-MS (+) m/z=951.7 (M+2H), 963.8 (M+H+Na).

Preparation of Example 7041

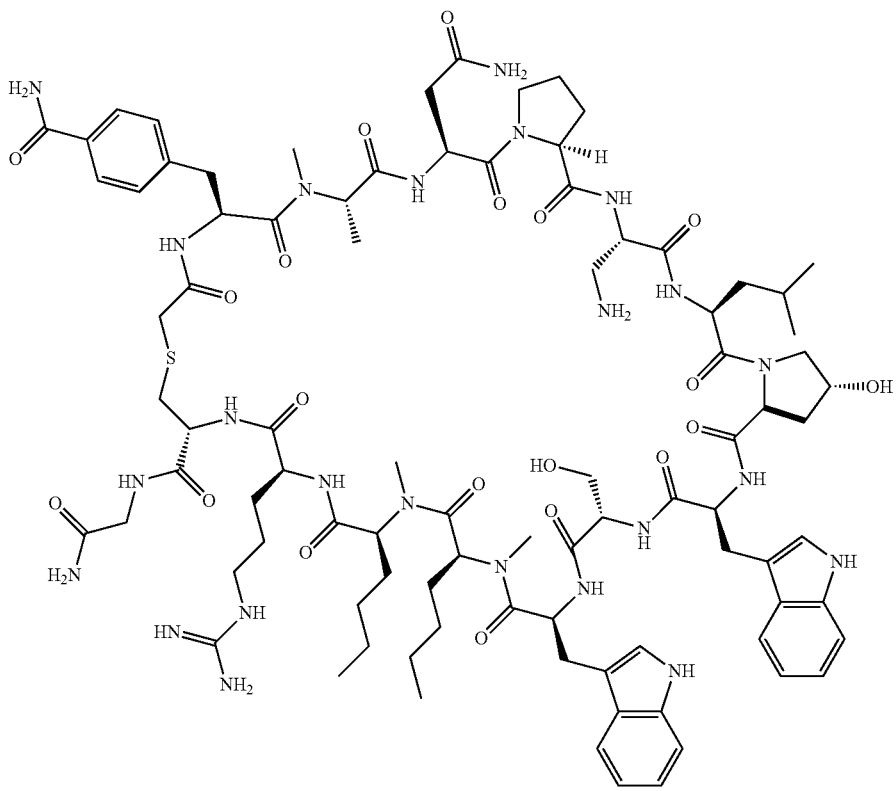 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C(N)=O)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-45% B over 30 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 96%.

Analysis condition A: Retention time=1.36 min; ESI-MS (+) m/z=944.1 (M+2H)

Analysis condition B: Retention time=2.45 min; ESI-MS (+) m/z=944.1 (M+2H).

Preparation of Example 7042

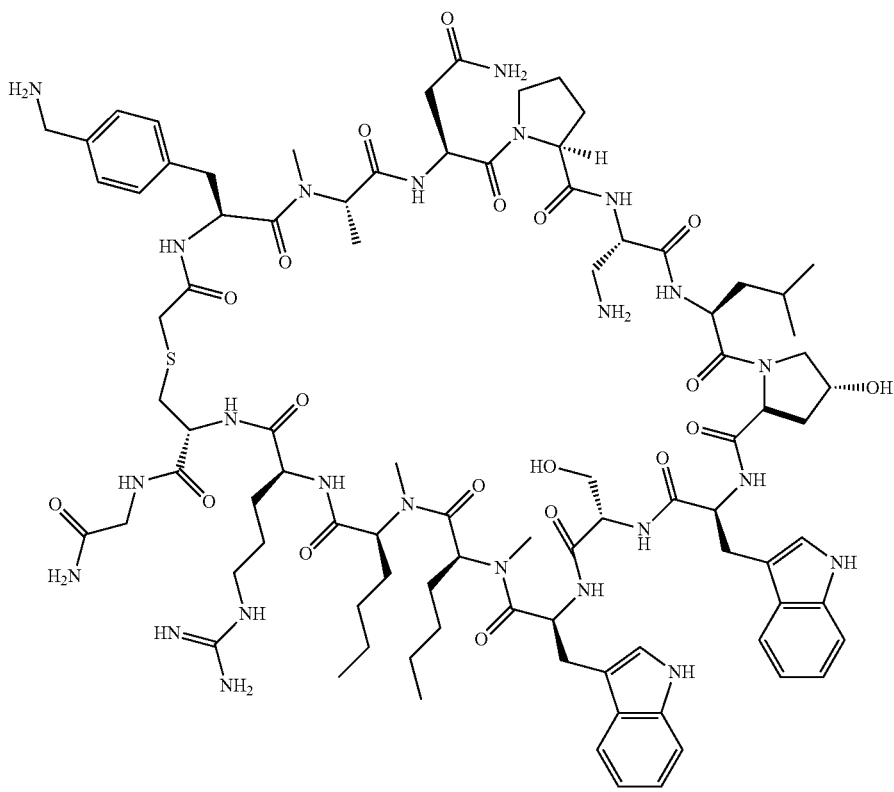 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(CN)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 97%.

Analysis condition A: Retention time=1.32 min; ESI-MS (+) m/z=937.2 (M+2H)

Analysis condition B: Retention time=2.84 min; ESI-MS (+) m/z=937.1 (M+2H).

Preparation of Example 7043

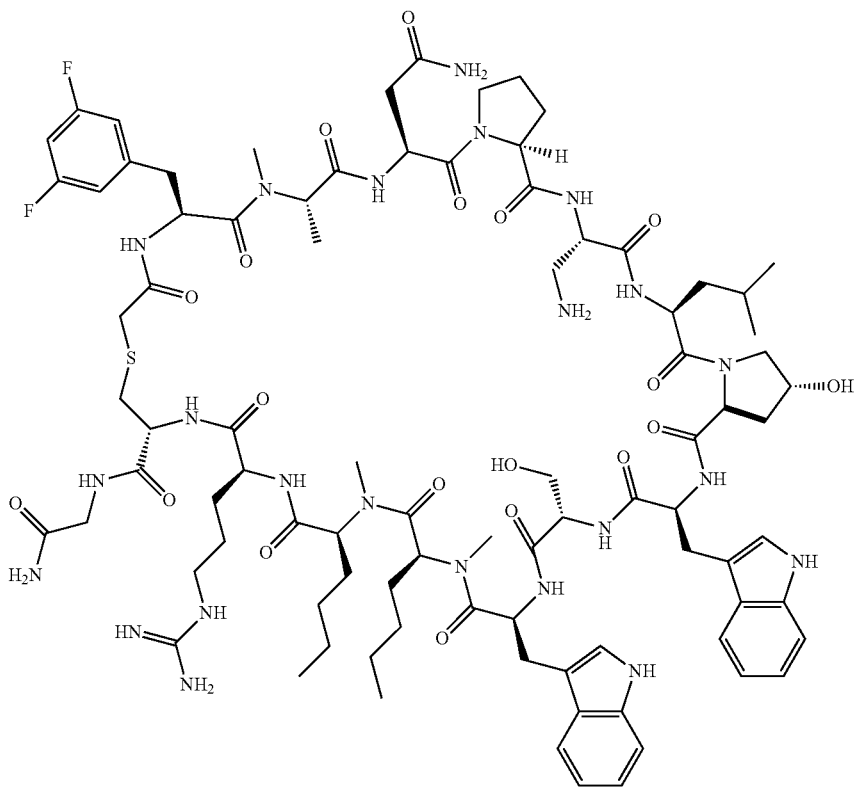 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cc(F)cc(F)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 60-100% B over 30 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 100%.

Analysis condition A: Retention time=1.78 min; ESI-MS (+) m/z=940.7 (M+2H)

Analysis condition B: Retention time=3.01 min; ESI-MS (+) m/z=940.7 (M+2H).

Preparation of Example 7044

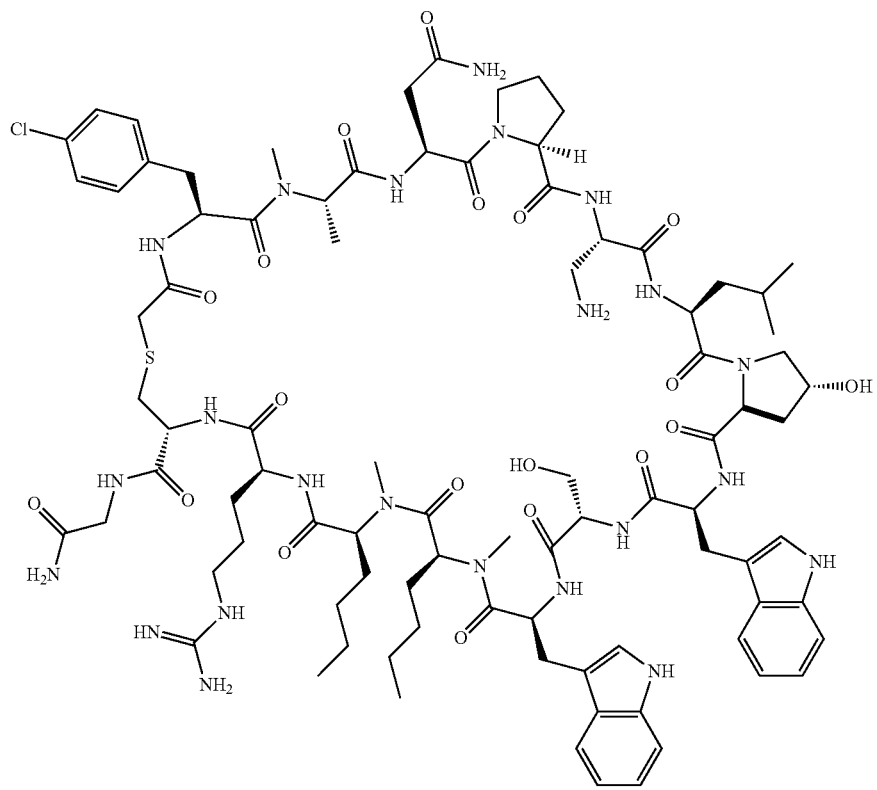 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 18.0 mg, and its estimated purity by LCMS analysis was 99%.

Analysis condition A: Retention time=2.08. min; ESI-MS (+) m/z=939.8 (M+2H)

Analysis condition B: Retention time=3.08 min; ESI-MS (+) m/z=939.3 (M+2H).

Preparation of Example 7045

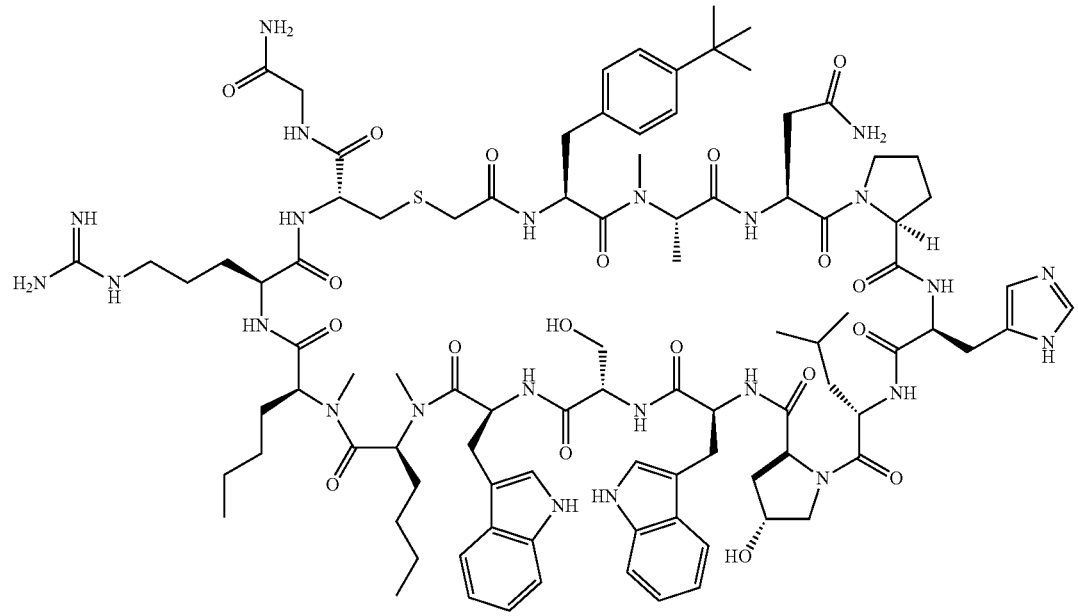 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C(C)(C)C)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 98%.

Analysis condition A: Retention time=2.18 min; ESI-MS (+) m/z=976.4 (M+2H)

Analysis condition B: Retention time=3.13 min; ESI-MS (+) m/z=976.7 (M+2H).

Preparation of Example 7046

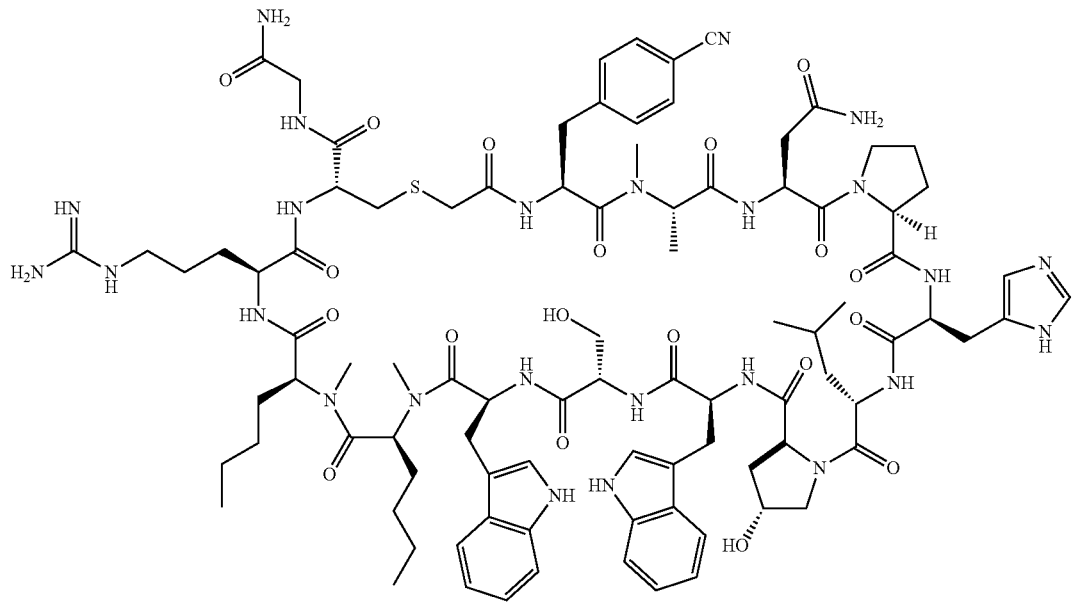 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C#N)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 100%.

Analysis condition A: Retention time=1.80 min; ESI-MS (+) m/z=960.7 (M+2H)

Analysis condition B: Retention time=2.75 min; ESI-MS (+) m/z=960.8 (M+2H).

Preparation of Example 7047

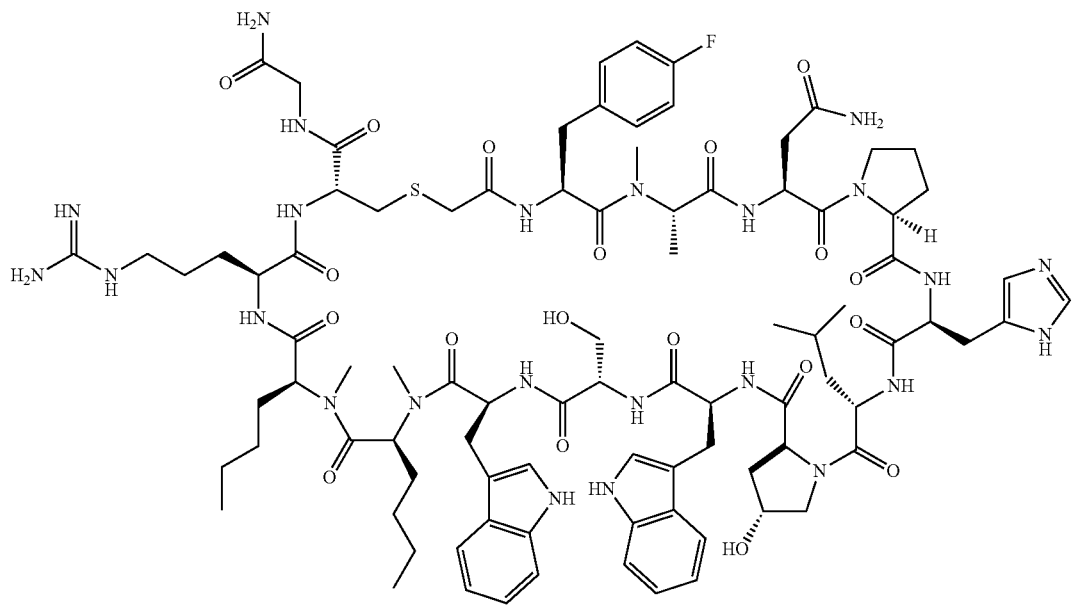

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 20.3 mg, and its estimated purity by LCMS analysis was 98%.

Analysis condition A: Retention time=1.84 min; ESI-MS (+) m/z=957.8 (M+2H)

Analysis condition B: Retention time=2.54 min; ESI-MS (+) m/z=957.9 (M+2H)

Preparation of Example 7048

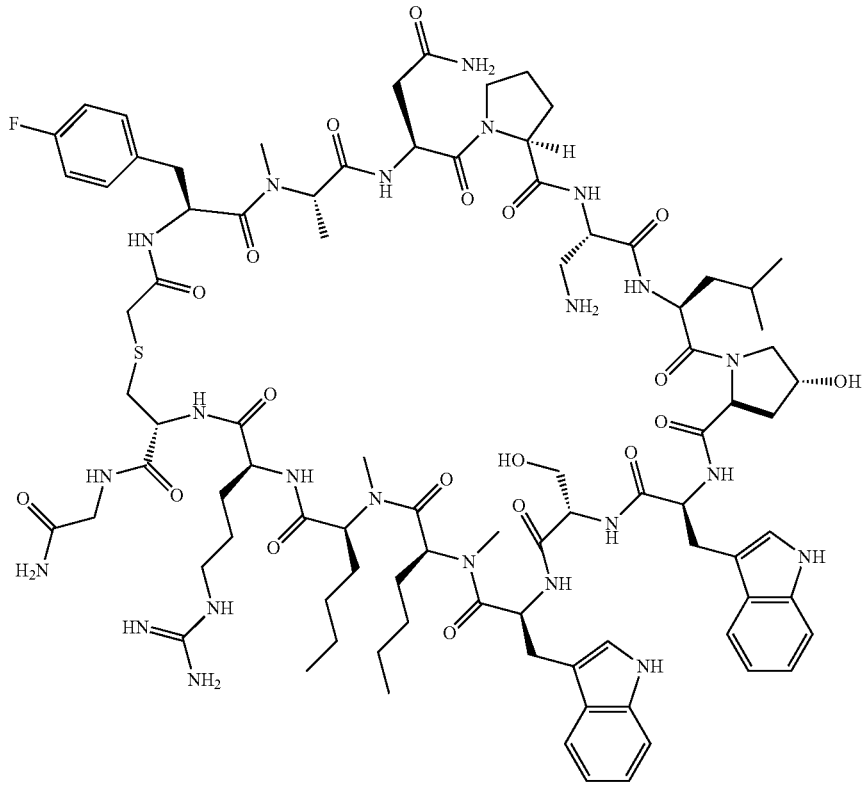 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(F)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 55.7 mg, and its estimated purity by LCMS analysis was 97%.

Analysis condition A: Retention time=1.90 min; ESI-MS (+) m/z=931.8 (M+2H)

Analysis condition B: Retention time=2. min; ESI-MS(+) m/z=931.7 (M+2H).

Preparation of Example 7049

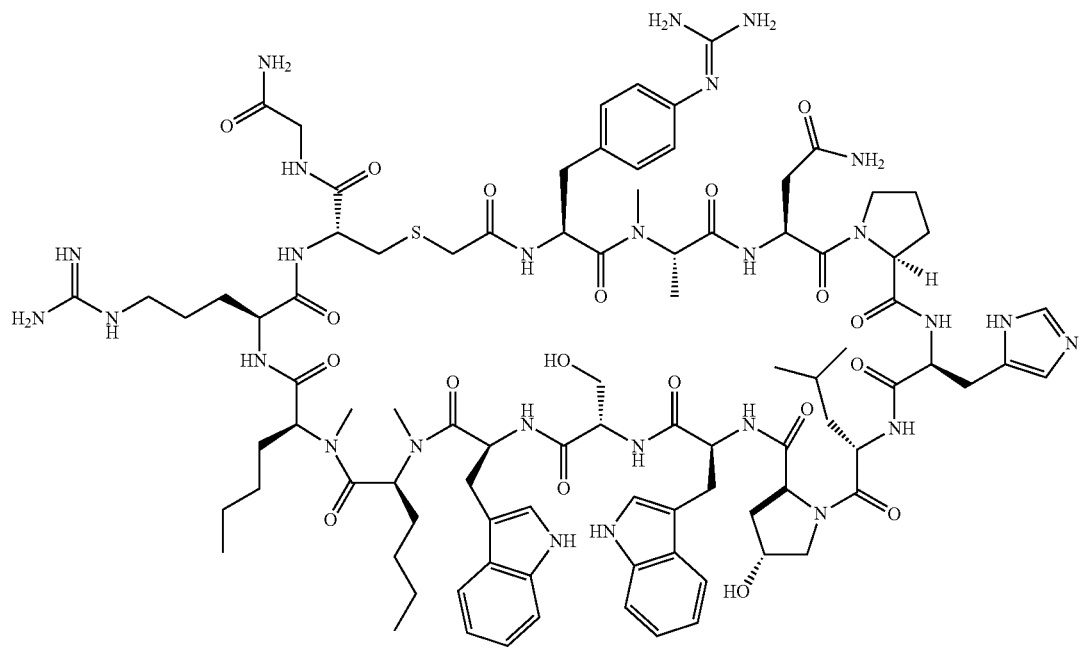 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(N=C(N)N)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 14.8 mg, and its estimated purity by LCMS analysis was 98%.

Analysis condition A: Retention time=1.34 min; ESI-MS (+) m/z=976.8 (M+2H)

Analysis condition B: Retention time=2.40 min; ESI-MS (+) m/z=976.8 (M+2H)

Preparation of Example 7050

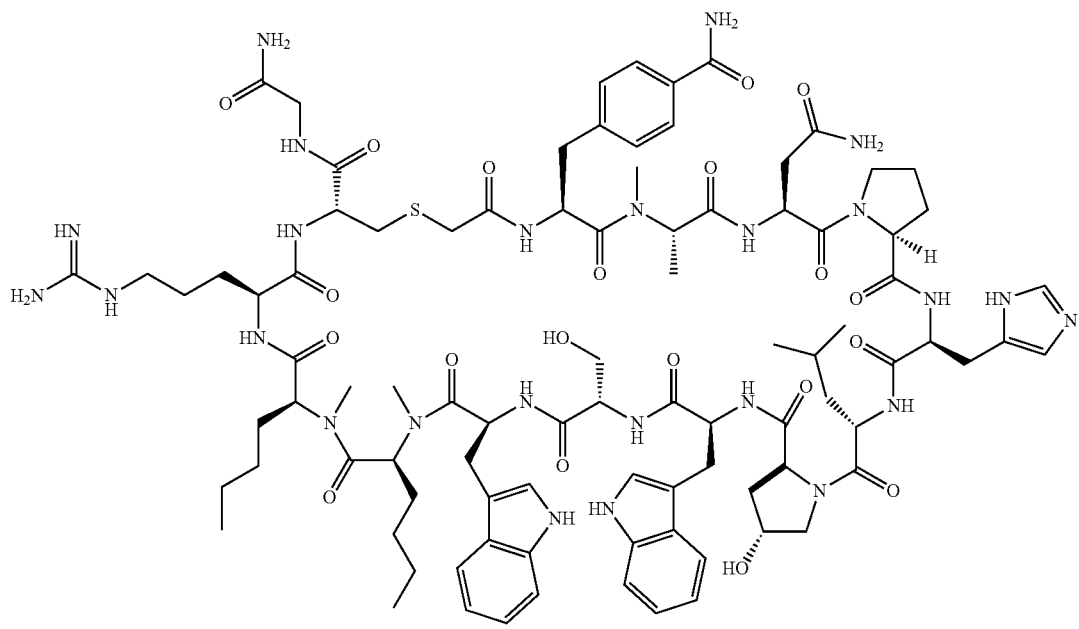 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(C(N)=O)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 14.7 mg, and its estimated purity by LCMS analysis was 96%.

Analysis condition A: Retention time=1.42 min; ESI-MS (+) m/z=969.6 (M+2H)

Analysis condition B: Retention time=2.44 min; ESI-MS (+) m/z=969.8 (M+2H).

Preparation of Example 7051

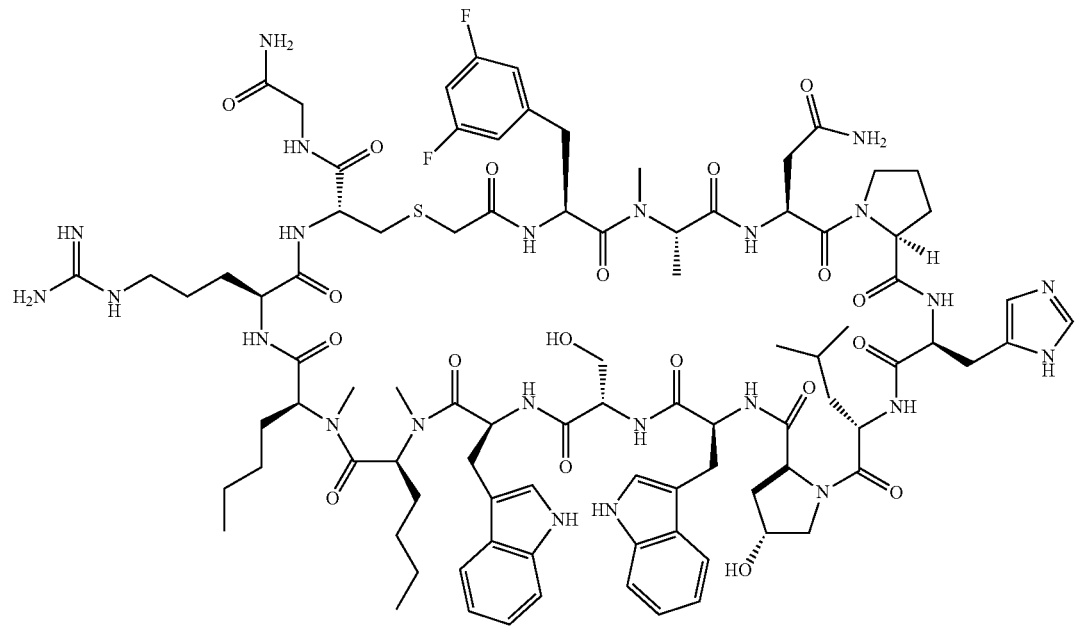 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cc(F)cc(F)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 100%.

Analysis condition A: Retention time=1.83 min; ESI-MS (+) m/z=966.7 (M+2H)

Analysis condition B: Retention time=3.00 min; ESI-MS (+) m/z=966.3 (M+2H).

Preparation of Example 7052

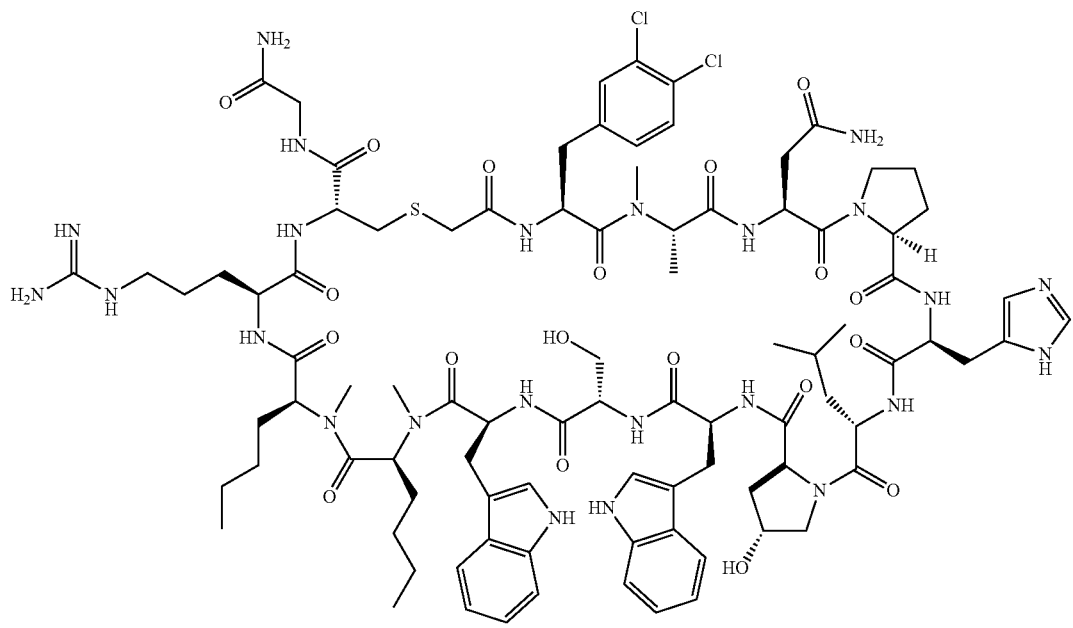 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)c(Cl)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 99%.

Analysis condition A: Retention time=1.95 min; ESI-MS (+) m/z=982.5 (M+2H)

Analysis condition B: Retention time=3.13 min; ESI-MS (+) m/z=982.2 (M+2H).

Preparation of Example 7053

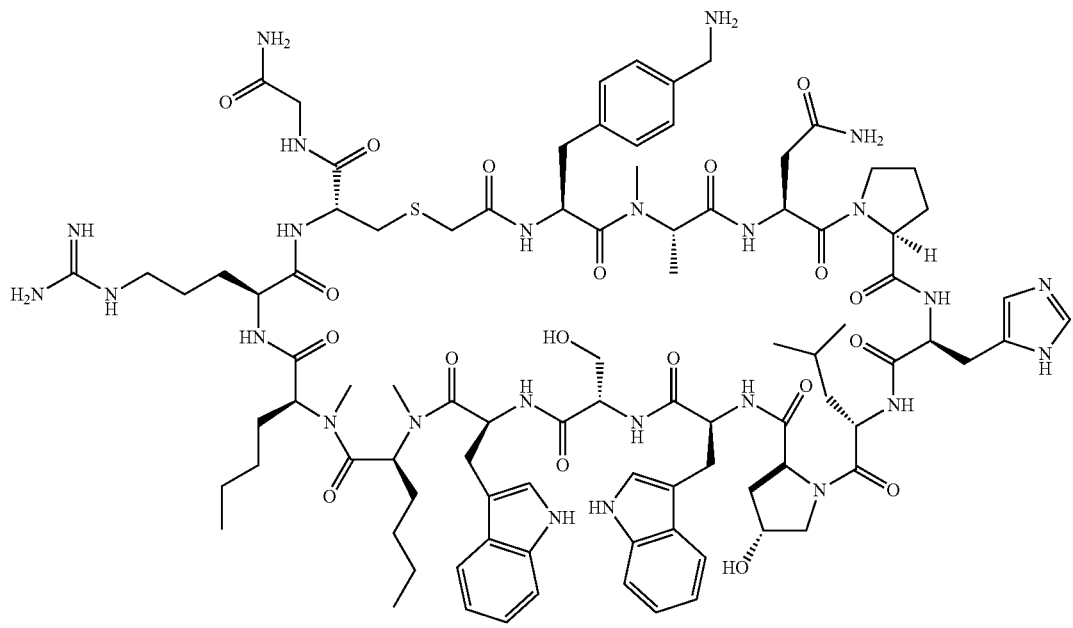 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(CN)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 14.5 mg, and its estimated purity by LCMS analysis was 100%.

Analysis condition A: Retention time=1.53 min; ESI-MS (+) m/z=962.8 (M+2H)

Analysis condition B: Retention time=2.43 min; ESI-MS (+) m/z=962.2 (M+2H).

Preparation of Example 7054

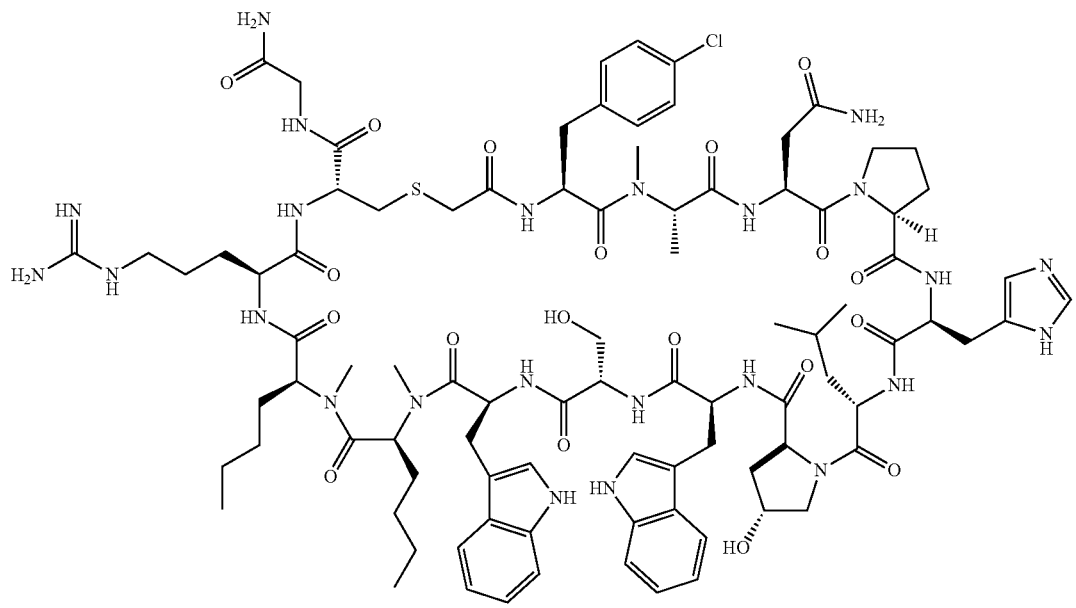

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 12.1 mg, and its estimated purity by LCMS analysis was 98%.

Analysis condition A: Retention time=2.04 min; ESI-MS (+) m/z=965.0 (M+2H)

Analysis condition B: Retention time=3.04 min; ESI-MS (+) m/z=965.4 (M+2H).

Preparation of Example 7055

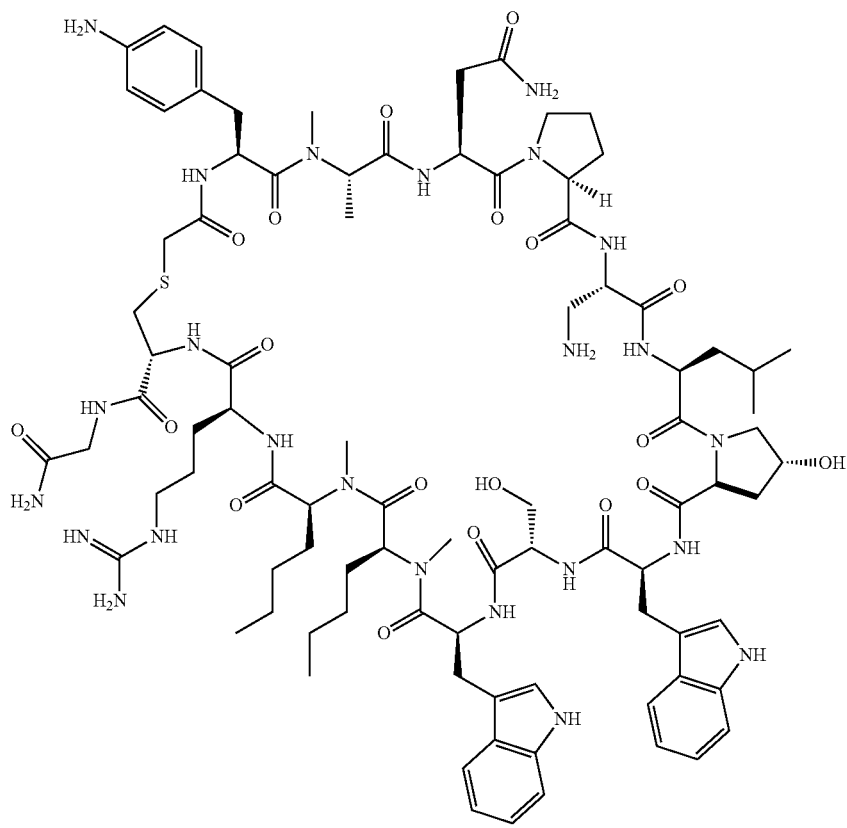 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(N)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. at 100% B; Flow: 20 mL/min. Fractions containing the desired product were combined and dried via centrifugal evaporation. The yield of the product was 14.0 mg, and its estimated purity by LCMS analysis was 95%.

Analysis condition A: Retention time=1.54 min; ESI-MS (+) m/z=930.2 (M+2H)

Analysis condition B: Retention time=2.63 min; ESI-MS (+) m/z=930.2 (M+2H).

Preparation of Example 7056

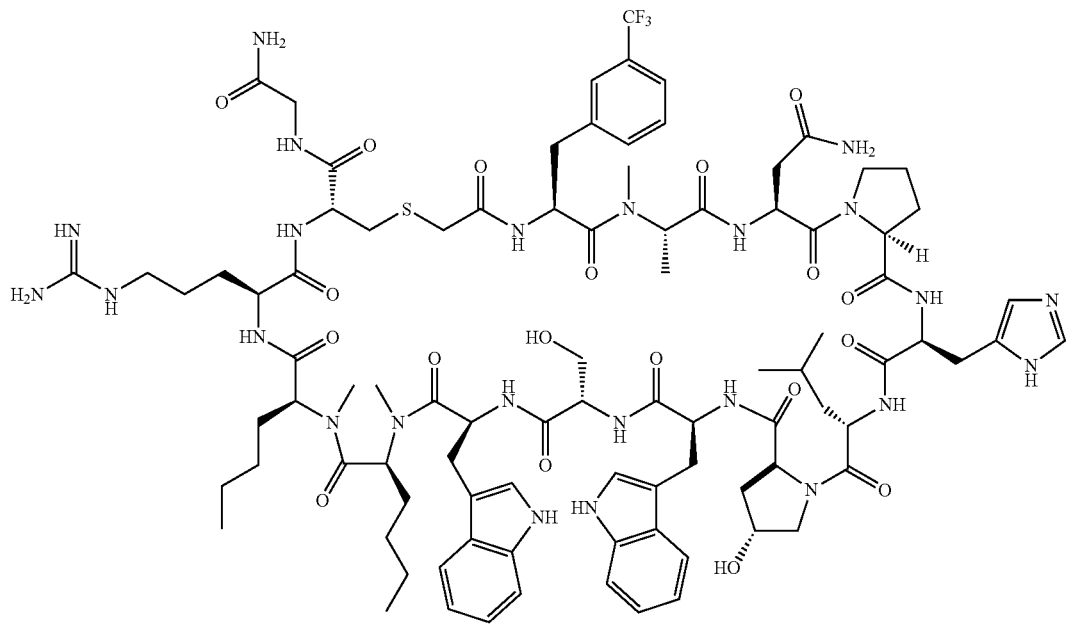 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(C(F)(F)F)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. at 100% B; Flow: 20 mL/min. Fractions containing the desired product were combined and dried via centrifugal evaporation. The yield of the product was 12.5 mg, and its estimated purity by LCMS analysis was 99%.

Analysis condition A: Retention time=1.93 min; ESI-MS (+) m/z=982.2 (M+2H)

Analysis condition B: Retention time=3.07 min; ESI-MS (+) m/z=982.2 (M+2H).

Preparation of Example 7057

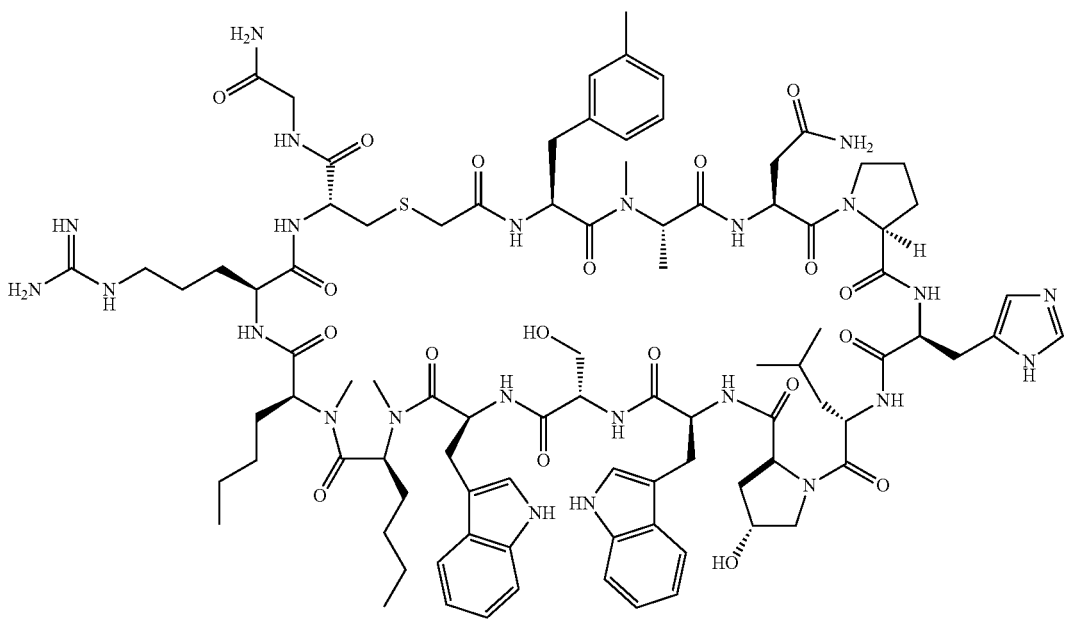 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(C)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 100%.

Analysis condition A: Retention time=1.90 min; ESI-MS (+) m/z=955.1 (M+2H)

Analysis condition B: Retention time=3.90 min; ESI-MS (+) m/z=955.1 (M+2H).

Preparation of Example 7058

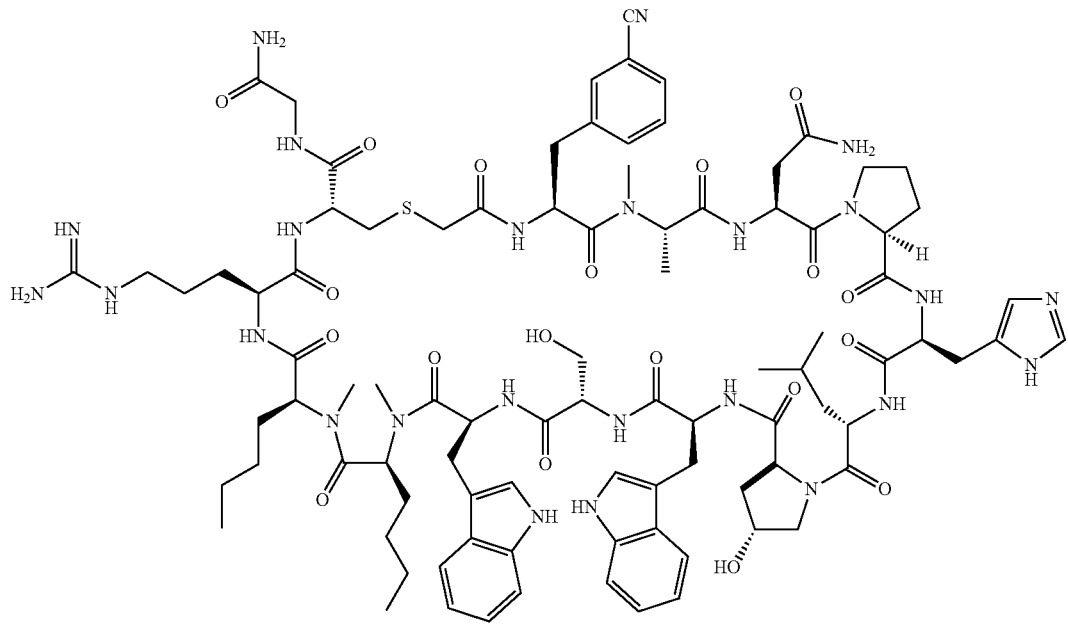 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2cccc(C#N)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. at 100% B; Flow: 20 mL/min. Fractions containing the desired product were combined and dried via centrifugal evaporation. The yield of the product was 21.9 mg, and its estimated purity by LCMS analysis was 99%.

Analysis condition A: Retention time=1. min; ESI-MS(+) m/z=960.4 (M+2H)

Analysis condition B: Retention time=2.78 min; ESI-MS (+) m/z=960.8 (M+2H).

Preparation of Example 7059

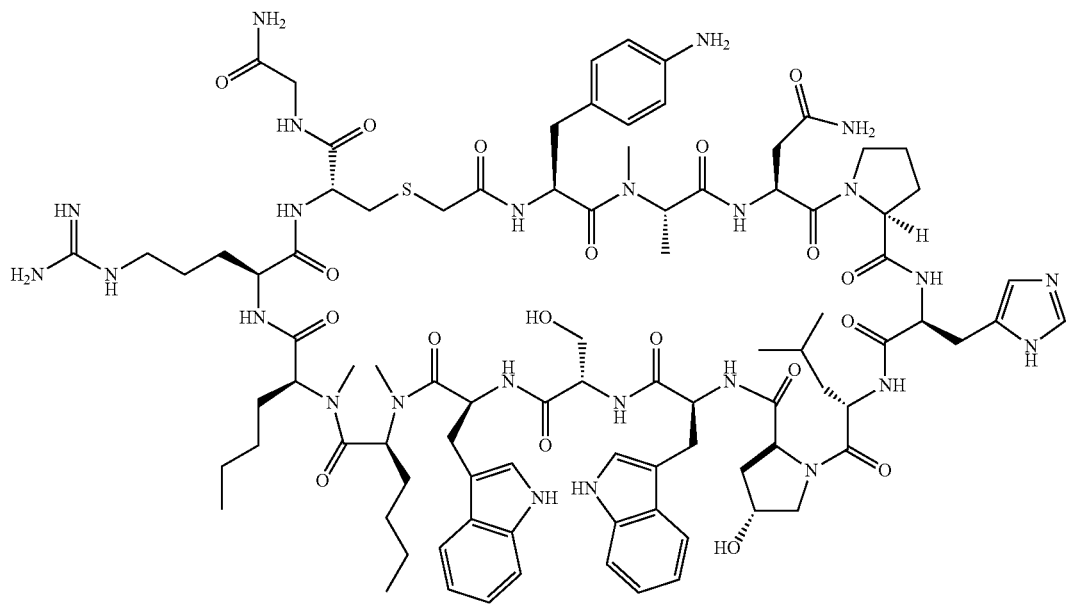 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(N)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. at 100% B; Flow: 20 mL/min. Fractions containing the desired product were combined and dried via centrifugal evaporation. The yield of the product was 15.3 mg, and its estimated purity by LCMS analysis was 99%.

Analysis condition A: Retention time=1.57 min; ESI-MS (+) m/z=955.4 (M+2H)

Analysis condition B: Retention time=2.62 min; ESI-MS (+) m/z=955.9 (M+2H).

Preparation of Example 7060

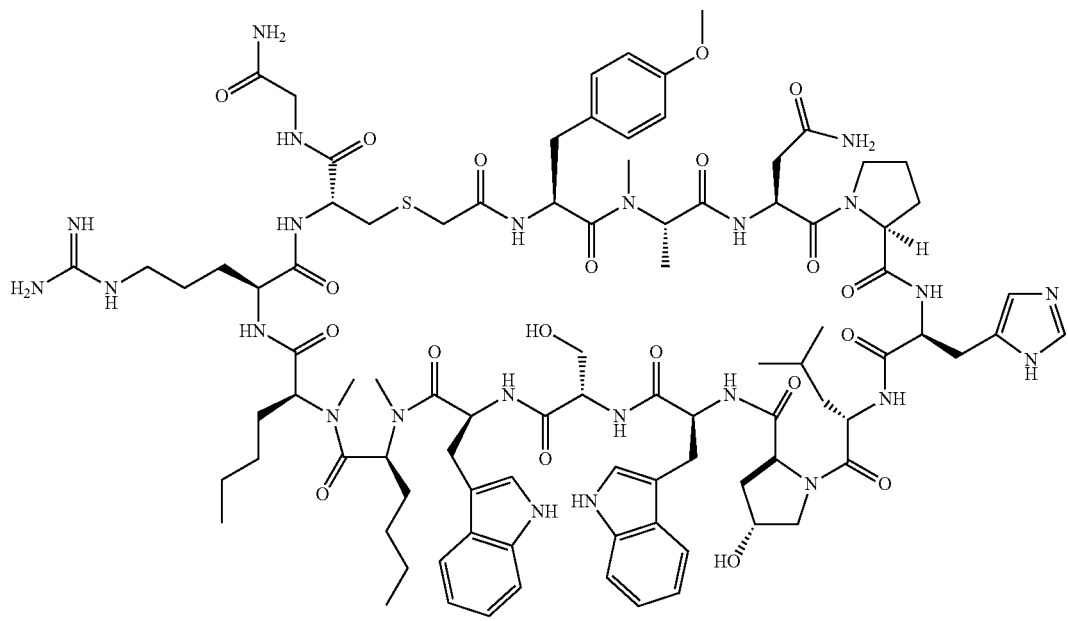 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(OC)cc2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation.

The yield of the product was 14.4 mg, and its estimated purity by LCMS analysis was 100%.

Analysis condition A: Retention time=1.82 min; ESI-MS (+) m/z=963.6 (M+2H)

Analysis condition B: Retention time=2.97 min; ESI-MS (+) m/z=963.3 (M+2H).

Preparation of Example 7061

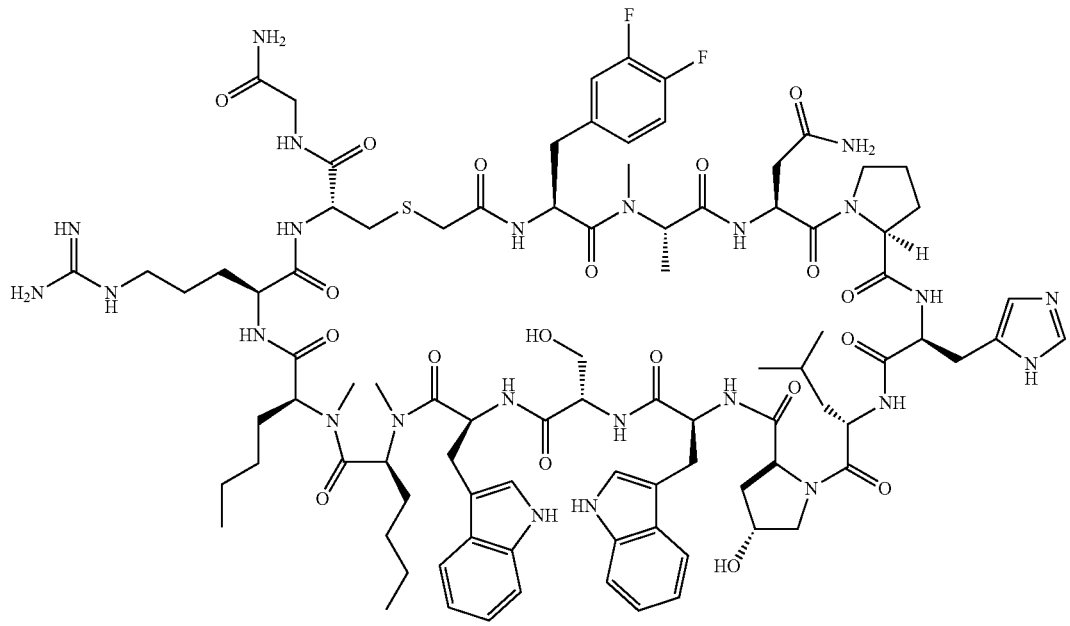 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(F)c(F)c2)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 20.0 mg, and its estimated purity by LCMS analysis was 99%.

Analysis condition A: Retention time=1.83 min; ESI-MS (+) m/z=966.2 (M+2H)

Analysis condition B: Retention time=3.04 min; ESI-MS (+) m/z=966.2 (M+2H).

Preparation of Example 7062

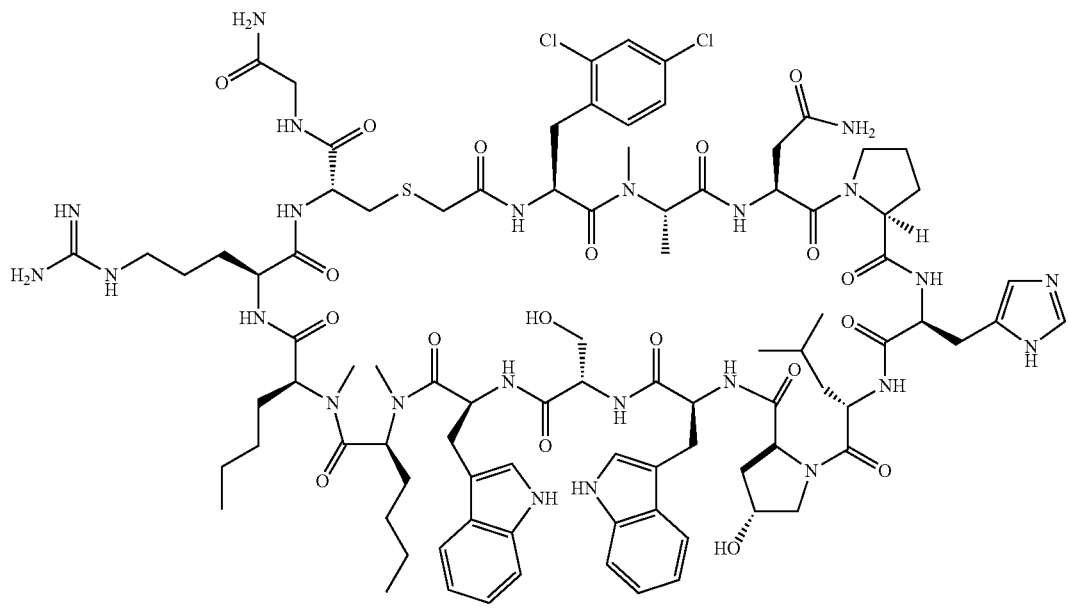 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)cc2Cl)C(=O)N(C)[C@@H](C)C(=O)N[C@@H](CC(N)=O)C(=O)N2CCC[C@H]2C(=O)N[C@@H](Cc2cnc[nH]2)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 µm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 36.8 mg, and its estimated purity by LCMS analysis was 97%.

Analysis condition A: Retention time=1.89 min; ESI-MS (+) m/z=983.1 (M+2H)

Analysis condition B: Retention time=3.11 min; ESI-MS (+) m/z=982.2 (M+2H).

Preparation of Example 7063

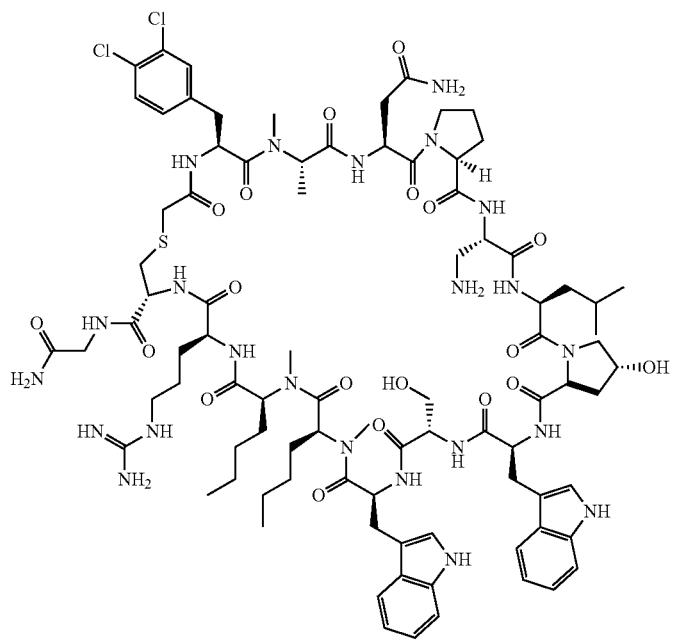 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(Cl)c(Cl)c2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 22.1 mg, and its estimated purity by LCMS analysis was 100%.

Analysis condition A: Retention time=1.92 min; ESI-MS (+) m/z=957.1 (M+2H)

Analysis condition B: Retention time=3.15 min; ESI-MS (+) m/z=957.3 (M+2H).

Preparation of Example 7064

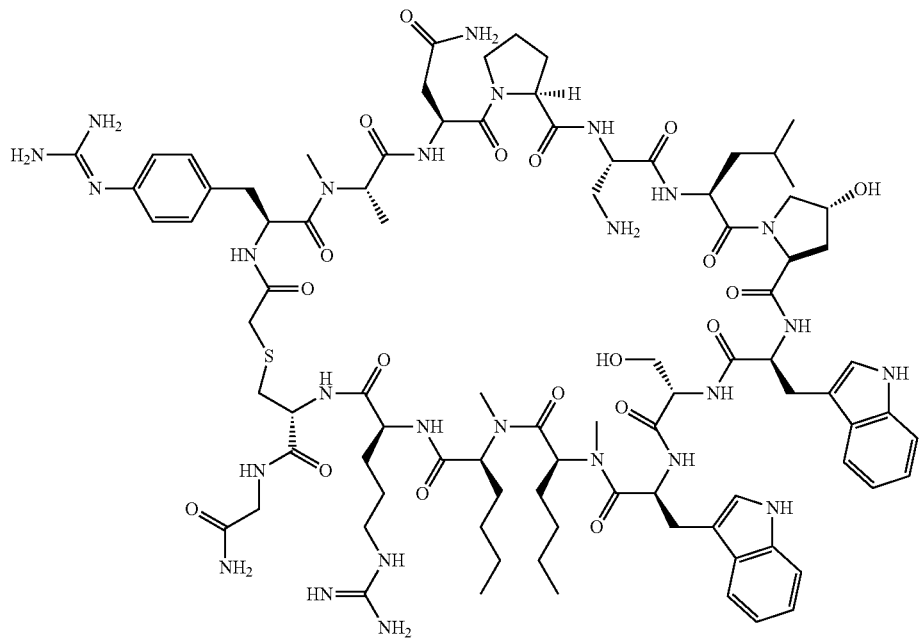 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)N[C@@H](Cc2ccc(N=C(N)N)cc2)C(=O)N(C)[C@@H](C)C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CO)C(=O)N[C@@H](Cc2c[nH]c3ccccc23)C(=O)N1C]

The crude material was purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min.

The material was further purified via preparative LC/MS with the following conditions: Column: XBridge C18, 5 μm, 19×200 mm, Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation.

The yield of the product was 7.7 mg, and its estimated purity by LCMS analysis was 99%.

Analysis condition A: Retention time=1.38 min; ESI-MS (+) m/z=951.0 (M+2H)

Analysis condition B: Retention time=2.40 min; ESI-MS (+) m/z=951.2 (M+2H), 634.5 (M+3H).

Series 9000

All 9000 series examples exemplified below were prepared by following above the "General Synthetic Sequence A"

Preparation of Example 9001

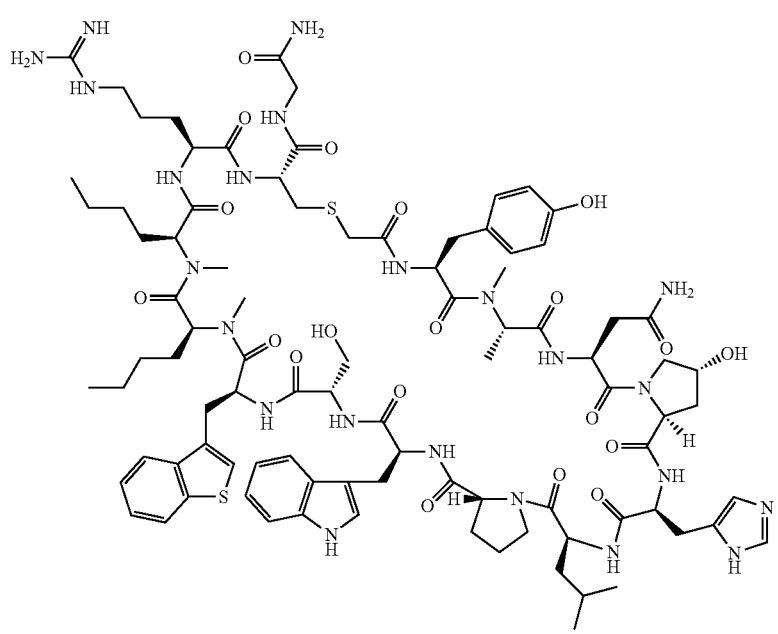

Example 9001

The crude material of Example 9001 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 95%.

Analysis condition A: Retention time=1.60 min; ESI-MS (+) m/z 964.8 (M+2H).

Analysis condition B: Retention time=2.77 min; ESI-MS (+) m/z 964.8 (M+2H).

Preparation of Example 9002

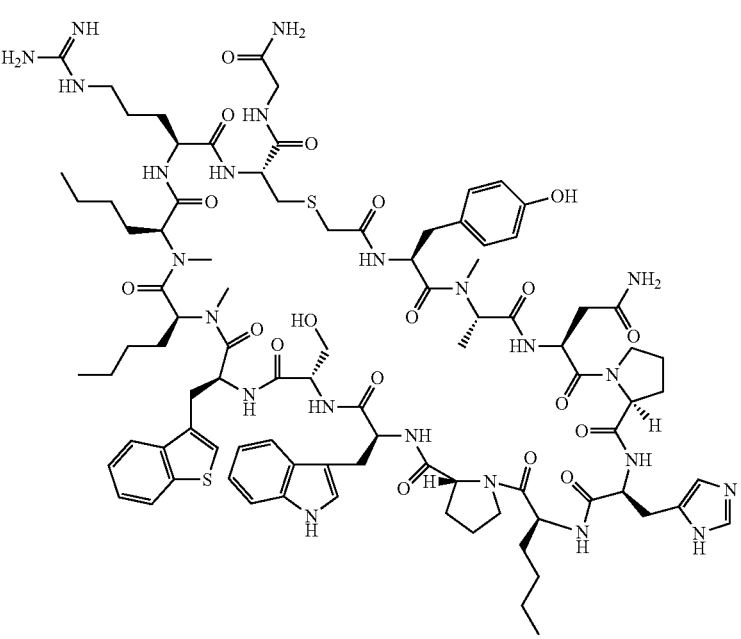

Example 9002

The crude material of Example 9002 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 16.4 mg, and its estimated purity by LCMS analysis was 96%.

Analysis condition A: Retention time=1.92 min; ESI-MS (+) m/z 956.6 (M+2H).

Analysis condition B: Retention time=2.91 min; ESI-MS (+) m/z 956.6 (M+2H).

Preparation of Example 9003

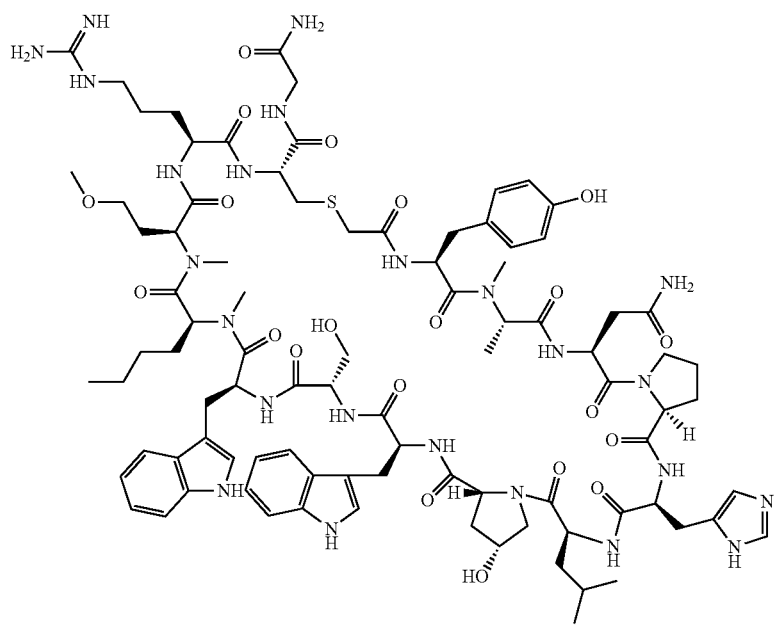

Example 9003

The crude material of Example 9003 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 99%.

Analysis condition A: Retention time=1.39 min; ESI-MS (+) m/z 957.5 (M+2H).

Analysis condition B: Retention time=2.40 min; ESI-MS (+) m/z 957.6 (M+2H).

Preparation of Example 9004

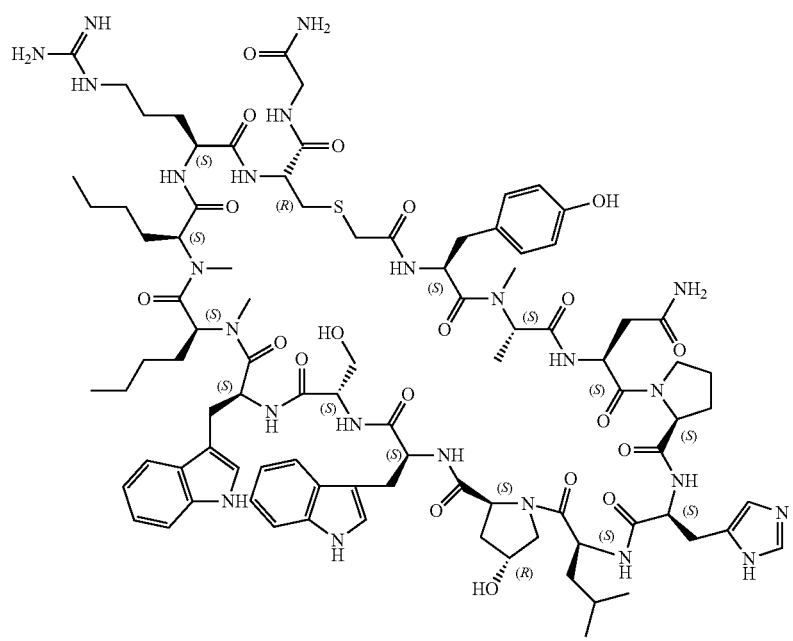

Example 9004

The crude material of Example 9004 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.3 mg, and its estimated purity by LCMS analysis was 100%.

Analysis condition A: Retention time=1.38 min; ESI-MS (+) m/z 957.5 (M+2H).

Analysis condition B: Retention time=2.38 min; ESI-MS (+) m/z 957.5 (M+2H).

Preparation of Example 9005

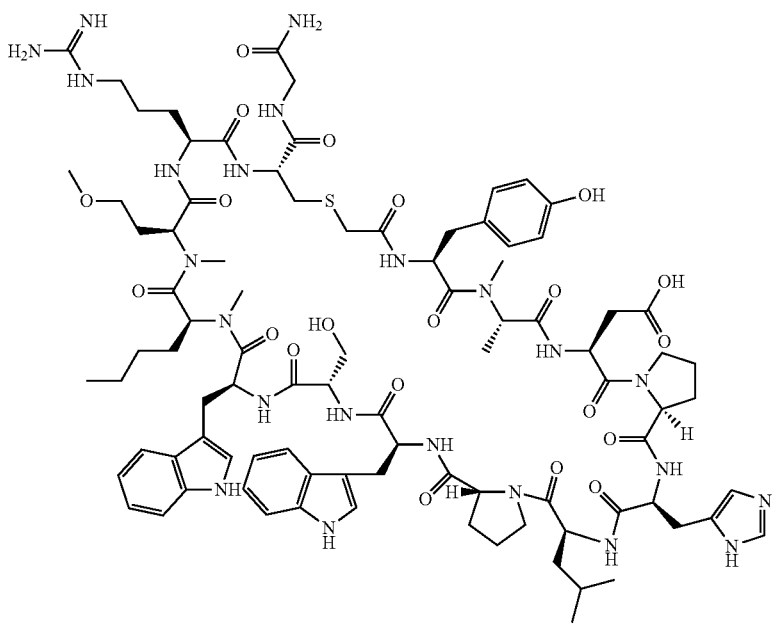

Example 9005

The crude material of Example 9005 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 98%.

Analysis condition A: Retention time=1.42 min; ESI-MS (+) m/z 950.1 (M+2H).

Analysis condition B: Retention time=2.45 min; ESI-MS (+) m/z 949.9 (M+2H).

Preparation of Example 9006

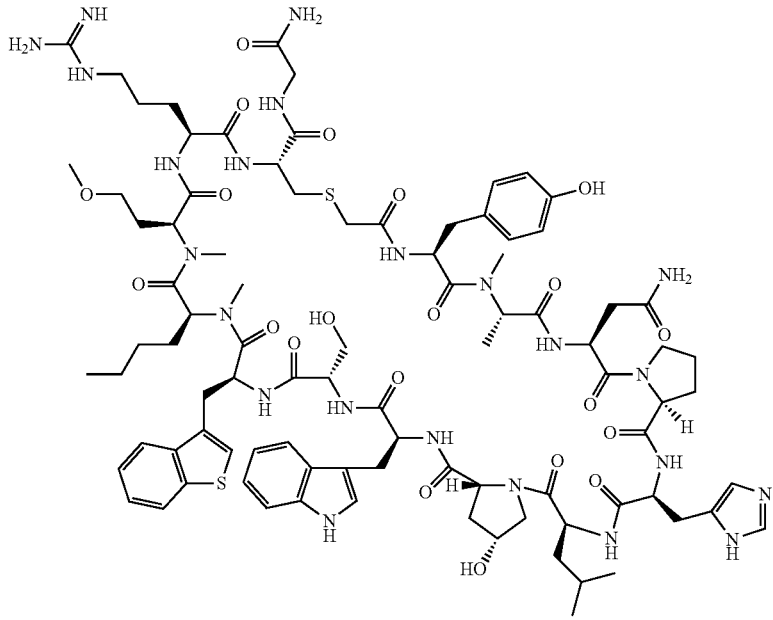

Example 9006

The crude material of Example 9006 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 17.5 mg, and its estimated purity by LCMS analysis was 100%.

Analysis condition A: Retention time=1.58 min; ESI-MS (+) m/z 964.9 (M+2H).

Analysis condition B: Retention time=2.40 min; ESI-MS (+) m/z 965.1 (M+2H).

Preparation of Example 9007

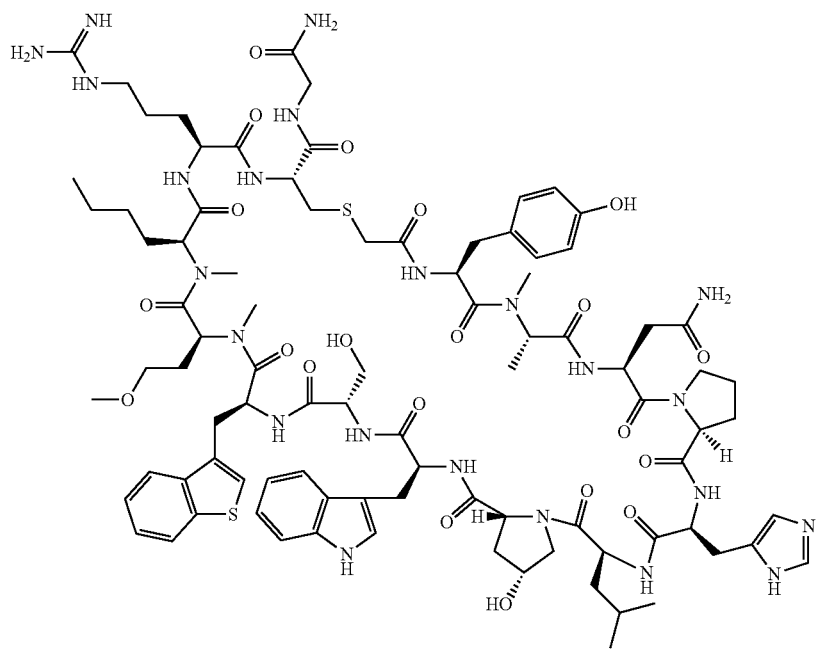

Example 9007

The crude material of Example 9007 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.6 mg, and its estimated purity by LCMS analysis was 99%.

Analysis condition A: Retention time=1.59 min; ESI-MS (+) m/z 965.0 (M+2H).

Analysis condition B: Retention time=2.40 min; ESI-MS (+) m/z 965.5 (M+2H).

Preparation of Example 9008

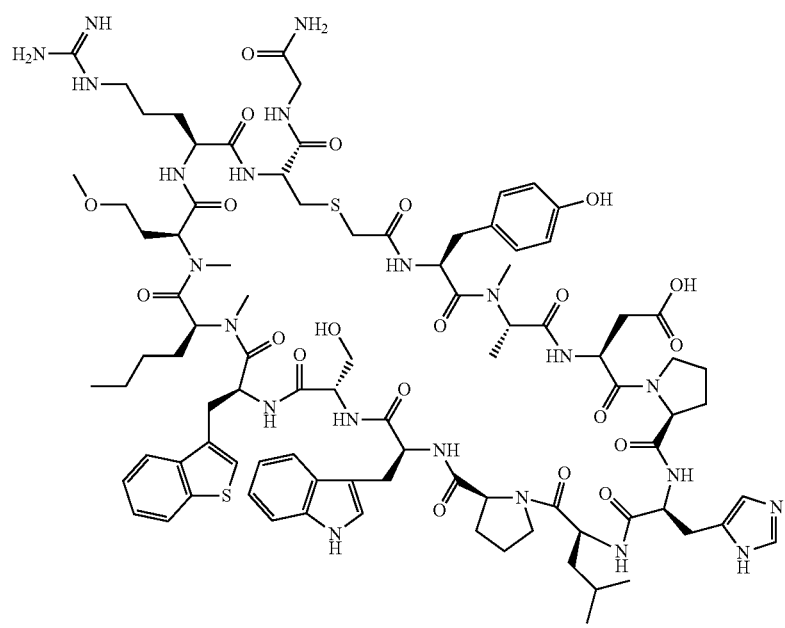

Example 9008

The crude material of Example 9008 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 34.5 mg, and its estimated purity by LCMS analysis was 97%.

Analysis condition A: Retention time=1.59 min; ESI-MS (+) m/z 957.3 (M+2H).

Analysis condition B: Retention time=2.67 min; ESI-MS (+) m/z 957.2 (M+2H).

Preparation of Example 9009

Example 9009

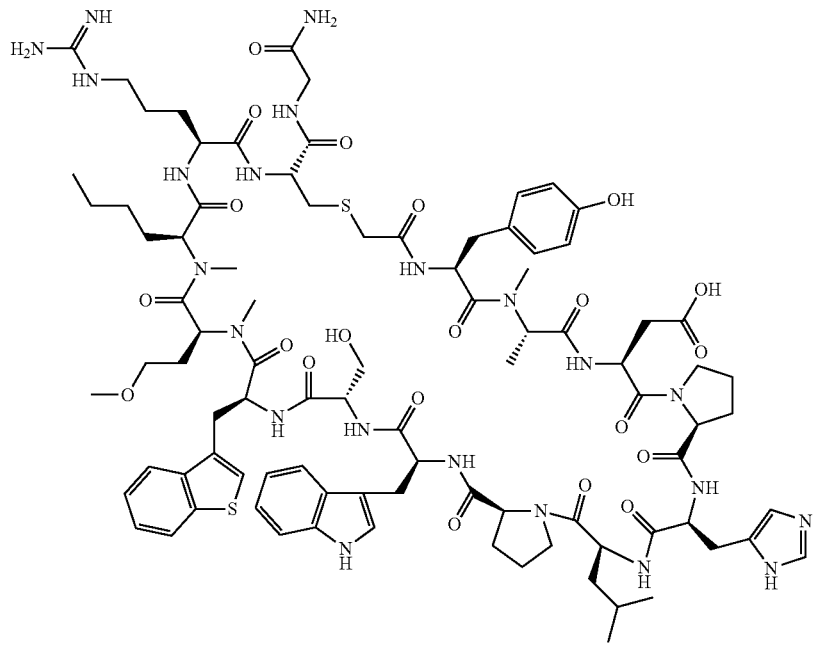

The crude material of Example 9009 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 99%.

Analysis condition A: Retention time=1.63 min; ESI-MS (+) m/z 957.1 (M+2H).

Analysis condition B: Retention time=2.65 min; ESI-MS (+) m/z 957.5 (M+2H).

Preparation of Example 9010

Example 9010

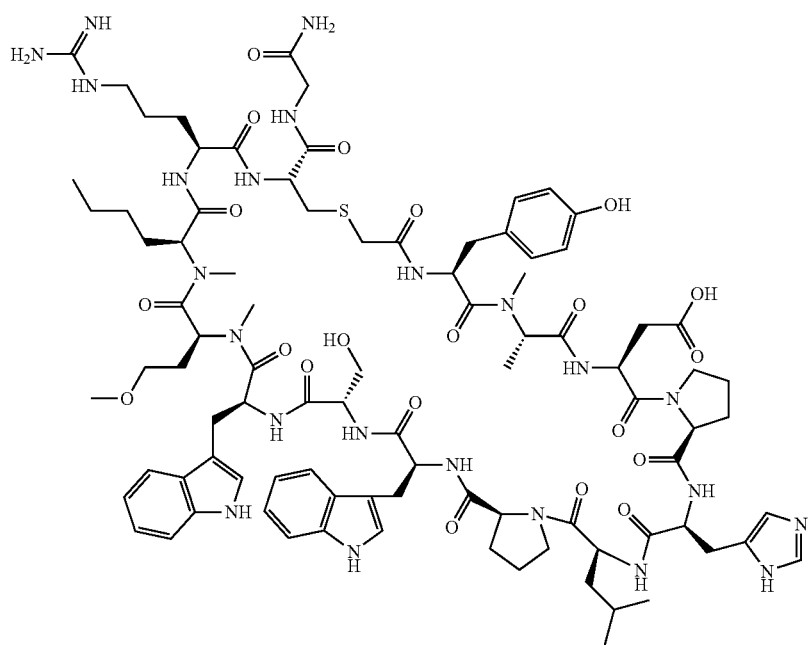

The crude material of Example 9010 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 32.0 mg, and its estimated purity by LCMS analysis was 100%.

Analysis condition A: Retention time=1.39 min; ESI-MS (+) m/z 949.3 (M+2H).

Analysis condition B: Retention time=2.46 min; ESI-MS (+) m/z 950.2 (M+2H).

Preparation of Example 9011

Example 9011

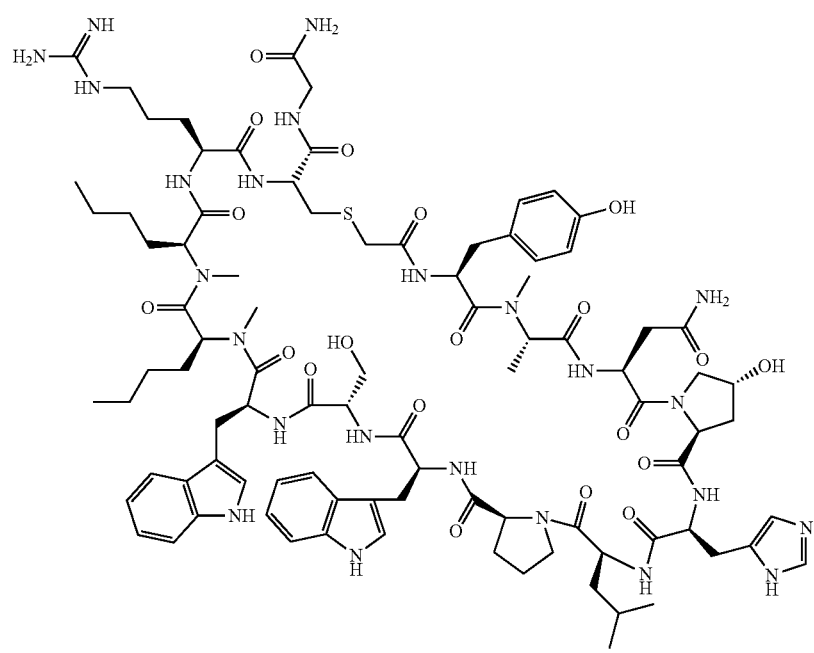

The crude material of Example 9011 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 100%.

Analysis condition A: Retention time=1.43 min; ESI-MS (+) m/z 956.1 (M+2H).

Analysis condition B: Retention time=2.53 min; ESI-MS (+) m/z 956.3 (M+2H).

Preparation of Example 9012

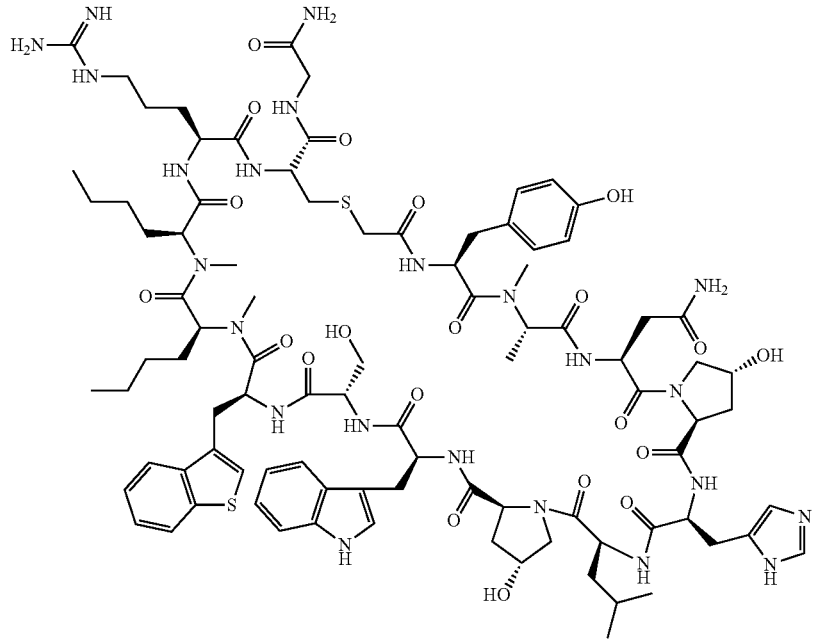

Example 9012

The crude material of Example 9012 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.4 mg, and its estimated purity by LCMS analysis was 98%.

Analysis condition A: Retention time=1.58 min; ESI-MS (+) m/z 972.7 (M+2H).

Analysis condition B: Retention time=2.75 min; ESI-MS (+) m/z 972.8 (M+2H).

Preparation of Example 9013

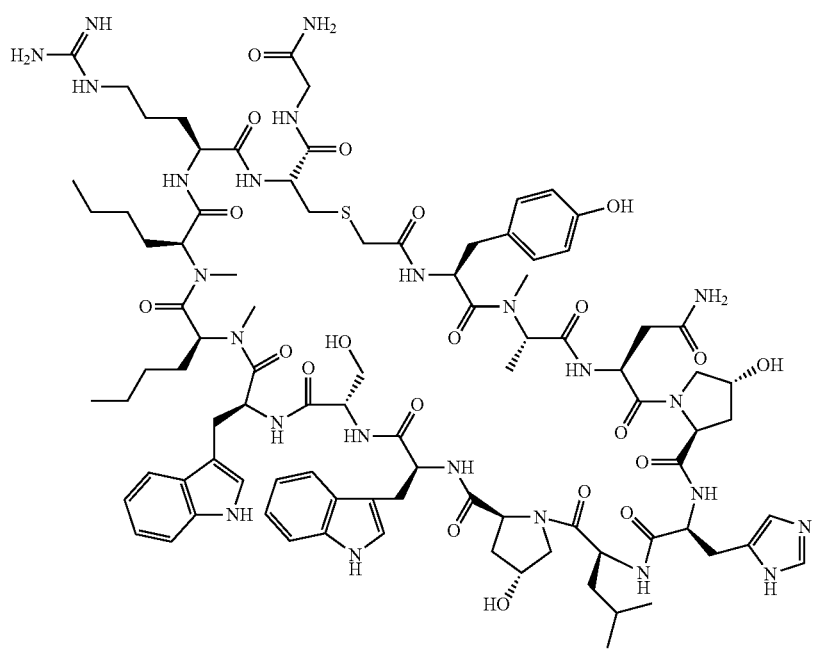

Example 9013

The crude material of Example 9013 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 99%.

Analysis condition A: Retention time=1.41 min; ESI-MS (+) m/z 964.4 (M+2H).

Analysis condition B: Retention time=2.49 min; ESI-MS (+) m/z 964.0 (M+2H).

Preparation of Example 9014

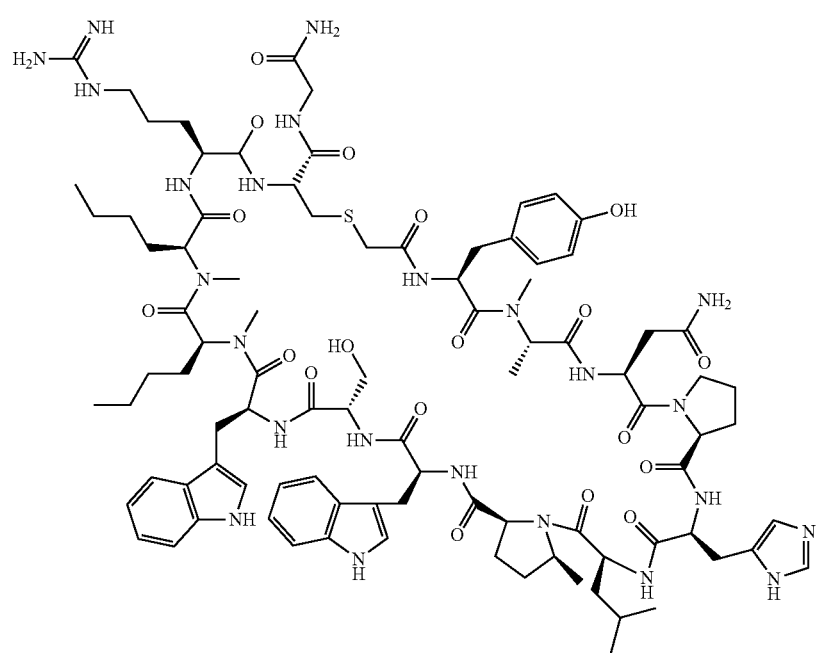

Example 9014

The crude material of Example 9014 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 13.8 mg, and its estimated purity by LCMS analysis was 99%.

Analysis condition A: Retention time=1.54 min; ESI-MS (+) m/z 955.3 (M+2H).

Analysis condition B: Retention time=2.65 min; ESI-MS (+) m/z 955.3 (M+2H).

Preparation of Example 9015

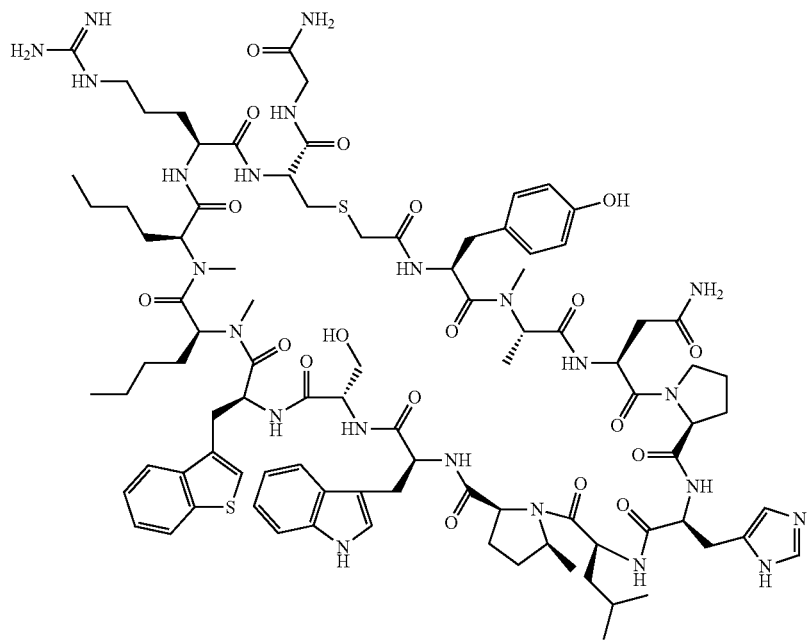

Example 9015

The crude material of Example 9015 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 17.4 mg, and its estimated purity by LCMS analysis was 98%.

Analysis condition A: Retention time=1.70 min; ESI-MS (+) m/z 963.9 (M+2H).

Analysis condition B: Retention time=2.84 min; ESI-MS (+) m/z 963.8 (M+2H).

Preparation of Example 9016

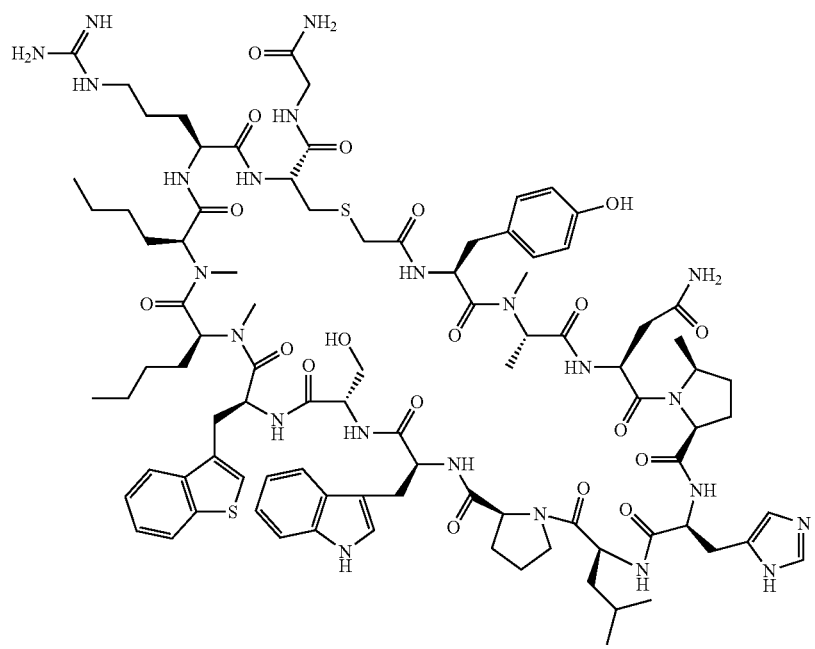

Example 9016

The crude material of Example 9016 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 10.8 mg, and its estimated purity by LCMS analysis was 100%.

Analysis condition A: Retention time=1.68 min; ESI-MS (+) m/z 963.7 (M+2H).

Analysis condition B: Retention time=2.86 min; ESI-MS (+) m/z 963.8 (M+2H).

Preparation of Example 9017

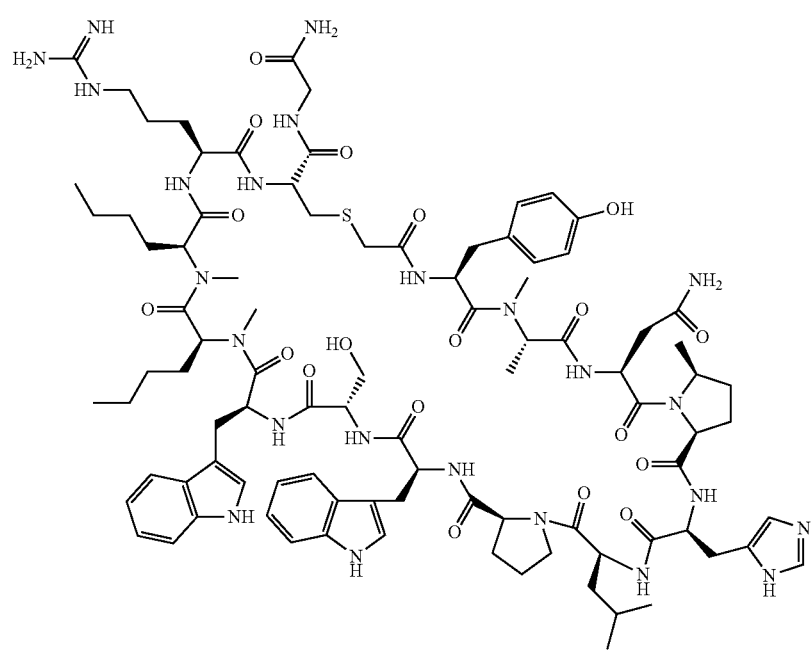

Example 9017

The crude material of Example 9017 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 100%.

Analysis condition A: Retention time=1.55 min; ESI-MS (+) m/z 955.1 (M+2H).

Analysis condition B: Retention time=2.65 min; ESI-MS (+) m/z 954.9 (M+2H).

Preparation of Example 9018

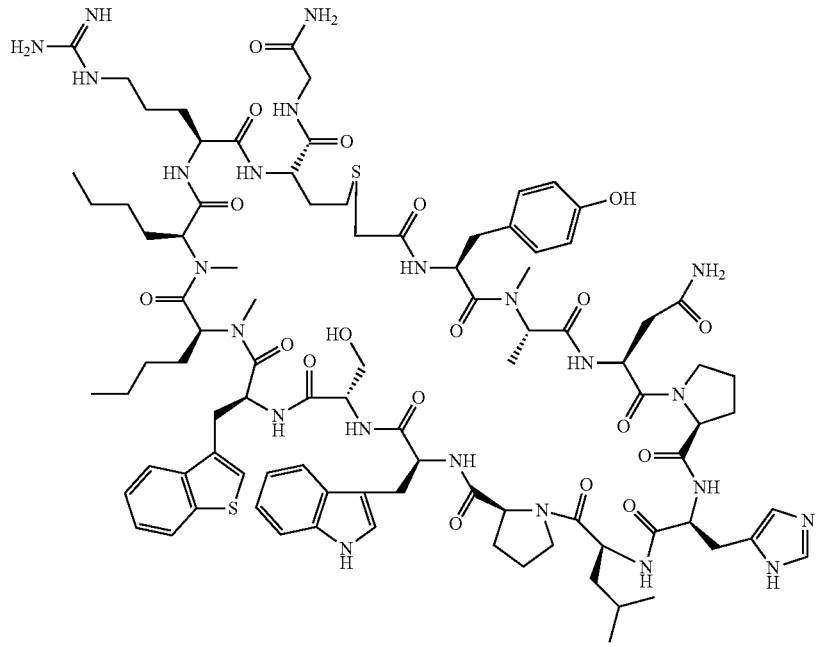

Example 9018

The crude material of Example was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 20.4 mg, and its estimated purity by LCMS analysis was 100%.

Analysis condition A: Retention time=1.62 min; ESI-MS (+) m/z 963.8 (M+2H).

Analysis condition B: Retention time=2.79 min; ESI-MS (+) m/z 963.8 (M+2H).

Preparation of Example 9019

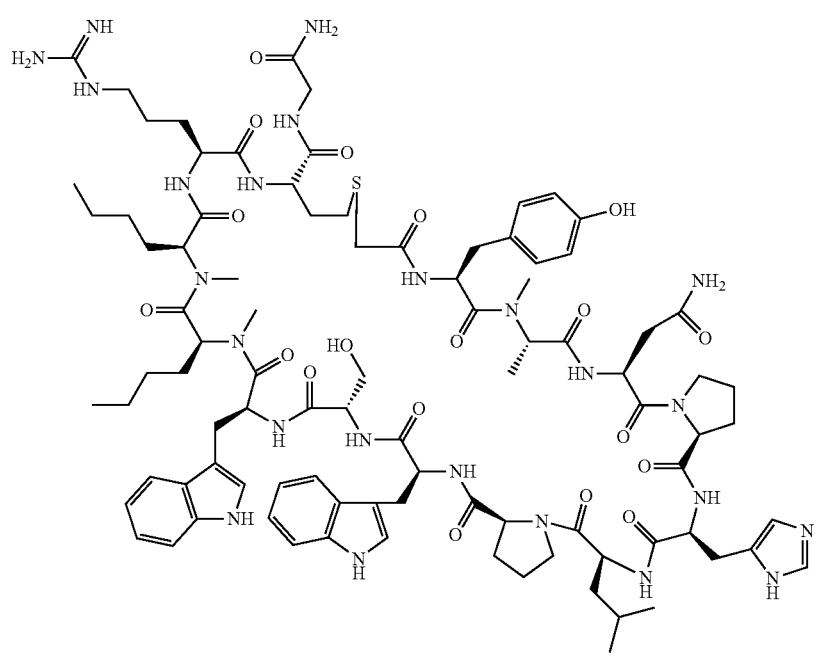

Example 9019

The crude material of Example 9019 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 14.5 mg, and its estimated purity by LCMS analysis was 100%.

Analysis condition A: Retention time=1.48 min; ESI-MS (+) m/z 954.9 (M+2H).

Analysis condition B: Retention time=2.63 min; ESI-MS (+) m/z 955.4 (M+2H).

Preparation of Example 9020

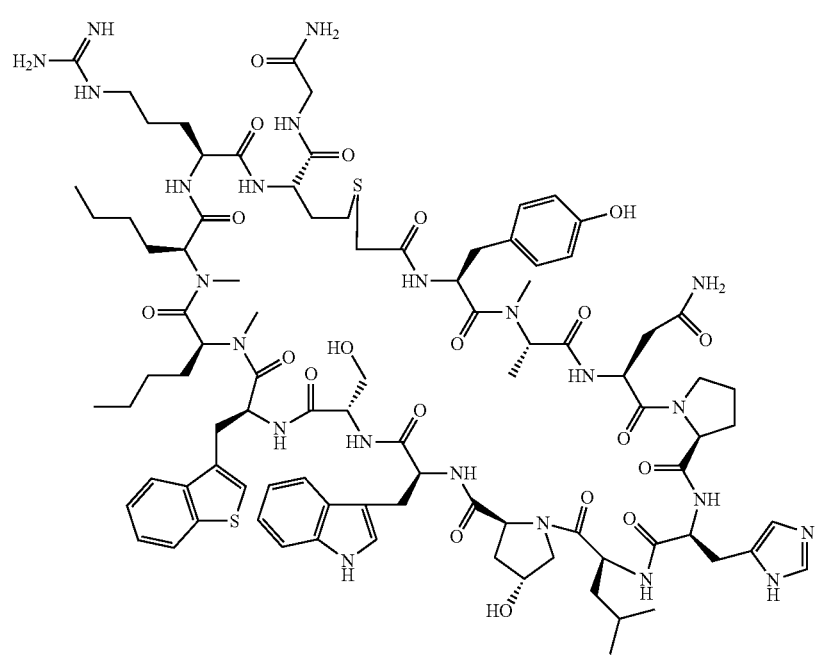

Example 9020

The crude material of Example 9020 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 12.0 mg, and its estimated purity by LCMS analysis was 100%.

Analysis condition A: Retention time=154. min; ESI-MS (+) m/z 969.8 (M+2H).

Analysis condition B: Retention time=2.74 min; ESI-MS (+) m/z 970.0 (M+2H).

Preparation of Example 9021

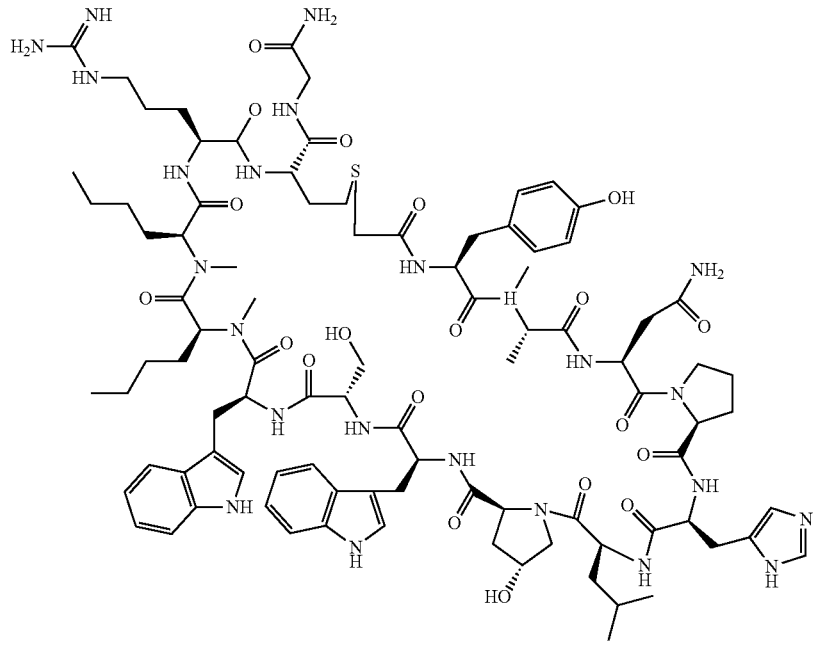

Example 9021

The crude material of Example 9021 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 100%.

Analysis condition B: Retention time=2.58 min; ESI-MS (+) m/z 963.4 (M+2H).

Preparation of Example 9022

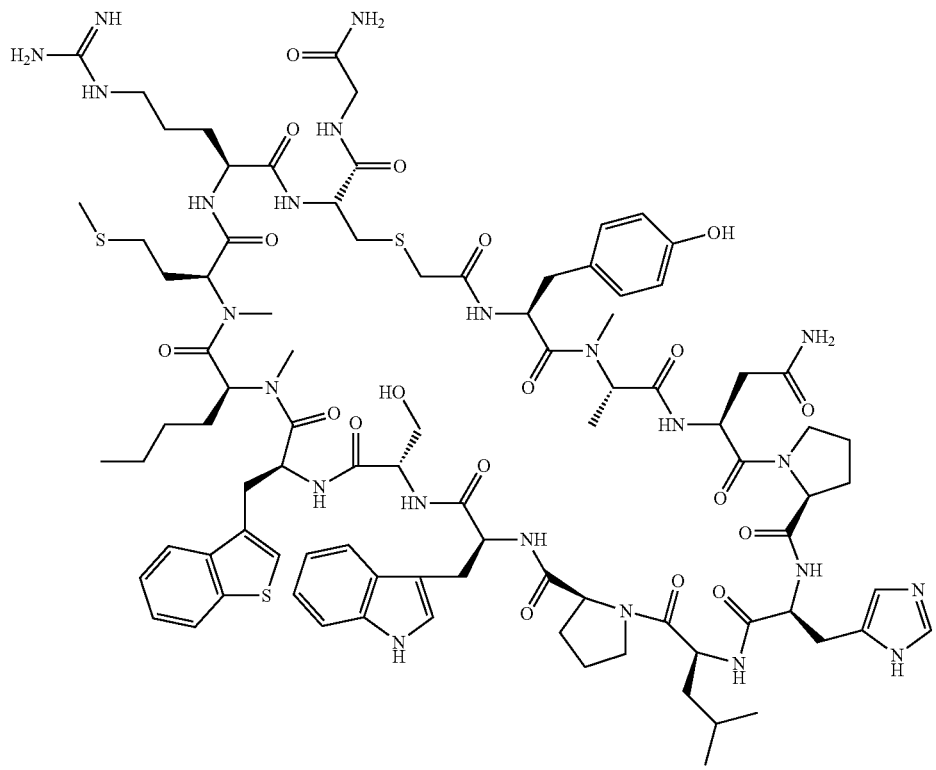

Example 9022

The crude material of Example 9022 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 20 minutes, then a 5-minute hold at 100% B; Flow: 20 mL/min. Fractions containing the desired product were combined and dried via centrifugal evaporation. The yield of the product was 17.6 mg, and its estimated purity by LCMS analysis was 100%.

Analysis condition A: Retention time=1.57 min; ESI-MS (+) m/z 965.8 (M+2H).

Analysis condition B: Retention time=2.77 min; ESI-MS (+) m/z 965.8 (M+2H).

Preparation of Example 9023

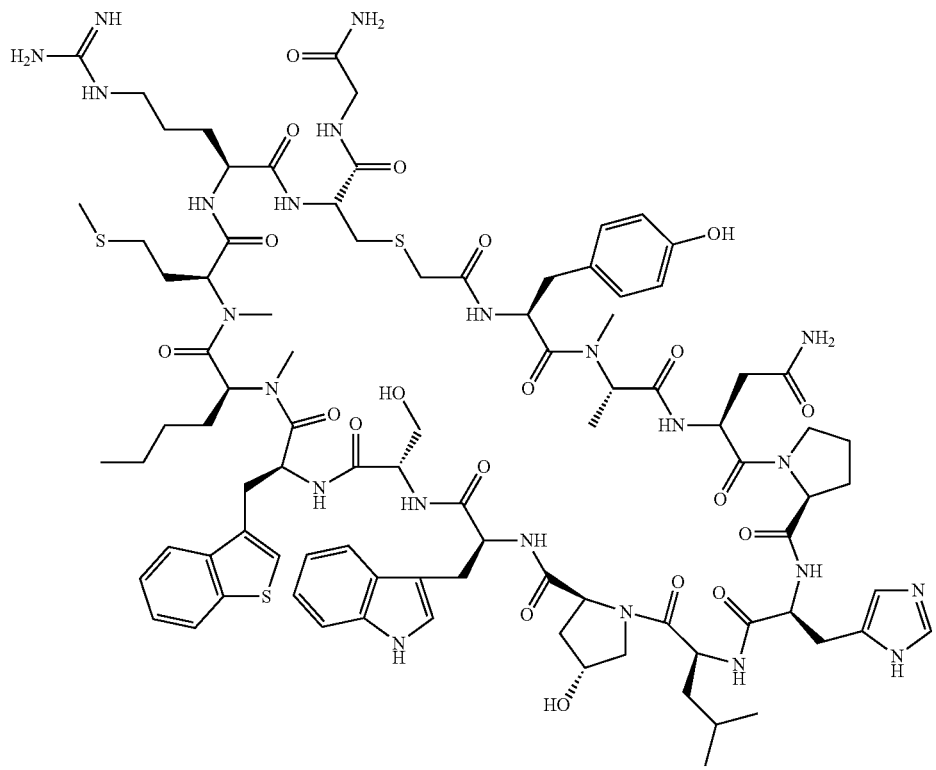

Example 9023

The crude material of Example 9023 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 100%.

Analysis condition A: Retention time=1.54 min; ESI-MS (+) m/z 973.9 (M+2H).

Analysis condition B: Retention time=2.73 min; ESI-MS (+) m/z 973.9 (M+2H).

Preparation of Example 9024

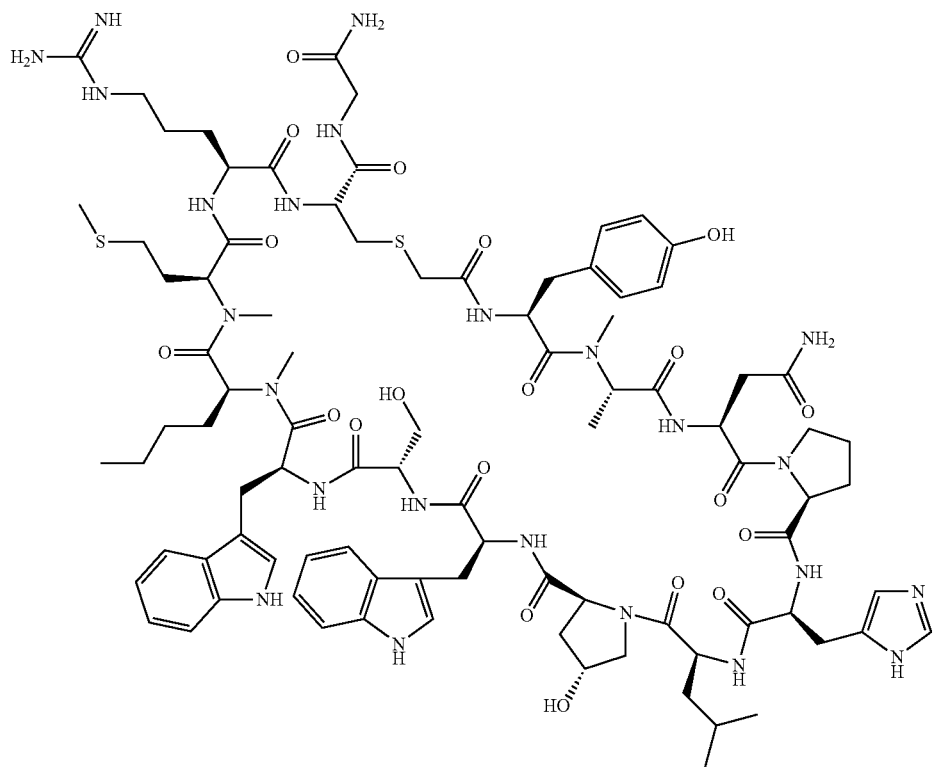

Example 9024

The crude material of Example 9024 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 29.8 mg, and its estimated purity by LCMS analysis was 100%.

Analysis condition A: Retention time=1.40 min; ESI-MS (+) m/z 965.0 (M+2H).

Analysis condition B: Retention time=2.52 min; ESI-MS (+) m/z 965.3 (M+2H).

Preparation of Example 9025

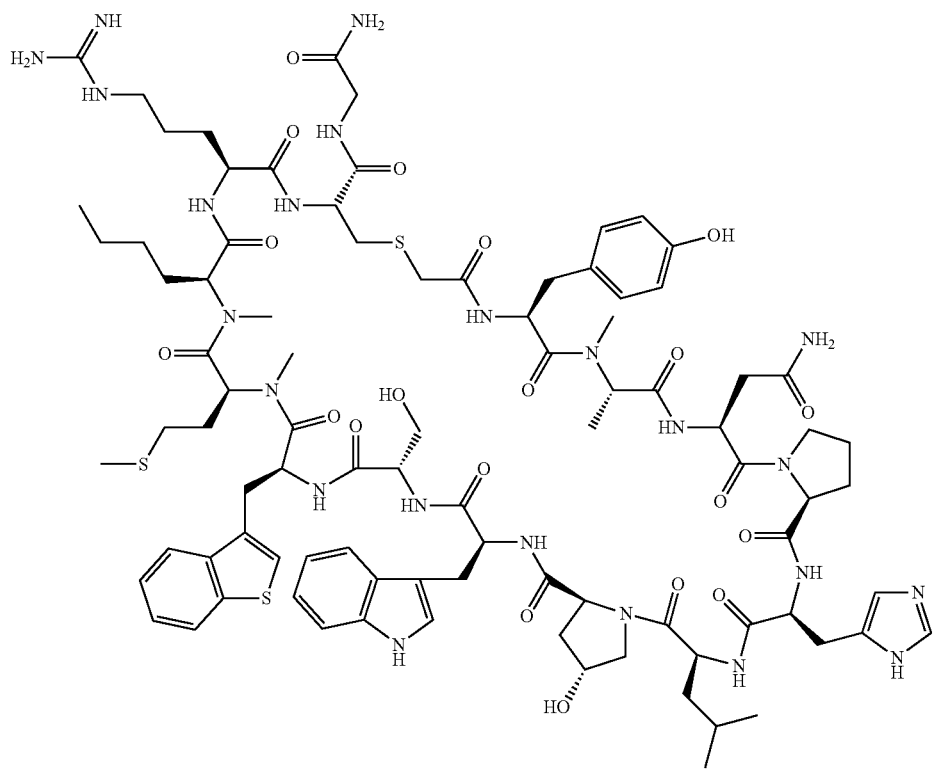

Example 9025

The crude material of Example 9025 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 100%.

Analysis condition A: Retention time=1.45 min; ESI-MS (+) m/z 973.5 (M+2H).

Analysis condition B: Retention time=2.64 min; ESI-MS (+) m/z 973.7 (M+2H).

Preparation of Example 9026

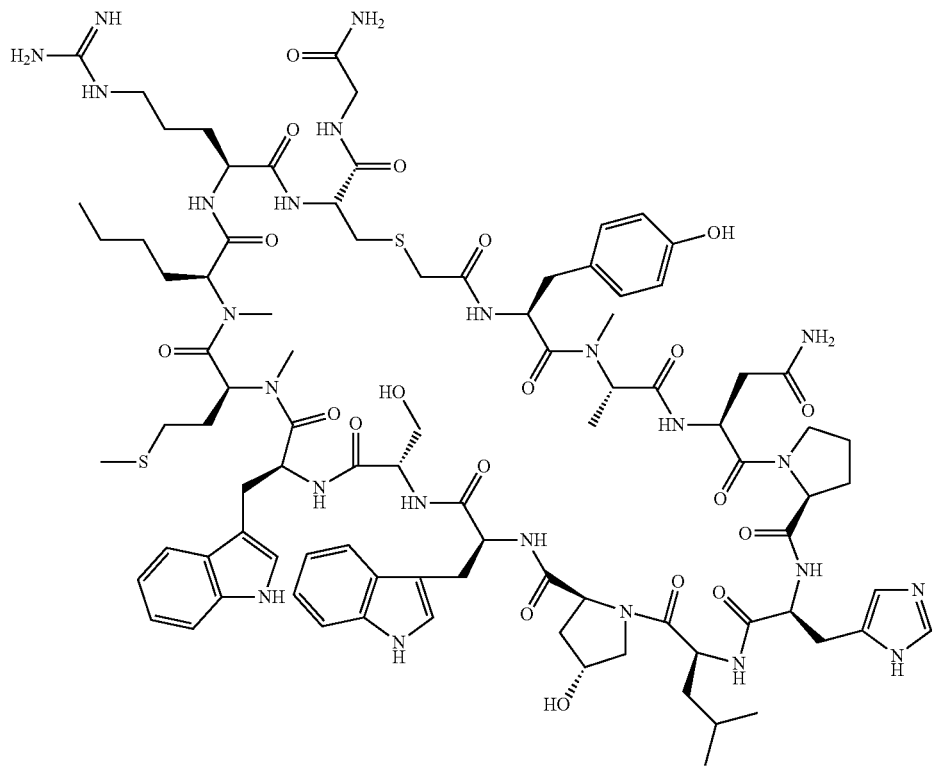

Example 9026

The crude material of Example 9026 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 20 minutes, then a 5-minute hold at 100% B; Flow: 20 mL/min. Fractions containing the desired product were combined and dried via centrifugal evaporation. The yield of the product was 14.6 mg, and its estimated purity by LCMS analysis was 100%.

Analysis condition A: Retention time=1.34 min; ESI-MS (+) m/z 965.2 (M+2H).

Analysis condition B: Retention time=2.47 min; ESI-MS (+) m/z 965.7 (M+2H).

Preparation of Example 9027

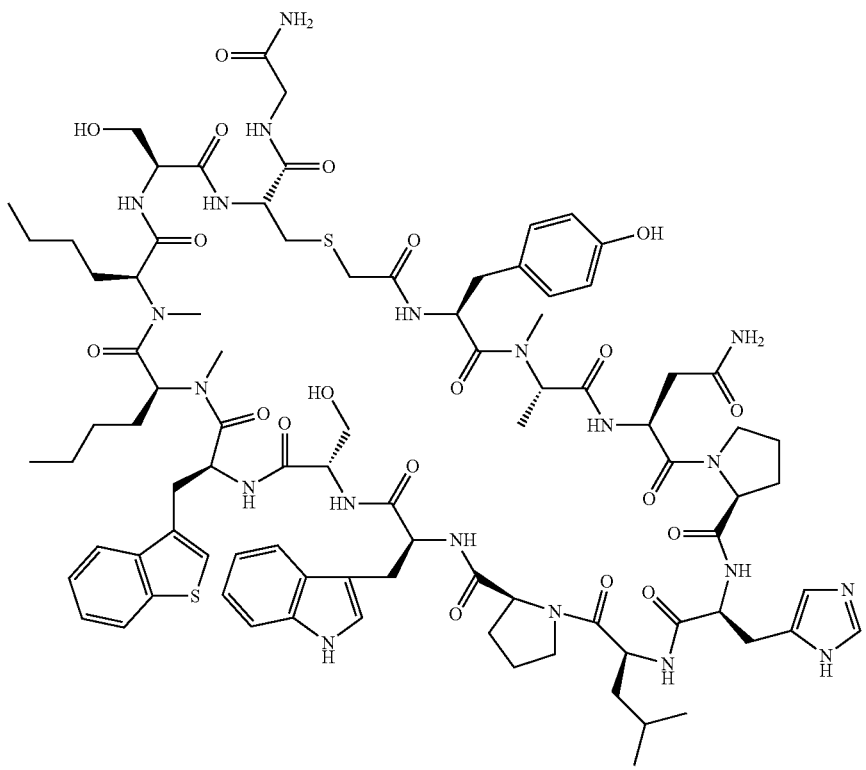

Example 9027

The crude material of Example 9027 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 18.9 mg, and its estimated purity by LCMS analysis was 97%.

Analysis condition A: Retention time=1.74 min; ESI-MS (+) m/z 922.5 (M+2H).

Analysis condition B: Retention time=2.92 min; ESI-MS (+) m/z 922.3 (M+2H).

Preparation of Example 9028

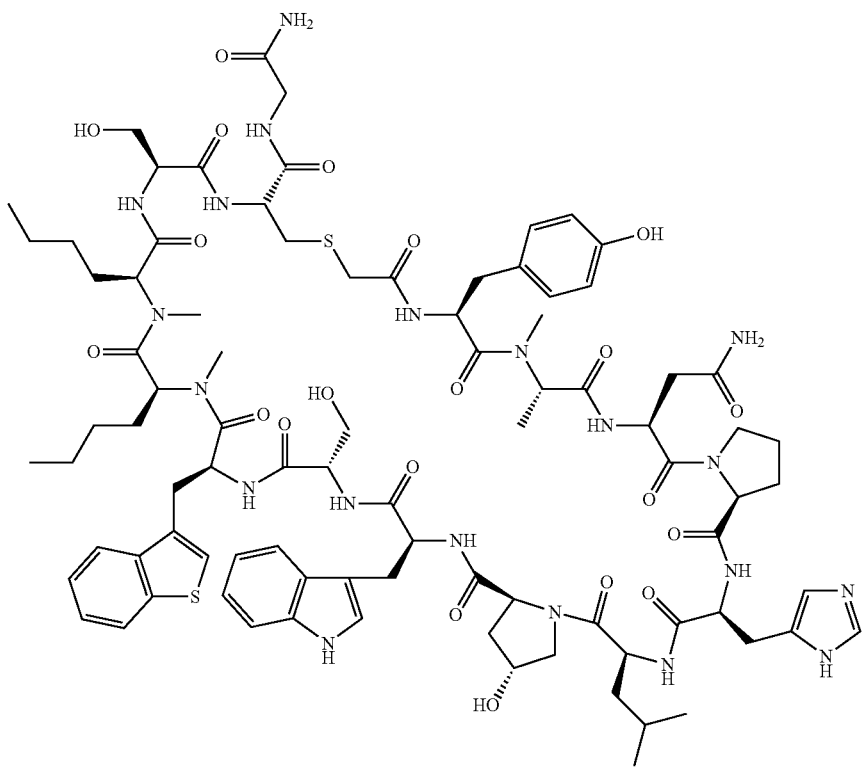

Example 9028

The crude material of Example 9028 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 19.6 mg, and its estimated purity by LCMS analysis was 99%.

Analysis condition A: Retention time=1.67 min; ESI-MS (+) m/z 930.3 (M+2H).

Analysis condition B: Retention time=2.90 min; ESI-MS (+) m/z 930.3 (M+2H).

Preparation of Example 9029

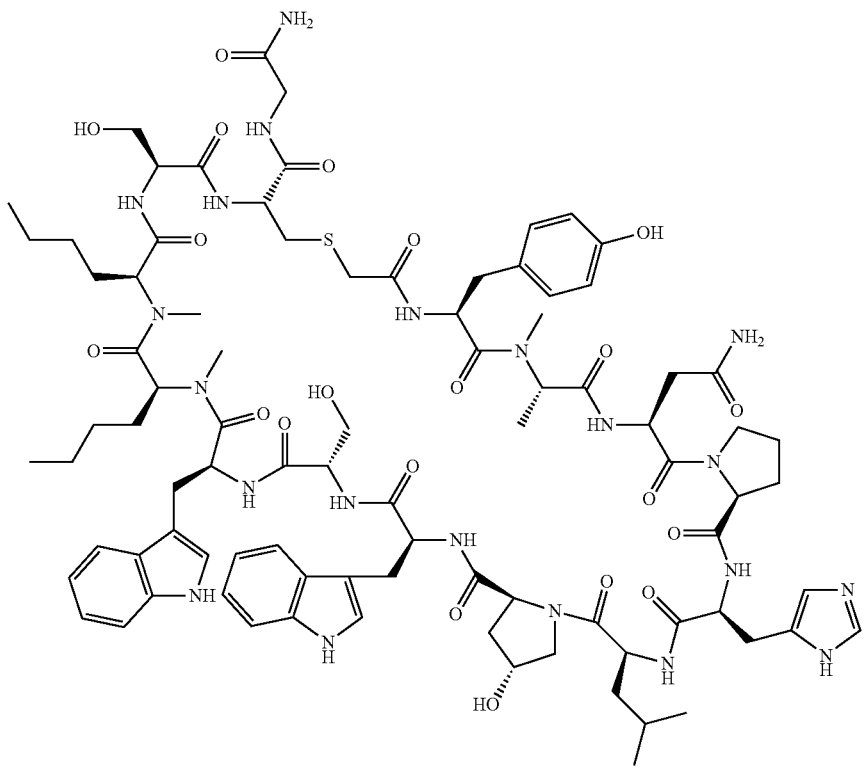

Example 9029

The crude material of Example 9029 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 99%.

Analysis condition A: Retention time=1.56 min; ESI-MS (+) m/z 921.7 (M+2H).

Analysis condition B: Retention time=2.66 min; ESI-MS (+) m/z 921.8 (M+2H).

Preparation of Example 9030

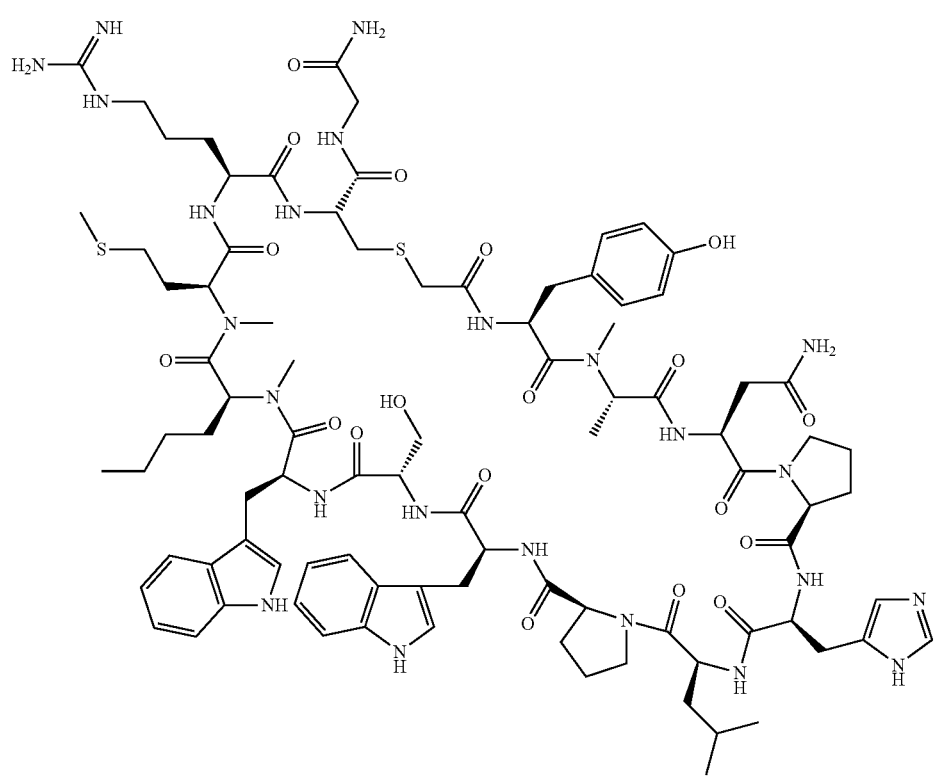

Example 9030

The crude material of Example 9030 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 98%.

Analysis condition A: Retention time=1.44 min; ESI-MS (+) m/z 957.2 (M+2H).

Analysis condition B: Retention time=2.55 min; ESI-MS (+) m/z 957.4 (M+2H).

Preparation of Example 9031

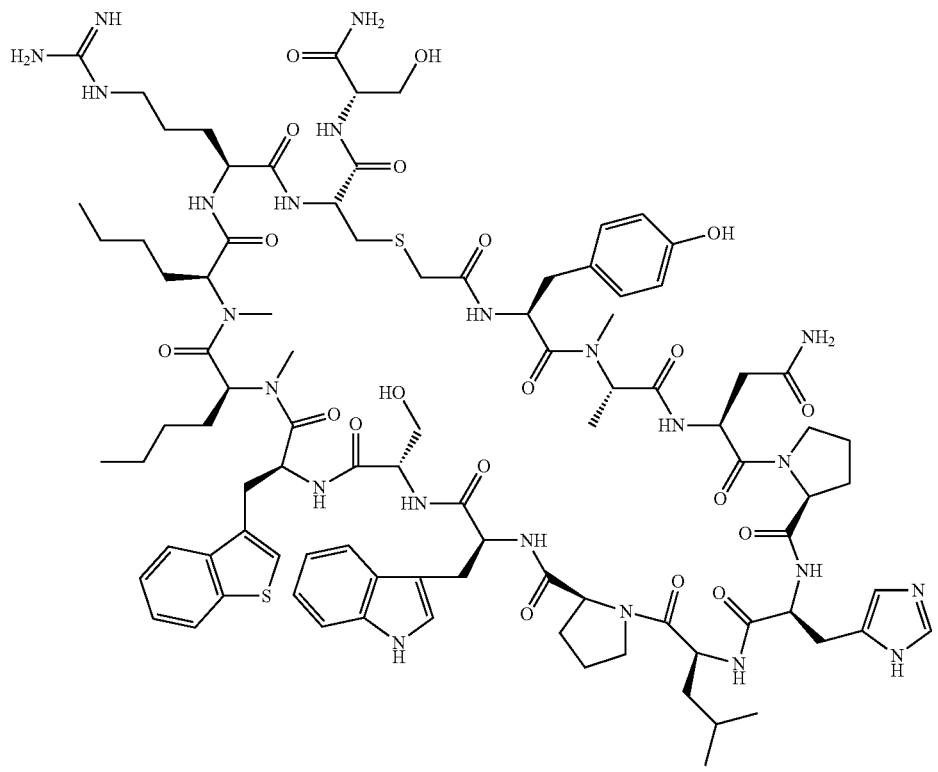

Example 9031

The crude material of Example 9031 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-60% B over 30 minutes, then a 5-minute hold at 100% B; Flow: 20 mL/min. Fractions containing the desired product were combined and dried via centrifugal evaporation. The yield of the product was 23.9 mg, and its estimated purity by LCMS analysis was 100%.

Analysis condition A: Retention time=1.64 min; ESI-MS (+) m/z 971.8 (M+2H).

Analysis condition B: Retention time=2.83 min; ESI-MS (+) m/z 971.4 (M+2H).

Preparation of Example 9032

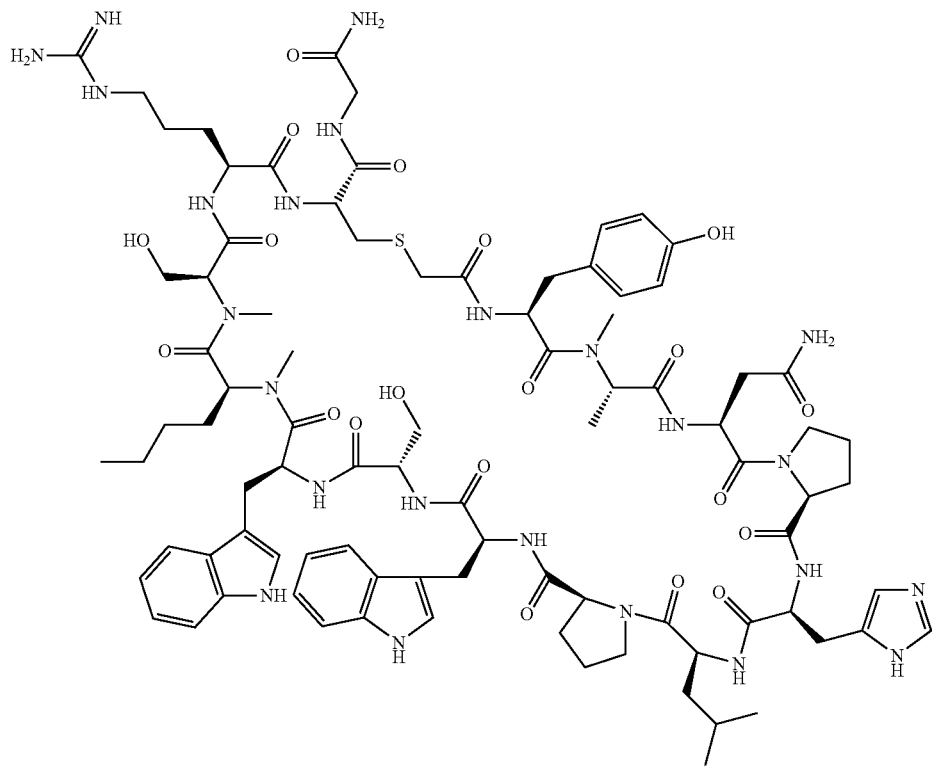

Example 9032

The crude material of Example 9032 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 21.5 mg, and its estimated purity by LCMS analysis was 100%.

Analysis condition A: Retention time=1.27 min; ESI-MS (+) m/z 935.0 (M+2H).

Analysis condition B: Retention time=2.32 min; ESI-MS (+) m/z 934.9 (M+2H).

Preparation of Example 9033

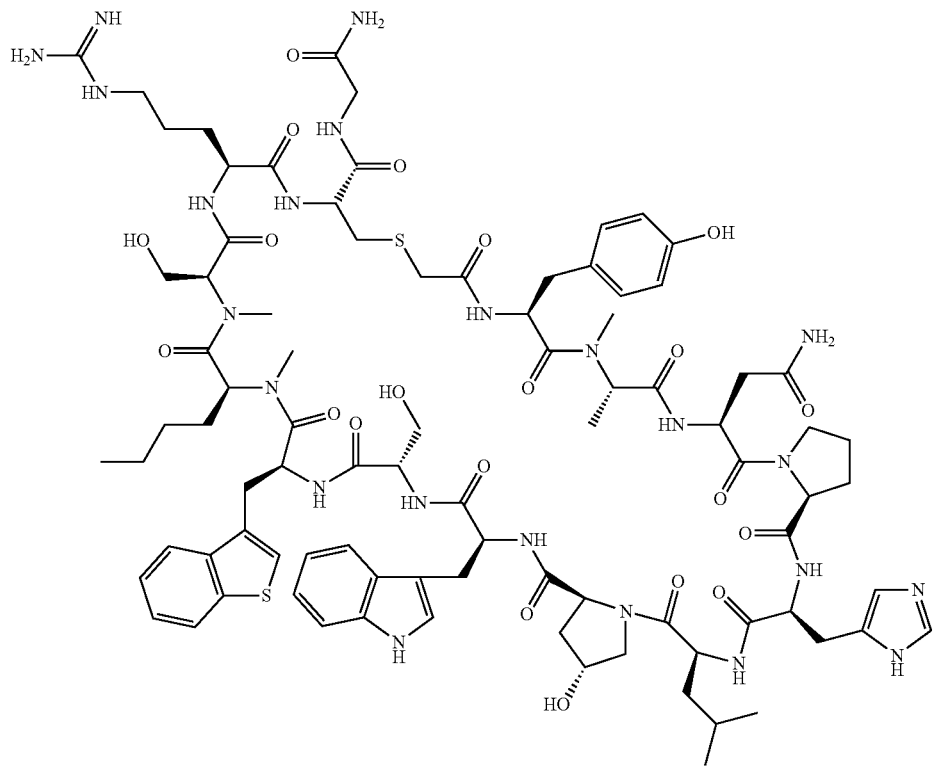

Example 9033

The crude material of Example 9033 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 100%.

Analysis condition A: Retention time=1.37 min; ESI-MS (+) m/z 952.1 (M+2H).

Analysis condition B: Retention time=2.48 min; ESI-MS (+) m/z 952.3 (M+2H).

Preparation of Example 9034

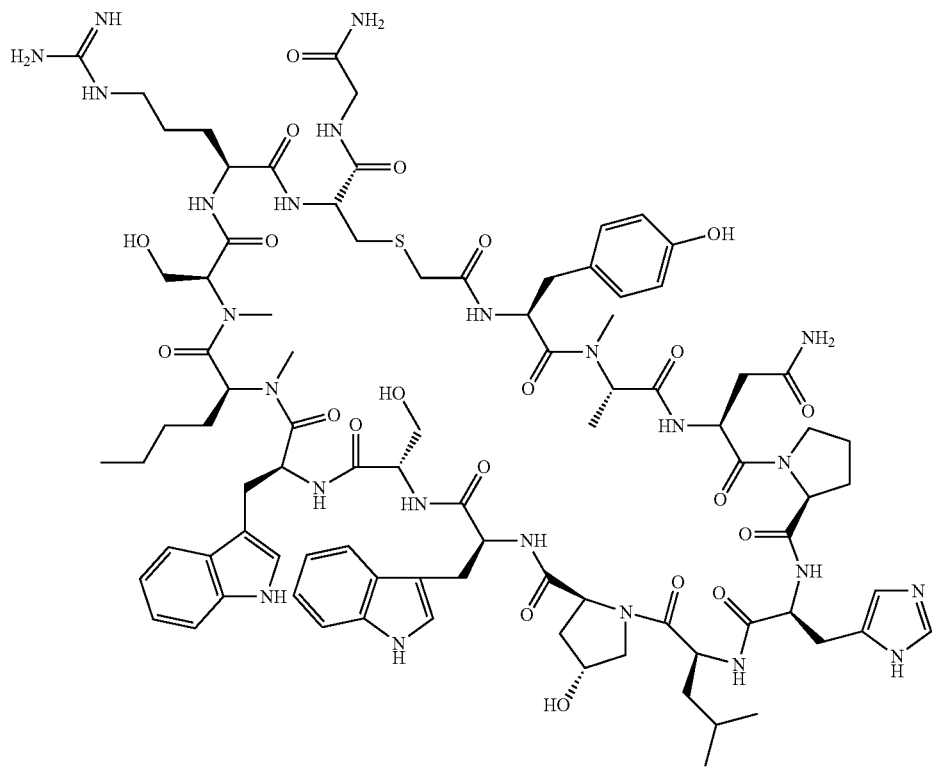

Example 9034

The crude material of Example 9034 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 17.7 mg, and its estimated purity by LCMS analysis was 100%.

Analysis condition A: Retention time=1.23 min; ESI-MS (+) m/z 943.3 (M+2H).

Analysis condition B: Retention time=2.24 min; ESI-MS (+) m/z 943.3 (M+2H).

Preparation of Example 9035

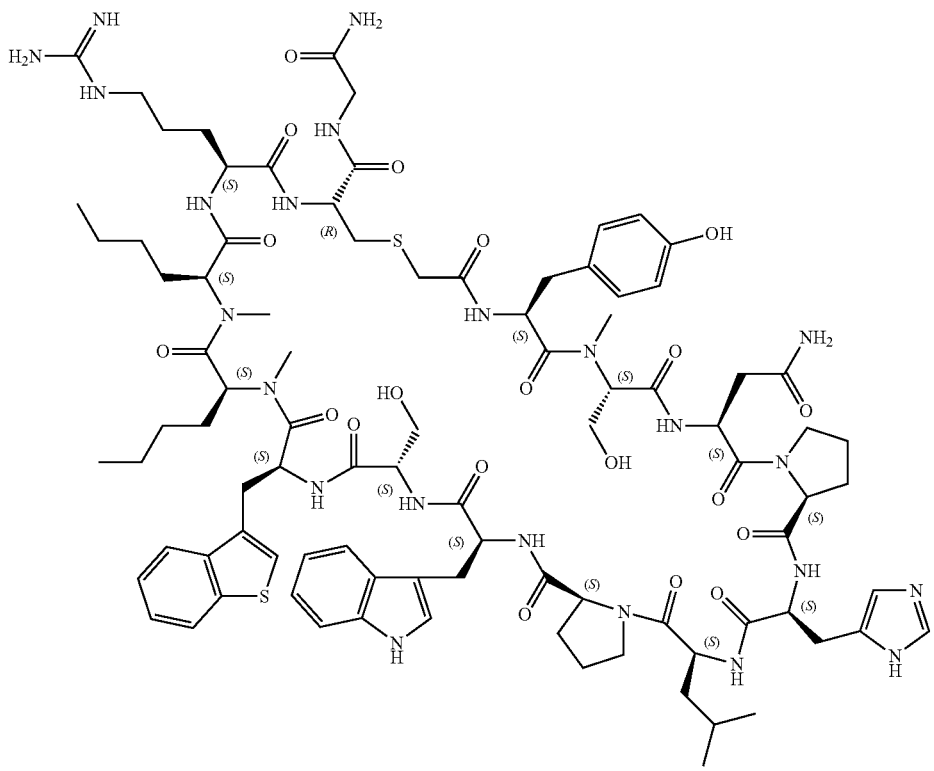

Example 9035

The crude material of Example 9035 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 13.5 mg, and its estimated purity by LCMS analysis was 100%.

Analysis condition A: Retention time=1.57 min; ESI-MS (+) m/z 965.0 (M+2H).

Analysis condition B: Retention time=2.77 min; ESI-MS (+) m/z 964.9 (M+2H).

Preparation of Example 9036

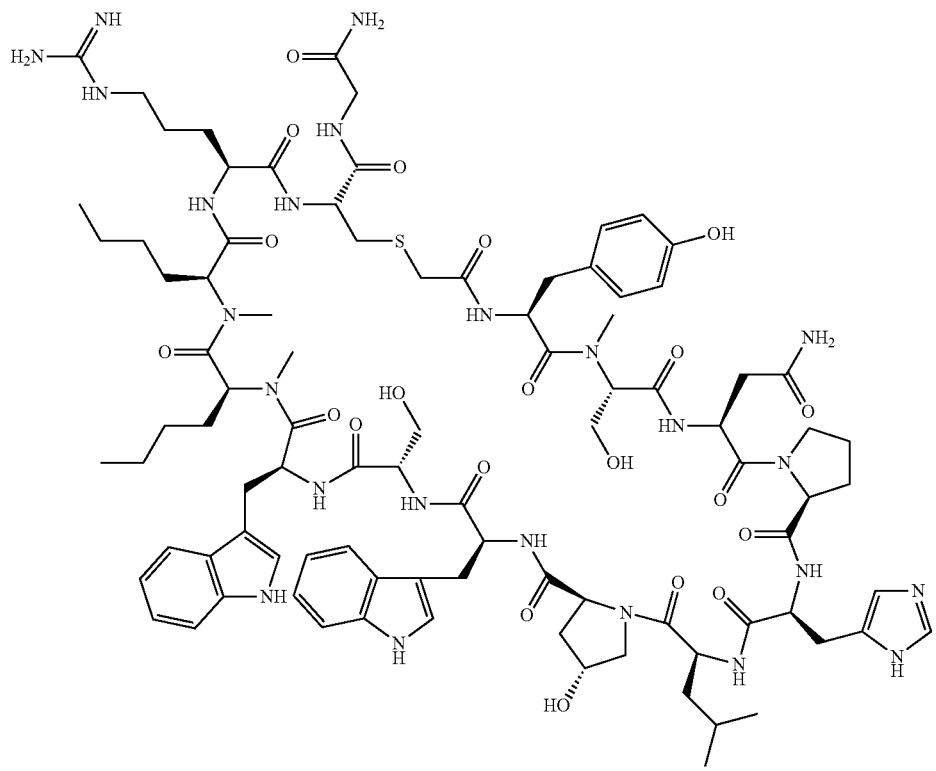

Example 9036

The crude material of Example 9036 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.39. min; ESI-MS (+) m/z 964.1 (M+2H).

Analysis condition B: Retention time=2.52 min; ESI-MS (+) m/z 964.3 (M+2H).

Preparation of Example 9037

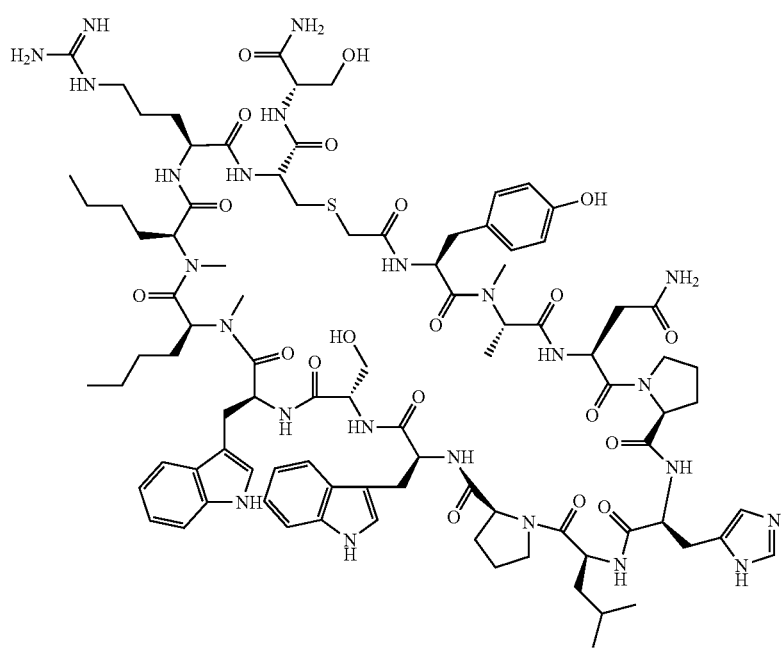

Example 9037

The crude material of Example 9037 was purified via preparative LC/MS with the following conditions: Column: Waters XBridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.9 mg, and its estimated purity by LCMS analysis was 92%.

Analysis condition A: Retention time=1.50 min; ESI-MS (+) m/z 963.3 (M+2H).

Analysis condition B: Retention time=2.61 min; ESI-MS (+) m/z 963.3 (M+2H).

Preparation of Example 9038

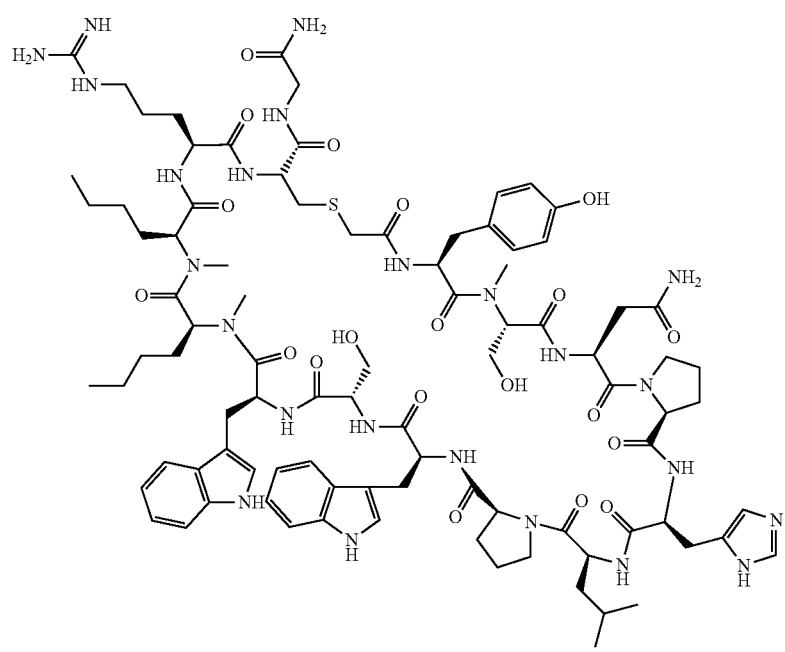

Example 9038

The crude material of Example 9038 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.0 mg, and its estimated purity by LCMS analysis was 96%.

Analysis condition A: Retention time=1.46 min; ESI-MS (+) m/z 956.3 (M+2H).

Analysis condition B: Retention time=2.61 min; ESI-MS (+) m/z 956.3 (M+2H).

Preparation of Example 9039

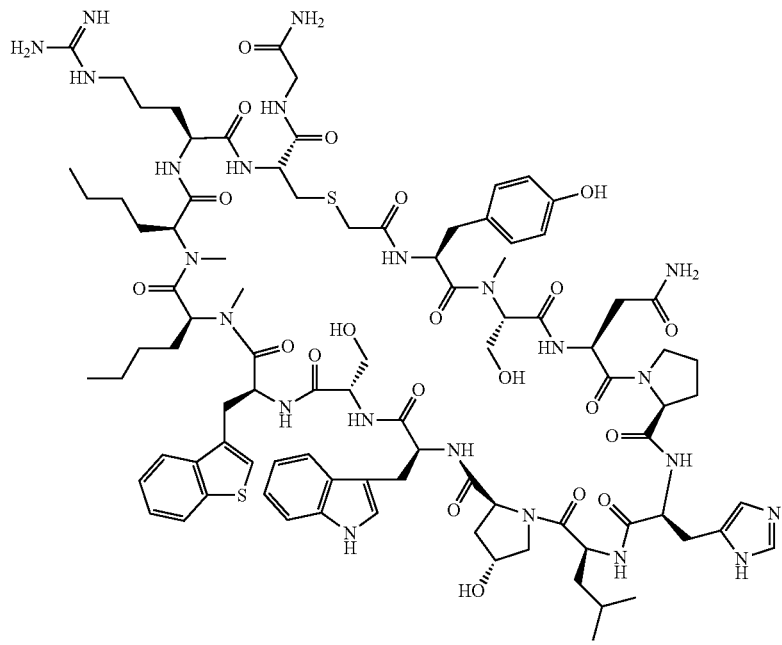

Example 9039

The crude material of Example 9039 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 40 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 98%.

Analysis condition A: Retention time=1.51 min; ESI-MS (+) m/z 973.0 (M+2H).

Analysis condition B: Retention time=2.71 min; ESI-MS (+) m/z 973.0 (M+2H).

Preparation of Example 9040

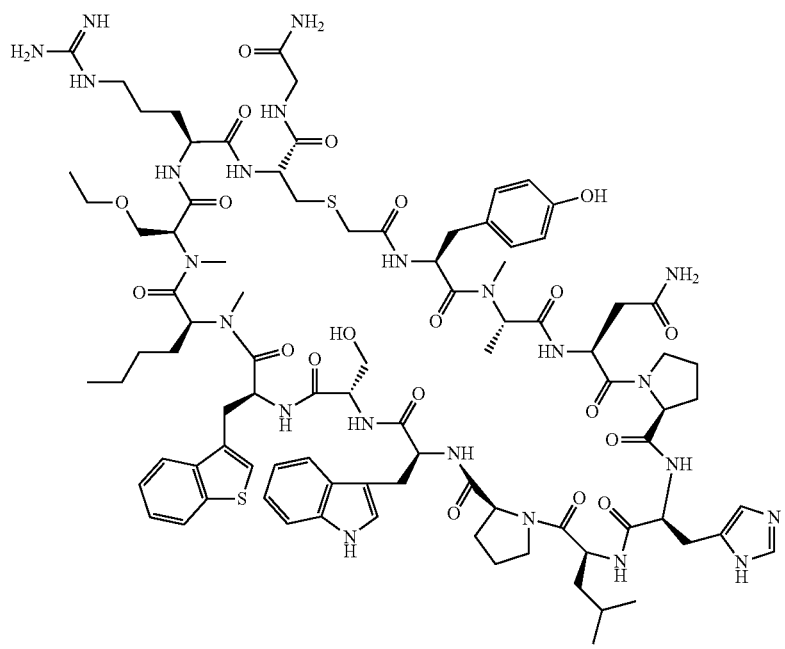

Example 9040

The crude material of Example 9040 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 16.2 mg, and its estimated purity by LCMS analysis was 98%.

Analysis condition A: Retention time=1.64 min; ESI-MS (+) m/z 957.2 (M+2H).

Analysis condition B: Retention time=2.78 min; ESI-MS (+) m/z 957.7 (M+2H).

Preparation of Example 9041

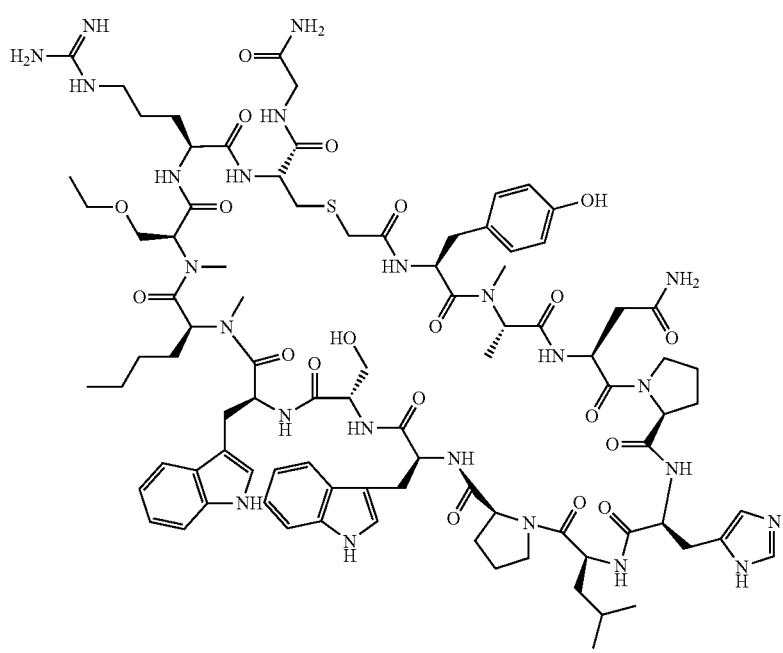

Example 9041

The crude material of Example 9041 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.5 mg, and its estimated purity by LCMS analysis was 95%.

Analysis condition A: Retention time=1.45 min; ESI-MS (+) m/z 949.2 (M+2H).

Analysis condition B: Retention time=2.54 min; ESI-MS (+) m/z 949.3 (M+2H).

Preparation of Example 9042

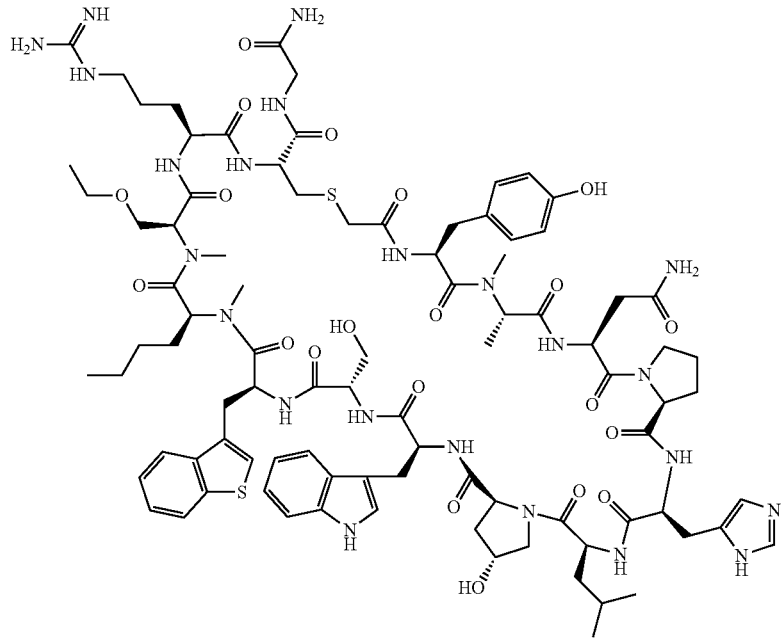

Example 9042

The crude material of Example 9042 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.8 mg, and its estimated purity by LCMS analysis was 96%.

Analysis condition A: Retention time=1.62 min; ESI-MS (+) m/z 965.4 (M+2H).

Analysis condition B: Retention time=2.76 min; ESI-MS (+) m/z 965.8 (M+2H).

Preparation of Example 9043

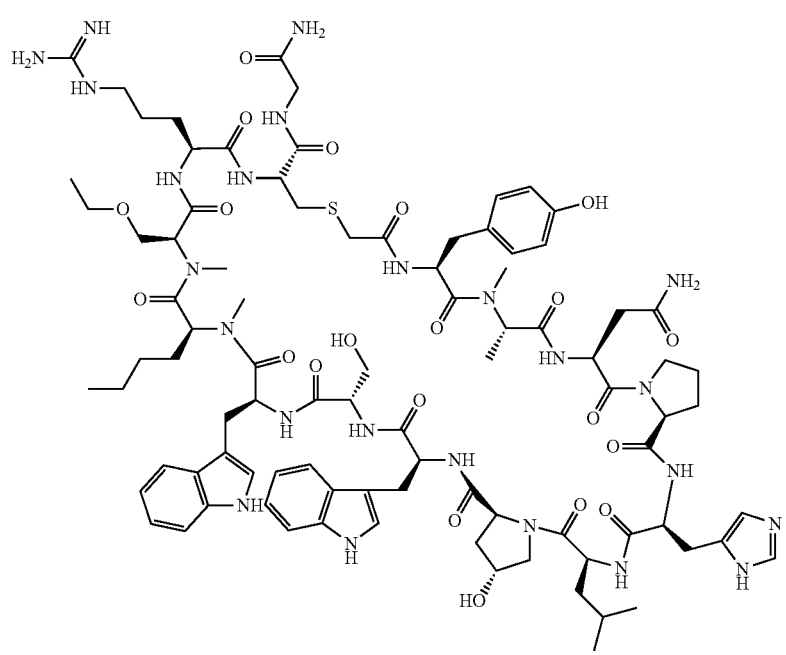

Example 9043

The crude material of Example 9043 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.1 mg, and its estimated purity by LCMS analysis was 98%.

Analysis condition A: Retention time=1.42 min; ESI-MS (+) m/z 958.1 (M+2H).

Analysis condition B: Retention time=2.51 min; ESI-MS (+) m/z 958.0 (M+2H).

Preparation of Example 9044

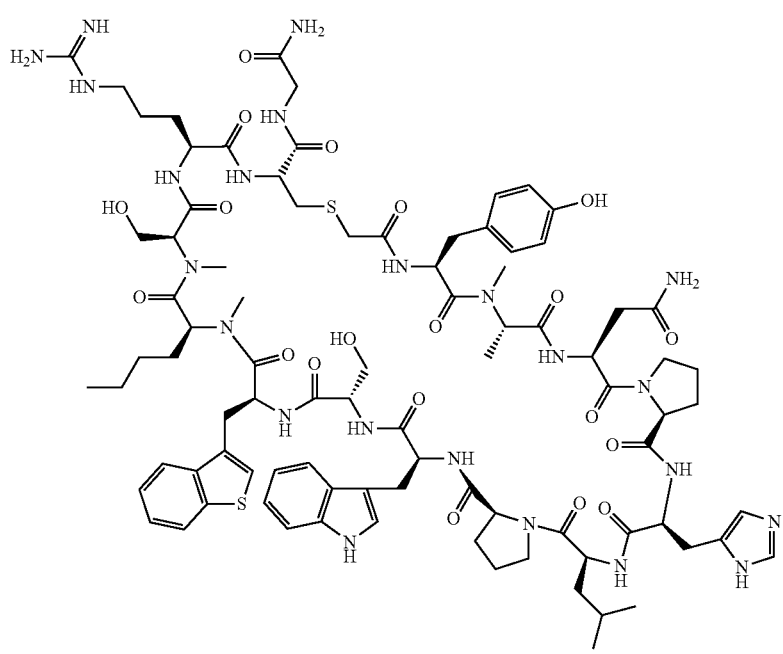

Example 9044

The crude material of Example 9044 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 40 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis condition A: Retention time=1.44 min; ESI-MS (+) m/z 943.8 (M+2H).

Analysis condition B: Retention time=2.55 min; ESI-MS (+) m/z 943.5 (M+2H).

Preparation of Example 9045

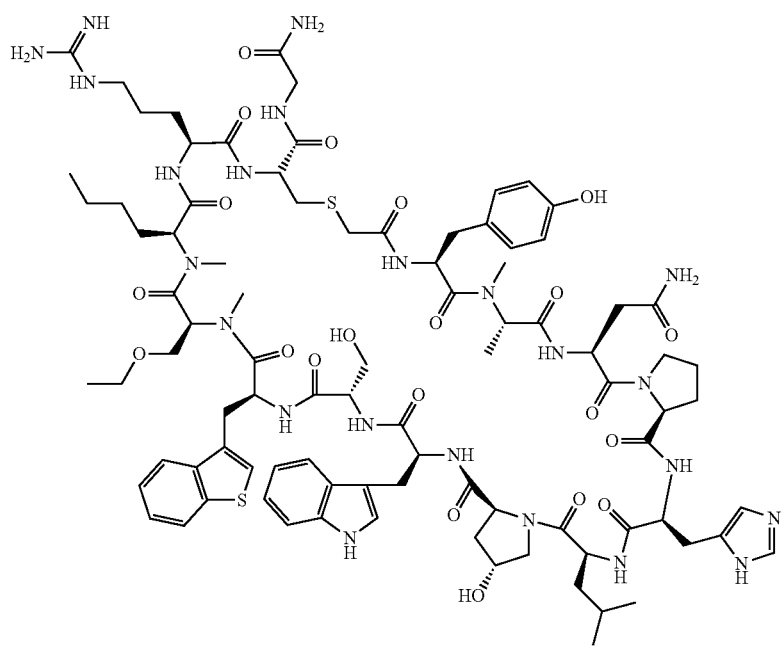

Example 9045

The crude material of Example 9045 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 24.2 mg, and its estimated purity by LCMS analysis was 99%.

Analysis condition A: Retention time=1.54 min; ESI-MS (+) m/z 965.8 (M+2H).

Analysis condition B: Retention time=2.71 min; ESI-MS (+) m/z 965.4 (M+2H).

Preparation of Example 9046

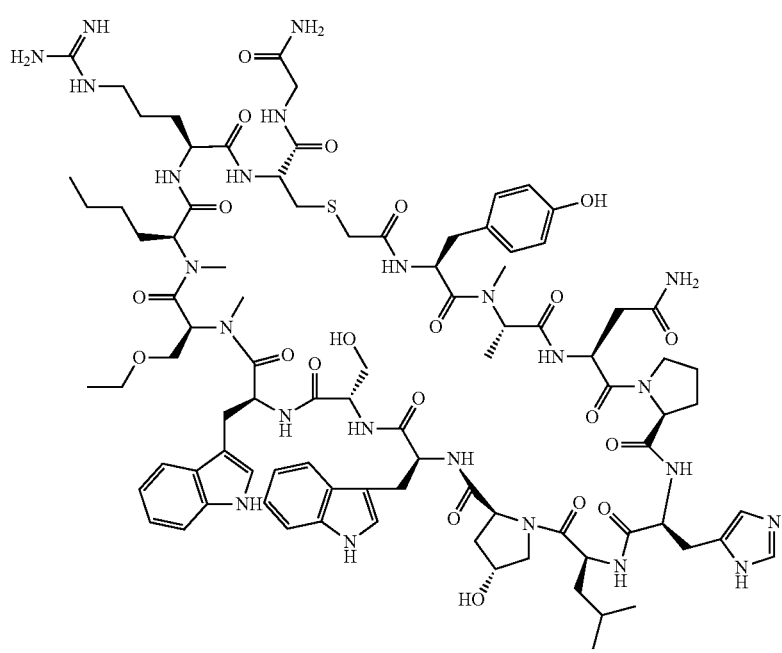

Example 9046

The crude material of Example 9046 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 17.3 mg, and its estimated purity by LCMS analysis was 100%.

Analysis condition A: Retention time=1.42 min; ESI-MS (+) m/z 957.2 (M+2H).

Analysis condition B: Retention time=2.49 min; ESI-MS (+) m/z 957.3 (M+2H).

Preparation of Example 9047

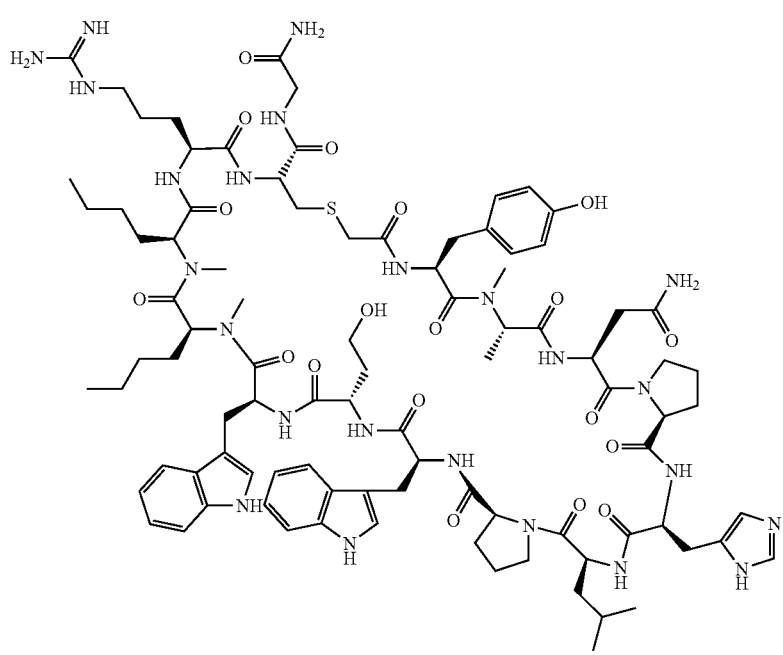

Example 9047

The crude material of Example 9047 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 97%.

Analysis condition A: Retention time=1.50 min; ESI-MS (+) m/z 955.0 (M+2H).

Analysis condition B: Retention time=2.60 min; ESI-MS (+) m/z 955.3 (M+2H).

Preparation of Example 9048

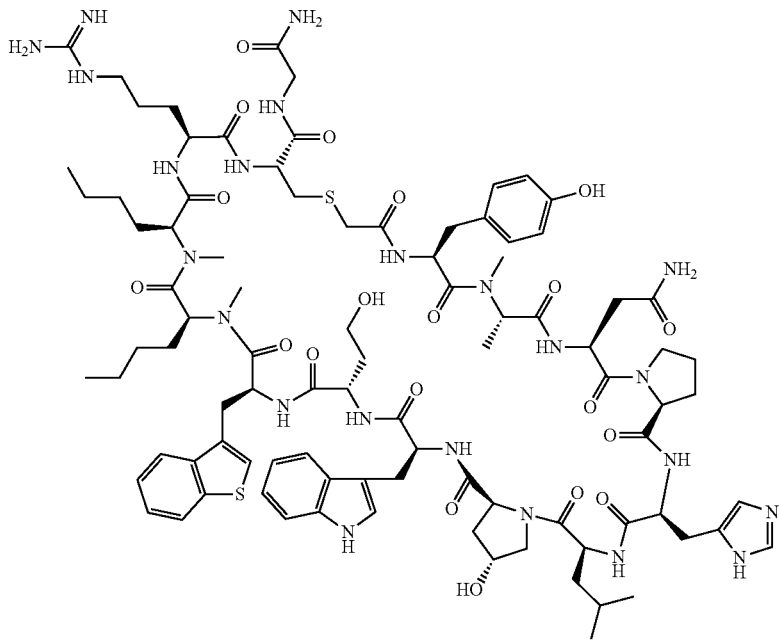

Example 9048

The crude material of Example 9048 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 55-95% B over 30 minutes, then a 5-minute hold at 100% B; Flow: 20 mL/min. Fractions containing the desired product were combined and dried via centrifugal evaporation. The yield of the product was 23.7 mg, and its estimated purity by LCMS analysis was 99%.

Analysis condition A: Retention time=1.64 min; ESI-MS (+) m/z 971.7 (M+2H).

Analysis condition B: Retention time=2.81 min; ESI-MS (+) m/z 971.4 (M+2H).

Preparation of Example 9049

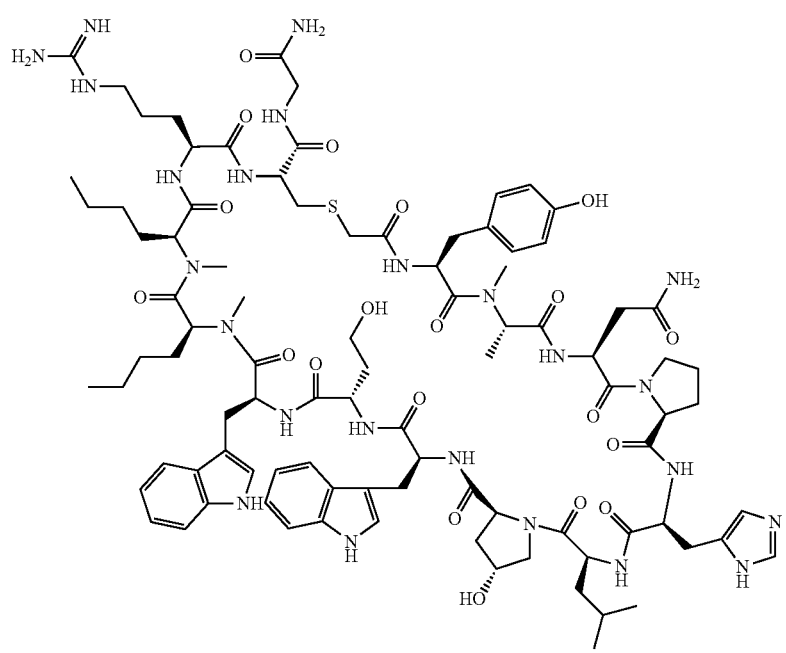

Example 9049

The crude material of Example 9049 was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 98%.

Analysis condition A: Retention time=1.49 min; ESI-MS (+) m/z 963.3 (M+2H).

Analysis condition B: Retention time=2.58 min; ESI-MS (+) m/z 963.3 (M+2H).

Preparation of Example 9050

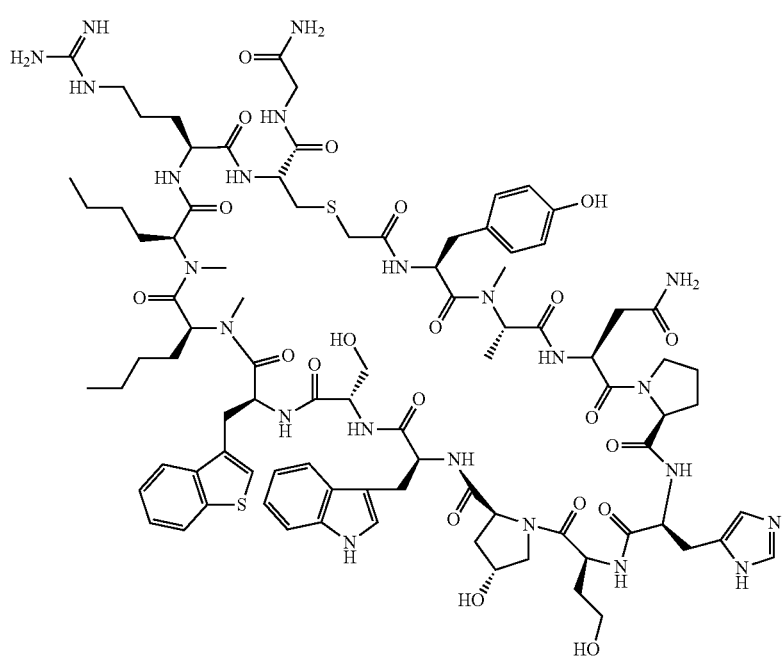

Example 9050

The crude material of Example 9050 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 34.5 mg, and its estimated purity by LCMS analysis was 98%.

Analysis condition A: Retention time=1.60 min; ESI-MS (+) m/z 958.7 (M+2H).

Analysis condition B: Retention time=2.79 min; ESI-MS (+) m/z 958.7 (M+2H).

Preparation of Example 9051

Example 9051

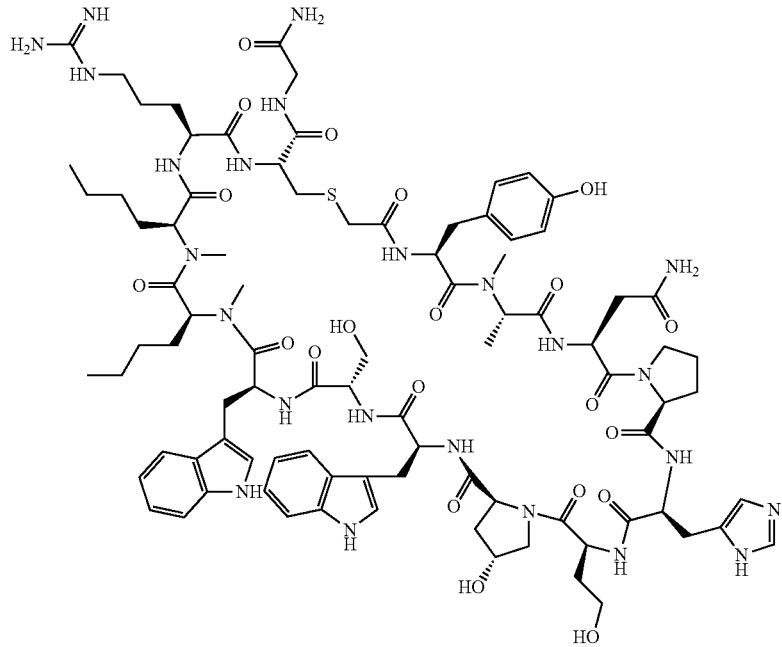

The crude material of Example 9051 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.2 mg, and its estimated purity by LCMS analysis was 97%.

Analysis condition A: Retention time=1.48 min; ESI-MS (+) m/z 950.3 (M+2H).

Analysis condition B: Retention time=2.55 min; ESI-MS (+) m/z 950.6 (M+2H).

Preparation of Example 9052

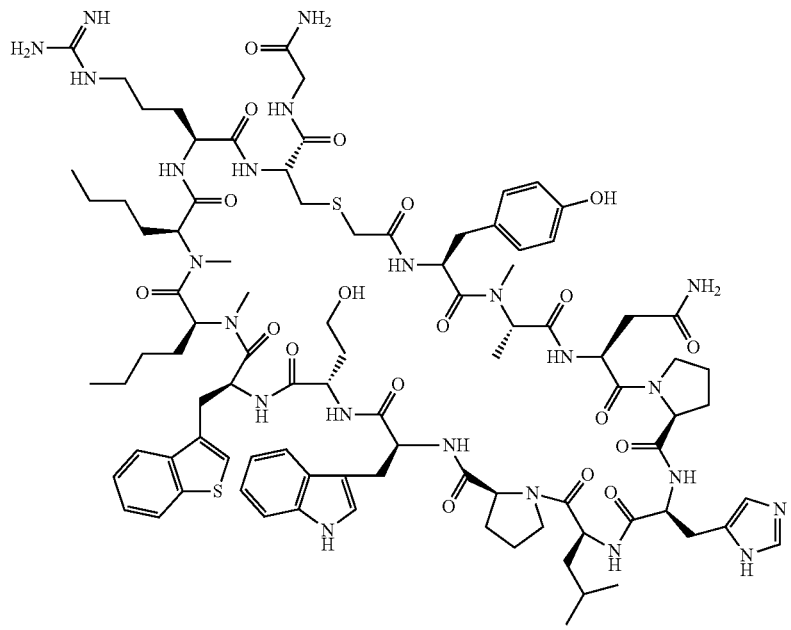

Example 9052

The crude material of Example 9052 was purified via preparative LC/MS with the following conditions: Column: Waters XBridge C18, 19×200 mm, 5-μm particles; Mobile Phase A: water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 9.2 mg, and its estimated purity by LCMS analysis was 99%.

Analysis condition A: Retention time=1.65 min; ESI-MS (+) m/z 963.5 (M+2H).

Analysis condition B: Retention time=2.83 min; ESI-MS (+) m/z 963.7 (M+2H).

Preparation of Example 9053

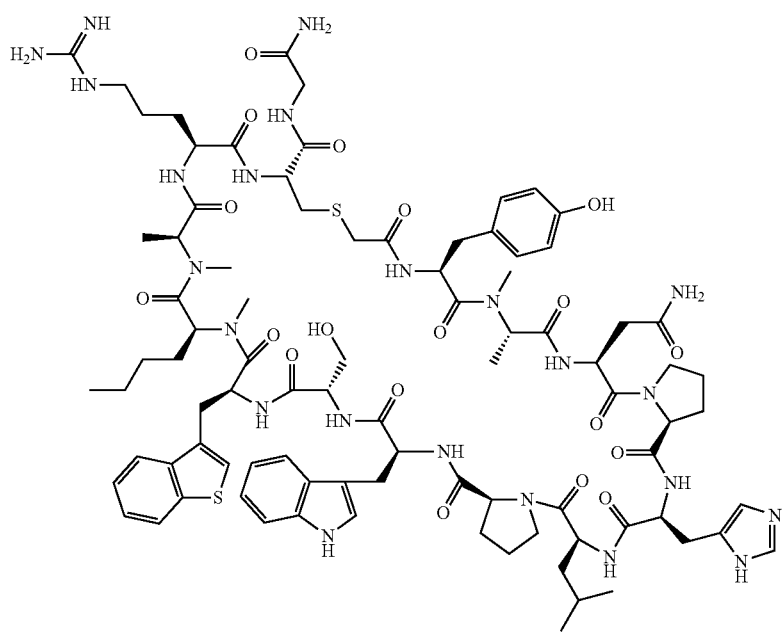

Example 9053

The crude material of Example 9053 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Mobile Phase A: water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The yield of the product was 20.6 mg, and its estimated purity by LCMS analysis was 99%.

Analysis condition A: Retention time=1.52 min; ESI-MS (+) m/z 935.6 (M+2H).

Analysis condition B: Retention time=2.63 min; ESI-MS (+) m/z 935.3 (M+2H).

Preparation of Example 9054

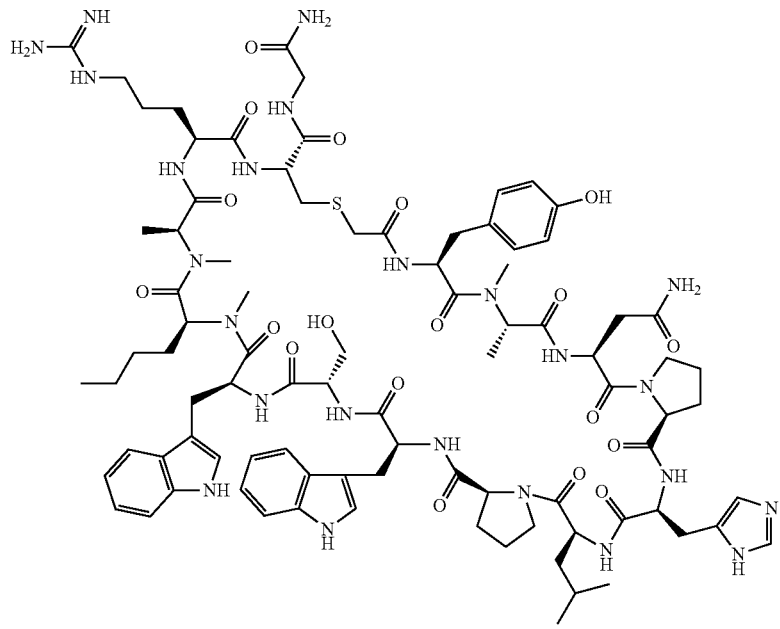

Example 9054

The crude material of Example 9054 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 96%.

Analysis condition A: Retention time=1.37 min; ESI-MS (+) m/z 927.1 (M+2H).

Analysis condition B: Retention time=2.39 min; ESI-MS (+) m/z 927.2 (M+2H).

Preparation of Example 9055

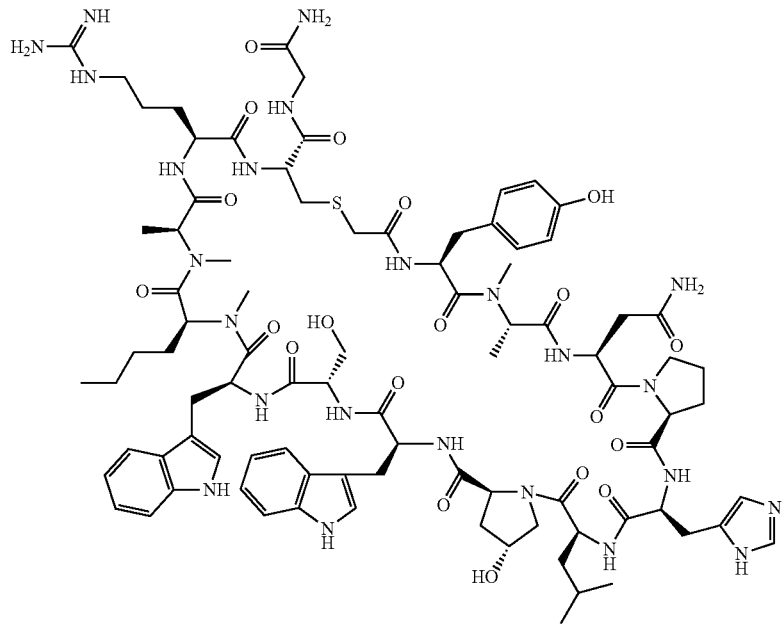

Example 9055

The crude material of Example 9055 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 99%.

Analysis condition A: Retention time=1.34 min; ESI-MS (+) m/z 934.9 (M+2H).

Analysis condition B: Retention time=2.36 min; ESI-MS (+) m/z 934.9 (M+2H).

Preparation of Example 9056

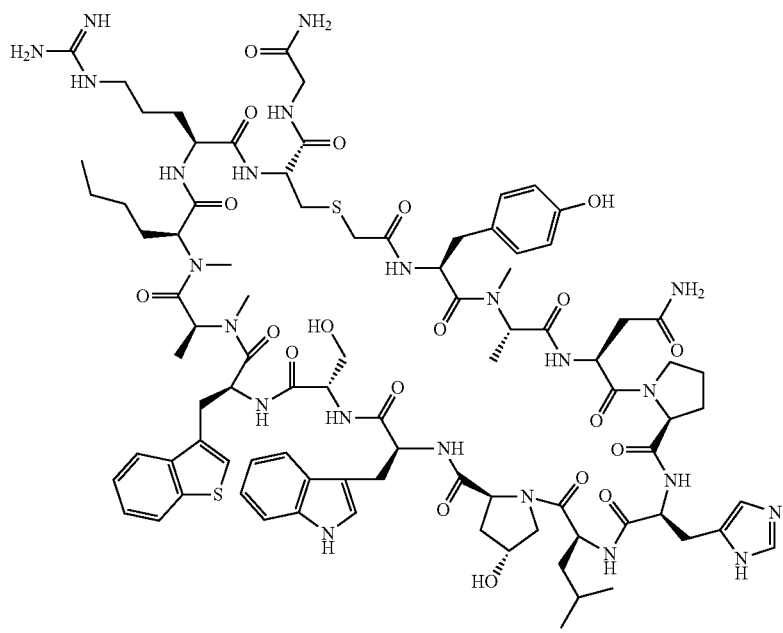

Example 9056

The crude material of Example 9056 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 100%.

Analysis condition A: Retention time=1.45 min; ESI-MS (+) m/z 943.4 (M+2H).

Analysis condition B: Retention time=2.56 min; ESI-MS (+) m/z 943.7 (M+2H).

Preparation of Example 9057

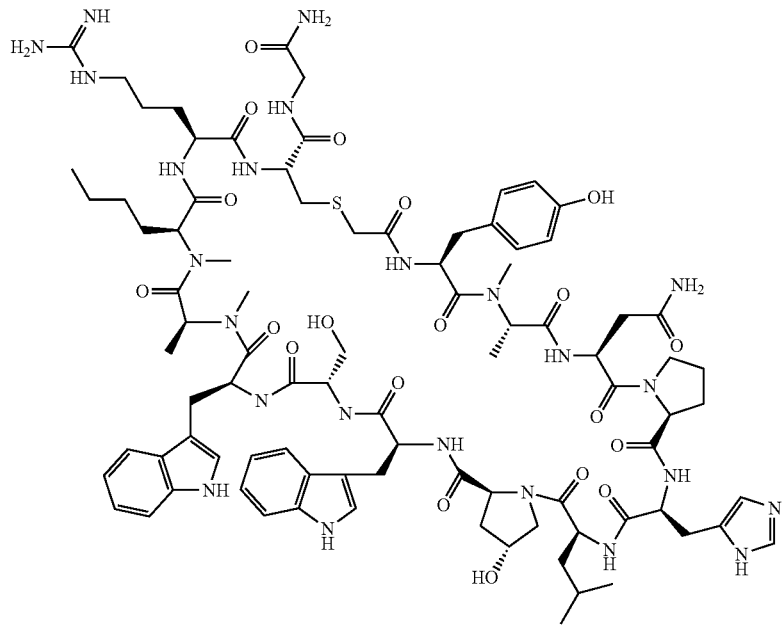

Example 9057

The crude material of Example 9057 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 18.6 mg, and its estimated purity by LCMS analysis was 95%.

Analysis condition A: Retention time=1.30 min; ESI-MS (+) m/z 934.8 (M+2H).
Analysis condition B: Retention time=2.33 min; ESI-MS (+) m/z 934.8 (M+2H).

Preparation of Example 9058

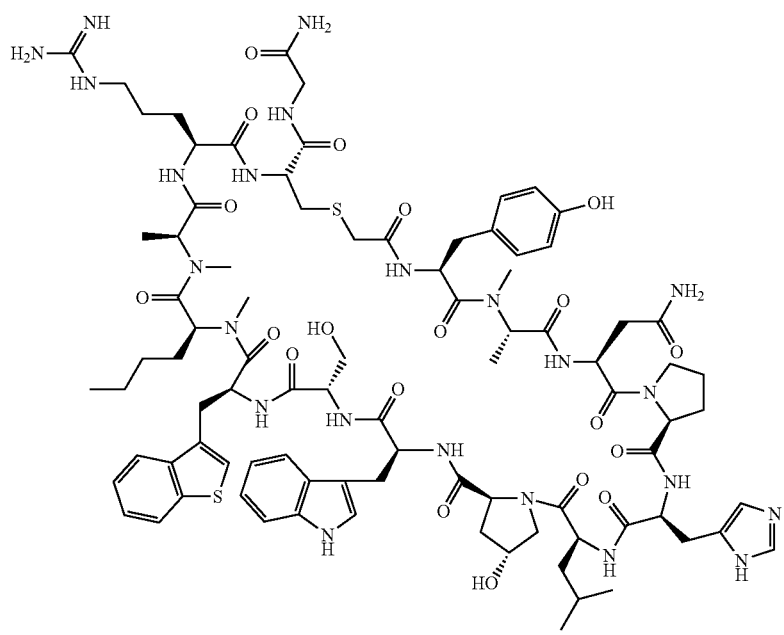

Example 9058

The crude material of Example 9058 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 9.2 mg, and its estimated purity by LCMS analysis was 98%.

Analysis condition A: Retention time=1.49 min; ESI-MS (+) m/z 943.6 (M+2H).
Analysis condition B: Retention time=2.60 min; ESI-MS (+) m/z 943.7 (M+2H).

Preparation of Example 9059

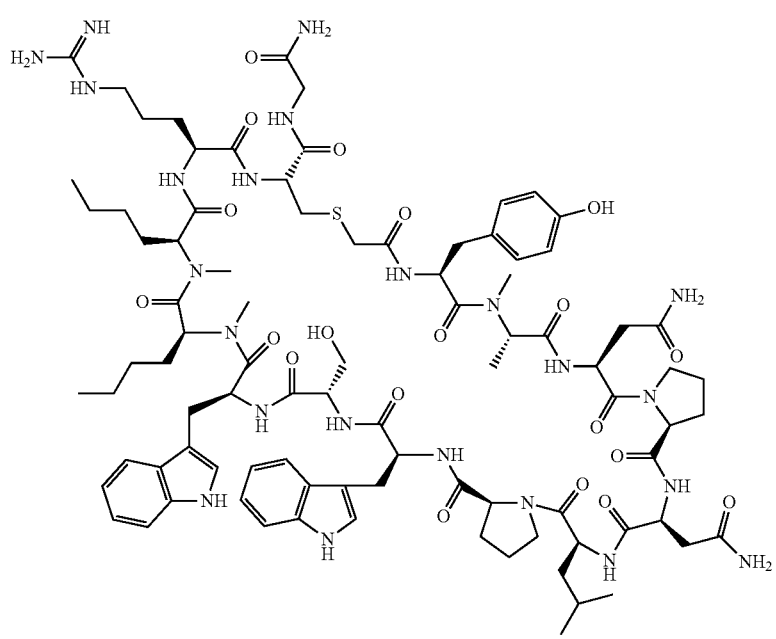

Example 9059

The crude material of Example 9059 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 36.4 mg, and its estimated purity by LCMS analysis was 94%.

Analysis condition A: Retention time=1.54 min; ESI-MS (+) m/z 936.5 (M+2H).

Analysis condition B: Retention time=2.54 min; ESI-MS (+) m/z 936.3 (M+2H).

Preparation of Example 9060

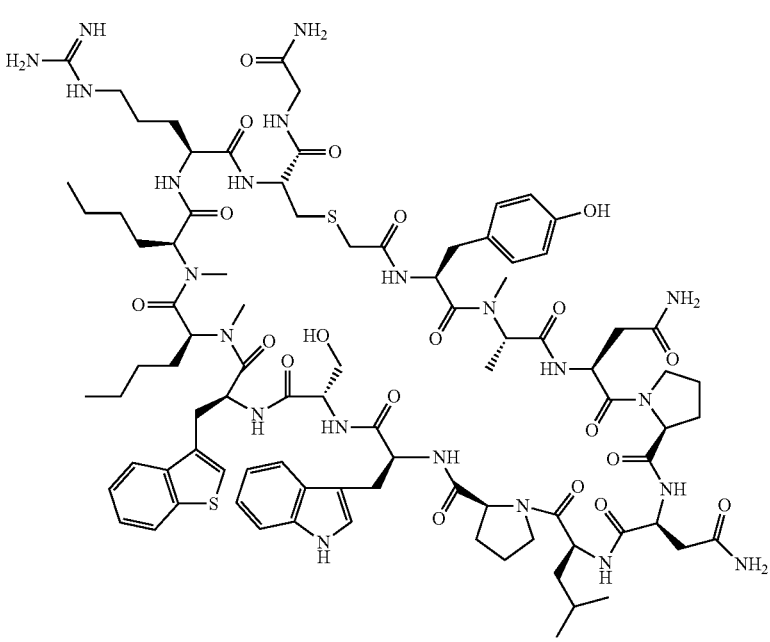

Example 9060

The crude material of Example 906 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 18.9 mg, and its estimated purity by LCMS analysis was 96%.

Analysis condition A: Retention time=1.73 min; ESI-MS (+) m/z 944.8 (M+2H).

Analysis condition B: Retention time=2.91 min; ESI-MS (+) m/z 944.9 (M+2H).

Preparation of Example 9061

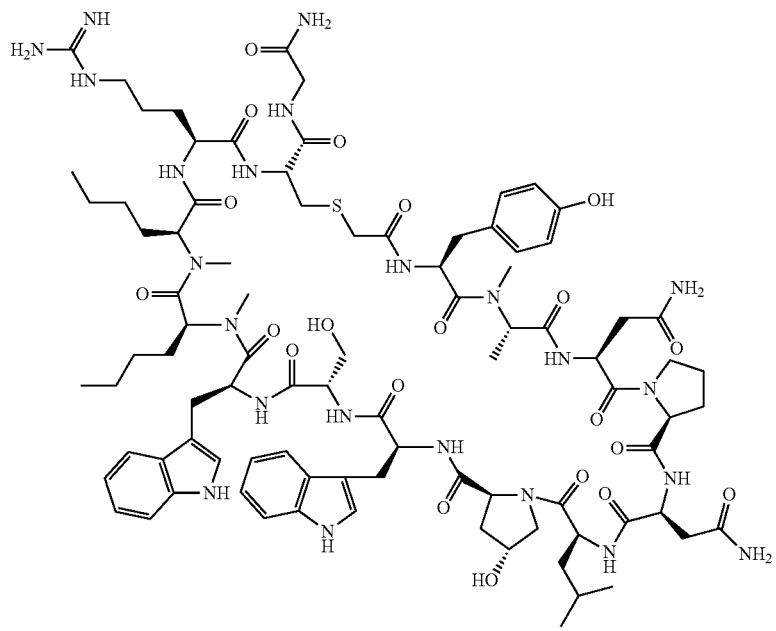

Example 9061

The crude material of Example 9061 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.3 mg, and its estimated purity by LCMS analysis was 96%.

Analysis condition A: Retention time=1.51 min; ESI-MS (+) m/z 944.6 (M+2H).

Analysis condition B: Retention time=2.65 min; ESI-MS (+) m/z 944.7 (M+2H).

Preparation of Example 9062

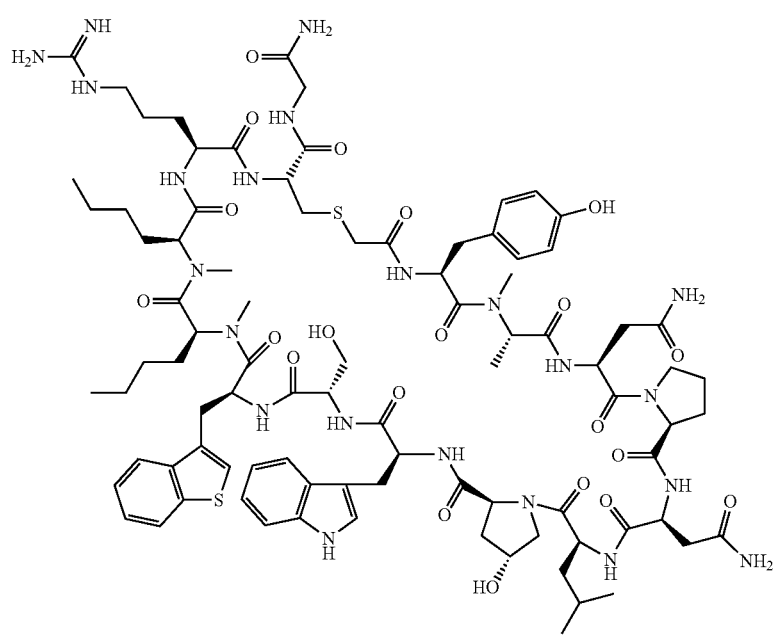

Example 9062

The crude material of Example 9062 was purified via preparative LC/MS with the following conditions: Column: Waters XBridge C18, 19×200 mm, 5-μm particles; Mobile Phase A: water with 20-mM ammonium acetate; Mobile Phase B: 95:5 methanol:water with 20-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 100%.

Analysis condition A: Retention time=1.66 min; ESI-MS (+) m/z 953.3 (M+2H).

Analysis condition B: Retention time=2.88 min; ESI-MS (+) m/z 952.9 (M+2H).

Preparation of Example 9063

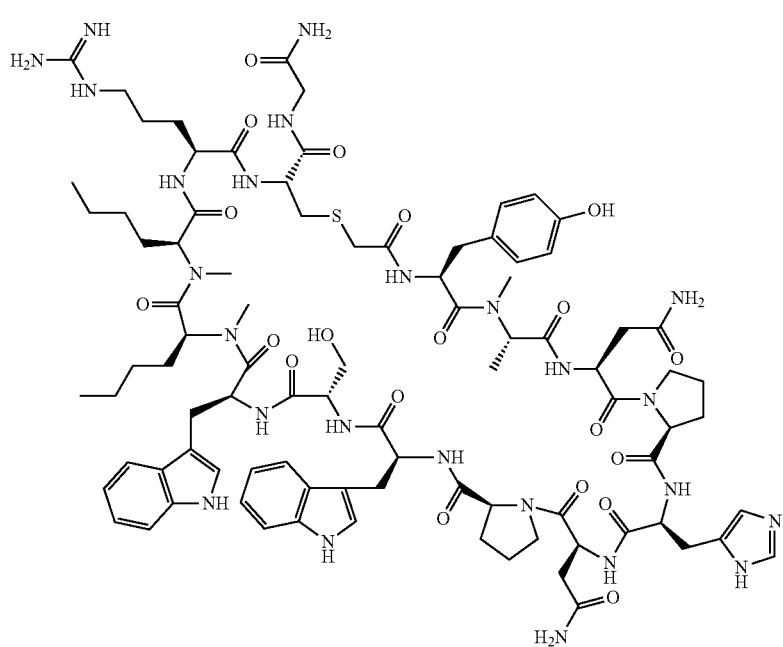

Example 9063

The crude material of Example 9063 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 100%.

Analysis condition A: Retention time=1.47 min; ESI-MS (+) m/z 948.5 (M+2H).

Analysis condition B: Retention time=2.64 min; ESI-MS (+) m/z 948.8 (M+2H).

Preparation of Example 9064

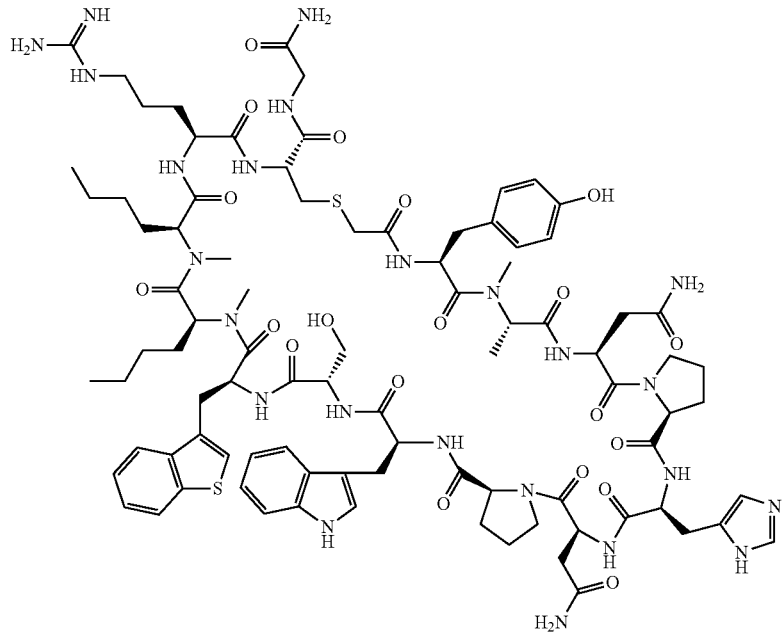

Example 9064

The crude material of Example 9064 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 12.4 mg, and its estimated purity by LCMS analysis was 99%.

Analysis condition A: Retention time=1.58 min; ESI-MS (+) m/z 956.9 (M+2H).

Analysis condition B: Retention time=2.81 min; ESI-MS (+) m/z 957.3 (M+2H).

Preparation of Example 9065

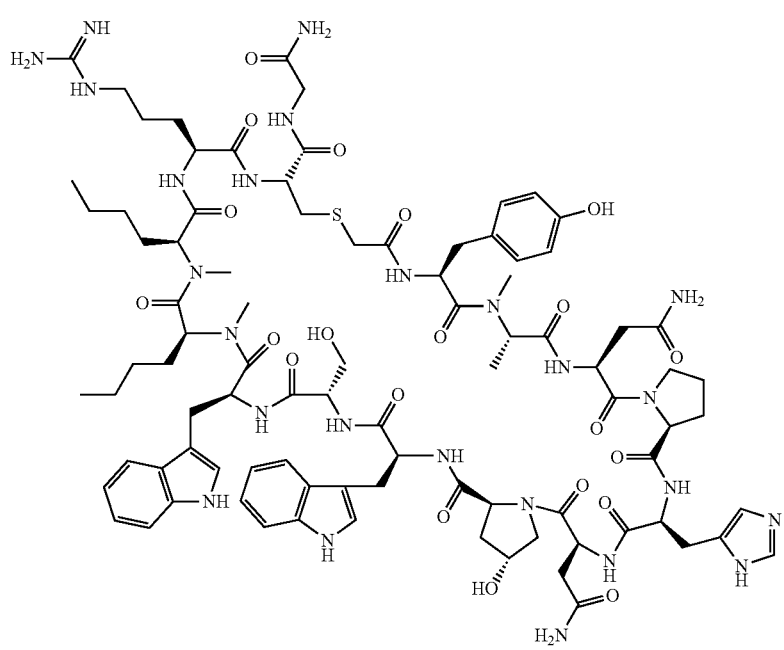

Example 9065

The crude material of Example 9065 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 11.4 mg, and its estimated purity by LCMS analysis was 100%.

Analysis condition A: Retention time=1.44 min; ESI-MS (+) m/z 956.8 (M+2H).

Analysis condition B: Retention time=2.60 min; ESI-MS (+) m/z 956.8 (M+2H).

Preparation of Example 9066

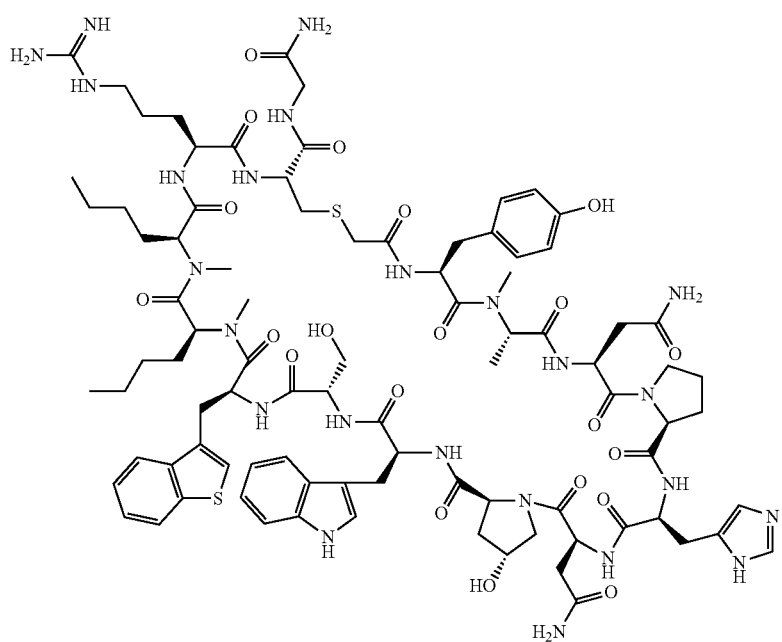

Example 9066

The crude material of Example 9066 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 97%.

Analysis condition A: Retention time=1.59 min; ESI-MS (+) m/z 964.9 (M+2H).

Analysis condition B: Retention time=2.78 min; ESI-MS (+) m/z 965.2 (M+2H).

Preparation of Example 9067

Example 9067

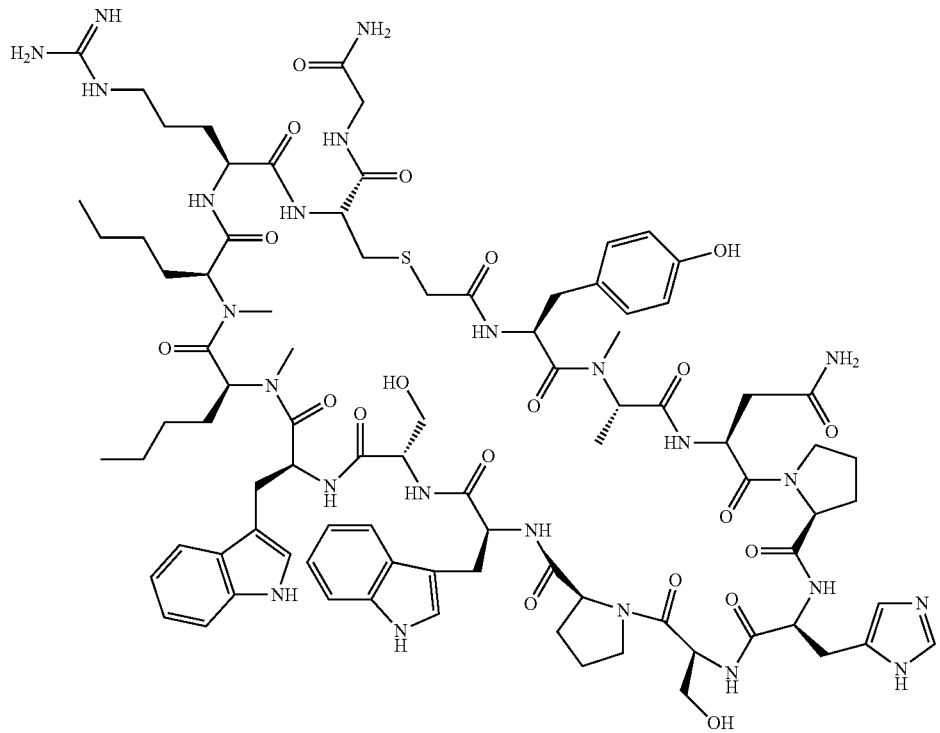

The crude material of Example 9067 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 29.8 mg, and its estimated purity by LCMS analysis was 100%.

Analysis condition A: Retention time=1.57 min; ESI-MS (+) m/z 934.9 (M+2H).

Analysis condition B: Retention time=2.57 min; ESI-MS (+) m/z 934.4 (M+2H).

Preparation of Example 9068

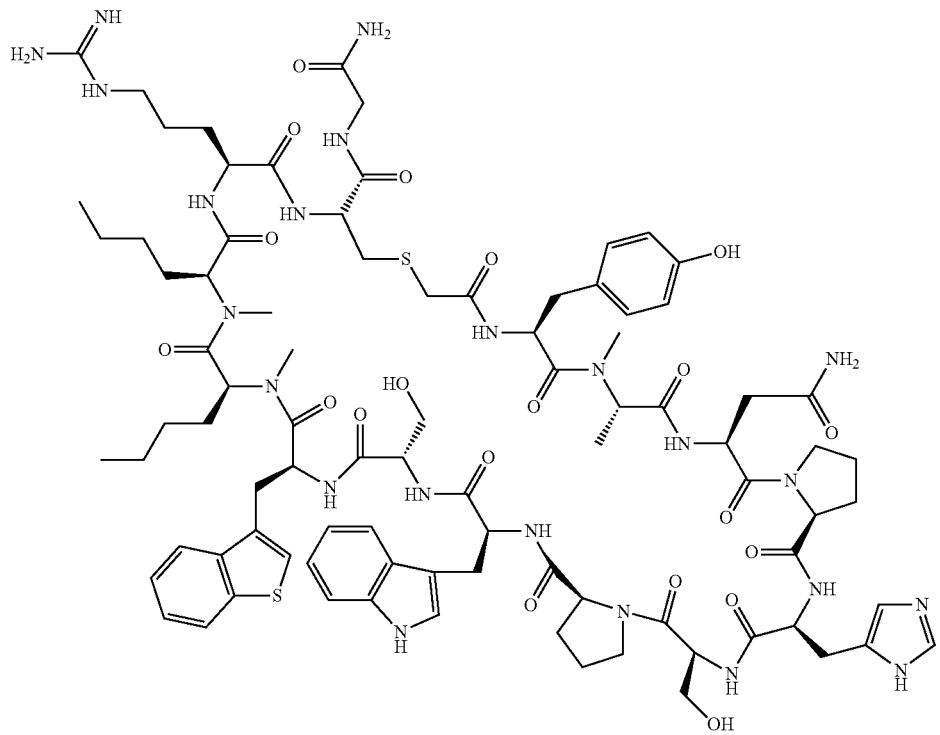

Example 9068

The crude material of Example 9068 was purified via preparative LC/MS with the following conditions: Column: Waters XBridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 100%.

Analysis condition A: Retention time=1.61 min; ESI-MS (+) m/z 943.3 (M+2H).

Analysis condition B: Retention time=2.84 min; ESI-MS (+) m/z 943.7 (M+2H).

Preparation of Example 9069

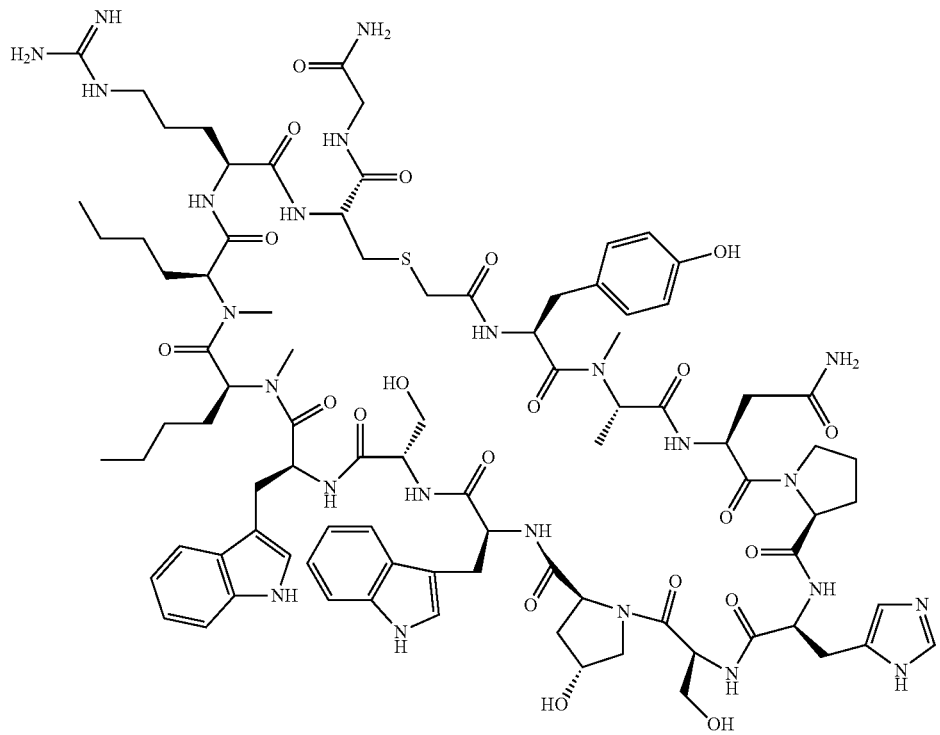

Example 9069

The crude material of Example 9069 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 25.1 mg, and its estimated purity by LCMS analysis was 100%.

Analysis condition A: Retention time=1.46 min; ESI-MS (+) m/z 943.2 (M+2H).

Analysis condition B: Retention time=2.64 min; ESI-MS (+) m/z 943.3 (M+2H).

Preparation of Example 9070

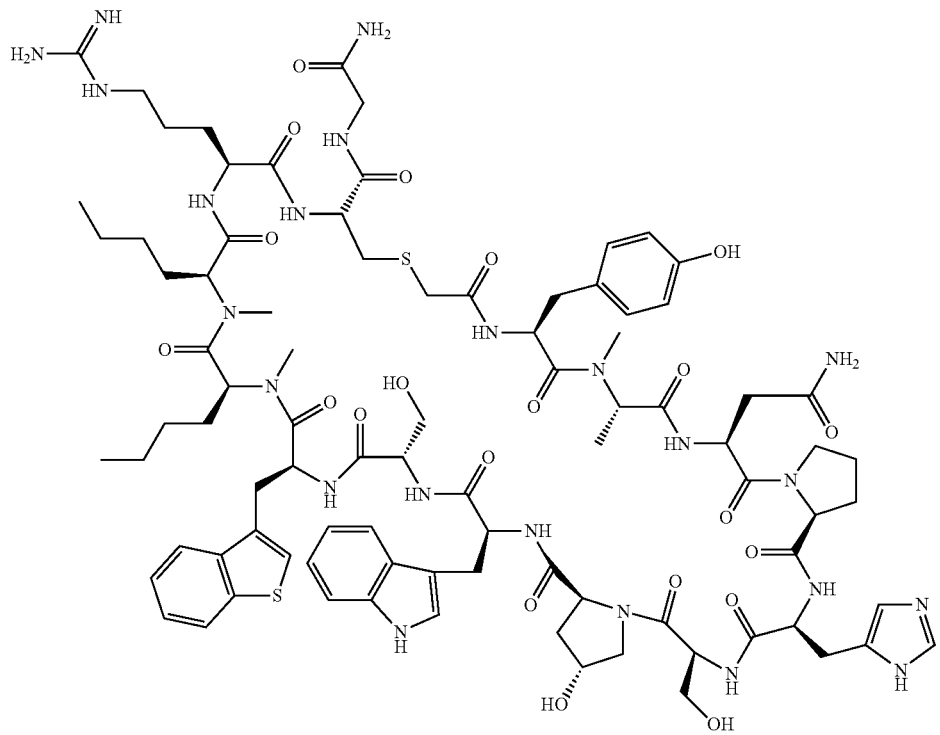

Example 9070

The crude material of Example 9070 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 22.9 mg, and its estimated purity by LCMS analysis was 100%.

Analysis condition A: Retention time=1.63 min; ESI-MS (+) m/z 951.7 (M+2H).

Analysis condition B: Retention time=2.85 min; ESI-MS (+) m/z 951.7 (M+2H).

Preparation of Example 9071

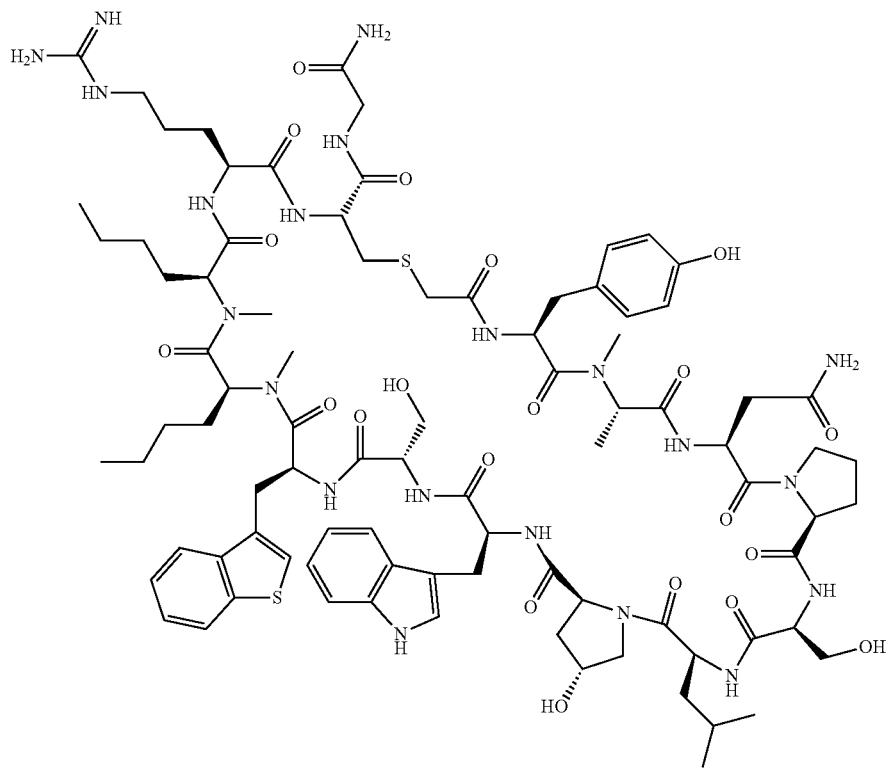

Example 9071

The crude material of Example 9071 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 13.6 mg, and its estimated purity by LCMS analysis was 100%.

Analysis condition B: Retention time=2.91 min; ESI-MS (+) m/z 939.8 (M+2H).

Preparation of Example 9072

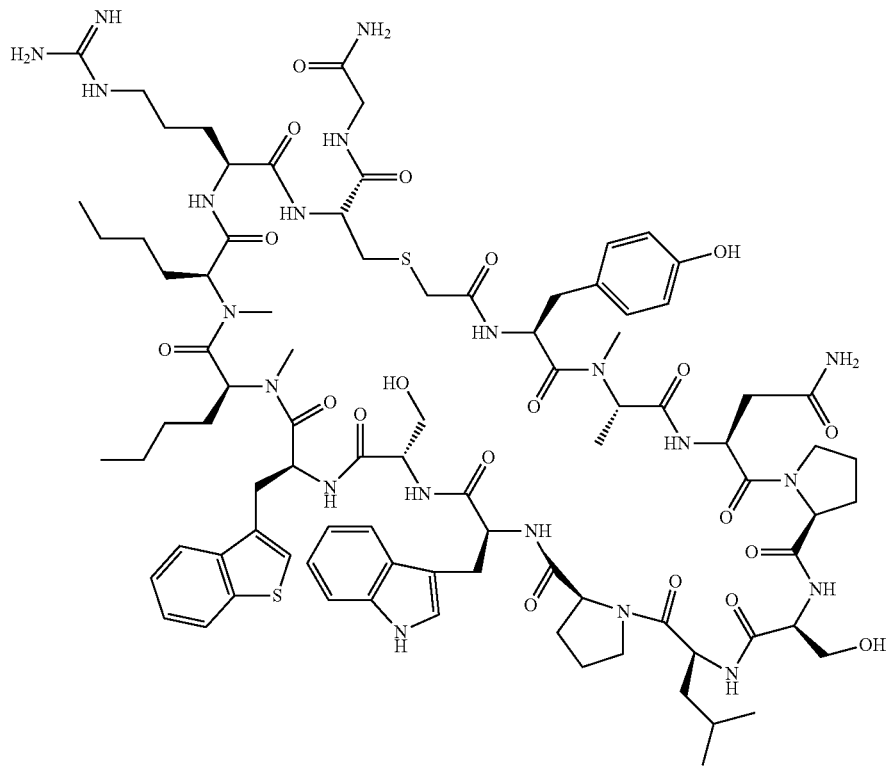

Example 9072

The crude material of Example 9072 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.2 mg, and its estimated purity by LCMS analysis was 97%.

Analysis condition A: Retention time=1.72 min; ESI-MS (+) m/z 931.8 (M+2H).

Analysis condition B: Retention time=2.93 min; ESI-MS (+) m/z 931.8 (M+2H).

Preparation of Example 9073

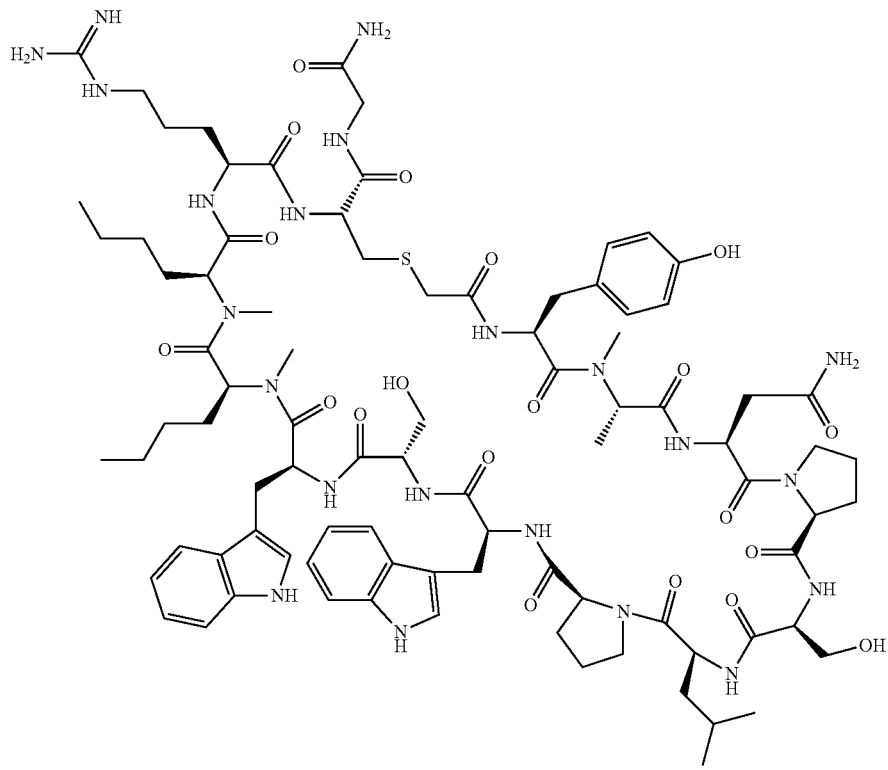

Example 9073

The crude material of Example 9073 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 96%.

Analysis condition A: Retention time=1.57 min; ESI-MS (+) m/z 922.7 (M+2H).

Analysis condition B: Retention time=2.74 min; ESI-MS (+) m/z 922.9 (M+2H).

Preparation of Example 9074

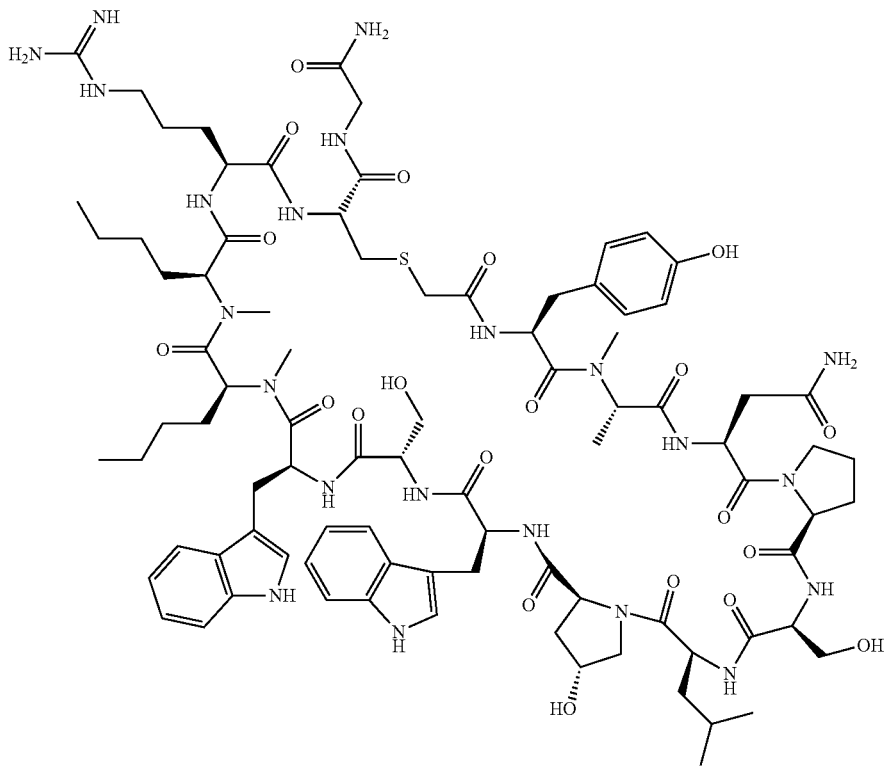

Example 9074

The crude material of Example 9074 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 99%.

Analysis condition A: Retention time=1.52 min; ESI-MS (+) m/z 931.0 (M+2H).

Analysis condition B: Retention time=2.98 min; ESI-MS (+) m/z 930.9 (M+2H).

Preparation of Example 9075

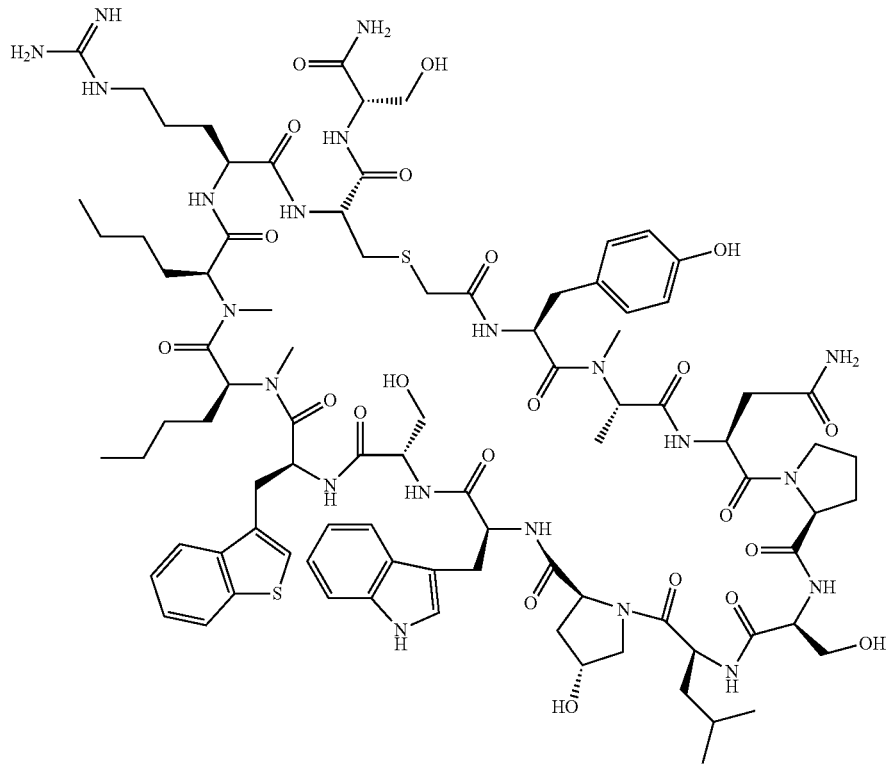

Example 9075

The crude material of Example 9075 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.1 mg, and its estimated purity by LCMS analysis was 99%.

Analysis condition A: Retention time=1.61 min; ESI-MS (+) m/z 954.5 (M+2H).

Analysis condition B: Retention time=3.18 min; ESI-MS (+) m/z 954.5 (M+2H).

Preparation of Example 9076

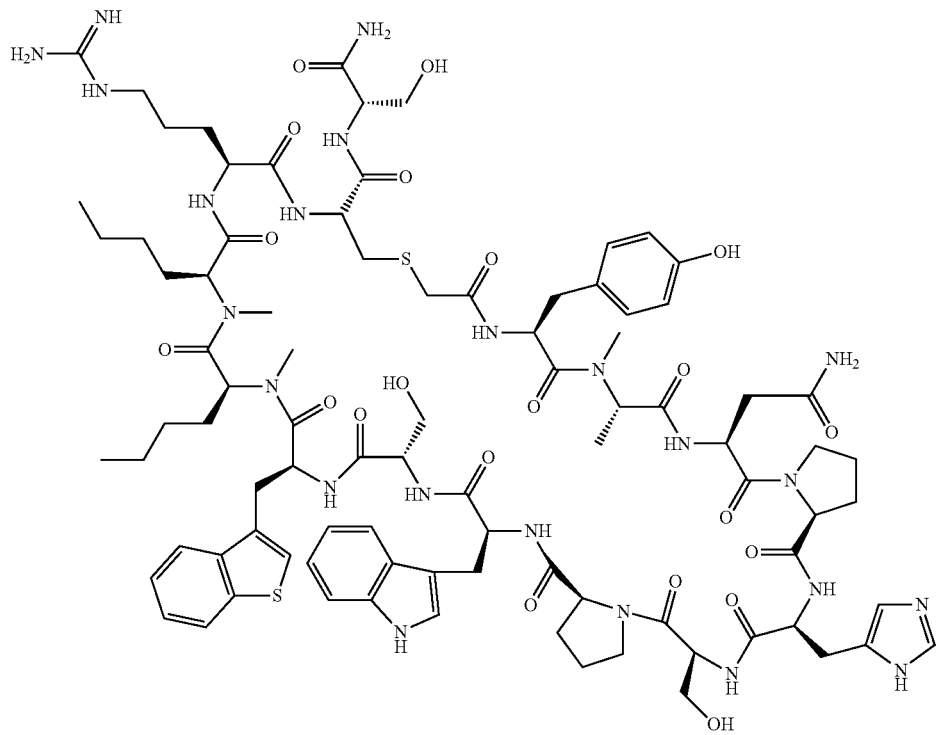

Example 9076

The crude material of Example 9076 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 44.3 mg, and its estimated purity by LCMS analysis was 99%.

Analysis condition A: Retention time=1.55 min; ESI-MS (+) m/z 958.5 (M+2H).

Analysis condition B: Retention time=3.11 min; ESI-MS (+) m/z 958.5 (M+2H).

Preparation of Example 9077

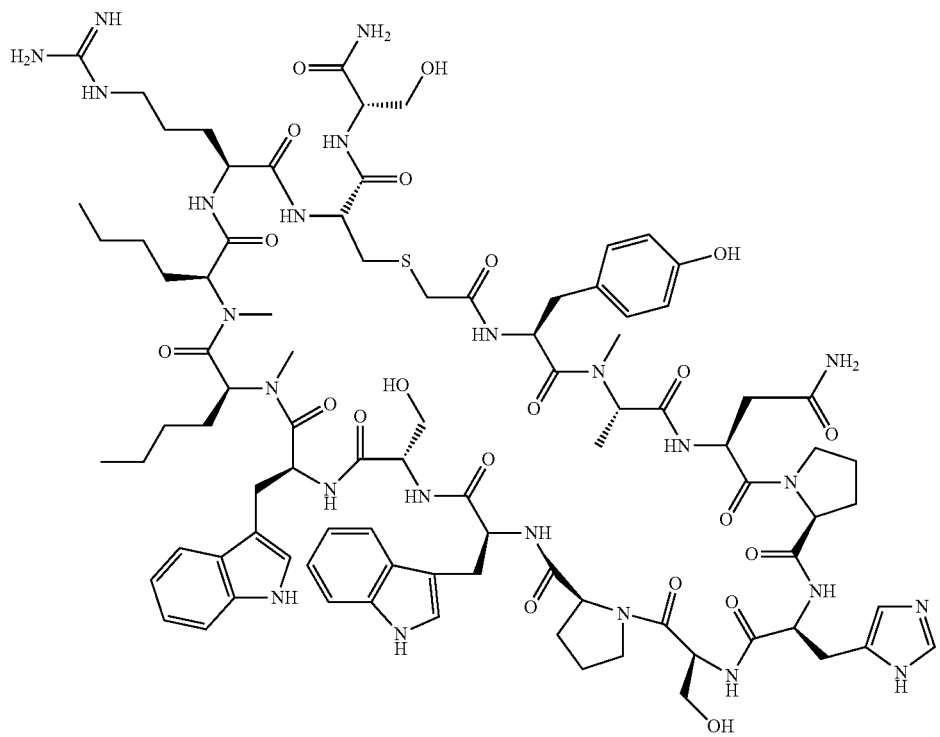

Example 9077

The crude material of Example 9077 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 30.3 mg, and its estimated purity by LCMS analysis was 100%.

Analysis condition A: Retention time=1.44 min; ESI-MS (+) m/z 950.8 (M+2H).

Analysis condition B: Retention time=2.92 min; ESI-MS (+) m/z 950.0 (M+2H).

Preparation of Example 9078

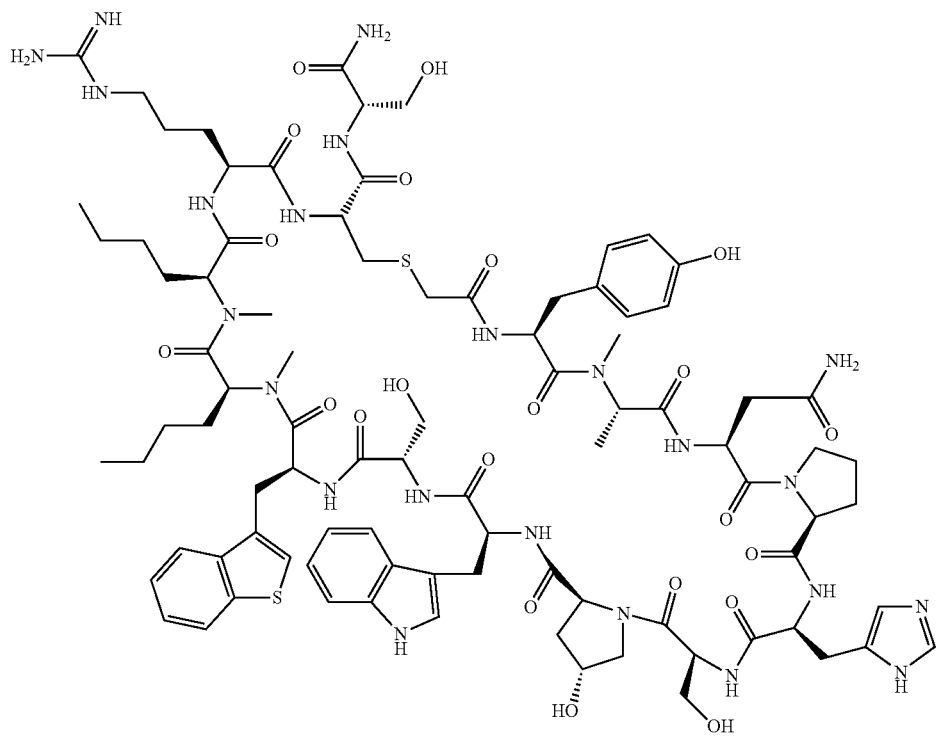

Example 9078

The crude material of Example 9078 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 39.1 mg, and its estimated purity by LCMS analysis was 100%.

Analysis condition A: Retention time=1.53 min; ESI-MS (+) m/z 966.5 (M+2H).

Analysis condition B: Retention time=3.09 min; ESI-MS (+) m/z 966.4 (M+2H).

Preparation of Example 9079

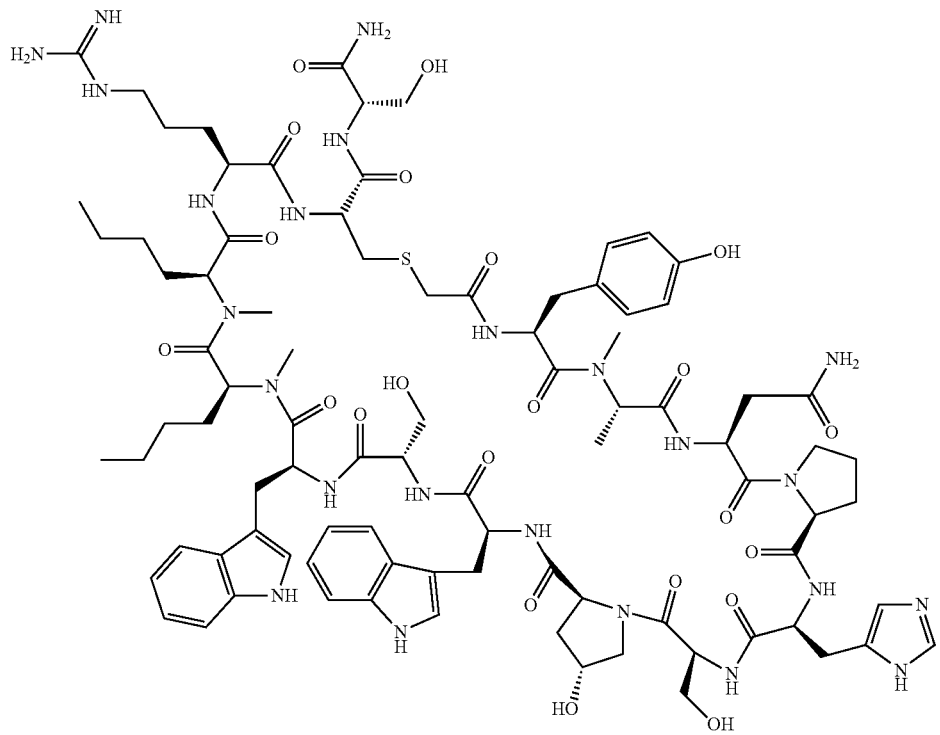

Example 9079

The crude material of Example 9079 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 23.7 mg, and its estimated purity by LCMS analysis was 100%.

Analysis condition A: Retention time=1.42 min; ESI-MS (+) m/z 957.9 (M+2H).

Analysis condition B: Retention time=2.89 min; ESI-MS (+) m/z 958.0 (M+2H).

Preparation of Example 9080

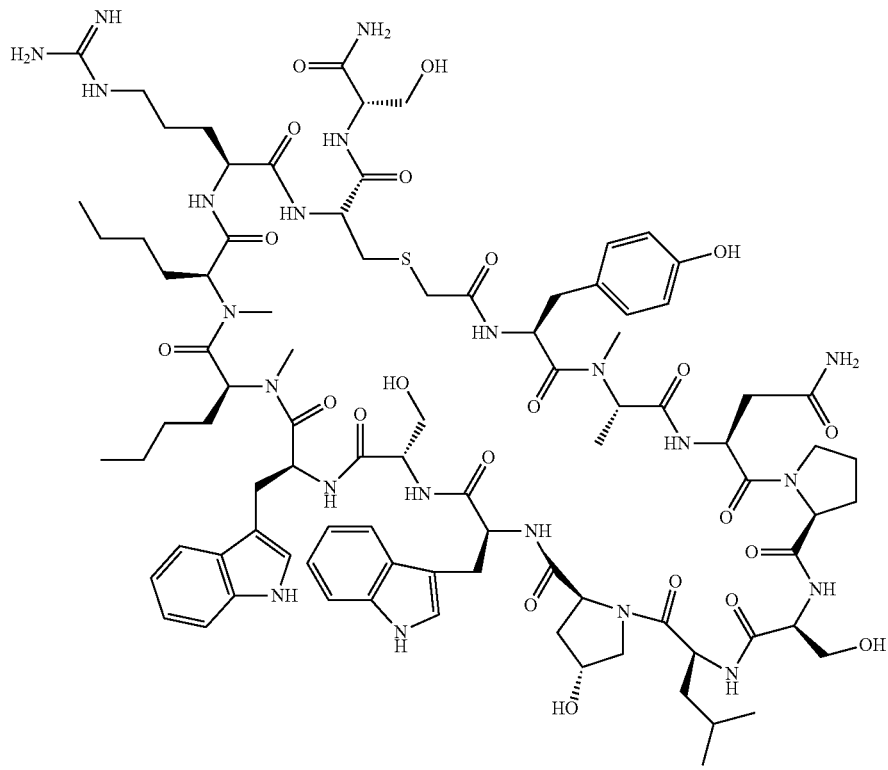

Example 9080

The crude material of Example 9080 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.8 mg, and its estimated purity by LCMS analysis was 99%.

Analysis condition A: Retention time=1.50 min; ESI-MS (+) m/z 945.9 (M+2H).

Analysis condition B: Retention time=2.97 min; ESI-MS (+) m/z 945.8 (M+2H).

Preparation of Example 9081

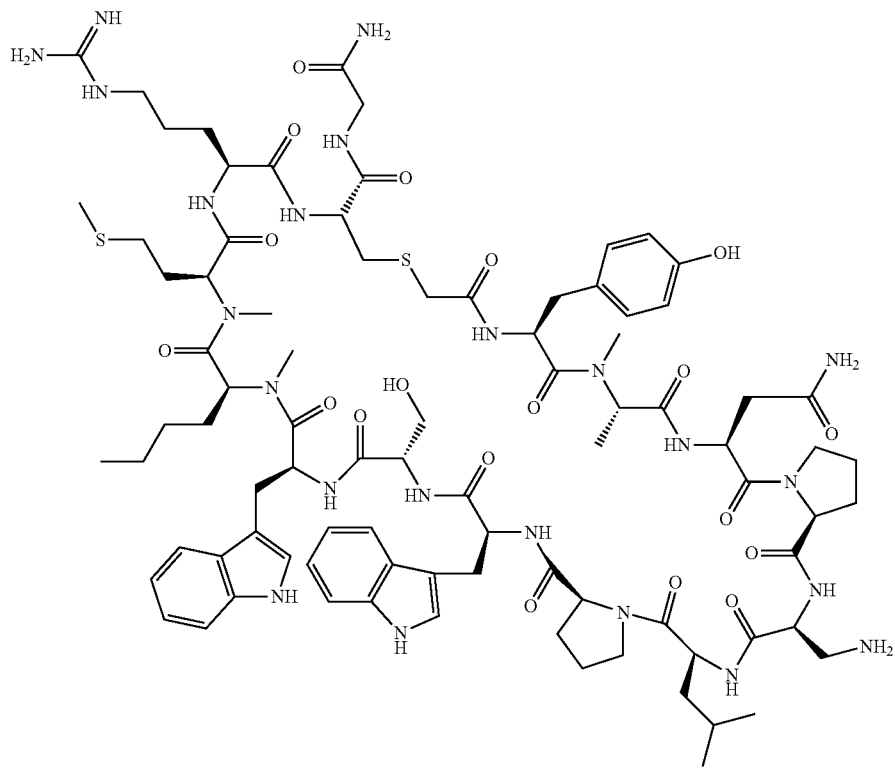

Example 9081

The crude material of Example 9081 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 11.1 mg, and its estimated purity by LCMS analysis was 100%.

Analysis condition A: Retention time=1.46 min; ESI-MS (+) m/z 931.6 (M+2H).

Analysis condition B: Retention time=2.60 min; ESI-MS (+) m/z 931.7 (M+2H).

Preparation of Example 9082

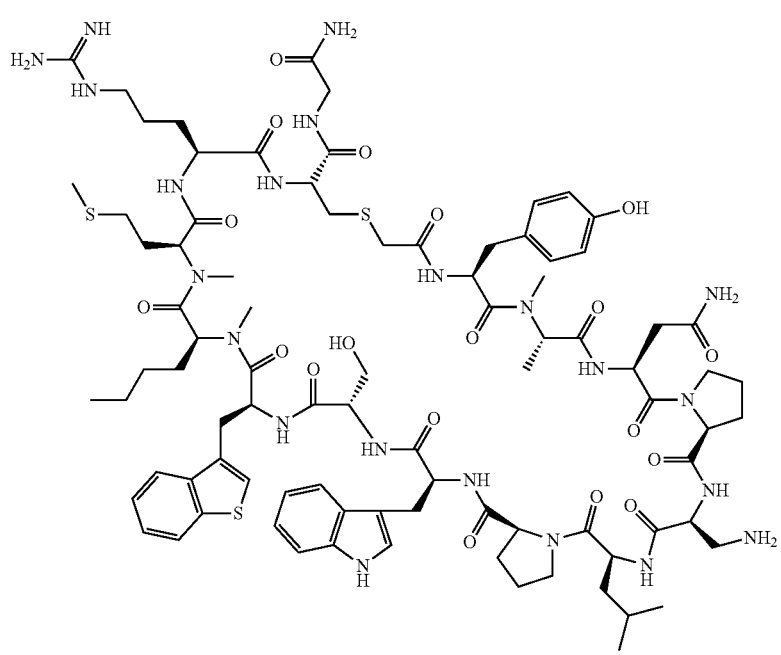

Example 9082

The crude material of Example 9082 was purified via preparative LC/MS with the following conditions: Column: Waters XBridge c-18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 12.3 mg, and its estimated purity by LCMS analysis was 98%.

Analysis condition A: Retention time=1.63 min; ESI-MS (+) m/z 939.7 (M+2H).

Analysis condition B: Retention time=2.82 min; ESI-MS (+) m/z 939.8 (M+2H).

Preparation of Example 9083

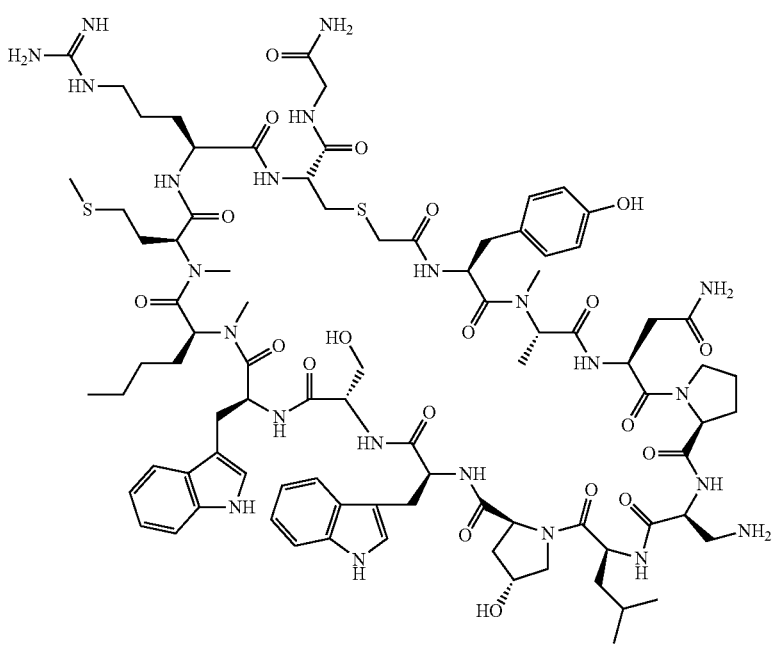

Example 9083

The crude material of Example 9083 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 99%.

Analysis condition A: Retention time=1.46 min; ESI-MS (+) m/z 939.7 (M+2H).

Analysis condition B: Retention time=2.58 min; ESI-MS (+) m/z 939.7 (M+2H).

Preparation of Example 9084

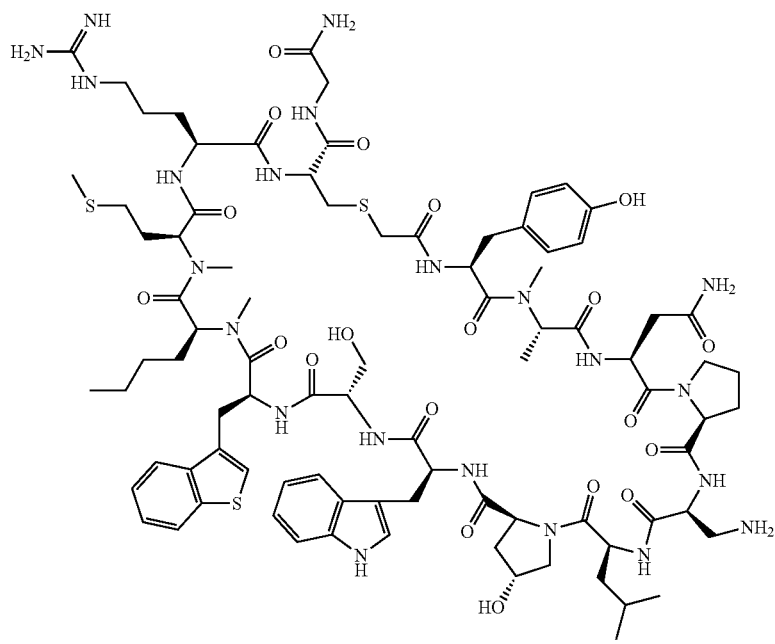

Example 9084

The crude material of Example 9084 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 100%.

Analysis condition A: Retention time=1.57 min; ESI-MS (+) m/z 948.1 (M+2H).

Analysis condition B: Retention time=2.79 min; ESI-MS (+) m/z 948.1 (M+2H).

Preparation of Example 9085

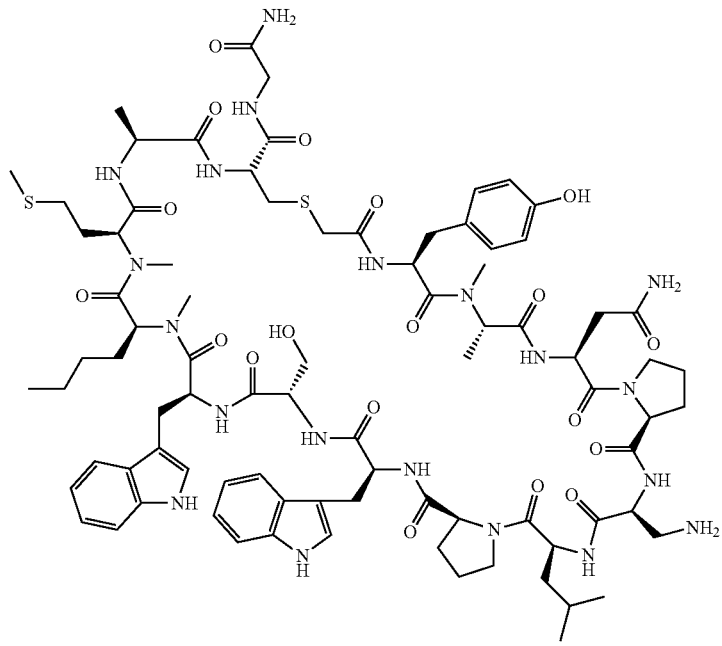

Example 9085

The crude material of Example 9085 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 21.8 mg, and its estimated purity by LCMS analysis was 90%.

Analysis condition A: Retention time=1.55 min; ESI-MS (+) m/z 889.1 (M+2H)$^+$.

Analysis condition B: Retention time=2.70 min; ESI-MS (+) m/z 889.1 (M+2H)$^+$.

Preparation of Example 9086

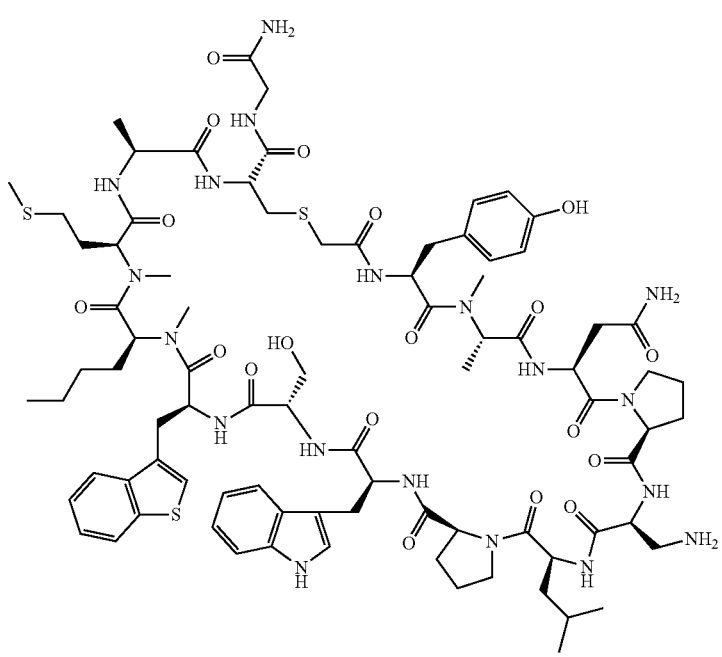

Example 9086

The crude material of Example 9086 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 25.5 mg, and its estimated purity by LCMS analysis was 98%.

Analysis condition A: Retention time=1.68 min; ESI-MS (+) m/z 897.4 (M+2H).

Analysis condition B: Retention time=2.90 min; ESI-MS (+) m/z 897.6 (M+2H).

Preparation of Example 9087

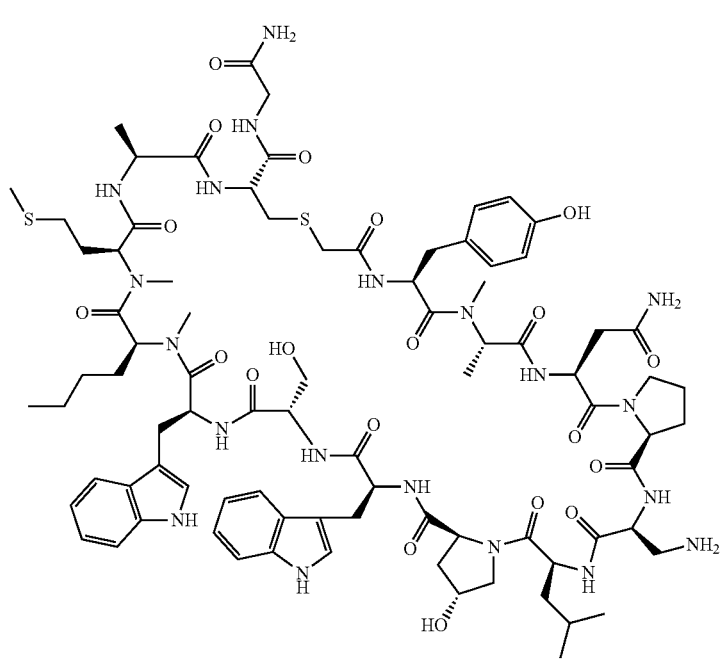

Example 9087

The crude material of Example 9087 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 24.6 mg, and its estimated purity by LCMS analysis was 99%.

Analysis condition A: Retention time=1.48 min; ESI-MS (+) m/z 897.0 (M+2H).

Analysis condition B: Retention time=2.66 min; ESI-MS (+) m/z 897.0 (M+2H).

Preparation of Example 9088

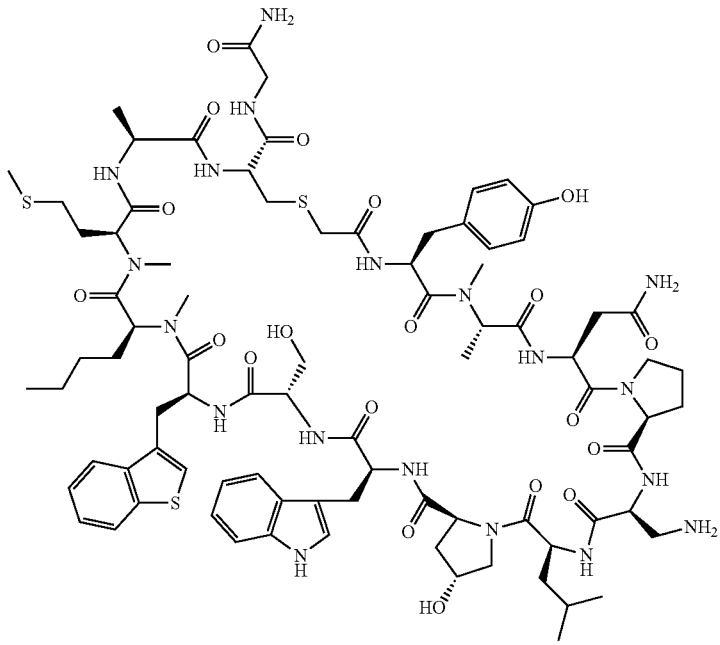

Example 9088

The crude material of Example 9088 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 18.3 mg, and its estimated purity by LCMS analysis was 100%.

Analysis condition A: Retention time=1.62 min; ESI-MS (+) m/z 905.6 (M+2H).

Analysis condition B: Retention time=2.88 min; ESI-MS (+) m/z 905.2 (M+2H).

Preparation of Example 9089

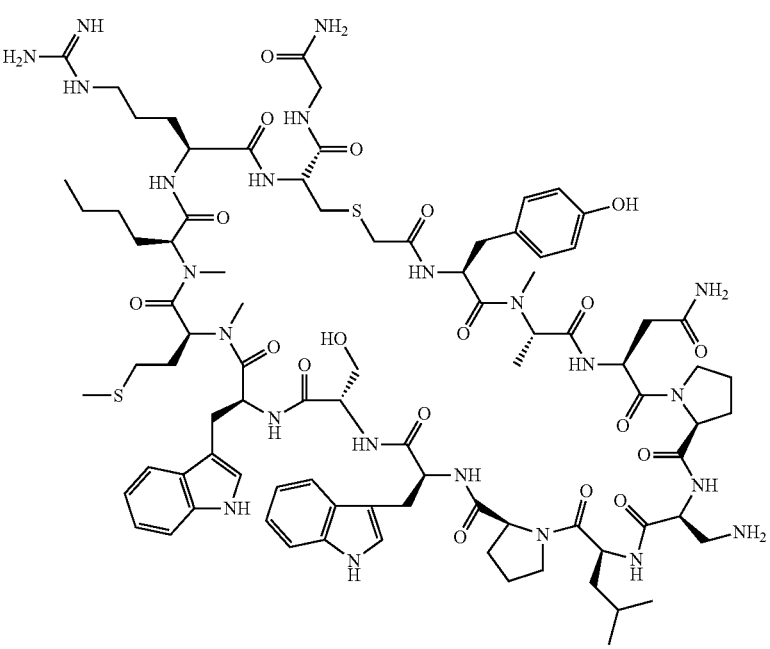

Example 9089

The crude material of Example 9089 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.5 mg, and its estimated purity by LCMS analysis was 92%.

Analysis condition A: Retention time=1.41 min; ESI-MS (+) m/z 931.6 (M+2H).

Analysis condition B: Retention time=2.56 min; ESI-MS (+) m/z 931.7 (M+2H).

Preparation of Example 9090

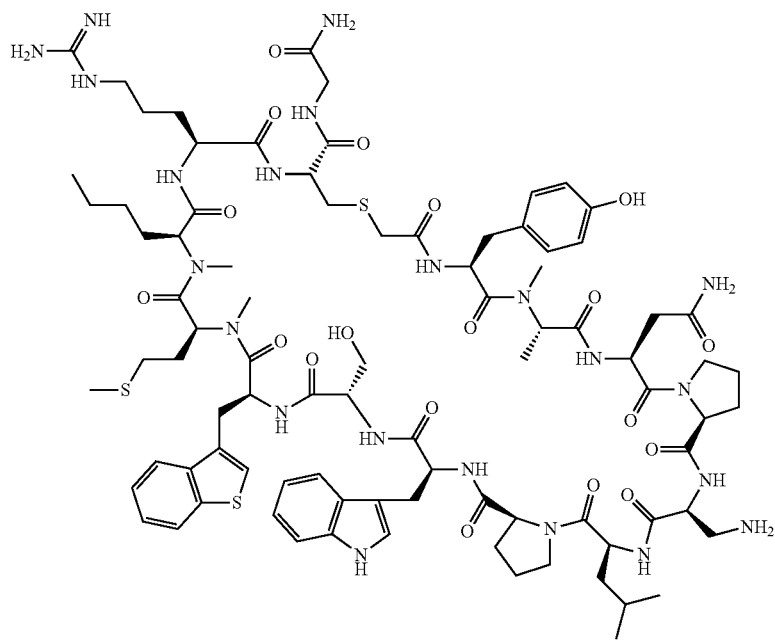

Example 9090

The crude material of Example 9090 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 28.6 mg, and its estimated purity by LCMS analysis was 94%.

Analysis condition A: Retention time=1.52 min; ESI-MS (+) m/z 940.1 (M+2H).

Analysis condition B: Retention time=2.75 min; ESI-MS (+) m/z 940.3 (M+2H).

Preparation of Example 9091

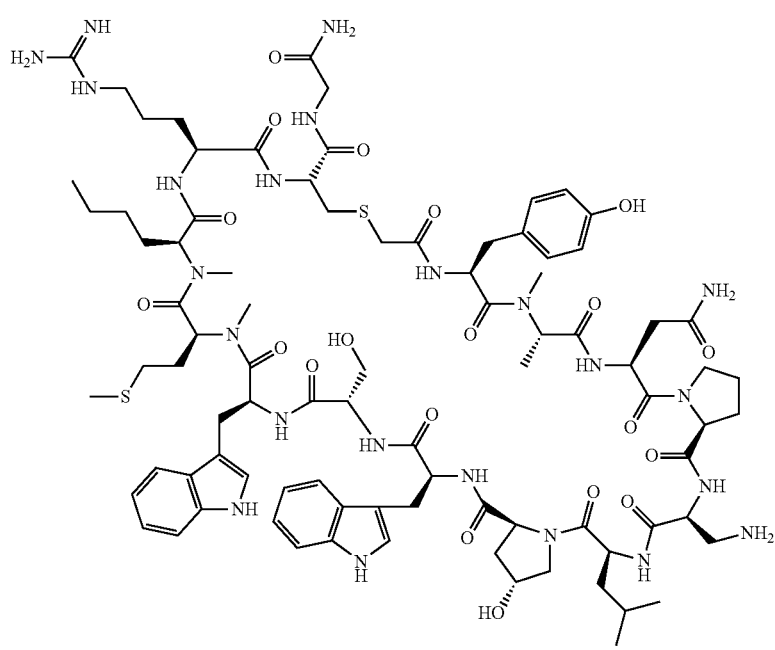

Example 9091

The crude material of Example 9091 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 24.7 mg, and its estimated purity by LCMS analysis was 98%.

Analysis condition A: Retention time=1.36 min; ESI-MS (+) m/z 939.7 (M+2H).

Analysis condition B: Retention time=2.51 min; ESI-MS (+) m/z 939.7 (M+2H).

Preparation of Example 9092

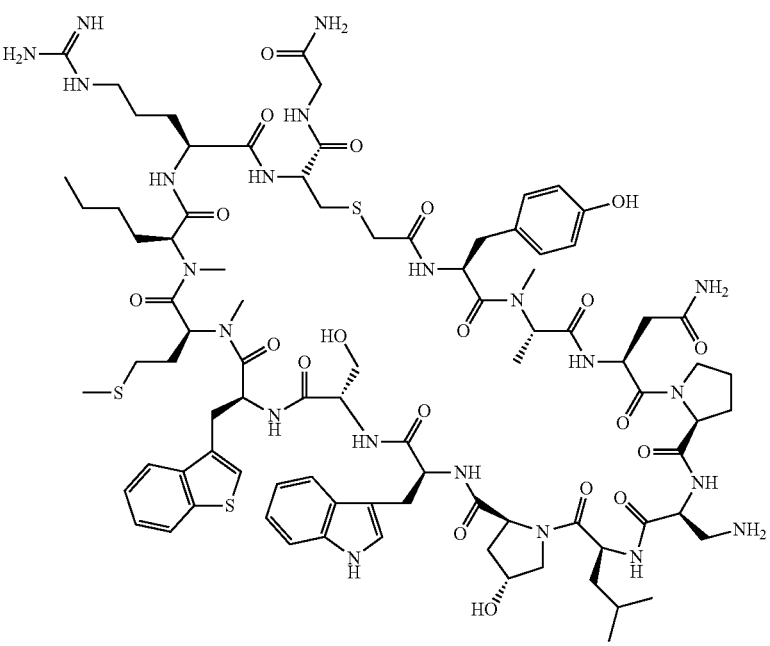

Example 9092

The crude material of Example 9092 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-80% B over 30 minutes, then a 5-minute hold at 100% B; Flow: 20 mL/min. Fractions containing the desired product were combined and dried via centrifugal evaporation. The yield of the product was 34.3 mg, and its estimated purity by LCMS analysis was 95%.

Analysis condition A: Retention time=1.47 min; ESI-MS (+) m/z 948.1 (M+2H).

Analysis condition B: Retention time=2.69 min; ESI-MS (+) m/z 948.2 (M+2H).

Preparation of Example 9093

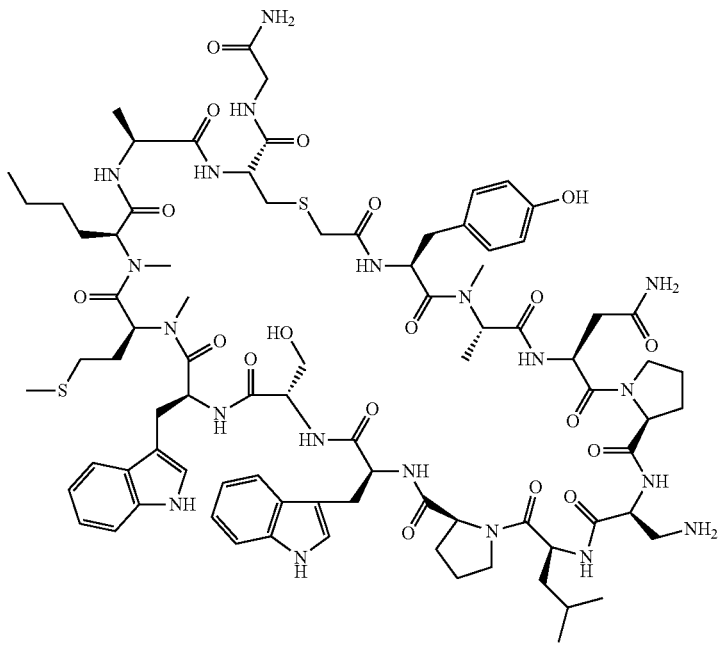

Example 9093

The crude material of Example 9093 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 22.4 mg, and its estimated purity by LCMS analysis was 100%.

Analysis condition A: Retention time=1.50 min; ESI-MS (+) m/z 889.4 (M+2H).

Analysis condition B: Retention time=2.64 min; ESI-MS (+) m/z 889.0 (M+2H).

Preparation of Example 9094

Example 9094

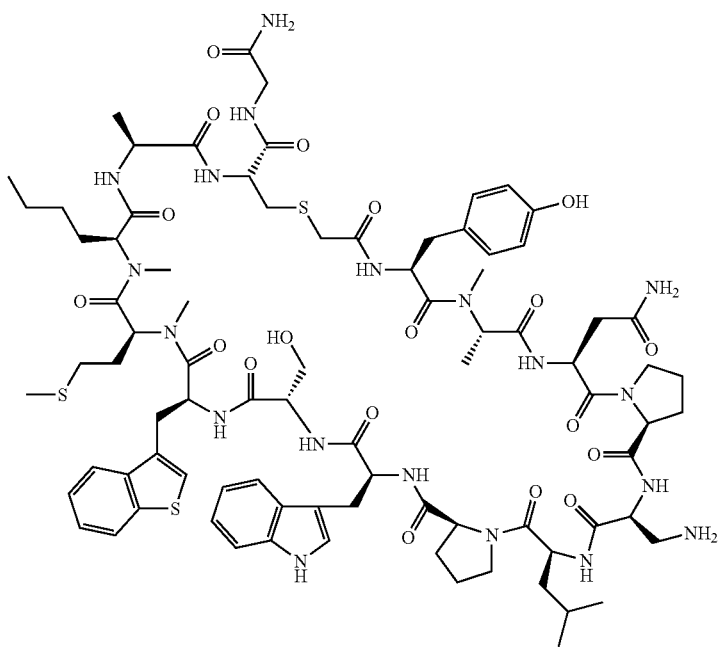

The crude material of Example 9094 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 24.9 mg, and its estimated purity by LCMS analysis was 99%.

Analysis condition A: Retention time=1.65 min; ESI-MS (+) m/z 897.5 (M+2H).

Analysis condition B: Retention time=2.84 min; ESI-MS (+) m/z 897.6 (M+2H).

Preparation of Example 9095

Example 9095

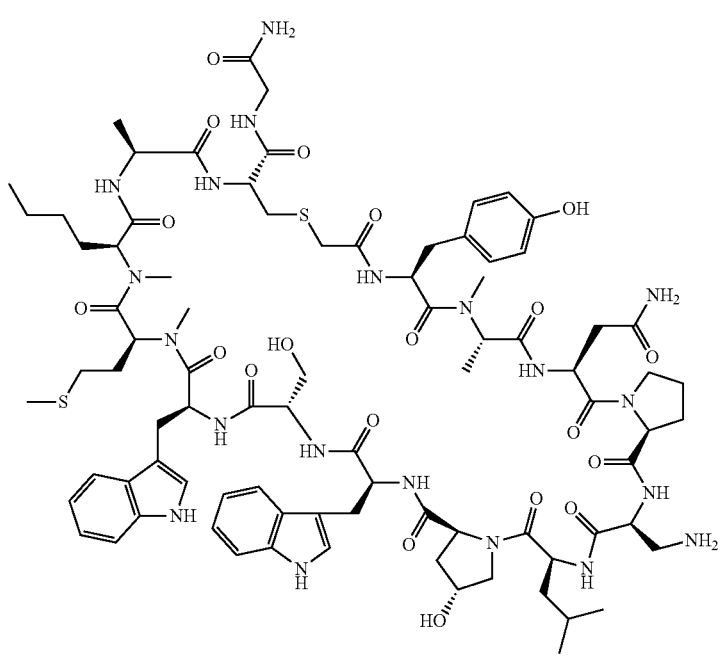

The crude material of Example 9095 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 19.3 mg, and its estimated purity by LCMS analysis was 96%.

Analysis condition A: Retention time=1.43 min; ESI-MS (+) m/z 896.9 (M+2H).

Analysis condition B: Retention time=2.58 min; ESI-MS (+) m/z 896.8 (M+2H).

Preparation of Example 9096

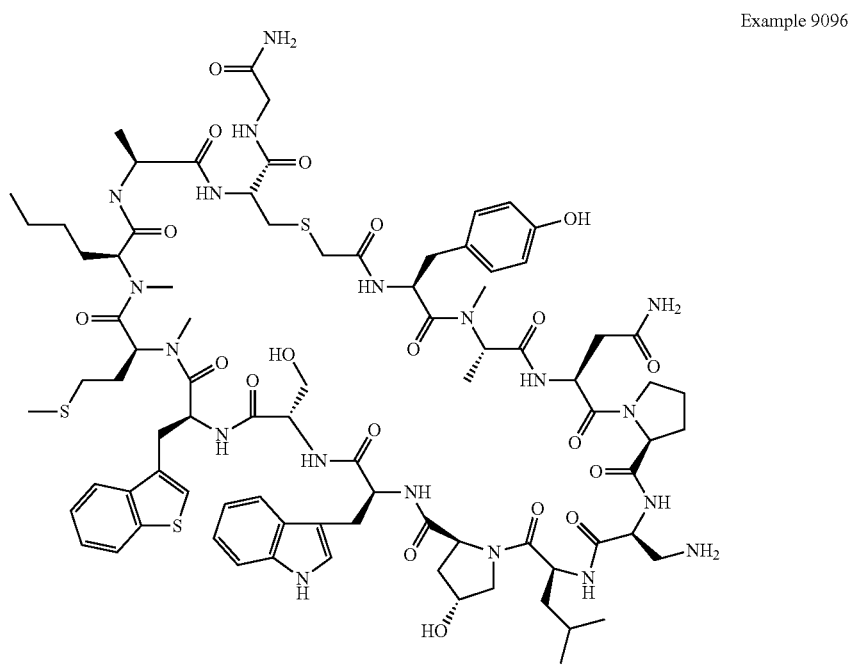

Example 9096

The crude material of Example 9096 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 27.4 mg, and its estimated purity by LCMS analysis was 95%.

Analysis condition A: Retention time=1.56 min; ESI-MS (+) m/z 905.2 (M+2H).

Analysis condition B: Retention time=2.79 min; ESI-MS (+) m/z 905.5 (M+2H).

Preparation of Example 9097

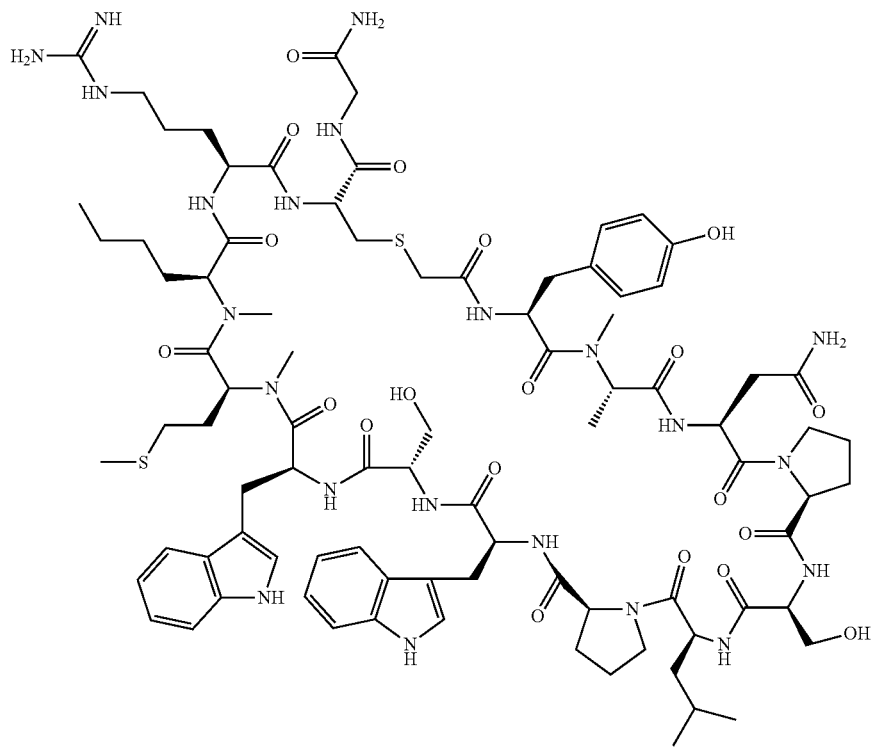

Example 9097

The crude material of Example 9097 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 16.5 mg, and its estimated purity by LCMS analysis was 96%.

Analysis condition A: Retention time=1.51 min; ESI-MS (+) m/z 931.7 (M+2H).

Analysis condition B: Retention time=2.62 min; ESI-MS (+) m/z 931.8 (M+2H).

Preparation of Example 9098

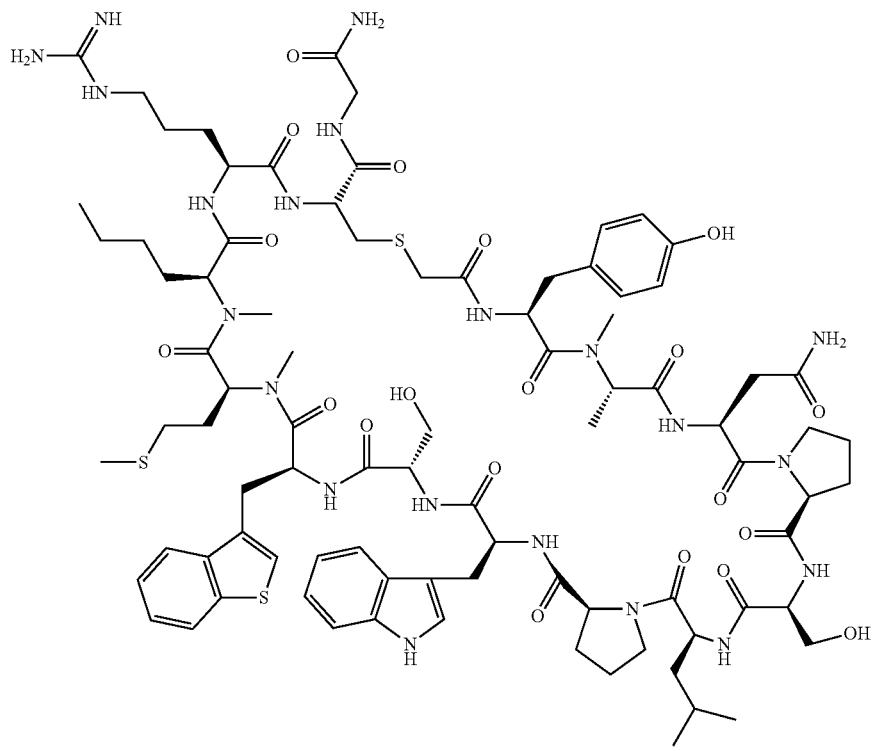

Example 9098

The crude material of Example 9098 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 14.3 mg, and its estimated purity by LCMS analysis was 98%.

Analysis condition A: Retention time=1.67 min; ESI-MS (+) m/z 940.2 (M+2H).

Analysis condition B: Retention time=2.83 min; ESI-MS (+) m/z 940.6 (M+2H).

Preparation of Example 9099

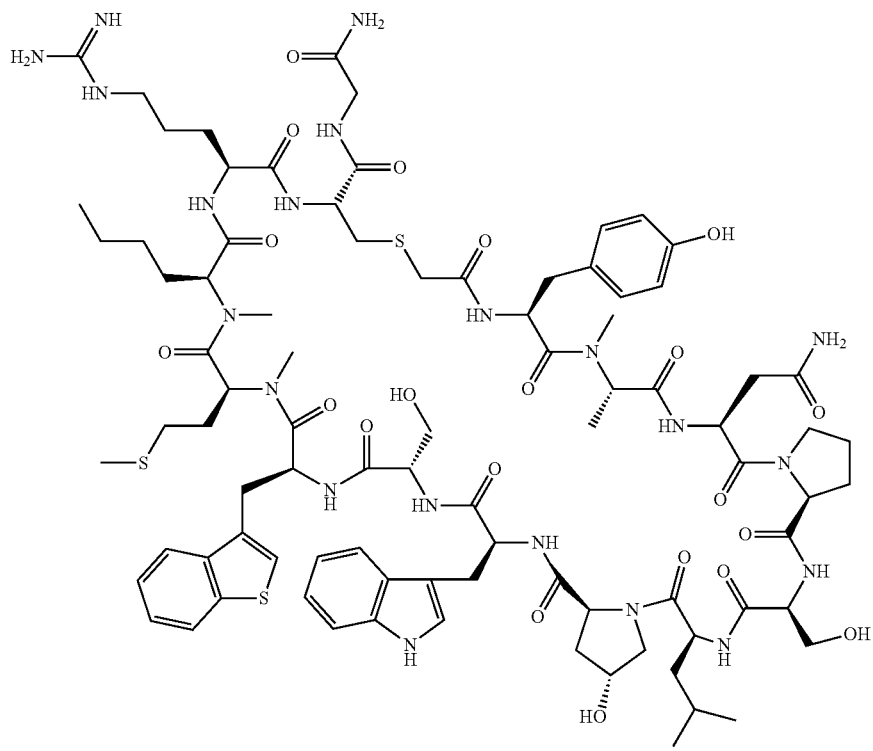

Example 9099

The crude material of Example 9099 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 11.5 mg, and its estimated purity by LCMS analysis was 98%

Analysis condition A: Retention time=1. min; ESI-MS(+) m/z 940.7 (M+2H).

Analysis condition B: Retention time=2. min; ESI-MS(+) m/z 940.3 (M+2H).

Preparation of Example 9100

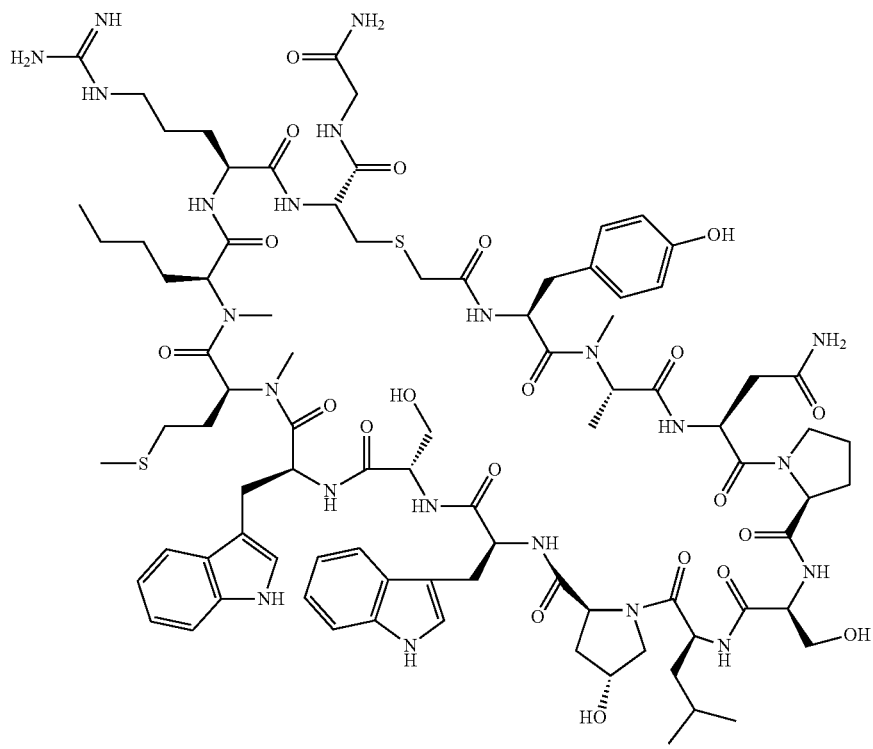

Example 9100

The crude material of Example 9100 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 20.7 mg, and its estimated purity by LCMS analysis was 99%.

Analysis condition A: Retention time=1.48 min; ESI-MS (+) m/z 940.8 (M+2H).

Analysis condition B: Retention time=2.59 min; ESI-MS (+) m/z 940.2 (M+2H).

Preparation of Example 9105

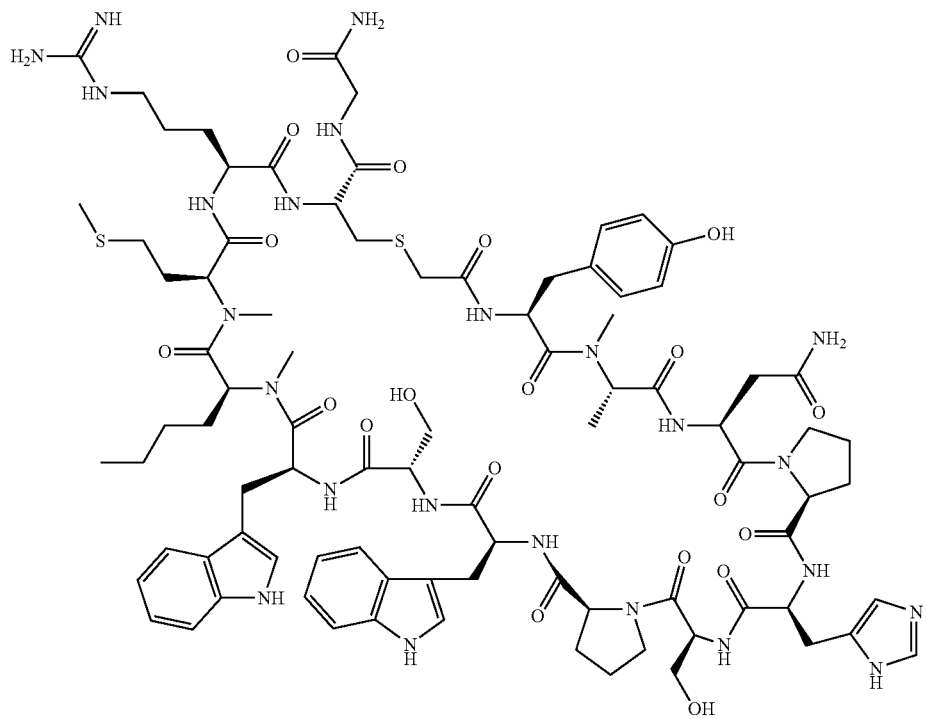

Example 9105

The crude material of Example 9105 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 16.0 mg, and its estimated purity by LCMS analysis was 98%.

Analysis condition A: Retention time=1.42 min; ESI-MS (+) m/z 944.0 (M+2H)$^+$.

Analysis condition B: Retention time=2.50 min; ESI-MS (+) m/z 944.2 (M+2H)$^+$.

Preparation of Example 9106

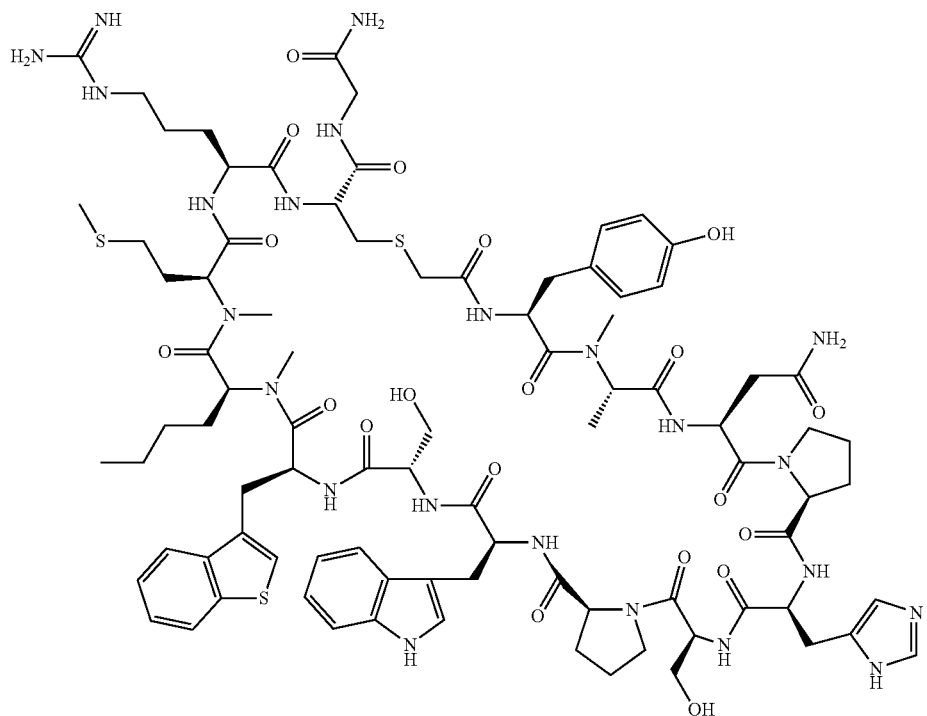

Example 9106

The crude material of Example 9106 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 100%.

Analysis condition A: Retention time=1.58 min; ESI-MS (+) m/z 952.7 (M+2H).

Analysis condition B: Retention time=2.70 min; ESI-MS (+) m/z 952.6 (M+2H).

Preparation of Example 9107

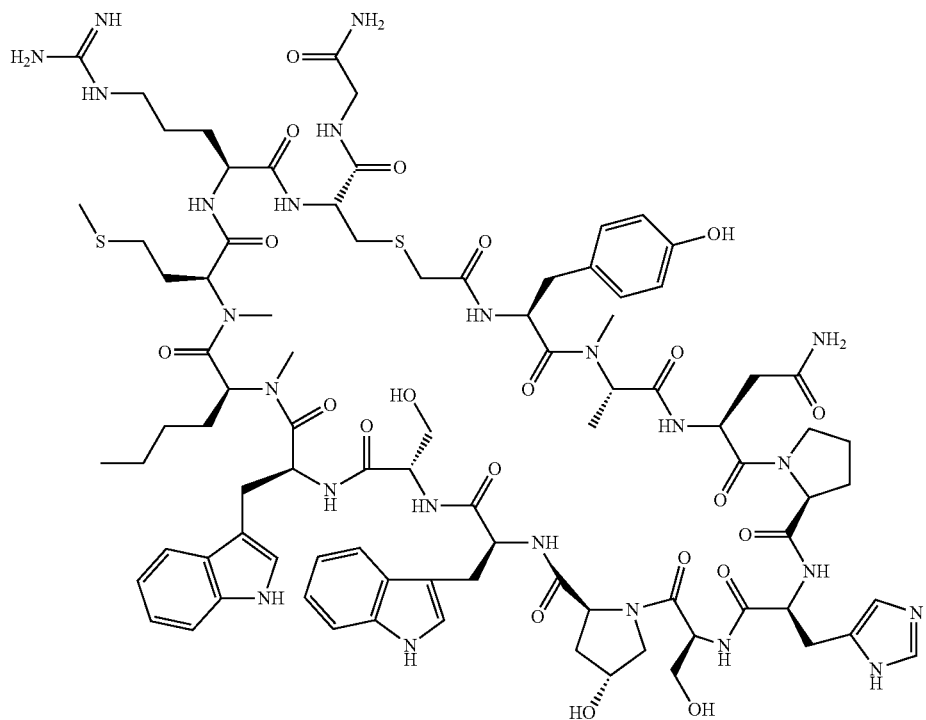

Example 9107

The crude material of Example 9107 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 100%.

Analysis condition A: Retention time=1.41 min; ESI-MS (+) m/z 952.2 (M+2H).

Analysis condition B: Retention time=2.49 min; ESI-MS (+) m/z 952.3 (M+2H).

Preparation of Example 9108

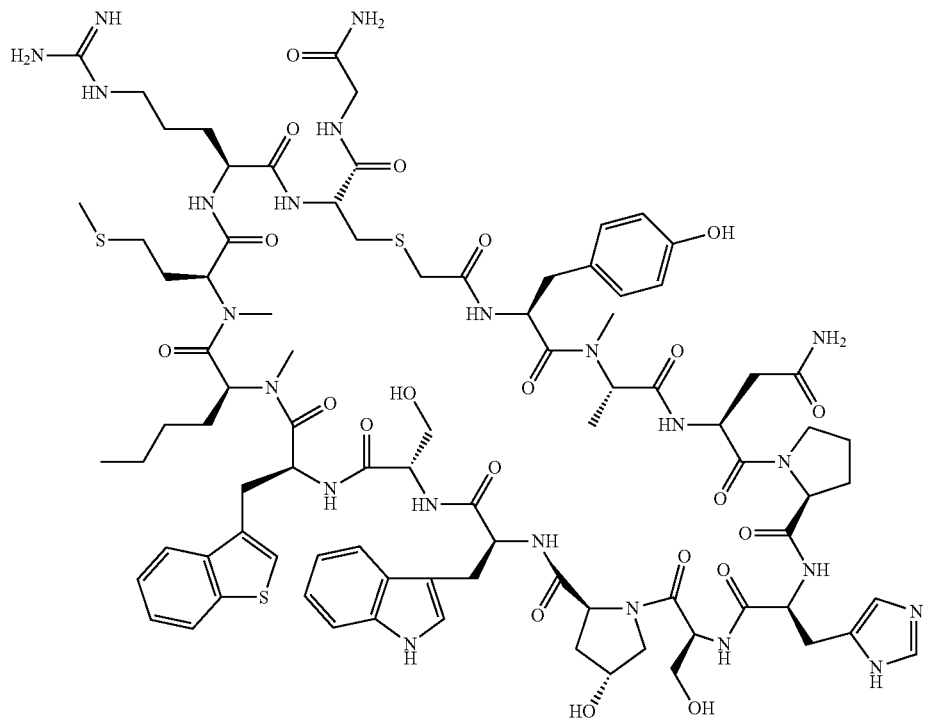

Example 9108

The crude material of Example 9108 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 100%.

Analysis condition A: Retention time=1.52 min; ESI-MS (+) m/z 960.2 (M+2H).

Analysis condition B: Retention time=2.68 min; ESI-MS (+) m/z 960.3 (M+2H).

Preparation of Example 9109

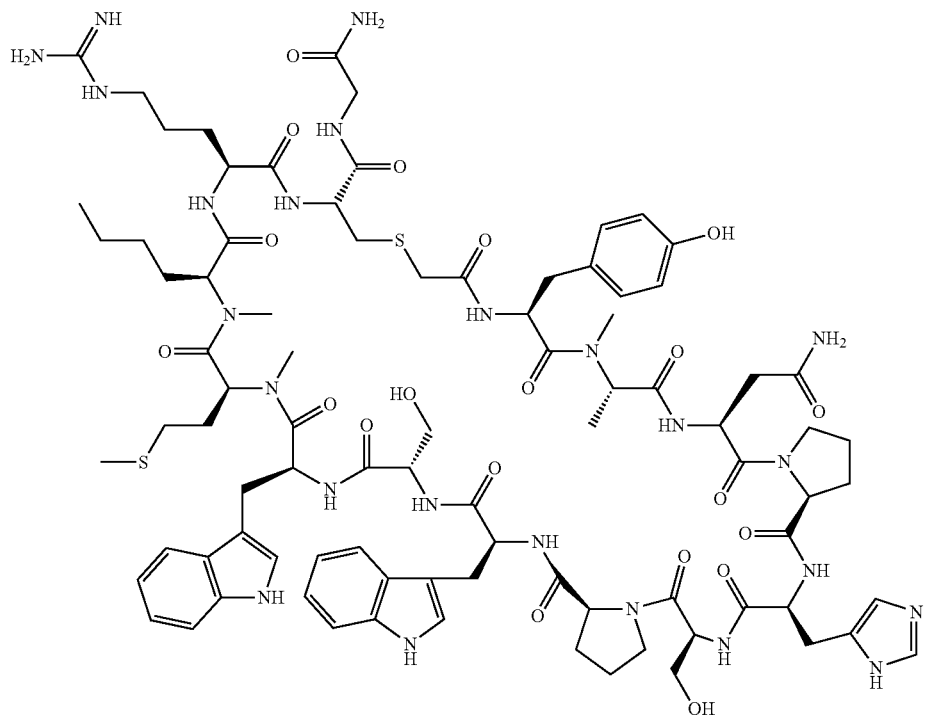

Example 9109

The crude material of Example 9109 was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 12.9 mg, and its estimated purity by LCMS analysis was 97%.

Analysis condition A: Retention time=1.39 min; ESI-MS (+) m/z 943.8 (M+2H).

Analysis condition B: Retention time=2.44 min; ESI-MS (+) m/z 944.1 (M+2H).

Preparation of Example 9110

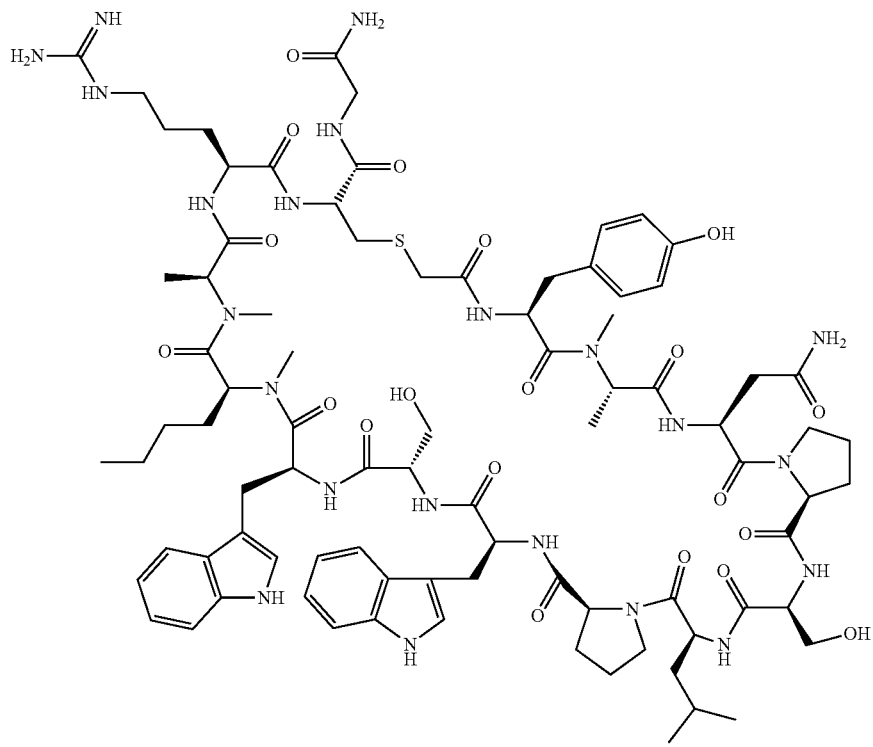

Example 9110

The crude material of Example 9110 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 35 minutes, then a 5-minute hold at 100% B; Flow: 20 mL/min. Fractions containing the desired product were combined and dried via centrifugal evaporation. The yield of the product was 7.7 mg, and its estimated purity by LCMS analysis was 96%.

Analysis condition A: Retention time=1.42 min; ESI-MS (+) m/z 902.2 (M+2H).

Analysis condition B: Retention time=2.46 min; ESI-MS (+) m/z 902.1 (M+2H).

Preparation of Example 9111

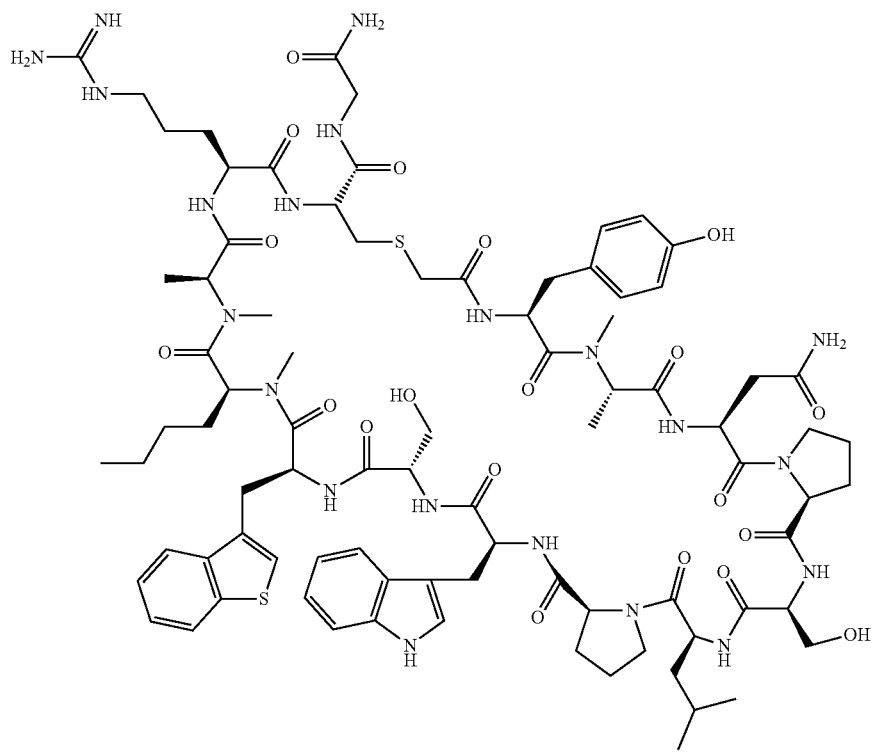

Example 9111

The crude material of Example 9111 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 8.9 mg, and its estimated purity by LCMS analysis was 100%.

Analysis condition A: Retention time=1.59 min; ESI-MS (+) m/z 910.2 (M+2H).

Analysis condition B: Retention time=2.68 min; ESI-MS (+) m/z 910.3 (M+2H).

Preparation of Example 9112

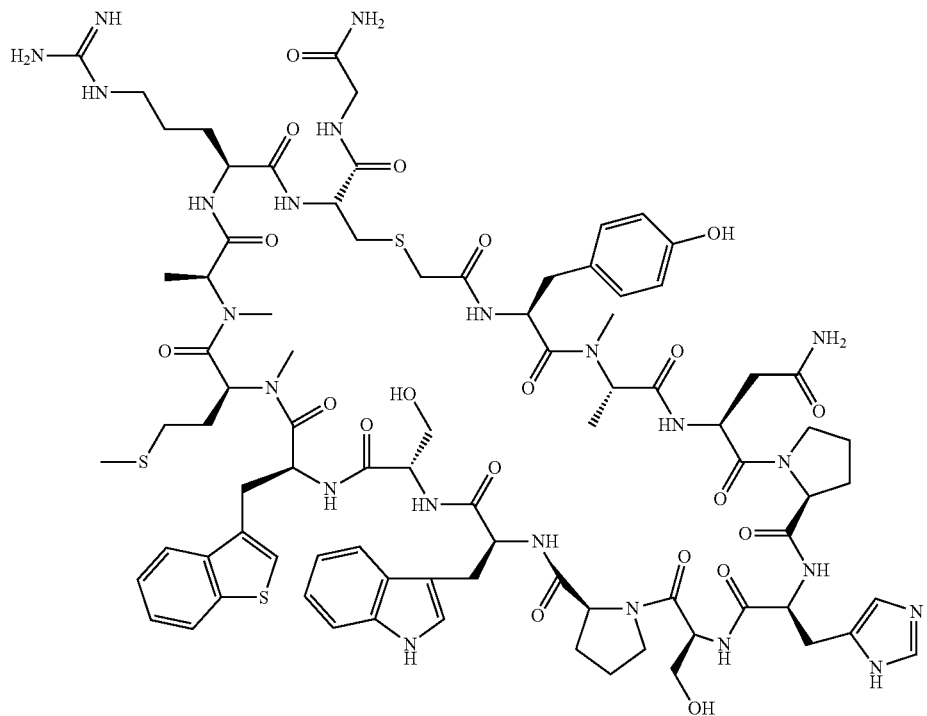

Example 9112

The crude material of Example 9112 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 13.4 mg, and its estimated purity by LCMS analysis was 95%.

Analysis condition A: Retention time=1.48 min; ESI-MS (+) m/z 952.2 (M+2H).

Analysis condition B: Retention time=2.59 min; ESI-MS (+) m/z 952.5 (M+2H).

Preparation of Example 9113

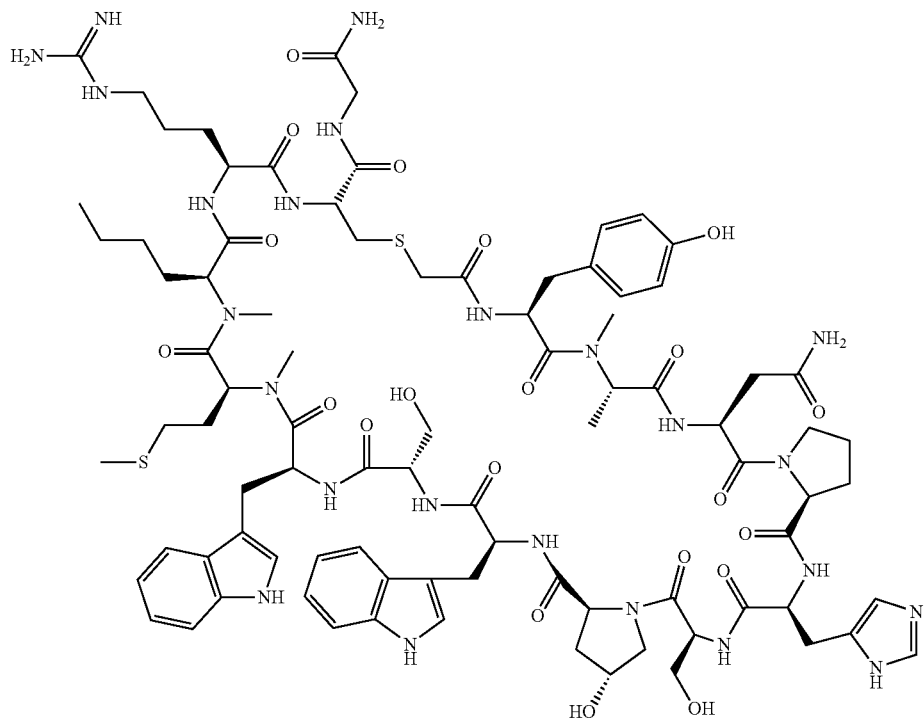

Example 9113

The crude material of Example 9113 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 93%.

Analysis condition A: Retention time=1.32 min; ESI-MS (+) m/z 951.7 (M+2H).

Analysis condition B: Retention time=2.39 min; ESI-MS (+) m/z 952.1 (M+2H).

Preparation of Example 9114

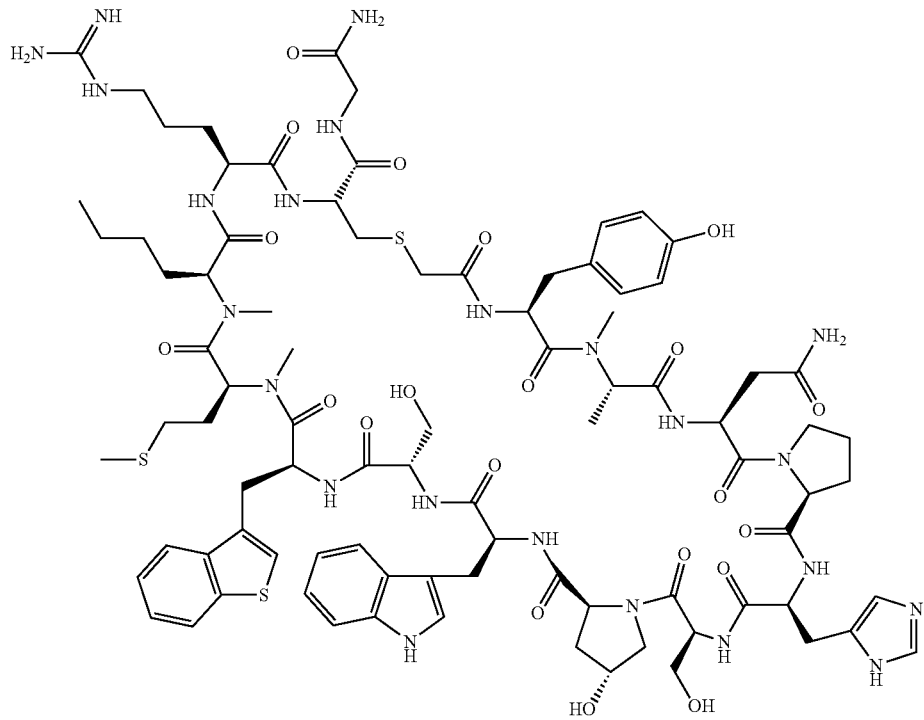

Example 9114

The crude material of Example 9114 was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 40 minutes, then a 5-minute hold at 100% B; Flow: 20 mL/min. Fractions containing the desired product were combined and dried via centrifugal evaporation. The material was further purified via preparative LC/MS with the following conditions: Column: XBridge Shield RP18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The yield of the product was 6.0 mg, and its estimated purity by LCMS analysis was 100%.

Analysis condition A: Retention time=1.45 min; ESI-MS (+) m/z 960.7 (M+2H).

Analysis condition B: Retention time=2.56 min; ESI-MS (+) m/z 960.6 (M+2H).

Preparation of Example 10001

Example 10001

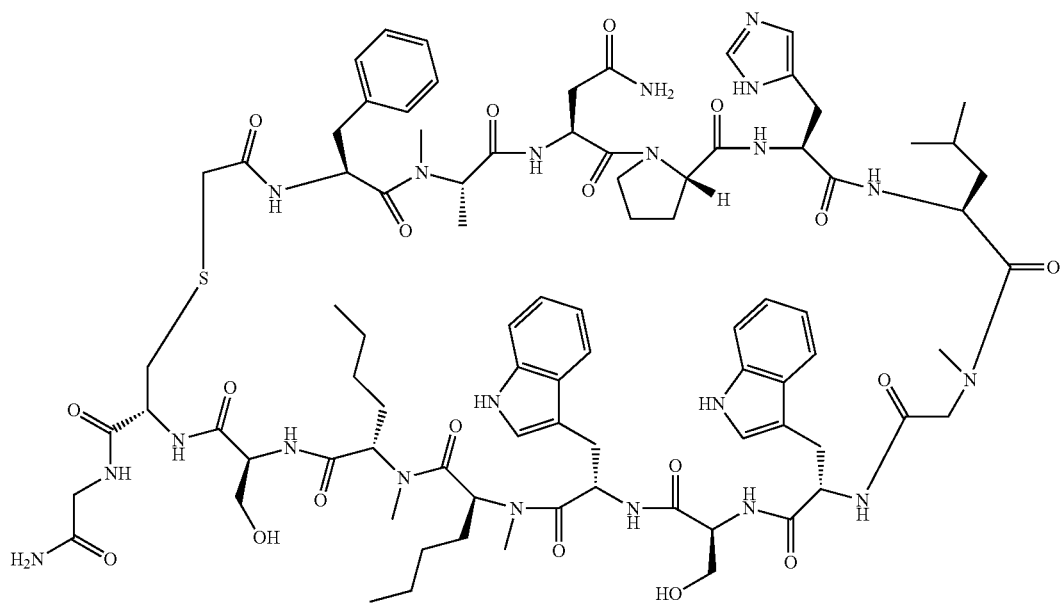

Example 10001 was prepared following the general synthetic sequence described for the preparation of Example 5001, composed of the following general procedures: "Prelude Method A: Resin-swelling procedure", "Prelude Method A: Single-coupling procedure", "Prelude Method A: Double-coupling procedure", "Prelude Method A: Chloroacetyl chloride coupling procedure", "Global Deprotection Method A", and "Cyclization Method A".

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 15 minutes, then a 4-minute hold at 100% B; Flow: 20 mL/min. Fractions containing the desired product were combined and dried via centrifugal evaporation. The yield of the product was 3.7 mg, and its estimated purity by LCMS analysis was 100%.

Analysis condition A: Retention time=1.81 min; ESI-MS (+) m/z 892.6 (M+2H).

Analysis condition B: Retention time=3.01 min; ESI-MS (+) m/z 892.6 (M+2H).

Preparation of (2S,3S)-2-((((9H-fluoren-9-yl)methoxy)carbonyl)amino)-3-(1-(tert-butoxycarbonyl)-1H-indol-3-yl)butanoic acid Scheme:

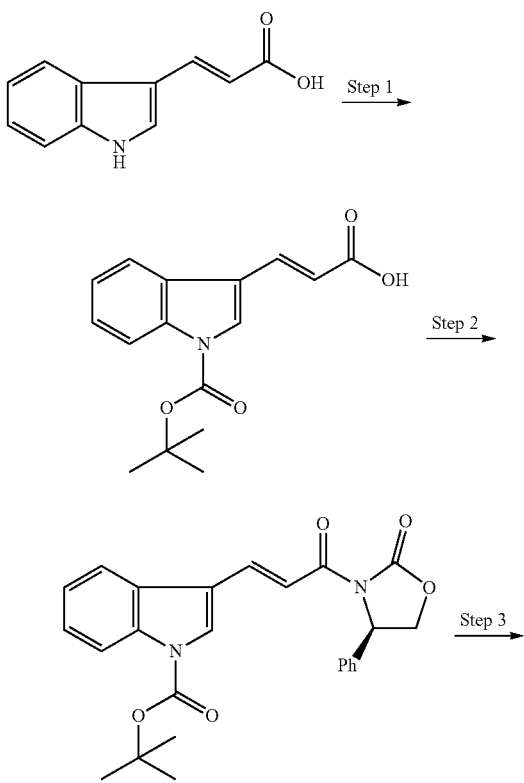

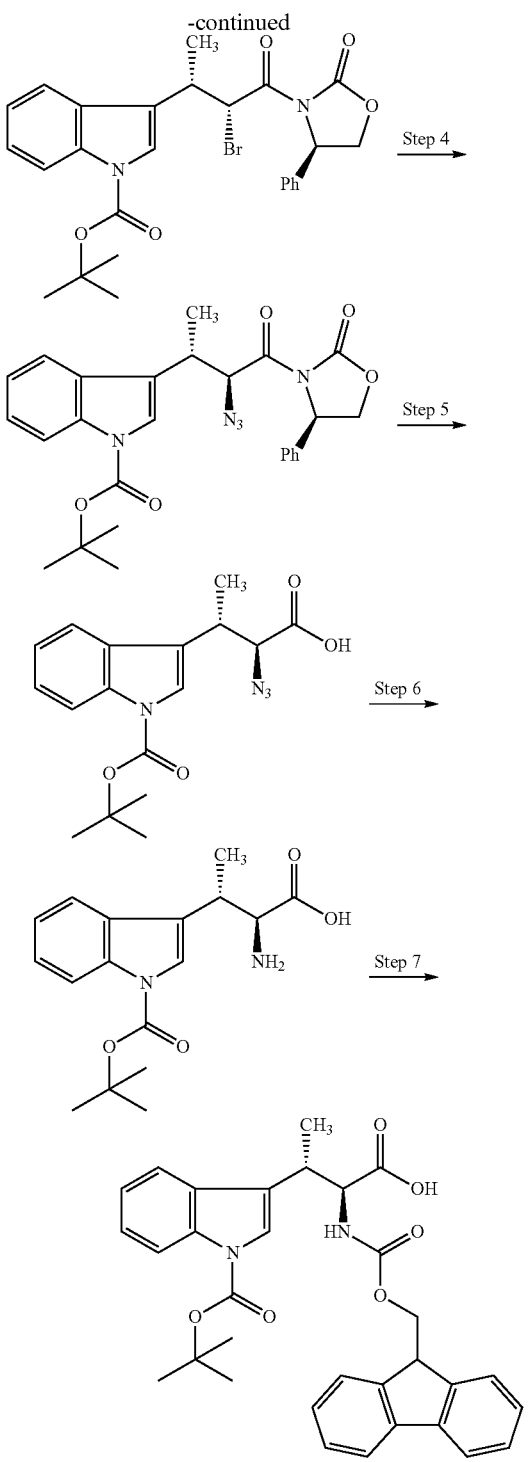

Step 1:
(E)-3-(1H-indol-3-yl)acrylic acid (4.2 g, 22.44 mmol), (Boc)$_2$O (10.42 ml, 44.9 mmol), and Et$_3$N (7.82 ml, 56.1 mmol) were stirred in THF (112 ml) followed by the addition of DMAP (0.137 g, 1.122 mmol). The reaction was stirred for 16 h. The reaction was quenched with saturated sodium bicarbonate and stirred vigorously for 10 min. The mixture was diluted with EtOAc and acidified with 1 N HCl. The organic layer was collected, dried over sodium sulfate, filtered and concentrated under vacuum to give (E)-3-(1-(tert-butoxycarbonyl)-1H-indol-3-yl)acrylic acid which was carried directly to step 2.

Step 2:
To a solution of (E)-3-(1-(tert-butoxycarbonyl)-1H-indol-3-yl)acrylic acid (7.14 g, 24.85 mmol) in THF (400 mL) at −78° C. were added Et$_3$N (10.39 ml, 74.6 mmol) and pivaloyl chloride (6.12 ml, 49.7 mmol). The mixture was stirred for 15 min at −78° C. then warmed to 0° C. for 1.5 h. The mixture was cooled to −78° C., to which was added n-Butyllithium (1.6 M in Hexanes)(14 mL, 22.4 mmol), then added the lithium salt of (R)-4-phenyl-2-oxazolidinone [prepared by adding n-Butyllithium (1.6 M in Hexanes)(31 ml, 49.7 mmol), to a solution of (R)-4-phenyloxazolidin-2-one (8.11 g, 49.7 mmol)] in THF (200 mL) at −78° C.) via cannula. The reaction was stirred at −78° C. for 2 h then at rt for 16 h. The reaction was quenched with saturated NH$_4$Cl aqueous solution. The organics were removed under vacuum and the aqueous was extracted with EtOAc. The organic layer was collected, washed with brine, dried over sodium sulfate, and concentrated under vacuum. The crude product was purified by silica gel chromatography using a gradient of 10-20% EtOAc/Hexanes. The product fractions were collected and the solvent removed under vacuum to give ((R,E)-tert-butyl 3-(3-oxo-3-(2-oxo-4-phenyloxazolidin-3-yl)prop-1-en-1-yl)-1H-indole-1-carboxylate, 7.12 g (66%). ESI-MS (+) m/z 433.4 (M+1).

Step 3:
To a mixture of Copper (I) bromide methylsulfide complex (5.08 g, 24.70 mmol) and dimethylsulfide (15 mL) in THF (30 mL) at −4° C. was added methylmagnesium bromide (3 M in diethylether) (5.49 ml, 16.46 mmol). After stirring for 10 min, (R,E)-tert-butyl 3-(3-oxo-3-(2-oxo-4-phenyloxazolidin-3-yl)prop-1-en-1-yl)-1H-indole-1-carboxylate (7.12 g, 16.46 mmol) in THF (70 mL) was added. The mixture was stirred at −4° C. for 1 h and at rt for 2 h. The mixture was cooled to −78° C. and NBS (5.86 g, 32.9 mmol) in THF (120 mL) was added via cannula into the reaction. The reaction was stirred for 1 h at −78° C. for 1 h then rt for 2 h. The reaction was quenched with 0.5 N NaHSO$_4$:brine (1:1, 200 mL). The organic layer was separated and washed with 0.5 N Na$_2$S$_2$O$_3$ (2×100 mL). The organic phase washed with NH$_4$Cl then brine. The organic layer was collected, dried over sodium sulfate, and concentrated under vacuum. The crude product was purified by silica gel chromatography using 10-20% EtOAc/Hexanes. The product fractions were collected and the solvent removed under vacuum to tert-butyl 3-((2S,3R)-3-bromo-4-oxo-4-((R)-2-oxo-4-phenyloxazolidin-3-yl)butan-2-yl)-1H-indole-1-carboxylate, 4.0 g, (46%). ESI-MS(+) m/z 549.2 (M+Na). $^1$H NMR (500 MHz, chloroform-d) d 8.16 (d, J=7.3 Hz, 1H), 7.64 (d, J=7.6 Hz, 1H), 7.48 (s, 1H), 7.43-7.22 (m, 7H), 6.18 (d, J=10.9 Hz, 1H), 5.16 (dd, J=8.8, 4.3 Hz, 1H), 4.45 (t, J=8.9 Hz, 1H), 4.16 (dd, J=8.9, 4.3 Hz, 1H), 3.75 (dq, J=10.8, 7.0 Hz, 1H), 1.69 (s, 9H), 1.60 (d, J=7.1 Hz, 3H).

Step 4:
tert-butyl 3-((2S,3R)-3-bromo-4-oxo-4-((R)-2-oxo-4-phenyloxazolidin-3-yl)butan-2-yl)-1H-indole-1-carboxylate (4 g, 7.58 mmol) was dissolved in DMSO (50.6 ml) followed by the addition of NaN$_3$ (1.972 g, 30.3 mmol). The reaction was stirred for 2 h. The reaction was diluted with EtOAc and water. The organic layer was collected, washed with water, then brine, dried over sodium sulfate and concentrated under vacuum to give the crude product which was purified by silica gel chromatography using a gradient of 15-20% EtOAc/Hexanes. The product fractions were collected and the solvent removed under vacuum to tert-butyl 3-((2S,3S)-3-azido-4-oxo-4-((R)-2-oxo-4-phenyloxazolidin-3-yl)butan-2-yl)-1H-indole-1-carboxylate, 3.4 g (91%). $^1$H NMR (400 MHz, chloroform-d) d 8.16 (d, J=7.6 Hz, 1H), 7.63 (d, J=7.6 Hz, 1H), 7.47 (s, 1H), 7.37-7.20 (m, 7H), 5.55 (d, J=8.8 Hz, 1H), 5.51 (dd, J=8.8, 4.4 Hz, 1H), 4.79 (t, J=8.9 Hz, 1H), 4.38 (dd, J=8.9, 4.3 Hz, 1H), 3.68-3.57 (m, 1H), 1.69-1.66 (m, 9H), 1.27 (d, J=6.8 Hz, 3H).

Step 5:

To a mixture of tert-butyl 3-((2S,3S)-3-azido-4-oxo-4-((R)-2-oxo-4-phenyloxazolidin-3-yl)butan-2-yl)-1H-indole-1-carboxylate (3.38 g, 6.90 mmol) in Water (29 mL) and THF (86 mL) at 0° C. was added hydrogen peroxide (4.67 ml, 45.7 mmol), then lithium hydroxide (0.331 g, 13.81 mmol). The reaction was stirred for 2 h. The reaction was quenched with $Na_2SO_3$ (7 g) in 40 mL water. The reaction was stirred for 30 min at rt. The solvent was removed under vacuum and then the reaction was diluted with EtOAc and water. The pH was adjusted to 2. The organic phase was collected, washed with brine, dried over sodium sulfate and concentrated under vacuum to give a residue which was triturated in $Et_2O$ to give a solid which was collected by filtration and dried to give (2S,3S)-2-azido-3-(1-(tert-butoxycarbonyl)-1H-indol-3-yl)butanoic acid, 2.38 g (100%). ESI-MS(−) m/z 343.3 (M−H). $^1$H NMR (500 MHz, chloroform-d) d 8.15 (d, J=5.5 Hz, 1H), 7.60 (d, J=7.7 Hz, 1H), 7.58-7.55 (m, 1H), 7.33 (td, J=7.7, 1.1 Hz, 1H), 7.27-7.23 (m, 1H), 4.29 (d, J=6.5 Hz, 1H), 3.68 (quin, J=6.9 Hz, 1H), 1.70 (s, 9H), 1.51 (d, J=7.1 Hz, 3H).

Step 6:

10% Pd on carbon (1.19 g, 1.118 mmol) was placed in a flask under a blanket of $N_2$ (g). The catalyst was wet with MeOH (5 mL). To the flask was added (2S,3S)-2-azido-3-(1-(tert-butoxycarbonyl)-1H-indol-3-yl)butanoic acid (2.38 g, 6.91 mmol) as a solution in MeOH (69.1 ml). The flask was evacuated then charged with $H_2$ (g). The reaction was stirred for 2 h. The flask was evacuated and purged with $N_2$ (g) 2×. The reaction was filtered through CELITE® and the filter cake washed with MeOH. The organics were concentrated under vacuum to give (2S,3S)-2-amino-3-(1-(tert-butoxycarbonyl)-1H-indol-3-yl)butanoic acid which was used in Step 7 as is. ESI-MS(+) m/z 319.4 (M+H).

Step 7:

(2S,3S)-2-amino-3-(1-(tert-butoxycarbonyl)-1H-indol-3-yl)butanoic acid (2197 mg, 6.9 mmol) was dissolved in a mixture of Water (35 mL) and THF (100 mL). Sodium bicarbonate (2174 mg, 25.9 mmol) and (9H-fluoren-9-yl)methyl 2,5-dioxopyrrolidine-1-carboxylate (4434 mg, 13.80 mmol) were added to the solution and the reaction was stirred for 16 h. Saturated ammonium chloride solution (200 mL) was added to the reaction and the solvent was then removed under vacuum. The remaining aqueous layer was extracted with EtOAc. The organic layer was then collected, dried over sodium sulfate, and concentrated under vacuum. The crude material was purified by rev. phase BIOTAGE® C-18 column using a gradient of 20-80% ACN/water with 0.1% TFA modifier over 20 min. The product fractions were collected, diluted with water and extracted with EtOAc. The organic layer washed with water, then brine, dried over sodium sulfate, and concentrated under vacuum to give (2S,3S)-2-((((9H-fluoren-9-yl)methoxy)carbonyl)amino)-3-(1-(tert-butoxycarbonyl)-1H-indol-3-yl)butanoic acid, 500 mg (13%). ESI-MS(+) m/z 541.5 (M+H). $^1$H NMR (500 MHz, DMSO-$d_6$) δ 12.79 (br. s., 1H), 8.03 (d, J=8.2 Hz, 1H), 7.90-7.85 (m, 2H), 7.73 (dd, J=8.1, 4.7 Hz, 2H), 7.62 (d, J=7.4 Hz, 1H), 7.56 (d, J=7.6 Hz, 1H), 7.53 (s, 1H), 7.39 (td, J=7.4, 4.0 Hz, 2H), 7.35-7.30 (m, 1H), 7.28-7.18 (m, 3H), 4.45 (t, J=8.2 Hz, 1H), 4.30-4.25 (m, 1H), 4.21-4.15 (m, 1H), 4.15-4.09 (m, 1H), 3.48 (quin, J=7.2 Hz, 1H), 1.57 (s, 9H), 1.34 (d, J=7.3 Hz, 3H).

Preparation of Example 10501

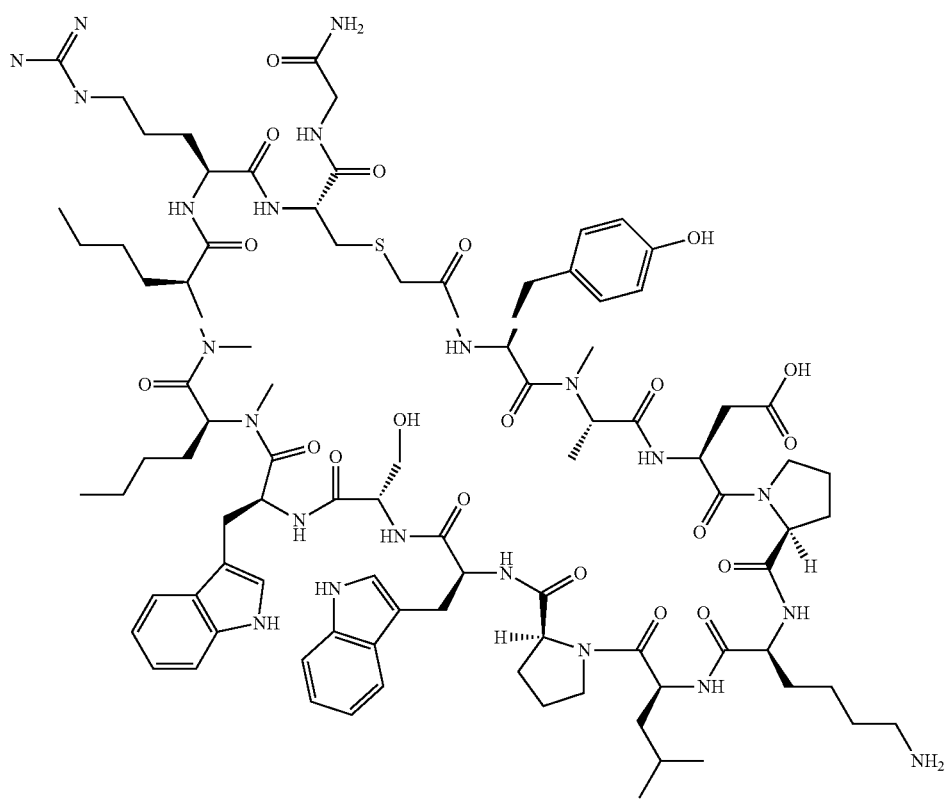

Example 10501

Example 10501 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.1 mg, and its estimated purity by LCMS analysis was 97%.

Analysis condition A: Retention time=1.60 min; ESI-MS (+) m/z 950.6 (M+2H)

Analysis condition B: Retention time=2.62 min; ESI-MS (+) m/z 950.5 (M+2H)

Preparation of Example 10502

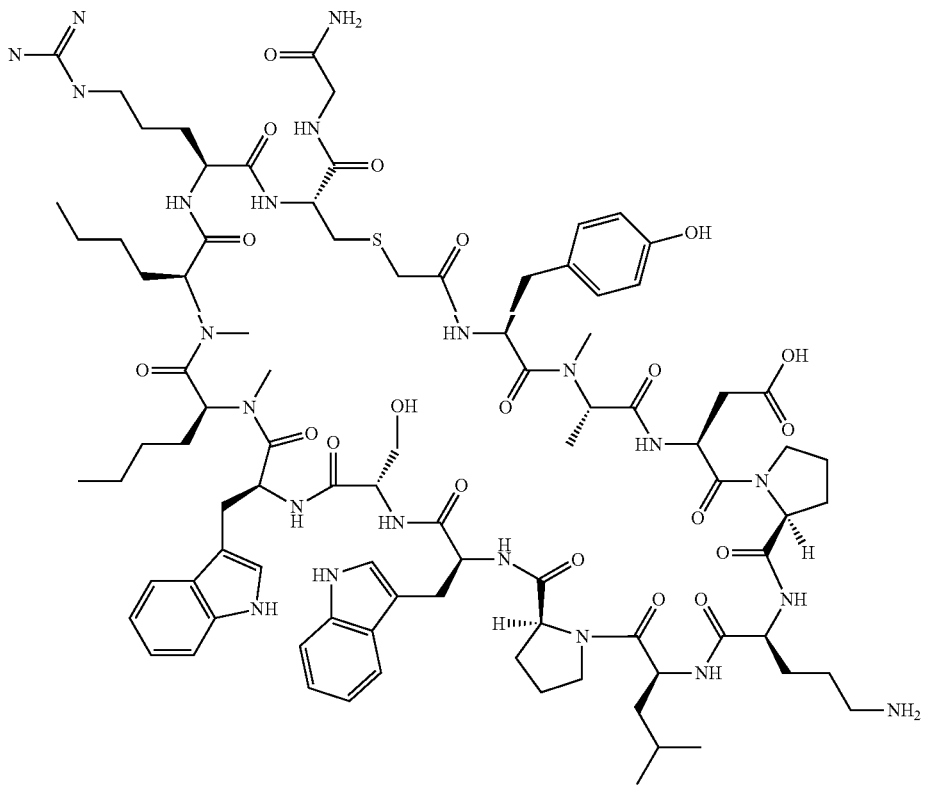

Example 10502

Example 10502 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 35.4 mg, and its estimated purity by LCMS analysis was 95%.

Analysis condition A: Retention time=1.44 min; ESI-MS (+) m/z 944.3 (M+2H)

Analysis condition B: Retention time=2.62 min; ESI-MS (+) m/z 944.0 (M+2H)

Preparation of Example 10503

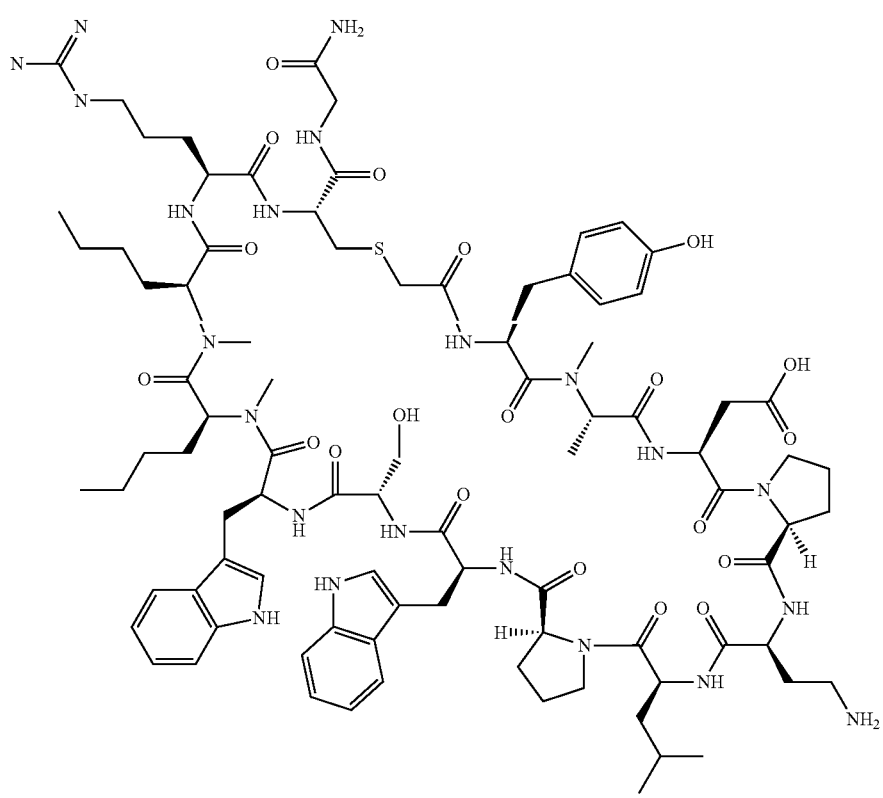

Example 10503

Example 10503 was prepared following "General Synthetic Sequence A". The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 44.9 mg, and its estimated purity by LCMS analysis was 95%.

Analysis condition A: Retention time=1.47 min; ESI-MS (+) m/z 937.4 (M+2H)

Analysis condition B: Retention time=2.61 min; ESI-MS (+) m/z 937.0 (M+2H)

Preparation of Example 10504

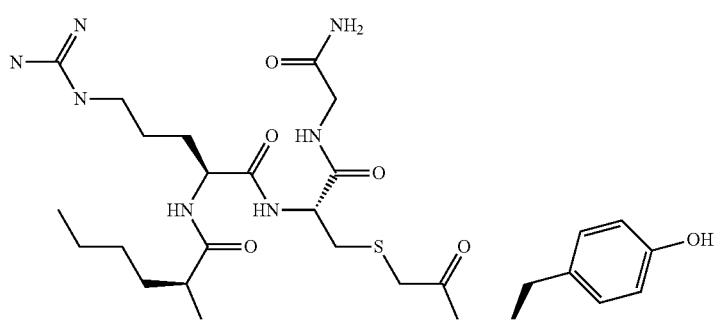

Example 10504

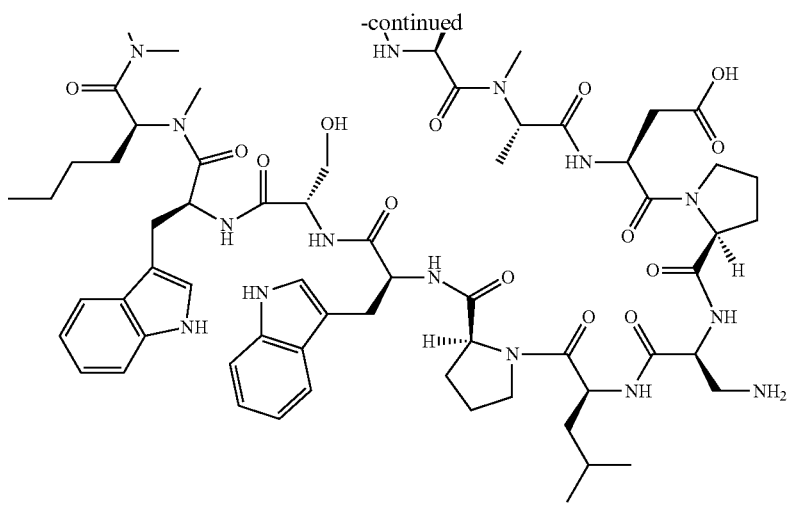

Example 10504 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 49.9 mg, and its estimated purity by LCMS analysis was 100%.

Analysis condition A: Retention time=1.45 min; ESI-MS (+) m/z 930.3 (M+2H)

Analysis condition B: Retention time=2.62 min; ESI-MS (+) m/z 930.4 (M+2H)

Preparation of Example 10505

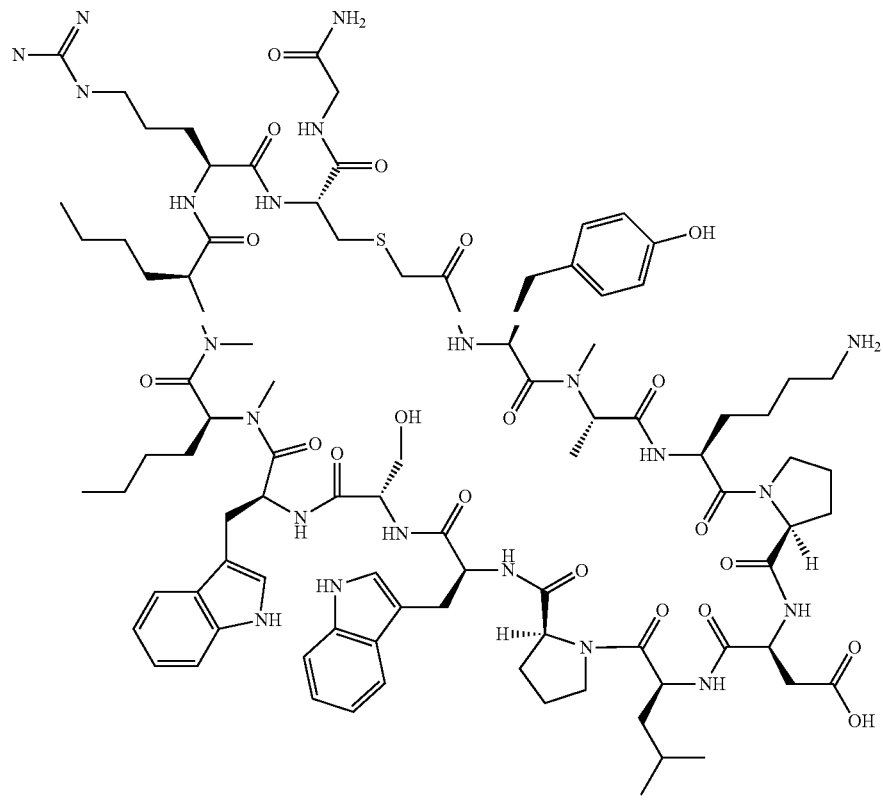

Example 10505

Example 10505 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.2 mg, and its estimated purity by LCMS analysis was 99%.

Analysis condition A: Retention time=1.44 min; ESI-MS (+) m/z 951.2 (M+2H)

Analysis condition B: Retention time=2.64 min; ESI-MS (+) m/z 951.3 (M+2H)

Preparation of Example 10506

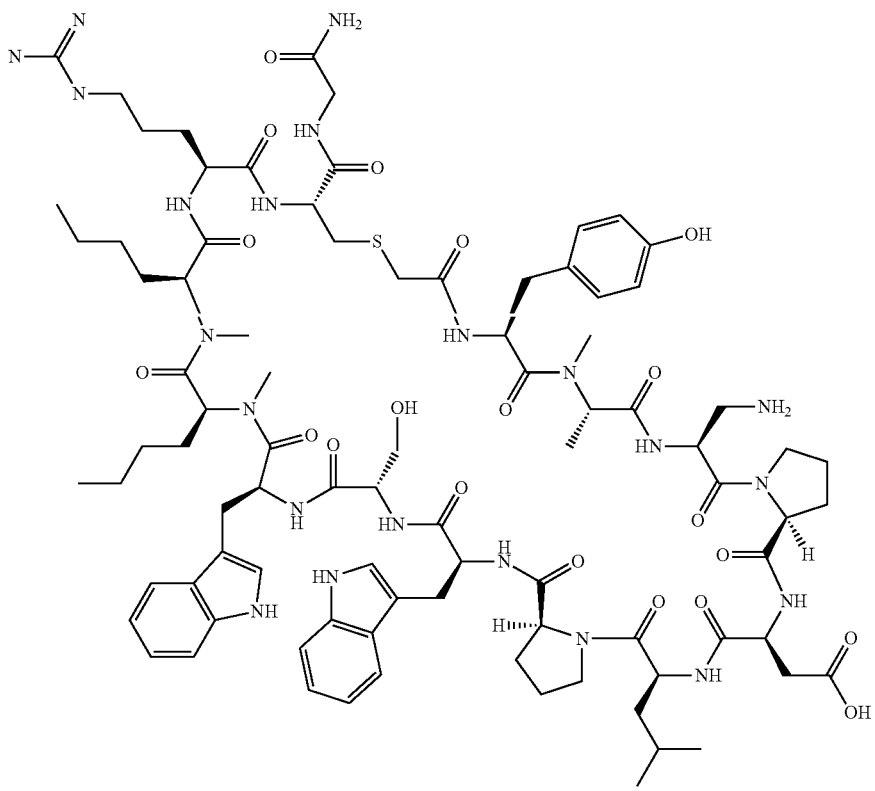

Example 10506

Example 10506 was prepared following "General Synthetic Sequence A". The crude material was purified via preparative LC/MS with the following conditions: Column: Waters XBridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 23.3 mg, and its estimated purity by LCMS analysis was 100%.

Analysis condition A: Retention time=1.53 min; ESI-MS (+) m/z 930.3 (M+2H)

Analysis condition B: Retention time=2.68 min; ESI-MS (+) m/z 930.4 (M+2H)

Preparation of Example 10507

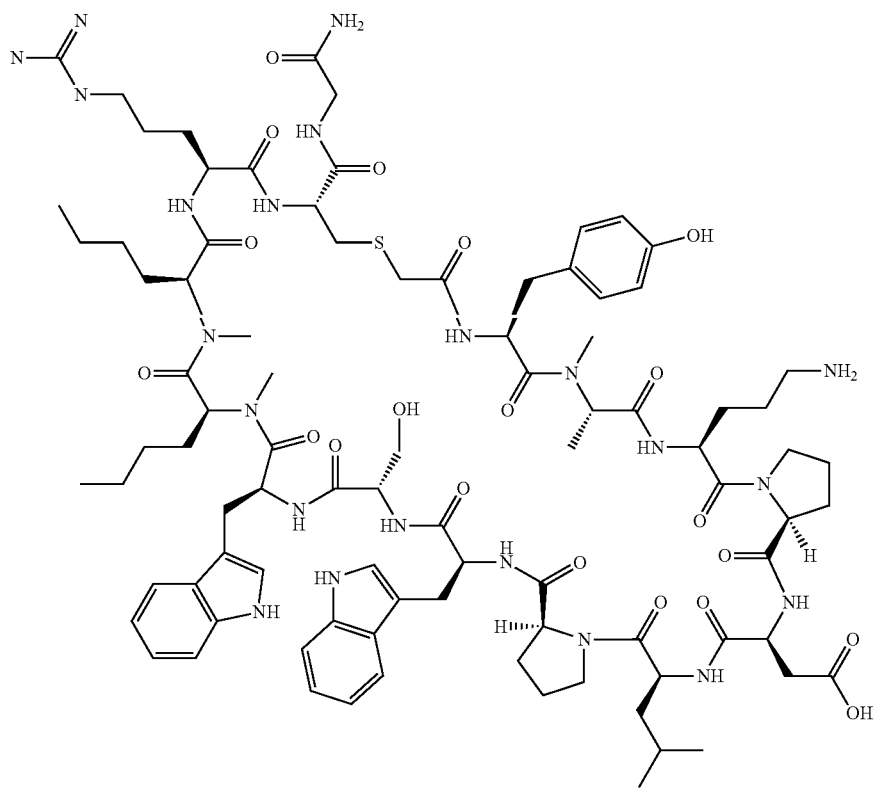

Example 10507

Example 10507 was prepared following "General Synthetic Sequence A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The yield of the product was 13.2 mg, and its estimated purity by LCMS analysis was 100%.

Analysis condition A: Retention time=1.50 min; ESI-MS (+) m/z 944.3 (M+2H)

Analysis condition B: Retention time=2.66 min; ESI-MS (+) m/z 943.7 (M+2H)

Preparation of Example 10508

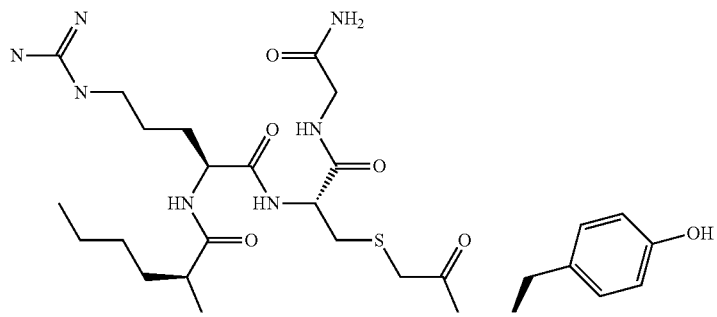

Example 10508

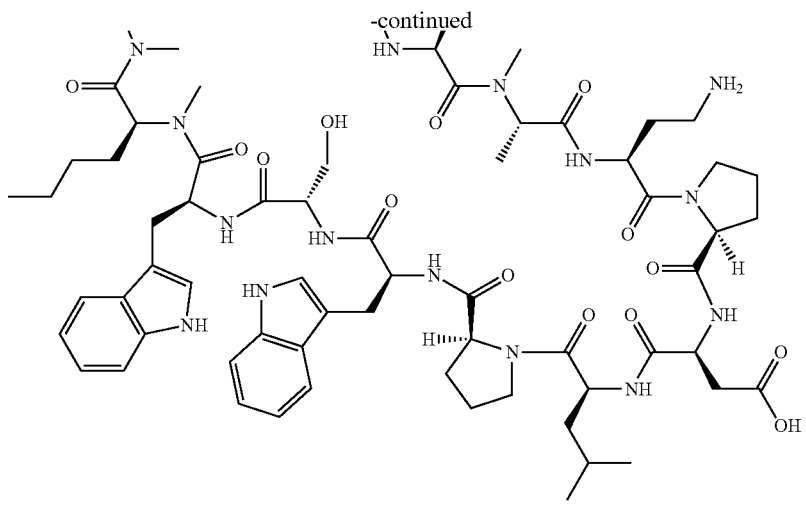

Example 10508 was prepared following "General Synthetic Sequence A". The crude material was purified via preparative LC/MS with the following conditions: Column: Waters XBridge c-18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 40 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 79%.

Analysis condition A: Retention time=1.52 min; ESI-MS (+) m/z 937.4 (M+2H)

Analysis condition B: Retention time=2.68 min; ESI-MS (+) m/z 937.3 (M+2H)

Preparation of Example 10509

Example 10509

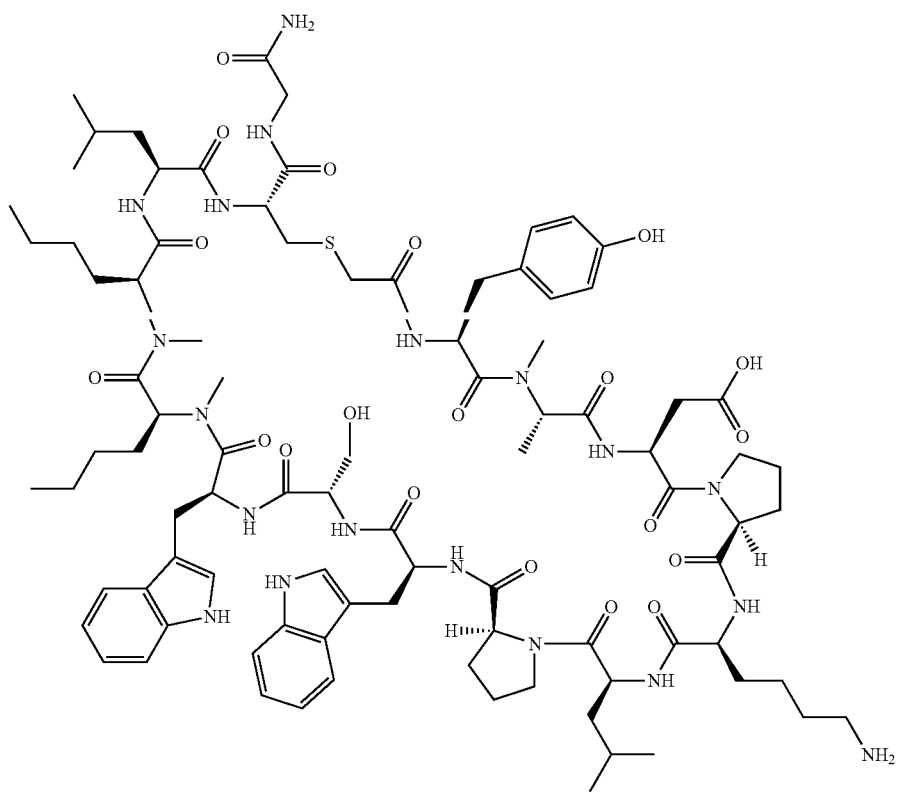

Example 10509 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 34.0 mg, and its estimated purity by LCMS analysis was 100%.

Analysis condition A: Retention time=1.64 min; ESI-MS (+) m/z 929.4 (M+2H)

Analysis condition B: Retention time=2.82 min; ESI-MS (+) m/z 929.8 (M+2H)

Preparation of Example 10510

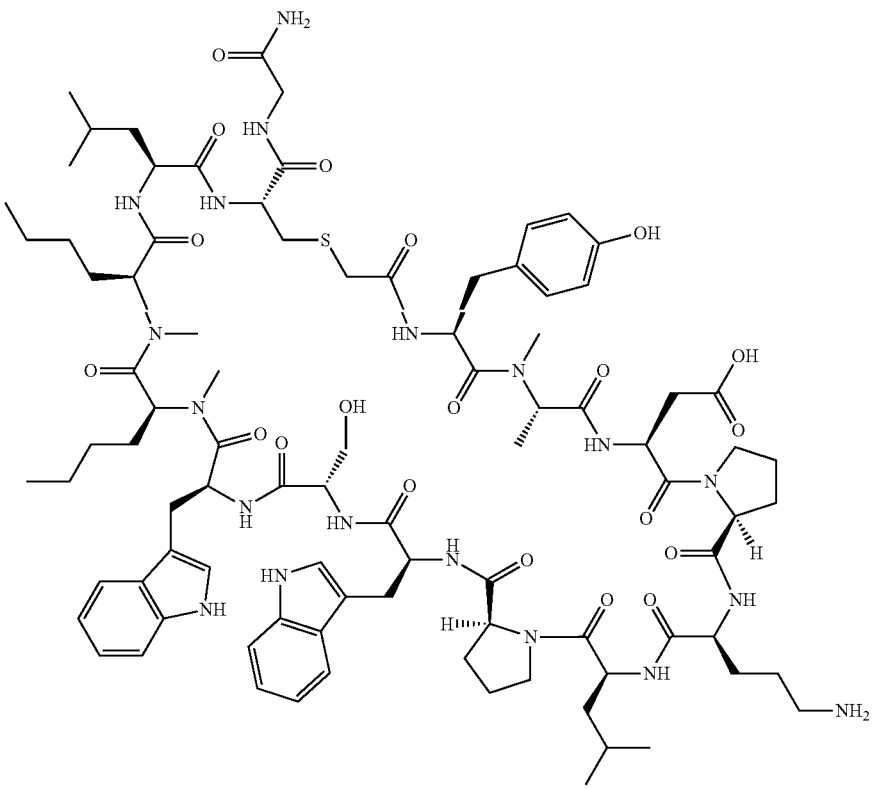

Example 10510

Example 10510 was prepared following "General Synthetic Sequence A". The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 34.0 mg, and its estimated purity by LCMS analysis was 100%.

Analysis condition A: Retention time=1.68 min; ESI-MS (+) m/z 922.5 (M+2H)

Analysis condition B: Retention time=2.83 min; ESI-MS (+) m/z 922.8 (M+2H)

Preparation of Example 10511

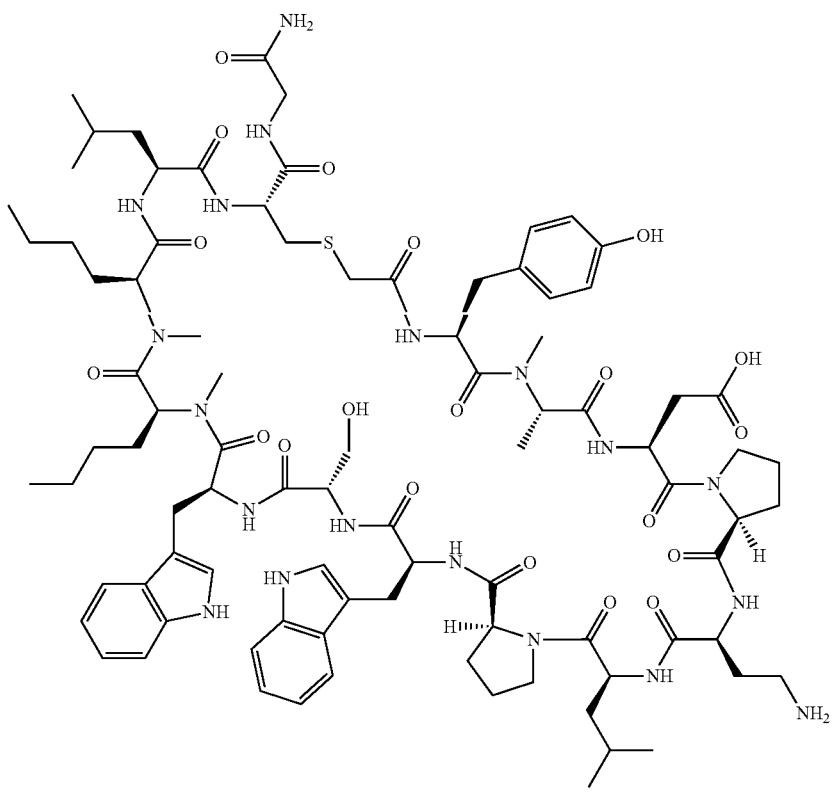

Example 10511

Example 10511 was prepared following "General Synthetic Sequence A". The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 100%.

Analysis condition A: Retention time=1.65 min; ESI-MS (+) m/z 915.8 (M+2H)

Analysis condition B: Retention time=2.84 min; ESI-MS (+) m/z 915.8 (M+2H)

Preparation of Example 10512

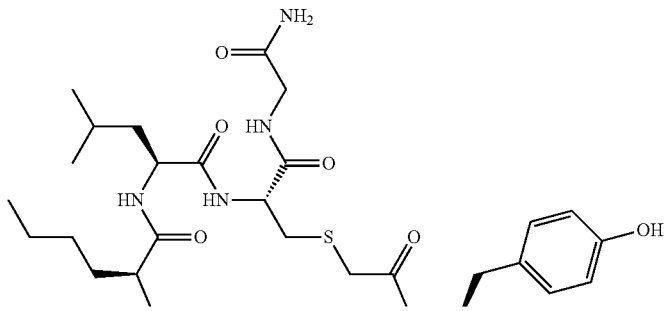

Example 10512

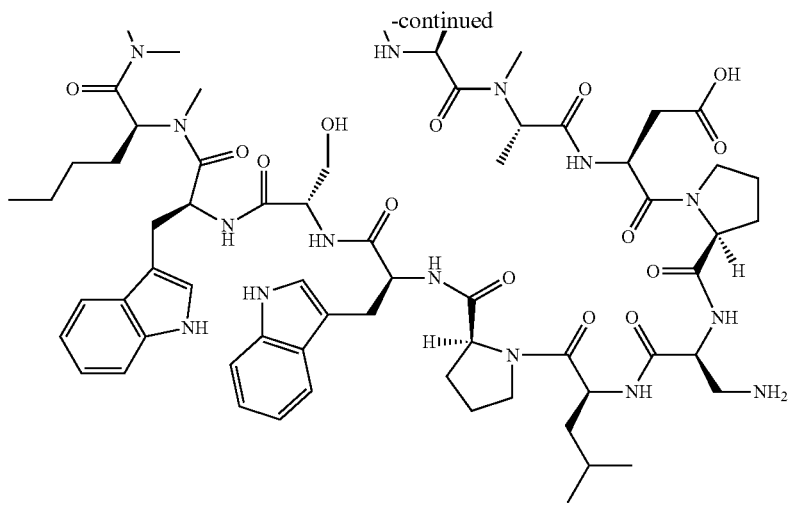

-continued

Example 10512 was prepared following "General Synthetic Sequence A". The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-50% B over 40 minutes, then a 5-minute hold at 100% B; Flow: 20 mL/min. Fractions containing the desired product were combined and dried via centrifugal evaporation. The yield of the product was 25.8 mg, and its estimated purity by LCMS analysis was 99%.

Analysis condition A: Retention time=1.66 min; ESI-MS (+) m/z 908.4 (M+2H)

Analysis condition B: Retention time=2.81 min; ESI-MS (+) m/z 908.4 (M+2H)

Preparation of Example 10513

Example 10513

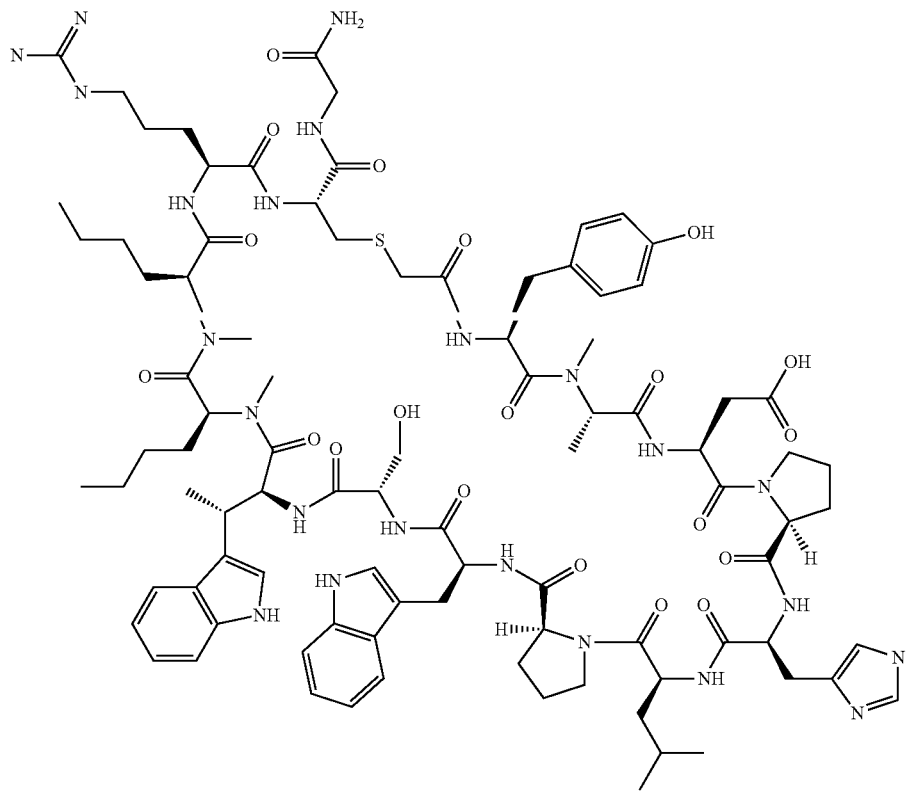

Example 10513 was prepared following "General Synthetic Sequence A" but using "Cyclization Method B" instead of "Cyclization Method A". (2S,3S)-2-((((9H-fluoren-9-yl)methoxy)carbonyl)amino)-3-(1-(tert-butoxycarbonyl)-1H-indol-3-yl)butanoic acid was used in the sixth amino acid coupling step. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 10.8 mg, and its estimated purity by LCMS analysis was 96%.

ESI-HRMS(+) m/z: Calculated: 954.4950 (M+2H). Found: 954.4874 (M+2H).

Preparation of Example 10514

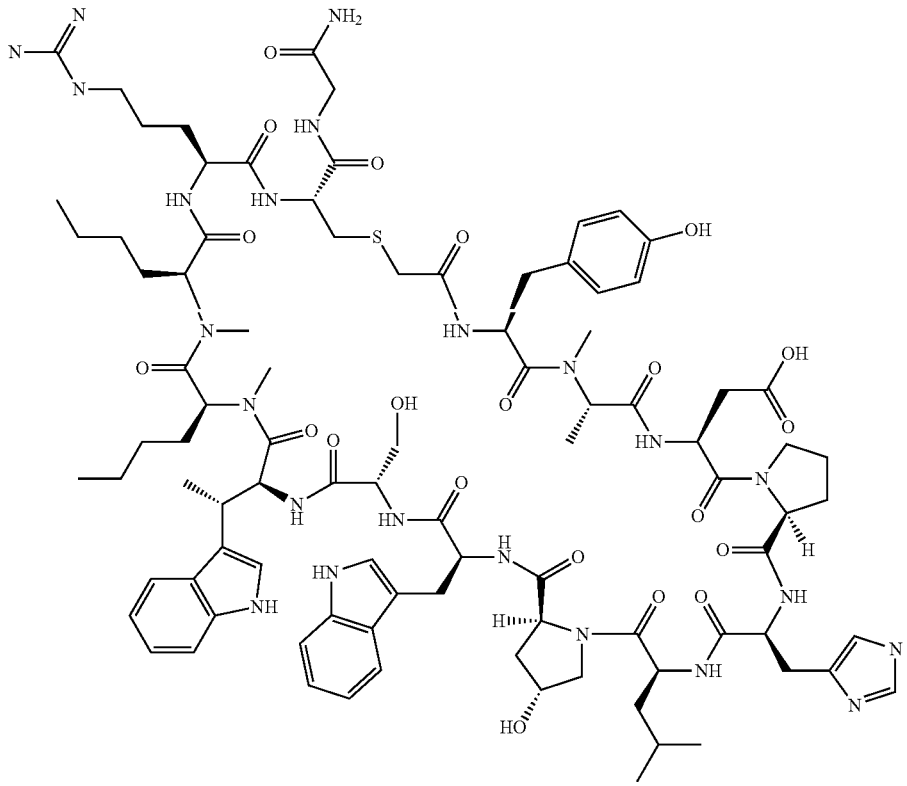

Example 10514

Example 10514 was prepared following "General Synthetic Sequence A" but using "Cyclization Method B" instead of "Cyclization Method A". (2S,3S)-2-((((9H-fluoren-9-yl)methoxy)carbonyl)amino)-3-(1-(tert-butoxycarbonyl)-1H-indol-3-yl)butanoic acid was used in the sixth amino acid coupling step. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 14.4 mg, and its estimated purity by LCMS analysis was 100%.

Analysis condition A: Retention time=1.52 min; ESI-MS (+) m/z 962.9 (M+2H)

Analysis condition B: Retention time=2.58 min; ESI-MS (+) m/z 962.9 (M+2H)

ESI-HRMS(+) m/z: Calculated: 962.4880 (M+2H). Found: 962.4851 (M+2H).

Preparation of Example 10515

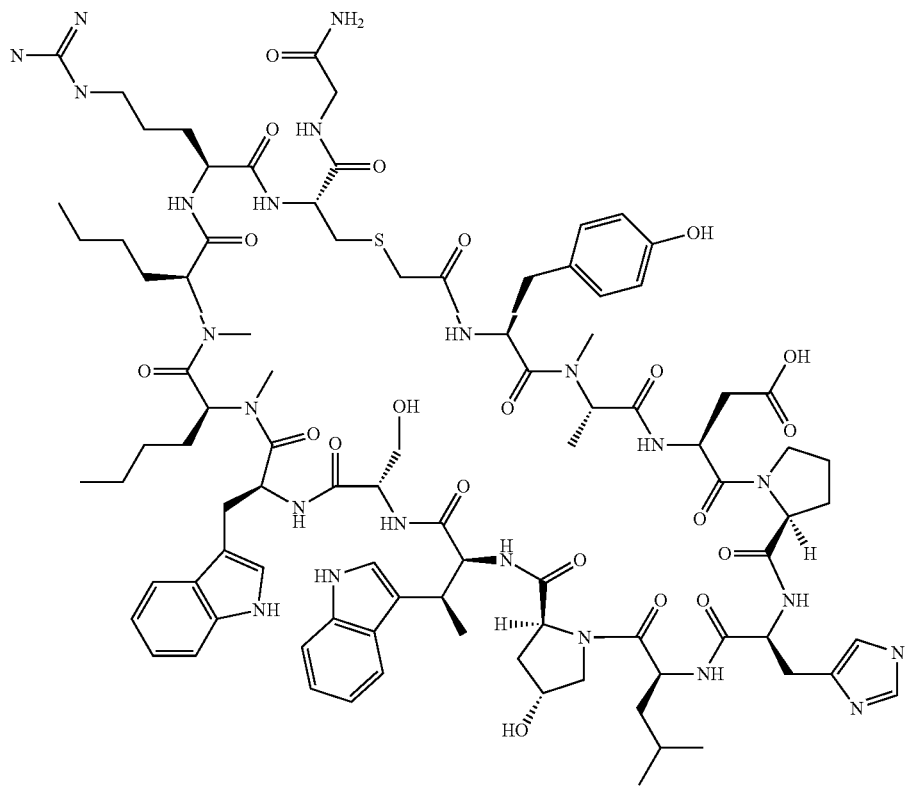

Example 10515

Example 10515 was prepared following "General Synthetic Sequence A" but using "Cyclization Method B" instead of "Cyclization Method A". (2S,3S)-2-((((9H-fluoren-9-yl)methoxy)carbonyl)amino)-3-(1-(tert-butoxycarbonyl)-1H-indol-3-yl)butanoic acid was used in the eighth amino acid coupling step. The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 15.1 mg, and its estimated purity by LCMS analysis was 97%.

Analysis condition B: Retention time=2.55 min; ESI-MS (+) m/z 963.0 (M+2H)

ESI-HRMS(+) m/z: Calculated: 962.4880 (M+2H). Found: 962.4844 (M+2H).

Preparation of Example 10516

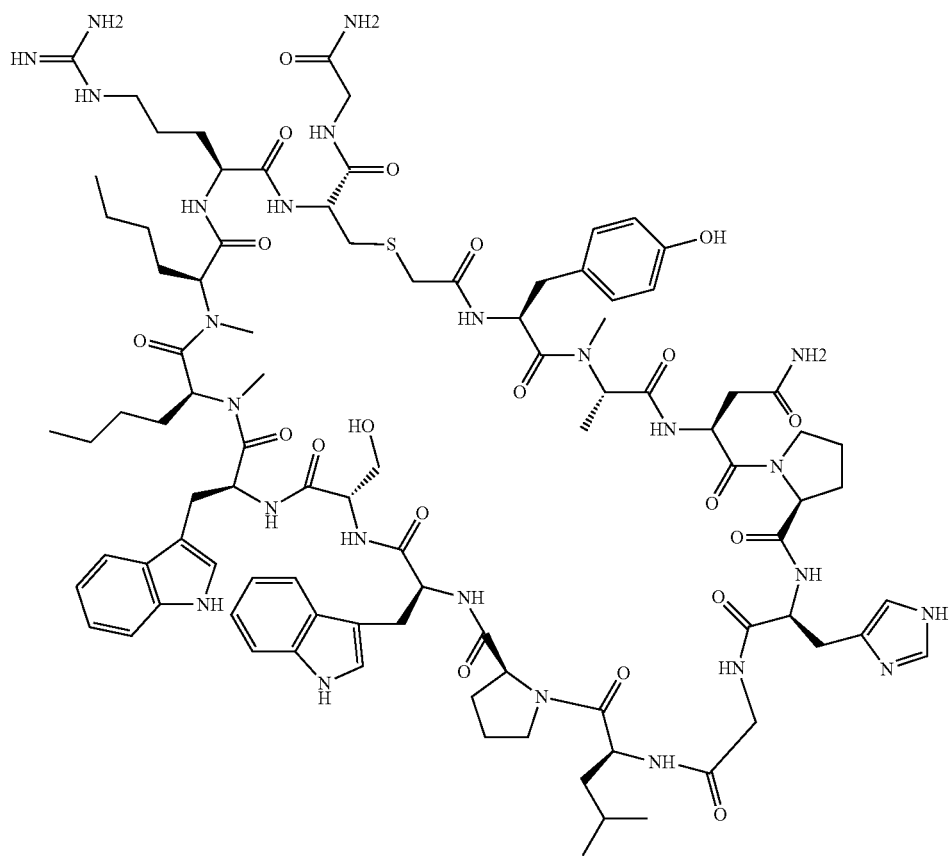

Example 10516

Example 10516 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 97%.

Analysis condition A: Retention time=1.58 min; ESI-MS (+) m/z 976.2 (M+2H)

Analysis condition B: Retention time=2.77 min; ESI-MS (+) m/z 976.4 (M+2H)

Preparation of Example 10517

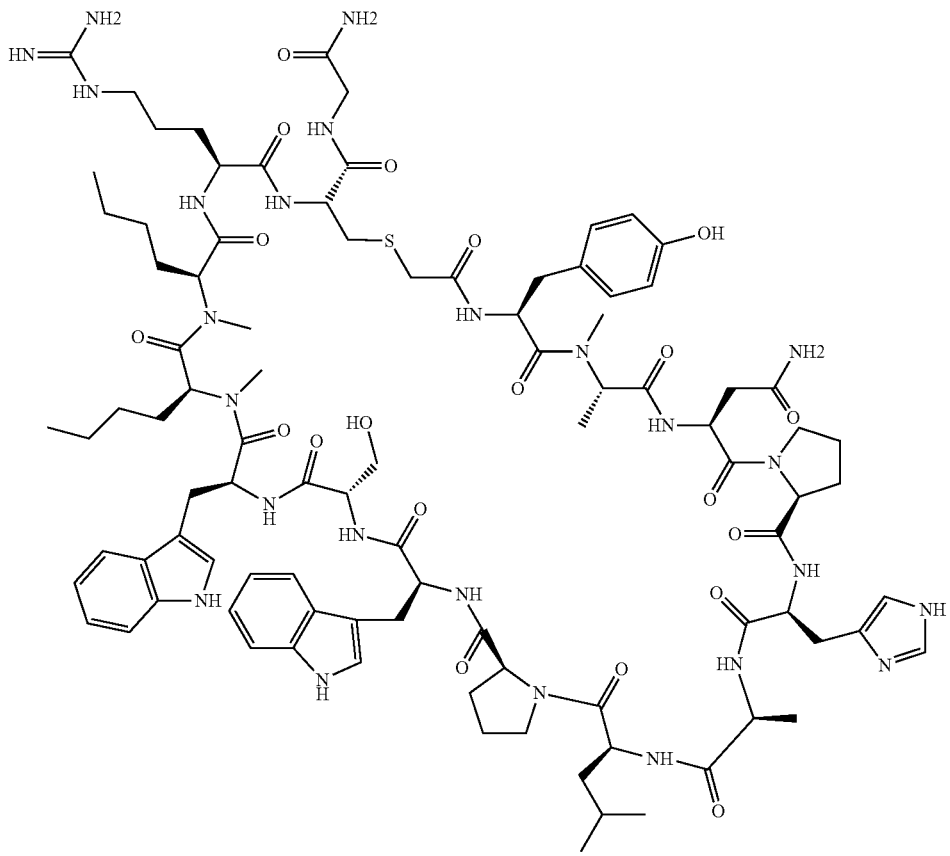

Example 10517

Example 10517 was prepared following "General Synthetic Sequence A" but using "Cyclization Method B" instead of "Cyclization Method A". The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.4 mg, and its estimated purity by LCMS analysis was 97%.

Analysis condition A: Retention time=1.57 min; ESI-MS (+) m/z 983.8 (M+2H)

Analysis condition B: Retention time=2.77 min; ESI-MS (+) m/z 983.8 (M+2H)

ESI-HRMS(+) m/z: Calculated: 983.0012 (M+2H). Found: 982.9986 (M+2H).

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:
Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:
Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

General Procedures for Examples 13001-14008:

All manipulations were performed under automation on a Symphony-X peptide synthesizer (Protein Technologies). All procedures unless noted were performed in a 10 mL polypropylene tube fitted with a bottom frit. The tube connects to the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solution was used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; Rink=(2,4-dimethoxyphenyl)(4-alkoxyphenyl)methanamine, where "4-alkoxy" describes the position and type of connectivity to the polystyrene resin. The resin used is Merrifield polymer (polystyrene) with a Rink linker (Fmoc-protected at nitrogen); 100-200 mesh, 1% DVB, 0.56 mmol/g loading. Common amino acids used are listed below with side-chain protecting groups indicated inside parenthesis. Fmoc-Ala-OH; Fmoc-Arg(Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc[N-Me]Ala-OH; Fmoc-[N-Me]Nle-OH; Fmoc-Phe-OH; Fmoc-Pro-OH; Fmoc-Sar-OH; Fmoc-Ser(tBu)-OH; Fmoc-Thr(tBu)-OH; Fmoc-Trp(Boc)-OH; Fmoc-Tyr(tBu)-OH; Fmoc-Val-OH The procedures describe an experiment performed on a 0.100 mmol scale, where the scale is determined by the amount of Rink linker bound to the resin. This scale corresponds to approximately 178 mg of the Rink-Merrifield resin described above. Prior to amino acid coupling, all peptide synthesis sequences began with a resin-swelling procedure, described below as "Resin-swelling procedure". Coupling of amino acids to a primary amine N-terminus used the "Single-coupling procedure" described below. Coupling of amino acids to a secondary amine N-terminus used the "Double-coupling procedure" described below. Coupling of chloroacetylchloride to the N-terminus of the peptide is described by the "Chloroacetyl chloride coupling procedure" detailed below.

Resin-Swelling Procedure:

To a 10 mL polypropylene solid-phase reaction vessel was added Merrifield:Rink resin (178 mg, 0.100 mmol). The resin washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin washed successively four times as follows: for each wash, DMF (2.0 mL) was added to top of the vessel (not through the bottom frit) and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin washed successively six times as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added to top of the vessel (not through the bottom frit) and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin washed successively four times as follows: for each wash, DMF (2.0 mL) was added to top of the vessel (not through the bottom frit) and the resulting mixture was periodically agitated for 90 seconds before the solution was drained through the frit. The resulting resin was used directly in the next step.

Chloroacetyl Chloride Coupling Procedure:

To the reaction vessel was added DIPEA (0.4M in DMF, 3.0 mL, 24 eq), then chloroacetyl chloride (0.8M in DMF, 1.5 mL, 13.2 eq). The mixture was periodically agitated for 30 minutes, then the solution was drained through the frit. The resin washed successively three times as follows: for each wash, DMF (2.0 mL) was added to top of the vessel (not through the bottom frit) and the resulting mixture was periodically agitated for 90 seconds before the solution was drained through the frit. The resin washed successively four times as follows: for each wash, $CH_2Cl_2$ (2.0 mL) was added to top of the vessel (not through the bottom frit) and the resulting mixture was periodically agitated for 90 seconds before the solution was drained through the frit. The resulting resin was placed under a $N_2$ stream for 15 minutes upon which the resin became rigid and easily handled.

Global Deprotection Procedure:

A "deprotection solution" was prepared by combining in a 40 mL glass vial trifluoroacetic acid (22 mL), phenol (1.325 g), water (1.25 mL) and triisopropylsilane (0.5 mL). The resin was removed from the reaction vessel and transferred to a 4 mL glass vial. To the vial was added the "deprotection solution" (2.0 mL). The mixture was vigorously mixed in a shaker (1000 RPM for 1 minute, then 500 RPM for 1.5 h). The mixture was filtered through a 0.2 micron syringe filter into a 18×150 mm test tube, and the solids were extracted with a second portion of the "deprotection solution" (1.0 mL). The combined filtrates, in the 18×150 mm test tube, were diluted with $Et_2O$ (15 mL) upon which a significant amount of a white solid precipitated. The mixture was centrifuged for 2 minutes, then the solution was decanted. The solids were suspended in $Et_2O$ (20 mL); the mixture was centrifuged for 5 minutes; and the solution was decanted. For a final time, the solids were suspended in $Et_2O$ (20 mL); the mixture was centrifuged for 5 minutes; and the solution was decanted.

Cyclization Procedure:
The solids were dissolved in 20 mL MeCN:aq. 0.1M NH₄OAc (1:1), and the solution was carefully adjusted to pH=8.5-9.0 using aq NaOH (1.0M). The solution was then allowed to stand (stirring not necessary) overnight (app. 18 h). 1 mL DMSO was added, and the reaction solution was concentrated in a SPEEDVAC® centrifuge evaporator overnight with mild heating. Approximately 1 mL of MeOH was added to the residue, and the resulting solution was purified by the method described in the individual examples.

Preparation of (2S,4R)-1-(((9H-fluoren-9-yl)methoxy)carbonyl)-4-phenylpyrrolidine-2-carboxylic acid Scheme:

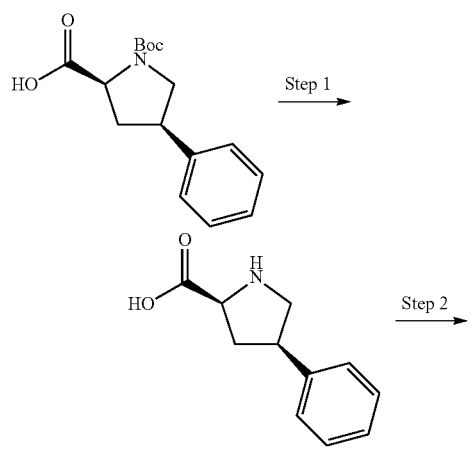

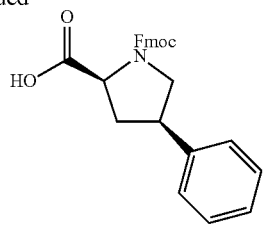

Step 1:
To a solution of (2S,4R)-1-(tert-butoxycarbonyl)-4-phenylpyrrolidine-2-carboxylic acid (1.20 g, 4.12 mmol) in CH₂Cl₂ (20.59 ml) was added TFA (4.13 ml, 53.5 mmol). The resulting solution was stirred at rt. When analysis by LC/MS showed the reaction to be complete, the volatiles were removed in vacuo, toluene (10 mL) was added, and the volitiles removed again.

Step 2:
The residue from step 1 was taken up in 1 M aq Na₂CO₃ (24.71 ml, 24.71 mmol) with ~5 mL THF added for solubility. FMOC-OSU (1.667 g, 4.94 mmol) was then added, and the mixture stirred overnight at rt. The reaction mixture was extracted twice with ether (discarded). The pH was adjusted to ~2 with the addition of 1 M HCl, and the resulting suspension extracted three times into EtOAc. The combined EtOAc extracts were dried over MgSO₄, filtered, and concentrated in vacuo. The crude (2S,4R)-1-(((9H-fluoren-9-yl)methoxy)carbonyl)-4-phenylpyrrolidine-2-carboxylic acid was used as-is for further chemistry.

Preparation of Example 13001

Example 13001

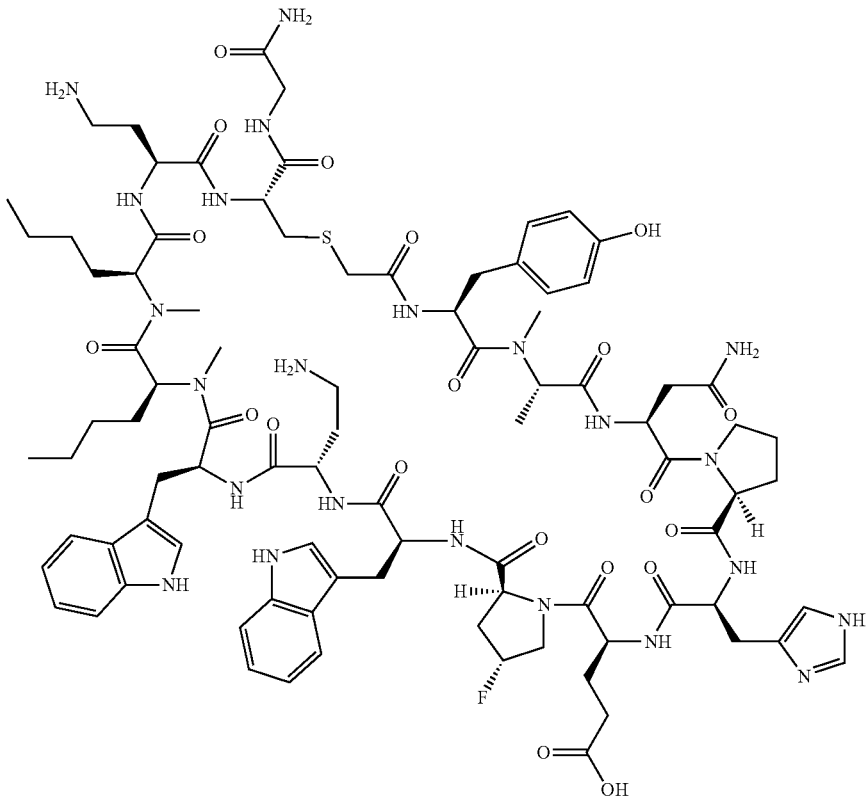

The following peptide was synthesized according to the procedures above. The underlined steps employed the double-coupling procedure.

ClAc-Tyr-[N-Me]Ala-Asn-Pro-His-Glu-[trans 4-fluoro-L-proline]-Trp-Dab-Trp-[N-Me]Nle-[N-Me]Nle-Dab-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 32.6 mg, and its estimated purity by LCMS analysis was 100%.

Analysis condition A: Retention time=1.42 min; ESI-MS (+) m/z 943.7 (M+2H), most abundant ion Analysis condition B: Retention time=2.62 min; ESI-MS (+) m/z 943.7 (M+2H), most abundant ion ESI-HRMS(+) m/z: Calculated: 942.9543 (M+2H). Found: 942.9517 (M+2H).

Preparation of Example 13002

The following peptide was synthesized according to the procedures above. The underlined steps employed the double-coupling procedure.

ClAc-Tyr-[N-Me]Ala-Asp-Pro-His-Glu-[trans 4-fluoro-L-proline]-Trp-Dab-Trp-[N-Me]Nle-[N-Me]Nle-Ala-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 26.7 mg, and its estimated purity by LCMS analysis was 100%.

Analysis condition A: Retention time=1.44 min; ESI-MS (+) m/z 929.3 (M+2H)

Analysis condition B: Retention time=2.66 min; ESI-MS (+) m/z 929.8 (M+2H), most abundant ion ESI-HRMS(+) m/z: Calculated: 928.9331 (M+2H). Found: 928.9306 (M+2H).

Example 13002

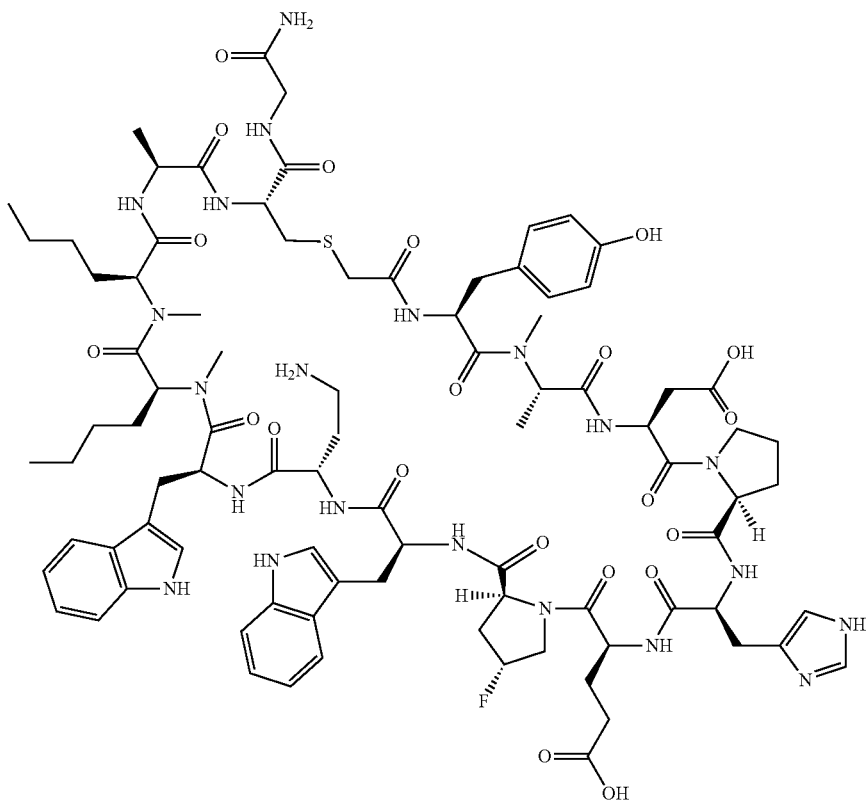

Preparation of Example 13003

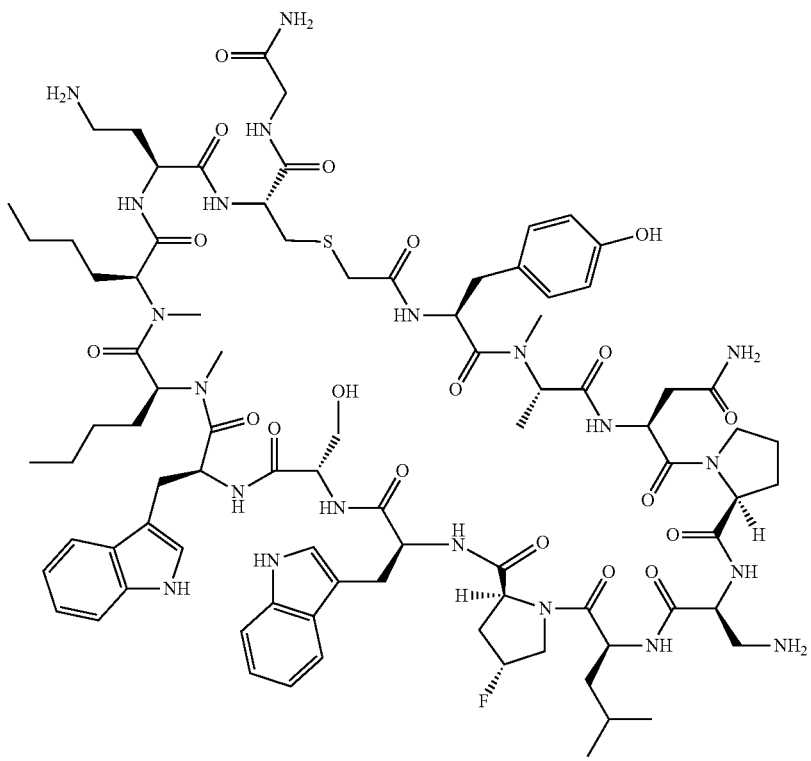

Example 13003

The following peptide was synthesized according to the procedures above. The underlined steps employed the double-coupling procedure.

ClAc-Tyr-[N-Me]Ala-Asn-Pro-Dap-Leu-[trans 4-fluoro-L-proline]-Trp-Ser-Trp-[N-Me]Nle-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 39.6 mg, and its estimated purity by LCMS analysis was 100%.

Analysis condition A: Retention time=1.63 min; ESI-MS (+) m/z 910.3 (M+2H)

Analysis condition B: Retention time=2.59 min; ESI-MS (+) m/z 910.3 (M+2H)

ESI-HRMS(+) m/z: Calculated: 909.9616 (M+2H). Found: 909.9587 (M+2H).

Preparation of Example 13004

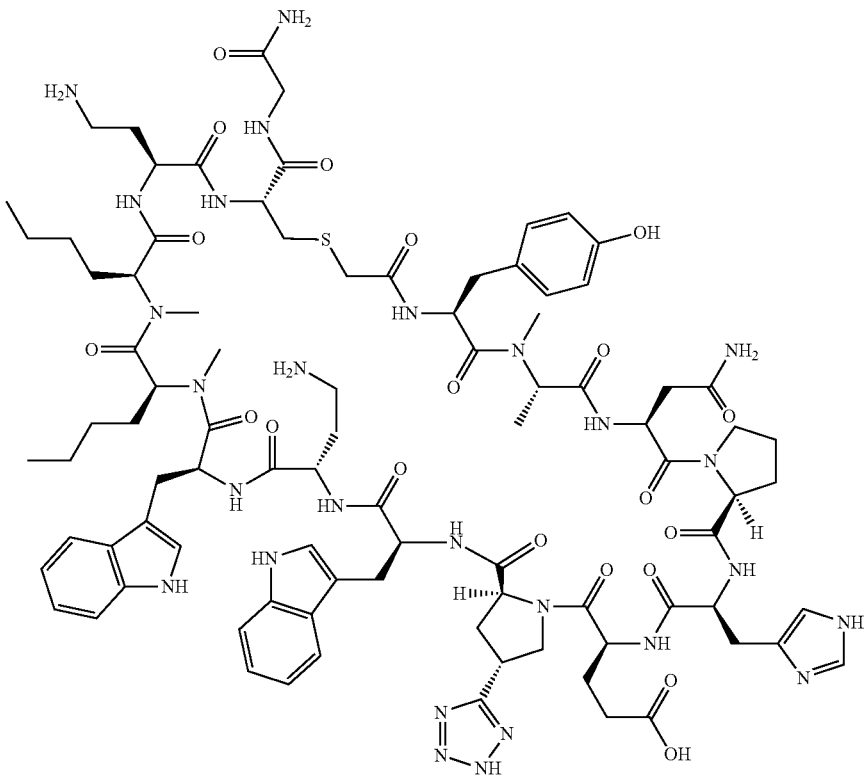

Example 13004

The following peptide was synthesized according to the procedures above. The underlined steps employed the double-coupling procedure.
ClAc-Tyr-[N-Me]Ala-Asn-Pro-His-Glu-[trans 4-(2H-tetrazol-5-yl)-L-proline]-Trp-Dab-Trp-[N-Me]Nle-[N-Me]Nle-Dab-Cys-Gly After deprotection and cyclization according to the procedures above, the compound was purified as follows:

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 100%.

Analysis condition A: Retention time=1.36 min; ESI-MS (+) m/z 968.2 (M+2H)

Analysis condition B: Retention time=2.55 min; ESI-MS (+) m/z 968.3 (M+2H)

ESI-HRMS(+) m/z: Calculated: 967.9652 (M+2H). Found: 967.9616 (M+2H).

Preparation of Example 13005

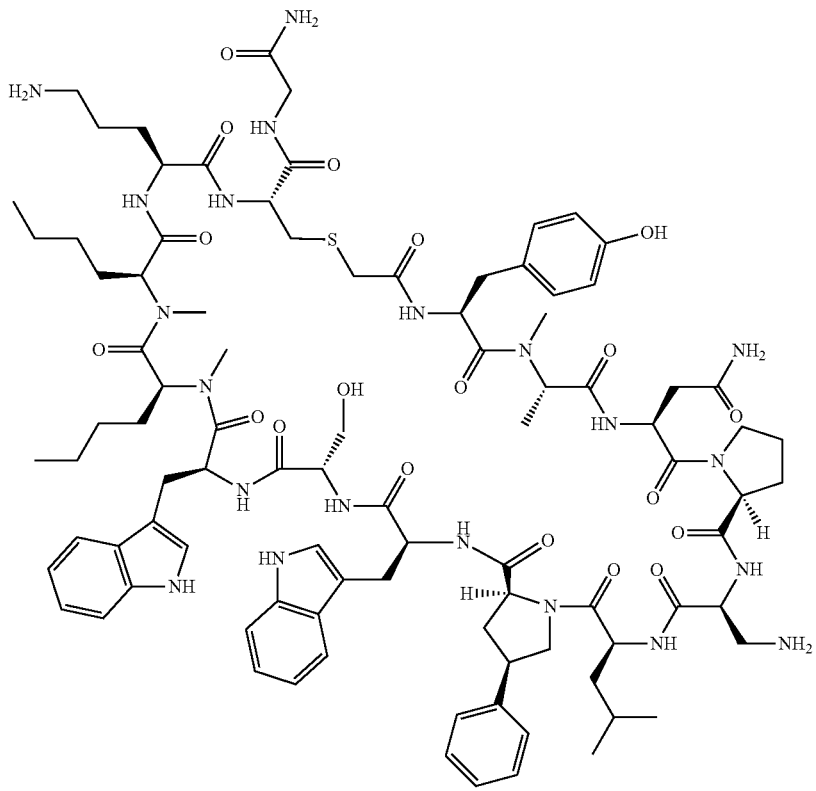

Example 13005

The following peptide was synthesized according to the procedures above. The underlined steps employed the double-coupling procedure.

ClAc-<u>Tyr</u>-[N-Me]Ala-<u>Asn</u>-Pro-Dap-<u>Leu</u>-[cis 4-phenyl-L-proline]-Trp-Ser-<u>Trp</u>-<u>[N-Me]Nle</u>-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 24.8 mg, and its estimated purity by LCMS analysis was 95%.

Analysis condition A: Retention time=1.62 min; ESI-MS (+) m/z 939.6 (M+2H), most abundant ion Analysis condition B: Retention time=2.75 min; ESI-MS (+) m/z 939.6 (M+2H), most abundant ion ESI-HRMS(+) m/z: Calculated: 938.9820 (M+2H). Found: 938.9804 (M+2H).

Preparation of Example 13006

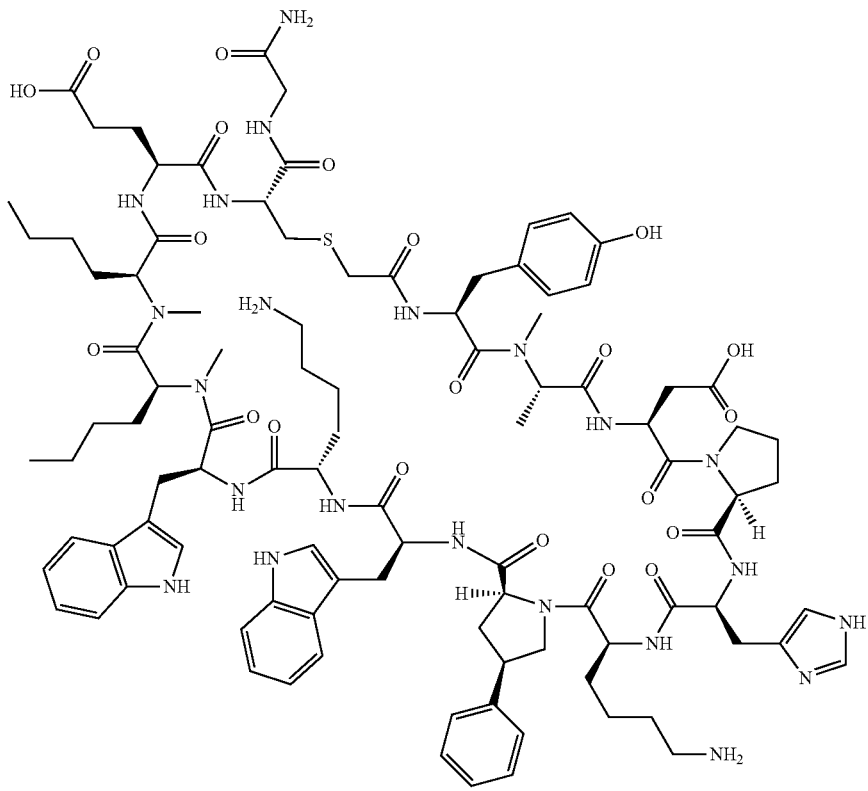

Example 13006

The following peptide was synthesized according to the procedures above. The underlined steps employed the double-coupling procedure.
ClAc-Tyr-[N-Me]Ala-Asp-Pro-His-Lys-[cis 4-phenyl-L-proline]-Trp-Lys-Trp-[N-Me]Nle-[N-Me]Nle-Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 28.0 mg, and its estimated purity by LCMS analysis was 98%.

Analysis condition A: Retention time=1.51 min; ESI-MS (+) m/z 1001.1 (M+2H), most abundant ion Analysis condition B: Retention time=2.67 min; ESI-MS (+) m/z 1001.1 (M+2H), most abundant ion ESI-HRMS(+) m/z: Calculated: 1000.4980 (M+2H). Found: 1000.4955 (M+2H).

Preparation of Example 13007

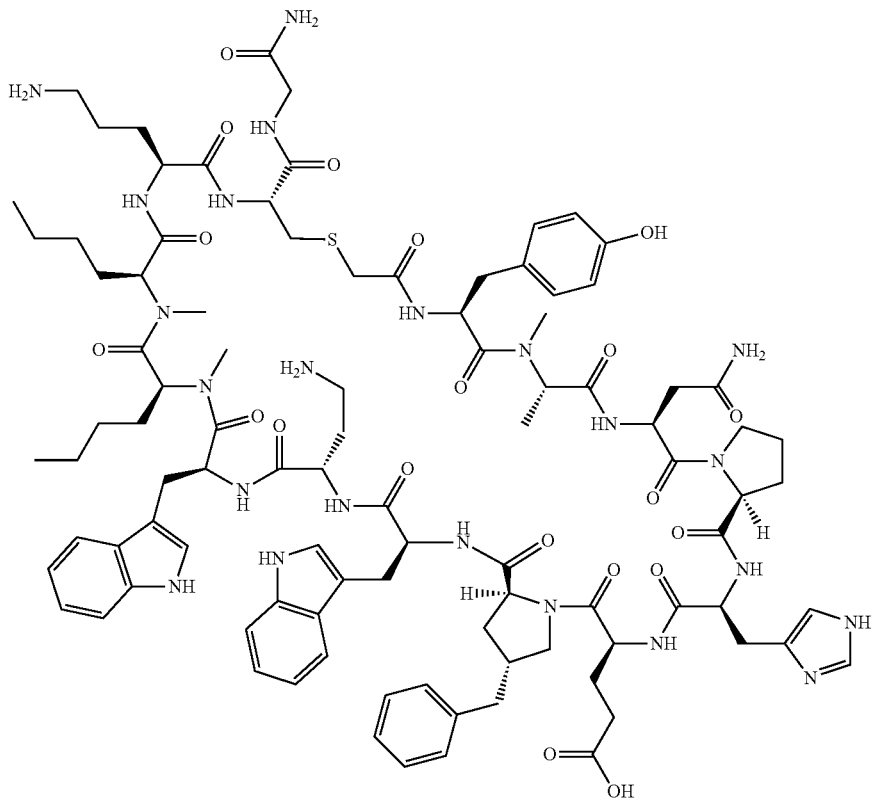

Example 13007

The following peptide was synthesized according to the procedures above. The underlined steps employed the double-coupling procedure.

ClAc-Tyr-[N-Me]Ala-Asn-Pro-His-Glu-[trans 4-benzyl-L-proline]-Trp-Dab-Trp-[N-Me]Nle-[N-Me]Nle-Dab-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 34.7 mg, and its estimated purity by LCMS analysis was 99%.

Analysis condition A: Retention time=1.62 min; ESI-MS (+) m/z 979.3 (M+2H), most abundant ion Analysis condition B: Retention time=2.86 min; ESI-MS (+) m/z 979.7 (M+2H), most abundant ion ESI-HRMS(+) m/z: Calculated: 978.9825 (M+2H). Found: 978.9810 (M+2H).

Preparation of Example 13008

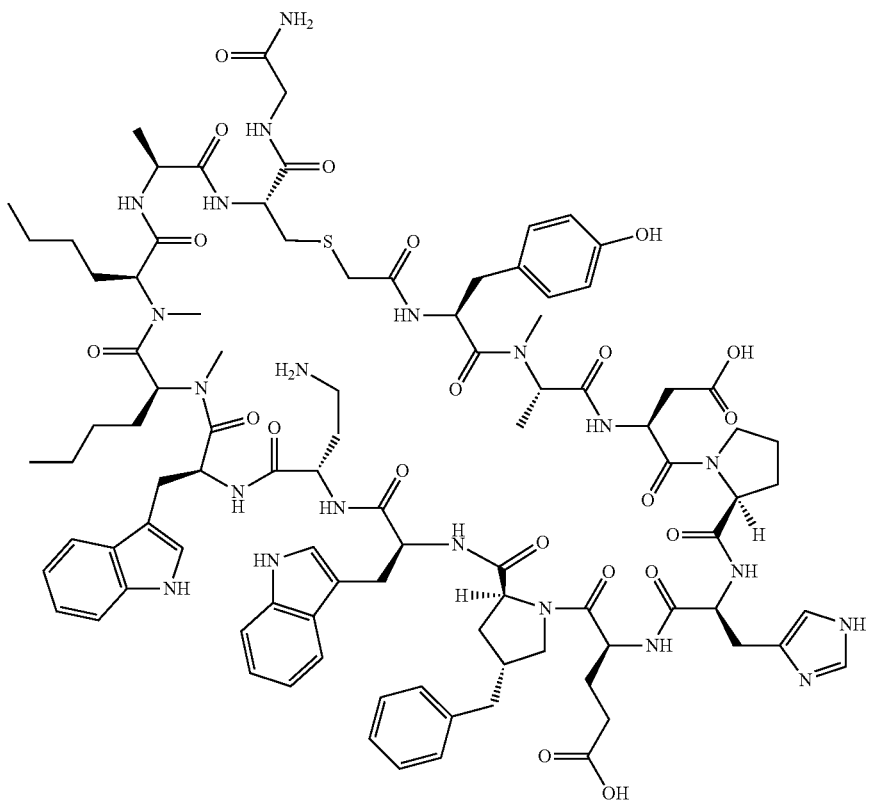

Example 13008

The following peptide was synthesized according to the procedures above. The underlined steps employed the double-coupling procedure.

ClAc-Tyr-[N-Me]Ala-Asp-Pro-His-Glu-[trans 4-benzyl-L-proline]-Trp-Dab-Trp-[N-Me]Nle-[N-Me]Nle-Ala-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 31.1 mg, and its estimated purity by LCMS analysis was 95%.

Analysis condition A: Retention time=1.68 min; ESI-MS (+) m/z 965.3 (M+2H)

Analysis condition B: Retention time=2.90 min; ESI-MS (+) m/z 965.7 (M+2H), most abundant ion ESI-HRMS(+) m/z: Calculated: 964.9613 (M+2H). Found: 964.9582 (M+2H).

Preparation of Example 13009

Example 13009

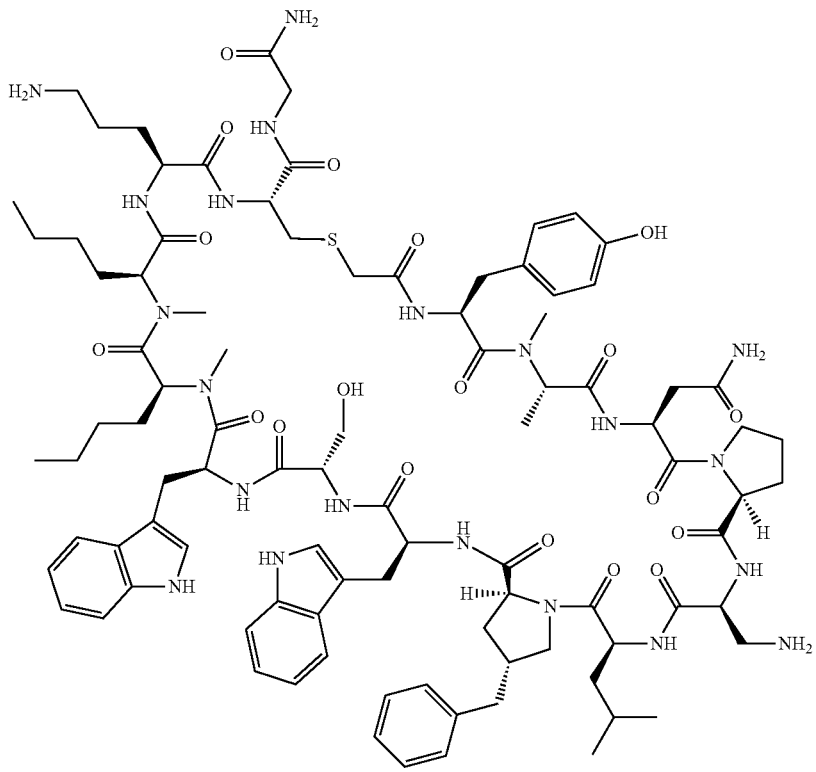

The following peptide was synthesized according to the procedures above. The underlined steps employed the double-coupling procedure.

ClAc-<u>Tyr</u>-[N-Me]Ala-<u>Asn</u>-Pro-Dap-<u>Leu</u>-[trans 4-benzyl-L-proline]-Trp-Ser-<u>Trp</u>-<u>[N-Me]Nle</u>-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The yield of the product was 23.5 mg, and its estimated purity by LCMS analysis was 99%.

Analysis condition A: Retention time=1.67 min; ESI-MS (+) m/z 946.5 (M+2H)

Analysis condition B: Retention time=2.78 min; ESI-MS (+) m/z 946.5 (M+2H)

ESI-HRMS(+) m/z: Calculated: 945.9898 (M+2H). Found: 945.9875 (M+2H).

Preparation of Example 13010

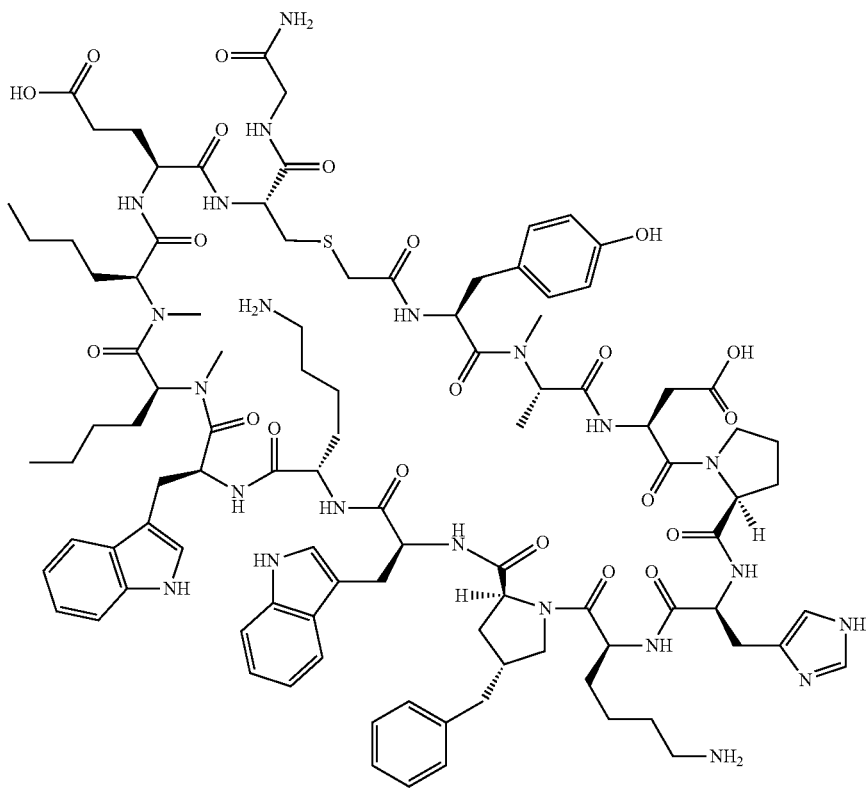

Example 13010

The following peptide was synthesized according to the procedures above. The underlined steps employed the double-coupling procedure.

ClAc-Tyr-[N-Me]Ala-Asp-Pro-His-Lys-[trans 4-benzyl-L-proline]-Trp-Lys-Trp-[N-Me]Nle-[N-Me]Nle-Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 33.3 mg, and its estimated purity by LCMS analysis was 99%.

Analysis condition A: Retention time=1.56 min; ESI-MS (+) m/z 1008.3 (M+2H), most abundant ion Analysis condition B: Retention time=2.75 min; ESI-MS (+) m/z 1008.3 (M+2H), most abundant ion ESI-HRMS(+) m/z: Calculated: 1007.5058 (M+2H). Found: 1007.5027 (M+2H).

Preparation of Example 13011

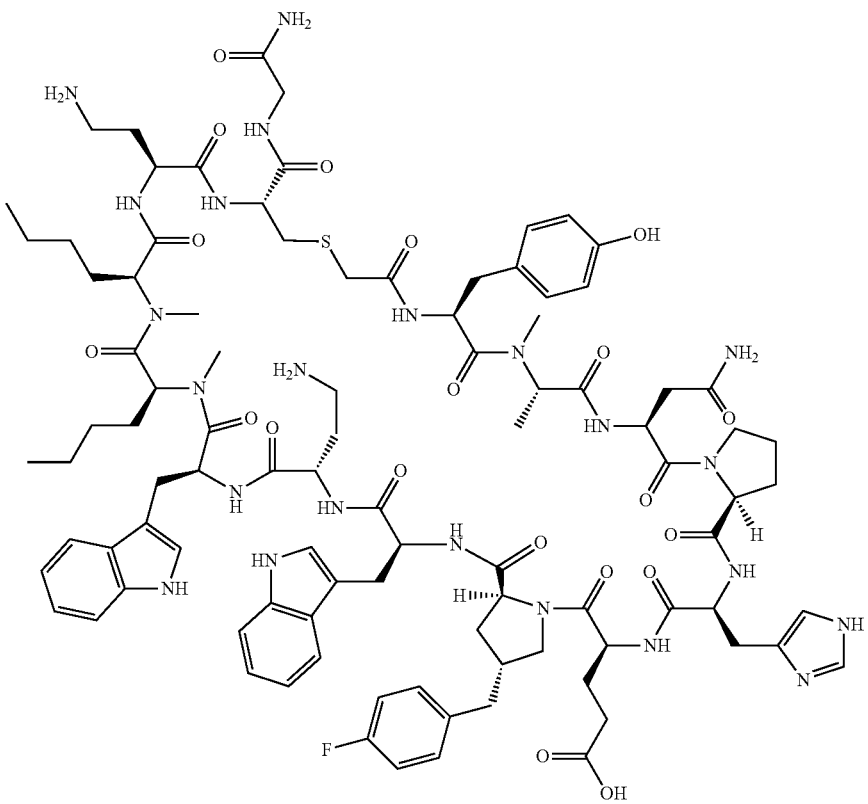

Example 13011

The following peptide was synthesized according to the procedures above. The underlined steps employed the double-coupling procedure.

ClAc-Tyr-[N-Me]Ala-Asn-Pro-His-Glu-[trans 4-(4-fluorobenzyl)-L-proline]-Trp-Dab-Trp-[N-Me]Nle-[N-Me]Nle-Dab-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 41.7 mg, and its estimated purity by LCMS analysis was 99%.

Analysis condition A: Retention time=1.63 min; ESI-MS (+) m/z 988.6 (M+2H)

Analysis condition B: Retention time=2.84 min; ESI-MS (+) m/z 988.7 (M+2H), most abundant ion ESI-HRMS(+) m/z: Calculated: 987.9778 (M+2H). Found: 987.9758 (M+2H).

Preparation of Example 13012

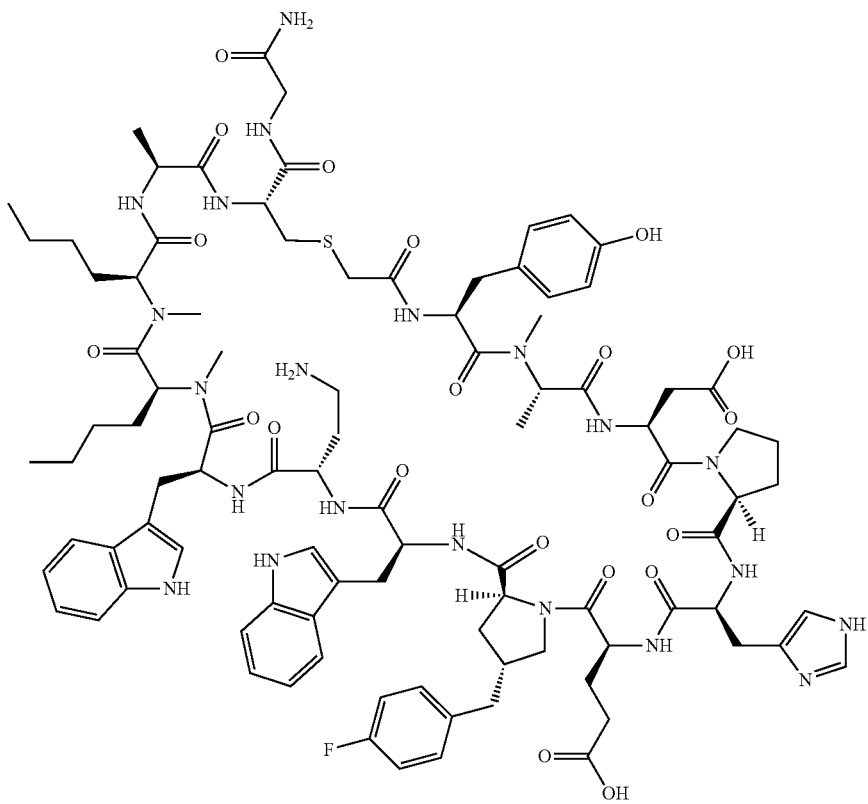

Example 13012

The following peptide was synthesized according to the procedures above. The underlined steps employed the double-coupling procedure.

ClAc-Tyr-[N-Me]Ala-Asp-Pro-His-Glu-[trans 4-(4-fluorobenzyl)-L-proline]-Trp-Dab-Trp-[N-Me]Nle-[N-Me]Nle-Ala-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.5 mg, and its estimated purity by LCMS analysis was 98%.

Analysis condition A: Retention time=1.68 min; ESI-MS (+) m/z 974.8 (M+2H), most abundant ion Analysis condition B: Retention time=2.90 min; ESI-MS (+) m/z 974.4 (M+2H)

ESI-HRMS(+) m/z: Calculated: 973.9565 (M+2H). Found: 973.9538 (M+2H).

Preparation of Example 13013

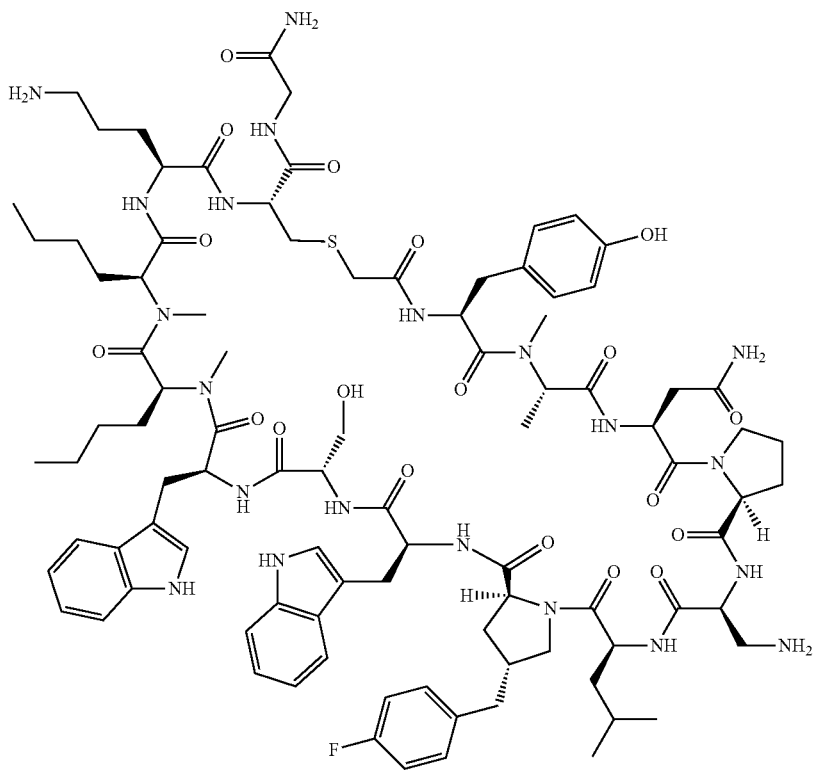

Example 13013

The following peptide was synthesized according to the procedures above. The underlined steps employed the double-coupling procedure.

ClAc-Tyr-[N-Me]Ala-Asn-Pro-Dap-Leu-[trans 4-(4-fluorobenzyl)-L-proline]-Trp-Ser-Trp-[N-Me]Nle-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 97%.

Analysis condition A: Retention time=1.69 min; ESI-MS (+) m/z 955.5 (M+2H)

Analysis condition B: Retention time=2.78 min; ESI-MS (+) m/z 955.8 (M+2H), most abundant ion ESI-HRMS(+) m/z: Calculated: 954.9851 (M+2H). Found: 954.9819 (M+2H).

Preparation of Example 13014

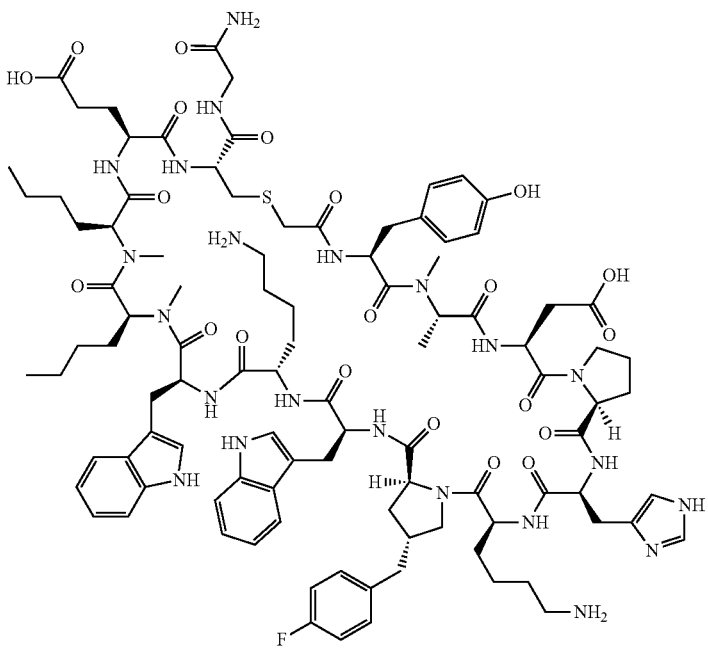

Example 13014

The following peptide was synthesized according to the procedures above. The underlined steps employed the double-coupling procedure.

ClAc-Tyr-[N-Me]Ala-Asp-Pro-His-Lys-[trans 4-(4-fluorobenzyl)-L-proline]-Trp-Lys-Trp-[N-Me]Nle-[N-Me]Nle-Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 18.1 mg, and its estimated purity by LCMS analysis was 100%.

Analysis condition A: Retention time=1.54 min; ESI-MS (+) m/z 1017.3 (M+2H), most abundant ion Analysis condition B: Retention time=2.76 min; ESI-MS (+) m/z 1016.9 (M+2H)

ESI-HRMS(+) m/z: Calculated: 1016.5011 (M+2H). Found: 1016.4991 (M+2H).

Preparation of Example 14001

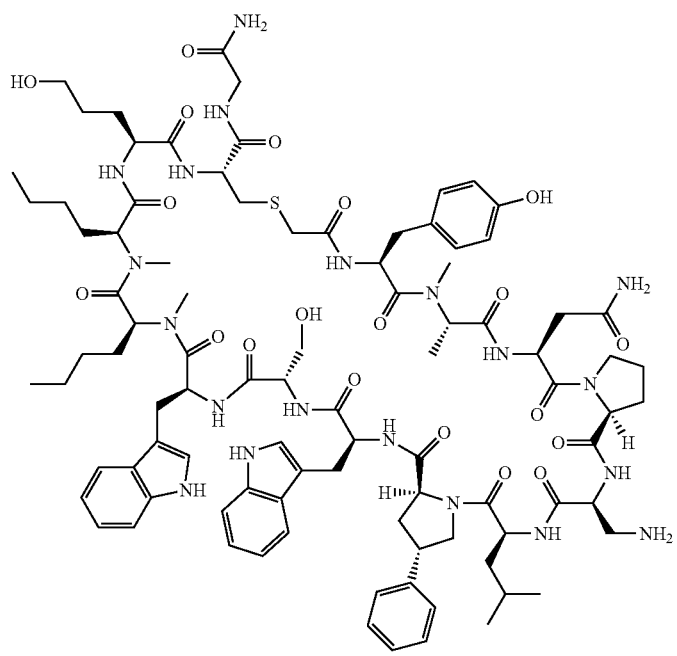

Example 14001

The following peptide was synthesized according to the procedures above. The underlined steps employed the double-coupling procedure.
ClAc-Tyr-[N-Me]Ala-Asn-Pro-Dap-Leu-[trans 4-phenyl-L-proline]-Trp-Ser-Trp-[N-Me]Nle-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 20.9 mg, and its estimated purity by LCMS analysis was 96%.

Analysis condition A: Retention time=1.64 min; ESI-MS (+) m/z 940.2 (M+2H), most abundant ion
Analysis condition B: Retention time=2.79 min; ESI-MS (+) m/z 939.6 (M+2H), most abundant ion
ESI-HRMS(+) m/z: Calculated: 938.9820 (M+2H). Found: 938.9799 (M+2H).

Preparation of Example 14002

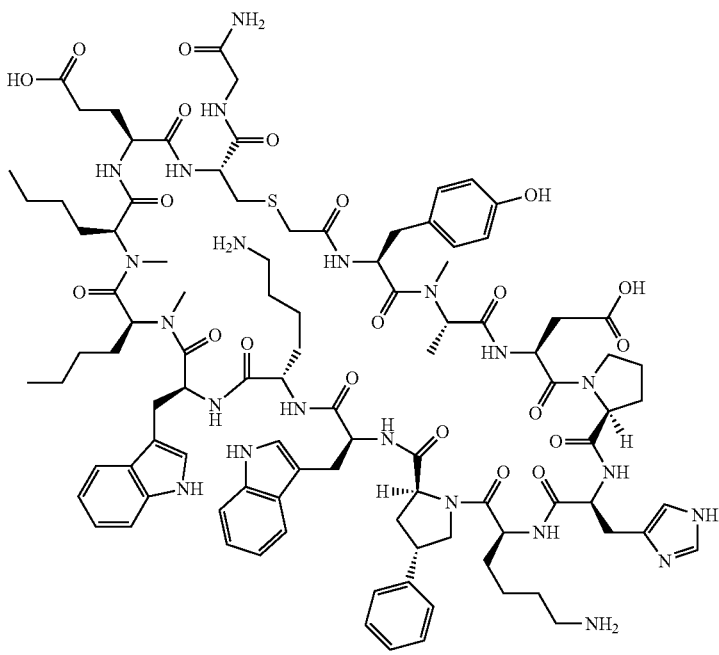

Example 14002

The following peptide was synthesized according to the procedures above. The underlined steps employed the double-coupling procedure.

ClAc-<u>Tyr</u>-[N-Me]Ala-<u>Asp</u>-Pro-His-<u>Lys</u>-[trans 4-phenyl-L-proline]-Trp-Lys-<u>Trp</u>-<u>[N-Me]Nle</u>-[N-Me]Nle-Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 51.0 mg, and its estimated purity by LCMS analysis was 99%.

Analysis condition A: Retention time=1.48 min; ESI-MS (+) m/z 1000.8 (M+2H)

Analysis condition B: Retention time=2.71 min; ESI-MS (+) m/z 1001.2 (M+2H)

ESI-HRMS(+) m/z: Calculated: 1000.4980 (M+2H). Found: 1000.4958 (M+2H).

Preparation of Example 14003

Example 14003

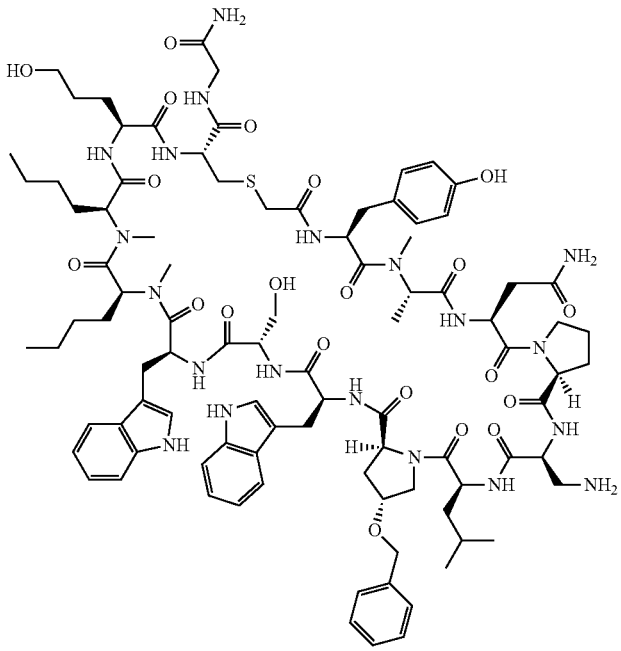

The following peptide was synthesized according to the procedures above. The underlined steps employed the double-coupling procedure.

ClAc-<u>Tyr</u>-[N-Me]Ala-<u>Asn</u>-Pro-Dap-<u>Leu</u>-[trans 4-benzyloxy-L-proline]-Trp-Ser-<u>Trp</u>-<u>[N-Me]Nle</u>-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 23.4 mg, and its estimated purity by LCMS analysis was 96%.

Analysis condition A: Retention time=1.66 min; ESI-MS (+) m/z 954.6 (M+2H), most abundant ion Analysis condition B: Retention time=2.79 min; ESI-MS (+) m/z 954.3 (M+2H)

Preparation of Example 14004

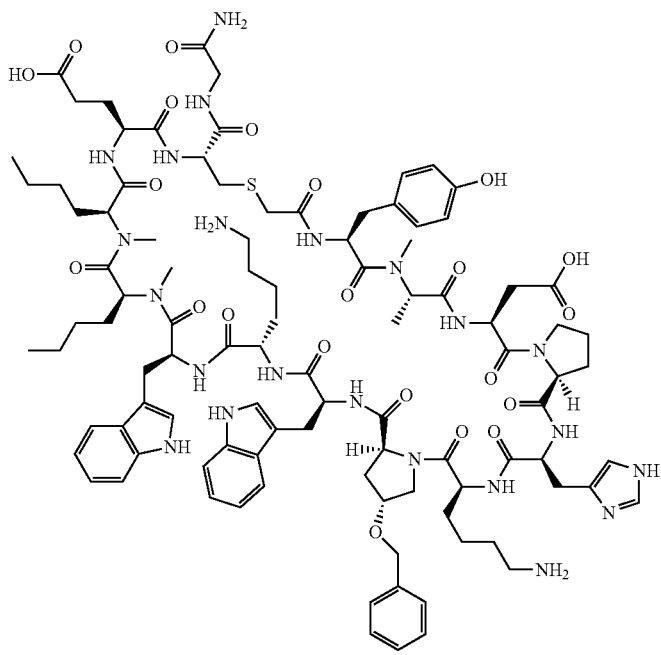

Example 14004

The following peptide was synthesized according to the procedures above. The underlined steps employed the double-coupling procedure.

ClAc-<u>Tyr</u>-[N-Me]Ala-<u>Asp</u>-Pro-His-<u>Lys</u>-[trans 4-benzyloxy-L-proline]-Trp-Lys-<u>Trp</u>-<u>[N-</u><u>Me]Nle</u>-[N-Me]Nle- Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The yield of the product was 35.6 mg, and its estimated purity by LCMS analysis was 94%.

Analysis condition A: Retention time=1.65 min; ESI-MS (+) m/z 1015.7 (M+2H)

Analysis condition B: Retention time=2.66 min; ESI-MS (+) m/z 1016.2 (M+2H), most abundant ion ESI-HRMS(+) m/z: Calculated: 1015.5033 (M+2H). Found: 1015.5008 (M+2H).

Preparation of Example 14005

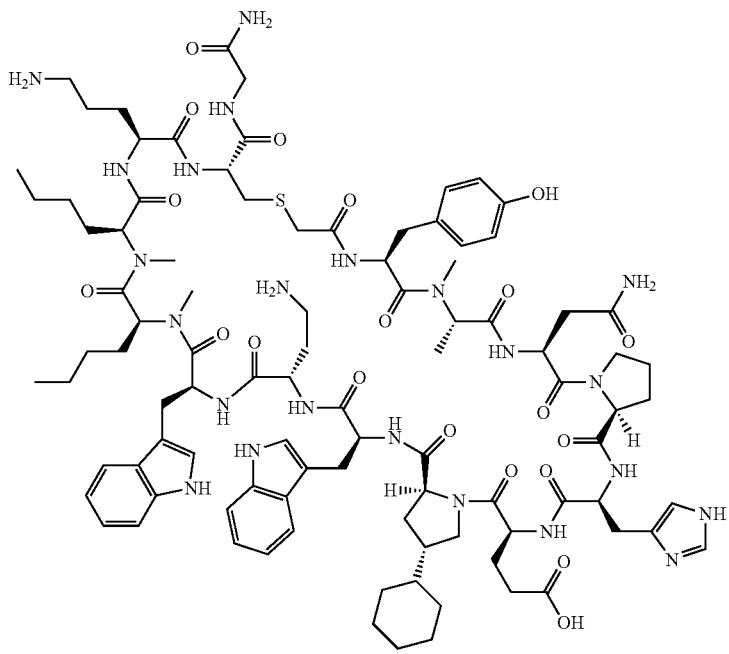

Example 14005

The following peptide was synthesized according to the procedures above. The underlined steps employed the double-coupling procedure.

ClAc-Tyr-[N-Me]Ala-Asn-Pro-His-Glu-[trans-4-cyclo-hexyl-L-proline]-Trp-Dab-Trp-[N-Me]Nle-[N-Me]Nle-Dab-Cys-Gly After deprotection and cyclization according to the procedures above, the compound was purified as follows:

The crude material was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 24.4 mg, and its estimated purity by LCMS analysis was 99%.

Analysis condition A: Retention time=1.76 min; ESI-MS (+) m/z 975.0 (M+2H)

Analysis condition B: Retention time=2.87 min; ESI-MS (+) m/z 975.1 (M+2H)

ESI-HRMS(+) m/z: Calculated: 974.9982 (M+2H). Found: 974.9954 (M+2H).

Preparation of Example 14006

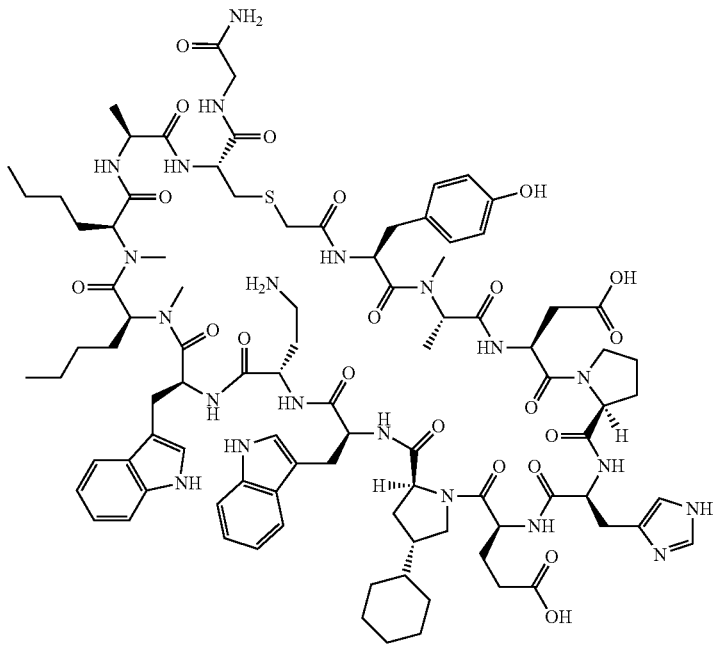

Example 14006

The following peptide was synthesized according to the procedures above. The underlined steps employed the double-coupling procedure.

ClAc-<u>Tyr</u>-[N-Me]Ala-<u>Asp</u>-Pro-His-<u>Glu</u>-[trans-4-cyclohexyl-L-proline]-Trp-Dab-<u>Trp</u>-<u>[N-Me]Nle</u>-[N-Me]Nle-Ala-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 29.2 mg, and its estimated purity by LCMS analysis was 99%.

Analysis condition A: Retention time=1.71 min; ESI-MS (+) m/z 961.3 (M+2H)

Analysis condition B: Retention time=2.99 min; ESI-MS (+) m/z 961.4 (M+2H)

ESI-HRMS(+) m/z: Calculated: 960.9769 (M+2H). Found: 960.9749 (M+2H).

Preparation of Example 14007

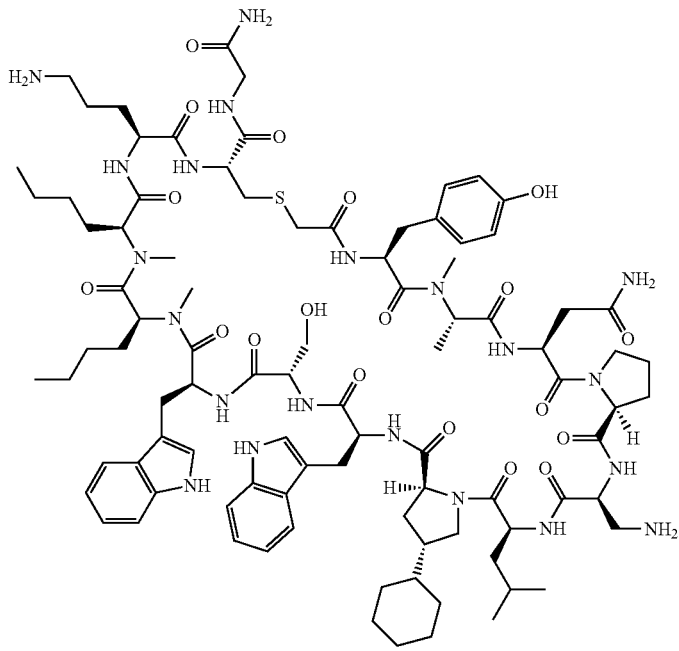

Example 14007

The following peptide was synthesized according to the procedures above. The underlined steps employed the double-coupling procedure.

ClAc-Tyr-[N-Me]Ala-Asn-Pro-Dap-Leu-[trans-4-cyclohexyl-L-proline]-Trp-Ser-Trp-[N-Me]Nle-[N-Me]Nle-Orn-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 20.3 mg, and its estimated purity by LCMS analysis was 98%.

Analysis condition A: Retention time=1.77 min; ESI-MS (+) m/z 942.8 (M+2H), most abundant ion Analysis condition B: Retention time=2.91 min; ESI-MS (+) m/z 942.8 (M+2H), most abundant ion Preparation of Example 14008

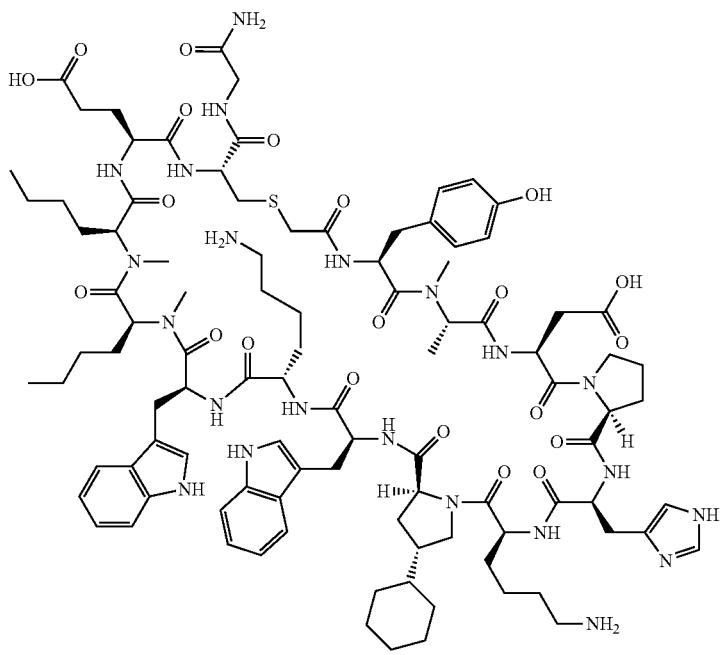

Example 14008

The following peptide was synthesized according to the procedures above. The underlined steps employed the double-coupling procedure.

ClAc-<u>Tyr</u>-[N-Me]Ala-<u>Asp</u>-Pro-His-<u>Lys</u>-[trans-4-cyclohexyl-L-proline]-Trp-Lys-<u>Trp</u>-[<u>N</u>-<u>Me</u>]<u>Nle</u>-[N-Me]Nle-Glu-Cys-Gly After deprotection and cyclization according to the procedures above, the compound was purified as follows:

The crude material was purified via preparative LC/MS with the following conditions: Column: XBridge C18, 19×200 mm, 5-μm particles; Mobile Phase A: 5:95 methanol: water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 21.7 mg, and its estimated purity by LCMS analysis was 99%.

Analysis condition A: Retention time=1.74 min; ESI-MS (+) m/z 1003.9 (M+2H)

Analysis condition B: Retention time=2.74 min; ESI-MS (+) m/z 1004.2 (M+2H), most abundant ion ESI-HRMS(+) m/z: Calculated: 1003.5215 (M+2H). Found: 1003.5189 (M+2H).

Example 120

Methods for Testing the Ability of Macrocyclic Peptides to Compete for the Binding of PD-1 to PD-L1 Using Homogenous Time-Resolved Fluorescence (HTRF) Binding Assays The ability of the macrocyclic peptides of the present disclosure to bind to PD-L1 was investigated using a PD-1/PD-L1 Homogenous Time-Resolved Fluorescence (HTRF) binding assay. A schematic of this assay is provided in FIG. 1.

Methods

Homogenous Time-Resolved Fluorescence (HTRF) Assays of Binding of Soluble PD-1 to Soluble PD-L1. Soluble PD-1 and soluble PD-L1 refers to proteins with carboxyl-end truncations that remove the transmembrane-spanning regions and are fused to heterologous sequences, specifically the Fc portion of the human immunoglobuling G sequence (Ig) or the hexahistidine epitope tag (His). All binding studies were performed in an HTRF assay buffer consisting of dPBS supplemented with 0.1% (w/v) bovine serum albumin and 0.05% (v/v) Tween-20. For the PD-1-Ig/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. PD-L1 fusion proteins from either human, cynomologous macaques, or mouse were used. HTRF detection was achieved using europium crypate-labeled anti-Ig monoclonal antibody (1 nM final) and allophycocyanin (APC) labeled anti-His monoclonal antibody (20 nM final). Antibodies were diluted in HTRF detection buffer and 5 μl was dispensed on top of binding reaction. The reaction was allowed to equilibrate for 30 minutes and signal (665 nm/620 nm ratio) was obtained using an EnVision fluorometer. Additional binding assays were established between PD-1-Ig/PD-L2-His (20 and 5 nM, respectively), CD80-His/PD-L1-Ig (100 and 10 nM, respectively) and CD80-His/CTLA4-Ig (10 and 5 nM, respectively). Competition studies between biotinylated Compound No. 71 and human PD-L1-His were performed as follows. Macrocyclic peptide inhibitors were pre-incubated with PD-L1-His (10 nM final) for 60 minutes in 4 μl of assay buffer followed by addition of biotinylated Compound No. 71 (0.5 nM final) in 1 μl of assay buffer. Binding was allowed to equilibrate for 30 minutes followed by addition of europium crypated labeled Streptavidin (2.5 pM final) and APC-labeled anti-His (20 nM final) in 5 μl of HTRF buffer. The reaction was allowed to equilibrate for 30 m and signal (665 nm/620 nm ratio) was obtained using an EnVision fluorometer.

Recombinant Proteins. Carboxyl-truncated human PD-1 (amino acids 25-167) with a C-terminal human Ig epitope tag [hPD-1 (25-167)-3S-IG] and human PD-L1 (amino acids 18-239) with a C-terminal His epitope tag [hPD-L1(19-239)-tobacco vein mottling virus protease cleavage site (TVMV)-His] were expressed in HEK293T cells and purified sequentially by rProteinA affinity chromatography and size exclusion chromatography. Human PD-L2-His (Sino Biologicals), CD80-His (Sino Biologicals), CTLA4-Ig (RnD Systems) were all obtained through commercial sources.

Sequence of Recombinant Human PD-1-Ig

```
hPD1(25-167)-3S-IG
                                          (SEQ ID NO: 1)
  1  LDSPDRPWNP PTFSPALLVV TEGDNATFTC SFSNTSESFV
     LNWYRMSPSN

51  QTDKLAAFPE DRSQPGQDCR FRVTQLPNGR DFHMSVVRAR
     RNDSGTYLCG

101  AISLAPKAQI KESLPAELRV TERRAEVPTA HPSPSPRPAG
     QFQGSPGGGG

151  GREPKSSDKT HTSPPSPAPE LLGGSSVFLF PPKPKDTLMI
     SRTPEVTCVV

201  VDVSHEDPEV KFNWYVDGVE VHNAKTKPRE EQYNSTYRVV
     SVLTVLHQDW

251  LNGKEYKCKV SNKALPAPIE KTISKAKGQP REPQVYTLPP
     SRDELTKNQV

301  SLTCLVKGFY PSDIAVEWES NGQPENNYKT TPPVLDSDGS
     FFLYSKLTVD

351  KSRWQQGNVF SCSVMHEALH NHYTQKSLSL SPGK
```

Sequence of Recombinant Human PD-L1-TVMV-His (PD-L1-His)

```
hPDL1(19-239)-TVMV-His
                                          (SEQ ID NO. 2)
  1  FTVTVPKDLY VVEYSSNMTI ECKFPVEKQL DLAALIVYWE
     MEDKNIIQFV

51  HGEEDLKVQH SSYRQRARLL KDQLSLGNAA LQITDVKLQD
     AGVYRCMISY

101  GGADYKRITV KVNAPYNKIN QRILVVDPVT SEHELTCQAE
     GYPKAEVIWT

151  SSDHQVLSGK TTTTNSKREE KLFNVTSTLR INTTTNEIFY
     CTFRRLDPEE

201  NHTAELVIPE LPLAHPPNER TGSSETVRFQ GHHHHHH
```

The results are shown in Table 6. As shown, the macrocyclic peptides of the present disclosure demonstrated potent inhibition of PD-1-Ig binding activity to PD-L1-TVMV-His (PD-L1-His).

TABLE 6

| Compound No. | HTRF Human PD-L1/PD-1 Binding Assay IC$_{50}$ (nM) |
| --- | --- |
| αhPD-L1 | 2.7 |
| 1 | 9 |
| 2 | 17 |
| 3 | 13 |
| 4 | 15 |

TABLE 6-continued

| Compound No. | HTRF Human PD-L1/PD-1 Binding Assay IC$_{50}$ (nM) |
| --- | --- |
| 71 | 7 |
| 99 | 153 |

Example 121

Methods for Testing the Ability of Compound No. 99 Variant Macrocyclic Peptides to Bind to PD-L1 Using Homogenous Time-Resolved Fluorescence (HTRF) Binding Assays The ability of variant macrocyclic peptides of Compound No. 99 peptide of the present disclosure to inhibit binding of PD-1-Ig binding to PD-L1-His was investigated in order to establish structure activity relationships.

HTRF Experiments were performed essentially as outlined supra. Variant macrocyclic peptides were created as outlined herein.

The results are shown in Table 7. Results for each parent macrocyclic peptide from other tables were included in this table for comparison purposes. As shown, the variant macrocyclic peptides of the present disclosure demonstrated potent inhibition of PD-1-Ig binding to PD-L1 and regions in which the activity was sensitive and resistant to variation were identified.

TABLE 7

COMPOUND NO. 99 VARIANT MACROCYCLIC PEPTIDES

| Compound No. | HTRF Human PD-L1/PD-1 Binding Assay IC$_{50}$ (nM) |
| --- | --- |
| 99 | 153 |
| 100 | 340 |
| 101 | 120 |
| 102 | >20000 |
| 103 | 1060 |
| 104 | 380 |
| 105 | 310 |
| 106 | 240 |
| 107 | 440 |
| 108 | 1780 |
| 109 | >20000 |
| 110 | 420 |
| 111 | 540 |
| 112 | 730 |
| 113 | 4490 |
| 114 | 30860 |
| 115 | 360 |

Example 122

Methods for Testing the Ability of Compound No. 1 Variant Macrocyclic Peptides to Inhibit PD-1 Binding to PD-L1 Using Homogenous Time-Resolved Fluorescence (HTRF) Binding Assays The ability of variant macrocyclic peptides of Compound No. 1 of the present disclosure to inhibit binding of PD-1 to PD-L1 was investigated in order to establish structure activity relationships.

HTRF Experiments were performed essentially as outlined supra. Variant macrocyclic peptides were created as outlined herein.

The results are shown in Table 8. Results for each parent macrocyclic peptide from other tables were included in this table for comparison purposes. As shown, the variant macrocyclic peptides of the present disclosure demonstrated potent inhibition of PD-1 binding to PD-L1 and regions sensitive and resistant to variation were identified.

TABLE 8

COMPOUND NO. 1 VARIANT MACROCYCLIC PEPTIDES

| Compound No. | HTRF Human PD-L1/PD-1 Binding Assay IC$_{50}$ (nM) |
|---|---|
| 1 | 9 |
| 5 | 6495 |
| 6 | 864 |
| 7 | 55 |
| 8 | 31 |
| 9 | 12 |
| 10 | 16 |
| 11 | 31 |
| 12 | 22 |
| 13 | 16 |
| 14 | 59 |
| 15 | >30,000 |
| 16 | 5 |
| 17 | 7535 |
| 18 | 36 |
| 19 | 33 |
| 20 | 8460 |
| 21 | 21 |
| 22 | 3 |
| 23 | 196 |
| 24 | 9 |
| 25 | 27 |
| 26 | 15 |
| 27 | 20 |
| 28 | 117 |
| 29 | 6833 |
| 30 | 5 |
| 31 | 18 |
| 32 | 18 |
| 33 | 9 |
| 34 | 4 |
| 35 | 56 |
| 36 | 9 |
| 37 | 1270 |
| 38 | 46 |
| 39 | 33 |
| 40 | 9 |
| 41 | 921 |
| 42 | >10000 |
| 43 | 554 |
| 44 | 34 |
| 45 | 105 |
| 46 | 873 |
| 47 | 27 |
| 48 | 40 |
| 49 | 34 |
| 50 | 71 |
| 51 | 23 |
| 52 | 24 |
| 53 | 34 |
| 54 | 26 |
| 55 | 4 |
| 56 | 13 |
| 57 | 9 |
| 58 | 8978 |
| 59 | >10000 |
| 60 | 43 |
| 61 | 31 |
| 62 | 475 |
| 63 | 3656 |
| 64 | 7 |

TABLE 8-continued

COMPOUND NO. 1 VARIANT MACROCYCLIC PEPTIDES

| Compound No. | HTRF Human PD-L1/PD-1 Binding Assay IC$_{50}$ (nM) |
|---|---|
| 65 | 43 |
| 66 | 144 |
| 67 | 108 |
| 68 | 2056 |
| 69 | 77 |
| 70 | 8683 |

Example 123

Methods for Testing the Ability of Compound No. 71 Variant Macrocyclic Peptides to Inhibit Binding of PD-1 to PD-L1 Using Homogenous Time-Resolved Fluorescence (HTRF) Binding Assays The ability of variant macrocyclic peptides of Compound No. 71 of the present disclosure to inhibit binding of PD-1 to PD-L1 was investigated in order to establish structure activity relationships.

HTRF experiments were performed essentially as outlined supra. Variant macrocyclic peptides were created as outlined herein.

The results are shown in Table 9. Results for each parent macrocyclic peptide from other tables were included in this table for comparison purposes. As shown, the variant macrocyclic peptides of the present disclosure demonstrated potent inhibition of PD-1 binding to PD-L1 and regions sensitive and resistant to variation were identified.

TABLE 9

| Compound No. | HTRF Human PD-L1/PD-1 Binding Assay IC$_{50}$ (nM) |
|---|---|
| 71 | 7 |
| 72 | 4229 |
| 73 | 39 |
| 74 | >10000 |
| 75 | 70 |
| 76 | >10000 |
| 77 | 24 |
| 78 | 14 |
| 79 | 80 |
| 80 | 264 |
| 81 | >10000 |
| 82 | 47 |
| 83 | 35 |
| 84 | 42 |
| 85 | 191 |
| 86 | 820 |
| 87 | 25 |

Example 124

Methods for Testing the Ability of Compound No. 116 Variant Macrocyclic Peptides to Bind to PD-L1 Using Homogenous Time-Resolved Fluorescence (HTRF) Binding Assays The ability of variant macrocyclic peptides of Compound No. 116 of the present disclosure to bind to PD-L1 was investigated in order to establish structure activity relationships.

HTRF Experiments were performed as outlined supra. Variant macrocyclic peptides were created as outlined herein.

The results are shown in Table 10. Results for each parent macrocyclic peptide from other tables were included in this table for comparison purposes. As shown, the variant macrocyclic peptides of the present disclosure demonstrated potent binding activity to PD-L1 and regions sensitive and resistant to variation were identified.

TABLE 10

COMPOUND NO. 116 VARIANT MACROCYCLIC PEPTIDES

| Compound No. | HTRF Human PD-L1/PD-1 Binding Assay $IC_{50}$ (nM) |
|---|---|
| 116 | 21 |
| 117 | 21 |
| 118 | 3 |

Example 125

Methods for Testing the Ability of Macrocyclic Peptides to Promote Interferon Gamma (IFNγ) Secretion in a Cytomegalovirus (CMV)-Specific T Cell Function Assay The ability of the macrocyclic peptides of the present disclosure to promote IFNγ secretion by CMV-specific T cells in a dose-dependent manner was investigated.

Methods

CMV-specific T Cell Function Assay. Peripheral blood mononuclear cells from a donor that was seropositive for CMV (PBMC, Astarte Biologics, Redmond, Wash.) were cultured at $2.5 \times 10^5$ cells/well in flat-bottom tissue culture (TC)-treated 96-well plates, in the presence of 0.5 μg/mL CMV+ cell lysate (Microbix Biosystems, Mississauga, Ontario) with or without increasing concentrations of anti-PD-L1 antibody or the indicated macrocyclic peptides. AIM-V medium (Life Technologies, Grand Island, N.Y.) supplemented with 10% heat-inactivated fetal bovine serum (FBS, Sigma, St Louis, Mo.) was used at a total volume of 200 μL/well in triplicate. The cells were cultured for 4 days at 37° C., 5% $CO_2$ at which time culture supernatant was harvested for determination of secreted IFNγ by ELISA (OptEIA hIFNγ ELISA Kit, BD Biosciences, San Jose, Calif.).

Figure 10B:
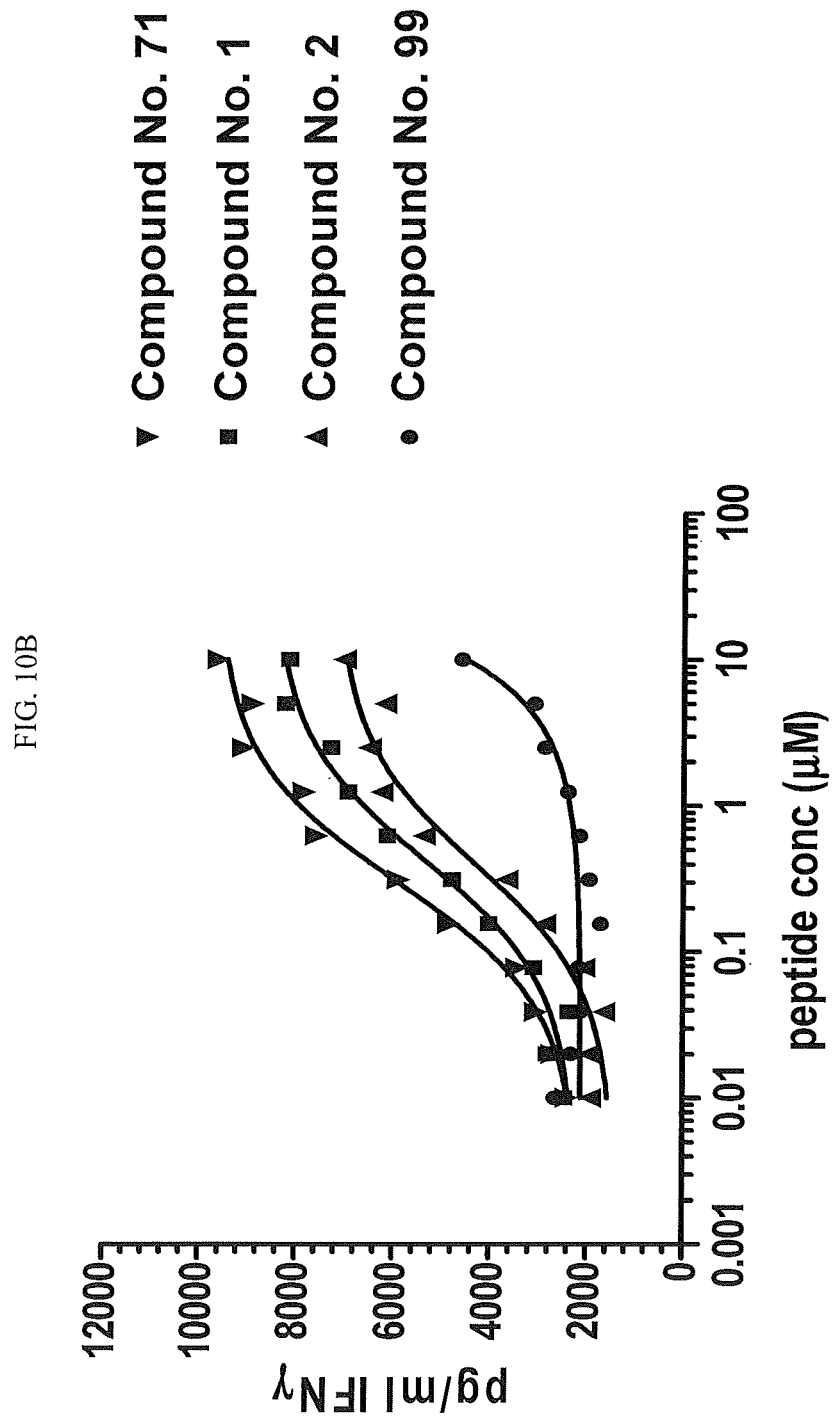
Figure 10C:
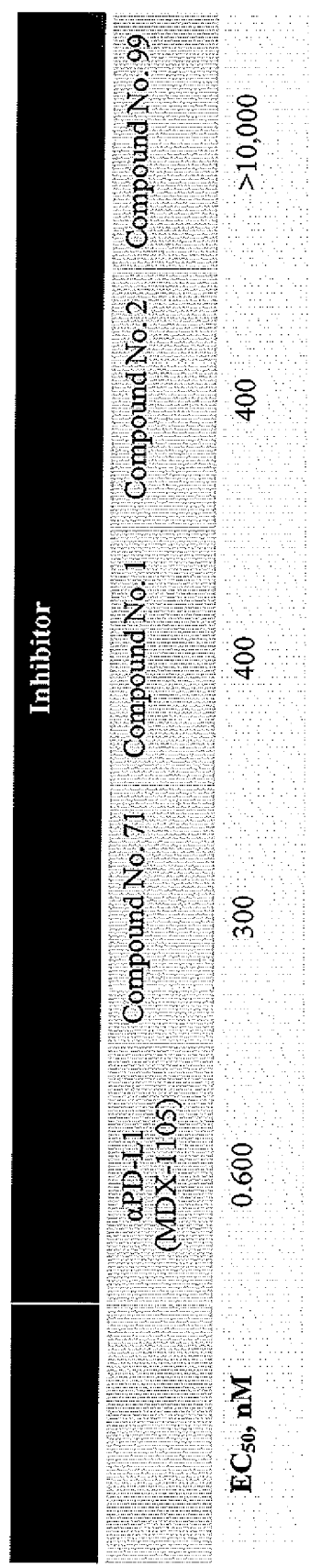

As shown in FIGS. 10A-C, the anti-PD-L1 antibody and peptides were both shown to promote IFNγ secretion by CMV-specific T cells in a dose-dependent manner. The most robust response was generated by the antibody directed to PD-L1 (MDX-1105, $EC_{50}$ 0.6 nM) followed by Compound No. 71 ($EC_{50}$ 300 nM), Compound No. 1 ($EC_{50}$ 400 nM), Compound No. 2 ($EC_{50}$ 400 nM), and Compound No. 99 ($EC_{50}$>10,000 nM). These results show that PD-L1 binding with the macrocyclic peptide inhibitors can enhance IFNγ release in a memory T cell population generated from previous exposure to a persistent antigen.

Example 126

Methods for Testing the Ability of Macrocyclic Peptides to Promote IFNγ Secretion in an HIV-Specific T Cell Function Assay The ability of the macrocyclic peptides of the present disclosure to promote IFNγ secretion by HIV-specific T cells in a dose-dependent manner was investigated.

Methods

HIV-specific T Cell Function Assay. Human PBMC (Bioreclamation LLC, Westbury, N.Y.) derived from a viremic HIV+ donor in the chronic stage of infection were cultured at $2.0 \times 10^6$ cells/well in TC-treated 48-well plates. Cells were stimulated with an HIV-Gag (capsid, Gag=group-specific antigen) peptide library (ProImmune, Sarasota, Fla.) consisting of 6 pools of 20 overlapping peptides (15-mers overlapping by 11 residues) each. The final concentration in culture was 2 μg/mL per peptide. HIV-Gag antigen stimulation was performed +/− anti-PD-L1 antibody (0.1 μM final) or peptide Compound No. 71 (7.5 μM final). RPMI medium (Life Technologies, Grand Island, N.Y.) supplemented with 10% heat-inactivated FBS (Sigma, St Louis, Mo.) and 10 U/ml rIL-2 (Peprotech, Rocky Hill, N.J.) was used at a total volume of 1 mL/well. The cells were cultured for 6 days at 37° C., 5% $CO_2$ at which time the cultures were washed and re-stimulated in anti-IFNγ coated ELISpot plates (hIFNγE-LISpot PRO Kit, Mabtech, Mariemont, Ohio) for 18 hours at 37° C., 5% $CO_2$. For re-stimulation, the in vitro expanded cells were cultured at $2.0 \times 10^5$ cells/well in RPMI medium devoid of rIL-2 at a total volume of 100 μL/well. The final concentrations of HIV-Gag antigen and anti-PD-L1 inhibitors were the same as stated above. ELISpot plates were air-dried for 5 days and read using an ImmunoSpot S6 Fluorospot analyzer (C.T.L., Shaker Heights, Ohio).

Figure 2:
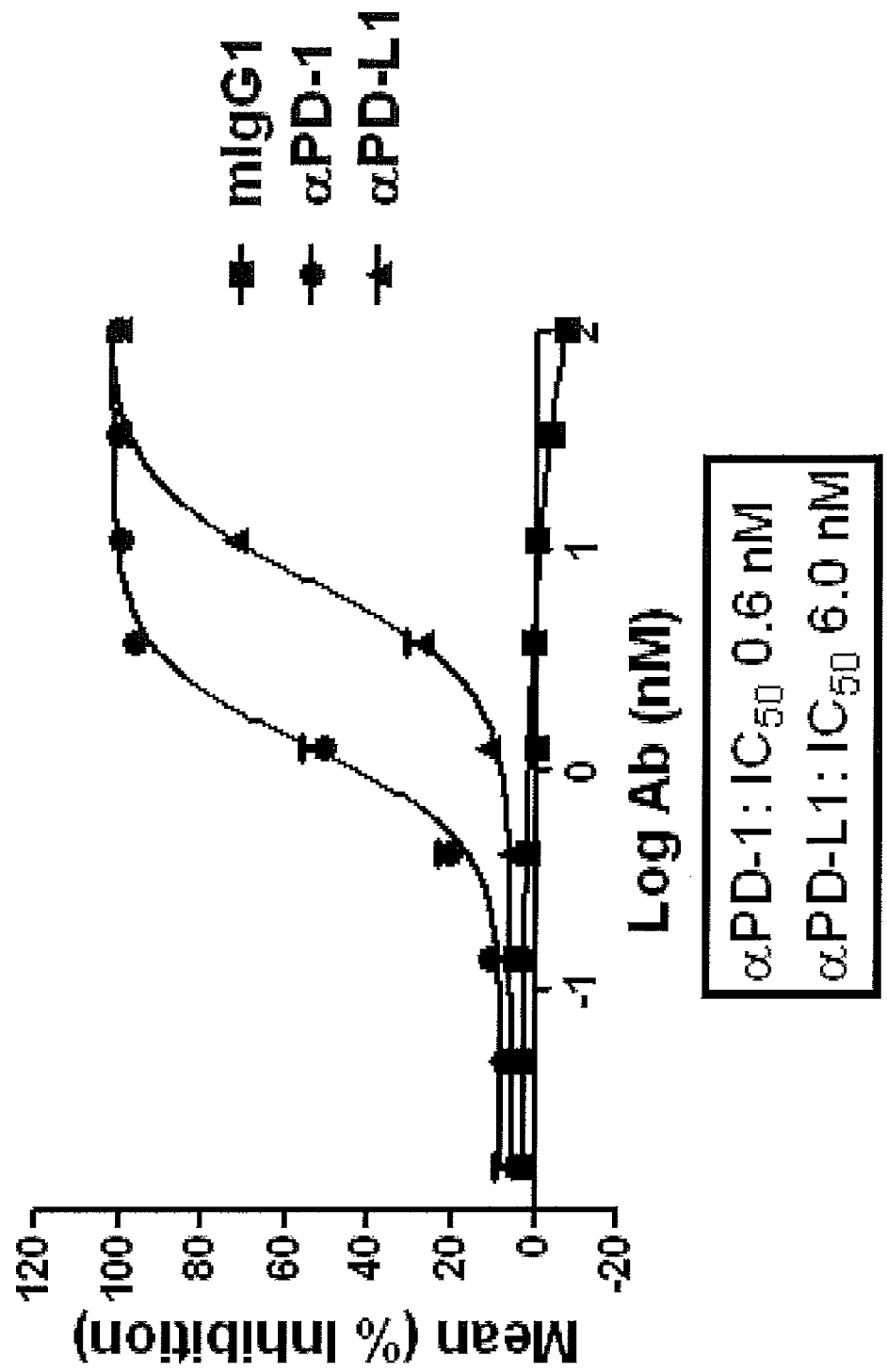
FIG. 2—Provides PD-1/PD-L1 control antibody dose-response curves for the HTRF used to measure the ability of the macrocyclic peptides to bind with PD-L1.
Figure 3:
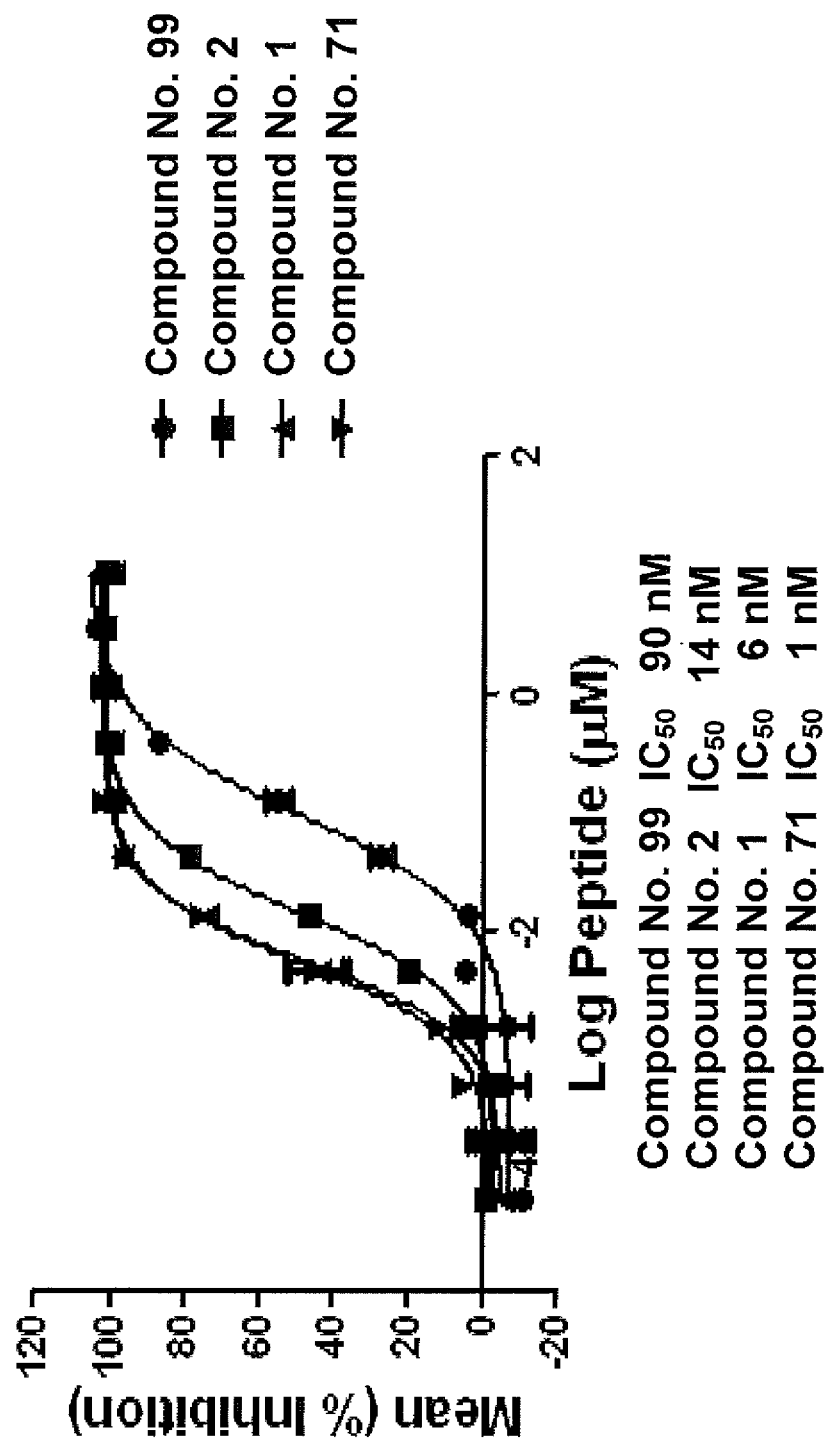
FIG. 3—Provides PD-1/PD-L1 HTRF dose-response curves for representative macrocyclic peptides of the present disclosure.
Figure 6:
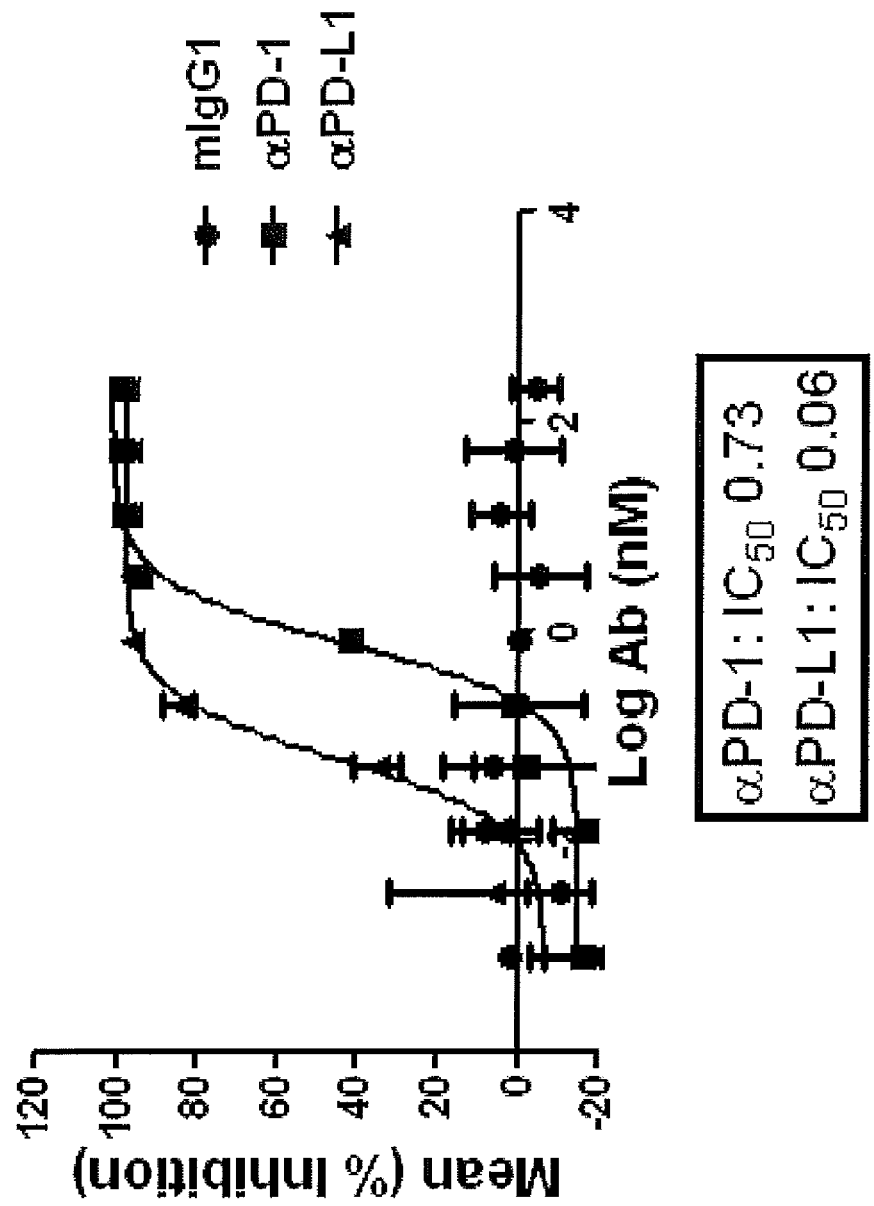
FIG. 6—Cell binding assay of control antibodies. As shown, the control antibodies (anti-PD-1 and anti-PD-L1) block binding of recombinant PD-1-Ig (phycoerythrin, PE, labeled) to LK35.2-hPD-L1 cells.
Figure 7:
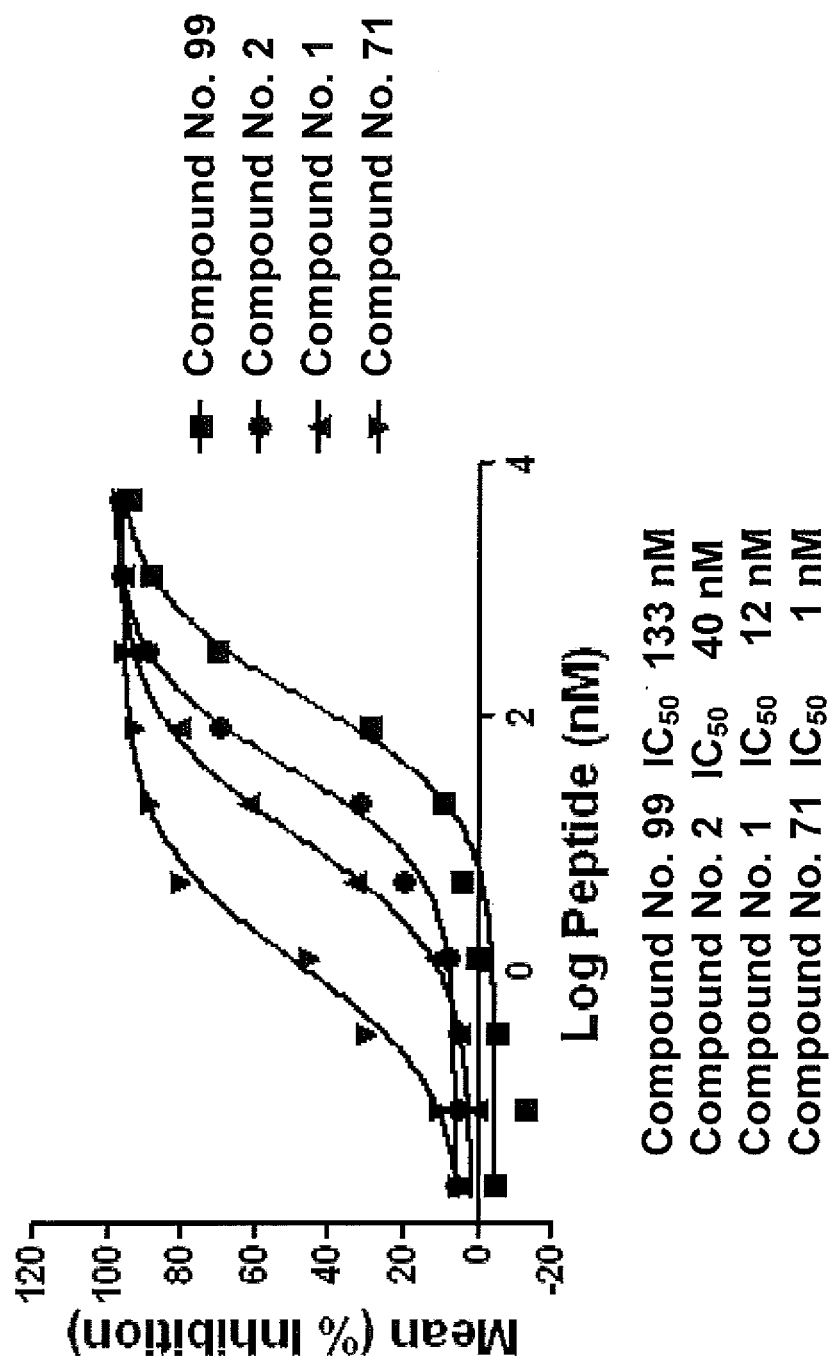
FIG. 7—Cell binding assay of select macrocyclic peptides of the present disclosure. As shown, the macrocyclic peptides block binding of recombinant PD-1-Ig (PE labeled) to LK35.2-hPD-L1 cells.
Figure 8:
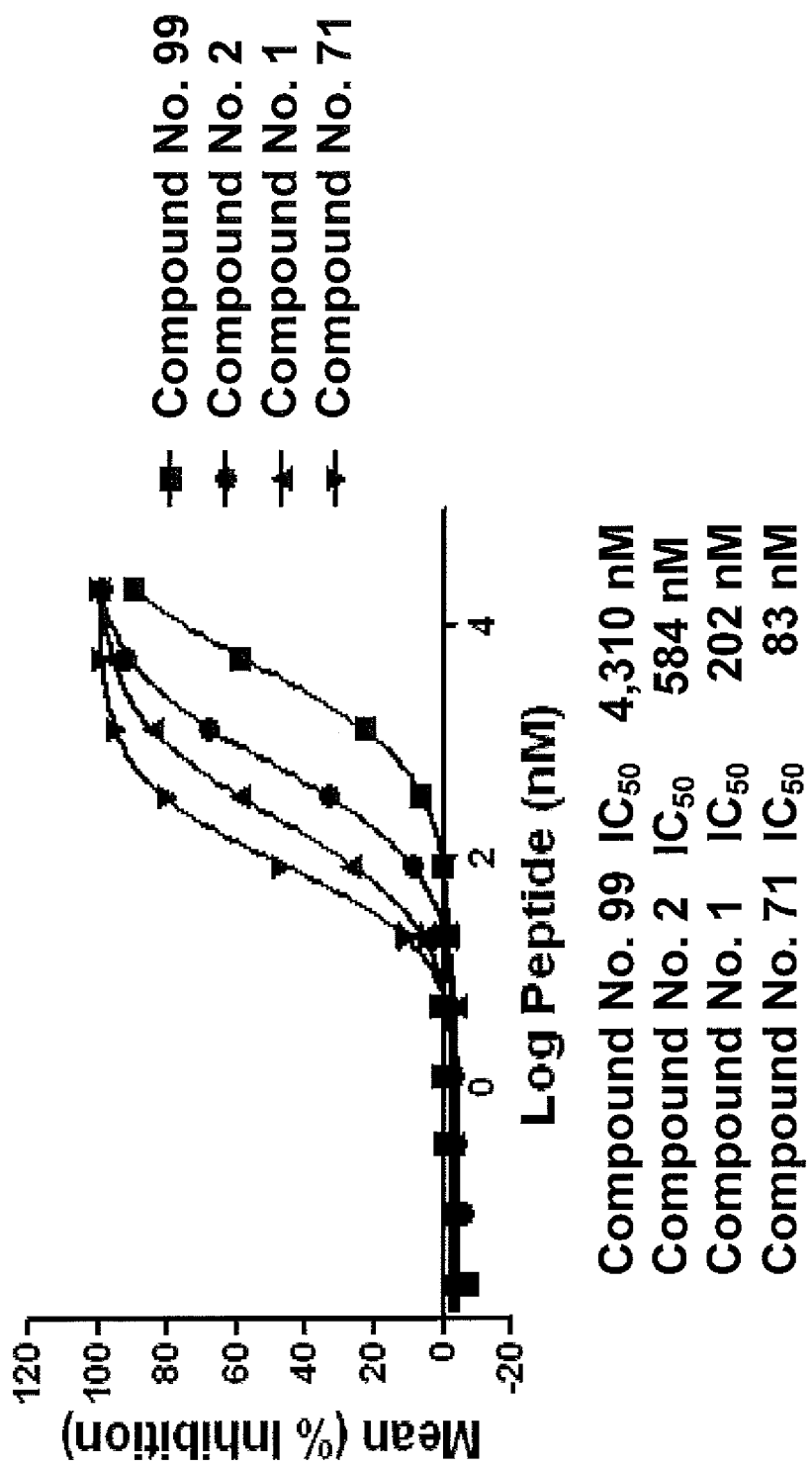
FIG. 8—Biotinylated Compound No. 71/PD-L1 Binding Assay. As shown, the Compound No. 99, 2, and 1 macrocyclic peptides are capable of blocking the binding of biotinylated Compound No. 71 peptide to PD-L1 using the HTRF assay. These results suggest these peptides bind to the same binding site.

As shown in FIG. 2, the anti-PD-L1 antibody and peptides were both shown to promote IFNγ secretion by HIV-specific T cells in a dose-dependent manner. The mean IFNγ spot forming cells (SFC) per well was calculated from duplicate wells and any background present in the unstimulated wells (<25 SFC) has been subtracted. Data are also presented as the fold increase over the DMSO control treatment. The anti-PD-L1 antibody and peptide both enhance IFNγ secretion by HIV-specific T cells responding to at least 1 of the 6 HIV-Gag antigen pools. These results show that PD-L1 binding with a peptide inhibitor can enhance IFNγ release from the T cell population responding to an ongoing chronic viral infection, similar to the anti-PD-L1 antibody.

Example 127

Methods for Testing the Ability of Macrocyclic Peptides to Bind to PD-L1 in Cell Binding Assays The ability of the macrocyclic peptides of the present disclosure to bind to Jurkat, mouse B cell line (LK35.2), and a human lung adenocarcinoma cell line (L2987) was investigated.

Methods

Jurkat-PD-1 Cell Binding Assay. Phycoerythrin (PE) was covalently linked to the Ig epitope tag of human PD-L1-Ig and fluorescently-labeled PD-L1-Ig was used for binding studies with a Jurkat cell line over-expressing human PD-1 (Jurkat-PD-1). Briefly, recombinant PD-L1-Ig (10 nM final) was pre-incubated with inhibitors for 15 m in a 30 μl volume of RPMI supplemented with 2% fetal calf serum. 1×105 Jurkat-PD-1 cells were dispensed on top of PD-L1-Ig and inhibitor in 20 μl RPMI supplemented with 2% fetal calf serum and binding was allowed to take place for 1 h at room temperature. Cells were washed 3× in dPBS. Cells were resuspended in 200 μl of dPBS and binding was measured by flow cytometry.

LK35.2-hPD-L1 Cell Binding Assay. Phycoerythrin (PE) was covalently linked to the Ig epitope tag of human PD-1-Ig and fluorescently-labeled PD-1-Ig was used for binding studies with a mouse B cell line (LK35.2) stably over-expressing human PD-L1 (LK35.2-hPD-L1). Briefly, 1×105 LK35.2- hPD-L1 cells were pre-incubated with inhibitor for 15 m in a 30 µl volume of RPMI supplemented with 2% fetal calf serum. 20 µl of PE-labeled PD-1-Ig (2 nM final), diluted in RPMI supplemented with 2% fetal calf serum, was dispensed on top of cells and inhibitor and binding was allowed to take place for 1 h at room temperature. Cells were washed 3× in dPBS. Cells were resuspended in 200 µl of dPBS and binding was measured by flow cytometry.

L2987 Cellomics Cell Binding Assay. Phycoerythrin (PE) was covalently linked to the Ig epitope tag of human PD-1-Ig and fluorescently-labeled PD-1-Ig was used for binding studies with a human lung adenocarcinoma cell line (L2987) which naturally expresses PD-L1. Briefly, 12,000 L2987 cells were seeded into clear 96 black, clear-bottom plates in 50 µl of DMEM supplemented with 5% fetal calf serum. The following day, inhibitors were diluted in serum-free DMEM and 25 µl was dispensed on top of cells. Following a 15 m incubation, sPD-1-Ig (30 nM final) was dispensed on top of cells and inhibitor in 25 µl of serum-free DMEM. Samples were incubated for 1 h at 37° C. followed by 2 washes in dPBS and fixation for 30 m with 4% paraformaldehyde. Samples were further washed 2× in dPBS. Hoechst (final 1 µg/ml) was added to final wash to stain nuclei. Plates were processed using a Cellomics ARRAYSCAN®.

The results are shown in FIGS. 2 thru 9. As shown, representative macrocyclic peptides of the present disclosure were able to bind to each of the Jurkat, mouse B cell line (LK35.2), and a human lung adenocarcinoma cell lines (L2987) that were tested. In addition, the PD-L1 macrocyclic peptides were appeared to bind to the same binding site of PD-L1 as each other as well as an internally developed anti-PD-L1 monoclonal antibody.

Additional cell binding assay results for the Compound No. 99, Compound No. 1, and Compound No. 71 series of peptides are shown in Tables 11 thru 13, respectively.

TABLE 11

CELL BINDING DATA FOR THE COMPOUND NO. 99 SERIES OF PEPTIDES

| Compound No. | Cell-Binding Hu PD-L1/PD-1 IC$_{50}$ (nM) |
|---|---|
| 1 | 11 |
| 2 | 43 |
| 4 | 15 |
| 71 | 10 |
| 99 | 1400 |

TABLE 12

CELL BINDING DATA FOR THE COMPOUND NO. 1 SERIES OF PEPTIDES

| Compound No. | Cell-Binding Hu PD-L1/PD-1 IC$_{50}$ (nM) |
|---|---|
| 1 | 11 |
| 5 | >10,000 |
| 8 | 223 |
| 9 | 71 |
| 10 | 82 |
| 13 | 35 |
| 14 | 242 |
| 15 | 1907 |
| 16 | 13 |
| 19 | 134 |
| 22 | 28 |
| 23 | 800 |
| 24 | 8 |

TABLE 12-continued

CELL BINDING DATA FOR THE COMPOUND NO. 1 SERIES OF PEPTIDES

| Compound No. | Cell-Binding Hu PD-L1/PD-1 IC$_{50}$ (nM) |
|---|---|
| 25 | 19 |
| 26 | 13 |
| 27 | 28 |
| 28 | 82 |
| 29 | 9105 |
| 30 | 3 |
| 31 | 11 |
| 32 | 25 |
| 33 | 7 |
| 34 | 37 |
| 36 | 11 |
| 37 | 2525 |
| 38 | 368 |
| 39 | 283 |
| 40 | 20 |
| 41 | >10000 |
| 43 | 5328 |
| 51 | 118 |
| 52 | 108 |
| 53 | 47 |
| 54 | 68 |
| 55 | 3 |
| 58 | >10000 |
| 61 | 195 |
| 62 | 3413 |
| 63 | >10000 |
| 65 | 258 |
| 67 | 143 |
| 69 | 351 |
| 70 | >10000 |

TABLE 13

CELL BINDING DATA FOR THE COMPOUND NO. 71 SERIES OF PEPTIDES

| Compound No. | Cell-Binding Hu PD-L1/PD-1 IC$_{50}$ (nM) |
|---|---|
| 71 | 10 |
| 72 | >10000 |
| 73 | 205 |
| 74 | >10000 |
| 75 | 438 |
| 76 | >10000 |
| 77 | 16 |
| 79 | 124 |
| 80 | 723 |
| 81 | >10000 |
| 82 | 203 |
| 83 | 75 |
| 84 | 50 |
| 85 | 255 |
| 86 | 7251 |
| 87 | 73 |

Example 128

Methods

LK35.2-hPD-L1 Cell Binding High-Content Screening Assay. Phycoerythrin (PE) was covalently linked to the Ig epitope tag of human PD-1-Ig and fluorescently-labeled PD-1-Ig was used for binding studies with a mouse B cell line (LK35.2) stably over-expressing human PD-L1 (LK35.2-hPD-L1). Briefly, 3×10$^3$ LK35.2-hPD-L1 cells were seeded into 384 well plates in 20 ul of RPMI supplemented with 10% fetal calf serum and cultured overnight. 125 nl of compound was added to cells, followed by 5 ul of PE-labeled PD-1-Ig (1 nM final), diluted in RPMI supplemented with 10% fetal calf serum, followed by incubation at 37° C. for 1 h. Cells were washed 3× in 100 ul dPBS followed by fixation with 30 ul of 4% paraformaldehyde in dPBS containing 10 ug/ml Hoechst 33342 for 30 min at room temperature. Cells were washed 3× in 100 ul of dPBS followed by final addition of 15 ul of dPBS. Data was collected and processed using a Cell Insight NXT High Content Imager and associated software.

293T-hPD-L1 Cell Binding High-Content Screening Assay. Phycoerythrin (PE) was covalently linked to the Ig epitope tag of human PD-1-Ig and fluorescently-labeled PD-1-Ig was used for binding studies with a human embryonic kidney cell line (293T) stably over-expressing human PD-L1 (293T-hPD-L1). Briefly, $2\times10^3$ 293T-hPD-L1 cells were seeded into 384 well plates in 20 ul of DMEM supplemented with 10% fetal calf serum and cultured overnight. 125 nl of compound was added to cells followed by 5 ul of PE-labeled PD-1-Ig (0.5 nM final), diluted in DMEM supplemented with 10% fetal calf serum, followed by incubation at 37° C. for 1 h. Cells were washed 3× in 100 ul dPBS followed by fixation with 30 ul of 4% paraformaldehyde in dPBS containing 10 ug/ml Hoechst 33342 for 30 min at room temperature. Cells were washed 3× in 100 ul of dPBS followed by final addition of 15 ul of dPBS. Data was collected and processed using a Cell Insight NXT High Content Imager and associated software.

TABLE 14

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 1001 | 3 | 3 | 3 |
| 1002 | 2 | 2 | 3 |
| 1003 | 3 | 3 | 3 |
| 1004 | 3 | 3 | 3 |
| 1005 | 3 | 3 | 3 |
| 1006 | 3 | 3 | 3 |
| 1007 | 3 | 3 | 3 |
| 1009 | 3 | 3 | 3 |
| 1010 | >10 | >10 | nd |
| 1011 | 3 | 3 | 3 |
| 1012 | 3 | 3 | 3 |
| 1013 | 3 | 3 | 3 |
| 1014 | 1 | 1 | 1 |
| 1015 | 2 | 2 | 2 |
| 1016 | 1 | 1 | 2 |
| 1017 | 3 | 3 | 3 |
| 1018 | 3 | 3 | 3 |
| 1019 | 3 | 3 | 3 |
| 1020 | 3 | 3 | 3 |
| 1021 | 0.1802 | 0.2617 | nd |
| 1022 | 3 | 3 | 3 |
| 1023 | 3 | 3 | 3 |
| 1024 | 3 | 3 | 3 |
| 1025 | 2 | 2 | 3 |
| 1026 | 3 | 3 | 3 |
| 1028 | 3 | 3 | 3 |
| 1029 | 3 | 3 | 3 |
| 1030 | 3 | 3 | 3 |
| 1031 | 3 | 3 | 3 |
| 1032 | 3 | 3 | 3 |
| 1033 | 3 | 3 | 3 |
| 1034 | 3 | 3 | 3 |
| 1035 | 2 | 1 | 1 |
| 1036 | 2 | 1 | 2 |
| 1037 | 2 | 1 | 1 |
| 1038 | 3 | 3 | 3 |
| 1039 | 3 | 2 | 3 |
| 1040 | 2 | 2 | 3 |
| 1041 | 2 | 1 | 1 |
| 1042 | 1 | 1 | 1 |
| 1043 | 2 | 2 | 3 |
| 1044 | 3 | 3 | 3 |
| 1045 | 2 | 2 | 3 |
| 1046 | 2 | 2 | 3 |
| 1047 | 3 | 3 | 3 |
| 1048 | 2 | 1 | 1 |
| 1049 | 2 | 1 | 2 |
| 1050 | 3 | 2 | 3 |
| 1051 | 2 | 1 | 1 |
| 1052 | 3 | 3 | 3 |
| 1053 | 3 | 3 | 3 |
| 1054 | 1 | 2 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or<br>not done (nd)<br>HTRF IC50 cluster<br>plus values (uM) | Clusters<br>1 = 0.0001584 to 0.004706<br>2 = 0.004776 to 0.07288<br>3 = 0.07431 to >10 or<br>not done (nd)<br>CBA IC50 cluster<br>plus values (uM) | Clusters<br>1 = 0.00002079 to 0.02258<br>2 = 0.02266 to >2.5<br>3 = not done (nd)<br>CMV Recall EC50 cluster<br>plus values (uM) |
|---|---|---|---|
| 1055 | 2 | 2 | 3 |
| 1056 | 2 | 2 | 3 |
| 1057 | 3 | 3 | 3 |
| 1058 | 3 | 3 | 3 |
| 1059 | 3 | 3 | 3 |
| 1060 | 2 | 2 | 3 |
| 1061 | 3 | 3 | 3 |
| 1062 | 2 | 2 | 3 |
| 1063 | 3 | 3 | 3 |
| 1064 | 3 | 3 | 3 |
| 1065 | 3 | 3 | 3 |
| 1066 | 3 | 3 | 3 |
| 1067 | 3 | 3 | 3 |
| 1068 | 3 | 3 | 3 |
| 1069 | 1 | 2 | 3 |
| 1070 | 2 | 2 | 3 |
| 1071 | 3 | 3 | 3 |
| 1072 | 3 | 3 | 3 |
| 1073 | 3 | 3 | 3 |
| 1074 | 3 | 3 | 3 |
| 1075 | 3 | 3 | 3 |
| 1076 | 2 | 2 | 3 |
| 1077 | 2 | 3 | 3 |
| 1078 | 3 | 3 | 3 |
| 1080 | 3 | 3 | 3 |
| 1081 | 3 | 3 | 3 |
| 1082 | 3 | 3 | 3 |
| 1083 | 1 | 2 | 3 |
| 1084 | 1 | 1 | 1 |
| 1085 | 3 | 3 | 3 |
| 1086 | 3 | 3 | 3 |
| 1087 | 1 | 1 | 2 |
| 1088 | 2 | 2 | 3 |
| 1089 | 3 | 3 | 3 |
| 1090 | 1 | 1 | 2 |
| 1091 | 1 | 1 | 2 |
| 1092 | 2 | 2 | 3 |
| 1093 | 3 | 3 | 3 |
| 1094 | 2 | 1 | 2 |
| 1095 | 3 | 3 | 3 |
| 1096 | 3 | 3 | 3 |
| 1097 | 2 | 2 | 3 |
| 1098 | 2 | 2 | 3 |
| 1099 | 3 | 3 | 3 |
| 1100 | 3 | 3 | 3 |
| 1101 | 3 | 3 | 3 |
| 1102 | 3 | 3 | 3 |
| 1103 | 2 | 2 | 3 |
| 1104 | 2 | 2 | 3 |
| 1105 | 2 | 2 | 3 |
| 1106 | 2 | 2 | 3 |
| 1107 | 3 | 3 | 3 |
| 1108 | 3 | 3 | 3 |
| 1110 | 3 | 3 | 3 |
| 1112 | 3 | 3 | 3 |
| 1113 | 1 | 1 | 1 |
| 1114 | 2 | 1 | 2 |
| 1115 | 1 | 1 | 1 |
| 1116 | 3 | 3 | 3 |
| 1117 | 2 | 2 | 3 |
| 1118 | 2 | 1 | 1 |
| 1119 | 2 | 1 | 1 |
| 1120 | 2 | 1 | 1 |
| 1121 | 2 | 1 | 2 |
| 1122 | 2 | 1 | 1 |
| 1123 | 1 | 1 | 1 |
| 1124 | 2 | 2 | 2 |
| 1125 | 0.005049 | nd | nd |
| 1126 | 2 | 1 | 3 |
| 1127 | 1 | 1 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 1128 | 2 | 1 | 3 |
| 1129 | 3 | 3 | 3 |
| 1130 | 3 | 1 | 3 |
| 1131 | 1 | 1 | 1 |
| 1132 | 2 | 1 | 1 |
| 1133 | 2 | 1 | 1 |
| 1134 | 2 | 1 | 1 |
| 1135 | 2 | 1 | 1 |
| 1136 | 2 | 2 | 2 |
| 1137 | 3 | 3 | 3 |
| 1138 | 2 | 1 | 2 |
| 1139 | 1 | 1 | 1 |
| 1140 | 1 | 1 | 1 |
| 1141 | 1 | 1 | 1 |
| 1142 | 2 | 2 | 2 |
| 1143 | 3 | 3 | 3 |
| 1144 | 3 | 2 | 3 |
| 1145 | 2 | 1 | 2 |
| 1146 | 2 | 3 | 3 |
| 1147 | 2 | 2 | 3 |
| 1148 | 2 | 2 | 3 |
| 1149 | 2 | 2 | 2 |
| 1150 | 1 | 1 | 1 |
| 1151 | 2 | 2 | 2 |
| 1152 | 2 | 2 | 2 |
| 1153 | 3 | 2 | 3 |
| 1154 | 2 | 3 | 3 |
| 1155 | 2 | 2 | 3 |
| 1156 | 1 | 1 | 3 |
| 1157 | 2 | 1 | 1 |
| 1158 | 1 | 1 | 2 |
| 1159 | 2 | 1 | 2 |
| 1160 | 2 | 1 | 2 |
| 1161 | 1 | 1 | 1 |
| 1162 | 1 | 1 | 1 |
| 1163 | 0.006241 | 0.00403755 | 0.002927 |
| 1164 | 2 | 2 | 3 |
| 1165 | 1 | 1 | 2 |
| 1166 | 1 | 1 | 1 |
| 1167 | 1 | 1 | 2 |
| 1168 | 1 | 1 | 1 |
| 1169 | 2 | 2 | 3 |
| 1170 | 1 | 2 | 3 |
| 1171 | 1 | 1 | 3 |
| 1172 | 1 | 2 | 3 |
| 1173 | 0.002714 | 0.010962 | 1 |
| 1174 | 1 | 1 | 1 |
| 1175 | 1 | 2 | 3 |
| 1176 | 2 | 2 | 3 |
| 1177 | 1 | 1 | 1 |
| 1178 | 1 | 2 | 3 |
| 1179 | 1 | 2 | 3 |
| 1180 | 1 | 1 | 3 |
| 1181 | 2 | 3 | 3 |
| 1182 | 1 | 1 | 1 |
| 1183 | 1 | 1 | 1 |
| 1184 | 1 | 1 | 1 |
| 1185 | 1 | 1 | 1 |
| 1186 | 1 | 1 | 1 |
| 1187 | 2 | 2 | 1 |
| 1188 | 2 | 2 | 3 |
| 1189 | 3 | 3 | 3 |
| 1190 | 3 | 3 | 3 |
| 1191 | 3 | 3 | 3 |
| 1192 | 0.006743 | 0.02152 | 1 |
| 1193 | 1 | 1 | 1 |
| 1194 | 1 | 1 | 1 |
| 1195 | 1 | 1 | 1 |
| 1196 | 3 | 2 | 3 |
| 1197 | 2 | 2 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 1198 | 1 | 1 | 1 |
| 1199 | 2 | 1 | 2 |
| 1200 | 1 | 2 | 2 |
| 1201 | 2 | 2 | 1 |
| 1202 | 1 | 1 | 2 |
| 1203 | 2 | 1 | 2 |
| 1204 | 2 | 1 | 2 |
| 1205 | 2 | 2 | 3 |
| 1206 | 1 | 1 | 2 |
| 1207 | 2 | 3 | 3 |
| 1208 | 1 | 2 | 2 |
| 1209 | 2 | 2 | 3 |
| 1210 | 3 | 3 | >2.5 |
| 1211 | 2 | 3 | 2 |
| 1212 | 3 | 3 | 3 |
| 1213 | 2 | 2 | 3 |
| 1214 | 2 | 2 | 3 |
| 1215 | 0.05086 | 0.09254 | 0.5077 |
| 1216 | 2 | 3 | 3 |
| 1217 | 2 | 2 | 2 |
| 1218 | 2 | 2 | 1 |
| 1219 | 2 | 1 | 3 |
| 1220 | 2 | 2 | 3 |
| 1221 | 3 | 3 | 3 |
| 1222 | 2 | 3 | 3 |
| 1223 | 1 | 1 | 1 |
| 1224 | 1 | 1 | 1 |
| 1225 | 1 | 1 | nd |
| 1226 | 1 | 1 | 2 |
| 1227 | 3 | 3 | 3 |
| 1228 | 2 | 2 | 3 |
| 1229 | 2 | 2 | 3 |
| 1230 | 3 | 3 | 3 |
| 1231 | 1 | 1 | 1 |
| 1232 | 3 | 3 | 3 |
| 1233 | 2 | 1 | 1 |
| 1234 | 2 | 1 | 1 |
| 1235 | 2 | 1 | 1 |
| 1236 | 2 | 1 | 3 |
| 1237 | 0.01647 | 0.004921 | 0.02189 |
| 1238 | 2 | 2 | 3 |
| 1239 | 2 | 2 | 3 |
| 3052 | 3 | 3 | 3 |
| 3053 | 3 | 3 | 3 |
| 3054 | 3 | 3 | 3 |
| 3055 | 3 | 3 | 3 |
| 3056-A | 3 | 3 | 3 |
| 3056-B | 2 | 3 | 3 |
| 3057 | 3 | 3 | 3 |
| 3058-A | 3 | 3 | 3 |
| 3058-B | 3 | 3 | 3 |
| 3059 | 2 | 2 | 3 |
| 3060-A | 2 | 2 | 3 |
| 3060-B | 3 | 3 | 3 |
| 3061 | 2 | 3 | 3 |
| 3062 | 1 | 2 | 3 |
| 3063 | 3 | 3 | 3 |
| 3064 | 2 | 3 | 3 |
| 3065 | 3 | 3 | 3 |
| 3066 | 3 | 3 | 3 |
| 3067 | 1 | 1 | 2 |
| 3068 | 3 | 3 | 3 |
| 3069 | 3 | 3 | 3 |
| 3070 | 3 | 3 | 3 |
| 3071 | 2 | 2 | 3 |
| 3072 | 3 | 3 | 3 |
| 3073 | 1 | 2 | 1 |
| 3074 | 2 | 2 | 3 |
| 3075 | 3 | 3 | 3 |
| 3076 | 1 | 2 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 3077 | 3 | 3 | 3 |
| 3078 | 3 | 3 | 3 |
| 3079 | 3 | 2 | 3 |
| 3080 | >10 | >10 | nd |
| 3081 | 3 | 2 | 3 |
| 3082 | 3 | 3 | 3 |
| 3083 | 4.266 | 7.662 | nd |
| 3084 | 3 | 3 | 3 |
| 3085 | 3 | 3 | 3 |
| 3086 | 1 | 1 | 2 |
| 3087 | 3 | 3 | 3 |
| 3088-A | 3 | 3 | 3 |
| 3088-B | nd | nd | nd |
| 3089 | 3 | 3 | 3 |
| 3090 | 3 | 3 | 3 |
| 3091 | 3 | 3 | 3 |
| 3092 | 3 | 3 | 3 |
| 3093 | 3 | 2 | 3 |
| 3094 | 2 | 2 | 3 |
| 3095 | 2 | 2 | 3 |
| 3096 | 2 | 2 | 3 |
| 3097 | 2 | 2 | 3 |
| 3098 | 3 | 2 | 3 |
| 3099 | 3 | 3 | 3 |
| 3100 | 3 | 3 | 3 |
| 3101 | 3 | 3 | 3 |
| 3102 | 3 | 3 | 3 |
| 3103 | 3 | 3 | 3 |
| 3104 | 3 | 3 | 3 |
| 3105 | 3 | 3 | 3 |
| 3106 | 3 | 2 | 2 |
| 3107 | 2 | 2 | 3 |
| 3108 | 3 | 3 | 3 |
| 3109 | 3 | 2 | 3 |
| 3110 | 2 | 1 | 2 |
| 3111 | 3 | 2 | 3 |
| 3112 | 3 | 3 | 3 |
| 3113 | 2 | 2 | 3 |
| 3114 | 2 | 2 | 3 |
| 3115 | 2 | 2 | 3 |
| 3116 | 1 | 1 | 3 |
| 3117 | 2 | 2 | 3 |
| 3118 | 2 | 2 | 3 |
| 3119 | 2 | 2 | 3 |
| 3120 | 2 | 1 | 2 |
| 3121 | 2 | 1 | 3 |
| 3122 | 2 | 2 | 3 |
| 3123 | 2 | 1 | 3 |
| 3124 | 2 | 1 | 3 |
| 3125 | 2 | 1 | 3 |
| 3130 | 2 | 1 | 2 |
| 3131 | 3 | 3 | 3 |
| 3132 | 2.228 | 3.785 | nd |
| 3133 | 3 | 3 | 3 |
| 3134 | 3 | 3 | 3 |
| 3135 | 3 | 3 | 3 |
| 3136 | 2 | 2 | 3 |
| 3137 | 3 | 3 | 3 |
| 3138 | 3 | 3 | 3 |
| 3139 | 2 | 2 | 3 |
| 3140 | 2 | 2 | 3 |
| 3141 | 2 | 2 | 3 |
| 3142 | 2 | 2 | 3 |
| 3143 | 2 | 1 | 3 |
| 3144 | 2 | 1 | 2 |
| 3145 | 3 | 3 | 3 |
| 3146 | 3 | 2 | 3 |
| 3147 | 0.7504 | 1.728 | nd |
| 3148 | 2 | 2 | 3 |
| 3149 | 0.03027 | 0.008858 | nd |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or<br>not done (nd)<br>HTRF IC50 cluster<br>plus values (uM) | Clusters<br>1 = 0.0001584 to 0.004706<br>2 = 0.004776 to 0.07288<br>3 = 0.07431 to >10 or<br>not done (nd)<br>CBA IC50 cluster<br>plus values (uM) | Clusters<br>1 = 0.00002079 to 0.02258<br>2 = 0.02266 to >2.5<br>3 = not done (nd)<br>CMV Recall EC50 cluster<br>plus values (uM) |
|---|---|---|---|
| 3150 | 3 | 3 | 3 |
| 3151 | 3 | 3 | 3 |
| 3152 | 2 | 2 | 2 |
| 3153 | 2 | 2 | 2 |
| 3154 | 0.2295 | 0.01841 | nd |
| 3155 | 3 | 3 | 3 |
| 3156 | 0.439 | 1.868 | nd |
| 3157 | 2 | 2 | 3 |
| 3158 | 3 | 2 | 3 |
| 3159 | 3 | 3 | 3 |
| 3160 | 3 | 3 | 3 |
| 3161 | 2 | 2 | 3 |
| 3162 | 2 | 2 | 3 |
| 3163 | 2 | 2 | 3 |
| 3164 | 2 | 2 | 3 |
| 3165 | 2 | 2 | 3 |
| 3166 | 2 | 1 | 2 |
| 3167 | 2 | 1 | 2 |
| 3168 | 3 | 3 | 3 |
| 3171 | 3 | 3 | 3 |
| 3172 | 3 | 3 | 3 |
| 3173 | 3 | 2 | 3 |
| 3174 | 3 | 2 | 3 |
| 3175 | 2 | 2 | 2 |
| 3176 | 3 | 3 | 3 |
| 3177 | 3 | 3 | 3 |
| 3178 | 2 | 2 | 3 |
| 3179 | 3 | 2 | 3 |
| 3180 | 2 | 1 | 3 |
| 3181 | 1 | 1 | 2 |
| 3182 | 1 | 1 | 2 |
| 3183 | 1 | 1 | 1 |
| 3184 | 3 | 3 | 3 |
| 3185 | 2 | 2 | 3 |
| 3186 | 2 | 1 | 3 |
| 3187 | 2 | 1 | 3 |
| 3188 | 2 | 1 | 3 |
| 3189 | 2 | 2 | 3 |
| 3190 | 1 | 1 | 3 |
| 3191 | 1 | 2 | 3 |
| 3192 | 1 | 1 | 2 |
| 3193 | 1 | 1 | 2 |
| 3194 | 0.004393 | 0.00114775 | 0.02524 |
| 3195 | 1 | 1 | 2 |
| 3196 | 1 | 1 | 2 |
| 3197 | 1 | 1 | 1 |
| 3198 | 2 | 1 | 1 |
| 3199 | 2 | 1 | 1 |
| 3200 | 2 | 1 | 2 |
| 3201 | 2 | 1 | 1 |
| 3202 | 2 | 1 | 1 |
| 3203 | 1 | 1 | 2 |
| 3204 | 2 | 3 | 3 |
| 3205 | 3 | 3 | 3 |
| 3206 | 2 | 2 | 2 |
| 3207 | 2 | 2 | 3 |
| 3208-A | 2 | 2 | 2 |
| 3208-B | 3 | 3 | 3 |
| 3209 | 2 | 2 | 2 |
| 3500 | 3 | 3 | 3 |
| 3501 | 2 | 2 | 3 |
| 3502 | 2 | 2 | 3 |
| 3503 | 3 | 3 | 3 |
| 3504 | 3 | 3 | 3 |
| 3505 | 2 | 2 | 3 |
| 3506 | 1 | 2 | 3 |
| 3507 | 2 | 3 | 3 |
| 3508 | 1 | 2 | 3 |
| 3509 | 2 | 3 | 3 |
| 3510 | 3 | 3 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or<br>not done (nd)<br>HTRF IC50 cluster<br>plus values (uM) | Clusters<br>1 = 0.0001584 to 0.004706<br>2 = 0.004776 to 0.07288<br>3 = 0.07431 to >10 or<br>not done (nd)<br>CBA IC50 cluster<br>plus values (uM) | Clusters<br>1 = 0.00002079 to 0.02258<br>2 = 0.02266 to >2.5<br>3 = not done (nd)<br>CMV Recall EC50 cluster<br>plus values (uM) |
|---|---|---|---|
| 3511 | 3 | 2 | 3 |
| 3512 | 1 | 2 | 2 |
| 3513 | 3 | 3 | 3 |
| 3514 | 2 | 2 | 3 |
| 3515 | 2 | 2 | 3 |
| 3516 | 3 | 3 | 3 |
| 3517 | 3 | 3 | 3 |
| 3518 | 3 | 3 | 3 |
| 3519 | 2 | 2 | 3 |
| 3520 | 2 | 1 | 2 |
| 3521 | 3 | 3 | 3 |
| 3522 | 3 | 2 | 3 |
| 3523 | 3 | 3 | 3 |
| 3524 | 2 | 1 | 2 |
| 3525 | 3 | 3 | 3 |
| 3526 | 0.1316 | 0.6292 | nd |
| 3527 | 2 | 2 | 3 |
| 3528 | 3 | 2 | 3 |
| 3529 | 3 | 2 | 3 |
| 3530 | 3 | 3 | 3 |
| 3531 | 3 | 3 | 3 |
| 3532 | 3 | 3 | 3 |
| 3533 | 2 | 2 | 3 |
| 3534 | 2 | 2 | 3 |
| 3535 | 3 | 2 | 3 |
| 3536 | 2 | 2 | 3 |
| 3537 | 2 | 2 | 3 |
| 3538 | 3 | 3 | 3 |
| 3539 | 3 | 3 | 3 |
| 3540 | 3 | 3 | 3 |
| 3541 | 3 | 3 | 3 |
| 3542 | 2 | 2 | 3 |
| 3543 | 3 | 3 | 3 |
| 3544 | 3 | 3 | 3 |
| 3545 | 3 | 3 | 3 |
| 3546 | 3 | 3 | 3 |
| 3547 | 3 | 3 | 3 |
| 3548 | 3 | 3 | 3 |
| 3549 | 0.2723 | 0.7282 | nd |
| 3550 | 0.04093 | 0.1495 | nd |
| 3551 | 2 | 2 | 3 |
| 3552 | 1 | 2 | 3 |
| 3553 | 1 | 2 | 3 |
| 3555 | 3 | 3 | 3 |
| 3556 | 3 | 3 | 3 |
| 3557 | 3 | 3 | 3 |
| 3558 | 3 | 3 | 3 |
| 3559 | 0.0121 | 0.04803 | nd |
| 3560 | 2 | 1 | 2 |
| 3561 | 3 | 3 | 3 |
| 3562 | 2 | 1 | 2 |
| 3563 | 3 | 3 | 3 |
| 3564 | >10 | >10 | nd |
| 3565 | 3 | 3 | 3 |
| 3566 | 3 | 3 | 3 |
| 3567 | 1 | 1 | 2 |
| 3568 | 3 | 2 | 3 |
| 3569 | 3 | 3 | 3 |
| 3570 | 3 | 3 | 3 |
| 3571 | 3 | 3 | 3 |
| 3572 | 1 | 1 | 2 |
| 3573 | 2 | 2 | 3 |
| 3574 | 2 | 1 | 2 |
| 3575 | 1 | 1 | 2 |
| 3576 | 2 | 2 | 3 |
| 3577 | 1 | 1 | 1 |
| 3578 | 1 | 1 | 2 |
| 3579 | 2 | 1 | 2 |
| 3580 | 1 | 1 | 2 |
| 3581 | 2 | 2 | 3 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 3582 | 2 | 2 | 3 |
| 3583 | 2 | 1 | 2 |
| 3584 | 2 | 1 | 3 |
| 3585-A | 3 | 3 | 3 |
| 3585-B | 2 | 2 | 3 |
| 3586 | 3 | 2 | 3 |
| 3587 | 3 | 3 | 3 |
| 3588 | 2 | 1 | 1 |
| 3589 | 1 | 1 | 1 |
| 3590 | 1 | 1 | 1.00000000 |
| 3591 | 1 | 1 | 1 |
| 3592 | 0.004004 | 0.0001584 | 0.0006202 |
| 3593 | 1 | 1 | 2 |
| 3594 | 2 | 1 | 3 |
| 3595 | 0.9908 | 0.1228 | nd |
| 3596 | 2 | 1 | 3 |
| 3597-A | 2 | 3 | 2 |
| 3597-B | 3 | 3 | 3 |
| 3598 | 1 | 1 | 2 |
| 3599 | 1 | 1 | 2 |
| 3600 | 0.006105 | 0.003898 | nd |
| 3601 | 0.006914 | 0.001791 | nd |
| 3602 | 2 | 3 | 3 |
| 3603 | 2 | 2 | 3 |
| 3604 | 3 | 3 | 3 |
| 3605 | 1 | 1 | 1 |
| 3606 | 1 | 1 | 1 |
| 3607 | 1 | 1 | 2 |
| 3608 | 1 | 1 | 1 |
| 3609 | 1 | 1 | 3 |
| 3610 | 2 | 2 | 3 |
| 3611 | 3 | 3 | 3 |
| 3613 | 1 | 1 | 1 |
| 3301 | 3 | 3 | 3 |
| 3302 | 3 | 3 | 3 |
| 3303 | 3 | 3 | 3 |
| 3304 | 3 | 3 | 3 |
| 3305 | 3 | 3 | 3 |
| 3306 | 2 | 2 | 3 |
| 3307 | 3 | 3 | 3 |
| 3308 | 2 | 3 | 3 |
| 3309 | 3 | 3 | 3 |
| 3310 | 3 | 3 | 3 |
| 3311 | 3 | 3 | 3 |
| 5001 | 1 | 2 | 3 |
| 5002 | 3 | 3 | 3 |
| 5004 | 2 | 2 | 1 |
| 5006 | 1 | 2 | 3 |
| 5007 | 2 | 2 | 3 |
| 5008 | 0.01812 | 0.02266 | nd |
| 5009 | 0.03045 | 3 | 3 |
| 5010 | 2 | 2 | 2 |
| 5011 | 2 | 2 | 1 |
| 5012 | 3 | 3 | 3 |
| 5013 | 3 | 3 | 3 |
| 5014 | 2 | 2 | 3 |
| 5015 | 2 | 2 | 3 |
| 5016 | 2 | 2 | 3 |
| 5017 | 0.01131 | 0.0129 | nd |
| 5018 | 2 | 2 | 3 |
| 5019 | 2 | 2 | 3 |
| 5020 | 3 | 3 | 3 |
| 5021 | 3 | 3 | 3 |
| 5022 | 2 | 1 | 1 |
| 5023 | 2 | 2 | 2 |
| 5024 | 1 | 1 | 1 |
| 5025 | 0.007431 | 0.00116 | 0.002304 |
| 5026 | 1 | 1 | 1 |
| 5027 | 3 | 3 | 3 |
| 5028 | 1 | 1 | 1 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 5029 | 1 | 1 | 1 |
| 5030 | 3 | 3 | 3 |
| 5031 | 1 | 1 | 1 |
| 5032 | 1 | 1 | 1 |
| 5033 | 2 | 2 | 2 |
| 5034 | 1 | 1 | 1 |
| 5035 | 1 | 1 | 1 |
| 5036 | 1 | 1 | 1 |
| 5037 | 1 | 1 | 1 |
| 5038 | 2 | 1 | 1 |
| 5039 | 1 | 1 | 1 |
| 5040 | 2 | 1 | 1 |
| 5041 | 2 | 1 | 1 |
| 5042 | 1 | 1 | 1 |
| 5043 | 2 | 1 | 1 |
| 5044 | 1 | 1 | 1 |
| 5045 | 1 | 1 | 1 |
| 5046 | 1 | 3 | 1 |
| 5047 | 2 | 2 | 3 |
| 5048 | 2 | 1 | 2 |
| 5049 | 1 | 1 | 1 |
| 5050 | 1 | 1 | 1 |
| 5051 | 3 | 3 | 3 |
| 5052 | 3 | 3 | 3 |
| 5053 | 3 | 3 | 3 |
| 5054 | 3 | 3 | 3 |
| 5055 | 3 | 3 | 3 |
| 5056 | 3 | 3 | 3 |
| 5057 | 2 | 2 | 2 |
| 5058 | 1 | 2 | 2 |
| 5059 | 1 | 2 | 1 |
| 5060 | 1 | 2 | 1 |
| 5061 | 1 | 1 | 2 |
| 5062 | 0.00515 | 0.00228325 | 0.0145 |
| 5063 | 1 | 1 | 1 |
| 5064 | 1 | 1 | 1 |
| 5065 | 1 | 1 | 1 |
| 5066 | 1 | 1 | 1 |
| 5067 | 0.00577 | 0.001814 | 0.003267 |
| 5068 | 2 | 1 | 1 |
| 5069 | 1 | 1 | 1 |
| 5070 | 1 | 1 | 1 |
| 5071 | 0.01053 | 0.001007 | 0.01404 |
| 5072 | 1 | 1 | 1 |
| 5073 | 1 | 1 | 1 |
| 5074 | 1 | 1 | 1 |
| 5075 | 1 | 1 | 1 |
| 5076 | 2 | 2 | 3 |
| 5077 | 2 | 1 | 3 |
| 5078 | 1 | 1 | 1 |
| 5079 | 1 | 2 | 1 |
| 5080 | 2 | 2 | 3 |
| 5081 | 1 | 2 | 2 |
| 5082 | 1 | 1 | 1 |
| 5083 | 1 | 1 | 1 |
| 5084 | 2 | 2 | 3 |
| 5085 | 1 | 1 | 2 |
| 5086 | 1 | 2 | 2 |
| 5087 | 1 | 2 | 2 |
| 5088 | 1 | 2 | 2 |
| 5089 | 1 | 1 | 1 |
| 5090 | 1 | 2 | 3 |
| 5091 | 2 | 2 | 3 |
| 5092 | 2 | 2 | 3 |
| 5093 | 0.006756 | 0.00314 | 0.1003 |
| 5094 | 1 | 2 | 2 |
| 5095 | 1 | 1 | 1 |
| 5096 | 1 | 1 | 1 |
| 5097 | 2 | 0.07431 | nd |
| 5098 | 1 | 2 | 1 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 5099 | 1 | 1 | 1 |
| 5100 | 2 | 1 | 1 |
| 5101 | 1 | 1 | 1 |
| 5102 | 2 | 2 | 2 |
| 5103 | 2 | 2 | 2 |
| 5104 | 1 | 1 | 1 |
| 5105 | 2 | 2 | 1 |
| 5106 | 1 | 1 | 1 |
| 5107 | 2 | 2 | 3 |
| 5108 | 2 | 2 | 3 |
| 5109 | 1 | 1 | 1 |
| 5110 | 1 | 1 | 1 |
| 5111 | 2 | 2 | 2 |
| 5112 | 1 | 1 | 1 |
| 5113 | 1 | 1 | 1 |
| 5114 | 1 | 1 | 1 |
| 5115 | 1 | 1 | 1 |
| 5116 | 1 | 2 | 2 |
| 5117 | 0.005334 | 0.006749 | 0.1028 |
| 5118 | 1 | 1 | 2 |
| 5119 | 1 | 2 | 2 |
| 5120 | 1 | 1 | 1 |
| 5121 | 2 | 2 | 2 |
| 5122 | 0.03483 | 0.1339 | nd |
| 5123 | 2 | 2 | 2 |
| 5124 | 1 | 1 | 2 |
| 5125 | 1 | 2 | 3 |
| 5126 | 1 | 2 | 2 |
| 5127 | 1 | 2 | 2 |
| 5128 | 1 | 1 | 2 |
| 5129 | 1 | 2 | 2 |
| 5130 | 2 | 1 | 2 |
| 5131 | 1 | 1 | 2 |
| 5132 | 2 | 2 | 3 |
| 5133 | 1 | 2 | 1 |
| 5134 | 1 | 2 | 2 |
| 5135 | 2 | 2 | 2 |
| 5137 | 1 | 1 | 1 |
| 5138 | 1 | 1 | 2 |
| 5139 | 1 | 1 | 1 |
| 5141 | 1 | 2 | 1 |
| 5142 | 2 | 2 | 3 |
| 5143 | 1 | 2 | 2 |
| 5144 | 1 | 1 | 1 |
| 5145 | 1 | 1 | 3 |
| 5146 | 2 | 2 | 3 |
| 5147 | 1 | 2 | 2 |
| 5140 | 2 | 2 | 2 |
| 5003 | 2 | 1 | 1 |
| 5005 | 2 | 2 | 2 |
| 6001 | 2 | 2 | 3 |
| 6002 | 2 | 1 | 2 |
| 6003 | 2 | 0.07288 | nd |
| 6004 | 2 | 2 | 3 |
| 6005 | 2 | 2 | 3 |
| 6006 | 2 | 2 | 2 |
| 6007 | 2 | 2 | 3 |
| 6008 | 3 | 3 | 3 |
| 6009 | 0.06968 | 0.1578 | nd |
| 6010 | 3 | 3 | 3 |
| 6011 | 2 | 2 | 3 |
| 6012 | 2 | 2 | 3 |
| 6013 | 2 | 2 | 3 |
| 6014 | 2 | 2 | 3 |
| 6015 | 3 | 2 | 3 |
| 6016 | 2 | 2 | 3 |
| 6017 | 1 | 1 | 1 |
| 6018 | 1 | 1 | 1 |
| 6019 | 1 | 1 | 1 |
| 6020 | 1 | 1 | 2 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 6021 | 1 | 1 | 1 |
| 6022 | 1 | 1 | 1 |
| 6023 | 2 | 1 | 1 |
| 6024 | 1 | 1 | 1 |
| 6025 | 1 | 1 | 1 |
| 6026 | 1 | 1 | 1 |
| 6027 | 1 | 1 | 1 |
| 6028 | 2 | 1 | 2 |
| 6029 | 1 | 2 | 1 |
| 6030 | 1 | 2 | 2 |
| 6031 | 1 | 2 | 2 |
| 6032 | 1 | 1 | 2 |
| 6033 | 1 | 1 | 1 |
| 6034 | 1 | 1 | 2 |
| 6035 | 0.004971 | 0.0007631 | 0.005747 |
| 6036 | 1 | 1 | 3 |
| 6037 | 3 | 3 | 3 |
| 6038 | 3 | 3 | 3 |
| 6039 | 3 | 3 | 3 |
| 6040 | 1 | 1 | 1 |
| 6041 | 2 | 2 | 3 |
| 6042 | 1 | 2 | 3 |
| 6043 | 1 | 2 | 3 |
| 6044 | 2 | 3 | 3 |
| 6045 | 0.09014 | 0.6254 | nd |
| 6046 | 1 | 1 | 1 |
| 6047 | 1 | 1 | 1 |
| 6048 | 2 | 2 | 3 |
| 6049 | 1 | 2 | 2 |
| 6050 | 1 | 2 | 2 |
| 7001 | 1 | 1 | 2 |
| 7002 | 1 | 1 | 1 |
| 7003 | 1 | 2 | 2 |
| 7004 | 1 | 2 | 3 |
| 7005 | 1 | 2 | 1 |
| 7006 | 1 | 1 | 1 |
| 7007 | 1 | 1 | 2 |
| 7008 | 1 | 1 | 1 |
| 7009 | 1 | 1 | 1 |
| 7010 | 1 | 2 | 2 |
| 7011 | 1 | 2 | 2 |
| 7012 | 3 | 3 | 3 |
| 7013 | 2 | 2 | 3 |
| 7014 | 1 | 1 | 2 |
| 7015 | 2 | 2 | 3 |
| 7016 | 2 | 2 | 3 |
| 7017 | 1 | 2 | 2 |
| 7018 | 0.01357 | 0.2284 | nd |
| 7019 | 1 | 1 | 2 |
| 7020 | 1 | 2 | 1 |
| 7021 | 3 | 3 | 3 |
| 7022 | 2 | 2 | 2 |
| 7023 | 3 | 3 | 3 |
| 7024 | 2 | 2 | 3 |
| 7025 | 3 | 3 | 3 |
| 7026 | 2 | 2 | 2 |
| 7027 | 2 | 1 | 2 |
| 7028 | 2 | 1 | 2 |
| 7029 | 3 | 2 | 2 |
| 7030 | 1 | 2 | 3 |
| 7031 | 1 | 2 | 1 |
| 7032 | 1 | 2 | 2 |
| 7033 | 1 | 1 | 3 |
| 7034 | 1 | 2 | 3 |
| 7035 | 1 | 2 | 1 |
| 7036 | 2 | 3 | 3 |
| 7037 | 2 | 2 | 3 |
| 7038 | 1 | 1 | 3 |
| 7039 | 1 | 1 | 1 |
| 7040 | 1 | 2 | 2 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or<br>not done (nd)<br>HTRF IC50 cluster<br>plus values (uM) | Clusters<br>1 = 0.0001584 to 0.004706<br>2 = 0.004776 to 0.07288<br>3 = 0.07431 to >10 or<br>not done (nd)<br>CBA IC50 cluster<br>plus values (uM) | Clusters<br>1 = 0.00002079 to 0.02258<br>2 = 0.02266 to >2.5<br>3 = not done (nd)<br>CMV Recall EC50 cluster<br>plus values (uM) |
|---|---|---|---|
| 7041 | 2 | 2 | 2 |
| 7042 | 2 | 2 | 3 |
| 7043 | 2 | 2 | 2 |
| 7044 | 1 | 2 | 2 |
| 7045 | 3 | 3 | 3 |
| 7046 | 1 | 1 | 1 |
| 7047 | 1 | 2 | 2 |
| 7048 | 1 | 3 | 3 |
| 7049 | 3 | 3 | 3 |
| 7050 | 1 | 2 | 1 |
| 7051 | 2 | 2 | 1 |
| 7052 | 2 | 2 | 3 |
| 7053 | 2 | 2 | 2 |
| 7054 | 1 | 1 | 1 |
| 7055 | 2 | 2 | 2 |
| 7056 | 2 | 3 | 3 |
| 7057 | 1 | 2 | 2 |
| 7058 | 2 | 3 | 3 |
| 7059 | 1 | 2 | 2 |
| 7060 | 1 | 1 | 1 |
| 7061 | 1 | 2 | 2 |
| 7062 | 1 | 2 | 2 |
| 7063 | 1 | 2 | 2 |
| 7064 | 3 | 3 | 3 |
| 13001 | 1 | 1 | 1 |
| 13002 | 1 | 1 | 1 |
| 13003 | 1 | 1 | 1 |
| 13004 | 1 | 1 | 3 |
| 13005 | 1 | 1 | 2 |
| 13006 | 0.004112 | 0.001465 | 0.02724 |
| 13007 | 1 | 1 | 1 |
| 13008 | 1 | 1 | 1 |
| 13009 | 1 | 1 | 2 |
| 13010 | 1 | 1 | 1 |
| 13011 | 0.00987 | 0.002687 | 0.03835 |
| 13012 | 1 | 1 | 2 |
| 13013 | 1 | 1 | 2 |
| 13014 | 1 | 3 | 3 |
| 14001 | 1 | 1 | 2 |
| 14002 | 1 | 1 | 2 |
| 14003 | 1 | 1 | 2 |
| 14004 | 1 | 1 | 1 |
| 14005 | 1 | 1 | 1 |
| 14006 | 1 | 1 | 1 |
| 14007 | 1 | 1 | 2 |
| 14008 | 1 | 1 | 1 |
| 9001 | 2 | 1 | 3 |
| 9002 | 2 | 2 | 3 |
| 9003 | 1 | 1 | 3 |
| 9004 | 1 | 2 | 3 |
| 9005 | 1 | 1 | 3 |
| 9006 | 1 | 1 | 1 |
| 9007 | 1 | 1 | 3 |
| 9008 | 1 | 1 | 3 |
| 9009 | 2 | 2 | 3 |
| 9010 | 2 | 2 | 3 |
| 9011 | 0.009402 | 0.01349 | nd |
| 9012 | 2 | 1 | 3 |
| 9013 | 0.008111 | 0.005974 | nd |
| 9014 | 1 | 1 | 1 |
| 9015 | 2 | 1 | 3 |
| 9016 | 0.005939 | 0.003278 | nd |
| 9017 | 2 | 2 | 3 |
| 9018 | 2 | 3 | 3 |
| 9019 | 2 | 3 | 3 |
| 9020 | 1 | 2 | 3 |
| 9021 | 2 | 3 | 3 |
| 9022 | 1 | 1 | 1 |
| 9023 | 1 | 1 | 1 |
| 9024 | 1 | 1 | 1 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or not done (nd)<br>HTRF IC50 cluster plus values (uM) | Clusters<br>1 = 0.0001584 to 0.004706<br>2 = 0.004776 to 0.07288<br>3 = 0.07431 to >10 or not done (nd)<br>CBA IC50 cluster plus values (uM) | Clusters<br>1 = 0.00002079 to 0.02258<br>2 = 0.02266 to >2.5<br>3 = not done (nd)<br>CMV Recall EC50 cluster plus values (uM) |
|---|---|---|---|
| 9025 | 1 | 1 | 2 |
| 9026 | 0.003466 | 0.00094785 | 0.03435 |
| 9027 | 1 | 1 | 2 |
| 9028 | 1 | 1 | 1 |
| 9029 | 2 | 1 | 1 |
| 9030 | 1 | 1 | 1 |
| 9031 | 0.007147 | 0.0006435 | 0.03943 |
| 9032 | 2 | 2 | 2 |
| 9033 | 2 | 1 | 2 |
| 9034 | 2 | 2 | 2 |
| 9035 | 2 | 2 | 2 |
| 9036 | 1 | 1 | 2 |
| 9037 | 2 | 1 | 2 |
| 9038 | 2 | 2 | 2 |
| 9039 | 1 | 1 | 2 |
| 9040 | 1 | 1 | 2 |
| 9041 | 1 | 1 | 2 |
| 9042 | 1 | 1 | 1 |
| 9043 | 1 | 1 | 2 |
| 9044 | 1 | 1 | 3 |
| 9045 | 1 | 1 | 1 |
| 9046 | 1 | 1 | 1 |
| 9047 | 1 | 1 | 1 |
| 9048 | 1 | 1 | 1 |
| 9049 | 1 | 1 | 1 |
| 9050 | 1 | 3 | 1 |
| 9051 | 2 | 1 | 1 |
| 9052 | 1 | 1 | 1 |
| 9053 | 2 | 2 | 1 |
| 9054 | 1 | 2 | 2 |
| 9055 | 1 | 1 | 2 |
| 9056 | 1 | 1 | 2 |
| 9057 | 0.01489 | 0.01948 | 0.112 |
| 9058 | 1 | 1 | 1 |
| 9059 | 2 | 2 | 2 |
| 9060 | 1 | 1 | 1 |
| 9061 | 1 | 1 | 1 |
| 9062 | 1 | 1 | 2 |
| 9063 | 1 | 1 | 2 |
| 9064 | 1 | 1 | 2 |
| 9065 | 1 | 1 | 2 |
| 9066 | 1 | 1 | 1 |
| 9067 | 1 | 1 | 2 |
| 9068 | 0.000385 | 0.002047 | 0.2488 |
| 9069 | 1 | 1 | 1 |
| 9070 | 2 | 1 | 2 |
| 9071 | 1 | 1 | 1 |
| 9072 | 1 | 1 | 2 |
| 9073 | 1 | 1 | 2 |
| 9074 | 1 | 1 | 1 |
| 9075 | 1 | 1 | 3 |
| 9076 | 1 | 2 | 3 |
| 9077 | 2 | 2 | 2 |
| 9078 | 2 | 1 | 1 |
| 9079 | 1 | 2 | 1 |
| 9080 | 1 | 1 | 1 |
| 9081 | 1 | 1 | 2 |
| 9082 | 1 | 1 | 2 |
| 9083 | 2 | 1 | 1 |
| 9084 | 1 | 1 | 1 |
| 9085 | 1 | 2 | 2 |
| 9086 | 1 | 1 | 1 |
| 9087 | 1 | 1 | 3 |
| 9088 | 1 | 1 | 1 |
| 9089 | 1 | 1 | 2 |
| 9090 | 1 | 1 | 2 |
| 9091 | 0.7736 | 0.003026 | 0.005603 |
| 9092 | 2 | 1 | 3 |
| 9093 | 2 | 2 | 2 |
| 9094 | 1 | 2 | 2 |

TABLE 14-continued

Biological Data for Examples 1001-10517

| Example No. | Clusters<br>1 = 0.000385 to 0.006743<br>2 = 0.006756 to 0.03027<br>3 = 0.03045 to >10 or<br>not done (nd)<br>HTRF IC50 cluster<br>plus values (uM) | Clusters<br>1 = 0.0001584 to 0.004706<br>2 = 0.004776 to 0.07288<br>3 = 0.07431 to >10 or<br>not done (nd)<br>CBA IC50 cluster<br>plus values (uM) | Clusters<br>1 = 0.00002079 to 0.02258<br>2 = 0.02266 to >2.5<br>3 = not done (nd)<br>CMV Recall EC50 cluster<br>plus values (uM) |
|---|---|---|---|
| 9095 | 1 | 2 | 2 |
| 9096 | 1 | 1 | 2 |
| 9097 | 1 | 2 | 2 |
| 9098 | 1 | 1 | 1 |
| 9099 | 1 | 1 | 2 |
| 9100 | 1 | 1 | 2 |
| 9105 | 1 | 2 | 1 |
| 9106 | 1 | 2 | 1 |
| 9107 | 2 | 2 | 1 |
| 9108 | 1 | 1 | 2 |
| 9109 | 2 | 2 | 2 |
| 9110 | 1 | 2 | 2 |
| 9111 | 1 | 2 | 2 |
| 9112 | 1 | 2 | 2 |
| 9113 | 2 | 2 | 2 |
| 9114 | 2 | 2 | 2 |
| 10001 | 2 | 3 | 3 |
| 10501 | 2 | 2 | 3 |
| 10502 | 1 | 2 | 3 |
| 10503 | 2 | 2 | 3 |
| 10504 | 2 | 1 | 3 |
| 10505 | 2 | 2 | 3 |
| 10506 | 2 | 3 | 3 |
| 10507 | 1 | 2 | 3 |
| 10508 | 2 | 2 | 2 |
| 10509 | 1 | 2 | 3 |
| 10510 | 0.008474 | 0.01661 | nd |
| 10511 | 1 | 2 | 3 |
| 10512 | 1 | 2 | 3 |
| 10513 | 1 | 1 | 2 |
| 10514 | 1 | 1 | 1 |
| 10515 | 0.003812 | 0.001559 | nd |
| 10516 | 3 | 3 | 3 |
| 10517 | 3 | 3 | 3 |

Numerous modifications and variations of the subject matter described and claimed herein are possible in light of the above teachings. It is therefore understood that within the scope of the appended claims, the subject matter recited in the claims may be practiced otherwise than as specifically described herein.

The present disclosure is not to be limited in scope by the embodiments disclosed herein, which are intended as single illustrations of individual aspects of the disclosure, and any that are functionally equivalent are within the scope of the disclosure. Various modifications to the models and methods of the disclosure, in addition to those described herein, will become apparent to those skilled in the art from the foregoing description and teachings, and are similarly intended to fall within the scope of the disclosure. Such modifications or other embodiments can be practiced without departing from the true scope and spirit of the disclosure.

The entire disclosure of each document cited (including patents, patent applications, journal articles, abstracts, laboratory manuals, books, GENBANK® Accession numbers, SWISS-PROT® Accession numbers, or other disclosures) herein is hereby incorporated by reference in its entirety. Further, the hard copy of the Sequence Listing submitted herewith, in addition to its corresponding Computer Readable Form, are incorporated herein by reference in their entireties.

What is claimed is:

1. A compound of formula (I),

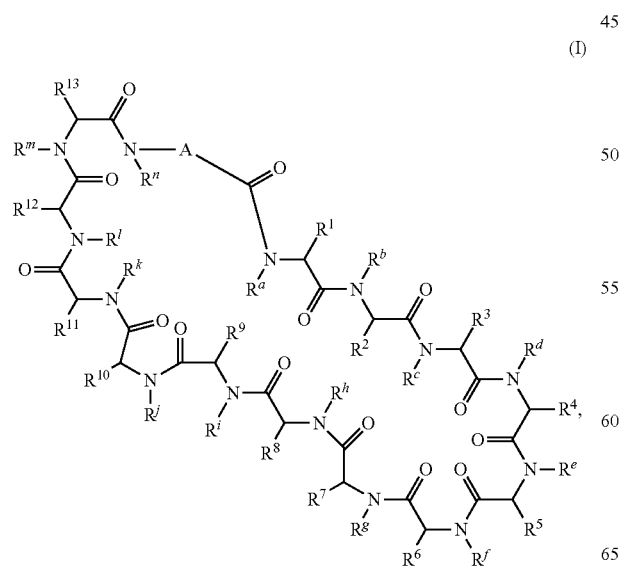

or a pharmaceutically acceptable salt thereof, wherein:

A is

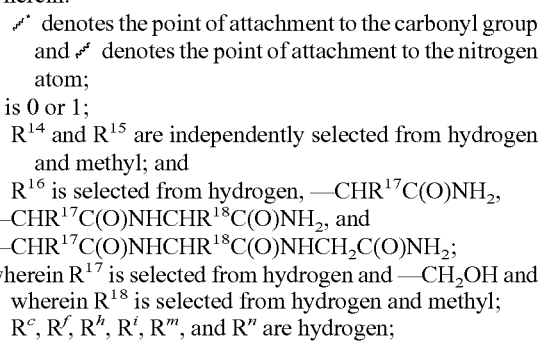

wherein:
 denotes the point of attachment to the carbonyl group and  denotes the point of attachment to the nitrogen atom;
n is 0 or 1;
$R^{14}$ and $R^{15}$ are independently selected from hydrogen and methyl; and
$R^{16}$ is selected from hydrogen, —$CHR^{17}C(O)NH_2$, —$CHR^{17}C(O)NHCHR^{18}C(O)NH_2$, and —$CHR^{17}C(O)NHCHR^{18}C(O)NHCH_2C(O)NH_2$;
wherein $R^{17}$ is selected from hydrogen and —$CH_2OH$ and wherein $R^{18}$ is selected from hydrogen and methyl;
$R^c$, $R^f$, $R^h$, $R^i$, $R^m$, and $R^n$ are hydrogen;

$R^a$, $R^e$, and $R^j$, are each independently selected from hydrogen and methyl;

$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;

$R^e$ can form a ring with the corresponding vicinal R group and the atoms to which it is attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^d$ is methyl or, $R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, hydroxy, and phenyl;

$R^g$ is methyl or, $R^g$ and $R^7$, together with the atoms to which they are attached, form a ring selected from azetidine, pyrollidine, morpholine, piperidine, piperazine, and tetrahydrothiazole; wherein each ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group;

$R^k$ is methyl or, $R^k$ and $R^{11}$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy; and $R^l$ is methyl or, $R^l$ and $R^{12}$, together with the atoms to which they are attached, form a ring selected from azetidine and pyrollidine, wherein each ring is optionally substituted with one to four groups independently selected from amino, cyano, methyl, halo, and hydroxy.

2. The compound of claim 1, or a pharmaceutically acceptable salt thereof, wherein $R^d$ and $R^4$, together with the atoms to which they are attached, form a ring selected from azetidine, pyrollidine, morpholine, piperidine, piperazine, and tetrahydrothiazole; wherein each ring is optionally substituted with one or two groups independently selected from amino, cyano, methyl, halo, and hydroxy;

$R^g$ and $R^7$, together with the atoms to which they are attached, form a pyrollidine ring, wherein said ring is optionally substituted with one or two groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^k$ is methyl.

3. The compound of claim 2, or a therapeutically acceptable salt thereof, wherein $R^8$ is selected from azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, diphenylmethyl, furanyl$C_1$-$C_3$alkyl, imidazolyl$C_1$-$C_3$alkyl, naphthyl$C_1$-$C_3$alkyl, pyridinyl$C_1$-$C_3$alkyl, thiazolyl$C_1$-$C_3$alkyl, thienyl$C_1$-$C_3$alkyl; and indolyl$C_1$-$C_3$alkyl, wherein the indolyl part is optionally substituted with one group selected from $C_1$-$C_3$alkyl, cyano, halo, and hydroxy.

4. The compound of claim 3, or a pharmaceutically acceptable salt thereof, wherein $R^8$ is 3-indolyl$C_1$-$C_3$alkyl optionally substituted with one group selected from $C_1$-$C_3$alkyl, halo, hydroxy, or cyano.

5. A method of blocking the interaction of PD-L1 with PD-1 and/or CD80 in a subject in need thereof, said method comprising administering to the subject a therapeutically effective amount of at least one macrocyclic peptide of claim 1.

* * * * *

SEQUENCE LISTING

```
<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

Leu Asp Ser Pro Asp Arg Pro Trp Asn Pro Pro Thr Phe Ser Pro Ala
1               5                   10                  15
```

-continued

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Asp Val Ser His Glu Asp Pro
        195                 200                 205

Glu Val Lys Phe Asn Trp Tyr Val Asp Gly Val Glu Val His Asn Ala
210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
            245                 250                 255

Lys Cys Lys Val Ser Asn Lys Ala Leu Pro Ala Pro Ile Glu Lys Thr
        260                 265                 270

Ile Ser Lys Ala Lys Gly Gln Pro Arg Glu Pro Gln Val Tyr Thr Leu
    275                 280                 285

Pro Pro Ser Arg Asp Glu Leu Thr Lys Asn Gln Val Ser Leu Thr Cys
290                 295                 300

Leu Val Lys Gly Phe Tyr Pro Ser Asp Ile Ala Val Glu Trp Glu Ser
305                 310                 315                 320

Asn Gly Gln Pro Glu Asn Asn Tyr Lys Thr Thr Pro Pro Val Leu Asp
            325                 330                 335

Ser Asp Gly Ser Phe Phe Leu Tyr Ser Lys Leu Thr Val Asp Lys Ser
        340                 345                 350

Arg Trp Gln Gln Gly Asn Val Phe Ser Cys Ser Val Met His Glu Ala
    355                 360                 365

Leu His Asn His Tyr Thr Gln Lys Ser Leu Ser Leu Ser Pro Gly Lys
370                 375                 380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

```
Asn Met Thr Ile Glu Cys Lys Phe Pro Val Glu Lys Gln Leu Asp Leu
            20              25              30

Ala Ala Leu Ile Val Tyr Trp Glu Met Glu Asp Lys Asn Ile Ile Gln
            35              40              45

Phe Val His Gly Glu Glu Asp Leu Lys Val Gln His Ser Ser Tyr Arg
    50              55              60

Gln Arg Ala Arg Leu Leu Lys Asp Gln Leu Ser Leu Gly Asn Ala Ala
65              70              75              80

Leu Gln Ile Thr Asp Val Lys Leu Gln Asp Ala Gly Val Tyr Arg Cys
            85              90              95

Met Ile Ser Tyr Gly Gly Ala Asp Tyr Lys Arg Ile Thr Val Lys Val
            100             105             110

Asn Ala Pro Tyr Asn Lys Ile Asn Gln Arg Ile Leu Val Val Asp Pro
            115             120             125

Val Thr Ser Glu His Glu Leu Thr Cys Gln Ala Glu Gly Tyr Pro Lys
    130             135             140

Ala Glu Val Ile Trp Thr Ser Ser Asp His Gln Val Leu Ser Gly Lys
145             150             155             160

Thr Thr Thr Thr Asn Ser Lys Arg Glu Glu Lys Leu Phe Asn Val Thr
                165             170             175

Ser Thr Leu Arg Ile Asn Thr Thr Thr Asn Glu Ile Phe Tyr Cys Thr
            180             185             190

Phe Arg Arg Leu Asp Pro Glu Glu Asn His Thr Ala Glu Leu Val Ile
        195             200             205

Pro Glu Leu Pro Leu Ala His Pro Pro Asn Glu Arg Thr Gly Ser Ser
    210             215             220

Glu Thr Val Arg Phe Gln Gly His His His His His His
225             230             235
```